US012171764B2

(12) United States Patent
Jones et al.

(10) Patent No.: US 12,171,764 B2
(45) **Date of Patent: *Dec. 24, 2024**

(54) TREATMENT OF A DISEASE OF THE GASTROINTESTINAL TRACT WITH A JAK OR OTHER KINASE INHIBITOR

(71) Applicant: BIORA THERAPEUTICS, INC., San Diego, CA (US)

(72) Inventors: Mitchell Lawrence Jones, La Jolla, CA (US); Sharat Singh, Rancho Santa Fe, CA (US); Christopher Loren Wahl, San Diego, CA (US); Harry Stylli, La Jolla, CA (US); Kevin David Howe, London (GB); Arana Perera, San Diego, CA (US)

(73) Assignee: BIORA THERAPEUTICS, INC., San Diego, CA (US)

(*) Notice: Subject to any disclaimer, the term of this patent is extended or adjusted under 35 U.S.C. 154(b) by 571 days.

This patent is subject to a terminal disclaimer.

(21) Appl. No.: 17/253,807

(22) PCT Filed: Jun. 19, 2019

(86) PCT No.: PCT/US2019/038003

§ 371 (c)(1),
(2) Date: Dec. 18, 2020

(87) PCT Pub. No.: WO2019/246273

PCT Pub. Date: Dec. 26, 2019

(65) Prior Publication Data

US 2022/0257600 A1 Aug. 18, 2022

Related U.S. Application Data

(60) Provisional application No. 62/804,385, filed on Feb. 12, 2019, provisional application No. 62/687,756, filed on Jun. 20, 2018.

(51) Int. Cl.

| | |
|---|---|
| ***A61K 31/519*** | (2006.01) |
| ***A61K 9/00*** | (2006.01) |
| ***A61K 31/4196*** | (2006.01) |
| ***A61K 31/437*** | (2006.01) |
| ***A61K 31/46*** | (2006.01) |
| ***A61K 31/4985*** | (2006.01) |
| ***A61K 31/501*** | (2006.01) |
| ***A61K 31/505*** | (2006.01) |
| ***A61K 31/506*** | (2006.01) |
| ***A61K 31/5377*** | (2006.01) |
| ***A61K 31/541*** | (2006.01) |
| ***A61P 1/00*** | (2006.01) |

(52) U.S. Cl.
CPC .......... *A61K 31/519* (2013.01); *A61K 9/0014* (2013.01); *A61K 9/0053* (2013.01); *A61K 9/0097* (2013.01); *A61K 31/4196* (2013.01); *A61K 31/437* (2013.01); *A61K 31/46* (2013.01); *A61K 31/4985* (2013.01); *A61K 31/501* (2013.01); *A61K 31/505* (2013.01); *A61K 31/506* (2013.01); *A61K 31/5377* (2013.01); *A61K 31/541* (2013.01); *A61P 1/00* (2018.01)

(58) Field of Classification Search
CPC .. A61K 31/519; A61K 9/0053; A61K 9/0097; A61K 31/4196; A61K 31/437; A61K 9/0014; A61K 31/46; A61K 31/4985; A61K 31/501; A61K 31/5377; A61K 31/541; A61P 1/00
See application file for complete search history.

(56) References Cited

U.S. PATENT DOCUMENTS

| | | | | |
|---|---|---|---|---|
| 11,033,490 B2 * | 6/2021 | Jones | A61K 9/4808 | |
| 2005/0266074 A1 * | 12/2005 | Zilberstein | A61B 1/00156 | 424/464 |
| 2013/0078248 A1 * | 3/2013 | Gschwind | A61P 35/00 | 435/328 |
| 2014/0275030 A1 * | 9/2014 | Combs | C07D 498/06 | 514/230.2 |

OTHER PUBLICATIONS

Xitian et al. "A novel remote controlled capsule for site-specific drug delivery in human GI tract." In International Journal of Pharmaceutics, 382 (2009) 160-164). (Year: 2009).*

Davoodi et al. "Drug delivery systems for programmed and on-demand release," in Advanced Drug Delivery Reviews 132 (2028) 104-138) (Year: 2018).*

* cited by examiner

*Primary Examiner* — Blessing M Fubara
(74) *Attorney, Agent, or Firm* — Procopio, Cory, Hargreaves & Savitch LLP

(57) ABSTRACT

This disclosure features methods and compositions for treating diseases of the gastrointestinal tract with a JAK or other kinase inhibitor.

19 Claims, 81 Drawing Sheets

Specification includes a Sequence Listing.

| Time | SQ Adalimumab Plasma concentration µgs/ml | Topical Adalimumab Plasma concentration µgs/ml |
|---|---|---|
| 6hrs | 16 +/-8 | 0.01 |
| 12hrs | 13 +/-4 | 0.01 |
| 24hrs | 13 +/-3 | 0.01 |
| 48hrs | 16 +/-5 | 0.01 |

FIG. 52

| Route | PO | IC | IC | IC |
|---|---|---|---|---|
| Dose (mg.kg) | 0.09 | 0.02 | 0.04 | 0.09 |
| Tmax | 1 | 1 | 1 | 1 |
| Cmax | 3.531 ± 3.84 | 2.39 ± 0.565 | 9.197 ± 3.30 | 21.8 ± 4.73 |
| Trough (12hr) | 0.568 ± 0.291 | 0.746 ± 0.038 | 1.96 ± 0.491 | 4.35 ± 0.516 |
| AUC 0-12hr (ng*h/ml) | 16.83 ± 3.641 | 15.29 ± 2.356 | 51.35 ± 4.04 | 129.6 ± 7.827 |

Quantitative histological grading of colitis.

| Feature graded | Grade | Description |
|---|---|---|
| Inflammation | 0 | None |
| | 1 | Slight |
| | 2 | Moderate |
| | 3 | Severe |
| Extent | 0 | None |
| | 1 | Mucosa |
| | 2 | Mucosa and submucosa |
| | 3 | Transmural |
| Regeneration | 0 | Complete regeneration or normal tissue |
| | 1 | Almost complete regeneration |
| | 2 | Regeneration with crypt depletion |
| | 3 | Surface epithelium not intact |
| | 4 | No tissue repair |
| Crypt damage | 0 | None |
| | 1 | Basal 1/3 damaged |
| | 2 | Basal 2/3 damaged |
| | 3 | Only surface epithelium intact |
| | 4 | Entire crypt and epithelium lost |
| Percent involvement | 1 | 1-25% |
| | 2 | 26-50% |
| | 3 | 51-75% |
| | 4 | 76-100% |

FIG. 93

Anti-TNFαIC
(IHC: CD4+)

Anti-TNFαIP
(IHC: CD4+)

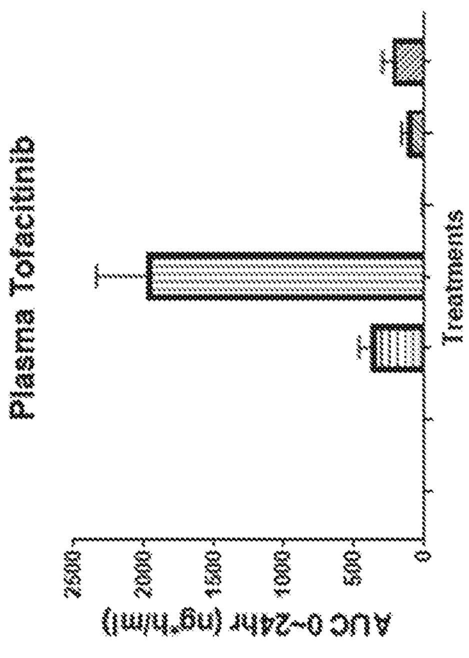
FIG. 111A
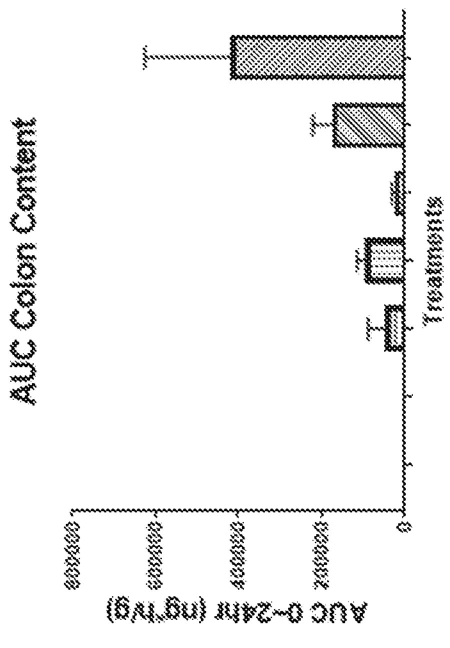
FIG. 111B
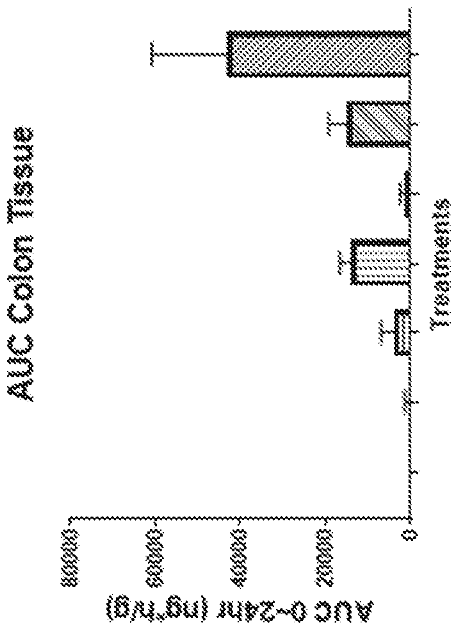
FIG. 111C

TREATMENT OF A DISEASE OF THE GASTROINTESTINAL TRACT WITH A JAK OR OTHER KINASE INHIBITOR

RELATED APPLICATIONS

This application claims the benefit of U.S. Provisional Application No. 62/687,756, filed Jun. 20, 2018; and 62/804,385, filed Feb. 12, 2019, each of which are incorporated herein by reference in their entirety.

INCORPORATION BY REFERENCE OF SEQUENCE LISTING FILED ELECTRONICALLY

An electronic version of the Sequence Listing is filed herewith, the contents of which are incorporated by reference in their entirety. The electronic file was created on Jun. 11, 2019 and is 97.7 KB and is titled 44090_0054WO1_ST25.txt.

TECHNICAL FIELD

This disclosure features methods and compositions for treating diseases of the gastrointestinal tract with a JAK or other kinase inhibitor.

BACKGROUND

The Janus kinase (JAK) proteins are a family of non-receptor tyrosine kinases that possess a highly conserved kinase domain responsible for its enzymatic activity. Mammals have four members of this family, JAK1, JAK2, JAK3 and Tyrosine kinase 2 (TYK2). These kinases associate with the intracellular portion of cytokine or hormone receptors, and transduce signals through seven members of the STAT transcription factors—STAT1, STAT2, STAT3, STAT4, STAT5A, STAT5B, and STAT6 in various combinations. JAK1 promotes signaling of multiple cytokines (e.g., certain type I and type II cytokines), including pro-inflammatory cytokines involved in the pathogenesis of autoimmune diseases. Single-nucleotide polymorphisms within the JAK/STAT pathway that confer susceptibility to IBD have been identified (Jostins et al., "Host-microbe interactions have shaped the genetic architecture of inflammatory bowel disease," Nature 491:119-124, 2012). Both in vivo and in vitro studies have confirmed the role of JAK/STAT signaling in regulating immune responses (O'Shea and Plenge, "JAK and STAT signaling molecules in immunoregulation and immune-mediated disease," Immunity 36:542-550, 2012). Tofacitinib, selective oral JAK inhibitor (including JAK1 and JAK3) has been tested in clinical trials for both ulcerative colitis (Sandborn et al., "Tofacitinib, an Oral Janus Kinase Inhibitor, in Active Ulcerative Colitis," New England J. Med 367:616-24, 2012; Panes et al., "Randomized trial of tofacitinib in active ulcerative colitis: analysis of efficacy base on patient-reported outcomes," BMC Gastroenterology 15:14, doi: 10.1186/s12876-015-0239-9, 2015) and Crohn's disease.

The gastrointestinal (GI) tract generally provides a therapeutic medium for an individual's body. One means of accessing the therapeutic medium of the GI tract is via oral administration, however, the convenience of per oral delivery is countered by well-established challenges. For instance, traditional oral delivery of a drug may lend itself to systemic exposure associated with undesirable or potentially harmful side effects. Another challenge associated with oral administration relates to potential instability of the drug upon exposure to the harsh chemical and/or enzymatic degradation conditions of the GI tract.

Yet at times, therapeutic drugs may need to be dispensed to specified locations within the small intestine or large intestine, which is more effective than traditional oral administration of the therapeutic drugs to cure or alleviate the symptoms of some medical conditions. For example, therapeutic drugs dispensed directly within the small intestine would not be contaminated, digested or otherwise compromised in the stomach, and thus allow a higher dose to be delivered at a specific location within the small intestine.

An effective way to provide topical, local delivery of a therapeutic drug to the GI tract (and/or to a particular portion or section of the GI tract) to treat the diseased tissue in the GI tract would be desirable, given the following advantages over systemic administration:

- Reduced systemic exposure;
- Increase bioavailability at disease site;
- Potential to reduce the therapeutic dose relative to that required when delivered systemically;
- Supply drug to the biophase only when required;
- Maintain drug in intact form as close as possible to the target site; and
- Provide high residence time of the drug in an environment with low digestive enzymatic activity, particularly for delivery to the colon. [Van den Mooter & Kinget, Drug Delivery, 2, pp. 81-93 (1995)].

In practice, however, there are several challenges to such an approach. To begin with, identifying a "go/no-go" trigger for delivery to a specific site is generally difficult (e.g., see Rubenstein A., "Approaches and Opportunities in Colon-Specific Drug Delivery"; Critical Reviews in Therapeutic Drug Carrier Systems, 12(2&3), pp. 101-149 (1995), p. 106: "A successful delivery of a drug molecule to the colon means that most of it has been transported intact through the stomach and the small intestine. Practically, one cannot find a physiologic feature that may serve as a "go no-go" trigger for [delivery of] colonic-specific drugs."). For example, dispensing therapeutic drugs directly within the small intestine inside a human body (e.g., the cecum, the ascending colon) can be difficult, because a device or mechanism or a particular formulation would be needed to transport a therapeutically effective dose of drug to a desired location within the small intestine and then automatically deliver the therapeutic drug at the desired location. Such a device or mechanism also would also need to be operated in a safe manner in that the device or mechanism needs to physically enter the human body. Dispensing therapeutic drugs directly within other locations in the GI tract of the human body can be similarly difficult. For diseased tissue in the colon an added challenge lies in the difficulty in reaching the site of disease due to its location.

A further hurdle exists when the drug is a biologic, such as a monoclonal antibody, in which case there is a need to achieve high concentrations of the therapeutic drug in the large intestine for diseases such as, for example, colitis, and Crohn's disease [Van den Mooter et al., Drug Delivery (1996)]. Monoclonal antibodies ("mAbs") are typically delivered in single doses, generally 100 mg to 1 g protein per dose; since formulations of mAbs typically have concentrations up to about 50 mg/mL, administration of a relatively high volume of 2-20 mL per dose is required [Yang et al., PNAS, 2003]. At the relatively high concentrations required to deliver efficacious doses, mAbs have a tendency to aggregate; in addition, these high concentrations often result in very high viscosity and poor overall stability [Yang et al.]. Increasing protein concentrations may also result in opalescence, complicating the visual inspection [Puhl et al., Asian J. Pharm. Sci. II (2016), pp. 469-477]. While the use of more dilute formulations may help overcome these drawbacks, the resulting large volumes may not be practical for oral delivery to treat diseases and conditions of the GI tract, and may instead be conducive to IV infusion—which, in turn, may enhance unwanted systemic exposure.

Methods typically employed to deliver drugs locally all have their own drawbacks. For example, the usefulness of formulations relying on pH-mediated release (including but not limited to enteric coated formulations) may be limited by the high inter- and intra-patient variability of pH and microflora. The utility may be further limited in patient populations having highly variable motility (e.g., patients with ulcerative colitis), contributing to unpredictable transit times (times for transitioning from one portion of the GI tract to an adjacent portion). For example, budesonide formulated using Multi Matrix (MMX®) colonic delivery technology (budesonide MMX®) is a once-daily oral tablet designed for controlled release of budesonide throughout the colon for the treatment of ulcerative colitis. The tablet relies on pH-mediated release. When $^{153}$Sm labelled budesonide MMX® tablets were administered to 12 healthy subjects and evaluated for initial tablet disintegration (ITD) within the GI tract via pharmaco-scintigraphy, high variability in the location and time of ITD were observed, ranging from release in the ileum or small intestine/ileum after 6 to 12 hours (4 subjects) to release in the sigmoid colon after greater than 24 h (1 subject) [Brunner M. et al., "Gastrointestinal transit, release and plasma pharmacokinetics of a new oral budesonide formulation," Br. J. Clin. Pharmacol. (2006) 61(1), pp. 31-38.]. Moreover, pH is dysregulated in ulcerative colitis patients, making MMX technology and other pH-dependent drug delivery technologies less predictable. Not only are release and emulsification of drug unpredictable, but such technologies also have poor compatibility with some preferred formulation systems, including emulsifying systems. Rectal delivery forms (suppositories and enemas) have varying effectiveness since here too high variability has been observed in the distribution of these forms. Suppositories are only effective in the rectum because of their confined spread, and enemas may only offer effective topical treatment only to the sigmoid colon and descending colon [Van den Mooter et al., Drug Delivery (1996)].

Additional proposed solutions to colonic delivery, and some associated disadvantages, are described in Van den Mooter et al., Drug Delivery (1995). For example, attempts have been made to modify the release profile of drugs using pH-sensitive polymers or bacterial-degradable polymers as coatings. The use of pH-sensitive polymers, however, is characterized by the 'unsteadiness' of the site where the polymer disintegration commences—so that polymer dissolution can be completed at the end of the ileum or deep in the colon, depending on the intensity of GI motility. Colonic pH reduction (e.g., to as low as about pH 6, due to the presence of short-chain fatty acids, bile acid residues, $CO_2$ or other fermentation products) can reduce the reliability of triggering drug release based on the colon pH. An additional disadvantage is the difficulty to formulate certain drugs in enteric coated delivery capsules. As for bacterial-degradable polymers, they suffer from variability in absorption rates, which may be attributed to intra- and inter-subject differences in microbial degradation of the coating. The same drawbacks apply to delivery of drugs through bacterial-degradable matrices.

Another approach involves the preparation of prodrugs of the therapeutic agent. This approach relies on selective cleavage of the prodrug to release the active form in the colon as a result of metabolic activity of the gut microflora. Once again, this approach relies on factors, such as the enzymatic activity in GI tract, that may be highly variable between and within subjects.

The use of a non-autonomous devices and/or procedures could be seen as offering a potential solution to the foregoing problems, but in practice this approach too faces several challenges, such as:

- Focal CT, scintigraphy, magnetic marker monitoring used to identify the anatomical location of the device each require external equipment and/or clinician monitoring.
- Capsule-based devices that require external triggering (there is no autonomous system in current practice) are not practical from a clinical/commercial point of view.
- Devices relying on the pH in the GI tract or a portion thereof suffer from the drawbacks discussed above, including poor accuracy and high variability, compounded in certain disease populations.
- Devices that rely on electrical, or chemical principles or on pressure difference may be of conceptual interest but are mainly at the research stage at this time.
- Capsule endoscopy requires an expert read and is characterized by its high complexity and cost. According to *Journal of Micro-Bio Robotics* 11.1-4 (2016):1-18, endoscopic capsules with enhanced diagnostic capabilities are available as a result of progress in microelectromechanical systems (MEMS). Endoscopic capsules, however, do not have the capability of accurately locating a disease site autonomously. They require doctor oversight over a period of hours in order to manually determine the location.
- The use of catheters, for example coupled to an endoscopic device, to place drug at or near the site if disease is highly invasive requiring patients need to be sedated, and regular dosing (e.g., daily, weekly) via spray catheter is not practical. Spray catheters also cannot readily access certain sections of GI tract such as the ascending colon, cecum and all portions of the small intestine.

In sum, there remains a significant unmet medical need for improved treatment regimens for gastrointestinal diseases, such as inflammatory bowel disease (IBD), including a need for regimens which can dispense therapeutics to specific locations within the GI tract, thereby reducing or avoiding the drawbacks of oral or other forms of systemic administration.

SUMMARY

The present disclosure provides devices and methods for the topical administration of drug/mAbs to the GI tract, and more particularly, proximate to one or more disease sites.

The present disclosure provides one or more advantages:

- autonomous topical delivery of a therapeutic drug to specific locations in the GI tract using a self-localizing device that does not require external triggering to release the drug;
- localization based on anatomy, not variable physiological conditions (not pH- or bacteria-dependent);
- reduced systemic absorption/exposure;
- possibility to deliver a higher local dose;
- possibility to employ novel combinations of active agents that otherwise may have a dangerous side effect profile if administered in combination;

the ability to dispense the drug in virtually any form, e.g., liquid, non-solid, semi-solid or solid forms, or formulation, such as emulsions or formulations in charged excipients/carriers (e.g., micelles, surfactants) to enable even distribution in the colon and/or the targeting of inflamed tissues, and/or such as GI-specific formulations (to increase GI stability and/or GI tissue penetration);

flexible dosing schedules, e.g., single (e.g., bolus) dosing, multiple dosing, continuous dosing; optimized local pharmacokinetic profiles at the site of disease through regular dosing;

stability of the drug or formulation independent of the GI environment, since the drug or formulation remains in the device or in a reservoir until its site-specific release is triggered; and patient convenience.

The present disclosure provides novel treatment paradigms for inflammatory conditions of the gastrointestinal tract. The methods and compositions described herein allow for the regio-specific release of therapeutic drugs at or near the site of disease in the gastrointestinal tract. By releasing a therapeutic drug locally instead of systemically, the bioavailability of the drug can be increased at the site of injury and/or decreased in the systemic circulation, thereby resulting in improved overall safety and/or efficacy and fewer adverse side effects. Advantages may include one or more of increased drug engagement at the target, leading to new and more efficacious treatment regimens, and/or lower systemic drug levels, which can translate to reduced toxicity and reduced immunogenicity, e.g., in the case of biologics. In some instances, releasing a therapeutic drug locally also provides for new modes of action that may be unique to local delivery in the GI tract as opposed to systemic administration. For patients, clinicians and payors, this can mean an easier or simpler route of administration, fewer co-medicaments (e.g., immunomodulators), fewer side effects, and/or better outcomes.

For example, a patient may present to a physician with one or more symptoms of a disorder of the GI tract (e.g., inflammatory bowel disease), and the physician can determine the specific discrete location(s) of diseased tissue (e.g., inflamed tissue or a lesion) in the patient's GI tract, and then use any of the devices described herein to topically administer a therapeutically effective amount of a JAK inhibitor proximate to or directly onto the specific discrete location(s) of diseased tissue in the patient.

In other examples, a patient may present to a physician with one or more symptoms of a disorder of the GI tract (e.g., inflammatory bowel disease) and the physician can use any of the devices provided herein to identify the specific discrete location(s) of diseased tissue (e.g., inflamed tissue or a lesion) in the patient's GI tract, and then use the same device or a different device (e.g., any of the devices described herein) to topically administer a therapeutically effective amount of a JAK inhibitor proximate to or directly onto the specific discrete locations of diseased tissue in the patient. In some embodiments, a therapeutically effective amount of a JAK inhibitor is administered to a section or subsection of the GI tract containing one or more disease sites. In some embodiments, a therapeutically effective amount of a JAK inhibitor is administered proximal to a section or subsection of the GI tract containing one or more disease sites.

As can be appreciated by those in the art, these methods may be performed periodically on a patient at periodic intervals, e.g., approximately twice a month, approximately once a month, approximately every two months, approximately every three months, approximately four months, approximately five months, or approximately every six months. In some examples, these methods can provide for increased efficacy of treatment (e.g., reduced negative side effects and/or increased reduction in the severity, frequency, or number of symptoms) as compared to a patient which is administered an oral dosage form of the same JAK inhibitor. In some embodiments, the dosage of the JAK inhibitor administered using any of the devices described herein can differ between the different clinical visits based on an observation or measurement of the severity of disease at the specific discrete location(s) of diseased tissue (e.g., inflamed tissue or a lesion) in the patient's GI tract at the time of each clinical visit, or based on one or more observations or measurements of systemic disease markers (e.g., inflammatory markers in the blood) or markers in stool (e.g., calprotectin and lactoferrin). In some examples, over time, new specific discrete location(s) of diseased tissue may be detected or observed in the patient, and any of the devices described herein can be used to administer a therapeutically effective amount of a JAK inhibitor onto or proximal to the new specific discrete location(s) of diseased tissue in the patient's GI tract.

In some examples, the identification of the specific discrete location(s) of diseased tissue (e.g., inflamed tissue or a lesion) in the patient's GI tract and the administration of a therapeutically effective amount of a JAK inhibitor using any of the devices described herein can be performed in a single clinical visit.

In some examples, the diagnosis of a disorder of the GI tract (e.g., irritable bowel syndrome), the identification of the specific discrete location(s) of diseased tissue (e.g., inflamed tissue or a lesion) in the patient's GI tract, and the topical administration of a therapeutically effective amount of a JAK inhibitor proximate to or directly onto the specific discrete locations of diseased tissue in the patient using any of the devices described herein, can be performed in a single clinical visit.

Accordingly, described herein are methods for treating disorders of the gastrointestinal (GI) tract. The methods can include one or more of:

diagnosing a GI disease in a subject;

mapping, sampling, and/or assessing the site, severity, pathology, and extent of a GI disease in the GI tract of a subject and/or mapping, sampling, and/or assessing a patient response to a therapeutic agent, e.g., in the patient's GI tract;

identifying, quantifying, and/or monitoring one or more markers of a GI disease in the GI tract of the subject and/or one or more markers of patient response to a therapeutic agent, e.g., in the patient's GI tract; and releasing a therapeutic agent proximate to the site of a GI disease, e.g., to a section or subsection of the GI tract containing one or more disease sites, proximal to a section or subsection of the GI tract containing one or more disease sites, or directly onto the specific discrete location(s) of diseased tissue in the patient.

The present disclosure accordingly provides patients and physicians more personalized treatment options for GI disorders by facilitating regimens which can release a therapeutic agent according to desired (e.g., customized or optimized) dosage, timing, and/or location parameters. In some cases, the treatment methods can employ one or more ingestible devices to achieve the benefits disclosed herein.

Provided in the present disclosure is a method of treating a gastrointestinal (GI) inflammatory disease or condition in a subject in need thereof that includes topically administering to the subject a pharmaceutical formulation that contains a therapeutically effective amount of a JAK inhibitor, said topical administration including orally administering an ingestible device to the subject, said device containing the pharmaceutical formulation; and releasing the pharmaceutical formulation from the device (a) to a section or subsection of the subject's GI tract containing one or more inflammatory disease sites; or (b) proximal to a section or subsection of the subject's GI tract containing one or more inflammatory disease sites; thereby treating at least one of the one or more disease sites.

In some embodiments, the GI inflammatory disease or condition is an inflammatory bowel disease. In some embodiments, the disease or condition is ulcerative colitis. In some embodiments, the disease or condition is Crohn's disease.

In some embodiments, the device includes a self-localization mechanism configured to determine the device location within the subject's GI tract, and the method further includes determining the device location within the subject's GI tract via the device self-localization mechanism. In some embodiments, determining the device location within the subject's GI tract via the device self-localization mechanism includes detecting one or more device transitions between portions of the subject's GI tract. In some embodiments, the one or more detected device transitions occurs between portions of the GI tract selected from the group consisting of: mouth and stomach; esophagus and stomach; stomach and duodenum; duodenum and jejunum; jejunum and ileum; ileum and cecum; and cecum and colon; and combinations of any two or more of the foregoing. In some embodiments, the portions are adjacent portions. In some embodiments, determining the device location within the subject's GI tract via the device self-localization mechanism includes confirming the one or more device transitions between the portions of the GI tract of the subject.

In some embodiments, the device self-localization mechanism is based on data comprising light reflectance occurring external to the device and within the GI tract of the subject. In some embodiments, the device self-localization mechanism is based on data comprising elapsed time after entry of the device into the GI tract of the subject, elapsed time after detecting at least one of the one or more device transitions between the portions of the subject's GI tract, or a combination thereof. In some embodiments, the device self-localizes to the stomach, duodenum, jejunum, ileum, cecum or colon with at least 80% accuracy. In some embodiments, the device self-localizes to the stomach, duodenum, jejunum, ileum, cecum or colon with at least 85% accuracy.

In some embodiments, the release of the formulation from the device is autonomously triggered based on the self-localization of the device to a pre-selected location within the subject's GI tract. In some embodiments, the pre-selected location is selected from the group consisting of the stomach, the duodenum, the jejunum, the ileum, the cecum and the colon. In some embodiments, the release of the formulation from the device occurs at substantially the same time as the device self-localizes to the pre-selected location. In some embodiments, the release of the formulation from the device commences within a period of time of at most about 5 minutes after the device detects or confirms the transition to the pre-selected location. In some embodiments, the period of time is at most about 1 minute, at most about 30 seconds, at most about 10 seconds, or at most about 1 second after the device detects or confirms the transition to the pre-selected location. In some embodiments, the release of the formulation is as a bolus.

In some embodiments, the release of the formulation from the device occurs over a pre-determined period of time. In some embodiments, the pre-determined period of time over which the formulation is released from the device is about 8 hours, about 7 hours, about 6 hours, about 5 hours, about 4 hours, about 3 hours, about 2 hours, about 1 hour, about 30 minutes, about 15 minutes, about 10 minutes, or about 5 minutes. In some embodiments, the pre-determined period of time commences within at most about 5 minutes, at most about 1 minute, at most about 30 seconds, at most about 10 seconds, or at most about 1 second after the device detects or confirms the transition to the pre-selected location.

In some embodiments, the method further includes identifying the section or subsection of the GI tract containing at least one of the one or more disease sites. In some embodiments, the one or more disease sites is identified prior to the administration, wherein the identification of the one or more disease sites prior to the administration comprises imaging the GI tract, endoscopy, biopsy, computer-aided (CT) enterography, magnetic resonance enterography, sampling the GI tract for one or more disease markers, or a combination of any two or more of the foregoing.

In some embodiments of the method, the release of the formulation from the device is proximal to the section or subsection of the GI tract containing the one or more disease sites. In some embodiments, the release of the formulation is to a section or subsection of the GI tract immediately proximal to (immediately preceding) the section or subsection of the subject's GI tract containing at least one of the one or more disease sites. In some embodiments, the immediately preceding section or subsection of the GI tract does not contain a disease site and/or has not been determined to contain a disease site.

In some embodiments, determining the device location as the cecum autonomously triggers the release of the formulation to the cecum, thereby delivering the JAK inhibitor to at least one of the one or more disease sites in the colon. In some embodiments, determining the device location as the cecum autonomously triggers the release of the formulation to the cecum, thereby treating at least one of the one or more disease sites in the colon. In some embodiments, determining the device location as the ileum autonomously triggers the release of the formulation to the ileum, thereby delivering the JAK inhibitor to at least one of the one or more disease sites in the cecum. In some embodiments, determining the device location as the ileum autonomously triggers the release of the formulation to the ileum, thereby treating at least one of the one or more disease sites in the cecum. In some embodiments, determining the device location as the duodenum autonomously triggers the release of the formulation to the duodenum, thereby delivering the JAK inhibitor to at least one of the one or more disease sites in the jejunum. In some embodiments, determining the device location as the duodenum autonomously triggers the release of the formulation to the duodenum, thereby treating at least one of the one or more disease sites in the jejunum. In some embodiments, determining the device location as the jejunum autonomously triggers the release of the formulation to the jejunum, thereby delivering the JAK inhibitor to at least one of the one or more disease sites in the ileum. In some embodiments, determining the device location as the jejunum autonomously triggers the release of the formulation to the jejunum, thereby treating at least one of the one or more disease sites in the ileum. In some embodiments, determining the device location as the jejunum autonomously triggers release of the formulation to the jejunum, and wherein the one or more disease sites is present in the ileum, the colon, or both. In some embodiments, determining the device location as the jejunum autonomously triggers release of the formulation to the jejunum, and wherein the disease to be treated is ileal or ileal colonic Crohn's disease. In some embodiments, the section or subsection of the GI tract where the device is determined to be located does not contain a disease site and/or has not been determined to contain a disease site. In some embodiments, the section or subsection of the GI tract where the formulation is released does not contain a disease site and/or has not been determined to contain a disease site. In some embodiments, the immediately preceding section or subsection of the GI tract does not contain a disease site and/or has not been determined to contain a disease site. In some embodiments, the device determines the location with at least 80% accuracy; preferably, with at least 85% accuracy.

In some embodiments of the method, the release of the formulation from the device is to the section or subsection of the subject's GI tract containing at least one of the one or more inflammatory disease sites. In some embodiments, determining the device location as the colon autonomously triggers the release of the formulation to the colon, thereby delivering the JAK inhibitor to at least one of the one or more disease sites in the colon. In some embodiments, determining the device location as the colon autonomously triggers the release of the formulation to the colon, thereby treating at least one of the one or more disease sites in the colon. In some embodiments, determining the device location as the ileum autonomously triggers the release of the formulation to the ileum, thereby delivering the JAK inhibitor to at least one of the one or more disease sites in the ileum. In some embodiments, determining the device location as the ileum autonomously triggers the release of the formulation to the ileum, thereby treating at least one of the one or more disease sites in the ileum. In some embodiments, determining the device location as the jejunum autonomously triggers the release of the formulation to the jejunum, thereby delivering the JAK inhibitor to at least one of the one or more disease sites in the jejunum. In some embodiments, determining the device location as the jejunum autonomously triggers the release of the formulation to the jejunum, thereby treating at least one of the one or more disease sites in the jejunum. In some embodiments, determining the device location as the duodenum autonomously triggers the release of the formulation to the duodenum, thereby delivering the JAK inhibitor to at least one of the one or more disease sites in the duodenum. In some embodiments, determining the device location as the duodenum autonomously triggers the release of the formulation to the duodenum, thereby treating at least one of the one or more disease sites in the duodenum. In some embodiments, the device determines the location with at least 80% accuracy; preferably, with at least 85% accuracy.

In some embodiments of the method, the section of the GI tract containing the one or more inflammatory disease sites is selected from the group consisting of the stomach, duodenum, jejunum, ileum, cecum, ascending colon, transverse colon, descending colon, sigmoid colon and rectum; and a combination of any two or more of the foregoing. In some embodiment, the subsection of the GI tract containing the one or more inflammatory disease sites is selected from the group consisting of the proximal duodenum, distal duodenum, proximal jejunum, distal jejunum, proximal ileum, distal ileum, proximal cecum, distal cecum, proximal ascending colon, distal ascending colon, proximal transverse colon, distal transverse colon, proximal descending colon and distal descending colon, and a combination of any two or more of the foregoing.

In some embodiments of the method, the device self-localization mechanism does not require monitoring the pH of the subject's GI tract. In some embodiments, the method excludes a pH-dependent drug release mechanism. In some embodiments, the device self-localization mechanism does not require monitoring the pressure of the subject's GI tract, the temperature of the subjects GI tract, or both.

In some embodiments, the method provides a ratio of JAK inhibitor concentration in the subject's GI tissue to JAK inhibitor concentration in the subject's blood, serum, or plasma ranging from about 2:1 to about 3000:1, about 2:1 to about 2000:1, about 2:1 to about 1000:1, or about 2:1 to about 600:1.

In some embodiments, the method suppresses the subject's local GI tract immune response as compared to the subject's peripheral immune response.

In some embodiments, the therapeutically effective amount of the JAK inhibitor is an induction dose. In some embodiments, the therapeutically effective amount of the JAK inhibitor is a maintenance dose.

In some embodiments of the methods, the JAK inhibitor is tofacitinib or a pharmaceutically acceptable salt thereof. In some embodiments, the JAK inhibitor is tofacitinib citrate.

In some embodiments of the method, the JAK inhibitor is a small molecule. In some embodiments, the JAK inhibitor is a small molecule and the formulation includes one or more pharmaceutically acceptable excipients. In some embodiments, the JAK inhibitor is selected from the group consisting of abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some embodiments, the JAK inhibitor is tofacitinib or a pharmaceutically acceptable salt thereof. In some embodiments, the JAK inhibitor is tofacitinib citrate.

In some embodiments of the method, the pharmaceutical formulation is provided as a solid, and the JAK inhibitor is present in the pharmaceutical formulation at a concentration of at least about 75% (w/w), about 80% (w/w), about 85% (w/w), or at least about 90% (w/w); optionally, at least about 95%, about 96%, about 97%, about 98% or about 99% (w/w). In some embodiments, the JAK inhibitor is tofacitinib or a pharmaceutically acceptable salt thereof. In some embodiments, the JAK inhibitor is tofacitinib citrate.

In some embodiments of the method, the pharmaceutical formulation is provided as a solution, a dispersion or a suspension. In some embodiments, the formulation is provided as a dispersion or a suspension that contains the JAK inhibitor in a suspending agent, where the suspending agent is selected from the group consisting of carboxymethyl cellulose (CMC), one or more PEGs (e.g., PEG 100 to 1000, PEG 3350), hydroxypropyl methylcellulose (HPMC), and combinations thereof. In some embodiments, the formulation includes one or more excipients selected from the group consisting of castor oil, modified starch, sorbitol, cellulose, pectin, sucrose, citric acid, poloxamers, EDTA, cocamide DE, glycerol, Cremophor RH40, dextrose, polyvinyl alcohol, hydroxyethyl cellulose, hydroxypropyl cellulose, propylene glycol, a gum, propylene glycol alginate, methyl paraben, povidone, water, and a surfactant, which is optionally polysorbate 20, 40, 60 or 80. In some embodiments, the JAK inhibitor is provided as a micronized solid dispersed or suspended in the suspending agent and the one or more optional excipients. In some embodiments, the pharmaceutical formulation contains the JAK inhibitor at a concentration of at least about 10 mg/mL or 10 mg/g or at least about 15 mg/mL or 15 mg/g. In some embodiments, the JAK inhibitor is tofacitinib or a pharmaceutically acceptable salt thereof. In some embodiments, the JAK inhibitor is tofacitinib citrate.

In some embodiments of the method, the JAK inhibitor selectively decreases the activity of JAK1, JAK3, or both.

In some embodiments, the method includes administering an additional agent in addition to the JAK inhibitor, wherein the additional agent is administered topically or by another form of administration. In some embodiment, the topical administration is via an ingestible device. In some embodiments, the additional agent is selected from the group consisting of an immunosuppressant, an aminosalicylate, a second JAK inhibitor, an S1P modulator, a PDE4 inhibitor, an integrin inhibitor, an IL-12/IL-23 inhibitor, a GM-CSF and an anti-TNF agent. In some embodiments, the immunosuppressant is a corticosteroid. In some embodiments, the JAK inhibitor is tofacitinib citrate.

In some embodiments, the additional agent is an IL-12/IL-23 inhibitor. In some embodiments, the IL-12/IL-23 inhibitor is selected from the group consisting of ustekinumab, guselkumab, risankizumab, brazikumab, and mirikizumab; and biosimilars thereof. In some embodiments, the IL-12/IL-23 inhibitor is ustekinumab or a biosimilar thereof. In some embodiments, the ustekinumab or the biosimilar thereof is administered systemically. In some embodiments, the IL-12/IL-23 inhibitor is a compound selected from the group consisting of PTG-200, apilimod mesylate, Compound A, Compound B, or Compound C as described in U.S. Pat. No. 9,624,268; and pharmaceutically acceptable salts thereof.

In some embodiments, the additional agent is an S1P modulator. In some embodiments, the S1P inhibitor is selected from the group consisting of fingolimod, KRP203, siponimod, ponesimod, cenerimod, ozanimod, ceralifimod, amiselimod, and etrasimod; and pharmaceutically acceptable salts thereof. In some embodiments, the S1P modulator is ozanimod, etrasimod, or amiselimod; or a pharmaceutically acceptable salt thereof.

In some embodiments, the additional agent is a GM-CSF. In some embodiments, the GM-CSF is sargramostim (Leukine®) or molgramostim; or a biosimilar thereof. In some preferred embodiments, the GM-CSF is sargramostim or a biosimilar thereof. In some embodiments, the GM-CSF is administered during maintenance therapy.

In some embodiments, the additional agent is a PDE4 inhibitor. In some embodiments, the PDE4 inhibitor is selected from the group consisting of apremilast, cilomilast, crisaborole, ibudilast, lotamilast, roflumilast, and tetomilast; and pharmaceutically acceptable salts thereof. In some embodiments, the PDE4 inhibitor is apremilast or a pharmaceutically acceptable salt thereof; or tetomilast or a pharmaceutically acceptable salt thereof.

In some embodiments, the additional agent is an integrin inhibitor. In some embodiments, the integrin inhibitor is selected from the group consisting of vedolizumab, natalizumab, etrolizumab, vatelizumab and PF-00547659; and biosimilars thereof. In some embodiments, the integrin inhibitor is vedolizumab or a biosimilar thereof. In some embodiments, the vedolizumab or the biosimilar thereof is administered systemically. In some embodiments, the additional agent is an integrin inhibitor selected from the group consisting of AJM-300, carotegrast (HCA2969), firategrast, valategrast, R00270608, CDP-323, CT7758, GW-559090, ELND-004, PN-10943 (PN-943) and PTG-100; and pharmaceutically acceptable salts thereof. In some embodiments, the integrin inhibitor is AJM-300 or a pharmaceutically acceptable salt thereof; or carotegrast or a pharmaceutically acceptable salt thereof.

In some embodiments, the additional agent is an anti-TNF agent selected from the group consisting of adalimumab, infliximab, golimumab, certolizumab, certolizumab pegol, and etanercept; and biosimilars thereof. In some embodiments, the anti-TNF agent is adalimumab or a biosimilar thereof. In some embodiments, the adalimumab is administered systemically.

In some embodiments, the additional agent is an immunosuppressant. In some embodiments, the immunosuppressant is a corticosteroid selected from the group consisting of prednisone, methylprednisolone, hydrocortisone and budesonide; and pharmaceutically acceptable salts thereof.

In some embodiments, the additional agent is an aminosalicylate. In some embodiments, the aminosalicylate is mesalazine or a pharmaceutically acceptable salt thereof.

In some embodiments, the additional agent is selected from the group consisting of methotrexate, Traficet-EN, alicaforsen (ISIS 2302), SB012, tacrolimus, cyclosporin A, and neuregulin-4; and pharmaceutically acceptable salts thereof.

In some embodiments, the additional agent is a second JAK inhibitor, where the second JAK inhibitor is different from the first JAK inhibitor. In some embodiments, the second JAK inhibitor is selected from the group consisting of baricitinib, filgotinib, upadacitinib, TD-1473, TD-3504 and tofacitinib; and pharmaceutically acceptable salts thereof.

In some embodiments, the additional agent is administered topically via an ingestible device. In some embodiments, the additional agent is administered together with the JAK inhibitor in the same ingestible device as the JAK inhibitor. In some embodiments, the additional agent is administered separately from the JAK inhibitor in a separate ingestible device from the JAK inhibitor. In some embodiments, the additional agent is administered orally. In some embodiments, the additional agent is administered systemically. In some embodiments, the additional agent is administered intravenously. In some embodiments, the additional agent is administered subcutaneously. In some embodiments, the additional agent is administered rectally.

Also provided in the present disclosure is a method of treating an inflammatory bowel disease (IBD) in a subject in need thereof, the method including topically administering a pharmaceutical formulation including a therapeutically effective amount of tofacitinib, or a pharmaceutically acceptable salt thereof, (a) to a section or subsection of the gastrointestinal (GI) tract of the subject; or (b) proximal to a section or subsection of the gastrointestinal (GI) tract of the subject; wherein said section or subsection contains one or more inflammatory disease sites; thereby treating at least one of the one or more inflammatory disease sites. In some embodiments, the IBD is Crohn's disease. In some embodiments, the IBD is ulcerative colitis. In some embodiments, the tofacitinib or the pharmaceutically acceptable salt thereof is tofacitinib citrate.

In some embodiments, the section or subsection of the GI tract containing the one or more disease sites is selected from the group consisting of stomach, duodenum, jejunum, ileum, cecum, ascending colon, transverse colon, descending colon, sigmoid colon and rectum; preferably, the section or subsection of the GI tract containing the one or more disease sites is selected from the group consisting of ileum, cecum, colon and rectum; and a combination thereof.

In some embodiments, the pharmaceutical formulation is contained in a device selected from an endoscope, an ingestible device, or a reservoir. In some embodiments, the endoscope comprises a catheter. In some embodiments, the catheter is a spray catheter. In some embodiments, the endoscope is connected to the reservoir. In some embodiments, the reservoir is an anchorable reservoir.

In some embodiments, the pharmaceutical formulation is a solid formulation, a solution formulation, a dispersion formulation, a suspension formulation, or an emulsion formulation. In some embodiments, the pharmaceutical formulation is a suppository for rectal administration. In some embodiments, the pharmaceutical formulation is an enema for rectal administration. In some embodiments, the enema for rectal administration is for sustained release or for delayed release.

In some embodiments, the pharmaceutical formulation containing tofacitinib, or a pharmaceutically acceptable salt thereof, is contained in an ingestible device, said device containing a self-localization mechanism configured to determine a device location within the subject's GI tract, and the method further includes determining the device location within the subject's GI tract via the device self-localization mechanism.

Thus, in some embodiments, the topical administration includes orally administering the ingestible device to the subject; and releasing the pharmaceutical formulation from the device (a) to a section or subsection of the subject's GI tract containing one or more inflammatory disease sites; or (b) proximal to a section or subsection of the subject's GI tract containing one or more inflammatory disease sites.

In some embodiments, determining the device location within the subject's GI tract via the device self-localization mechanism includes detecting one or more device transitions between portions of the subject's GI tract. In some embodiments, the one or more device transitions occurs between portions of the GI tract selected from the group consisting of: mouth and stomach; esophagus and stomach; stomach and duodenum; duodenum and jejunum; jejunum and ileum; ileum and cecum; and cecum and colon; and combinations of any two or more of the foregoing. In some embodiments, the portions are adjacent portions.

In some embodiments, the device self-localization mechanism is based on data comprising light reflectance occurring external to the device and within the GI tract of the subject. In some embodiments, the device self-localization mechanism is based on data comprising elapsed time after entry of the device into the GI tract of the subject, elapsed time after detecting at least one of the one or more device transitions between the portions of the subject's GI tract, or a combination thereof. In some embodiments, determining the device location within the subject's GI tract via the device self-localization mechanism further includes confirming the one or more device transition between the portions of the GI tract of the subject.

In some embodiments, the device self-localizes to the stomach, duodenum, jejunum, ileum, cecum or colon with at least 80% accuracy. In some embodiments, the device self-localizes to the stomach, duodenum, jejunum, ileum, cecum or colon with at least 85% accuracy.

In some embodiments, the self-localization of the device to a pre-selected location within the subject's GI tract autonomously triggers a release of the formulation from the device. In some embodiments, the release of the formulation from the device is proximal to the section or subsection of the subject's GI tract containing at least one of the one or more disease sites. In some embodiments, the release of the formulation is to a section or subsection of the GI tract immediately proximal (immediately preceding) the section or subsection of the subject's GI tract containing at least one of the one or more disease sites. In some embodiments, the release of the formulation is as a bolus.

In some embodiments, the release of the formulation from the device occurs at substantially the same time as the device self-localizes to the pre-selected location. In some embodiments, the release of the formulation from the device commences within a period of time of at most about 5 minutes after the device detects or confirms the transition to the pre-selected location. In some embodiments, the period of time is at most about 1 minute, at most about 30 seconds, at most about 10 seconds, or at most about 1 second after the device detects or confirms the transition to the pre-selected location. In some embodiments, the release of the formulation from the device occurs over a pre-determined period of time. In some embodiments, the pre-determined period of time is about 8 hours, about 7 hours, about 6 hours, about 5 hours, about 4 hours, about 3 hours, about 2 hours, about 1 hour, about 30 minutes, about 15 minutes, about 10 minutes, or about 5 minutes. In some embodiments, the pre-determined period of time commences within at most about 5 minutes, at most about 1 minute, at most about 30 seconds, at most about 10 seconds, or at most about 1 second after the device detects or confirms the transition to the pre-selected location.

In some embodiments, the method comprises administering an additional agent in addition to the tofacitinib, or a pharmaceutically acceptable salt thereof, where the additional agent is administered topically or by another form of administration. In some embodiments, the topical administration is via an ingestible device.

In some embodiments, the additional agent is selected from the group consisting of an immunosuppressant, an aminosalicylate, an IL-12/IL-23 inhibitor, an S1P modulator, a PDE4 inhibitor, an integrin inhibitor, a second JAK inhibitor, a GM-CSF and an anti-TNF agent. In some embodiments, the immunosuppressant is a corticosteroid. In some embodiments, the additional agent is an IL-12/IL-23 inhibitor. In some embodiments, the IL-12/IL-23 inhibitor is ustekinumab or a biosimilar thereof. In some embodiments, the additional agent is an integrin inhibitor. In some embodiments, the integrin inhibitor is vedolizumab or a biosimilar thereof. In some embodiments, the vedolizumab or the biosimilar thereof is administered systemically. In some embodiments, the additional agent is a GM-CSF. In some embodiments, the GM-CSF is sargramostim (Leukine®) or molgramostim; or a biosimilar thereof. In some embodiments, the GM-CSF is administered during maintenance therapy. In some embodiments, the additional agent is an anti-TNF agent. In some embodiments, the anti-TNF agent is adalimumab or a biosimilar thereof. In some embodiments, the adalimumab or the biosimilar thereof is administered systemically.

Also provided in the present disclosure is a device that includes a pharmaceutical formulation containing a JAK inhibitor; one or more processing devices; and one more machine-readable hardware storage devices storing instructions that are executable by the one or more processing devices to (a) determine a location of the ingestible device in the GI tract of the subject; and (b) release the formulation from the device at a pre-selected location of the GI tract; where the device is a self-localizing ingestible device configured for use in treating an inflammatory gastrointestinal disease or condition in a subject. In some embodiments, the device self-localizes in the pre-selected location of the GI tract of the subject with an accuracy of at least 80%. In some embodiments, the pre-selected location is selected from the group consisting of stomach, duodenum, jejunum, ileum, cecum and colon.

In some embodiments, the device includes a first light source and a second light source, where the first light source is configured to emit light at a first wavelength, and the second light source is configured to emit light at a second wavelength different from the first wavelength. In some embodiments, the device includes a first detector and a second detector, where the first detector is configured to detect light at the first wavelength, and the second detector is configured to detect light at the second wavelength. In some embodiments, the first wavelength and the second wavelength are each independently selected from the group consisting of red light, green light and blue light. In some embodiments, each of the first and second wavelengths is selected from the group consisting of 600 nm to 750 nm; 495 nm to 600 nm; and 400 nm to 495 nm. In some embodiments, the first and second wavelengths are separated by at least 50 nm.

In some embodiments, the device is configured to detect a transition between a first section or subsection and a second section or subsection of the GI tract. In some embodiments, the first and second section of the GI tract is selected from the group consisting of the mouth and stomach; the esophagus and stomach; the stomach and duodenum; the duodenum and jejunum; the jejunum and ileum; the ileum and cecum; and the cecum and colon; and a combination of any two or more of the foregoing.

In some embodiments, the device includes a mechanism configured to monitor elapsed time after entry of the device into the GI tract of the subject. In some embodiments, the mechanism is further configured to monitor elapsed time after detecting a device transition between a first section or subsection and a second section or subsection of the subject's GI tract.

In some embodiments, at least one of the one or more storage device stores instructions to release the formulation from the device into the pre-selected location at substantially the same time as the device self-localizes to the pre-selected location. In some embodiments, the pre-selected location is selected from the group consisting of the stomach, the duodenum, the jejunum, the ileum, the cecum, and the colon.

In some embodiments, the device further includes a housing; a force generator located within the housing; and a storage reservoir located within the housing, where the storage reservoir stores the pharmaceutical formulation; and where the ingestible device is configured such that the force generator generates a force, thereby initiating the release of the formulation from the ingestible device into the pre-selected location of the GI tract. In some embodiments, the force generator is a gas generating cell that generates a gas.

In some embodiments, the device is not configured to release the formulation based on the pH of the subject's GI tract. In some embodiments, determining the location of the ingestible device in the GI tract of the subject is not based on pressure in the GI tract of the subject. In some embodiments, releasing the formulation from the device is not based on temperature of the GI tract of the subject.

In some embodiments, the pharmaceutical formulation consists of, or consists essentially of, the JAK inhibitor. In some embodiments, the pharmaceutical formulation contains a therapeutically effective amount of the JAK inhibitor.

In some embodiments of the device, the JAK inhibitor is a small molecule, and the formulation optionally further comprises one or more pharmaceutically acceptable excipients; optionally, the JAK inhibitor is selected from the group consisting of abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof; alternatively, the JAK inhibitor is selected from the group consisting of baricitinib, filgotinib, upadacitinib, TD-1473, TD-3504 and tofacitinib; and pharmaceutically acceptable salts thereof. In some embodiments, the JAK inhibitor is tofacitinib or a pharmaceutically acceptable salt thereof. In some embodiments, the JAK inhibitor is tofacitinib citrate.

In some embodiments, the device does not contain an environmental pH sensor, an environmental temperature sensor, and/or an environmental pressure sensor.

Aspects and embodiments as described herein are intended to be freely combinable. For example, any details or embodiments described herein for methods of treatment apply equally to a JAK inhibitor, composition or ingestible device for use in said treatment. Any details or embodiments described for a device apply equally to methods of treatment using the device, or to a JAK inhibitor or composition for use in a method of treatment involving the device.

every third day (Q3D) or intracecally (10 mg/kg and 1 mg/kg) administered daily (QD), when compared to vehicle control (Vehicle). Data presented as mean±SEM. Mann-Whitney's U-test and Student's t-test were used for statistical analysis on non-Gaussian and Gaussian data respectively. A value of $p<0.05$ was considered significant (Graph Pad Software, Inc.).

Figure 39:
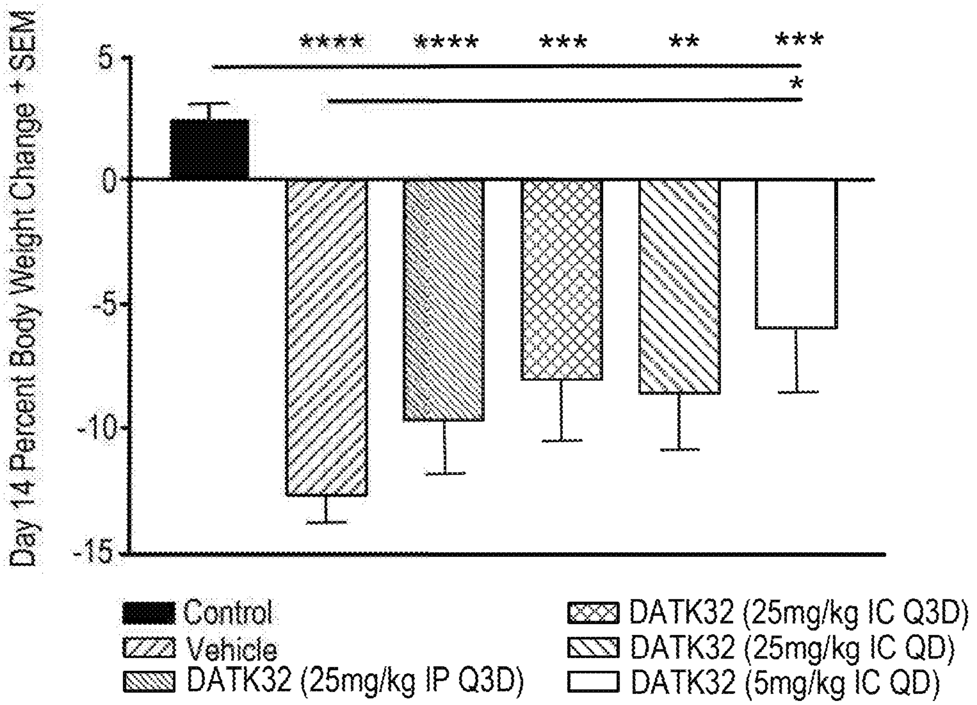

FIG. 39 is a graph showing the percentage (%) change in body weight at day 14 (±SEM) for DSS mice treated with DATK32 (anti-α4β7) antibody intraperitoneally (25 mg/kg) every third day (Q3D) or intracecally (25 mg/kg or 5 mg/kg) administered daily (QD), when compared to vehicle control (Vehicle) and when IC is compared to IP. Data presented as mean±SEM. Mann-Whitney's U-test and Student's t-test were used for statistical analysis on non-Gaussian and Gaussian data respectively. A value of $p<0.05$ was considered significant (Graph Pad Software, Inc.).

Figure 40:
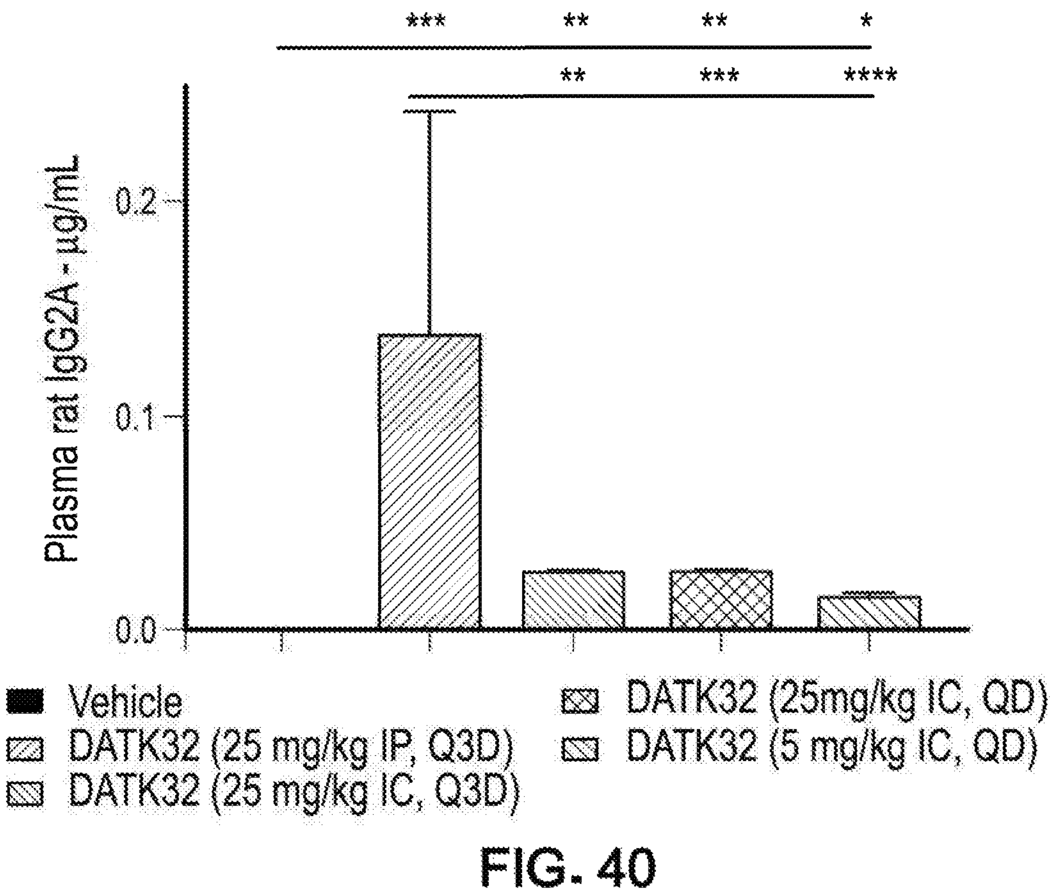

FIG. 40 is a graph showing the plasma concentration of DATK32 rat IgG2A (μg/mL) of intraperitoneally (25 mg/kg) and intracecally (25 mg/kg and 5 mg/kg) administered treatment groups given daily (QD) or every third day (Q3D), where IP is compared to IC. Data presented as mean±SEM. Mann-Whitney's U-test and Student's t-test were used for statistical analysis on non-Gaussian and Gaussian data respectively. A value of $p<0.05$ was considered significant (Graph Pad Software, Inc.).

Figure 41:
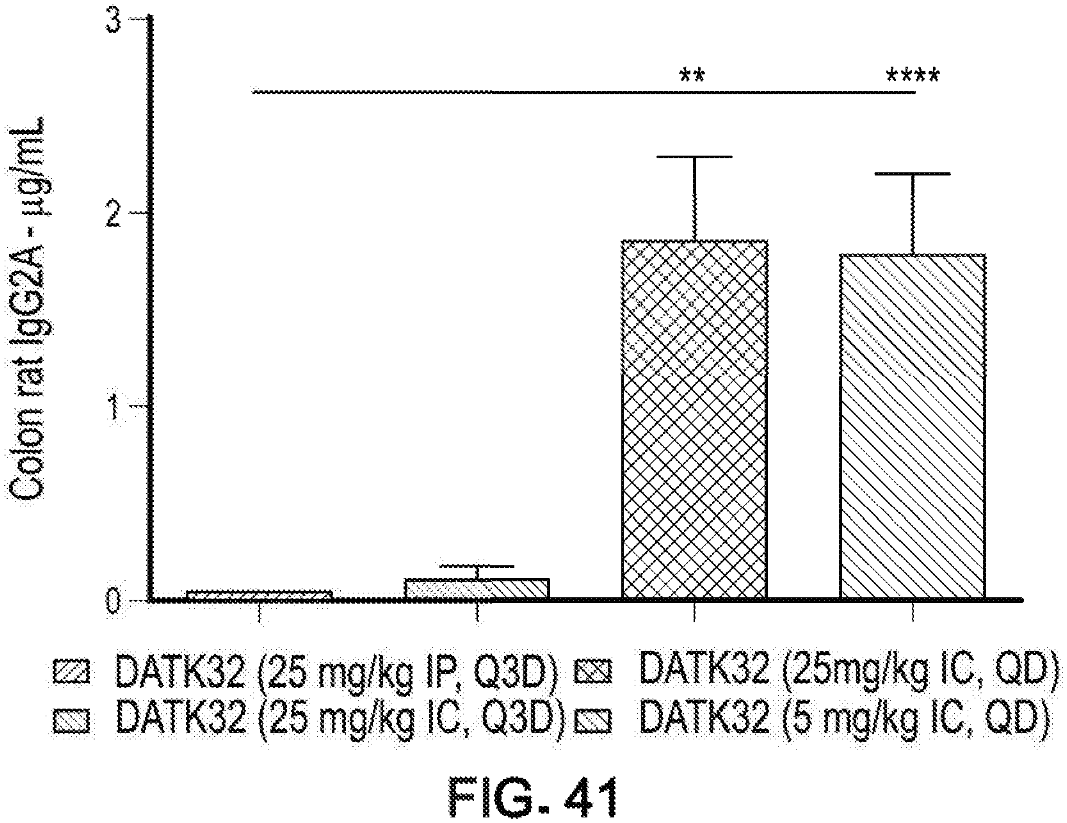

FIG. 41 is a graph showing the concentration of DATK32 rat IgG2A antibody (μg/mL) in cecum and colon content of intraperitoneally (25 mg/kg) or intracecally (25 mg/kg and 5 mg/kg) administered treatment groups given daily (QD) or every third day (Q3D), where IP is compared to IC. Data presented as mean f SEM. Mann-Whitney's U-test and Student's t-test were used for statistical analysis on non-Gaussian and Gaussian data respectively. A value of $p<0.05$ was considered significant (Graph Pad Software, Inc.).

Figure 42:
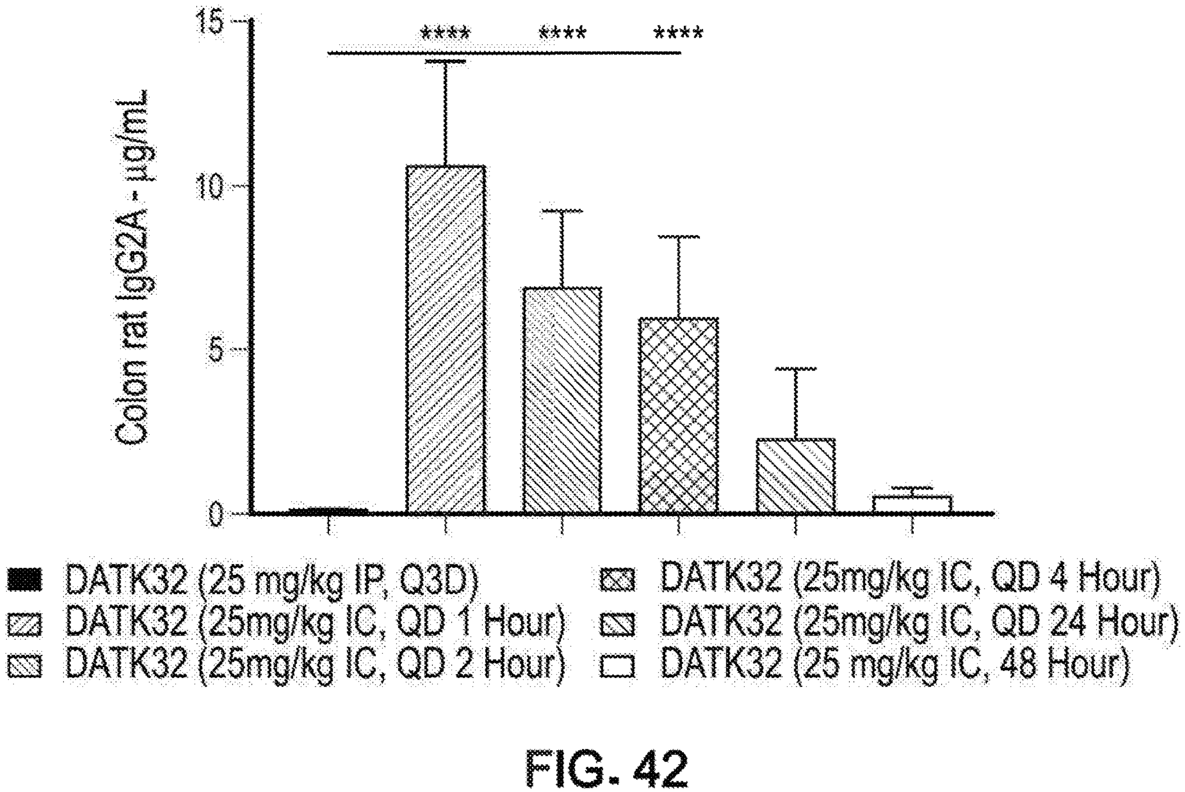

FIG. 42 is a graph showing the concentration of DATK32 rat IgG2A (μg/mL) in the colon content of intraperitoneally (25 mg/kg) or intracecally (25 mg/kg and 5 mg/kg) administered treatment groups given daily (QD), and concentration over time (1, 2, 4, 24, and 48 hours), where IP is compared to IC. Data presented as mean±SEM. Mann-Whitney's U-test and Student's t-test were used for statistical analysis on non-Gaussian and Gaussian data respectively. A value of $p<0.05$ was considered significant (Graph Pad Software, Inc.).

Figure 43:
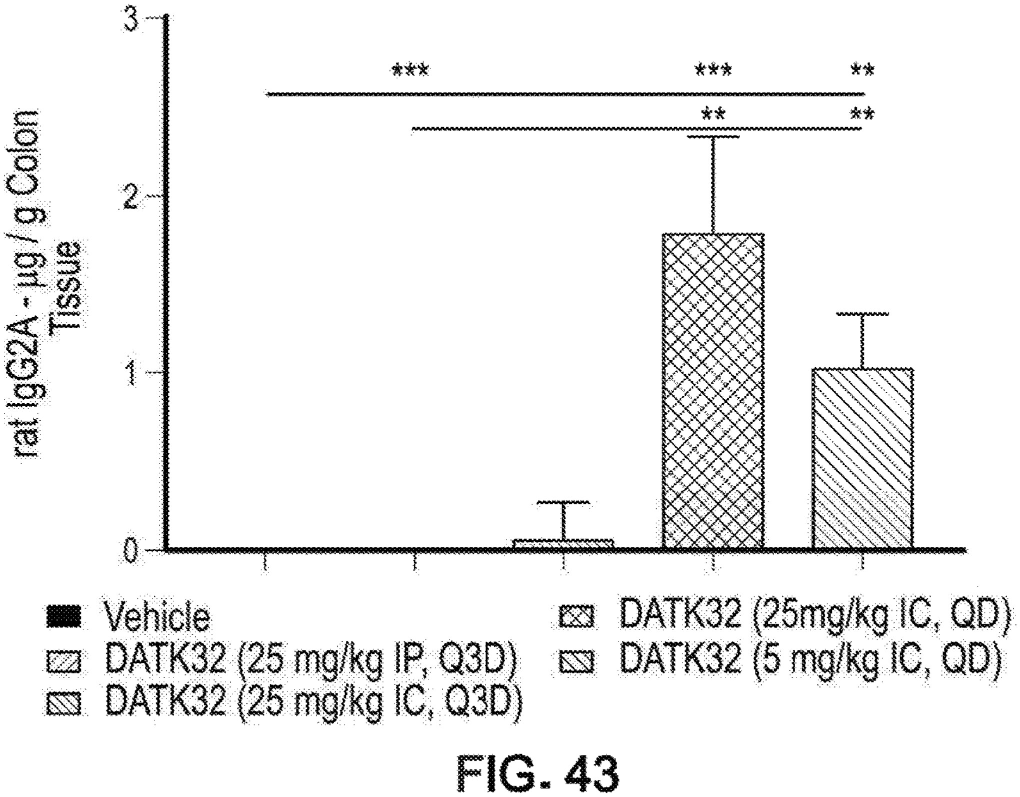

FIG. 43 is a graph showing the concentration of DATK32 rat IgG2A (μg/g) in colon tissue of intraperitoneally (25 mg/kg) or intracecally (25 mg/kg and 5 mg/kg) administered treatment groups given daily (QD) or every third day (Q3D), where IP is compared to IC. Data presented as mean±SEM. Mann-Whitney's U-test and Student's t-test were used for statistical analysis on non-Gaussian and Gaussian data respectively. A value of $p<0.05$ was considered significant (Graph Pad Software, Inc.).

Figure 44:
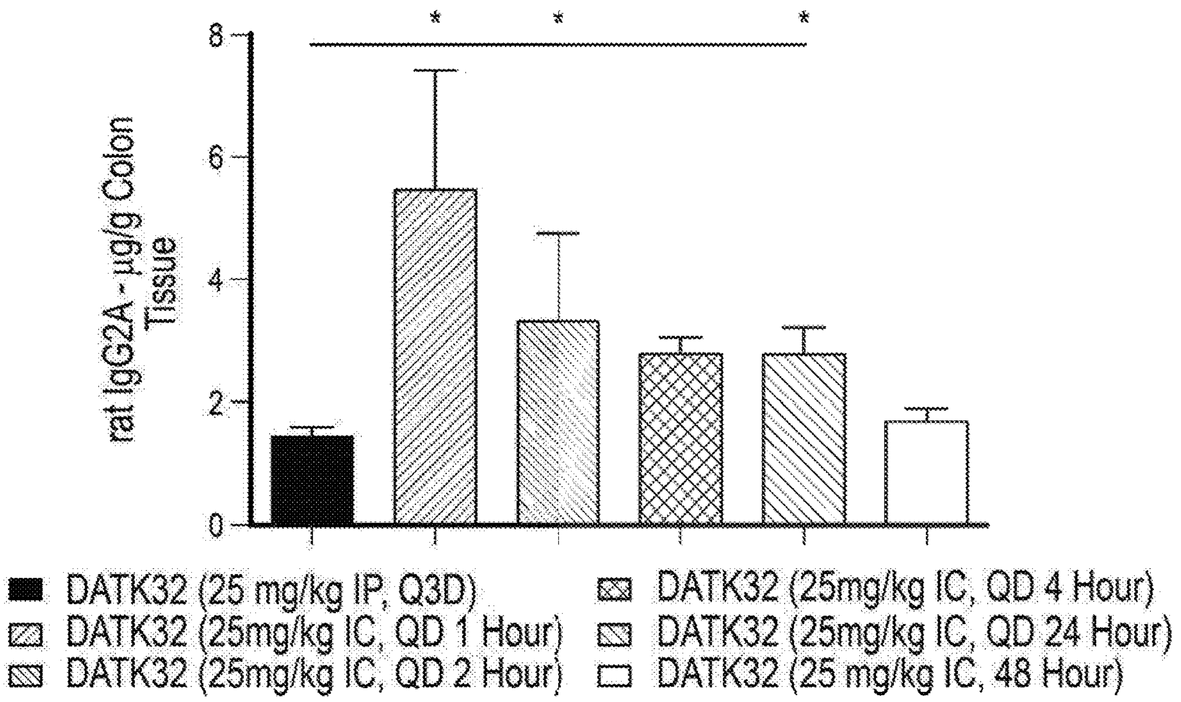

FIG. 44 is a graph showing the concentration of DATK32 rat IgG2A (μg/g) in the colon tissue of intraperitoneally (25 mg/kg) or intracecally (25 mg/kg and 5 mg/kg) administered treatment groups given daily (QD), and the concentration over time (1, 2, 4, 24, and 48 hours) was determined, where IP is compared to IC. Data presented as mean±SEM. Mann-Whitney's U-test and Student's t-test were used for statistical analysis on non-Gaussian and Gaussian data respectively. A value of $p<0.05$ was considered significant (Graph Pad Software, Inc.).

Figure 45:
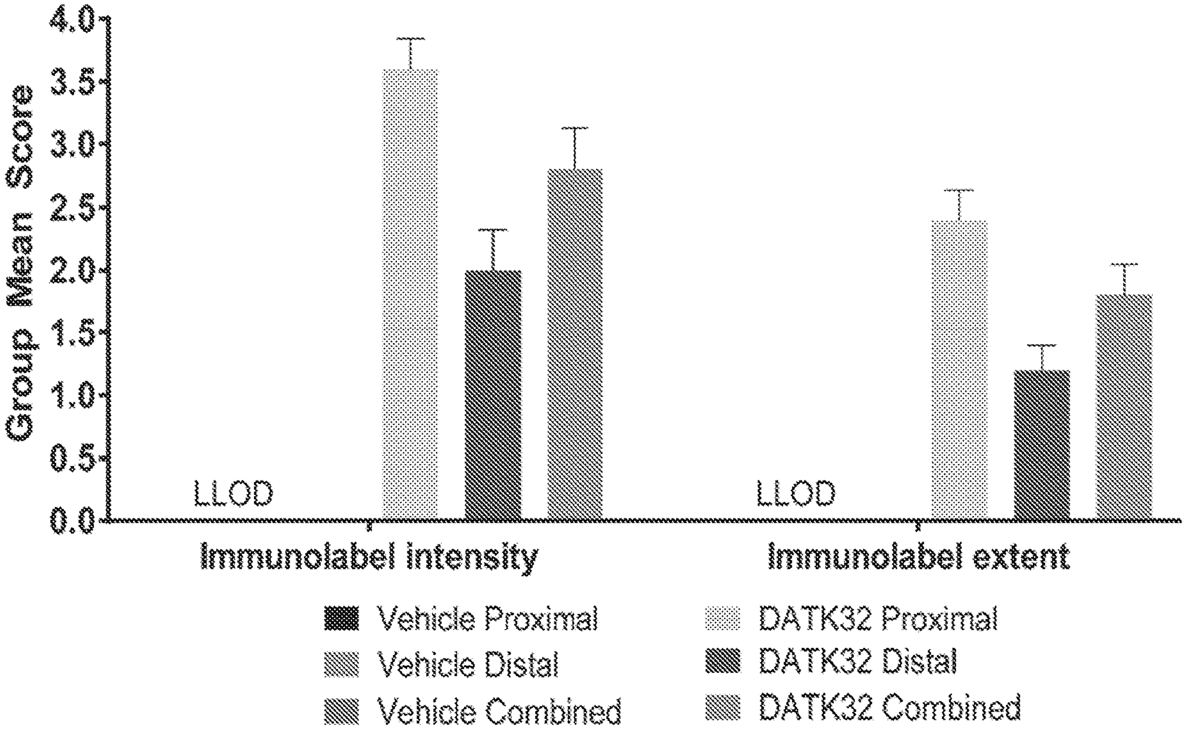

FIG. 45 is a graph showing the mean overall tissue immunolabel scores (intensity and extent) in acute DSS colitis mouse colon of DATK32 (anti-α4β7) antibody treated versus vehicle control (Vehicle) treated DSS mice. The data are presented as mean±SEM.

Figure 46:
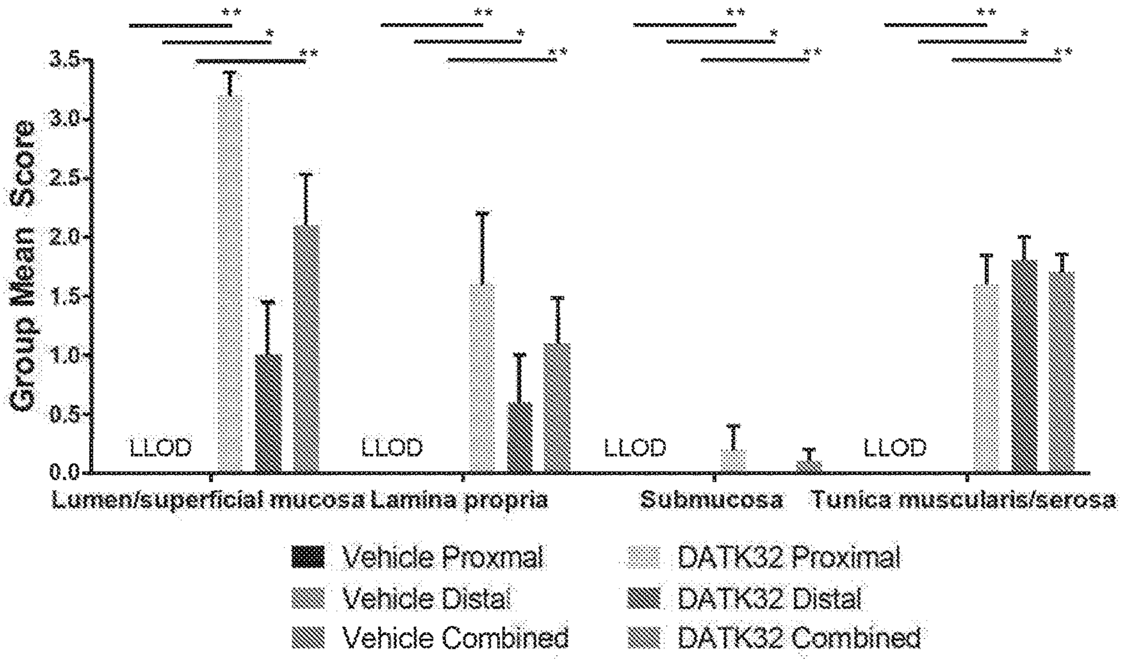

FIG. 46 is a graph showing the mean location-specific immunolabel scores in acute DSS colitis mouse colon of DATK32 (anti-α4β7) antibody-treated versus vehicle control (Vehicle)-treated DSS mice. Data presented as mean±SEM. Mann-Whitney's U-test and Student's t-test were used for statistical analysis on non-Gaussian and Gaussian data respectively. A value of $p<0.05$ was considered significant (Graph Pad Software, Inc.).

Figure 47:
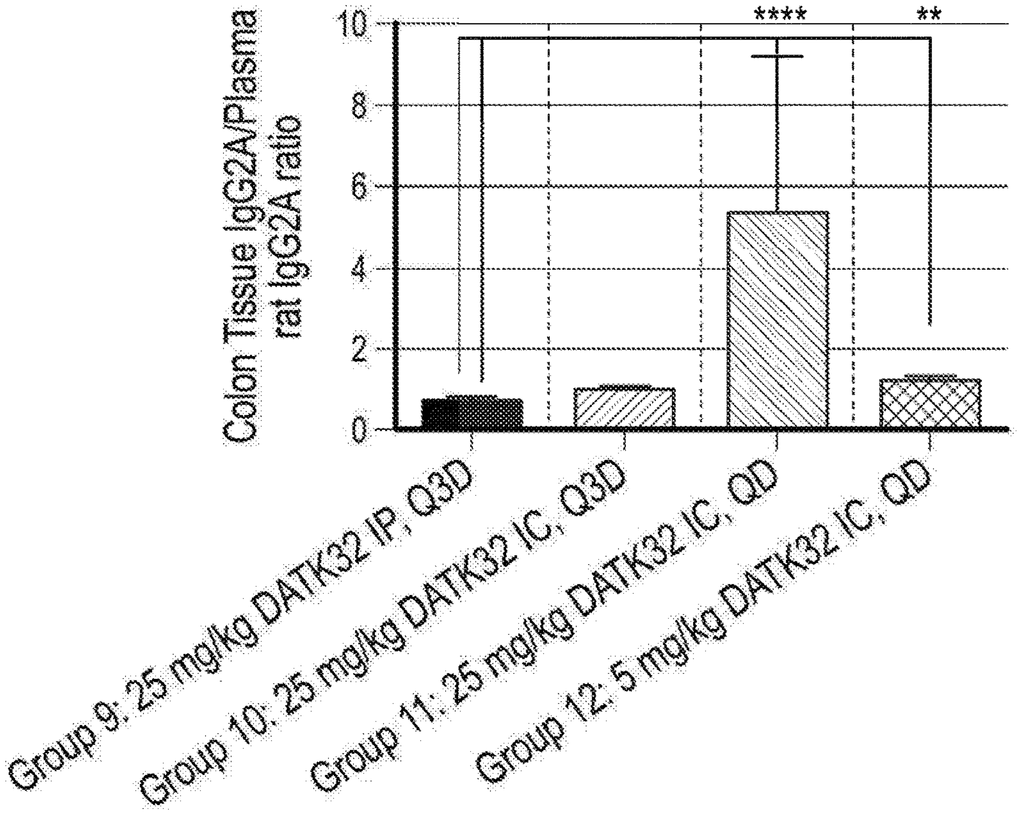

FIG. 47 is a graph showing the ratio of the DATK-32 antibody in the colon tissue to the plasma concentration of the DATK-32 antibody in mice treated with the DATK-32 antibody on day 0 (Q0) or day 3 (Q3D) of the study (Groups 9-12), when measured after initial dosing.

Figure 48:
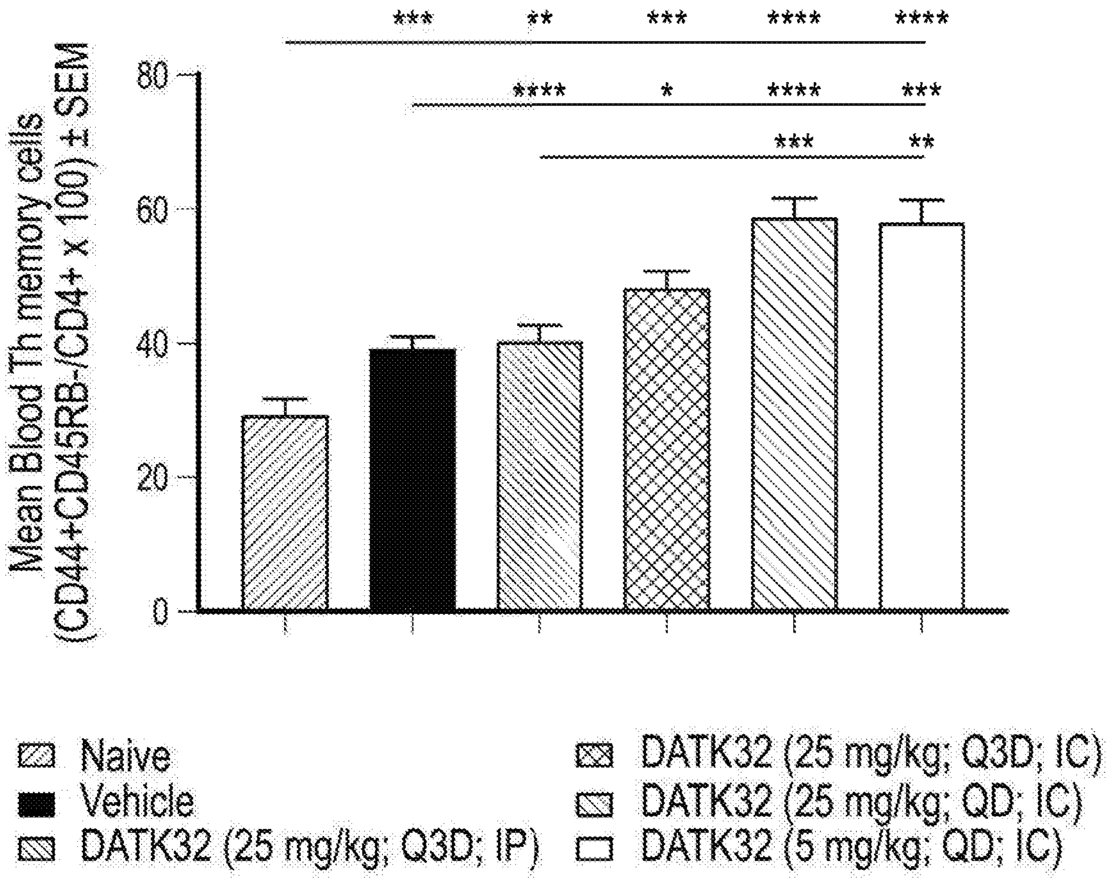

FIG. 48 is a graph showing the mean percentage of Th memory cells (mean±SEM) in blood for DATK32 (anti-α4β7) antibody intraperitoneally (25 mg/kg) or intracecally (25 mg/kg or 5 mg/kg) administered treatment groups given daily (QD) or every third day (Q3D), when compared to vehicle control (Vehicle) and when IP is compared to IC. Mean percentage Th memory cells were measured using FACS analysis. Data presented as mean±SEM. Mann-Whitney's U-test and Student's t-test were used for statistical analysis on non-Gaussian and Gaussian data respectively. A value of $p<0.05$ was considered significant (Graph Pad Software, Inc.).

Figure 49:
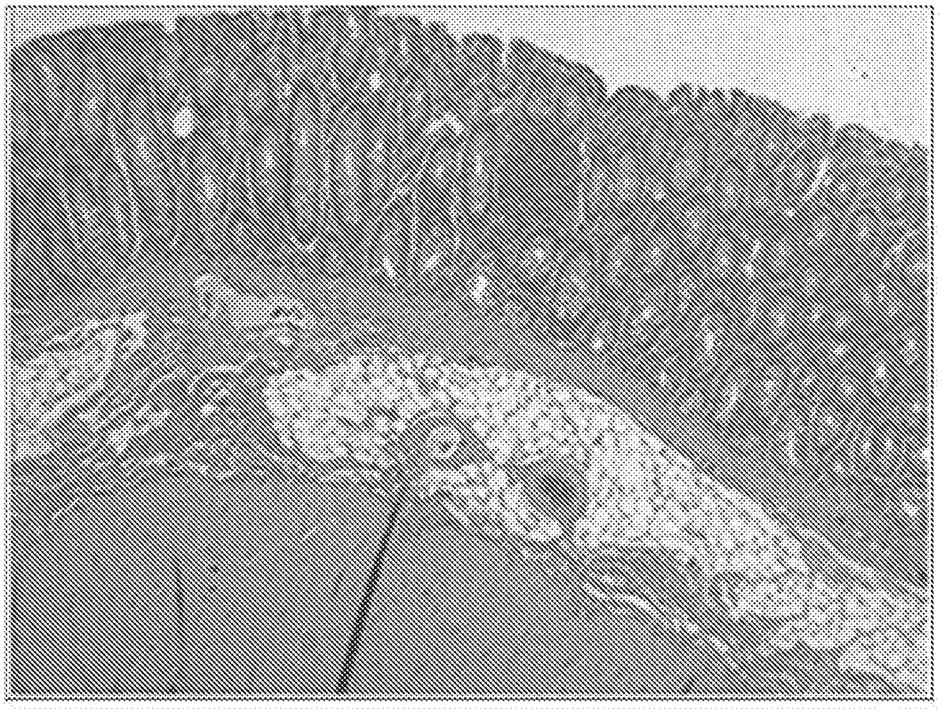

FIG. 49 is an exemplary image of a histological section of a distal transverse colon of Animal 1501 showing no significant lesions (i.e., normal colon).

Figure 50:

FIG. 50 is an exemplary image of a histological section of a distal transverse colon of Animal 2501 (treated with TNBS) showing areas of necrosis and inflammation.

Figure 51:
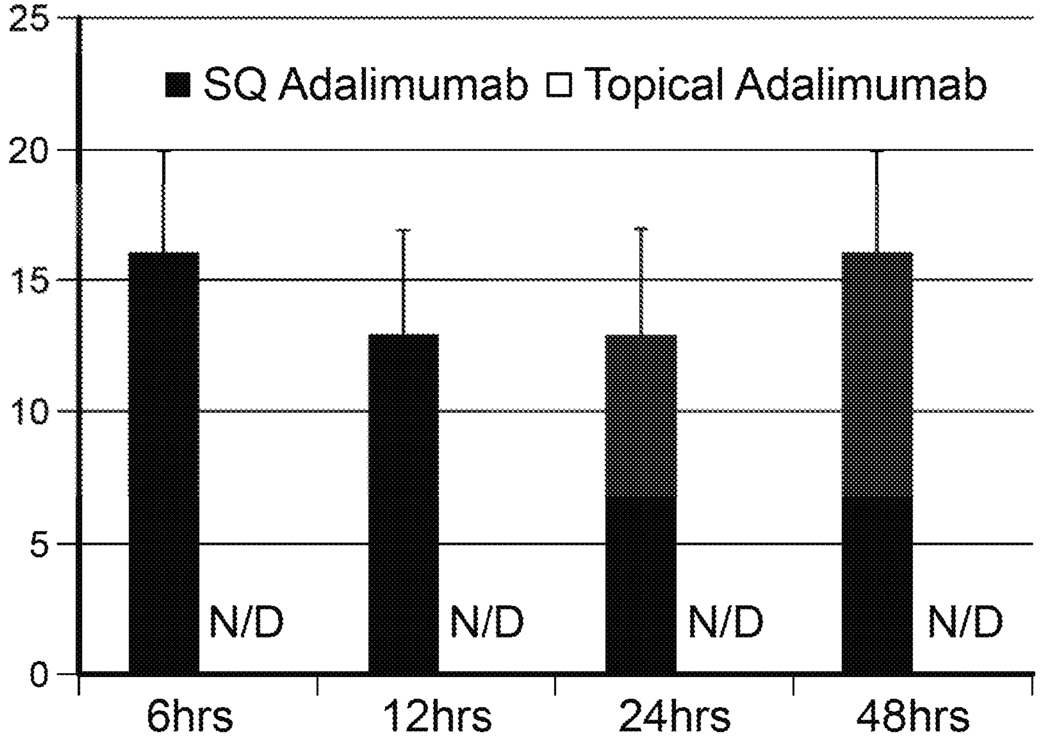

FIG. 51 is a representative graph of plasma adalimumab concentrations over time following a single subcutaneous (SQ) or topical administration of adalimumab. The plasma concentrations of adalimumab were determined 6, 12, 24, and 48 hours after administration of adalimumab. N/D=not detectable.

FIG. 52 is a representative table of the plasma adalimumab concentrations (μg/mL) as shown in FIG. 51.

Figure 53:
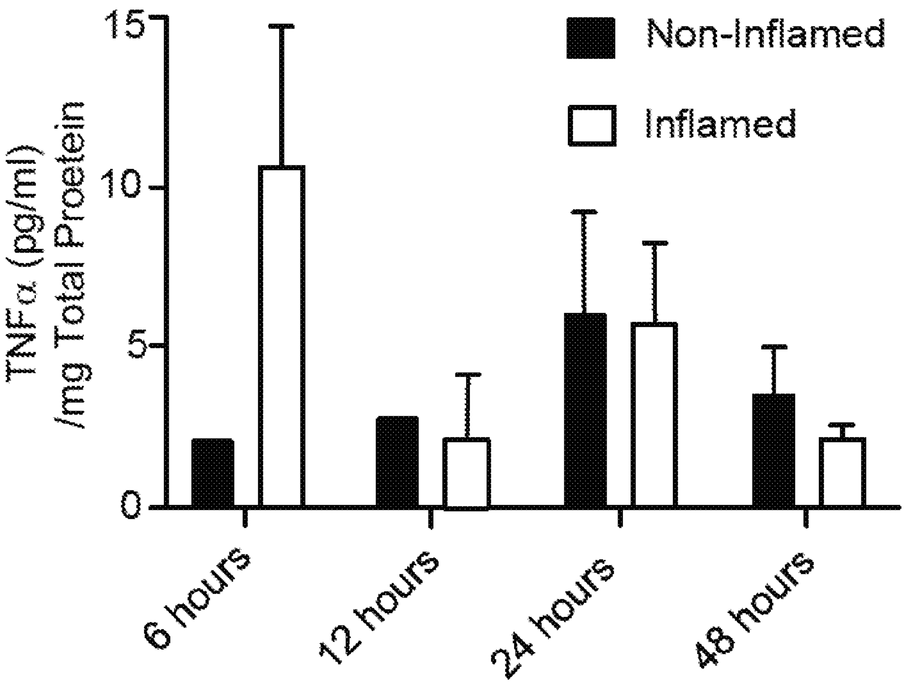

FIG. 53 is a graph showing the concentration of TNFα (μg/mL per mg of total protein) in non-inflamed and inflamed colon tissue after intracecal administration of adalimumab, as measured 6, 12, 24, and 24 hours after the initial dosing.

Figure 54:
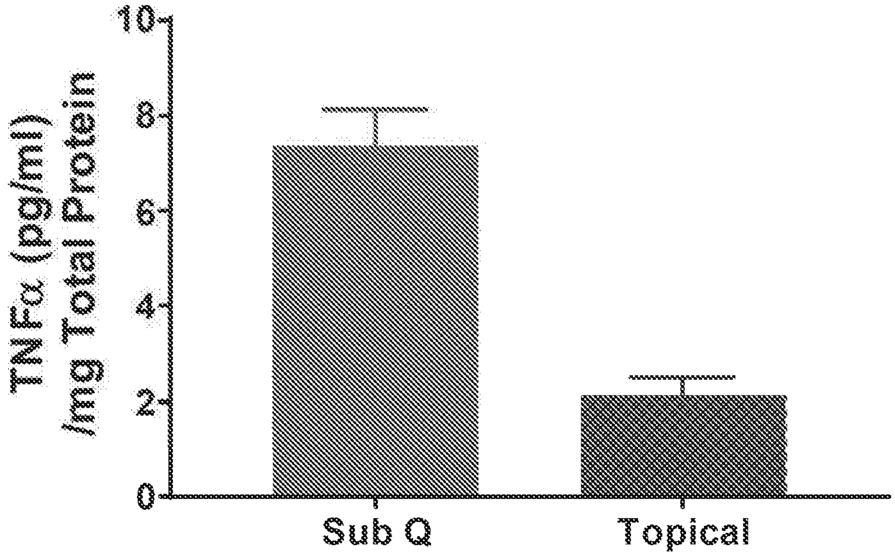

FIG. 54 is a graph showing the concentration of TNFα (μg/mL per mg of total protein) in colon tissue after subcutaneous or intracecal (topical) administration of adalimumab, as measured 48 hours after the initial dosing.

Figure 55:
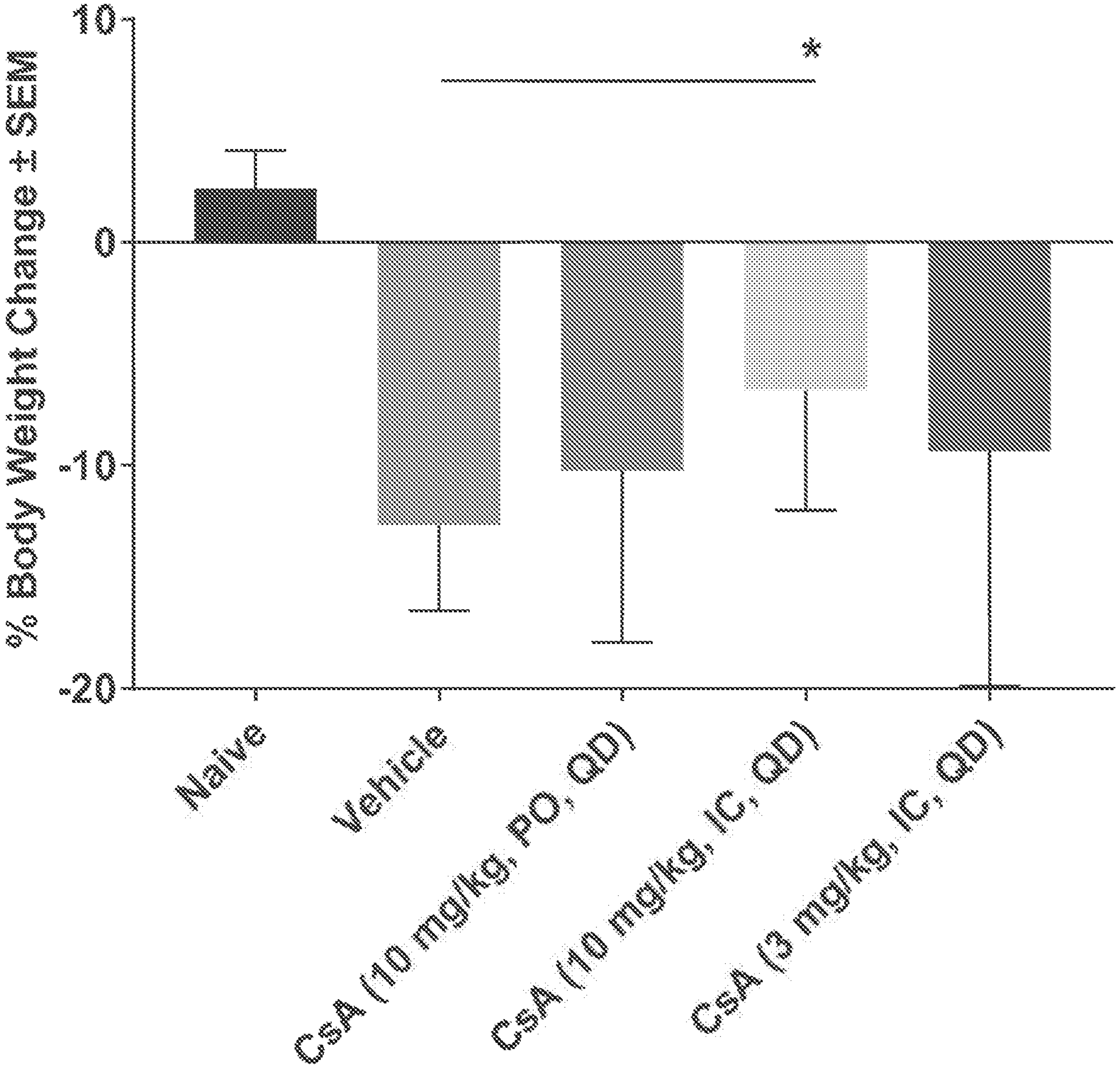

FIG. 55 is a graph showing the percentage (%) change in body weight at day 14 (±SEM) in acute DSS colitis mice treated with cyclosporin A orally (10 mg/kg) every third day (Q3D) or intracecally (10 mg/kg or 3 mg/kg) daily (QD), when compared to vehicle control (Vehicle). Data presented as mean f SEM. Mann-Whitney's U-test and Student's t-test were used for statistical analysis on non-Gaussian and Gaussian data respectively. A value of $p<0.05$ was considered significant (Graph Pad Software, Inc.).

Figure 56:
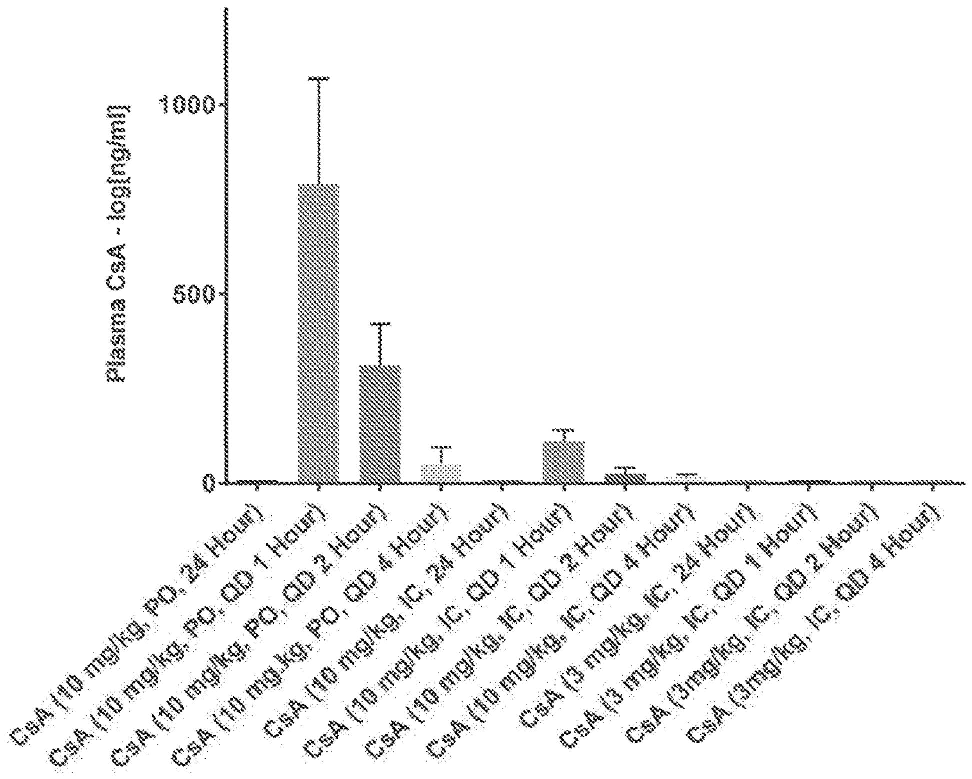

FIG. 56 is a graph showing the plasma cyclosporin A (CsA) (ng/mL) concentration over time (1 h, 2 h, 4 h, and 24 h) in acute DSS colitis mice treated daily (QD) with orally (PO) (10 mg/kg) or intracecally (IC) (10 mg/kg or 3 mg/kg) administered CsA. Data presented as mean±SEM.

Figure 57:
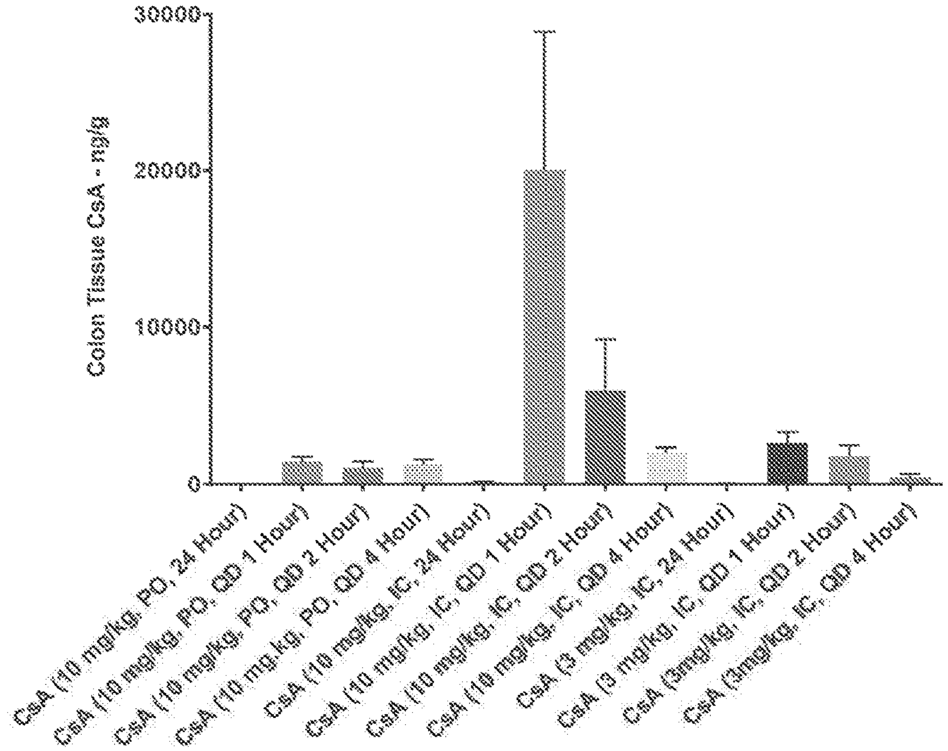

FIG. 57 is a graph showing the colon tissue cyclosporin A (CsA) (ng/g) concentration over time (1 h, 2 h, 4 h and 24 h) in acute DSS colitis mice treated daily (QD) with orally (PO) (10 mg/kg) or intracecally (IC) (10 mg/kg or 3 mg/kg) administered CsA. Data presented as mean±SEM.

Figure 58:
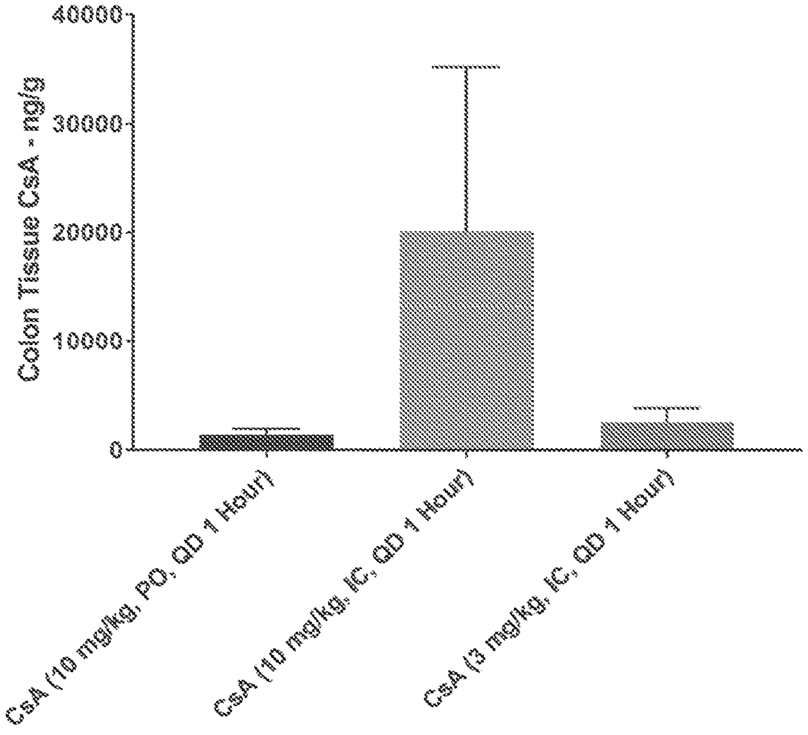

FIG. 58 is a graph showing the peak colon tissue cyclosporin A (CsA) (ng/g) concentration in acute DSS colitis mice treated daily (QD) with orally (PO) (10 mg/kg) or intracecally (IC) (10 mg/kg or 3 mg/kg) administered CsA. Data presented as mean±SEM.

Figure 59:
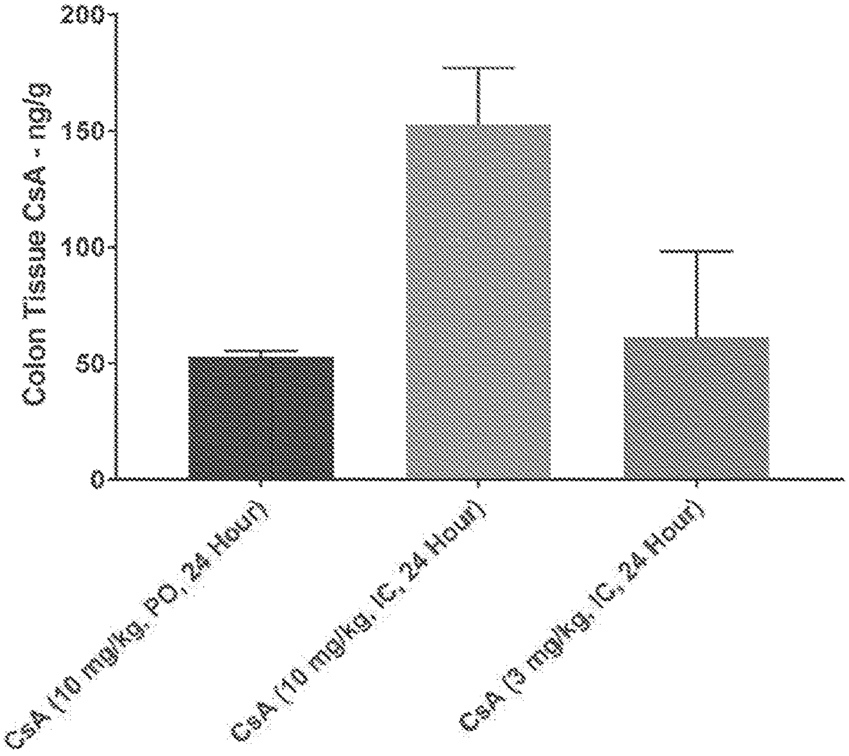

FIG. 59 is a graph showing the trough tissue concentration of cyclosporin (CsA) (ng/g) in colon of acute DSS colitis mice treated daily (QD) with orally (PO) (10 mg/kg) or intracecally (IC) (10 mg/kg or 3 mg/kg) administered CsA. Data presented as mean±SEM.

Figure 60:
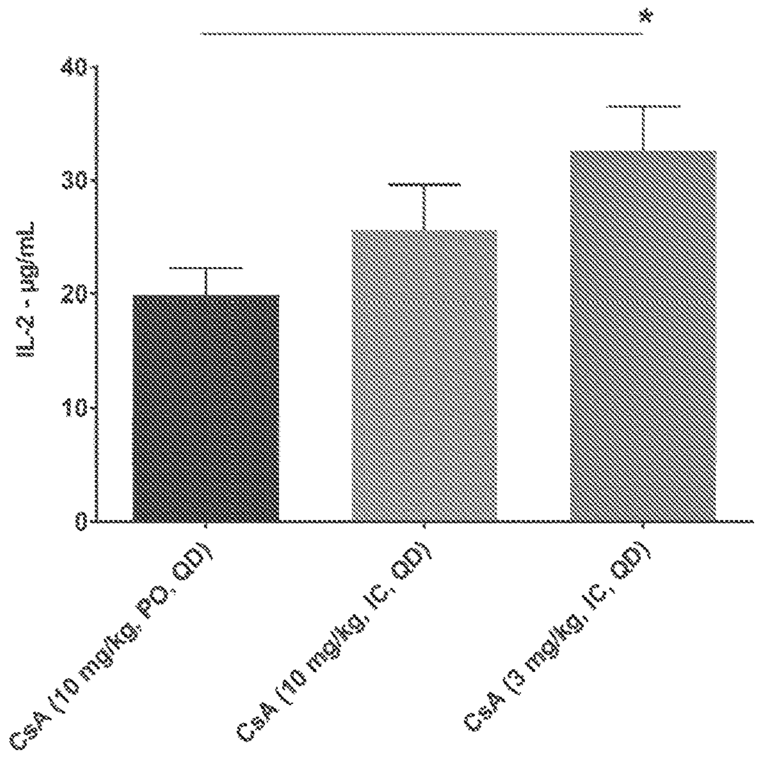

FIG. 60 is a graph showing the interleukin-2 (Il-2) concentration (μg/mL) in colon tissue of acute DSS colitis mice treated daily (QD) with orally (PO) (10 mg/kg) or intracecally (IC) (10 mg/kg or 3 mg/kg) administered CsA, where PO is compared to IC. Data presented as mean±SEM. Mann-Whitney's U-test and Student's t-test were used for statistical analysis on non-Gaussian and Gaussian data respectively. A value of $p<0.05$ was considered significant (Graph Pad Software, Inc.).

Figure 61:
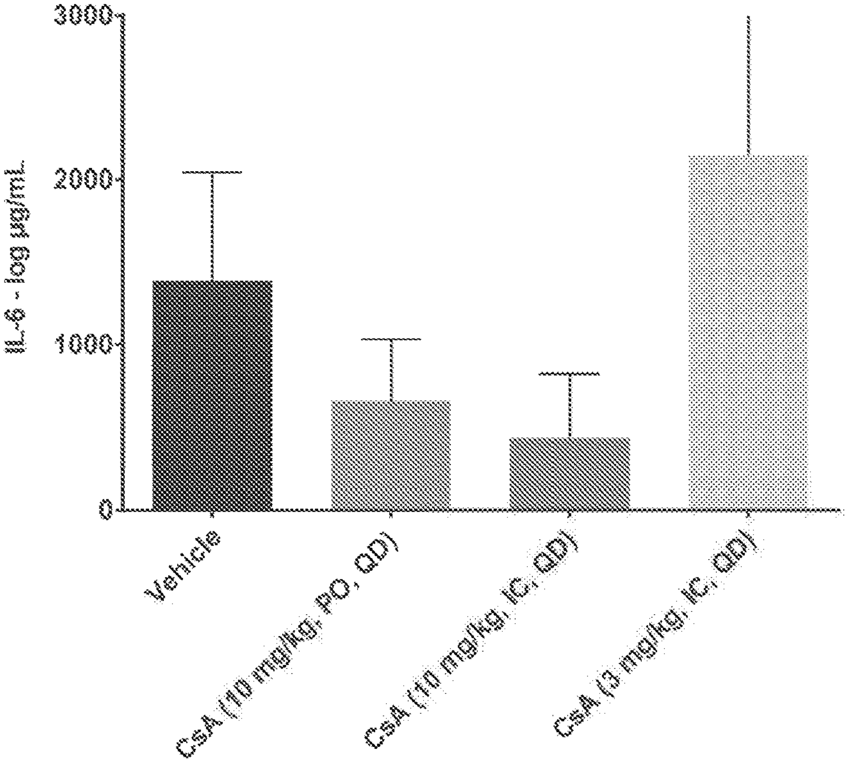

FIG. 61 is a graph showing the interleukin-6 (Il-6) concentration (μg/mL) in colon tissue of acute DSS colitis mice treated daily (QD) with orally (PO) (10 mg/kg) or intracecally (IC) (10 mg/kg or 3 mg/kg) administered CsA. Data presented as mean f SEM.

Figure 62:
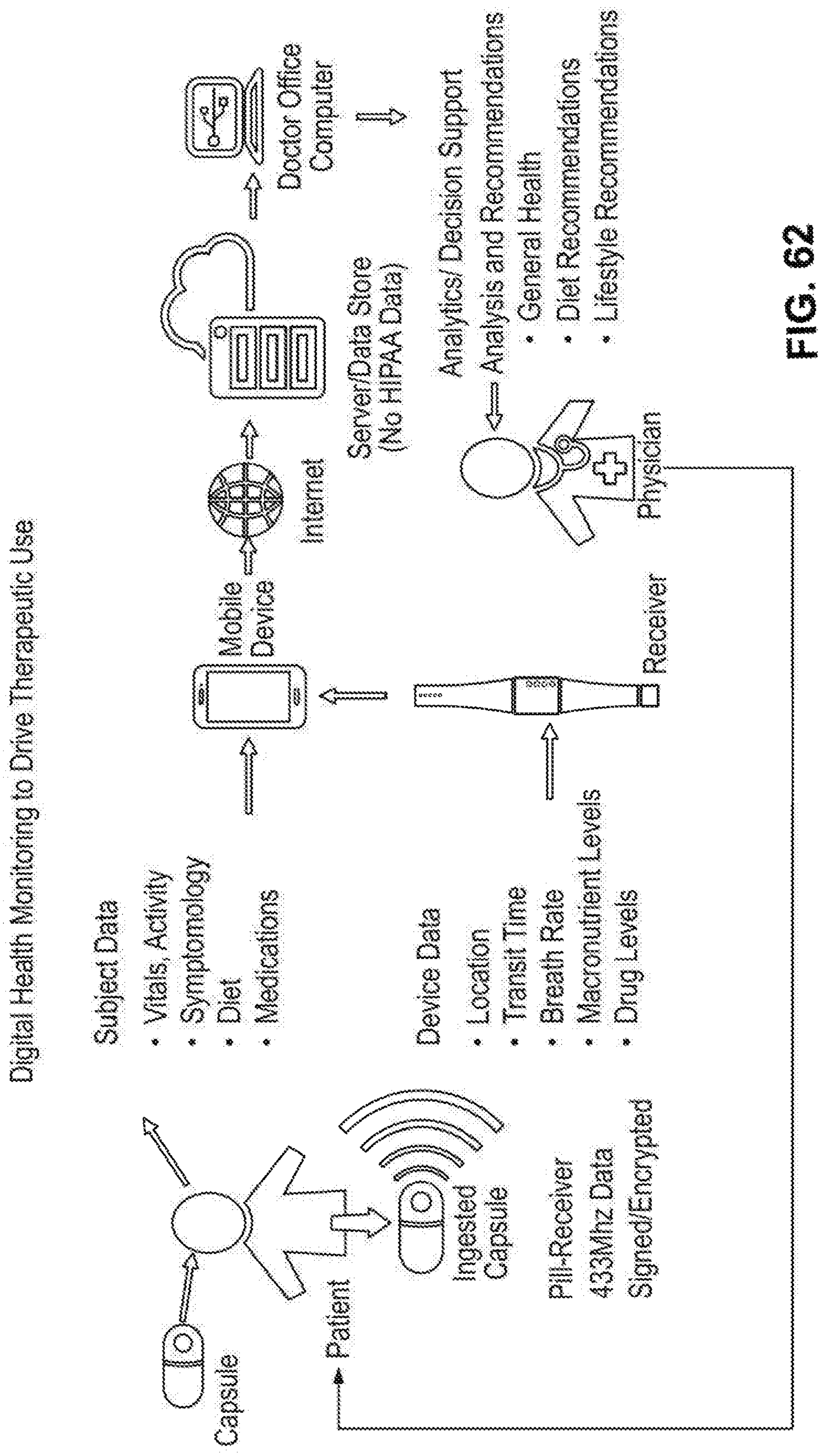
Figure 63A:
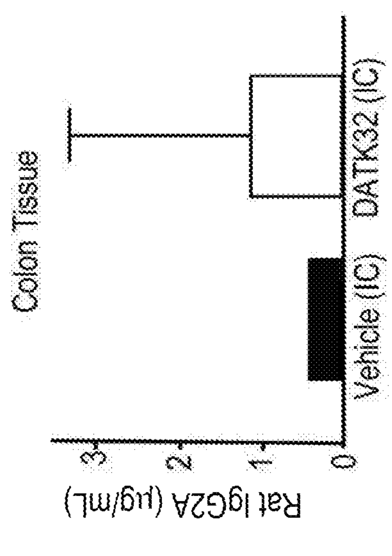
Figure 63B:
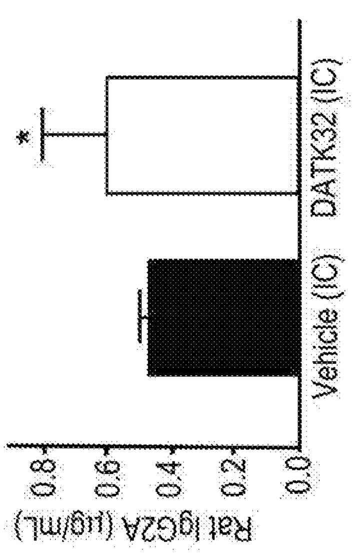
Figure 63C:
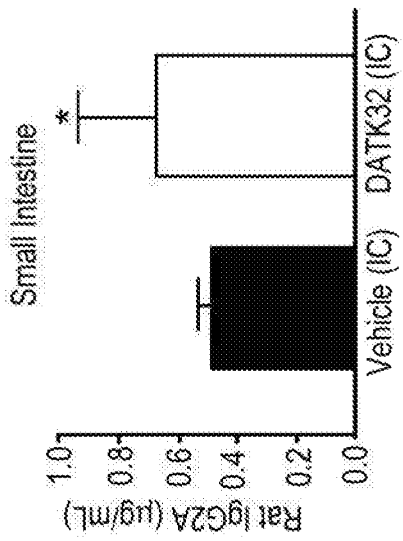
Figure 63D:
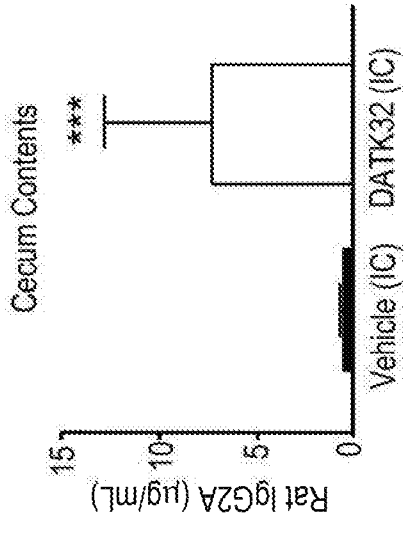
Figure 63E:
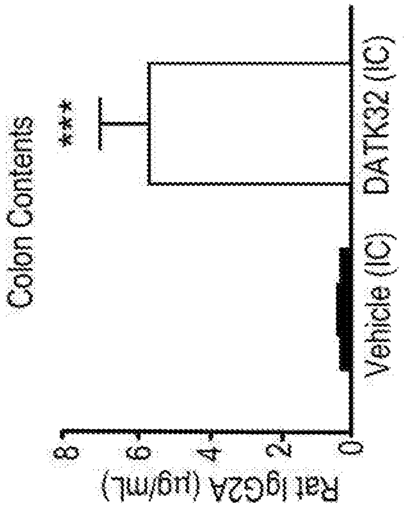
Figure 63F:
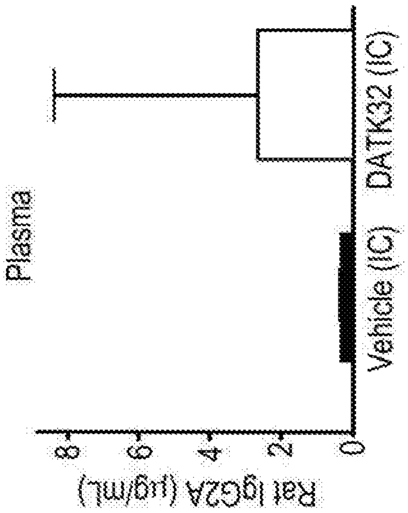

FIG. 62 illustrates a nonlimiting example of a system for collecting, communicating and/or analyzing data about a subject, using an ingestible device.

FIGS. 63A-63F are graphs showing rat IgG2A concentration as measured in (A) colon homogenate, (B) mLN homogenate, (C) small intestine homogenate, (D) cecum contents, (E) colon contents, and (F) plasma by ELISA. Standards were prepared with plasma matrix. Samples were diluted 1:50 before analysis. Sample 20 was removed from cecum contents analysis graph (outlier). *$p<0.05$; $p<0.01$; **$p<0.001$ were determined using the unpaired t test.

Figure 64:
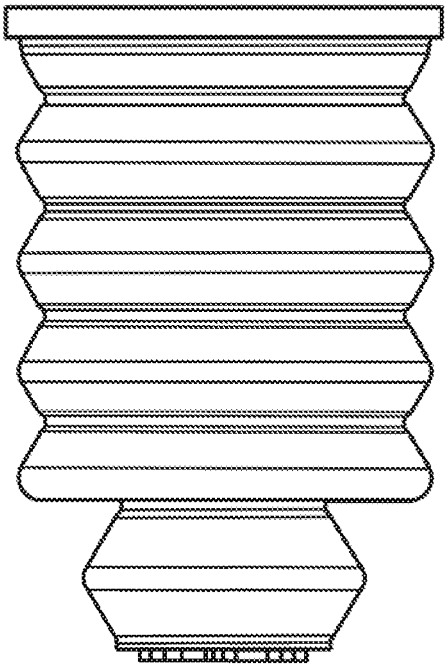

FIG. 64 illustrates a tapered silicon bellows.

Figure 65:
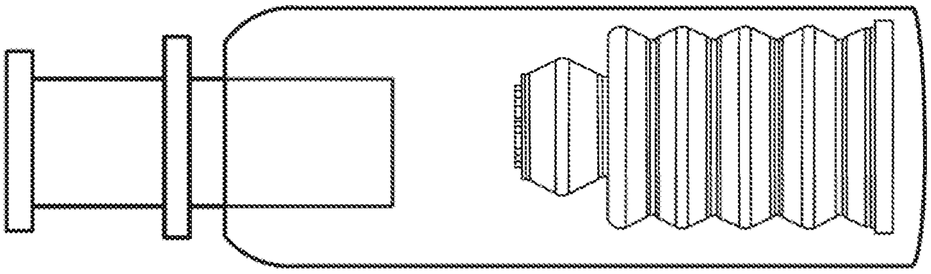

FIG. 65 illustrates a tapered silicone bellows in the simulated device jig.

Figure 66:
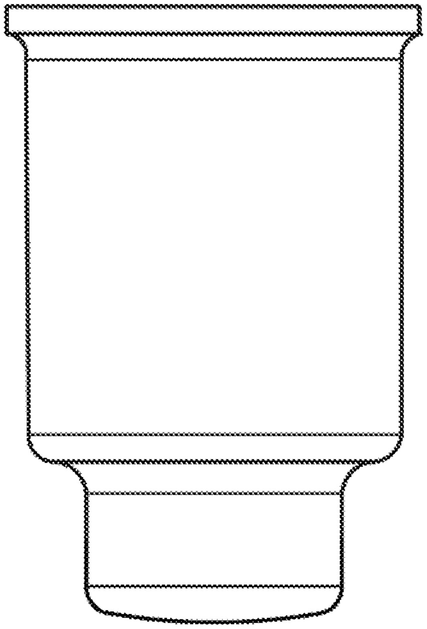

FIG. 66 illustrates a smooth PVC bellows.

Figure 67:
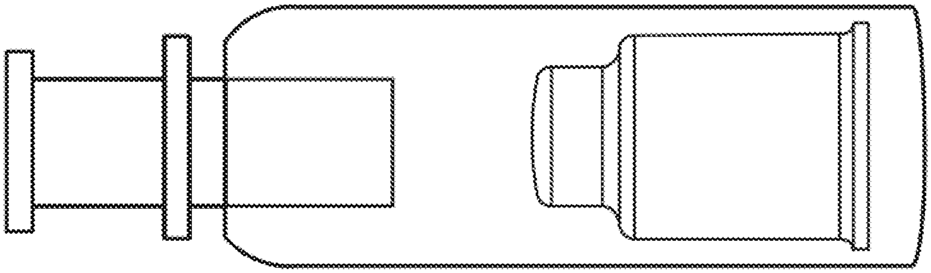

FIG. 67 illustrates a smooth PVC bellows in the simulated device jig.

Figures 68A, 68B:
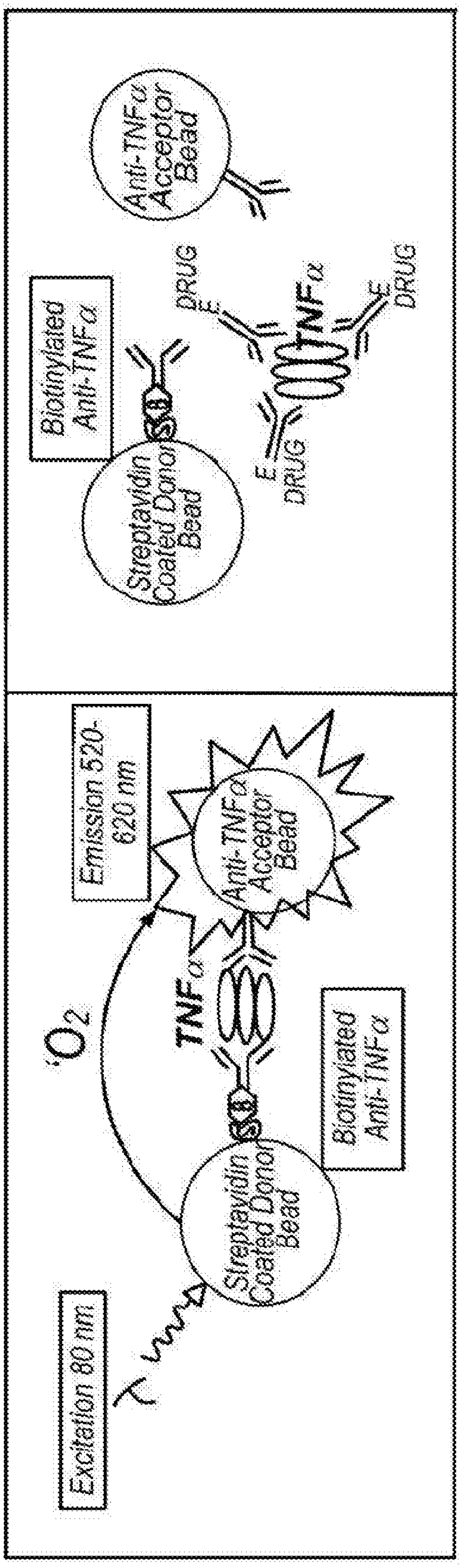

FIGS. 68A-68B demonstrate a principle of a competition assay performed in an experiment. FIG. 68A shows binding of anti-TNFα to TNFα receptor without drug. FIG. 68B shows binding of anti-TNFα to TNFα with drug.

Figure 69:
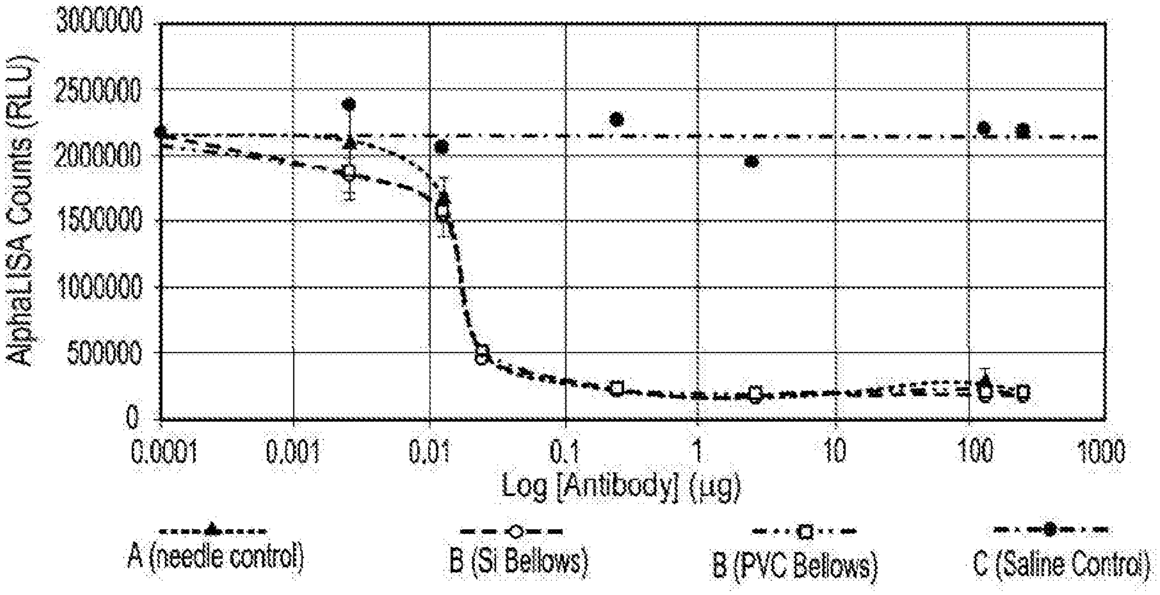

FIG. 69 shows AlphaLISA data. Dose response curves after 4 hours exposure show drug (Exemptia® (adalimumab biosimilar)) binding to TNFα (10,000 pg) of drug dispensed from a standard injector, Si bellows or PVC bellows.

Figure 70:
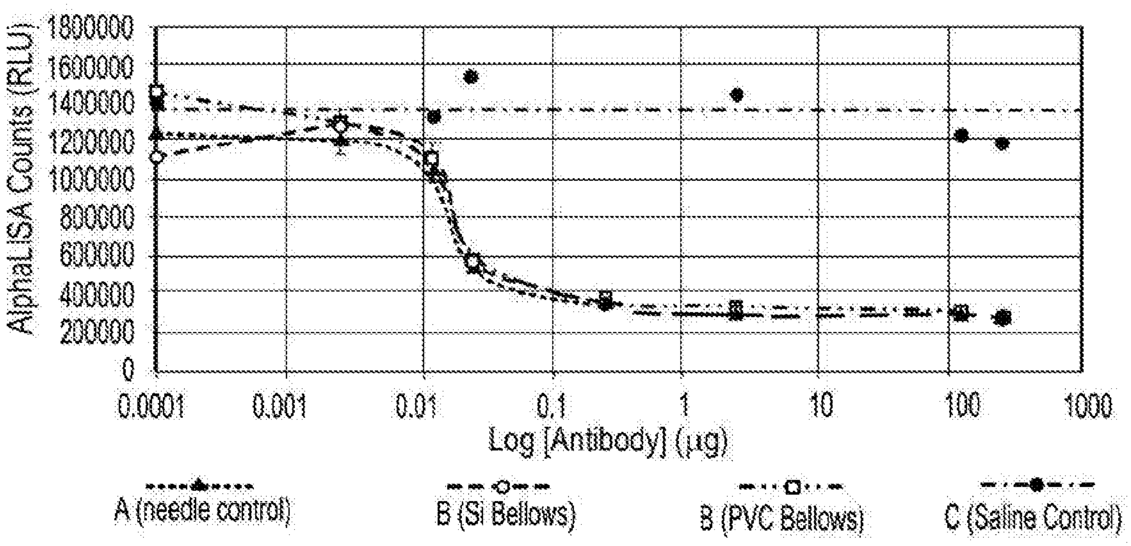

FIG. 70 shows AlphaLISA data. Dose response curves after 24 hours exposure show drug (Exemptia® (adalimumab biosimilar)) binding to TNFα (10,000 pg) of drug dispensed from a standard injector, Si bellows or PVC bellows.

Figure 71:
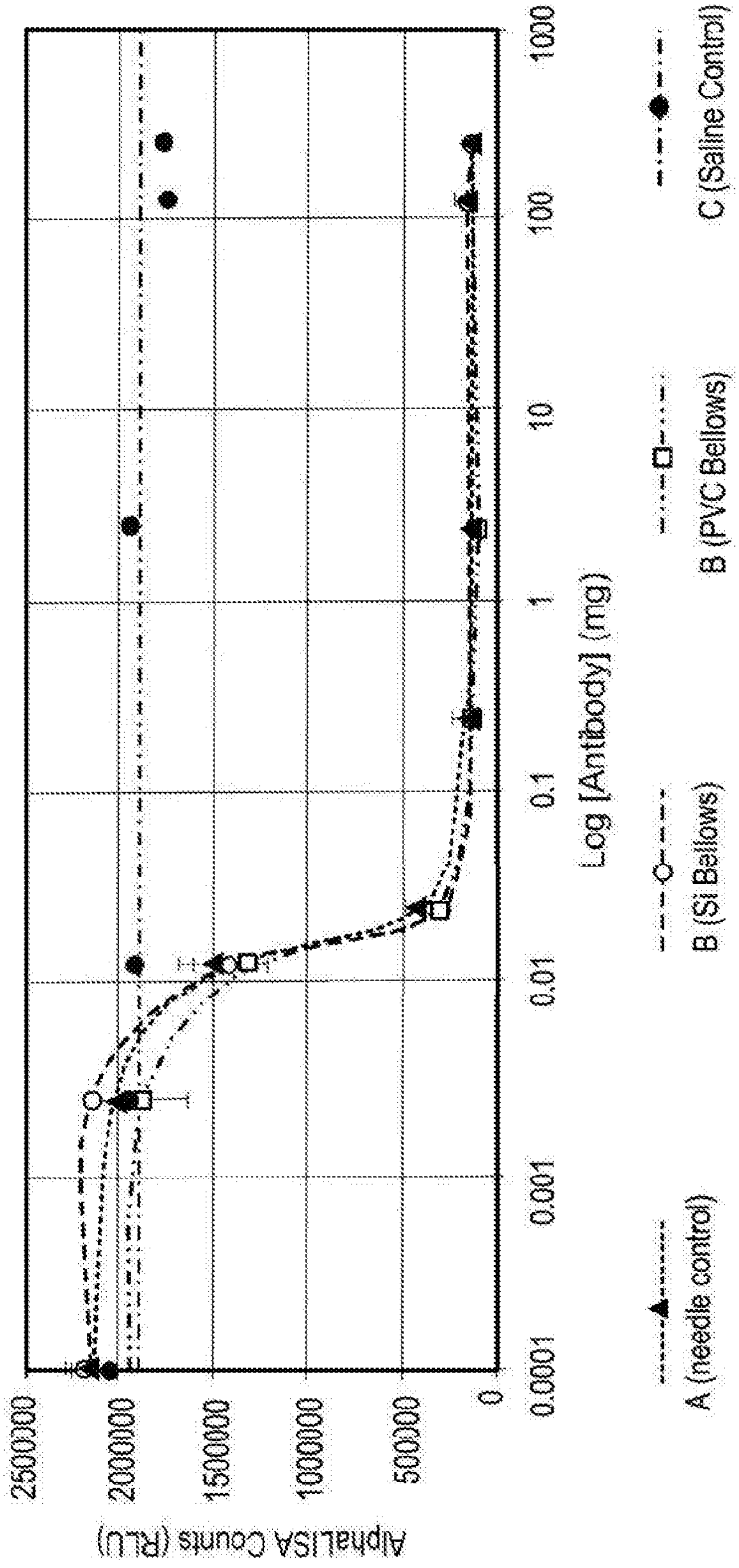

FIG. 71 shows AlphaLISA data. Dose response curves after 336 hours exposure show drug (Exemptia® (adalimumab biosimilar)) binding to TNFα (10,000 pg) of drug dispensed from a standard injector, Si bellows or PVC bellows.

Figure 72:
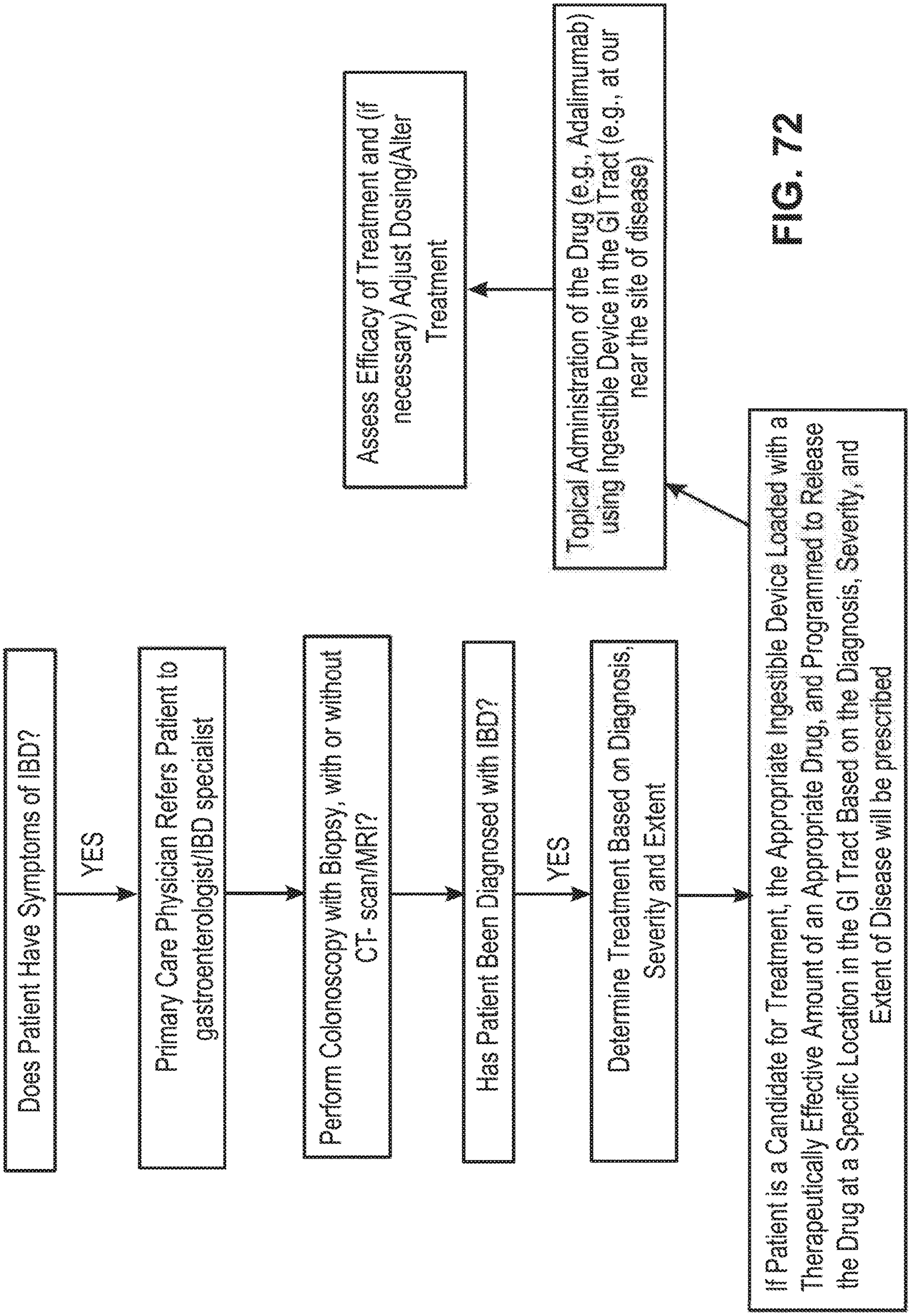

FIG. 72 is a flowchart of illustrative steps of a clinical protocol, in accordance with some embodiments of the disclosure.

Figure 73:
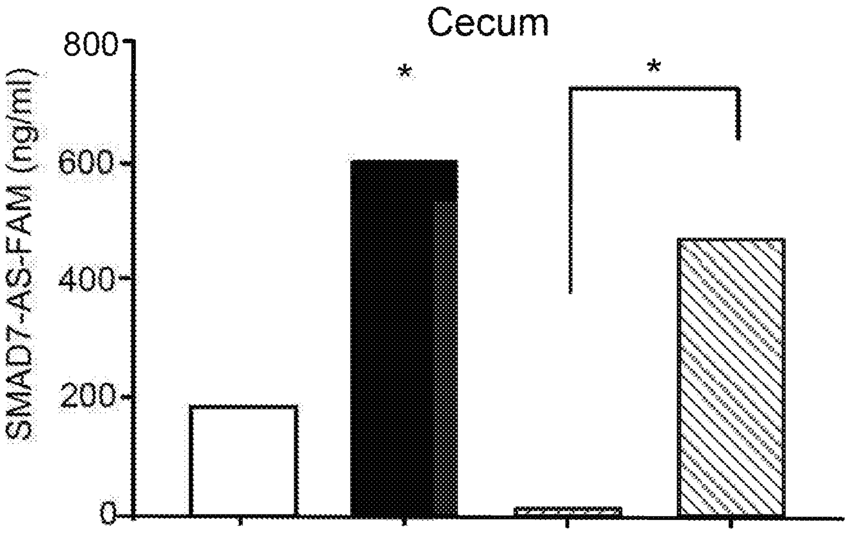

FIG. 73 is a graph showing the level of FAM-SMAD7-AS oligonucleotide in the cecum tissue of DSS-induced colitis mice at 12-hours. The bars represent from left to right, Groups 2 through 5 in the experiment described in Example 9.

Figure 74:
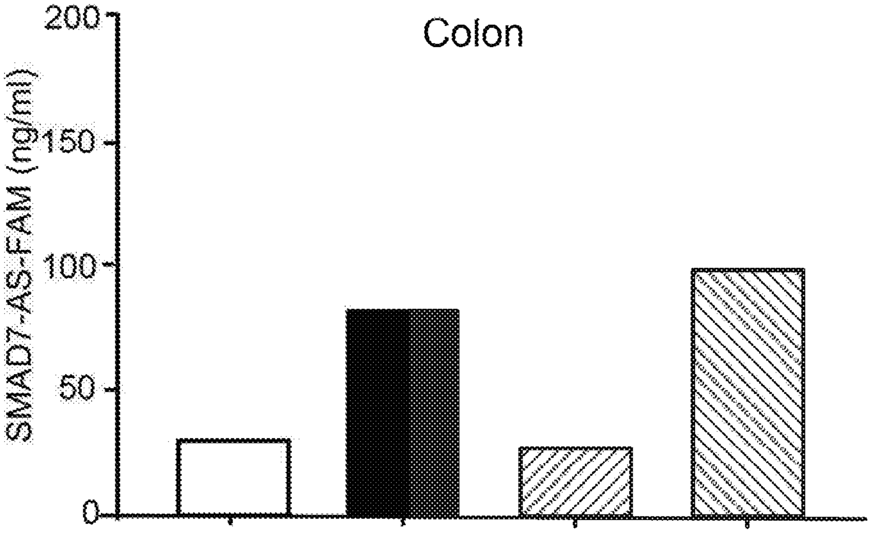

FIG. 74 is a graph showing the level of FAM-SMAD7-AS oligonucleotide in the colon tissue of DSS-induced colitis mice at 12-hours. The bars represent from left to right, Groups 2 through 5 in the experiment described in Example 9.

Figure 75:
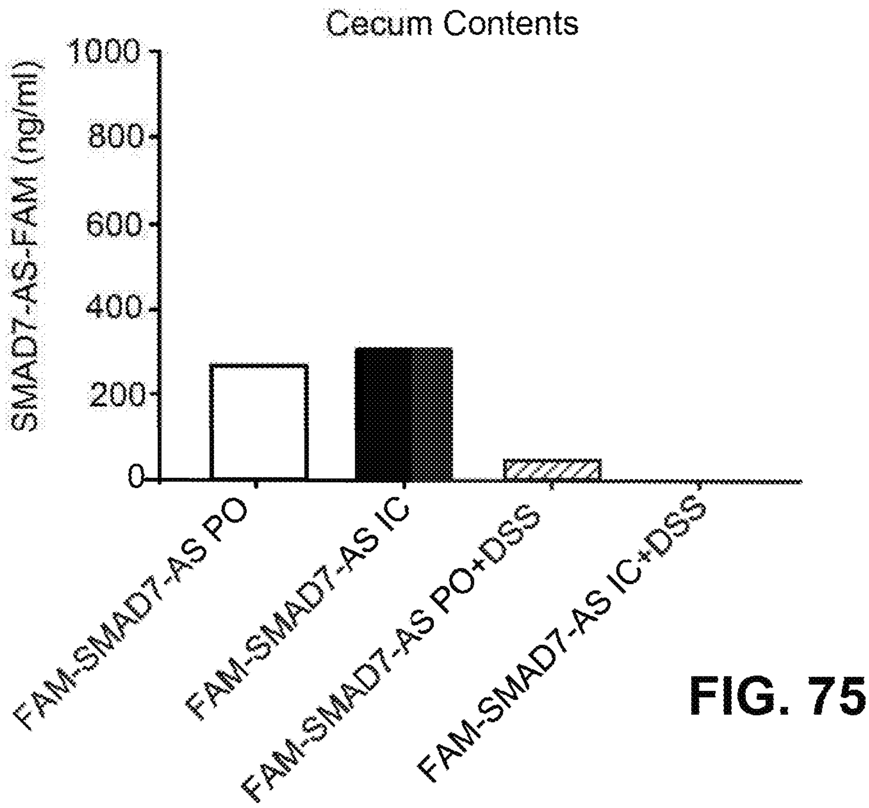

FIG. 75 is a graph showing the level of FAM-SMAD7-AS oligonucleotide in the cecum contents of DSS-induced colitis mice at 12-hours. The bars represent from left to right, Groups 2 through 5 in the experiment described in Example 9.

Figure 76:
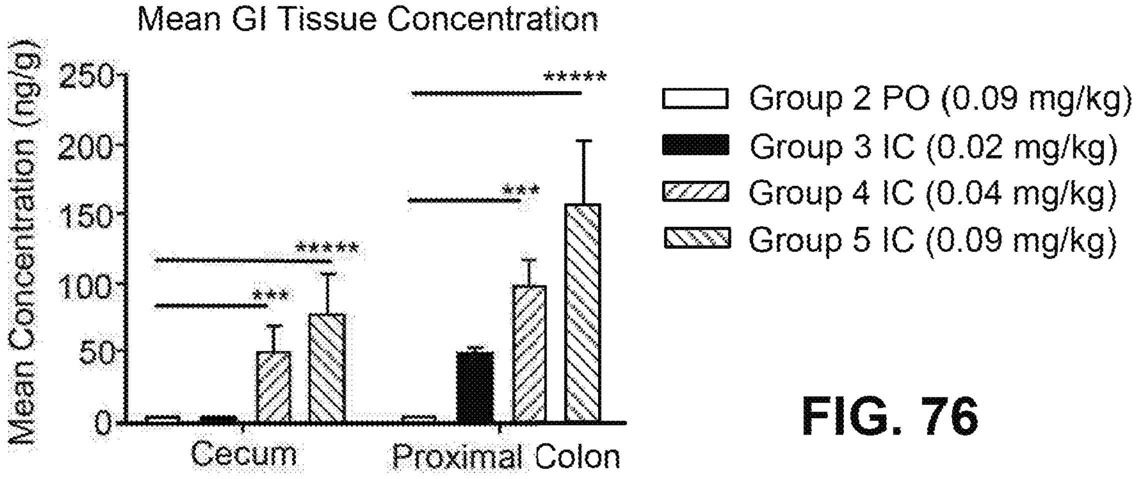

FIG. 76 is a graph showing the mean concentration of tacrolimus in the cecum tissue and the proximal colon tissue 12 hours after intra-cecal or oral administration of tacrolimus to swine as described in Example 10.

Figure 77:
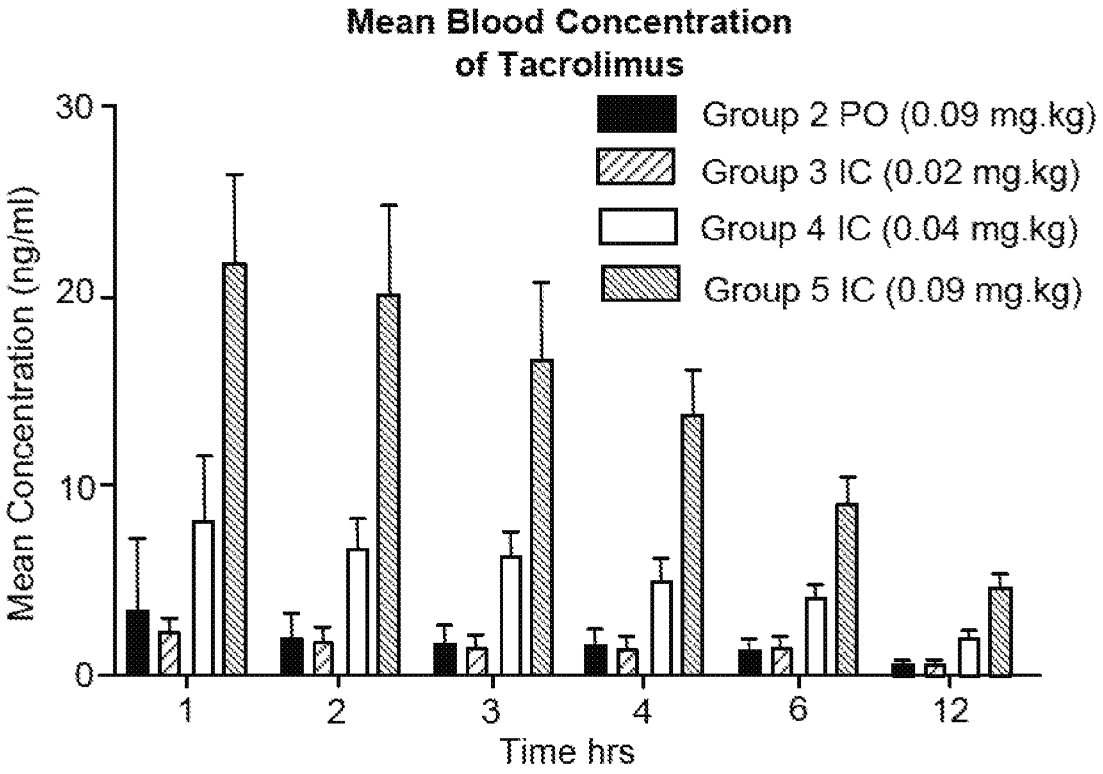

FIG. 77 is a graph showing the mean concentration of tacrolimus in the blood 1 hour, 2 hours, 3 hours, 4 hours, 6 hours and 12 hours after intra-cecal (IC) or oral administration (PO) of tacrolimus to swine as described in Example 13.

Figure 78:
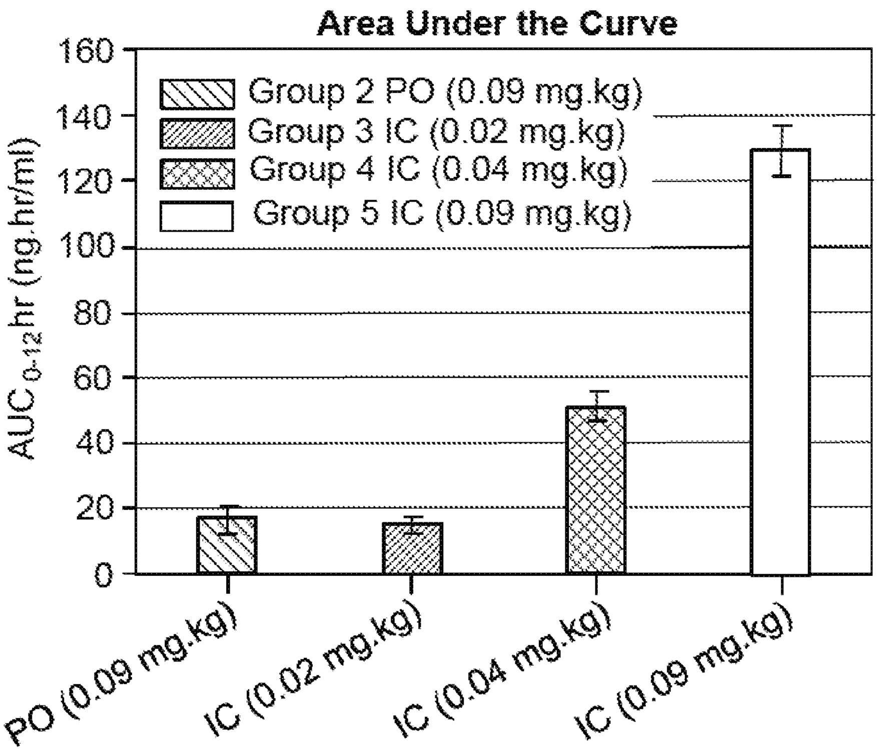

FIG. 78 is a graph showing the $AUC_{0-12}$ hours of tacrolimus in the blood after intra-cecal (IC) or oral administration (PO) of tacrolimus in swine as described in Example 13.

Figure 79:
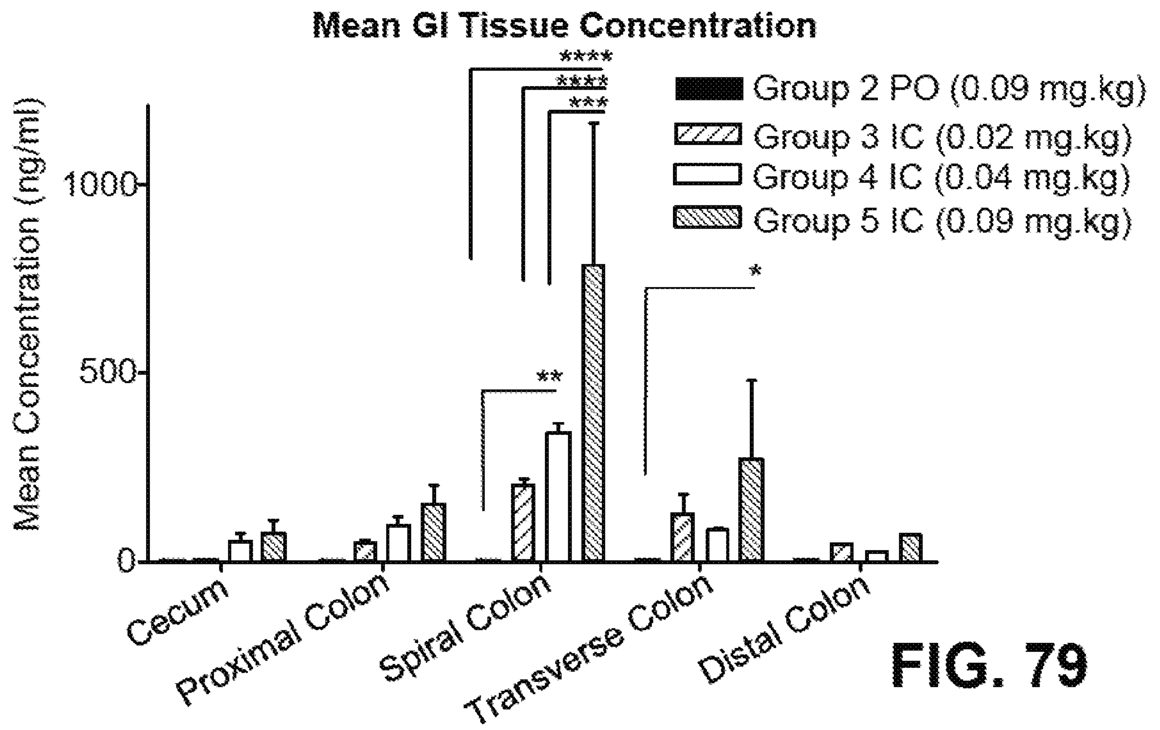

FIG. 79 is a graph showing the mean concentration of tacrolimus in the cecum tissue, the proximal colon tissue, the spiral colon tissue, the transverse colon tissue, and the distal colon tissue after intra-cecal (IC) or oral administration (PO) of tacrolimus in swine as described in Example 13. ** $P<0.0001$, * $P<0.001$.

Figure 80:
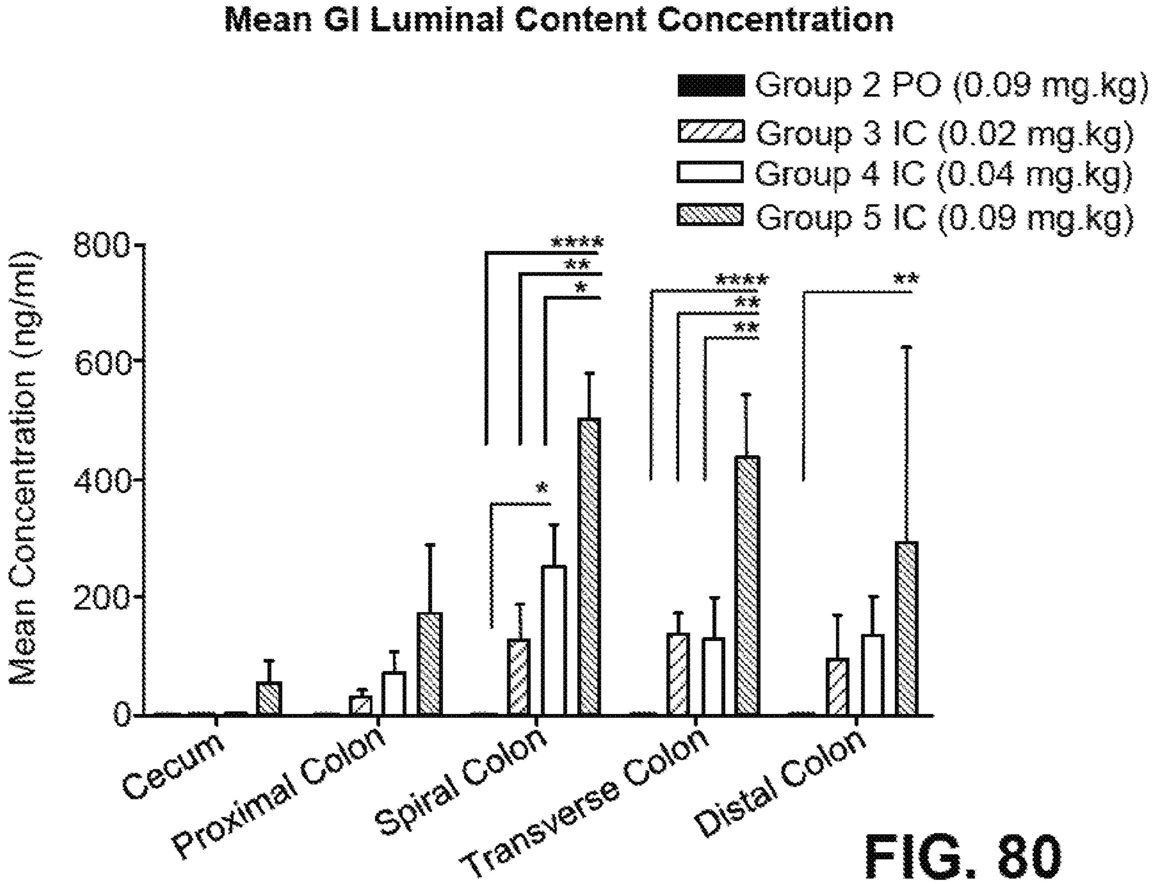
Figure 81:
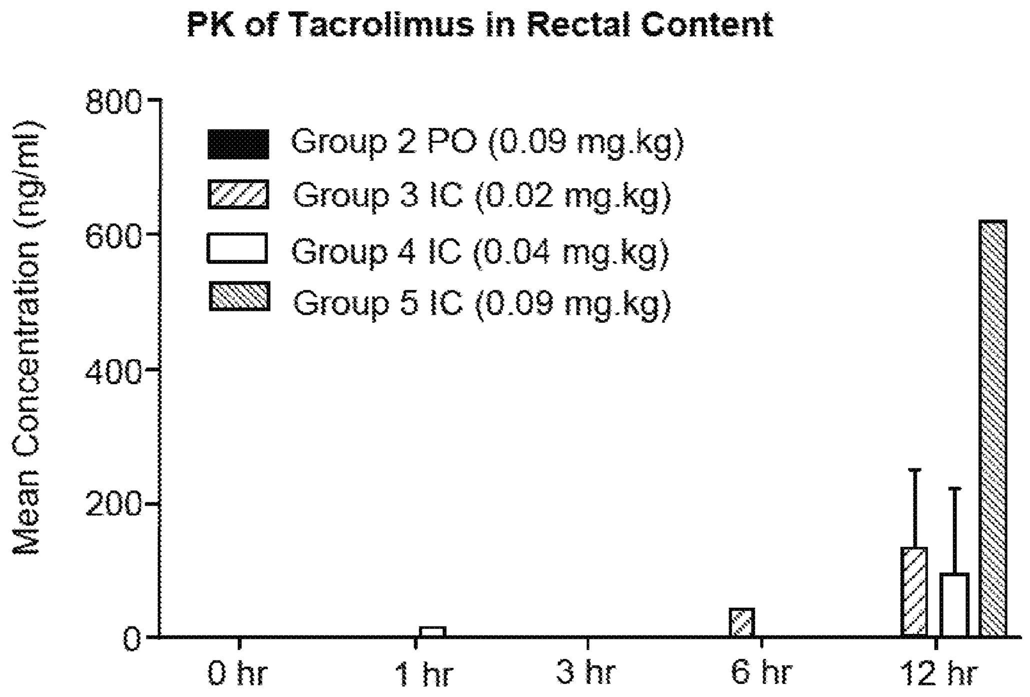

FIG. 80 is a graph showing the mean concentation of tacrolimus in the cecum lumen, the proximal lumen, the spiral colon lumen, the transverse colon lumen, and the distal colon lumen in swine after intra-cecal (IC) or oral administration (PO) of tacrolimus in swine as described in Example 13. ** $P<0.0001$, * $P<0.001$ FIG. 81 is a bar graph showing the mean concentration of tacrolimus in the rectal content 1 hour, 3 hours, 6 hours and 12 hours after intra-cecal (IC) or oral administration (PO) of tacrolimus to swine as described in Example 13.

Figure 82:
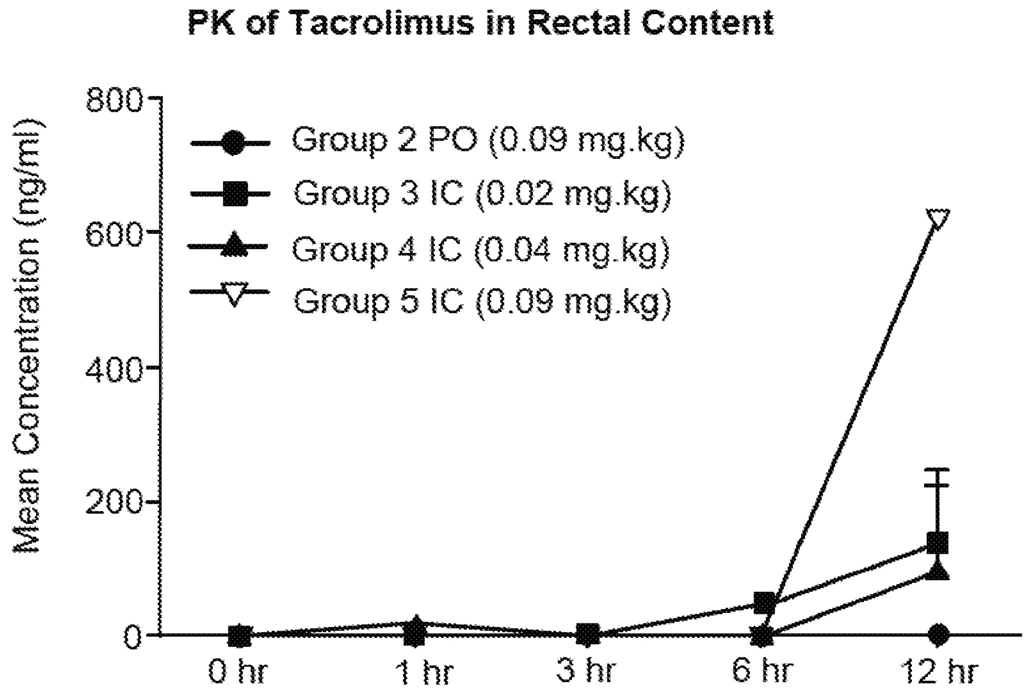

FIG. 82 is a line graph showing the mean concentration of tacrolimus in the rectal content 1 hour, 3 hours, 6 hours and 12 hours after intra-cecal (IC) or oral administration (PO) of tacrolimus to swine as described in Example 13.

Figure 83:
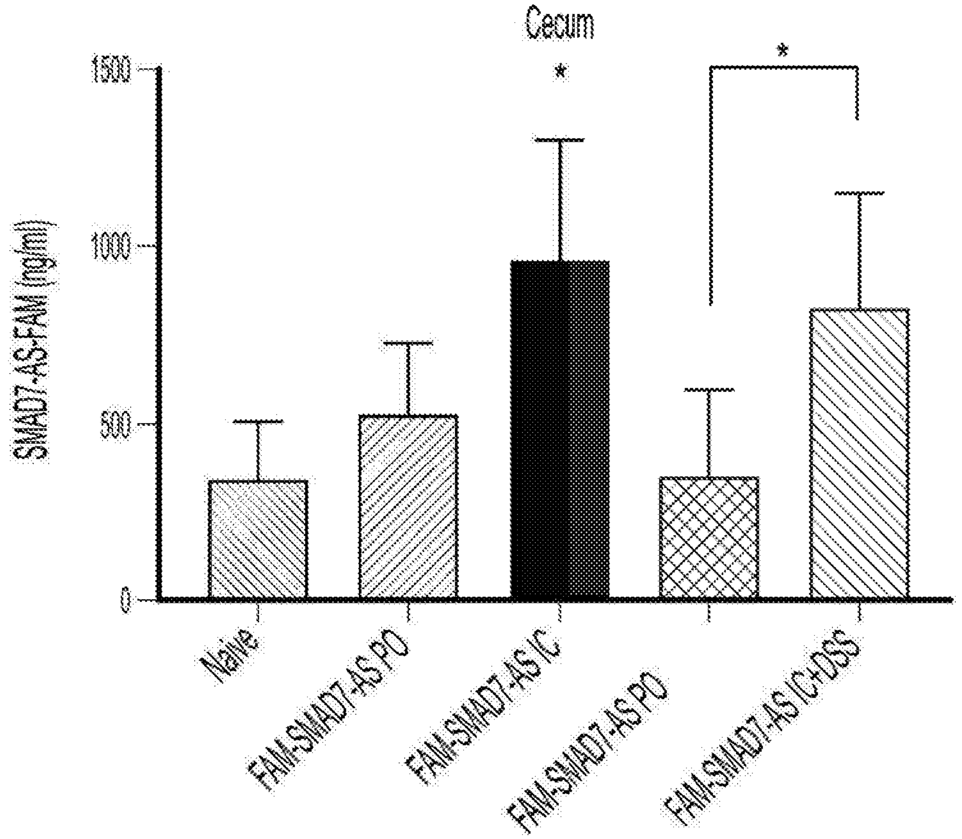

FIG. 83 is a graph showing the mean concentration of a SMAD7 antisense molecuile (SMAD7-AS-FAM) in the cecum tissue in untreated swine or in swine after intra-cecal (IC) or oral administration (PO) of SMAD7-AS-FAM as described in Example 9.

Figure 84:
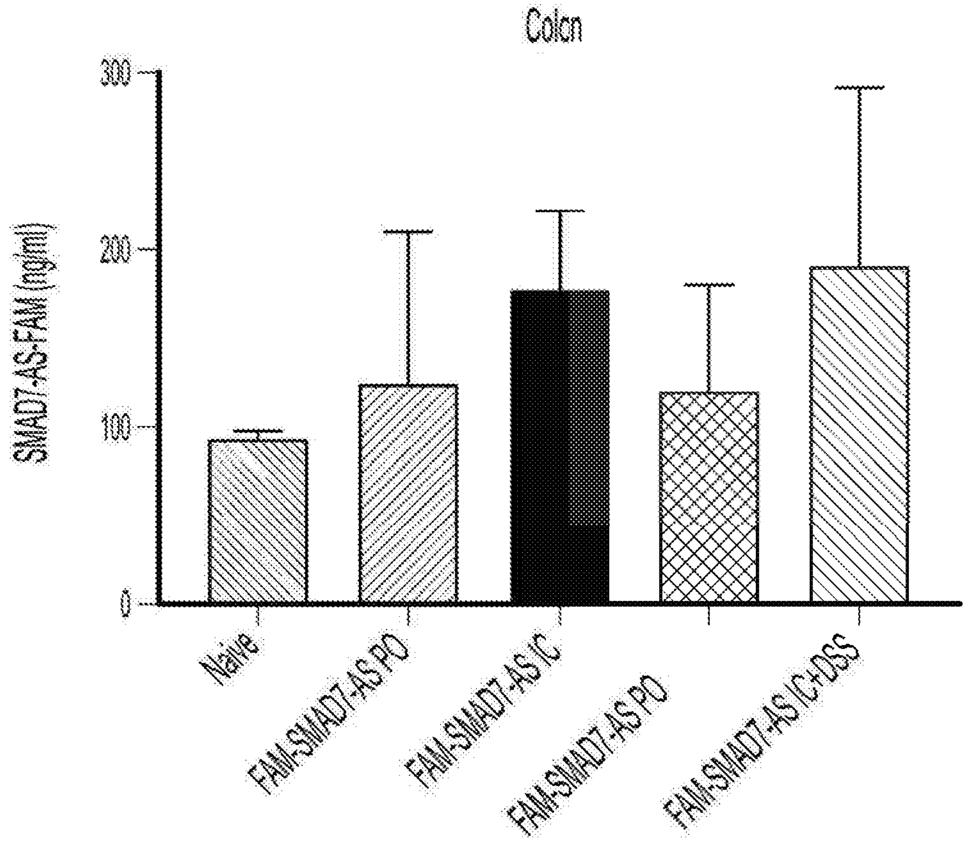

FIG. 84 is a graph showing the mean concentration of SMAD7-AS-FAM in the colon tissue in untreated swine or in swine after intra-cecal (IC) or oral administration (PO) of SMAD7-AS-FAM as described in Example 9.

Figure 85:
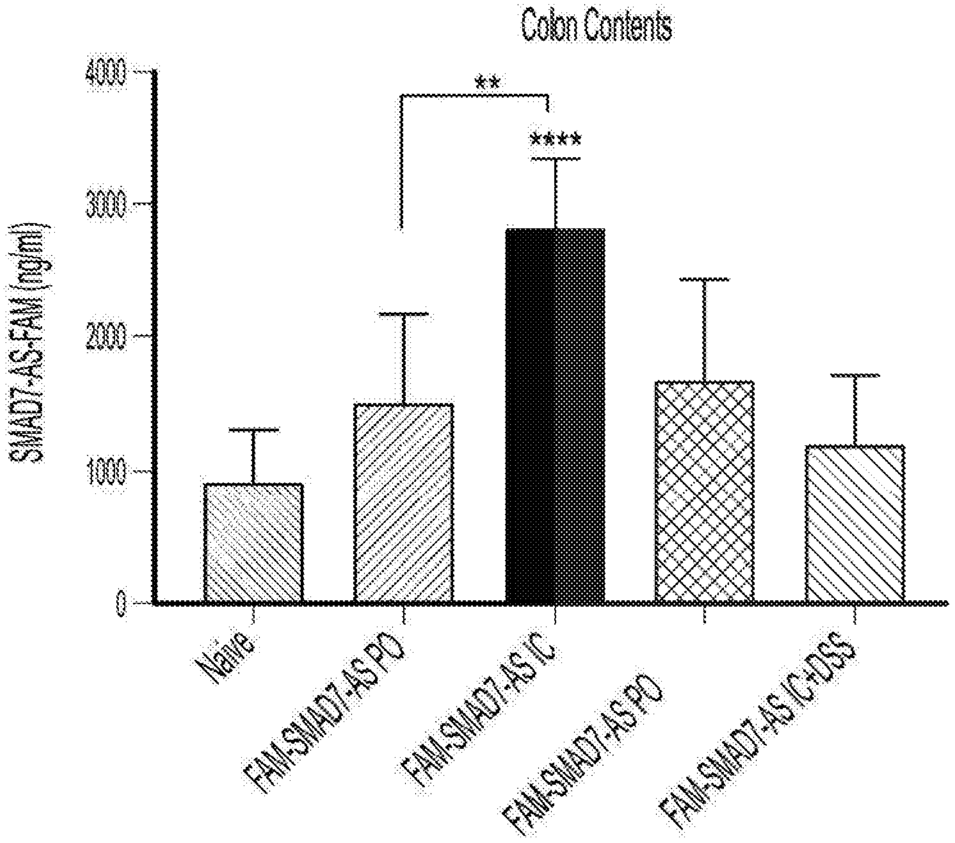

FIG. 85 is a graph showing the mean concentration of SMAD7-AS-FAM in the colon contents in untreated swine or in swine after intra-cecal (IC) or oral administration (PO) of SMAD7-AS-FAM as described in Example 9.

Figure 86:
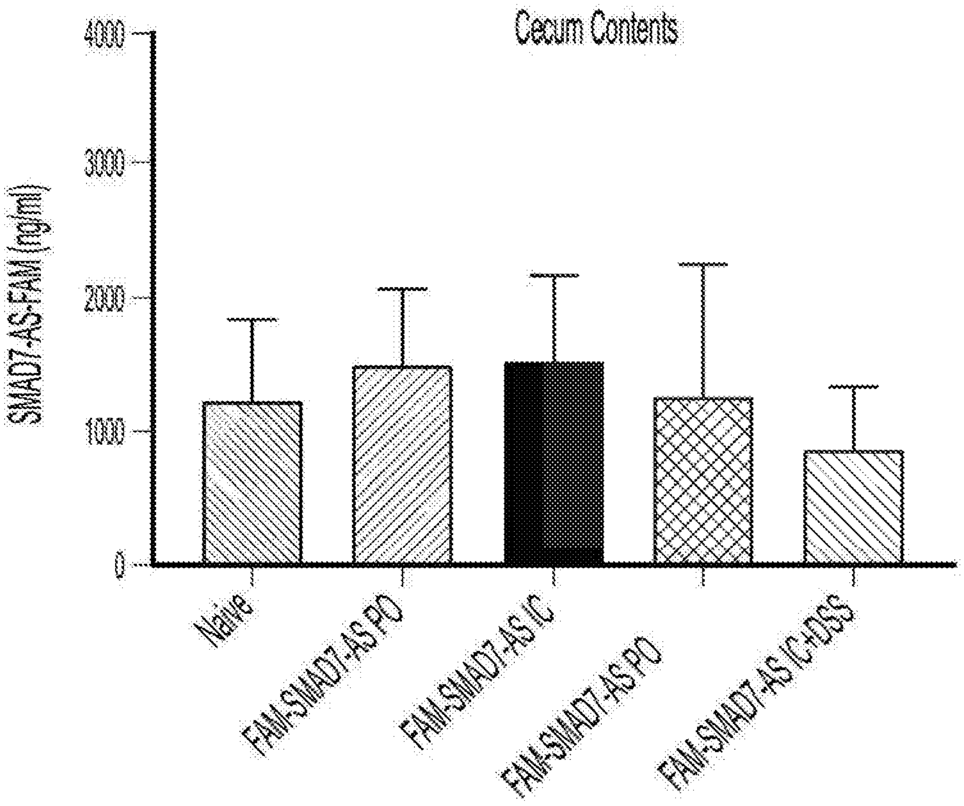

FIG. 86 is a graph showing the mean concentration of SMAD7-AS-FAM in the cecum contents in untreated swine or in swine after intra-cecal (IC) or oral administration (PO) of SMAD7-AS-FAM as described in Example 9.

Figure 87:
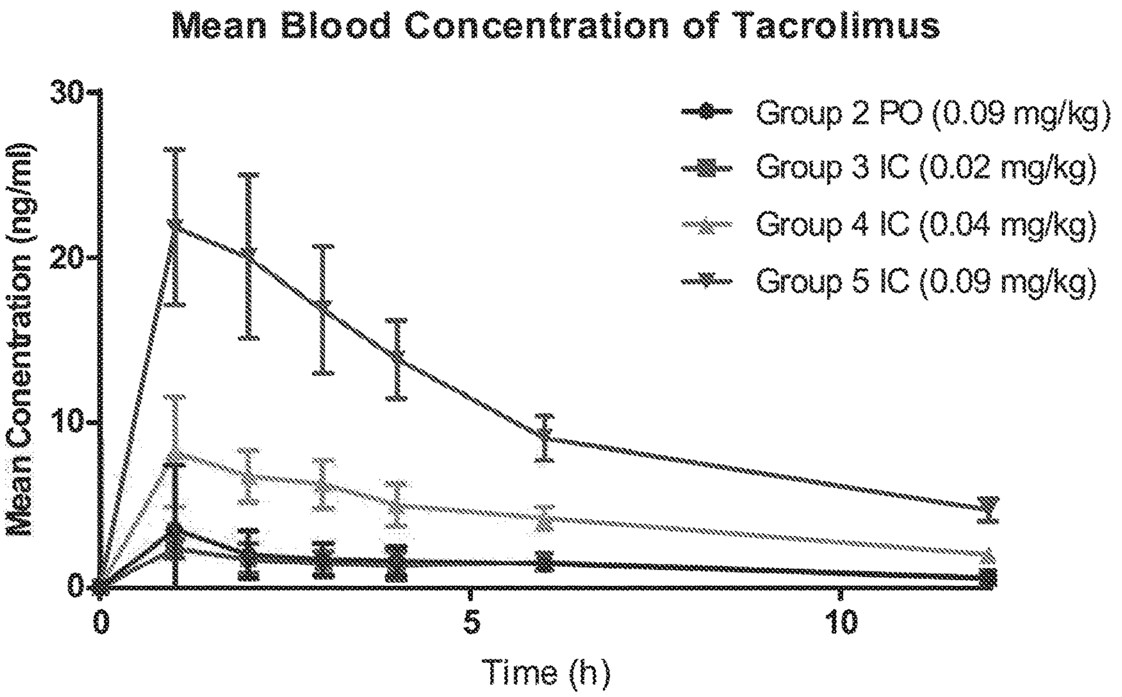

FIG. 87 is a graph showing the mean concentration of tacrolimus in the blood of swine 1 hour, 2 hours, 3 hours, 4 hours, 6 hours, and 12 hours after intra-cecal (IC) or oral administration (PO) of tacrolimus as described in Example 10.

Figure 88:
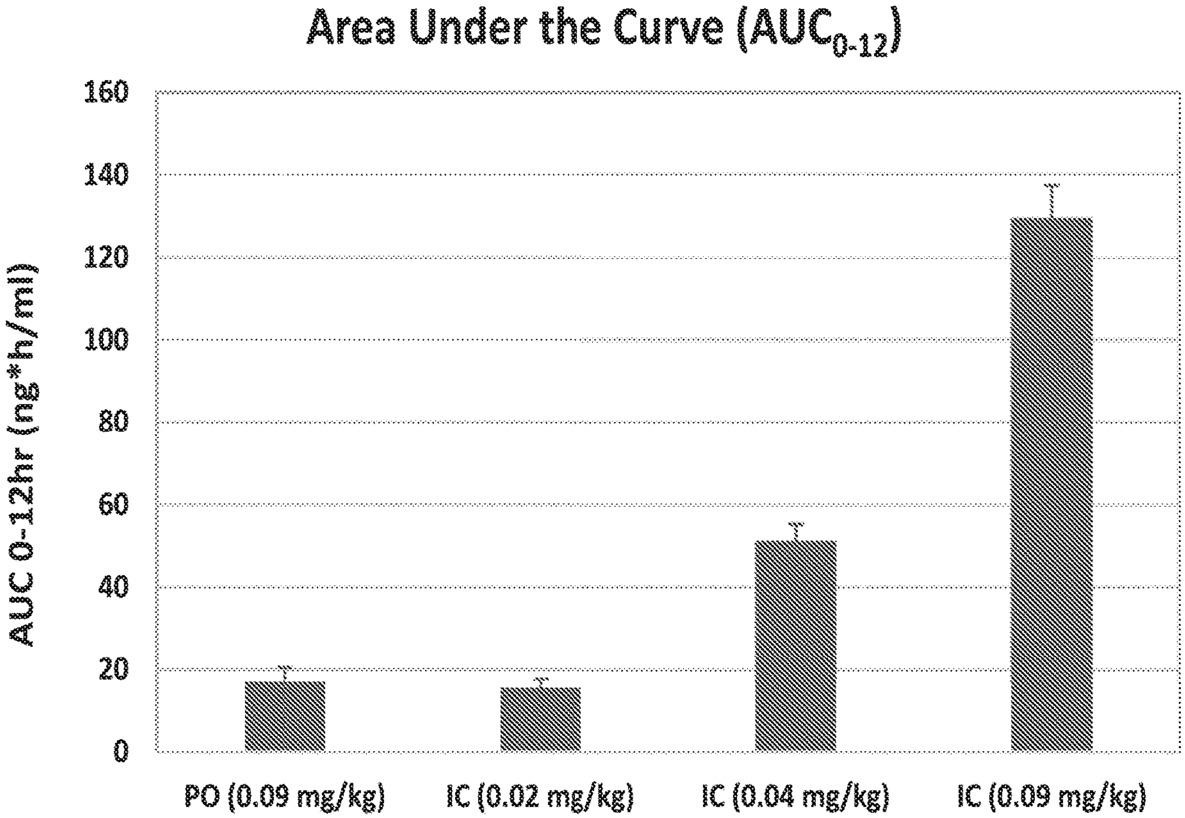

FIG. 88 is a graph showing the $AUC_{0-12}$ hours of tacrolimus in the blood of swine after intra-cecal (IC) or oral administration (PO) of tacrolimus as described in Example 10.

Figures 89, 90:
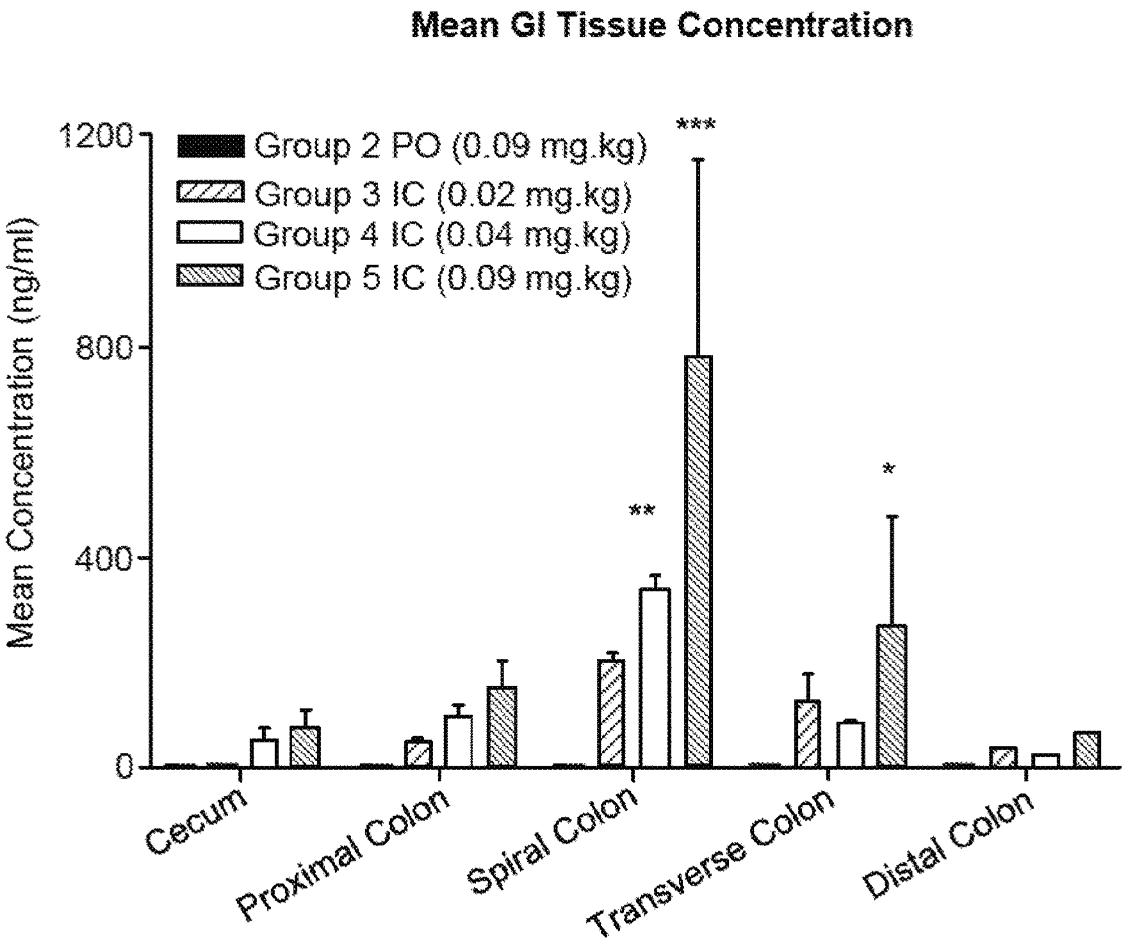

FIG. 89 is a representative table showing the $T_{max}$, $C_{max}$, trough (at 12 hours post-administration), and $AUC_{0-12}$ hours of tacrolimus in swine after intra-cecal (IC) or oral administration (PO) as described in Example 10.

FIG. 90 is a graph showing the mean concentration of tacrolimus in the cecum, the proximal colon, the spiral colon, the transverse colon, and the distal colon of swine after intra-cecal (IC) or oral administration (PO) of tacrolimus as described in Example 10.

Figure 91:
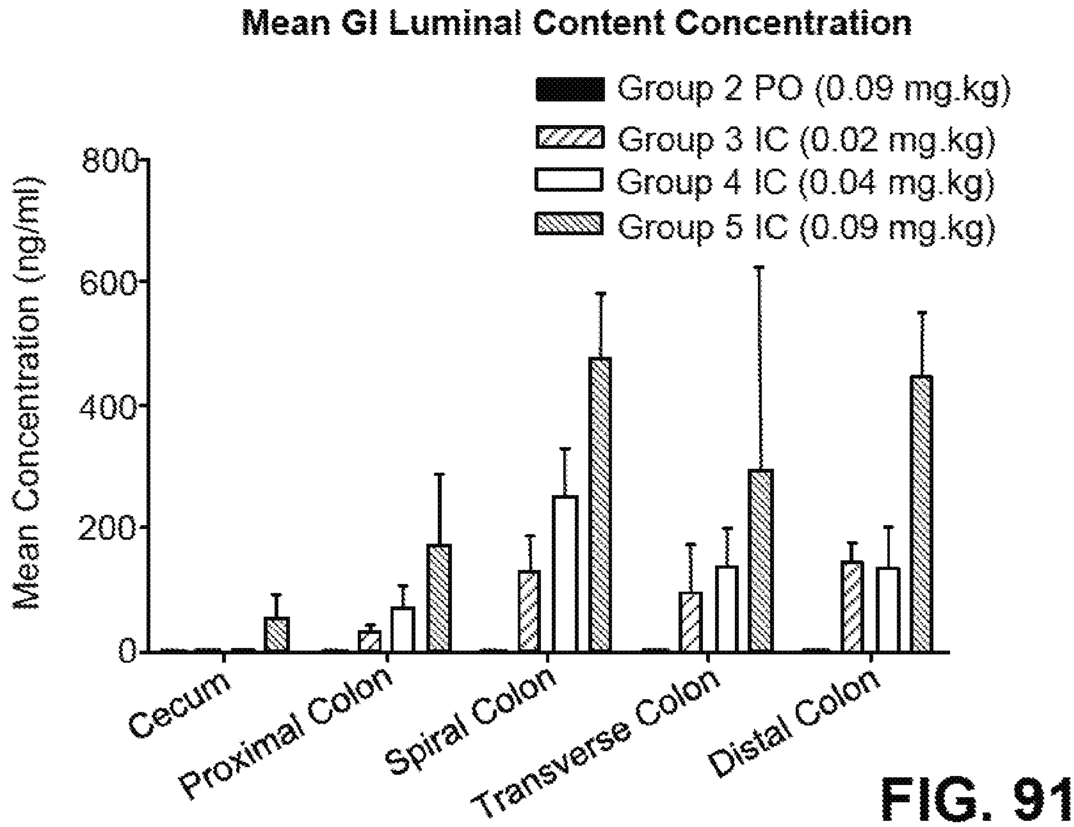

FIG. 91 is a graph showing the mean concentration of tacrolimus in the cecum lumen, the proximal colon lumen, the spiral colon lumen, the transverse colon lumen, and the distal colon lumen of swine after intra-cecal (IC) or oral administration (PO) of tacrolimus as described in Example 10.

Figure 92:
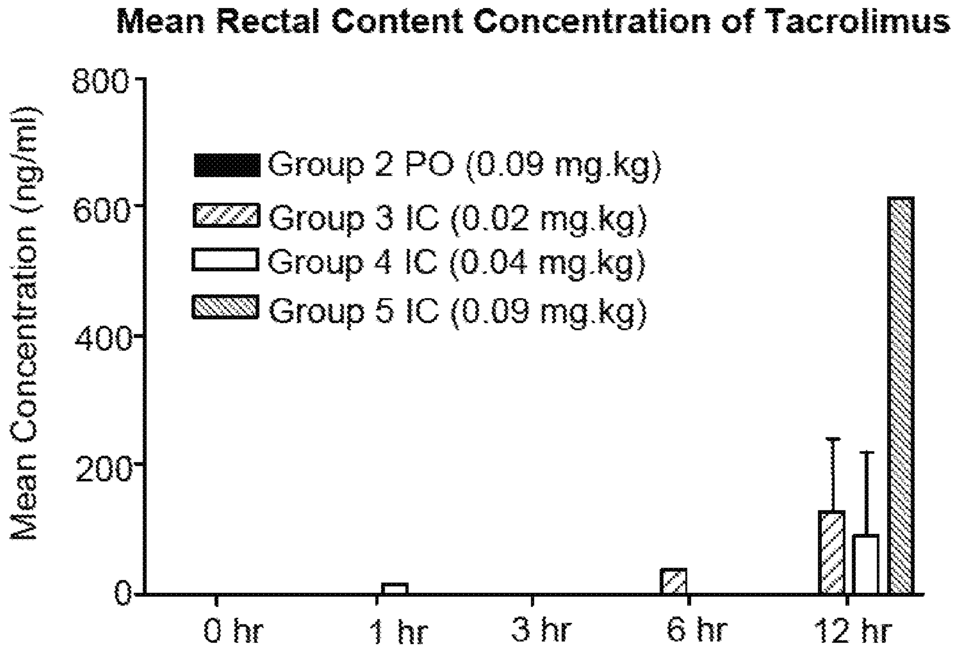

FIG. 92 is a graph showing the mean concentration of tacrolimus in the rectal content of swine at 1 hour, 3 hours, 6 hours, and 12 hours after intra-cecal (IC) or oral administration (PO) of tacrolimus as described in Example 10.

FIG. 93 is a representative table showing the quantitative histological grading of colitis as described in Example 11.

Figure 94:
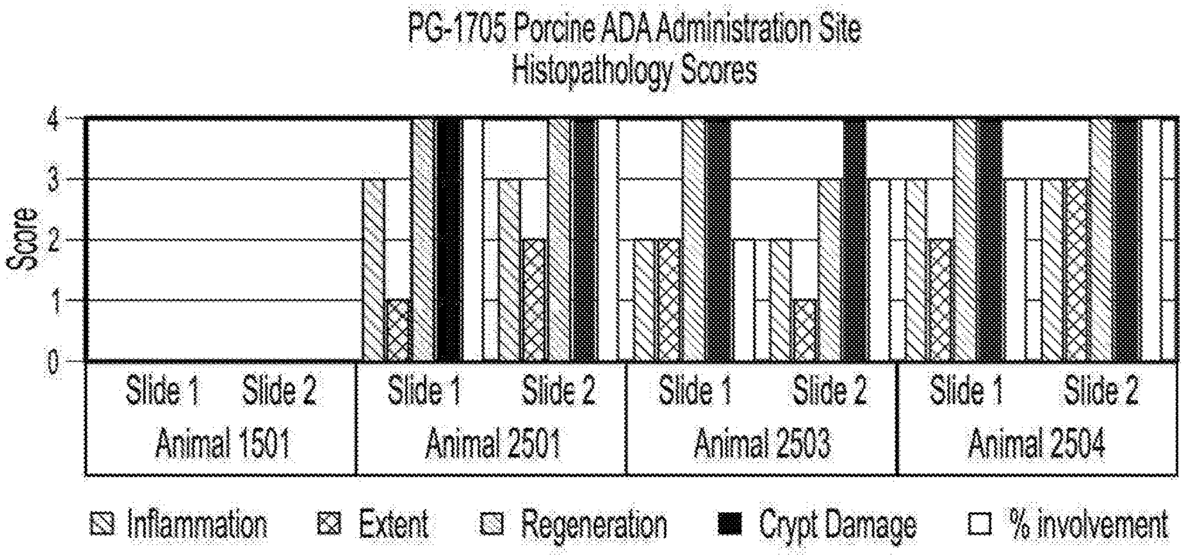

FIG. 94 is a graph showing the histopathological scores of two slides for animal 1502 (healthy control swine treated with placebo), animal 2501 (swine with 8.5% DSS-induced colitis treated with 1.86 mg/kg adalimumab), animal 2503 (swine with 8.5% DSS-induced colitis treated with 1.86 mg/kg adalimumab), and animal 2504 (swine with 8.5% DSS-induced colitis treated with 1.86 mg/kg adalimumab) at the placebo or adalimumab administration site prior to administration of placebo or adalimumab, respect tively. Absence of a bar for a particular parameter indicates that the value for this parameter was 0.

Figure 95:
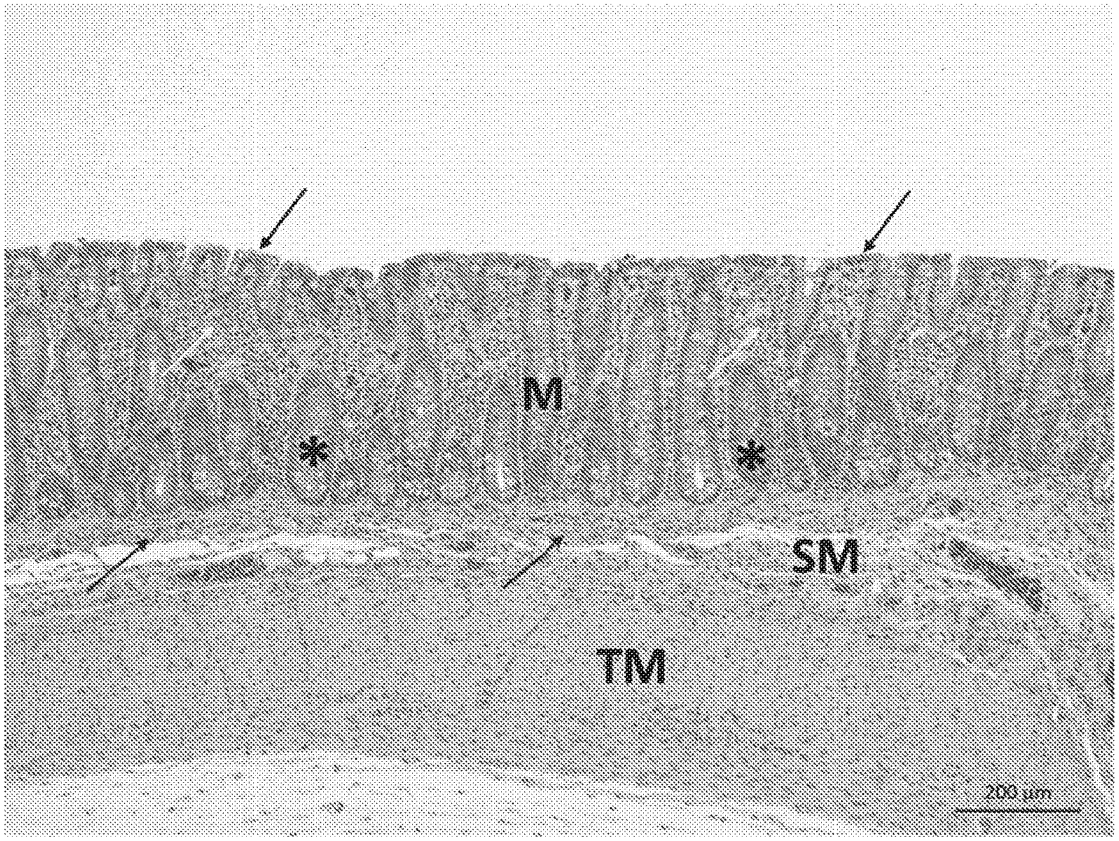

FIG. 95 is a representative hematoxylin- and eosin-stained image of the transverse colon of animal 1501 (healthy control swine). M, mucosa; SM, submucosa; TM, tunica muscularis. Numerous intestinal crypts (asterisks) are present and the surface epithelium (top two arrows) is intact. Mononuclear inflammatory cells are prominent in the lamina propria (light arrows) of the mucosa and extend a short distance into the submucosa (bottom two arrows). This amount of inflammatory cell infiltrate was expected background change and considered unrelated to the experimental protocol.

Figure 96:
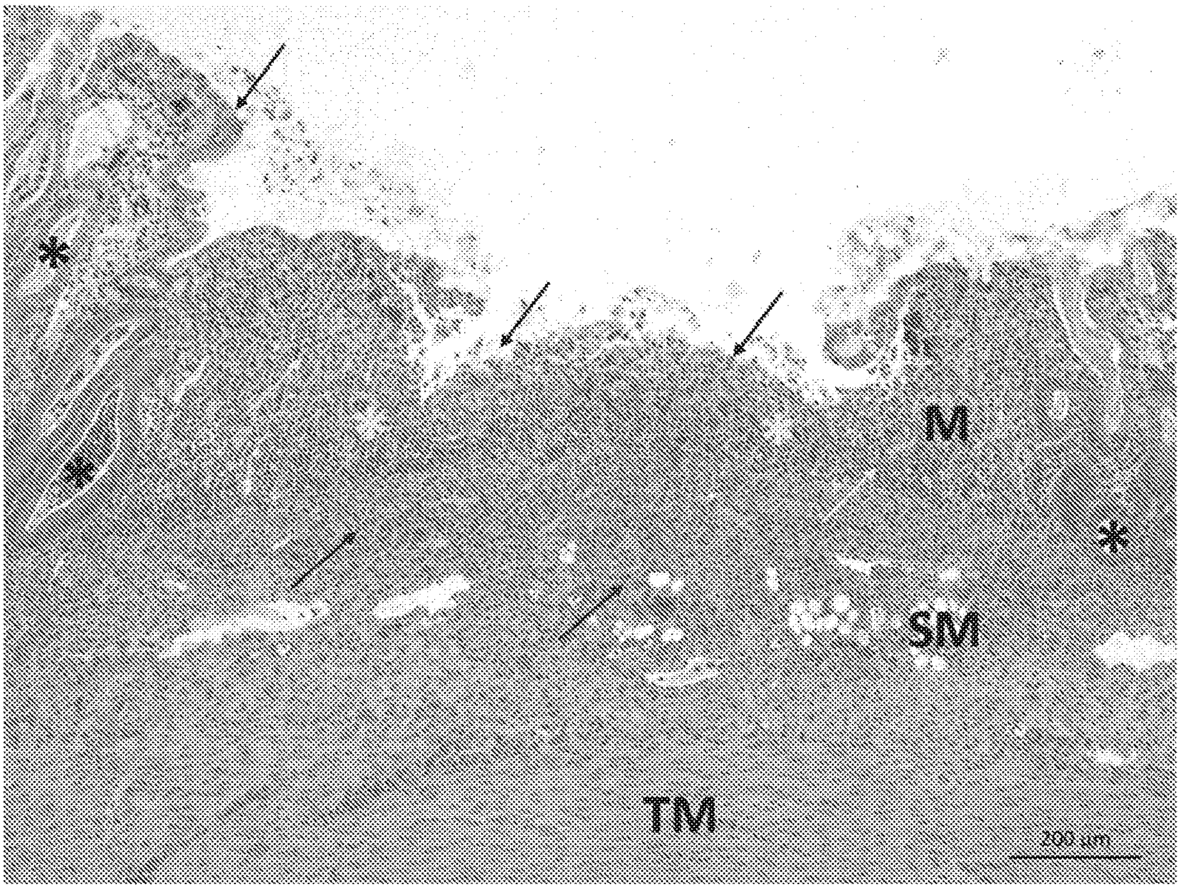

FIG. 96 is a representative hematoxylin- and eosin-stained image of the transverse colon of animal 2504 (8.5% DSS-induced colitis swine administered 1.86 mg/kg adalimumab) prior to administration of adalimumab. M, mucosa; SM, submucosa; TM, tunica muscularis. Extensive loss (light asterisks) of intestinal crypts is present in the mucosa. Scattered crypts remain (dark asterisks) and are often dilated and filled with inflammatory cell debris and mucus. The luminal epithelium persists in some areas (upper left arrow), but is absent in others (erosion; top middle and top right arrows). Inflammatory cells in the mucosa (light arrow) are abundant and extend into the submucosa (bottom left and bottom middle arrows).

Figure 97:
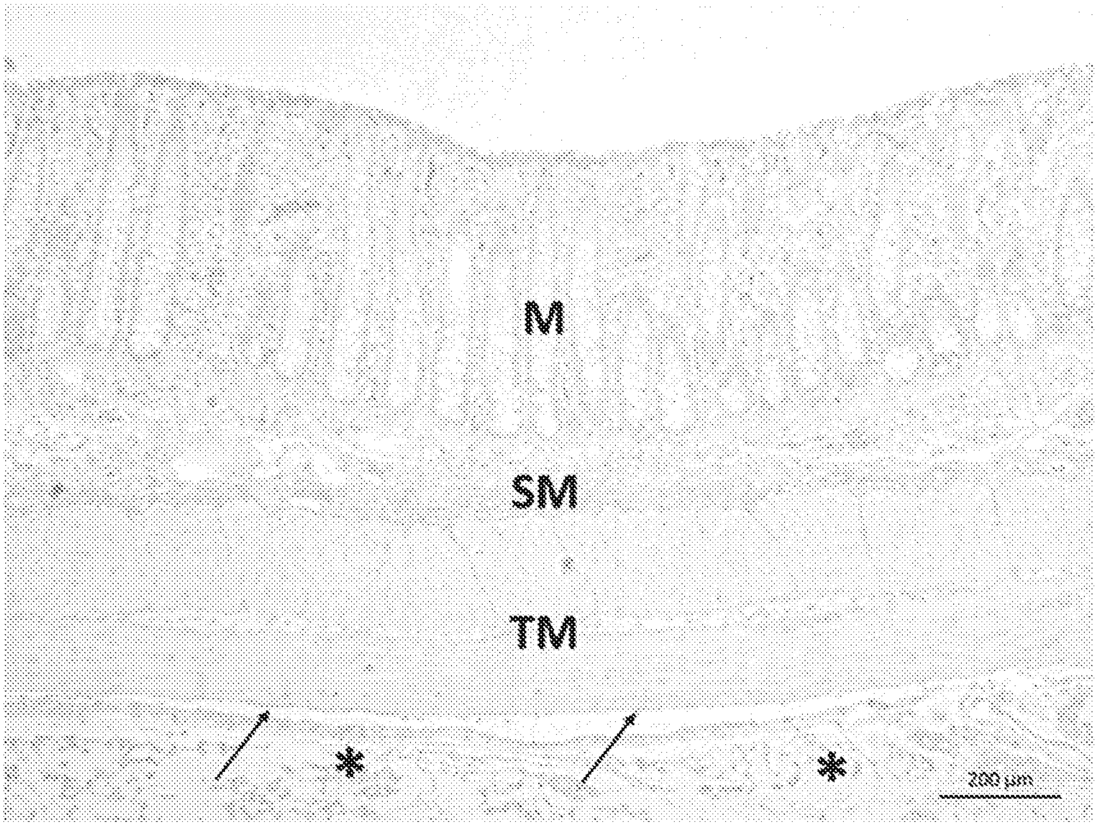

FIG. 97 is a representative immunohistochemistry micrograph of the transverse colon of animal 1501 (healthy control swine) stained for human IgG. M, mucosa; SM, submucosa; TM, tunica muscularis. Serosal surface (arrows) and loose connective mesentery tissue (asterisks) are indicated. Faint 3,3-diaminobenzidine (DAB) staining in this tissue was considered a background effect and not indicative of human IgG.

Figure 98:
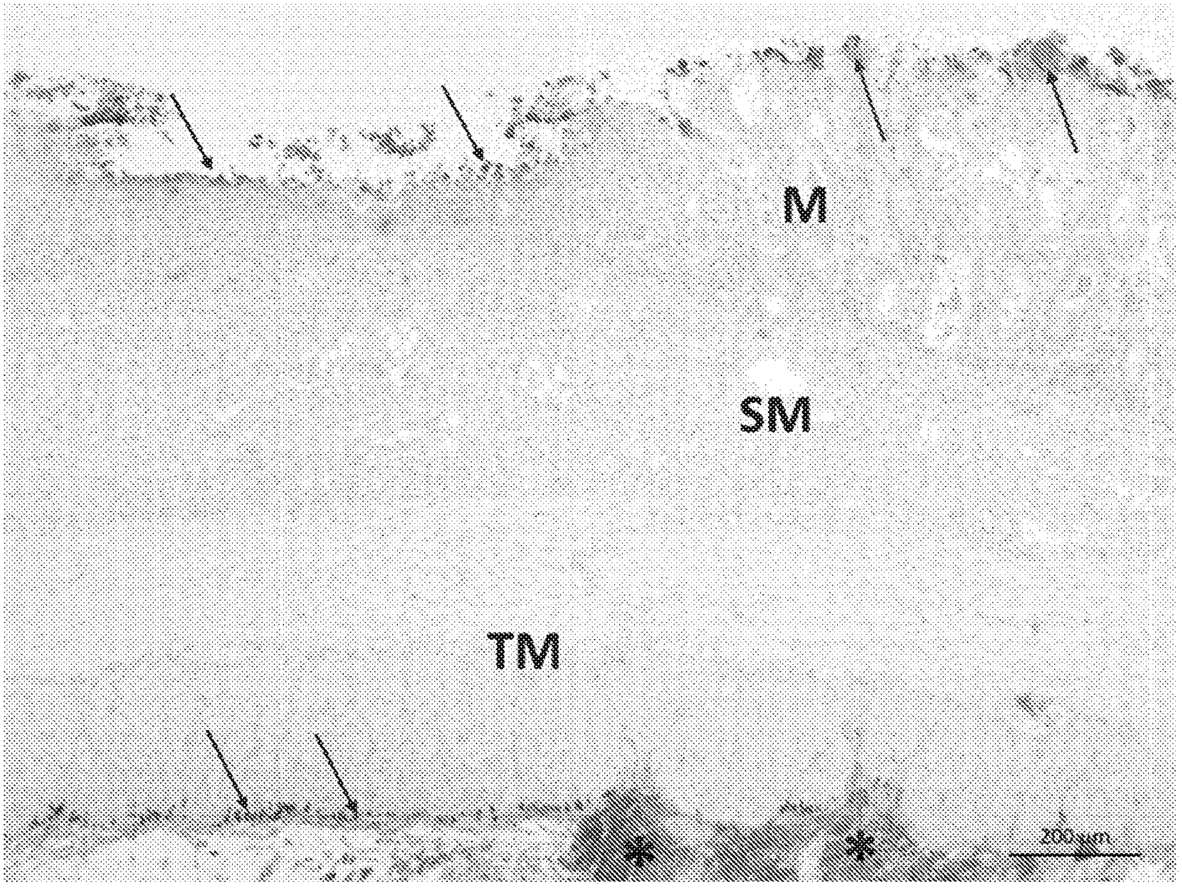

FIG. 98 is a representative immunohistochemistry micrograph of the transverse colon of animal 2504 (8.5% DSS-induced colitis swine treated with 1.86 mg/kg dose of adsalimumab) stained for human IgG. M, mucosa; SM, submucosa; TM, tunica muscularis. DAB staining demonstrates the presence of human IgG at the surface of luminal epithelium (two top right arrows) and at the luminal surface of an area of inflammation and erosion (top two left arrows). Intense staining is also present in the loose connective mesentery tissue (asterisks) and extends a short distance into the outer edge of the tunica muscularis (bottom left two arrows). This type of staining was considered strong (grade 4) or very strong (grade 5).

Figure 99:
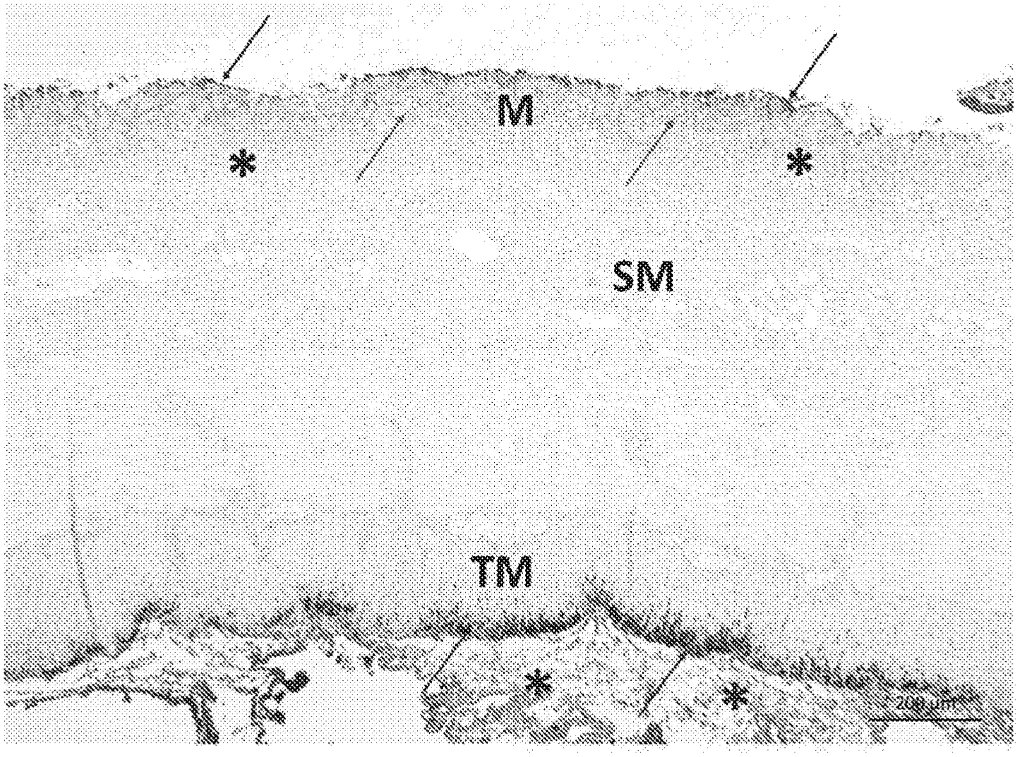

FIG. 99 is a representative immunohistochemistry micrograph of the large intestine of animal 2504 (8.5% DSS-induced colitis swine treated with 1.86 mg/kg adalimumab) stained for human IgG. M, mucosa; SM, submucosa; TM, tunica muscularis. Lesions of DSS-induced colitis are present in this section. The luminal epithelium is absent (erosion) and diffuse loss of crypts (glands) is seen (top two asterisks). Very strong (grade 5) DAB (brown) staining demonstrates the presence of human IgG in the loose mesentery connective tissue (bottom two arterisks) and extending a short distance into the outer edge of the tunica muscularis (bottom two arrows). Strong (grade 4) staining for human IgG is seen at the eroded luminal surface (top two arrows pointing down) and within the inflammatory exudate. Weak (grade 2) staining for human IgG extends into the lamina propria (top two arrows pointing up) near the luminal surface.

Figure 100:
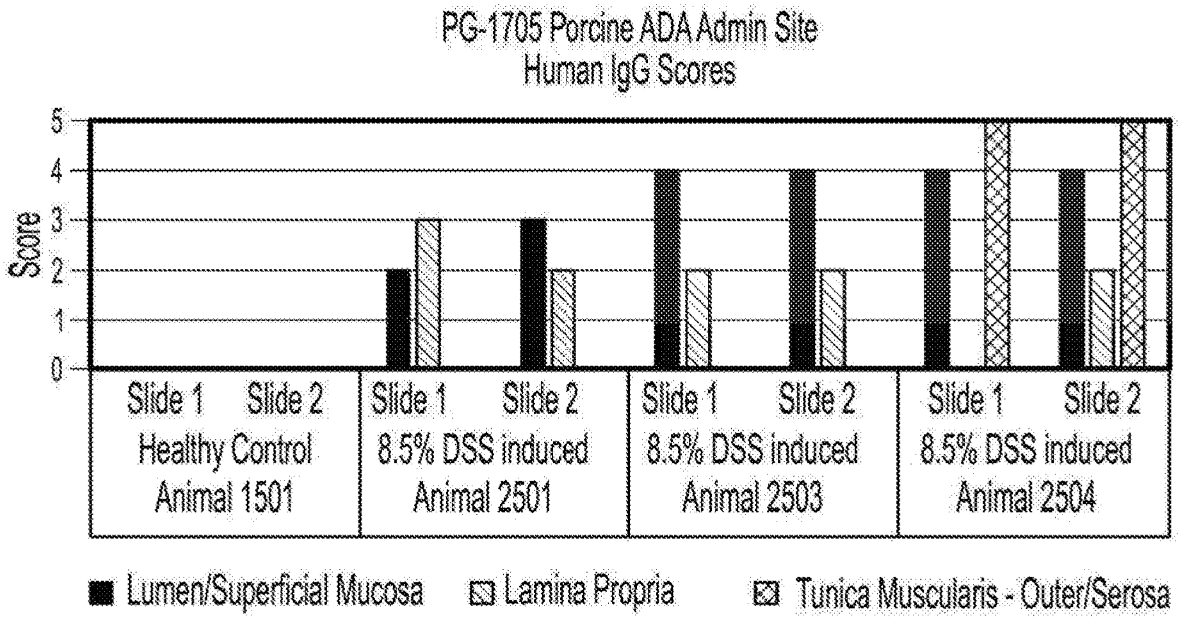

FIG. 100 is a graph showing the presence of human IgG (adalimumab) at the specified locations (lumen/superficial mucosa, lamina propria, and tunica muscularis-outer/serosa) (scored level) in two slides from each of animal 1502 (placebo-treated healthy control swine), animal 2501 (swine with 8.5% DSS-induced colitis treated with 1.86 mg/kg adalimumab), animal 2503 (swine with 8.5% DSS-induced colitis treated with 1.86 mg/kg adalimumab) and animal 2504 (swine with 8.5% DSS-induced colitis treated with 1.86 mg/kg adalimumab) at the placebo or adalimumab administration site. Absence of a bar for a particular location indicates that the value for this location was 0. Scoring: 0=not present; 1=minimal; 2=weak; 3=moderate; 4=strong; and 5=very strong immunolabel.

Figure 101:
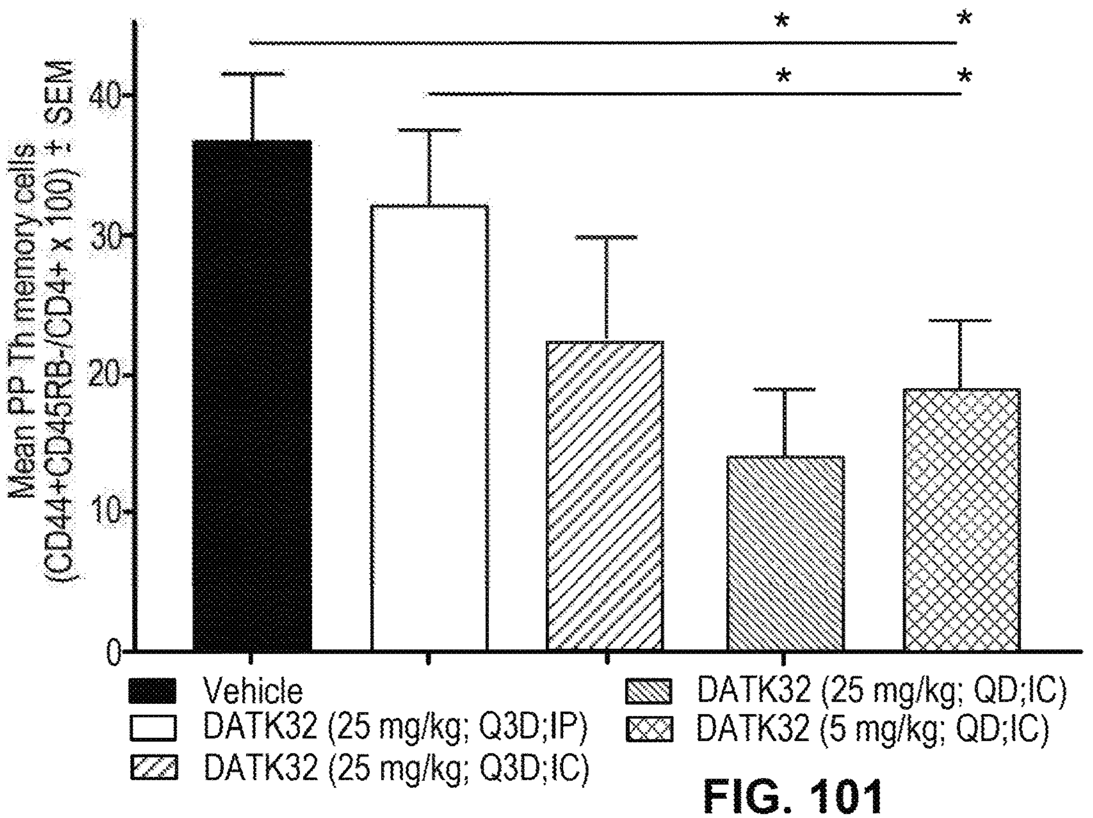

FIG. 101 is a graph showing the mean of Th memory cells (mean±SEM) in Peyer's Patches (PP) for DATK32 antibody (anti-$\alpha 4\beta 7$ integrin antibody) intraperitoneally (25 mg/kg) or intracecally (25 mg/kg or 5 mg/kg) administered treatment groups given daily (QD) or every third day (Q3D), when compared to vehicle control (Vehicle) and when IP is compared to IC. Mean Th memory cells were measured using FACS analysis. Mann-Whitney's U-test and Student's t-test were used for statistical analysis on non-Gaussian and Gaussian data respectively. A value of $p<0.05$ was considered significant (Graph Pad Software, Inc.).

Figure 102:
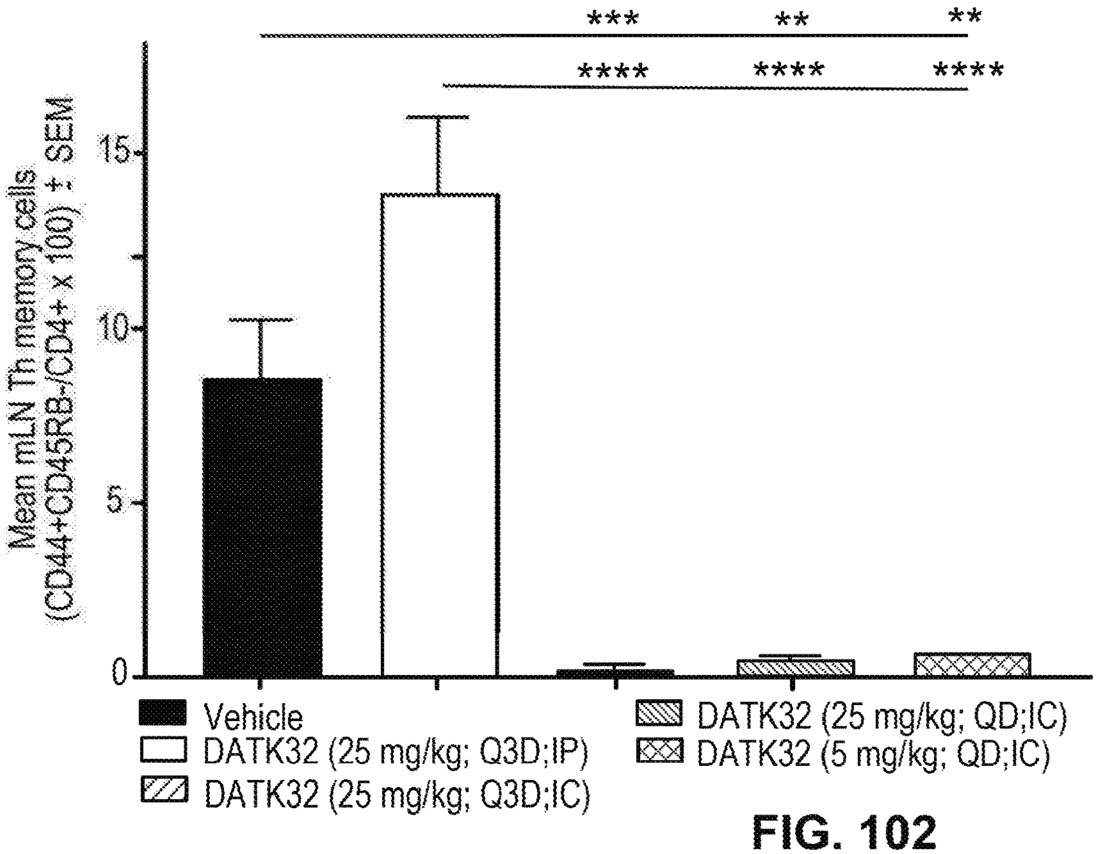

FIG. 102 is a graph showing the mean of Th memory cells (mean±SEM) in mesenteric lymph nodes (mLN) for DATK32 antibody (anti-$\alpha 4\beta 7$ integrin antibody) intraperitoneally (25 mg/kg) or intracecally (25 mg/kg or 5 mg/kg) administered treatment groups given daily (QD) or every third day (Q3D), when compared to vehicle control (Vehicle) and when IP is compared to IC. Mean Th memory cells were measured using FACS analysis. Mann-Whitney's U-test and Student's t-test were used for statistical analysis on non-Gaussian and Gaussian data respectively. A value of $p<0.05$ was considered significant (Graph Pad Software, Inc.).

Figure 103:
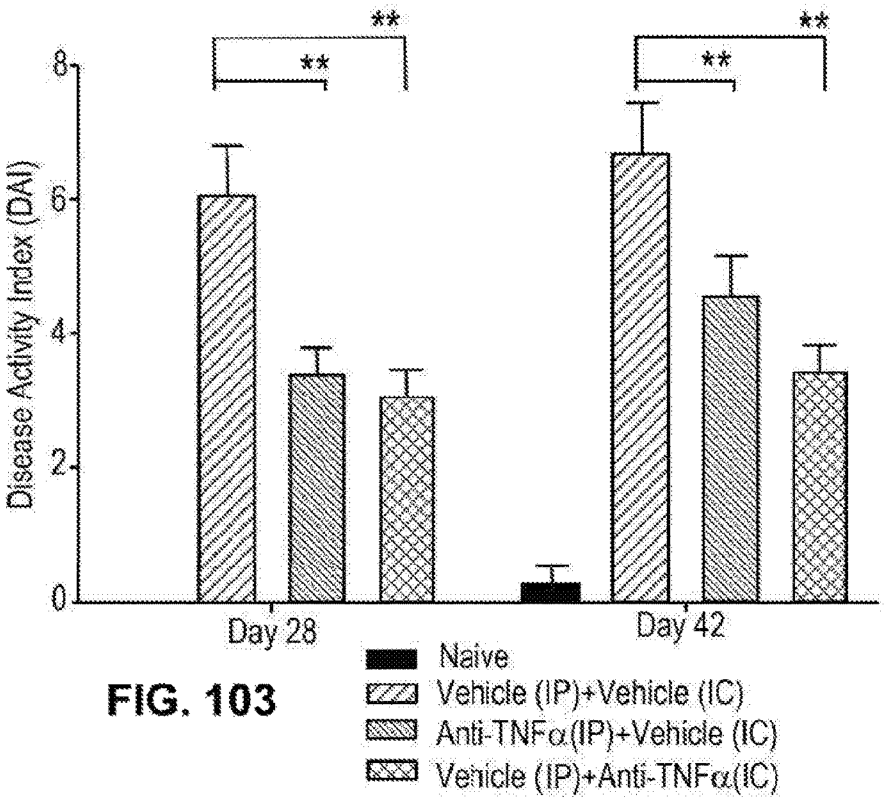

FIG. 103 is a graph showing the Disease Activity Index (DAI) of naïve mice (Group 1), mice administered vehicle only both intraperitoneally (IP) and intra-cecally (IC) (Group 2), mice administered an anti-TNFα antibody IP and vehicle IC (Group 7), and mice administered an anti-TNFα antibody IC and vehicle IP (Group 8) at Day 28 and Day 42 of the study described in Example 16.

Figure 104:
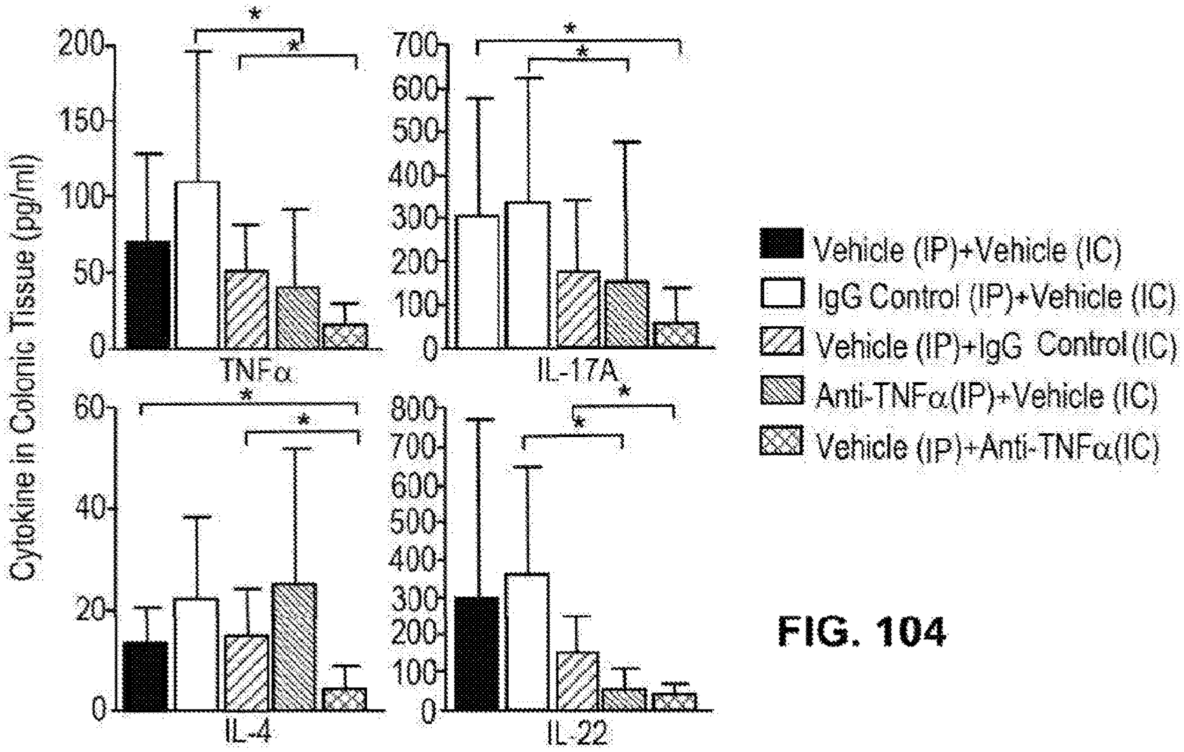

FIG. 104 is a set of graphs showing the colonic tissue concentration of TNFα, IL-17A, IL-4, and IL-22 in mice administered vehicle only both IP and IC (Group 2), mice administered IgG control antibody IP and vehicle IC (Group 3), mice administered IgG control IC and vehicle IP (Group 4), mice administered anti-TNFα antibody IP and vehicle IC (Group 7), and mice administered anti-TNFα antibody IC and vehicle IP (Group 8) at Day 42 of the study described in Example 16.

Figure 105:
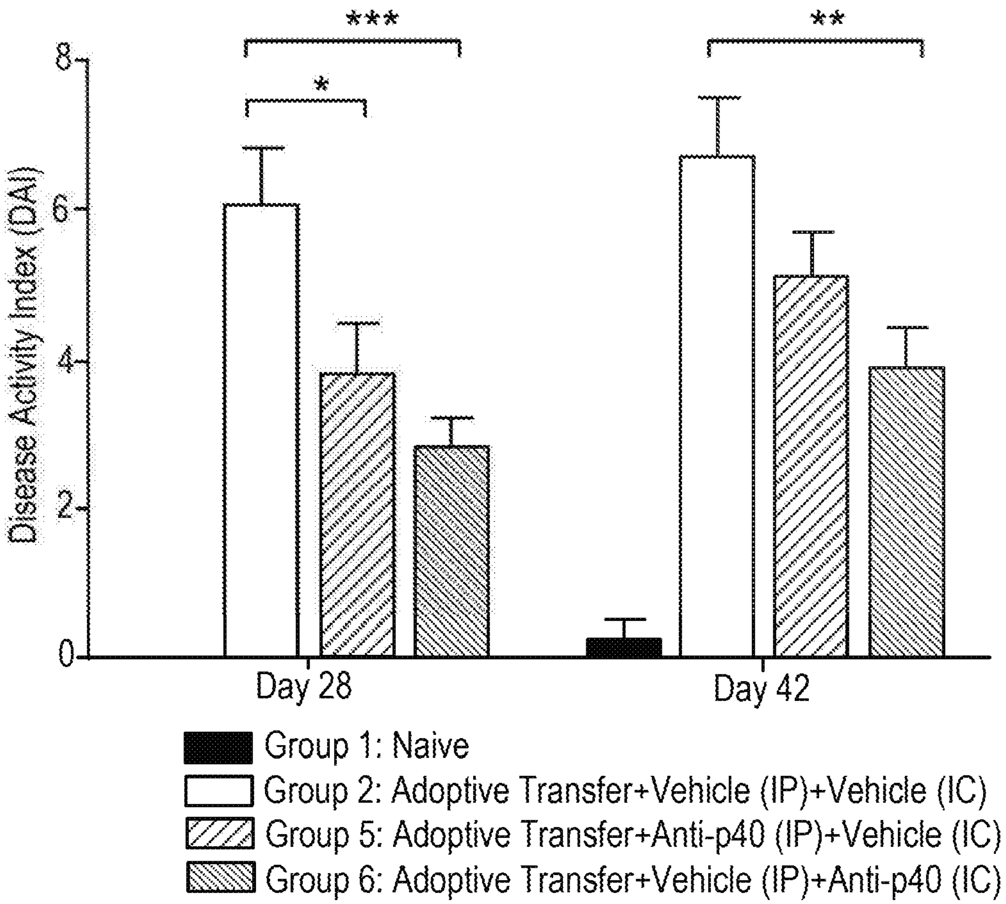

FIG. 105 is a graph showing the Disease Activity Index (DAI) of naïve mice (Group 1), mice administered vehicle only both IP and IC (Group 2), mice administered an anti-IL12 p40 antibody IP and vehicle IC (Group 5), and mice an anti-IL12 p40 antibody IC and vehicle IP (Group 6) at Day 28 and Day 42 of the study described in Example 16.

Figure 106:
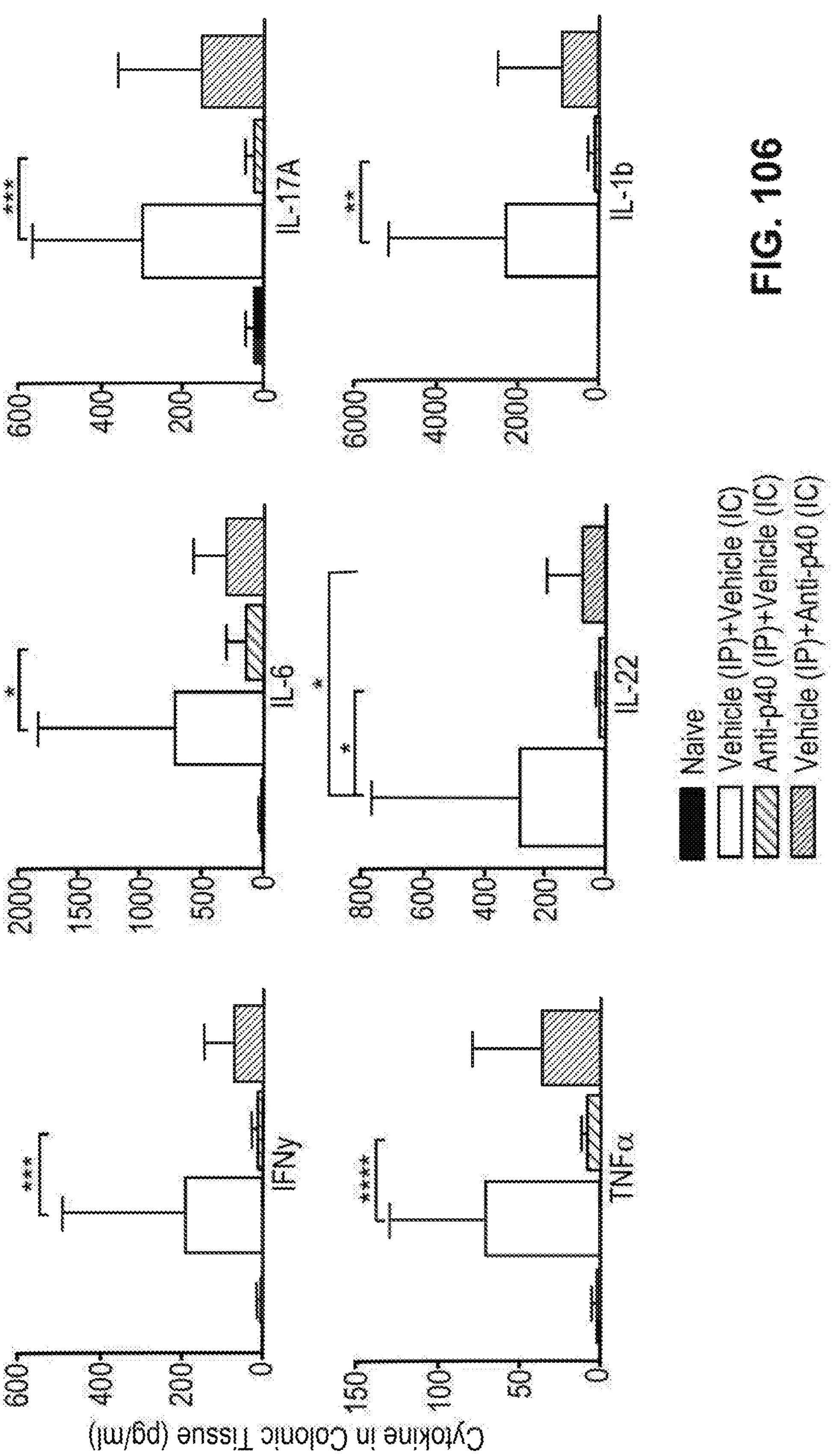

FIG. 106 is a set of graphs showing the colonic tissue concentration of IFN-gamma, IL-6, IL-17A, TNFα, IL-22, and IL-1b in naïve mice (Group 1), mice administered vehicle only both IP and IC (Group 2), mice administered anti-IL 12 p40 antibody IP and vehicle IC (Group 5), and mice administered anti-IL12 p40 antibody IC and vehicle IP (Group 8) at Day 42 of the study described in Example 16.

Figure 107A:
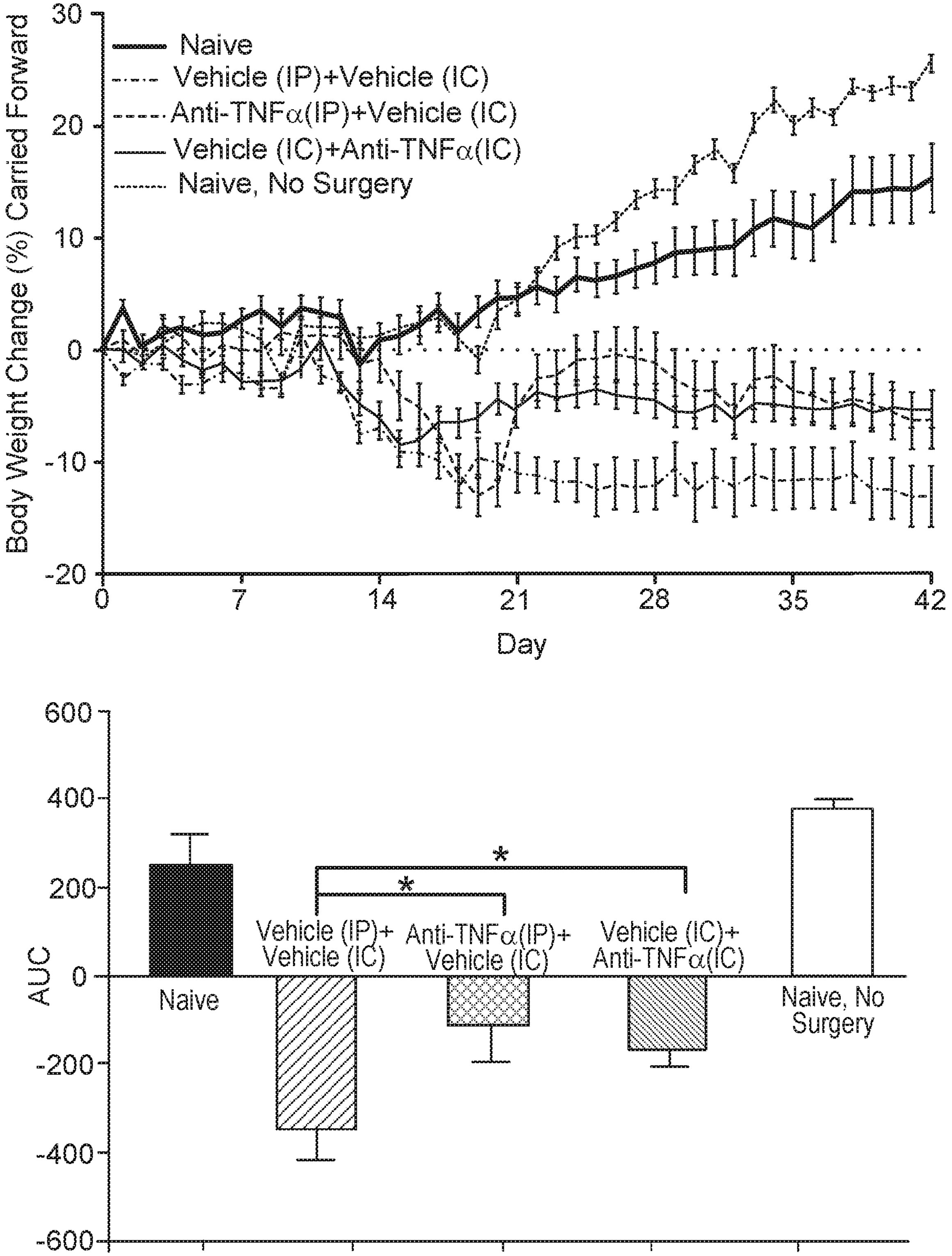
Figure 107B:
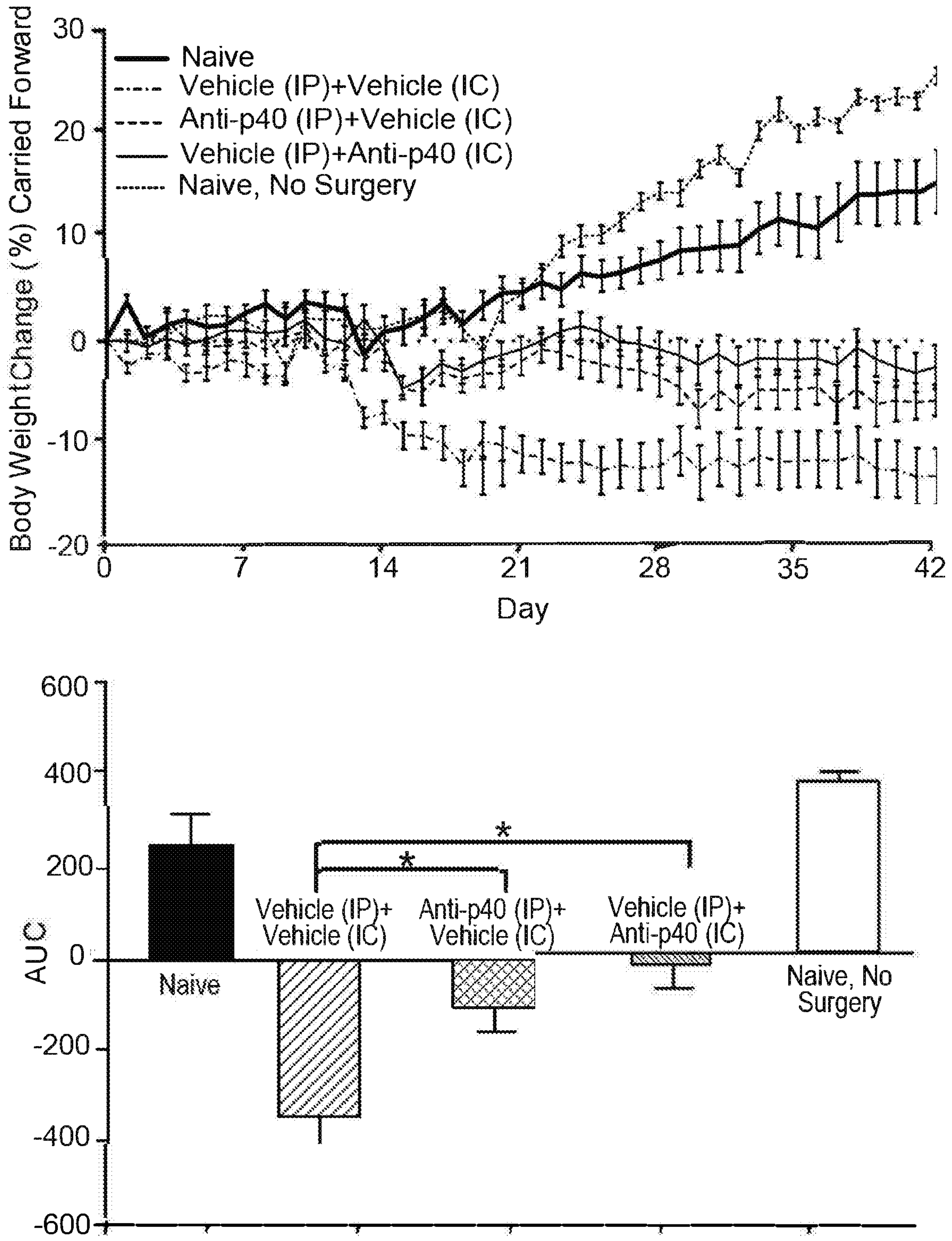

FIGS. 107A-107B show body weight changes (mean % SEM). FIG. 107A shows the influence of anti-TNF alpha; FIG. 107B shows the influence of anti-IL12p40. The AUC was calculated using the trapezoidal rule and is shown in the figure inset. Differences in body weight loss were calculated as AUC for individual mouse from Days 0 to 42. Two-tailed Mann-Whitney U-Test; $p<0.05$*; $p<0.01$; $p<0.005$*, n=5-9.

Figure 108:
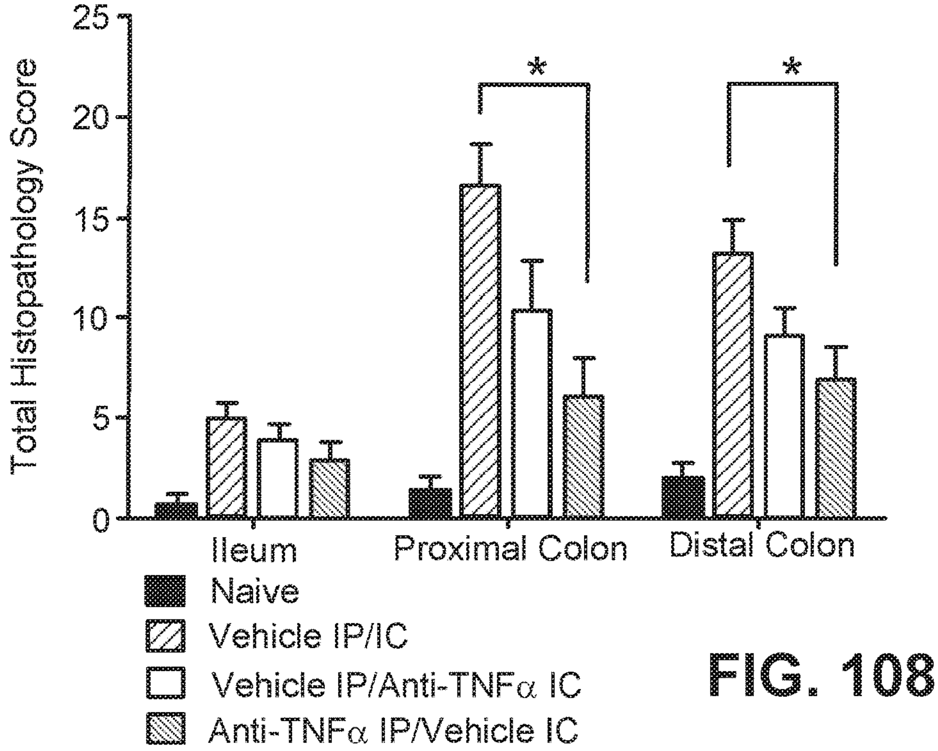

FIG. 108 shows total histopathology score (mean %±SEM) in ileum, proximal colon and distal colon tissues after targeted IC anti-TNF alpha treatment compared with vehicle and IP treatment groups. Pair-wise comparisons by two-tailed Mann-Whitney U-Test for treatment effects; $p<0.05$*.

Figure 109A:
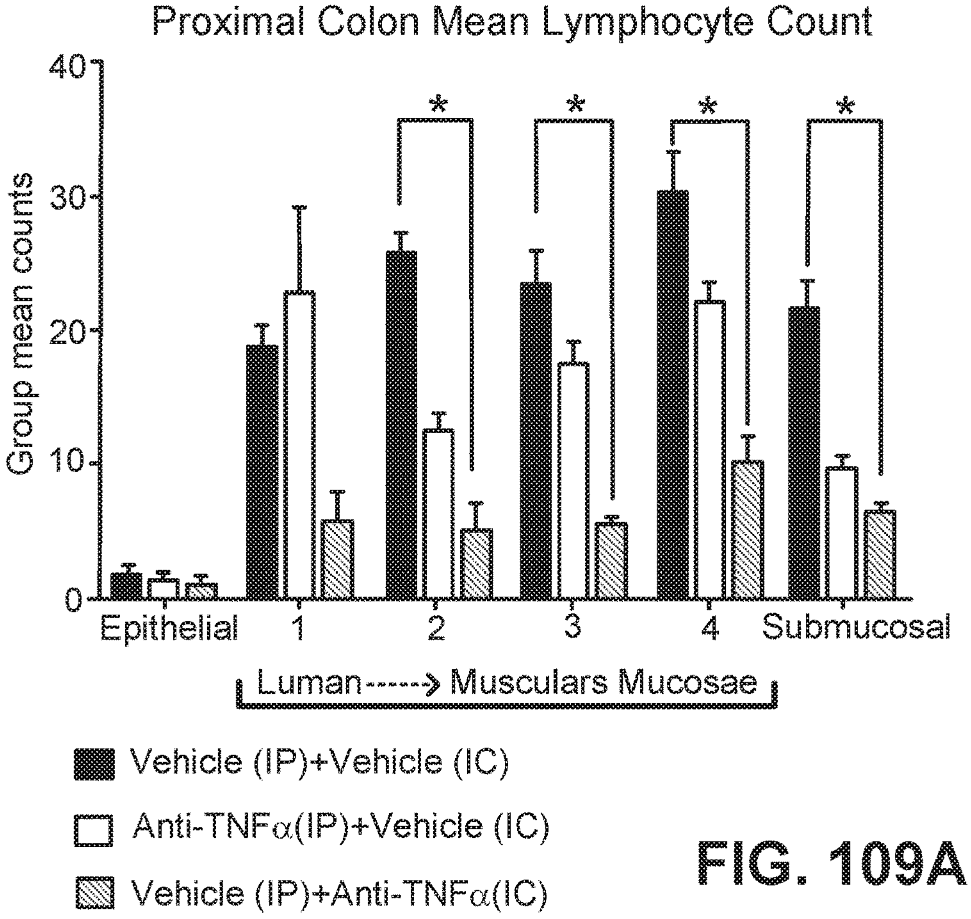
Figure 109B:
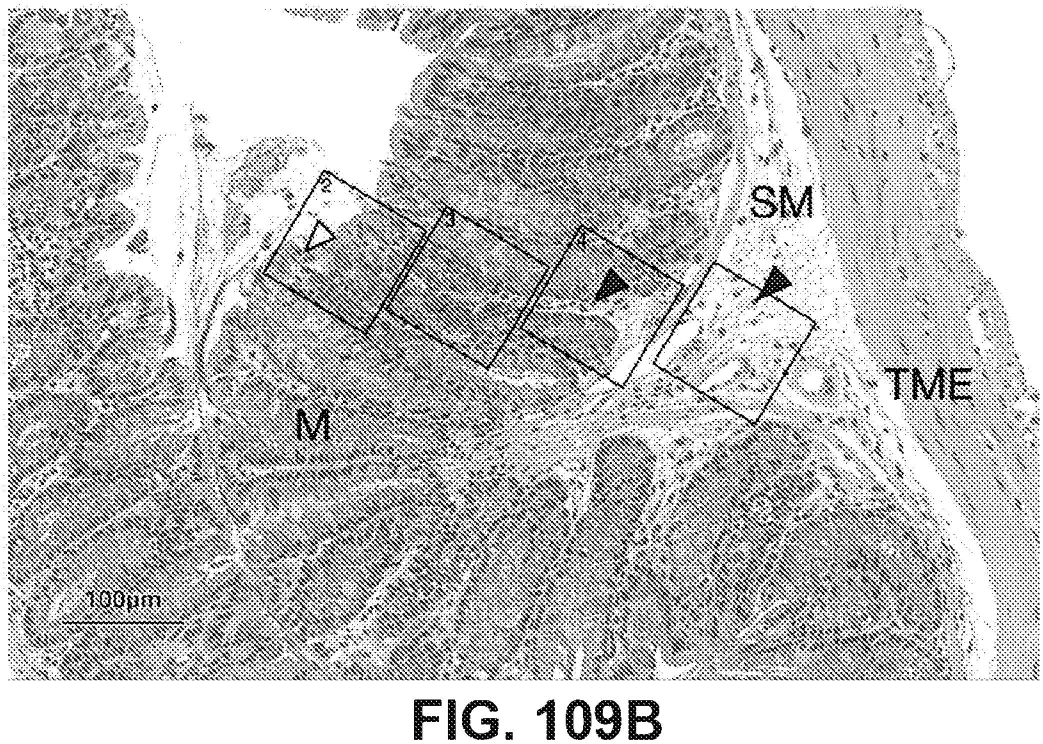
Figure 109C:
Figure 109D:
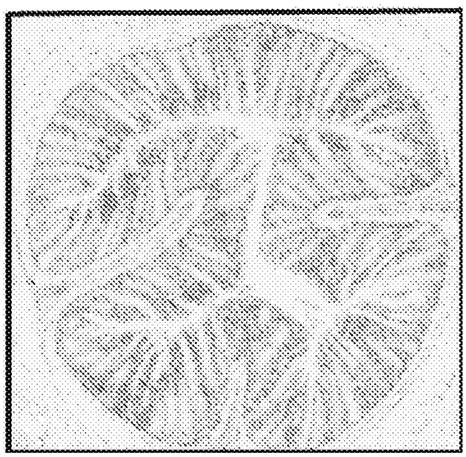

FIGS. 109A-109D show mean lymphocyte counts from luminal to external submucosa of proximal colon and represented images of H&E stains and IHC stains of the proximal colon. FIG. 109A shows the mean lymphocyte count from most inner lumen to submucosal of the proximal colon in groups treated with Vehicle controls, anti-TNFα (IP) and anti-TNFα (IC), Group mean±/−SEM. Kruskal-Wallis Test with Dunn's multiple comparison for treatment effects; $p<0.05$*. FIG. 109B is a representative image of H&E stain of proximal colon in proximal colon of anti-TNFα (IC) group. An intraepithelial lymphocyte (white arrowhead), example lamina proprial lymphocytes (black arrowheads), and the tunica muscularis externa (TME) are indicate. FIGS. 109C and 109D are representative images of IHC stain of CD4 marker for lymphocytes in proximal colon of anti-TNFα (IC) (FIG. 109C) or anti-TNFα (IP) (FIG. 109D) group.

Figure 110B:
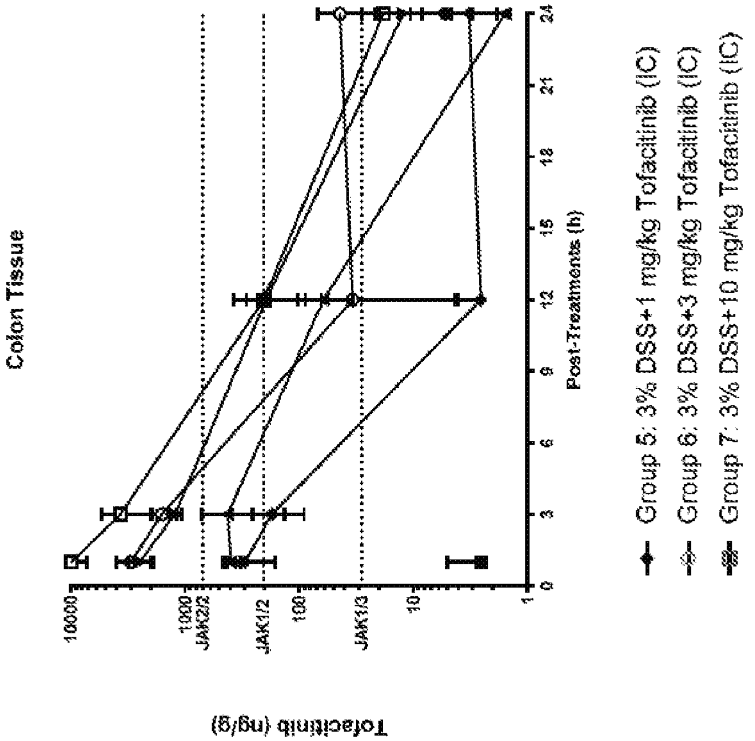
Figure 110A:
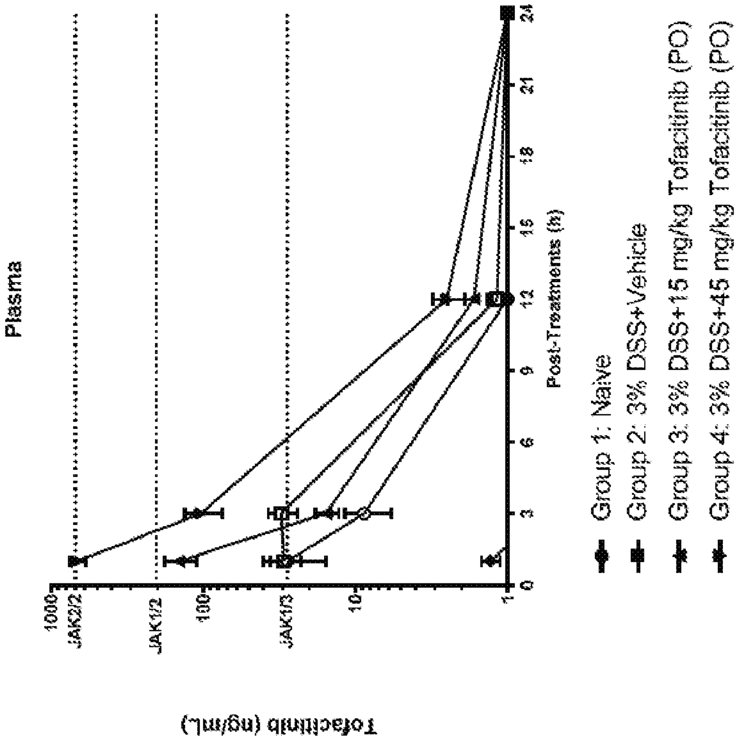

FIGS. 110A-110B show mean plasma (FIG. 110A) and colon tissue (FIG. 110B) concentrations of tofacitinib (free base) over a 24-hour period post-treatment with tofacitinib citrate or vehicle in a DSS-induced colitis mouse model. Dashed lines indicate in vitro $IC_{50}$ values for JAK1/3, JAK1/2 and JAK2/2 in whole blood. Error bars represent standard deviation.

FIGS. 111A-111C show plasma (FIG. 111A), colon content (FIG. 111B) and colon tissue (FIG. 111C) tofacitinib exposure ($AUC_{0\text{-}24\ h}$) after treatment with vehicle or tofacitinib citrate via per oral (PO) or intracecal (IC) administration in a DSS-induced colitis mouse model.

Figure 112A:
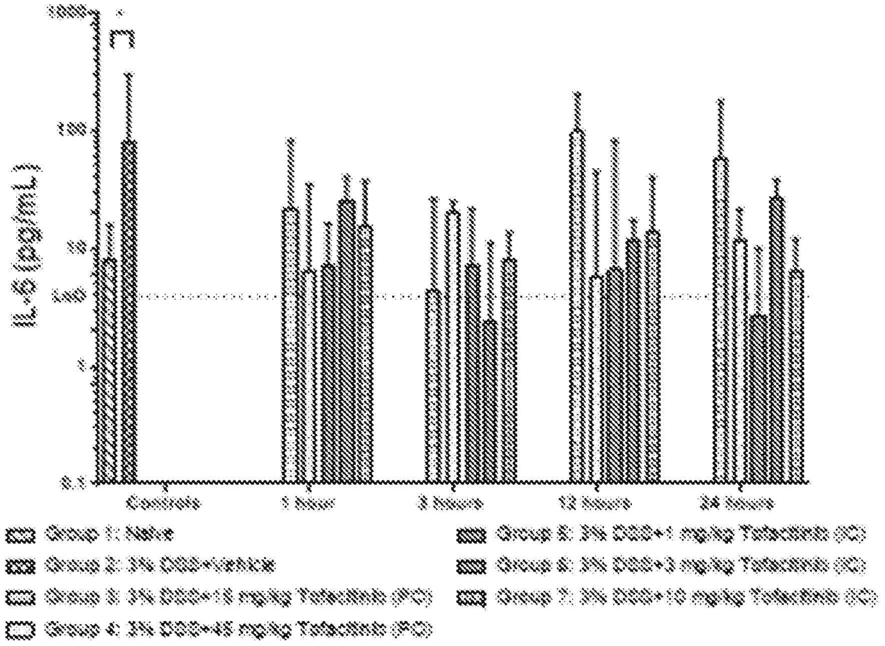
Figure 112B:
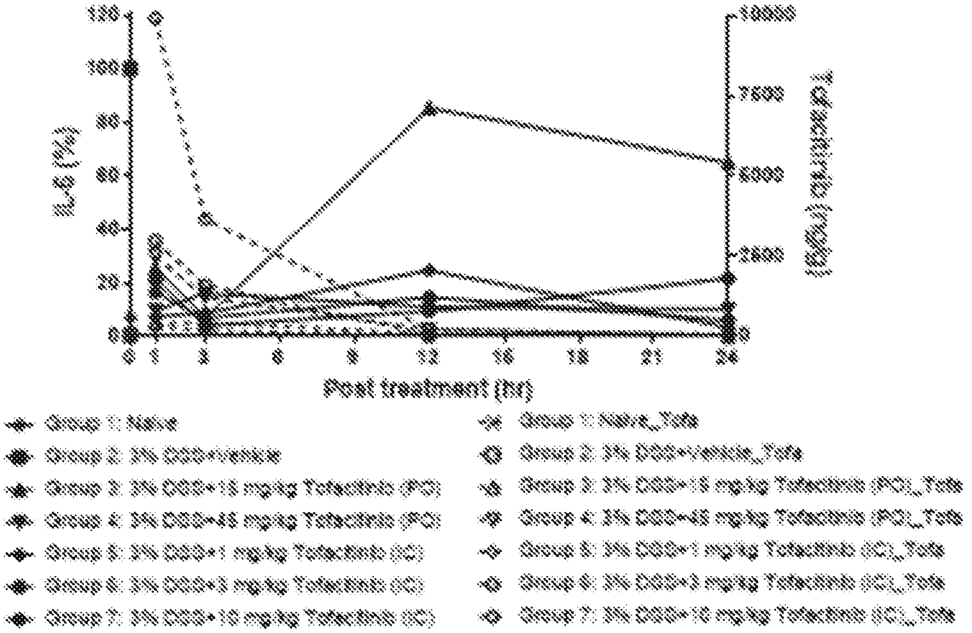

FIGS. 112A-112B show IL-6 concentrations in colon tissue over a 24-hour period post-treatment with vehicle or tofacitinib citrate via per oral (PO) or intracecal (IC) administration in a DSS-induced colitis mouse model on Study Day 12. FIG. 112A shows IL-6 concentrations in colon tissue at various timepoints on Study Day 12. FIG. 112B shows the relationship between tofacitinib concentration in colon tissue (open shapes and dotted lines; right y-axis) and % IL-6 in colon tissue after treatment with tofacitinib citrate, normalized to DSS vehicle control (Group 2) (solid shapes and solid lines; left y-axis).

DETAILED DESCRIPTION

The present disclosure is directed to various methods and formulations for treating diseases of the gastrointestinal tract with a JAK inhibitor. For example, in an embodiment, a method of treating a disease of the gastrointestinal tract in a subject comprises administering to the subject a pharmaceutical formulation comprising a JAK inhibitor wherein the pharmaceutical formulation is released in the subject's gastrointestinal tract proximate to one or more sites of disease. For example, in an embodiment, the pharmaceutical formulation comprises a therapeutically effective amount of a JAK inhibitor.

In some embodiments, the formulation is contained in an ingestible device, and the device releases the formulation at a location proximate to the site of disease. The location of the site of disease may be predetermined. For example, an ingestible device, the location of which within the GI tract can be accurately determined as disclosed herein, may be used to sample one or more locations in the GI tract and to detect one or more analytes, including markers of the disease, in the GI tract of the subject. A pharmaceutical formulation may be then administered via an ingestible device and released at a location proximate to the predetermined site of disease. The release of the formulation may be triggered autonomously, as further described herein.

The following disclosure illustrates aspects of the formulations and methods embodied in the claims.

Formulations and Pharmaceutical Formulations

As used herein, a "formulation" of a JAK inhibitor may refer to either the JAK inhibitor in pure form, such as, for example, a lyophilized JAK inhibitor, or a mixture of the JAK inhibitor with one or more physiologically acceptable carriers, excipients or stabilizers. Thus, therapeutic formulations or medicaments can be prepared by mixing the JAK inhibitor having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) antibody; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases. Exemplary lyophilized formulations are described in U.S. Pat. No. 6,267,958. Aqueous formulations include those described in U.S. Pat. No. 6,171,586 and WO 2006/044908, the latter formulations including a histidine-acetate buffer.

A formulation of a JAK inhibitor as disclosed herein, e.g., sustained-release formulations, can further include a mucoadhesive agent, e.g., one or more of polyvinyl pyrolidine, methyl cellulose, sodium carboxyl methyl cellulose, hydroxyl propyl cellulose, carbopol, a polyacrylate, chitosan, a eudragit analogue, a polymer, and a thiomer. Additional examples of mucoadhesive agents that can be included in a formulation with a JAK inhibitor are described in, e.g., Peppas et al., *Biomaterials* 17(16):1553-1561, 1996; Kharenko et al., *Pharmaceutical Chemistry J.* 43(4):200-208, 2009; Salamat-Miller et al., *Adv. Drug Deliv. Reviews* 57(11):1666-1691, 2005; Bernkop-Schnurch, *Adv. Drug Deliv. Rev.* 57(11):1569-1582, 2005; and Harding et al., *Biotechnol. Genet. Eng. News* 16(1):41-86, 1999.

In some embodiments, components of a formulation may include any one of the following components, or any combination thereof: Acacia, Alginate, Alginic Acid, Aluminum Acetate, an antiseptic, Benzyl Alcohol, Butyl Paraben, Butylated Hydroxy Toluene, an antioxidant. Citric acid, Calcium carbonate, Candelilla wax, a binder, Croscarmellose sodium, Confectioner sugar, Colloidal silicone dioxide, Cellulose, Carnuba wax, Corn starch, Carboxymethylcellulose calcium, Calcium stearate, Calcium disodium EDTA, Chelation agents, Copolyvidone, Castor oil hydrogenated, Calcium hydrogen phosphate dehydrate, Cetylpyridine chloride, Cysteine HCl, Crosspovidone, Dibasic Calcium Phosphate, Disodium hydrogen phosphate, Dimethicone, Erythrosine Sodium, Ethyl Cellulose, Gelatin, Glyceryl monooleate, Glycerin, Glycine, Glyceryl monostearate, Glyceryl behenate, Hydroxy propyl cellulose, Hydroxyl propyl methyl cellulose, Hypromellose, HPMC Pthalate, Iron oxides or ferric oxide, Iron oxide yellow, Iron oxide red or ferric oxide, Lactose (hydrous or anhydrous or monohydrate or spray dried), Magnesium stearate, Microcrystalline cellulose, Mannitol, Methyl cellulose, Magnesium carbonate, Mineral oil, Methacrylic acid copolymer, Magnesium oxide, Methyl paraben, PEG, Polysorbate 80, Propylene glycol, Polyethylene oxide, Propylene paraben, Polaxamer 407 or 188 or plain, Potassium bicarbonate, Potassium sorbate, Potato starch, Phosphoric acid, Polyoxy140 stearate, Sodium starch glycolate, Starch pregelatinized, Sodium crossmellose, Sodium lauryl sulfate, Starch, Silicon dioxide, Sodium benzoate, Stearic acid, Sucrose base for medicated confectionery, a granulating agent, Sorbic acid, Sodium carbonate, Saccharin sodium, Sodium alginate, Silica gel, Sorbiton monooleate, Sodium stearyl fumarate, Sodium chloride, Sodium metabisulfite, Sodium citrate dehydrate, Sodium starch, Sodium carboxy methyl cellulose, Succinic acid, Sodium propionate, Titanium dioxide, Talc, Triacetin, Triethyl citrate.

Accordingly, in some embodiments of the method of treating a disease as disclosed herein, the method comprises administering to the subject a pharmaceutical composition that is a formulation as disclosed herein. In some embodiments the formulation is a dosage form, which may be, as an example, a solid form such as, for example, a capsule, a tablet, a sachet, or a lozenge; or which may be, as an example, a liquid form such as, for example, a solution, a suspension, an emulsion, or a syrup.

In some embodiments, the formulation is not comprised in an ingestible device. In some embodiments wherein the formulation is not comprised in an ingestible device, the formulation may be suitable for oral administration. The formulation may be, for example, a solid dosage form or a liquid dosage form as disclosed herein. In some embodiments wherein the formulation is not comprised in an ingestible device, the formulation may be suitable for rectal administration. The formulation may be, for example, a dosage form such as a suppository or an enema. In embodiments where the formulation is not comprised in an ingestible device, the formulation releases the JAK inhibitor at a location in the gastrointestinal tract of the subject that is proximate to one or more sites of disease. Such localized release may be achieved, for example, with a formulation comprising an enteric coating. Such localized release may be achieved, an another example, with a formulation comprising a core comprising one or more polymers suitable for controlled release of an active substance. A non-limiting list of such polymers includes: poly(2-(diethylamino)ethyl methacrylate, 2-(dimethylamino)ethyl methacrylate, poly(ethylene glycol), poly(2-aminoethyl methacrylate), (2-hydroxypropyl)methacrylamide, poly(β-benzyl-l-aspartate), poly(N-isopropylacrylamide), and cellulose derivatives.

In some embodiments, the formulation is comprised in an ingestible device as disclosed herein. In some embodiments wherein the formulation is comprised in an ingestible device, the formulation may be suitable for oral administration. The formulation may be, for example, a solid dosage form or a liquid dosage form as disclosed herein. In some embodiments the formulation is suitable for introduction and optionally for storage in the device. In some embodiments the formulation is suitable for introduction and optionally for storage in a reservoir comprised in the device. In some embodiments the formulation is suitable for introduction and optionally for storage in a reservoir comprised in the device. Thus, in some embodiments, provided herein is a reservoir comprising a therapeutically effective amount of a JAK inhibitor, wherein the reservoir is configured to fit into an ingestible device. In some embodiments, the reservoir comprising a therapeutically effective amount of a JAK inhibitor is attachable to an ingestible device. In some embodiments, the reservoir comprising a therapeutically effective amount of a JAK inhibitor is capable of anchoring itself to the subject's tissue. As an example, the reservoir capable of anchoring itself to the subject's tissue comprises silicone. As an example, the reservoir capable of anchoring itself to the subject's tissue comprises polyvinyl chloride.

In some embodiments the formulation is suitable for introduction in a spray catheter, as disclosed herein.

The formulation herein may also contain more than one active compound as necessary for the particular indication being treated, for example, those with complementary activities that do not adversely affect each other. For instance, the formulation may further comprise another JAK inhibitor or a chemotherapeutic agent. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the JAK inhibitor, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated JAK inhibitors remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Pharmaceutical formulations may contain one or more JAK inhibitors. The pharmaceutical formulations may be formulated in any manner known in the art. In some embodiments the formulations include one or more of the following components: a sterile diluent (e.g., sterile water or saline), a fixed oil, polyethylene glycol, glycerin, propylene glycol, or other synthetic solvents, antibacterial or antifungal agents, such as benzyl alcohol or methyl parabens, chlorobutanol, phenol, ascorbic acid, thimerosal, and the like, antioxidants, such as ascorbic acid or sodium bisulfite, chelating agents, such as ethylenediaminetetraacetic acid, buffers, such as acetates, citrates, or phosphates, and isotonic agents, such as sugars (e.g., dextrose), polyalcohols (e.g., mannitol or sorbitol), or salts (e.g., sodium chloride), or any combination thereof. Liposomal suspensions can also be used as pharmaceutically acceptable carriers (see, e.g., U.S. Pat. No. 4,522,811, incorporated by reference herein in its entirety). The formulations can be formulated and enclosed in ampules, disposable syringes, or multiple dose vials. Where required, proper fluidity can be maintained by, for example, the use of a coating, such as lecithin, or a surfactant. Controlled release of the JAK inhibitor can be achieved by implants and microencapsulated delivery systems, which can include biodegradable, biocompatible polymers (e.g., ethylene vinyl acetate, polyanhydrides, polyglycolic acid, collagen, polyorthoesters, and polylactic acid; Alza Corporation and Nova Pharmaceutical, Inc.).

In some embodiments, the JAK inhibitor is present in a pharmaceutical formulation within the device.

In some embodiments, the JAK inhibitor is present in solution within the device.

In some embodiments, the JAK inhibitor is present in a suspension in a liquid medium within the device.

In some embodiments, the JAK inhibitor is present as a pure, powder (e.g., lyophilized) form of the JAK inhibitor.

Liquid pharmaceutically administrable formulations can, for example, be prepared by dissolving, dispersing, etc. a therapeutic agent provided herein and optional pharmaceutical adjuvants in a carrier (e.g., water, saline, aqueous dextrose, glycerol, glycols, ethanol or the like) to form a solution, colloid, liposome, emulsion, complexes, coacervate or suspension. If desired, the pharmaceutical formulation can also contain minor amounts of nontoxic auxiliary substances such as wetting agents, emulsifying agents, co-solvents, solubilizing agents, pH buffering agents and the like (e.g., sodium acetate, sodium citrate, cyclodextrin derivatives, sorbitan monolaurate, triethanolamine acetate, triethanolamine oleate, and the like).

Small Molecule Drug Formulations—General Properties

In one embodiment, the formulation comprises a small molecule drug. In some embodiments, the small molecule drug formulation is suitable for topical delivery to the GI tract, especially for topical delivery to the small intestine, including the duodenum, the jejunum and/or the ileum; the large intestine; the cecum; and/or the colon. In a further embodiment, the formulation is suitable for topical delivery of the drug to the GI tract containing one or more sites of disease. In some aspects, the small molecule drug formulation, when released into the GI tract, is dispersed such that the formulation and/or the drug is topically administered to one or more tissues of the GI tract, including tissue comprising one or more disease site(s). In some embodiments, the drug formulation when released in the GI tract, is dispersed into the mucosa, and the formulation and/or the drug is distributed locally to the site of administration and or/distal to the site of administration, thereby providing topical administration of the drug to one or more tissues of the GI tract, including tissue comprising one or more disease site(s).

Preferably, the formulation provides one or more of the following characteristics: substantial distribution of the formulation and/or drug in the target tissue; highly localized drug tissue concentration; low systemic drug exposure; stability of the formulation and/or drug in the drug product (e.g., stability within a delivery device, such as an ingestible device as described herein, prior to and/or after administration); stability of the formulation and/or drug in the GI environment upon administration, including a disease state GI environment (for example, temperature stability, pH stability, oxidative stability); and the ability of the formulation and/or drug to permeate into disease tissue.

In some aspects, the drug substance is provided as a solid for direct use in a drug delivery system (for example, in an ingestible device as described herein), or for combination with one or more excipients to provide a formulation suitable for delivery to the GI tract. In some embodiments, the drug substance is provided in amorphous form. In other embodiments, the drug substance is provided in crystalline form.

In some embodiments, the drug substance is provided as micronized drug particles. In some aspects, the micronized drug particles have been sized to enhance absorption and/or penetration in the GI tract and/or at the disease site. In other aspects, the micronized drug particles have been sized to optimize topical administration and absorption of the drug to the mucosal layer. In yet other aspects, the micronized drug particles have been sized to increase the dispersion loading of a suspension, i.e., to increase the concentration of the drug in the suspension in order to increase the drug load to the site of delivery upon dispersion.

In some embodiments, the drug is provided as a lyophilized powder. In some aspects, the lyophilized drug powder comprises, consists of or consists essentially of the drug. In some embodiments, the small molecule drug formulation is provided as a liquid. Preferably, the liquid formulation has a viscosity that does not exceed 5000 cps. In some embodiments, the liquid formulation has a viscosity ranging from about 0.8 to about 1000 cps.

Preferably, the small molecule drug formulation is a high concentration formulation. In some embodiments, the concentration of the drug in the formulation is expressed in units of mg/mL, for example, when the formulation is a solution formulation. In some aspects, the concentration of the drug in the formulation is at least 3 mg/mL. In other aspects, the concentration of the drug in the formulation is at least 5 mg/mL. In yet other aspects, the concentration of the drug in the formulation ranges from about 5 mg/mL to about 20 mg/mL, from about 5 mg/mL to about 15 mg/mL, or from about 10 mg/mL to about 15 mg/mL. Preferably, the concentration of the drug in the formulation is at least about 10 mg/mL, or at least about 15 mg/mL. In some embodiments, the concentration of the drug in the formulation is expressed in units of mg/g, for example, when the formulation is a solid formulation or a suspension or dispersion formulation. In some aspects, the concentration of drug in the formulation is at least 3 mg/g. In other aspects, the concentration of the drug in the formulation is at least 5 mg/g. In yet other aspects, the concentration of the drug in the formulation ranges from about 5 mg/g to about 20 mg/g, from about 5 mg/g to about 15 mg/g, or from about 10 mg/g to about 15 mg/g. Preferably, the concentration of the drug in the formulation is at least about 10 mg/g, or at least about 15 mg/g.

In one embodiment, the small molecule formulation is provided as a solution formulation, such as a fully solubilized formulation or a stabilized solution formulation. In another embodiment, the small molecule drug formulation is provided as a solid formulation, for example a solid drug alone or in combination with one or more excipients. In yet another embodiment, the small molecule formulation is provided as a dispersion or suspension formulation. In another embodiment, the formulation is provided as an emulsion formulation, including but not limited to a micelle-solubilized formulation, a lipid-based or liposomal formulation, a self-micro-emulsifying drug delivery system (SMEDDS) or a self-nano-emulsifying drug delivery system (SNEDDS). The foregoing categories are also not intended to be mutually exclusive. Thus, for example, a stabilized solution, a suspension or an emulsion formulation may incorporate micelles or liposomes.

In some aspects, the formulations in the foregoing categories further comprise one or more additional excipients to enhance performance, such as GI penetration/absorption and/or stability. Excipients that may be incorporated to enhance absorption by the GI tract and/or at the disease site within the GI tract include bile salts, chelators, surfactants, anti-oxidants, fatty acids and derivatives thereof, cationic polymers, anionic polymers, and acylcarnitines.

Bile salts may be incorporated into a formulation of the present disclosure, for example, in order to form reverse micelles, disrupt a cell membrane, open up tight junctions between cells, and/or to inhibit enzymes and/or mucolytic activity. Non-limiting examples of suitable bile salts include sodium deoxycholate, sodium taurocholate, sodium glycodeoxycholate, sodium taurodihydrofusidate, and sodium glycodihydrofudisate.

Chelators may be incorporated into a formulation of the present disclosure, for example, in order to interfere with calcium ions, disrupt intracellular junctions and/or decrease transepithelial electrical resistance. Non-limiting examples of suitable chelators include EDTA, citric acid, succinic acid and salycilates.

Surfactants may be incorporated into a formulation of the present disclosure, for example, in order to perturb intercellular lipids, lipid order, orientation and/or fluidity, and/or to inhibit efflux mechanisms. Non-limiting examples of suitable surfactants include sodium lauryl sulfate, laureth-9, sodium dodecylsulfate, sodium taurodihydrofusidate, polyoxyethylene ethers, polysorbate (polyoxyethylene sorbitan monolaurate, for example, polysorbate 20, polysorbate 40, polysorbate 60 and polysorbate 80); TRITON (t-octylphenoxypolyethoxyethanol, nonionic detergent, Union Carbide subsidiary of Dow Chemical Co., Midland Mich.); sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palmidopropyl-, or isostearamidopropyl-betaine (e.g. lauroamidopropyl); myristamidopropyl-, palmidopropyl-, or isostearamidopropyl-dimethylamine; sodium methyl cocoyl-, or disodium methyl oleyl-taurate; sorbitan monopalmitate; and the MONAQUAT series (Mona Industries, Inc., Paterson, N.J.); polyethyl glycol (PEG), polypropylene glycol (PPG), and copolymers of poloxyethylene and poloxypropylene glycol (e.g. Pluronics/Poloxamer, PF68, etc.); etc.

Fatty acids or derivatives thereof (for example, salts, esters or ethers thereof) may be incorporated into a formulation of the present disclosure, for example, in order to increase the fluidity of phospholipid membranes, contraction of actin myofilaments and/or the opening of tight junctions. Non-limiting examples of suitable fatty acids or derivatives thereof include oleic acid, linoleic acid, caprylic acid, capric acid, acyl carnitines, mono-glyceride and di-glycerides.

In some embodiments, the formulation comprises at least one adhesive agent, such as a mucoadhesive agent, In some embodiments, the formulation containing the (muco)adhesive agent is particularly useful in the topical treatment of gastrointestinal mucosal lesions. Non-limiting examples of the at least one adhesive agent for incorporation into formulations of the present disclosure include alginate, gelatin, collagen, poly(acrylic acid), poly(methacrylic acid), poly(L-lysine), poly(ethyleneimine), poly(ethylene oxide), poly(2-hydroxyethyl methacrylate), P(MAA-g-EG) hydrogel microparticles, lectin-conjugated alginate microparticles, thiolated polymer, natural oligosaccharides gum, drum dried waxy maize starch, Carbopol 974P, chitin, chitosan and derivatives thereof (for example, trimethyl chitosan), sea curve 240, scleroglucan, HE-starch, hydroxyl propyl cellulose, cellulose derivatives, pectin, xanthan gum, polycarbophil, amino dextran, DEAE-dextran, aminocaprylate, hyaluronic acid and/or a hyaluronate salt, polyvinyl acetate (PVA), cellulose derivatives such as cellulose sodium glycolate, methyl cellulose, carboxy methylhydroxyethyl cellulose, hydroxyethyl cellulose, propyl cellulose, hydroxypropyl methylcellulose, ethylcellulose, 3-O-ethylcellulose, hydroxypropyl methylcellulose phthalate, ethyl(hydroxyethyl)cellulose, 6-O-alkylated cellulose, cellulose octanoate sulfate, cellulose lauroate sulfate, cellulose stearate sulfate, and cationic derivatives thereof, 6-O-benzylcellulose, 2,3-di-O-methyl-6-O-benzylcellulose, 2,3-di-O-benzylcellulose, 2,3-di-O-benzyl-6-O-methylcellulose, 2,3,6-tri-O-benzylcellulose, hydroxypropyl methylcellulose acetate succinate, O-2-[2-(2-methoxyethoxy)ethoxy]acetyl cellulose, sodium alginate, starch, dextrin, a polyvinyl alcohol, a (poly)vinyl resin, sodium silicate, poloxamers, and the like. When the adhesive agent is sodium alginate, a compound containing divalent ions, such as CaCl2, is preferably present in the composition. Other mucoadhesive agents include cationic and anionic polymers, as described below.

Cationic polymers may be incorporated into a formulation of the present disclosure, for example, in order to enhance mucoadhesion, to open tight junctions, or both, for example, via ionic interactions with cell membrane(s). Non-limiting examples of suitable cationic polymers include chitin, chitosan and derivatives thereof (for example, trimethyl chitosan).

Anionic polymers may be incorporated into a formulation of the present disclosure, for example, in order to inhibit enzymes, to open tight junctions, or both, for example, via removal of extracellular calcium ions. Non-limiting examples of suitable anionic polymers include polymers of acrylic acid cross-linked with polyalkenyl ethers or divinyl glycol (e.g., Carbopol®) and polyacrylic acid derivatives, including salts, esters and ethers thereof.

Acylcarnities may be incorporated into a formulation of the present disclosure, for example, in order to disrupt membranes and/or open tight junctions via a calcium-independent mechanism. Non-limiting examples of suitable acylcarnitines include lauroyl-L-camitine chloride and palmitoylcarnitine chloride.

Antioxidants may be incorporated into a formulation of the present disclosure, for example, in order to reduce the viscosity of the mucus layer, which may involve breaking and/or preventing the formation of disulfide bonds. In a non-limiting embodiment, the antioxidant is N-acetylcysteine.

Other excipients that may be incorporated to enhance drug and/or drug formulation stability include antioxidants, reducing agents and preservatives. Non-limiting examples of these agents include those present in some commercial drug products listed in the tables below. The concentration ranges are illustrative and non-limiting.

TABLE 1

Antioxidants and reducing agents and usage in some commercial products

| Excipient | Range | Example |
|---|---|---|
| Ascorbate (sodium/acid) | 0.1-4.8% w/v | Vibramycin ® (Roerig) 4.8% |
| Bisulfite sodium | 0.02-0.66% w/v | Amikin ® (Bristol Myers) 0.66% |
| Butylated hydroxy anisole (BRA) | 0.00028-0.03% w/v | Aquasol ® (Astra) 0.03% |
| Butylated hydroxy toluene (BHT) | 0.00116-0.03% w/v | Aquasol ® (Astra) 0.03% |
| Cystein/Cysteinate, HCl | 0.07-0.10% w/v | Acthar Gel ® (Rhone-Poulanc) 0.1% w/v |
| Dithionite sodium (Na hydrosulfite, Na sulfoxylate) | 0.10% | Nurorphan ® (DuPont) 0.10% |
| Gentisic acid | 0.02% w/v | OctreoScan ® (Mallinckrodt) |
| Gentisic acid ethanolamine | 2% | M.V.I. 12 ® (Astra) 2% |
| Glutamate monosodium | 0.1% w/v | Varivas ® (Merck) 0.1% w/v |
| Formaldehyde sulfoxylate sodium | 0.075-0.5% w/v | Terramycin Solution (Roerig) 0.5% |
| Metabisulfite potassium | 0.10% | Vasoxyl ® (Glaxo-Wellcome) 0.10% |
| Metabisulfite sodium | 0.02-1% w/v | Intropin ® (DuPont) 1% w/v |
| Monothioglycerol (Thioglycerol) | 0.1-1% | Terramycin Solution (Roerig) 1% |
| Propyl gallate | 0.02% | Navane ® (Roerig) |
| Sulfite, sodium | 0.05-0.2% w/v | Enion ® (Ohmeda) 0.2% w/v |
| Thioglycolate, sodium | 0.66% w/v | Sus-Phrine ® (Forest) 0.66% w/v |

TABLE 2

Preservatives and usage in some commercial products

| Excipient | Range | Example |
|---|---|---|
| Benzethonium chloride | 0.01% | Benadryl ® (Parke-Davis) 0.01% w/v |
| Benzyl alcohol | 0.75-5% | Dimenhydrinate ® (Steris) 5% |
| Chlorobutanol | 0.25-0.5% | Codine phosphate (Wyeth-Ayerst) 0.5% |
| m-Cresol | 0.1-0.3% | Humatrope ® (Lilly) 0.30% |
| Myristyl gamma-picolinium | 0.0195-0.169% | Depo-Provera ® (Upjohn) 0.169% w/v |
| Paraben methyl | 0.05-0.18% | Inapsine ® (Janssen) 0.18% w/v |
| Paraben propyl | 0.01-0.1% | Xylocaine w/Epinephrine (Astra) 0.1% w/v |
| Phenol | 0.2-0.5% | Calcimar ® (Rhone Poulanc) 0.5% w/v |

TABLE 2-continued

| Preservatives and usage in some commercial products | | |
|---|---|---|
| Excipient | Range | Example |
| 2-Phenoxyethanol | 0.50% | Havrix ® (SmithKline Beecham) 0.50% w/v |
| Phenyl mercuric nitrate | 0.001% | Antivenin ® (Wyeth-Ayerst) 0.001% |
| Thimerosal | 0.003-0.01% | Atgam ® (Upjohn) 0.01% |

Solution Formulations

Solutions

In one embodiment, the small molecule drug formulation is provided as a solution. In some aspects, the solution formulation comprises the drug dissolved in one or more solvents, i.e., the drug is fully solubilized in the one or more solvents. Preferably, the one or more solvents is generally regarded as safe (GRAS). Non-limiting examples of solvents suitable for providing the small molecule solution formulation include water (e.g., WFI or a pH-adjusted water), one or more aqueous buffers, polyethylene glycol (PEG) 300-600 (e.g., PEG 300, PEG 400, PEG 500 or PEG 600), ethanol, propylene glycol, glycerin, N-methyl-2-pyrrolidone, dimethylacetamide, dimethylsulfoxide, and combinations of any two or more of the foregoing. In some embodiments, the solution formulation consists of or consists essentially of the drug and the one or more solvents.

Non-limiting examples of aqueous buffers for use as a solution formulation solvent include a phosphate buffer, a phosphate buffered saline (PBS, TBS, TNT, PBT), a histidine buffer, a citrate buffer, a TRIS buffer, a glycine-HCl buffer, a glycine-NaOH buffer, an acetate buffer, a cacodylate buffer, a maleate buffer, a PIPES buffer, a HEPES buffer, an MES buffer, a MOPS buffer, a phosphate-citrate buffer, and a barbital buffer. In some aspects, the pH of the aqueous buffer, and/or the pH of the final solution formulation containing the buffer, ranges from about pH 5.5 to about pH 8.5, or about pH 6 to about pH 8; preferably, the pH ranges from about pH 6.5 to about pH 7.2. In some embodiments, the buffer and/or final solution formulation pH is about 7.

In some embodiments, the solution formulation comprises a co-solvent system, wherein the co-solvent system consists of or consists essentially of a mixture of an organic solvent (such as ethanol) and an aqueous solvent (such as water, water for injection (WFI), a pH-adjusted water, a saline solution (e.g., normal saline), a dextrose solution (e.g., dextrose 5% for injection), or an aqueous buffer, such as phosphate buffer, a phosphate buffered saline (PBS, TBS, TNT, PBT), a histidine buffer, a citrate buffer, a TRIS buffer, a glycine-HCl buffer, a glycine-NaOH buffer, an acetate buffer, a cacodylate buffer, a maleate buffer, a PIPES buffer, a HEPES buffer, an MES buffer, a MOPS buffer, a phosphate-citrate buffer, and a barbital buffer.

In one embodiment, the formulation is an ethanolic solution formulation. In some aspects, the ethanolic solution formulation comprises at least about 50% ethanol, at least about 60% ethanol, at least about 70% ethanol, at least about 75% ethanol, or at least 80% ethanol, wherein the % is (w/w) with respect to the total mass of the solvent(s). In yet further aspects, the ethanolic solution formulation comprises an aqueous medium (e.g., water, water for injection (WFI), a pH-adjusted water, a saline solution (e.g., normal saline), a dextrose solution (e.g., dextrose 5% for injection), or an aqueous buffer (e.g., a phosphate buffer, a phosphate buffered saline (PBS, TBS, TNT, PBT), a histidine buffer, a citrate buffer, a TRIS buffer, a glycine-HCl buffer, a glycine-NaOH buffer, an acetate buffer, a cacodylate buffer, a maleate buffer, a PIPES buffer, a HEPES buffer, an MES buffer, a MOPS buffer, a phosphate-citrate buffer, and a barbital buffer). In some embodiments, the ethanolic solution formulation comprises at most about 20%, about 25%, about 30%, about 40% or about 50% water (e.g., WFI or pH-adjusted water) or aqueous buffer, wherein the % is (w/w) with respect to the total mass of the solvent(s).

In some embodiments, the small molecule drug formulation is a solution comprising polyethylene glycol (PEG) 300-600 (e.g., PEG 300, PEG 400, PEG 500, or PEG 600). In some embodiments, the solution further comprises an aqueous vehicle. For example, the aqueous vehicle can be water, water-for-injection (WFI), pH-adjusted water, or a buffer, such as an aqueous buffer, for example, a phosphate buffer, a phosphate buffered saline (PBS, TBS, TNT, PBT), a histidine buffer, a citrate buffer, a TRIS buffer, a glycine-HCl buffer, a glycine-NaOH buffer, an acetate buffer, a cacodylate buffer, a maleate buffer, a PIPES buffer, a HEPES buffer, an MES buffer, a MOPS buffer, a phosphate-citrate buffer, and a barbital buffer.

Stabilized Solutions

In another embodiment, the small molecule drug formulation is provided as a stabilized solution. In some aspects, the stabilized solution comprises the drug, one or more solvents and a stabilizing agent. The stabilizing agent may facilitate and maintain the dissolution of the drug in the one or more solvents. Non-limiting examples of solvents suitable for providing the stabilized solution formulation include water (e.g., WFI or pH-adjusted water), one or more aqueous buffers, polyethylene glycol 300-600 (e.g., PEG 300, PEG 400, PEG 500 or PEG 600), ethanol, propylene glycol, glycerin, N-methyl-2-pyrrolidone, dimethylacetamide, dimethylsulfoxide, and combinations of two or more of the foregoing.

Non-limiting examples of aqueous buffers for use in a small molecule stabilized solution formulation solvent include a phosphate buffer, a phosphate buffered saline (PBS, TBS, TNT, PBT), a histidine buffer, a citrate buffer, a TRIS buffer, a glycine-HCl buffer, a glycine-NaOH buffer, an acetate buffer, a cacodylate buffer, a maleate buffer, a PIPES buffer, a HEPES buffer, an MES buffer, a MOPS buffer, a phosphate-citrate buffer, and a barbital buffer. In some aspects, the pH of the aqueous buffer, and/or the pH of the final solution formulation containing the buffer, ranges from about pH 5.5 to about pH 8.5, or about pH 6 to about pH 8; preferably, the pH ranges from about pH 6.5 to about pH 7.2. In some embodiments, the buffer and/or final solution formulation pH is about 7.

Non-limiting examples of a stabilizing agent to be combined with the one or more solvents to provide the small molecule drug stabilized solution formulation include surfactants, water-insoluble lipids, organic liquids or semi-solids, cyclodextrins, phospholipids, and combinations of two or more of the foregoing.

In some embodiments, the stabilizing agent is a surfactant. Non-limiting examples of surfactants for incorporation into the stabilized solution formulation include Cremophor EL, Cremophor RH 40, Cremophor RH 60, d-alpha-tocopherol polyethylene glycol 1000 succinate, polysorbate 20, polysorbate 40, polysorbate 60, polysorbate 80, Solutol HS 15, sorbitan monooleate, poloxamer 407, Labrafil M-1944CS, Labrafil M-2125CS, Labrasol, Gellucire 44/14, Softigen 767, mono- and di-fatty acid esters of PEG 300, 400 or 1750; and combinations of two or more of the foregoing.

In some embodiments, the stabilizing agent is a water-insoluble lipid. Non-limiting examples of water-insoluble lipids for incorporation into the stabilized solution formulation include castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil and palm seed oil; and combinations of two or more of the foregoing.

In some embodiments, the stabilizing agent is an organic liquid or semi-solid. Non-limiting examples of an organic liquid or semi-solid for incorporation into the stabilized solution formulation include beeswax, d-alpha-tocopherol, oleic acid, medium-chain mono- and diglycerides; and combinations of two or more of the foregoing.

In some embodiments, the stabilizing agent is a cyclodextrin. Non-limiting examples of a cyclodextrin for incorporation into the stabilized solution formulation include alpha-cyclodextrin, beta-cyclodextrin, hydroxypropyl-beta-cyclodextrin and sulfobutylether-beta-cyclodextrin.

In some embodiments, the stabilizing agent is a phospholipid. Non-limiting examples of a phospholipid for incorporation into the stabilized solution formulation include hydrogenated soy phosphatidylcholine, distearoylphosphatidylglycerol, L-alpha-dimyristoylphosphatidylcholine and L-alpha-dimyristoylphosphatidylglycerol; and combinations of two or more of the foregoing.

In one embodiment, the stabilized solution formulation comprises, consists essentially of or consists of the drug, one or more solvents (such as ethanol), and a water insoluble lipid; optionally, the formulation further comprises a polyol, such as a sugar or sugar alcohol; in some embodiments, the polyol is sucrose, mannitol, sorbitol, trehalose, raffinose, maltose, or a combination thereof.

In another embodiment, the stabilized solution formulation comprises, consists essentially of or consists of the drug, one or more solvents, and an organic liquid or semi-solid.

In another embodiment, the stabilized solution formulation comprises, consists essentially of or consists of the drug, one or more solvents, and a cyclodextrin.

In another embodiment, the stabilized solution formulation comprises, consists essentially of or consists of the drug, one or more solvents, and a phospholipid.

In another embodiment, the stabilized solution formulation comprises, consists essentially of or consists of the drug, one or more solvents, and a surfactant.

In one embodiment, the formulation is a stabilized ethanolic solution formulation comprising the drug, ethanol, a stabilizing agent, and optionally, a second solvent. In further aspects of this embodiment, the ethanolic formulation comprises at least about 50% ethanol, at least about 60% ethanol, at least about 70% ethanol, at least about 75% ethanol, t least 80% ethanol, at least about 85% ethanol, or at least about 90% ethanol, wherein the % is (w/w) with respect to the total mass of the solvent(s) or the total mass of the solvent(s) and the stabilizing agent. In yet further aspects, the stabilized ethanolic solution formulation further comprises water (e.g., WFI or a pH-adjusted water) or an aqueous buffer as the second solvent. In some embodiments, the stabilized ethanolic solution formulation comprises at most about 20%, at most about 25%, at most about 30%, at most about 40% or at most about 50% water or aqueous buffer, wherein the % is (w/w) with respect to the total mass of the solvent(s) or the total mass of the solvent(s) and the stabilizing agent. In some embodiments, the stabilized ethanolic solution formulation comprises between about 0.1% and about 50% of the stabilizing agent, wherein the % is (w/w) with respect to the total mass of the solvent(s) and the stabilizing agent. Non-limiting examples of a stabilizing agent suitable for providing the stabilized ethanolic solution formulation include surfactants (e.g., Cremophor EL, Cremophor RH 40, Cremophor RH 60, d-alpha-tocopherol polyethylene glycol 1000 succinate, polysorbate 20, polysorbate 40, polysorbate 60, polysorbate 80, Solutol HS 15, sorbitan monooleate, poloxamer 407, Labrafil M-1944CS, Labrafil M-2125CS, Labrasol, Gellucire 44/14, Softigen 767, mono- and di-fatty acid esters of PEG 300, 400, or 1750), water-insoluble lipids (e.g., castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, palm seed oil), organic liquids or semi-solids (e.g., beeswax, d-alpha-tocopherol, oleic acid, medium-chain mono- and diglycerides), cyclodextrins (e.g., (alpha-cyclodextrin, beta-cyclodextrin, hydroxypropyl-beta-cyclodextrin, and sulfobutylether-beta-cyclodextrin), phospholipids (e.g., hydrogenated soy phosphatidylcholine, distearoylphosphatidylglycerol, L-alpha-dimyristoylphosphatidylcholine and L-alpha-dimyristoylphosphatidylglycerol), and combinations of two or more of the foregoing.

In another embodiment, the formulation is a stabilized ethanolic solution formulation comprising the drug, ethanol, a stabilizing agent or carrier, and optionally, a second solvent. In further aspects of this embodiment, the ethanolic formulation comprises from 0.1 to 99.9% of the stabilizing agent or carrier, wherein the % is (w/w) with respect to the total mass of the solvent(s) or the total mass of the solvent(s) and the stabilizing agent. In yet further aspects, the stabilized ethanolic solution formulation further comprises water (e.g., WFI or a pH-adjusted water) or an aqueous buffer as the second solvent. Non-limiting examples of a stabilizing agent or carrier suitable for providing the stabilized ethanolic solution formulation include surfactants (e.g., Cremophor EL, Cremophor RH 40, Cremophor RH 60, d-alpha-tocopherol polyethylene glycol 1000 succinate, polysorbate 20, polysorbate 40, polysorbate 60, polysorbate 80, Solutol HS 15, sorbitan monooleate, poloxamer 407, Labrafil M-1944CS, Labrafil M-2125CS, Labrasol, Gellucire 44/14, Softigen 767, mono- and di-fatty acid esters of PEG 300, 400, or 1750), water-insoluble lipids (e.g., castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, palm seed oil), organic liquids or semi-solids (e.g., beeswax, d-alpha-tocopherol, oleic acid, medium-chain mono- and diglycerides), cyclodextrins (e.g., (alpha-cyclodextrin, beta-cyclodextrin, hydroxypropyl-beta-cyclodextrin, and sulfobutylether-beta-cyclodextrin), phospholipids (e.g., hydrogenated soy phosphatidylcholine, distearoylphosphatidylglycerol, L-alpha-dimyristoylphosphatidylcholine and L-alpha-dimyristoylphosphatidylglycerol), and combinations of two or more of the foregoing.

In a particular embodiment, the formulation comprises, consists essentially of or consists of the drug, ethanol, and a surfactant, such as Labrasol or a a polyoxyethylene hydrogenated castor oil such as Cremophor. In a more particular embodiment, the formulation comprises, consists essentially of or consists of the drug, ethanol, and a polyoxyethylene hydrogenated castor oil (e.g., Cremophor).

In one embodiment, the formulation comprises, consists essentially of or consists of the drug, ethanol and Cremophor.

Optionally, each of the foregoing formulations comprising the drug, the ethanol and the Cremophor further comprises a second solvent. Optionally, the second solvent is a PEG (for example, PEG 300 or PEG 400). Alternatively, the second solvent is water (e.g., WFI or a pH-adjusted water) or an aqueous buffer, thereby optionally providing the formulation as a micelle-solubilized formulation.

In another embodiment, the comprises, consists essentially of or consists of the drug and a solvent, such as a PEG (for example, PEG 300 or PEG400), optionally further comprising a stabilizing agent or carrier, and/or a second solvent. In some embodiments, the second solvent is water (e.g., WFI or a pH-adjusted water) or an aqueous buffer. In other embodiments, the second solvent is ethanol. Non-limiting examples of a stabilizing agent or carrier suitable for providing the formulation include surfactants (e.g., Cremophor EL, Cremophor RH 40, Cremophor RH 60, d-alpha-tocopherol polyethylene glycol 1000 succinate, polysorbate 20, polysorbate 40, polysorbate 60, polysorbate 80, Solutol HS 15, sorbitan monooleate, poloxamer 407, Labrafil M-1944CS, Labrafil M-2125CS, Labrasol, Gellucire 44/14, Softigen 767, mono- and di-fatty acid esters of PEG 300, 400, or 1750), water-insoluble lipids (e.g., castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, palm seed oil), organic liquids or semi-solids (e.g., beeswax, d-alpha-tocopherol, oleic acid, medium-chain mono- and diglycerides), cyclodextrins (e.g., (alpha-cyclodextrin, beta-cyclodextrin, hydroxypropyl-beta-cyclodextrin, and sulfobutylether-beta-cyclodextrin), phospholipids (e.g., hydrogenated soy phosphatidylcholine, distearoylphosphatidylglycerol, L-alpha-dimyristoylphosphatidylcholine and L-alpha-dimyristoylphosphatidylglycerol), and combinations of two or more of the foregoing. In some embodiments, the stabilizing agent is Cremophor.

Solid Formulations

In one embodiment, the small molecule drug formulation is provided as a solid. In some aspects, the solid formulation, upon administration, is released into the GI tract where it is dispersed and distributed locally and or/distal to the site of administration. In some embodiments, the solid drug formulation is dispersed into the mucosa and distributed locally and or/distal to the site of administration. In a non-limiting example, the solid drug formulation is released in the cecum, dispersed into the mucosa, and distributed to the colon. In some embodiments, the solid drug formulation is loaded into an ingestible device for release into the GI tract. In some aspects, upon administration, the solid drug formulation is emulsified in the GI tract via contact with one or more substances present in the local environment, for example, with bile salts present in the GI tract; in further aspects, the emulsification enhances drug distribution to and/or absorption by the surrounding tissues, and/or enhances the stability of the formulation.

In one embodiment, the solid drug formulation comprises, consists of or consists essentially of the drug. In some aspects, the drug is in crystalline form. In other aspects, the drug is in amorphous form. In some embodiments, the drug is provided in as micronized drug particles, a lyophilized powder or in extruded form.

In another embodiment, the solid formulation comprises the drug and one or more excipients. In some aspects, the drug (which may be crystalline or amorphous, micronized or lyophilized) is physically admixed with the one or more excipients. In some embodiments, the one or more excipients is selected from the group consisting of preservatives and anti-oxidants. In some embodiments, the drug is physically admixed with an excipient such as a solvent (for example, PEG) and extruded.

In another embodiment, the solid drug formulation is an enteric-coated formulation.

In another embodiment, the solid drug formulation is not an enteric-coated formulation.

In another embodiment, the solid drug formulation does not contain a pH-dependent drug release matrix.

Dispersion or Suspension Formulations

Dispersion Formulations

In one embodiment, the small molecule drug formulation is provided as a dispersion formulation. Typically, the dispersion formulation comprises at least two phases, a dispersed phase and a dispersion medium or vehicle. In one embodiment, solid drug particles (the dispersed phase) are dispersed in a continuous dispersion vehicle, which is preferably a solution in which the drug is insoluble or poorly soluble, and throughout which the drug particles are distributed.

In some embodiments, the solid drug particles comprise micronized drug particles; advantageously, the micronized drug particles increase dispersion loading. In other embodiments, the solid drug is provided in an extruded form, for example, the drug may be admixed with an excipient (for example, a solvent such as PEG and extruded; advantageously, the extruded drug formulation increases dispersion loading. In other embodiments, the solid drug is provided in a lyophilized form; advantageously, the lyophilized drug formulation increases dispersion loading.

In some aspects, the dispersion formulation is prepared using solvent evaporation techniques, which may increase dispersion loading.

In other embodiments, the drug is a liquid or a semi-solid, and the dispersion formulation comprises the drug in the form of droplets dispersed throughout the dispersion vehicle, which may be a solution phase in which the drug is insoluble or poorly soluble, and throughout which the drug droplets are distributed.

Suspension Formulations

In one embodiment, the formulation is provided as a suspension. In some aspects, the suspension formulation comprises the drug suspended via a suspending agent in an aqueous media, such as an aqueous buffer.

Non-limiting examples of suitable suspending agents include carboxymethyl cellulose (CMC), PEGs (e.g., PEG 100-1000, PEG 3350), hydroxypropyl methylcellulose (HPMC), and combinations thereof. The formulation may further comprise one or more excipients, such as castor oil, modified starch, sorbitol, cellulose, pectin, sucrose, citric acid, poloxamers, tetrasodium edetate (EDTA), PEG(s), cocamide DE, glycerol, Cremophor RH40, dextrose, polyvinyl alcohol, hydroxyethyl cellulose, hydroxypropyl cellulose, propylene glycol, gums (various), propylene glycol alginate, methyl paraben, providone, water, and surfactants (such as polysorbate 20, 40, 60 or 80).

In one example, the suspension formulation comprises the drug solubilized in a lipid, which is further suspended in an aqueous vehicle (e.g., WIFI, a pH-adjusted water, or an aqueous buffer). In another example, the suspension formulation comprises micronized drug substance suspended in an excipient, such as an excipient suitable for solution formulations as disclosed herein. In another example, the suspension formulation comprises micronized drug substance suspended in a solvent, such as a solvent suitable for solution formulations as disclosed herein. In a further example, the suspension formulation comprises drug solubilized in a lipid, which is further suspended in an excipient, such as an excipient suitable for solution formulations as disclosed herein. In another example, the suspension formulation comprises drug solubilized in a lipid, which is further suspended in a solvent, such as a solvent suitable for solution formulations as disclosed herein.

Emulsion Formulations

In one embodiment, the formulation is provided as an emulsion.

Water-In-Oil Emulsions

In some aspects, the emulsion formulation is a water-in-oil emulsion formulation. In further aspects, the water-in-oil emulsion formulation comprises a water-insoluble excipient, a triglyceride and one or more surfactants. Typically, the water-in-oil emulsion will contain two (2) surfactants.

In one embodiment, the emulsion comprises a non-ionic surfactant. In some embodiments, the non-ionic surfactant contains the following functionality or agent: ethoxylated aliphatic alcohol; polyoxyethylene surfactants; carboxylic esters; polyethylene glycol esters; anhydrosorbitol ester and its ethoxylated derivatives; glycol esters of fatty acids; amides; monoalkanolamine condensates; polyoxyethylene fatty acid amides.

In one embodiment, the emulsion comprises an amphoteric surfactant. In some embodiments, the amphoteric surfactant contains the following functionality or agent: n-coco 3-aminopropionic acid/sodium salt; n-tallow 3-iminodipropionate, disodium salt; n-carboxymethyl n-dimethyl n-9 octadecenyl ammonium hydroxide; n-cocoamidethyl n-hydroxyethylglycine, sodium salt.

In other embodiments, the emulsion is a cationic emulsion, which preferably interacts with negatively charged tissue of the GI tract, thereby facilitating the topical administration of the drug to the GI tissue. In some embodiments, the cationic emulsion comprises one or more excipients comprising one or more of the following functional groups: quaternary ammonium salts; amines with amide linkages; polyoxyethylene alkyl and alicyclic amines; N,N,N',N' tetrakis substituted ethylenediamines; 2-alkyl 1-hydroxethyl 2-imidazolines.

In some embodiments, the emulsion is an anionic emulsion, which preferably interacts with positively charged inflamed tissue at a disease site, thereby facilitating the targeted topical administration of the drug to the disease site. In some embodiments, the anionic emulsion comprises one or more excipients comprising one or more of the following functional groups: carboxylates; sulfonates; petroleum sulfonates; alkylbenzenesulfonates; naphthalenesulfonates; olefin sulfonates; alkyl sulfates; sulfates; sulfated natural oils and fats; sulfated esters; sulfated alkanolamides; alkylphenols, and ethoxylated and sulfated derivatives.

Non-limiting examples of water-insoluble excipients for incorporation into the emulsion formulation include bees wax, oleic acid, soy fatty acids, d-alpha-tocopherol (vitamin E), corn oil monoglycerides, corn oil diglycerides, corn oil triglycerides, medium chain (C8-C10) monoglycerides, medium chain (C8-C10) diglycerides, propylene glycol esters of fatty acids, and combinations of two or more of the foregoing.

Non-limiting examples of triglycerides for incorporation into the emulsion formulation include long-chain triglycerides, such as hydrogenated soybean oil, hydrogenated vegetable oil, corn oil, olive oil, peanut oil, sesame oil; and medium-chain triglycerides, such as caprylic/capric triglycerides, triglycerides derived from coconut oil or palm seed oil; and combinations thereof.

Non-limiting examples of surfactants for incorporation into the emulsion formulation include polysorbate 20 (Tween 20), polysorbate 80 (Tween 80), sorbitanmonolaurate (Span 20), d-alpha-tocopheryl PEG 1000 succinate (TPGS), glycerylmonoolate, polyoxyl 35 castor oil (Cremophor EL), polyoxyl 40 hydrogenated castor oil (Cremophor RH40), polyoxyl 60 hydrogenated castor oil (Cremophor RH60), PEG 300 oleic glycerides (Labrafil® M-1944CS), PEG 300 linoleic glycerides (Labrafil® M-2125CS), PEG 400 caprylic/capric glycerides (Labrasol®), PEG 1500 lauric glycerides (Gelucire® 44/14); and combinations thereof.

Lipid-Based Emulsions

In some embodiments, the formulation is a lipid-based formulation comprising the drug, an aqueous phase (e.g., water, water for injection (WFI), a pH-adjusted water, a saline solution (e.g., normal saline), a dextrose solution (e.g., dextrose 5% for injection), or an aqueous buffer) and an emulsifier. Non-limiting examples of the emulsifiers suitable for use in the lipid-based emulsion formulations are listed in Table 3. Optionally, the formulation further comprises a non-aqueous co-solvent; non-limiting examples of the cosolvent include ethanol, propylene glycol, glycerol, and a PEG (e.g, PEG 400). Suitable combinations of agents used to formulate the small molecule drug are found in Table 4, which discloses some commercial lipid-based formulations.

TABLE 3

| Emulsifiers used in lipid-based formulations | |
|---|---|
| Low hydrophilic lipophilic balance (HLB) (<10) emulsifier | |
| Phosphatidylcholine and phosphatidylcholine/ solvent mixtures | Phosphatidylcholine, phosphatidylcholine in propylene glycol, phosphatidylcholine in medium chain triglycerides, and phosphatidylcholine in safflower oil/ethanol |
| Unsaturated poly-glycolized glycerides | Oleoyl macrogolglycerides, linoleoyl macrogolglycerides |
| Sorbitan esters | Sorbitan monooleate, sorbitan monostearate, sorbitan monolaurate, and sorbitan monopalmitate |
| High HLB (>10) emulsifier | |
| Polyoxyethylene sorbitan esters | Polysorbate 20, polysorbate 40, polysorbate 60, and polysorbate 80 |
| Polyoxyl castor oil derivatives | Polyoxyl 35 castor oil, polyoxyl 40 hydrogenated castor oil |
| Polyoxyethylene polyoxypropylene block copolymer | Poloxamer 188, poloxamer 407 |
| Saturated poly-glycolized glycerides | Lauroyl macrogolglycerides, stearoyl macrogolglycerides |
| PEG-8 caprylic/capric glycerides | Caprylocaproyl macrogolglycerides |
| Vitamin E derivative | Tocopherol PEG succinate |

TABLE 4

| Some Commercial Lipid formulations | | | | |
|---|---|---|---|---|
| Drug | Oils: triglycerides or mixed mono and diglycerides | Water-insoluble surfactants (HLB < 12) | Water-soluble surfactants (HLB > 12) | Hydrophilic cosolvent |
| Isotretinoin (Accutane ®) Discontinued | Beeswax, hydrogenated soybean oil flakes, hydrogenated vegetable oil, soybean oil | | | |
| Cyclosporin A (Sandimmune ®) | Olive oil | | polyoxyethylated oleic glycerides | Ethanol 12.5% |
| Dronabinol (Marinol ®) | Sesame oil | | | |
| Clofazimine (Lamprene ®) 100 mg Discontinued | Beeswax | | | |
| Cyclosporin A (Sandimmune ®) | Corn oil | Linoleic macroglycerides | | Ethanol 12.7% |
| Ranitidine (Zantac ®) Discontinued | Medium chain triglycerides | Mixed glycerides of long chain fatty acids (Gelucire 33/01) | | |
| Cyclosporin A (Neoral ®) | Corn oil mono-di-triglycerides | | Polyoxyl 40 hydrogenated castor oil | Ethanol 11.9%, glycerol, propylene glycol |
| Cyclosporin A (Neoral ®) | Corn oil-mono-di-triglycerides | | Polyoxyl 40 hydrogenated castor oil | Ethanol 11.9%, propylene glycol |
| Tretinoin (Vesanoid ®) Discontinued | Beeswax, hydrogenated soybean oil flakes, hydrogenated vegetable oil, soybean oil | | | |
| Ritonavir (Norvir ®) | | Oleic acid | Polyoxyl 35 castor oil | Ethanol |
| Saquinavir (Fortovase ®) Discontinued | Medium chain mono- and di-glycerides | | | |
| Progesterone (Prometrium ®) | Peanut oil | | | |
| Amprenavir (Agenerase ®) discontinued | | | Vitamin E TPGS | PEG400, propylene glycol |
| Bexarotene (Targretin ®) | | | Polysorbate 20 | PEG400 |
| Doxercalciferol (Hectorol ®) | Coconut oil | | | Alcohol |
| Sirolimus (Rapamune ®) | Phosphatidylcholine, mono- and di-glycerides, soy fatty acids, ascorbyl palmitate | | Polysorbate 80 | 1.5-2.5% ethanol, propylene glycol |
| Cyclosporin A (Gengraf ®) | | | Polysorbate 80, Polyoxyl 35 castor oil | Propylene glycol, alcohol 12.8% v/v |
| Cyclosporin A (Gengraf ®) | | | Polyoxyl 40 hydrogenated castor oil, Polysorbate 80 | Propylene glycol |
| Ritonavir/ lopinavir (Kaletra ®) Discontinued | | Oleic acid | Polyoxyl 35 castor oil | Propylene glycol |
| Dutasteride (Avodart ®) | Mono-di-glycerides of caprylic/capric acid | | | |
| Isotretinoin (Claravis ®) | Hydrogenated vegetable oil, soybean oil, white wax | | Polysorbate 80 | |

TABLE 4-continued

| Some Commercial Lipid formulations | | | | |
|---|---|---|---|---|
| Drug | Oils: triglycerides or mixed mono and diglycerides | Water-insoluble surfactants (HLB < 12) | Water-soluble surfactants (HLB > 12) | Hydrophilic cosolvent |
| Omega-3-acid ethyl esters (Lovaza ®) | Soybean oil | | | |
| Tipranavir (Aptivus ®) | Mono-/di-glycerides of caprylic/capric acids | | Polyoxyl 35 castor oil | Ethanol, propylene glycol |
| Tipranavir (Aptivus ®) | | | Vitamin E TPGS | PEG 400, propylene glycol, water |
| Paricalcitol (Zemplar ®) | Medium chain triglycerides fractionated from coconut oil or palm kernel oil | | | Alcohol |
| Lubiprostone (Amitiza ®) | Medium chain triglycerides | | | |
| Fenofibrate (Lipofen ®) | | | Gelucire 44/14 (lauroyl macrogol glyceride type 1500) | |
| Topotecan HCl (Hycamtin ®) | Hydrogenated vegetable oil | Glyceryl monostearate | | |
| Loratadine (Claritin ®) | Caprylic/capric glycerides | | Polysorbate 80 | |
| Isotretinoin (Absorica ®) | Soybean oil, stearoyl polyoxylglycerides | Sorbitan monooleate | | |
| Enzalutamide (Xtandi ®) | Caprylocaproyl polyoxyglycerides | | | |
| Nintedanib (Ofev ®) | MCTs, hard fat | Lecithin | | |
| Calcifediol (Rayaldee ™) | | Mixture of lipophilic emulsifier with a HLB <7 and an absorption enhancer with HLB of 13-18 Oily vehicle—mineral oil, liquid paraffins, or squalene | | |

Formulations Containing Tofacitinib

In some embodiments, the pharmaceutical formulation comprising tofacitinib is tofacitinib in the form of micronized particles, such as particles micronized with PEG.

In some more particular embodiments, the pharmaceutical formulation comprises tofacitinib citrate. More particularly, the pharmaceutical formulation is XELJANZ®.

Thus, in some more particular embodiments, the pharmaceutical formulation comprises tofacitinib citrate and the pharmaceutical formulation comprises microcrystalline cellulose, lactose monohydrate, croscarmellose sodium, magnesium stearate, HPMC 2910/Hypromellose 6 cP, titanium dioxide, macrogol/PEG3350, and triacetin.

In other embodiments, the pharmaceutical formulation is provided as a dispersion or a suspension comprising the tofacitinib in a suspending agent, wherein the suspending agent is optionally carboxymethyl cellulose (CMC), one or more PEGs (e.g., PEG 100 to 1000, PEG 3350), hydroxypropyl methylcellulose (HPMC), or a combination thereof. Optionally, the formulation further comprises one or more excipients selected from the group consisting of castor oil, modified starch, sorbitol, cellulose, pectin, sucrose, citric acid, poloxamers, EDTA, cocamide DE, glycerol, Cremophor RH40, dextrose, polyvinyl alcohol, hydroxyethyl cellulose, hydroxypropyl cellulose, propylene glycol, a gum, propylene glycol alginate, methyl paraben, providone, water, and a surfactant, which is optionally polysorbate 20, 40, 60 or 80. Optionally, the tofacitinab is provided as a micronized solid dispersed or suspended in the suspending agent and the one or more optional excipients. Preferably, the pharmaceutical formulation contains the tofacitinib at a concentration of at least about 5 mg/mL or 5 mg/g, at least about 10 mg/mL or 10 mg/g; optionally, at least about 15 mg/mL or 15 mg/g. In some embodiments, the tofacitinib is tofacitinib citrate.

In other embodiments, the formulation is provided as a solid, and the tofacitinib is present in the pharmaceutical formulation at a concentration of at least about 75% (w/w), about 80% (w/w), about 85% (w/w), or at least about 90% (w/w); optionally, at least about 95%, about 96%, about 97%, about 98% or about 99% (w/w). In some embodiments, the tofacitinib is tofacitinib citrate.

Formulations for Delivery of Antibodies and Other Therapeutic Proteins

In some aspects, a JAK inhibitor is administered in combination with a second agent, wherein the second agent is an antibody or other therapeutic protein. In some embodiments, the JAK inhibitor itself is an antibody or other therapeutic protein. The antibody or other therapeutic protein (i.e., the JAK inhibitor itself or the second agent) can be delivered systemically, for example, via intravenous or subcutaneous administration, or can be administered using the devices and methods described herein, including an ingestible device as disclosed herein. The antibodies or other therapeutic proteins can be incorporated into pharmaceutical formulations, which may be loaded into a device for release and delivery to a subject, or more particularly, for topical delivery of the formulation and/or antibody or therapeutic protein to the gastrointestinal tract of a subject. The formulations can be liquid, semi-solid, or solid formulations, and can comprise the agent and a physiologically acceptable carrier. Exemplary carriers include water, saline, phosphate buffered saline, dextrose, glycerol, ethanol and the like. Polyamines or polyols, including sugars and polyalcohols (e.g., mannitol or sorbitol), may be incorporated into the present formulations, for example, for use as stabilizing agents, e.g., to preserve the biological activity of an antibody or other therapeutic protein under various stress conditions. Formulations can include other substances, such as wetting or emulsifying agents, preservatives, buffers, and/or mucoadhesive agents, which can enhance the shelf life and/or effectiveness of the agent. Formulations that are particularly useful for the methods and compositions described herein are described in detail below. Some formulations disclosed herein, which may be commercially or otherwise available for IV or subcutaneous delivery, and which may be available in pre-loaded syringes or pens, may alternatively be incorporated or loaded into a device, such as an ingestible device, as disclosed herein, for release and topical delivery of the formulation and/or antibody or therapeutic protein to the gastrointestinal tract of a subject.

General Description of Formulations and Ingredients

An antibody or other therapeutic protein can be formulated in a solution (e.g., aqueous formulation), dry formulation (e.g., lyophilized solid formulation), microemulsion, nanoemulsion, solid composition, semi-solid composition, dispersion, liposome, or a particulate composition containing a micro- or nanoencapsulated antibody or other therapeutic protein. In some embodiments, the formulation can be suitable for high antibody concentration (e.g., about 150 mg/mL and greater). Solutions can be prepared, e.g., by incorporating an antibody in the required amount in an appropriate solvent with at least one, or a combination of, ingredients described above. Generally, dispersions can be prepared by incorporating an antibody into a vehicle that contains a basic dispersion medium and the required other ingredients from those described above. In some embodiments, proper fluidity of a solution may be maintained, for example, using a coating such as lecithin, by the maintenance of the required particle size in the case of dispersion, and by the use of surfactants. Prolonged absorption of compositions can be brought about by including in the composition an agent that delays absorption, for example, monostearate salts and/or gelatin. In some embodiments, formulations containing an antibody or therapeutic protein further comprises one or more additional excipients to enhance performance, such as GI penetration/absorption and/or stability. Excipients that may be incorporated to enhance absorption by the GI tract and/or at the disease site within the GI tract include bile salts, chelators, surfactants, anti-oxidants, fatty acids and derivatives thereof, cationic polymers, anionic polymers, and acylcarnitines, such as lauroyl-L-carnitine chloride or palmitoylcarnitine chloride.

Polyols

In some embodiments, the present disclosure provides a formulation comprising a polyol. As used herein, the term "polyol" refers an excipient with multiple hydroxyl groups, and includes sugars (e.g., reducing and nonreducing sugars), sugar alcohols and sugar acids. In some embodiments, the polyol is a small molecule. A "reducing sugar" is one which contains a hemiacetal group that can reduce metal ions or react covalently with lysine and other amino groups in proteins. A "nonreducing sugar" is one which does not have these properties of a reducing sugar. Polyols that are suitable for use in formulations of the present application include, for example, polyols selected from the group consisting of mannitol, sucrose, trehalose, sorbitol, erythritol, isomalt, lactitol, maltitol, maltose, xylitol, raffinose, stachyose, melezitose, dextran, palatinit, glycerol, lactitol, propylene glycol, polyethylene glycol, inositol, and mixtures thereof.

In some embodiments, the present disclosure provides a composition comprising an antibody and a polyol, which may be a sugar (e.g., a non-reducing sugar). In one example, these excipients increase stability of an antibody or another therapeutic protein in the formulation that is susceptible to deamidation, oxidation, isomerization and/or aggregation. Hence, inclusion of a sugar in the formulation improves stability, reduces aggregate formation, and retards degradation of the therapeutic protein therein. Suitable examples of polyols include mannitol, sorbitol, sucrose, trehalose, raffinose, maltose, and a combination thereof.

A molar ratio of the polyol to the antibody or other therapeutic protein can be, e.g., at least about 600:1; about 625:1; about 650:1; about 675:1, about 700:1; about 750:1, about 800:1, about 1000:1, about 1200:1, about 1400:1, about 1500:1, about 1600:1, about 1700:1, about 1800:1, about 1900:1, or about 2000:1. In some embodiments, sucrose, mannitol, sorbitol, trehalose, or any combination thereof, is the non-reducing sugar for use in an antibody formulation (solid or liquid). In some embodiments, the molar ratio of the non-reducing sugar to the antibody (mole:mole) is at least about 600:1.

Amino Acids

In some embodiments, a formulation can include any desired free amino acid, a salt thereof, or a combination thereof, which can be in the L-form, the D-form or any desired mixture of these forms. Free amino acids that can be included in the formulation include, for example, any one of the 20 essential amino acids, or more particular amino acids, such as histidine, alanine, arginine, glycine, glutamic acid, serine, lysine, tryptophan, valine, cysteine, methionine, and any combination thereof. The amino acids can stabilize an antibody against degradation during manufacturing, drying, lyophilization and/or storage, e.g., through hydrogen bonds, salt bridges antioxidant properties or hydrophobic interactions or by exclusion from the protein surface. Amino acids can act as tonicity modifiers or can act to decrease viscosity of the formulation. Free amino acids, such as histidine and arginine, can act as cryoprotectants and lyoprotectants, and do not crystallize when lyophilized as components of the formulation.

Free amino acids, such as glutamic acid and histidine, alone or in combination, can act as buffering agents in an aqueous formulation in the pH range of about 5 to about 7.5, or about 4.7 to about 5.7. In some embodiments, when a combination of amino acids, such as histidine and arginine, is used in a formulation, the molar ratio of total amino acid amount to antibody ratio can be at least about 200:1, about 200:1 to about 500:1, or at least about 400:1. In some embodiments, the free amino acid in the formulation is histidine, alanine, arginine, glycine, glutamic acid, or any combination thereof. The molar ratio of free amino acid to antibody may be at least about 200:1, about 250:1, about 300:1, about 400:1, or about 500:1.

Surfactants

In some embodiments, a formulation may contain a surfactant. When present, the surfactant is generally included in an amount which reduces formation of insoluble aggregates of an antibody, e.g., during bottling, freezing, drying, lyophilization and/or reconstitution. A "surfactant" herein refers to an agent that lowers surface tension of a liquid. The surfactant can be a nonionic surfactant. Non-limiting examples of useful surfactants include polysorbate (polyoxyethylene sorbitan monolaurate, for example, polysorbate 20, polysorbate 40, polysorbate 60, and polysorbate 80); TRITON (t-octylphenoxypolyethoxyethanol, nonionic detergent); sodium dodecyl sulfate (SDS); sodium laurel sulfate; sodium octyl glycoside; lauryl-, myristyl-, linoleyl-, or stearyl-sulfobetaine; lauryl-, myristyl-, linoleyl- or stearylsarcosine; linoleyl-, myristyl-, or cetyl-betaine; lauroamidopropyl-, cocamidopropyl-, linoleamidopropyl-, myristamidopropyl-, palmidopropyl-, or isostearamidopropylbetaine (e.g. lauroamidopropyl); myristamidopropyl-, palmidopropyl-, or isostearamidopropyl-dimethylamine; sodium methyl cocoyl-, or disodium methyl oleyl-taurate; sorbitan monopalmitate; and the MONAQUAT series; polyethyl glycol (PEG), polypropylene glycol (PPG), and copolymers of polyoxyethylene and polyoxypropylene glycol (e.g., pluronics/poloxamer, PF68, etc.); etc. In some embodiments, the surfactant is polysorbate 80. In some embodiments, the surfactant:antibody molar ratio is about 1:1.

Bile Salts

In some embodiments, the formulation comprises at least one bile salt. When present, the one or more bile salts is generally included in an amount enhances absorption of the formulation and/or antibody by the GI tract and/or at the disease site within the GI tract include. Non-limiting examples of bile salts for incorporation into a formulation of the present disclosure include sodium deoxycholate, sodium taurocholate, sodium glycodeoxycholate, sodium taurodihydrofusidate, sodium glycodihydrofusidate.

Mucoadhesive Agents

In some embodiments, the formulation comprises at least one adhesive agent, such as a mucoadhesive agent, wherein the adhesive agent is optionally a thermoreversible adhesive agent. In some embodiments, the formulation is particularly useful in the topical treatment of gastrointestinal mucosal lesions. Non-limiting examples of the at least one adhesive agent for incorporation into formulations of the present disclosure include alginate, gelatin, collagen, poly(acrylic acid), poly(methacrylic acid), poly(L-lysine), poly(ethyleneimine), poly(ethylene oxide), poly(2-hydroxyethyl methacrylate), P(MAA-g-EG) hydrogel microparticles, lectin-conjugated alginate microparticles, thiolated polymer, natural oligosaccharides gum, drum dried waxy maize starch, Carbopol 974P, chitin, chitosan and derivatives thereof (for example, trimethyl chitosan), sea curve 240, scleroglucan, HE-starch, hydroxyl propyl cellulose, cellulose derivatives, pectin, xanthan gum, polycarbophil, amino dextran, DEAE-dextran, aminocaprylate, hyaluronic acid and/or a hyaluronate salt, polyvinyl acetate (PVA), cellulose derivatives such as cellulose sodium glycolate, methyl cellulose, carboxy methylhydroxyethyl cellulose, hydroxyethyl cellulose, propyl cellulose, hydroxypropyl methylcellulose, ethylcellulose, 3-O-ethylcellulose, hydroxypropyl methylcellulose phthalate, ethyl(hydroxyethyl)cellulose, 6-O-alkylated cellulose, cellulose octanoate sulfate, cellulose lauroate sulfate, cellulose stearate sulfate, and cationic derivatives thereof, 6-O-benzylcellulose, 2,3-di-O-methyl-6-O-benzylcellulose, 2,3-di-O-benzylcellulose, 2,3-di-O-benzyl-6-O-methylcellulose, 2,3,6-tri-O-benzylcellulose, hydroxypropyl methylcellulose acetate succinate, O-2-[2-(2-methoxyethoxy)ethoxy]acetyl cellulose, sodium alginate, starch, dextrin, a polyvinyl alcohol, a (poly)vinyl resin, sodium silicate, poloxamers, and the like. When the adhesive agent is sodium alginate, a compound containing divalent ions, such as $CaCl_2$, can be present in the composition.

In some embodiments, the mucoadhesive agent is a cationic polymer. When present, the cationic polymer is generally included in an amount which enhances mucoadhesion, opens tight junctions between cells, or both, for example, via ionic interactions with cell membrane(s). Non-limiting examples of suitable cationic polymers include chitin, chitosan and derivatives thereof (for example, trimethyl chitosan).

In some embodiments, the mucoadhesive agent is an anionic polymer. When present, the anionic polymer is generally included in an amount which enhances mucoadhesion, opens tight junctions between cells, or both. Non-limiting examples of suitable anionic polymers include polymers of acrylic acid cross-linked with polyalkenyl ethers or divinyl glycol (e.g., Carbopol®), polyacrylic acid derivatives, including salts, esters and ethers thereof, and hyaluronic acid, including salts thereof.

In some embodiments, the formulation comprises the antibody and one or more adhesive agents, such as a poloxamer, a hyaluronic acid and/or hyaluronate salt, or a combination thereof.

In some more particular embodiments, the one or more adhesive agents includes a thermoreversible adhesive agent, and the formulation comprising the thermoreversible adhesive agent may be a thermoreversible formulation, essentially as described in WO 2018/019881, which is hereby incorporated by reference in its entirety. Accordingly, in some embodiments, a formulation of the present disclosure comprises the antibody, a hyaluronic acid or a salt thereof and two thermoreversible adhesive agents, wherein one of the two thermoreversible agents is a poloxamer, and wherein the poloxamer and the hyaluronic acid or salt thereof are present in a specific ratio. In some embodiments, the weight ratio between the poloxamer and the hyaluronic acid or its salt is from 60:1 to 10:1. In more particular embodiments, the weight ratio between the poloxamer and the hyaluronic acid or its salt is from 60:1 to 20:1, more particularly from 50:1 to 30:1, more particularly is from 45:1 to 35:1, and even more particularly about 40:1. In some more particular embodiments, the weight ratio between the poloxamer and the second thermoreversible adhesive agent is from about 4:1 to about 25:1, more particularly from about 8:1 to about 12:1, more particularly still from about 9:1 to about 11:1, even more particularly the ratio is 10:1. In some embodiments, the formulation comprises, consists essentially of, or consists of the antibody, the hyaluronic acid or salt thereof, and the one or more mucoadhesive agents, wherein one of the two thermoreversible agents is a poloxamer. In other embodiments, the formulation comprises, consists essentially of, or consists of the antibody, the hyaluronic acid or salt thereof, the one or more mucoadhesive agents, wherein one of the two thermoreversible agents is a poloxamer, and an aqueous medium, such as water, a pH-adjusted water or an aqueous buffer. In some more particular embodiments, the hyaluronic acid or salt thereof is present in an amount ranging from about 0.1 to about 2% (w/w), about 0.25 to about 1.5%, about 0.3 to about 0.8% (w/w), or more particularly about 0.4% (w/w) with respect to the total weight of all formulation excipients (including the aqueous medium), or with respect to the total mass of the formulation, including the antibody. In some further embodiments, the formulation comprises from about 10 to about 25% (w/w) of two thermoreversible adhesive agents, with respect to the total weight of all formulation excipients (including the aqueous medium), or with respect to the total mass of the formulation, including the antibody; wherein one of the thermoreversible adhesive agents is a poloxamer.

In some embodiments, the formulation comprises the antibody and one or more thermoreversible adhesive agents, such as a poloxamer, and does not contain a hyaluronic acid or salt thereof.

In some embodiments, the antibody is a monoclonal antibody; optionally, the monoclonal antibody is selected from the group consisting of adalimumab, vedolizumab, infliximab, etrolizumab, golimumab, certolizumab, certolizumab pegol, ustekinumab, risankizumab, etanercept, brazikumab, natalizumab, PF-00547659, guselkumab, mirikizumab, or any antigen-binding fragment thereof, glycosylation variant thereof, or biosimilar thereof.

Other Excipients

Metal chelators may be a useful component to a formulation. Suitable metal chelators include, for example, methylamine, ethylenediamine, desferoxamine, trientine, histidine, malate, succinate, phosphonate compounds, e.g., etidronic acid, succinic acid, citric acid, salicylates, ethylenediaminetetraacetic acid (EDTA), ethyleneglycoltetraacetic acid (EGTA), and the like.

Formulations may include an anti-oxidant. Suitable antioxidants include, for example, citric acid, uric acid, ascorbic acid, lipoic acid, glutathione, methionine, tocopherol, carotene, lycopene, cysteine and the like.

A preservative may be a useful addition to a formulation. Suitable examples of preservatives include benzyl alcohol, phenol, m-cresol, chlorobutanol and benzethonium Cl.

In some embodiments, a formulation can include an antibody and at least one amphiphilic polysaccharide. Suitable examples of amphiphilic polysaccharides are described, for example, in US 2011/0014189, the disclosure of which is incorporated herein by reference in its entirety.

In some embodiments, a formulation can include an antibody and at least one alkylglycoside. Alkylglycoside may have a critical micelle concentration (CMC) of less than about 1 mM. Presence of an alkylglycoside may reduce aggregation and immunogenicity of the antibody in the formulation. Suitable examples of alkylglycosides include dodecyl maltoside, tridecyl maltoside, tetradecyl maltoside, sucrose mono-dodecanoate, sucrose mono-tridecanoate, and sucrose mono-tetradecanoate. Examples of formulations containing an alkylglycoside are described, for example, in U.S. Pat. No. 8,226,949, which is incorporated herein by reference in its entirety.

A formulation may include N-methyl pyrrolidone (NMP). Concentration of N-methyl pyrrolidone may be, for example, from about 1 mM to about 1000 mM. N-methyl pyrrolidone provides reduced viscosity of the formulation. Exemplary concentrations of NMP include about 50 mM, about 60 mM, about 70 mM, about 80 mM, about 90 mM, about 100 mM, about 110 mM, about 120 mM, about 130 mM, about 140 mM, about 150 mM, about 160 mM, about 170 mM, about 180 mM, about 190 mM, about 200 mM, about 250 mM, about 275 mM, about 300 mM, about 325 mM, about 350 mM, about 375 mM, about 400 mM, about 425 mM, about 450 mM, about 475 mM, about 500 mM, about 525 mM, about 550 mM, about 575 mM, about 600 mM, about 625 mM, about 650 mM, about 675 mM, or about 700 mM. Ranges of amounts of NMP include, but are not limited to, about 50 mM to about 600 mM, about 50 mM to about 150 mM, about 50 mM to about 200 mM, and about 370-600 mM. Additional examples of NMP formulations are disclosed, for example, in WO 2018/067987, which is incorporated herein by reference in its entirety.

Effective Dose

In some embodiments, a formulation can include a dose of about 30-90 mg, about 70-90 mg, about 30-110 mg, about 70-110 mg, about 150-450 mg, or about 300-1200 mg of an antibody, an antigen-binding portion or a biosimilar thereof, or other therapeutic protein. In some embodiments, an effective dose of an antibody, or an antigen-binding portion or a biosimilar thereof, or other therapeutic protein, in a formulation is about 30 mg, about 40 mg, about 50 mg, about 60 mg, about 70 mg, about 80 mg, about 90 mg, about 100 mg, about 125 mg, about 150 mg, about 160 mg, about 175 mg, about 200 mg, about 300 mg, about 400 mg, about 450 mg, about 500 mg, about 600 mg, about 750 mg, about 1000 mg, or about 1200 mg. In some embodiments, the dose is an induction dose. In other embodiments, the dose is a maintenance dose.

Exemplary Antibodies for Formulations

A formulation described herein may include any antibody or fragment thereof, or other therapeutic protein (e.g., a recombinant protein, therapeutic enzyme, etc.). Antibodies can be of any type, e.g., a human, humanized, chimeric, or murine antibody (e.g., a human IgG1 kappa antibody). For example, a formulation described herein may include an anti-TNF-alpha antibody. Exemplary antibodies useful for inclusion in a formulation described herein include adalimumab, vedolizumab, infliximab, etrolizumab, golimumab, certolizumab, certolizumab pegol, ustekinumab, risankizumab, etanercept, brazikumab, natalizumab, PF-00547659 (SHP647), guselkumab, mirikizumab, or any antigen-binding fragment thereof, glycosylation variant thereof, or biosimilar thereof. In some embodiments, a formulation includes an antibody, or antigen-binding fragment thereof, selected from the group consisting of: adalimumab, vedolimumab, vatelizumab, golimumab, certolizumab, certolizumab pegol, and ustekinumab, any antigen binding fragment thereof or a biosimilar thereof. Additional pharmaceutical formulations of antibodies potentially useful in the presently described compositions and methods are disclosed in US Publication Nos. 2012/0282249, US 2009/0291062; U.S. Pat. Nos. 8,420,081 and 8,883,146; and PCT Publication No. WO 02/072636, the disclosures of which are incorporated herein by reference in their entireties.

Antibodies in Crystalline Form

In some embodiments, an antibody or other therapeutic protein is crystalline. Advantages afforded by crystalline protein particles include their dense packing, allowing high drug loading; reduced surface area, which reducing interactions with solvent and polymeric scaffolds and thus may show improved stability over amorphous formulations; potential for controlled/sustained release, which may be attributable to delayed dissolution of crystals even absent polymeric encapsulation (Puhl et al., "Recent Advances in Crystalline and Amorphous Particulate Protein Formulations for Controlled Delivery"; Asian J. Pharm. Sci. 11 (2016), pp. 469-477, which is hereby incorporated by reference in its entirety). In some embodiments, antibody crystals are prepared by batch crystallization. Suitable methods for batch crystallization of antibodies and crystals obtained by those methods include those described in, e.g., U.S. Pat. Nos. 8,034,906 and 8,436,149; and U.S. Patent Application Publication No. 2010/0034823, the disclosures of each of which are incorporated herein by reference in their entirety; examples of needle morphology of the antibody crystals include needles with a maximum length l of about 2-500 m or about 100-300 μm and an l/d ratio of about 3 to 30. In a more particular embodiment, the antibody is adalimumab or a biosimilar thereof. Other suitable methods for antibody batch crystallization are disclosed in Yang et al., "Crystalline monoclonal antibodies for subcutaneous delivery," PNAS, 100(12), 2003, 6934-6939, the disclosure of which is incorporated herein by reference in its entirety.

Exemplary Formulations

In many embodiments, a formulation, at a bare minimum, comprises an antibody and a polyol. In one example, the polyol in the formulation is selected from: sucrose, mannitol, sorbitol, trehalose, raffinose, maltose, and any combination thereof. In another example, the polyol in the formulation is sucrose. In yet another example, the polyol in the formulation is mannitol. In yet another example, the polyol in the formulation is sorbitol.

In many embodiments, a formulation, at a bare minimum, comprises an antibody and a surfactant. In one example, the surfactant in the formulation is non-ionic. In one example, the non-ionic surfactant is a polysorbate. The polysorbate is typically selected from polysorbate 80, polysorbate 60, polysorbate 40, and polysorbate 20. In another example, the non-ionic surfactant is a poloxamer such as poloxamer 188.

In many embodiments, a formulation, at a bare minimum, comprises an antibody and at least one amino acid (e.g., one, two, or three amino acids). In one example, the amino acid in the formulation is selected from arginine, histidine, alanine, glycine, glutamic acid, and methionine. In another example, the formulation comprises L-arginine hydrochloride. In yet another example, the formulation comprises arginine and histidine (e.g., L-arginine and L-histidine). In yet another example, the formulation comprises L-histidine and L-histidine monohydrochloride monohydrate. In yet another example, the formulation comprises L-histidine, L-histidine monohydrochloride monohydrate, and L-methionine. In yet another example, the formulation comprises L-histidine, L-histidine monohydrochloride monohydrate, and L-arginine.

In many embodiments, a formulation, at a bare minimum, comprises an antibody and sodium chloride.

In many embodiments, a formulation, at a bare minimum, comprises an antibody and a buffer. In some embodiments, the buffer comprises a phosphate. In one example, the phosphate is selected from: monobasic sodium phosphate, dibasic sodium phosphate, sodium phosphate monobasic monohydrate, sodium phosphate dibasic heptahydrate, sodium phosphate monobasic dihydrate, and sodium phosphate dibasic dihydrate. In some embodiments, the buffer comprises a citrate. In one example, the citrate is selected from: sodium citrate and citric acid monohydrate. In some embodiments, the buffer comprises an acetate. In one example, the acetate is sodium acetate trihydrate. In some embodiments, a formulation, at a bare minimum, comprises an antibody and a buffer which is not phosphate or citrate. In one example, an amount of phosphate or citrate in the formulation is negligible or non-detectable.

In many embodiments, a formulation, at a bare minimum, comprises an antibody, a polyol, and a surfactant. In other embodiments, a formulation, at a bare minimum, comprises an antibody, a polyol, a surfactant, and at least one amino acid. In yet other embodiments, the formulation, at a bare minimum, comprises an antibody, a polyol, a surfactant, and a buffer. In yet other embodiments, a formulation, at a bare minimum, comprises an antibody, a polyol, a surfactant, at least one amino acid, and a buffer.

In some embodiments, a formulation, at a bare minimum, comprises an antibody, sodium chloride, a phosphate buffer (for example, containing sodium phosphate monobasic monohydrate, sodium phosphate dibasic heptahydrate), and polysorbate 80. In one example, the formulation is liquid and comprises water for injection. In some embodiments, the formulation consists of or consists essentially of the foregoing components.

In some embodiments, a formulation, at a bare minimum, comprises an antibody, a buffer, which is optionally a phosphate and/or citrate buffer, and an excipient selected from a polyol (such as a sugar or sugar alcohol) and a non-ionic surfactant, such as a polysorbate. In one example, the formulation is liquid and contains water for injection. In another example, the formulation contains low levels of ionic excipients and has low conductivity. In some embodiments, the formulation consists of or consists essentially of the foregoing components.

In some embodiments, a formulation, at a bare minimum, comprises an antibody, sodium chloride, a phosphate buffer (for example, containing sodium phosphate monobasic dihydrate, sodium phosphate dibasic dihydrate, or a combination thereof), L-arginine hydrochloride, and sucrose. In one example, the formulation is liquid and contains water for injection. In some embodiments, the formulation consists of or consists essentially of the foregoing components.

In some embodiments, a formulation, at a bare minimum, comprises an antibody, sodium chloride, a phosphate buffer (for example, containing sodium phosphate monobasic dihydrate, sodium phosphate dibasic dihydrate, or a combination thereof), a citrate buffer (for example, containing sodium citrate, citric acid monohydrate, or a combination thereof), mannitol, and polysorbate 80. In one example, the formulation is liquid and contains water for injection. In another example, pH of the liquid formulation is adjusted with NaOH to about 5.2. In some embodiments, the formulation consists of or consists essentially of the foregoing components.

In some embodiments, a formulation, at a bare minimum, comprises an antibody, a buffer, which is optionally a phosphate and/or citrate buffer, a polyol selected from: mannitol, sorbitol, sucrose, trehalose, raffinose, maltose; and a combination thereof, and a non-ionic surfactant selected from polysorbate 20, polysorbate 40, polysorbate 60, and polysorbate 80. In one example, the formulation contains low levels of ionic excipients and has low conductivity. In another example, the concentration of the antibody in the formulation is at least about 10 mg/mL, about 50 mg/mL, about 100 mg/mL, about 150 mg/mL, about 200 mg/mL, or about 250 mg/mL. In some embodiments, the formulation consists of or consists essentially of the foregoing components.

In some embodiments, a formulation, at a bare minimum, comprises an antibody, a phosphate buffer (for example, containing monobasic sodium phosphate and dibasic sodium phosphate), sucrose, and polysorbate 80.

In some embodiments, a formulation, at a bare minimum, comprises an antibody, an amino acid selected from arginine, histidine, and a combination thereof, sucrose, and polysorbate 80. Optionally, the formulation further comprises a buffer. In one example, the formulation is a lyophilized powder. In some embodiments, the formulation consists of or consists essentially of the foregoing components.

In some embodiments, a formulation, at a bare minimum, comprises an antibody, a free amino acid selected from histidine, alanine, arginine, glycine, and glutamic acid, a polyol selected from mannitol, sorbitol, sucrose, trehalose, and a combination thereof, and a surfactant. Optionally, the formulation further comprises a buffer. In one example, the formulation is liquid. In another example, the formulation is solid (e.g., lyophilized powder for reconstitution). In some embodiments, the formulation consists of or consists essentially of the foregoing components.

In some embodiments, a formulation, at a bare minimum, comprises an antibody, an acetate salt, such as sodium acetate trihydrate, an amino acid which is histidine and/or a salt thereof, sorbitol, and a non-ionic surfactant such as polysorbate 80; optionally, the formulation further comprises arginine and/or a salt thereof. In one example, the formulation is liquid and comprises water for injection. In another example, pH of the liquid formulation is from about 5.1 to about 5.3. In yet another example, the formulation contains a negligible or non-detectable amount of sodium chloride. In yet another example, the formulation does not contain phosphate or citrate. In some embodiments, the formulation consists of or consists essentially of the foregoing components.

In some embodiments, a formulation, at a bare minimum, comprises an antibody, an amino acid selected from L-histidine and/or a salt thereof (for example, wherein the L-histidine salt is L-histidine monohydrochloride monohydrate), and a combination thereof, sorbitol and polysorbate 80. In one example, the formulation is liquid and comprises water for injection. In some embodiments, the formulation consists of or consists essentially of the foregoing components.

In some embodiments, a formulation, at a bare minimum, comprises an antibody, an amino acid selected from L-histidine, a L-histidine salt (for example, L-histidine monohydrochloride monohydrate), L-methionine, and a combination of any two or more of the foregoing, sucrose, and polysorbate 80. In one example, the formulation also contains a metal chelating agent such as EDTA disodium salt dihydrate. In another example, the formulation is liquid and contains water for injection. In some embodiments, the formulation consists of or consists essentially of the foregoing components.

In some embodiments, a formulation, at a bare minimum, comprises an antibody, an amino acid selected from L-histidine and a L-histidine salt (for example, L-histidine monohydrochloride monohydrate), and a combination thereof, sucrose, and polysorbate 80. In some embodiments, the formulation consists of or consists essentially of the foregoing components. In other embodiments, the formulation further comprises water for injection (WFI), or a pH-adjusted water (e.g., pH-adjusted WFI). In further embodiments, the pH-adjusted water is pH-adjusted to pH 5.8.

In some embodiments, a formulation, at a bare minimum, comprises an antibody, an amino acid selected from L-histidine, a L-histidine salt (for example, L-histidine monohydrochloride monohydrate), a L-arginine salt (for example, L-arginine hydrochloride), and a combination of any two or more of the foregoing, sucrose, and polysorbate 80. In some embodiments, the formulation consists of or consists essentially of the foregoing components.

In some embodiments, a formulation, at a bare minimum, comprises an antibody, an amino acid selected from L-histidine and L-arginine, and a combination thereof, polysorbate 20, and succinic acid. In some embodiments, the formulation consists of or consists essentially of the foregoing components.

In some embodiments, a formulation, at a bare minimum, comprises an antibody (for example, at a concentration of at least about 100 mg/mL, or at least about 110 mg/mL or 125 mg/mL), mannitol, and polysorbate 80. In one example, the formulation is liquid and contains water for injection. In some embodiments, the formulation consists of or consists essentially of the foregoing components.

In some embodiments, a formulation, at a bare minimum, comprises an antibody, a polyol such as mannitol, and a surfactant selected from a polysorbate (e.g., polysorbate 20 or 80) and a poloxamer (for example, poloxamer 188); and wherein the formulation contains a negligible or non-detectable amount of salt, and a negligible or non-detectable amount of buffer. In one example, the formulation has an antibody concentration of at least about 50 mg/mL, about 75 mg/mL, or about 100 mg/mL or greater, and has low conductivity. In some embodiments, the formulation consists of or consists essentially of the foregoing components.

In some embodiments, a formulation, at a bare minimum, comprises an antibody, a mineral salt such as sodium chloride and an acetate salt, such as sodium acetate. In one example, the formulation is a liquid formulation which comprises a water for injection. In some embodiments, the formulation consists of or consists essentially of the foregoing components.

In one embodiment, the formulation comprises, consists essentially of, or consists of an antibody, such as a monoclonal antibody, a salt, a buffer system, a polyol and a non-ionic surfactant. The formulation may be provided in an aqueous medium or in dry powder form. In more particular embodiments, the buffer system includes a citrate buffer system (for example, sodium citrate and citric acid monohydrate), a phosphate buffer system (for example, monobasic sodium phosphate dihydrate and dibasic sodium phosphate) or both. In more particular embodiments, the polyol is mannitol, sorbitol, sucrose, trehalose, raffinose, maltose, or a combination thereof. In more particular embodiments still, the non-ionic surfactant is a polysorbate (e.g., polysorbate, 20, 40, 60, 80, or a combination thereof) and/or a poloxamer (e.g., 188). In some embodiments, the salt is sodium chloride. In some embodiments, the pH of the formulation ranges from about 5 to about 8. In other embodiments, the pH ranges from about 5 to about 5.5, from about 5.1 to about 5.3, or is about 5.2. Optionally, the monoclonal antibody is adalimumab or a biosimilar thereof.

In another embodiment, the formulation comprises, consists essentially of, or consists of an antibody, such as a monoclonal antibody, an acetate salt, a polyol, a non-ionic surfactant, one or more amino acids, and negligible or non-detectable levels of salts other than the acetate salt (e.g., the formulation may exclude sodium chloride); the formulation contains negligible or non-detectable levels of citrate and phosphate buffer systems. The formulation may be provided in an aqueous medium or in dry powder form. The aqueous formulation or the reconstituted dry powder has an acidic pH, e.g., less than 6. In more particular embodiments, the acetate salt is sodium acetate trihydrate. In more particular embodiments, the polyol is mannitol, sorbitol, sucrose, trehalose, raffinose, maltose, or a combination thereof; in some embodiments, the polyol is sorbitol. In more particular embodiments still, the non-ionic surfactant is a polysorbate (e.g., polysorbate, 20, 40, 60, 80, or a combination thereof) and/or a poloxamer (e.g., 188); in some embodiments, the non-ionic surfactant is polysorbate 80. In yet more particular embodiments, the one or more amino acids is histidine or a salt thereof, optionally further including arginine or a salt thereof. Optionally, the monoclonal antibody is adalimumab or a biosimilar thereof. In some embodiments, the pH of the formulation ranges from about 5 to about 8.

In another embodiment, the formulation comprises, consists essentially of, or consists of an antibody, such as a monoclonal antibody, a polyol, a non-ionic surfactant and one or more free amino acids; the formulation contains negligible or non-detectable levels of ionic excipients, and thus negligible or non-detectable levels of an acetate buffer or salt, negligible or non-detectable levels a citrate buffering system and negligible or non-detectable levels of a phosphate buffering system. The formulation may be provided in an aqueous medium or in dry powder form. Accordingly, when the formulation is in an aqueous media or the dry powder form is reconstituted or exposed to an aqueous media, the resulting composition has a low conductivity. In more particular embodiments, the polyol is mannitol, sorbitol, sucrose, trehalose, raffinose, maltose, or a combination thereof; in some embodiments, the polyol is mannitol or sucrose. In more particular embodiments, the non-ionic surfactant is a polysorbate (e.g., polysorbate, 20, 40, 60, 80, or a combination thereof) and/or a poloxamer (e.g., 188); in some embodiments, the non-ionic surfactant is polysorbate 80. In yet more particular embodiments, the one or more free amino acids is selected from histidine, alanine, arginine, glycine, glutamic acid, and combinations of any two or more of the foregoing; in some embodiments, the amino acid is histidine and/or arginine. In some embodiments, the monoclonal antibody is vedolizumab or a biosimilar thereof. In some embodiments, the pH of the formulation ranges from about 5 to about 8.

In another embodiment, the formulation consists essentially of or consists of an antibody, such as a monoclonal antibody, a polyol, and a non-ionic surfactant; the formulation contains low, negligible or non-detectable levels of salts and/or buffering systems; for example, the formulation contains negligible or non-detectable levels of acetate salt, citrate buffers, phosphate buffers, and amino acids salts. The formulation may be provided in an aqueous medium or in dry powder form. In more particular embodiments, the polyol is mannitol, sorbitol, sucrose, trehalose, raffinose, maltose, or a combination thereof; in some embodiments, the polyol is mannitol. In more particular embodiments, the non-ionic surfactant is a polysorbate (e.g., polysorbate, 20, 40, 60, 80, or a combination thereof) and/or a poloxamer (e.g., 188); in some embodiments, the non-ionic surfactant is polysorbate 80. In some embodiments, the monoclonal antibody is adalimumab or a biosimilar thereof.

Aqueous/Liquid Formulations

In some embodiments, the present disclosure provides a liquid pharmaceutical formulation comprising a therapeutically effective amount of an antibody, which is a solution, suspension, or a dispersion (e.g., a buffered aqueous solution). A buffered solution can include a citrate buffer or a phosphate buffer, e.g., citric acid, sodium citrate, disodium phosphate dihydrate, and sodium dihydrogen phosphate dihydrate; polyols, such as mannitol or sucrose; salts, such as sodium chloride or sodium acetate; a detergent, such as a non-ionic surfactant, including polysorbate 20 or 80; and a mineral base or acid, such as sodium hydroxide or hydrochloric acid, for pH adjustment.

pH of Liquid Formulations

In some embodiments, the pH of a liquid composition can be from about 4 to about 8, from about 4.5 to about 6.0, from about 4.7 to about 5.7, from about 4.8 to about 5.5, or from about 5.0 to about 5.2. In some embodiments, the pH of a liquid composition can be from about 5 to about 8, from about 5.5 to about 7.5, about 6.0 to about 7.0, or about 6.0 to about 6.5, such as about 6.0, about 6.1, about 6.2, about 6.3, about 6.4 or about 6.5.

Concentration of Antibody in a Liquid Composition

In some embodiments, a liquid aqueous pharmaceutical formulation can include a high concentration of an antibody, e.g., ranging from about 40 to about 400 mg/mL, about 1 to about 150 mg/mL, or about 50 to about 200 mg/mL. In some embodiments, the formulation is stable without the need for any additional agents. Concentration of an antibody in a liquid aqueous pharmaceutical formulation may for example be greater than about 45 mg/mL, about 50 mg/mL, about 150 mg/mL, or about 200 mg/mL. In some embodiments, an antibody, or an antigen-binding portion or a biosimilar, or other therapeutic protein, can remain soluble at a high protein concentration (e.g., at least about 40 mg/mL, about 45 mg/mL, about 50 mg/mL, about 55 mg/mL, about 60 mg/mL, about 65 mg/mL, about 70 mg/mL, about 75 mg/mL, about 80 mg/mL, about 85 mg/mL, about 90 mg/mL, about 96 mg/mL, about 100 mg/mL, about 105 mg/mL, about 110 mg/mL, or more) and does not contain a buffer or a salt. In some embodiments, the concentration of an antibody, or an antigen-binding fragment or a biosimilar thereof, in the formulation can be about 90-110 mg/mL, about 95-105 mg/mL, or about 75-125 mg/mL.

In some embodiments, the formulation is a high concentration formulation wherein the concentration of the antibody in the formulation is greater than 100 mg/mL. In other aspects, the concentration of the antibody in the formulation is at least about 110 mg/mL or at least about or at least about 125 mg/mL. In other aspects, the concentration of the antibody in the formulation is at least about 150 mg/mL. In other aspects, the concentration of the antibody in the formulation is at least about 175 mg/mL. In yet other aspects, the concentration of the antibody in the formulation ranges from about 100 mg/mL to about 200 mg/mL, from about 110 mg/mL to about 250 mg/mL, from about 125 mg/mL to about 200 mg/mL, or from about 150 mg/mL to about 200 mg/mL. In some aspects, the concentration of the antibody in the formulation ranges from about 140 mg/mL to about 180 mg/mL. In some aspects, the concentration of the antibody is about 150 mg/mL. In some aspects, the concentration of the antibody is about 175 mg/mL.

Concentration of Surfactant in a Liquid Composition

In some embodiments, a surfactant used in a liquid formulation is a polysorbate (e.g., polysorbate 80). For example, the concentration of a surfactant (such as polysorbate) in a liquid formulation may be about 0.1-1.5 mg/mL, about 0.2-1.4 mg/mL, about 0.3-1.3 mg/mL, about 0.4-1.2 mg/mL, about 0.5-1.1 mg/mL, about 0.6-1.0 mg/mL, about 0.6-1.1 mg/mL, about 0.7-1.1 mg/mL, about 0.8-1.1 mg/mL, or about 0.9-1.1 mg/mL. In some embodiments, the polysorbate in a liquid formulation is at a concentration of about 0.1-10 mg/mL, about 0.5-5 mg/mL, about 0.1-2 mg/mL, or about 1 mg/mL. In another example, the concentration of the surfactant in a formulation may be from about 10 mg/mL to about 200 mg/mL, such as for example about 20 mg/mL, about 30 mg/mL, about 40 mg/mL, about 50 mg/mL, about 60 mg/mL, about 70 mg/mL, about 80 mg/mL, about 90 mg/mL, about 100 mg/mL, about 110 mg/mL, about 120 mg/mL, about 130 mg/mL, about 140 mg/mL, about 150 mg/mL, about 180 mg/mL, or about 200 mg/mL.

Concentration of a Polyol in a Liquid Composition

In some embodiments, the concentration of a polyol in a liquid formulation is less than about 50 mg/mL or about 45 mg/mL. In others, a liquid formulation contains about 38-46 mg/mL of the polyol (e.g., mannitol). That is, a liquid formulation can include about 35 mg/mL, about 36 mg/mL, about 37 mg/mL, about 38 mg/mL, about 39 mg/mL, about 40 mg/mL, about 41 mg/mL, about 42 mg/mL, about 43 mg/mL, about 44 mg/mL, about 45 mg/mL, about 46 mg/mL, about 47 mg/mL, about 48 mg/mL, about 49 mg/mL, about 50 mg/mL, about 51 mg/mL, about 52 mg/mL, about 53 mg/mL, about 54 mg/mL, or about 55 mg/mL of the polyol. In addition, ranges of values using a combination of any of the above recited values as upper and/or lower limits are intended to be included, e.g., there may be about 39-45 mg/mL, about 40-44 mg/mL, or about 37-47 mg/mL of polyol in the composition. In some embodiments, a liquid formulation includes about 12-72 mg/mL of polyol, e.g., mannitol. A liquid formulation may include mannitol or sorbitol.

In some embodiments, a liquid formulation comprises an antibody, or an antigen binding portion or a biosimilar thereof, at a concentration of more than about 50 mg/mL, less than about 50 mg/mL of a polyol (such as mannitol), and a surfactant, such as polysorbate. In some embodiments, a liquid formulation comprises an antibody at a concentration of about 90-110 mg/mL, and a polyol at a concentration of less than about 50 mg/mL, and a surfactant (e.g., polysorbate 80).

In some embodiments, the concentration of polyol (e.g., non-reducing sugar) in a liquid antibody formulation (e.g., pre-drying or post-reconstitution) can be in the range from about 10 mM to about 1 M, for example, from about 60 mM to about 600 mM, about 100 mM to about 450 mM, about 200 mM to about 350 mM, about 250 mM to about 325 mM, or about 275 mM to about 300 mM.

Amino Acids in Liquid Formulations

In some embodiments, a liquid formulation can include one or more amino acids and/or salts thereof, such as histidine or a combination of histidine and arginine, or more particularly, L-histidine and/or L-arginine. In some embodiments, the concentrations of the amino acid and/or salts thereof for liquid formulations are in the range from about 10 mM to about 0.5 M, about 15 mM to about 300 mM, about 20 mM to about 200 mM, about 25 mM to about 150 mM, about 50 mM, or about 125 mM.

Exemplary Liquid Formulations

In some embodiments, a liquid aqueous formulation comprises an antibody or antigen-binding fragment thereof (or other therapeutic protein), a surfactant, and a polyol, and does not contain a buffer or a salt. In some embodiments, a liquid aqueous formulation comprises less than 50 mg/mL of a polyol. In some embodiments, a liquid aqueous formulation comprises an antibody or antigen-binding fragment thereof (or other therapeutic protein), a surfactant, and a polyol; wherein the concentration of the antibody, or antigen-binding portion or a biosimilar thereof, is at least about 50 mg/mL, about 75 mg/mL, about 100 mg/mL, or greater than about 100 mg/mL. In some embodiments, a liquid aqueous formulation comprises an antibody or antigen-binding fragment thereof (or other therapeutic protein), at a concentration of at least about 50 mg/mL, about 75 mg/mL, about 100 mg/mL, or greater than about 150 mg/mL, a surfactant, and a polyol; wherein the formulation does not contain a buffer and a salt. In some embodiments, a liquid aqueous formulation consists essentially of a surfactant and about 30-90 mg of an antibody or antigen-binding fragment thereof (or other therapeutic protein), wherein concentration of the antibody is about 90-110 mg/mL.

In one example, the polyol is mannitol and the surfactant is polysorbate 80. In another example, the liquid composition includes about 5-20 mg/mL of mannitol and about 0.1-10 mg/mL of polysorbate 80. In some embodiments, a liquid formulation comprises at least about 50 mg/mL to about 100 mg/mL of an antibody, a buffering agent (e.g., histidine), and at least about 9% (w/w) of a non-reducing sugar (e.g., sucrose, trehalose or mannitol). In some embodiments, a liquid formulation comprises at least about 50 mg/mL to about 80 mg/mL (or about 60 mg/mL) of an antibody, a buffering agent (e.g., histidine), a free amino acid (e.g., arginine) and at least about 9% or 10% (w/w) of a non-reducing sugar (e.g., sucrose, trehalose or mannitol). In some embodiments, a liquid formulation comprises at least about 60 mg/mL of an antibody, at least about 10% (w/v) of a non-reducing sugar, and at least about 125 mM of one or more free amino acids. In some embodiments, a liquid formulation comprises at least about 60 mg/mL of an antibody, at least about 10% (w/v) of a non-reducing sugar, and at least about 175 mM of one or more free amino acids. In some embodiments, a liquid formulation comprises from about 60 mg/mL to about 80 mg/mL of an antibody, a buffering agent and at least about 10% (w/w) of a sugar. In some embodiments, a liquid formulation comprises from about 60 mg/mL to about 80 mg/mL of an antibody, histidine and at least about 10% (w/w) of sucrose.

Special Properties of Liquid Formulations/Conductivity

An antibody or antigen-binding fragment thereof (or other therapeutic protein), may be formulated in an aqueous formulation essentially as described in US 2009/0291062 A1 and U.S. Pat. No. 8,420,081, each of which is incorporated herein by reference in its entirety. In some cases, despite the high concentration of protein, the formulation can have minimal aggregation and can be stored using various methods and forms, e.g., freezing, without deleterious effects that might be expected with high protein formulations. Formulations of the disclosure may in some embodiments not require excipients, such as, for example, surfactants and buffering systems, which are used in traditional formulations to stabilize proteins in solution. However, the formulations may contain these excipients for enhanced stability.

In some embodiments, an aqueous formulation of the disclosure can include low levels of ionic excipients, and thus has low conductivity, e.g., less than 2 mS/cm. The methods and compositions also provide aqueous antibody formulations having low osmolality, e.g., no greater than 30 mOsmol/kg. In some embodiments, a formulation has a low conductivity, including, for example, a conductivity of less than about 2.5 mS/cm, about 2 mS/cm, about 1.5 mS/cm, about 1 mS/cm, about 0.9 mS/cm, or about 0.5 mS/cm. In some embodiments, a formulation has an osmolality of no more than about 15 mOsmol/kg. In some embodiments, the disclosure provides for an aqueous formulation comprising an antibody, or an antigen-binding fragment thereof, wherein the protein has a hydrodynamic diameter ($D_h$) of less than about 5 μm, about 4 μm, about 3 μm, about 2 μm, or about 1 μm.

In some embodiments, the liquid aqueous formulation comprises an antibody or antigen-binding fragment thereof (or other therapeutic protein), at a concentration of at least about 50 mg/mL, a surfactant and a polyol, wherein the formulation has a conductivity of less than about 2 mS/cm. In some embodiments, the liquid aqueous formulation comprises an antibody or antigen-binding fragment thereof (or other therapeutic protein) at a concentration of at least about 50 mg/mL, a surfactant, and a polyol; wherein the antibody or antigen-binding fragment thereof (or other therapeutic protein), has a hydrodynamic diameter of less than about 5 nm, about 4 nm, or about 3 nm in the formulation. In some embodiments, a liquid aqueous formulation comprises an antibody or antigen-binding fragment thereof (or other therapeutic protein), a surfactant, and less than about 50 mg/mL of a polyol, wherein the formulation has a conductivity of less than about 2 mS/cm, a hydrodynamic diameter ($D_h$) which is at least about 50% less than the $D_h$ of the protein in a buffered solution at a given concentration; and a hydrodynamic diameter ($D_h$) of less than about 4 nm. In some embodiments, the formulation has a conductivity of less than about 1 mS/cm, or about 0.9 mS/cm.

Water-based formulations may comprise non-ionizable excipients that improve, for example, the osmolality or viscosity features of the formulation. Examples of non-ionizable excipients which may be included in aqueous formulations for altering desired characteristics of the formulation include, but are not limited to, mannitol, sorbitol, a non-ionic surfactant (e.g., polysorbate 20, polysorbate 40, polysorbate 60 or polysorbate 80), sucrose, trehalose, raffinose, and maltose.

In some embodiments, the disclosure provides for an aqueous formulation comprising an antibody or antigen-binding fragment thereof (or other therapeutic protein) at a concentration of at least 20 mg/mL and water, wherein the formulation has a conductivity of less than about 2.5 mS/cm and the antibody or antigen-binding fragment thereof (or other therapeutic protein), has a molecular weight greater than about 47 kDa. In some embodiments, the concentration of the antibody or antigen-binding fragment thereof is at least 50 mg/mL, and the formulation has an osmolality of no more than about 30 mOsmol/kg. In some embodiments, the antibody or antigen-binding fragment thereof has a hydrodynamic diameter ($D_h$) which is at least about 50% less than the $D_h$ of the antibody, or antigen-binding fragment thereof, in a buffered solution at the same concentration; more particularly, wherein the buffered solution is PBS.

Methods of Making Aqueous Formulations

Skilled practitioners will appreciate that any number of methods may be used to make an aqueous formulation. Methods of making aqueous formulations, as disclosed in US 2009/0291062 and U.S. Pat. No. 8,420,081, may be based on a diafiltration process wherein a first solution containing a protein is diafiltered using water as a diafiltration medium. Protein production operations often involve final diafiltration of a protein solution into a formulation buffer once the protein has been purified from impurities resulting from its expression. For example, an aqueous formulation may be made by subjecting a protein solution to diafiltration using water alone as a diafiltration solution. Proteins may be transferred into pure water for use in a stable formulation, wherein the protein remains in solution and can be concentrated at high levels without the use of other agents to maintain its stability. Diafiltration uses membranes to remove, replace, or lower the concentration of salts or solvents from the protein solutions. Diafiltration or diafiltration/ultrafiltration (DF/UF) selectively utilizes permeable (porous) membrane filters to separate the components of solutions and suspensions based on their molecular size. One parameter for selecting a membrane for concentration is its retention characteristics for the sample to be concentrated. To assure complete retention, the molecular weight cut-off (MWCO) of the membrane should be about ⅓$^{rd}$ to about ⅙$^{th}$ of the molecular weight of the molecule to be retained. In order to prepare a low-ionic protein formulation, the protein solution (which may be solubilized in a buffered formulation) is subjected to a DF/UF process, whereby water is used as a DF/UF medium. In some embodiments, the DF/UF medium consists of water and does not include any other excipients. Any water can be used in the DF/UF process, although particularly useful water is purified or deionized water. The process may be performed such that there is at least a determined volume exchange, e.g., a five-fold volume exchange, with the water. The resulting aqueous formulation has a significant decrease in the overall percentage of excipients in comparison to the initial protein solution. For example, 95-99% less excipients may be found in the aqueous formulation in comparison to the initial protein solution. Despite the decrease in excipients, the protein can remain soluble and retain its biological activity, even at high concentrations. In some embodiments, the methods of the present disclosure result in compositions comprising an increase in concentration of the protein while decreasing additional components, such as ionic excipients. As such, the hydrodynamic diameter of the protein in the aqueous formulation is smaller relative to the same protein in a standard buffering solution, such as phosphate buffered saline (PBS). Methods may include diafiltering a protein solution using water as a diafiltration medium and subsequently concentrating the resulting aqueous solution. Concentration following diafiltration results in an aqueous formulation containing water and an increased protein concentration relative to the first protein solution. Concentration of the diafiltered protein solution may be achieved through means known in the art, including centrifugation. There are two forms of DF/UF, including DF/UF in discontinuous mode and DF/UF in continuous mode. Useful methods described herein may be performed according to either mode.

In some embodiments, the first protein solution is subjected to a repeated volume exchange with the water, such that an aqueous formulation, which is essentially water and protein, is achieved. The diafiltration step may be performed any number of times, depending on the protein in solution, wherein one diafiltration step equals one total volume exchange. As a result of the diafiltration methods, the concentration of solutes in the first protein solution is significantly reduced in the final aqueous formulation comprising essentially water and protein. For example, the aqueous formulation can have a final concentration of excipients which is at least 95% less than the first protein solution, for example, at least 99% less than the first protein solution. For example, in one embodiment, to dissolve a protein in WFI is a process that creates a theoretical final excipient concentration, reached by constant volume diafiltration with five diafiltration volumes, that is equal or approximate to Ci e=0.00674, i.e., an approximate 99.3% maximum excipient reduction.

The terms "excipient-free" or "free of excipients" indicate that the formulation is essentially free of excipients. In some embodiments, excipient-free indicates buffer-free, salt free, sugar-free, amino acid-free, surfactant-free, and/or polyol free. In some embodiments, the term "essentially free of excipients" indicates that the solution or formulation is at least 99% free of excipients. It should be noted, however, that in certain embodiments, a formulation may comprise a certain specified non-ionic excipient, e.g., sucrose or mannitol, and yet the formulation is otherwise excipient free. For example, a formulation may comprise water, a protein, and mannitol, wherein the formulation is otherwise excipient free. In another example, a formulation may comprise water, a protein, and polysorbate 80, wherein the formulation is otherwise excipient free. In yet another example, the formulation may comprise water, a protein, a sorbitol, and polysorbate 80, wherein the formulation is otherwise excipient free.

In some embodiments, certain characteristics of the formulation may be adjusted, such as the osmolality and/or viscosity, as desired in high protein concentration-water solutions, by adding non-ionic excipients (e.g., mannitol) without changing other desired features, such as non-opalescence. As such, either during or following the transfer of the protein to water or during the course of the diafiltration, excipients may be added that improve, for example, the osmolality or viscosity features of the formulation. Such non-ionic excipients could be added during the process of the transfer of the protein into the final low ionic formulation. Examples of non-ionizable excipients that may be added to the aqueous formulation for altering desired characteristics of the formulation include, but are not limited to, mannitol, sorbitol, a non-ionic surfactant (e.g., polysorbate 20, polysorbate 40, polysorbate 60 or polysorbate 80), sucrose, trehalose, raffinose, and maltose.

In some embodiments, a liquid formulation can be a solution or suspension prepared in a suitable aqueous solvent, e.g., water or aqueous/organic mixture, such as a water/alcohol mixture. Liquid formulations may be refrigerated (e.g., 2-8° C.) or frozen (e.g., at −20° C. or −80° C.) for storage.

In some embodiments, the present disclosure provides a method for generating a high concentration, aqueous protein suspension preparation, wherein proteins can be therapeutic antibodies. The suspension comprises a protein and a polyamino acid, which serves as a precipitant. The protein and polyamino acid (e.g., poly-L-lysine or poly-L-glutamic acid) form a complex at low ionic strength that is suspended in the buffer. In one example, proteins at about 1.0 mg/mL to about 200 mg/mL are fully precipitated by the addition of about 0.05-0.3 mg/mL poly(amino acid). The protein is stabilized and can be concentrated by removing water or supernatant from the aqueous suspension, for example, following centrifugation of the precipitates. The precipitates are then dissolved by addition of a buffer with salt, for example, at physiological ionic strength of 150 mM sodium chloride (NaCl).

These methods result in redissolved proteins that retain the original activity and native secondary structure of the protein. Also, the method of the present disclosure eliminates the need for the addition of additives that may be necessary for other formulations. In some embodiments, the suspension preparation does not need a dissolving step. The preparation method also has the advantage of producing a concentrated suspension with a relatively low viscosity as compared to other high concentration protein formulations. Exemplary methods and preparations for generating high concentration protein formulations via precipitation and re-dissolution using polyamino acid are described, for example, in US application publication No. 2016/0206752 and Kurinomaru, Takaaki, et al., "Protein-poly (amino acid) complex precipitation for high-concentration protein formulation," Journal of Pharmaceutical Sciences 103.8 (2014): 2248-2254, the disclosure of which is incorporated herein by reference in its entirety.

Solid Formulations

In some aspects, the antibody is provide as a solid. In some aspects, the antibody is provided in crystalline form. In other embodiments, the antibody is provided in amorphous form. In some embodiments, the drug is provided as a lyophilized powder or in extruded form. In one embodiment, the solid drug formulation comprises, consists of or consists essentially of the antibody.

In the case of such solid formulations, such as powders (e.g., for direct incorporation into a device as disclosed herein, or for the preparation of solutions for incorporation into a device as disclosed herein), useful methods of preparation are vacuum drying and freeze-drying that yields a powder of the antibody plus any additional desired ingredient from a previously prepared solution thereof. In some embodiments, a solid formulation (e.g., in a dried state) can be stable for at least three months at about 40° C. and 75% relative humidity (RH). A solid formulation may also have a moisture content of no more than about 5%, about 4.5%, about 4%, about 3.5%, about 3%, about 2.5%, about 2%, about 1.5%, or about 1%; or the solid formulation is substantially anhydrous.

Amount of Antibody in Solid Formulations

In some embodiments, a lyophile after the lyophilization contains, for example, from about 50 wt. % to about 100 wt. %, from about 55 wt. % to about 95 wt. %, from about 60 wt. % to about 90 wt. %, or from about 70 wt. % to about 80 wt. % of an antibody. In some embodiments, a liquid formulation can be reconstituted from a solid lyophilized formulation (e.g., reconstituted to comprise a stable liquid formulation as described herein).

Amount of Polyol in Solid Formulations

The amount of a polyol (e.g., mannitol, sorbitol, sucrose, trehalose, raffinose, maltose, etc.), in a dry (e.g., lyophilized) antibody formulation can be, e.g., in the range from about 40% to about 70% (w/w of dry formulation). More particularly, an amount of the polyol in the dry (e.g., lyophilized) antibody formulation can be in the range from about 40% to about 60%, from about 45% to about 55% or about 51% (w/w). In some embodiments, an amount of the polyol in the dry (e.g., lyophilized) antibody formulation is greater than about 51% (w/w of dry formulation) when the antibody amount is about 31% (w/w of dry formulation) or greater than about a 1.6:1 mass ratio of the polyol (e.g., non-reducing sugar) to the antibody in the dry formulation.

Amount of Amino Acid in Solid Formulations

In some embodiments, an amount of a free amino acid (and/or salt thereof) in a dry, (e.g., lyophilized) formulation can be in the range from about 1% to about 10% (w/w of dry formulation), or from about 3% to about 6% (w/w). In some embodiments, an amount of amino acid in a dry, (e.g., lyophilized) formulation can be greater than about 4% (w/w of the dry formulation) when the antibody amount is about 31% (w/w of the dry formulation) or greater than about a 0.15:1 mass ratio of the amino acid to protein in the dry formulation. In still yet another embodiment, an amount of free amino acid in a dry (e.g., lyophilized) formulation can be in the range from about 4% to about 20% (w/w of dry formulation), or from about 10% to about 15% (w/w). In some embodiments, an amount of amino acid in a dry (e.g., lyophilized) formulation can be greater than about 13% (w/w of the dry formulation) when the protein amount is about 31% (w/w of the dry formulation) or greater than about a 0.4:1 mass ratio of amino acid to protein in the dry formulation. In some embodiments, the amino acid is histidine or arginine or a combination of both.

Amount of Surfactant in Solid Formulations

A surfactant concentration, e.g., in a pre-drying, (e.g., before lyophilization) or post-reconstitution formulation, can be, e.g., from about 0.0001% to about 1.0%, from about 0.01% to about 0.1%, for example about 0.02%, about 0.03%, about 0.04%, about 0.05%, about 0.06%, about 0.07%, about 0.08,%, about 0.09% (w/v), about 0.05% to about 0.07%, or about 0.06% (w/v). A surfactant amount, e.g., in a dry (e.g., lyophilized) formulation, can generally be from about 0.01% to about 3.0% (w/w), from about 0.10% to about 1.0%, for example about 0.15%, about 0.20%, about 0.25%, about 0.30%, about 0.35%, about 0.40%, or about 0.50% (w/w). In some embodiments, the surfactant is polysorbate 80.

Exemplary Solid Formulations

In some embodiments, a solid (e.g., lyophilized) formulation comprises a mixture of a polyol, such as a non-reducing sugar, an antibody, histidine, arginine, and polysorbate 80, and the molar ratio of polyol (e.g., non-reducing sugar) to the antibody (mole:mole) is greater than about 600:1. In some embodiments, a solid (e.g., lyophilized) formulation comprises a mixture of a polyol, such as a non-reducing sugar, an antibody, histidine, arginine, and polysorbate 80, molar ratio of non-reducing sugar to the antibody (mole:mole) is greater than about 600:1, and the molar ratio of arginine to the antibody (mole:mole) in the formulation is greater than 250:1.

Methods of Making Solid Formulations

Freeze-drying is a commonly employed technique for preserving proteins; freeze-drying serves to remove water from the protein preparation of interest. Freeze-drying, or lyophilization, is a process by which the material to be dried is first frozen and then the ice or frozen solvent is removed by sublimation under vacuum. Excipients can be included in the pre-lyophilized formulation to stabilize proteins during the lyophilization process and/or to improve the stability of the lyophilized protein formulation (Pikal M., *Biopharm.* 3(9)26-30 (1990) and Arakawa et al. *Pharm. Res.* 8(3):285-291 (1991)).

Amorphous proteins can be obtained by any suitable means, including freeze drying, spray-drying, spray-freeze drying, or precipitation, for example, from supercritical fluids. The foregoing processes, being relatively mild, advantageously provide the biologic protein in stable form with retention of the therapeutic activity.

Reconstitution of Solid Formulations

In some embodiments, a solid formulation can be dissolved (e.g., reconstituted) in a suitable medium or solvent to become a liquid formulation as described herein, suitable for administration to a patient by any suitable route, including incorporation into a device as disclosed herein. Suitable examples of solvents for reconstituting the solid formulation include water, isotonic saline, buffer, e.g., phosphate-buffered saline, citrate-buffered saline, Ringer's (lactated or dextrose) solution, minimal essential medium, alcohol/aqueous solutions, dextrose solution, etc. The amount of solvent can result in an antibody concentration higher, the same, or lower than the concentration of the antibody in the composition prior to drying.

In some embodiments, a liquid formulation is lyophilized and stored as a single dose in a container which may contain at least about 120 mg, about 180 mg, about 240 mg, about 300 mg, about 360 mg, about 540 mg, or about 900 mg of an antibody. The final dosage form, e.g., after dilution of the reconstituted antibody (e.g., in a saline or 5% dextrose), concentration of the antibody can be from about 0.5 mg/mL to about 500 mg/mL, for example, about 50 mg/mL, about 100 mg/mL, about 110 mg/mL, about 125 mg/mL, about 150 mg/mL, about 175 mg/mL, about 200 mg/mL, or greater.

Controlled-Release Formulations and Formulations with Encapsulated Therapeutic Proteins An antibody or another therapeutic protein may be prepared with a carrier that will protect it against rapid release, such as in a controlled-release formulation, including microencapsulated delivery systems. Biodegradable, biocompatible polymers can be used in these formulations, such as ethylene vinyl acetate, polyanhydrides, polyglycolic acid, collagen, polyorthoesters, and polylactic acid. Many methods for preparing such formulations are known to skilled practitioners. See, e.g., Sustained and Controlled Release Drug Delivery Systems, J. R. Robinson, ed., Marcel Dekker, Inc., New York, 1978.

In some embodiments, when antibody is crystalline, the protein crystals in the formulation can be embedded in, or encapsulated by, an excipient. Suitable examples of such excipients include any one or more of the polymers described herein. In some embodiments, crystals can then be embedded by drying the crystals and combining these dried crystals with a carrier, e.g., by compression, melt dispersion, etc. In some embodiments, crystals may be encapsulated/embedded by combining a crystal suspension with a carrier solution that is not miscible with water. The carrier precipitates after removal of the solvent of the carrier. Subsequently, the material is dried. In some embodiments, antibody crystals are encapsulated/embedded by combining a crystal suspension with a water miscible carrier solution. The carrier precipitates as its solubility limit is exceeded in the mixture. In some embodiments, antibody crystals are embedded by combining dried crystals or a crystal suspension with a water miscible carrier solution.

Antibody crystals may be encapsulated within a polymeric carrier to form coated particles. The coated particles of an antibody crystal formulation may have a spherical morphology and be microspheres of up to 500 micrometers in diameter or they may have some other morphology and be microparticulates. Formulations and methods of preparing the formulations comprising antibody crystals are described in WO 02/072636, which is incorporated by reference herein.

Also useful are formulations comprising an antibody or other therapeutic protein, and a controlled release matrix comprising at least one lipid or lipophilic vehicle; at least one hydrophilic polymer; at least one hygroscopic polymer; and at least one non-ionic surfactant. In one example, the matrix dissolves in the colon. Suitable examples of liquid lipid or lipophilic vehicle include, e.g., olive oil, sunflower oil, canola oil, palmitoleic acid, oleic acid, myristoleic acid, linoleic acid, arachidonic acid, paraffin oil, and mineral oil. Suitable examples of hygroscopic polymers include, e.g., polyvinylpyrrolidone, copovidone, hydroxypropylmethylcellulose, hydroxypropylcellulose, ethyl cellulose, methylcellulose, and polyethylene oxide. Suitable examples of non-ionic surfactants include, e.g., pluronic, lutrol, tween 80, span 80, egetal, and triton X-100. Additional examples of extended release matrixes are provided, for example, in US 2016/0287525, which is incorporated herein by reference in its entirety.

A formulation may comprise a semi-crystalline matrix, and an antibody or other therapeutic protein in microparticulate or nanoparticulate form entrapped in the matrix. In some embodiments, the matrix can comprise at least one semi-crystalline water soluble polymer in an amount of at least 50% by weight of the total mass of the matrix. In one example, the matrix is characterized by a melting point of at least about 40° C. and is water soluble. Suitable examples of semi-crystalline water soluble polymers include, e.g., polyalkylene glycols, polyalkylene glycol copolymers, polyvinyl alcohols, hydroxyalkyl celluloses, polysorbates, polyoxyethylene stearates, carrageenans, and alginates, and mixtures thereof. Other examples of such formulations are described in US 2017/0273909, which is incorporated by reference in its entirety.

Exemplified Controlled-Release Formulations

In some embodiments, a formulation of the present disclosure comprises oleic acid; a polyethylene glycol glyceride ester; a poloxamer non-ionic surfactant; a mixture of polyvinylpyrrolidone and polyvinyl acetate; a carbomer polymer; dimethylaminoethyl methacrylate copolymer; and an antibody.

In some embodiments, a formulation of the present disclosure comprises a controlled release matrix comprising about 40% to about 55% oleic acid; about 5% to about 20% GELUCIRE® 43/01; about 1% to about 10% LUTROL® 127U; about 2% to about 8% KOLLIDON® SR; about 1% to about 6% CARBOPOL® 971 A; about 2% to about 8% EUDRAGIT® EPO; and about 25% to about 33% of an antibody.

Formulations Containing Adalimumab

In some embodiments, the present application provides a pharmaceutical formulation comprising adalimumab (also known as antibody D2E7). The formulation can be a liquid, semi-solid, or solid formulation. As used herein, the term "adalimumab" includes antibody or monoclonal adalimumab, any antigen-binding portion thereof, any glycosylation pattern variant thereof, and any biosimilar thereof.

Low Acidic Species of Adalimumab in Liquid and Solid Formulations

In some embodiments, formulations of adalimumab comprise the antibody having a percentage of acidic species (AR) that is not the same as the percentage of AR present in adalimumab formulated as HUMIRA® as currently approved and described in the "Highlights of Prescribing Information" for HUMIRA® (adalimumab) Injection (Revised January 2008), the contents of which are incorporated herein by reference. In one example, the low AR adalimumab has a percentage of AR that is lower than the percentage of AR present in adalimumab formulated as HUMIRA®. In some embodiments, the formulation comprises any one of the low acidic species described, for example, in US 2015/0110799, the disclosure of which is incorporated herein by reference in its entirety.

In some embodiments, a formulation of adalimumab can include less than about 10% total acidic species of adalimumab, wherein the acidic species of adalimumab have a net negative charge relative to the adalimumab main species and the acidic species comprise species selected from the group consisting of charge variants, structure variants, fragmentation variants and any combinations thereof, and wherein the acidic species of adalimumab do not include process-related impurities selected from the group consisting of host cell proteins, host cell nucleic acids, chromatographic materials and media components.

Formulations Containing Crystalline Forms of Adalimumab

In some embodiments, a formulation of adalimumab comprises the antibody in a crystalline form. In one example, the formulation comprises a crystal of adalimumab wherein the crystal has a needle morphology with a length of about 2-500 μm, or about 100-300 μm, and an l/d ratio of about 3 to 30, for example, as described in U.S. Pat. No. 8,436,149. Crystals can be obtained from a polyclonal antibody or a monoclonal antibody, or both.

The crystal of the antibody can be obtained by a batch crystallization method, which can include (a) combining an aqueous solution of adalimumab, an inorganic phosphate salt, and an acetate buffer to obtain an aqueous crystallization mixture, wherein the aqueous crystallization mixture has a pH about 3 to about 5, has an acetate buffer concentration of about 0 M to about 0.5 M, has an inorganic phosphate salt concentration of about 1 M to about 6 M, and has an antibody concentration of about 0.5 mg/mL to about 100 mg/mL; and incubating the aqueous crystallization mixture at a temperature of about 4° C. to about 37° C. until a crystal of the antibody is formed. In some embodiments, the formulation is a crystal slurry, having an adalimumab concentration greater than about 100 mg/mL or about 100 mg/g.

pH of Aqueous Formulation of Adalimumab

In some embodiments, a formulation of adalimumab is a liquid pharmaceutical formulation as described herein. The pH of such a formulation can be, e.g., from about 4 to about 8, from about 4.5 to about 6.0, from about 4.7 to about 5.7, from about 4.8 to about 5.5, or from about 5.0 to about 5.2, inclusive. In some embodiments, the pH of the liquid formulation is from about 5 to about 8.

Concentration of Adalimumab in Liquid Formulations

In some embodiments, a liquid formulation of adalimumab contains a high concentration of adalimumab, including, for example, a concentration greater than about 45 mg/mL, greater than about 50 mg/mL, or up to about 100 mg/mL. In other embodiments, the liquid formulation of adalimumab contains an even higher concentration of adalimumab, including, for example, a concentration greater than about 100 mg/mL, greater than about 110 mg/mL, greater than about 125 mg/mL, greater than about 150 mg/mL, or greater than about 175 mg/mL. In some embodiments, the formulation is an aqueous pharmaceutical composition comprising adalimumab, a polyol, a surfactant, and a buffer system comprising citrate and/or phosphate with a pH of about 4 to 8, in amounts sufficient to formulate the antibody for therapeutic use at a concentration of greater than about 100 mg/mL. In some embodiments, a liquid formulation of adalimumab comprises the antibody at a concentration of at least about 110 mg/mL, at least about 125 mg/mL, at least about 150 mg/mL, or at least about 175 mg/mL.

In some embodiments, the concentration of adalimumab in the formulation is between about 1 mg and about 150 mg, inclusive, of antibody per mL of a liquid formulation. In others, the concentration of is between about 5 mg and about 80 mg per mL. In still others, the concentration of adalimumab in the formulation is between about 25 mg/mL and about 50 mg/mL, inclusive. In some embodiments, the concentration of adalimumab in a liquid formulation is about 1-150 mg/mL, about 5-145 mg/mL, about 10-140 mg/mL, about 15-135 mg/mL, about 20-130 mg/mL, about 25-125 mg/mL, about 30-120 mg/mL, about 35-115 mg/mL, about 40-110 mg/mL, about 45-105 mg/mL, about 50-100 mg/mL, about 55-95 mg/mL, about 60-90 mg/mL, about 65-85 mg/mL, about 70-80 mg/mL, or about 75 mg/mL. Ranges intermediate to the above recited concentrations, for example, about 6-144 mg/mL, are also intended to be part of this disclosure. For example, ranges of values using a combination of any of the above recited values as upper and/or lower limits are intended to be included. In some embodiments, the formulation of adalimumab contains a high antibody concentration, for example, about 50 mg/mL, about 55 mg/mL, about 60 mg/mL, about 65 mg/mL, about 70 mg/mL, about 75 mg/mL, about 80 mg/mL, about 85 mg/mL, about 90 mg/mL, about 95 mg/mL, about 100 mg/mL, about 105 mg/mL, about 110 mg/mL, or about 115 mg/mL adalimumab, or higher. In some embodiments, the concentration of adalimumab in a liquid formulation is about 40-125 mg/mL, about 50-150 mg/mL, about 55-150 mg/mL, about 60-150 mg/mL, about 65-150 mg/mL, about 70-150 mg/mL, about 75-150 mg/mL, about 80-150 mg/mL, about 85-150 mg/mL, about 90-150 mg/mL, about 90-110 mg/mL, about 95-105 mg/mL, about 95-150 mg/mL, about 100-150 mg/mL, about 105-150 mg/mL, about 110-150 mg/mL, about 115-150 mg/mL, about 120-150 mg/mL, about 125-150 mg/mL, about 125-200 mg/mL, about 50-130 mg/mL, about 95-105 mg/mL, about 75-125 mg/mL, or at least about 200 mg/mL adalimumab.

Buffering Agents in Aqueous Solutions of Adalimumab

The present disclosure provides an aqueous formulation comprising adalimumab in a pH-buffered solution. In one example, a liquid formulation comprises adalimumab in combination with mannitol, citric acid monohydrate, sodium citrate, disodium phosphate dihydrate, sodium dihydrogen phosphate dihydrate, sodium chloride, polysorbate 80, water, and sodium hydroxide. The buffer can have a pH ranging from about 4 to about 8, from about 5 to about 8, from about 5 to about 7.5, from about 5 to about 7, from about 4.5 to about 6.0, from about 4.7 to about 5.7, from about 4.8 to about 5.5, or from about 5.0 to about 5.2. Suitable examples of buffers that can control the pH within the above ranges include acetate (e.g., sodium acetate), succinate (e.g., sodium succinate), gluconate, histidine, citrate and other organic acid buffers.

In some embodiments, a liquid formulation is buffered with histidine (and optionally arginine) amino acids and an acetate, while minimizing sodium chloride, with the buffers enhancing the thermal and colloidal stability of the antibody, even more so than formulations of adalimumab currently approved for patient use (e.g., currently approved injectable solutions). In some embodiments, the formulation contains a fine balance of an acidic pH of about 5.2 with the appropriate salts and buffer components. High levels of salt can induce aggregation and degradation, which could be improved by lowering the salt level. Accordingly, the present disclosure provides a buffered formulation of adalimumab comprising an aqueous carrier comprising buffer comprising histidine (and optionally arginine) amino acids and an acetate, and comprising mannitol, a non-ionic surfactant, and a minimal amount of sodium chloride.

In some embodiments, a formulation of adalimumab comprises a buffer system that contains citrate and phosphate to maintain the pH in a range of about 4 to about 8, from about 4.5 to about 6.0, from about 4.8 to about 5.5, or from about 5.0 to about 5.2. In one example, the buffer system includes citric acid monohydrate, sodium citrate, disodium phosphate dihydrate, and/or sodium dihydrogen phosphate dihydrate. In another example, the buffer system includes about 1.3 mg/mL of citric acid (e.g., 1.305 mg/mL), about 0.3 mg/mL of sodium citrate (e.g., 0.305 mg/mL), about 1.5 mg/mL of disodium phosphate dihydrate (e.g., 1.53 mg/mL), about 0.9 mg/mL of sodium dihydrogen phosphate dihydrate (e.g., 0.86), and about 6.2 mg/mL of sodium chloride (e.g., 6.165 mg/mL). In additional examples, the buffer system includes about 1-1.5 mg/mL of citric acid, about 0.25 mg/mL to about 0.5 mg/mL of sodium citrate, about 1.25 mg/mL to about 1.75 mg/mL of disodium phosphate dihydrate, about 0.7 mg/mL to about 1.1 mg/mL of sodium dihydrogen phosphate dihydrate, and about 6.0 mg/mL to about 6.4 mg/mL of sodium chloride. The pH of a formulation can be adjusted with an appropriate amount of sodium hydroxide.

In some embodiments, a liquid pharmaceutical formulation of adalimumab comprises about 1.3 mg/mL of citric acid, about 0.3 mg/mL of sodium citrate, about 1.5 mg/mL of disodium phosphate dihydrate, about 0.9 mg/mL of sodium dihydrogen phosphate dihydrate, and about 6.2 mg/mL of sodium chloride. In other embodiments, a liquid aqueous pharmaceutical formulation of adalimumab comprises about 1.305 mg/mL of citric acid, about 0.305 mg/mL of sodium citrate, about 1.53 mg/mL of disodium phosphate dihydrate, about 0.86 mg/mL of sodium dihydrogen phosphate dihydrate, and about 6.165 mg/mL of sodium chloride.

Polyols in Solid and Liquid Formulations of Adalimumab

A polyol, which acts as a tonicifier and can stabilize adalimumab, can be included in a formulation of adalimumab. The polyol can be added to the formulation in an amount that can vary with respect to the desired isotonicity of the formulation. In some embodiments, the aqueous formulation is isotonic. The amount of polyol added can also vary with respect to the molecular weight of the polyol. For example, a lower amount of a monosaccharide (e.g., mannitol) can be added, compared to a disaccharide (such as trehalose). In some embodiments, the polyol used in the formulation as a tonicity agent is mannitol. For example, the mannitol concentration can be about 5-20 mg/mL, about 7.5-15 mg/mL, about 10-14 mg/mL, or about 12 mg/mL. In some embodiments, the polyol sorbitol is included in the formulation.

Surfactants in Solid and Liquid Formulations of Adalimumab

A detergent or surfactant can be added to a formulation of adalimumab. Exemplary detergents include nonionic surfactants such as polysorbates (e.g., polysorbates 20, 80, etc.) or poloxamers (e.g., poloxamer 188 or 407). The amount of detergent added can be such that it reduces aggregation of adalimumab, minimizes the formation of particulates in the formulation and reduces adsorption. In some embodiments, the formulation includes a surfactant which is a polysorbate such as polysorbate 80 or Tween 80. Tween 80 is a term used to describe polyoxyethylene (20) sorbitanmonooleate (see Fiedler, Lexikon der Hifsstoffe, Editio Cantor Verlag Aulendorf, 4th edi., 1996). In some embodiments, the formulation is liquid and contains from about 0.1 mg/mL to about 10 mg/mL, from about 0.5 mg/mL to about 5 mg/mL, about 0.1%, or about 0.2% of polysorbate 80. In some embodiments, the formulation of adalimumab contains about 0.1-2 mg/mL, about 0.1-1.5 mg/mL, about 0.2-1.4 mg/mL, about 0.3-1.3 mg/mL, about 0.4-1.2 mg/mL, about 0.5-1.1 mg/mL, about 0.6-1.0 mg/mL, about 0.6-1.1 mg/mL, about 0.7-1.1 mg/mL, about 0.8-1.1 mg/mL, or about 0.9-1.1 mg/mL of a surfactant such as polysorbate 80.

Exemplary Dosage of Adalimumab in Solid and Liquid Formulations

In some embodiments, a formulation of adalimumab includes about 20-100 mg, about 20-110 mg, about 20-90 mg, about 30-80 mg, about 30-90 mg, about 30-100 mg, about 60-100 mg, about 40-90 mg, or about 40-100 mg of adalimumab. In some embodiments, the formulation includes about 30 mg, about 31 mg, about 32 mg, about 33 mg, about 34 mg, about 35 mg, about 36 mg, about 37 mg, about 38 mg, about 39 mg, about 40 mg, about 41 mg, about 42 mg, about 43 mg, about 44 mg, about 45 mg, about 46 mg, about 47 mg, about 48 mg, about 49 mg, about 50 mg, about 51 mg, about 52 mg, about 53 mg, about 54 mg, about 55 mg, about 56 mg, about 57 mg, about 58 mg, about 59 mg, about 60 mg, about 61 mg, about 62 mg, about 63 mg, about 64 mg, about 65 mg, about 66 mg, about 67 mg, about 68 mg, about 69 mg, about 70 mg, about 71 mg, about 72 mg, about 73 mg, about 74 mg, about 75 mg, about 76 mg, about 77 mg, about 78 mg, about 79 mg, about 80 mg, about 81 mg, about 82 mg, about 83 mg, about 84 mg. 85 mg, about 86 mg, about 87 mg, about 88 mg, about 89 mg, about 90 mg, about 91 mg, about 92 mg, about 93 mg, about 94 mg, about 95 mg, about 96 mg, about 97 mg, about 98 mg, about 99 mg, about 100 mg, about 101 mg, about 102 mg, about 103 mg, about 104 mg, about 105 mg, about 106 mg, about 107 mg, about 108 mg, about 109 mg, or about 110 mg of adalimumab. Ranges including the aforementioned numbers are also included in the disclosure, e.g., about 70-90 mg, about 65-95 mg, about 75-85 mg, or about 60-85 mg of adalimumab. In some embodiments, an effective amount of adalimumab is about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, or about 100 mg.

In some embodiments, a formulation of adalimumab includes about 1 mg to about 500 mg, about 1 mg to about 100 mg, about 5 mg to about 40 mg, about 40 mg to about 80 mg, about 160 mg, about 80 mg or about 40 mg of adalimumab. In some embodiments, the formulation contains an induction dose of about 160 mg of adalimumab. In other embodiments, the formulation contains a maintenance dose of about 80 mg, about 40 mg, or about 40 mg to about 80 mg of adalimumab.

Special Properties of Liquid Formulations of Adalimumab/ Conductivity

In some embodiments, a formulation of adalimumab does not contain any buffer(s) (e.g., citrate and phosphate) or salt(s). It should be noted, however, that although said formulation may not contain buffer or salt (e.g., NaCl), a small trace amount of a buffer and/or a salt may be present in the formulation. In some embodiments, the formulation does not contain detectable levels of a buffer(s) and/or a salt.

In some embodiments, the formulation contains adalimumab at a concentration of about 100 mg/mL (or about 75-125 mg/mL), a surfactant (e.g., polysorbate 80), and has a conductivity of less than about 2 mS/cm. In one example, the formulation also contains a polyol (e.g., sorbitol or mannitol).

In some embodiments, a formulation contains adalimumab at a concentration of about 100 mg/mL (or about 75-125 mg/mL), about 0.8-1.3 mg/mL of a surfactant (e.g., polysorbate 80), and has a conductivity of less than 2 mS/cm. In one example, the formulation also contains less than about 50 mg/mL of a polyol (e.g., sorbitol or mannitol).

In some embodiments, a liquid aqueous formulation of adalimumab comprises adalimumab, a surfactant, and less than 50 mg/mL of a polyol, where the formulation has a conductivity of less than about 2 mS/cm and a hydrodynamic diameter ($D_h$) which is at least about 50% less than the $D_h$ of the protein in a buffered solution at a given concentration.

Formulations of Adalimumab for Administration in Combination with Methotrexate

In some embodiments, a formulation of adalimumab is administered to a patient in combination with methotrexate, or a pharmaceutically acceptable salt thereof. In one example, the formulation of adalimumab and methotrexate, or a pharmaceutically acceptable salt thereof, are administered to a patient simultaneously or consecutively, for example, in separate dosage forms. In another example, formulation of adalimumab is administered to the subject in a device as described herein, and methotrexate, or a pharmaceutically acceptable salt thereof, is administered to the subject in a conventional dosage form, such as a tablet or gelatin capsule. In some embodiments, a formulation of adalimumab and a therapeutically effective amount of methotrexate, or a pharmaceutically acceptable salt thereof, is administered to a patient in the same dosage form (e.g., in a device as described herein).

Exemplified Adalimumab Formulations

In some embodiments, a formulation comprises adalimumab, polysorbate 80, mannitol, and water for injection. In some more particular embodiments, the formulation consists essentially of or consists of adalimumab, polysorbate 80, mannitol, and water for injection. In even more particular embodiments, the concentration of adalimumab in the formulation is about 100 mg/mL. In one particular embodiment, the formulation is HUMIRA® 40 mg concentrate for injection, as provided in commercially available pre-filled syringes or pens (AbbVie Limited, Summary of Product Characteristics Updated 2 May 2018). In other embodiments, the formulation comprises, consists of or consists essentially of adalimumab, polysorbate 80, mannitol and water for injection, and the concentration of adalimumab in the formulation is greater than about 100 mg/mL. In yet other embodiments, the formulation comprises, consists of or consists essentially of adalimumab, polysorbate 80, mannitol and water for injection, and the concentration of adalimumab in the formulation is at least about 110 mg/mL, at least about 125 mg/mL, at least about 150 mg/mL or at least about 175 mg/mL.

In some embodiments, a formulation comprises, consists essentially of or consists of adalimumab, sodium chloride, a buffer including sodium phosphate monobasic monohydrate, sodium phosphate dibasic heptahydrate, and polysorbate 80. In one example, the formulation is liquid and comprises water for injection. In some embodiments, the formulation consists essentially of or consists of the foregoing components.

In some embodiments, a formulation comprises, consists essentially of or consists of adalimumab, a buffer which is optionally a phosphate or citrate buffer, and an excipient selected from a polyol (such as a sugar or sugar alcohol) and a non-ionic surfactant, such as a polysorbate. In one example, the formulation is liquid and contains water for injection. In another example, the formulation contains low levels of ionic excipients and has low conductivity.

In some embodiments, a formulation comprises, consists essentially of or consists of adalimumab, sodium chloride, a buffer containing a phosphate such as sodium phosphate monobasic dihydrate, sodium phosphate dibasic dihydrate, or a combination thereof, L-arginine hydrochloride, and sucrose. In one example, the formulation is liquid and contains water for injection.

In some embodiments, a formulation comprises, consists essentially of or consists of adalimumab, sodium chloride, a buffer containing a phosphate such as sodium phosphate monobasic dihydrate, sodium phosphate dibasic dihydrate, or a combination thereof, a citrate such as sodium citrate, citric acid monohydrate, or a combination thereof, mannitol, and polysorbate 80. In one example, the formulation is liquid and contains water for injection. In another example, the pH of the liquid formulation is adjusted with NaOH to about 5.2. In one embodiment, the formulation is HUMIRA® (adalimumab) for injection, for subcutaneous use, for example, as initially approved in the U.S. in 2002. In some embodiments, a formulation comprises, consists essentially of or consists of adalimumab, a buffer, which is optionally a phosphate or citrate buffer, a polyol selected from mannitol, sorbitol, sucrose, trehalose, raffinose, maltose, and a combination thereof, and a non-ionic surfactant selected from polysorbate 20, polysorbate 40, polysorbate 60, and polysorbate 80. In one example, the formulation contains low levels of ionic excipients and has low conductivity. In another example, the concentration of adalimumab in the formulation is at least about 10 mg/mL, about 50 mg/mL, about 100 mg/mL, about 150 mg/mL, about 200 mg/mL, or about 250 mg/mL.

In some embodiments, a formulation comprises, consists essentially of or consists of adalimumab, a buffer containing a phosphate selected from monobasic sodium phosphate and dibasic sodium phosphate, sucrose, and polysorbate 80.

In some embodiments, a formulation comprises, consists essentially of or consists of adalimumab, arginine, histidine, or a combination thereof, sucrose, and polysorbate 80. Optionally, the formulation further comprises a buffer. In one example, the formulation is a lyophilized powder.

In some embodiments, a formulation comprises, consists essentially of or consists of adalimumab, a free amino acid selected from histidine, alanine, arginine, glycine, and glutamic acid, a polyol selected from mannitol, sorbitol, sucrose, trehalose, and a combination thereof, and a surfactant. Optionally, the formulation further comprises a buffer. In one example, the formulation is liquid. In another example, the formulation is solid (e.g., lyophilized powder for reconstitution).

In some embodiments, a formulation comprises, consists essentially of or consists of adalimumab, an acetate salt, such as sodium acetate trihydrate, an amino acid which is histidine and/or a salt thereof, sorbitol, and a non-ionic surfactant such as polysorbate 80; optionally, the formulation further comprises arginine and/or a salt thereof. In one example, the formulation is liquid and comprises water for injection. In another example, the pH of the liquid formulation is from about 5.1 to about 5.3. In yet another example, the formulation contains negligible or non-detectable amount of sodium chloride. In yet another example, the formulation does not contain phosphate or citrate.

In some embodiments, a formulation comprises, consists essentially of or consists of adalimumab, an amino acid selected from L-histidine, L-histidine monohydrochloride monohydrate, and a combination thereof, sorbitol and polysorbate 80. In one example, the formulation is liquid and comprises water for injection.

In some embodiments, a formulation comprises, consists essentially of or consists of adalimumab, an amino acid selected from L-histidine, L-histidine monohydrochloride monohydrate, L-methionine, and a combination thereof, sucrose, and polysorbate 80. In one example, the formulation also contains a metal chelating agent such as EDTA disodium salt dihydrate. In another example, the formulation is liquid and contains water for injection.

In some embodiments, a formulation comprises, consists essentially of or consists of adalimumab, an amino acid selected from L-histidine, L-histidine monohydrochloride monohydrate, L-arginine hydrochloride, and a combination thereof, sucrose, and polysorbate 80.

In some embodiments, a formulation comprises, consists essentially of or consists of adalimumab, an amino acid selected from L-histidine and L-arginine, and a combination thereof, polysorbate 20, and succinic acid.

In some embodiments, a formulation comprises, consists essentially of or consists of adalimumab at a concentration of at least about 100 mg/mL, mannitol, and polysorbate 80. In one example, the formulation is liquid and contains water for injection. In one embodiment, the formulation is HUMIRA® 40 mg concentrate for injection, as provided in commercially available pre-filled syringes or pens (AbbVie Limited, Summary of Product Characteristics Updated 2 May 2018).

In some embodiments, a formulation comprises, consists essentially of or consists of adalimumab, a buffer containing a negligible or non-detectable amount of sodium chloride, phosphate and citrate, a polyol such as mannitol, and a surfactant selected from a polysorbate and a poloxamer. In one example, the formulation has an adalimumab concentration of at least about 50 mg/mL, about 75 mg/mL, or about 100 mg/mL or greater, and has low conductivity.

In some embodiments, a formulation comprises, consists essentially of or consists of adalimumab, sodium chloride, and an acetate such as sodium acetate.

In some embodiments, a formulation comprises about 80 mg of adalimumab, water for injection, about 42 mg/mL of mannitol, and about 1 mg/mL of polysorbate 80. In some embodiments, a formulation comprises about 80 mg of adalimumab, water for injection, and about 1 mg/mL polysorbate 80.

In some embodiments, a liquid aqueous pharmaceutical formulation comprises about 1-150 mg/mL of adalimumab, about 5-20 mg/mL of mannitol, about 0.1-10 mg/mL of Tween-80, and a buffer system comprising citrate and/or phosphate, with a pH of about 4 to about 8. In one example, the formulation comprises about 40 mg of adalimumab.

In some embodiments, a liquid aqueous pharmaceutical formulation comprises about 50 mg/mL of adalimumab, about 12 mg/mL of mannitol, about 1 mg/mL of Tween-80, and a buffer system comprising citrate and/or phosphate, with a pH of about 4 to about 8. In one example, the formulation comprises about 40 mg of adalimumab.

In some embodiments, a liquid aqueous formulation of adalimumab consists essentially of a surfactant and about 30-90 mg of adalimumab, wherein the formulation has an antibody concentration of about 90-110 mg/mL.

In some embodiments, a liquid aqueous formulation comprises about 100 mg/mL of adalimumab; about 1.0 mg/mL of polysorbate-80; and about 42 mg/mL of mannitol; where the formulation has a pH of about 4.7 to about 5.7 and does not contain a buffer or a salt.

In some embodiments, a liquid aqueous formulation consists essentially of about 100 mg/mL of adalimumab; about 1.0 mg/mL of polysorbate-80; and about 42 mg/mL of mannitol, where the formulation has a pH of about 4.7 to about 5.7.

In some embodiments, a liquid aqueous formulation comprises about 100 mg/mL of adalimumab; about 1.0 mg/mL of polysorbate-80; and about 42 mg/mL of mannitol; where the formulation has a pH of about 4.7 to about 5.7, and where the formulation is stable up to about 30° C. for at least 6 days.

In some embodiments, a liquid aqueous formulation comprises about 100 mg/mL of adalimumab; about 1.0 mg/mL of polysorbate-80; and about 42 mg/mL of mannitol; where the formulation has a pH of about 4.7 to about 5.7, and where the formulation has a characteristic selected from the group consisting of a conductivity of less than about 2 mS/cm; a hydrodynamic diameter ($D_h$) which is at least about 50% less than the $D_h$ of the protein in a buffered solution at a given concentration; and a hydrodynamic diameter ($D_h$) of less than about 4 nm.

In some embodiments, a liquid aqueous formulation consists essentially of about 1.0 mg/mL of polysorbate-80 and about 40 mg of adalimumab, where the concentration of adalimumab is about 100 mg/mL, and where the formulation has a pH of about 4.7 to about 5.7.

In some embodiments, a liquid aqueous pharmaceutical formulation comprises about 20 to about 150 mg/mL of adalimumab, about 5-20 mg/mL of mannitol, about 0.1-10 mg/mL of polysorbate-80, and a buffer system comprising citrate and phosphate, with a pH of about 4 to about 8.

In some embodiments, a liquid aqueous pharmaceutical formulation comprises about 40 mg/mL to about 100 mg/mL of adalimumab, about 7.5 to about 15 mg/mL of mannitol, and about 0.5 to about 5 mg/mL of polysorbate 80.

In some embodiments, a liquid aqueous formulation comprises about 50-100 mg/mL of adalimumab, about 7.5-15 mg/mL of mannitol, and about 0.5-5 mg/mL of polysorbate 80, where the pH of the formulation is about 5.0-6.5.

In some embodiments, a liquid aqueous formulation comprises about 50 mg/mL of adalimumab, about 7.5-15 mg/mL of mannitol, and about 0.5-5 mg/mL of polysorbate 80, where the pH of the formulation is about 4.5 to about 6.0.

In some embodiments, a liquid aqueous formulation comprises about 45-105 mg/mL of adalimumab, a polyol, about 0.1-10 mg/mL of polysorbate 80, and a buffer system having a pH of about 4.5 to about 7.0.

In some embodiments, a liquid aqueous formulation comprises about 45-150 mg/mL of adalimumab, a polyol, about 0.1-10 mg/mL of polysorbate 80, and a buffer system having a pH of about 4.5 to about 7.0.

In some embodiments, a liquid aqueous formulation comprises about 50 mg/mL to about 100 mg/mL of adalimumab, trehalose, and about 0.5-5 mg/mL of polysorbate 80, where the formulation has a pH of about 5.0 to about 6.5.

In some embodiments, a liquid aqueous formulation comprises about 45 to about 105 mg/mL of adalimumab, trehalose, about 0.1-10 mg/mL of polysorbate 80, and a buffer system comprising acetate and having a pH of about 4.5 to about 7.0.

In some embodiments, a liquid aqueous formulation comprises about 100 mg/mL of adalimumab; about 1.0 mg/mL of polysorbate-80; and about 42 mg/mL of mannitol; where the formulation has a pH of about 4.7 to about 5.7.

In some embodiments, a liquid aqueous formulation comprises about 50 to about 100 mg/mL adalimumab, trehalose, and about 0.5-5 mg/mL of polysorbate 80, where the formulation has a pH of about 5.0 to about 6.5.

In some embodiments, a liquid formulation of adalimumab comprises an aqueous buffer comprising from about 10 mM to about 30 mM of acetate or an acetate salt (e.g., sodium acetate trihydrate), from about 15 mM to about 20 mM of histidine and/or a histidine salt and from about 0 mM to about 30 mM of arginine, from about 200 mM to about 206 mM of sorbitol, and about 0.07% (v/v) to about 0.15% (v/v) of a non-ionic surfactant (e.g., polysorbate 80). In these embodiments, the formulation has a pH of from about 5.1 to about 5.3 (e.g., about 5.2).

In some embodiments, a liquid formulation of adalimumab comprises a buffer comprising from about 1 mM to about 30 mM of an acetate salt, from about 10 mM to about 30 mM of histidine and/or a histidine salt, about 201 mM to about 205 mM of sorbitol, and about 0.08% (v/v) to about 0.12% (v/v) of polysorbate 80. In one example, the antibody formulation has a pH of from about 5.1 to about 5.3 (e.g., about 5.2). In another example, the buffer comprises from about 0.1 to about 30 mM of arginine and/or an arginine salt. In another example, the acetate salt comprises sodium acetate trihydrate. In another example, the formulation comprises from about 35 mg to about 45 mg of adalimumab, e.g., from about 37 mg to about 43 mg, or about 40 mg of adalimumab. In another example, the formulation does not comprise NaCl, a citrate, or a phosphate.

In some embodiments, a formulation of adalimumab comprises adalimumab, sodium chloride, monobasic sodium phosphate dihydrate, dibasic sodium phosphate dihydrate, sodium citrate, citric acid monohydrate, mannitol, and polysorbate 80. In one example, the formulation is a liquid formulation (e.g., aqueous solution) or a solid formulation (e.g., lyophilized cake).

In some embodiments, a liquid formulation of adalimumab comprises adalimumab, sodium chloride, monobasic sodium phosphate dihydrate, dibasic sodium phosphate dihydrate, sodium citrate, citric acid monohydrate, mannitol, polysorbate 80, and water.

In some embodiments, an aqueous formulation of adalimumab comprises about 0.8 mL of a solution for injection comprising:

| Name of ingredient | Quantity | Function |
|---|---|---|
| Adalimumab (used as a concentrate) | 40.0 mg | 40.0 mg Active substance |
| Mannitol | 9.6 mg | Tonicity agent |
| Citric acid monohydrate Citric acid | 1.044 mg | Buffer |
| Sodium citrate | 0.244 mg | Buffer |
| Sodium phosphate dihydrate Dibasic sodium phosphate dihydrate | 1.224 mg | Buffer |
| Sodium dihydrogen phosphate dihydrate Monobasic sodium phosphate dihydrate | 0.688 mg | Buffer |
| Sodium chloride | 4.932 mg | Tonicity agent |
| Polysorbate 80 | 0.8 mg | Detergent |
| Water for injection | 759.028-759.048 mg | Solvent |
| Sodium hydroxide (1M solution) | 0.02-0.04 mg | pH adjustment |
| Total | 817.6 mg | |

In some embodiments, the density of the solution for injection is about 1.022 g/mL. In some embodiments, smaller volumes are used, for example, for incorporation into a device of the present disclosure, for example, a volume of about 0.4 mg/mL is incorporated into the device or device reservoir.

In some embodiments, each 0.8 mL of a liquid formulation of adalimumab comprises about 40 mg adalimumab, about 4.93 mg sodium chloride, about 0.69 mg monobasic sodium phosphate dihydrate, about 1.22 mg dibasic sodium phosphate dihydrate, about 0.24 mg sodium citrate, about 1.04 mg citric acid monohydrate, about 9.6 mg mannitol, about 0.8 mg polysorbate 80, and water for injection. In some embodiments, the pH of the liquid formulation is about 5.2.

In some embodiments, each 0.2 mL of a liquid formulation of adalimumab comprises about 20 mg adalimumab, mannitol and polysorbate 80. In one example, the formulation also comprises citric acid monohydrate, sodium citrate, sodium dihydrogen phosphate dihydrate, disodium phosphate dihydrate, sodium chloride and sodium hydroxide.

In some embodiments, each 0.8 mL of a liquid formulation of adalimumab comprises about 80 mg adalimumab, about 33.6 mg mannitol, about 0.8 mg polysorbate 80, and water for injection. In some embodiments, the pH of the liquid formulation is about 5.2.

In some embodiments, each 0.4 mL of a liquid formulation of adalimumab comprises about 40 mg adalimumab, about 16.8 mg mannitol, about 0.4 mg polysorbate 80, and water for injection. In some embodiments, the pH of the liquid formulation is about 5.2.

In some embodiments, each 0.4 mL of a liquid formulation of adalimumab comprises about 20 mg adalimumab, about 0.52 mg citric acid monohydrate, about 0.61 mg dibasic sodium phosphate dihydrate, about 4.8 mg mannitol, about 0.34 mg monobasic sodium phosphate dihydrate, about 0.4 mg polysorbate 80, about 2.47 mg sodium chloride, about 0.12 mg sodium citrate, and water for injection. In some embodiments, the pH of the liquid formulation is about 5.2.

In some embodiments, each 0.2 mL of a liquid formulation of adalimumab comprises about 10 mg adalimumab, about 0.26 mg citric acid monohydrate, about 0.31 mg dibasic sodium phosphate dihydrate, about 2.4 mg mannitol, about 0.17 mg monobasic sodium phosphate dihydrate, about 0.2 mg polysorbate 80, about 1.23 mg sodium chloride, about 0.06 mg sodium citrate, and water for injection. In some embodiments, the pH of the liquid formulation is about 5.2.

Additional pharmaceutical formulations of adalimumab are disclosed, for example, in US Publication Nos. 2015/0110799, 2012/026373, 2012/0263731, and 2010/0034823; U.S. Pat. Nos. 8,821,865, 8,034,906, and 8,436,149; and PCT Publication Nos. WO 2004/016286 and WO 2017/136433, the disclosures of each of which are incorporated herein by reference in their entireties.

Formulations Containing Vedolizumab

In some embodiments, the present application provides a pharmaceutical formulation comprising vedolizumab. The formulation can be a liquid, semi-solid, or solid formulation. As used herein, the term "vedolizumab" includes antibody or monoclonal vedolizumab, any antigen-binding portion thereof, any glycosylation pattern variant thereof, and any biosimilar thereof.

In some embodiments, an aqueous formulation comprises vedolizumab, at least one amino acid, a sugar, and a surfactant. In one example, the amino acid is histidine, arginine, or a combination thereof. In other embodiments, the sugar is sucrose. In yet other embodiments, the surfactant is polysorbate 80.

In some embodiments, a formulation of vedolizumab is stable for a prolonged period of time. A dry (e.g., lyophilized) formulation of vedolizumab can be stable at about 40° C., at about 75% RH for at least about 2-4 weeks, at least about 2 months, at least about 3 months, at least about 6 months, at least about 9 months, at least about 12 months, or at least about 18 months. In some embodiments, a formulation (liquid or dry (e.g., lyophilized)) of vedolizumab is stable at about 5° C. and/or 25° C. and about 60% RH for at least about 3 months, at least about 6 months, at least about 9 months, at least about 12 months, at least about 18 months, at least about 24 months, at least about 30 months, at least about 36 months, or at least about 48 months. In another example, a formulation (liquid or dry (e.g., lyophilized)) of vedolizumab is stable at about −20° C. for at least about 3 months, at least about 6 months, at least about 9 months, at least about 12 months, at least about 18 months, at least about 24 months, at least about 30 months, at least about 36 months, at least about 42 months, or at least about 48 months. In some embodiments, the liquid formulation is stable following freezing (to, e.g., −80° C.) and thawing, such as, for example, following 1, 2 or 3 cycles of freezing and thawing.

Concentration of Vedolizumab in Liquid Formulations

In some embodiments, a liquid (e.g., aqueous) formulation of vedolizumab contains a high concentration of the antibody, for example, from about 1 mg/mL to about 200 mg/mL of vedolizumab. In some embodiments, a liquid formulation of vedolizumab contains a high concentration of vedolizumab, including, for example, a concentration greater than about 45 mg/mL, greater than about 50 mg/mL, greater than about 100 mg/mL, greater than about 110 mg/mL, greater than about 125 mg/mL, greater than about 150 mg/mL, or greater than about 175 mg/mL.

In some embodiments, the pH of the liquid formulation of vedolizumab is from about 5 to about 8. The liquid formulation can include a buffer having a pH ranging from about 4 to about 8, from about 5 to about 8, from about 5 to about 7.5, from about 5 to about 7, from about 4.5 to about 6.0, from about 4.7 to about 5.7, from about 4.8 to about 5.5, or from about 5.0 to about 5.2.

Polyols in Solid and Liquid Vedolizumab Formulations

A polyol or sugar in the vedolizumab composition can be a non-reducing sugar. In some embodiments, the polyol or sugar is selected from the group consisting of: mannitol, sorbitol, sucrose, trehalose, raffinose, stachyose, melezitose, dextran, maltitol, lactitol, isomaltulose, palatinit, and a combination thereof. A molar ratio of the sugar to vedolizumab can be at least about 600:1; about 625:1; about 650:1; about 675:1, about 700:1; about 750:1, about 800:1, about 1000:1, about 1200:1, about 1400:1, about 1500:1, about 1600:1, about 1700:1, about 1800:1, about 1900:1, or about 2000:1. In some embodiments, the non-reducing sugar concentration in a liquid vedolizumab formulation (e.g., pre-drying or post-reconstitution) is in the range from about 10 mM to about 1 M, for example, from about 60 mM to about 600 mM, about 100 mM to about 450 mM, about 200 mM to about 350 mM, about 250 mM to about 325 mM, or about 275 mM to about 300 mM. In some embodiments, the amount of non-reducing sugar in a dry (e.g., lyophilized) vedolizumab formulation is in the range from about 40% to about 70% (w/w of dry formulation). In some embodiments, the amount of non-reducing sugar in a dry (e.g., lyophilized) vedolizumab formulation is in the range from about 40% to about 60%, from about 45% to about 55% or about 51% (w/w). In some embodiments, the amount of non-reducing sugar in a dry (e.g., lyophilized) vedolizumab formulation is greater than about 51% (w/w of dry formulation) when the vedolizumab amount is about 31% (w/w of dry formulation) or greater than about a 1.6:1 mass ratio of the non-reducing sugar to the antibody in the dry formulation. In some embodiments, sucrose is the non-reducing sugar for use in the vedolizumab formulation.

Methods of Preparation of Liquid and Solid Vedolizumab Formulations

A formulation of vedolizumab can be prepared, for example, as follows. Bottles of frozen, high concentration antibody preparation (vedolizumab, 50 mM histidine, 125 mM arginine, 0.06% polysorbate 80, pH 6.3) are thawed at room temperature for about 16-24 hours. Thawed bottles are pooled into a stainless steel compounding vessel and mixed. The preparation is then diluted with dilution buffer A (50 mM histidine, 125 mM arginine, 0.06% polysorbate 80, pH 6.3) to 80 mg/mL of vedolizumab and mixed. Sucrose is then added by diluting the preparation with dilution buffer B, which contains sucrose (50 mM histidine, 125 mM arginine, 40% sucrose, 0.06% polysorbate 80, pH 6.3). This step dilutes the antibody preparation to a liquid formulation of 60 mg/mL vedolizumab, 50 mM histidine, 125 mM arginine, 10% sucrose, 0.06% polysorbate 80, pH of about 6.3.

In some embodiments, the pre-lyophilization vedolizumab formulation volume is the same as the pre-administration reconstituted solution volume. For example, a formulation that is about 5.5 mL pre-lyophilization can be reconstituted to a volume of about 5.5 mL, by adding an amount of liquid, e.g., water or saline, that takes into account the volume of the dry solids. In other embodiments, it is desirable to lyophilize the formulation in a different volume than the reconstituted solution volume. For example, the vedolizumab formulation can be lyophilized as a dilute solution, e.g., 0.25×, 0.5×, or 0.75× and reconstituted to 1× by adding less liquid, e.g., about 75% less, about half, or about 25% less than the pre-lyophilization volume. In some embodiments, a 300 mg dose of vedolizumab is lyophilized as a 30 mg/mL antibody solution in 5% sucrose and reconstituted to a 60 mg/mL antibody solution in 10% sucrose. Alternatively, a lyophilized vedolizumab formulation can be reconstituted into a more dilute solution than the pre-lyophilized formulation.

Exemplary Dosage of Liquid and Solid Vedolizumab Formulations

In some embodiments, a formulation of vedolizumab as described herein is administered to a patient, for example in a device as described herein, to achieve a therapeutically effective dose of about 0.2 mg/kg, about 0.5 mg/kg, about 2.0 mg/kg, about 6.0 mg/kg, or about 10.0 mg/kg. In some embodiments, the effective dose of vedolizumab in the formulation is about 30 mg, about 40 mg, about 50 mg, about 60 mg, about 80 mg, about 100 mg, about 120 mg, about 150 mg, about 180 mg, about 200 mg, about 225 mg, about 250 mg, about 300 mg, about 350 mg, 400 mg, about 450 mg, about 500 mg, about 600 mg, about 700 mg, or about 750 mg. In some embodiments, a 750 mg dose is about 2.5 times the recommended dose for administration to a patient. In some embodiments, the effective dose is about 0.2-10 mg/kg, or about 1-100 mg/kg. In some embodiments, the effective dose of vedolizumab is about 0.1 mg/kg body weight to about 10.0 mg/kg body weight per treatment, for example about 2 mg/kg to about 7 mg/kg, about 3 mg/kg to about 6 mg/kg, or about 3.5 mg/kg to about 5 mg/kg. In some embodiments, the dose administered is about 0.3 mg/kg, about 0.5 mg/kg, about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, or about 10 mg/kg. In some embodiments, the vedolizumab is administered at a dose of about 50 mg, about 100 mg, about 300 mg, about 500 mg or about 600 mg. In some embodiments, the vedolizumab is administered at a dose of about 108 mg, about 216 mg, about 160 mg, about 165 mg, about 155 to about 180 mg, about 170 mg or about 180 mg.

In some embodiments, a formulation of vedolizumab includes about 1 mg to about 500 mg, about 1 mg to about 100 mg, or about 5 mg to about 40 mg of vedolizumab.

Exemplary Liquid and Solid Vedolizumab Formulations

In some embodiments, a formulation comprises, consists essentially of, or consists of vedolizumab, sodium chloride, a buffer including sodium phosphate monobasic monohydrate, sodium phosphate dibasic heptahydrate, and polysorbate 80. In one example, the formulation is liquid and comprises water for injection.

In some embodiments, a formulation comprises, consists essentially of, or consists of vedolizumab, a buffer which is optionally a phosphate or citrate buffer, and an excipient selected from a polyol (such as a sugar or sugar alcohol) and a non-ionic surfactant, such as a polysorbate. In one example, the formulation is liquid and contains water for injection. In another example, the formulation contains low levels of ionic excipients and has low conductivity.

In some embodiments, a formulation comprises, consists essentially of, or consists of vedolizumab, sodium chloride, a buffer containing a phosphate such as sodium phosphate monobasic dihydrate, sodium phosphate dibasic dihydrate, or a combination thereof, L-arginine hydrochloride, and sucrose. In one example, the formulation is liquid and contains water for injection.

In some embodiments, a formulation comprises, consists essentially of, or consists of vedolizumab, sodium chloride, a buffer containing a phosphate such as sodium phosphate monobasic dihydrate, sodium phosphate dibasic dihydrate, or a combination thereof, a citrate such as sodium citrate, citric acid monohydrate, or a combination thereof, mannitol, and polysorbate 80. In one example, the formulation is liquid and contains water for injection. In another example, the pH of the liquid formulation is adjusted with NaOH to about 5.2.

In some embodiments, a formulation comprises, consists essentially of, or consists of vedolizumab, a buffer, which is optionally a phosphate or citrate buffer, a polyol selected from mannitol, sorbitol, sucrose, trehalose, raffinose, maltose, and a combination thereof, and a non-ionic surfactant selected from polysorbate 20, polysorbate 40, polysorbate 60, and polysorbate 80. In one example, the formulation contains low levels of ionic excipients and has low conductivity. In another example, the concentration of the antibody in the formulation is at least about 10 mg/mL, about 50 mg/mL, about 100 mg/mL, about 150 mg/mL, about 200 mg/mL, or about 250 mg/mL.

In some embodiments, a formulation comprises, consists essentially of, or consists of vedolizumab, a buffer containing a phosphate selected from monobasic sodium phosphate and dibasic sodium phosphate, sucrose, and polysorbate 80.

In some embodiments, a formulation comprises, consists essentially of, or consists of vedolizumab, arginine, histidine, or a combination thereof, sucrose, and polysorbate 80. Optionally, the formulation further comprises a buffer. In one example, the formulation is a lyophilized powder.

In some embodiments, a formulation comprises, consists essentially of, or consists of vedolizumab, a free amino acid selected from histidine, alanine, arginine, glycine, and glutamic acid, a polyol selected from mannitol, sorbitol, sucrose, trehalose, and a combination thereof, and a surfactant. Optionally, the formulation further comprises a buffer. In one example, the formulation is liquid. In another example, the formulation is solid (e.g., lyophilized powder for reconstitution).

In some embodiments, a formulation comprises, consists essentially of, or consists of vedolizumab, an acetate salt, such as sodium acetate trihydrate, an amino acid which is histidine and/or a salt thereof, sorbitol, and a non-ionic surfactant such as polysorbate 80; optionally, the formulation further comprises arginine and/or a salt thereof. In one example, the formulation is liquid and comprises water for injection. In another example, the pH of the liquid formulation is from about 5.1 to about 5.3. In yet another example, the formulation contains a negligible or non-detectable amount of sodium chloride. In yet another example, the formulation does not contain phosphate or citrate.

In some embodiments, a formulation comprises, consists essentially of, or consists of vedolizumab, an amino acid selected from L-histidine, L-histidine monohydrochloride monohydrate, and a combination thereof, sorbitol and polysorbate 80. In one example, the formulation is liquid and comprises water for injection.

In some embodiments, a formulation comprises, consists essentially of, or consists of vedolizumab, an amino acid selected from L-histidine, L-histidine monohydrochloride monohydrate, L-methionine, and a combination thereof, sucrose, and polysorbate 80. In one example, the formulation also contains a metal chelating agent such as EDTA disodium salt dihydrate. In another example, the formulation is liquid and contains water for injection.

In some embodiments, a formulation comprises, consists essentially of, or consists of vedolizumab, an amino acid selected from L-histidine, L-histidine monohydrochloride monohydrate, L-arginine hydrochloride, and a combination thereof, sucrose, and polysorbate 80. In one particular embodiment, the formulation is ENTYVIO®.

In some embodiments, a formulation comprises, consists essentially of, or consists of vedolizumab, an amino acid selected from L-histidine and L-arginine, and a combination thereof, polysorbate 20, and succinic acid.

In some embodiments, a formulation comprises, consists essentially of, or consists of vedolizumab at a concentration of at least about 100 mg/mL, mannitol, and polysorbate 80. In one example, the formulation is liquid and contains water for injection.

In some embodiments, a formulation comprises, consists essentially of, or consists of vedolizumab, a buffer containing a negligible or non-detectable amount of sodium chloride, phosphate and citrate, a polyol such as mannitol, and a surfactant selected from a polysorbate and a poloxamer. In one example, the formulation has an antibody concentration of at least about 50 mg/mL, about 75 mg/mL, or about 100 mg/mL or greater, and low conductivity.

In some embodiments, a formulation comprises, consists essentially of, or consists of vedolizumab, sodium chloride, and an acetate such as sodium acetate.

In some embodiments, a formulation of vedolizumab is a liquid formulation comprising at least about 50 mg/mL to about 100 mg/mL of vedolizumab, a buffering agent (e.g., histidine), and at least about 9% (w/w) non-reducing sugar (e.g., sucrose, trehalose or mannitol). In some embodiments, the formulation comprises at least about 50 mg/mL to about 80 mg/mL (e.g., about 60 mg/mL) of vedolizumab, a buffering agent (e.g., histidine), a free amino acid (e.g., arginine) and at least about 9% or about 10% (w/w) non-reducing sugar (e.g., sucrose, trehalose or mannitol).

A formulation of vedolizumab can be lyophilized and stored as a single dose in one container (e.g., a device as described herein). The container can be stored at about 2-8° C. until it is administered to a subject in need thereof. The container can contain, for example, a 60 mg/mL dose of vedolizumab. The container can contain at least about 120 mg, about 180 mg, about 240 mg, about 300 mg, about 360 mg, about 540 mg, or about 900 mg of the total amount of vedolizumab.

In some embodiments, an aqueous formulation comprises vedolizumab, about 50 mM histidine, about 125 mM arginine, about 0.06% polysorbate 80, and the pH of the formulation is about 6.3.

In some embodiments, an aqueous composition comprises about 5 mg/mL of vedolizumab, about 20 mM of citrate/citric acid, about 125 mM of sodium chloride, and about 0.05% polysorbate 80, and has a pH of about 6.0. This formulation can be stored long term at about −70° C. and up to 3 months at about −20° C.

In some embodiments, an aqueous formulation comprises about 60 mg/mL vedolizumab, about 25 mM histidine, about 75 mM arginine, about 2% sucrose, about 0.05% polysorbate 80, and has a pH of about 6.3.

In some embodiments, an aqueous formulation comprises about 60 mg/mL vedolizumab, about 25 mM histidine, about 75 mM arginine, about 4% sucrose, about 0.05% polysorbate 80, and has a pH of about 6.9.

In some embodiments, an aqueous formulation comprises about 60 mg/mL vedolizumab, about 50 mM histidine, about 125 mM arginine, about 2% sucrose, about 0.05% polysorbate 80, and has a pH of about 6.7.

In some embodiments, an aqueous formulation comprises about 60 mg/mL vedolizumab, about 50 mM histidine, about 125 mM arginine, about 4% sucrose, about 0.05% polysorbate 80, and has a pH of about 6.9.

In some embodiments, an aqueous formulation comprises about 60 mg/mL vedolizumab, about 50 mM histidine, about 125 mM arginine, about 6% sucrose, about 1.5% mannitol, about 0.06% polysorbate 80, and has a pH of about 6.3.

In some embodiments, an aqueous formulation comprises about 60 mg/mL vedolizumab, about 50 mM histidine, about 125 mM arginine, about 9% sucrose, about 0.06% polysorbate 80, and has a pH of about 6.3.

In some embodiments, a single dose of a liquid formulation contains about 300 mg vedolizumab, about 23 mg L-histidine, about 21.4 mg L-histidine monohydrochloride, about 131.7 mg L-arginine hydrochloride, about 500 mg sucrose and about 3 mg polysorbate 80. In some embodiments, this formulation is a lyophilized cake, and when reconstituted with about 4.8 mL of water for injection, the pH of the formulation is about 6.3. The formulation can be stored for up to about four hours at about 2-8° C. (about 36° F. to about 46° F.) without freezing.

In some embodiments, a dosage form (e.g., a container as described herein) contains about 1-20 mL of a 60 mg/mL solution of vedolizumab for a total dose of the antibody of about 60-1200 mg, for example about 300 mg. In some embodiments, the formulation is lyophilized and stored as a single dose in one container at about 2-8° C. until it is administered to a subject in need thereof.

Additional pharmaceutical formulations of vedolizumab are disclosed, for example, in US Publication Nos. 2012/0282249 and 2017/0002078; U.S. Pat. No. 9,764,033; and PCT Publication Nos. WO 2012/151248, WO 2016/086147, and WO 2016/105572, the disclosures of each of which are incorporated herein by reference in their entireties.

Formulations Containing Infliximab

In some embodiments, a pharmaceutical formulation described herein includes infliximab. The formulation can be a liquid, semi-solid, or solid formulation. The term "infliximab" includes antibody or monoclonal infliximab, any antigen-binding portion thereof, any glycosylation pattern variant thereof, and any biosimilar thereof.

Exemplary Dosage of Infliximab in Solid and Liquid Formulations

In some embodiments, a formulation of infliximab as described herein is administered to a patient, for example in a device as described herein, to achieve a therapeutically effective dose of, e.g., about 0.2 mg/kg, about 0.5 mg/kg, about 2.0 mg/kg, about 3.0 mg/kg, about 6.0 mg/kg, about 10.0 mg/kg, about 20.0 mg/kg, or about 40.0 mg/kg. In some embodiments, infliximab is administered at a dose of, e.g., about 80 mg, about 90 mg, about 100 mg, about 120 mg, about 150, about 160 mg, about 170 mg, about 180 mg, or about 200 mg.

In some embodiments, a liquid formulation of infliximab contains a high concentration of infliximab, including, for example, a concentration greater than about 45 mg/mL, greater than about 50 mg/mL, greater than about 100 mg/mL, greater than about 110 mg/mL, greater than about 125 mg/mL, greater than about 150 mg/mL, greater than about 175 mg/mL, or greater than about 200 mg/mL.

In some embodiments, the formulation of infliximab is a liquid, and the pH of the liquid formulation is from about 5 to about 8. In some embodiments, the liquid formulation includes a buffer. In some embodiments, the pH of the buffer, and/or the pH of the final liquid formulation containing the buffer, ranges from about 4 to about 8, from about 5 to about 8, from about 5 to about 7.5, from about 5 to about 7, from about 4.5 to about 6.0, from about 4.7 to about 5.7, from about 4.8 to about 5.5, or from about 5.0 to about 5.2.

Exemplary Formulations of Infliximab

In some embodiments, a formulation comprises, consists essentially of or consists of infliximab, sodium chloride, a buffer including sodium phosphate monobasic monohydrate, sodium phosphate dibasic heptahydrate, and polysorbate 80. In one example, the formulation is liquid and comprises water for injection.

In some embodiments, a formulation comprises, consists essentially of or consists of infliximab, a buffer which is optionally a phosphate or citrate buffer, and an excipient selected from a polyol (such as a sugar or sugar alcohol) and a non-ionic surfactant, such as a polysorbate. In one example, the formulation is liquid and contains water for injection. In another example, the formulation contains low levels of ionic excipients and has low conductivity.

In some embodiments, a formulation comprises, consists essentially of or consists of infliximab, sodium chloride, a buffer containing a phosphate such as sodium phosphate monobasic dihydrate, sodium phosphate dibasic dihydrate, or a combination thereof, L-arginine hydrochloride, and sucrose. In one example, the formulation is liquid and contains water for injection.

In some embodiments, a formulation comprises, consists essentially of or consists of infliximab, sodium chloride, a buffer containing a phosphate such as sodium phosphate monobasic dihydrate, sodium phosphate dibasic dihydrate, or a combination thereof, a citrate such as sodium citrate, citric acid monohydrate, or a combination thereof, mannitol, and polysorbate 80. In one example, the formulation is liquid and contains water for injection. In another example, the pH of the liquid formulation is adjusted with NaOH to about 5.2.

In some embodiments, a formulation comprises, consists essentially of or consists of infliximab, a buffer, which is optionally a phosphate or citrate buffer, a polyol selected from mannitol, sorbitol, sucrose, trehalose, raffinose, maltose, and a combination thereof, and a non-ionic surfactant selected from polysorbate 20, polysorbate 40, polysorbate 60, and polysorbate 80. In one example, the formulation contains low levels of ionic excipients and has low conductivity. In another example, the concentration of the antibody in the formulation is at least about 10 mg/mL, about 50 mg/mL, about 100 mg/mL, about 150 mg/mL, about 200 mg/mL, or about 250 mg/mL.

In some embodiments, a formulation comprises, consists essentially of or consists of infliximab, a buffer containing a phosphate selected from monobasic sodium phosphate and dibasic sodium phosphate, sucrose, and polysorbate 80. In some embodiments, the formulation is REMICADE®.

In some embodiments, a formulation comprises, consists essentially of or consists of infliximab, arginine, histidine, or a combination thereof, sucrose, and polysorbate 80. Optionally, the formulation further comprises a buffer. In one example, the formulation is a lyophilized powder.

In some embodiments, a formulation comprises, consists essentially of or consists of infliximab, a free amino acid selected from histidine, alanine, arginine, glycine, and glutamic acid, a polyol selected from mannitol, sorbitol, sucrose, trehalose, and a combination thereof, and a surfactant. Optionally, the formulation further comprises a buffer. In one example, the formulation is liquid. In another example, the formulation is solid (e.g., lyophilized powder for reconstitution).

In some embodiments, a formulation comprises, consists essentially of or consists of infliximab, an acetate salt, such as sodium acetate trihydrate, an amino acid which is histidine and/or a salt thereof, sorbitol, and a non-ionic surfactant such as polysorbate 80; optionally, the formulation further comprises arginine and/or a salt thereof. In one example, the formulation is liquid and comprises water for injection. In another example, the pH of the liquid formulation is from about 5.1 to about 5.3. In yet another example, the formulation contains a negligible or non-detectable amount of sodium chloride. In yet another example, the formulation does not contain phosphate or citrate.

In some embodiments, a formulation comprises, consists essentially of or consists of infliximab, an amino acid selected from L-histidine, L-histidine monohydrochloride monohydrate, and a combination thereof, sorbitol and polysorbate 80. In one example, the formulation is liquid and comprises water for injection.

In some embodiments, a formulation comprises, consists essentially of or consists of infliximab, an amino acid selected from L-histidine, L-histidine monohydrochloride monohydrate, L-methionine, and a combination thereof, sucrose, and polysorbate 80. In one example, the formulation also contains a metal chelating agent such as EDTA disodium salt dihydrate. In another example, the formulation is liquid and contains water for injection.

In some embodiments, a formulation comprises, consists essentially of or consists of infliximab, an amino acid selected from L-histidine, L-histidine monohydrochloride monohydrate, L-arginine hydrochloride, and a combination thereof, sucrose, and polysorbate 80.

In some embodiments, a formulation comprises, consists essentially of or consists of infliximab, an amino acid selected from L-histidine and L-arginine, and a combination thereof, polysorbate 20, and succinic acid.

In some embodiments, a formulation comprises, consists essentially of or consists of infliximab at a concentration of at least about 100 mg/mL, mannitol, and polysorbate 80. In one example, the formulation is liquid and contains water for injection.

In some embodiments, a formulation comprises, consists essentially of or consists of infliximab, a buffer containing a negligible or non-detectable amount of sodium chloride, phosphate and citrate, a polyol such as mannitol, and a surfactant selected from a polysorbate and a poloxamer. In one example, the formulation has an antibody concentration of at least about 50 mg/mL, about 75 mg/mL, or about 100 mg/mL or greater, and low conductivity.

In some embodiments, a formulation, at a bare minimum, comprises, consists essentially of or consists of infliximab, sodium chloride, and an acetate such as sodium acetate.

In some embodiments, a single dose of a formulation of infliximab (e.g., in a device as described herein) includes about 100 mg infliximab, about 500 mg sucrose, about 0.5 mg polysorbate 80, about 2.2 mg monobasic sodium phosphate, monohydrate, and about 6.1 mg dibasic sodium phosphate, dihydrate. In some embodiments, the pH of the formulation is about 7.2. In some embodiments, the formulation does not contain any preservatives. In some embodiments, a formulation of infliximab is a lyophilized powder that can be reconstituted. Infliximab can be supplied in a single container (e.g., in a device as described herein) as a liquid formulation containing about 10 mg/mL. In some embodiments, the formulation comprises about 100 mg infliximab, sucrose, polysorbate 80, monobasic sodium phosphate, monohydrate, and dibasic sodium phosphate.

Formulations Containing Etrolizumab

In some embodiments, a pharmaceutical formulation includes etrolizumab. The formulation can be a liquid, semi-solid, or solid formulation. As used herein, the term "etrolizumab" includes antibody or monoclonal etrolizumab, any antigen-binding portion thereof, any glycosylation pattern variant thereof, and any biosimilar thereof.

Exemplary Dosage of Etrolizumab in Solid and Liquid Formulations

In some embodiments, etrolizumab is administered at a dose of about 80 mg, about 90 mg, about 100 mg, about 105 mg, about 120 mg, about 150, about 160 mg, about 170 mg, about 180 mg, or about 200 mg. In some embodiments, an effective dose of etrolizumab is about 100 mg, about 200 mg, about 210 mg, about 300 mg, about 400 mg, or about 450 mg. In certain embodiments, the effective dose is about 105 mg or about 210 mg.

In some embodiments, a formulation of etrolizumab includes about 1 mg to about 500 mg, about 1 mg to about 100 mg, or about 5 mg to about 40 mg of etrolizumab.

In some embodiments, a liquid formulation of etrolizumab contains a high concentration of etrolizumab, including, for example, a concentration greater than about 45 mg/mL, greater than about 50 mg/mL, greater than about 100 mg/mL, greater than about 110 mg/mL, greater than about 125 mg/mL, greater than about 150 mg/mL, greater than about 175 mg/mL, or greater than about 200 mg/mL.

In some embodiments, the formulation of etrolizumab is a liquid, and the pH of the liquid formulation is from about 5 to about 8. In some embodiments, the liquid formulation includes a buffer. In some embodiments, the pH of the buffer, and/or the pH of the final liquid formulation containing the buffer, ranges from about 4 to about 8, from about 5 to about 8, from about 5 to about 7.5, from about 5 to about 7, from about 4.5 to about 6.0, from about 4.7 to about 5.7, from about 4.8 to about 5.5, or from about 5.0 to about 5.2.

Exemplary Formulations of Etrolizumab

In some embodiments, a formulation comprises, consists essentially of, or consists of etrolizumab, sodium chloride, a buffer including sodium phosphate monobasic monohydrate, sodium phosphate dibasic heptahydrate, and polysorbate 80. In one example, the formulation is liquid and comprises water for injection.

In some embodiments, a formulation comprises, consists essentially of, or consists of etrolizumab, a buffer which is optionally a phosphate or citrate buffer, and an excipient selected from a polyol (such as a sugar or sugar alcohol) and a non-ionic surfactant, such as a polysorbate. In one example, the formulation is liquid and contains water for injection. In another example, the formulation contains low levels of ionic excipients and has low conductivity.

In some embodiments, a formulation comprises, consists essentially of, or consists of etrolizumab, sodium chloride, a buffer containing a phosphate such as sodium phosphate monobasic dihydrate, sodium phosphate dibasic dihydrate, or a combination thereof, L-arginine hydrochloride, and sucrose. In one example, the formulation is liquid and contains water for injection.

In some embodiments, a formulation comprises, consists essentially of, or consists of etrolizumab, sodium chloride, a buffer containing a phosphate such as sodium phosphate monobasic dihydrate, sodium phosphate dibasic dihydrate, or a combination thereof, a citrate such as sodium citrate, citric acid monohydrate, or a combination thereof, mannitol, and polysorbate 80. In one example, the formulation is liquid and contains water for injection. In another example, the pH of the liquid formulation is adjusted with NaOH to about 5.2.

In some embodiments, a formulation comprises, consists essentially of, or consists of etrolizumab, a buffer, which is optionally a phosphate or citrate buffer, a polyol selected from mannitol, sorbitol, sucrose, trehalose, raffinose, maltose, and a combination thereof, and a non-ionic surfactant selected from polysorbate 20, polysorbate 40, polysorbate 60, and polysorbate 80. In one example, the formulation contains low levels of ionic excipients and has low conductivity. In another example, the concentration of the antibody in the formulation is at least about 10 mg/mL, about 50 mg/mL, about 100 mg/mL, about 150 mg/mL, about 200 mg/mL, or about 250 mg/mL.

In some embodiments, a formulation comprises, consists essentially of, or consists of etrolizumab, a buffer containing a phosphate selected from monobasic sodium phosphate and dibasic sodium phosphate, sucrose, and polysorbate 80.

In some embodiments, a formulation comprises, consists essentially of, or consists of etrolizumab, arginine, histidine, or a combination thereof, sucrose, and polysorbate 80. Optionally, the formulation further comprises a buffer. In one example, the formulation is a lyophilized powder.

In some embodiments, a formulation comprises, consists essentially of, or consists of etrolizumab, a free amino acid selected from histidine, alanine, arginine, glycine, and glutamic acid, a polyol selected from mannitol, sorbitol, sucrose, trehalose, and a combination thereof, and a surfactant. Optionally, the formulation further comprises a buffer. In one example, the formulation is liquid. In another example, the formulation is solid (e.g., lyophilized powder for reconstitution).

In some embodiments, a formulation comprises, consists essentially of, or consists of etrolizumab, an acetate salt, such as sodium acetate trihydrate, an amino acid which is histidine and/or a salt thereof, sorbitol, and a non-ionic surfactant such as polysorbate 80; optionally, the formulation further comprises arginine and/or a salt thereof. In one example, the formulation is liquid and comprises water for injection. In another example, the pH of the liquid formulation is from about 5.1 to about 5.3. In yet another example, the formulation contains a negligible or non-detectable amount of sodium chloride. In yet another example, the formulation does not contain phosphate or citrate.

In some embodiments, a formulation comprises, consists essentially of, or consists of etrolizumab, an amino acid selected from L-histidine, L-histidine monohydrochloride monohydrate, and a combination thereof, sorbitol and polysorbate 80. In one example, the formulation is liquid and comprises water for injection.

In some embodiments, a formulation comprises, consists essentially of, or consists of etrolizumab, an amino acid selected from L-histidine, L-histidine monohydrochloride monohydrate, L-methionine, and a combination thereof, sucrose, and polysorbate 80. In one example, the formulation also contains a metal chelating agent such as EDTA disodium salt dihydrate. In another example, the formulation is liquid and contains water for injection.

In some embodiments, a formulation comprises, consists essentially of, or consists of etrolizumab, an amino acid selected from L-histidine, L-histidine monohydrochloride monohydrate, L-arginine hydrochloride, and a combination thereof, sucrose, and polysorbate 80.

In some embodiments, a formulation comprises, consists essentially of, or consists of etrolizumab, an amino acid selected from L-histidine and L-arginine, and a combination thereof, polysorbate 20, and succinic acid.

In some embodiments, a formulation comprises, consists essentially of, or consists of etrolizumab at a concentration of at least about 100 mg/mL, mannitol, and polysorbate 80. In one example, the formulation is liquid and contains water for injection.

In some embodiments, a formulation comprises, consists essentially of, or consists of etrolizumab, a buffer containing a negligible or non-detectable amount of sodium chloride, phosphate and citrate, a polyol such as mannitol, and a surfactant selected from a polysorbate and a poloxamer. In one example, the formulation has an antibody concentration of at least about 50 mg/mL, about 75 mg/mL, or about 100 mg/mL or greater, and low conductivity.

In some embodiments, a formulation comprises, consists essentially of, or consists of etrolizumab, sodium chloride, and an acetate such as sodium acetate.

In some embodiments, a formulation of etrolizumab is a liquid formulation comprising about 105 mg at a concentration of the antibody of about 150 mg/mL. Additional pharmaceutical formulations of etrolizumab are disclosed, for example, in PCT Publication No. WO 2016/138207, the disclosure of which is incorporated herein by reference in its entirety.

Formulations Containing Golimumab

In some embodiments, a pharmaceutical formulation comprises golimumab. The formulation can be a liquid, semi-solid, or solid formulation. As used herein, the term "golimumab" includes antibody or monoclonal golimumab, any antigen-binding portion thereof, any glycosylation pattern variant thereof, and any biosimilar thereof.

Exemplary Dosage of Golimumab in Solid and Liquid Formulations

In some embodiments, golimumab is administered to a patient at a dose of about 20 mg, about 30 mg, about 40 mg, about 50 mg, about 60 mg, about 70 mg, about 80 mg, about 100 mg, about 150 mg, or about 200 mg. In some embodiments, a formulation of golimumab includes about 1 mg to about 500 mg, about 1 mg to about 100 mg, about 5 mg to about 40 mg, about 40 mg to about 80 mg, about 160 mg, about 80 mg or about 40 mg of golimumab. In some embodiments, the formulation contains an induction dose of about 160 mg of golimumab. In other embodiments, the formulation contains a maintenance dose of about 80 mg, about 40 mg, or about 40 mg to about 80 mg of golimumab.

In some embodiments, a liquid formulation of golimumab contains a high concentration of golimumab, including, for example, a concentration greater than about 45 mg/mL, greater than about 50 mg/mL, greater than about 100 mg/mL, greater than about 110 mg/mL, greater than about 125 mg/mL, greater than about 150 mg/mL, greater than about 175 mg/mL, or greater than about 200 mg/mL.

In some embodiments, the formulation of golimumab is a liquid, and the pH of the liquid formulation is from about 5 to about 8. In some embodiments, the liquid formulation includes a buffer. In some embodiments, the pH of the buffer, and/or the pH of the final liquid formulation containing the buffer, ranges from about 4 to about 8, from about 5 to about 8, from about 5 to about 7.5, from about 5 to about 7, from about 4.5 to about 6.0, from about 4.7 to about 5.7, from about 4.8 to about 5.5, or from about 5.0 to about 5.2.

Exemplary Formulations of Golimumab

In some embodiments, a formulation comprises, consists essentially of or consists of golimumab, sodium chloride, a buffer including sodium phosphate monobasic monohydrate, sodium phosphate dibasic heptahydrate, and polysorbate 80. In one example, the formulation is liquid and comprises water for injection.

In some embodiments, a formulation comprises, consists essentially of or consists of golimumab, a buffer which is optionally a phosphate or citrate buffer, and an excipient selected from a polyol (such as a sugar or sugar alcohol) and a non-ionic surfactant, such as a polysorbate. In one example, the formulation is liquid and contains water for injection. In another example, the formulation contains low levels of ionic excipients and has low conductivity.

In some embodiments, a formulation comprises, consists essentially of or consists of golimumab, sodium chloride, a buffer containing a phosphate such as sodium phosphate monobasic dihydrate, sodium phosphate dibasic dihydrate, or a combination thereof, L-arginine hydrochloride, and sucrose. In one example, the formulation is liquid and contains water for injection.

In some embodiments, a formulation comprises, consists essentially of or consists of golimumab, sodium chloride, a buffer containing a phosphate such as sodium phosphate monobasic dihydrate, sodium phosphate dibasic dihydrate, or a combination thereof, a citrate such as sodium citrate, citric acid monohydrate, or a combination thereof, mannitol, and polysorbate 80. In one example, the formulation is liquid and contains water for injection. In another example, the pH of the liquid formulation is adjusted with NaOH to about 5.2.

In some embodiments, a formulation comprises, consists essentially of or consists of golimumab, a buffer, which is optionally a phosphate or citrate buffer, a polyol selected from mannitol, sorbitol, sucrose, trehalose, raffinose, maltose, and a combination thereof, and a non-ionic surfactant selected from polysorbate 20, polysorbate 40, polysorbate 60, and polysorbate 80. In one example, the formulation contains low levels of ionic excipients and has low conductivity. In another example, concentration of the antibody in the formulation is at least about 10 mg/mL, about 50 mg/mL, about 100 mg/mL, about 150 mg/mL, about 200 mg/mL, or about 250 mg/mL.

In some embodiments, a formulation comprises, consists essentially of or consists of golimumab, a buffer containing a phosphate selected from monobasic sodium phosphate and dibasic sodium phosphate, sucrose, and polysorbate 80.

In some embodiments, a formulation comprises, consists essentially of or consists of golimumab, arginine, histidine, or a combination thereof, sucrose, and polysorbate 80. Optionally, the formulation further comprises a buffer. In one example, the formulation is a lyophilized powder.

In some embodiments, a formulation comprises, consists essentially of or consists of golimumab, a free amino acid selected from histidine, alanine, arginine, glycine, and glutamic acid, a polyol selected from mannitol, sorbitol, sucrose, trehalose, and a combination thereof, and a surfactant. Optionally, the formulation further comprises a buffer. In one example, the formulation is liquid. In another example, the formulation is solid (e.g., lyophilized powder for reconstitution).

In some embodiments, a formulation comprises, consists essentially of or consists of golimumab, an acetate salt, such as sodium acetate trihydrate, an amino acid which is histidine and/or a salt thereof, sorbitol, and a non-ionic surfactant such as polysorbate 80; optionally, the formulation further comprises arginine and/or a salt thereof. In one example, the formulation is liquid and comprises water for injection. In another example, pH of the liquid formulation is from about 5.1 to about 5.3. In yet another example, the formulation contains a negligible or non-detectable amount of sodium chloride. In yet another example, the formulation does not contain phosphate or citrate.

In some embodiments, a formulation comprises, consists essentially of or consists of golimumab, an amino acid selected from L-histidine, L-histidine monohydrochloride monohydrate, and a combination thereof, sorbitol and polysorbate 80. In one example, the formulation is liquid and comprises water for injection. In one particular embodiment, the formulation is SIMPONI® 50 mg solution for injection (e.g., the solution as commercially provided in pre-filled syringes).

In some embodiments, a formulation comprises, consists essentially of or consists of golimumab, an amino acid selected from L-histidine, L-histidine monohydrochloride monohydrate, L-methionine, and a combination thereof, sucrose, and polysorbate 80. In one example, the formulation also contains a metal chelating agent such as EDTA disodium salt dihydrate. In another example, the formulation is liquid and contains water for injection.

In some embodiments, a formulation comprises, consists essentially of or consists of golimumab, an amino acid selected from L-histidine, L-histidine monohydrochloride monohydrate, L-arginine hydrochloride, and a combination thereof, sucrose, and polysorbate 80.

In some embodiments, a formulation comprises, consists essentially of or consists of golimumab, an amino acid selected from L-histidine and L-arginine, and a combination thereof, polysorbate 20, and succinic acid.

In some embodiments, a formulation comprises, consists essentially of or consists of golimumab at a concentration of at least about 100 mg/mL, mannitol, and polysorbate 80. In one example, the formulation is liquid and contains water for injection.

In some embodiments, a formulation comprises, consists essentially of or consists of golimumab, a buffer containing a negligible or non-detectable amount of sodium chloride, phosphate and citrate, a polyol such as mannitol, and a surfactant selected from a polysorbate and a poloxamer. In one example, the formulation has an antibody concentration of at least about 50 mg/mL, about 75 mg/mL, or about 100 mg/mL or greater, and low conductivity.

In some embodiments, a formulation comprises about 50 mg of the golimumab antibody, about 0.44 mg of L-histidine and L-histidine monohydrochloride monohydrate, about 20.5 mg of sorbitol, about 0.08 mg of polysorbate 80, and water for injection. In some embodiments, the formulation is liquid and the pH of the formulation is about 5.5. In some embodiments, the formulation is a solid lyophilized powder. In some embodiments, neither the liquid nor the solid formulation contains preservatives.

In some embodiments, a formulation comprises about 100 mg of the golimumab antibody, about 0.87 mg of L-histidine and L-histidine monohydrochloride monohydrate, about 41.0 mg of sorbitol, about 0.15 mg of polysorbate 80, and water for injection. In some embodiments, the formulation is liquid and the pH of the formulation is about 5.5. In some embodiments, the formulation is a solid lyophilized powder. In some embodiments, neither the liquid nor the solid formulation contains preservatives.

In some embodiments, a single container (e.g., a device as described herein) comprises about 50 mg or about 100 mg of golimumab, sorbitol, L-histidine, L-histidine monohydrochloride monohydrate, and polysorbate 80.

Additional pharmaceutical formulations of golimumab are disclosed, for example, in US Publication Nos. 2011/0014189, 2012/0263731, 2014/0127227, 2016/0287525, and 2017/0273909; U.S. Pat. Nos. 8,226,949 and 8,420,081; and PCT Publication Nos. WO 2017/106595 and WO 2018/067987, the disclosures of each of which are incorporated herein by reference in their entireties.

Formulations Containing Certolizumab Pegol

In some embodiments, a pharmaceutical formulation includes certolizumab pegol. The formulation can be a liquid, semi-solid, or solid formulation. As used herein, the term "certolizumab pegol" includes antibody or monoclonal certolizumab pegol, any antigen-binding portion thereof, any glycosylation pattern variant thereof, and any biosimilar thereof.

Exemplary Dosage of Certolizumab Pegol in Solid and Liquid Formulations

In some embodiments, certolizumab pegol is administered at a dose of about 50 mg, about 60 mg, about 70 mg, about 80 mg, about 100 mg, about 150 mg, about 200 mg, about 250 mg, about 400 mg, about 500 mg, about 600 mg, about 800 mg, or about 1000 mg. In some embodiments, a formulation of certolizumab pegol includes about 1 mg to about 500 mg, about 1 mg to about 100 mg, about 5 mg to about 40 mg, about 40 mg to about 80 mg, about 160 mg, about 80 mg or about 40 mg of certolizumab pegol. In some embodiments, the formulation contains an induction dose of about 160 mg of certolizumab pegol. In other embodiments, the formulation contains a maintenance dose of about 80 mg, about 40 mg, or about 40 mg to about 80 mg of certolizumab pegol.

In some embodiments, the formulation is liquid and the concentration of certolizumab pegol in the formulation is about 200 mg/mL. In some embodiments, a single dosage form (e.g., a device as described herein) comprises about 200 mg of a liquid formulation comprising about 200 mg/mL concentration of certolizumab pegol. In some embodiments, an effective dose of certolizumab pegol is about 10-20 mg/kg.

In some embodiments, a liquid formulation of certolizumab pegol contains a high concentration of certolizumab pegol, including, for example, a concentration greater than about 45 mg/mL, greater than about 50 mg/mL, greater than about 100 mg/mL, greater than about 110 mg/mL, greater than about 125 mg/mL, greater than about 150 mg/mL, greater than about 175 mg/mL, or greater than about 200 mg/mL.

In some embodiments, the formulation of certolizumab pegol is a liquid, and the pH of the liquid formulation is from about 5 to about 8. In some embodiments, the liquid formulation includes a buffer. In some embodiments, the pH of the buffer, and/or the pH of the final liquid formulation containing the buffer, ranges from about 4 to about 8, from about 5 to about 8, from about 5 to about 7.5, from about 5 to about 7, from about 4.5 to about 6.0, from about 4.7 to about 5.7, from about 4.8 to about 5.5, or from about 5.0 to about 5.2.

Exemplary Formulations of Certolizumab Pegol

In some embodiments, a formulation comprises, consists essentially of or consists of certolizumab pegol, sodium chloride, a buffer including sodium phosphate monobasic monohydrate, sodium phosphate dibasic heptahydrate, and polysorbate 80. In one example, the formulation is liquid and comprises water for injection.

In some embodiments, a formulation comprises, consists essentially of or consists of certolizumab pegol, a buffer which is optionally a phosphate or citrate buffer, and an excipient selected from a polyol (such as a sugar or sugar alcohol) and a non-ionic surfactant, such as a polysorbate. In one example, the formulation is liquid and contains water for injection. In another example, the formulation contains low levels of ionic excipients and has low conductivity.

In some embodiments, a formulation comprises, consists essentially of or consists of certolizumab pegol, sodium chloride, a buffer containing a phosphate such as sodium phosphate monobasic dihydrate, sodium phosphate dibasic dihydrate, or a combination thereof, L-arginine hydrochloride, and sucrose. In one example, the formulation is liquid and contains water for injection.

In some embodiments, a formulation comprises, consists essentially of or consists of certolizumab pegol, sodium chloride, a buffer containing a phosphate such as sodium phosphate monobasic dihydrate, sodium phosphate dibasic dihydrate, or a combination thereof, a citrate such as sodium citrate, citric acid monohydrate, or a combination thereof, mannitol, and polysorbate 80. In one example, the formulation is liquid and contains water for injection. In another example, the pH of the liquid formulation is adjusted with NaOH to about 5.2.

In some embodiments, a formulation comprises, consists essentially of or consists of certolizumab pegol, a buffer, which is optionally a phosphate or citrate buffer, a polyol selected from mannitol, sorbitol, sucrose, trehalose, raffinose, maltose, and a combination thereof, and a non-ionic surfactant selected from polysorbate 20, polysorbate 40, polysorbate 60, and polysorbate 80. In one example, the formulation contains low levels of ionic excipients and has low conductivity. In another example, the concentration of the antibody in the formulation is at least about 10 mg/mL, about 50 mg/mL, about 100 mg/mL, about 150 mg/mL, about 200 mg/mL, or about 250 mg/mL.

In some embodiments, a formulation comprises, consists essentially of or consists of certolizumab pegol, a buffer containing a phosphate selected from monobasic sodium phosphate and dibasic sodium phosphate, sucrose, and polysorbate 80.

In some embodiments, a formulation comprises, consists essentially of or consists of certolizumab pegol, arginine, histidine, or a combination thereof, sucrose, and polysorbate 80. Optionally, the formulation further comprises a buffer. In one example, the formulation is a lyophilized powder.

In some embodiments, a formulation comprises, consists essentially of or consists of certolizumab pegol, a free amino acid selected from histidine, alanine, arginine, glycine, and glutamic acid, a polyol selected from mannitol, sorbitol, sucrose, trehalose, and a combination thereof, and a surfactant. Optionally, the formulation further comprises a buffer. In one example, the formulation is liquid. In another example, the formulation is solid (e.g., lyophilized powder for reconstitution).

In some embodiments, a formulation comprises, consists essentially of or consists of certolizumab pegol, an acetate salt, such as sodium acetate trihydrate, an amino acid which is histidine and/or a salt thereof, sorbitol, and a non-ionic surfactant such as polysorbate 80; optionally, the formulation further comprises arginine and/or a salt thereof. In one example, the formulation is liquid and comprises water for injection. In another example, the pH of the liquid formulation is from about 5.1 to about 5.3. In yet another example, the formulation contains a negligible or non-detectable amount of sodium chloride. In yet another example, the formulation does not contain phosphate or citrate.

In some embodiments, a formulation comprises, consists essentially of or consists of certolizumab pegol, an amino acid selected from L-histidine, L-histidine monohydrochloride monohydrate, and a combination thereof, sorbitol and polysorbate 80. In one example, the formulation is liquid and comprises water for injection.

In some embodiments, a formulation comprises, consists essentially of or consists of certolizumab pegol, an amino acid selected from L-histidine, L-histidine monohydrochloride monohydrate, L-methionine, and a combination thereof, sucrose, and polysorbate 80. In one example, the formulation also contains a metal chelating agent such as EDTA disodium salt dihydrate. In another example, the formulation is liquid and contains water for injection.

In some embodiments, a formulation comprises, consists essentially of or consists of certolizumab pegol, an amino acid selected from L-histidine, L-histidine monohydrochloride monohydrate, L-arginine hydrochloride, and a combination thereof, sucrose, and polysorbate 80.

In some embodiments, a formulation comprises, consists essentially of or consists of certolizumab pegol, an amino acid selected from L-histidine and L-arginine, and a combination thereof, polysorbate 20, and succinic acid.

In some embodiments, a formulation comprises, consists essentially of or consists of certolizumab pegol at a concentration of at least about 100 mg/mL, mannitol, and polysorbate 80. In one example, the formulation is liquid and contains water for injection.

In some embodiments, a formulation comprises, consists essentially of or consists of certolizumab pegol, a buffer containing a negligible or non-detectable amount of sodium chloride, phosphate and citrate, a polyol such as mannitol, and a surfactant selected from a polysorbate and a poloxamer. In one example, the formulation has an antibody concentration of at least about 50 mg/mL, about 75 mg/mL, or about 100 mg/mL or greater, and low conductivity.

In some embodiments, a formulation comprises, consists essentially of or consists of certolizumab pegol, sodium chloride, and an acetate such as sodium acetate. In one particular embodiment, the formulation is CIMZIA®.

In some embodiments, a formulation comprises about 200 mg certolizumab pegol, about 0.9 mg lactic acid, about 0.1 mg polysorbate, and about 100 mg sucrose. In some embodiments, the formulation is liquid and the pH of the formulation is about 5.2. In some embodiments, the formulation is a solid lyophilized powder. In some embodiments, a formulation is a liquid formulation which comprises about 200 mg certolizumab pegol, about 1.36 mg sodium acetate, about 7.31 mg sodium chloride, and water for injection. In some embodiments, the pH of the formulation is about 4.7.

Formulations Containing Ustekinumab

In some embodiments, a pharmaceutical formulation comprises ustekinumab. The formulation can be a liquid, semi-solid, or solid formulation. As used herein, the term "ustekinumab" includes antibody or monoclonal ustekinumab, any antigen-binding portion thereof, any glycosylation pattern variant thereof, and any biosimilar thereof.

Exemplary Dosages of Ustekinumab in Solid and Liquid Formulations

In some embodiments, ustekinumab is administered at a dose of about 20 mg, about 30 mg, about 40 mg, about 45 mg, about 50 mg, about 60 mg, about 70 mg, about 80 mg, about 90 mg, about 100 mg, about 130 mg, about 150 mg, about 200 mg, about 260 mg, about 300 mg, 390 mg, about 500 mg, about 520 mg, or about 600 mg. In some embodiments, a formulation of ustekinumab includes about 1 mg to about 650 mg, about 1 mg to about 600 mg, about 1 mg to about 500 mg, about 1 mg to about 100 mg, or about 5 mg to about 40 mg of ustekinumab.

In some embodiments, the formulation is liquid and the concentration of ustekinumab in the formulation is from about 5 mg/mL to about 90 mg/mL. In some embodiments, a single dosage form (e.g., a device as described herein) comprises about 130 mg of a liquid formulation comprising about 5 mg/mL concentration of ustekinumab. In some embodiments, an effective dose of ustekinumab is about 1-50 mg/kg. In some embodiments, an effective dose of ustekinumab is about 6 mg/kg.

In some embodiments, a liquid formulation of ustekinumab contains a high concentration of ustekinumab, including, for example, a concentration greater than about 45 mg/mL, greater than about 50 mg/mL, greater than about 100 mg/mL, greater than about 110 mg/mL, greater than about 125 mg/mL, greater than about 150 mg/mL, greater than about 175 mg/mL, or greater than about 200 mg/mL.

In some embodiments, the formulation of ustekinumab is a liquid, and the pH of the liquid formulation is from about 5 to about 8. In some embodiments, the liquid formulation includes a buffer. In some embodiments, the pH of the buffer, and/or the pH of the final liquid formulation containing the buffer, ranges from about 4 to about 8, from about 5 to about 8, from about 5 to about 7.5, from about 5 to about 7, from about 4.5 to about 6.0, from about 4.7 to about 5.7, from about 4.8 to about 5.5, or from about 5.0 to about 5.2.

Exemplary Formulations of Ustekinumab

In some embodiments, a formulation comprises, consists essentially of or consists of ustekinumab, sodium chloride, a buffer including sodium phosphate monobasic monohydrate, sodium phosphate dibasic heptahydrate, and polysorbate 80. In one example, the formulation is liquid and comprises water for injection.

In some embodiments, a formulation comprises, consists essentially of or consists of ustekinumab, a buffer which is optionally a phosphate or citrate buffer, and an excipient selected from a polyol (such as a sugar or sugar alcohol) and a non-ionic surfactant, such as a polysorbate. In one example, the formulation is liquid and contains water for injection. In another example, the formulation contains low levels of ionic excipients and has low conductivity.

In some embodiments, a formulation comprises, consists essentially of or consists of ustekinumab, sodium chloride, a buffer containing a phosphate such as sodium phosphate monobasic dihydrate, sodium phosphate dibasic dihydrate, or a combination thereof, L-arginine hydrochloride, and sucrose. In one example, the formulation is liquid and contains water for injection.

In some embodiments, a formulation comprises, consists essentially of or consists of ustekinumab, sodium chloride, a buffer containing a phosphate such as sodium phosphate monobasic dihydrate, sodium phosphate dibasic dihydrate, or a combination thereof, a citrate such as sodium citrate, citric acid monohydrate, or a combination thereof, mannitol, and polysorbate 80. In one example, the formulation is liquid and contains water for injection. In another example, the pH of the liquid formulation is adjusted with NaOH to about 5.2.

In some embodiments, a formulation comprises, consists essentially of or consists of ustekinumab, a buffer, which is optionally a phosphate or citrate buffer, a polyol selected from mannitol, sorbitol, sucrose, trehalose, raffinose, maltose, and a combination thereof, and a non-ionic surfactant selected from polysorbate 20, polysorbate 40, polysorbate 60, and polysorbate 80. In one example, the formulation contains low levels of ionic excipients and has low conductivity. In another example, the concentration of the antibody in the formulation is at least about 10 mg/mL, about 50 mg/mL, about 100 mg/mL, about 150 mg/mL, about 200 mg/mL, or about 250 mg/mL.

In some embodiments, a formulation comprises, consists essentially of or consists of ustekinumab, a buffer containing a phosphate selected from monobasic sodium phosphate and dibasic sodium phosphate, sucrose, and polysorbate 80.

In some embodiments, a formulation comprises, consists essentially of or consists of ustekinumab, arginine, histidine, or a combination thereof, sucrose, and polysorbate 80. Optionally, the formulation further comprises a buffer. In one example, the formulation is a lyophilized powder.

In some embodiments, a formulation comprises, consists essentially of or consists of ustekinumab, a free amino acid selected from histidine, alanine, arginine, glycine, and glutamic acid, a polyol selected from mannitol, sorbitol, sucrose, trehalose, and a combination thereof, and a surfactant. Optionally, the formulation further comprises a buffer. In one example, the formulation is liquid. In another example, the formulation is solid (e.g., lyophilized powder for reconstitution).

In some embodiments, a formulation comprises, consists essentially of or consists of ustekinumab, an acetate salt, such as sodium acetate trihydrate, an amino acid which is histidine and/or a salt thereof, sorbitol, and a non-ionic surfactant such as polysorbate 80; optionally, the formulation further comprises arginine and/or a salt thereof. In one example, the formulation is liquid and comprises water for injection. In another example, the pH of the liquid formulation is from about 5.1 to about 5.3. In yet another example, the formulation contains a negligible or non-detectable amount of sodium chloride. In yet another example, the formulation does not contain phosphate or citrate.

In some embodiments, a formulation comprises, consists essentially of or consists of ustekinumab, an amino acid selected from L-histidine, L-histidine monohydrochloride monohydrate, and a combination thereof, sorbitol and polysorbate 80. In one example, the formulation is liquid and comprises water for injection.

In some embodiments, a formulation comprises, consists essentially of or consists of ustekinumab, an amino acid selected from L-histidine, L-histidine monohydrochloride monohydrate, L-methionine, and a combination thereof, sucrose, and polysorbate 80. In one example, the formulation also contains a metal chelating agent such as EDTA disodium salt dihydrate. In another example, the formulation is liquid and contains water for injection. In one particular embodiment, the formulation is STELARA®.

In some embodiments, a formulation comprises, consists essentially of or consists of ustekinumab, an amino acid selected from L-histidine, L-histidine monohydrochloride monohydrate, L-arginine hydrochloride, and a combination thereof, sucrose, and polysorbate 80.

In some embodiments, a formulation comprises, consists essentially of or consists of ustekinumab, an amino acid selected from L-histidine and L-arginine, and a combination thereof, polysorbate 20, and succinic acid.

In some embodiments, a formulation comprises, consists essentially of or consists of ustekinumab at a concentration of at least about 100 mg/mL, mannitol, and polysorbate 80. In one example, the formulation is liquid and contains water for injection.

In some embodiments, a formulation comprises, consists essentially of or consists of ustekinumab, a buffer containing a negligible or non-detectable amount of sodium chloride, phosphate and citrate, a polyol such as mannitol, and a surfactant selected from a polysorbate and a poloxamer. In one example, the formulation has an antibody concentration of at least about 50 mg/mL, about 75 mg/mL, or about 100 mg/mL or greater, and low conductivity.

In some embodiments, a formulation comprises, consists essentially of or consists of ustekinumab, sodium chloride, and an acetate such as sodium acetate.

In some embodiments, each 0.5 mL of a liquid formulation of ustekinumab comprises about 45 mg ustekinumab, about 0.5 mg of L-histidine and L-histidine monohydrochloride monohydrate, about 0.02 mg of polysorbate 80, and about 38 mg of sucrose.

In some embodiments, each 1 mL of a liquid formulation of ustekinumab comprises about 90 mg ustekinumab, about 1 mg of L-histidine and L-histidine monohydrochloride monohydrate, about 0.04 mg of polysorbate 80, and about 76 mg of sucrose.

In some embodiments, a formulation of ustekinumab comprises about 130 mg of ustekinumab, about 0.52 mg of EDTA disodium salt dihydrate, about 20 mg of L-histidine, about 27 mg of L-histidine hydrochloride monohydrate, about 10.4 mg of L-methionine, about 10.4 mg of polysorbate 80 and about 2210 mg of sucrose. In some embodiments, the formulation is liquid. In others, the formulation is a solid lyophilized powder.

In some embodiments, a formulation of ustekinumab comprises about 130 mg, about 260 mg, about 390 mg, or about 520 mg of ustekinumab, L-histidine, L-histidine monohydrochloride monohydrate, L-methionine, polysorbate 80, and sucrose. In one example, when the formulation is a liquid formulation, the formulation comprises water for injection.

Formulations Containing Risankizumab

In some embodiments, a pharmaceutical formulation comprises risankizumab. The formulation can be a liquid, semi-solid, or solid formulation. As used herein, the term "risankizumab" includes antibody or monoclonal risankizumab, any antigen-binding portion thereof, any glycosylation pattern variant thereof, and any biosimilar thereof.

Exemplary Dosages of Risankizumab in Solid and Liquid Formulations

In some embodiments, risankizumab is administered at a dose of about 15 mg, about 18 mg, about 20 mg, about 30 mg, about 36 mg, about 40 mg, about 50 mg, about 60 mg, about 70 mg, about 80 mg, about 90 mg, about 100 mg, about 130 mg, about 150 mg, about 200 mg, or about 500 mg. In some embodiments, a formulation of risankizumab includes about 1 mg to about 650 mg, about 1 mg to about 600 mg, about 1 mg to about 500 mg, about 1 mg to about 100 mg, or about 5 mg to about 40 mg of risankizumab.

In some embodiments, a liquid formulation of risankizumab contains a high concentration of risankizumab, including, for example, a concentration greater than about 45 mg/mL, greater than about 50 mg/mL, greater than about 100 mg/mL, greater than about 110 mg/mL, greater than about 125 mg/mL, greater than about 150 mg/mL, greater than about 175 mg/mL, or greater than about 200 mg/mL.

In some embodiments, the formulation of risankizumab is a liquid, and the pH of the liquid formulation is from about 5 to about 8. In some embodiments, the liquid formulation includes a buffer. In some embodiments, the pH of the buffer, and/or the pH of the final liquid formulation containing the buffer, ranges from about 4 to about 8, from about 5 to about 8, from about 5 to about 7.5, from about 5 to about 7, from about 4.5 to about 6.0, from about 4.7 to about 5.7, from about 4.8 to about 5.5, or from about 5.0 to about 5.2.

Exemplary Formulations of Risankizumab

In some embodiments, a formulation comprises, consists essentially of or consists of risankizumab, sodium chloride, a buffer including sodium phosphate monobasic monohydrate, sodium phosphate dibasic heptahydrate, and polysorbate 80. In one example, the formulation is liquid and comprises water for injection.

In some embodiments, a formulation comprises, consists essentially of or consists of risankizumab, a buffer which is optionally a phosphate or citrate buffer, and an excipient selected from a polyol (such as a sugar or sugar alcohol) and a non-ionic surfactant, such as a polysorbate. In one example, the formulation is liquid and contains water for injection. In another example, the formulation contains low levels of ionic excipients and has low conductivity.

In some embodiments, a formulation comprises, consists essentially of or consists of risankizumab, sodium chloride, a buffer containing a phosphate such as sodium phosphate monobasic dihydrate, sodium phosphate dibasic dihydrate, or a combination thereof, L-arginine hydrochloride, and sucrose. In one example, the formulation is liquid and contains water for injection.

In some embodiments, a formulation comprises, consists essentially of or consists of risankizumab, sodium chloride, a buffer containing a phosphate such as sodium phosphate monobasic dihydrate, sodium phosphate dibasic dihydrate, or a combination thereof, a citrate such as sodium citrate, citric acid monohydrate, or a combination thereof, mannitol, and polysorbate 80. In one example, the formulation is liquid and contains water for injection. In another example, the pH of the liquid formulation is adjusted with NaOH to about 5.2.

In some embodiments, a formulation comprises, consists essentially of or consists of risankizumab, a buffer, which is optionally a phosphate or citrate buffer, a polyol selected from mannitol, sorbitol, sucrose, trehalose, raffinose, maltose, and a combination thereof, and a non-ionic surfactant selected from polysorbate 20, polysorbate 40, polysorbate 60, and polysorbate 80. In one example, the formulation contains low levels of ionic excipients and has low conductivity. In another example, concentration of the antibody in the formulation is at least about 10 mg/mL, about 50 mg/mL, about 100 mg/mL, about 150 mg/mL, about 200 mg/mL, or about 250 mg/mL.

In some embodiments, a formulation comprises, consists essentially of or consists of risankizumab, a buffer containing a phosphate selected from monobasic sodium phosphate and dibasic sodium phosphate, sucrose, and polysorbate 80.

In some embodiments, a formulation comprises, consists essentially of or consists of risankizumab, arginine, histidine, or a combination thereof, sucrose, and polysorbate 80. Optionally, the formulation further comprises a buffer. In one example, the formulation is a lyophilized powder.

In some embodiments, a formulation comprises, consists essentially of or consists of risankizumab, a free amino acid selected from histidine, alanine, arginine, glycine, and glutamic acid, a polyol selected from mannitol, sorbitol, sucrose, trehalose, and a combination thereof, and a surfactant. Optionally, the formulation further comprises a buffer. In one example, the formulation is liquid. In another example, the formulation is solid (e.g., lyophilized powder for reconstitution).

In some embodiments, a formulation comprises, consists essentially of or consists of risankizumab, an acetate salt, such as sodium acetate trihydrate, an amino acid which is histidine and/or a salt thereof, sorbitol, and a non-ionic surfactant such as polysorbate 80; optionally, the formulation further comprises arginine and/or a salt thereof. In one example, the formulation is liquid and comprises water for injection. In another example, the pH of the liquid formulation is from about 5.1 to about 5.3. In yet another example, the formulation contains a negligible or non-detectable amount of sodium chloride. In yet another example, the formulation does not contain phosphate or citrate.

In some embodiments, a formulation comprises, consists essentially of or consists of risankizumab, an amino acid selected from L-histidine, L-histidine monohydrochloride monohydrate, and a combination thereof, sorbitol and polysorbate 80. In one example, the formulation is liquid and comprises water for injection.

In some embodiments, a formulation comprises, consists essentially of or consists of risankizumab, an amino acid selected from L-histidine, L-histidine monohydrochloride monohydrate, L-methionine, and a combination thereof, sucrose, and polysorbate 80. In one example, the formulation also contains a metal chelating agent such as EDTA disodium salt dihydrate. In another example, the formulation is liquid and contains water for injection.

In some embodiments, a formulation comprises, consists essentially of or consists of risankizumab, an amino acid selected from L-histidine, L-histidine monohydrochloride monohydrate, L-arginine hydrochloride, and a combination thereof, sucrose, and polysorbate 80.

In some embodiments, a formulation comprises, consists essentially of or consists of risankizumab, an amino acid selected from L-histidine and L-arginine, and a combination thereof, polysorbate 20, and succinic acid.

In some embodiments, a formulation comprises, consists essentially of or consists of risankizumab at a concentration of at least about 100 mg/mL, mannitol, and polysorbate 80. In one example, the formulation is liquid and contains water for injection.

In some embodiments, a formulation comprises, consists essentially of or consists of risankizumab, a buffer containing a negligible or non-detectable amount of sodium chloride, phosphate and citrate, a polyol such as mannitol, and a surfactant selected from a polysorbate and a poloxamer. In one example, the formulation has an antibody concentration of at least about 50 mg/mL, about 75 mg/mL, or about 100 mg/mL or greater, and low conductivity.

In some embodiments, a formulation comprises, consists essentially of or consists of risankizumab, sodium chloride, and an acetate such as sodium acetate.

Formulations Containing Etanercept

In some embodiments, a pharmaceutical formulation comprises etanercept. The formulation can be a liquid, semi-solid, or solid formulation. As used herein, the term "etanercept" includes antibody or monoclonal etanercept, any antigen-binding portion thereof, any glycosylation pattern variant thereof, and any biosimilar thereof.

Exemplary Dosages of Etanercept in Solid and Liquid Formulations

In some embodiments, etanercept is administered to a patient at a dose of about 5 mg, about 10 mg, about 15 mg, about 20 mg, about 25 mg, about 30 mg, about 40 mg, about 50 mg, about 60 mg, about 70 mg, about 80 mg, about 90 mg, or about 100 mg.

In some embodiments, a formulation of etanercept includes about 1 mg to about 500 mg, about 1 mg to about 100 mg, about 5 mg to about 40 mg, about 40 mg to about 80 mg, about 160 mg, about 80 mg or about 40 mg of etanercept. In some embodiments, the formulation contains an induction dose of about 160 mg of etanercept. In other embodiments, the formulation contains a maintenance dose of about 80 mg, about 40 mg, or about 40 mg to about 80 mg of etanercept.

In some embodiments, when the formulation is liquid, the formulation comprises about 10 mg, about 25 mg, or about 50 mg of etanercept at a concentration of about 50 mg/mL.

In some embodiments, a liquid formulation of etanercept contains a high concentration of etanercept, including, for example, a concentration greater than about 45 mg/mL, greater than about 50 mg/mL, greater than about 100 mg/mL, greater than about 110 mg/mL, greater than about 125 mg/mL, greater than about 150 mg/mL, greater than about 175 mg/mL, or greater than about 200 mg/mL.

In some embodiments, the formulation of etanercept is a liquid, and the pH of the liquid formulation is from about 5 to about 8. In some embodiments, the liquid formulation includes a buffer. In some embodiments, the pH of the buffer, and/or the pH of the final liquid formulation containing the buffer, ranges from about 4 to about 8, from about 5 to about 8, from about 5 to about 7.5, from about 5 to about 7, from about 4.5 to about 6.0, from about 4.7 to about 5.7, from about 4.8 to about 5.5, or from about 5.0 to about 5.2.

Exemplary Formulations of Etanercept

In some embodiments, a formulation comprises, consists essentially of or consists of etanercept, sodium chloride, a buffer including sodium phosphate monobasic monohydrate, sodium phosphate dibasic heptahydrate, and polysorbate 80. In one example, the formulation is liquid and comprises water for injection.

In some embodiments, a formulation comprises, consists essentially of or consists of etanercept, a buffer which is optionally a phosphate or citrate buffer, and an excipient selected from a polyol (such as a sugar or sugar alcohol) and a non-ionic surfactant, such as a polysorbate. In one example, the formulation is liquid and contains water for injection. In another example, the formulation contains low levels of ionic excipients and has low conductivity.

In some embodiments, a formulation comprises, consists essentially of or consists of etanercept, sodium chloride, a buffer containing a phosphate such as sodium phosphate monobasic dihydrate, sodium phosphate dibasic dihydrate, or a combination thereof, L-arginine hydrochloride, and sucrose. In one example, the formulation is liquid and contains water for injection. In one particular embodiment, the formulation is ENBREL®.

In some embodiments, a formulation comprises, consists essentially of or consists of etanercept, sodium chloride, a buffer containing a phosphate such as sodium phosphate monobasic dihydrate, sodium phosphate dibasic dihydrate, or a combination thereof, a citrate such as sodium citrate, citric acid monohydrate, or a combination thereof, mannitol, and polysorbate 80. In one example, the formulation is liquid and contains water for injection. In another example, the pH of the liquid formulation is adjusted with NaOH to about 5.2.

In some embodiments, a formulation comprises, consists essentially of or consists of etanercept, a buffer, which is optionally a phosphate or citrate buffer, a polyol selected from mannitol, sorbitol, sucrose, trehalose, raffinose, maltose, and a combination thereof, and a non-ionic surfactant selected from polysorbate 20, polysorbate 40, polysorbate 60, and polysorbate 80. In one example, the formulation contains low levels of ionic excipients and has low conductivity. In another example, the concentration of the antibody in the formulation is at least about 10 mg/mL, about 50 mg/mL, about 100 mg/mL, about 150 mg/mL, about 200 mg/mL, or about 250 mg/mL.

In some embodiments, a formulation comprises, consists essentially of or consists of etanercept, a buffer containing a phosphate selected from monobasic sodium phosphate and dibasic sodium phosphate, sucrose, and polysorbate 80.

In some embodiments, a formulation comprises, consists essentially of or consists of etanercept, arginine, histidine, or a combination thereof, sucrose, and polysorbate 80. Optionally, the formulation further comprises a buffer. In one example, the formulation is a lyophilized powder.

In some embodiments, a formulation comprises, consists essentially of or consists of etanercept, a free amino acid selected from histidine, alanine, arginine, glycine, and glutamic acid, a polyol selected from mannitol, sorbitol, sucrose, trehalose, and a combination thereof, and a surfactant. Optionally, the formulation further comprises a buffer. In one example, the formulation is liquid. In another example, the formulation is solid (e.g., lyophilized powder for reconstitution).

In some embodiments, a formulation comprises, consists essentially of or consists of etanercept, an acetate salt, such as sodium acetate trihydrate, an amino acid which is histidine and/or a salt thereof, sorbitol, and a non-ionic surfactant such as polysorbate 80; optionally, the formulation further comprises arginine and/or a salt thereof. In one example, the formulation is liquid and comprises water for injection. In another example, the pH of the liquid formulation is from about 5.1 to about 5.3. In yet another example, the formulation contains a negligible or non-detectable amount of sodium chloride. In yet another example, the formulation does not contain phosphate or citrate.

In some embodiments, a formulation comprises, consists essentially of or consists of etanercept, an amino acid selected from L-histidine, L-histidine monohydrochloride monohydrate, and a combination thereof, sorbitol and polysorbate 80. In one example, the formulation is liquid and comprises water for injection.

In some embodiments, a formulation comprises, consists essentially of or consists of etanercept, an amino acid selected from L-histidine, L-histidine monohydrochloride monohydrate, L-methionine, and a combination thereof, sucrose, and polysorbate 80. In one example, the formulation also contains a metal chelating agent such as EDTA disodium salt dihydrate. In another example, the formulation is liquid and contains water for injection.

In some embodiments, a formulation comprises, consists essentially of or consists of etanercept, an amino acid selected from L-histidine, L-histidine monohydrochloride monohydrate, L-arginine hydrochloride, and a combination thereof, sucrose, and polysorbate 80.

In some embodiments, a formulation comprises, consists essentially of or consists of etanercept, an amino acid selected from L-histidine and L-arginine, and a combination thereof, polysorbate 20, and succinic acid.

In some embodiments, a formulation comprises, consists essentially of or consists of etanercept at a concentration of at least about 100 mg/mL, mannitol, and polysorbate 80. In one example, the formulation is liquid and contains water for injection.

In some embodiments, a formulation comprises, consists essentially of or consists of etanercept, a buffer containing a negligible or non-detectable amount of sodium chloride, phosphate and citrate, a polyol such as mannitol, and a surfactant selected from a polysorbate and a poloxamer. In one example, the formulation has an antibody concentration of at least about 50 mg/mL, about 75 mg/mL, or about 100 mg/mL or greater, and low conductivity.

In some embodiments, a formulation comprises, consists essentially of or consists of etanercept, sodium chloride, and an acetate such as sodium acetate.

In some embodiments, a liquid formulation of etanercept comprises from about 25 to about 50 mg/mL of etanercept, about 25 mM L-arginine, about 25 mM sodium phosphate, about 100 mM sodium chloride, and about 1% sucrose. In some embodiments, the pH of the formulation is about 6.0 to about 7.0.

In some embodiments, a liquid formulation comprises from about 10 mg/mL to about 100 mg/mL of etanercept, and further comprises L-arginine, sodium phosphate, sodium chloride and sucrose.

In some embodiments, a liquid formulation comprises from about 10 mg/mL to about 100 mg/mL etanercept, from about 10 mM to about 75 mM of L-arginine, from about 5 mM to about 100 mM of sodium phosphate, from about 5 mM to about 200 mM of sodium chloride, from about 0.5% to about 1.5% of sucrose. In some embodiments, the pH of the formulation is from about 5.5 to about 7.8.

In some embodiments, a liquid formulation comprises from about 25 mg to about 50 mg of etanercept, from about 10 mM to about 100 mM of L-arginine, from about 10 mM to about 50 mM of sodium phosphate, from about 0.75% to about 1.25% of sucrose, from about 50 mM to about 150 mM of NaCl, and the pH of the formulation is from about 6.0 to about 7.0.

In some embodiments, a liquid formulation comprises about 50 mg etanercept, about 1% sucrose, about 100 mM sodium chloride, about 25 mM L-arginine hydrochloride, and about 25 mM sodium phosphate.

In some embodiments, a liquid formulation comprises about 25 mg etanercept, about 1% sucrose, about 100 mM sodium chloride, about 25 mM L-arginine hydrochloride, and about 25 mM sodium phosphate.

In some embodiments, a formulation comprises about 25 mg etanercept, about 40 mg mannitol, about 10 mg sucrose, and about 1.2 mg tromethamine. In one example, the formulation is a liquid formulation or a solid (e.g., lyophilized cake) formulation.

In some embodiments, a formulation of etanercept comprises about 10 mg, about 25 mg, or about 50 mg of etanercept, mannitol, sucrose, and tromethamine. In some embodiments, when the formulation is a liquid formulation, the formulation also comprises water for injection.

In some embodiments, a formulation of etanercept comprises about 10 mg, about 25 mg, or about 50 mg of etanercept, sucrose, sodium chloride, L-arginine hydrochloride, sodium phosphate monobasic dihydrate, and sodium phosphate dibasic dihydrate. In other embodiments, when the formulation is a liquid formulation, the formulation also comprises water for injection.

Additional pharmaceutical formulations of etanercept are disclosed, for example, in U.S. Pat. Nos. 7,648,702, 8,163,522, and 8,063,182; and EP Patent No. 1,478,394, the disclosures of each of which are incorporated herein by reference in their entireties.

Formulations Containing Brazikumab

In some embodiments, a pharmaceutical formulation comprises brazikumab. The formulation can be a liquid, semi-solid, or solid formulation. As used herein, the term "brazikumab" includes antibody or monoclonal brazikumab, any antigen-binding portion thereof, any glycosylation pattern variant thereof, and any biosimilar thereof.

Exemplary Dosages of Brazikumab in Solid and Liquid Formulations

In some embodiments, brazikumab is administered at a dose of about 15 mg, about 20 mg, about 30 mg, about 40 mg, about 50 mg, about 60 mg, about 70 mg, about 80 mg, about 90 mg, about 100 mg, about 105 mg, about 130 mg, about 150 mg, about 200 mg, about 210 mg, about 500 mg, about 700 mg, or about 1000 mg. In some embodiments, a formulation of brazikumab includes about 1 mg to about 650 mg, about 1 mg to about 600 mg, about 1 mg to about 500 mg, about 1 mg to about 100 mg, or about 5 mg to about 40 mg of brazikumab.

In some embodiments, a liquid formulation of brazikumab contains a high concentration of brazikumab, including, for example, a concentration greater than about 45 mg/mL, greater than about 50 mg/mL, greater than about 100 mg/mL, greater than about 110 mg/mL, greater than about 125 mg/mL, greater than about 150 mg/mL, greater than about 175 mg/mL, or greater than about 200 mg/mL.

In some embodiments, the formulation of brazikumab is a liquid, and the pH of the liquid formulation is from about 5 to about 8. In some embodiments, the liquid formulation includes a buffer. In some embodiments, the pH of the buffer, and/or the pH of the final liquid formulation containing the buffer, ranges from about 4 to about 8, from about 5 to about 8, from about 5 to about 7.5, from about 5 to about 7, from about 4.5 to about 6.0, from about 4.7 to about 5.7, from about 4.8 to about 5.5, or from about 5.0 to about 5.2.

Exemplary Formulations of Brazikumab

In some embodiments, a formulation comprises, consists essentially of or consists of brazikumab, sodium chloride, a buffer including sodium phosphate monobasic monohydrate, sodium phosphate dibasic heptahydrate, and polysorbate 80. In one example, the formulation is liquid and comprises water for injection.

In some embodiments, a formulation comprises, consists essentially of or consists of brazikumab, a buffer which is optionally a phosphate or citrate buffer, and an excipient selected from a polyol (such as a sugar or sugar alcohol) and a non-ionic surfactant, such as a polysorbate. In one example, the formulation is liquid and contains water for injection. In another example, the formulation contains low levels of ionic excipients and has low conductivity.

In some embodiments, a formulation comprises, consists essentially of or consists of brazikumab, sodium chloride, a buffer containing a phosphate such as sodium phosphate monobasic dihydrate, sodium phosphate dibasic dihydrate, or a combination thereof, L-arginine hydrochloride, and sucrose. In one example, the formulation is liquid and contains water for injection.

In some embodiments, a formulation comprises, consists essentially of or consists of brazikumab, sodium chloride, a buffer containing a phosphate such as sodium phosphate monobasic dihydrate, sodium phosphate dibasic dihydrate, or a combination thereof, a citrate such as sodium citrate, citric acid monohydrate, or a combination thereof, mannitol, and polysorbate 80. In one example, the formulation is liquid and contains water for injection. In another example, the pH of the liquid formulation is adjusted with NaOH to about 5.2.

In some embodiments, a formulation comprises, consists essentially of or consists of brazikumab, a buffer, which is optionally a phosphate or citrate buffer, a polyol selected from mannitol, sorbitol, sucrose, trehalose, raffinose, maltose, and a combination thereof, and a non-ionic surfactant selected from polysorbate 20, polysorbate 40, polysorbate 60, and polysorbate 80. In one example, the formulation contains low levels of ionic excipients and has low conductivity. In another example, the concentration of the antibody in the formulation is at least about 10 mg/mL, about 50 mg/mL, about 100 mg/mL, about 150 mg/mL, about 200 mg/mL, or about 250 mg/mL.

In some embodiments, a formulation comprises, consists essentially of or consists of brazikumab, a buffer containing a phosphate selected from monobasic sodium phosphate and dibasic sodium phosphate, sucrose, and polysorbate 80.

In some embodiments, a formulation comprises, consists essentially of or consists of brazikumab, arginine, histidine, or a combination thereof, sucrose, and polysorbate 80. Optionally, the formulation further comprises a buffer. In one example, the formulation is a lyophilized powder.

In some embodiments, a formulation comprises, consists essentially of or consists of brazikumab, a free amino acid selected from histidine, alanine, arginine, glycine, and glutamic acid, a polyol selected from mannitol, sorbitol, sucrose, trehalose, and a combination thereof, and a surfactant. Optionally, the formulation further comprises a buffer. In one example, the formulation is liquid. In another example, the formulation is solid (e.g., lyophilized powder for reconstitution).

In some embodiments, a formulation comprises, consists essentially of or consists of brazikumab, an acetate salt, such as sodium acetate trihydrate, an amino acid which is histidine and/or a salt thereof, sorbitol, and a non-ionic surfactant such as polysorbate 80; optionally, the formulation further comprises arginine and/or a salt thereof. In one example, the formulation is liquid and comprises water for injection. In another example, the pH of the liquid formulation is from about 5.1 to about 5.3. In yet another example, the formulation contains a negligible or non-detectable amount of sodium chloride. In yet another example, the formulation does not contain phosphate or citrate.

In some embodiments, a formulation comprises, consists essentially of or consists of brazikumab, an amino acid selected from L-histidine, L-histidine monohydrochloride monohydrate, and a combination thereof, sorbitol and polysorbate 80. In one example, the formulation is liquid and comprises water for injection.

In some embodiments, a formulation comprises, consists essentially of or consists of brazikumab, an amino acid selected from L-histidine, L-histidine monohydrochloride monohydrate, L-methionine, and a combination thereof, sucrose, and polysorbate 80. In one example, the formulation also contains a metal chelating agent such as EDTA disodium salt dihydrate. In another example, the formulation is liquid and contains water for injection.

In some embodiments, a formulation comprises, consists essentially of or consists of brazikumab, an amino acid selected from L-histidine, L-histidine monohydrochloride monohydrate, L-arginine hydrochloride, and a combination thereof, sucrose, and polysorbate 80.

In some embodiments, a formulation comprises, consists essentially of or consists of brazikumab, an amino acid selected from L-histidine and L-arginine, and a combination thereof, polysorbate 20, and succinic acid.

In some embodiments, a formulation comprises, consists essentially of or consists of brazikumab at a concentration of at least about 100 mg/mL, mannitol, and polysorbate 80. In one example, the formulation is liquid and contains water for injection.

In some embodiments, a formulation comprises, consists essentially of or consists of brazikumab, a buffer containing a negligible or non-detectable amount of sodium chloride, phosphate and citrate, a polyol such as mannitol, and a surfactant selected from a polysorbate and a poloxamer. In one example, the formulation has an antibody concentration of at least about 50 mg/mL, about 75 mg/mL, or about 100 mg/mL or greater, and low conductivity.

In some embodiments, a formulation comprises, consists essentially of or consists of brazikumab, sodium chloride, and an acetate such as sodium acetate.

Formulations Containing Natalizumab

In some embodiments, a pharmaceutical formulation comprises natalizumab. The formulation can be a liquid, semi-solid, or solid formulation. As used herein, the term "natalizumab" includes antibody or monoclonal natalizumab, any antigen-binding portion thereof, any glycosylation pattern variant thereof, and any biosimilar thereof.

Exemplary Dosages of Natalizumab in Solid and Liquid Formulations

In some embodiments, a formulation comprises an effective amount of natalizumab of about 1 mg, about 1.7 mg, about 5 mg, about 10 mg, about 20 mg, about 50 mg, about 100 mg, about 150 mg, about 200 mg, about 250 mg, about 300 mg, about 400 mg, about 500 mg, about 600 mg, about 700 mg, or about 1000 mg.

In some embodiments, a formulation of natalizumab includes about 1 mg to about 500 mg, about 1 mg to about 100 mg, about 5 mg to about 40 mg of natalizumab.

Natalizumab can be administered to a subject (e.g., a human) at a concentration of about 0.01 mg/mL to about 200 mg/mL. For example, natalizumab can range in concentration from about 0.1 mg/mL to about 150 mg/mL. However, embodiments exist when greater concentrations are required for administration to a patient, e.g., about 15 to about 200 mg/mL, about 15 mg/mL to 150 mg/mL, about 20 to about 50 mg/mL, or about 20 mg/mL of natalizumab, and any integer value in between. In some embodiments, a liquid formulation of natalizumab contains a high concentration of natalizumab, including, for example, a concentration greater than about 45 mg/mL, greater than about 50 mg/mL, greater than about 100 mg/mL, greater than about 110 mg/mL, greater than about 125 mg/mL, greater than about 150 mg/mL, greater than about 175 mg/mL, or greater than about 200 mg/mL.

In some embodiments, the formulation of natalizumab is a liquid, and the pH of the liquid formulation is from about 5 to about 8. In some embodiments, the liquid formulation includes a buffer. In some embodiments, the pH of the buffer, and/or the pH of the final liquid formulation containing the buffer, ranges from about 4 to about 8, from about 5 to about 8, from about 5 to about 7.5, from about 5 to about 7, from about 4.5 to about 6.0, from about 4.7 to about 5.7, from about 4.8 to about 5.5, or from about 5.0 to about 5.2.

Exemplary Formulations of Natalizumab

In some embodiments, a formulation comprises, consists essentially of, or consists of natalizumab, sodium chloride, a buffer including sodium phosphate monobasic monohydrate, sodium phosphate dibasic heptahydrate, and polysorbate 80. In one example, the formulation is liquid and comprises water for injection. In one particular embodiment, the formulation is TYSABRI®.

In some embodiments, a formulation comprises, consists essentially of, or consists of natalizumab, a buffer which is optionally a phosphate or citrate buffer, and an excipient selected from a polyol (such as a sugar or sugar alcohol) and a non-ionic surfactant, such as a polysorbate. In one example, the formulation is liquid and contains water for injection. In another example, the formulation contains low levels of ionic excipients and has low conductivity.

In some embodiments, a formulation comprises, consists essentially of, or consists of natalizumab, sodium chloride, a buffer containing a phosphate such as sodium phosphate monobasic dihydrate, sodium phosphate dibasic dihydrate, or a combination thereof, L-arginine hydrochloride, and sucrose. In one example, the formulation is liquid and contains water for injection.

In some embodiments, a formulation comprises, consists essentially of, or consists of natalizumab, sodium chloride, a buffer containing a phosphate such as sodium phosphate monobasic dihydrate, sodium phosphate dibasic dihydrate, or a combination thereof, a citrate such as sodium citrate, citric acid monohydrate, or a combination thereof, mannitol, and polysorbate 80. In one example, the formulation is liquid and contains water for injection. In another example, the pH of the liquid formulation is adjusted with NaOH to about 5.2.

In some embodiments, a formulation comprises, consists essentially of, or consists of natalizumab, a buffer, which is optionally a phosphate or citrate buffer, a polyol selected from mannitol, sorbitol, sucrose, trehalose, raffinose, maltose, and a combination thereof, and a non-ionic surfactant selected from polysorbate 20, polysorbate 40, polysorbate 60, and polysorbate 80. In one example, the formulation contains low levels of ionic excipients and has low conductivity. In another example, the concentration of the antibody in the formulation is at least about 10 mg/mL, about 50 mg/mL, about 100 mg/mL, about 150 mg/mL, about 200 mg/mL, or about 250 mg/mL.

In some embodiments, a formulation comprises, consists essentially of, or consists of natalizumab, a buffer containing a phosphate selected from monobasic sodium phosphate and dibasic sodium phosphate, sucrose, and polysorbate 80.

In some embodiments, a formulation comprises, consists essentially of, or consists of natalizumab, arginine, histidine, or a combination thereof, sucrose, and polysorbate 80. Optionally, the formulation further comprises a buffer. In one example, the formulation is a lyophilized powder.

In some embodiments, a formulation comprises, consists essentially of, or consists of natalizumab, a free amino acid selected from histidine, alanine, arginine, glycine, and glutamic acid, a polyol selected from mannitol, sorbitol, sucrose, trehalose, and a combination thereof, and a surfactant. Optionally, the formulation further comprises a buffer. In one example, the formulation is liquid. In another example, the formulation is solid (e.g., lyophilized powder for reconstitution).

In some embodiments, a formulation comprises, consists essentially of, or consists of natalizumab, an acetate salt, such as sodium acetate trihydrate, an amino acid which is histidine and/or a salt thereof, sorbitol, and a non-ionic surfactant such as polysorbate 80; optionally, the formulation further comprises arginine and/or a salt thereof. In one example, the formulation is liquid and comprises water for injection. In another example, the pH of the liquid formulation is from about 5.1 to about 5.3. In yet another example, the formulation contains a negligible or non-detectable amount of sodium chloride. In yet another example, the formulation does not contain phosphate or citrate.

In some embodiments, a formulation comprises, consists essentially of, or consists of natalizumab, an amino acid selected from L-histidine, L-histidine monohydrochloride monohydrate, and a combination thereof, sorbitol and polysorbate 80. In one example, the formulation is liquid and comprises water for injection.

In some embodiments, a formulation comprises, consists essentially of, or consists of natalizumab, an amino acid selected from L-histidine, L-histidine monohydrochloride monohydrate, L-methionine, and a combination thereof, sucrose, and polysorbate 80. In one example, the formulation also contains a metal chelating agent such as EDTA disodium salt dihydrate. In another example, the formulation is liquid and contains water for injection.

In some embodiments, a formulation comprises, consists essentially of, or consists of natalizumab, an amino acid selected from L-histidine, L-histidine monohydrochloride monohydrate, L-arginine hydrochloride, and a combination thereof, sucrose, and polysorbate 80.

In some embodiments, a formulation comprises, consists essentially of, or consists of natalizumab, an amino acid selected from L-histidine and L-arginine, and a combination thereof, polysorbate 20, and succinic acid.

In some embodiments, a formulation comprises, consists essentially of, or consists of natalizumab at a concentration of at least about 100 mg/mL, mannitol, and polysorbate 80. In one example, the formulation is liquid and contains water for injection.

In some embodiments, a formulation comprises, consists essentially of, or consists of natalizumab, a buffer containing a negligible or non-detectable amount of sodium chloride, phosphate and citrate, a polyol such as mannitol, and a surfactant selected from a polysorbate and a poloxamer. In one example, the formulation has an antibody concentration of at least about 50 mg/mL, about 75 mg/mL, or about 100 mg/mL or greater, and low conductivity.

In some embodiments, a formulation comprises, consists essentially of, or consists of natalizumab, sodium chloride, and an acetate such as sodium acetate.

In some embodiments, a liquid formulation comprises about 300 mg of natalizumab at a concentration of about 20 mg/mL.

In some embodiments, a liquid formulation comprises about 20 mg/mL of natalizumab, about 10 mM sodium phosphate buffer, about 8.18 mg/mL of sodium chloride, and about 0.2 mg/mL of polysorbate 80, and has a pH of about 6.1.

In some embodiments, a liquid formulation comprises about 20.0 mg/mL of natalizumab, about 140 mM NaCl, about 0.02% Polysorbate 80 (w/v), and about 10 mM sodium phosphate. In these embodiments, the pH of the formulation is about 6.0.

In some embodiments, a formulation comprises about 10.0 mg or natalizumab, about 1.4 mg of sodium phosphate, about 8.2 mg of sodium chloride, and about 0.1 mg of polysorbate 80. In these embodiments, the pH of the formulation is about 6.0.

In some embodiments, a formulation comprises about 10.0 mg or natalizumab, about 1.4 mg of sodium phosphate, about 8.2 mg of sodium chloride, and about 0.2 mg of polysorbate 80. In these embodiments, the pH of the formulation is about 6.0.

In some embodiments, a liquid formulation comprises about 5.0 mg/mL natalizumab, about 140 mM NaCl, about 0.02% Polysorbate 80 (w/v), and about 10 mM sodium phosphate. In these embodiments, the pH of the formulation is about 6.0.

In some embodiments, a formulation comprises about 50.0 mg of natalizumab, about 1.4 mg of sodium phosphate, about 8.2 mg sodium chloride, and about 0.2 mg of polysorbate 80. In these embodiments, when the formulation is liquid, the pH of the formulation is about 6.0.

In some embodiments, a formulation comprises about 20.0 mg of natalizumab, about 1.4 mg of sodium phosphate, about 8.2 mg sodium chloride, and about 0.2 mg of polysorbate 80. In these embodiments, when the formulation is liquid, the pH of the formulation is about 6.0.

In some embodiments, a formulation comprises about 5.0 mg of natalizumab, about 1.4 mg of sodium phosphate, about 8.2 mg sodium chloride, and about 0.2 mg of polysorbate 80. In these embodiments, when the formulation is liquid, the pH of the formulation is about 6.0.

In some embodiments, a formulation comprises about 1.7 mg of natalizumab, about 1.4 mg of sodium phosphate, about 8.2 mg sodium chloride, and about 0.2 mg of polysorbate 80. In these embodiments, when the formulation is liquid, the pH of the formulation is about 6.0.

In some embodiments, a liquid formulation comprises from about 20 mg/mL to about 150 mg/mL of natalizumab, about 10 mM phosphate buffer, about 140 mM sodium chloride, and from about 0.001% to about 2% (w/v) of polysorbate 80.

In some embodiments, a formulation comprises about 300 mg natalizumab, about 123 mg sodium chloride, about 17.0 mg sodium phosphate, monobasic, monohydrate, about 7.24 mg sodium phosphate, dibasic, heptahydrate, and about 3.0 mg polysorbate 80. In some embodiments, the formulation is liquid (e.g., an aqueous solution). In other embodiments, the formulation is solid (e.g., a lyophilized cake).

In some embodiments, each 15 mL unit dose (e.g., in a device as described herein) comprises about 300 mg natalizumab, about 123 mg sodium chloride, about 17.0 mg sodium phosphate monobasic monohydrate, about 7.24 mg sodium phosphate dibasic heptahydrate, about 3.0 mg polysorbate 80, and water for injection. In some embodiments, the pH of the formulation is about 6.1.

In some embodiments, a liquid formulation comprises natalizumab at a concentration of about 2.6 mg/mL.

In some embodiments, a formulation comprises about 300 mg of natalizumab, sodium phosphate monobasic monohydrate, sodium phosphate dibasic heptahydrate, sodium chloride, and polysorbate 80. In one example, the formulation is liquid (e.g., an aqueous solution). In another example, the formulation is solid (e.g., lyophilized cake).

Additional pharmaceutical formulations of natalizumab are disclosed, for example, in US Publication No. 2015/0044206; and U.S. Pat. Nos. 8,349,321, 8,815,236, and 8,900,577; the disclosures of each of which are incorporated herein by reference in their entireties.

Formulations Containing PF-00547659

In some embodiments, a pharmaceutical formulation comprises PF-00547659 (SHP647). The formulation can be a liquid, semi-solid, or solid formulation. As used herein, the term "PF-00547659" includes antibody or monoclonal PF-00547659, any antigen-binding portion thereof, any glycosylation pattern variant thereof, and any biosimilar thereof.

Exemplary Dosages of PF-00547659 in Solid and Liquid Formulations

In some embodiments, a formulation comprises an effective amount of PF-00547659 of about 7.5 mg, about 15 mg, about 22.5 mg, about 45 mg, about 75 mg, about 150 mg, about 225 mg, about 450 mg, or about 900 mg.

In some embodiments, a liquid formulation of PF-00547659 contains a high concentration of PF-00547659, including, for example, a concentration greater than about 45 mg/mL, greater than about 50 mg/mL, greater than about 100 mg/mL, greater than about 110 mg/mL, greater than about 125 mg/mL, greater than about 150 mg/mL, greater than about 175 mg/mL, or greater than about 200 mg/mL.

In some embodiments, the formulation of PF-00547659 is a liquid, and the pH of the liquid formulation is from about 5 to about 8. In some embodiments, the liquid formulation includes a buffer. In some embodiments, the pH of the buffer, and/or the pH of the final liquid formulation containing the buffer, ranges from about 4 to about 8, from about 5 to about 8, from about 5 to about 7.5, from about 5 to about 7, from about 4.5 to about 6.0, from about 4.7 to about 5.7, from about 4.8 to about 5.5, or from about 5.0 to about 5.2.

Exemplary Formulations of PF-00547659

In some embodiments, a formulation comprises, consists essentially of, or consists of PF-00547659, sodium chloride, a buffer including sodium phosphate monobasic monohydrate, sodium phosphate dibasic heptahydrate, and polysorbate 80. In one example, the formulation is liquid and comprises water for injection.

In some embodiments, a formulation comprises, consists essentially of, or consists of PF-00547659, a buffer which is optionally a phosphate or citrate buffer, and an excipient selected from a polyol (such as a sugar or sugar alcohol) and a non-ionic surfactant, such as a polysorbate. In one example, the formulation is liquid and contains water for injection. In another example, the formulation contains low levels of ionic excipients and has low conductivity.

In some embodiments, a formulation comprises, consists essentially of, or consists of PF-00547659, sodium chloride, a buffer containing a phosphate such as sodium phosphate monobasic dihydrate, sodium phosphate dibasic dihydrate, or a combination thereof, L-arginine hydrochloride, and sucrose. In one example, the formulation is liquid and contains water for injection.

In some embodiments, a formulation comprises, consists essentially of, or consists of PF-00547659, sodium chloride, a buffer containing a phosphate such as sodium phosphate monobasic dihydrate, sodium phosphate dibasic dihydrate, or a combination thereof, a citrate such as sodium citrate, citric acid monohydrate, or a combination thereof, mannitol, and polysorbate 80. In one example, the formulation is liquid and contains water for injection. In another example, the pH of the liquid formulation is adjusted with NaOH to about 5.2.

In some embodiments, a formulation comprises, consists essentially of, or consists of PF-00547659, a buffer, which is optionally a phosphate or citrate buffer, a polyol selected from mannitol, sorbitol, sucrose, trehalose, raffinose, maltose, and a combination thereof, and a non-ionic surfactant selected from polysorbate 20, polysorbate 40, polysorbate 60, and polysorbate 80. In one example, the formulation contains low levels of ionic excipients and has low conductivity. In another example, the concentration of the antibody in the formulation is at least about 10 mg/mL, about 50 mg/mL, about 100 mg/mL, about 150 mg/mL, about 200 mg/mL, or about 250 mg/mL.

In some embodiments, a formulation comprises, consists essentially of, or consists of PF-00547659, a buffer containing a phosphate selected from monobasic sodium phosphate and dibasic sodium phosphate, sucrose, and polysorbate 80.

In some embodiments, a formulation comprises, consists essentially of, or consists of PF-00547659, arginine, histidine, or a combination thereof, sucrose, and polysorbate 80. Optionally, the formulation further comprises a buffer. In one example, the formulation is a lyophilized powder.

In some embodiments, a formulation comprises, consists essentially of, or consists of PF-00547659, a free amino acid selected from histidine, alanine, arginine, glycine, and glutamic acid, a polyol selected from mannitol, sorbitol, sucrose, trehalose, and a combination thereof, and a surfactant. Optionally, the formulation further comprises a buffer. In one example, the formulation is liquid. In another example, the formulation is solid (e.g., lyophilized powder for reconstitution).

In some embodiments, a formulation comprises, consists essentially of, or consists of PF-00547659, an acetate salt, such as sodium acetate trihydrate, an amino acid which is histidine and/or a salt thereof, sorbitol, and a non-ionic surfactant such as polysorbate 80; optionally, the formulation further comprises arginine and/or a salt thereof. In one example, the formulation is liquid and comprises water for injection. In another example, the pH of the liquid formulation is from about 5.1 to about 5.3. In yet another example, the formulation contains a negligible or non-detectable amount of sodium chloride. In yet another example, the formulation does not contain phosphate or citrate.

In some embodiments, a formulation comprises, consists essentially of, or consists of PF-00547659, an amino acid selected from L-histidine, L-histidine monohydrochloride monohydrate, and a combination thereof, sorbitol and polysorbate 80. In one example, the formulation is liquid and comprises water for injection.

In some embodiments, a formulation comprises, consists essentially of, or consists of PF-00547659, an amino acid selected from L-histidine, L-histidine monohydrochloride monohydrate, L-methionine, and a combination thereof, sucrose, and polysorbate 80. In one example, the formulation also contains a metal chelating agent such as EDTA disodium salt dihydrate. In another example, the formulation is liquid and contains water for injection.

In some embodiments, a formulation comprises, consists essentially of, or consists of PF-00547659, an amino acid selected from L-histidine, L-histidine monohydrochloride monohydrate, L-arginine hydrochloride, and a combination thereof, sucrose, and polysorbate 80.

In some embodiments, a formulation comprises, consists essentially of, or consists of PF-00547659, an amino acid selected from L-histidine and L-arginine, and a combination thereof, polysorbate 20, and succinic acid.

In some embodiments, a formulation comprises, consists essentially of, or consists of PF-00547659 at a concentration of at least about 100 mg/mL, mannitol, and polysorbate 80. In one example, the formulation is liquid and contains water for injection.

In some embodiments, a formulation comprises, consists essentially of, or consists of PF-00547659, a buffer containing a negligible or non-detectable amount of sodium chloride, phosphate and citrate, a polyol such as mannitol, and a surfactant selected from a polysorbate and a poloxamer. In one example, the formulation has an antibody concentration of at least about 50 mg/mL, about 75 mg/mL, or about 100 mg/mL or greater, and low conductivity.

In some embodiments, a formulation comprises, consists essentially of, or consists of PF-00547659, sodium chloride, and an acetate such as sodium acetate.

Formulations Containing Guselkumab

In some embodiments, a pharmaceutical formulation comprises guselkumab. The formulation can be a liquid, semi-solid, or solid formulation. As used herein, the term "guselkumab" includes antibody or monoclonal guselkumab, any antigen-binding portion thereof, any glycosylation pattern variant thereof, and any biosimilar thereof.

Exemplary Dosages of Guselkumab in Solid and Liquid Formulations

In some embodiments, guselkumab is administered at a dose of about 30 mg, about 40 mg, about 50 mg, about 60 mg, about 70 mg, about 80 mg, about 90 mg, about 100 mg, about 130 mg, about 150 mg, about 200 mg, about 500 mg, about 700 mg, or about 1000 mg. In some embodiments, a dosage form (e.g., a device as described herein) comprises a liquid formulation of guselkumab at a concentration of about 100 mg/mL.

In some embodiments, a liquid formulation of guselkumab contains a high concentration of guselkumab, including, for example, a concentration greater than about 45 mg/mL, greater than about 50 mg/mL, greater than about 100 mg/mL, greater than about 110 mg/mL, greater than about 125 mg/mL, greater than about 150 mg/mL, greater than about 175 mg/mL, or greater than about 200 mg/mL.

In some embodiments, the formulation of guselkumab is a liquid, and the pH of the liquid formulation is from about 5 to about 8. In some embodiments, the liquid formulation includes a buffer. In some embodiments, the pH of the buffer, and/or the pH of the final liquid formulation containing the buffer, ranges from about 4 to about 8, from about 5 to about 8, from about 5 to about 7.5, from about 5 to about 7, from about 4.5 to about 6.0, from about 4.7 to about 5.7, from about 4.8 to about 5.5, or from about 5.0 to about 5.2.

Exemplary Formulations of Guselkumab

In some embodiments, a formulation comprises, consists essentially of or consists of guselkumab, sodium chloride, a buffer including sodium phosphate monobasic monohydrate, sodium phosphate dibasic heptahydrate, and polysorbate 80. In one example, the formulation is liquid and comprises water for injection.

In some embodiments, a formulation comprises, consists essentially of or consists of guselkumab, a buffer which is optionally a phosphate or citrate buffer, and an excipient selected from a polyol (such as a sugar or sugar alcohol) and a non-ionic surfactant, such as a polysorbate. In one example, the formulation is liquid and contains water for injection. In another example, the formulation contains low levels of ionic excipients and has low conductivity.

In some embodiments, a formulation comprises, consists essentially of or consists of guselkumab, sodium chloride, a buffer containing a phosphate such as sodium phosphate monobasic dihydrate, sodium phosphate dibasic dihydrate, or a combination thereof, L-arginine hydrochloride, and sucrose. In one example, the formulation is liquid and contains water for injection.

In some embodiments, a formulation comprises, consists essentially of or consists of guselkumab, sodium chloride, a buffer containing a phosphate such as sodium phosphate monobasic dihydrate, sodium phosphate dibasic dihydrate, or a combination thereof, a citrate such as sodium citrate, citric acid monohydrate, or a combination thereof, mannitol, and polysorbate 80. In one example, the formulation is liquid and contains water for injection. In another example, the pH of the liquid formulation is adjusted with NaOH to about 5.2.

In some embodiments, a formulation comprises, consists essentially of or consists of guselkumab, a buffer, which is optionally a phosphate or citrate buffer, a polyol selected from mannitol, sorbitol, sucrose, trehalose, raffinose, maltose, and a combination thereof, and a non-ionic surfactant selected from polysorbate 20, polysorbate 40, polysorbate 60, and polysorbate 80. In one example, the formulation contains low levels of ionic excipients and has low conductivity. In another example, the concentration of the antibody in the formulation is at least about 10 mg/mL, about 50 mg/mL, about 100 mg/mL, about 150 mg/mL, about 200 mg/mL, or about 250 mg/mL.

In some embodiments, a formulation comprises, consists essentially of or consists of guselkumab, a buffer containing a phosphate selected from monobasic sodium phosphate and dibasic sodium phosphate, sucrose, and polysorbate 80.

In some embodiments, a formulation comprises, consists essentially of or consists of guselkumab, arginine, histidine, or a combination thereof, sucrose, and polysorbate 80. Optionally, the formulation further comprises a buffer. In one example, the formulation is a lyophilized powder.

In some embodiments, a formulation comprises, consists essentially of or consists of guselkumab, a free amino acid selected from histidine, alanine, arginine, glycine, and glutamic acid, a polyol selected from mannitol, sorbitol, sucrose, trehalose, and a combination thereof, and a surfactant. Optionally, the formulation further comprises a buffer. In one example, the formulation is liquid. In another example, the formulation is solid (e.g., lyophilized powder for reconstitution).

In some embodiments, a formulation comprises, consists essentially of or consists of guselkumab, an acetate salt, such as sodium acetate trihydrate, an amino acid which is histidine and/or a salt thereof, sorbitol, and a non-ionic surfactant such as polysorbate 80; optionally, the formulation further comprises arginine and/or a salt thereof. In one example, the formulation is liquid and comprises water for injection. In another example, the pH of the liquid formulation is from about 5.1 to about 5.3. In yet another example, the formulation contains a negligible or non-detectable amount of sodium chloride. In yet another example, the formulation does not contain phosphate or citrate.

In some embodiments, a formulation comprises, consists essentially of or consists of guselkumab, an amino acid selected from L-histidine, L-histidine monohydrochloride monohydrate, and a combination thereof, sorbitol and polysorbate 80. In one example, the formulation is liquid and comprises water for injection.

In some embodiments, a formulation comprises, consists essentially of or consists of guselkumab, an amino acid selected from L-histidine, L-histidine monohydrochloride monohydrate, L-methionine, and a combination thereof, sucrose, and polysorbate 80. In one example, the formulation also contains a metal chelating agent such as EDTA disodium salt dihydrate. In another example, the formulation is liquid and contains water for injection.

In some embodiments, a formulation comprises, consists essentially of or consists of guselkumab, an amino acid selected from L-histidine, L-histidine monohydrochloride monohydrate, L-arginine hydrochloride, and a combination thereof, sucrose, and polysorbate 80.

In some embodiments, a formulation comprises, consists essentially of or consists of guselkumab, an amino acid selected from L-histidine and L-arginine, and a combination thereof, polysorbate 20, and succinic acid.

In some embodiments, a formulation comprises, consists essentially of or consists of guselkumab at a concentration of at least about 100 mg/mL, mannitol, and polysorbate 80. In one example, the formulation is liquid and contains water for injection.

In some embodiments, a formulation comprises, consists essentially of or consists of guselkumab, a buffer containing a negligible or non-detectable amount of sodium chloride, phosphate and citrate, a polyol such as mannitol, and a surfactant selected from a polysorbate and a poloxamer. In one example, the formulation has an antibody concentration of at least about 50 mg/mL, about 75 mg/mL, or about 100 mg/mL or greater, and low conductivity.

In some embodiments, a formulation comprises, consists essentially of or consists of guselkumab, sodium chloride, and an acetate such as sodium acetate.

In some embodiments, a liquid formulation comprises about 100 mg guselkumab, about 0.6 mg of L-histidine, about 1.5 mg of L-histidine monohydrochloride monohydrate, about 0.5 mg of polysorbate 80, and about 79 mg of sucrose. In one example, the formulation is liquid and the pH of the formulation is about 5.8.

In some embodiments, a formulation comprises about 100 mg of guselkumab, histidine, histidine monohydrochloride monohydrate, polysorbate 80, and sucrose. In one example, the formulation is a liquid formulation or a solid formulation (e.g., lyophilized cake) as described herein.

Formulations Containing Mirikizumab

In some embodiments, a pharmaceutical formulation comprises mirikizumab. The formulation can be a liquid, semi-solid, or solid formulation. As used herein, the term "mirikizumab" includes antibody or monoclonal mirikizumab, any antigen-binding portion thereof, any glycosylation pattern variant thereof, and any biosimilar thereof.

Exemplary Dosages of Mirikizumab in Solid and Liquid Formulations

In some embodiments, an effective dose of mirikizumab is about 5 mg, about 20 mg, about 60 mg, about 120 mg, about 200 mg, about 350 mg, or about 600 mg.

In some embodiments, a liquid formulation of mirikizumab contains a high concentration of mirikizumab, including, for example, a concentration greater than about 45 mg/mL, greater than about 50 mg/mL, greater than about 100 mg/mL, greater than about 110 mg/mL, greater than about 125 mg/mL, greater than about 150 mg/mL, greater than about 175 mg/mL, or greater than about 200 mg/mL.

In some embodiments, the formulation of mirikizumab is a liquid, and the pH of the liquid formulation is from about 5 to about 8. In some embodiments, the liquid formulation includes a buffer. In some embodiments, the pH of the buffer, and/or the pH of the final liquid formulation containing the buffer, ranges from about 4 to about 8, from about 5 to about 8, from about 5 to about 7.5, from about 5 to about 7, from about 4.5 to about 6.0, from about 4.7 to about 5.7, from about 4.8 to about 5.5, or from about 5.0 to about 5.2.

Exemplary Formulations of Mirikizumab

In some embodiments, a formulation comprises, consists essentially of or consists of mirikizumab, sodium chloride, a buffer including sodium phosphate monobasic monohydrate, sodium phosphate dibasic heptahydrate, and polysorbate 80. In one example, the formulation is liquid and comprises water for injection.

In some embodiments, a formulation comprises, consists essentially of or consists of mirikizumab, a buffer which is optionally a phosphate or citrate buffer, and an excipient selected from a polyol (such as a sugar or sugar alcohol) and a non-ionic surfactant, such as a polysorbate. In one example, the formulation is liquid and contains water for injection. In another example, the formulation contains low levels of ionic excipients and has low conductivity.

In some embodiments, a formulation comprises, consists essentially of or consists of mirikizumab, sodium chloride, a buffer containing a phosphate such as sodium phosphate monobasic dihydrate, sodium phosphate dibasic dihydrate, or a combination thereof, L-arginine hydrochloride, and sucrose. In one example, the formulation is liquid and contains water for injection.

In some embodiments, a formulation comprises, consists essentially of or consists of mirikizumab, sodium chloride, a buffer containing a phosphate such as sodium phosphate monobasic dihydrate, sodium phosphate dibasic dihydrate, or a combination thereof, a citrate such as sodium citrate, citric acid monohydrate, or a combination thereof, mannitol, and polysorbate 80. In one example, the formulation is liquid and contains water for injection. In another example, the pH of the liquid formulation is adjusted with NaOH to about 5.2.

In some embodiments, a formulation comprises, consists essentially of or consists of mirikizumab, a buffer, which is optionally a phosphate or citrate buffer, a polyol selected from mannitol, sorbitol, sucrose, trehalose, raffinose, maltose, and a combination thereof, and a non-ionic surfactant selected from polysorbate 20, polysorbate 40, polysorbate 60, and polysorbate 80. In one example, the formulation contains low levels of ionic excipients and has low conductivity. In another example, the concentration of the antibody in the formulation is at least about 10 mg/mL, about 50 mg/mL, about 100 mg/mL, about 150 mg/mL, about 200 mg/mL, or about 250 mg/mL.

In some embodiments, a formulation comprises, consists essentially of or consists of mirikizumab, a buffer containing a phosphate selected from monobasic sodium phosphate and dibasic sodium phosphate, sucrose, and polysorbate 80.

In some embodiments, a formulation comprises, consists essentially of or consists of mirikizumab, arginine, histidine, or a combination thereof, sucrose, and polysorbate 80. Optionally, the formulation further comprises a buffer. In one example, the formulation is a lyophilized powder.

In some embodiments, a formulation comprises, consists essentially of or consists of mirikizumab, a free amino acid selected from histidine, alanine, arginine, glycine, and glutamic acid, a polyol selected from mannitol, sorbitol, sucrose, trehalose, and a combination thereof, and a surfactant. Optionally, the formulation further comprises a buffer. In one example, the formulation is liquid. In another example, the formulation is solid (e.g., lyophilized powder for reconstitution).

In some embodiments, a formulation comprises, consists essentially of or consists of mirikizumab, an acetate salt, such as sodium acetate trihydrate, an amino acid which is histidine and/or a salt thereof, sorbitol, and a non-ionic surfactant such as polysorbate 80; optionally, the formulation further comprises arginine and/or a salt thereof. In one example, the formulation is liquid and comprises water for injection. In another example, the pH of the liquid formulation is from about 5.1 to about 5.3. In yet another example, the formulation contains a negligible or non-detectable amount of sodium chloride. In yet another example, the formulation does not contain phosphate or citrate.

In some embodiments, a formulation comprises, consists essentially of or consists of mirikizumab, an amino acid selected from L-histidine, L-histidine monohydrochloride monohydrate, and a combination thereof, sorbitol and polysorbate 80. In one example, the formulation is liquid and comprises water for injection.

In some embodiments, a formulation comprises, consists essentially of or consists of mirikizumab, an amino acid selected from L-histidine, L-histidine monohydrochloride monohydrate, L-methionine, and a combination thereof, sucrose, and polysorbate 80. In one example, the formulation also contains a metal chelating agent such as EDTA disodium salt dihydrate. In another example, the formulation is liquid and contains water for injection.

In some embodiments, a formulation comprises, consists essentially of or consists of mirikizumab, an amino acid selected from L-histidine, L-histidine monohydrochloride monohydrate, L-arginine hydrochloride, and a combination thereof, sucrose, and polysorbate 80.

In some embodiments, a formulation comprises, consists essentially of or consists of mirikizumab, an amino acid selected from L-histidine and L-arginine, and a combination thereof, polysorbate 20, and succinic acid.

In some embodiments, a formulation comprises, consists essentially of or consists of mirikizumab at a concentration of at least about 100 mg/mL, mannitol, and polysorbate 80. In one example, the formulation is liquid and contains water for injection.

In some embodiments, a formulation comprises, consists essentially of or consists of mirikizumab, a buffer containing a negligible or non-detectable amount of sodium chloride, phosphate and citrate, a polyol such as mannitol, and a surfactant selected from a polysorbate and a poloxamer. In one example, the formulation has an antibody concentration of at least about 50 mg/mL, about 75 mg/mL, or about 100 mg/mL or greater, and low conductivity.

In some embodiments, a formulation comprises, consists essentially of or consists of mirikizumab, sodium chloride, and an acetate such as sodium acetate.

Formulations Containing Vatelizumab

In some embodiments, a pharmaceutical formulation includes vatelizumab. The formulation can be a liquid, semi-solid, or solid formulation. As used herein, the term "vatelizumab" includes antibody vatelizumab, any antigen-binding portion thereof, and any biosimilar thereof.

Exemplary Dosage of Vatelizumab in Solid and Liquid Formulations

In some embodiments, vatelizumab is administered at a dose of, e.g., about 80 mg, about 90 mg, about 100 mg, about 105 mg, about 120 mg, about 150, about 160 mg, about 170 mg, about 180 mg, or about 200 mg. In some embodiments, an effective dose of vatelizumab is about 100 mg, about 200 mg, about 210 mg, about 300 mg, about 400 mg, or about 450 mg. In certain embodiments, the effective dose is about 105 mg or about 210 mg.

In some embodiments, a formulation of vatelizumab includes about 1 mg to about 500 mg, about 1 mg to about 100 mg, or about 5 mg to about 40 mg of vatelizumab.

In some embodiments, a liquid formulation of vatelizumab contains a high concentration of vatelizumab, including, for example, a concentration greater than about 45 mg/mL, greater than about 50 mg/mL, greater than about 100 mg/mL, greater than about 110 mg/mL, greater than about 125 mg/mL, greater than about 150 mg/mL, greater than about 175 mg/mL, or greater than about 200 mg/mL.

In some embodiments, the formulation of vatelizumab is a liquid, and the pH of the liquid formulation is from about 5 to about 8. In some embodiments, the liquid formulation includes a buffer. In some embodiments, the pH of the buffer, and/or the pH of the final liquid formulation containing the buffer ranges from about 4 to about 8, from about 5 to about 8, from about 5 to about 7.5, from about 5 to about 7, from about 4.5 to about 6.0, from about 4.7 to about 5.7, from about 4.8 to about 5.5, or from about 5.0 to about 5.2.

Formulations Containing Daclizumab

In some embodiments, a pharmaceutical formulation comprises daclizumab. The formulation can be a liquid, semi-solid, or solid formulation. As used herein, the term "daclizumab" includes antibody or monoclonal daclizumab, any antigen-binding portion thereof, any glycosylation pattern variant thereof, and any biosimilar thereof.

Exemplary Dosage of Daclizumab in Solid and Liquid Formulations

In some embodiments, daclizumab is administered to a patient at a dose of about 20 mg, about 30 mg, about 40 mg, about 50 mg, about 60 mg, about 70 mg, about 80 mg, about 100 mg, about 150 mg, or about 200 mg. In some embodiments, a formulation of daclizumab includes about 1 mg to about 500 mg, about 1 mg to about 100 mg, about 5 mg to about 40 mg, about 40 mg to about 80 mg, about 160 mg, about 80 mg or about 40 mg of daclizumab. In some embodiments, the formulation contains an induction dose of about 160 mg of daclizumab. In other embodiments, the formulation contains a maintenance dose of about 80 mg, about 40 mg, or about 40 mg to about 80 mg of daclizumab.

In some embodiments, a liquid formulation of daclizumab contains a high concentration of daclizumab, including, for example, a concentration greater than about 45 mg/mL, greater than about 50 mg/mL, greater than about 100 mg/mL, greater than about 110 mg/mL, greater than about 125 mg/mL, greater than about 150 mg/mL, greater than about 175 mg/mL, or greater than about 200 mg/mL.

In some embodiments, the formulation of daclizumab is a liquid, and the pH of the liquid formulation is from about 5 to about 8. In some embodiments, the liquid formulation includes a buffer. In some embodiments, the pH of the buffer, and/or the pH of the final liquid formulation containing the buffer, ranges from about 4 to about 8, from about 5 to about 8, from about 5 to about 7.5, from about 5 to about 7, from about 4.5 to about 6.0, from about 4.7 to about 5.7, from about 4.8 to about 5.5, or from about 5.0 to about 5.2. In some embodiments, the liquid formulation pH is 6.8, 6.9, 7.0 or 7.1, for example, pH 6.9. In other embodiments, the liquid formulation pH is 5.8, 5.9, 6.0 or 6.1, for example, pH 6.0.

Exemplary Formulations of Daclizumab

In some embodiments, a formulation comprises, consists essentially of or consists of daclizumab, an aqueous medium (such as water, a pH-adjusted water or an aqueous buffer), and a non-ionic surfactant.

In some embodiments, a formulation comprises, consists essentially of or consists of daclizumab, a buffer (e.g., a phosphate buffer), a salt, and a non-ionic surfactant, such as a polysorbate. In some embodiments, the formulation pH is 6.9, 7.0 or 7.1. In some further embodiments, the buffer is a phosphate buffer comprising sodium phosphate monobasic monohydrate and sodium phosphate dibasic heptahydrate. In some embodiments, the salt is sodium chloride. In some further embodiments, the non-ionic surfactant is polysorbate 80. In some more particular embodiments, the formulation comprises, consists essentially of or consists of daclizumab, sodium phosphate monobasic monohydrate, sodium phosphate dibasic heptahydrate, sodium chloride, polysorbate 80, and can further contain hydrochloric acid or sodium hydroxide to adjust the pH to 6.9. In some embodiments, the formulation does not contain additional agent(s) that act as preservatives. In a more particular embodiment, the formulation is, or contains essentially the same chemical composition as, ZENAPAX® 25 mg/5 mL concentrate, wherein each milliliter of ZENAPAX® contains 5 mg of daclizumab and 3.6 mg sodium phosphate monobasic monohydrate, 11 mg sodium phosphate dibasic heptahydrate, 4.6 mg sodium chloride, 0.2 mg polysorbate 80, and optionally, hydrochloric acid or sodium hydroxide to adjust the pH to 6.9; no preservatives are added. In some embodiments, the ZENAPAX® 25 mg/5 mL concentrate formulation, or the formulation containing essentially the same chemical composition as ZENAPAX® 25 mg/5 mL concentrate, is further diluted prior to administration. In some embodiments, the calculated dose volume is diluted into 0.9% sodium chloride solution prior to administration.

In some embodiments, a formulation comprises, consists essentially of or consists of daclizumab, a non-ionic surfactant (e.g., a polysorbate), succinic acid, one or more salts, and water (e.g., water for injection). In some further embodiments, the non-ionic surfactant is polysorbate 80. In some embodiments, the one or more salts is sodium chloride, sodium succinate, or both. In some more particular embodiments, the formulation comprises, consists essentially of or consists of daclizumab, polysorbate 80, sodium chloride, sodium succinate, succinic acid and water for injection, and the formulation pH is about 6. In some embodiments, the formulation is preservative-free. In a more particular embodiment, the formulation is, or contains essentially the same chemical composition as, ZINBRYTA® injection, where each 1 mL contains 150 mg daclizumab; polysorbate 80, USP (0.3 mg); sodium chloride (5.84 mg); sodium succinate, anhydrous (5.94 mg); succinic acid (0.35 mg); and water for injection, USP, and the pH is 6.0. In some embodiments, the ZINBRYTA® injection formulation, or the formulation containing essentially the same chemical composition as ZINBRYTA® injection, is further diluted prior to administration.

In some embodiments, a single container (e.g., a device as described herein) comprises about 50 mg or about 100 mg or more of daclizumab.

Definitions

By "ingestible," it is meant that the device can be swallowed whole.

As used herein, "topical delivery" refers to a route of administration of a medicament (i.e., a drug or a pharmaceutical formulation containing a drug) where the medicament is applied to a localized area of the body or to the surface of a body part, regardless of the location of the effect; more particularly, the topical administration of the medicament comprises applying the medicament to a mucous membrane or lining of the gastrointestinal tract of a subject, including, but not limited to, a mucous membrane or lining containing one or more disease sites, such as gastrointestinal mucosal lesions. The effect of the topical delivery or topical administration of the medicament may be local to, or away from, the site of the topical administration. "Topical delivery," "topical administration," "topical application" and "topical treatment" are used interchangeably herein.

"Gastrointestinal inflammatory disorders" are a group of chronic disorders that cause inflammation and/or ulceration in the mucous membrane. These disorders include, for example, inflammatory bowel disease (e.g., Crohn's disease, ulcerative colitis, indeterminate colitis and infectious colitis), mucositis (e.g., oral mucositis, gastrointestinal mucositis, nasal mucositis and proctitis), necrotizing enterocolitis and esophagitis.

"Inflammatory Bowel Disease" or "IBD" is a chronic inflammatory autoimmune condition of the gastrointestinal (GI) tract. The GI tract can be divided into four main different sections, the oesophagus, stomach, small intestine and large intestine or colon. The small intestine possesses three main subcompartments: the duodenum, jejunum and ileum. Similarly, the large intestine consists of six sections: the cecum, ascending colon, transverse colon, ascending colon, sigmoid colon, and the rectum. The small intestine is about 6 m long, its diameter is about 2.5 to about 3 cm and the transit time through it is typically about 3 hours. The duodenum has a C-shape, and is about 30 cm long. Due to its direct connection with the stomach, it is physically more stable than the jejunum and ileum, which are sections that can freely move. The jejunum is about 2.4 m in length and the ileum is about 3.6 m in length and their surface areas are about 180 $m^2$ and about 280 $m^2$, respectively. The large intestine is about 1.5 m long, its diameter is between about 6.3 and about 6.5 cm, the transit time though this section is about 20 hours and has a reduced surface area of about 150 $m^2$. The higher surface area of the small intestine enhances its capacity for systemic drug absorption.

The etiology of IBD is complex, and many aspects of the pathogenesis remain unclear. The treatment of moderate to severe IBD poses significant challenges to treating physicians, because conventional therapy with corticosteroids and immunomodulator therapy (e.g., azathioprine, 6-mercaptopurine, and methotrexate administered via traditional routes such as tablet form, oral suspension, or intravenously) is associated with side effects and intolerance and has not shown proven benefit in maintenance therapy (steroids). Monoclonal antibodies targeting tumor necrosis factor alpha (TNF-α), such as infliximab (a chimeric antibody) and adalimumab (a fully human antibody), are currently used in the management of CD. Infliximab has also shown efficacy and has been approved for use in UC. However, approximately 10%-20% of patients with CD are primary nonresponders to anti-TNF therapy, and another ~20%-30% of CD patients lose response over time (Schnitzler et al., Gut 58:492-500 (2009)). Other adverse events (AEs) associated with anti-TNFs include elevated rates of bacterial infection, including tuberculosis, and, more rarely, lymphoma and demyelination (Chang et al., Nat. Clin. Pract. Gastroenterol. Hepatol. 3:220 (2006); Hoentjen et al., World J. Gastroenterol. 15(17):2067 (2009)). No currently available therapy achieves sustained remission in more than 20%-30% of IBD patients with chronic disease (Hanauer et al., Lancet 359:1541-49 (2002); Sandborn et al., N. Engl. J. Med. 353:1912-25 (2005)). In addition, most patients do not achieve sustained steroid-free remission and mucosal healing, clinical outcomes that correlate with true disease modification.

Although the cause of IBD remains unknown, several factors such as genetic, infectious and immunologic susceptibility have been implicated. IBD is much more common in Caucasians, especially those of Jewish descent. The chronic inflammatory nature of the condition has prompted an intense search for a possible infectious cause. Although agents have been found which stimulate acute inflammation, none has been found to cause the chronic inflammation associated with IBD. The hypothesis that IBD is an autoimmune disease is supported by the previously mentioned extraintestinal manifestation of IBD as joint arthritis, and the known positive response to IBD by treatment with therapeutic agents such as adrenal glucocorticoids, cyclosporin A and azathioprine, which are known to suppress immune response. In addition, the GI tract, more than any other organ of the body, is continuously exposed to potential antigenic substances such as proteins from food, bacterial byproducts (LPS), etc.

A chronic inflammatory autoimmune condition of the gastrointestinal (GI) tract presents clinically as either ulcerative colitis (UC) or Crohn's disease (CD). Both IBD conditions are associated with an increased risk for malignancy of the GI tract.

"Crohn's disease" ("CD") is a chronic transmural inflammatory disease with the potential to affect any part of the entire GI tract, and UC is a mucosal inflammation of the colon. Both conditions are characterized clinically by frequent bowel motions, malnutrition, and dehydration, with disruption in the activities of daily living.

CD is frequently complicated by the development of malabsorption, strictures, and fistulae and may require repeated surgery. UC, less frequently, may be complicated by severe bloody diarrhea and toxic megacolon, also requiring surgery. The most prominent feature Crohn's disease is the granular, reddish-purple edematous thickening of the bowel wall. With the development of inflammation, these granulomas often lose their circumscribed borders and integrate with the surrounding tissue. Diarrhea and obstruction of the bowel are the predominant clinical features. As with ulcerative colitis, the course of Crohn's disease may be continuous or relapsing, mild or severe, but unlike ulcerative colitis, Crohn's disease is not curable by resection of the involved segment of bowel. Most patients with Crohn's disease require surgery at some point, but subsequent relapse is common and continuous medical treatment is usual.

Crohn's disease may involve any part of the alimentary tract from the mouth to the anus, although typically it appears in the ileocolic, small-intestinal or colonic-anorectal regions. Histopathologically, the disease manifests by discontinuous granulomatomas, crypt abscesses, fissures and aphthous ulcers. The inflammatory infiltrate is mixed, consisting of lymphocytes (both T and B cells), plasma cells, macrophages, and neutrophils. There is a disproportionate increase in IgM- and IgG-secreting plasma cells, macrophages and neutrophils.

To date, the primary outcome measure in Crohn's Disease clinical trials is the Crohn's Disease Activity Index (CDAI), which has served as the basis for approval of multiple drug treatments, including for example, vedolizumab and natalizumab. The CDAI was developed by regressing clinician global assessment of disease activity on eighteen potential items representing patient reported outcomes (PROs) (i.e., abdominal pain, pain awakening patient from sleep, appetite), physical signs (i.e., average daily temperature, abdominal mass), medication use (i.e., loperamide or opiate use for diarrhea) and a laboratory test (i.e., hematocrit). Backward stepwise regression analysis identified eight independent predictors which are the number of liquid or soft stools, severity of abdominal pain, general well-being, occurrence of extra-intestinal symptoms, need for anti-diarrheal drugs, presence of an abdominal mass, hematocrit, and body weight. The final score is a composite of these eight items, adjusted using regression coefficients and standardization to construct an overall CDAI score, ranging from 0 to 600 with higher score indicating greater disease activity. Widely used benchmarks are: CDAI <150 is defined as clinical remission, 150 to 219 is defined as mildly active disease, 220 to 450 is defined as moderately active disease, and above 450 is defined as very severe disease (Best W. R., et al., Gastroenterology 77:843-6, 1979). Vedolizumab and natalizumab have been approved on the basis of demonstrated clinical remission, i.e., CDAI <150.

Although the CDAI has been in use for over 40 years, and has served as the basis for drug approval, it has several limitations as an outcome measure for clinical trials. For example, most of the overall score comes from the patient diary card items (pain, number of liquid bowel movements, and general well-being), which are vaguely defined and not standardized terms (Sandler et al., J. Clin. Epidemiol. 41:451-8, 1988; Thia et al., Inflamm. Bowel Dis. 17:105-11, 2011). In addition, measurement of pain is based on a four-point scale rather than an updated seven-point scale. The remaining 5 index items contribute very little to identifying an efficacy signal and may be a source of measurement noise. Furthermore, concerns have been raised about poor criterion validity for the CDAI, a reported lack of correlation between the CDAI and endoscopic measures of inflammation (which may render the CDAI as a poor discriminator of active CD and irritable bowel syndrome) and high reported placebo rates (Korzenik et al., N. Engl. J. Med. 352:2193-201, 2005; Sandborn W. J., et al., N. Engl. J. Med. 353:1912-25, 2005; Sandborn W. J., et al., Ann. Intern. 19; 146:829-38, 2007, Epub 2007 Apr. 30; Kim et al., Gastroenterology 146:(5 supplement 1) S-368, 2014).

It is, thus, generally recognized that additional or alternative measures of CD symptoms are needed, such as new PRO tools or adaptations of the CDAI to derive a new PRO. The PRO2 and PRO3 tools are such adaptations of the CDAI and have been recently described in Khanna et al., Aliment Pharmacol. Ther. 41:77-86, 2015. The PRO2 evaluates the frequency of loose/liquid stools and abdominal pain (Id). These items are derived and weighted accordingly from the CDAI and are the CDAI diary card items, along with general well-being, that contribute most to the observed clinical benefit measured by CDAI (Sandler et al., J. Clin. Epidemiol. 41:451-8, 1988; Thia et al., Inflamm. Bowel Dis. 17:105-11, 2011; Kim et al., Gastroenterology 146:(5 supplement 1) S-368, 2014). The remission score of <11 is the CDAI-weighted sum of the average stool frequency and pain scores in a 7-day period, which yielded optimum sensitivity and specificity for identification of CDAI remission (score of <150) in a retrospective data analysis of ustekinumab induction treatment for moderate to severe CD in a Phase II clinical study (Gasink C., et al., Abstract, ACG Annual Meeting 2014). The PRO2 was shown to be sensitive and responsive when used as a continuous outcome measure in a retrospective data analysis of MTX treatment in active CD (Khanna R., et al., Inflamm. Bowel Dis. 20:1850-61, 2014) measured by CDAI. Additional outcome measures include the Mayo Clinic Score, the Crohn disease endoscopic index of severity (CDEIS), and the Ulcerative colitis endoscopic index of severity (UCEIS). Additional outcome measures include Clinical remission, Mucosal healing, Histological healing (transmural), MRI or ultrasound for measurement or evaluation of bowel wall thickness, abscesses, fistula and histology.

An additional means of assessing the extent and severity of Crohn's Disease is endoscopy. Endoscopic lesions typical of Crohn's disease have been described in numerous studies and include, e.g., aphthoid ulcerations, "punched-out ulcers," cobblestoning and stenosis. Endoscopic evaluation of such lesions was used to develop the first validated endoscopic score, the Crohn's Disease Endoscopic Index of Severity (CDEIS) (Mary et al., Gut 39:983-9, 1989). More recently, because the CDEIS is time-consuming, complicated and impractical for routine use, a Simplified Endoscopic Activity Score for Crohn's Disease (SES-CD) was developed and validated (Daperno et al., Gastrointest. Endosc. 60(4):505-12, 2004). The SES-CD consists of four endoscopic variables (size of ulcers, proportion of surface covered by ulcers, proportion of surface with any other lesions (e.g., inflammation), and presence of narrowings [stenosis]) that are scored in five ileocolonic segments, with each variable, or assessment, rated from 0 to 3.

To date, there is no cure for CD. Accordingly, the current treatment goals for CD are to induce and maintain symptom improvement, induce mucosal healing, avoid surgery, and improve quality of life (Lichtenstein G. R., et al., Am. J. Gastroenterol. 104:465-83, 2009; Van Assche G., et al., J. Crohns Colitis, 4:63-101, 2010). The current therapy of IBD usually involves the administration of antiinflammatory or immunosuppressive agents, such as sulfasalazine, corticosteroids, 6-mercaptopurine/azathioprine, or cyclosporin A, all of which are not typically delivered by localized release of a drug at the site or location of disease. More recently, biologics like TNF-alpha inhibitors and IL-12/IL-23 blockers, are used to treat IBD. If anti-inflammatory/immunosuppressive/biologic therapies fail, colectomies are the last line of defense. The typical operation for CD not involving the rectum is resection (removal of a diseased segment of bowel) and anastomosis (reconnection) without an ostomy. Sections of the small or large intestine may be removed. About 30% of CD patients will need surgery within the first year after diagnosis. In the subsequent years, the rate is about 5% per year. Unfortunately, CD is characterized by a high rate of recurrence; about 5% of patients need a second surgery each year after initial surgery.

Refining a diagnosis of inflammatory bowel disease involves evaluating the progression status of the diseases using standard classification criteria. The classification systems used in IBD include the Truelove and Witts Index (Truelove S. C. and Witts, L. J., Br. Med. J. 1955; 2:1041-1048), which classifies colitis as mild, moderate, or severe, as well as Lennard-Jones (Lennard-Jones J. E., Scand. J. Gastroenterol. Suppl. 1989; 170:2-6) and the simple clinical colitis activity index (SCCAI) (Walmsley et al., Gut, 1998; 43:29-32). These systems track such variables as daily bowel movements, rectal bleeding, temperature, heart rate, hemoglobin levels, erythrocyte sedimentation rate, weight, hematocrit score, and the level of serum albumin.

There is sufficient overlap in the diagnostic criteria for UC and CD that it is sometimes impossible to say which a given patient has; however, the type of lesion typically seen is different, as is the localization. UC mostly appears in the colon, proximal to the rectum, and the characteristic lesion is a superficial ulcer of the mucosa; CD can appear anywhere in the bowel, with occasional involvement of stomach, esophagus and duodenum, and the lesions are usually described as extensive linear fissures.

In approximately 10-15% of cases, a definitive diagnosis of ulcerative colitis or Crohn's disease cannot be made and such cases are often referred to as "indeterminate colitis." Two antibody detection tests are available that can help the diagnosis, each of which assays for antibodies in the blood. The antibodies are "perinuclear anti-neutrophil antibody" (pANCA) and "anti-*Saccharomyces cerevisiae* antibody" (ASCA). Most patients with ulcerative colitis have the pANCA antibody but not the ASCA antibody, while most patients with Crohn's disease have the ASCA antibody but not the pANCA antibody. However, these two tests have shortcomings as some patients have neither antibody and some Crohn's disease patients may have only the pANCA antibody. A third test, which measures the presence and accumulation of circulating anti-microbial antibodies—particularly flagellin antibodies, has proven to be useful for detecting susceptibility to Crohn's Disease before disease development. See Choung, R. S., et al., "Serologic microbial associated markers can predict Crohn's disease behaviour years before disease diagnosis," Alimentary Pharmacology and Therapeutics 43.12 (2016):1300-1310.

"Ulcerative colitis (UC)" afflicts the large intestine. The course of the disease may be continuous or relapsing, mild or severe. The earliest lesion is an inflammatory infiltration with abscess formation at the base of the crypts of Lieberkuhn. Coalescence of these distended and ruptured crypts tends to separate the overlying mucosa from its blood supply, leading to ulceration. Symptoms of the disease include cramping, lower abdominal pain, rectal bleeding, and frequent, loose discharges consisting mainly of blood, pus and mucus with scanty fecal particles. A total colectomy may be required for acute, severe or chronic, unremitting ulcerative colitis.

The clinical features of UC are highly variable, and the onset may be insidious or abrupt, and may include diarrhea, tenesmus and relapsing rectal bleeding. With fulminant involvement of the entire colon, toxic megacolon, a life-threatening emergency, may occur. Extraintestinal manifestations include arthritis, pyoderma gangrenoum, uveitis, and erythema nodosum.

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. The terms "antibody" and "immunoglobulin" are used interchangeably in the broadest sense. As used herein, the terms encompass monoclonal antibodies (for example, full length or intact monoclonal antibodies), polyclonal antibodies (for example, full length or intact polyclonal antibodies), and fragments thereof (such as Fab, Fab', F(ab')2, Fv), single chain (ScFv) and domain antibodies), fusion proteins including an antibody portion, multivalent antibodies, multispecific antibodies (e.g., bispecific, trispecific, etc. antibodies so long as they exhibit the desired biological activity), and any other modified configuration of the immunoglobulin molecule that includes an antigen recognition site. An antibody can be human, humanized and/or affinity matured.

The term antibody includes antibody fragments (e.g., antigen-binding fragments) such as an Fv fragment, a Fab fragment, a F(ab')2 fragment, and a Fab' fragment. "Antibody fragments" comprise only a portion of an intact antibody, where in certain embodiments, the portion retains at least one, and typically most or all, of the functions normally associated with that portion when present in an intact antibody. In one embodiment, an antibody fragment comprises an antigen binding site of the intact antibody and thus retains the ability to bind antigen. In another embodiment, an antibody fragment, for example one that comprises the Fc region, retains at least one of the biological functions normally associated with the Fc region when present in an intact antibody, such as FcRn binding, antibody half-life modulation, ADCC function and complement binding. In one embodiment, an antibody fragment is a monovalent antibody that has an in vivo half-life substantially similar to an intact antibody. For example, such an antibody fragment may comprise on antigen binding arm linked to an Fc sequence capable of conferring in vivo stability to the fragment. Additional examples of antigen-binding fragments include an antigen-binding fragment of an IgG (e.g., an antigen-binding fragment of IgG1, IgG2, IgG3, or IgG4) (e.g., an antigen-binding fragment of a human or humanized IgG, e.g., human or humanized IgG1, IgG2, IgG3, or IgG4); an antigen-binding fragment of an IgA (e.g., an antigen-binding fragment of IgA1 or IgA2) (e.g., an antigen-binding fragment of a human or humanized IgA, e.g., a human or humanized IgA1 or IgA2); an antigen-binding fragment of an IgD (e.g., an antigen-binding fragment of a human or humanized IgD); an antigen-binding fragment of an IgE (e.g., an antigen-binding fragment of a human or humanized IgE); or an antigen-binding fragment of an IgM (e.g., an antigen-binding fragment of a human or humanized IgM). An antibody includes an antibody of any class, such as IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively.

The subunit structures and three-dimensional configurations of different classes of immunoglobulins are well known.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigen or antigenic site. Furthermore, in contrast to polyclonal antibody preparations that typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present disclosure may be made by the hybridoma method first described by Kohler and Milstein, 1975, Nature 256:495, or may be made by recombinant DNA methods such as described in U.S. Pat. No. 4,816,567. The monoclonal antibodies may also be isolated from phage libraries generated using the techniques described in McCafferty et al., 1990, Nature 348:552-554, for example.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA 81:6851-6855 (1984)).

A "variable region" of an antibody refers to the variable region of the antibody light chain or the variable region of the antibody heavy chain, either alone or in combination. As known in the art, the variable regions of the heavy and light chain each consist of four framework regions (FR) connected by three complementarity determining regions (CDRs) that contain hypervariable regions. The CDRs in each chain are held together in close proximity by the FRs and, with the CDRs from the other chain, contribute to the formation of the antigen-binding site of antibodies. There are at least two techniques for determining CDRs: (1) an approach based on cross-species sequence variability (i.e., Kabat et al., Sequences of Proteins of Immunological Interest, (5th ed., 1991, National Institutes of Health, Bethesda MD)); and (2) an approach based on crystallographic studies of antigen-antibody complexes (Al-Lazikani et al., 1997, J. Molec. Biol. 273:927-948). As used herein, a CDR may refer to CDRs defined by either approach or by a combination of both approaches.

As known in the art, a "constant region" of an antibody refers to the constant region of the antibody light chain or the constant region of the antibody heavy chain, either alone or in combination.

As used herein, "TNF" is interchangeable with the terms "TNF-alpha" and "TNF-α" and the term "TNF inhibitor," as used herein, is interchangeable with the term "anti-TNF agent."

An "IL-12/IL-23 inhibitor," as used herein, refers to an agent which decreases the activity of IL-12 and/or IL-23, wherein the decrease in activity includes one or more of: (1) a decrease in the expression of IL-12 and/or IL-23, e.g., as compared to the level of IL-12 and/or IL-23 expression in the absence of the agent; (2) a decrease in the ability of IL-12 to bind to an IL-12 receptor or the ability of IL-23 to bind to an IL-23 receptor, e.g., as compared to the level of IL-12/IL-23 activity in the absence of the agent; and (3) a decrease in the level of an IL-12/IL-23 protein in a mammalian cell contacted with the agent, e.g., as compared to the same mammalian cell not contacted with the agent. IL-12 is a heterodimeric cytokine that includes both IL-12A (p35) and IL-12B (p40) polypeptides. IL-23 is a heterodimeric cytokine that includes both IL-23 (p19) and IL-12B (p40) polypeptides. The receptor for IL-12 is a heterodimeric receptor that includes IL-12R β1 and IL-12R β2. The receptor for IL-23 is a heterodimeric receptor that includes IL-12R β1 and IL-23R. Non-limiting examples of IL-12/IL-23 inhibitors include antibodies such as ustekinumab, guselkumab, risankizumab, brazikumab and mirikizumab; small molecules such as apilimod mesylate; and peptide inhibitors of the IL-23 receptor, such as those disclosed in U.S. Pat. No. 9,624,268, e.g., Compound A (SEQ ID NO: 276) having the following structure:

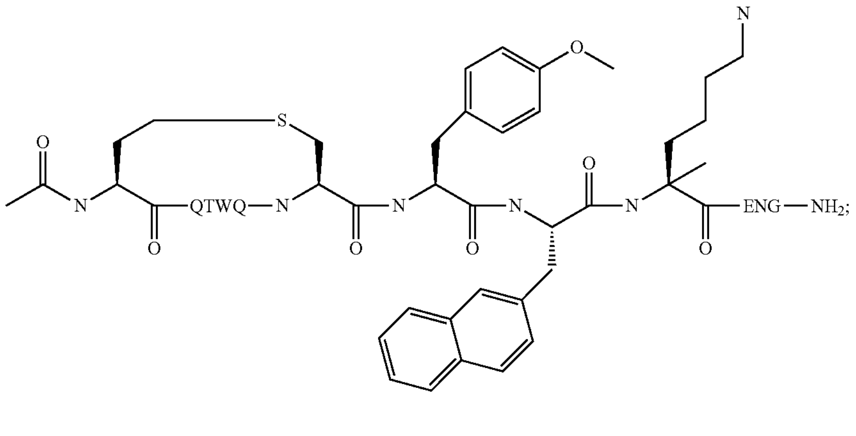

Compound B (SEQ ID NO: 279) having the following structure:

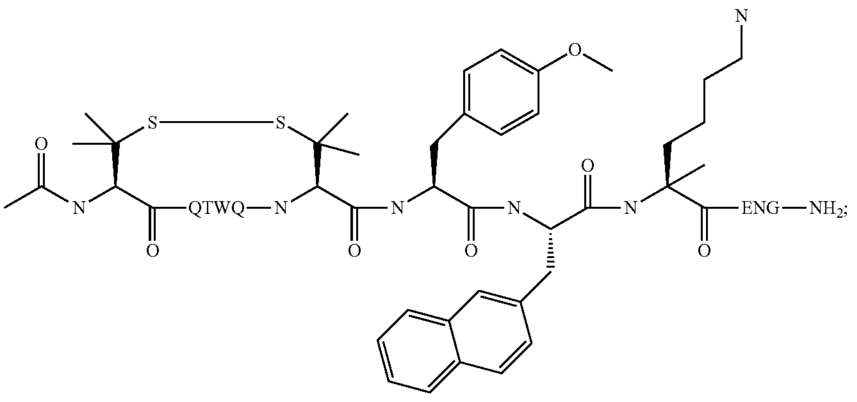

Compound C (SEQ ID NO: 280) having the following structure:

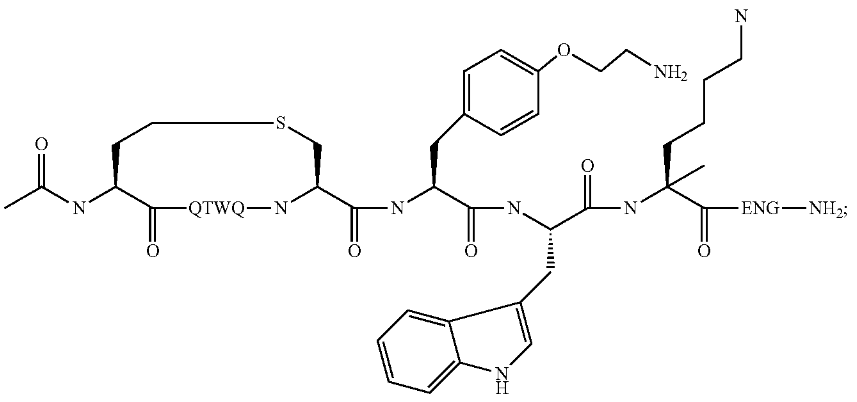

or a pharmaceutically acceptable salt thereof.

"Treatment regimen" refers to a combination of dosage, frequency of administration, or duration of treatment, with or without addition of a second medication.

"Effective treatment regimen" refers to a treatment regimen that will offer beneficial response to a patient receiving the treatment.

"Effective amount" refers to an amount of drug that offers beneficial response to a patient receiving the treatment. For example, an effective amount may be a Human Equivalent Dose (HED).

"Dispensable," with reference to any substance, refers to any substance that may be released from an ingestible device as disclosed herein, or from a component of the device such as a reservoir. For example, a dispensable substance may be a JAK inhibitor, and/or a formulation comprising a JAK inhibitor.

"Patient response" or "patient responsiveness" can be assessed using any endpoint indicating a benefit to the patient, including, without limitation, (1) inhibition, to some extent, of disease progression, including slowing down and complete arrest; (2) reduction in the number of disease episodes and/or symptoms; (3) reduction in lesional size; (4) inhibition (i.e., reduction, slowing down or complete stopping) of disease cell infiltration into adjacent peripheral organs and/or tissues; (5) inhibition (i.e., reduction, slowing down or complete stopping) of disease spread; (6) decrease of auto-immune response, which may, but does not have to, result in the regression or ablation of the disease lesion; (7) relief, to some extent, of one or more symptoms associated with the disorder; (8) increase in the length of disease-free presentation following treatment; and/or (9) decreased mortality at a given point of time following treatment. The term "responsiveness" refers to a measurable response, including complete response (CR) and partial response (PR).

As used herein, "complete response" or "CR" means the disappearance of all signs of inflammation or remission in response to treatment. This does not necessarily mean the disease has been cured.

"Partial response" or "PR" refers to a decrease of at least 50% in the severity of inflammation, in response to treatment.

A "beneficial response" of a patient to treatment with a therapeutic agent and similar wording refers to the clinical or therapeutic benefit imparted to a patient at risk for or suffering from a gastrointestinal inflammatory disorder from or as a result of the treatment with the agent. Such benefit includes cellular or biological responses, a complete response, a partial response, a stable disease (without progression or relapse), or a response with a later relapse of the patient from or as a result of the treatment with the agent.

As used herein, "non-response" or "lack of response" or similar wording means an absence of a complete,response, a partial response, or a beneficial response to treatment with a therapeutic agent.

"A patient maintains responsiveness to a treatment" when the patient's responsiveness does not decrease with time during the course of a treatment.

A "symptom" of a disease or disorder (e.g., inflammatory bowel disease, e.g., ulcerative colitis or Crohn's disease) is any morbid phenomenon or departure from the normal in structure, function, or sensation, experienced by a subject and indicative of disease.

As used herein, "accuracy," when disclosed in connection with a specified location of a device within the GI tract of a subject, refers to the degree to which the location determined by the device conforms to the correct location, wherein the correct location is based on a generally accepted standard. The location within the GI tract of the subject determined by the device can be based on data, for example, light reflectance data, collected by the ingestible device. In some embodiments, the correct location can be based on external imaging devices, such as computer-aided tomography (CT), interpreted, for example, by a qualified clinician or physician. Therefore, percent accuracy ("% accuracy") can refer to the percentage agreement between the location of the device in the GI tract as determined by the device, and the correct location, for example, as determined by CT, e.g., expressed as [(number of devices in which location determined by the device agrees with location as determined by CT/total devices administered to the subject or subjects)×100%], or, where only one device is administered per subject, [(number of subjects in which location determined by the device agrees with location as determined by CT/total number of subjects)×100%]. The latter formula for determining % accuracy was used in Example 14. In some embodiments, the accuracy with which the device determines a location refers to the accuracy with which the device determines that it is at a location pre-selected for drug release.

As used herein, an "autonomous device" refers to a device comprising one or more processors configured to independently control certain mechanisms or operations of the device while in the GI tract of a subject. Preferably, an autonomous device of the present disclosure has no external electrical or wireless connections that control device mechanisms or operations, although connections such as wireless connections may be present to enable alternative device functions, such as transmitting data collected by the device to an external (ex vivo) system or receiver. The independently controlled mechanisms or operations of the autonomous device include, for example, triggering the release of a drug (or the formulation comprising the drug), triggering collection of one or more samples, and/or triggering the analysis of one or more samples; and/or determining the location of the device within the GI tract of the subject. Such mechanisms are referred to herein as "autonomous mechanisms," or, for example, an "autonomous triggering mechanism" or an "autonomous localization mechanism," respectively. Actively implementing such an autonomous triggering or autonomous localization mechanism is referred to as "autonomous triggering" or "autonomous localizing," respectively. An "autonomous localization mechanism" is synonymous with a "self-localization mechanism."

As used herein, a "housing" is a portion of an ingestible device that defines the boundary between the interior of the device and the environment exterior to the device.

As used herein, a "self-localizing device" refers to a device comprising a mechanism or system that can be implemented autonomously to determine the location of the ingestible device in vivo, e.g., within the GI tract of a subject. Such a mechanism is referred to as a "self-localization mechanism." A "self-localization mechanism" is synonymous with an "autonomous localization mechanism." A self-localizing device does not require ex vivo visualization devices or systems, for example, using scintigraphy or computer-aided tomography (CT), to localize in the GI tract.

As used herein, "localizing a device" refers to determining a location of the device.

As used herein, "self-localizing a device" refers to determining a location of the device via a device self-localization mechanism, e.g., determining a location of the within the GI tract of a subject via a device self-localization mechanism.

As used herein, "sensor" refers to a mechanism or portion of a mechanism configured to collect information regarding the surroundings of the ingestible device. Examples of "sensors" include environmental sensors and light sensors. Examples of environmental sensors include pH sensors and sensors capable to identifying muscle contractions and/or peristalsis.

As used herein, "time of transition" of the device refers to elapsed time during passage of the device from one portion of the GI tract into a second portion of the GI tract. In some embodiments, the second portion of the GI tract is adjacent to the first portion. Non-limiting examples of time of transition include the elapsed time during passage of the device between mouth and stomach, esophagus and stomach, stomach and duodenum, duodenum and jejunum, jejunum and ileum, ileum and cecum, or cecum and colon.

As used herein, "time following transition" of the device refers to elapsed time after passage of the device from one portion of the GI tract into a second portion of the GI tract. In some embodiments, the second portion of the GI tract is adjacent to the first portion. Non-limiting examples of time following transition include elapsed time following passage of the device between mouth and stomach, esophagus and stomach, stomach and duodenum, duodenum and jejunum, jejunum and ileum, ileum and cecum, or cecum and colon.

As used herein, a "portion" of the GI tract refers to an anatomical section or subsection of the GI tract. Non-limiting examples of a portion of the GI tract include the mouth, the esophagus, the stomach, the duodenum, the jejunum, the ileum, the cecum, the colon, the ascending colon, the transverse colon, the descending colon, and the rectum.

As used herein, "proximate" as disclosed in connection with release of a drug from a device to one or more disease sites, refers to a location that is sufficiently spatially close to the one or more disease sites such that releasing the drug at the location treats the disease. For example, when the drug is released proximate to the one or more disease sites, the drug may be released 150 cm or less, such as 125 cm or less, such as 100 cm or less, such as 50 cm or less, such as 40 cm or less, such as 30 cm or less, such as 20 cm or less, such as 10 cm or less, such as 5 cm or less, such as 2 cm or less, from the one or more sites of disease. In some embodiments, the proximate location for drug release is the same section or subsection of the gastrointestinal tract containing the one or more disease sites. Thus, where the present application refers to release of a drug proximate to a site of disease, this in some embodiments refers to release of the drug to a section or subsection of the GI tract that contains a site of disease. For example, when a disease site is in the ileum, the drug may be released proximate to the disease site by releasing the drug to the ileum. In some embodiments, the proximate location for drug release is a different section or subsection of the GI tract than that containing the disease site; for example, the drug release may be proximal to the disease site. Thus, where the present application refers to release of a drug proximate to a site of disease, this in some embodiments refers to release of the drug to a section or subsection of the GI tract that is proximal to the section or subsection containing the disease site. For example, when a disease site is in the ileum, the drug may be released to the jejunum.

As used herein, "proximal," when used in connection with an anatomical structure, refers to a portion that precedes, or is upstream of, an adjacent portion of the anatomical structure. In some embodiments, proximal refers to a portion of an anatomical structure that immediately precedes, or is immediately upstream of, an immediately adjacent portion of the anatomical structure. "Proximal," when used in connection with release of a drug from a device to one or more disease sites, refers to release of the drug from the device to a portion of an anatomical structure that precedes, or is upstream of, an adjacent portion of an anatomical structure that contains one or more disease sites. The portion may be a section of the GI tract, which may be selected from mouth, esophagus, stomach, duodenum, jejunum, ileum, cecum, ascending colon, transverse colon, descending colon, and rectum. The portion may be a subsection of the GI tract, which may be selected from proximal duodenum, proximal jejunum, proximal ileum, proximal cecum, proximal ascending colon, proximal transverse colon, proximal descending colon, distal duodenum, distal jejunum, distal ileum, distal cecum, distal ascending colon, distal transverse colon, distal descending colon. In some exemplary embodiments, the drug is released to the cecum (e.g., to a location proximal to the ascending colon) to treat a site of disease tissue in the ascending colon (i.e., a site of disease distal to the cecum). In another embodiment, the drug is released to the cecum (e.g., to a location proximal to the colon) to treat a site of disease tissue in one or more of the ascending colon, transverse colon, descending colon, or a combination thereof (e.g., a site of disease distal to the cecum).

As used herein, "distal," when used in connection with an anatomical structure, refers to a portion, section, or subsection that follows, or is downstream of, an adjacent portion, section, or subsection of the anatomical structure. In some embodiments, distal refers to a portion, section, or subsection that immediately follows, or is immediately downstream of, an immediately adjacent portion, section, or subsection of the anatomical structure.

As used herein, the "total induction dose" is the sum of induction doses over a given time period.

As used herein, the term "adhesion" refers to the ability of the formulations of the present disclosure to bind to the site of topical administration, e.g., mucoses (e.g., a mucosal lining of the gastrointestinal tract of a subject), upon contact, whereby when they are brought into contact work must be done in order to separate them. The adhesion can be measured by a texture analyzer, e.g., TA.XT Plus (Texture Technologies). For example, a 40-mm diameter disk can be compressed into the gel and redrawn. The method settings, including speed rate at 1 mm/second and distance (depth of the insertion) of 9-mm can be assessed at the desired temperature, e.g., at 22° C., 25° C. or at 37° C. The adhesion is measured in mN/s units. The more negative the value in mN/s, the more adhesive the composition will be. Thus, for example a composition showing a measurement value of −100 mN/s is more adhesive than a composition showing a lower measurement value of e.g., −50 mN/s.

As used herein, the term "thermoreversible" or equivalent expressions thereof such as "thermally reversible" applied to the composition means that it exhibits reverse thermogellation, i.e., it undergoes a change in viscosity when the temperature varies. In some embodiments, the composition is liquid at room temperature and forms a gel at body temperature. The liquid state at room temperature facilitates the administration of the composition when it is to be administered, e.g., to the gastrointestinal mucosa, by using an appropriate delivery device, such as for example an ingestible device as disclosed herein. When the composition is released from the device and comes into contact with the mucosa at body temperature, its viscosity increases to a higher viscosity state, hence acquiring the consistency of a gel. This has the advantage that the composition remains on the surface of the affected area.

The terms "pharmaceutically acceptable carrier," "pharmaceutically acceptable diluent" and "pharmaceutically acceptable excipient" include any and all solvents, cosolvents, complexing agents, dispersion media, coatings, isotonic and absorption delaying agents and the like which are not biologically or otherwise undesirable. The use of such media and agents for pharmaceutically active substances is well known in the art. Except insofar as any conventional media or agent is incompatible with the active ingredient, its use in the therapeutic formulations is contemplated. Supplementary active ingredients can also be incorporated into the formulations. In addition, various adjuvants such as are commonly used in the art may be included. These and other such therapeutic agents are described in the literature, e.g., in the Merck Index, Merck & Company, Rahway, N.J. Considerations for the inclusion of various components in pharmaceutical formulations are described, e.g., in Gilman et al. (Eds.) (2010); Goodman and Gilman's: The Pharmacological Basis of Therapeutics, 12th Ed., The McGraw-Hill Companies.

As used herein, the term "pharmaceutically acceptable salt" refers to those salts of compounds disclosed herein that are safe and effective for use in mammals, including humans, and that possess the desired biological activity. Pharmaceutically acceptable salts are known to the person of ordinary skill in the art. In a non-limiting example, when the compound has an acidic group such as carboxyl group in the formula, the salts can be salts thereof with alkali metals, e.g. sodium, potassium and ammonium, salts thereof with alkaline earth metals, e.g. calcium and magnesium, salts thereof with aluminum and zinc, salts thereof with organic amines, e.g. triethylamine, ethanolamine, morpholine, piperidine and dicyclohexylamine, and salts thereof with basic amino acids, e.g. arginine and lysine. In a non-limiting example, when the compound has a basic group in the formula, the salts can be those with inorganic acids, e.g., hydrochloric acid, sulfuric acid and phosphoric acid; those with organic carboxylic acids, e.g. acetic acid, citric acid, benzoic acid, maleic acid, fumaric acid, tartaric acid and succinic acid; and those with organosulfonic acids, e.g., methanesulfonic acid and p-toluenesulfonic acid. The salts can be formed by mixing a compound with a necessitated acid or base in a proper ratio in a solvent or dispersing agent or by the cation exchange or anion exchange reaction with another salt.

As used herein, a reference to a drug's international nonproprietary name (INN) is to be interpreted as including generic, bioequivalent and biosimilar versions of that drug, including but not limited to any drug that has received abbreviated regulatory approval by reference to an earlier regulatory approval of that drug. Additionally, all drugs disclosed herein optionally include the pharmaceutically acceptable salts and solvates of the drugs thereof, unless expressly indicated otherwise.

As used herein, each listed small molecule, peptide or nucleic acid agent optionally includes a pharmaceutically acceptable salt thereof, whether or not such a form is expressly indicated. Each listed antibody agent optionally includes a biosimilar thereof, whether or not such a biosimilar is expressly indicated.

Inhibitory Agents of Janus Kinase (JAK) Activity and/or Expression

The term "JAK inhibitor" refers to an agent which decreases the activity of Janus kinase 1 (JAK1), JAK2, JAK3, or non-receptor protein tyrosine kinase 2 (TYK-2), wherein the decrease in activity includes one or more of: (1) a decrease in the expression of at least one of JAK1, JAK2, JAK3, and TYK-2, e.g., as compared to the level of JAK expression in the absence of the agent; (2) a decrease in the kinase activity of at least one of JAK1, JAK2, JAK3, and TYK-2, e.g., as compared to the level of activity in the absence of the agent; and (3) a decrease in the level of a JAK protein in a mammalian cell contacted with the agent, e.g., as compared to the same mammalian cell not contacted with the agent. In some further embodiments, the JAK inhibitor decreases the activity of at least one of JAK1, JAK2, JAK3 and TYK-2 and interferes with the Janus kinase-signal transducer and activator of transcription (JAK-STAT) signaling pathway.

In some embodiments, the JAK inhibitor decreases the activity of JAK1. In some embodiments, the JAK inhibitor decreases the activity of JAK2. In some embodiments, the JAK inhibitor decreases the activity of JAK3. In some embodiments, the JAK inhibitor decreases the activity of TYK-2. In some preferred embodiments, the JAK inhibitor selectively decreases the activity of JAK 1, JAK3, or both. In some other preferred embodiments, the JAK inhibitor selectively decreases the activity of JAK3. In some embodiments, the JAK inhibitor covalently binds to JAK1, JAK3 or both. In some embodiments, the JAK inhibitor is a Michael acceptor.

In some embodiments, the JAK inhibitor decreases the expression of JAK1. In some embodiments, the JAK inhibitor decreases the expression of JAK2. In some embodiments, the JAK inhibitor decreases the expression of JAK3. In some embodiments, the JAK inhibitor decreases the expression of TYK-2.

In some embodiments, the JAK inhibitor decreases the kinase activity of JAK1. In some embodiments, the JAK inhibitor decreases the kinase activity of JAK2. In some embodiments, the JAK inhibitor decreases the kinase activity of JAK3. In some embodiments, the JAK inhibitor decreases the kinase activity of TYK-2. In some embodiments, the JAK inhibitor is a decreases the kinase activity of JAK1, JAK2, JAK3, and TYK2. In some embodiments, the JAK inhibitor decreases the kinase activity of two or more (e.g., 3 or 4) of: JAK1, JAK2, JAK3 and TYK2. In some embodiments, the JAK inhibitor decreases the kinase activity of a single JAK isoform (e.g., JAK1, JAK2, JAK3, or TYK2).

In some embodiments, the JAK inhibitor decreases the kinase activity of JAK1 and JAK2. In some embodiments, the JAK inhibitor decreases the kinase activity of JAK1 and JAK3. In some embodiments, the JAK inhibitor decreases the kinase activity of JAK2 and JAK3. In some embodiments, the JAK inhibitor decreases the kinase activity of JAK1, JAK2 and JAK3. In some preferred embodiments, the JAK inhibitor selectively decreases the kinase activity of JAK 1, JAK3, or both. In some other preferred embodiments, the JAK inhibitor selectively decreases the kinase activity of JAK3.

In some embodiments, a JAK inhibitor can decrease JAK activity, e.g., decrease one or more of: JAK1, JAK2, JAK3, and/or TYK-2 expression; JAK1, JAK2, JAK3, and/or TYK-2 kinase activity, or the level of JAK protein in a mammalian cell contacted with the agent, for example, as compared to the level of JAK protein in the same mammalian cell not contacted with the agent, e.g., by about 1% to about 99%, by about 1% to about 95%, by about 1% to about 90%, by about 1% to about 85%, by about 1% to about 80%, by about 1% to about 75%, by about 1% to about 70%, by about 1% to about 65%, by about 1% to about 60%, by about 1% to about 55%, by about 1% to about 50%, by about 1% to about 45%, by about 1% to about 40%, by about 1% to about 35%, by about 1% to about 30%, by about 1% to about 25%, by about 1% to about 20%, by about 1% to about 20%, by about 1% to about 15%, by about 1% to about 10%, by about 1% to about 5%, by about 5% to about 99%, by about 5% to about 90%, by about 5% to about 85%, by about 5% to about 80%, by about 5% to about 75%, by about 5% to about 70%, by about 5% to about 65%, by about 5% to about 60%, by about 5% to about 55%, by about 5% to about 50%, by about 5% to about 45%, by about 5% to about 40%, by about 5% to about 35%, by about 5% to about 30%, by about 5% to about 25%, by about 5% to about 20%, by about 5% to about 15%, by about 5% to about 10%, by about 10% to about 99%, about 10% to about 95%, about 10% to about 90%, about 10% to about 85%, by about 10% to about 80%, by about 10% to about 75%, by about 10% to about 70%, by about 10% to about 65%, by about 10% to about 60%, by about 10% to about 55%, by about 10% to about 50%, by about 10% to about 45%, by about 10% to about 40%, by about 10% to about 35%, by about 10% to about 30%, by about 10% to about 25%, by about 10% to about 20%, by about 10% to about 15%, by about 15% to about 99%, by about 15% to about 95%, by about 15% to about 90%, by about 15% to about 85%, by about 15% to about 80%, by about 15% to about 75%, by about 15% to about 70%, by about 15% to about 65%, by about 15% to about 60%, by about 15% to about 55%, by about 15% to about 50%, by about 15% to about 45%, by about 15% to about 40%, by about 15% to about 35%, by about 15% to about 30%, by about 15% to about 25%, by about 15% to about 20%, by about 20% to about 99%, by about 20% to about 95%, by about 20% to about 90%, by about 20% to about 85%, by about 20% to about 80%, by about 20% to about 75%, by about 20% to about 70%, by about 20% to about 65%, by about 20% to about 60%, by about 20% to about 55%, by about 20% to about 50%, by about 20% to about 45%, by about 20% to about 40%, by about 20% to about 35%, by about 20% to about 30%, by about 20% to about 25%, by about 25% to about 99%, about 25% to about 95%, by about 25% to about 90%, by about 25% to about 85%, by about 25% to about 80%, by about 25% to about 75%, by about 25% to about 70%, by about 25% to about 65%, by about 25% to about 60%, by about 25% to about 55%, by about 25% to about 50%, by about 25% to about 45%, by about 25% to about 40%, by about 25% to about 35%, by about 25% to about 30%, by about 30% to about 99%, by about 30% to about 95%, by about 30% to about 90%, by about 30% to about 85%, by about 30% to about 80%, by about 30% to about 75%, by about 30% to about 70%, by about 30% to about 65%, by about 30% to about 60%, by about 30% to about 55%, by about 30% to about 50%, by about 30% to about 45%, by about 30% to about 40%, by about 30% to about 35%, by about 35% to about 99%, by about 35% to about 95%, by about 35% to about 90%, by about 35% to about 85%, by about 35% to about 80%, by about 35% to about 75%, by about 35% to about 70%, by about 35% to about 65%, by about 35% to about 60%, by about 35% to about 55%, by about 35% to about 50%, by about 35% to about 45%, by about 35% to about 40%, by about 40% to about 99%, by about 40% to about 95%, by about 40% to about 90%, by about 40% to about 85%, by about 40% to about 80%, by about 40% to about 75%, by about 40% to about 70%, by about 40% to about 65%, by about 40% to about 60%, by about 40% to about 55%, by about 40% to about 50%, by about 40% to about 45%, by about 45% to about 99%, by about 45% to about 95%, by about 45% to about 90%, by about 45% to about 85%, by about 45% to about 80%, by about 45% to about 75%, by about 45% to about 70%, by about 45% to about 65%, by about 45% to about 60%, by about 45% to about 55%, by about 45% to about 50%, by about 50% to about 99%, by about 50% to about 95%, by about 50% to about 90%, by about 50% to about 85%, by about 50% to about 80%, by about 50% to about 75%, by about 50% to about 70%, by about 50% to about 65%, by about 50% to about 60%, by about 50% to about 55%, by about 55% to about 99%, by about 55% to about 95%, by about 55% to about 90%, by about 55% to about 85%, by about 55% to about 80%, by about 55% to about 75%, by about 55% to about 70%, by about 55% to about 65%, by about 55% to about 60%, by about 60% to about 99%, by about 60% to about 95%, by about 60% to about 90%, by about 60% to about 85%, by about 60% to about 80%, by about 60% to about 75%, by about 60% to about 70%, by about 60% to about 65%, by about 65% to about 99%, by about 65% to about 95%, by about 65% to about 90%, by about 65% to about 85%, by about 65% to about 80%, by about 65% to about 75%, by about 65% to about 70%, by about 70% to about 99%, by about 70% to about 95%, by about 70% to about 90%, by about 70% to about 85%, by about 70% to about 80%, by about 70% to about 75%, by about 75% to about 99%, by about 75% to about 95%, by about 75% to about 90%, by about 75% to about 85%, by about 75% to about 80%, by about 80% to about 99%, by about 80% to about 95%, by about 80% to about 90%, by about 80% to about 85%, by about 85% to about 99%, by about 85% to about 95%, by about 85% to about 90%, by about 90% to about 99%, by about 90% to about 95%, or by about 95% to about 99%.

In some embodiments, a JAK inhibitor can inhibit JAK activity with an $IC_{50}$ of about 1 pM to about 100 TM, about 1 pM to about 95 TM, about 1 pM to about 90 TM, about 1 pM to about 85 TM, about 1 pM to about 80 TM, about 1 pM to about 75 TM, about 1 pM to about 70 TM, about 1 pM to about 65 TM, about 1 pM to about 60 TM, about 1 pM to about 55 TM, about 1 pM to about 50 TM, about 1 pM to about 45 TM, about 1 pM to about 40 TM, about 1 pM to about 35 TM, about 1 pM to about 30 TM, about 1 pM to about 25 TM, about 1 pM to about 20 TM, about 1 pM to about 15 TM, about 1 pM to about 10 TM, about 1 pM to about 5 TM, about 1 pM to about 1 TM, about 1 pM to about 900 nM, about 1 pM to about 800 nM, about 1 pM to about 700 nM, about 1 pM to about 600 nM, about 1 pM to about 500 nM, about 1 pM to about 400 nM, about 1 pM to about 300 nM, about 1 pM to about 200 nM, about 1 pM to about 100 nM, about 1 pM to about 50 nM, about 1 pM to about 1 nM, about 1 pM to about 800 pM, about 1 pM to about 600 pM, about 1 pM to about 400 pM, about 1 pM to about 200 pM, about 200 pM to about 100 TM, about 200 pM to about 95 TM, about 200 pM to about 90 TM, about 200 pM to about 85 TM, about 200 pM to about 80 TM, about 200 pM to about 75 TM, about 200 pM to about 70 TM, about 200 pM to about 65 TM, about 200 pM to about 60 TM, about 200 pM to about 55 TM, about 200 pM to about 50 TM, about 200 pM to about 45 TM, about 200 pM to about 40 TM, about 200 pM to about 35 TM, about 200 pM to about 30 TM, about 200 pM to about 25 TM, about 200 pM to about 20 TM, about 200 pM to about 15 TM, about 200 pM to about 10 TM, about 200 pM to about 5 TM, about 200 pM to about 1 TM, about 200 pM to about 900 nM, about 200 pM to about 800 nM, about 200 pM to about 700 nM, about 200 pM to about 600 nM, about 200 pM to about 500 nM, about 200 pM to about 400 nM, about 200 pM to about 300 nM, about 200 pM to about 200 nM, about 200 pM to about 100 nM, about 200 pM to about 50 nM, about 200 pM to about 1 nM, about 200 pM to about 800 pM, about 200 pM to about 600 pM, about 200 pM to about 400 pM, about 400 pM to about 100 TM, about 400 pM to about 95 TM, about 400 pM to about 90 TM, about 400 pM to about 85 TM, about 400 pM to about 80 TM, about 400 pM to about 75 TM, about 400 pM to about 70 TM, about 400 pM to about 65 TM, about 400 pM to about 60 TM, about 400 pM to about 55 TM, about 400 pM to about 50 TM, about 400 pM to about 45 TM, about 400 pM to about 40 TM, about 400 pM to about 35 TM, about 400 pM to about 30 TM, about 400 pM to about 25 TM, about 400 pM to about 20 TM, about 400 pM to about 15 TM, about 400 pM to about 10 TM, about 400 pM to about 5 TM, about 400 pM to about 1 TM, about 400 pM to about 900 nM, about 400 pM to about 800 nM, about 400 pM to about 700 nM, about 400 pM to about 600 nM, about 400 pM to about 500 nM, about 400 pM to about 400 nM, about 400 pM to about 300 nM, about 400 pM to about 200 nM, about 400 pM to about 100 nM, about 400 pM to about 50 nM, about 400 pM to about 1 nM, about 400 pM to about 800 pM, 400 pM to about 600 pM, about 600 pM to about 100 TM, about 600 pM to about 95 TM, about 600 pM to about 90 TM, about 600 pM to about 85 TM, about 600 pM to about 80 TM, about 600 pM to about 75 TM, about 600 pM to about 70 TM, about 600 pM to about 65 TM, about 600 pM to about 60 TM, about 600 pM to about 55 TM, about 600 pM to about 50 TM, about 600 pM to about 45 TM, about 600 pM to about 40 TM, about 600 pM to about 35 TM, about 600 pM to about 30 TM, about 600 pM to about 25 TM, about 600 pM to about 20 TM, about 600 pM to about 15 TM, about 600 pM to about 10 TM, about 600 pM to about 5 TM, about 600 pM to about 1 TM, about 600 pM to about 900 nM, about 600 pM to about 800 nM, about 600 pM to about 700 nM, about 600 pM to about 600 nM, about 600 pM to about 500 nM, about 600 pM to about 400 nM, about 600 pM to about 300 nM, about 600 pM to about 200 nM, about 600 pM to about 100 nM, about 600 pM to about 50 nM, about 600 pM to about 1 nM, about 600 pM to about 800 pM, about 800 pM to about 100 TM, about 800 pM to about 95 TM, about 800 pM to about 90 TM, about 800 pM to about 85 TM, about 800 pM to about 80 TM, about 800 pM to about 75 TM, about 800 pM to about 70 TM, about 800 pM to about 65 TM, about 800 pM to about 60 TM, about 800 pM to about 55 TM, about 800 pM to about 50 TM, about 800 pM to about 45 TM, about 800 pM to about 40 TM, about 800 pM to about 35 TM, about 800 pM to about 30 TM, about 800 pM to about 25 TM, about 800 pM to about 20 TM, about 800 pM to about 15 TM, about 800 pM to about 10 TM, about 800 pM to about 5 TM, about 800 pM to about 1 TM, about 800 pM to about 900 nM, about 800 pM to about 800 nM, about 800 pM to about 700 nM, about 800 pM to about 600 nM, about 800 pM to about 500 nM, about 800 pM to about 400 nM, about 800 pM to about 300 nM, about 800 pM to about 200 nM, about 800 pM to about 100 nM, about 800 pM to about 50 nM, about 800 pM to about 1 nM, about 1 nM to about 100 TM, about 1 nM to about 95 TM, about 1 nM to about 90 TM, about 1 nM to about 85 TM, about 1 nM to about 80 TM, about 1 nM to about 75 TM, about 1 nM to about 70 TM, about 1 nM to about 65 TM, about 1 nM to about 60 TM, about 1 nM to about 55 TM, about 1 nM to about 50 TM, about 1 nM to about 45 TM, about 1 nM to about 40 TM, about 1 nM to about 35 TM, about 1 nM to about 30 TM, about 1 nM to about 25 TM, about 1 nM to about 20 TM, about 1 nM to about 15 TM, about 1 nM to about 10 TM, about 1 nM to about 5 TM, about 1 nM to about 1 TM, about 1 nM to about 900 nM, about 1 nM to about 800 nM, about 1 nM to about 700 nM, about 1 nM to about 600 nM, about 1 nM to about 500 nM, about 1 nM to about 400 nM, about 1 nM to about 300 nM, about 1 nM to about 200 nM, about 1 nM to about 100 nM, about 1 nM to about 50 nM, about 50 nM to about 100 TM, about 50 nM to about 95 TM, about 50 nM to about 90 TM, about 50 nM to about 85 TM, about 50 nM to about 80 TM, about 50 nM to about 75 TM, about 50 nM to about 70 TM, about 50 nM to about 65 TM, about 50 nM to about 60 TM, about 50 nM to about 55 TM, about 50 nM to about 50 TM, about 50 nM to about 45 TM, about 50 nM to about 40 TM, about 50 nM to about 35 TM, about 50 nM to about 30 TM, about 50 nM to about 25 TM, about 50 nM to about 20 TM, about 50 nM to about 15 TM, about 50 nM to about 10 TM, about 50 nM to about 5 TM, about 50 nM to about 1 TM, about 50 nM to about 900 nM, about 50 nM to about 800 nM, about 50 nM to about 700 nM, about 50 nM to about 600 nM, about 50 nM to about 500 nM, about 50 nM to about 400 nM, about 50 nM to about 300 n, about 50 nM to about 200 nM, about 50 nM to about 100 nM, about 100 nM to about 100 TM, about 100 nM to about 95 TM, about 100 nM to about 90 TM, about 100 nM to about 85 TM, about 100 nM to about 80 TM, about 100 nM to about 75 TM, about 100 nM to about 70 TM, about 100 nM to about 65 TM, about 100 nM to about 60 TM, about 100 nM to about 55 TM, about 100 nM to about 50 TM, about 100 nM to about 45 TM, about 100 nM to about 40 TM, about 100 nM to about 35 TM, about 100 nM to about 30 TM, about 100 nM to about 25 TM, about 100 nM to about 20 TM, about 100 nM to about 15 TM, about 100 nM to about 10 TM, about 100 nM to about 5 TM, about 100 nM to about 1 TM, about 100 nM to about 900 nM, about 100 nM to about 800 nM, about 100 nM to about 700 nM, about 100 nM to about 600 nM, about 100 nM to about 500 nM, about 100 nM to about 400 nM, about 100 nM to about 300 nM, about 100 nM to about 200 nM, about 200 nM to about 100 TM, about 200 nM to about 95 TM, about 200 nM to about 90 TM, about 200 nM to about 85 TM, about 200 nM to about 80 TM, about 200 nM to about 75 TM, about 200 nM to about 70 TM, about 200 nM to about 65 TM, about 200 nM to about 60 TM, about 200 nM to about 55 TM, about 200 nM to about 50 TM, about 200 nM to about 45 TM, about 200 nM to about 40 TM, about 200 nM to about 35 TM, about 200 nM to about 30 TM, about 200 nM to about 25 TM, about 200 nM to about 20 TM, about 200 nM to about 15 TM, about 200 nM to about 10 TM, about 200 nM to about 5 TM, about 200 nM to about 1 TM, about 200 nM to about 900 nM, about 200 nM to about 800 nM, about 200 nM to about 700 nM, about 200 nM to about 600 nM, about 200 nM to about 500 nM, about 200 nM to about 400 nM, about 200 nM to about 300 nM, about 300 nM to about 100 TM, about 300 nM to about 95 TM, about 300 nM to about 90 TM, about 300 nM to about 85 TM, about 300 nM to about 80 TM, about 300 nM to about 75 TM, about 300 nM to about 70 TM, about 300 nM to about 65 TM, about 300 nM to about 60 TM, about 300 nM to about 55 TM, about 300 nM to about 50 TM, about 300 nM to about 45 TM, about 300 nM to about 40 TM, about 300 nM to about 35 TM, about 300 nM to about 30 TM, about 300 nM to about 25 TM, about 300 nM to about 20 TM, about 300 nM to about 15 TM, about 300 nM to about 10 TM, about 300 nM to about 5 TM, about 300 nM to about 1 TM, about 300 nM to about 900 nM, about 300 nM to about 800 nM, about 300 nM to about 700 nM, about 300 nM to about 600 nM, about 300 nM to about 500 nM, about 300 nM to about 400 nM, about 400 nM to about 100 TM, about 400 nM to about 95 TM, about 400 nM to about 90 TM, about 400 nM to about 85 TM, about 400 nM to about 80 TM, about 400 nM to about 75 TM, about 400 nM to about 70 TM, about 400 nM to about 65 TM, about 400 nM to about 60 TM, about 400 nM to about 55 TM, about 400 nM to about 50 TM, about 400 nM to about 45 TM, about 400 nM to about 40 TM, about 400 nM to about 35 TM, about 400 nM to about 30 TM, about 400 nM to about 25 TM, about 400 nM to about 20 TM, about 400 nM to about 15 TM, about 400 nM to about 10 TM, about 400 nM to about 5 TM, about 400 nM to about 1 TM, about 400 nM to about 900 nM, about 400 nM to about 800 nM, about 400 nM to about 700 nM, about 400 nM to about 600 nM, about 400 nM to about 500 nM, about 500 nM to about 100 TM, about 500 nM to about 95 TM, about 500 nM to about 90 TM, about 500 nM to about 85 TM, about 500 nM to about 80 TM, about 500 nM to about 75 TM, about 500 nM to about 70 TM, about 500 nM to about 65 TM, about 500 nM to about 60 TM, about 500 nM to about 55 TM, about 500 nM to about 50 TM, about 500 nM to about 45 TM, about 500 nM to about 40 TM, about 500 nM to about 35 TM, about 500 nM to about 30 TM, about 500 nM to about 25 TM, about 500 nM to about 20 TM, about 500 nM to about 15 TM, about 500 nM to about 10 TM, about 500 nM to about 5 TM, about 500 nM to about 1 TM, about 500 nM to about 900 nM, about 500 nM to about 800 nM, about 500 nM to about 700 nM, about 500 nM to about 600 nM, about 600 nM to about 100 TM, about 600 nM to about 95 TM, about 600 nM to about 90 TM, about 600 nM to about 85 TM, about 600 nM to about 80 TM, about 600 nM to about 75 TM, about 600 nM to about 70 TM, about 600 nM to about 65 TM, about 600 nM to about 60 TM, about 600 nM to about 55 TM, about 600 nM to about 50 TM, about 600 nM to about 45 TM, about 600 nM to about 40 TM, about 600 nM to about 35 TM, about 600 nM to about 30 TM, about 600 nM to about 25 TM, about 600 nM to about 20 TM, about 600 nM to about 15 TM, about 600 nM to about 10 TM, about 600 nM to about 5 TM, about 600 nM to about 1 TM, about 600 nM to about 900 nM, about 600 nM to about 800 nM, about 600 nM to about 700 nM, about 700 nM to about 100 TM, about 700 nM to about 95 TM, about 700 nM to about 90 TM, about 700 nM to about 85 TM, about 700 nM to about 80 TM, about 700 nM to about 75 TM, about 700 nM to about 70 TM, about 700 nM to about 65 TM, about 700 nM to about 60 TM, about 700 nM to about 55 TM, about 700 nM to about 50 TM, about 700 nM to about 45 TM, about 700 nM to about 40 TM, about 700 nM to about 35 TM, about 700 nM to about 30 TM, about 700 nM to about 25 TM, about 700 nM to about 20 TM, about 700 nM to about 15 TM, about 700 nM to about 10 TM, about 700 nM to about 5 TM, about 700 nM to about 1 TM, about 700 nM to about 900 nM, about 700 nM to about 800 nM, about 800 nM to about 100 TM, about 800 nM to about 95 TM, about 800 nM to about 90 TM, about 800 nM to about 85 TM, about 800 nM to about 80 TM, about 800 nM to about 75 TM, about 800 nM to about 70 TM, about 800 nM to about 65 TM, about 800 nM to about 60 TM, about 800 nM to about 55

TM, about 800 nM to about 50 TM, about 800 nM to about 45 TM, about 800 nM to about 40 TM, about 800 nM to about 35 TM, about 800 nM to about 30 TM, about 800 nM to about 25 TM, about 800 nM to about 20 TM, about 800 nM to about 15 TM, about 800 nM to about 10 TM, about 800 nM to about 5 TM, about 800 nM to about 1 TM, about 800 nM to about 900 nM, about 900 nM to about 100 TM, about 900 nM to about 95 TM, about 900 nM to about 90 TM, about 900 nM to about 85 TM, about 900 nM to about 80 TM, about 900 nM to about 75 TM, about 900 nM to about 70 TM, about 900 nM to about 65 TM, about 900 nM to about 60 TM, about 900 nM to about 55 TM, about 900 nM to about 50 TM, about 900 nM to about 45 TM, about 900 nM to about 40 TM, about 900 nM to about 35 TM, about 900 nM to about 30 TM, about 900 nM to about 25 TM, about 900 nM to about 20 TM, about 900 nM to about 15 TM, about 900 nM to about 10 TM, about 900 nM to about 5 TM, about 900 nM to about 1 TM, about 1 TM to about 100 TM, about 1 TM to about 95 TM, about 1 TM to about 90 TM, about 1 TM to about 85 TM, about 1 TM to about 80 TM, about 1 TM to about 75 TM, about 1 TM to about 70 TM, about 1 TM to about 65 TM, about 1 TM to about 60 TM, about 1 TM to about 55 TM, about 1 TM to about 50 TM, about 1 TM to about 45 TM, about 1 TM to about 40 TM, about 1 TM to about 35 TM, about 1 TM to about 30 TM, about 1 TM to about 25 TM, about 1 TM to about 20 TM, about 1 TM to about 15 TM, about 1 TM to about 10 TM, about 1 TM to about 5 TM, about 5 TM to about 100 TM, about 5 TM to about 95 TM, about 5 TM to about 90 TM, about 5 TM to about 85 TM, about 5 TM to about 80 TM, about 5 TM to about 75 TM, about 5 TM to about 70 TM, about 5 TM to about 65 TM, about 5 TM to about 60 TM, about 5 TM to about 55 TM, about 5 TM to about 50 TM, about 5 TM to about 45 TM, about 5 TM to about 40 TM, about 5 TM to about 35 TM, about 5 TM to about 30 TM, about 5 TM to about 25 TM, about 5 TM to about 20 TM, about 5 TM to about 15 TM, about 5 TM to about 10 TM, about 10 TM to about 100 TM, about 10 TM to about 95 TM, about 10 TM to about 90 TM, about 10 TM to about 85 TM, about 10 TM to about 80 TM, about 10 TM to about 75 TM, about 10 TM to about 70 TM, about 10 TM to about 65 TM, about 10 TM to about 60 TM, about 10 TM to about 55 TM, about 10 TM to about 50 TM, about 10 TM to about 45 TM, about 10 TM to about 40 TM, about 10 TM to about 35 TM, about 10 TM to about 30 TM, about 10 TM to about 25 TM, about 10 TM to about 20 TM, about 10 TM to about 15 TM, about 15 TM to about 100 TM, about 15 TM to about 95 TM, about 15 TM to about 90 TM, about 15 TM to about 85 TM, about 15 TM to about 80 TM, about 15 TM to about 75 TM, about 15 TM to about 70 TM, about 15 TM to about 65 TM, about 15 TM to about 60 TM, about 15 TM to about 55 TM, about 15 TM to about 50 TM, about 15 TM to about 45 TM, about 15 TM to about 40 TM, about 15 TM to about 35 TM, about 15 TM to about 30 TM, about 15 TM to about 25 TM, about 15 TM to about 20 TM, about 20 TM to about 100 TM, about 20 TM to about 95 TM, about 20 TM to about 90 TM, about 20 TM to about 85 TM, about 20 TM to about 80 TM, about 20 TM to about 75 TM, about 20 TM to about 70 TM, about 20 TM to about 65 TM, about 20 TM to about 60 TM, about 20 TM to about 55 TM, about 20 TM to about 50 TM, about 20 TM to about 45 TM, about 20 TM to about 40 TM, about 20 TM to about 35 TM, about 20 TM to about 30 TM, about 20 TM to about 25 TM, about 25 TM to about 100 TM, about 25 TM to about 95 TM, about 25 TM to about 90 TM, about 25 TM to about 85 TM, about 25 TM to about 80 TM, about 25 TM to about 75 TM, about 25 TM to about 70 TM, about 25 TM to about 65 TM, about 25 TM to about 60 TM, about 25 TM to about 55 TM, about 25 TM to about 50 TM, about 25 TM to about 45 TM, about 25 TM to about 40 TM, about 25 TM to about 35 TM, about 25 TM to about 30 TM, about 30 TM to about 100 TM, about 30 TM to about 95 TM, about 30 TM to about 90 TM, about 30 TM to about 85 TM, about 30 TM to about 80 TM, about 30 TM to about 75 TM, about 30 TM to about 70 TM, about 30 TM to about 65 TM, about 30 TM to about 60 TM, about 30 TM to about 55 TM, about 30 TM to about 50 TM, about 30 TM to about 45 TM, about 30 TM to about 40 TM, about 30 TM to about 35 TM, about 35 TM to about 100 TM, about 35 TM to about 95 TM, about 35 TM to about 90 TM, about 35 TM to about 85 TM, about 35 TM to about 80 TM, about 35 TM to about 75 TM, about 35 TM to about 70 TM, about 35 TM to about 65 TM, about 35 TM to about 60 TM, about 35 TM to about 55 TM, about 35 TM to about 50 TM, about 35 TM to about 45 TM, about 35 TM to about 40 TM, about 40 TM to about 100 TM, about 40 TM to about 95 TM, about 40 TM to about 90 TM, about 40 TM to about 85 TM, about 40 TM to about 80 TM, about 40 TM to about 75 TM, about 40 TM to about 70 TM, about 40 TM to about 65 TM, about 40 TM to about 60 TM, about 40 TM to about 55 TM, about 40 TM to about 50 TM, about 40 TM to about 45 TM, about 45 TM to about 100 TM, about 45 TM to about 95 TM, about 45 TM to about 90 TM, about 45 TM to about 85 TM, about 45 TM to about 80 TM, about 45 TM to about 75 TM, about 45 TM to about 70 TM, about 45 TM to about 65 TM, about 45 TM to about 60 TM, about 45 TM to about 55 TM, about 45 TM to about 50 TM, about 50 TM to about 100 TM, about 50 TM to about 95 TM, about 50 TM to about 90 TM, about 50 TM to about 85 TM, about 50 TM to about 80 TM, about 50 TM to about 75 TM, about 50 TM to about 70 TM, about 50 TM to about 65 TM, about 50 TM to about 60 TM, about 50 TM to about 55 TM, about 55 TM to about 100 TM, about 55 TM to about 95 TM, about 55 TM to about 90 TM, about 55 TM to about 85 TM, about 55 TM to about 80 TM, about 55 TM to about 75 TM, about 55 TM to about 70 TM, about 55 TM to about 65 TM, about 55 TM to about 60 TM, about 60 TM to about 100 TM, about 60 TM to about 95 TM, about 60 TM to about 90 TM, about 60 TM to about 85 TM, about 60 TM to about 80 TM, about 60 TM to about 75 TM, about 60 TM to about 70 TM, about 60 TM to about 65 TM, about 65 TM to about 100 TM, about 65 TM to about 95 TM, about 65 TM to about 90 TM, about 65 TM to about 85 TM, about 65 TM to about 80 TM, about 65 TM to about 75 TM, about 65 TM to about 70 TM, about 70 TM to about 100 TM, about 70 TM to about 95 TM, about 70 TM to about 90 TM, about 70 TM to about 85 TM, about 70 TM to about 80 TM, about 70 TM to about 75 TM, about 75 TM to about 100 TM, about 75 TM to about 95 TM, about 75 TM to about 90 TM, about 75 TM to about 85 TM, about 75 TM to about 80 TM, about 80 TM to about 100 TM, about 80 TM to about 95 TM, about 80 TM to about 90 TM, about 80 TM to about 85 TM, about 85 TM to about 100 TM, about 85 TM to about 95 TM, about 85 TM to about 90 TM, about 90 TM to about 100 TM, about 90 TM to about 95 TM, or about 95 TM to about 100 TM.

In some embodiments, the JAK inhibitor is a pan-JAK inhibitor. As used herein, the term "pan-JAK inhibitor" is an agent that inhibits JAK1, JAK2 and JAK3 activity under the conditions of use by at least about 50%. In some embodiments, a pan-JAK inhibitor can be an agent that has an $IC_{50}$ for wildtype human JAK1, wildtype human JAK2, and wildtype human JAK3 that are less than about ±10-fold of each other when each of the $IC_{50}$ values is assayed under the same or similar assay conditions. In some embodiments, a pan-JAK inhibitor can be an agent that has an $IC_{50}$ for wildtype human JAK1, wildtype human JAK2, and wildtype human JAK3 that are within about 5-fold of each other when each of the $IC_{50}$ values is assayed under the same or similar assay conditions. In some embodiments, a pan-JAK inhibitor can be an agent that has an $IC_{50}$ for wildtype human JAK1, wildtype human JAK2, and wildtype human JAK3 that are within about 2-fold of each other when each of the $IC_{50}$ values is assayed under the same or similar assay conditions. In some embodiments, a pan-JAK inhibitor can be an agent that has an $IC_{50}$ for wildtype human JAK1, wildtype human JAK2, and wildtype human JAK3 that are within t 10% of each other when each of the $IC_{50}$ values is assayed under the same or similar assay conditions (e.g., the human wildtype JAK1, wildtype human JAK2, and wildtype human JAK3 assays described in Kim et al., *J. Med. Chem.* 58(18):7596-5602, 2015).

In some embodiments, the JAK inhibitor is a selective JAK1, JAK3 inhibitor. As used herein, the term "selective JAK1, JAK3 inhibitor" means an agent that has an $IC_{50}$ for wildtype human JAK1 and wildtype human JAK3, that are each greater than about 10-fold lower (e.g., at least about 20-fold lower) than the $IC_{50}$ for wildtype human JAK2 when the $IC_{50}$ is determined for each of wildtype human JAK1, wildtype human JAK2, and wildtype human JAK3 using the same or similar assay conditions (e.g., the human wildtype JAK1, wildtype human JAK2, and wildtype human JAK3 assays described in Kim et al., *J Med. Chem.* 58(18):7596-5602, 2015). In some embodiments, the selective JAK1, JAK3 inhibitor is ZM 39923 (Brown et al., *Bioorg. Med. Chem. Lett.* 10(6):575-579, 2000; and Lai et al., *Chem. Biol.* 15(9):969-978, 2008); or peficitinib (ASP015K; JNJ-54781532; Ito et al., *J. Pharmacol. Sci.* 133(1):25-33, 2017; Cao et al., *Clin. Pharmacol. Drug Dev.* 5(6):435-449, 2016; Takeuchi et al., Ann. Rheum. Dis. 75(6):1057-1064, 2016); and Papp et al., *Br. J. Dermatol.* 173(3):767-776, 2015).

In some embodiments, the JAK inhibitor is a selective JAK1 inhibitor. As used herein, the term "selective JAK1 inhibitor" means an agent that has an $IC_{50}$ for wildtype human JAK1 that is greater than about 10-fold lower (e.g., at least 20-fold lower) than each of the $IC_{50}$ for wildtype human JAK2 and the $IC_{50}$ for wildtype human JAK3 when measured using the same or similar assay conditions (e.g., the human wildtype JAK1, wildtype human JAK2, and wildtype human JAK3 assays described in Kim et al., *J. Med. Chem.* 58(18):7596-5602, 2015). In some embodiments, the JAK1 inhibitor is (31S,4R)-3-ethyl-4-(3H-imidazo[1,2-a]pyrrolo[2,3-e]pyrazin-8-yl)-N-(2,2,2-trifluoroethyl)pyrrolidine-1-carboxamide as disclosed in international patent application PCT/US2014/062145, incorporated by reference herein in its entirety.

In some embodiments, the JAK inhibitor is a selective JAK3 inhibitor. As used herein, the term "selective JAK3 inhibitor" means an agent that has an $IC_{50}$ for wildtype human JAK3 that is greater than about 10-fold lower (e.g., at least about 20-fold lower) than each of the $IC_{50}$ for wildtype human JAK2 and the $IC_{50}$ for wildtype human JAK1 when measured using the same or similar assay conditions (e.g., the human wildtype JAK1, wildtype human JAK2, and wildtype human JAK3 assays described in Kim et al., *J. Med. Chem.* 58(18):7596-5602, 2015).

In some embodiments, a JAK inhibitor is a small molecule (e.g., an organic, an inorganic, or bioinorganic molecule) having a molecule weight of less than about 900 Daltons (e.g., less than about 500 Daltons). In some embodiments, a JAK inhibitor is an inhibitory nucleic acid. In some embodiments, a JAK inhibitor is an anti-JAK antibody.

Inhibitory Nucleic Acids

In some embodiments, a JAK inhibitory agent is an inhibitory nucleic acid. In some embodiments, the inhibitory nucleic acid is an antisense nucleic acid, a ribozyme, a small interfering RNA (siRNA), a small hairpin RNA, or a microRNA. Examples of aspects of these different inhibitory nucleic acids are described below. Any of the examples of inhibitory nucleic acids that can decrease expression of a JAK1, JAK2, JAK3, or TYK2 mRNA in a mammalian cell can be synthesized in vitro.

Inhibitory nucleic acids that can decrease the expression of JAK1, JAK2, JAK3, or TYK2 mRNA expression in a mammalian cell include antisense nucleic acid molecules, i.e., nucleic acid molecules whose nucleotide sequence is complementary to all or part of a JAK1, JAK2, JAK3, or TYK2 mRNA (e.g., complementary to all or a part of any one of SEQ ID NOs: 1-15).

```
Human JAK1 mRNA Variant 1
                                                        (SEQ ID NO: 1)
  1 ggggcgggac gggaggcggt gcgtcgctga gcgcaggccg cggcggccgc ggagtatcct

 61 ggagctgcag acagtgcggg cctgcgccca gtcccggctg tcctcgccgc gacccctcct

121 cagccctggg cgcgcgcacg ctggggcccc gcggggctgg ccgcctagcg agcctgccgg

181 tcgaccccag ccagcgcagc gacggggcgc tgcctggccc aggcgcacac ggaagtgcgc

241 ttctctgaag tagctttgga aagtagagaa gaaaatccag tttgcttctt ggagaacact

301 ggacagctga ataaatgcag tatctaaata taaaagagga ctgcaatgcc atggctttct

361 gtgctaaaat gaggagctcc aagaagactg aggtgaacct ggaggcccct gagccagggg

421 tggaagtgat cttctatctg tcggacaggg agcccctccg gctgggcagt ggagagtaca

481 cagcagagga actgtgcatc agggctgcac aggcatgccg tatctctcct ctttgtcaca

541 acctctttgc cctgtatgac gagaacacca agctctggta tgctccaaat cgcaccatca

601 ccgttgatga caagatgtcc ctccggctcc actaccggat gaggttctat ttcaccaatt

661 ggcatggaac caacgacaat gagcagtcag tgtggcgtca ttctccaaag aagcagaaaa

721 atggctacga gaaaaaaaag attccagatg caacccctct ccttgatgcc agctcactgg

781 agtatctgtt tgctcaggga cagtatgatt tggtgaaatg cctggctcct attcgagacc
```

-continued

```
 841 ccaagaccga gcaggatgga catgatattg agaacgagtg tctagggatg gctgtcctgg
 901 ccatctcaca ctatgccatg atgaagaaga tgcagttgcc agaactgccc aaggacatca
 961 gctacaagcg atatattcca gaaacattga ataagtccat cagacagagg aaccttctca
1021 ccaggatgcg gataaataat gttttcaagg atttcctaaa ggaatttaac aacaagacca
1081 tttgtgacag cagcgtgtcc acgcatgacc tgaaggtgaa atacttggct accttggaaa
1141 ctttgacaaa acattacggt gctgaaatat ttgagacttc catgttactg atttcatcag
1201 aaaatgagat gaattggttt cattcgaatg acggtggaaa cgttctctac tacgaagtga
1261 tggtgactgg gaatcttgga atccagtgga ggcataaacc aaatgttgtt tctgttgaaa
1321 aggaaaaaaa taaactgaag cggaaaaaac tggaaaataa acacaagaag gatgaggaga
1381 aaaacaagat ccgggaagag tggaacaatt tttcttactt ccctgaaatc actcacattg
1441 taataaagga gtctgtggtc agcattaaca agcaggacaa caagaaaatg gaactgaagc
1501 tctcttccca cgaggaggcc ttgtcctttg tgtccctggt agatggctac ttccggctca
1561 cagcagatgc ccatcattac ctctgcaccg acgtggcccc cccgttgatc gtccacaaca
1621 tacagaatgg ctgtcatggt ccaatctgta cagaatacgc catcaataaa ttgcggcaag
1681 aaggaagcga ggaggggatg tacgtgctga ggtggagctg caccgacttt gacaacatcc
1741 tcatgaccgt cacctgcttt gagaagtctg agcaggtgca gggtgcccag aagcagttca
1801 agaactttca gatcgaggtg cagaagggcc gctacagtct gcacggttcg gaccgcagct
1861 tccccagctt gggagacctc atgagccacc tcaagaagca gatcctgcgc acggataaca
1921 tcagcttcat gctaaaacgc tgctgccagc ccaagccccg agaaatctcc aacctgctgg
1981 tggctactaa gaaagcccag gagtggcagc ccgtctaccc catgagccag ctgagtttcg
2041 atcggatcct caagaaggat ctggtgcagg gcgagcacct tgggagaggc acgagaacac
2101 acatctattc tgggaccctg atggattaca aggatgacga aggaacttct gaagagaaga
2161 agataaaagt gatcctcaaa gtcttagacc ccagccacag ggatatttcc ctggccttct
2221 tcgaggcagc cagcatgatg agacaggtct cccacaaaca catcgtgtac ctctatggcg
2281 tctgtgtccg cgacgtggag aatatcatgg tggaagagtt tgtggaaggg ggtcctctgg
2341 atctcttcat gcaccggaaa agcgatgtcc ttaccacacc atggaaattc aaagttgcca
2401 aacagctggc cagtgccctg agctacttgg aggataaaga cctggtccat ggaaatgtgt
2461 gtactaaaaa cctcctcctg gcccgtgagg gcatcgacag tgagtgtggc ccattcatca
2521 agctcagtga ccccggcatc cccattacgg tgctgtctag gcaagaatgc attgaacgaa
2581 tcccatggat tgctcctgag tgtgttgagg actccaagaa cctgagtgtg gctgctgaca
2641 agtggagctt tggaaccacg ctctgggaaa tctgctacaa tggcgagatc cccttgaaag
2701 acaagacgct gattgagaaa gagagattct atgaaagccg gtgcaggcca gtgacaccat
2761 catgtaagga gctggctgac ctcatgaccc gctgcatgaa ctatgacccc aatcagaggc
2821 ctttcttccg agccatcatg agagacatta ataagcttga agagcagaat ccagatattg
2881 tttcagaaaa aaaaccagca actgaagtgg accccacaca ttttgaaaag cgcttcctaa
2941 agaggatccg tgacttggga gagggccact ttgggaaggt tgagctctgc aggtatgacc
3001 ccgaagggga caatacaggg gagcaggtgg ctgttaaatc tctgaagcct gagagtggag
3061 gtaaccacat agctgatctg aaaaaggaaa tcgagatctt aaggaacctc tatcatgaga
3121 acattgtgaa gtacaaagga atctgcacag aagacggagg aaatggtatt aagctcatca
3181 tggaatttct gccttcggga agccttaagg aatatcttcc aaagaataag aacaaaataa
```

-continued 3241 acctcaaaca gcagctaaaa tatgccgttc agatttgtaa ggggatggac tatttgggtt 3301 ctcggcaata cgttcaccgg gacttggcag caagaaatgt ccttgttgag agtgaacacc 3361 aagtgaaaat tggagacttc ggtttaacca aagcaattga aaccgataag gagtattaca 3421 ccgtcaagga tgaccgggac agccctgtgt tttggtatgc tccagaatgt ttaatgcaat 3481 ctaaatttta tattgcctct gacgtctggt cttttggagt cactctgcat gagctgctga 3541 cttactgtga ttcagattct agtcccatgg ctttgttcct gaaaatgata ggcccaaccc 3601 atggccagat gacagtcaca agacttgtga atacgttaaa agaaggaaaa cgcctgccgt 3661 gcccacctaa ctgtccagat gaggtttatc aacttatgag gaaatgctgg gaattccaac 3721 catccaatcg gacaagcttt cagaacctta ttgaaggatt tgaagcactt ttaaaataag 3781 aagcatgaat aacatttaaa ttccacagat tatcaagtcc ttctcctgca acaaatgccc 3841 aagtcatttt ttaaaaattt ctaatgaaag aagtttgtgt tctgtccaaa aagtcactga 3901 actcatactt cagtacatat acatgtataa ggcacactgt agtgcttaat atgtgtaagg 3961 acttcctctt taaatttggt accagtaact tagtgacaca taatgacaac caaaatattt 4021 gaaagcactt aagcactcct ccttgtggaa agaatatacc accatttcat ctggctagtt 4081 caccatcaca actgcattac caaaagggga tttttgaaaa cgaggagttg accaaaataa 4141 tatctgaaga tgattgcttt tccctgctgc cagctgatct gaaatgtttt gctggcacat 4201 taatcataga taaagaaaga ttgatggact tagccctcaa atttcagtat ctatacagta 4261 ctagaccatg cattcttaaa atattagata ccaggtagta tatattgttt ctgtacaaaa 4321 atgactgtat tctctcacca gtaggactta aactttgttt ctccagtggc ttagctcctg 4381 ttcctttggg tgatcactag cacccatttt tgagaaagct ggttctacat gggggggatag 4441 ctgtggaata gataatttgc tgcatgttaa ttctcaagaa ctaagcctgt gccagtgctt 4501 tcctaagcag tataccttta atcagaactc attcccagaa cctggatgct attacacatg 4561 cttttaagaa acgtcaatgt atatcctttt ataactctac cactttgggg caagctattc 4621 cagcactggt tttgaatgct gtatgcaacc agtctgaata ccacatacgc tgcactgttc 4681 ttagagggtt tccatactta ccaccgatct acaagggttg atccctgttt ttaccatcaa 4741 tcatcaccct gtggtgcaac acttgaaaga cccggctaga ggcactatgg acttcaggat 4801 ccactagaca gttttcagtt tgcttggagg tagctgggta atcaaaaatg tttagtcatt 4861 gattcaatgt gaacgattac ggtctttatg accaagagtc tgaaaatctt tttgttatgc 4921 tgtttagtat tcgtttgata ttgttacttt tcacctgttg agcccaaatt caggattggt 4981 tcagtggcag caatgaagtt gccatttaaa tttgttcata gcctacatca ccaaggtctc 5041 tgtgtcaaac ctgtggccac tctatatgca ctttgtttac tctttataca aataaatata 5101 ctaaagactt tacatgca Human JAK1 mRNA Variant 2

(SEQ ID NO: 2)

1 agaagcggag cgtatacgga ggaggcggga tgcatttctg catcgagcgc acaaagttat 61 ctaaaacagt tcatgctgct gaaaacctcc ttcctggcag atgtccctca accctactgg 121 tgcctggctt ctgagacaca cgcttctctg aagtagcttt ggaaagtaga gaagaaaatc 181 cagtttgctt cttggagaac actggacagc tgaataaatg cagtatctaa atataaaaga 241 ggactgcaat gccatggctt tctgtgctaa aatgaggagc tccaagaaga ctgaggtgaa 301 cctggaggcc cctgagccag gggtggaagt gatcttctat ctgtcggaca gggagcccct 361 ccggctgggc agtggagagt acacagcaga ggaactgtgc atcagggctg cacaggcatg 421 ccgtatctct cctctttgtc acaacctctt tgccctgtat gacgagaaca ccaagctctg -continued

```
481 gtatgctcca aatcgcacca tcaccgttga tgacaagatg tccctccggc tccactaccg
541 gatgaggttc tatttcacca attggcatgg aaccaacgac aatgagcagt cagtgtggcg
601 tcattctcca aagaagcaga aaaatggcta cgagaaaaaa aagattccag atgcaacccc
661 tctccttgat gccagctcac tggagtatct gtttgctcag ggacagtatg atttggtgaa
721 atgcctggct cctattcgag accccaagac cgagcaggat ggacatgata ttgagaacga
781 gtgtctaggg atggctgtcc tggccatctc acactatgcc atgatgaaga agatgcagtt
841 gccagaactg cccaaggaca tcagctacaa gcgatatatt ccagaaacat tgaataagtc
901 catcagacag aggaaccttc tcaccaggat gcggataaat aatgttttca aggatttcct
961 aaaggaattt aacaacaaga ccatttgtga cagcagcgtg tccacgcatg acctgaaggt
1021 gaaatacttg gctaccttgg aaactttgac aaaacattac ggtgctgaaa tatttgagac
1081 ttccatgtta ctgatttcat cagaaaatga gatgaattgg tttcattcga atgacggtgg
1141 aaacgttctc tactacgaag tgatggtgac tgggaatctt ggaatccagt ggaggcataa
1201 accaaatgtt gtttctgttg aaaaggaaaa aaataaactg aagcggaaaa aactggaaaa
1261 taaacacaag aaggatgagg agaaaaacaa gatccgggaa gagtggaaca atttttctta
1321 cttccctgaa atcactcaca ttgtaataaa ggagtctgtg gtcagcatta acaagcagga
1381 caacaagaaa atggaactga agctctcttc ccacgaggag gccttgtcct ttgtgtccct
1441 ggtagatggc tacttccggc tcacagcaga tgcccatcat tacctctgca ccgacgtggc
1501 ccccccgttg atcgtccaca acatacagaa tggctgtcat ggtccaatct gtacagaata
1561 cgccatcaat aaattgcggc aagaaggaag cgaggagggg atgtacgtgc tgaggtggag
1621 ctgcaccgac tttgacaaca tcctcatgac cgtcacctgc tttgagaagt ctgagcaggt
1681 gcagggtgcc cagaagcagt tcaagaactt tcagatcgag gtgcagaagg gccgctacag
1741 tctgcacggt tcggaccgca gcttccccag cttgggagac ctcatgagcc acctcaagaa
1801 gcagatcctg cgcacggata acatcagctt catgctaaaa cgctgctgcc agcccaagcc
1861 ccgagaaatc tccaacctgc tggtggctac taagaaagcc caggagtggc agcccgtcta
1921 ccccatgagc cagctgagtt tcgatcggat cctcaagaag gatctggtgc agggcgagca
1981 ccttgggaga ggcacgagaa cacacatcta ttctgggacc ctgatggatt acaaggatga
2041 cgaaggaact tctgaagaga agaagataaa agtgatcctc aaagtcttag accccagcca
2101 cagggatatt tccctggcct tcttcgaggc agccagcatg atgagacagg tctcccacaa
2161 acacatcgtg tacctctatg gcgtctgtgt ccgcgacgtg gagaatatca tggtggaaga
2221 gtttgtggaa gggggtcctc tggatctctt catgcaccgg aaaagcgatg tccttaccac
2281 accatggaaa ttcaaagttg ccaaacagct ggccagtgcc ctgagctact tggaggataa
2341 agacctggtc catggaaatg tgtgtactaa aaacctcctc ctggcccgtg agggcatcga
2401 cagtgagtgt ggcccattca tcaagctcag tgaccccggc atccccatta cggtgctgtc
2461 taggcaagaa tgcattgaac gaatcccatg gattgctcct gagtgtgttg aggactccaa
2521 gaacctgagt gtggctgctg acaagtggag ctttggaacc acgctctggg aaatctgcta
2581 caatggcgag atccccttga aagacaagac gctgattgag aaagagagat tctatgaaag
2641 ccggtgcagg ccagtgacac catcatgtaa ggagctggct gacctcatga cccgctgcat
2701 gaactatgac cccaatcaga ggcctttctt ccgagccatc atgagagaca ttaataagct
2761 tgaagagcag aatccagata ttgtttcaga aaaaaaacca gcaactgaag tggaccccac
2821 acattttgaa aagcgcttcc taaagaggat ccgtgacttg ggagagggcc actttgggaa
```

-continued

```
2881 ggttgagctc tgcaggtatg accccgaagg ggacaataca ggggagcagg tggctgttaa
2941 atctctgaag cctgagagtg gaggtaacca catagctgat ctgaaaaagg aaatcgagat
3001 cttaaggaac ctctatcatg agaacattgt gaagtacaaa ggaatctgca cagaagacgg
3061 aggaaatggt attaagctca tcatggaatt tctgccttcg ggaagcctta aggaatatct
3121 tccaaagaat aagaacaaaa taaacctcaa acagcagcta aaatatgccg ttcagatttg
3181 taaggggatg gactatttgg gttctcggca atacgttcac cgggacttgg cagcaagaaa
3241 tgtccttgtt gagagtgaac accaagtgaa aattggagac ttcggtttaa ccaaagcaat
3301 tgaaaccgat aaggagtatt acaccgtcaa ggatgaccgg gacagccctg tgttttggta
3361 tgctccagaa tgtttaatgc aatctaaatt ttatattgcc tctgacgtct ggtcttttgg
3421 agtcactctg catgagctgc tgacttactg tgattcagat tctagtccca tggctttgtt
3481 cctgaaaatg ataggcccaa cccatggcca gatgacagtc acaagacttg tgaatacgtt
3541 aaaagaagga aaacgcctgc cgtgcccacc taactgtcca gatgaggttt atcaacttat
3601 gaggaaatgc tgggaattcc aaccatccaa tcggacaagc tttcagaacc ttattgaagg
3661 atttgaagca cttttaaaat aagaagcatg aataacattt aaattccaca gattatcaag
3721 tccttctcct gcaacaaatg cccaagtcat tttttaaaaa tttctaatga aagaagtttg
3781 tgttctgtcc aaaaagtcac tgaactcata cttcagtaca tatacatgta taaggcacac
3841 tgtagtgctt aatatgtgta aggacttcct ctttaaattt ggtaccagta acttagtgac
3901 acataatgac aaccaaaata tttgaaagca cttaagcact cctccttgtg gaaagaatat
3961 accaccattt catctggcta gttcaccatc acaactgcat taccaaaagg ggatttttga
4021 aaacgaggag ttgaccaaaa taatatctga agatgattgc ttttccctgc tgccagctga
4081 tctgaaatgt tttgctggca cattaatcat agataaagaa agattgatgg acttagccct
4141 caaatttcag tatctataca gtactagacc atgcattctt aaaatattag ataccaggta
4201 gtatatattg tttctgtaca aaaatgactg tattctctca ccagtaggac ttaaactttg
4261 tttctccagt ggcttagctc ctgttccttt gggtgatcac tagcacccat ttttgagaaa
4321 gctggttcta catgggggga tagctgtgga atagataatt tgctgcatgt taattctcaa
4381 gaactaagcc tgtgccagtg ctttcctaag cagtatacct ttaatcagaa ctcattccca
4441 gaacctggat gctattacac atgcttttaa gaaacgtcaa tgtatatcct tttataactc
4501 taccactttg gggcaagcta ttccagcact ggttttgaat gctgtatgca accagtctga
4561 ataccacata cgctgcactg ttcttagagg gtttccatac ttaccaccga tctacaaggg
4621 ttgatccctg tttttaccat caatcatcac cctgtggtgc aacacttgaa agacccggct
4681 agaggcacta tggacttcag gatccactag acagttttca gtttgcttgg aggtagctgg
4741 gtaatcaaaa atgtttagtc attgattcaa tgtgaacgat tacggtcttt atgaccaaga
4801 gtctgaaaat ctttttgtta tgctgtttag tattcgtttg atattgttac ttttcacctg
4861 ttgagcccaa attcaggatt ggttcagtgg cagcaatgaa gttgccattt aaatttgttc
4921 atagcctaca tcaccaaggt ctctgtgtca aacctgtggc cactctatat gcactttgtt
4981 tactctttat acaaataaat atactaaaga ctttacatgc a
```

Human JAK1 mRNA Variant 3

(SEQ ID NO: 3)

```
  1 atctatcaca tggcagagat agaataaaaa cagaaaaatg gcgacggtca cgttgtggcg
 61 agccttgctg cgtcattaga taatcctcat gcaaatagcg ggaagaacaa aggaagggga
121 gcccgggacc cccgggggcg cagcgcttct ctgaagtagc tttggaaagt agagaagaaa
181 atccagtttg cttcttggag aacactggac agctgaataa atgcagtatc taaatataaa
```

-continued

```
 241 agaggactgc aatgccatgg ctttctgtgc taaaatgagg agctccaaga agactgaggt
 301 gaacctggag gcccctgagc caggggtgga agtgatcttc tatctgtcgg acagggagcc
 361 cctccggctg ggcagtggag agtacacagc agaggaactg tgcatcaggg ctgcacaggc
 421 atgccgtatc tctcctcttt gtcacaacct ctttgccctg tatgacgaga acaccaagct
 481 ctggtatgct ccaaatcgca ccatcaccgt tgatgacaag atgtccctcc ggctccacta
 541 ccggatgagg ttctatttca ccaattggca tggaaccaac gacaatgagc agtcagtgtg
 601 gcgtcattct ccaaagaagc agaaaaatgg ctacgagaaa aaaaagattc cagatgcaac
 661 ccctctcctt gatgccagct cactggagta tctgtttgct cagggacagt atgatttggt
 721 gaaatgcctg gctcctattc gagaccccaa gaccgagcag gatggacatg atattgagaa
 781 cgagtgtcta gggatggctg tcctggccat ctcacactat gccatgatga agaagatgca
 841 gttgccagaa ctgcccaagg acatcagcta caagcgatat attccagaaa cattgaataa
 901 gtccatcaga cagaggaacc ttctcaccag gatgcggata aataatgttt tcaaggattt
 961 cctaaaggaa tttaacaaca agaccatttg tgacagcagc gtgtccacgc atgacctgaa
1021 ggtgaaatac ttggctacct tggaaacttt gacaaaacat tacggtgctg aaatatttga
1081 gacttccatg ttactgattt catcagaaaa tgagatgaat tggtttcatt cgaatgacgg
1141 tggaaacgtt ctctactacg aagtgatggt gactgggaat cttggaatcc agtggaggca
1201 taaaccaaat gttgtttctg ttgaaaagga aaaaaataaa ctgaagcgga aaaaactgga
1261 aaataaacac aagaaggatg aggagaaaaa caagatccgg gaagagtgga acaatttttc
1321 ttacttccct gaaatcactc acattgtaat aaaggagtct gtggtcagca ttaacaagca
1381 ggacaacaag aaaatggaac tgaagctctc ttcccacgag gaggccttgt cctttgtgtc
1441 cctggtagat ggctacttcc ggctcacagc agatgcccat cattacctct gcaccgacgt
1501 ggcccccccg ttgatcgtcc acaacataca gaatggctgt catggtccaa tctgtacaga
1561 atacgccatc aataaattgc ggcaagaagg aagcgaggag gggatgtacg tgctgaggtg
1621 gagctgcacc gactttgaca acatcctcat gaccgtcacc tgctttgaga agtctgagca
1681 ggtgcagggt gcccagaagc agttcaagaa ctttcagatc gaggtgcaga agggccgcta
1741 cagtctgcac ggttcggacc gcagcttccc cagcttggga gacctcatga gccacctcaa
1801 gaagcagatc ctgcgcacgg ataacatcag cttcatgcta aaacgctgct gccagcccaa
1861 gccccgagaa atctccaacc tgctggtggc tactaagaaa gcccaggagt ggcagcccgt
1921 ctaccccatg agccagctga gtttcgatcg gatcctcaag aaggatctgg tgcagggcga
1981 gcaccttggg agaggcacga gaacacacat ctattctggg accctgatgg attacaagga
2041 tgacgaagga acttctgaag agaagaagat aaaagtgatc ctcaaagtct tagaccccag
2101 ccacagggat atttccctgg ccttcttcga ggcagccagc atgatgagac aggtctccca
2161 caaacacatc gtgtacctct atggcgtctg tgtccgcgac gtggagaata tcatggtgga
2221 agagtttgtg gaagggggtc ctctggatct cttcatgcac cggaaaagcg atgtccttac
2281 cacaccatgg aaattcaaag ttgccaaaca gctggccagt gccctgagct acttggagga
2341 taaagacctg gtccatggaa atgtgtgtac taaaaacctc ctcctggccc gtgagggcat
2401 cgacagtgag tgtggcccat tcatcaagct cagtgacccc ggcatcccca ttacggtgct
2461 gtctaggcaa gaatgcattg aacgaatccc atggattgct cctgagtgtg ttgaggactc
2521 caagaacctg agtgtggctg ctgacaagtg gagctttgga accacgctct gggaaatctg
2581 ctacaatggc gagatcccct tgaaagacaa gacgctgatt gagaaagaga gattctatga
```

-continued 2641 aagccggtgc aggccagtga caccatcatg taaggagctg gctgacctca tgacccgctg
2701 catgaactat gaccccaatc agaggccttt cttccgagcc atcatgagag acattaataa
2761 gcttgaagag cagaatccag atattgtttc agaaaaaaaa ccagcaactg aagtggaccc
2821 cacacatttt gaaaagcgct tcctaaagag gatccgtgac ttgggagagg gccactttgg
2881 gaaggttgag ctctgcaggt atgaccccga aggggacaat acaggggagc aggtggctgt
2941 taaatctctg aagcctgaga gtggaggtaa ccacatagct gatctgaaaa aggaaatcga
3001 gatcttaagg aacctctatc atgagaacat tgtgaagtac aaaggaatct gcacagaaga
3061 cggaggaaat ggtattaagc tcatcatgga atttctgcct tcgggaagcc ttaaggaata
3121 tcttccaaag aataagaaca aaataaacct caaacagcag ctaaaatatg ccgttcagat
3181 ttgtaagggg atggactatt tgggttctcg gcaatacgtt caccgggact tggcagcaag
3241 aaatgtcctt gttgagagtg aacaccaagt gaaaattgga gacttcggtt taaccaaagc
3301 aattgaaacc gataaggagt attacaccgt caaggatgac cgggacagcc ctgtgttttg
3361 gtatgctcca gaatgtttaa tgcaatctaa attttatatt gcctctgacg tctggtcttt
3421 tggagtcact ctgcatgagc tgctgactta ctgtgattca gattctagtc ccatggcttt
3481 gttcctgaaa atgataggcc caacccatgg ccagatgaca gtcacaagac ttgtgaatac
3541 gttaaaagaa ggaaaacgcc tgccgtgccc acctaactgt ccagatgagg tttatcaact
3601 tatgaggaaa tgctgggaat tccaaccatc caatcggaca agctttcaga accttattga
3661 aggatttgaa gcacttttaa aataagaagc atgaataaca tttaaattcc acagattatc
3721 aagtccttct cctgcaacaa atgcccaagt catttttttaa aaatttctaa tgaaagaagt
3781 ttgtgttctg tccaaaaagt cactgaactc atacttcagt acatatacat gtataaggca
3841 cactgtagtg cttaatatgt gtaaggactt cctctttaaa tttggtacca gtaacttagt
3901 gacacataat gacaaccaaa atatttgaaa gcacttaagc actcctcctt gtggaaagaa
3961 tataccacca tttcatctgg ctagttcacc atcacaactg cattaccaaa aggggatttt
4021 tgaaaacgag gagttgacca aaataatatc tgaagatgat tgcttttccc tgctgccagc
4081 tgatctgaaa tgttttgctg gcacattaat catagataaa gaaagattga tggacttagc
4141 cctcaaattt cagtatctat acagtactag accatgcatt cttaaaatat tagataccag
4201 gtagtatata ttgtttctgt acaaaaatga ctgtattctc tcaccagtag gacttaaact
4261 ttgtttctcc agtggcttag ctcctgttcc tttgggtgat cactagcacc catttttgag
4321 aaagctggtt ctacatgggg ggatagctgt ggaatagata atttgctgca tgttaattct
4381 caagaactaa gcctgtgcca gtgctttcct aagcagtata cctttaatca gaactcattc
4441 ccagaacctg gatgctatta cacatgcttt taagaaacgt caatgtatat ccttttataa
4501 ctctaccact ttggggcaag ctattccagc actggttttg aatgctgtat gcaaccagtc
4561 tgaataccac atacgctgca ctgttcttag agggtttcca tacttaccac cgatctacaa
4621 gggttgatcc ctgtttttac catcaatcat caccctgtgg tgcaacactt gaaagacccg
4681 gctagaggca ctatggactt caggatccac tagacagttt tcagtttgct tggaggtagc
4741 tgggtaatca aaaatgttta gtcattgatt caatgtgaac gattacggtc tttatgacca
4801 agagtctgaa aatctttttg ttatgctgtt tagtattcgt ttgatattgt tacttttcac
4861 ctgttgagcc caaattcagg attggttcag tggcagcaat gaagttgcca tttaaatttg
4921 ttcatagcct acatcaccaa ggtctctgtg tcaaacctgt ggccactcta tatgcacttt
4981 gtttactctt tatacaaata aatatactaa agactttaca tgca Human JAK1 mRNA Variant 4

-continued (SEQ ID NO: 4)

```
   1 atctatcaca tggcagagat agaataaaaa cagaaaaatg gcgacggtca cgttgtggcg
  61 agccttgctg cgtcattaga taatcctcat gcaaatagcg ggaagaacaa aggaagggga
 121 gcccgggacc cccgggggcg caggatccgg cgggaggagt ctaagaggag gaggcggcgg
 181 tgccggagga ggaggaggag ggagggagaa gagaggaaga ccggagtccc cgcggcggcg
 241 gcggtccgga gagagggcga gccccgcgcg gcgccgggga ccgggcgcta ccacgaggcc
 301 gggacgctgg agtctgggtt atctaaaaca gttcatgctg ctgaaaacct ccttcctggc
 361 agatgtccct caaccctact ggtgcctggc ttctgagaca cacgcttctc tgaagtagct
 421 ttggaaagta gagaagaaaa tccagtttgc ttcttggaga acactggaca gctgaataaa
 481 tgcagtatct aaatataaaa gaggactgca atgccatggc tttctgtgct aaaatgagga
 541 gctccaagaa gactgaggtg aacctggagg cccctgagcc aggggtggaa gtgatcttct
 601 atctgtcgga cagggagccc ctccggctgg gcagtggaga gtacacagca gaggaactgt
 661 gcatcagggc tgcacaggca tgccgtatct ctcctctttg tcacaacctc tttgccctgt
 721 atgacgagaa caccaagctc tggtatgctc caaatcgcac catcaccgtt gatgacaaga
 781 tgtccctccg gctccactac cggatgaggt tctatttcac caattggcat ggaaccaacg
 841 acaatgagca gtcagtgtgg cgtcattctc caaagaagca gaaaaatggc tacgagaaaa
 901 aaaagattcc agatgcaacc cctctccttg atgccagctc actggagtat ctgtttgctc
 961 agggacagta tgatttggtg aaatgcctgg ctcctattcg agaccccaag accgagcagg
1021 atggacatga tattgagaac gagtgtctag ggatggctgt cctggccatc tcacactatg
1081 ccatgatgaa gaagatgcag ttgccagaac tgcccaagga catcagctac aagcgatata
1141 ttccagaaac attgaataag tccatcagac agaggaacct tctcaccagg atgcggataa
1201 ataatgtttt caaggatttc ctaaaggaat ttaacaacaa gaccatttgt gacagcagcg
1261 tgtccacgca tgacctgaag gtgaaatact tggctacctt ggaaactttg acaaaacatt
1321 acggtgctga aatatttgag acttccatgt tactgatttc atcagaaaat gagatgaatt
1381 ggtttcattc gaatgacggt ggaaacgttc tctactacga agtgatggtg actgggaatc
1441 ttggaatcca gtggaggcat aaaccaaatg ttgtttctgt tgaaaaggaa aaaaataaac
1501 tgaagcggaa aaaactggaa aataaacaca agaaggatga ggagaaaaac aagatccggg
1561 aagagtggaa caatttttct tacttccctg aaatcactca cattgtaata aaggagtctg
1621 tggtcagcat taacaagcag gacaacaaga aaatggaact gaagctctct tcccacgagg
1681 aggccttgtc ctttgtgtcc ctggtagatg gctacttccg gctcacagca gatgcccatc
1741 attacctctg caccgacgtg gcccccccgt tgatcgtcca caacatacag aatggctgtc
1801 atggtccaat ctgtacagaa tacgccatca ataaattgcg gcaagaagga agcgaggagg
1861 ggatgtacgt gctgaggtgg agctgcaccg actttgacaa catcctcatg accgtcacct
1921 gctttgagaa gtctgagcag gtgcagggtg cccagaagca gttcaagaac tttcagatcg
1981 aggtgcagaa gggccgctac agtctgcacg gttcggaccg cagcttcccc agcttgggag
2041 acctcatgag ccacctcaag aagcagatcc tgcgcacgga taacatcagc ttcatgctaa
2101 aacgctgctg ccagcccaag ccccgagaaa tctccaacct gctggtggct actaagaaag
2161 cccaggagtg gcagcccgtc taccccatga gccagctgag tttcgatcgg atcctcaaga
2221 aggatctggt gcagggcgag caccttggga gaggcacgag aacacacatc tattctggga
2281 ccctgatgga ttacaaggat gacgaaggaa cttctgaaga gaagaagata aaagtgatcc
2341 tcaaagtctt agaccccagc cacagggata tttccctggc cttcttcgag gcagccagca
```

-continued 2401 tgatgagaca ggtctcccac aaacacatcg tgtacctcta tggcgtctgt gtccgcgacg 2461 tggagaatat catggtggaa gagtttgtgg aagggggtcc tctggatctc ttcatgcacc 2521 ggaaaagcga tgtccttacc acaccatgga aattcaaagt tgccaaacag ctggccagtg 2581 ccctgagcta cttggaggat aaagacctgg tccatggaaa tgtgtgtact aaaaacctcc 2641 tcctggcccg tgagggcatc gacagtgagt gtggcccatt catcaagctc agtgaccccg 2701 gcatccccat tacggtgctg tctaggcaag aatgcattga acgaatccca tggattgctc 2761 ctgagtgtgt tgaggactcc aagaacctga gtgtggctgc tgacaagtgg agctttggaa 2821 ccacgctctg ggaaatctgc tacaatggcg agatcccctt gaaagacaag acgctgattg 2881 agaaagagag attctatgaa agccggtgca ggccagtgac accatcatgt aaggagctgg 2941 ctgacctcat gacccgctgc atgaactatg accccaatca gaggcctttc ttccgagcca 3001 tcatgagaga cattaataag cttgaagagc agaatccaga tattgtttca gaaaaaaaac 3061 cagcaactga agtggacccc acacattttg aaaagcgctt cctaaagagg atccgtgact 3121 tgggagaggg ccactttggg aaggttgagc tctgcaggta tgaccccgaa ggggacaata 3181 caggggagca ggtggctgtt aaatctctga agcctgagag tggaggtaac cacatagctg 3241 atctgaaaaa ggaaatcgag atcttaagga acctctatca tgagaacatt gtgaagtaca 3301 aaggaatctg cacagaagac ggaggaaatg gtattaagct catcatggaa tttctgcctt 3361 cgggaagcct taaggaatat cttccaaaga ataagaacaa aataaacctc aaacagcagc 3421 taaaatatgc cgttcagatt tgtaagggga tggactattt gggttctcgg caatacgttc 3481 accgggactt ggcagcaaga aatgtccttg ttgagagtga acaccaagtg aaaattggag 3541 acttcggttt aaccaaagca attgaaaccg ataaggagta ttacaccgtc aaggatgacc 3601 gggacagccc tgtgttttgg tatgctccag aatgtttaat gcaatctaaa ttttatattg 3661 cctctgacgt ctggtctttt ggagtcactc tgcatgagct gctgacttac tgtgattcag 3721 attctagtcc catggctttg ttcctgaaaa tgataggccc aacccatggc cagatgacag 3781 tcacaagact tgtgaatacg ttaaaagaag gaaaacgcct gccgtgccca cctaactgtc 3841 cagatgaggt ttatcaactt atgaggaaat gctgggaatt ccaaccatcc aatcggacaa 3901 gctttcagaa ccttattgaa ggatttgaag cacttttaaa ataagaagca tgaataacat 3961 ttaaattcca cagattatca agtccttctc ctgcaacaaa tgcccaagtc atttttttaaa 4021 aatttctaat gaaagaagtt tgtgttctgt ccaaaaagtc actgaactca tacttcagta 4081 catatacatg tataaggcac actgtagtgc ttaatatgtg taaggacttc ctctttaaat 4141 ttggtaccag taacttagtg acacataatg acaaccaaaa tatttgaaag cacttaagca 4201 ctcctccttg tggaaagaat ataccaccat ttcatctggc tagttcacca tcacaactgc 4261 attaccaaaa ggggattttt gaaaacgagg agttgaccaa aataatatct gaagatgatt 4321 gcttttccct gctgccagct gatctgaaat gttttgctgg cacattaatc atagataaag 4381 aaagattgat ggacttagcc ctcaaatttc agtatctata cagtactaga ccatgcattc 4441 ttaaaatatt agataccagg tagtatatat tgtttctgta caaaaatgac tgtattctct 4501 caccagtagg acttaaactt tgtttctcca gtggcttagc tcctgttcct ttgggtgatc 4561 actagcaccc atttttgaga aagctggttc tacatggggg gatagctgtg gaatagataa 4621 tttgctgcat gttaattctc aagaactaag cctgtgccag tgctttccta agcagtatac 4681 ctttaatcag aactcattcc cagaacctgg atgctattac acatgctttt aagaaacgtc 4741 aatgtatatc cttttataac tctaccactt tggggcaagc tattccagca ctggttttga 4801 atgctgtatg caaccagtct gaataccaca tacgctgcac tgttcttaga gggtttccat -continued 4861 acttaccacc gatctacaag ggttgatccc tgtttttacc atcaatcatc accctgtggt 4921 gcaacacttg aaagacccgg ctagaggcac tatggacttc aggatccact agacagtttt 4981 cagtttgctt ggaggtagct gggtaatcaa aaatgtttag tcattgattc aatgtgaacg 5041 attacggtct ttatgaccaa gagtctgaaa atctttttgt tatgctgttt agtattcgtt 5101 tgatattgtt acttttcacc tgttgagccc aaattcagga ttggttcagt ggcagcaatg 5161 aagttgccat ttaaatttgt tcatagccta catcaccaag gtctctgtgt caaacctgtg 5221 gccactctat atgcactttg tttactcttt atacaaataa atatactaaa gactttacat 5281 gca Human JAK1 mRNA Variant 5

(SEQ ID NO: 5)

1 atctatcaca tggcagagat agaataaaaa cagaaaaatg gcgacggtca cgttgtggcg 61 agccttgctg cgtcattaga taatcctcat gcaaatagcg ggaagaacaa aggaagggga 121 gcccgggacc cccgggggcg caggatccgg cgggaggagt ctaagaggag gaggcggcgg 181 tgccggagga ggaggaggag ggagggagaa gagaggaaga ccggagtccc cgcggcggcg 241 gcggtccgga gagagggcga gccccgcgcg gcgccgggga ccgggcgcta ccacgaggcc 301 gggacgctgg agtctgggcg cttctctgaa gtagctttgg aaagtagaga agaaaatcca 361 gtttgcttct tggagaacac tggacagctg aataaatgca gtatctaaat ataaaagagg 421 actgcaatgc catggctttc tgtgctaaaa tgaggagctc caagaagact gaggtgaacc 481 tggaggcccc tgagccaggg gtggaagtga tcttctatct gtcggacagg gagcccctcc 541 ggctgggcag tggagagtac acagcagagg aactgtgcat cagggctgca caggcatgcc 601 gtatctctcc tctttgtcac aacctctttg ccctgtatga cgagaacacc aagctctggt 661 atgctccaaa tcgcaccatc accgttgatg acaagatgtc cctccggctc cactaccgga 721 tgaggttcta tttcaccaat tggcatggaa ccaacgacaa tgagcagtca gtgtggcgtc 781 attctccaaa gaagcagaaa aatggctacg agaaaaaaaa gattccagat gcaacccctc 841 tccttgatgc cagctcactg gagtatctgt ttgctcaggg acagtatgat ttggtgaaat 901 gcctggctcc tattcgagac cccaagaccg agcaggatgg acatgatatt gagaacgagt 961 gtctagggat ggctgtcctg gccatctcac actatgccat gatgaagaag atgcagttgc 1021 cagaactgcc caaggacatc agctacaagc gatatattcc agaaacattg aataagtcca 1081 tcagacagag gaaccttctc accaggatgc ggataaataa tgttttcaag gatttcctaa 1141 aggaatttaa caacaagacc atttgtgaca gcagcgtgtc cacgcatgac ctgaaggtga 1201 aatacttggc taccttggaa actttgacaa aacattacgg tgctgaaata tttgagactt 1261 ccatgttact gatttcatca gaaaatgaga tgaattggtt tcattcgaat gacggtggaa 1321 acgttctcta ctacgaagtg atggtgactg ggaatcttgg aatccagtgg aggcataaac 1381 caaatgttgt ttctgttgaa aaggaaaaaa ataaactgaa gcggaaaaaa ctggaaaata 1441 aacacaagaa ggatgaggag aaaaacaaga tccgggaaga gtggaacaat ttttcttact 1501 tccctgaaat cactcacatt gtaataaagg agtctgtggt cagcattaac aagcaggaca 1561 acaagaaaat ggaactgaag ctctcttccc acgaggaggc cttgtccttt gtgtccctgg 1621 tagatggcta cttccggctc acagcagatg cccatcatta cctctgcacc gacgtggccc 1681 ccccgttgat cgtccacaac atacagaatg gctgtcatgg tccaatctgt acagaatacg 1741 ccatcaataa attgcggcaa gaaggaagcg aggaggggat gtacgtgctg aggtggagct 1801 gcaccgactt tgacaacatc ctcatgaccg tcacctgctt tgagaagtct gagcaggtgc -continued 1861 agggtgccca gaagcagttc aagaactttc agatcgaggt gcagaagggc cgctacagtc 1921 tgcacggttc ggaccgcagc ttccccagct tgggagacct catgagccac ctcaagaagc 1981 agatcctgcg cacggataac atcagcttca tgctaaaacg ctgctgccag cccaagcccc 2041 gagaaatctc caacctgctg gtggctacta agaaagccca ggagtggcag cccgtctacc 2101 ccatgagcca gctgagtttc gatcggatcc tcaagaagga tctggtgcag ggcgagcacc 2161 ttgggagagg cacgagaaca cacatctatt ctgggaccct gatggattac aaggatgacg 2221 aaggaacttc tgaagagaag aagataaaag tgatcctcaa agtcttagac cccagccaca 2281 gggatatttc cctggccttc ttcgaggcag ccagcatgat gagacaggtc tcccacaaac 2341 acatcgtgta cctctatggc gtctgtgtcc gcgacgtgga gaatatcatg gtggaagagt 2401 ttgtggaagg gggtcctctg gatctcttca tgcaccggaa aagcgatgtc cttaccacac 2461 catggaaatt caaagttgcc aaacagctgg ccagtgccct gagctacttg gaggataaag 2521 acctggtcca tggaaatgtg tgtactaaaa acctcctcct ggcccgtgag ggcatcgaca 2581 gtgagtgtgg cccattcatc aagctcagtg accccggcat ccccattacg gtgctgtcta 2641 ggcaagaatg cattgaacga atcccatgga ttgctcctga gtgtgttgag gactccaaga 2701 acctgagtgt ggctgctgac aagtggagct ttggaaccac gctctgggaa atctgctaca 2761 atggcgagat ccccttgaaa gacaagacgc tgattgagaa agagagattc tatgaaagcc 2821 ggtgcaggcc agtgacacca tcatgtaagg agctggctga cctcatgacc cgctgcatga 2881 actatgaccc caatcagagg cctttcttcc gagccatcat gagagacatt aataagcttg 2941 aagagcagaa tccagatatt gtttcagaaa aaaaaccagc aactgaagtg gaccccacac 3001 attttgaaaa gcgcttccta aagaggatcc gtgacttggg agagggccac tttgggaagg 3061 ttgagctctg caggtatgac cccgaagggg acaatacagg ggagcaggtg gctgttaaat 3121 ctctgaagcc tgagagtgga ggtaaccaca tagctgatct gaaaaaggaa atcgagatct 3181 taaggaacct ctatcatgag aacattgtga agtacaaagg aatctgcaca gaagacggag 3241 gaaatggtat taagctcatc atggaatttc tgccttcggg aagccttaag gaatatcttc 3301 caaagaataa gaacaaaata aacctcaaac agcagctaaa atatgccgtt cagatttgta 3361 aggggatgga ctatttgggt tctcggcaat acgttcaccg ggacttggca gcaagaaatg 3421 tccttgttga gagtgaacac caagtgaaaa ttggagactt cggtttaacc aaagcaattg 3481 aaaccgataa ggagtattac accgtcaagg atgaccggga cagccctgtg ttttggtatg 3541 ctccagaatg tttaatgcaa tctaaatttt atattgcctc tgacgtctgg tcttttggag 3601 tcactctgca tgagctgctg acttactgtg attcagattc tagtcccatg gctttgttcc 3661 tgaaaatgat aggcccaacc catggccaga tgacagtcac aagacttgtg aatacgttaa 3721 aagaaggaaa acgcctgccg tgcccaccta actgtccaga tgaggtttat caacttatga 3781 ggaaatgctg ggaattccaa ccatccaatc ggacaagctt tcagaacctt attgaaggat 3841 ttgaagcact tttaaaataa gaagcatgaa taacatttaa attccacaga ttatcaagtc 3901 cttctcctgc aacaaatgcc caagtcattt tttaaaaatt tctaatgaaa gaagtttgtg 3961 ttctgtccaa aaagtcactg aactcatact tcagtacata tacatgtata aggcacactg 4021 tagtgcttaa tatgtgtaag gacttcctct ttaaatttgg taccagtaac ttagtgacac 4081 ataatgacaa ccaaaatatt tgaaagcact taagcactcc tccttgtgga aagaatatac 4141 caccatttca tctggctagt tcaccatcac aactgcatta ccaaaagggg atttttgaaa 4201 acgaggagtt gaccaaaata atatctgaag atgattgctt ttccctgctg ccagctgatc 4261 tgaaatgttt tgctggcaca ttaatcatag ataaagaaag attgatggac ttagccctca -continued 4321 aatttcagta tctatacagt actagaccat gcattcttaa aatattagat accaggtagt 4381 atatattgtt tctgtacaaa aatgactgta ttctctcacc agtaggactt aaactttgtt 4441 tctccagtgg cttagctcct gttcctttgg gtgatcacta gcacccattt ttgagaaagc 4501 tggttctaca tggggggata gctgtggaat agataatttg ctgcatgtta attctcaaga 4561 actaagcctg tgccagtgct ttcctaagca gtataccttt aatcagaact cattcccaga 4621 acctggatgc tattacacat gcttttaaga aacgtcaatg tatatccttt tataactcta 4681 ccactttggg gcaagctatt ccagcactgg ttttgaatgc tgtatgcaac cagtctgaat 4741 accacatacg ctgcactgtt cttagagggt ttccatactt accaccgatc tacaagggtt 4801 gatccctgtt tttaccatca atcatcaccc tgtggtgcaa cacttgaaag acccggctag 4861 aggcactatg gacttcagga tccactagac agttttcagt ttgcttggag gtagctgggt 4921 aatcaaaaat gtttagtcat tgattcaatg tgaacgatta cggtctttat gaccaagagt 4981 ctgaaaatct ttttgttatg ctgtttagta ttcgtttgat attgttactt ttcacctgtt 5041 gagcccaaat tcaggattgg ttcagtggca gcaatgaagt tgccatttaa atttgttcat 5101 agcctacatc accaaggtct ctgtgtcaaa cctgtggcca ctctatatgc actttgttta 5161 ctctttatac aaataaatat actaaagact ttacatgca Huma JAK1 mRNA Variant 6

(SEQ ID NO: 6)

1 ggggcgggac gggaggcggt gcgtcgctga gcgcaggccg cggcggccgc ggagtatcct 61 ggagctgcag acagtgcggg cctgcgccca gtcccggctg tcctcgccgc gacccctcct 121 cagccctggg cgcgcgcacg ctggggcccc gcggggctgg ccgcctagcg agcctgccgg 181 tcgaccccag ccagcgcagc gacggggcgc tgcctggccc aggcgcacac ggaagtgtta 241 tctaaaacag ttcatgctgc tgaaaacctc cttcctggca gatgtccctc aaccctactg 301 gtgcctggct tctgagacac acgcttctct gaagtagctt tggaaagtag agaagaaaat 361 ccagtttgct tcttggagaa cactggacag ctgaataaat gcagtatcta aatataaaag 421 aggactgcaa tgccatggct ttctgtgcta aaatgaggag ctccaagaag actgaggtga 481 acctggaggc ccctgagcca ggggtggaag tgatcttcta tctgtcggac agggagcccc 541 tccggctggg cagtggagag tacacagcag aggaactgtg catcagggct gcacaggcat 601 gccgtatctc tectetttgt cacaacctct ttgccctgta tgacgagaac accaagctct 661 ggtatgctcc aaatcgcacc atcaccgttg atgacaagat gtccctccgg ctccactacc 721 ggatgaggtt ctatttcacc aattggcatg gaaccaacga caatgagcag tcagtgtggc 781 gtcattctcc aaagaagcag aaaaatggct acgagaaaaa aaagattcca gatgcaaccc 841 ctctccttga tgccagctca ctggagtatc tgtttgctca gggacagtat gatttggtga 901 aatgcctggc tcctattcga gaccccaaga ccgagcagga tggacatgat attgagaacg 961 agtgtctagg gatggctgtc ctggccatct cacactatgc catgatgaag aagatgcagt 1021 tgccagaact gcccaaggac atcagctaca agcgatatat tccagaaaca ttgaataagt 1081 ccatcagaca gaggaacctt ctcaccagga tgcggataaa taatgttttc aaggatttcc 1141 taaaggaatt taacaacaag accatttgtg acagcagcgt gtccacgcat gacctgaagg 1201 tgaaatactt ggctaccttg gaaactttga caaaacatta cggtgctgaa atatttgaga 1261 cttccatgtt actgatttca tcagaaaatg agatgaattg gtttcattcg aatgacggtg 1321 gaaacgttct ctactacgaa gtgatggtga ctgggaatct tggaatccag tggaggcata 1381 aaccaaatgt tgtttctgtt gaaaaggaaa aaaataaact gaagcggaaa aaactggaaa -continued 1441 ataaacacaa gaaggatgag gagaaaaaca agatccggga agagtggaac aatttttctt
1501 acttccctga aatcactcac attgtaataa aggagtctgt ggtcagcatt aacaagcagg
1561 acaacaagaa aatggaactg aagctctctt cccacgagga ggccttgtcc tttgtgtccc
1621 tggtagatgg ctacttccgg ctcacagcag atgcccatca ttacctctgc accgacgtgg
1681 cccccccgtt gatcgtccac aacatacaga atggctgtca tggtccaatc tgtacagaat
1741 acgccatcaa taaattgcgg caagaaggaa gcgaggaggg gatgtacgtg ctgaggtgga
1801 gctgcaccga ctttgacaac atcctcatga ccgtcacctg ctttgagaag tctgagcagg
1861 tgcagggtgc ccagaagcag ttcaagaact ttcagatcga ggtgcagaag ggccgctaca
1921 gtctgcacgg ttcggaccgc agcttcccca gcttgggaga cctcatgagc cacctcaaga
1981 agcagatcct gcgcacggat aacatcagct tcatgctaaa acgctgctgc cagcccaagc
2041 cccgagaaat ctccaacctg ctggtggcta ctaagaaagc ccaggagtgg cagcccgtct
2101 accccatgag ccagctgagt ttcgatcgga tcctcaagaa ggatctggtg cagggcgagc
2161 accttgggag aggcacgaga acacacatct attctgggac cctgatggat tacaaggatg
2221 acgaaggaac ttctgaagag aagaagataa aagtgatcct caaagtctta gaccccagcc
2281 acagggatat ttccctggcc ttcttcgagg cagccagcat gatgagacag gtctcccaca
2341 aacacatcgt gtacctctat ggcgtctgtg tccgcgacgt ggagaatatc atggtggaag
2401 agtttgtgga agggggtcct ctggatctct tcatgcaccg gaaaagcgat gtccttacca
2461 caccatggaa attcaaagtt gccaaacagc tggccagtgc cctgagctac ttggaggata
2521 aagacctggt ccatggaaat gtgtgtacta aaaacctcct cctggcccgt gagggcatcg
2581 acagtgagtg tggcccattc atcaagctca gtgaccccgg catccccatt acggtgctgt
2641 ctaggcaaga atgcattgaa cgaatcccat ggattgctcc tgagtgtgtt gaggactcca
2701 agaacctgag tgtggctgct gacaagtgga gctttggaac cacgctctgg gaaatctgct
2761 acaatggcga gatccccttg aaagacaaga cgctgattga gaaagagaga ttctatgaaa
2821 gccggtgcag gccagtgaca ccatcatgta aggagctggc tgacctcatg acccgctgca
2881 tgaactatga ccccaatcag aggcctttct tccgagccat catgagagac attaataagc
2941 ttgaagagca gaatccagat attgtttcag aaaaaaaacc agcaactgaa gtggacccca
3001 cacattttga aaagcgcttc ctaaagagga tccgtgactt gggagagggc cactttggga
3061 aggttgagct ctgcaggtat gaccccgaag gggacaatac aggggagcag gtggctgtta
3121 aatctctgaa gcctgagagt ggaggtaacc acatagctga tctgaaaaag gaaatcgaga
3181 tcttaaggaa cctctatcat gagaacattg tgaagtacaa aggaatctgc acagaagacg
3241 gaggaaatgg tattaagctc atcatggaat ttctgccttc gggaagcctt aaggaatatc
3301 ttccaaagaa taagaacaaa ataaacctca aacagcagct aaaatatgcc gttcagattt
3361 gtaaggggat ggactatttg ggttctcggc aatacgttca ccgggacttg gcagcaagaa
3421 atgtccttgt tgagagtgaa caccaagtga aaattggaga cttcggttta accaaagcaa
3481 ttgaaaccga taaggagtat tacaccgtca aggatgaccg ggacagccct gtgttttggt
3541 atgctccaga atgtttaatg caatctaaat tttatattgc ctctgacgtc tggtcttttg
3601 gagtcactct gcatgagctg ctgacttact gtgattcaga ttctagtccc atggctttgt
3661 tcctgaaaat gataggccca acccatggcc agatgacagt cacaagactt gtgaatacgt
3721 taaaagaagg aaaacgcctg ccgtgcccac ctaactgtcc agatgaggtt tatcaactta
3781 tgaggaaatg ctgggaattc caaccatcca atcggacaag ctttcagaac cttattgaag
3841 gatttgaagc acttttaaaa taagaagcat gaataacatt taaattccac agattatcaa -continued

```
3901 gtccttctcc tgcaacaaat gcccaagtca ttttttaaaa atttctaatg aaagaagttt
3961 gtgttctgtc caaaaagtca ctgaactcat acttcagtac atatacatgt ataaggcaca
4021 ctgtagtgct taatatgtgt aaggacttcc tctttaaatt tggtaccagt aacttagtga
4081 cacataatga caaccaaaat atttgaaagc acttaagcac tcctccttgt ggaaagaata
4141 taccaccatt tcatctggct agttcaccat cacaactgca ttaccaaaag ggatttttg
4201 aaaacgagga gttgaccaaa ataatatctg aagatgattg cttttccctg ctgccagctg
4261 atctgaaatg ttttgctggc acattaatca tagataaaga aagattgatg gacttagccc
4321 tcaaatttca gtatctatac agtactagac catgcattct taaaatatta gataccaggt
4381 agtatatatt gtttctgtac aaaaatgact gtattctctc accagtagga cttaaacttt
4441 gtttctccag tggcttagct cctgttcctt tgggtgatca ctagcaccca tttttgagaa
4501 agctggttct acatgggggg atagctgtgg aatagataat ttgctgcatg ttaattctca
4561 agaactaagc ctgtgccagt gctttcctaa gcagtatacc tttaatcaga actcattccc
4621 agaacctgga tgctattaca catgctttta agaaacgtca atgtatatcc ttttataact
4681 ctaccacttt ggggcaagct attccagcac tggttttgaa tgctgtatgc aaccagtctg
4741 aataccacat acgctgcact gttcttagag ggtttccata cttaccaccg atctacaagg
4801 gttgatccct gtttttacca tcaatcatca ccctgtggtg caacacttga aagacccggc
4861 tagaggcact atggacttca ggatccacta gacagttttc agtttgcttg gaggtagctg
4921 ggtaatcaaa aatgtttagt cattgattca atgtgaacga ttacggtctt tatgaccaag
4981 agtctgaaaa tettitttgtt atgctgttta gtattcgttt gatattgtta cttttcacct
5041 gttgagccca aattcaggat tggttcagtg gcagcaatga agttgccatt taaatttgtt
5101 catagcctac atcaccaagg tctctgtgtc aaacctgtgg ccactctata tgcactttgt
5161 ttactcttta tacaaataaa tatactaaag actttacatg ca
```

Human JAK1 mRNA Variant 7

(SEQ ID NO: 7)

```
   1 agaagcggag cgtatacgga ggaggcggga tgcatttctg catcgagcgc acaaagcgct
  61 tctctgaagt agctttggaa agtagagaag aaaatccagt ttgcttcttg gagaacactg
 121 gacagctgaa taaatgcagt atctaaatat aaaagaggac tgcaatgcca tggctttctg
 181 tgctaaaatg aggagctcca agaagactga ggtgaacctg gaggcccctg agccaggggt
 241 ggaagtgatc ttctatctgt cggacaggga gcccctccgg ctgggcagtg gagagtacac
 301 agcagaggaa ctgtgcatca gggctgcaca ggcatgccgt atctctcctc tttgtcacaa
 361 cctctttgcc ctgtatgacg agaacaccaa gctctggtat gctccaaatc gcaccatcac
 421 cgttgatgac aagatgtccc tccggctcca ctaccggatg aggttctatt tcaccaattg
 481 gcatggaacc aacgacaatg agcagtcagt gtggcgtcat tctccaaaga agcagaaaaa
 541 tggctacgag aaaaaaaaga ttccagatgc aacccctctc cttgatgcca gctcactgga
 601 gtatctgttt gctcagggac agtatgattt ggtgaaatgc ctggctccta ttcgagaccc
 661 caagaccgag caggatggac atgatattga gaacgagtgt ctagggatgg ctgtcctggc
 721 catctcacac tatgccatga tgaagaagat gcagttgcca gaactgccca aggacatcag
 781 ctacaagcga tatattccag aaacattgaa taagtccatc agacagagga accttctcac
 841 caggatgcgg ataaataatg ttttcaagga tttcctaaag gaatttaaca acaagaccat
 901 ttgtgacagc agcgtgtcca cgcatgacct gaaggtgaaa tacttggcta ccttggaaac
 961 tttgacaaaa cattacggtg ctgaaatatt tgagacttcc atgttactga tttcatcaga
```

-continued 1021 aaatgagatg aattggtttc attcgaatga cggtggaaac gttctctact acgaagtgat 1081 ggtgactggg aatcttggaa tccagtggag gcataaacca aatgttgttt ctgttgaaaa 1141 ggaaaaaaat aaactgaagc ggaaaaaact ggaaaataaa cacaagaagg atgaggagaa 1201 aaacaagatc cgggaagagt ggaacaattt ttcttacttc cctgaaatca ctcacattgt 1261 aataaaggag tctgtggtca gcattaacaa gcaggacaac aagaaaatgg aactgaagct 1321 ctcttcccac gaggaggcct tgtcctttgt gtccctggta gatggctact tccggctcac 1381 agcagatgcc catcattacc tctgcaccga cgtggccccc ccgttgatcg tccacaacat 1441 acagaatggc tgtcatggtc caatctgtac agaatacgcc atcaataaat tgcggcaaga 1501 aggaagcgag gaggggatgt acgtgctgag gtggagctgc accgactttg acaacatcct 1561 catgaccgtc acctgctttg agaagtctga gcaggtgcag ggtgcccaga agcagttcaa 1621 gaactttcag atcgaggtgc agaagggccg ctacagtctg cacggttcgg accgcagctt 1681 ccccagcttg ggagacctca tgagccacct caagaagcag atcctgcgca cggataacat 1741 cagcttcatg ctaaaacgct gctgccagcc caagccccga gaaatctcca acctgctggt 1801 ggctactaag aaagcccagg agtggcagcc cgtctacccc atgagccagc tgagtttcga 1861 tcggatcctc aagaaggatc tggtgcaggg cgagcacctt gggagaggca cgagaacaca 1921 catctattct gggaccctga tggattacaa ggatgacgaa ggaacttctg aagagaagaa 1981 gataaaagtg atcctcaaag tcttagaccc cagccacagg gatatttccc tggccttctt 2041 cgaggcagcc agcatgatga gacaggtctc ccacaaacac atcgtgtacc tctatggcgt 2101 ctgtgtccgc gacgtggaga atatcatggt ggaagagttt gtggaagggg gtcctctgga 2161 tctcttcatg caccggaaaa gcgatgtcct taccacacca tggaaattca aagttgccaa 2221 acagctggcc agtgccctga gctacttgga ggataaagac ctggtccatg gaaatgtgtg 2281 tactaaaaac ctcctcctgg cccgtgaggg catcgacagt gagtgtggcc cattcatcaa 2341 gctcagtgac cccggcatcc ccattacggt gctgtctagg caagaatgca ttgaacgaat 2401 cccatggatt gctcctgagt gtgttgagga ctccaagaac ctgagtgtgg ctgctgacaa 2461 gtggagcttt ggaaccacgc tctgggaaat ctgctacaat ggcgagatcc ccttgaaaga 2521 caagacgctg attgagaaag agagattcta tgaaagccgg tgcaggccag tgacaccatc 2581 atgtaaggag ctggctgacc tcatgacccg ctgcatgaac tatgacccca atcagaggcc 2641 tttcttccga gccatcatga gagacattaa taagcttgaa gagcagaatc cagatattgt 2701 ttcagaaaaa aaaccagcaa ctgaagtgga ccccacacat tttgaaaagc gcttcctaaa 2761 gaggatccgt gacttgggag agggccactt tgggaaggtt gagctctgca ggtatgaccc 2821 cgaaggggac aatacagggg agcaggtggc tgttaaatct ctgaagcctg agagtggagg 2881 taaccacata gctgatctga aaaaggaaat cgagatctta aggaacctct atcatgagaa 2941 cattgtgaag tacaaaggaa tctgcacaga agacggagga aatggtatta agctcatcat 3001 ggaatttctg ccttcgggaa gccttaagga atatcttcca aagaataaga acaaaataaa 3061 cctcaaacag cagctaaaat atgccgttca gatttgtaag gggatggact atttgggttc 3121 tcggcaatac gttcaccggg acttggcagc aagaaatgtc cttgttgaga gtgaacacca 3181 agtgaaaatt ggagacttcg gtttaaccaa agcaattgaa accgataagg agtattacac 3241 cgtcaaggat gaccgggaca gccctgtgtt ttggtatgct ccagaatgtt taatgcaatc 3301 taaattttat attgcctctg acgtctggtc ttttggagtc actctgcatg agctgctgac 3361 ttactgtgat tcagattcta gtcccatggc tttgttcctg aaaatgatag gcccaaccca 3421 tggccagatg acagtcacaa gacttgtgaa tacgttaaaa gaaggaaaac gcctgccgtg -continued 3481 cccacctaac tgtccagatg aggtttatca acttatgagg aaatgctggg aattccaacc 3541 atccaatcgg acaagctttc agaaccttat tgaaggattt gaagcacttt taaaataaga 3601 agcatgaata acatttaaat tccacagatt atcaagtcct tctcctgcaa caaatgccca 3661 agtcattttt taaaaatttc taatgaaaga agtttgtgtt ctgtccaaaa agtcactgaa 3721 ctcatacttc agtacatata catgtataag gcacactgta gtgcttaata tgtgtaagga 3781 cttcctcttt aaatttggta ccagtaactt agtgacacat aatgacaacc aaaatatttg 3841 aaagcactta agcactcctc cttgtggaaa gaatatacca ccatttcatc tggctagttc 3901 accatcacaa ctgcattacc aaaaggggat ttttgaaaac gaggagttga ccaaaataat 3961 atctgaagat gattgctttt ccctgctgcc agctgatctg aaatgttttg ctggcacatt 4021 aatcatagat aaagaaagat tgatggactt agccctcaaa tttcagtatc tatacagtac 4081 tagaccatgc attcttaaaa tattagatac caggtagtat atattgtttc tgtacaaaaa 4141 tgactgtatt ctctcaccag taggacttaa actttgtttc tccagtggct tagctcctgt 4201 tcctttgggt gatcactagc acccattttt gagaaagctg gttctacatg gggggatagc 4261 tgtggaatag ataatttgct gcatgttaat tctcaagaac taagcctgtg ccagtgcttt 4321 cctaagcagt ataccttta tcagaactca ttcccagaac ctggatgcta ttacacatgc 4381 ttttaagaaa cgtcaatgta tatcctttta taactctacc actttggggc aagctattcc 4441 agcactggtt ttgaatgctg tatgcaacca gtctgaatac cacatacgct gcactgttct 4501 tagagggttt ccatacttac caccgatcta caagggttga tccctgtttt taccatcaat 4561 catcaccctg tggtgcaaca cttgaaagac ccggctagag gcactatgga cttcaggatc 4621 cactagacag ttttcagttt gcttggaggt agctgggtaa tcaaaaatgt ttagtcattg 4681 attcaatgtg aacgattacg gtctttatga ccaagagtct gaaaatcttt ttgttatgct 4741 gtttagtatt cgtttgatat tgttactttt cacctgttga gcccaaattc aggattggtt 4801 cagtggcagc aatgaagttg ccatttaaat ttgttcatag cctacatcac caaggtctct 4861 gtgtcaaacc tgtggccact ctatatgcac tttgtttact ctttatacaa ataaatatac 4921 taaagacttt acatgca Human JAK1 mRNA Variant 8

(SEQ ID NO: 8)

1 ggggcgggac gggaggcggt gcgtcgctga gcgcaggccg cggcggccgc ggagtatcct 61 ggagctgcag acagtgcggg cctgcgccca gtcccggctg tcctcgccgc gacccctcct 121 cagccctggg cgcgcgcacg ctggggcccc gcggggctgg ccgcctagcg agcctgccgg 181 tcgaccccag ccagcgcagc gacggggcgc tgcctggccc aggcgcacac ggaagtgcgc 241 ttctctgaag tagctttgga aagtagagaa gaaaatccag tttgcttctt ggagaacact 301 ggacagctga ataaatgcag tatctaaata taaaagagga ctgcaatgcc atggctttct 361 gtgctaaaat gaggagctcc aagaagactg aggtgaacct ggaggcccct gagccagggg 421 tggaagtgat cttctatctg tcggacaggg agcccctccg gctgggcagt ggagagtaca 481 cagcagagga actgtgcatc agggctgcac aggcatgccg tatctctcct ctttgtcaca 541 acctctttgc cctgtatgac gagaacacca agctctggta tgctccaaat cgcaccatca 601 ccgttgatga caagatgtcc ctccggctcc actaccggat gaggttctat ttcaccaatt 661 ggcatggaac caacgacaat gagcagtcag tgtggcgtca ttctccaaag aagcagaaaa 721 atggctacga gaaaaaaaag attccagatg caacccctct ccttgatgcc agctcactgg 781 agtatctgtt tgctcaggga cagtatgatt tggtgaaatg cctggctcct attcgagacc -continued 841 ccaagaccga gcaggatgga catgatattg agaacgagtg tctagggatg gctgtcctgg 901 ccatctcaca ctatgccatg atgaagaaga tgcagttgcc agaactgccc aaggacatca 961 gctacaagcg atatattcca gaaacattga ataagtccat cagacagagg aaccttctca 1021 ccaggatgcg gataaataat gttttcaagg atttcctaaa ggaatttaac aacaagacca 1081 tttgtgacag cagcgtgtcc acgcatgacc tgaaggtgaa atacttggct accttggaaa 1141 ctttgacaaa acattacggt gctgaaatat ttgagacttc catgttactg atttcatcag 1201 aaaatgagat gaattggttt cattcgaatg acggtggaaa cgttctctac tacgaagtga 1261 tggtgactgg gaatcttgga atccagtgga ggcataaacc aaatgttgtt tctgttgaaa 1321 aggaaaaaaa taaactgaag cggaaaaaac tggaaaataa acacaagaag gatgaggaga 1381 aaaacaagat ccgggaagag tggaacaatt tttcttactt ccctgaaatc actcacattg 1441 taataaagga gtctgtggtc agcattaaca agcaggacaa caagaaaatg gaactgaagc 1501 tctcttccca cgaggaggcc ttgtcctttg tgtccctggt agatggctac ttccggctca 1561 cagcagatgc ccatcattac ctctgcaccg acgtggcccc cccgttgatc gtccacaaca 1621 tacagaatgg ctgtcatggt ccaatctgta cagaatacgc catcaataaa ttgcggcaag 1681 aaggaagcga ggaggggatg tacgtgctga ggtggagctg caccgacttt gacaacatcc 1741 tcatgaccgt cacctgcttt gagaagtctg aggtgcaggg tgcccagaag cagttcaaga 1801 actttcagat cgaggtgcag aagggccgct acagtctgca cggttcggac cgcagcttcc 1861 ccagcttggg agacctcatg agccacctca agaagcagat cctgcgcacg gataacatca 1921 gcttcatgct aaaacgctgc tgccagccca agccccgaga aatctccaac ctgctggtgg 1981 ctactaagaa agcccaggag tggcagcccg tctaccccat gagccagctg agtttcgatc 2041 ggatcctcaa gaaggatctg gtgcagggcg agcaccttgg gagaggcacg agaacacaca 2101 tctattctgg gaccctgatg gattacaagg atgacgaagg aacttctgaa gagaagaaga 2161 taaaagtgat cctcaaagtc ttagacccca gccacaggga tatttccctg gccttcttcg 2221 aggcagccag catgatgaga caggtctccc acaaacacat cgtgtacctc tatggcgtct 2281 gtgtccgcga cgtggagaat atcatggtgg aagagtttgt ggaaggggggt cctctggatc 2341 tcttcatgca ccggaaaagc gatgtcctta ccacaccatg gaaattcaaa gttgccaaac 2401 agctggccag tgccctgagc tacttggagg ataaagacct ggtccatgga aatgtgtgta 2461 ctaaaaacct cctcctggcc cgtgagggca tcgacagtga gtgtggccca ttcatcaagc 2521 tcagtgaccc cggcatcccc attacggtgc tgtctaggca agaatgcatt gaacgaatcc 2581 catggattgc tcctgagtgt gttgaggact ccaagaacct gagtgtggct gctgacaagt 2641 ggagctttgg aaccacgctc tgggaaatct gctacaatgg cgagatcccc ttgaaagaca 2701 agacgctgat tgagaaagag agattctatg aaagccggtg caggccagtg acaccatcat 2761 gtaaggagct ggctgacctc atgacccgct gcatgaacta tgaccccaat cagaggcctt 2821 tcttccgagc catcatgaga gacattaata agcttgaaga gcagaatcca gatattgttt 2881 cagaaaaaaa accagcaact gaagtggacc ccacacattt tgaaaagcgc ttcctaaaga 2941 ggatccgtga cttgggagag ggccactttg ggaaggttga gctctgcagg tatgaccccg 3001 aaggggacaa tacaggggag caggtggctg ttaaatctct gaagcctgag agtggaggta 3061 accacatagc tgatctgaaa aaggaaatcg agatcttaag gaacctctat catgagaaca 3121 ttgtgaagta caaaggaatc tgcacagaag acggaggaas tggtattaag ctcatcatgg 3181 aatttctgcc ttcgggaagc cttaaggaat atcttccaaa gaataagaac aaaataaacc 3241 tcaaacagca gctaaaatat gccgttcaga tttgtaaggg gatggactat ttgggttctc -continued 3301 ggcaatacgt tcaccgggac ttggcagcaa gaaatgtcct tgttgagagt gaacaccaag
3361 tgaaaattgg agacttcggt ttaaccaaag caattgaaac cgataaggag tattacaccg
3421 tcaaggatga ccgggacagc cctgtgtttt ggtatgctcc agaatgttta atgcaatcta
3481 aattttatat tgcctctgac gtctggtctt ttggagtcac tctgcatgag ctgctgactt
3541 actgtgattc agattctagt cccatggctt tgttcctgaa aatgataggc ccaacccatg
3601 gccagatgac agtcacaaga cttgtgaata cgttaaaaga aggaaaacgc ctgccgtgcc
3661 cacctaactg tccagatgag gtttatcaac ttatgaggaa atgctgggaa ttccaaccat
3721 ccaatcggac aagctttcag aaccttattg aaggatttga agcactttta aaataagaag
3781 catgaataac atttaaattc cacagattat caagtccttc tcctgcaaca aatgcccaag
3841 tcattttttta aaaatttcta atgaaagaag tttgtgttct gtccaaaaag tcactgaact
3901 catacttcag tacatataca tgtataaggc acactgtagt gcttaatatg tgtaaggact
3961 tectetttaa atttggtacc agtaacttag tgacacataa tgacaaccaa aatatttgaa
4021 agcacttaag cactcctcct tgtggaaaga atataccacc atttcatctg gctagttcac
4081 catcacaact gcattaccaa aaggggattt ttgaaaacga ggagttgacc aaaataatat
4141 ctgaagatga ttgcttttcc ctgctgccag ctgatctgaa atgttttgct ggcacattaa
4201 tcatagataa agaaagattg atggacttag ccctcaaatt tcagtatcta tacagtacta
4261 gaccatgcat tcttaaaata ttagatacca ggtagtatat attgtttctg tacaaaaatg
4321 actgtattct ctcaccagta ggacttaaac tttgtttctc cagtggctta gctcctgttc
4381 ctttgggtga tcactagcac ccatttttga gaaagctggt tctacatggg gggatagctg
4441 tggaatagat aatttgctgc atgttaattc tcaagaacta agcctgtgcc agtgctttcc
4501 taagcagtat acctttaatc agaactcatt cccagaacct ggatgctatt acacatgctt
4561 ttaagaaacg tcaatgtata tccttttata actctaccac tttggggcaa gctattccag
4621 cactggtttt gaatgctgta tgcaaccagt ctgaatacca catacgctgc actgttctta
4681 gagggtttcc atacttacca ccgatctaca agggttgatc cctgttttta ccatcaatca
4741 tcaccctgtg gtgcaacact tgaaagaccc ggctagaggc actatggact tcaggatcca
4801 ctagacagtt ttcagtttgc ttggaggtag ctgggtaatc aaaaatgttt agtcattgat
4861 tcaatgtgaa cgattacggt ctttatgacc aagagtctga aaatcttttt gttatgctgt
4921 ttagtattcg tttgatattg ttacttttca cctgttgagc ccaaattcag gattggttca
4981 gtggcagcaa tgaagttgcc atttaaattt gttcatagcc tacatcacca aggtctctgt
5041 gtcaaacctg tggccactct atatgcactt tgtttactct ttatacaaat aaatatacta
5101 aagactttac atgca Human JAK2 mRNA Variant 1

(SEQ ID NO: 9)

1 ctgcaggaag gagagaggaa gaggagcaga agggggcagc agcggacgcc gctaacggcc
61 tccctcggcg ctgacaggct gggccggcgc ccggctcgct tgggtgttcg cgtcgccact
121 tcggcttctc ggccggtcgg gcccctcggc ccgggcttgc ggcgcgcgtc ggggctgagg
181 gctgctgcgg cgcagggaga ggcctggtcc tcgctgccga gggatgtgag tgggagctga
241 gcccacactg gagggccccc gagggcccag cctggaggtc gttcagagcc gtgcccgtcc
301 cggggcttcg cagaccttga cccgccgggt aggagccgcc cctgcgggct cgagggcgcg
361 ctctggtcgc ccgatctgtg tagccggttt cagaagcagg caacaggaac aagatgtgaa
421 ctgtttctct tctgcagaaa aagaggctct tcctcctcct cccgcgacgg caaatgttct -continued

```
481 gaaaaagact ctgcatggga atggcctgcc ttacgatgac agaaatggag ggaacatcca
541 cctcttctat atatcagaat ggtgatattt ctggaaatgc caattctatg aagcaaatag
601 atccagttct tcaggtgtat ctttaccatt cccttgggaa atctgaggca gattatctga
661 cctttccatc tggggagtat gttgcagaag aaatctgtat tgctgcttct aaagcttgtg
721 gtatcacacc tgtgtatcat aatatgtttg ctttaatgag tgaaacagaa aggatctggt
781 atccacccaa ccatgtcttc catatagatg agtcaaccag gcataatgta ctctacagaa
841 taagatttta ctttcctcgt tggtattgca gtggcagcaa cagagcctat cggcatggaa
901 tatctcgagg tgctgaagct cctcttcttg atgactttgt catgtcttac ctctttgctc
961 agtggcggca tgattttgtg cacggatgga taaaagtacc tgtgactcat gaaacacagg
1021 aagaatgtct tgggatggca gtgttagata tgatgagaat agccaaagaa aacgatcaaa
1081 ccccactggc catctataac tctatcagct acaagacatt cttaccaaaa tgtattcgag
1141 caaagatcca agactatcat attttgacaa ggaagcgaat aaggtacaga tttcgcagat
1201 ttattcagca attcagccaa tgcaaagcca ctgccagaaa cttgaaactt aagtatctta
1261 taaatctgga aactctgcag tctgccttct acacagagaa atttgaagta aaagaacctg
1321 gaagtggtcc ttcaggtgag gagattttg caaccattat aataactgga aacggtggaa
1381 ttcagtggtc aagagggaaa cataaagaaa gtgagacact gacagaacag gatttacagt
1441 tatattgcga ttttcctaat attattgatg tcagtattaa gcaagcaaac caagagggtt
1501 caaatgaaag ccgagttgta actatccata agcaagatgg taaaaatctg gaaattgaac
1561 ttagctcatt aagggaagct ttgtctttcg tgtcattaat tgatggatat tatagattaa
1621 ctgcagatgc acatcattac ctctgtaaag aagtagcacc tccagccgtg cttgaaaata
1681 tacaaagcaa ctgtcatggc ccaatttcga tggattttgc cattagtaaa ctgaagaaag
1741 caggtaatca gactggactg tatgtacttc gatgcagtcc taaggacttt aataaatatt
1801 ttttgacttt tgctgtcgag cgagaaaatg tcattgaata taaacactgt ttgattacaa
1861 aaaatgagaa tgaagagtac aacctcagtg ggacaaagaa gaacttcagc agtcttaaag
1921 atcttttgaa ttgttaccag atggaaactg ttcgctcaga caatataatt ttccagttta
1981 ctaaatgctg tcccccaaag ccaaaagata aatcaaacct tctagtcttc agaacgaatg
2041 gtgtttctga tgtaccaacc tcaccaacat tacagaggcc tactcatatg aaccaaatgg
2101 tgtttcacaa aatcagaaat gaagatttga tatttaatga aagccttggc caaggcactt
2161 ttacaaagat tttaaaggc gtacgaagag aagtaggaga ctacggtcaa ctgcatgaaa
2221 cagaagttct tttaaaagtt ctggataaag cacacagaaa ctattcagag tetttetttg
2281 aagcagcaag tatgatgagc aagetttctc acaagcattt ggttttaaat tatggagtat
2341 gtgtctgtgg agacgagaat attctggttc aggagtttgt aaaatttgga tcactagata
2401 catatctgaa aaagaataaa aattgtataa atatattatg gaaacttgaa gttgctaaac
2461 agttggcatg ggccatgcat tttctagaag aaaacaccct tattcatggg aatgtatgtg
2521 ccaaaaatat tctgcttatc agagaagaag acaggaagac aggaaatcct cctttcatca
2581 aacttagtga tcctggcatt agtattacag ttttgccaaa ggacattctt caggagagaa
2641 taccatgggt accacctgaa tgcattgaaa atcctaaaaa tttaaatttg gcaacagaca
2701 aatggagttt tggtaccact ttgtgggaaa tctgcagtgg aggagataaa cctctaagtg
2761 ctctggattc tcaaagaaag ctacaatttt atgaagatag gcatcagctt cctgcaccaa
2821 agtgggcaga attagcaaac cttataaata attgtatgga ttatgaacca gatttcaggc
2881 cttctttcag agccatcata cgagatctta acagtttgtt tactccagat tatgaactat
```

-continued 2941 taacagaaaa tgacatgtta ccaaatatga ggataggtgc cctggggttt tctggtgcct 3001 ttgaagaccg ggatcctaca cagtttgaag agagacattt gaaatttcta cagcaacttg 3061 gcaagggtaa ttttgggagt gtggagatgt gccggtatga ccctctacag gacaacactg 3121 gggaggtggt cgctgtaaaa aagcttcagc atagtactga agagcaccta agagactttg 3181 aaagggaaat tgaaatcctg aaatccctac agcatgacaa cattgtaaag tacaagggag 3241 tgtgctacag tgctggtcgg cgtaatctaa aattaattat ggaatattta ccatatggaa 3301 gtttacgaga ctatcttcaa aaacataaag aacggataga tcacataaaa cttctgcagt 3361 acacatctca gatatgcaag ggtatggagt atcttggtac aaaaaggtat atccacaggg 3421 atctggcaac gagaaatata ttggtggaga acgagaacag agttaaaatt ggagattttg 3481 ggttaaccaa agtcttgcca caagacaaag aatactataa agtaaaagaa cctggtgaaa 3541 gtcccatatt ctggtatgct ccagaatcac tgacagagag caagttttct gtggcctcag 3601 atgtttggag ctttggagtg gttctgtatg aacttttcac atacattgag aagagtaaaa 3661 gtccaccagc ggaatttatg cgtatgattg gcaatgacaa acaaggacag atgatcgtgt 3721 tccatttgat agaacttttg aagaataatg gaagattacc aagaccagat ggatgcccag 3781 atgagatcta tatgatcatg acagaatgct ggaacaataa tgtaaatcaa cgcccctcct 3841 ttagggatct agctcttcga gtggatcaaa taagggataa catggctgga tgaaagaaat 3901 gaccttcatt ctgagaccaa agtagattta cagaacaaag ttttatattt cacattgctg 3961 tggactatta ttacatatat cattattata taaatcatga tgctagccag caaagatgtg 4021 aaaatatctg ctcaaaactt tcaaagttta gtaagttttt cttcatgagg ccaccagtaa 4081 aagacattaa tgagaattcc ttagcaagga ttttgtaaga agtttcttaa acattgtcag 4141 ttaacatcac tcttgtctgg caaaagaaaa aaaatagact tttcaactc agctttttga 4201 gacctgaaaa aattattatg taaattttgc aatgttaaag atgcacagaa tatgtatgta 4261 tagtttttac cacagtggat gtataatacc ttggcatctt gtgtgatgtt ttacacacat 4321 gagggctggt gttcattaat actgttttct aatttttcca tagttaatct ataattaatt 4381 acttcactat acaaacaaat taagatgttc agataattga ataagtacct ttgtgtcctt 4441 gttcatttat atcgctggcc agcattataa gcaggtgtat acttttagct tgtagttcca 4501 tgtactgtaa atatttttca cataaaggga acaaatgtct agttttattt gtataggaaa 4561 tttccctgac cctaaataat acattttgaa atgaaacaag cttacaaaga tataatctat 4621 tttattatgg tttcccttgt atctatttgt ggtgaatgtg ttttttaaat ggaactatct 4681 ccaaattttt ctaagactac tatgaacagt tttcttttaa aattttgaga ttaagaatgc 4741 caggaatatt gtcatccttt gagctgctga ctgccaataa cattcttcga tctctgggat 4801 ttatgctcat gaactaaatt taagcttaag ccataaaata gattagattg tttttaaaa 4861 atggatagct cattaagaag tgcagcaggt taagaatttt ttcctaaaga ctgtatattt 4921 gaggggtttc agaattttgc attgcagtca tagaagagat ttatttcctt tttagagggg 4981 aaatgaggta aataagtaaa aaagtatgct tgttaatttt attcaagaat gccagtagaa 5041 aattcataac gtgtatcttt aagaaaaatg agcatacatc ttaaatcttt tcaattaagt 5101 ataaggggtt gttcgttgtt gtcatttgtt atagtgctac tccactttag acaccatagc 5161 taaaataaaa tatggtgggt tttgtgtgtg tgtgtgtgtg tgtgtgtgtg tgtgtgtgtg 5221 tgttatttat acaaaactta aaatacttgc tgttttgatt aaaaagaaaa tagtttctta 5281 cttta -continued Human JAK2 mRNA Variant 2

(SEQ ID NO: 10)

```
   1 attcggggag actgcaggcc aaccgggagg ctgagttcga agctagcagg gcggcgaagc

  61 cagtgtcgcc cgcggcgttg agaagacggt gtggccccgg agagggtgga gacaactgtg

 121 acgggcttcc cggctgcccg aagtgggagt ggtgtggggc tgcaggaagg agagaggaag

 181 aggagcagaa gggggcagca gcggacgccg ctaacggcct ccctcggcgc tgacaggctg

 241 ggccggcgcc cggctcgctt gggtgttcgc gtcgccactt cggcttctcg gccggtcggg

 301 cccctcggcc cgggcttgcg gcgcgcgtcg ggctgaggg ctgctgcggc gcagggagag

 361 gcctggtcct cgctgccgag ggatgtgagt gggagctgag cccacactgg agggcccccg

 421 agggcccagc ctggaggtcg ttcagagccg tgcccgtccc ggggcttcgc agaccttgac

 481 ccgccgggtt tcagaagcag gcaacaggaa caagatgtga actgtttctc ttctgcagaa

 541 aaagaggctc ttcctcctcc tcccgcgacg gcaaatgttc tgaaaaagac tctgcatggg

 601 aatggcctgc cttacgatga cagaaatgga gggaacatcc acctcttcta tatatcagaa

 661 tggtgatatt tctggaaatg ccaattctat gaagcaaata gatccagttc ttcaggtgta

 721 tctttaccat tcccttggga aatctgaggc agattatctg acctttccat ctggggagta

 781 tgttgcagaa gaaatctgta ttgctgcttc taaagcttgt ggtatcacac ctgtgtatca

 841 taatatgttt gctttaatga gtgaaacaga aaggatctgg tatccaccca accatgtctt

 901 ccatatagat gagtcaacca ggcataatgt actctacaga ataagatttt actttcctcg

 961 ttggtattgc agtggcagca acagagccta tcggcatgga atatctcgag gtgctgaagc

1021 tcctcttctt gatgactttg tcatgtctta cctctttgct cagtggcggc atgattttgt

1081 gcacggatgg ataaaagtac ctgtgactca tgaaacacag gaagaatgtc ttgggatggc

1141 agtgttagat atgatgagaa tagccaaaga aaacgatcaa accccactgg ccatctataa

1201 ctctatcagc tacaagacat tcttaccaaa atgtattcga gcaaagatcc aagactatca

1261 tattttgaca aggaagcgaa taaggtacag atttcgcaga tttattcagc aattcagcca

1321 atgcaaagcc actgccagaa acttgaaact taagtatctt ataaatctgg aaactctgca

1381 gtctgccttc tacacagaga aatttgaagt aaaagaacct ggaagtggtc cttcaggtga

1441 ggagattttt gcaaccatta taataactgg aaacggtgga attcagtggt caagagggaa

1501 acataaagaa agtgagacac tgacagaaca ggatttacag ttatattgcg attttcctaa

1561 tattattgat gtcagtatta agcaagcaaa ccaagagggt tcaaatgaaa gccgagttgt

1621 aactatccat aagcaagatg gtaaaaatct ggaaattgaa cttagctcat taagggaagc

1681 tttgtctttc gtgtcattaa ttgatggata ttatagatta actgcagatg cacatcatta

1741 cctctgtaaa gaagtagcac ctccagccgt gcttgaaaat atacaaagca actgtcatgg

1801 cccaatttcg atggattttg ccattagtaa actgaagaaa gcaggtaatc agactggact

1861 gtatgtactt cgatgcagtc ctaaggactt taataaatat tttttgactt ttgctgtcga

1921 gcgagaaaat gtcattgaat ataaacactg tttgattaca aaaaatgaga atgaagagta

1981 caacctcagt gggacaaaga agaacttcag cagtcttaaa gatcttttga attgttacca

2041 gatggaaact gttcgctcag acaatataat tttccagttt actaaatgct gtcccccaaa

2101 gccaaaagat aaatcaaacc ttctagtctt cagaacgaat ggtgtttctg atgtaccaac

2161 ctcaccaaca ttacagaggc ctactcatat gaaccaaatg gtgtttcaca aaatcagaaa

2221 tgaagatttg atatttaatg aaagccttgg ccaaggcact tttacaaaga tttttaaagg

2281 cgtacgaaga gaagtaggag actacggtca actgcatgaa acagaagttc ttttaaaagt

2341 tctggataaa gcacacagaa actattcaga gtctttcttt gaagcagcaa gtatgatgag
```

-continued 2401 caagctttct cacaagcatt tggttttaaa ttatggagta tgtgtctgtg gagacgagaa
2461 tattctggtt caggagtttg taaaatttgg atcactagat acatatctga aaaagaataa
2521 aaattgtata aatatattat ggaaacttga agttgctaaa cagttggcat gggccatgca
2581 ttttctagaa gaaaacaccc ttattcatgg gaatgtatgt gccaaaaata ttctgcttat
2641 cagagaagaa gacaggaaga caggaaatcc tcctttcatc aaacttagtg atcctggcat
2701 tagtattaca gttttgccaa aggacattct tcaggagaga ataccatggg taccacctga
2761 atgcattgaa aatcctaaaa atttaaattt ggcaacagac aaatggagtt ttggtaccac
2821 tttgtgggaa atctgcagtg gaggagataa acctctaagt gctctggatt ctcaaagaaa
2881 gctacaattt tatgaagata ggcatcagct tcctgcacca aagtgggcag aattagcaaa
2941 ccttataaat aattgtatgg attatgaacc agatttcagg ccttctttca gagccatcat
3001 acgagatctt aacagtttgt ttactccaga ttatgaacta ttaacagaaa atgacatgtt
3061 accaaatatg aggataggtg ccctggggtt ttctggtgcc tttgaagacc gggatcctac
3121 acagtttgaa gagagacatt tgaaatttct acagcaactt ggcaagggta attttgggag
3181 tgtggagatg tgccggtatg accctctaca ggacaacact ggggaggtgg tcgctgtaaa
3241 aaagcttcag catagtactg aagagcacct aagagacttt gaaagggaaa ttgaaatcct
3301 gaaatcccta cagcatgaca acattgtaaa gtacaaggga gtgtgctaca gtgctggtcg
3361 gcgtaatcta aaattaatta tggaatattt accatatgga agtttacgag actatcttca
3421 aaaacataaa gaacggatag atcacataaa acttctgcag tacacatctc agatatgcaa
3481 gggtatggag tatcttggta caaaaaggta tatccacagg gatctggcaa cgagaaatat
3541 attggtggag aacgagaaca gagttaaaat tggagatttt gggttaacca aagtcttgcc
3601 acaagacaaa gaatactata aagtaaaaga acctggtgaa agtcccatat tctggtatgc
3661 tccagaatca ctgacagaga gcaagttttc tgtggcctca gatgtttgga gctttggagt
3721 ggttctgtat gaacttttca catacattga gaagagtaaa agtccaccag cggaatttat
3781 gcgtatgatt ggcaatgaca aacaaggaca gatgatcgtg ttccatttga tagaactttt
3841 gaagaataat ggaagattac caagaccaga tggatgccca gatgagatct atatgatcat
3901 gacagaatgc tggaacaata atgtaaatca acgcccctcc tttagggatc tagctcttcg
3961 agtggatcaa ataagggata acatggctgg atgaaagaaa tgaccttcat tctgagacca
4021 aagtagattt acagaacaaa gttttatatt tcacattgct gtggactatt attacatata
4081 tcattattat ataaatcatg atgctagcca gcaaagatgt gaaaatatct gctcaaaact
4141 ttcaaagttt agtaagtttt tcttcatgag gccaccagta aaagacatta atgagaattc
4201 cttagcaagg attttgtaag aagtttctta aacattgtca gttaacatca ctcttgtctg
4261 gcaaaagaaa aaaaatagac tttttcaact cagcttttttg agacctgaaa aaattattat
4321 gtaaattttg caatgttaaa gatgcacaga atatgtatgt atagttttta ccacagtgga
4381 tgtataatac cttggcatct tgtgtgatgt tttacacaca tgagggctgg tgttcattaa
4441 tactgttttc taatttttcc atagttaatc tataattaat tacttcacta tacaaacaaa
4501 ttaagatgtt cagataattg aataagtacc tttgtgtcct tgttcattta tatcgctggc
4561 cagcattata agcaggtgta tacttttagc ttgtagttcc atgtactgta aatatttttc
4621 acataaaggg aacaaatgtc tagttttatt tgtataggaa atttccctga ccctaaataa
4681 tacattttga aatgaaacaa gcttacaaag atataatcta ttttattatg gtttcccttg
4741 tatctatttg tggtgaatgt gtttttaaa tggaactatc tccaaatttt tctaagacta -continued

```
4801 ctatgaacag ttttctttta aaattttgag attaagaatg ccaggaatat tgtcatcctt
4861 tgagctgctg actgccaata acattcttcg atctctggga tttatgctca tgaactaaat
4921 ttaagcttaa gccataaaat agattagatt gtttttttaaa aatggatagc tcattaagaa
4981 gtgcagcagg ttaagaattt tttcctaaag actgtatatt tgaggggttt cagaattttg
5041 cattgcagtc atagaagaga tttatttcct ttttagaggg gaaatgaggt aaataagtaa
5101 aaaagtatgc ttgttaattt tattcaagaa tgccagtaga aaattcataa cgtgtatctt
5161 taagaaaaat gagcatacat cttaaatctt ttcaattaag tataaggggt tgttcgttgt
5221 tgtcatttgt tatagtgcta ctccacttta gacaccatag ctaaaataaa atatggtggg
5281 ttttgtgtgt gtgtgtgtgt gtgtgtgtgt gtgtgtgtgt gtgttattta tacaaaactt
5341 aaaatacttg ctgttttgat taaaaagaaa atagtttctt acttta
```

Human JAK2 mRNA Variant 3

(SEQ ID NO: 11)

```
   1 attcggggag actgcaggcc aaccgggagg ctgagttcga agctagcagg gcggcgaagc
  61 cagtgtcgcc cgcggcgttg agaagacggc aaatgttctg aaaaagactc tgcatgggaa
 121 tggcctgcct tacgatgaca gaaatggagg gaacatccac ctcttctata tatcagaatg
 181 gtgatatttc tggaaatgcc aattctatga agcaaataga tccagttctt caggtgtatc
 241 tttaccattc ccttgggaaa tctgaggcag attatctgac ctttccatct ggggagtatg
 301 ttgcagaaga aatctgtatt gctgcttcta aagcttgtgg tatcacacct gtgtatcata
 361 atatgtttgc tttaatgagt gaaacagaaa ggatctggta tccacccaac catgtcttcc
 421 atatagatga gtcaaccagg cataatgtac tctacagaat aagattttac tttcctcgtt
 481 ggtattgcag tggcagcaac agagcctatc ggcatggaat atctcgaggt gctgaagctc
 541 ctcttcttga tgactttgtc atgtcttacc tctttgctca gtggcggcat gattttgtgc
 601 acggatggat aaaagtacct gtgactcatg aaacacagga agaatgtctt gggatggcag
 661 tgttagatat gatgagaata gccaaagaaa acgatcaaac ccccactggcc atctataact
 721 ctatcagcta caagacattc ttaccaaaat gtattcgagc aaagatccaa gactatcata
 781 ttttgacaag gaagcgaata aggtacagat ttcgcagatt tattcagcaa ttcagccaat
 841 gcaaagccac tgccagaaac ttgaaactta agtatcttat aaatctggaa actctgcagt
 901 ctgccttcta cacagagaaa tttgaagtaa aagaacctgg aagtggtcct tcaggtgagg
 961 agatttttgc aaccattata ataactggaa acggtggaat tcagtggtca agagggaaac
1021 ataaagaaag tgagacactg acagaacagg atttacagtt atattgcgat tttcctaata
1081 ttattgatgt cagtattaag caagcaaacc aagagggttc aaatgaaagc cgagttgtaa
1141 ctatccataa gcaagatggt aaaaatctgg aaattgaact tagctcatta agggaagctt
1201 tgtctttcgt gtcattaatt gatggatatt atagattaac tgcagatgca catcattacc
1261 tctgtaaaga agtagcacct ccagccgtgc ttgaaaatat acaaagcaac tgtcatggcc
1321 caatttcgat ggattttgcc attagtaaac tgaagaaagc aggtaatcag actggactgt
1381 atgtacttcg atgcagtcct aaggacttta ataaatattt tttgactttt gctgtcgagc
1441 gagaaaatgt cattgaatat aaacactgtt tgattacaaa aaatgagaat gaagagtaca
1501 acctcagtgg gacaaagaag aacttcagca gtcttaaaga tcttttgaat tgttaccaga
1561 tggaaactgt tcgctcagac aatataattt tccagtttac taaatgctgt cccccaaagc
1621 caaaagataa atcaaacctt ctagtcttca gaacgaatgg tgtttctgat gtaccaacct
1681 caccaacatt acagaggcct actcatatga accaaatggt gtttcacaaa atcagaaatg
1741 aagatttgat atttaatgaa agccttggcc aaggcacttt tacaaagatt tttaaaggcg
```

-continued 1801 tacgaagaga agtaggagac tacggtcaac tgcatgaaac agaagttctt ttaaaagttc
1861 tggataaagc acacagaaac tattcagagt ctttctttga agcagcaagt atgatgagca
1921 agctttctca caagcatttg gttttaaatt atggagtatg tgtctgtgga gacgagaata
1981 ttctggttca ggagtttgta aaatttggat cactagatac atatctgaaa aagaataaaa
2041 attgtataaa tatattatgg aaacttgaag ttgctaaaca gttggcatgg gccatgcatt
2101 ttctagaaga aaacaccctt attcatggga atgtatgtgc caaaaatatt ctgcttatca
2161 gagaagaaga caggaagaca ggaaatcctc ctttcatcaa acttagtgat cctggcatta
2221 gtattacagt tttgccaaag gacattcttc aggagagaat accatgggta ccacctgaat
2281 gcattgaaaa tcctaaaaat ttaaatttgg caacagacaa atggagtttt ggtaccactt
2341 tgtgggaaat ctgcagtgga ggagataaac ctctaagtgc tctggattct caaagaaagc
2401 tacaatttta tgaagatagg catcagcttc ctgcaccaaa gtgggcagaa ttagcaaacc
2461 ttataaataa ttgtatggat tatgaaccag atttcaggcc ttctttcaga gccatcatac
2521 gagatcttaa cagtttgttt actccagatt atgaactatt aacagaaaat gacatgttac
2581 caaatatgag gataggtgcc ctggggtttt ctggtgcctt tgaagaccgg gatcctacac
2641 agtttgaaga gagacatttg aaatttctac agcaacttgg caagggtaat tttgggagtg
2701 tggagatgtg ccggtatgac cctctacagg acaacactgg ggaggtggtc gctgtaaaaa
2761 agcttcagca tagtactgaa gagcacctaa gagactttga aagggaaatt gaaatcctga
2821 aatccctaca gcatgacaac attgtaaagt acaagggagt gtgctacagt gctggtcggc
2881 gtaatctaaa attaattatg gaatatttac catatggaag tttacgagac tatcttcaaa
2941 aacataaaga acggatagat cacataaaac ttctgcagta cacatctcag atatgcaagg
3001 gtatggagta tcttggtaca aaaaggtata tccacaggga tctggcaacg agaaatatat
3061 tggtggagaa cgagaacaga gttaaaattg gagattttgg gttaaccaaa gtcttgccac
3121 aagacaaaga atactataaa gtaaaagaac ctggtgaaag tcccatattc tggtatgctc
3181 cagaatcact gacagagagc aagttttctg tggcctcaga tgtttggagc tttggagtgg
3241 ttctgtatga acttttcaca tacattgaga agagtaaaag tccaccagcg gaatttatgc
3301 gtatgattgg caatgacaaa caaggacaga tgatcgtgtt ccatttgata gaacttttga
3361 agaataatgg aagattacca agaccagatg gatgcccaga tgagatctat atgatcatga
3421 cagaatgctg gaacaataat gtaaatcaac gcccctcctt tagggatcta gctcttcgag
3481 tggatcaaat aagggataac atggctggat gaaagaaatg accttcattc tgagaccaaa
3541 gtagatttac agaacaaagt tttatatttc acattgctgt ggactattat tacatatatc
3601 attattatat aaatcatgat gctagccagc aaagatgtga aaatatctgc tcaaaacttt
3661 caaagtttag taagtttttc ttcatgaggc caccagtaaa agacattaat gagaattcct
3721 tagcaaggat tttgtaagaa gtttcttaaa cattgtcagt taacatcact cttgtctggc
3781 aaaagaaaaa aaatagactt tttcaactca gctttttgag acctgaaaaa attattatgt
3841 aaattttgca atgttaaaga tgcacagaat atgtatgtat agtttttacc acagtggatg
3901 tataatacct tggcatcttg tgtgatgttt tacacacatg agggctggtg ttcattaata
3961 ctgttttcta atttttccat agttaatcta taattaatta cttcactata caaacaaatt
4021 aagatgttca gataattgaa taagtacctt tgtgtccttg ttcatttata tcgctggcca
4081 gcattataag caggtgtata cttttagctt gtagttccat gtactgtaaa tatttttcac
4141 ataaagggaa caaatgtcta gttttatttg tataggaaat ttccctgacc ctaaataata -continued 4201 cattttgaaa tgaaacaagc ttacaaagat ataatctatt ttattatggt ttcccttgta
4261 tctatttgtg gtgaatgtgt tttttaaatg gaactatctc caaatttttc taagactact
4321 atgaacagtt ttcttttaaa attttgagat taagaatgcc aggaatattg tcatcctttg
4381 agctgctgac tgccaataac attcttcgat ctctgggatt tatgctcatg aactaaattt
4441 aagcttaagc cataaaatag attagattgt tttttaaaaa tggatagctc attaagaagt
4501 gcagcaggtt aagaattttt tcctaaagac tgtatatttg aggggtttca gaattttgca
4561 ttgcagtcat agaagagatt tatttccttt ttagagggga aatgaggtaa ataagtaaaa
4621 aagtatgctt gttaatttta ttcaagaatg ccagtagaaa attcataacg tgtatcttta
4681 agaaaaatga gcatacatct taaatctttt caattaagta taaggggttg ttcgttgttg
4741 tcatttgtta tagtgctact ccactttaga caccatagct aaaataaaat atggtgggtt
4801 ttgtgtgtgt gtgtgtgtgt gtgtgtgtgt gtgtgtgtgt gttatttata caaaacttaa
4861 aatacttgct gttttgatta aaaagaaaat agtttcttac ttta Human JAK2 mRNA Variant 4

(SEQ ID NO: 12)

1 gggagtggtg tggggctgca ggaaggagag aggaagagga gcagaagggg gcagcagcgg
61 acgccgctaa cggcctccct cggcgctgac aggctgggcc ggcgcccggc tcgcttgggt
121 gttcgcgtcg ccacttcggc ttctcggccg gtcgggcccc tcggcccggg cttgcggcgc
181 gcgtcggggc tgagggctgc tgcggcgcag ggagaggcct ggtcctcgct gccgagggat
241 gtgagtggga gctgagccca cactggaggg cccccgaggg cccagcctgg aggtcgttca
301 gagccgtgcc cgtcccgggg cttcgcagac cttgacccgc cgggtaggag ccgcccctgc
361 gggctcgagg gcgcgctctg gtcgcccgat ctgtgtagcc ggcaaatgtt ctgaaaaaga
421 ctctgcatgg gaatggcctg ccttacgatg acagaaatgg agggaacatc cacctcttct
481 atatatcaga atggtgatat ttctggaaat gccaattcta tgaagcaaat agatccagtt
541 cttcaggtgt atctttacca ttcccttggg aaatctgagg cagattatct gacctttcca
601 tctggggagt atgttgcaga agaaatctgt attgctgctt ctaaagcttg tggtatcaca
661 cctgtgtatc ataatatgtt tgctttaatg agtgaaacag aaaggatctg gtatccaccc
721 aaccatgtct tccatataga tgagtcaacc aggcataatg tactctacag aataagattt
781 tactttcctc gttggtattg cagtggcagc aacagagcct atcggcatgg aatatctcga
841 ggtgctgaag ctcctcttct tgatgacttt gtcatgtctt acctctttgc tcagtggcgg
901 catgattttg tgcacggatg gataaaagta cctgtgactc atgaaacaca ggaagaatgt
961 cttgggatgg cagtgttaga tatgatgaga atagccaaag aaaacgatca aaccccactg
1021 gccatctata actctatcag ctacaagaca ttcttaccaa aatgtattcg agcaaagatc
1081 caagactatc atattttgac aaggaagcga ataaggtaca gatttcgcag atttattcag
1141 caattcagcc aatgcaaagc cactgccaga aacttgaaac ttaagtatct tataaatctg
1201 gaaactctgc agtctgcctt ctacacagag aaatttgaag taaaagaacc tggaagtggt
1261 ccttcaggtg aggagatttt tgcaaccatt ataataactg gaaacggtgg aattcagtgg
1321 tcaagaggga aacataaaga aagtgagaca ctgacagaac aggatttaca gttatattgc
1381 gattttccta atattattga tgtcagtatt aagcaagcaa accaagaggg ttcaaatgaa
1441 agccgagttg taactatcca taagcaagat ggtaaaaatc tggaaattga acttagctca
1501 ttaagggaag ctttgtcttt cgtgtcatta attgatggat attatagatt aactgcagat
1561 gcacatcatt acctctgtaa agaagtagca cctccagccg tgcttgaaaa tatacaaagc
1621 aactgtcatg gcccaatttc gatggatttt gccattagta aactgaagaa agcaggtaat -continued 1681 cagactggac tgtatgtact tcgatgcagt cctaaggact ttaataaata tttttgact
1741 tttgctgtcg agcgagaaaa tgtcattgaa tataaacact gtttgattac aaaaaatgag
1801 aatgaagagt acaacctcag tgggacaaag aagaacttca gcagtcttaa agatcttttg
1861 aattgttacc agatggaaac tgttcgctca gacaatataa ttttccagtt tactaaatgc
1921 tgtcccccaa agccaaaaga taaatcaaac cttctagtct tcagaacgaa tggtgtttct
1981 gatgtaccaa cctcaccaac attacagagg cctactcata tgaaccaaat ggtgtttcac
2041 aaaatcagaa atgaagattt gatatttaat gaaagccttg gccaaggcac ttttacaaag
2101 atttttaaag gcgtacgaag agaagtagga gactacggtc aactgcatga aacagaagtt
2161 cttttaaaag ttctggataa agcacacaga aactattcag agtetttett tgaagcagca
2221 agtatgatga gcaagctttc tcacaagcat ttggttttaa attatggagt atgtgtctgt
2281 ggagacgaga atattctggt tcaggagttt gtaaaatttg gatcactaga tacatatctg
2341 aaaaagaata aaaattgtat aaatatatta tggaaacttg aagttgctaa acagttggca
2401 tgggccatgc atttctaga agaaaacacc cttattcatg ggaatgtatg tgccaaaaat
2461 attctgctta tcagagaaga agacaggaag acaggaaatc ctcctttcat caaacttagt
2521 gatcctggca ttagtattac agttttgcca aaggacattc ttcaggagag aataccatgg
2581 gtaccacctg aatgcattga aaatcctaaa aatttaaatt tggcaacaga caaatggagt
2641 tttggtacca ctttgtggga aatctgcagt ggaggagata aacctctaag tgctctggat
2701 tctcaaagaa agctacaatt ttatgaagat aggcatcagc ttcctgcacc aaagtgggca
2761 gaattagcaa accttataaa taattgtatg gattatgaac cagatttcag gccttctttc
2821 agagccatca tacgagatct taacagtttg tttactccag attatgaact attaacagaa
2881 aatgacatgt taccaaatat gaggataggt gccctggggt tttctggtgc ctttgaagac
2941 cgggatccta cacagtttga agagagacat ttgaaatttc tacagcaact tggcaagggt
3001 aattttggga gtgtggagat gtgccggtat gaccctctac aggacaacac tggggaggtg
3061 gtcgctgtaa aaaagcttca gcatagtact gaagagcacc taagagactt tgaaagggaa
3121 attgaaatcc tgaaatccct acagcatgac aacattgtaa agtacaaggg agtgtgctac
3181 agtgctggtc ggcgtaatct aaaattaatt atggaatatt taccatatgg aagtttacga
3241 gactatcttc aaaaacataa agaacggata gatcacataa aacttctgca gtacacatct
3301 cagatatgca agggtatgga gtatcttggt acaaaaaggt atatccacag ggatctggca
3361 acgagaaata tattggtgga gaacgagaac agagttaaaa ttggagattt tgggttaacc
3421 aaagtcttgc cacaagacaa agaatactat aaagtaaaag aacctggtga aagtcccata
3481 ttctggtatg ctccagaatc actgacagag agcaagtttt ctgtggcctc agatgtttgg
3541 agctttggag tggttctgta tgaacttttc acatacattg agaagagtaa aagtccacca
3601 gcggaattta tgcgtatgat tggcaatgac aaacaaggac agatgatcgt gttccatttg
3661 atagaacttt tgaagaataa tggaagatta ccaagaccag atggatgccc agatgagatc
3721 tatatgatca tgacagaatg ctggaacaat aatgtaaatc aacgcccctc ctttagggat
3781 ctagctcttc gagtggatca aataagggat aacatggctg gatgaaagaa atgaccttca
3841 ttctgagacc aaagtagatt tacagaacaa agttttatat ttcacattgc tgtggactat
3901 tattacatat atcattatta tataaatcat gatgctagcc agcaaagatg tgaaaatatc
3961 tgctcaaaac tttcaaagtt tagtaagttt ttcttcatga ggccaccagt aaaagacatt
4021 aatgagaatt ccttagcaag gattttgtaa gaagtttctt aaacattgtc agttaacatc -continued

```
4081 actcttgtct ggcaaaagaa aaaaaataga ctttttcaac tcagcttttt gagacctgaa
4141 aaaattatta tgtaaatttt gcaatgttaa agatgcacag aatatgtatg tatagttttt
4201 accacagtgg atgtataata ccttggcatc ttgtgtgatg ttttacacac atgagggctg
4261 gtgttcatta atactgtttt ctaatttttc catagttaat ctataattaa ttacttcact
4321 atacaaacaa attaagatgt tcagataatt gaataagtac ctttgtgtcc ttgttcattt
4381 atatcgctgg ccagcattat aagcaggtgt atacttttag cttgtagttc catgtactgt
4441 aaatattttt cacataaagg gaacaaatgt ctagttttat ttgtatagga aatttccctg
4501 accctaaata atacattttg aaatgaaaca agcttacaaa gatataatct attttattat
4561 ggtttccctt gtatctattt gtggtgaatg tgttttttaa atggaactat ctccaaattt
4621 ttctaagact actatgaaca gttttctttt aaaatttttga gattaagaat gccaggaata
4681 ttgtcatcct ttgagctgct gactgccaat aacattcttc gatctctggg atttatgctc
4741 atgaactaaa tttaagctta agccataaaa tagattagat tgttttttaa aaatggatag
4801 ctcattaaga agtgcagcag gttaagaatt ttttcctaaa gactgtatat ttgaggggtt
4861 tcagaatttt gcattgcagt catagaagag atttatttcc tttttagagg ggaaatgagg
4921 taaataagta aaaaagtatg cttgttaatt ttattcaaga atgccagtag aaaattcata
4981 acgtgtatct ttaagaaaaa tgagcataca tcttaaatct tttcaattaa gtataagggg
5041 ttgttcgttg ttgtcatttg ttatagtgct actccacttt agacaccata gctaaaataa
5101 aatatggtgg gttttgtgtg tgtgtgtgtg tgtgtgtgtg tgtgtgtgtg tgtgttattt
5161 atacaaaact taaaatactt gctgttttga ttaaaaagaa aatagtttct tacttta
```

Human JAK3 mRNA (SEQ ID NO: 13)

```
   1 cacacaggaa ggagccgagt gggactttcc tctcgctgcc tcccggctct gcccgccctt
  61 cgaaagtcca gggtccctgc ccgctaggca agttgcactc atggcacctc caagtgaaga
 121 gacgcccctg atccctcagc gttcatgcag cctcttgtcc acggaggctg gtgccctgca
 181 tgtgctgctg cccgctcggg gccccgggcc cccccagcgc ctatctttct cctttgggga
 241 ccacttggct gaggacctgt gcgtgcaggc tgccaaggcc agcggcatcc tgcctgtgta
 301 ccactccctc tttgctctgg ccacggagga cctgtcctgc tggttccccc cgagccacat
 361 cttctccgtg gaggatgcca gcacccaagt cctgctgtac aggattcgct tttacttccc
 421 caattggttt gggctggaga agtgccaccg cttcgggcta cgcaaggatt tggccagtgc
 481 tatccttgac ctgccagtcc tggagcacct ctttgcccag caccgcagtg acctggtgag
 541 tgggcgcctc cccgtgggcc tcagtctcaa ggagcagggt gagtgtctca gcctggccgt
 601 gttggacctg gcccggatgg cgcgagagca ggcccagcgg ccgggagagc tgctgaagac
 661 tgtcagctac aaggcctgcc tacccccaag cctgcgcgac ctgatccagg gcctgagctt
 721 cgtgacgcgg aggcgtattc ggaggacggt gcgcagagcc ctgcgccgcg tggccgcctg
 781 ccaggcagac cggcactcgc tcatggccaa gtacatcatg gacctggagc ggctggatcc
 841 agccggggcc gccgagacct tccacgtggg cctccctggg gcccttggtg gccacgacgg
 901 gctggggctg ctccgcgtgg ctggtgacgg cggcatcgcc tggacccagg gagaacagga
 961 ggtcctccag ccctttctgcg actttccaga aatcgtagac attagcatca agcaggcccc
1021 gcgcgttggc ccggccggag agcaccgcct ggtcactgtt accaggacag acaaccagat
1081 tttagaggcc gagttcccag ggctgcccga ggctctgtcg ttcgtggcgc tcgtggacgg
1141 ctacttccgg ctgaccacgg actcccagca cttcttctgc aaggaggtgg caccgccgag
1201 gctgctggag gaagtggccg agcagtgcca cggccccatc actctggact ttgccatcaa
```

-continued 1261 caagctcaag actgggggct cacgtcctgg ctcctatgtt ctccgccgca gcccccagga
1321 ctttgacagc ttcctcctca ctgtctgtgt ccagaacccc cttggtcctg attataaggg
1381 ctgcctcatc cggcgcagcc ccacaggaac cttccttctg gttggcctca gccgacccca
1441 cagcagtctt cgagagctcc tggcaacctg ctgggatggg ggctgcacg tagatggggt
1501 ggcagtgacc ctcacttcct gctgtatccc cagacccaaa gaaaagtcca acctgatcgt
1561 ggtccagaga ggtcacagcc cacccacatc atccttggtt cagccccaat cccaatacca
1621 gctgagtcag atgacatttc acaagatccc tgctgacagc ctggagtggc atgagaacct
1681 gggccatggg tccttcacca agatttaccg gggctgtcgc catgaggtgg tggatgggga
1741 ggcccgaaag acagaggtgc tgctgaaggt catggatgcc aagcacaaga actgcatgga
1801 gtcattcctg gaagcagcga gcttgatgag ccaagtgtcg taccggcatc tcgtgctgct
1861 ccacggcgtg tgcatggctg gagacagcac catggtgcag gaatttgtac acctgggggc
1921 catagacatg tatctgcgaa aacgtggcca cctggtgcca gccagctgga agctgcaggt
1981 ggtcaaacag ctggcctacg ccctcaacta tctggaggac aaaggcctgc cccatggcaa
2041 tgtctctgcc cggaaggtgc tcctggctcg ggagggggct gatgggagcc cgcccttcat
2101 caagctgagt gaccctgggg tcagccccgc tgtgttaagc ctggagatgc tcaccgacag
2161 gatcccctgg gtggcccccg agtgtctccg ggaggcgcag acacttagct tggaagctga
2221 caagtggggc ttcggcgcca cggtctggga agtgtttagt ggcgtcacca tgcccatcag
2281 tgccctggat cctgctaaga aactccaatt ttatgaggac cggcagcagc tgccggcccc
2341 caagtggaca gagctggccc tgctgattca acagtgcatg gcctatgagc cggtccagag
2401 gccctccttc cgagccgtca ttcgtgacct caatagcctc atctcttcag actatgagct
2461 cctctcagac cccacacctg gtgccctggc acctcgtgat gggctgtgga atggtgccca
2521 gctctatgcc tgccaagacc ccacgatctt cgaggagaga cacctcaagt acatctcaca
2581 gctgggcaag ggcaactttg gcagcgtgga gctgtgccgc tatgacccgc taggcgacaa
2641 tacaggtgcc ctggtggccg tgaaacagct gcagcacagc gggccagacc agcagaggga
2701 ctttcagcgg gagattcaga tcctcaaagc actgcacagt gatttcattg tcaagtatcg
2761 tggtgtcagc tatggcccgg gccgccagag cctgcggctg gtcatggagt acctgcccag
2821 cggctgcttg cgcgacttcc tgcagcggca ccgcgcgcgc ctcgatgcca gccgcctcct
2881 tctctattcc tcgcagatct gcaagggcat ggagtacctg ggctcccgcc gctgcgtgca
2941 ccgcgacctg gccgcccgaa acatcctcgt ggagagcgag gcacacgtca agatcgctga
3001 cttcggccta gctaagctgc tgccgcttga caaagactac tacgtggtcc gcgagccagg
3061 ccagagcccc attttctggt atgcccccga atccctctcg gacaacatct tctctcgcca
3121 gtcagacgtc tggagcttcg gggtcgtcct gtacgagctc ttcacctact gcgacaaaag
3181 ctgcagcccc tcggccgagt tcctgcggat gatgggatgt gagcgggatg tccccgccct
3241 ctgccgcctc ttggaactgc tggaggaggg ccagaggctg ccggcgcctc ctgcctgccc
3301 tgctgaggtt cacgagctca tgaagctgtg ctgggcccct agcccacagg accggccatc
3361 attcagcgcc ctgggccccc agctggacat gctgtggagc ggaagccggg ggtgtgagac
3421 tcatgccttc actgctcacc cagagggcaa acaccactcc ctgtcctttt catagctcct
3481 gcccgcagac ctctggatta ggtctctgtt gactggctgt gtgaccttag gcccggagct
3541 gcccctctct gggcctcaga ggccttatga gggtcctcta cttcaggaac acccccatga
3601 cattgcattt ggggggctc ccgtggcctg tagaatagcc tgtggccttt gcaatttgtt -continued 3661 aaggttcaag acagatgggc atatgtgtca gtggggctct ctgagtcctg gcccaaagaa 3721 gcaaggaacc aaatttaaga ctctcgcatc ttcccaaccc cttaagccct ggcccccctga 3781 gtttcctttt ctgtctctct ctttttattt tttttatttt tatttttatt tttgagacag 3841 agcctcgctc tgttacccag ggtggagtgc agtggtgcga tctcggctca gtgcaacctc 3901 tgcttcccag gttcaagcga ttctcctgcc tcagcctccc gagtagctgg gattacaggt 3961 gtgcaccacc acacccggct aatttttttt atttttaata gagatgaggt ttcaccatga 4021 tggccaggct gatctcgaac tcctaacctc aagtgatcct cccacctcag cctcccaaag 4081 tgttggaata ataggcatga gccactgcac ccaggctttt ttttttttaa atttattatt 4141 attattttta agagacagga tcttgctacg ttgcccaggc tggtcttgaa ctcctgggct 4201 acagtgatcc tcctgcctta tcctcctaaa tagctgggac tacagcacct agttttgagt 4261 ttcctgtctt atttccaatg gggacattca tgtagctttt tttttttttt ttttttttgag 4321 acggagtctc gctctgtcgc ccaggctgga gtacagtggc gcaatctagg ctcactgcaa 4381 gctccgcctc ctgggttcac accattctct cgcctcagcc tcccaagtag ctgggactac 4441 aggcgcccgc caccacaccc ggctaatttt ttgtattttt agtagagacg gggtttcacc 4501 ttgttagcca ggatggtttc catctcctga cctcgtgatc tgcccgtctc ggcctcccaa 4561 agtgctggga ttacaggcat gagccactgc gcccggccct catgtagctt taaatgtatg 4621 atctgacttc tgctccccga tctctgtttc tctggaggaa gccaaggaca agagcagttg 4681 ctgtggctgg gactctgcct tttaggggag cccgtgtatc tctttgggat cctgaaaggg 4741 ggcaggaaag gctggggtcc cagtccaccc taatggtatc tgagtgtcct agggcttcag 4801 ttttcccacc tgtccaatgg gaccctttct gtcctcaccc tacaaggggc acaaagggat 4861 gacaccaaac ctggcaggaa cttttcacgc aatcaaggga aggaaaggca ttcctggcag 4921 agggaacagc atgccaagcg tgagaaggct cagagtaagg aggttaagag cccaagtatt 4981 ggagcctaca gttttgcccc ttccatgcag tgtgacagtg ggcaagttcc tttccctctc 5041 tgggtctcag ttctgtcccc tgcaaaatgg tcagagctta ccccttggct gtgcagggtc 5101 aactttctga ctggtgagag ggattctcat gcaggttaag cttctgctgc tcctcctcac 5161 ctgcaaagct tttctgccac ttttgcctcc ttggaaaact cttatccatc tctcaaaact 5221 ccagctacca catccttgca gccttccctc atataccccc actactactg tagccctgtc 5281 cttccctcca gccccactct ggccctgggg ctggggaagt gtctgtgtcc agctgtctcc 5341 cctgacctca gggttccttg ggggctgggc tgaggcctca gtacagaggg ggctctggaa 5401 atgtttgttg actgaataaa ggaattcagt ggaaaaaaaa aaaaaaaaa Human JAK3 mRNA (SEQ ID NO: 14)

1 ccctctgacc aggactgagg ggetttttct ctctgtgccc caggcaagtt gcactcatta 61 tggaattccg gcggcccgct aggcaagttg cactcatggc acctccaagt gaagagacgc 121 ccctgatccc tcagcgttca tgcagcctct tgtccacgga ggctggtgcc ctgcatgtgc 181 tgctgcccgc tcgggccccg gggccccccc agcgcctatc tttctccttt ggggaccact 241 tggctgagga cctgtgcgtg caggctgcca aggccagcgg catcctgcct gtgtaccact 301 ccctctttgc tctggccacg gaggacctgt cctgctggtt ccccccgagc cacatcttct 361 ccgtggagga tgccagcacc caagtcctgc tgtacaggat tcgcttttac ttccccaatt 421 ggtttgggct ggagaagtgc caccgcttcg ggctacgcaa ggatttggcc agtgctatcc 481 ttgacctgcc agtcctggag cacctctttg cccagcaccg cagtgacctg gtgagtgggc 541 gcctccccgt gggcctcagt ctcaaggagc agggtgagtg tctcagcctg gccgtgttgg -continued 601 acctggcccg gatggcgcga gagcaggccc agcggccggg agagctgctg aagactgtca
661 gctacaaggc ctgcctaccc ccaagcctgc gcgacctgat ccagggcctg agcttcgtga
721 cgcggagggc tattcggagg acggtgcgca gagccctgcc gcgcgtggcc gcctgccagg
781 cagaccggca ctcgctcatg gccaagtaca tcatggacct ggagcggctg gatccagccg
841 gggccgccga gaccttccac gtgggcctcc ctggggccct tggtggccac gacgggctgg
901 ggctgctccg cgtggctggt gacggcggca tcgcctggac ccagggagaa caggaggtcc
961 tccagccctt ctgcgacttt ccagaaatcg tagacattag catcaagcag gccccgcgcg
1021 ttggcccggc cggagagcac cgcctggtca ctgttaccag gacagacaac cagattttag
1081 aggccgagtt cccagggctg cccgaggctc tgtcgttcgt ggcgctcgtg gacggctact
1141 tccggctgac cacggactcc cagcacttct tctgcaagga ggtggcaccg ccgaggctgc
1201 tggaggaagt ggccgagcag tgccacggcc ccatcactct ggactttgcc atcaacaagc
1261 tcaagactgg ggctcacgt cctggctcct atgttctccg ccgcagcccc caggactttg
1321 acagcttcct cctcactgtc tgtgtccaga accccttgg tcctgattat aagggctgcc
1381 tcatccggcg cagccccaca ggaaccttcc ttctggttgg cctcagccga ccccacagca
1441 gtcttcgaga gctcctggca acctgctggg atgggggct gcacgtagat ggggtggcag
1501 tgaccctcac ttcctgctgt atccccagac ccaaagaaaa gtccaacctg atcgtggtcc
1561 agagaggtca cagcccaccc acatcatcct tggttcagcc ccaatcccaa taccagctga
1621 gtcagatgac atttcacaag atccctgctg acagcctgga gtggcatgag aacctgggcc
1681 atgggtcctt caccaagatt taccggggct gtcgccatga ggtggtggat ggggaggccc
1741 gaaagacaga ggtgctgctg aaggtcatgg atgccaagca caagaactgc atggagtcat
1801 tcctggaagc agcgagcttg atgagccaag tgtcgtaccg gcatctcgtg ctgctccacg
1861 gcgtgtgcat ggctggagac agcaccatgg tgcaggaatt tgtacacctg gggccatag
1921 acatgtatct gcgaaaacgt ggccacctgg tgccagccag ctggaagctg caggtggtca
1981 aacagctggc ctacgccctc aactatctgg aggacaaagg cctgccccat ggcaatgtct
2041 ctgcccggaa ggtgctcctg gctcgggagg gggctgatgg gagcccgccc ttcatcaagc
2101 tgagtgaccc tggggtcagc cccgctgtgt taagcctgga gatgctcacc gacaggatcc
2161 cctgggtggc ccccgagtgt ctccgggagg cgcagacact tagcttggaa gctgacaagt
2221 ggggcttcgg cgccacggtc tgggaagtgt ttagtggcgt caccatgccc atcagtgccc
2281 tggatcctgc taagaaactc caattttatg aggaccggca gcagctgccg gcccccaagt
2341 ggacagagct ggccctgctg attcaacagt gcatggccta tgagccggtc cagaggccct
2401 ccttccgagc cgtcattcgt gacctcaata gcctcatctc ttcagactat gagctcctct
2461 cagaccccac acctggtgcc ctggcacctc gtgatgggct gtggaatggt gcccagctct
2521 atgcctgcca agaccccacg atcttcgagg agagacacct caagtacatc tcacagctgg
2581 gcaagggcaa ctttggcagc gtggagctgt gccgctatga cccgctagcc cacaatacag
2641 gtgccctggt ggccgtgaaa cagctgcagc acagcgggcc agaccagcag agggactttc
2701 agcgggagat tcagatcctc aaagcactgc acagtgattt cattgtcaag tatcgtggtg
2761 tcagctatgg cccgggccgg ccagagctgc ggctggtcat ggagtacctg cccagcggct
2821 gcttgcgcga cttcctgcag cggcaccgcg cgcgcctcga tgccagccgc ctccttctct
2881 attcctcgca gatctgcaag ggcatggagt acctgggctc ccgccgctgc gtgcaccgcg
2941 acctggccgc ccgaaacatc ctcgtggaga gcgaggcaca cgtcaagatc gctgacttcg -continued 3001 gcctagctaa gctgctgccg cttgacaaag actactacgt ggtccgcgag ccaggccaga 3061 gccccatttt ctggtatgcc cccgaatccc tctcggacaa catcttctct cgccagtcag 3121 acgtctggag cttcggggtc gtcctgtacg agctcttcac ctactgcgac aaaagctgca 3181 gcccctcggc cgagttcctg cggatgatgg gatgtgagcg ggatgtcccc gccctctgcc 3241 gcctcttgga actgctggag gagggccaga ggctgccggc gcctcctgcc tgccctgctg 3301 aggttcacga gctcatgaag ctgtgctggg cccctagccc acaggaccgg ccatcattca 3361 gcgccctggg cccccagctg gacatgctgt ggagcggaag ccgggggtgt gagactcatg 3421 ccttcactgc tcacccagag ggcaaacacc actccctgtc cttttcatag ctcctgcccg 3481 cagacctctg gattaggtct ctgttgactg gctgtgtgac cttaggcccg gagctgcccc 3541 tctctgggcc tcagaggcct tatgagggtc ctctacttca ggaacacccc catgacattg 3601 catttggggg ggctcccgtg gcctgtagaa tagcctgtgg cctttgcaat ttgttaaggt 3661 tcaagacaga tgggcatatg tgtcagtggg gctctctgag tcctggccca aagaagcaag 3721 gaaccaaatt taagactctc gcatcttccc aaccccttaa gccctggccc cctgagtttc 3781 cttttctcgt ctctctcttt ttattttttt tatttttatt tttatttttg agacagagcc 3841 tcgctcgtta cccagggtgg agtgcagtgg tagcgatctc ggctcacagt gcaacctctg 3901 cttcccaggt tcaagcgatt ctcctgcctc agcctcccga gtagctggga ttacaggtgt 3961 gcaccaccac acccggctaa ttttttttat ttttaataga gatgaggttt caccatgatg 4021 gccaggctga tctcgaactc ctaacctcaa gtgatcctcc cacc Human TYK2 mRNA (SEQ ID NO: 15)

1 aagcagtagc tacccgcggg agcggggagg ggtccgggtt cgagcttgtg ttcccccgga 61 agggtgagtc tggacgcggg cgcggaagga gcgcggccgg aggtcctcag gaagaagccg 121 cggggactgg ctgcgcttga caggctgcac ttggatggga gcacctggtg cctcgggact 181 gctccgatgc ccgggtctgt gctgaatgtg taatatgcgg aactatattg aaacattaca 241 accatctttt gatggcaaca ccctgaggac ctcccttttc cagatgggga aactgaggcc 301 cagaattgct aagtggcttg cttgagttga cacagggagc tccaggactc accctcagct 361 gagccacctg ccgggagcat gcctctgcgc cactggggga tggccagggg cagtaagccc 421 gttggggatg gagcccagcc catggctgcc atgggaggcc tgaaggtgct tctgcactgg 481 gctggtccag gcggcgggga gccctgggtc actttcagtg agtcatcgct gacagctgag 541 gaagtctgca tccacattgc acataaagtt ggtatcactc ctccttgctt caatctcttt 601 gccctcttcg atgctcaggc ccaagtctgg ttgcccccaa accacatcct agagatcccc 661 agagatgcaa gcctgatgct atatttccgc ataaggtttt atttccggaa ctggcatggc 721 atgaatcctc gggaaccggc tgtgtaccgt tgtgggcccc caggaaccga ggcatcctca 781 gatcagacag cacaggggat gcaactcctg gacccagcct catttgagta cctctttgag 841 cagggcaagc atgagtttgt gaatgacgtg gcatcactgt gggagctgtc gaccgaggag 901 gagatccacc actttaagaa tgagagcctg ggcatggcct ttctgcacct ctgtcacctc 961 gctctccgcc atggcatccc cctggaggag gtggccaaga agaccagctt caaggactgc 1021 atcccgcgct ccttccgccg gcatatccgg cagcacagcg ccctgacccg gctgcgcctt 1081 cggaacgtct tccgcaggtt cctgcgggac ttccagccgg gccgactctc ccagcagatg 1141 gtcatggtca aatacctagc cacactcgag cggctggcac cccgcttcgg cacagagcgt 1201 gtgcccgtgt gccacctgag gctgctggcc caggccgagg gggagccctg ctacatccgg 1261 gacagtgggg tggcccctac agaccctggc cctgagtctg ctgctgggcc cccaacccac -continued 1321 gaggtgctgg tgacaggcac tggtggcatc cagtggtggc cagtagagga ggaggtgaac 1381 aaggaggagg gttctagtgg cagcagtggc aggaaccccc aagccagcct gtttgggaag 1441 aaggccaagg ctcacaaggc agtcggccag ccggcagaca ggccgcggga gccactgtgg 1501 gcctacttct gtgacttccg ggacatcacc cacgtggtgc tgaaagagca ctgtgtcagc 1561 atccaccggc aggacaacaa gtgcctggag ctgagcttgc cttcccgggc tgcggcgctg 1621 tccttcgtgt cgctggtgga cggctatttc cgcctgacgg ccgactccag ccactacctg 1681 tgccacgagg tggctccccc acggctggtg atgagcatcc gggatgggat ccacggaccc 1741 ctgctggagc catttgtgca ggccaagctg cggcccgagg acggcctgta cctcattcac 1801 tggagcacca gccaccccta ccgcctgatc ctcacagtgg cccagcgtag ccaggcacca 1861 gacggcatgc agagcttgcg gctccgaaag ttccccattg agcagcagga cggggccttc 1921 gtgctggagg gctggggccg gtccttcccc agcgttcggg aacttggggc tgccttgcag 1981 ggctgcttgc tgagggccgg ggatgactgc ttctctctgc gtcgctgttg cctgccccaa 2041 ccaggagaaa cctccaatct catcatcatg cggggggctc gggccagccc caggacactc 2101 aacctcagcc agctcagctt ccaccgggtt gaccagaagg agatcaccca gctgtcccac 2161 ttgggccagg gcacaaggac caacgtgtat gagggccgcc tgcgagtgga gggcagcggg 2221 gaccctgagg agggcaagat ggatgacgag gacccccctcg tgcctggcag ggaccgtggg 2281 caggagctac gagtggtgct caaagtgctg gaccctagtc accatgacat cgccctggcc 2341 ttctacgaga cagccagcct catgagccag gtctcccaca cgcacctggc cttcgtgcat 2401 ggcgtctgtg tgcgcggccc tgaaaatatc atggtgacag agtacgtgga gcacggaccc 2461 ctggatgtgt ggctgcggag ggagcggggc catgtgccca tggcttggaa gatggtggtg 2521 gcccagcagc tggccagcgc cctcagctac ctggagaaca agaacctggt tcatggtaat 2581 gtgtgtggcc ggaacatcct gctggcccgg ctggggttgg cagagggcac cagccccttc 2641 atcaagctga gtgatcctgg cgtgggcctg ggcgccctct ccagggagga gcgggtggag 2701 aggatcccct ggctggcccc cgaatgccta ccaggtgggg ccaacagcct aagcaccgcc 2761 atggacaagt gggggtttgg cgccaccctc ctggagatct gctttgacgg agaggcccct 2821 ctgcagagcc gcagtccctc cgagaaggag catttctacc agaggcagca ccggctgccc 2881 gagccctcct gcccacagct ggccacactc accagccagt gtctgaccta tgagccaacc 2941 cagaggccat cattccgcac catcctgcgt gacctcaccc ggctgcagcc ccacaatctt 3001 gctgacgtct tgactgtgaa cccggactca ccggcgtcgg accctacggt tttccacaag 3061 cgctatttga aaaagatccg agatctgggc gagggtcact tcggcaaggt cagcttgtac 3121 tgctacgatc cgaccaacga cggcactggc gagatggtgg cggtgaaagc cctcaaggca 3181 gactgcggcc cccagcaccg ctcgggctgg aagcaggaga ttgacattct gcgcacgctc 3241 taccacgagc acatcatcaa gtacaagggc tgctgcgagg accaaggcga gaagtcgctg 3301 cagctggtca tggagtacgt gcccctgggc agcctccgag actacctgcc ccggcacagc 3361 atcgggctgg cccagctgct gctcttcgcc cagcagatct gcgagggcat ggcctatctg 3421 cacgcgcagc actacatcca ccgagaccta gccgcgcgca acgtgctgct ggacaacgac 3481 aggctggtca agatcgggga ctttggccta gccaaggccg tgcccgaagg ccacgagtac 3541 taccgcgtgc gcgaggatgg ggacagcccc gtgttctggt atgccccaga gtgcctgaag 3601 gagtataagt tctactatgc gtcagatgtc tggtccttcg ggtgaccct gtatgagctg 3661 ctgacgcact gtgactccag ccagagcccc cccacgaaat tccttgagct cataggcatt -continued

```
3721 gctcagggtc agatgacagt tctgagactc actgagttgc tggaacgagg ggagaggctg

3781 ccacggcccg acaaatgtcc ctgtgaggtc tatcatctca tgaagaactg ctgggagaca

3841 gaggcgtcct ttcgcccaac cttcgagaac ctcataccca ttctgaagac agtccatgag

3901 aagtaccaag gccaggcccc ttcagtgttc agcgtgtgct gaggcacaat ggcagccctg

3961 cctgggagga ctggaccagg cagtggctgc agagggagcc tcctgctccc tgctccagga

4021 tgaaaccaag agggggatgt cagcctcacc cacaccgtgt gccttactcc tgtctagaga

4081 ccccacctct gtgaacttat ttttctttct tggccgtgag cctaaccatg atcttgaggg

4141 acccaacatt tgtaggggca ctaatccagc ccttaaatcc cccagcttcc aaacttgagg

4201 cccaccatct ccaccatctg gtaataaact catgttttct ctgctggaaa aaaaaaaaaa

4261 aa
```

In some embodiments, an antisense nucleic acid molecule is complementary to all or part of a non-coding region of the coding strand of a nucleotide sequence encoding a JAK1, JAK2, JAK3, or TYK2 protein. Non-coding regions (5' and 3' untranslated regions) are the 5' and 3' sequences that flank the coding region in a gene and are not translated into amino acids.

Based upon the sequences disclosed herein, one of skill in the art can easily choose and synthesize any of a number of appropriate antisense nucleic acids to target a nucleic acid encoding a JAK1, JAK2, JAK3, or TYK2 protein described herein. Antisense nucleic acids targeting a nucleic acid encoding a JAK1, JAK2, JAK3, or TYK2 protein can be designed using the software available at the Integrated DNA Technologies website.

In some embodiments, an antisense nucleic acid is about 5, 10, 15, 20, 25, 30, 35, 40, 45, or 50 nucleotides or more in length. An antisense oligonucleotide can be constructed using chemical synthesis and enzymatic ligation reactions using procedures known in the art. For example, an antisense nucleic acid can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used.

Examples of modified nucleotides which can be used to generate an antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest).

The antisense nucleic acid molecules described herein can be prepared in vitro and administered to a mammal, e.g., a human. Alternatively, they can be generated in situ such that they hybridize with or bind to cellular mRNA and/or genomic DNA encoding a JAK1, JAK2, JAK3, or TYK2 protein to thereby inhibit expression, e.g., by inhibiting transcription and/or translation. The hybridization can be by conventional nucleotide complementarities to form a stable duplex, or, for example, in the case of an antisense nucleic acid molecule that binds to DNA duplexes, through specific interactions in the major groove of the double helix. The antisense nucleic acid molecules can be delivered to a mammalian cell using a vector (e.g., a lentivirus, a retrovirus, or an adenovirus vector).

In some embodiments, an antisense nucleic acid is an α-anomeric nucleic acid molecule. An α-anomeric nucleic acid molecule forms specific double-stranded hybrids with complementary RNA in which, contrary to the usual, β-units, the strands run parallel to each other (Gaultier et al., *Nucleic Acids Res.* 15:6625-6641, 1987). The antisense nucleic acid can also comprise a 2'-O-methylribonucleotide (Inoue et al., *Nucleic Acids Res.* 15:6131-6148, 1987) or a chimeric RNA-DNA analog (Inoue et al., *FEBS Lett.* 215: 327-330, 1987).

In some embodiments, an inhibitory nucleic acid is a ribozyme that has specificity for a nucleic acid encoding a JAK1, JAK2, JAK3, or TYK2 protein (e.g., specificity for a JAK1, JAK2, JAK3, or TYK2 mRNA, e.g., specificity for any one of SEQ ID NOs: 1-15). Ribozymes are catalytic RNA molecules with ribonuclease activity that are capable of cleaving a single-stranded nucleic acid, such as an mRNA, to which they have a complementary region. Thus, ribozymes (e.g., hammerhead ribozymes (described in Haselhoff and Gerlach, *Nature* 334:585-591, 1988)) can be used to catalytically cleave mRNA transcripts to thereby inhibit translation of the protein encoded by the mRNA. A ribozyme having specificity for a JAK1, JAK2, JAK3, or TYK2 mRNA can be designed based upon the nucleotide sequence of any of the JAK1, JAK2, JAK3, or TYK2 mRNA sequences disclosed herein. For example, a derivative of a Tetrahymena L-19 IVS RNA can be constructed in which the nucleotide sequence of the active site is complementary to the nucleotide sequence to be cleaved in a JAK1, JAK2, JAK3, or TYK2 mRNA (see, e.g., U.S. Pat. Nos. 4,987,071 and 5,116,742). Alternatively, a JAK1, JAK2, JAK3, or TYK2 mRNA can be used to select a catalytic RNA having a specific ribonuclease activity from a pool of RNA molecules. See, e.g., Bartel et al., *Science* 261:1411-1418, 1993.

In some embodiments, an inhibitory nucleic acid is a nucleic acid molecule that forms triple helical structures. For example, expression of a JAK1, JAK2, JAK3, or JAK4 polypeptide can be inhibited by targeting nucleotide sequences complementary to the regulatory region of the gene encoding the JAK1, JAK2, JAK3, or TYK2 polypeptide (e.g., the promoter and/or enhancer, e.g., a sequence that is at least 1 kb, 2 kb, 3 kb, 4 kb, or 5 kb upstream of the transcription initiation start state) to form triple helical structures that prevent transcription of the gene in target cells. See generally Helene, *Anticancer Drug Des.* 6(6):569-84, 1991; Helene, *Ann. N.Y. Acad. Sci.* 660:27-36, 1992; and Maher, *Bioassays* 14(12):807-15, 1992.

In various embodiments, inhibitory nucleic acids can be modified at the base moiety, sugar moiety, or phosphate backbone to improve, e.g., the stability, hybridization, or solubility of the molecule. For example, the deoxyribose phosphate backbone of the nucleic acids can be modified to generate peptide nucleic acids (see, e.g., Hyrup et al., *Bioorganic Medicinal Chem.* 4(1):5-23, 1996). Peptide nucleic acids (PNAs) are nucleic acid mimics, e.g., DNA mimics, in which the deoxyribose phosphate backbone is replaced by a pseudopeptide backbone and only the four natural nucleobases are retained. The neutral backbone of PNAs allows for specific hybridization to DNA and RNA under conditions of low ionic strength. The synthesis of PNA oligomers can be performed using standard solid phase peptide synthesis protocols (see, e.g., Perry-O'Keefe et al., *Proc. Natl. Acad. Sci. U.S.A.* 93:14670-675, 1996). PNAs can be used as antisense or antigene agents for sequence-specific modulation of gene expression by, e.g., inducing transcription or translation arrest or inhibiting replication.

PNAs can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras can be generated which may combine the advantageous properties of PNA and DNA. Such chimeras allow DNA recognition enzymes, e.g., RNAse H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation.

The synthesis of PNA-DNA chimeras can be performed as described in Finn et al., *Nucleic Acids Res.* 24:3357-63, 1996. For example, a DNA chain can be synthesized on a solid support using standard phosphoramidite coupling chemistry and modified nucleoside analogs. Compounds such as 5'-(4-methoxytrityl)amino-5'-deoxy-thymidine phosphoramidite can be used as a link between the PNA and the 5' end of DNA (Mag et al., *Nucleic Acids Res.* 17:5973-88, 1989). PNA monomers are then coupled in a stepwise manner to produce a chimeric molecule with a 5' PNA segment and a 3' DNA segment (Finn et al., *Nucleic Acids Res.* 24:3357-63, 1996). Alternatively, chimeric molecules can be synthesized with a 5' DNA segment and a 3' PNA segment (Peterser et al., *Bioorganic Med. Chem. Lett.* 5:1119-11124, 1975).

In some embodiments, the inhibitory nucleic acids include other appended groups such as peptides, or agents facilitating transport across the cell membrane (see, Letsinger et al., *Proc. Natl. Acad. Sci. U.S.A.* 86:6553-6556, 1989; Lemaitre et al., *Proc. Natl. Acad. Sci. U.S.A.* 84:648-652, 1989; and WO 88/09810). In addition, the inhibitory nucleic acids can be modified with hybridization-triggered cleavage agents (see, e.g., Krol et al., *Bio/Techniques* 6:958-976, 1988) or intercalating agents (see, e.g., Zon, Pharm. Res., 5:539-549, 1988). To this end, the oligonucleotide may be conjugated to another molecule, e.g., a peptide, hybridization triggered cross-linking agent, transport agent, hybridization-triggered cleavage agent, etc.

In some embodiments, expression of a JAK1, JAK2, JAK3, or TYK2 mRNA is decreased in a mammalian cell by RNA interference (RNAi). RNAi is a process in which mRNA is degraded in host cells. To inhibit an mRNA, double-stranded RNA (dsRNA) corresponding to a portion of the gene to be silenced (e.g., a gene encoding a JAK1, JAK2, JAK3, or TYK2 polypeptide) is introduced into a mammalian cell. The dsRNA is digested into 21-23 nucleotide-long duplexes called short interfering RNAs (or siRNAs), which bind to a nuclease complex to form what is known as the RNA-induced silencing complex (or RISC). The RISC targets the homologous transcript by base pairing interactions between one of the siRNA strands and the endogenous mRNA. It then cleaves the mRNA about 12 nucleotides from the 3' terminus of the siRNA (see Sharp et al., *Genes Dev.* 15:485-490, 2001, and Hammond et al., *Nature Rev. Gen.* 2:110-119, 2001).

RNA-mediated gene silencing can be induced in a mammalian cell in many ways, e.g., by enforcing endogenous expression of RNA hairpins (see, Paddison et al., *Proc. Natl. Acad. Sci. U.S.A.* 99:1443-1448, 2002) or, as noted above, by transfection of small (21-23 nt) dsRNA (reviewed in Caplen, *Trends Biotech.* 20:49-51, 2002). Methods for modulating gene expression with RNAi are described, e.g., in U.S. Pat. No. 6,506,559 and US 2003/0056235, which are hereby incorporated by reference.

Standard molecular biology techniques can be used to generate siRNAs. Short interfering RNAs can be chemically synthesized, recombinantly produced, e.g., by expressing RNA from a template DNA, such as a plasmid, or obtained from commercial vendors, such as Dharmacon. The RNA used to mediate RNAi can include synthetic or modified nucleotides, such as phosphorothioate nucleotides. Methods of transfecting cells with siRNA or with plasmids engineered to make siRNA are routine in the art.

The siRNA molecules used to decrease expression of a JAK1, JAK2, JAK3, or TYK2 mRNA can vary in a number of ways. For example, they can include a 3' hydroxyl group and strands of 21, 22, or 23 consecutive nucleotides. They can be blunt ended or include an overhanging end at either the 3' end, the 5' end, or both ends. For example, at least one strand of the RNA molecule can have a 3' overhang from about 1 to about 6 nucleotides (e.g., 1-5, 1-3, 2-4, or 3-5 nucleotides (whether pyrimidine or purine nucleotides) in length. Where both strands include an overhang, the length of the overhangs may be the same or different for each strand.

To further enhance the stability of the RNA duplexes, the 3' overhangs can be stabilized against degradation (by, e.g., including purine nucleotides, such as adenosine or guanosine nucleotides or replacing pyrimidine nucleotides by modified analogues (e.g., substitution of uridine 2-nucleotide 3' overhangs by 2'-deoxythymidine is tolerated and does not affect the efficiency of RNAi). Any siRNA can be used in the methods of decreasing a JAK1, JAK2, JAK3, or TYK2 mRNA, provided it has sufficient homology to the target of interest (e.g., a sequence present in any one of SEQ ID NOs: 1-15, e.g., a target sequence encompassing the translation start site or the first exon of the mRNA). There is no upper limit on the length of the siRNA that can be used (e.g., the siRNA can range from about 21 base pairs of the gene to the full length of the gene or more (e.g., about 20 to about 30 base pairs, about 50 to about 60 base pairs, about 60 to about 70 base pairs, about 70 to about 80 base pairs, about 80 to about 90 base pairs, or about 90 to about 100 base pairs).

Non-limiting examples of JAK inhibitors that are siRNAs are described in Cook et al., *Blood* 123:2826-2837, 2014. Non-limiting examples of JAK inhibitors that are short hairpin RNAs (shRNAs) are described in Koppikar et al., *Nature* 489(7414):155-159, 2012).

In certain embodiments, a therapeutically effective amount of an inhibitory nucleic acid targeting a nucleic acid encoding a JAK1, JAK2, JAK3, or TYK2 protein is administered to a subject (e.g., a human subject) in need thereof.

In some embodiments, the inhibitory nucleic acid is about 10 nucleotides to about 40 nucleotides (e.g., about 10 to about 30 nucleotides, about 10 to about 25 nucleotides, about 10 to about 20 nucleotides, about 10 to about 15 nucleotides, 10 nucleotides, 11 nucleotides, 12 nucleotides, 13 nucleotides, 14 nucleotides, 15 nucleotides, 16 nucleotides, 17 nucleotides, 18 nucleotides, 19 nucleotides, 20 nucleotides, 21 nucleotides, 22 nucleotides, 23 nucleotides, 24 nucleotides, 25 nucleotides, 26 nucleotides, 27 nucleotides, 28 nucleotides, 29 nucleotides, 30 nucleotides, 31 nucleotides, 32 nucleotides, 33 nucleotides, 34 nucleotides, 35 nucleotides, 36 nucleotides, 37 nucleotides, 38 nucleotides, 39 nucleotides, or 40 nucleotides) in length. One skilled in the art will appreciate that inhibitory nucleic acids may comprise at least one modified nucleic acid at either the 5' or 3'end of DNA or RNA.

As is known in the art, the term "thermal melting point (Tm)" refers to the temperature, under defined ionic strength, pH, and inhibitory nucleic acid concentration, at which 50% of the inhibitory nucleic acids complementary to the target sequence hybridize to the target sequence at equilibrium. In some embodiments, an inhibitory nucleic acid can bind specifically to a target nucleic acid under stingent conditions, e.g., those in which the salt concentration is at least about 0.01 to 1.0 M Na ion concentration (or other salts) at pH 7.0 to 8.3 and the temperature is at least about 30° C. for short oligonucleotides (e.g., 10 to 50 nucleotide). Stringent conditions can also be achieved with the addition of destabilizing agents such as formamide.

In some embodiments of any of the inhibitory nucleic acids described herein, the inhibitory nucleic acid binds to a target nucleic acid (e.g., a nucleic acid encoding JAK1, JAK2, JAK3, or TYK2) with a $T_m$ of greater than 20° C., greater than 22° C., greater than 24° C., greater than 26° C., greater than 28° C., greater than 30° C., greater than 32° C., greater than 34° C., greater than 36° C., greater than 38° C., greater than 40° C., greater than 42° C., greater than 44° C., greater than 46° C., greater than 48° C., greater than 50° C., greater than 52° C., greater than 54° C., greater than 56° C., greater than 58° C., greater than 60° C., greater than 62° C., greater than 64° C., greater than 66° C., greater than 68° C., greater than 70° C., greater than 72° C., greater than 74° C., greater than 76° C., greater than 78° C., or greater than 80° C., e.g., as measured in phosphate buffered saline using a UV spectrophotometer.

In some embodiments of any of the inhibitor nucleic acids described herein, the inhibitory nucleic acid binds to a target nucleic acid (e.g., a nucleic acid encoding a JAK1, JAK2, JAK3, or TYK2) with a Tm of about 20° C. to about 80° C., about 78° C., about 76° C., about 74° C., about 72° C., about 70° C., about 68° C., about 66° C., about 64° C., about 62° C., about 60° C., about 58° C., about 56° C., about 54° C., about 52° C., about 50° C., about 48° C., about 46° C., about 44° C., about 42° C., about 40° C., about 38° C., about 36° C., about 34° C., about 32° C., about 30° C., about 28° C., about 26° C., about 24° C., or about 22° C. (inclusive); about 22° C. to about 80° C., about 78° C., about 76° C., about 74° C., about 72° C., about 70° C., about 68° C., about 66° C., about 64° C., about 62° C., about 60° C., about 58° C., about 56° C., about 54° C., about 52° C., about 50° C., about 48° C., about 46° C., about 44° C., about 42° C., about 40° C., about 38° C., about 36° C., about 34° C., about 32° C., about 30° C., about 28° C., about 26° C., or about 24° C. (inclusive); about 24° C. to about 80° C., about 78° C., about 76° C., about 74° C., about 72° C., about 70° C., about 68° C., about 66° C., about 64° C., about 62° C., about 60° C., about 58° C., about 56° C., about 54° C., about 52° C., about 50° C., about 48° C., about 46° C., about 44° C., about 42° C., about 40° C., about 38° C., about 36° C., about 34° C., about 32° C., about 30° C., about 28° C., or about 26° C. (inclusive); about 26° C. to about 80° C., about 78° C., about 76° C., about 74° C., about 72° C., about 70° C., about 68° C., about 66° C., about 64° C., about 62° C., about 60° C., about 58° C., about 56° C., about 54° C., about 52° C., about 50° C., about 48° C., about 46° C., about 44° C., about 42° C., about 40° C., about 38° C., about 36° C., about 34° C., about 32° C., about 30° C., or about 28° C. (inclusive); about 28° C. to about 80° C., about 78° C., about 76° C., about 74° C., about 72° C., about 70° C., about 68° C., about 66° C., about 64° C., about 62° C., about 60° C., about 58° C., about 56° C., about 54° C., about 52° C., about 50° C., about 48° C., about 46° C., about 44° C., about 42° C., about 40° C., about 38° C., about 36° C., about 34° C., about 32° C., or about 30° C. (inclusive); about 30° C. to about 80° C., about 78° C., about 76° C., about 74° C., about 72° C., about 70° C., about 68° C., about 66° C., about 64° C., about 62° C., about 60° C., about 58° C., about 56° C., about 54° C., about 52° C., about 50° C., about 48° C., about 46° C., about 44° C., about 42° C., about 40° C., about 38° C., about 36° C., about 34° C., or about 32° C. (inclusive); about 32° C. to about 80° C., about 78° C., about 76° C., about 74° C., about 72° C., about 70° C., about 68° C., about 66° C., about 64° C., about 62° C., about 60° C., about 58° C., about 56° C., about 54° C., about 52° C., about 50° C., about 48° C., about 46° C., about 44° C., about 42° C., about 40° C., about 38° C., about 36° C., or about 34° C. (inclusive); about 34° C. to about 80° C., about 78° C., about 76° C., about 74° C., about 72° C., about 70° C., about 68° C., about 66° C., about 64° C., about 62° C., about 60° C., about 58° C., about 56° C., about 54° C., about 52° C., about 50° C., about 48° C., about 46° C., about 44° C., about 42° C., about 40° C., about 38° C., or about 36° C. (inclusive); about 36° C. to about 80° C., about 78° C., about 76° C., about 74° C., about 72° C., about 70° C., about 68° C., about 66° C., about 64° C., about 62° C., about 60° C., about 58° C., about 56° C., about 54° C., about 52° C., about 50° C., about 48° C., about 46° C., about 44° C., about 42° C., about 40° C., or about 38° C. (inclusive); about 38° C. to about 80° C., about 78° C., about 76° C., about 74° C., about 72° C., about 70° C., about 68° C., about 66° C., about 64° C., about 62° C., about 60° C., about 58° C., about 56° C., about 54° C., about 52° C., about 50° C., about 48° C., about 46° C., about 44° C., about 42° C., or about 40° C. (inclusive); about 40° C. to about 80° C., about 78° C., about 76° C., about 74° C., about 72° C., about 70° C., about 68° C., about 66° C., about 64° C., about 62° C., about 60° C., about 58° C., about 56° C., about 54° C., about 52° C., about 50° C., about 48° C., about 46° C., about 44° C., or about 42° C. (inclusive); about 42° C. to about 80°

C., about 78° C., about 76° C., about 74° C., about 72° C., about 70° C., about 68° C., about 66° C., about 64° C., about 62° C., about 60° C., about 58° C., about 56° C., about 54° C., about 52° C., about 50° C., about 48° C., about 46° C., or about 44° C. (inclusive); about 44° C. to about 80° C., about 78° C., about 76° C., about 74° C., about 72° C., about 70° C., about 68° C., about 66° C., about 64° C., about 62° C., about 60° C., about 58° C., about 56° C., about 54° C., about 52° C., about 50° C., about 48° C., or about 46° C. (inclusive); about 46° C. to about 80° C., about 78° C., about 76° C., about 74° C., about 72° C., about 70° C., about 68° C., about 66° C., about 64° C., about 62° C., about 60° C., about 58° C., about 56° C., about 54° C., about 52° C., about 50° C., or about 48° C. (inclusive); about 48° C. to about 80° C., about 78° C., about 76° C., about 74° C., about 72° C., about 70° C., about 68° C., about 66° C., about 64° C., about 62° C., about 60° C., about 58° C., about 56° C., about 54° C., about 52° C., or about 50° C. (inclusive); about 50° C. to about 80° C., about 78° C., about 76° C., about 74° C., about 72° C., about 70° C., about 68° C., about 66° C., about 64° C., about 62° C., about 60° C., about 58° C., about 56° C., about 54° C., or about 52° C. (inclusive); about 52° C. to about 80° C., about 78° C., about 76° C., about 74° C., about 72° C., about 70° C., about 68° C., about 66° C., about 64° C., about 62° C., about 60° C., about 58° C., about 56° C., or about 54° C. (inclusive); about 54° C. to about 80° C., about 78° C., about 76° C., about 74° C., about 72° C., about 70° C., about 68° C., about 66° C., about 64° C., about 62° C., about 60° C., about 58° C., or about 56° C. (inclusive); about 56° C. to about 80° C., about 78° C., about 76° C., about 74° C., about 72° C., about 70° C., about 68° C., about 66° C., about 64° C., about 62° C., about 60° C., or about 58° C. (inclusive); about 58° C. to about 80° C., about 78° C., about 76° C., about 74° C., about 72° C., about 70° C., about 68° C., about 66° C., about 64° C., about 62° C., or about 60° C. (inclusive); about 60° C. to about 80° C., about 78° C., about 76° C., about 74° C., about 72° C., about 70° C., about 68° C., about 66° C., about 64° C., or about 62° C. (inclusive); about 62° C. to about 80° C., about 78° C., about 76° C., about 74° C., about 72° C., about 70° C., about 68° C., about 66° C., or about 64° C. (inclusive); about 64° C. to about 80° C., about 78° C., about 76° C., about 74° C., about 72° C., about 70° C., about 68° C., or about 66° C. (inclusive); about 66° C. to about 80° C., about 78° C., about 76° C., about 74° C., about 72° C., about 70° C., or about 68° C. (inclusive); about 68° C. to about 80° C., about 78° C., about 76° C., about 74° C., about 72° C., or about 70° C. (inclusive); about 70° C. to about 80° C., about 78° C., about 76° C., about 74° C., or about 72° C. (inclusive); about 72° C. to about 80° C., about 78° C., about 76° C., or about 74° C. (inclusive); about 74° C. to about 80° C., about 78° C., or about 76° C. (inclusive); about 76° C. to about 80° C. or about 78° C. (inclusive); or about 78° C. to about 80° C. (inclusive), In some embodiments, the inhibitory nucleic acid is formulated in a nanoparticle (e.g., a nanoparticle including one or more synthetic polymers, e.g., Patil et al., *Pharmaceutical Nanotechnol.* 367:195-203, 2009; Yang et al., *ACS Appl. Mater. Interfaces, doi:* 10.1021/acsami.6b16556, 2017; Perepelyuk et al., *Mol. Ther. Nucleic Acids* 6:259-268, 2017). In some embodiments, the nanoparticle can be a mucoadhesive particle (e.g., nanoparticles having a positively-charged exterior surface) (Andersen et al., *Methods Mol. Biol.* 555:77-86, 2009). In some embodiments, the nanoparticle can have a neutrally-charged exterior surface.

In some embodiments, the inhibitory nucleic acid is formulated, e.g., as a liposome (Buyens et al., *J. Control Release* 158(3): 362-370, 2012; Scarabel et al., *Expert Opin. Drug Deliv.* 17:1-14, 2017), a micelle (e.g., a mixed micelle) (Tangsangasaksri et al., *BioMacromolecules* 17:246-255, 2016; Wu et al., *Nanotechnology, doi:* 10.1088/1361-6528/aa6519, 2017), a microemulsion (WO 11/004395), a nanoemulsion, or a solid lipid nanoparticle (Sahay et al., *Nature Biotechnol.* 31:653-658, 2013; and Lin et al., *Nanomedicine* 9(1):105-120, 2014). Additional exemplary structural features of inhibitory nucleic acids and formulations of inhibitory nucleic acids are described in US 2016/0090598.

In some embodiments, a pharmaceutical composition includes a sterile saline solution and one or more inhibitory nucleic acid (e.g., any of the inhibitory nucleic acids described herein). In some examples, a pharmaceutical composition consists of a sterile saline solution and one or more inhibitory nucleic acid (e.g., any of the inhibitory nucleic acids described herein). In certain embodiments, the sterile saline is a pharmaceutical grade saline. In certain embodiments, a pharmaceutical composition can include one or more inhibitory nucleic acid (e.g., any of the inhibitory nucleic acids described herein) and sterile water. In certain embodiments, a pharmaceutical composition consists of one or more inhibitory nucleic acid (e.g., any of the inhibitory nucleic acids described herein) and sterile water. In certain embodiments, a pharmaceutical composition includes one or more inhibitory nucleic acid (e.g., any of the inhibitory nucleic acids described herein) and phosphate-buffered saline (PBS). In certain embodiments, a pharmaceutical composition consists of one or more inhibitory nucleic acids (e.g., any of the inhibitory nucleic acids described herein) and sterile phosphate-buffered saline (PBS). In some examples, the sterile saline is a pharmaceutical grade PBS.

In certain embodiments, one or more inhibitory nucleic acids (e.g., any of the inhibitory nucleic acids described herein) is admixed with pharmaceutically acceptable active and/or inert substances for the preparation of pharmaceutical compositions or formulations. Compositions and methods for the formulation of pharmaceutical compositions depend on a number of criteria, including, but not limited to, route of administration, extent of disease, or dose to be administered.

Pharmaceutical compositions including one or more inhibitory nucleic acids encompass any pharmaceutically acceptable salts, esters, or salts of such esters. Non-limiting examples of pharmaceutical compositions include pharmaceutically acceptable salts of inhibitory nucleic acids. Suitable pharmaceutically acceptable salts include, but are not limited to, sodium and potassium salts.

Also provided herein are prodrugs that include additional nucleosides at one or both ends of an inhibitory nucleic acid which are cleaved by endogenous nucleases within the body, to form the active inhibitory nucleic acid.

In some embodiments, lipid moieties are used to formulate an inhibitory nucleic acid. In certain such methods, the inhibitory nucleic acid is introduced into preformed liposomes or lipoplexes made of mixtures of cationic lipids and neutral lipids. In certain methods, inhibitory nucleic acid complexes with mono- or poly-cationic lipids are formed without the presence of a neutral lipid. In certain embodiments, a lipid moiety is selected to increase distribution of an inhibitory nucleic acid to a particular cell or tissue in a mammal. In some examples, a lipid moiety is selected to increase distribution of an inhibitory nucleic acid to fat tissue in a mammal. In certain embodiments, a lipid moiety is selected to increase distribution of an inhibitory nucleic acid to muscle tissue.

In certain embodiments, pharmaceutical compositions provided herein comprise one or more inhibitory nucleic acid and one or more excipients. In certain such embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In some examples, a pharmaceutical composition provided herein includes liposomes and emulsions. Liposomes and emulsions can be used to formulate hydrophobic compounds. In some examples, certain organic solvents such as dimethylsulfoxide are used.

In some examples, a pharmaceutical composition provided herein includes one or more tissue-specific delivery molecules designed to deliver one or more inhibitory nucleic acids to specific tissues or cell types in a mammal. For example, a pharmaceutical composition can include liposomes coated with a tissue-specific antibody.

In some embodiments, a pharmaceutical composition provided herein includes a co-solvent system. Examples of such co-solvent systems include benzyl alcohol, a nonpolar surfactant, a water-miscible organic polymer, and an aqueous phase. A non-limiting example of such a co-solvent system is the VPD co-solvent system, which is a solution of absolute ethanol comprising 3% w/v benzyl alcohol, 8% w/v of the nonpolar surfactant Polysorbate 80™ and 65% w/v polyethylene glycol 300. As can be appreciated, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In some examples, a pharmaceutical composition is formulated for oral administration. In some examples, pharmaceutical compositions are formulated for buccal administration.

In some examples, a pharmaceutical composition is formulated for administration by injection (e.g., intravenous, subcutaneous, intramuscular, etc.). In some of these embodiments, a pharmaceutical composition includes a carrier and is formulated in aqueous solution, such as water or physiologically compatible buffers such as Hanks's solution, Ringer's solution, or physiological saline buffer. In some examples, other ingredients are included (e.g., ingredients that aid in solubility or serve as preservatives). In some examples, injectable suspensions are prepared using appropriate liquid carriers, suspending agents, and the like. Some pharmaceutical compositions for injection are formulated in unit dosage form, e.g., in ampoules or in multi-dose containers. Some pharmaceutical compositions for injection are suspensions, solutions, or emulsions in oily or aqueous vehicles, and may contain formulatory agents such as suspending, stabilizing, and/or dispersing agents. Solvents suitable for use in pharmaceutical compositions for injection include, but are not limited to, lipophilic solvents and fatty oils, such as sesame oil, synthetic fatty acid esters, such as ethyl oleate or triglycerides, and liposomes.

Small Molecule Inhibitors of Janus Kinase or Other Protein Kinases

Ini some embodiments, the protein kinase inhibitor is a small molecule JAK inhibitor.

In some embodiments, the JAK inhibitor is filgotinib (GLPG0634, G146034) (Vermeire et al., Lancet 389 (10066):266-275, 2017; Menet et al., *J. Med. Chem.* 57(22): 9323-9342, 2014; Van Rompaey et al., *J. Immunol.* 191(7): 3568-3577, 2013; Namour et al., *Clin. Pharmacokinet.* 54(8):859-874, 2015), having the following structure:

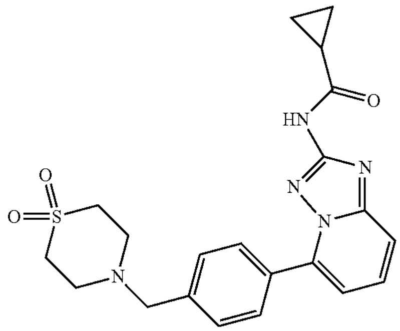

;

or a pharmaceutically acceptable salt thereof.

In some embodiments, the JAK inhibitor is a metabolite of filgotinib, such as 4-(4-(2-amino-[1,2,4]triazolo[1,5-a] pyridin-5-yl)benzyl)thiomorpholine-1,1-dioxide (WO2018087202A1, US2016/0296529A1, U.S. Pat. No. 9,284,311B2), having the following structure:

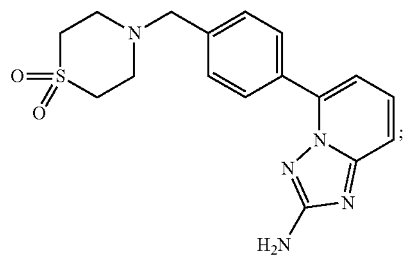 [SMILES: Nc1nc2cccc(-c3ccc(CN4CCS(=O)(=O)CC4)cc3)n2n1]

;

or a pharmaceutically acceptable salt thereof.

In some embodiments, the JAK inhibitor is a mixture of filgotinib and the foregoing metabolite thereof (US 2016/0296529A1, U.S. Pat. No. 9,284,311B2).

In some embodiments, the JAK inhibitor is solcitinib (GSK2586184, GLPG0778; Kahl et al., Lupus 25(13):1420-1430, 2016; Ludbrook et al., *Br. J. Dermatol.* 174(5):985-995, 2016; van Vollenhoven et al., Lupus 24(6):648-649, 2015), having the following structure:

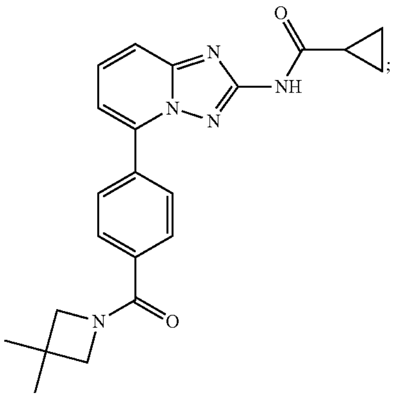 [SMILES: CC1(C)CN(C(=O)c2ccc(-c3cccc4nc(NC(=O)C5CC5)nn34)cc2)C1]

;

or a pharmaceutically acceptable salt thereof.

In some embodiments, the JAK inhibitor is oclacitinib (PF03394197, Apoquel®) (Gonzales et al., *J. Vet. Pharmacol. Ther.* 37(4):317-324, 2014; Collard et al., *J. Vet. Pharmacol. Ther.* 37(3):279-285, 2014; Cosgrove et al., *Vet. Dermatol.* 24(6):587-597, 2013), having the following structure:

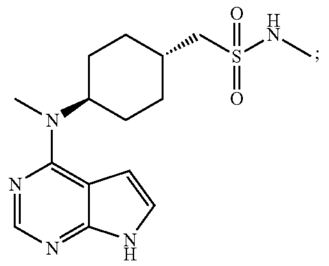 [SMILES: CNS(=O)(=O)C[C@H]1CC[C@H](N(C)c2ncnc3[nH]ccc23)CC1]

or a pharmaceutically acceptable salt thereof.

In some embodiments, the JAK inhibitor is upadacitinib (ABT494) (Kremer et al., *Arthritis Rheumatol.* 68(12):2867-2877, 2016; Mohamed et al., *Clin. Pharmaco.* 55(12):1547-1558, 2016), GLG0778 (O'Shea et al., *Ann. Rev. Med.* 66(1):311-28, 2015; Schwartz et al., *Nat. Rev. Rheum.* 12:25-36, 2016), having the following structure:

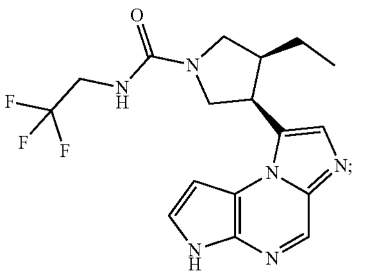 [SMILES: CC[C@@H]1CN(C(=O)NCC(F)(F)F)C[C@@H]1c1cnc2cnc3[nH]ccc3n12]

or a pharmaceutically acceptable salt thereof.

In some embodiments, the JAK inhibitor is itacitinib (INCB039110) (Mascarenhas et al., *Haematologica* 102(2): 327-335, 2017; Bissonnette et al., *J. Dermatolog. Treat.* 27(4):332-338, 2016; Rosenthal et al., *Exp. Opin. Pharmacother.* 15(9):1265-1276, 2014), having the following structure:

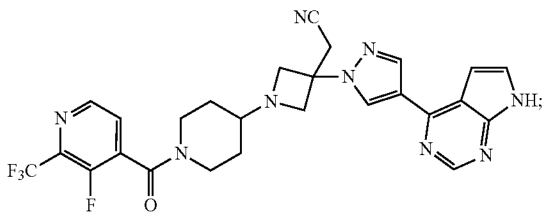 [SMILES: N#CCC1(n2cc(-c3ncnc4[nH]ccc34)cn2)CN(C2CCN(C(=O)c3ccnc(C(F)(F)F)c3F)CC2)C1]

or a pharmaceutically acceptable salt thereof (e.g., itacitinib adipate).

In some embodiments, the JAK inhibitor is abrocitinib (PF04965842) (Gadina et al., *Curr. Opin. Rheumatol.* 26(2): 237-243, 2014; Degryset et al., *J. Hematol. Oncol.* 8:91, 2015), having the following structure:

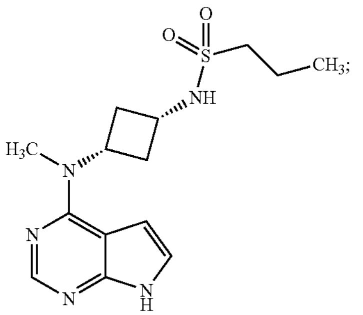 [SMILES: CCCS(=O)(=O)N[C@H]1C[C@@H](N(C)c2ncnc3[nH]ccc23)C1]

or a pharmaceutically acceptable salt thereof;

In some embodiments, the JAK inhibitor is INCB047986 or a variant thereof (Norman, *Exp. Opin. Investig. Drugs* 23(8):1067-1077, 2014); or a pharmaceutically acceptable salt thereof.

In some embodiments, the JAK inhibitor is SAR-20347 (Works et al., *J. Immunol.* 193(7):3278-3287, 2014)), having the following structure:

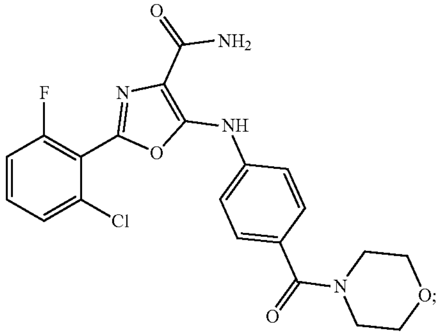 [SMILES: NC(=O)c1nc(-c2c(F)cccc2Cl)oc1Nc1ccc(C(=O)N2CCOCC2)cc1]

or a pharmaceutically acceptable salt thereof. In some embodiments, the JAK inhibitor is, PF-06700841 (D'Amico, F. et al., Expert Opin. Invest. Drugs, 27(7):595-599 (2018)), having the following structure:

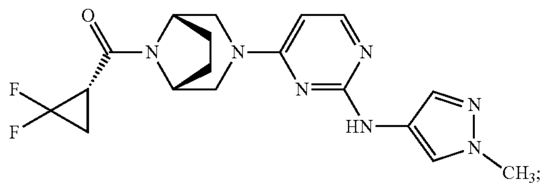 [SMILES: Cn1cc(Nc2nccc(N3C[C@H]4CC[C@@H](C3)N4C(=O)[C@@H]3CC3(F)F)n2)cn1]

or a pharmaceutically acceptable salt thereof.

In some embodiments, the JAK inhibitor is INCB16562 or a variant thereof (Koppikar et al., *Blood* 115(4):2919-2927, 2010; Li et al., *Neoplasia* 12(1):28-38, 2010), said INCB16562 having the following structure:

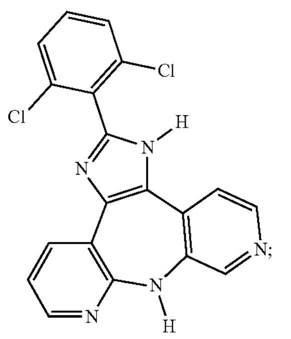 [SMILES: Clc1cccc(Cl)c1-c1nc2c([nH]1)-c1ccncc1Nc1ncccc1-2]

or a pharmaceutically acceptable salt thereof.

In some embodiments, the JAK inhibitor is ruxolitinib (Jakafi®, Jakavi®, INCB018424) (Harrison et al., *N. Engl. J. Med.* 366:787-798, 2012; Pieri et al., *Am. J. Hematol.* 92(2):187-195, 2017; Mackay-Wiggan et al., *JCI Insight* 1(15):e89790, 2016; Rudolph et al., *Leukemia* 30(10):2119-2123, 2016; Furqan et al., *Biomark Res.* 1(1):5, 2013), having the following structure:

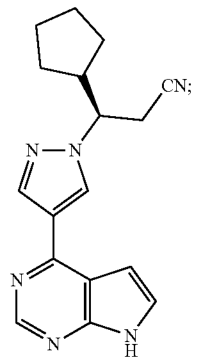 [SMILES: N#CC[C@H](C1CCCC1)n1cc(-c2ncnc3[nH]ccc23)cn1]

or pharmaceutically acceptable salt thereof.

In some embodiments, the JAK inhibitor is baricitinib (Olumiant®; INCB028050, LY3009104) (Gras, *Drugs Today* (*Barc*) 52(10):543-550, 2016; Smolen et al., *Ann. Rheum. Dis.* 76(4):694-700, 2016; Kubo et al., *Expert. Rev. Clin. Immunol.* 12(9):911-919, 2016; Fridman et al., *J. Immunol.* 84(9):5298-5307, 2010; Hsu and Armstrong, *J. Immunol. Res.* Article ID 283617, 2014), having the following structure:

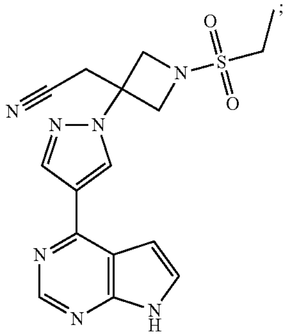 [SMILES: CCS(=O)(=O)N1CC(CC#N)(n2cc(-c3ncnc4[nH]ccc34)cn2)C1]

or pharmaceutically acceptable salt thereof.

In some embodiments, the JAK inhibitor is momelotinib (GS-0387, CYT387) (Pardanani et al., *Leukemia* 23: 1441-1445, 2009; Gupta et al., *Haematologica* 102(1):94-102, 2017; Hu et al., *Mol. Pharm.* 13(2):689-697, 2016; Abubaker et al., *BMC Cancer* 14:317, 2014; Durmus et al., *Pharmacol. Res.* 76:9-16, 2013; Pardanani et al., *Leukemia* 27(6):1322-1327, 2013; Monaghan et al., *Leukemia* 25(12): 1891-1899, 2011; Tyner et al., *Blood* 115(25):5232-5240, 2010) having the following structure:

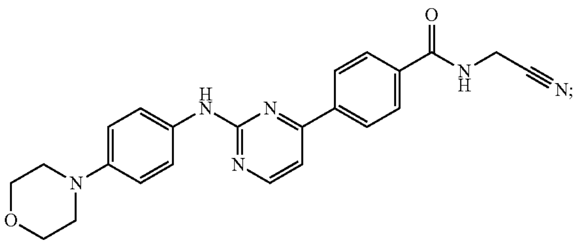 [SMILES: N#CCNC(=O)c1ccc(-c2ccnc(Nc3ccc(N4CCOCC4)cc3)n2)cc1]

or a pharmaceutically acceptable salt thereof.

In some embodiments, the JAK inhibitor is AZD1480 (Ioannidis et al., *J. Med. Chem.* 54: 262-276, 2011; Moisan et al., *Nat. Cell Biol.* 17(1):57-67, 2015; Qin et al., *J. Neurosci.* 36(18):5144059, 2016; Jiang et al., *Biochem. Biophys. Res. Commun.* 458(4):908-912, 2015; Verstovsek et al., *Leuk. Res.* 39(2):157-163, 2015; Plimack et al., *Oncologist* 18(7): 819-820, 2013; Yan et al., *Oncotarget* 4(3):433-445, 2013), having the following structure:

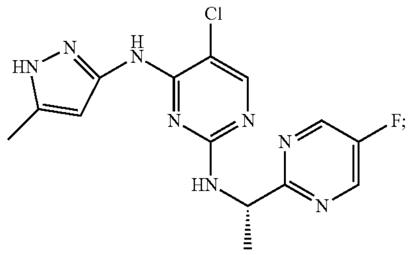 [SMILES: Cc1cc(Nc2nc(N[C@@H](C)c3ncc(F)cn3)ncc2Cl)n[nH]1]

or pharmaceutically acceptable salt thereof.

In some embodiment, the JAK inhibitor is CEP-33779 (Dugan et al., *J. Med. Chem.* 55(11):5243-5254, 2012; Seavey et al., *Mol. Cancer Ther.* 11(4):984-993, 2012; Stump et al., *Arthritis Res. Ther.* 13(2):R68, 2011), having the following structure:

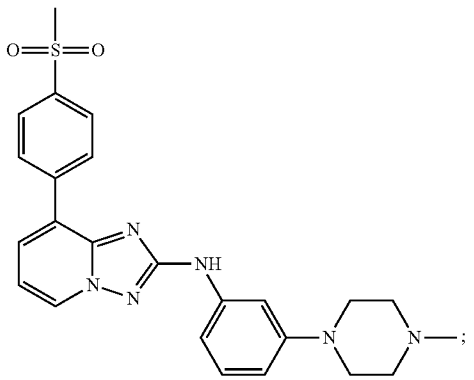 [SMILES: CN1CCN(c2cccc(Nc3nc4c(-c5ccc(S(C)(=O)=O)cc5)cccn4n3)c2)CC1]

or a pharmaceutically acceptable salt thereof.

In some embodiments, the JAK inhibitor is fedratinib (TG101348, SAR302503) (Pardanani et al., *J. Clin. Oncol.* 29:789-796, 2011; Jamieson et al., *J. Transl. Med.* 13:294, 2015; Zhang et al., *Oncotarget* 6(16):14329-14343, 2015; Wernig et al., *Blood* 105:4508-4515, 2008), having the following structure:

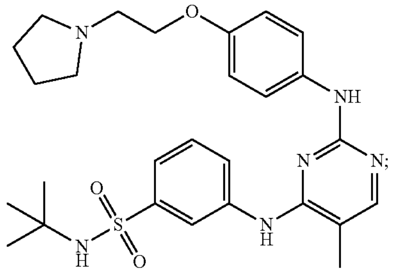 [SMILES: Cc1cnc(Nc2ccc(OCCN3CCCC3)cc2)nc1Nc1cccc(S(=O)(=O)NC(C)(C)C)c1]

or a pharmaceutically acceptable salt thereof.

In some embodiments, the JAK inhibitor is lestaurtinib (CEP-701) (Hexnet et al., *Blood* 111:5663-5671, 2008; Santos et al., *Blood* 115: 1131-1136, 2010; Smith et al., *Blood* 103: 3669-3676, 2004; Hexner et al., *Leuk. Lymphoma.* 56(9):2543, 2015; Geyer et al., *Hematology* 17(Suppll):S129-132, 2012; Diaz et al., *PLoS One* 6(4):e18856, 2011; Minturn et al., *Cancer Chemother. Pharmacol.* 68(4): 1057-1065, 2011), having the following structure:

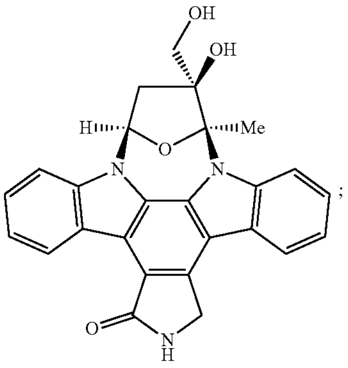 [SMILES: C[C@]12O[C@H](C[C@]1(O)CO)n1c3ccccc3c3c4c(c5c6ccccc6n2c5c31)CNC4=O]

or a pharmaceutically acceptable salt thereof.

In some embodiments, the JAK inhibitor is AC-430 ((R)-(4-fluorophenyl)-[4-[(5-methyl-1H-pyrazol-3-yl) amino]quinazolin-2-yl]methanol) (O'Shea et al., *Immunity* 36(4):542-550, 2012; Patterson et al., *Clin. Exp. Immunol.* 176:1-10, 2014; U.S. Pat. No. 8,927,711; ClinicalTrials.gov identifier (NCT number): NCTO1287858), having the following structure:

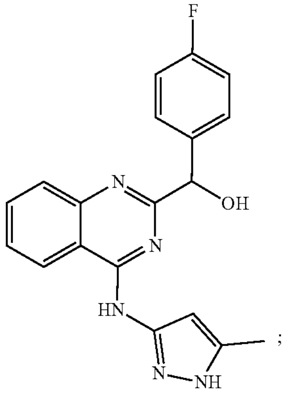 [SMILES: Cc1cc(Nc2nc(C(O)c3ccc(F)cc3)nc3ccccc23)n[nH]1]

or a pharmaceutically acceptable salt thereof.

In some embodiments, the JAK inhibitor is pacritinib (SB1518) (Deeg et al., *J. Clin. Oncol.* 29: Abstract 6515, 2011; Verstovsek et al., *J. Hematol. Oncol.* 9(1):137, 2016; Chow et al., *Onco Targets. Ther.* 9:2655-2665, 2016; Komrokji et al., *Blood* 125(17):2649-2655, 2015; Jayaraman et al., *Drug Metab. Lett.* 9(1):28-47, 2015; clinicaltrials.gov identifier (NCT number): NCT02055781), having the following structure:

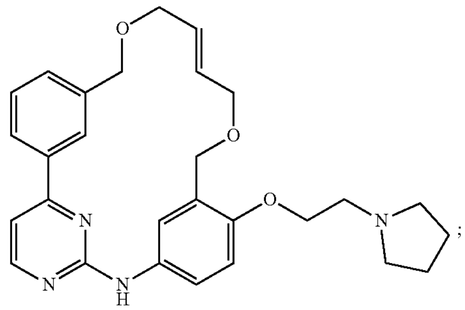 [SMILES: C1=C/COCc2cc(ccc2OCCN2CCCC2)Nc2nccc(n2)-c2cccc(c2)COC/1]

or a pharmaceutically acceptable salt thereof.

In some embodiments, the JAK inhibitor is BMS-911543 (Mace et al., *Oncotarget* 6(42):44509-44522, 2015; Wan et al., *ACS Med. Chem. Lett.* 6(8):850-855, 2015; Purandare et al., *Leukemia* 26(2):280-288, 2012), having the following structure:

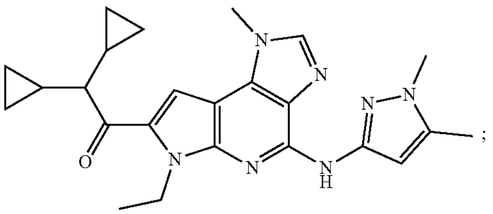 [SMILES: CCn1c(C(=O)C(C2CC2)C2CC2)cc2c3c(ncn3C)c(Nc3cc(C)n(C)n3)nc21]

or a pharmaceutically acceptable salt thereof.

In some embodiments, the JAK inhibitor is XL019 (Verstovsek et al., *Leuk. Res.* 38(3):316-322, 2014; Forsyth et al., *Bioorg. Med. Chem. Lett.* 22(24):7653-7658, 2012), having the following structure:

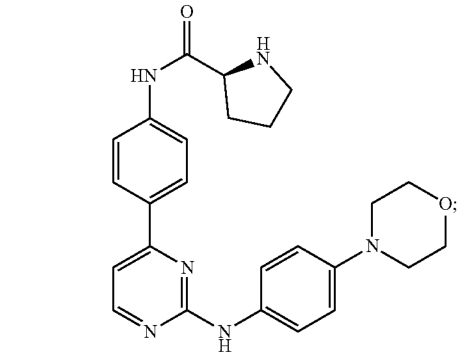 [SMILES: O=C(Nc1ccc(-c2ccnc(Nc3ccc(N4CCOCC4)cc3)n2)cc1)[C@@H]1CCCN1]

or a pharmaceutically acceptable salt thereof.

In some embodiments, the JAK inhibitor is Gandotinib® (LY2784544) (Ma et al., *Blood Cancer J.* 3:e109, 2013; Verstovsek et al., *Blood* 122: 665, 2013; Mitchell et al., *Org. Process Res. Dev.* 16(1):70-81. 2012), having the following structure:

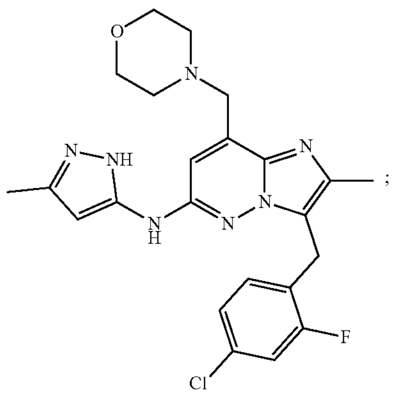

or a pharmaceutically acceptable salt thereof.

In some embodiments, the JAK inhibitor is a compound as described in US 2009/0258864 A1, which is hereby incorporated by reference in its entirety. In a more particular embodiment, the JAK inhibitor is R723 (Shide et al., *Blood* 117(25):6866-6875, 2011; US 2009/0258864 A1) having the following structure:

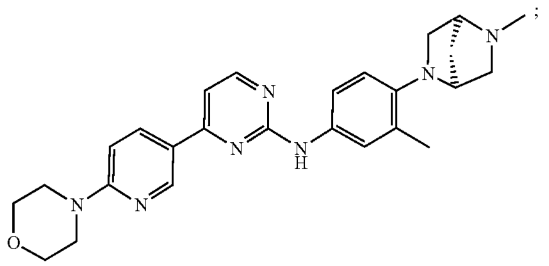

or a pharmaceutically acceptable salt thereof.

In some embodiments, the JAK inhibitor is tyrphostin B42 ((E)-N-benzyl-2-cyano-3-(3,4-dihydroxyphenyl)acrylamide; Sugimoto et al., *Eur. J. Immunol.,* 33(1):243-51, 2003), having the following structure:

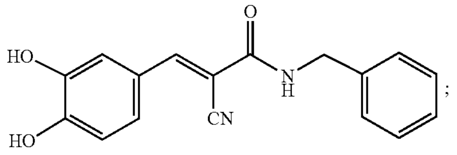 [SMILES: N#C/C(=C\c1ccc(O)c(O)c1)C(=O)NCc1ccccc1]

or a pharmaceutically acceptable salt thereof.

In some embodiments, the JAK inhibitor is Z3 (2-methyl-1-phenyl-4-pyridin-2-yl-2-(2-pyridin-2-ylethyl)butan-1-one) (Sayyah et al., *Mol. Cancer. Ther.* 7(8):2308-2318, 2008) or a variant thereof, said Z3 having the following structure:

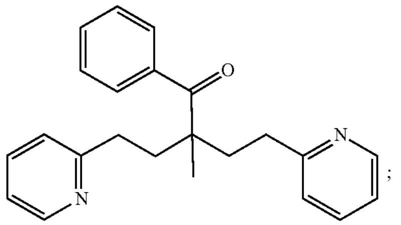 [SMILES: CC(CCc1ccccn1)(CCc1ccccn1)C(=O)c1ccccc1]

or a pharmaceutically acceptable salt thereof.

In some embodiments, the JAK inhibitor is NVP-BSK805 or a variant thereof (Ringel et al., *Acta Haematol.* 132(1): 75-86, 2014; Baffert et al., *Mol. Cancer. Ther.* 9(7):1945-1955, 2010), said NVP-BSK805 having the following structure:

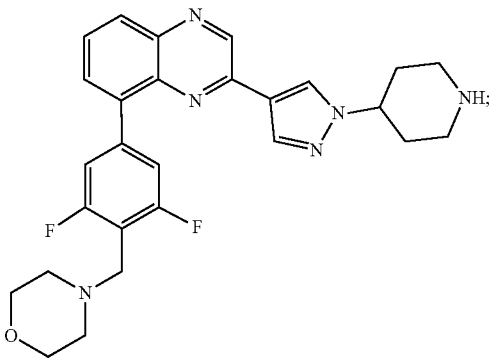 [SMILES: Fc1cc(-c2cccc3ncc(-c4cnn(C5CCNCC5)c4)nc23)cc(F)c1CN1CCOCC1]

or a pharmaceutically acceptable salt thereof (for example, the dihydrochloride salt thereof).

In some embodiments, JAK inhibitor is CHZ868 or a variant thereof (Wu et al., *Cancer Cell* 28(1):29-41, 2015; Meyer et al., *Cancer Cell* 28(1):15-28, 2015), said CHZ868 having the following structure:

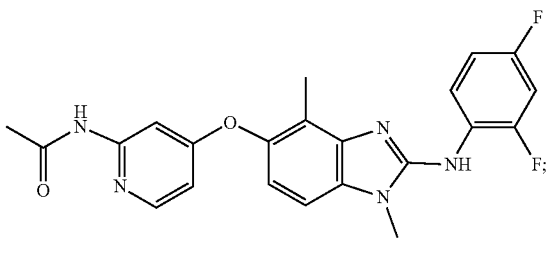 [SMILES: CC(=O)Nc1cc(Oc2ccc3c(nc(Nc4ccc(F)cc4F)n3C)c2C)ccn1]

or a pharmaceutically acceptable salt thereof.

In some embodiments, the JAK inhibitor is decernotinib (VX-509) (Elwood et al., *J. Pharmacol. Exp. Ther.* 2017; Genovese et al., *Ann Rheum Dis.* 75(11):1979-1983, 2016; Gadina et al., *Arthritis Rheumatol.* 68(1):31-34, 2016; Farmer et al., *J. Med. Chem.* 58(18):7195-7216, 2015; Fleischmann et al., *Arthritis Rheumatol.* 67(2):334-343, 2015; Mahajan et al., *J. Pharmacol.* 353(2):405-414, 2015), having the following structure:

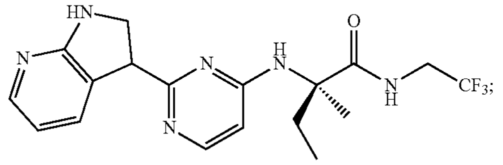 [SMILES: CC[C@@](C)(Nc1ccnc(C2CNc3ncccc32)n1)C(=O)NCC(F)(F)F]

or a pharmaceutically acceptable salt thereof.

In some embodiments, the JAK inhibitor is PF-06651600 (Thorarensen A. et al., *J. Med. Chem.,* 60(5):1971-1993, 2017), having the following structure:

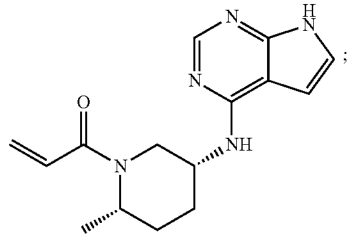 [SMILES: C=CC(=O)N1C[C@H](Nc2ncnc3[nH]ccc23)CC[C@@H]1C]

or a pharmaceutically acceptable salt thereof.

In some embodiments, the JAK inhibitor is R348 (R932348) or a variant thereof (Velotta et al., *Transplantation* 87(5):653-659, 2009; Deuse et al., *Transplantation* 85(6):885-892, 2008), said R348 having the following structure:

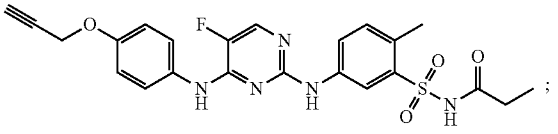 [SMILES: C#CCOc1ccc(Nc2nc(Nc3ccc(C)c(S(=O)(=O)NC(=O)CC)c3)ncc2F)cc1]

or a pharmaceutically acceptable salt thereof.

In some embodiments, the JAK inhibitor is the active metabolite of R348, also known as R333 (R932333) (Neuro-Oncol, 2014:16, suppl 3: iii35; Presto et al., *Br. J. Derm.,* 2018, 178(6):1308-1314; Velotta et al., *Transplantation* 87(5):653-659, 2009); or a pharmaceutically acceptable salt thereof.

In some embodiments, the JAK inhibitor is cucurbitacin I (JSI-124) or a variant thereof (Oi et al., *Int. J. Oncol.* 49(6):2275-2284, 2016; Qi et al., *Am. J. Chin. Med.* 43(2): 337-347, 2015; Seo et al., *Food Chem. Toxicol.* 64:217-224, 2014), said cucurbitacin I having the following structure:

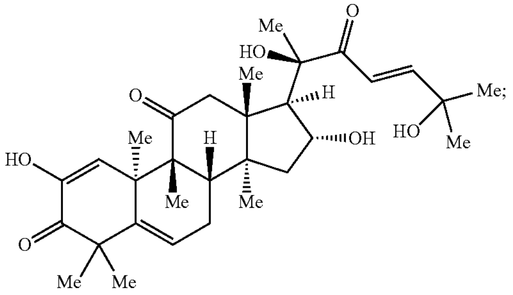

or a pharmaceutically acceptable salt thereof.

In some preferred embodiments, the JAK inhibitor is tofacitinib (3-[(3R,4R)-4-methyl-3-[methyl(7H-pyrrolo[2,3-d]pyrimidin-4-yl)amino]piperidin-1-yl]-3-oxopropanenitrile) having the following structure:

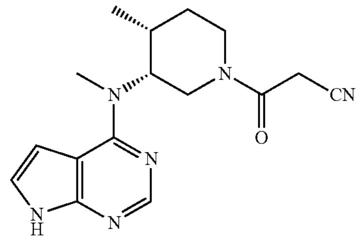 [SMILES: C[C@@H]1CCN(C(=O)CC#N)C[C@@H]1N(C)c1ncnc2[nH]ccc12]

or a pharmaceutically acceptable salt thereof. In a more particular embodiment, the JAK inhibitor is tofacitinib citrate (Xeljanz®, Jakvinus®, tasocitinib, CP-690,550). In some embodiments, the JAK inhibitor is a variant of tofacitinib, or a pharmaceutically acceptable salt thereof. Tofacitinib and variants thereof are described in, for example, Ghoreschi et al., *J. Immunol.* 186(7):4234-4243, 2011; Yoshida et al., *Biochem. Biophys. Res. Commun* 418(2):234-240, 2012; Calama et al., *Pulm. Pharmacol. Ther. S*1094-5539(16):30060-30068, 2017; Cutolo et al., *J. Inflamm. Res.* 6:129-137, 2013; Yokoyama et al., J. Clin. Immunol. 33(3): 586-594, 2013; Thoma et al., J. Med. Chem. 54(1):284-288, 2011; and Meyer et al. (2010) J. Inflamm. 7-41.

In some embodiments, the tofacitinib variant is a prodrug of tofacitinib. In some more particular embodiments, the tofacitinib prodrug is a glucuronide-containing prodrug, for example, as described in US 2017/0145044 A1, which is incorporated by reference herein in its entirety. In some embodiments, the glucuronide-containing prodrug of tofacitinib is a compound of formula I:

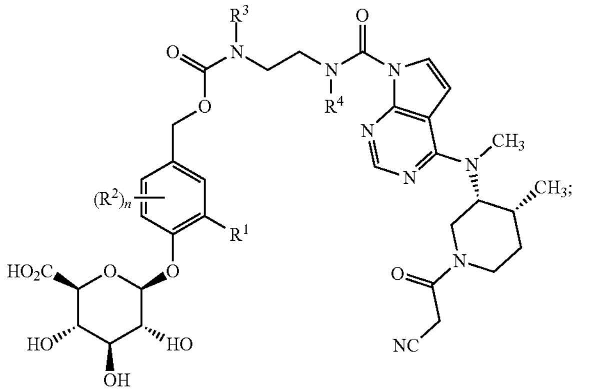

wherein:

n is 0, 1 or 2;

$R^1$ is selected from the group consisting of hydrogen, $C_{1-4}$ alkyl, $C_{1-3}$ alkoxy, amino, nitro, fluoro, chloro, bromo, iodo, cyano, hydroxy and trifluoromethyl;

each $R^2$, when present, is independently selected from the group consisting of $C_{1-4}$ alkyl, $C_{1-3}$ alkoxy, amino, nitro, fluoro, chloro, bromo, iodo, cyano, hydroxyl and trifluoromethyl;

$R^3$ is hydrogen, methyl or ethyl;

$R^4$ is hydrogen, methyl or ethyl;

or a pharmaceutically acceptable salt thereof.

In some more particular embodiments, the glucuronide-containing prodrug of tofacitinib is a compound of formula I, as described above, wherein n is 0, $R^3$ is methyl, and $R^4$ is methyl; or a pharmaceutically acceptable salt thereof.

In some more particular embodiments, the glucuronide-containing prodrug of tofacitinib is (2S,3S,4S,5R,6S)-6-(2-amino-4-((((2-(4-(((3R,4R)-1-(2-cyanoacetyl)-4-methylpiperidin-3-yl)(methyl)amino)-N-methyl-7H-pyrrolo[2,3-d]pyrimidine-7-carboxamido)ethyl)(methyl)carbamoyl)oxy)methyl)phenoxy)-3,4,5-trihydroxytetrahydro-2H-pyran-2-carboxylic acid having the following structure:

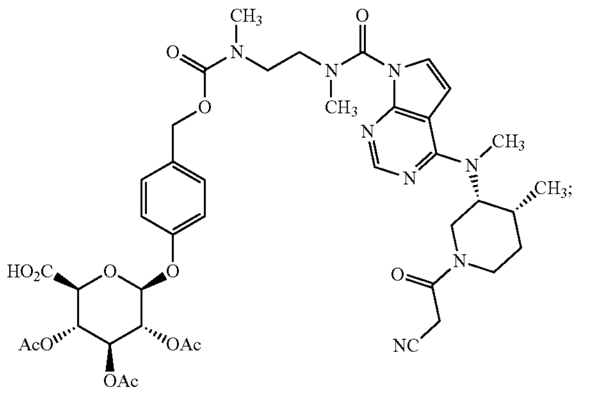 [SMILES: CC(=O)O[C@@H]1[C@@H](OC(C)=O)[C@H](Oc2ccc(COC(=O)N(C)CCN(C)C(=O)n3ccc4c(N(C)[C@H]5CN(C(=O)CC#N)CC[C@H]5C)ncnc43)cc2)O[C@H](C(=O)O)[C@H]1OC(C)=O]

or a pharmaceutically acceptable salt thereof.

In some more particular embodiments, the glucuronide-containing prodrug of tofacitinib is (2S,3S,4S,5R,6S)-6-(4-((((2-(4-(((3R,4R)-1-(2-cyanoacetyl)-4-methylpiperidin-3-yl)(methyl)amino)-N-methyl-7H-pyrrolo[2,3-d]pyrimidine-7-carboxamido)ethyl)(methyl) carbamoyl)oxy)methyl)phenoxy)-3,4,5-trihydroxytetrahydro-2H-pyran-2-carboxylic acid having the following structure:

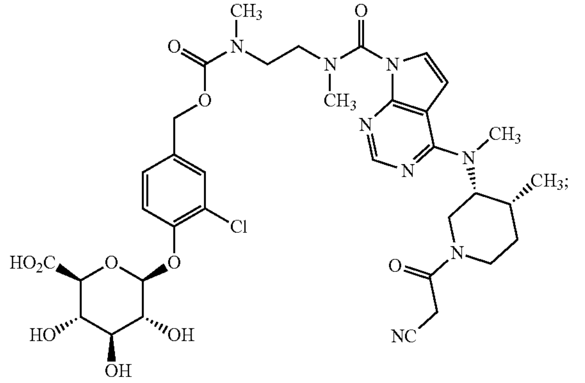

or a pharmaceutically acceptable salt thereof.

In some more particular embodiments, the glucuronide-containing prodrug of tofacitinib is a (2S,3S,4S,5R,6S)-6-(4-((((2-(4-(((3R,4R)-1-(2-cyanoacetyl)-4-methylpiperidin-3-yl)(methyl)amino)-N-methyl-7H-pyrrolo[2,3-d]pyrimidine-7-carboxamido)ethyl)(methyl)carbamoyl)oxy)methyl)-2-methylphenoxy)-3,4,5-trihydroxytetrahydro-2H-pyran-2-carboxylic acid having the following structure:

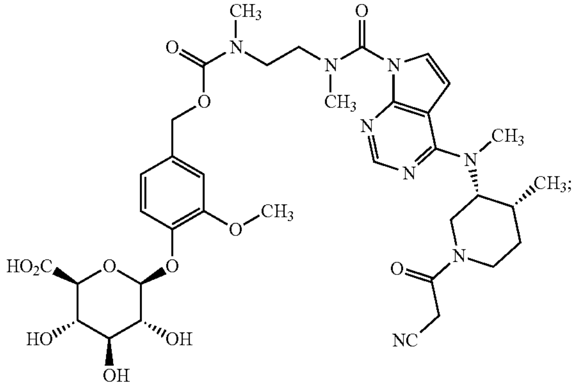 [SMILES: COc1cc(COC(=O)N(C)CCN(C)C(=O)n2ccc3c(N(C)[C@H]4CN(C(=O)CC#N)CC[C@H]4C)ncnc32)ccc1O[C@@H]1O[C@H](C(=O)O)[C@@H](O)[C@H](O)[C@H]1O]

or a pharmaceutically acceptable salt thereof.

In some more particular embodiments, the glucuronide-containing prodrug of tofacitinib is (2S,3S,4S,5R,6S)-6-(2-chloro-4-((((2-(4-(((3R,4R)-1-(2-cyanoacetyl)-4-methylpiperidin-3-yl)(methyl)amino)-N-methyl-7H-pyrrolo[2,3-d]pyrimidine-7-carboxamido)ethyl)(methyl)carbamoyl)oxy)methyl)phenoxy)-3,4,5-trihydroxytetrahydro-2H-pyran-2-carboxylic acid having the following structure:

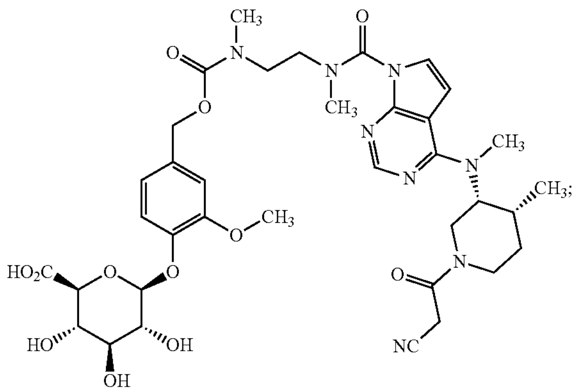 [SMILES: COc1cc(COC(=O)N(C)CCN(C)C(=O)n2ccc3c(N(C)[C@H]4CN(C(=O)CC#N)CC[C@H]4C)ncnc32)ccc1O[C@@H]1O[C@H](C(=O)O)[C@@H](O)[C@H](O)[C@H]1O]

or a pharmaceutically acceptable salt thereof.

In some more particular embodiments, the glucuronide-containing prodrug of tofacitinib is (2S,3S,4S,5R,6S)-6-(4-((((2-(4-(((3R,4R)-1-(2-cyanoacetyl)-4-methylpiperidin-3-yl)(methyl)amino)-N-methyl-7H-pyrrolo[2,3-d]pyrimidine-7-carboxamido)ethyl)(methyl)carbamoyl)oxy)methyl)-2-methoxyphenoxy)-3,4,5-trihydroxytetrahydro-2H-pyran-2-carboxylic acid having the following structure:

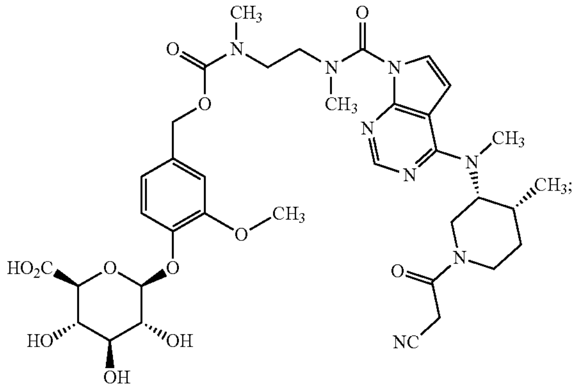

or a pharmaceutically acceptable salt thereof.

In some more particular embodiments, the glucuronide-containing prodrug of tofacitinib is TD-3504 (Theravance Biopharma) or a pharmaceutically acceptable salt thereof. In some embodiments, the glucuronide-containing prodrug of tofacitinib is (2S,3S,4S,5R,6S)-6-(4-((((2-(4-(((3R,4R)-1-(2-cyano-acetyl)-4-methylpiperidin-3-yl)(methyl)amino)-N-methyl-7H-pyrrolo[2,3-d]pyrimidine-7-carboxamido) ethyl)(methyl)carbamoyl)-oxy)methyl)-2-nitrophenoxy)-3,4,5-trihydroxytetrahydro-2H-pyran-2-carboxylic acid having the following structure:

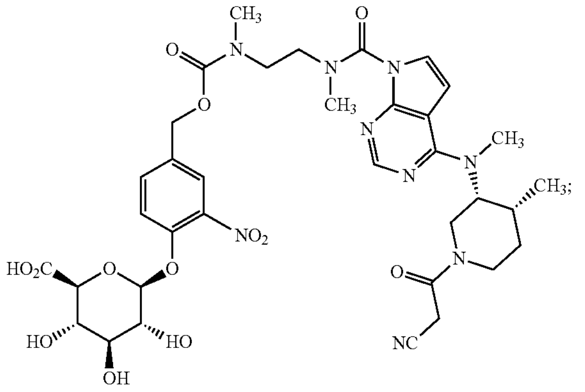

or a pharmaceutically acceptable salt thereof.

In some embodiments, the tofacitinib variant is a thiocarbamate prodrug of tafacitinib, for example, as described in US 2018/0339980 A1, which is incorporated by reference herein in its entirety. In some embodiments, the thiocarbamate prodrug of tofacitinib is a compound of formula Ia:

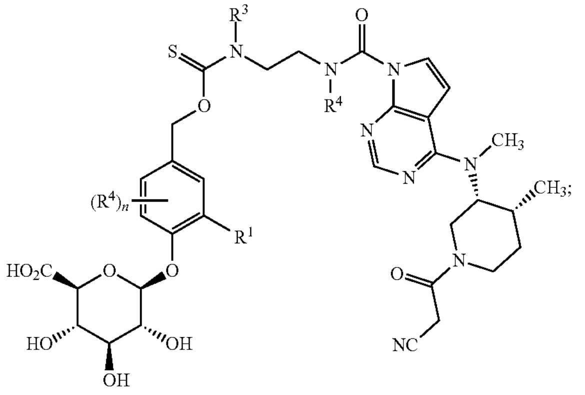

wherein:

n is 0, 1, or 2;

$R^1$ is selected from the group consisting of hydrogen, $C_{1-4}$ alkyl, $C_{1-3}$ alkoxy, amino, nitro, halo, cyano, hydroxy and trifluoromethyl;

each $R^2$, when present, is independently selected from the group consisting of $C_{1-4}$ alkyl, $C_{1-3}$ alkoxy, amino, nitro, halo, cyano, hydroxyl and trifluoromethyl;

$R^3$ is selected from the group consisting of hydrogen, methyl and ethyl;

$R^4$ is selected from the group consisting of hydrogen, methyl and ethyl;

or a pharmaceutically acceptable salt thereof.

In some more particular embodiments, the thiocarbamate prodrug of tofacitinib is a compound of formula La, as described above, wherein n is 0, $R^3$ is methyl, and $R^4$ is methyl; or a pharmaceutically acceptable salt thereof.

In some more particular embodiments, the thiocarbamate prodrug of tofacitinib is (2S,3S,4S,5R,6S)-6-(4-((((2-(4-

(((3R,4R)-1-(2-cyanoacetyl)-4-methylpiperidin-3-yl) (methyl) amino)-N-methyl-7H-pyrrolo[2,3-d]pyrimidine-7-carboxamido)ethyl)(methyl)carbamothioyl) oxy)methyl)-2-nitrophenoxy)-3,4,5-trihydroxytetrahydro-2H-pyran-2-carboxylic acid having the following structure:

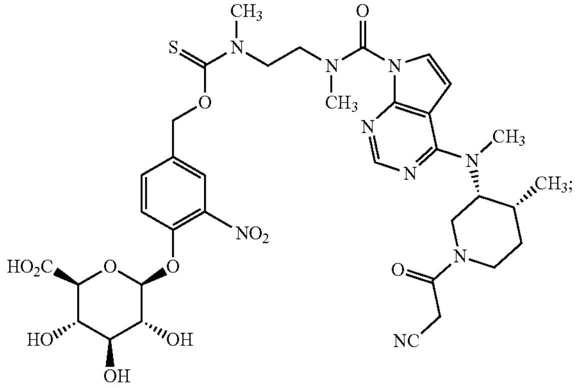 [SMILES: C[C@@H]1CCN(C(=O)CC#N)C[C@@H]1N(C)c1ncnc2c1ccn2C(=O)N(C)CCN(C)C(=S)OCc1ccc(O[C@@H]2O[C@H](C(=O)O)[C@@H](O)[C@H](O)[C@H]2O)c([N+](=O)[O-])c1]

or a pharmaceutically acceptable salt thereof.

In some more particular embodiments, the thiocarbamate prodrug of tofacitinib is (2S,3S,4S,5R,6S)-6-(4-((((2-(4-(((3R,4R)-1-(2-cyanoacetyl)-4-methylpiperidin-3-yl) (methyl) amino)-N-methyl-7H-pyrrolo[2,3-d]pyrimidine-7-carboxamido)ethyl)(methyl)carbamothioyl) oxy)methyl) phenoxy)-3,4,5-trihydroxytetrahydro-2H-pyran-2-carboxylic acid having the following structure:

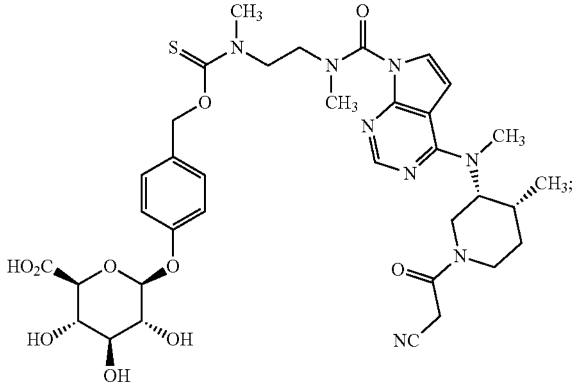 [SMILES: C[C@@H]1CCN(C(=O)CC#N)C[C@@H]1N(C)c1ncnc2c1ccn2C(=O)N(C)CCN(C)C(=S)OCc1ccc(O[C@@H]2O[C@H](C(=O)O)[C@@H](O)[C@H](O)[C@H]2O)cc1]

or a pharmaceutically acceptable salt thereof.

In some more particular embodiments, the thiocarbamate prodrug of tofacitinib is (2S,3S,4S,5R,6S)-6-(4-((((2-(4-(((3R,4R)-11-(2-cyanoacetyl)-4-methylpiperidin-3-yl) (methyl)amino)-N-methyl-7H-pyrrolo[2,3-d]pyrimidine-7-carboxamido)ethyl)(methyl) carbamothioyl)oxy)methyl)-2-methylphenoxy)-3,4,5-trihydroxytetrahydro-2H-pyran-2-carboxylic acid having the following structure:

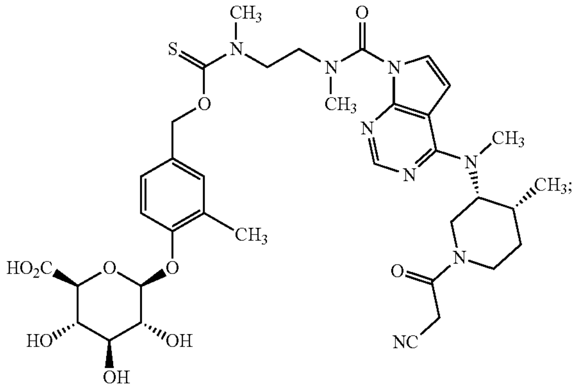

or a pharmaceutically acceptable salt thereof.

In some more particular embodiments, the thiocarbamate prodrug of tofacitinib is (2S,3S,4S,5R,6S)-6-(2-chloro-4-((((2-(4-(((3R,4R)-1-(2-cyanoacetyl)-4-methylpiperidin-3-yl)(methyl)amino)-N-methyl-7H-pyrrolo[2,3-d]pyrimidine-7-carboxamido)ethyl)(methyl) carbamothioyl)oxy)methyl) phenoxy)-3,4,5-trihydroxytetrahydro-2H-pyran-2-carboxylic acid having the following structure:

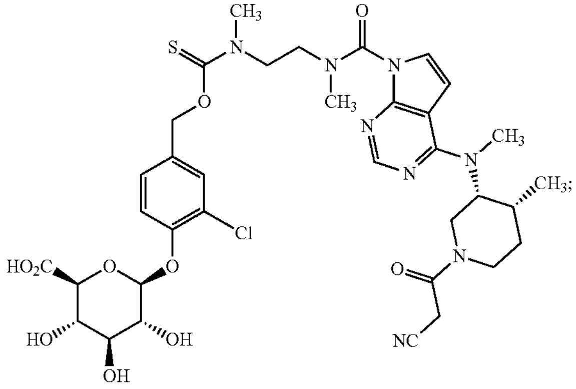 [SMILES: C[C@@H]1CCN(C(=O)CC#N)C[C@@H]1N(C)c1ncnc2c1ccn2C(=O)N(C)CCN(C)C(=S)OCc1ccc(O[C@@H]2O[C@H](C(=O)O)[C@@H](O)[C@H](O)[C@H]2O)c(Cl)c1]

or a pharmaceutically acceptable salt thereof.

In some more particular embodiments, the thiocarbamate prodrug of tofacitinib is (2S,3S,4S,5R,6S)-6-(4-((((2-(4-(((3R,4R)-1-(2-cyanoacetyl)-4-methylpiperidin-3-yl) (methyl) amino)-N-methyl-7H-pyrrolo[2,3-d]pyrimidine-7-carboxamido)ethyl)(methyl)carbamothioyl) oxy)methyl)-2-methoxyphenoxy)-3,4,5-trihydroxytetrahydro-2H-pyran-2-carboxylic acid having the following structure:

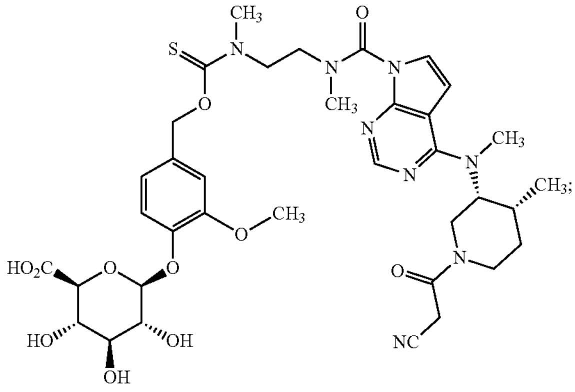

or a pharmaceutically acceptable salt thereof.

In some embodiments, the JAK inhibitor is 3-O-methylthespesilactam (Li et al., *Biochem. Pharmacol.* 86(10):1411-8, 2013)), having the following structure:

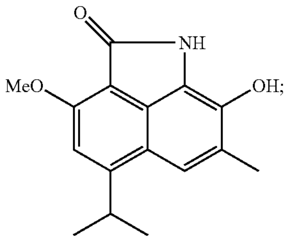 [SMILES: COc1cc(C(C)C)c2cc(C)c(O)c3c2c1C(=O)N3]

or a pharmaceutically acceptable salt thereof.

In some embodiments, the JAK inhibitor is peficitinib (ASP015K, JNJ-54781532) or a variant thereof (Genovese et al., *Arthritis Rheumatol.,* 2017; Ito et al., *J. Pharmacol. Sci.* 133(1):25-33, 2017; Cao et al. (2016) *Clin. Pharmacol. Drug Dev.* 5(6):435-449, 2016; Takeuchi et al., *Ann. Rheum. Dis.* 75(6):1057-1064, 2016), said peficitinib having the following structure:

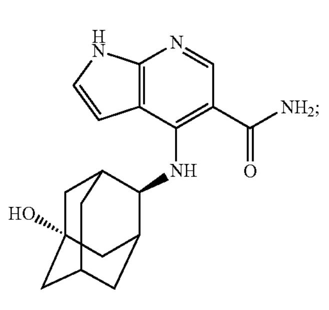 [SMILES: NC(=O)c1cnc2[nH]ccc2c1N[C@H]1C2CC3CC1C[C@](O)(C3)C2]

or a pharmaceutically acceptable salt thereof.

In some embodiments, the JAK inhibitor is a naphthyridine compound as described in US 2016/0347772 A1, U.S. Pat. No. 9,725,470 B2 or 10,072,026, each of which are incorporated by reference in their entirety herein. In some embodiments, the JAK inhibitor is a compound of the following formula:

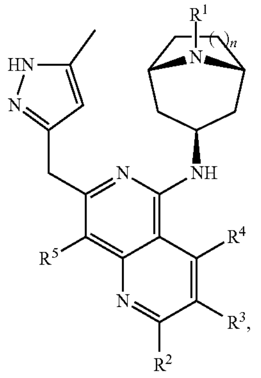

wherein:

$R^1$ is selected from:

(a) $C_{1-4}$alkyl, wherein $C_{1-4}$alkyl is optionally substituted with one, two, or three fluoro or with a substituent selected from —CN; —$OC_{1-3}$alkyl; —$C(O)OC_{1-4}$alkyl; phenyl, wherein phenyl is optionally substituted with —OH; pyridinyl, wherein pyridinyl is optionally substituted with —CN; tetrahydropyranyl; —C(O)$NR^aR^b$, wherein $R^a$ and $R^b$ are independently hydrogen or $C_{1-3}$alkyl or $R^a$ is hydrogen and $R^b$ is

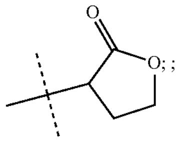

and a group selected from

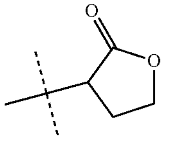

and

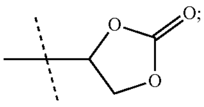

(b) a group selected from

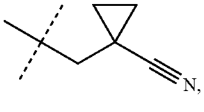

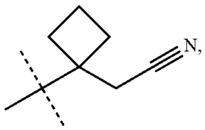

and

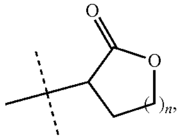

wherein m is 1 or 2;

(c) —$C(O)R^6$, wherein $R^6$ is selected from $C_{1-4}$alkyl, wherein $C_{1-4}$alkyl is optionally substituted with one, two, or three fluoro or with a substituent selected from —OH, —CN, —$OC_{1-4}$alkyl, phenyl, and —$NR^eR^f$, wherein $R^e$ and $R^f$ are independently hydrogen or $C_{1-3}$alkyl;

$C_{3-6}$cycloalkyl, wherein $C_{3-6}$cycloalkyl is optionally substituted with $C_{1-3}$alkyl;

pyridinyl, wherein pyridinyl is optionally substituted with —CN; and

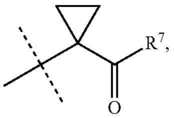

wherein $R^7$ is —CN, —$CF_3$, or —$OCH_3$;

(d) —$C(O)OR^8$, wherein $R^8$ is selected from $C_{1-4}$alkyl, wherein $C_{1-4}$alkyl is optionally substituted with —CN, $C_{3-6}$cycloalkyl, tetrahydrofuranyl, or —$OR^m$, wherein $R^m$ is hydrogen or $C_{1-3}$alkyl; and $C_{1-4}$alkenyl; and (e) —$S(O)_2R^9$, wherein $R^9$ is selected from $C_{1-4}$alkyl, wherein $C_{1-4}$alkyl is optionally substituted with —CN, —$OC_{1-3}$alkyl, phenyl, pyridinyl, or $C_{3-6}$cycloalkyl, $C_{1-4}$alkenyl, $C_{3-6}$cycloalkyl, wherein $C_{3-6}$cycloalkyl is optionally substituted with $C_{1-3}$alkyl, phenyl, pyridinyl, wherein pyridinyl is optionally substituted with fluoro, heterocycle containing 4 to 6 ring atoms including one nitrogen atom, wherein the heterocycle is optionally substituted with —CN or $C_{1-3}$alkyl, wherein $C_{1-3}$alkyl is optionally substituted with —CN or —$OC_{1-3}$alkyl; and

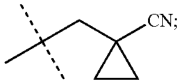

$R^2$ is selected from hydrogen, —$OC_{1-3}$alkyl, and —$CH_2$—$R^{10}$, wherein $R^{10}$ is selected from —OH, morpholinyl, piperidinyl, wherein piperidinyl is optionally substituted with two fluoro, and piperazinyl, wherein piperazinyl is optionally substituted with methyl;

$R^3$ is selected from hydrogen, $C_{1-3}$alkyl, —$OC_{1-3}$alkyl, —$C(O)OC_{1-3}$alkyl, —$S(O)_2C_{1-3}$alkyl, and —$CH_2S(O)_2$ $C_{1-3}$alkyl;

$R^4$ is hydrogen or —$OC_{1-3}$alkyl;

$R^5$ is hydrogen or fluoro; and n is 1 or 2;

provided that when $R^3$ is —$OC_{1-3}$ alkyl and $R^2$, $R^4$, and $R^5$ are each hydrogen, $R^9$ is not phenyl;

when $R^5$ is fluoro, n is 1, and $R^2$, $R^3$, and $R^4$ are each hydrogen, $R^9$ is not phenyl; and when $R^5$ is fluoro, $R^3$ is methyl, and $R^2$ and $R^4$ are each hydrogen, $R^1$ is not —$C(O)OR^8$;

or a pharmaceutically acceptable salt or stereoisomer thereof.

In some more particular embodiments, the JAK inhibitor is naphthyridine compound TD-1473 or a pharmaceutically acceptable salt thereof. In some embodiments, the JAK inhibitor is a compound having the following structure:

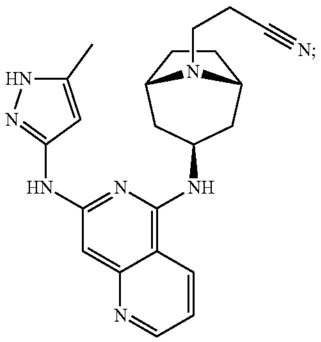 [SMILES: Cc1cc(Nc2cc3ncccc3c(N[C@@H]3C[C@H]4CC[C@@H](C3)N4CCC#N)n2)n[nH]1]

or a pharmaceutically acceptable salt thereof.

In another particular embodiment, the JAK inhibitor is a naphthyridine compound having the following structure:

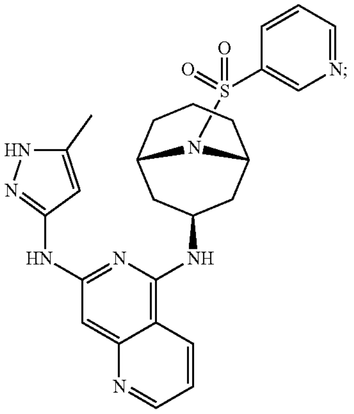 [SMILES: Cc1cc(Nc2cc3ncccc3c(N[C@@H]3C[C@H]4CCC[C@@H](C3)N4S(=O)(=O)c3cccnc3)n2)n[nH]1]

or a pharmaceutically acceptable salt thereof.

In some embodiments, the JAK inhibitor is a pyrimidine compound as described in WO 2017/189822 A1, US 2017/0312280 A1, and U.S. Pat. No. 10,028,960, each of which are incorporated by reference herein in their entirety. In some embodiments, the pan-JAK inhibitor is a compound of the following Formula:

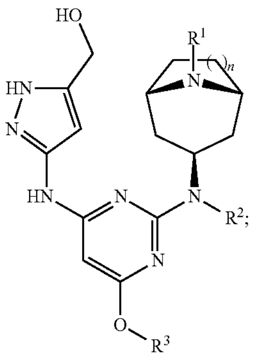

wherein:

$R^1$ is selected from:

(a) —$S(O)_2R^4$, wherein $R^4$ is selected from:

$C_{1-4}$alkyl, wherein $C_{1-4}$alkyl is optionally substituted with —CN, —$OC_{1-3}$alkyl, or $C_{3-6}$cycloalkyl, heterocyclyl containing 4 to 6 ring atoms including one nitrogen atom, wherein any heterocyclyl is optionally substituted with —CN, $C_{3-6}$cycloalkyl, pyridinyl, wherein pyridinyl is optionally substituted with fluoro, and phenyl;

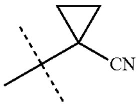

(b) $C_{1-4}$alkyl, wherein $C_{1-4}$alkyl is optionally substituted with —CN, CN or pyridinyl, wherein pyridinyl is optionally substituted with CN; and (c) —$C(O)R^5$, wherein $R^5$ is selected from:

$C_{1-4}$alkyl, wherein $C_{1-4}$alkyl is optionally substituted with $C_{3-6}$cycloalkyl, or with one or two fluoro, $OC_{1-4}$alkyl, $C_{3-6}$cycloalkyl, and morpholinyl;

$R^2$ is hydrogen or methyl;

$R^3$ is $C_{1-3}$alkyl; and n is 1 or 2;

or a pharmaceutically acceptable salt thereof.

In some more particular embodiments, the pyrimidine compound is a compound having the following structure:

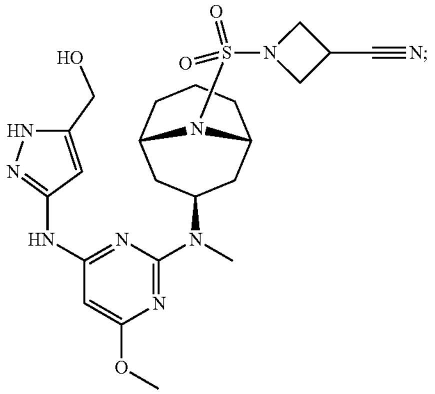 [SMILES: COc1cc(Nc2cc(CO)[nH]n2)nc(N(C)[C@@H]2C[C@H]3CCC[C@@H](C2)N3S(=O)(=O)N2CC(C#N)C2)n1]

or a pharmaceutically acceptable salt thereof.

In some embodiments, the JAK inhibitor is a compound as described in US 2017/0121327 A1, U.S. Pat. No. 10,100,049 or U.S. Pat. No. 10,183,942, each of which are herein incorporated by reference in their entirety. In some embodiments, the compound is selected from the group consisting of:

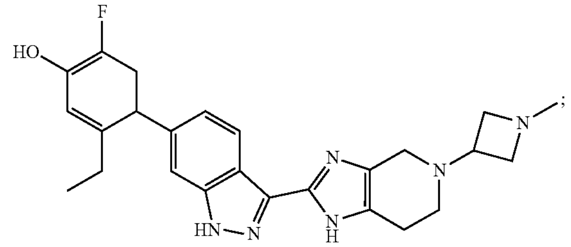

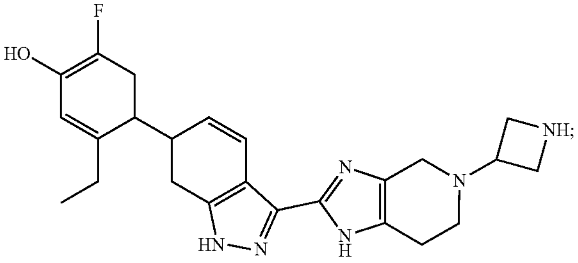

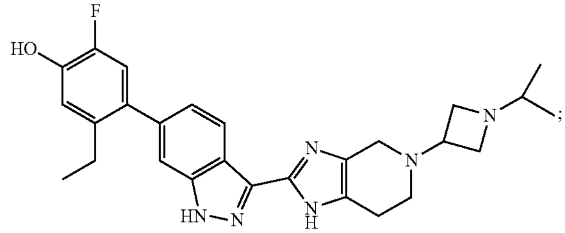

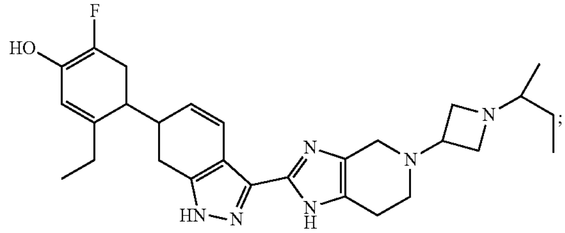

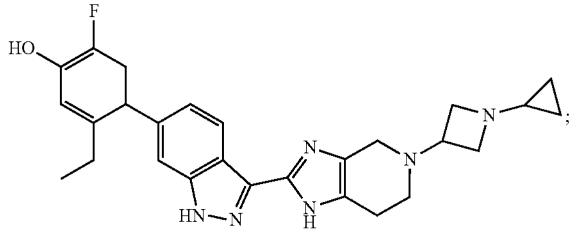

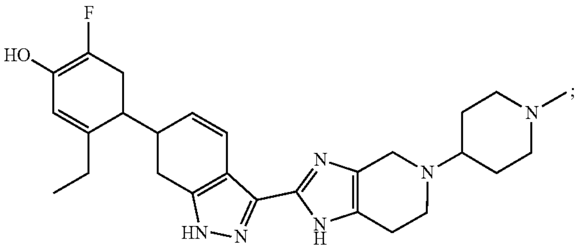

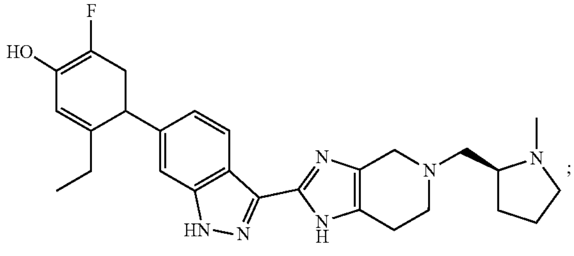

-continued
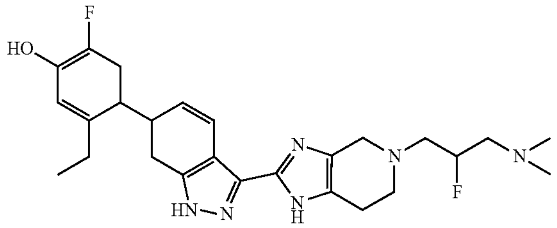
;
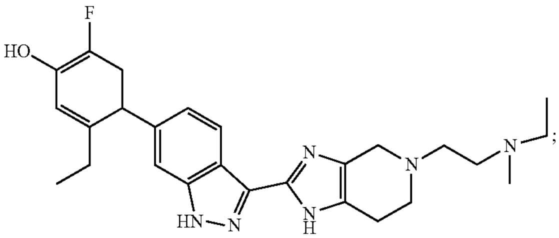
;
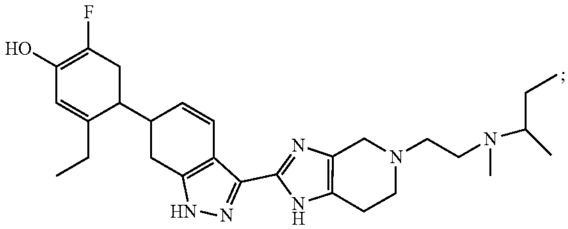
;
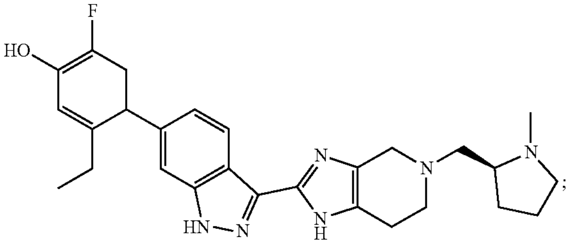
;
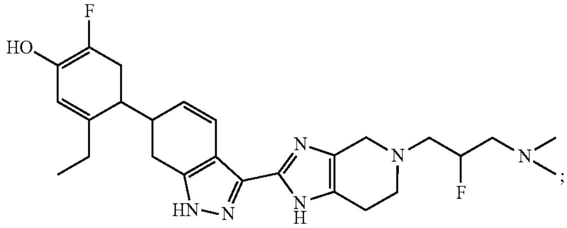
;
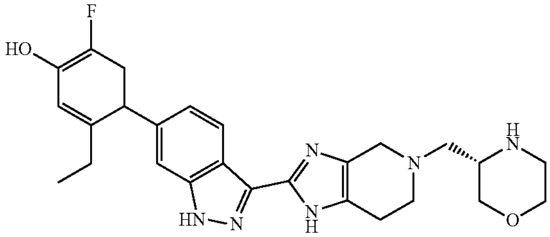
;
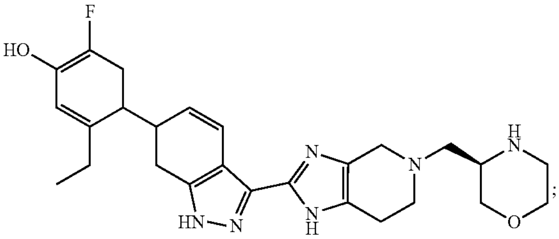
;
-continued
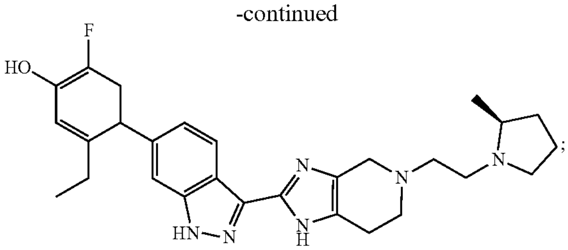
;
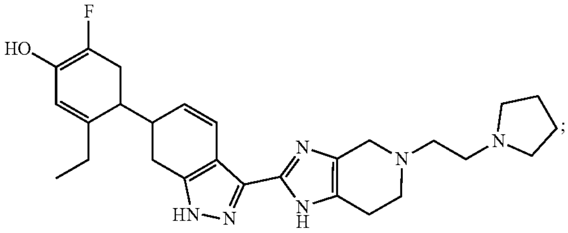
;
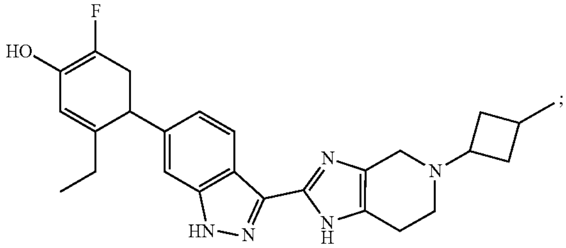
;
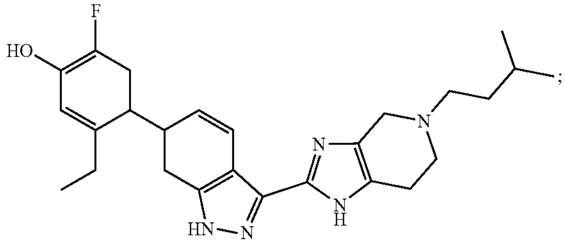
;
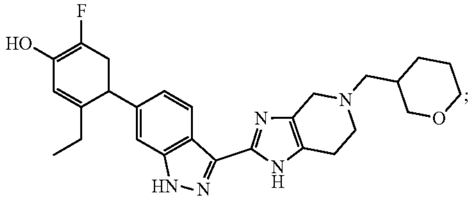
; and
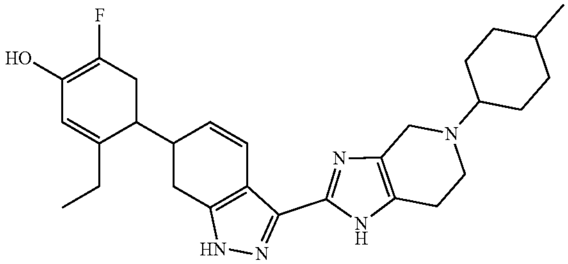
;
and pharmaceutically acceptable salts thereof.

In some embodiments, JAK inhibitor is:

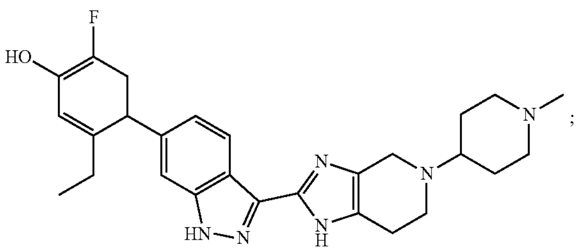 [SMILES: CCC1=CC(O)=C(F)CC1c1ccc2c(-c3nc4c([nH]3)CCN(C3CCN(C)CC3)C4)n[nH]c2c1]

or a pharmaceutically acceptable salt thereof.

In other embodiments, the JAK inhibitor is:

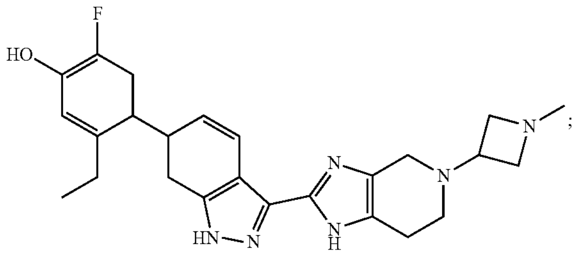 [SMILES: CCC1=CC(O)=C(F)CC1C1C=Cc2c(-c3nc4c([nH]3)CCN(C3CN(C)C3)C4)n[nH]c2C1]

or a pharmaceutically acceptable salt thereof.

In some embodiments, the JAK inhibitor is cerdulatinib (PRT2070, PRT062070) (Coffey et al. (2014) *J. Pharmacol. Exp. Ther.* 351(3):538-548, 2014; and Ma et al., *Oncotarget* 6(41):43881-43896, 2015) having the following structure:

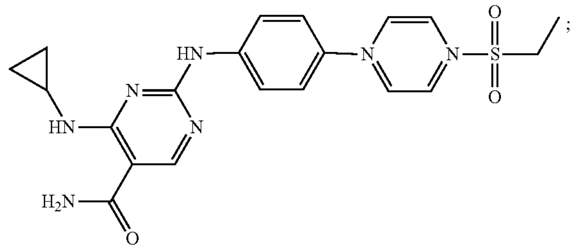

or a pharmaceutically acceptable salt thereof.

In some embodiments, the JAK inhibitor is pyridone 6 (P6; JAK Inhibitor 1; CAS Registry No. 457081-03-07) (Nakagawa et al., *J. Immunol.* 187(9):4611-4620, 2011; Pedranzini et al., *Cancer Res.* 66(19):9714-9721, 2006; Bordonaro et al., *PLoS One* 9:e115068, 2014), having the following structure:

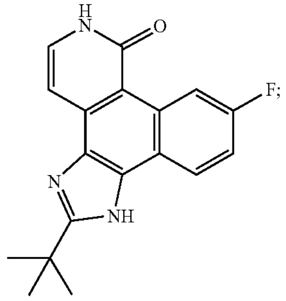 [SMILES: CC(C)(C)c1nc2c3cc[nH]c(=O)c3c3cc(F)ccc3c2[nH]1]

or a pharmaceutically acceptable salt thereof.

In some embodiments, the JAK inhibitor is PF-06263276 (Jones et al., "Design and Synthesis of a Pan-Janus Kinase Inhibitor Clinical Candidate (PF-06263276) Suitable for Inhaled and Topical Delivery for the Treatment of Inflammatory Diseases of the Lungs and Skin," J. Med. Chem., 2017, 60 (2), pp 767-786) having the following structure:

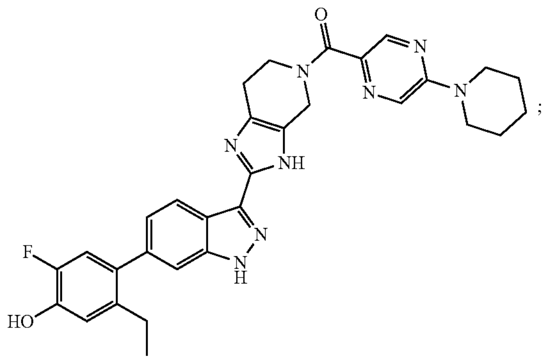 [SMILES: CCc1cc(O)c(F)cc1-c1ccc2c(-c3nc4c([nH]3)CN(C(=O)c3cnc(N5CCCCC5)cn3)CC4)n[nH]c2c1]

or a pharmaceutically acceptable salt thereof.

In some embodiments, the JAK inhibitor is NDI-031301 (Akahane et al., Blood 128:1596, 2016); or a pharmaceutically acceptable salt thereof.

In some embodments, the JAK inhibitor is BMS-986165 (Gillooly et al., 2016 *ACR/ARHP Annual Meeting*, Abstract 11L, 2016), having the following structure:

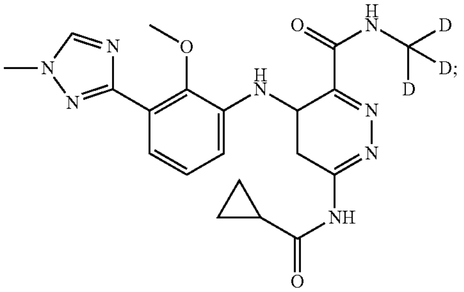

or a pharmaceutically acceptable salt thereof.

In some embodiments, the JAK inhibitor is tyrphostin A1 (Ishizaki et al., *Int. Immunol.* 26(5):257-267, 2014; Sugimoto et al., *Eur. J. Immunol.*, 33(1):243-51, 2003), having the following structure:

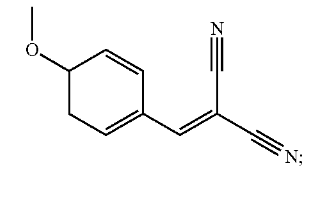

or a pharmaceutically acceptable salt thereof.

In some embodiments, the JAK inhibitor is a triazolopyridine, for example, as disclosed in US 2013/0143915; or a variant thereof, for example, a triazolopyridine having the following structure:

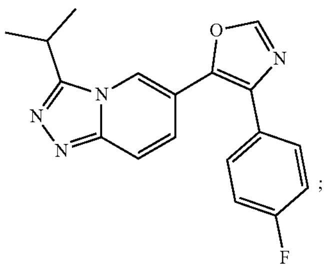 [SMILES: CC(C)c1nnc2ccc(-c3ocnc3-c3ccc(F)cc3)cn12]

or a pharmaceutically acceptable salt thereof.

In some embodiments, the JAK inhibitor is a compound as described by Tokarski J. S. et al., J. Biol. Chem., V290, No. 17, pp. 11061-11074 (2015), which is hereby incorporated by reference in its entirety, wherein the compound has the following structure:

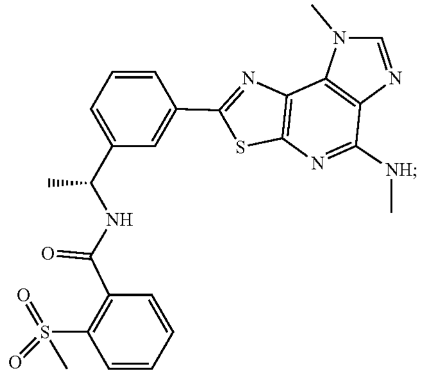 [SMILES: CNc1nc2sc(-c3cccc([C@@H](C)NC(=O)c4ccccc4S(C)(=O)=O)c3)nc2c2c1ncn2C]

or a pharmaceutically acceptable salt thereof.

In some embodiments, the JAK inhibitor is NDI-031407 (Miao et al., "Potent and Selective Tyk2 Inhibitor Highly Efficacious in Rodent Models of Inflammatory Bowel Disease and Psoriasis," Nimbus Therapeutics, 2016 ACR/ARHP Annual Meeting; Sep. 28, 2016; Abstract number 1911).

In some embodiments, the JAK inhibitor is R256 (AZD0449) or a variant thereof (Ashino et al., *J. Allergy Clin. Immunol.* 133(4):1162-1174, 2014); or a pharmaceutically acceptable salt thereof.

In some embodiments, the JAK inhibitor is SDC-1801; or a pharmaceutically acceptable salt thereof. SDC-1801 (Sareum PLC) demonstrates high selectivity for TYK2 and JAK1 kinases relative to JAK2 and JAK3.

In some embodiments, the JAK inhibitor is GSK-2864192A; or a pharmaceutically acceptable salt thereof.

Additional examples of JAK inhibitors are described in, e.g., Furomoto et al., *BioDrugs* 27(5):431-438, 2013; O' Shea et al., *Ann. Rheum. Dis.* 72(2):ii111-ii-115, 2013; Sonbol et al., *Ther. Adv. Hematol.* 4(1):15-35, 2013; Tanaka et al. (2015) *J. Biochem.* 158(3):173-179, 2015; Masse et al., *J. Immunol.* 194(1):67, 2015; Menet, *Pharm. Pat. Anal.* 3(4):449-466, 2014; Liang et al., *Euro. J. Med. Chem.* 67: 175-187, 2013; Jang et al., *Bioorg. Med. Chem. Lett.* 25(18): 3947-3952, 2015); U.S. Pat. Nos. 9,296,725; 9,309,240; US 2013/0231340; and US 2016/0251376.

In some embodiments, the JAK inhibitor is selected from the group consisting of abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. Preferably, the JAK inhibitor is tofacitinib or a pharmaceutically acceptable salt thereof. In a most preferred embodiment, the JAK inhibitor is tofacitinib citrate.

In some embodiments, the kinase inhibitor is a tyrosine kinase inhibitor, for example, a CSF-1R inhibitor. In some embodiments, the tyrosine kinase inhibitor is edicotinib (PRV-6527; JNJ-40346527) having the following structure:

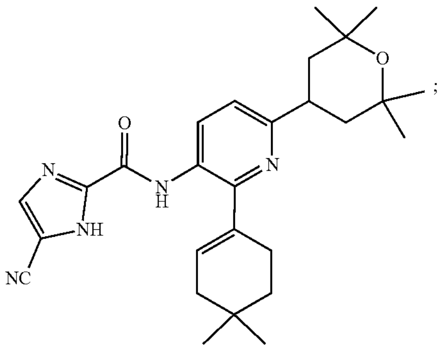 [SMILES: CC1(C)CC=C(c2nc(C3CC(C)(C)OC(C)(C)C3)ccc2NC(=O)c2ncc(C#N)[nH]2)CC1]

or a pharmaceutically acceptable salt thereof.

In some embodiments, the tyrosine kinase inhibitor is TOP-1288 (Foster, Martyn et al., "The Pharmacological Profile of TOP1288, a Narrow Spectrum Kinase Inhibitor (NSKI) in Clinical Development as an Anti-Inflammatory Treatment for Ulcerative Colitis," Gastroenterology, Volume 152, Issue 5, S766).

In some embodiments, the kinase inhibitor is GLPG-0555, which inhibits GT622 (ClinicalTrials.gov Identifier NCTO1023321).

In some embodiments, the tyrosine kinase inhibitor is a compound described in WO 2008/068751, which is incorporated by reference herein in its entirety. In some embodiments, the small molecule is a compound represented by the following structure:

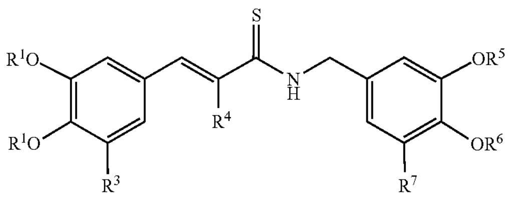

wherein:

$R^1$, $R^2$, $R^5$ and $R^6$ are independently selected from H, $C_1$-$C_4$ alkyl, acyl and a functional group that gives rise to hydroxyl upon hydrolysis;

$R^3$ and $R^7$ are independently selected from H, halogen, haloalkyl and $OR^8$, wherein R is H, $C_1$-$C_4$ alkyl, acyl or a functional group that gives rise to hydroxyl upon hydrolysis;

$R^4$ is H or CN;

including salts, hydrates, solvates, polymorphs, optical isomers, geometrical isomers, enantiomers, diastereomers, and mixtures thereof.

In some embodiments, the protein tyrosine kinase inhibitor is a compound having the structure:

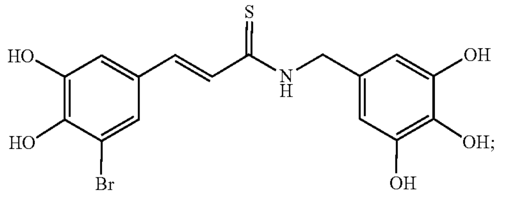 [SMILES: Oc1cc(CNC(=S)/C=C/c2cc(O)c(O)c(Br)c2)cc(O)c1O]

or a pharmaceutically acceptable salt thereof. In some embodiments, the compound is an agent that targets IRS1/2 and STAT3. In some embodiments, the compound is NT219 (El-Ami et al., Aging Cell (2014) 13:165-174; Kitov Pharmaceuticals, Inc), having the following structure:

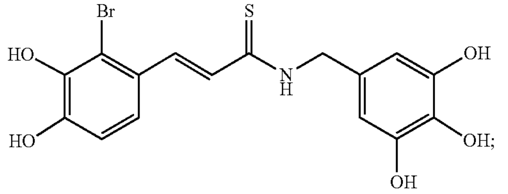 [SMILES: Oc1cc(CNC(=S)/C=C/c2ccc(O)c(O)c2Br)cc(O)c1O]

or a pharmaceutically acceptable salt thereof.

In some embodiments, the protein tyrosine kinase inhibitor is a compound described in Reuveni et al., Cancer Res. (2013) 73:4383-4394, for example, NT52, NT75, NT157, NT205 or C133; or a pharmaceutically acceptable salt thereof.

In some embodiments, the protein kinase inhibitor is a small molecule inhibitor of receptor interacting serine/threonine kinase 1 (RIP-1 kinase), for example, GSK-2982772 (Harris, P. A. et al., J. Med. Chem. 60(4):1247-1261 (2017); clinicaltrials.gov study identifier NCT02903966 entitled GSK2982772 Study in Subjects With Ulcerative Colitis) having the following structure:

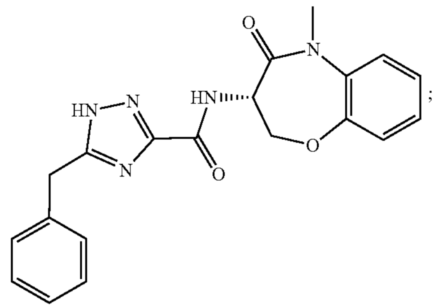 [SMILES: CN1C(=O)[C@@H](NC(=O)c2n[nH]c(Cc3ccccc3)n2)COc2ccccc21]

or a pharmaceutically acceptable salt thereof.

In some embodiments, the kinase inhibitor is semapimod (N,N'-Bis{3,5-bis(1-(carbamimidoylhydrazono)ethyl) phenyl}decanediamide; CNI-1493; CAS Registry No. 352513-83-8) (ClinicalTrials.gov Identifier NCT00739986). Semapimod inhibits c-Raf, a MAPK kinase kinase upstream of ERK (Lowenberg M, Verhaar A, van den Blink B, ten Kate F, van Deventer S, Peppelenbosch M, Hommes D. Specific inhibition of c-Raf activity by semapimod induces clinical remission in severe Crohn's disease. J. Immunol. 2005; 175:2293-2300).

In some embodiments, the kinase inhibitor is doramapimod (BIRB 796; CAS Registry No. 285983-48-4), having the following structure:

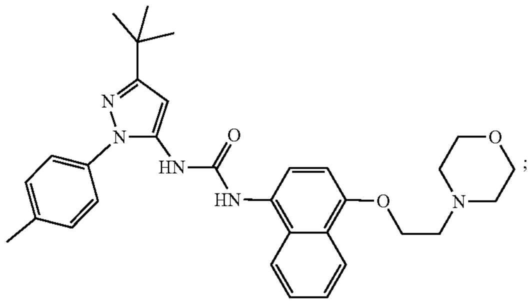 [SMILES: Cc1ccc(-n2nc(C(C)(C)C)cc2NC(=O)Nc2ccc(OCCN3CCOCC3)c3ccccc23)cc1]

or a pharmaceutically acceptable salt thereof. Doramapimod is a p38 mitogen-activated protein kinase inhibitor (Schreiber S, Feagan B, D'Haens G, et al., "Oral p38 mitogen-activated protein kinase inhibition with BIRB 796 for active Crohn's disease: a randomized, double-blind, placebo-controlled trial," Clin. Gastroenterol. Hepatol. 2006; 4:325-34).

In some embodiments, the kinase inhibitor is RWJ-68354 having the following structure:

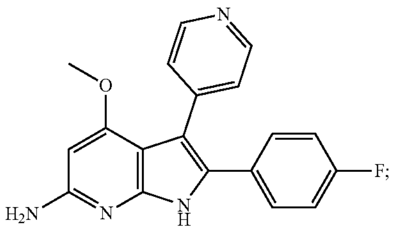 [SMILES: COc1cc(N)nc2[nH]c(-c3ccc(F)cc3)c(-c3ccncc3)c12]

or a pharmaceutically acceptable salt thereof. RWJ-68354 is a p38 mitogen-activated protein kinase inhibitor (Henry, J. R. et al., "6-Amino-2-(4-fluorophenyl)-4-methoxy-3-(4-pyridyl)-1H-pyrrolo[2,3-b]pyridine (RWJ 68354): a potent and selective p38 kinase inhibitor," J. Med. Chem., 41(22): 4196-8, 1998).

In some embodiments, the kinase inhibitor is PF-06650833 having the following structure:

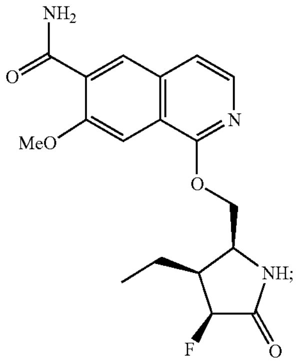 [SMILES: CC[C@@H]1[C@H](F)C(=O)N[C@@H]1COc1nccc2cc(C(N)=O)c(OC)cc12]

or a pharmaceutically acceptable salt thereof. PF-06650833 is an interleukin-1 receptor-associated kinase 4 (IRAK4) inhibitor (Lee, K. L. et al., "Discovery of Clinical Candidate 1-{[(2S,3S,4S)-3-Ethyl-4-fluoro-5-oxopyrrolidin-2-yl] methoxy}-7-methoxyisoquinoline-6-carboxamide (PF-06650833), a Potent, Selective Inhibitor of Interleukin-1 Receptor Associated Kinase 4 (IRAK4), by Fragment-Based Drug Design," J. Med. Chem. 60(13):5521-5542, 2017).

Exemplary Methods of Treating a Disease or Condition of the Gastrointestinal (GI) Tract with a JAK Inhibitor 1. Topical Administration of Drug to the GI Tract of a Subject Exemplary non-limiting embodiments follow.

In some embodiments, provided herein is a method of treating a disease or condition of the GI tract of a subject, comprising:

- topically administering to the GI tract of the subject (i) a JAK inhibitor or (ii) a pharmaceutical formulation that comprises a JAK inhibitor;
- wherein the topical administration comprises administering the JAK inhibitor or the pharmaceutical formulation that comprises the JAK inhibitor (a) to a section or subsection of the GI tract containing one or more disease sites, or (b) proximal to a section or subsection of the GI tract containing one or more disease sites.

Preferably, the disease or condition is an inflammatory gastrointestinal disease or condition. More preferably, the disease or condition is an inflammatory bowel disease. In a more particular embodiment, the inflammatory bowel disease is ulcerative colitis. In another more particular embodiment, the inflammatory bowel disease is Crohn's disease. In yet another more particular embodiment, the inflammatory bowel disease is ileal Crohn's disease.

In some embodiments, the section or subsection of the GI tract of the subject containing the one or more disease sites is the duodenum, and the JAK inhibitor or the pharmaceutical formulation that comprises the JAK inhibitor is administered to the stomach. In some embodiments, the disease or condition is Crohn's disease.

In some embodiments, the section or subsection of the GI tract of the subject containing the one or more disease sites is the duodenum, and the JAK inhibitor or the pharmaceutical formulation that comprises the JAK inhibitor is administered to the duodenum. In some embodiments, the disease or condition is Crohn's disease.

In some embodiments, the section or subsection of the GI tract of the subject containing the one or more disease sites is the jejunum, and the JAK inhibitor or the pharmaceutical formulation that comprises the JAK inhibitor is administered to the duodenum. In some embodiments, the disease or condition is Crohn's disease.

In some embodiments, the section or subsection of the GI tract of the subject containing the one or more disease sites is the jejunum, and the JAK inhibitor or the pharmaceutical formulation that comprises the JAK inhibitor is administered to the jejunum. In some embodiments, the disease or condition is Crohn's disease.

In some embodiments, the section or subsection of the GI tract of the subject containing the one or more disease sites is the ileum, and the JAK inhibitor or the pharmaceutical formulation that comprises the JAK inhibitor is administered to the jejunum. In some embodiments, the disease or condition is Crohn's disease. In some further embodiments, the disease or condition is ileal Crohn's disease. In some other embodiments, the disease or condition is ulcerative colitis with at least one or more disease sites in the terminal ileum.

In some embodiments, the section or subsection of the GI tract of the subject containing the one or more disease sites is the ileum, and the JAK inhibitor or the pharmaceutical formulation that comprises the JAK inhibitor is released to the ileum. In some embodiments, the disease or condition is Crohn's disease. In some further embodiments, the disease or condition is ileal Crohn's disease. In some other embodiments, the disease or condition is ulcerative colitis with at least one or more disease sites in the terminal ileum.

In some embodiments, the section or subsection of the GI tract of the subject containing the one or more disease sites is the cecum, and the JAK inhibitor or the pharmaceutical formulation that comprises the JAK inhibitor is released to the ileum. In some embodiments, the disease or condition is ulcerative colitis.

In some embodiments, the section or subsection of the GI tract of the subject containing the one or more disease sites is the cecum, and the JAK inhibitor or the pharmaceutical formulation that comprises the JAK inhibitor is released to the cecum. In some embodiments, the disease or condition is ulcerative colitis.

In some embodiments, the section or subsection of the GI tract of the subject containing the one or more disease sites is the colon, and the JAK inhibitor or the pharmaceutical formulation that comprises the JAK inhibitor is released to the cecum. In some embodiments, the disease or condition is ulcerative colitis.

In some embodiments, the section or subsection of the GI tract of the subject containing the one or more disease sites is the colon, and the JAK inhibitor or the pharmaceutical formulation that comprises the JAK inhibitor is released to the colon. In some embodiments, the disease or condition is ulcerative colitis.

In some embodiments, the section or subsection of the GI tract of the subject containing the one or more disease sites is the ascending colon, and the JAK inhibitor or the pharmaceutical formulation that comprises the JAK inhibitor is released to the cecum. In some embodiments, the disease or condition is ulcerative colitis.

In some embodiments, the section or subsection of the GI tract of the subject containing the one or more disease sites is the ascending colon, and the JAK inhibitor or the pharmaceutical formulation that comprises the JAK inhibitor is released to the ascending colon. In some embodiments, the disease or condition is ulcerative colitis.

In some embodiments, the section or subsection of the GI tract of the subject containing the one or more disease sites is the transverse colon, and the JAK inhibitor or the pharmaceutical formulation that comprises the JAK inhibitor is released to the cecum or ascending colon. In some embodiments, the disease or condition is ulcerative colitis.

In some embodiments, the section or subsection of the GI tract of the subject containing the one or more disease sites is the transverse colon, and the JAK inhibitor or the pharmaceutical formulation that comprises the JAK inhibitor is released to the transverse colon. In some embodiments, the disease or condition is ulcerative colitis.

In some embodiments, the section or subsection of the GI tract of the subject containing the one or more disease sites is the descending colon, and the JAK inhibitor or the pharmaceutical formulation that comprises the JAK inhibitor is released to the ascending or transverse colon. In some embodiments, the disease or condition is ulcerative colitis.

In some embodiments, the section or subsection of the GI tract of the subject containing the one or more disease sites is the descending colon, and the JAK inhibitor or the pharmaceutical formulation that comprises the JAK inhibitor is released to the descending colon. In some embodiments, the disease or condition is ulcerative colitis.

In some embodiments, the method of treating the disease or condition of the GI tract of the subject comprises administering a therapeutically effective amount of the JAK inhibitor. In some embodiments, the therapeutically effective amount of the JAK inhibitor is an induction dose. In some embodiments, the therapeutically effective amount of the JAK inhibitor is a maintenance dose. In some embodiments, the method comprises administering an induction dose and subsequently administering a maintenance dose of the JAK inhibitor.

In some embodiments, the method provides a concentration of the JAK inhibitor in the subject's blood, serum, or plasma of less than about 2000 ng/mL. In some further embodiments, the method provides a concentration of the JAK inhibitor in the subject's blood, serum, or plasma of less than about 1000 ng/mL. In some further embodiments, the method provides a concentration of the JAK inhibitor in the subject's blood, serum, or plasma of less than about 500 ng/mL. In some further embodiments, the method provides a concentration of the JAK inhibitor in the subject's blood, serum, or plasma of less than or equal to about 100 ng/mL. In yet some further embodiments, the method provides a concentration of the JAK inhibitor in the subject's blood, serum, or plasma of less than or equal to about 50 ng/mL. In some even further embodiments, the method provides a concentration of the JAK inhibitor in the subject's blood, serum, or plasma of less than or equal to about 10 ng/mL.

In some embodiments, the method provides a concentration of the JAK inhibitor in the subject's blood, serum, or plasma of about 1 ng/mL to about 100 ng/mL. In some further embodiments, the method provides a concentration of the JAK inhibitor in the subject's blood, serum, or plasma of about 1 ng/mL to about 50 ng/mL, about 1 ng/mL to about 30 ng/mL, about 1 ng/mL to about 10 ng/mL, or about 1 ng/mL to about 5 ng/mL.

In some embodiments, the method provides a ratio of GI tissue concentration of the JAK inhibitor to blood, serum, or plasma concentration of the JAK inhibitor of about 2:1 to about 3000:1, about 2:1 to about 2000:1, about 2:1 to about 1000:1, or about 2:1 to about 600:1.

In some embodiments, the method provides a plasma concentration of the JAK inhibitor that is reduced relative to the plasma concentration after systemic administration of the same amount of the JAK inhibitor.

In some embodiments, the JAK inhibitor is a JAK inhibitor as disclosed herein. In some embodiments, the JAK inhibitor is a small molecule, an antibody, a peptide, a peptide fragment or a nucleic acid. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In some preferred embodiments, the JAK inhibitor is tofacitinib or a pharmaceutically acceptable salt thereof, or more particularly, tofacitinib citrate.

In some embodiments, the JAK inhibitor or the pharmaceutical formulation comprising the JAK inhibitor is contained in a device selected from an endoscope, an ingestible device, or a reservoir. In some embodiments, the endoscope comprises a catheter. In some embodiments, the catheter is a spray catheter. In some embodiments, the endoscope is connected to the reservoir. In some embodiments, the reservoir is an anchorable reservoir.

In some embodiments, the pharmaceutical formulation is a suppository for rectal administration. In other embodiments, the pharmaceutical formulation is an enema for rectal administration. In some further embodiments, the enema for rectal administration is for sustained release or for delayed release.

In some embodiments, the JAK inhibitor is a small molecule or peptide, and the formulation is a formulation as disclosed herein. In some embodiments, the concentration of the JAK inhibitor in the formulation is at least about 5 mg/mL, such as at least about 10 mg/mL, such as at least about 15 mg/mL.

In some embodiments, the JAK inhibitor is a therapeutic protein or an antibody, such as a monoclonal antibody, and the formulation is a formulation as disclosed herein. In some embodiments, the concentration of the JAK inhibitor in the formulation is at least about 110 mg/mL, or at least about 125 mg/mL.

2. Topical Administration of Drug to the GI Tract of a Subject Via Oral Administration of an Ingestible Device as Disclosed Herein Exemplary non-limiting embodiments follow.

In some embodiments, provided herein is a method of treating an inflammatory disease or condition of the GI tract of a subject, comprising:

- topically administering to the GI tract of the subject (i) a JAK inhibitor or (ii) a pharmaceutical formulation that comprises a JAK inhibitor, said topical administration comprising:
- orally administering to the subject an ingestible device comprising the JAK inhibitor or the pharmaceutical formulation that comprises a JAK inhibitor; and
- releasing the JAK inhibitor or the pharmaceutical formulation that comprises the JAK inhibitor from the ingestible device (a) to a section or subsection of the GI tract containing one or more disease sites, or (b) proximal to a section or subsection of the GI tract containing one or more disease sites.

Preferably, the inflammatory disease or condition is an inflammatory bowel disease. In a more particular embodiment, the inflammatory bowel disease is ulcerative colitis. In another more particular embodiment, the inflammatory bowel disease is Crohn's disease. In yet another more particular embodiment, the inflammatory bowel disease is ileal Crohn's disease.

In some embodiments, the section or subsection of the GI tract of the subject containing the one or more disease sites is the duodenum, and the JAK inhibitor or the pharmaceutical formulation that comprises the JAK inhibitor is released from the device to the stomach. In some embodiments, the disease or condition is Crohn's disease.

In some embodiments, the section or subsection of the GI tract of the subject containing the one or more disease sites is the duodenum, and the JAK inhibitor or the pharmaceutical formulation that comprises the JAK inhibitor is released from the device to the duodenum. In some embodiments, the disease or condition is Crohn's disease.

In some embodiments, the section or subsection of the GI tract of the subject containing the one or more disease sites is the jejunum, and the JAK inhibitor or the pharmaceutical formulation that comprises the JAK inhibitor is released from the device to the duodenum. In some embodiments, the disease or condition is Crohn's disease.

In some embodiments, the section or subsection of the GI tract of the subject containing the one or more disease sites is the jejunum, and the JAK inhibitor or the pharmaceutical formulation that comprises the JAK inhibitor is released from the device to the jejunum. In some embodiments, the disease or condition is Crohn's disease.

In some embodiments, the section or subsection of the GI tract of the subject containing the one or more disease sites is the ileum, and the JAK inhibitor or the pharmaceutical formulation that comprises the JAK inhibitor is released from the device to the jejunum. In some embodiments, the disease or condition is Crohn's disease. In some further embodiments, the disease or condition is ileal Crohn's disease. In some other embodiments, the disease or condition is ulcerative colitis with at least one or more disease sites in the terminal ileum.

In some embodiments, the section or subsection of the GI tract of the subject containing the one or more disease sites is the ileum, and the JAK inhibitor or the pharmaceutical formulation that comprises the JAK inhibitor is released from the device to the ileum. In some embodiments, the disease or condition is Crohn's disease. In some further embodiments, the disease or condition is ileal Crohn's disease. In some other embodiments, the disease or condition is ulcerative colitis with at least one or more disease sites in the terminal ileum.

In some embodiments, the section or subsection of the GI tract of the subject containing the one or more disease sites is the cecum, and the JAK inhibitor or the pharmaceutical formulation that comprises the JAK inhibitor is released to the ileum. In some embodiments, the disease or condition is ulcerative colitis.

In some embodiments, the section or subsection of the GI tract of the subject containing the one or more disease sites is the cecum, and the JAK inhibitor or the pharmaceutical formulation that comprises the JAK inhibitor is released from the device to the cecum. In some embodiments, the disease or condition is ulcerative colitis.

In some embodiments, the section or subsection of the GI tract of the subject containing the one or more disease sites is the colon, and the JAK inhibitor or the pharmaceutical formulation that comprises the JAK inhibitor is released from the device to the cecum. In some embodiments, the disease or condition is ulcerative colitis.

In some embodiments, the section or subsection of the GI tract of the subject containing the one or more disease sites is the colon, and the JAK inhibitor or the pharmaceutical formulation that comprises the JAK inhibitor is released from the device to the colon. In some embodiments, the disease or condition is ulcerative colitis.

In some embodiments, the section or subsection of the GI tract of the subject containing the one or more disease sites is the ascending colon, and the JAK inhibitor or the pharmaceutical formulation that comprises the JAK inhibitor is released from the device to the cecum. In some embodiments, the disease or condition is ulcerative colitis.

In some embodiments, the section or subsection of the GI tract of the subject containing the one or more disease sites is the ascending colon, and the JAK inhibitor or the pharmaceutical formulation that comprises the JAK inhibitor is released from the device to the ascending colon. In some embodiments, the disease or condition is ulcerative colitis.

In some embodiments, the section or subsection of the GI tract of the subject containing the one or more disease sites is the transverse colon, and the JAK inhibitor or the pharmaceutical formulation that comprises the JAK inhibitor is released from the device to the cecum or ascending colon. In some embodiments, the disease or condition is ulcerative colitis.

In some embodiments, the section or subsection of the GI tract of the subject containing the one or more disease sites is the transverse colon, and the JAK inhibitor or the pharmaceutical formulation that comprises the JAK inhibitor is released from the device to the transverse colon. In some embodiments, the disease or condition is ulcerative colitis.

In some embodiments, the section or subsection of the GI tract of the subject containing the one or more disease sites is the descending colon, and the JAK inhibitor or the pharmaceutical formulation that comprises the JAK inhibitor is released from the device to the ascending or transverse colon. In some embodiments, the disease or condition is ulcerative colitis.

In some embodiments, the section or subsection of the GI tract of the subject containing the one or more disease sites is the descending colon, and the JAK inhibitor or the pharmaceutical formulation that comprises the JAK inhibitor is released from the device to the descending colon. In some embodiments, the disease or condition is ulcerative colitis.

In some embodiments, the JAK inhibitor, or the pharmaceutical formulation comprising the JAK inhibitor, is released by a mechanism capable of releasing the JAK inhibitor or the pharmaceutical formulation comprising the JAK inhibitor from the device. In some more particular embodiments, the release mechanism is a gas-generating cell capable of generating a gas in an amount sufficient to release the JAK inhibitor, or the pharmaceutical formulation comprising the JAK inhibitor, from the device.

In some embodiments, the ingestible device is equipped with a triggering mechanism for releasing the JAK inhibitor or the pharmaceutical formulation comprising the JAK inhibitor from the ingestible device. In some embodiments, the triggering mechanism comprises a processor or controller communicably coupled to one or more sensors. In some embodiments, the sensor is capable of detecting reflectance (e.g., light reflected from the environment in the GI tract and external to the device). In some embodiments, the sensor is capable of detecting muscle contractions and/or peristalsis. In some embodiments, the sensor is not a pH sensor. In some embodiments, the sensor is not a pressure sensor. In some embodiments, the sensor is not a temperature sensor. In some further embodiments, the processor or controller activates the triggering mechanism. In some embodiments, the device is programmed to release the JAK inhibitor or the pharmaceutical formulation comprising the JAK inhibitor to a location in the GI tract of the subject. In some embodiments, the location in the GI tract of the subject is a pre-selected location.

Thus, in some further embodiments, the method further comprises releasing the JAK inhibitor, or the pharmaceutical formulation comprising the JAK inhibitor, from the device, said device comprising the triggering mechanism. In some more particular embodiments, the release is triggered autonomously. In some more particular embodiments, the release is autonomously triggered based on reflectance (light reflectance) detected by the sensor. In some more particular embodiments, the release is autonomously triggered based on one or more pre-established parameters. In some more particular embodiments, the one or more pre-established parameters are selected from reflectance (light reflectance) in the GI tract, time following entry of the device into the GI tract of the subject, and a combination thereof. Additional pre-established parameters optionally include detected muscle contractions in the GI tract, pH in the GI tract, temperature in the GI tract, blood detected in the GI tract, and the level of analyte or biomarker determined in a sample obtained in the GI tract. In some more particular embodiments, the one or more pre-established parameters do not comprise the pH in the GI tract. In some more particular embodiments, the one or more pre-established parameters do not comprise the temperature in the GI tract. In some more particular embodiments, the one or more pre-established parameters do not comprise the pressure in the GI tract. In some more particular embodiments, the JAK inhibitor or the pharmaceutical formulation that comprises the JAK inhibitor is triggered for release from the device within a period of time equal to or less than about 5 minutes after the device is localized at a desired selected location in the GI tract of the subject, such as a pre-selected location.

In some embodiments, the ingestible device contains a therapeutically effective amount of the JAK inhibitor. In some embodiments, the therapeutically effective amount of the JAK inhibitor is an induction dose. In some other embodiments, the therapeutically effective amount of the JAK inhibitor is a maintenance dose.

In some embodiments, the ingestible device further comprises a mechanism to monitor elapsed time. In some embodiments, the elapsed time is a period of time that begins after entry of the ingestible device into the GI tract of the subject. In some embodiments, the elapsed time is a period of time that begins after entry of the ingestible device into the mouth of the subject. In some embodiments, the elapsed time is a period of time that begins after the ingestible device is swallowed by the subject. In some embodiments, the elapsed time is a period of time that ends after the device exits the GI tract. In some embodiments, the elapsed time is a period of time that ends when the device exits the GI tract. In some embodiments, the elapsed time is a period of time that ends after the device has localized to a portion of the GI tract. In some embodiments, the elapsed time is a period of time that ends after the mechanism to monitor elapsed time is inactivated. In some embodiments, the elapsed time includes or consists of time of transition, or the elapsed time during passage of the device from one portion of the GI tract into a second portion of the GI tract. In some embodiments, the elapsed time includes or consists of time following transition, or the elapsed time after passage of the device from one portion of the GI tract into a second portion of the GI tract. In some further embodiments, the elapsed time after entry of the device into the GI tract of the subject comprises time of transition, time following transition, or a combination thereof. In some embodiments, the mechanism configured to monitor elapsed time is a clock circuitry.

In some embodiments, the method provides a concentration of the JAK inhibitor in the subject's blood, serum, or plasma of less than about 2000 ng/mL. In some further embodiments, the method provides a concentration of the JAK inhibitor in the subject's blood, serum, or plasma of less than about 1000 ng/mL. In some further embodiments, the method provides a concentration of the JAK inhibitor in the subject's blood, serum, or plasma of less than about 500 ng/mL. In some further embodiments, the method provides a concentration of the JAK inhibitor in the subject's blood, serum, or plasma of less than or equal to about 100 ng/mL. In yet some further embodiments, the method provides a concentration of the JAK inhibitor in the subject's blood, serum, or plasma of less than or equal to about 50 ng/mL. In some even further embodiments, the method provides a concentration of the JAK inhibitor in the subject's blood, serum, or plasma of less than or equal to about 10 ng/mL.

In some embodiments, the method provides a concentration of the JAK inhibitor in the subject's blood, serum, or plasma of about 1 ng/mL to about 100 ng/mL. In some further embodiments, the method provides a concentration of the JAK inhibitor in the subject's blood, serum, or plasma of about 1 ng/mL to about 50 ng/mL, about 1 ng/mL to about 30 ng/mL, about 1 ng/mL to about 10 ng/mL, or about 1 ng/mL to about 5 ng/mL.

In some embodiments, the method provides a ratio of GI tissue concentration of the JAK inhibitor to blood, serum, or plasma concentration of the JAK inhibitor of about 2:1 to about 3000:1, about 2:1 to about 2000:1, about 2:1 to about 1000:1, or about 2:1 to about 600:1.

In some embodiments, the method provides a plasma concentration of the JAK inhibitor that is reduced relative to the plasma concentration after systemic administration of the same amount of the JAK inhibitor.

In some embodiments, the JAK inhibitor is a JAK inhibitor as disclosed herein. In some embodiments, the JAK inhibitor is a small molecule, an antibody, a peptide, a peptide fragment or a nucleic acid. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In some preferred embodiments, the JAK inhibitor is tofacitinib or a pharmaceutically acceptable salt thereof, or more particularly, tofacitinib citrate.

In some embodiments, the JAK inhibitor is a small molecule or peptide, and the formulation is a formulation as disclosed herein. In some embodiments, the concentration of the JAK inhibitor in the formulation is at least about 5 mg/mL, such as at least about 10 mg/mL, such as at least about 15 mg/mL.

In some embodiments, the JAK inhibitor is a therapeutic protein or an antibody, such as a monoclonal antibody, and the formulation is a formulation as disclosed herein. In some embodiments, the concentration of the JAK inhibitor in the formulation is at least about 110 mg/mL, or at least about 125 mg/mL.

3. Topical Administration of Drug to the GI Tract of a Subject Via Oral Administration of an Ingestible Device as Disclosed Herein, Further Comprising Localizing the Ingestible Device to a Pre-Selected Location of the GI Tract of the Subject Exemplary non-limiting embodiments follow.

In some embodiments, provided herein is a method of treating an inflammatory disease or condition of the GI tract of a subject, comprising:

topically administering to the GI tract of the subject (i) a JAK inhibitor or (ii) a pharmaceutical formulation that comprises a JAK inhibitor, said topical administration comprising:

orally administering to the subject an ingestible device comprising the JAK inhibitor or the pharmaceutical formulation that comprises the JAK inhibitor;

localizing the device to a pre-selected location of the GI tract of the subject; and releasing the JAK inhibitor or the pharmaceutical formulation that comprises the JAK inhibitor from the ingestible device (a) to a section or subsection of the GI tract containing one or more disease sites, or (b) proximal to a section or subsection of the GI tract containing one or more disease sites.

Preferably, the inflammatory disease or condition is an inflammatory bowel disease. In a more particular embodiment, the inflammatory bowel disease is ulcerative colitis. In another more particular embodiment, the inflammatory bowel disease is Crohn's disease. In yet another more particular embodiment, the inflammatory bowel disease is ileal Crohn's disease.

In some embodiments, the pre-selected location is the section or subsection of the GI tract containing the one or more inflammatory disease sites.

In some embodiments, the section or subsection of the GI tract of the subject containing the one or more disease sites is the duodenum, and the JAK inhibitor or the pharmaceutical formulation that comprises the JAK inhibitor is released from the device to the duodenum. In some embodiments, the disease or condition is Crohn's disease.

In some embodiments, the section or subsection of the GI tract of the subject containing the one or more disease sites is the jejunum, and the JAK inhibitor or the pharmaceutical formulation that comprises the JAK inhibitor is released from the device to the jejunum. In some embodiments, the disease or condition is Crohn's disease.

In some embodiments, the section or subsection of the GI tract of the subject containing the one or more disease sites is the ileum, and the JAK inhibitor or the pharmaceutical formulation that comprises the JAK inhibitor is released from the device to the ileum. In some embodiments, the disease or condition is Crohn's disease. In some further embodiments, the disease or condition is ileal Crohn's disease. In some other embodiments, the disease or condition is ulcerative colitis with at least one or more disease sites in the terminal ileum.

In some embodiments, the section or subsection of the GI tract of the subject containing the one or more disease sites is the cecum, and the JAK inhibitor or the pharmaceutical formulation that comprises the JAK inhibitor is released from the device to the cecum. In some embodiments, the disease or condition is ulcerative colitis.

In some embodiments, the section or subsection of the GI tract of the subject containing the one or more disease sites is the colon, and the JAK inhibitor or the pharmaceutical formulation that comprises the JAK inhibitor is released from the device to the colon. In some embodiments, the disease or condition is ulcerative colitis.

In some embodiments, the section or subsection of the GI tract of the subject containing the one or more disease sites is the ascending colon, and the JAK inhibitor or the pharmaceutical formulation that comprises the JAK inhibitor is released from the device to the ascending colon. In some embodiments, the disease or condition is ulcerative colitis.

In some embodiments, the section or subsection of the GI tract of the subject containing the one or more disease sites is the transverse colon, and the JAK inhibitor or the pharmaceutical formulation that comprises the JAK inhibitor is released from the device to the transverse colon. In some embodiments, the disease or condition is ulcerative colitis.

In some embodiments, the section or subsection of the GI tract of the subject containing the one or more disease sites is the descending colon, and the JAK inhibitor or the pharmaceutical formulation that comprises the JAK inhibitor is released from the device to the descending colon. In some embodiments, the disease or condition is ulcerative colitis.

In other embodiments, the pre-selected location is proximal to the section or subsection of the GI tract containing the one or more inflammatory disease sites. In some further embodiments, the pre-selected location immediately precedes the section or subsection of the subject's GI tract containing the one or more inflammatory disease sites. In yet some further embodiments, the pre-selected location does not contain or has not been determined to contain a disease site.

In some embodiments, the section or subsection of the GI tract of the subject containing the one or more disease sites is the duodenum, and the JAK inhibitor or the pharmaceutical formulation that comprises the JAK inhibitor is released from the device to the stomach. In some embodiments, the disease or condition is Crohn's disease.

In some embodiments, the section or subsection of the GI tract of the subject containing the one or more disease sites is the jejunum, and the JAK inhibitor or the pharmaceutical formulation that comprises the JAK inhibitor is released from the device to the duodenum. In some further embodiments, the duodenum does not contain or has not been determined to contain one or more disease sites. In some embodiments, the disease or condition is Crohn's disease.

In some embodiments, the section or subsection of the GI tract of the subject containing the one or more disease sites is the ileum, and the JAK inhibitor or the pharmaceutical formulation that comprises the JAK inhibitor is released from the device to the jejunum. In some further embodiments, the jejunum does not contain or has not been determined to contain one or more disease sites. In some embodiments, the disease or condition is Crohn's disease. In some further embodiments, the disease or condition is ileal Crohn's disease. In some other embodiments, the disease or condition is ulcerative colitis with at least one or more disease sites in the terminal ileum.

In some embodiments, the section or subsection of the GI tract of the subject containing the one or more disease sites is the cecum, and the JAK inhibitor or the pharmaceutical formulation that comprises the JAK inhibitor is released to the ileum. In some further embodiments, the ileum does not contain or has not been determined to contain one or more disease sites. In some embodiments, the disease or condition is ulcerative colitis.

In some embodiments, the section or subsection of the GI tract of the subject containing the one or more disease sites is the colon, and the JAK inhibitor or the pharmaceutical formulation that comprises the JAK inhibitor is released from the device to the cecum. In some further embodiments, the cecum does not contain or has not been determined to contain one or more disease sites. In some embodiments, the disease or condition is ulcerative colitis.

In some embodiments, the section or subsection of the GI tract of the subject containing the one or more disease sites is the ascending colon, and the JAK inhibitor or the pharmaceutical formulation that comprises the JAK inhibitor is released from the device to the cecum. In some further embodiments, the cecum does not contain or has not been determined to contain one or more disease sites. In some embodiments, the disease or condition is ulcerative colitis.

In some embodiments, the section or subsection of the GI tract of the subject containing the one or more disease sites is the transverse colon, and the JAK inhibitor or the pharmaceutical formulation that comprises the JAK inhibitor is released from the device to the cecum or ascending colon. In some embodiments, the disease or condition is ulcerative colitis.

In some embodiments, the section or subsection of the GI tract of the subject containing the one or more disease sites is the descending colon, and the JAK inhibitor or the pharmaceutical formulation that comprises the JAK inhibitor is released from the device to the ascending or transverse colon. In some embodiments, the disease or condition is ulcerative colitis.

In some embodiments, the JAK inhibitor, or the pharmaceutical formulation comprising the JAK inhibitor, is released by a mechanism capable of releasing the JAK inhibitor or the pharmaceutical formulation comprising the JAK inhibitor from the device. In some more particular embodiments, the release mechanism is a gas-generating cell capable of generating a gas in an amount sufficient to release the JAK inhibitor, or the pharmaceutical formulation comprising the JAK inhibitor, from the device.

In some embodiments, the ingestible device is equipped with a triggering mechanism for releasing the JAK inhibitor or the pharmaceutical formulation comprising the JAK inhibitor from the ingestible device. In some embodiments, the triggering mechanism comprises a processor or controller communicably coupled to one or more sensors. In some embodiments, the sensor is capable of detecting reflectance (e.g., light reflected from the environment in the GI tract and external to the device). In some embodiments, the sensor is capable of detecting muscle contractions and/or peristalsis. In some embodiments, the sensor is not a pH sensor. In some embodiments, the sensor is not a pressure sensor. In some embodiments, the sensor is not a temperature sensor. In some further embodiments, the processor or controller activates the triggering mechanism. In some embodiments, the device is programmed to release the JAK inhibitor or the pharmaceutical formulation comprising the JAK inhibitor to a location in the GI tract of the subject. In some embodiments, the location in the GI tract of the subject is the pre-selected location.

Thus, in some further embodiments, the method further comprises releasing the JAK inhibitor, or the pharmaceutical formulation comprising the JAK inhibitor, from the device, said device comprising the triggering mechanism. In some more particular embodiments, the release is triggered autonomously. In some more particular embodiments, the release is autonomously triggered based on reflectance (light reflectance) detected by the sensor. In some more particular embodiments, the release is autonomously triggered based on one or more pre-established parameters. In some more particular embodiments, the one or more pre-established parameters are selected from reflectance (light reflectance) in the GI tract, time following entry of the device into the GI tract of the subject, and a combination thereof. Additional pre-established parameters optionally include detected muscle contractions in the GI tract, pH in the GI tract, temperature in the GI tract, blood detected in the GI tract, and the level of analyte or biomarker determined in a sample obtained in the GI tract. In some more particular embodiments, the one or more pre-established parameters do not comprise the pH in the GI tract. In some more particular embodiments, the one or more pre-established parameters do not comprise the temperature in the GI tract. In some more particular embodiments, the one or more pre-established parameters do not comprise the pressure in the GI tract. In some more particular embodiments, the JAK inhibitor or the pharmaceutical formulation that comprises the JAK inhibitor is triggered for release from the device within a period of time equal to or less than about 5 minutes after the device is localized at a desired selected location in the GI tract of the subject, such as a pre-selected location.

In some embodiments, the ingestible device contains a therapeutically effective amount of the JAK inhibitor. In some embodiments, the therapeutically effective amount of the JAK inhibitor is an induction dose. In some other embodiments, the therapeutically effective amount of the JAK inhibitor is a maintenance dose.

In some embodiments, the ingestible device further comprises a mechanism to monitor elapsed time. In some embodiments, the elapsed time is a period of time that begins after entry of the ingestible device into the GI tract of the subject. In some embodiments, the elapsed time is a period of time that begins after entry of the ingestible device into the mouth of the subject. In some embodiments, the elapsed time is a period of time that begins after the ingestible device is swallowed by the subject. In some embodiments, the elapsed time is a period of time that ends after the device exits the GI tract. In some embodiments, the elapsed time is a period of time that ends when the device exits the GI tract. In some embodiments, the elapsed time is a period of time that ends after the device has localized to a portion of the GI tract. In some embodiments, the elapsed time is a period of time that ends after the mechanism to monitor elapsed time is inactivated. In some embodiments, the elapsed time includes or consists of time of transition, or the elapsed time during passage of the device from one portion of the GI tract into a second portion of the GI tract. In some embodiments, the elapsed time includes or consists of time following transition, or the elapsed time after passage of the device from one portion of the GI tract into a second portion of the GI tract. In some further embodiments, the elapsed time after entry of the device into the GI tract of the subject comprises time of transition, time following transition, or a combination thereof. In some embodiments, the mechanism configured to monitor elapsed time is a clock circuitry.

In some embodiments, the method provides a concentration of the JAK inhibitor in the subject's blood, serum, or plasma of less than about 2000 ng/mL. In some further embodiments, the method provides a concentration of the JAK inhibitor in the subject's blood, serum, or plasma of less than about 1000 ng/mL. In some further embodiments, the method provides a concentration of the JAK inhibitor in the subject's blood, serum, or plasma of less than about 500 ng/mL. In some further embodiments, the method provides a concentration of the JAK inhibitor in the subject's blood, serum, or plasma of less than or equal to about 100 ng/mL. In yet some further embodiments, the method provides a concentration of the JAK inhibitor in the subject's blood, serum, or plasma of less than or equal to about 50 ng/mL. In some even further embodiments, the method provides a concentration of the JAK inhibitor in the subject's blood, serum, or plasma of less than or equal to about 10 ng/mL.

In some embodiments, the method provides a concentration of the JAK inhibitor in the subject's blood, serum, or plasma of about 1 ng/mL to about 100 ng/mL. In some further embodiments, the method provides a concentration of the JAK inhibitor in the subject's blood, serum, or plasma of about 1 ng/mL to about 50 ng/mL, about 1 ng/mL to about 30 ng/mL, about 1 ng/mL to about 10 ng/mL, or about 1 ng/mL to about 5 ng/mL.

In some embodiments, the method provides a ratio of GI tissue concentration of the JAK inhibitor to blood, serum, or plasma concentration of the JAK inhibitor of about 2:1 to about 3000:1, about 2:1 to about 2000:1, about 2:1 to about 1000:1, or about 2:1 to about 600:1.

In some embodiments, the method provides a plasma concentration of the JAK inhibitor that is reduced relative to the plasma concentration after systemic administration of the same amount of the JAK inhibitor.

In some embodiments, the JAK inhibitor is a JAK inhibitor as disclosed herein. In some embodiments, the JAK inhibitor is a small molecule, an antibody, a peptide, a peptide fragment or a nucleic acid. In some embodiments, the JAK inhibitor is selected from the group consisting abrocitinib, baricitinib, BMS-986165, decemotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In some preferred embodiments, the JAK inhibitor is tofacitinib or a pharmaceutically acceptable salt thereof, or more particularly, tofacitinib citrate.

In some embodiments, the JAK inhibitor is a small molecule or peptide, and the formulation is a formulation as disclosed herein. In some embodiments, the concentration of the JAK inhibitor in the formulation is at least about 5 mg/mL, such as at least about 10 mg/mL, such as at least about 15 mg/mL.

In some embodiments, the JAK inhibitor is a therapeutic protein or an antibody, such as a monoclonal antibody, and the formulation is a formulation as disclosed herein. In some embodiments, the concentration of the JAK inhibitor in the formulation is at least about 110 mg/mL, or at least about 125 mg/mL.

In some embodiments, provided herein is a method of treating an inflammatory disease or condition of the GI tract of a subject, comprising:

topically administering to the GI tract of the subject (i) a JAK inhibitor or (ii) a pharmaceutical formulation that comprises a JAK inhibitor, said topical administration comprising:

orally administering to the subject an ingestible device comprising the JAK inhibitor or the pharmaceutical formulation that comprises the JAK inhibitor;

localizing the device to a pre-selected location of the GI tract of the subject, wherein said pre-selected location is the cecum; and releasing the JAK inhibitor or the pharmaceutical formulation that comprises the JAK inhibitor from the ingestible device to the cecum, wherein at least one of the one or more disease sites is in the colon.

In some embodiments, the one or more disease sites is in the ascending colon, the transverse colon, the descending colon, or a combination thereof.

In some embodiments, the cecum does not contain or has not been determined to contain a disease site.

Preferably, the inflammatory disease or condition is an inflammatory bowel disease. In some more particular embodiments, the inflammatory bowel disease is ulcerative colitis.

In some embodiments, the JAK inhibitor, or the pharmaceutical formulation comprising the JAK inhibitor, is released by a mechanism capable of releasing the JAK inhibitor or the pharmaceutical formulation comprising the JAK inhibitor from the device. In some more particular embodiments, the release mechanism is a gas-generating cell capable of generating a gas in an amount sufficient to release the JAK inhibitor, or the pharmaceutical formulation comprising the JAK inhibitor, from the device.

In some embodiments, the ingestible device is equipped with a triggering mechanism for releasing the JAK inhibitor or the pharmaceutical formulation comprising the JAK inhibitor from the ingestible device. In some embodiments, the triggering mechanism comprises a processor or controller communicably coupled to one or more sensors. In some embodiments, the sensor is capable of detecting reflectance (e.g., light reflected from the environment in the GI tract and external to the device). In some embodiments, the sensor is capable of detecting muscle contractions and/or peristalsis. In some embodiments, the sensor is not a pH sensor. In some embodiments, the sensor is not a pressure sensor. In some embodiments, the sensor is not a temperature sensor. In some further embodiments, the processor or controller activates the triggering mechanism. In some embodiments, the device is programmed to release the JAK inhibitor or the pharmaceutical formulation comprising the JAK inhibitor to a location in the GI tract of the subject. In some embodiments, the location in the GI tract of the subject is the pre-selected location.

Thus, in some further embodiments, the method further comprises releasing the JAK inhibitor, or the pharmaceutical formulation comprising the JAK inhibitor, from the device, said device comprising the triggering mechanism. In some more particular embodiments, the release is triggered autonomously. In some more particular embodiments, the release is autonomously triggered based on reflectance (light reflectance) detected by the sensor. In some more particular embodiments, the release is autonomously triggered based on one or more pre-established parameters. In some more particular embodiments, the one or more pre-established parameters are selected from reflectance (light reflectance) in the GI tract, time following entry of the device into the GI tract of the subject, and a combination thereof. Additional pre-established parameters optionally include detected muscle contractions in the GI tract, pH in the GI tract, temperature in the GI tract, blood detected in the GI tract, and the level of analyte or biomarker determined in a sample obtained in the GI tract. In some more particular embodiments, the one or more pre-established parameters do not comprise the pH in the GI tract. In some more particular embodiments, the one or more pre-established parameters do not comprise the temperature in the GI tract. In some more particular embodiments, the one or more pre-established parameters do not comprise the pressure in the GI tract. In some more particular embodiments, the JAK inhibitor or the pharmaceutical formulation that comprises the JAK inhibitor is triggered for release from the device within a period of time of equal to or less than about 5 minutes after the device localized at a desired location in the GI tract of the subject, such as a pre-selected location.

In some embodiments, the ingestible device contains a therapeutically effective amount of the JAK inhibitor. In some embodiments, the therapeutically effective amount of the JAK inhibitor is an induction dose. In some other embodiments, the therapeutically effective amount of the JAK inhibitor is a maintenance dose.

In some embodiments, the ingestible device further comprises a mechanism to monitor elapsed time. In some embodiments, the elapsed time is a period of time that begins after entry of the ingestible device into the GI tract of the subject. In some embodiments, the elapsed time is a period of time that begins after entry of the ingestible device into the mouth of the subject. In some embodiments, the elapsed time is a period of time that begins after the ingestible device is swallowed by the subject. In some embodiments, the elapsed time is a period of time that ends after the device exits the GI tract. In some embodiments, the elapsed time is a period of time that ends when the device exits the GI tract. In some embodiments, the elapsed time is a period of time that ends after the device has localized to a portion of the GI tract. In some embodiments, the elapsed time is a period of time that ends after the mechanism to monitor elapsed time is inactivated. In some embodiments, the elapsed time includes or consists of time of transition, or the elapsed time during passage of the device from one portion of the GI tract into a second portion of the GI tract. In some embodiments, the elapsed time includes or consists of time following transition, or the elapsed time after passage of the device from one portion of the GI tract into a second portion of the GI tract. In some further embodiments, the elapsed time after entry of the device into the GI tract of the subject comprises time of transition, time following transition, or a combination thereof. In some embodiments, the mechanism configured to monitor elapsed time is a clock circuitry.

In some more particular embodiments, the time of transition is elapsed time during passage of the device from mouth to stomach. In some embodiments, the time of transition is elapsed time during passage of the device from esophagus to stomach. In some embodiments, the time following transition is elapsed time after passage of the device from stomach to duodenum.

In some embodiments, the method provides a concentration of the JAK inhibitor in the subject's blood, serum, or plasma of less than about 2000 ng/mL. In some further embodiments, the method provides a concentration of the JAK inhibitor in the subject's blood, serum, or plasma of less than about 1000 ng/mL. In some further embodiments, the method provides a concentration of the JAK inhibitor in the subject's blood, serum, or plasma of less than about 500 ng/mL. In some further embodiments, the method provides a concentration of the JAK inhibitor in the subject's blood, serum, or plasma of less than or equal to about 100 ng/mL. In yet some further embodiments, the method provides a concentration of the JAK inhibitor in the subject's blood, serum, or plasma of less than or equal to about 50 ng/mL. In some even further embodiments, the method provides a concentration of the JAK inhibitor in the subject's blood, serum, or plasma of less than or equal to about 10 ng/mL.

In some embodiments, the method provides a concentration of the JAK inhibitor in the subject's blood, serum, or plasma of about 1 ng/mL to about 100 ng/mL. In some further embodiments, the method provides a concentration of the JAK inhibitor in the subject's blood, serum, or plasma of about 1 ng/mL to about 50 ng/mL, about 1 ng/mL to about 30 ng/mL, about 1 ng/mL to about 10 ng/mL, or about 1 ng/mL to about 5 ng/mL.

In some embodiments, the method provides a ratio of GI tissue concentration of the JAK inhibitor to blood, serum, or plasma concentration of the JAK inhibitor of about 2:1 to about 3000:1, about 2:1 to about 2000:1, about 2:1 to about 1000:1, or about 2:1 to about 600:1.

In some embodiments, the method provides a plasma concentration of the JAK inhibitor that is reduced relative to the plasma concentration after systemic administration of the same amount of the JAK inhibitor.

In some embodiments, the JAK inhibitor is a JAK inhibitor as disclosed herein. In some embodiments, the JAK inhibitor is a small molecule, an antibody, a peptide, a peptide fragment or a nucleic acid. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In some preferred embodiments, the JAK inhibitor is tofacitinib or a pharmaceutically acceptable salt thereof, or more particularly, tofacitinib citrate.

In some embodiments, the JAK inhibitor is a small molecule or peptide, and the formulation is a formulation as disclosed herein. In some embodiments, the concentration of the JAK inhibitor in the formulation is at least about 5 mg/mL, such as at least about 10 mg/mL, such as at least about 15 mg/mL.

In some embodiments, the JAK inhibitor is a therapeutic protein or an antibody, such as a monoclonal antibody, and the formulation is a formulation as disclosed herein. In some embodiments, the concentration of the JAK inhibitor in the formulation is at least about 110 mg/mL, or at least about 125 mg/mL.

In some embodiments, provided herein is a method of treating an inflammatory disease or condition of the GI tract of a subject, comprising:

- topically administering to the GI tract of the subject (i) a JAK inhibitor or (ii) a pharmaceutical formulation that comprises a JAK inhibitor, said topical administration comprising:
- orally administering to the subject an ingestible device comprising the JAK inhibitor or the pharmaceutical formulation that comprises the JAK inhibitor;
- localizing the device to a pre-selected location of the GI tract of the subject, wherein said pre-selected location is the colon; and
- releasing the JAK inhibitor or the pharmaceutical formulation that comprises the JAK inhibitor from the ingestible device to the colon, wherein at least one of the one or more disease sites is in the colon.

In some embodiments, the one or more disease sites is in the ascending colon, the transverse colon, the descending colon, or a combination thereof.

Preferably, the inflammatory disease or condition is an inflammatory bowel disease. In some more particular embodiments, the inflammatory bowel disease is ulcerative colitis.

In some embodiments, the JAK inhibitor, or the pharmaceutical formulation comprising the JAK inhibitor, is released by a mechanism capable of releasing the JAK inhibitor or the pharmaceutical formulation comprising the JAK inhibitor from the device. In some more particular embodiments, the release mechanism is a gas-generating cell capable of generating a gas in an amount sufficient to release the JAK inhibitor, or the pharmaceutical formulation comprising the JAK inhibitor, from the device.

In some embodiments, the ingestible device is equipped with a triggering mechanism for releasing the JAK inhibitor or the pharmaceutical formulation comprising the JAK inhibitor from the ingestible device. In some embodiments, the triggering mechanism comprises a processor or controller communicably coupled to one or more sensors. In some embodiments, the sensor is capable of detecting reflectance (e.g., light reflected from the environment in the GI tract and external to the device). In some embodiments, the sensor is capable of detecting muscle contractions and/or peristalsis. In some embodiments, the sensor is not a pH sensor. In some embodiments, the sensor is not a pressure sensor. In some embodiments, the sensor is not a temperature sensor. In some further embodiments, the processor or controller activates the triggering mechanism. In some embodiments, the device is programmed to release the JAK inhibitor or the pharmaceutical formulation comprising the JAK inhibitor to a location in the GI tract of the subject. In some embodiments, the location in the GI tract of the subject is the pre-selected location.

Thus, in some further embodiments, the method further comprises releasing the JAK inhibitor, or the pharmaceutical formulation comprising the JAK inhibitor, from the device, said device comprising the triggering mechanism. In some more particular embodiments, the release is triggered autonomously. In some more particular embodiments, the release is autonomously triggered based on reflectance (light reflectance) detected by the sensor. In some more particular embodiments, the release is autonomously triggered based on one or more pre-established parameters. In some more particular embodiments, the one or more pre-established parameters are selected from reflectance (light reflectance) in the GI tract, time following entry of the device into the GI tract of the subject, and a combination thereof. Additional pre-established parameters optionally include detected muscle contractions in the GI tract, pH in the GI tract, temperature in the GI tract, blood detected in the GI tract, and the level of analyte or biomarker determined in a sample obtained in the GI tract. In some more particular embodiments, the one or more pre-established parameters do not comprise the pH in the GI tract. In some more particular embodiments, the one or more pre-established parameters do not comprise the temperature in the GI tract. In some more particular embodiments, the one or more pre-established parameters do not comprise the pressure in the GI tract. In some more particular embodiments, the JAK inhibitor or the pharmaceutical formulation that comprises the JAK inhibitor is triggered for release from the device within a period of time of equal to or less than about 5 minutes after the device is localized at a desired location in the GI tract of the subject, such as a pre-selected location.

In some embodiments, the ingestible device contains a therapeutically effective amount of the JAK inhibitor. In some embodiments, the therapeutically effective amount of the JAK inhibitor is an induction dose. In some other embodiments, the therapeutically effective amount of the JAK inhibitor is a maintenance dose.

In some embodiments, the ingestible device further comprises a mechanism to monitor elapsed time. In some embodiments, the elapsed time is a period of time that begins after entry of the ingestible device into the GI tract of the subject. In some embodiments, the elapsed time is a period of time that begins after entry of the ingestible device into the mouth of the subject. In some embodiments, the elapsed time is a period of time that begins after the ingestible device is swallowed by the subject. In some embodiments, the elapsed time is a period of time that ends after the device exits the GI tract. In some embodiments, the elapsed time is a period of time that ends when the device exits the GI tract. In some embodiments, the elapsed time is a period of time that ends after the device has localized to a portion of the GI tract. In some embodiments, the elapsed time is a period of time that ends after the mechanism to monitor elapsed time is inactivated. In some embodiments, the elapsed time includes or consists of time of transition, or the elapsed time during passage of the device from one portion of the GI tract into a second portion of the GI tract. In some embodiments, the elapsed time includes or consists of time following transition, or the elapsed time after passage of the device from one portion of the GI tract into a second portion of the GI tract. In some further embodiments, the elapsed time after entry of the device into the GI tract of the subject comprises time of transition, time following transition, or a combination thereof. In some embodiments, the mechanism configured to monitor elapsed time is a clock circuitry.

In some more particular embodiments, the time of transition is elapsed time during passage of the device from mouth to stomach. In some embodiments, the time of transition is elapsed time during passage of the device from esophagus to stomach. In some embodiments, the time following transition is elapsed time after passage of the device from stomach to duodenum.

In some embodiments, the method provides a concentration of the JAK inhibitor in the subject's blood, serum, or plasma of less than about 2000 ng/mL. In some further embodiments, the method provides a concentration of the JAK inhibitor in the subject's blood, serum, or plasma of less than about 1000 ng/mL. In some further embodiments, the method provides a concentration of the JAK inhibitor in the subject's blood, serum, or plasma of less than about 500 ng/mL. In some further embodiments, the method provides a concentration of the JAK inhibitor in the subject's blood, serum, or plasma of less than or equal to about 100 ng/mL. In yet some further embodiments, the method provides a concentration of the JAK inhibitor in the subject's blood, serum, or plasma of less than or equal to about 50 ng/mL. In some even further embodiments, the method provides a concentration of the JAK inhibitor in the subject's blood, serum, or plasma of less than or equal to about 10 ng/mL.

In some embodiments, the method provides a concentration of the JAK inhibitor in the subject's blood, serum, or plasma of about 1 ng/mL to about 100 ng/mL. In some further embodiments, the method provides a concentration of the JAK inhibitor in the subject's blood, serum, or plasma of about 1 ng/mL to about 50 ng/mL, about 1 ng/mL to about 30 ng/mL, about 1 ng/mL to about 10 ng/mL, or about 1 ng/mL to about 5 ng/mL.

In some embodiments, the method provides a ratio of GI tissue concentration of the JAK inhibitor to blood, serum, or plasma concentration of the JAK inhibitor of about 2:1 to about 3000:1, about 2:1 to about 2000:1, about 2:1 to about 1000:1, or about 2:1 to about 600:1.

In some embodiments, the method provides a plasma concentration of the JAK inhibitor that is reduced relative to the plasma concentration after systemic administration of the same amount of the JAK inhibitor.

In some embodiments, the JAK inhibitor is a JAK inhibitor as disclosed herein. In some embodiments, the JAK inhibitor is a small molecule, an antibody, a peptide, a peptide fragment or a nucleic acid. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In some preferred embodiments, the JAK inhibitor is tofacitinib or a pharmaceutically acceptable salt thereof, or more particularly, tofacitinib citrate.

In some embodiments, the JAK inhibitor is a small molecule or peptide, and the formulation is a formulation as disclosed herein. In some embodiments, the concentration of the JAK inhibitor in the formulation is at least about 5 mg/mL, such as at least about 10 mg/mL, such as at least about 15 mg/mL.

In some embodiments, the JAK inhibitor is a therapeutic protein or an antibody, such as a monoclonal antibody, and the formulation is a formulation as disclosed herein. In some embodiments, the concentration of the JAK inhibitor in the formulation is at least about 110 mg/mL, or at least about 125 mg/mL.

4. Topical Administration of Drug to the GI Tract of a Subject Via Oral Administration of an Ingestible Device as Disclosed Herein, Further Comprising Localizing the Ingestible Device to a Pre-Selected Location of the GI Tract of the Subject. Wherein the Device is a Self-Localizing Device In some embodiments, the ingestible device is configured to determine the device location within the subject's GI tract. In some embodiments, the ingestible device comprises a self-localization mechanism configured to determine the device location within the subject's GI tract, and is thus a self-localizing device.

In some embodiments, the device is self-localized to a pre-selected location in the GI tract of the subject. Thus, in some further embodiments, the method of treating a disease or condition of the GI tract comprises localizing the device to a pre-selected location in the GI tract of the subject. In some embodiments, the pre-selected location is the section or subsection of the GI tract containing the one or more inflammatory disease sites. In other embodiments, the pre-selected location is proximal to the section or subsection of the GI tract containing the one or more inflammatory disease sites. In some further embodiments, the pre-selected location immediately precedes the section or subsection of the subject's GI tract containing the one or more inflammatory disease sites. In yet some further embodiments, the pre-selected location does not contain or has not been determined to contain a disease site.

In some exemplary embodiments, the method of treating a disease or condition of the GI tract of the subject comprises using a self-localizing device comprising at least one sensor configured to collect data, such as optical data, from the portions of the GI tract through which the device has travelled, including the portion of the GI tract in which the device is presently located. In some more particular embodiments, the device determines its location based on data collected by at least one sensor. In some more particular embodiments, the sensor comprises a light sensor and the data comprises optical data. In some more particular embodiments, the optical data is data collected by a system that includes at least one light source and at least one light detector. In some more particular embodiments, the light detector comprises a light sensor.

In some more particular embodiments, the device determines its location (self-localizes) to the stomach about one (1) minute following transition of the device into the GI tract (e.g., time after entry of the device into the mouth, or time after swallowing the device). In some more particular embodiments, the device determines its location to the jejunum about three (3) minutes following transition of the device from the stomach to the duodenum. In some more particular embodiments, the device is also localized in response to detection of a temperature change in the GI tract or in the portion of the GI tract where the device is located, relative to a portion of the GI trace where the device was previously located. In some more particular embodiments, the device is also localized upon detection of a pH change in the GI tract or in the portion of the GI tract where the device is located, relative to a portion of the GI trace where the device was previously located. In other more particular embodiments, localizing the device does not comprise measuring the pH in the GI tract or in the portion of the GI tract where the device is or was previously located. In some more particular embodiments, the device includes one or more machine readable hardware storage devices that store instructions that are executable by one or more processing devices to determine the location of the device.

In some more particular embodiments, the device determines its location within the GI tract of the subject with an accuracy of at least about 85%. In some more particular embodiments, transition of the device from one portion of the GI tract into an adjacent portion of the GI tract is determined by the device with an accuracy of at least about 85%. In some more particular embodiments, transition of the device from the stomach to the duodenum is determined with an accuracy of at least about 90%. In some more particular embodiments, transition of the device from the duodenum to the jejunum is determined with an accuracy of at least about 90%. In some more particular embodiments, transition of the device from the jejunum to the ileum is determined with an accuracy of at least about 80%. In some more particular embodiments, transition of the device from the ileum to the cecum is determined with an accuracy of at least about 80%.

Exemplary non-limiting embodiments follow.

In some embodiments, provided herein is a method of treating an inflammatory disease or condition of the GI tract of a subject, comprising:

- topically administering to the GI tract of the subject (i) a JAK inhibitor or (ii) a pharmaceutical formulation that comprises a JAK inhibitor, said topical administration comprising:
- orally administering to the subject an ingestible device comprising the JAK inhibitor or the pharmaceutical formulation that comprises the JAK inhibitor;
- localizing the device to a pre-selected location of the GI tract of the subject; and
- releasing the JAK inhibitor or the pharmaceutical formulation that comprises the JAK inhibitor from the ingestible device (a) to a section or subsection of the GI tract containing one or more disease sites, or (b) proximal to a section or subsection of the GI tract containing one or more disease sites;

wherein the device comprises a self-localization mechanism, and the device is self-localized to the pre-selected location via the device self-localization mechanism.

Preferably, the inflammatory disease or condition is an inflammatory bowel disease. In a more particular embodiment, the inflammatory bowel disease is ulcerative colitis. In another more particular embodiment, the inflammatory bowel disease is Crohn's disease. In yet another more particular embodiment, the inflammatory bowel disease is ileal Crohn's disease.

In some embodiments, the pre-selected location is the section or subsection of the GI tract containing the one or more inflammatory disease sites.

In some embodiments, the section or subsection of the GI tract of the subject containing the one or more disease sites is the duodenum, and the JAK inhibitor or the pharmaceutical formulation that comprises the JAK inhibitor is released from the device to the duodenum. In some embodiments, the disease or condition is Crohn's disease.

In some embodiments, the section or subsection of the GI tract of the subject containing the one or more disease sites is the jejunum, and the JAK inhibitor or the pharmaceutical formulation that comprises the JAK inhibitor is released from the device to the jejunum. In some embodiments, the disease or condition is Crohn's disease.

In some embodiments, the section or subsection of the GI tract of the subject containing the one or more disease sites is the ileum, and the JAK inhibitor or the pharmaceutical formulation that comprises the JAK inhibitor is released from the device to the ileum. In some embodiments, the disease or condition is Crohn's disease. In some further embodiments, the disease or condition is ileal Crohn's disease. In some other embodiments, the disease or condition is ulcerative colitis with at least one or more disease sites in the terminal ileum.

In some embodiments, the section or subsection of the GI tract of the subject containing the one or more disease sites is the cecum, and the JAK inhibitor or the pharmaceutical formulation that comprises the JAK inhibitor is released from the device to the cecum. In some embodiments, the disease or condition is ulcerative colitis.

In some embodiments, the section or subsection of the GI tract of the subject containing the one or more disease sites is the colon, and the JAK inhibitor or the pharmaceutical formulation that comprises the JAK inhibitor is released from the device to the colon. In some embodiments, the disease or condition is ulcerative colitis.

In some embodiments, the section or subsection of the GI tract of the subject containing the one or more disease sites is the ascending colon, and the JAK inhibitor or the pharmaceutical formulation that comprises the JAK inhibitor is released from the device to the ascending colon. In some embodiments, the disease or condition is ulcerative colitis.

In some embodiments, the section or subsection of the GI tract of the subject containing the one or more disease sites is the transverse colon, and the JAK inhibitor or the pharmaceutical formulation that comprises the JAK inhibitor is released from the device to the transverse colon. In some embodiments, the disease or condition is ulcerative colitis.

In some embodiments, the section or subsection of the GI tract of the subject containing the one or more disease sites is the descending colon, and the JAK inhibitor or the pharmaceutical formulation that comprises the JAK inhibitor is released from the device to the descending colon. In some embodiments, the disease or condition is ulcerative colitis.

In other embodiments, the pre-selected location is proximal to the section or subsection of the GI tract containing the one or more inflammatory disease sites. In some further embodiments, the pre-selected location immediately precedes the section or subsection of the subject's GI tract containing the one or more inflammatory disease sites. In yet some further embodiments, the pre-selected location does not contain or has not been determined to contain a disease site.

In some embodiments, the section or subsection of the GI tract of the subject containing the one or more disease sites is the duodenum, and the JAK inhibitor or the pharmaceutical formulation that comprises the JAK inhibitor is released from the device to the stomach. In some embodiments, the disease or condition is Crohn's disease.

In some embodiments, the section or subsection of the GI tract of the subject containing the one or more disease sites is the jejunum, and the JAK inhibitor or the pharmaceutical formulation that comprises the JAK inhibitor is released from the device to the duodenum. In some further embodiments, the duodenum does not contain or has not been determined to contain one or more disease sites. In some embodiments, the disease or condition is Crohn's disease.

In some embodiments, the section or subsection of the GI tract of the subject containing the one or more disease sites is the ileum, and the JAK inhibitor or the pharmaceutical formulation that comprises the JAK inhibitor is released from the device to the jejunum. In some further embodiments, the jejunum does not contain or has not been determined to contain one or more disease sites. In some embodiments, the disease or condition is Crohn's disease.

In some further embodiments, the disease or condition is ileal Crohn's disease. In some other embodiments, the disease or condition is ulcerative colitis with at least one or more disease sites in the terminal ileum.

In some embodiments, the section or subsection of the GI tract of the subject containing the one or more disease sites is the cecum, and the JAK inhibitor or the pharmaceutical formulation that comprises the JAK inhibitor is released to the ileum. In some further embodiments, the ileum does not contain or has not been determined to contain one or more disease sites. In some embodiments, the disease or condition is ulcerative colitis.

In some embodiments, the section or subsection of the GI tract of the subject containing the one or more disease sites is the colon, and the JAK inhibitor or the pharmaceutical formulation that comprises the JAK inhibitor is released from the device to the cecum. In some further embodiments, the cecum does not contain or has not been determined to contain one or more disease sites. In some embodiments, the disease or condition is ulcerative colitis.

In some embodiments, the section or subsection of the GI tract of the subject containing the one or more disease sites is the ascending colon, and the JAK inhibitor or the pharmaceutical formulation that comprises the JAK inhibitor is released from the device to the cecum. In some further embodiments, the cecum does not contain or has not been determined to contain one or more disease sites. In some embodiments, the disease or condition is ulcerative colitis.

In some embodiments, the section or subsection of the GI tract of the subject containing the one or more disease sites is the transverse colon, and the JAK inhibitor or the pharmaceutical formulation that comprises the JAK inhibitor is released from the device to the cecum or ascending colon. In some embodiments, the disease or condition is ulcerative colitis.

In some embodiments, the section or subsection of the GI tract of the subject containing the one or more disease sites is the descending colon, and the JAK inhibitor or the pharmaceutical formulation that comprises the JAK inhibitor is released from the device to the ascending or transverse colon. In some embodiments, the disease or condition is ulcerative colitis.

In some embodiments, the device self-localization mechanism is based on optical data, elapsed time, or a combination thereof. In some embodiments, the optical data comprises reflected light. Thus, in some embodiments, the device self-localization mechanism is based on data comprising light reflectance occurring external to the device and within the GI tract of the subject, elapsed time after entry of the ingestible device into the GI tract of the subject, or a combination thereof. In some embodiments, the device comprising the self-localization mechanism (the self-localizing device) comprises a first light source and a second light source. In some embodiments, the first light source is configured to emit light at a first wavelength, and the second light source is configured to emit light at a second wavelength different from the first wavelength. In some embodiments, the self-localizing device further comprises a first detector and a second detector, wherein the first detector is configured to detect light at the first wavelength, and the second detector is configured to detect light at the second wavelength. In some further embodiments, the first wavelength and second wavelength are each independently selected from the group consisting of red light, green light and blue light.

In some embodiments, the ingestible device further comprises a mechanism to monitor elapsed time. In some embodiments, the elapsed time is a period of time that begins after entry of the ingestible device into the GI tract of the subject. In some embodiments, the elapsed time is a period of time that begins after entry of the ingestible device into the mouth of the subject. In some embodiments, the elapsed time is a period of time that begins after the ingestible device is swallowed by the subject. In some embodiments, the elapsed time is a period of time that ends after the device exits the GI tract. In some embodiments, the elapsed time is a period of time that ends when the device exits the GI tract. In some embodiments, the elapsed time is a period of time that ends after the device has localized to a portion of the GI tract. In some embodiments, the elapsed time is a period of time that ends after the mechanism to monitor elapsed time is inactivated. In some embodiments, the elapsed time includes or consists of time of transition, or the elapsed time during passage of the device from one portion of the GI tract into a second portion of the GI tract. In some embodiments, the elapsed time includes or consists of time following transition, or the elapsed time after passage of the device from one portion of the GI tract into a second portion of the GI tract. In some further embodiments, the elapsed time after entry of the device into the GI tract of the subject comprises time of transition, time following transition, or a combination thereof. In some embodiments, the mechanism configured to monitor elapsed time is a clock circuitry.

In some more particular embodiments, the time of transition is elapsed time during passage of the device from mouth to stomach. In some embodiments, the time of transition is elapsed time during passage of the device from esophagus to stomach. In some embodiments, the time following transition is elapsed time after passage of the device from stomach to duodenum.

Thus, in some embodiments, the method further comprises self-localizing the device to the pre-selected location within the subject's GI tract, wherein the self-localization comprises detecting one or more device transitions between portions of the subject's GI tract. In some further embodiments, detecting one or more device transitions between portions of the subject's GI tract is based on optical data, such as data comprising light reflectance occurring external to the device and within the GI tract of the subject, elapsed time after entry of the device into the GI tract of the subject, or a combination thereof. In some embodiments, the one or more device transitions occurs between portions of the GI tract selected from the group consisting of: mouth and stomach; esophagus and stomach; stomach and duodenum; duodenum and jejunum; jejunum and ileum; ileum and cecum; and cecum and colon; and combinations of any two or more of the foregoing.

In some embodiments, the JAK inhibitor, or the pharmaceutical formulation comprising the JAK inhibitor, is released by a mechanism capable of releasing the JAK inhibitor or the pharmaceutical formulation comprising the JAK inhibitor from the device. In some more particular embodiments, the release mechanism is a gas-generating cell capable of generating a gas in an amount sufficient to release the JAK inhibitor, or the pharmaceutical formulation comprising the JAK inhibitor, from the device.

In some embodiments, the ingestible device is equipped with a triggering mechanism for releasing the JAK inhibitor or the pharmaceutical formulation comprising the JAK inhibitor from the ingestible device. In some embodiments, the triggering mechanism comprises a processor or controller communicably coupled to one or more sensors. In some embodiments, the sensor is capable of detecting reflectance (e.g., light reflected from the environment in the GI tract and external to the device). In some embodiments, the sensor is capable of detecting muscle contractions and/or peristalsis. In some embodiments, the sensor is not a pH sensor. In some embodiments, the sensor is not a pressure sensor. In some embodiments, the sensor is not a temperature sensor. In some further embodiments, the processor or controller activates the triggering mechanism. In some embodiments, the device is programmed to release the JAK inhibitor or the pharmaceutical formulation comprising the JAK inhibitor to a location in the GI tract of the subject. In some embodiments, the location in the GI tract of the subject is the pre-selected location.

Thus, in some further embodiments, the method further comprises releasing the JAK inhibitor, or the pharmaceutical formulation comprising the JAK inhibitor, from the device, said device comprising the triggering mechanism. In some more particular embodiments, the release is triggered autonomously. In some more particular embodiments, the release is autonomously triggered based on reflectance (light reflectance) detected by the sensor. In some more particular embodiments, the release is autonomously triggered based on one or more pre-established parameters. In some more particular embodiments, the one or more pre-established parameters are selected from reflectance (light reflectance) in the GI tract, time following entry of the device into the GI tract of the subject, and a combination thereof. Additional pre-established parameters optionally include detected muscle contractions in the GI tract, pH in the GI tract, temperature in the GI tract, blood detected in the GI tract, and the level of analyte or biomarker determined in a sample obtained in the GI tract. In some more particular embodiments, the one or more pre-established parameters do not comprise the pH in the GI tract. In some more particular embodiments, the one or more pre-established parameters do not comprise the temperature in the GI tract. In some more particular embodiments, the one or more pre-established parameters do not comprise the pressure in the GI tract. In some more particular embodiments, the JAK inhibitor or the pharmaceutical formulation that comprises the JAK inhibitor is triggered for release from the device within a period of time of equal to or less than about 5 minutes after the device is self-localized at the pre-selected location in the GI tract of the subject.

In some embodiments, the ingestible device contains a therapeutically effective amount of the JAK inhibitor. In some embodiments, the therapeutically effective amount of the JAK inhibitor is an induction dose. In some other embodiments, the therapeutically effective amount of the JAK inhibitor is a maintenance dose.

In some embodiments, the method provides a concentration of the JAK inhibitor in the subject's blood, serum, or plasma of less than about 2000 ng/mL. In some further embodiments, the method provides a concentration of the JAK inhibitor in the subject's blood, serum, or plasma of less than about 1000 ng/mL. In some further embodiments, the method provides a concentration of the JAK inhibitor in the subject's blood, serum, or plasma of less than about 500 ng/mL. In some further embodiments, the method provides a concentration of the JAK inhibitor in the subject's blood, serum, or plasma of less than or equal to about 100 ng/mL. In yet some further embodiments, the method provides a concentration of the JAK inhibitor in the subject's blood, serum, or plasma of less than or equal to about 50 ng/mL. In some even further embodiments, the method provides a concentration of the JAK inhibitor in the subject's blood, serum, or plasma of less than or equal to about 10 ng/mL.

In some embodiments, the method provides a concentration of the JAK inhibitor in the subject's blood, serum, or plasma of about 1 ng/mL to about 100 ng/mL. In some further embodiments, the method provides a concentration of the JAK inhibitor in the subject's blood, serum, or plasma of about 1 ng/mL to about 50 ng/mL, about 1 ng/mL to about 30 ng/mL, about 1 ng/mL to about 10 ng/mL, or about 1 ng/mL to about 5 ng/mL.

In some embodiments, the method provides a ratio of GI tissue concentration of the JAK inhibitor to blood, serum, or plasma concentration of the JAK inhibitor of about 2:1 to about 3000:1, about 2:1 to about 2000:1, about 2:1 to about 1000:1, or about 2:1 to about 600:1.

In some embodiments, the method provides a plasma concentration of the JAK inhibitor that is reduced relative to the plasma concentration after systemic administration of the same amount of the JAK inhibitor.

In some embodiments, the JAK inhibitor is a JAK inhibitor as disclosed herein. In some embodiments, the JAK inhibitor is a small molecule, an antibody, a peptide, a peptide fragment or a nucleic acid. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In some preferred embodiments, the JAK inhibitor is tofacitinib or a pharmaceutically acceptable salt thereof, or more particularly, tofacitinib citrate.

In some embodiments, the JAK inhibitor is a small molecule or peptide, and the formulation is a formulation as disclosed herein. In some embodiments, the concentration of the JAK inhibitor in the formulation is at least about 5 mg/mL, such as at least about 10 mg/mL, such as at least about 15 mg/mL.

In some embodiments, the JAK inhibitor is a therapeutic protein or an antibody, such as a monoclonal antibody, and the formulation is a formulation as disclosed herein. In some embodiments, the concentration of the JAK inhibitor in the formulation is at least about 110 mg/mL, or at least about 125 mg/mL.

In some embodiments, provided herein is a method of treating an inflammatory disease or condition of the GI tract of a subject, comprising:

topically administering to the GI tract of the subject (i) a JAK inhibitor or (ii) a pharmaceutical formulation that comprises a JAK inhibitor, said topical administration comprising:

orally administering to the subject an ingestible device comprising the JAK inhibitor or the pharmaceutical formulation that comprises the JAK inhibitor;

localizing the device to a pre-selected location of the GI tract of the subject; and releasing the JAK inhibitor or the pharmaceutical formulation that comprises the JAK inhibitor from the ingestible device (a) to a section or subsection of the GI tract containing one or more disease sites, or (b) proximal to a section or subsection of the GI tract containing one or more disease sites;

wherein the device further comprises a mechanism configured to measure elapsed time, and the device is self-localized to the pre-selected location based on data comprising elapsed time that begins after entry of the device into the GI tract of the subject.

In some embodiments, the elapsed time is a period of time that begins after entry of the ingestible device into the mouth of the subject. In some embodiments, the elapsed time is a period of time that begins after the ingestible device is swallowed by the subject. In some embodiments, the elapsed time is a period of time that ends after the device exits the GI tract. In some embodiments, the elapsed time is a period of time that ends when the device exits the GI tract. In some embodiments, the elapsed time is a period of time that ends after the device has localized to a portion of the GI tract. In some embodiments, the elapsed time is a period of time that ends after the mechanism to monitor elapsed time is inactivated. In some embodiments, the elapsed time includes or consists of time of transition, or the elapsed time during passage of the device from one portion of the GI tract into a second portion of the GI tract. In some embodiments, the elapsed time includes or consists of time following transition, or the elapsed time after passage of the device from one portion of the GI tract into a second portion of the GI tract. In some further embodiments, the elapsed time after entry of the device into the GI tract of the subject comprises time of transition, time following transition, or a combination thereof. In some embodiments, the mechanism configured to monitor elapsed time is a clock circuitry.

In some more particular embodiments, the time of transition is elapsed time during passage of the device from mouth to stomach. In some embodiments, the time of transition is elapsed time during passage of the device from esophagus to stomach. In some embodiments, the time following transition is elapsed time after passage of the device from stomach to duodenum.

In some embodiments, the time during transition of the device from the first portion of the GI tract to the second portion of the GI tract is pre-determined. In some embodiment, the time following transition of the device from the first portion of the GI tract to the second portion of the GI tract is pre-determined. In some embodiments, the second portion is an adjacent portion.

In some embodiments, the device is self-localized to the preselected location by detecting one or more device transitions between the portions of the subject's GI tract.

In some embodiments, the device is self-localized to the pre-selected location based on data consisting of elapsed time that begins after entry of the device into the GI tract of the subject. In some more particular embodiments, the elapsed time is time of transition of the device from mouth to stomach or from esophagus to stomach.

In some further embodiments, the pre-selected location is the stomach.

Preferably, the inflammatory disease or condition is an inflammatory bowel disease.

In some embodiments, the section or subsection of the GI tract of the subject containing the one or more disease sites is the duodenum, and the JAK inhibitor or the pharmaceutical formulation that comprises the JAK inhibitor is released from the device to the stomach. In some more particular embodiments, the inflammatory bowel disease is Crohn's disease.

In some embodiments, the JAK inhibitor, or the pharmaceutical formulation comprising the JAK inhibitor, is released by a mechanism capable of releasing the JAK inhibitor or the pharmaceutical formulation comprising the JAK inhibitor from the device. In some more particular embodiments, the release mechanism is a gas-generating cell capable of generating a gas in an amount sufficient to release the JAK inhibitor, or the pharmaceutical formulation comprising the JAK inhibitor, from the device.

In some embodiments, the ingestible device is equipped with a triggering mechanism for releasing the JAK inhibitor or the pharmaceutical formulation comprising the JAK inhibitor from the ingestible device. In some embodiments, the triggering mechanism comprises a processor or controller communicably coupled to one or more sensors. In some embodiments, the sensor is capable of detecting reflectance (e.g., light reflected from the environment in the GI tract and external to the device). In some embodiments, the sensor is capable of detecting muscle contractions and/or peristalsis. In some embodiments, the sensor is not a pH sensor. In some embodiments, the sensor is not a pressure sensor. In some embodiments, the sensor is not a temperature sensor. In some further embodiments, the processor or controller activates the triggering mechanism. In some embodiments, the device is programmed to release the JAK inhibitor or the pharmaceutical formulation comprising the JAK inhibitor to a location in the GI tract of the subject. In some embodiments, the location in the GI tract of the subject is the pre-selected location.

Thus, in some further embodiments, the method further comprises releasing the JAK inhibitor, or the pharmaceutical formulation comprising the JAK inhibitor, from the device, said device comprising the triggering mechanism. In some more particular embodiments, the release is triggered autonomously. In some more particular embodiments, the release is autonomously triggered based on reflectance (light reflectance) detected by the sensor. In some more particular embodiments, the release is autonomously triggered based on one or more pre-established parameters. In some more particular embodiments, the one or more pre-established parameters are selected from reflectance (light reflectance) in the GI tract, time following entry of the device into the GI tract of the subject, and a combination thereof. Additional pre-established parameters optionally include detected muscle contractions in the GI tract, pH in the GI tract, temperature in the GI tract, blood detected in the GI tract, and the level of analyte or biomarker determined in a sample obtained in the GI tract. In some more particular embodiments, the one or more pre-established parameters do not comprise the pH in the GI tract. In some more particular embodiments, the one or more pre-established parameters do not comprise the temperature in the GI tract. In some more particular embodiments, the one or more pre-established parameters do not comprise the pressure in the GI tract. In some more particular embodiments, the JAK inhibitor or the pharmaceutical formulation that comprises the JAK inhibitor is triggered for release from the device within a period of time of equal to or less than about 5 minutes after the device is self-localized at the pre-selected location in the GI tract of the subject.

In some embodiments, the ingestible device contains a therapeutically effective amount of the JAK inhibitor. In some embodiments, the therapeutically effective amount of the JAK inhibitor is an induction dose. In some other embodiments, the therapeutically effective amount of the JAK inhibitor is a maintenance dose.

In some embodiments, the method provides a concentration of the JAK inhibitor in the subject's blood, serum, or plasma of less than about 2000 ng/mL. In some further embodiments, the method provides a concentration of the JAK inhibitor in the subject's blood, serum, or plasma of less than about 1000 ng/mL. In some further embodiments, the method provides a concentration of the JAK inhibitor in the subject's blood, serum, or plasma of less than about 500 ng/mL. In some further embodiments, the method provides a concentration of the JAK inhibitor in the subject's blood, serum, or plasma of less than or equal to about 100 ng/mL. In yet some further embodiments, the method provides a concentration of the JAK inhibitor in the subject's blood, serum, or plasma of less than or equal to about 50 ng/mL. In some even further embodiments, the method provides a concentration of the JAK inhibitor in the subject's blood, serum, or plasma of less than or equal to about 10 ng/mL.

In some embodiments, the method provides a concentration of the JAK inhibitor in the subject's blood, serum, or plasma of about 1 ng/mL to about 100 ng/mL. In some further embodiments, the method provides a concentration of the JAK inhibitor in the subject's blood, serum, or plasma of about 1 ng/mL to about 50 ng/mL, about 1 ng/mL to about 30 ng/mL, about 1 ng/mL to about 10 ng/mL, or about 1 ng/mL to about 5 ng/mL.

In some embodiments, the method provides a ratio of GI tissue concentration of the JAK inhibitor to blood, serum, or plasma concentration of the JAK inhibitor of about 2:1 to about 3000:1, about 2:1 to about 2000:1, about 2:1 to about 1000:1, or about 2:1 to about 600:1.

In some embodiments, the method provides a plasma concentration of the JAK inhibitor that is reduced relative to the plasma concentration after systemic administration of the same amount of the JAK inhibitor.

In some embodiments, the JAK inhibitor is a JAK inhibitor as disclosed herein. In some embodiments, the JAK inhibitor is a small molecule, an antibody, a peptide, a peptide fragment or a nucleic acid. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In some preferred embodiments, the JAK inhibitor is tofacitinib or a pharmaceutically acceptable salt thereof, or more particularly, tofacitinib citrate.

In some embodiments, the JAK inhibitor is a small molecule or peptide, and the formulation is a formulation as disclosed herein. In some embodiments, the concentration of the JAK inhibitor in the formulation is at least about 5 mg/mL, such as at least about 10 mg/mL, such as at least about 15 mg/mL.

In some embodiments, the JAK inhibitor is a therapeutic protein or an antibody, such as a monoclonal antibody, and the formulation is a formulation as disclosed herein. In some embodiments, the concentration of the JAK inhibitor in the formulation is at least about 110 mg/mL, or at least about 125 mg/mL.

In some embodiments, provided herein is a method of treating an inflammatory disease or condition of the GI tract of a subject, comprising:

topically administering to the GI tract of the subject (i) a JAK inhibitor or (ii) a pharmaceutical formulation that comprises a JAK inhibitor, said topical administration comprising:

orally administering to the subject an ingestible device comprising the JAK inhibitor or the pharmaceutical formulation that comprises the JAK inhibitor;

localizing the device to a pre-selected location of the GI tract of the subject; and releasing the JAK inhibitor or the pharmaceutical formulation that comprises the JAK inhibitor from the ingestible (a) to a section or subsection of the GI tract containing one or more disease sites, or (b) proximal to a section or subsection of the GI tract containing one or more disease sites;

wherein the device is self-localized to the pre-selected location based on data comprising:

(a) optical data;

(b) elapsed time after entry of the device into the GI tract of the subject; or (c) a combination of (a) and (b).

In some embodiments, the optical data comprises light reflectance that is external to the device and within the GI tract of the subject.

Preferably, the inflammatory disease or condition is an inflammatory bowel disease. In a more particular embodiment, the inflammatory bowel disease is ulcerative colitis. In another more particular embodiment, the inflammatory bowel disease is Crohn's disease. In yet another more particular embodiment, the inflammatory bowel disease is ileal Crohn's disease.

In some embodiments, the pre-selected location is the section or subsection of the GI tract containing the one or more inflammatory disease sites.

In some embodiments, the section or subsection of the GI tract of the subject containing the one or more disease sites is the duodenum, and the JAK inhibitor or the pharmaceutical formulation that comprises the JAK inhibitor is released from the device to the duodenum. In some embodiments, the disease or condition is Crohn's disease.

In some embodiments, the section or subsection of the GI tract of the subject containing the one or more disease sites is the jejunum, and the JAK inhibitor or the pharmaceutical formulation that comprises the JAK inhibitor is released from the device to the jejunum. In some embodiments, the disease or condition is Crohn's disease.

In some embodiments, the section or subsection of the GI tract of the subject containing the one or more disease sites is the ileum, and the JAK inhibitor or the pharmaceutical formulation that comprises the JAK inhibitor is released from the device to the ileum. In some embodiments, the disease or condition is Crohn's disease. In some further embodiments, the disease or condition is ileal Crohn's disease. In some other embodiments, the disease or condition is ulcerative colitis with at least one or more disease sites in the terminal ileum.

In some embodiments, the section or subsection of the GI tract of the subject containing the one or more disease sites is the cecum, and the JAK inhibitor or the pharmaceutical formulation that comprises the JAK inhibitor is released from the device to the cecum. In some embodiments, the disease or condition is ulcerative colitis.

In some embodiments, the section or subsection of the GI tract of the subject containing the one or more disease sites is the colon, and the JAK inhibitor or the pharmaceutical formulation that comprises the JAK inhibitor is released from the device to the colon. In some embodiments, the disease or condition is ulcerative colitis.

In some embodiments, the section or subsection of the GI tract of the subject containing the one or more disease sites is the ascending colon, and the JAK inhibitor or the pharmaceutical formulation that comprises the JAK inhibitor is released from the device to the ascending colon. In some embodiments, the disease or condition is ulcerative colitis.

In some embodiments, the section or subsection of the GI tract of the subject containing the one or more disease sites is the transverse colon, and the JAK inhibitor or the pharmaceutical formulation that comprises the JAK inhibitor is released from the device to the transverse colon. In some embodiments, the disease or condition is ulcerative colitis.

In some embodiments, the section or subsection of the GI tract of the subject containing the one or more disease sites is the descending colon, and the JAK inhibitor or the pharmaceutical formulation that comprises the JAK inhibitor is released from the device to the descending colon. In some embodiments, the disease or condition is ulcerative colitis.

In other embodiments, the pre-selected location is proximal to the section or subsection of the GI tract containing the one or more inflammatory disease sites. In some further embodiments, the pre-selected location immediately precedes the section or subsection of the subject's GI tract containing the one or more inflammatory disease sites. In yet some further embodiments, the pre-selected location does not contain or has not been determined to contain a disease site.

In some embodiments, the section or subsection of the GI tract of the subject containing the one or more disease sites is the duodenum, and the JAK inhibitor or the pharmaceutical formulation that comprises the JAK inhibitor is released from the device to the stomach. In some embodiments, the disease or condition is Crohn's disease.

In some embodiments, the section or subsection of the GI tract of the subject containing the one or more disease sites is the jejunum, and the JAK inhibitor or the pharmaceutical formulation that comprises the JAK inhibitor is released from the device to the duodenum. In some further embodiments, the duodenum does not contain or has not been determined to contain one or more disease sites. In some embodiments, the disease or condition is Crohn's disease.

In some embodiments, the section or subsection of the GI tract of the subject containing the one or more disease sites is the ileum, and the JAK inhibitor or the pharmaceutical formulation that comprises the JAK inhibitor is released from the device to the jejunum. In some further embodiments, the jejunum does not contain or has not been determined to contain one or more disease sites. In some embodiments, the disease or condition is Crohn's disease. In some further embodiments, the disease or condition is ileal Crohn's disease. In some other embodiments, the disease or condition is ulcerative colitis with at least one or more disease sites in the terminal ileum.

In some embodiments, the section or subsection of the GI tract of the subject containing the one or more disease sites is the cecum, and the JAK inhibitor or the pharmaceutical formulation that comprises the JAK inhibitor is released to the ileum. In some further embodiments, the ileum does not contain or has not been determined to contain one or more disease sites. In some embodiments, the disease or condition is ulcerative colitis.

In some embodiments, the section or subsection of the GI tract of the subject containing the one or more disease sites is the colon, and the JAK inhibitor or the pharmaceutical formulation that comprises the JAK inhibitor is released from the device to the cecum. In some further embodiments, the cecum does not contain or has not been determined to contain one or more disease sites. In some embodiments, the disease or condition is ulcerative colitis.

In some embodiments, the section or subsection of the GI tract of the subject containing the one or more disease sites is the ascending colon, and the JAK inhibitor or the pharmaceutical formulation that comprises the JAK inhibitor is released from the device to the cecum. In some further embodiments, the cecum does not contain or has not been determined to contain one or more disease sites. In some embodiments, the disease or condition is ulcerative colitis.

In some embodiments, the section or subsection of the GI tract of the subject containing the one or more disease sites is the transverse colon, and the JAK inhibitor or the pharmaceutical formulation that comprises the JAK inhibitor is released from the device to the cecum or ascending colon. In some embodiments, the disease or condition is ulcerative colitis.

In some embodiments, the section or subsection of the GI tract of the subject containing the one or more disease sites is the descending colon, and the JAK inhibitor or the pharmaceutical formulation that comprises the JAK inhibitor is released from the device to the ascending or transverse colon. In some embodiments, the disease or condition is ulcerative colitis.

In some embodiments, the device self-localization mechanism is based on data comprising light reflectance occurring external to the device and within the GI tract of the subject, elapsed time after entry of the device into the GI tract of the subject, or a combination thereof. In some embodiments, the device comprising the self-localization mechanism (the self-localizing device) comprises a first light source and a second light source. In some embodiments, the first light source is configured to emit light at a first wavelength, and the second light source is configured to emit light at a second wavelength different from the first wavelength. In some embodiments, the self-localizing device further comprises a first detector and a second detector, wherein the first detector is configured to detect light at the first wavelength, and the second detector is configured to detect light at the second wavelength. In some further embodiments, the first wavelength and second wavelength are each independently selected from the group consisting of red light, green light and blue light.

In some embodiments, the ingestible device further comprises a mechanism to monitor elapsed time. In some embodiments, the elapsed time is a period of time that begins after entry of the ingestible device into the GI tract of the subject. In some embodiments, the elapsed time is a period of time that begins after entry of the ingestible device into the mouth of the subject. In some embodiments, the elapsed time is a period of time that begins after the ingestible device is swallowed by the subject. In some embodiments, the elapsed time is a period of time that ends after the device exits the GI tract. In some embodiments, the elapsed time is a period of time that ends when the device exits the GI tract. In some embodiments, the elapsed time is a period of time that ends after the device has localized to a portion of the GI tract. In some embodiments, the elapsed time is a period of time that ends after the mechanism to monitor elapsed time is inactivated. In some embodiments, the elapsed time includes or consists of time of transition, or the elapsed time during passage of the device from one portion of the GI tract into a second portion of the GI tract. In some embodiments, the elapsed time includes or consists of time following transition, or the elapsed time after passage of the device from one portion of the GI tract into a second portion of the GI tract. In some further embodiments, the elapsed time after entry of the device into the GI tract of the subject comprises time of transition, time following transition, or a combination thereof. In some embodiments, the mechanism configured to monitor elapsed time is a clock circuitry.

In some more particular embodiments, the time of transition is elapsed time during passage of the device from mouth to stomach. In some embodiments, the time of transition is elapsed time during passage of the device from esophagus to stomach. In some embodiments, the time following transition is elapsed time after passage of the device from stomach to duodenum.

Thus, in some embodiments, the method further comprises self-localizing the device to the pre-selected location within the subject's GI tract, wherein the self-localization comprises detecting one or more device transitions between portions of the subject's GI tract. In some further embodiments, detecting one or more device transitions between portions of the subject's GI tract is based on optical data, such as data comprising light reflectance occurring external to the device and within the GI tract of the subject, elapsed time after entry of the device into the GI tract of the subject, or a combination thereof. In some embodiments, the one or more device transitions occurs between portions of the GI tract selected from the group consisting of: mouth and stomach; esophagus and stomach; stomach and duodenum; duodenum and jejunum; jejunum and ileum; ileum and cecum; and cecum and colon; and combinations of any two or more of the foregoing.

In some embodiments, the JAK inhibitor, or the pharmaceutical formulation comprising the JAK inhibitor, is released by a mechanism capable of releasing the JAK inhibitor or the pharmaceutical formulation comprising the JAK inhibitor from the device. In some more particular embodiments, the release mechanism is a gas-generating cell capable of generating a gas in an amount sufficient to release the JAK inhibitor, or the pharmaceutical formulation comprising the JAK inhibitor, from the device.

In some embodiments, the ingestible device is equipped with a triggering mechanism for releasing the JAK inhibitor or the pharmaceutical formulation comprising the JAK inhibitor from the ingestible device. In some embodiments, the triggering mechanism comprises a processor or controller communicably coupled to one or more sensors. In some embodiments, the sensor is capable of detecting reflectance (e.g., light reflected from the environment in the GI tract and external to the device). In some embodiments, the sensor is capable of detecting muscle contractions and/or peristalsis. In some embodiments, the sensor is not a pH sensor. In some embodiments, the sensor is not a pressure sensor. In some embodiments, the sensor is not a temperature sensor. In some further embodiments, the processor or controller activates the triggering mechanism. In some embodiments, the device is programmed to release the JAK inhibitor or the pharmaceutical formulation comprising the JAK inhibitor to a location in the GI tract of the subject. In some embodiments, the location in the GI tract of the subject is the pre-selected location.

Thus, in some further embodiments, the method further comprises releasing the JAK inhibitor, or the pharmaceutical formulation comprising the JAK inhibitor, from the device, said device comprising the triggering mechanism. In some more particular embodiments, the release is triggered autonomously. In some more particular embodiments, the release is autonomously triggered based on reflectance (light reflectance) detected by the sensor. In some more particular embodiments, the release is autonomously triggered based on one or more pre-established parameters. In some more particular embodiments, the one or more pre-established parameters are selected from reflectance (light reflectance) in the GI tract, time following entry of the device into the GI tract of the subject, and a combination thereof. Additional pre-established parameters optionally include detected muscle contractions in the GI tract, pH in the GI tract, temperature in the GI tract, blood detected in the GI tract, and the level of analyte or biomarker determined in a sample obtained in the GI tract. In some more particular embodiments, the one or more pre-established parameters do not comprise the pH in the GI tract. In some more particular embodiments, the one or more pre-established parameters do not comprise the temperature in the GI tract. In some more particular embodiments, the one or more pre-established parameters do not comprise the pressure in the GI tract. In some more particular embodiments, the JAK inhibitor or the pharmaceutical formulation that comprises the JAK inhibitor is triggered for release from the device within a period of time of equal to or less than about 5 minutes after the device is self-localized at the pre-selected location in the GI tract of the subject.

Preferably, the inflammatory disease or condition is an inflammatory bowel disease. In a more particular embodiment, the inflammatory bowel disease is ulcerative colitis. In another more particular embodiment, the inflammatory bowel disease is Crohn's disease. In yet another more particular embodiment, the inflammatory bowel disease is ileal Crohn's disease.

In some embodiments, the ingestible device contains a therapeutically effective amount of the JAK inhibitor. In some embodiments, the therapeutically effective amount of the JAK inhibitor is an induction dose. In some other embodiments, the therapeutically effective amount of the JAK inhibitor is a maintenance dose.

In some embodiments, the method provides a concentration of the JAK inhibitor in the subject's blood, serum, or plasma of less than about 2000 ng/mL. In some further embodiments, the method provides a concentration of the JAK inhibitor in the subject's blood, serum, or plasma of less than about 1000 ng/mL. In some further embodiments, the method provides a concentration of the JAK inhibitor in the subject's blood, serum, or plasma of less than about 500 ng/mL. In some further embodiments, the method provides a concentration of the JAK inhibitor in the subject's blood, serum, or plasma of less than or equal to about 100 ng/mL. In yet some further embodiments, the method provides a concentration of the JAK inhibitor in the subject's blood, serum, or plasma of less than or equal to about 50 ng/mL. In some even further embodiments, the method provides a concentration of the JAK inhibitor in the subject's blood, serum, or plasma of less than or equal to about 10 ng/mL.

In some embodiments, the method provides a concentration of the JAK inhibitor in the subject's blood, serum, or plasma of about 1 ng/mL to about 100 ng/mL. In some further embodiments, the method provides a concentration of the JAK inhibitor in the subject's blood, serum, or plasma of about 1 ng/mL to about 50 ng/mL, about 1 ng/mL to about 30 ng/mL, about 1 ng/mL to about 10 ng/mL, or about 1 ng/mL to about 5 ng/mL.

In some embodiments, the method provides a ratio of GI tissue concentration of the JAK inhibitor to blood, serum, or plasma concentration of the JAK inhibitor of about 2:1 to about 3000:1, about 2:1 to about 2000:1, about 2:1 to about 1000:1, or about 2:1 to about 600:1.

In some embodiments, the method provides a plasma concentration of the JAK inhibitor that is reduced relative to the plasma concentration after systemic administration of the same amount of the JAK inhibitor.

In some embodiments, the JAK inhibitor is a JAK inhibitor as disclosed herein. In some embodiments, the JAK inhibitor is a small molecule, an antibody, a peptide, a peptide fragment or a nucleic acid. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting ofbaricitinib, filgotinib, upadacitinib, TD-1473, TD-3504 and tofacitinib; and pharmaceutically acceptable salts thereof. In some preferred embodiments, the JAK inhibitor is tofacitinib or a pharmaceutically acceptable salt thereof, or more particularly, tofacitinib citrate.

In some embodiments, the JAK inhibitor is a small molecule or peptide, and the formulation is a formulation as disclosed herein. In some embodiments, the concentration of the JAK inhibitor in the formulation is at least about 5 mg/mL, such as at least about 10 mg/mL, such as at least about 15 mg/mL.

In some embodiments, the JAK inhibitor is a therapeutic protein or an antibody, such as a monoclonal antibody, and the formulation is a formulation as disclosed herein. In some embodiments, the concentration of the JAK inhibitor in the formulation is at least about 110 mg/mL, or at least about 125 mg/mL.

In some embodiments, provided herein is a method of treating an inflammatory disease or condition of the GI tract of a subject, comprising:

topically administering to the GI tract of the subject (i) a JAK inhibitor or (ii) a pharmaceutical formulation that comprises a JAK inhibitor, said topical administration comprising:

orally administering to the subject an ingestible device comprising the JAK inhibitor or the pharmaceutical formulation that comprises the JAK inhibitor;

localizing the device to a pre-selected location of the GI tract of the subject; and releasing the JAK inhibitor or the pharmaceutical formulation that comprises the JAK inhibitor from the ingestible device (a) to a section or subsection of the GI tract containing one or more disease sites, or (b) proximal to a section or subsection of the GI tract containing one or more disease sites;

wherein the device comprises at least one light source and at least one light detector; and the device is self-localized to the pre-selected location based on optical data collected by the device.

In some embodiments, the optical data comprises light reflectance that is external to the device and within the GI tract of the subject. Preferably, the inflammatory disease or condition is an inflammatory bowel disease. In a more particular embodiment, the inflammatory bowel disease is ulcerative colitis. In another more particular embodiment, the inflammatory bowel disease is Crohn's disease. In yet another more particular embodiment, the inflammatory bowel disease is ileal Crohn's disease.

In some embodiments, the pre-selected location is the section or subsection of the GI tract containing the one or more inflammatory disease sites.

In some embodiments, the section or subsection of the GI tract of the subject containing the one or more disease sites is the duodenum, and the JAK inhibitor or the pharmaceutical formulation that comprises the JAK inhibitor is released from the device to the duodenum. In some embodiments, the disease or condition is Crohn's disease.

In some embodiments, the section or subsection of the GI tract of the subject containing the one or more disease sites is the jejunum, and the JAK inhibitor or the pharmaceutical formulation that comprises the JAK inhibitor is released from the device to the jejunum. In some embodiments, the disease or condition is Crohn's disease.

In some embodiments, the section or subsection of the GI tract of the subject containing the one or more disease sites is the ileum, and the JAK inhibitor or the pharmaceutical formulation that comprises the JAK inhibitor is released from the device to the ileum. In some embodiments, the disease or condition is Crohn's disease. In some further embodiments, the disease or condition is ileal Crohn's disease. In some other embodiments, the disease or condition is ulcerative colitis with at least one or more disease sites in the terminal ileum.

In some embodiments, the section or subsection of the GI tract of the subject containing the one or more disease sites is the cecum, and the JAK inhibitor or the pharmaceutical formulation that comprises the JAK inhibitor is released from the device to the cecum. In some embodiments, the disease or condition is ulcerative colitis.

In some embodiments, the section or subsection of the GI tract of the subject containing the one or more disease sites is the colon, and the JAK inhibitor or the pharmaceutical formulation that comprises the JAK inhibitor is released from the device to the colon. In some embodiments, the disease or condition is ulcerative colitis.

In some embodiments, the section or subsection of the GI tract of the subject containing the one or more disease sites is the ascending colon, and the JAK inhibitor or the pharmaceutical formulation that comprises the JAK inhibitor is released from the device to the ascending colon. In some embodiments, the disease or condition is ulcerative colitis.

In some embodiments, the section or subsection of the GI tract of the subject containing the one or more disease sites is the transverse colon, and the JAK inhibitor or the pharmaceutical formulation that comprises the JAK inhibitor is released from the device to the transverse colon. In some embodiments, the disease or condition is ulcerative colitis.

In some embodiments, the section or subsection of the GI tract of the subject containing the one or more disease sites is the descending colon, and the JAK inhibitor or the pharmaceutical formulation that comprises the JAK inhibitor is released from the device to the descending colon. In some embodiments, the disease or condition is ulcerative colitis.

In other embodiments, the pre-selected location is proximal to the section or subsection of the GI tract containing the one or more inflammatory disease sites. In some further embodiments, the pre-selected location immediately precedes the section or subsection of the subject's GI tract containing the one or more inflammatory disease sites. In yet some further embodiments, the pre-selected location does not contain or has not been determined to contain a disease site.

In some embodiments, the section or subsection of the GI tract of the subject containing the one or more disease sites is the duodenum, and the JAK inhibitor or the pharmaceutical formulation that comprises the JAK inhibitor is released from the device to the stomach. In some embodiments, the disease or condition is Crohn's disease.

In some embodiments, the section or subsection of the GI tract of the subject containing the one or more disease sites is the jejunum, and the JAK inhibitor or the pharmaceutical formulation that comprises the JAK inhibitor is released from the device to the duodenum. In some further embodiments, the duodenum does not contain or has not been determined to contain one or more disease sites. In some embodiments, the disease or condition is Crohn's disease.

In some embodiments, the section or subsection of the GI tract of the subject containing the one or more disease sites is the ileum, and the JAK inhibitor or the pharmaceutical formulation that comprises the JAK inhibitor is released from the device to the jejunum. In some further embodiments, the jejunum does not contain or has not been determined to contain one or more disease sites. In some embodiments, the disease or condition is Crohn's disease. In some further embodiments, the disease or condition is ileal Crohn's disease. In some other embodiments, the disease or condition is ulcerative colitis with at least one or more disease sites in the terminal ileum.

In some embodiments, the section or subsection of the GI tract of the subject containing the one or more disease sites is the cecum, and the JAK inhibitor or the pharmaceutical formulation that comprises the JAK inhibitor is released to the ileum. In some further embodiments, the ileum does not contain or has not been determined to contain one or more disease sites. In some embodiments, the disease or condition is ulcerative colitis.

In some embodiments, the section or subsection of the GI tract of the subject containing the one or more disease sites is the colon, and the JAK inhibitor or the pharmaceutical formulation that comprises the JAK inhibitor is released from the device to the cecum. In some further embodiments, the cecum does not contain or has not been determined to contain one or more disease sites. In some embodiments, the disease or condition is ulcerative colitis.

In some embodiments, the section or subsection of the GI tract of the subject containing the one or more disease sites is the ascending colon, and the JAK inhibitor or the pharmaceutical formulation that comprises the JAK inhibitor is released from the device to the cecum. In some further embodiments, the cecum does not contain or has not been determined to contain one or more disease sites. In some embodiments, the disease or condition is ulcerative colitis.

In some embodiments, the section or subsection of the GI tract of the subject containing the one or more disease sites is the transverse colon, and the JAK inhibitor or the pharmaceutical formulation that comprises the JAK inhibitor is released from the device to the cecum or ascending colon. In some embodiments, the disease or condition is ulcerative colitis.

In some embodiments, the section or subsection of the GI tract of the subject containing the one or more disease sites is the descending colon, and the JAK inhibitor or the pharmaceutical formulation that comprises the JAK inhibitor is released from the device to the ascending or transverse colon. In some embodiments, the disease or condition is ulcerative colitis.

In some embodiments, the device self-localization mechanism is based on data comprising light reflectance occurring external to the device and within the GI tract of the subject, elapsed time after entry of the device into the GI tract of the subject, or a combination thereof. In some embodiments, the device comprising the self-localization mechanism (the self-localizing device) comprises a first light source and a second light source. In some embodiments, the first light source is configured to emit light at a first wavelength, and the second light source is configured to emit light at a second wavelength different from the first wavelength. In some embodiments, the self-localizing device further comprises a first detector and a second detector, wherein the first detector is configured to detect light at the first wavelength, and the second detector is configured to detect light at the second wavelength. In some further embodiments, the first wavelength and second wavelength are each independently selected from the group consisting of red light, green light and blue light.

In some embodiments, the ingestible device further comprises a mechanism to monitor elapsed time. In some embodiments, the elapsed time is a period of time that begins after entry of the ingestible device into the GI tract of the subject. In some embodiments, the elapsed time is a period of time that begins after entry of the ingestible device into the mouth of the subject. In some embodiments, the elapsed time is a period of time that begins after the ingestible device is swallowed by the subject. In some embodiments, the elapsed time is a period of time that ends after the device exits the GI tract. In some embodiments, the elapsed time is a period of time that ends when the device exits the GI tract. In some embodiments, the elapsed time is a period of time that ends after the device has localized to a portion of the GI tract. In some embodiments, the elapsed time is a period of time that ends after the mechanism to monitor elapsed time is inactivated. In some embodiments, the elapsed time includes or consists of time of transition, or the elapsed time during passage of the device from one portion of the GI tract into a second portion of the GI tract. In some embodiments, the elapsed time includes or consists of time following transition, or the elapsed time after passage of the device from one portion of the GI tract into a second portion of the GI tract. In some further embodiments, the elapsed time after entry of the device into the GI tract of the subject comprises time of transition, time following transition, or a combination thereof. In some embodiments, the mechanism configured to monitor elapsed time is a clock circuitry.

In some more particular embodiments, the time of transition is elapsed time during passage of the device from mouth to stomach. In some embodiments, the time of transition is elapsed time during passage of the device from esophagus to stomach. In some embodiments, the time following transition is elapsed time after passage of the device from stomach to duodenum.

Thus, in some embodiments, the method further comprises self-localizing the device to the pre-selected location within the subject's GI tract, wherein the self-localization comprises detecting one or more device transitions between portions of the subject's GI tract. In some further embodiments, detecting one or more device transitions between portions of the subject's GI tract is based on light reflectance occurring external to the device and within the GI tract of the subject, elapsed time after entry of the device into the GI tract of the subject, or a combination thereof. In some embodiments, the one or more device transitions occurs between portions of the GI tract selected from the group consisting of: mouth and stomach; esophagus and stomach; stomach and duodenum; duodenum and jejunum; jejunum and ileum; ileum and cecum; and cecum and colon; and combinations of any two or more of the foregoing.

In some embodiments, the JAK inhibitor, or the pharmaceutical formulation comprising the JAK inhibitor, is released by a mechanism capable of releasing the JAK inhibitor or the pharmaceutical formulation comprising the JAK inhibitor from the device. In some more particular embodiments, the release mechanism is a gas-generating cell capable of generating a gas in an amount sufficient to release the JAK inhibitor, or the pharmaceutical formulation comprising the JAK inhibitor, from the device.

In some embodiments, the ingestible device is equipped with a triggering mechanism for releasing the JAK inhibitor or the pharmaceutical formulation comprising the JAK inhibitor from the ingestible device. In some embodiments, the triggering mechanism comprises a processor or controller communicably coupled to one or more sensors. In some embodiments, the sensor is capable of detecting reflectance (e.g., light reflected from the environment in the GI tract and external to the device). In some embodiments, the sensor is capable of detecting muscle contractions and/or peristalsis. In some embodiments, the sensor is not a pH sensor. In some embodiments, the sensor is not a pressure sensor. In some embodiments, the sensor is not a temperature sensor. In some further embodiments, the processor or controller activates the triggering mechanism. In some embodiments, the device is programmed to release the JAK inhibitor or the pharmaceutical formulation comprising the JAK inhibitor to a location in the GI tract of the subject. In some embodiments, the location in the GI tract of the subject is the pre-selected location.

Thus, in some further embodiments, the method further comprises releasing the JAK inhibitor, or the pharmaceutical formulation comprising the JAK inhibitor, from the device, said device comprising the triggering mechanism. In some more particular embodiments, the release is triggered autonomously. In some more particular embodiments, the release is autonomously triggered based on reflectance (light reflectance) detected by the sensor. In some more particular embodiments, the release is autonomously triggered based on one or more pre-established parameters. In some more particular embodiments, the one or more pre-established parameters are selected from reflectance (light reflectance) in the GI tract, time following entry of the device into the GI tract of the subject, and a combination thereof. Additional pre-established parameters optionally include detected muscle contractions in the GI tract, pH in the GI tract, temperature in the GI tract, blood detected in the GI tract, and the level of analyte or biomarker determined in a sample obtained in the GI tract. In some more particular embodiments, the one or more pre-established parameters do not comprise the pH in the GI tract. In some more particular embodiments, the one or more pre-established parameters do not comprise the temperature in the GI tract. In some more particular embodiments, the one or more pre-established parameters do not comprise the pressure in the GI tract. In some more particular embodiments, the JAK inhibitor or the pharmaceutical formulation that comprises the JAK inhibitor is triggered for release from the device within a period of time of equal to or less than about 5 minutes after the device is self-localized at the pre-selected location in the GI tract of the subject.

Preferably, the inflammatory disease or condition is an inflammatory bowel disease. In a more particular embodiment, the inflammatory bowel disease is ulcerative colitis. In another more particular embodiment, the inflammatory bowel disease is Crohn's disease. In yet another more particular embodiment, the inflammatory bowel disease is ileal Crohn's disease.

In some embodiments, the ingestible device contains a therapeutically effective amount of the JAK inhibitor. In some embodiments, the therapeutically effective amount of the JAK inhibitor is an induction dose. In some other embodiments, the therapeutically effective amount of the JAK inhibitor is a maintenance dose.

In some embodiments, the method provides a concentration of the JAK inhibitor in the subject's blood, serum, or plasma of less than about 2000 ng/mL. In some further embodiments, the method provides a concentration of the JAK inhibitor in the subject's blood, serum, or plasma of less than about 1000 ng/mL. In some further embodiments, the method provides a concentration of the JAK inhibitor in the subject's blood, serum, or plasma of less than about 500 ng/mL. In some further embodiments, the method provides a concentration of the JAK inhibitor in the subject's blood, serum, or plasma of less than or equal to about 100 ng/mL. In yet some further embodiments, the method provides a concentration of the JAK inhibitor in the subject's blood, serum, or plasma of less than or equal to about 50 ng/mL. In some even further embodiments, the method provides a concentration of the JAK inhibitor in the subject's blood, serum, or plasma of less than or equal to about 10 ng/mL.

In some embodiments, the method provides a concentration of the JAK inhibitor in the subject's blood, serum, or plasma of about 1 ng/mL to about 100 ng/mL. In some further embodiments, the method provides a concentration of the JAK inhibitor in the subject's blood, serum, or plasma of about 1 ng/mL to about 50 ng/mL, about 1 ng/mL to about 30 ng/mL, about 1 ng/mL to about 10 ng/mL, or about 1 ng/mL to about 5 ng/mL.

In some embodiments, the method provides a ratio of GI tissue concentration of the JAK inhibitor to blood, serum, or plasma concentration of the JAK inhibitor of about 2:1 to about 3000:1, about 2:1 to about 2000:1, about 2:1 to about 1000:1, or about 2:1 to about 600:1.

In some embodiments, the method provides a plasma concentration of the JAK inhibitor that is reduced relative to the plasma concentration after systemic administration of the same amount of the JAK inhibitor.

In some embodiments, the JAK inhibitor is a JAK inhibitor as disclosed herein. In some embodiments, the JAK inhibitor is a small molecule, an antibody, a peptide, a peptide fragment or a nucleic acid. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In some preferred embodiments, the JAK inhibitor is tofacitinib or a pharmaceutically acceptable salt thereof, or more particularly, tofacitinib citrate.

In some embodiments, the JAK inhibitor is a small molecule or peptide, and the formulation is a formulation as disclosed herein. In some embodiments, the concentration of the JAK inhibitor in the formulation is at least about 5 mg/mL, such as at least about 10 mg/mL, such as at least about 15 mg/mL.

In some embodiments, the JAK inhibitor is a therapeutic protein or an antibody, such as a monoclonal antibody, and the formulation is a formulation as disclosed herein. In some embodiments, the concentration of the JAK inhibitor in the fonnulation is at least about 110 mg/mL, or at least about 125 mg/mL.

In some embodiments, provided herein is a method of treating a disease or condition of the GI tract of a subject, comprising:

topically administering to the GI tract of the subject (i) a JAK inhibitor or (ii) a pharmaceutical formulation that comprises a JAK inhibitor, said topical administration comprising:

orally administering to the subject an ingestible device comprising the JAK inhibitor or the pharmaceutical formulation that comprises the JAK inhibitor;

localizing the device to a pre-selected location of the GI tract of the subject; and releasing the JAK inhibitor or the pharmaceutical formulation that comprises the JAK inhibitor from the ingestible device (a) to a section or subsection of the GI tract containing one or more disease sites, or (b) proximal to a section or subsection of the GI tract containing one or more disease sites;

wherein the device comprises a first light source and a second light source, wherein the first light source is configured to emit light at a first wavelength, and the second light source is configured to emit light at a second wavelength different from the first wavelength;

a first detector and a second detector, wherein the first detector is configured to detect light at the first wavelength, and the second detector is configured to detect light at the second wavelength; and the device is self-localized to the pre-selected location based on data comprising reflected light detected by the first detector, the second detector, or both.

In some embodiments, the reflected light is light that is external to the device and present in the GI tract.

In some further embodiments, the first wavelength and second wavelength are each independently selected from the group consisting of red light, green light and blue light.

In some embodiments, the device self-localization mechanism is based on data further comprising elapsed time after entry of the device into the GI tract of the subject.

In some embodiments, the ingestible device further comprises a mechanism to monitor elapsed time. In some embodiments, the elapsed time is a period of time that begins after entry of the ingestible device into the GI tract of the subject. In some embodiments, the elapsed time is a period of time that begins after entry of the ingestible device into the mouth of the subject. In some embodiments, the elapsed time is a period of time that begins after the ingestible device is swallowed by the subject. In some embodiments, the elapsed time is a period of time that ends after the device exits the GI tract. In some embodiments, the elapsed time is a period of time that ends when the device exits the GI tract. In some embodiments, the elapsed time is a period of time that ends after the device has localized to a portion of the GI tract. In some embodiments, the elapsed time is a period of time that ends after the mechanism to monitor elapsed time is inactivated. In some embodiments, the elapsed time includes or consists of time of transition, or the elapsed time during passage of the device from one portion of the GI tract into a second portion of the GI tract. In some embodiments, the elapsed time includes or consists of time following transition, or the elapsed time after passage of the device from one portion of the GI tract into a second portion of the GI tract. In some further embodiments, the elapsed time after entry of the device into the GI tract of the subject comprises time of transition, time following transition, or a combination thereof. In some embodiments, the mechanism configured to monitor elapsed time is a clock circuitry.

In some more particular embodiments, the time of transition is elapsed time during passage of the device from mouth to stomach. In some embodiments, the time of transition is elapsed time during passage of the device from esophagus to stomach. In some embodiments, the time following transition is elapsed time after passage of the device from stomach to duodenum.

Thus, in some embodiments, the method further comprises self-localizing the device to the pre-selected location within the subject's GI tract, wherein the self-localization comprises detecting one or more device transitions between portions of the subject's GI tract. In some further embodiments, detecting one or more device transitions between portions of the subject's GI tract is based on data comprising the reflected light detected by the first detector, the second detector, or both, wherein the reflected light is external to the device and within the GI tract of the subject; elapsed time after entry of the device into the GI tract of the subject; or a combination thereof. In some embodiments, the one or more device transitions occurs between portions of the GI tract selected from the group consisting of: mouth and stomach; esophagus and stomach; stomach and duodenum; duodenum and jejunum; jejunum and ileum; ileum and cecum; and cecum and colon; and combinations of any two or more of the foregoing.

In some more particular embodiments, the detected reflectance includes green light and blue light, wherein an increase in the ratio of the green to blue reflectance detected indicates that the device has transitioned from the stomach to the duodenum.

In other more particular embodiments, the detected reflectance includes red light, wherein a decrease in red light reflectance detected indicates that the device has transitioned from the jejunum to the ileum.

In other more particular embodiments, the detected reflectance includes red light, green light and blue light, wherein a change in the ratio of the red to green reflectance detected, and/or a change in the coefficient of variation (CV) of the detected blue reflectance, indicates that the device has transitioned from the cecum further into the colon.

Preferably, the inflammatory disease or condition is an inflammatory bowel disease. In a more particular embodiment, the inflammatory bowel disease is ulcerative colitis. In another more particular embodiment, the inflammatory bowel disease is Crohn's disease. In yet another more particular embodiment, the inflammatory bowel disease is ileal Crohn's disease.

In some embodiments, the pre-selected location is the section or subsection of the GI tract containing the one or more inflammatory disease sites.

In some embodiments, the section or subsection of the GI tract of the subject containing the one or more disease sites is the duodenum, and the JAK inhibitor or the pharmaceutical formulation that comprises the JAK inhibitor is released from the device to the duodenum. In some embodiments, the disease or condition is Crohn's disease.

In some embodiments, the section or subsection of the GI tract of the subject containing the one or more disease sites is the jejunum, and the JAK inhibitor or the pharmaceutical formulation that comprises the JAK inhibitor is released from the device to the jejunum. In some embodiments, the disease or condition is Crohn's disease.

In some embodiments, the section or subsection of the GI tract of the subject containing the one or more disease sites is the ileum, and the JAK inhibitor or the pharmaceutical formulation that comprises the JAK inhibitor is released from the device to the ileum. In some embodiments, the disease or condition is Crohn's disease. In some further embodiments, the disease or condition is ileal Crohn's disease. In some other embodiments, the disease or condition is ulcerative colitis with at least one or more disease sites in the terminal ileum.

In some embodiments, the section or subsection of the GI tract of the subject containing the one or more disease sites is the cecum, and the JAK inhibitor or the pharmaceutical formulation that comprises the JAK inhibitor is released from the device to the cecum. In some embodiments, the disease or condition is ulcerative colitis.

In some embodiments, the section or subsection of the GI tract of the subject containing the one or more disease sites is the colon, and the JAK inhibitor or the pharmaceutical formulation that comprises the JAK inhibitor is released from the device to the colon. In some embodiments, the disease or condition is ulcerative colitis.

In some embodiments, the section or subsection of the GI tract of the subject containing the one or more disease sites is the ascending colon, and the JAK inhibitor or the pharmaceutical formulation that comprises the JAK inhibitor is released from the device to the ascending colon. In some embodiments, the disease or condition is ulcerative colitis.

In some embodiments, the section or subsection of the GI tract of the subject containing the one or more disease sites is the transverse colon, and the JAK inhibitor or the pharmaceutical formulation that comprises the JAK inhibitor is released from the device to the transverse colon. In some embodiments, the disease or condition is ulcerative colitis.

In some embodiments, the section or subsection of the GI tract of the subject containing the one or more disease sites is the descending colon, and the JAK inhibitor or the pharmaceutical formulation that comprises the JAK inhibitor is released from the device to the descending colon. In some embodiments, the disease or condition is ulcerative colitis.

In other embodiments, the pre-selected location is proximal to the section or subsection of the GI tract containing the one or more inflammatory disease sites. In some further embodiments, the pre-selected location immediately precedes the section or subsection of the subject's GI tract containing the one or more inflammatory disease sites. In yet some further embodiments, the pre-selected location does not contain or has not been determined to contain a disease site.

In some embodiments, the section or subsection of the GI tract of the subject containing the one or more disease sites is the duodenum, and the JAK inhibitor or the pharmaceutical formulation that comprises the JAK inhibitor is released from the device to the stomach. In some embodiments, the disease or condition is Crohn's disease.

In some embodiments, the section or subsection of the GI tract of the subject containing the one or more disease sites is the jejunum, and the JAK inhibitor or the pharmaceutical formulation that comprises the JAK inhibitor is released from the device to the duodenum. In some further embodiments, the duodenum does not contain or has not been determined to contain one or more disease sites. In some embodiments, the disease or condition is Crohn's disease.

In some embodiments, the section or subsection of the GI tract of the subject containing the one or more disease sites is the ileum, and the JAK inhibitor or the pharmaceutical formulation that comprises the JAK inhibitor is released from the device to the jejunum. In some further embodiments, the jejunum does not contain or has not been determined to contain one or more disease sites. In some embodiments, the disease or condition is Crohn's disease. In some further embodiments, the disease or condition is ileal Crohn's disease. In some other embodiments, the disease or condition is ulcerative colitis with at least one or more disease sites in the terminal ileum.

In some embodiments, the section or subsection of the GI tract of the subject containing the one or more disease sites is the cecum, and the JAK inhibitor or the pharmaceutical formulation that comprises the JAK inhibitor is released to the ileum. In some further embodiments, the ileum does not contain or has not been determined to contain one or more disease sites. In some embodiments, the disease or condition is ulcerative colitis.

In some embodiments, the section or subsection of the GI tract of the subject containing the one or more disease sites is the colon, and the JAK inhibitor or the pharmaceutical formulation that comprises the JAK inhibitor is released from the device to the cecum. In some further embodiments, the cecum does not contain or has not been determined to contain one or more disease sites. In some embodiments, the disease or condition is ulcerative colitis.

In some embodiments, the section or subsection of the GI tract of the subject containing the one or more disease sites is the ascending colon, and the JAK inhibitor or the pharmaceutical formulation that comprises the JAK inhibitor is released from the device to the cecum. In some further embodiments, the cecum does not contain or has not been determined to contain one or more disease sites. In some embodiments, the disease or condition is ulcerative colitis.

In some embodiments, the section or subsection of the GI tract of the subject containing the one or more disease sites is the transverse colon, and the JAK inhibitor or the pharmaceutical formulation that comprises the JAK inhibitor is released from the device to the cecum or ascending colon. In some embodiments, the disease or condition is ulcerative colitis.

In some embodiments, the section or subsection of the GI tract of the subject containing the one or more disease sites is the descending colon, and the JAK inhibitor or the pharmaceutical formulation that comprises the JAK inhibitor is released from the device to the ascending or transverse colon. In some embodiments, the disease or condition is ulcerative colitis.

In some embodiments, the JAK inhibitor, or the pharmaceutical formulation comprising the JAK inhibitor, is released by a mechanism capable of releasing the JAK inhibitor or the pharmaceutical formulation comprising the JAK inhibitor from the device. In some more particular embodiments, the release mechanism is a gas-generating cell capable of generating a gas in an amount sufficient to release the JAK inhibitor, or the pharmaceutical formulation comprising the JAK inhibitor, from the device.

In some embodiments, the ingestible device is equipped with a triggering mechanism for releasing the JAK inhibitor or the pharmaceutical formulation comprising the JAK inhibitor from the ingestible device. In some embodiments, the triggering mechanism comprises a processor or controller communicably coupled to one or more sensors. In some embodiments, the sensor is capable of detecting reflectance (e.g., light reflected from the environment in the GI tract and external to the device). In some embodiments, the sensor is capable of detecting muscle contractions and/or peristalsis. In some embodiments, the sensor is not a pH sensor. In some embodiments, the sensor is not a pressure sensor. In some embodiments, the sensor is not a temperature sensor. In some further embodiments, the processor or controller activates the triggering mechanism. In some embodiments, the device is programmed to release the JAK inhibitor or the pharmaceutical formulation comprising the JAK inhibitor to a location in the GI tract of the subject. In some embodiments, the location in the GI tract of the subject is the pre-selected location.

Thus, in some further embodiments, the method further comprises releasing the JAK inhibitor, or the pharmaceutical formulation comprising the JAK inhibitor, from the device, said device comprising the triggering mechanism. In some more particular embodiments, the release is triggered autonomously. In some more particular embodiments, the release is autonomously triggered based on reflectance (light reflectance) detected by the sensor. In some more particular embodiments, the release is autonomously triggered based on one or more pre-established parameters. In some more particular embodiments, the one or more pre-established parameters are selected from reflectance (light reflectance) in the GI tract, time following entry of the device into the GI tract of the subject, and a combination thereof. Additional pre-established parameters optionally include detected muscle contractions in the GI tract, pH in the GI tract, temperature in the GI tract, blood detected in the GI tract, and the level of analyte or biomarker determined in a sample obtained in the GI tract. In some more particular embodiments, the one or more pre-established parameters do not comprise the pH in the GI tract. In some more particular embodiments, the one or more pre-established parameters do not comprise the temperature in the GI tract. In some more particular embodiments, the one or more pre-established parameters do not comprise the pressure in the GI tract. In some more particular embodiments, the JAK inhibitor or the pharmaceutical formulation that comprises the JAK inhibitor is triggered for release from the device within a period of time of equal to or less than about 5 minutes after the device is self-localized at the pre-selected location in the GI tract of the subject.

In some embodiments, the ingestible device contains a therapeutically effective amount of the JAK inhibitor. In some embodiments, the therapeutically effective amount of the JAK inhibitor is an induction dose. In some other embodiments, the therapeutically effective amount of the JAK inhibitor is a maintenance dose.

In some embodiments, the method provides a concentration of the JAK inhibitor in the subject's blood, serum, or plasma of less than about 2000 ng/mL. In some further embodiments, the method provides a concentration of the JAK inhibitor in the subject's blood, serum, or plasma of less than about 1000 ng/mL. In some further embodiments, the method provides a concentration of the JAK inhibitor in the subject's blood, serum, or plasma of less than about 500 ng/mL. In some further embodiments, the method provides a concentration of the JAK inhibitor in the subject's blood, serum, or plasma of less than or equal to about 100 ng/mL. In yet some further embodiments, the method provides a concentration of the JAK inhibitor in the subject's blood, serum, or plasma of less than or equal to about 50 ng/mL. In some even further embodiments, the method provides a concentration of the JAK inhibitor in the subject's blood, serum, or plasma of less than or equal to about 10 ng/mL.

In some embodiments, the method provides a concentration of the JAK inhibitor in the subject's blood, serum, or plasma of about 1 ng/mL to about 100 ng/mL. In some further embodiments, the method provides a concentration of the JAK inhibitor in the subject's blood, serum, or plasma of about 1 ng/mL to about 50 ng/mL, about 1 ng/mL to about 30 ng/mL, about 1 ng/mL to about 10 ng/mL, or about 1 ng/mL to about 5 ng/mL.

In some embodiments, the method provides a ratio of GI tissue concentration of the JAK inhibitor to blood, serum, or plasma concentration of the JAK inhibitor of about 2:1 to about 3000:1, about 2:1 to about 2000:1, about 2:1 to about 1000:1, or about 2:1 to about 600:1.

In some embodiments, the method provides a plasma concentration of the JAK inhibitor that is reduced relative to the plasma concentration after systemic administration of the same amount of the JAK inhibitor.

In some embodiments, the JAK inhibitor is a JAK inhibitor as disclosed herein. In some embodiments, the JAK inhibitor is a small molecule, an antibody, a peptide, a peptide fragment or a nucleic acid. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In some preferred embodiments, the JAK inhibitor is tofacitinib or a pharmaceutically acceptable salt thereof, or more particularly, tofacitinib citrate.

In some embodiments, the JAK inhibitor is a small molecule or peptide, and the formulation is a formulation as disclosed herein. In some embodiments, the concentration of the JAK inhibitor in the formulation is at least about 5 mg/mL, such as at least about 10 mg/mL, such as at least about 15 mg/mL.

In some embodiments, the JAK inhibitor is a therapeutic protein or an antibody, such as a monoclonal antibody, and the formulation is a formulation as disclosed herein. In some embodiments, the concentration of the JAK inhibitor in the formulation is at least about 110 mg/mL, or at least about 125 mg/mL.

In some embodiments, provided herein is a method of treating an inflammatory disease or condition of the GI tract of a subject, comprising:

topically administering to the GI tract of the subject (i) a JAK inhibitor or (ii) a pharmaceutical formulation that comprises a JAK inhibitor, said topical administration comprising:

orally administering to the subject an ingestible device comprising the JAK inhibitor or the pharmaceutical formulation that comprises the JAK inhibitor;

localizing the device to a pre-selected location of the GI tract of the subject; and releasing the JAK inhibitor or the pharmaceutical formulation that comprises the JAK inhibitor from the ingestible device (a) to a section or subsection of the GI tract containing one or more disease sites, or (b) proximal to a section or subsection of the GI tract containing one or more disease sites;

wherein the device is self-localized to the pre-selected location based on detecting one or more device transitions between portions of the subject's GI tract; and optionally, the one or more device transitions occurs between the portions of the GI tract selected from the group consisting of mouth and stomach; esophagus and stomach; stomach and duodenum; duodenum and jejunum; jejunum and ileum; ileum and cecum; and cecum and colon; and combinations of any two or more of the foregoing device transitions.

In some embodiments, the detection of the one or more device transitions is based on data comprising light reflectance occurring external to the device and within the GI tract of the subject, elapsed time after entry of the device into the GI tract of the subject, or a combination thereof. In some embodiments, the device comprising the self-localization mechanism (the self-localizing device) comprises a first light source and a second light source. In some embodiments, the first light source is configured to emit light at a first wavelength, and the second light source is configured to emit light at a second wavelength different from the first wavelength. In some embodiments, the self-localizing device further comprises a first detector and a second detector, wherein the first detector is configured to detect light at the first wavelength, and the second detector is configured to detect light at the second wavelength. In some further embodiments, the first wavelength and second wavelength are each independently selected from the group consisting of red light, green light and blue light.

In another more particular embodiment, the detected reflectance includes green light and blue light, wherein an increase in the ratio of the green to blue reflectance detected indicates that the device has transitioned from the stomach to the duodenum.

In other more particular embodiments, the detected reflectance includes red light, wherein a decrease in red light reflectance detected indicates that the device has transitioned from the jejunum to the ileum.

In other more particular embodiments, the detected reflectance includes red light, green light and blue light, wherein a change in the ratio of the red to green reflectance detected, and/or a change in the coefficient of variation (CV) of the detected blue reflectance, indicates that the device has transitioned from the cecum further into the colon.

In some embodiments, the ingestible device further comprises a mechanism to monitor elapsed time. In some embodiments, the elapsed time is a period of time that begins after entry of the ingestible device into the GI tract of the subject. In some embodiments, the elapsed time is a period of time that begins after entry of the ingestible device into the mouth of the subject. In some embodiments, the elapsed time is a period of time that begins after the ingestible device is swallowed by the subject. In some embodiments, the elapsed time is a period of time that ends after the device exits the GI tract. In some embodiments, the elapsed time is a period of time that ends when the device exits the GI tract. In some embodiments, the elapsed time is a period of time that ends after the device has localized to a portion of the GI tract. In some embodiments, the elapsed time is a period of time that ends after the mechanism to monitor elapsed time is inactivated. In some embodiments, the elapsed time includes or consists of time of transition, or the elapsed time during passage of the device from one portion of the GI tract into a second portion of the GI tract. In some embodiments, the elapsed time includes or consists of time following transition, or the elapsed time after passage of the device from one portion of the GI tract into a second portion of the GI tract. In some further embodiments, the elapsed time after entry of the device into the GI tract of the subject comprises time of transition, time following transition, or a combination thereof. In some embodiments, the mechanism configured to monitor elapsed time is a clock circuitry.

In some more particular embodiments, the time of transition is elapsed time during passage of the device from mouth to stomach. In some embodiments, the time of transition is elapsed time during passage of the device from esophagus to stomach. In some embodiments, the time following transition is elapsed time after passage of the device from stomach to duodenum.

Preferably, the inflammatory disease or condition is an inflammatory bowel disease. In a more particular embodiment, the inflammatory bowel disease is ulcerative colitis. In another more particular embodiment, the inflammatory bowel disease is Crohn's disease. In yet another more particular embodiment, the inflammatory bowel disease is ileal Crohn's disease.

In some embodiments, the pre-selected location is the section or subsection of the GI tract containing the one or more inflammatory disease sites.

In some embodiments, the section or subsection of the GI tract of the subject containing the one or more disease sites is the duodenum, and the JAK inhibitor or the pharmaceutical formulation that comprises the JAK inhibitor is released from the device to the duodenum. In some embodiments, the disease or condition is Crohn's disease.

In some embodiments, the section or subsection of the GI tract of the subject containing the one or more disease sites is the jejunum, and the JAK inhibitor or the pharmaceutical formulation that comprises the JAK inhibitor is released from the device to the jejunum. In some embodiments, the disease or condition is Crohn's disease.

In some embodiments, the section or subsection of the GI tract of the subject containing the one or more disease sites is the ileum, and the JAK inhibitor or the pharmaceutical formulation that comprises the JAK inhibitor is released from the device to the ileum. In some embodiments, the disease or condition is Crohn's disease. In some further embodiments, the disease or condition is ileal Crohn's disease. In some other embodiments, the disease or condition is ulcerative colitis with at least one or more disease sites in the terminal ileum.

In some embodiments, the section or subsection of the GI tract of the subject containing the one or more disease sites is the cecum, and the JAK inhibitor or the pharmaceutical formulation that comprises the JAK inhibitor is released from the device to the cecum. In some embodiments, the disease or condition is ulcerative colitis.

In some embodiments, the section or subsection of the GI tract of the subject containing the one or more disease sites is the colon, and the JAK inhibitor or the pharmaceutical formulation that comprises the JAK inhibitor is released from the device to the colon. In some embodiments, the disease or condition is ulcerative colitis.

In some embodiments, the section or subsection of the GI tract of the subject containing the one or more disease sites is the ascending colon, and the JAK inhibitor or the pharmaceutical formulation that comprises the JAK inhibitor is released from the device to the ascending colon. In some embodiments, the disease or condition is ulcerative colitis.

In some embodiments, the section or subsection of the GI tract of the subject containing the one or more disease sites is the transverse colon, and the JAK inhibitor or the pharmaceutical formulation that comprises the JAK inhibitor is released from the device to the transverse colon. In some embodiments, the disease or condition is ulcerative colitis.

In some embodiments, the section or subsection of the GI tract of the subject containing the one or more disease sites is the descending colon, and the JAK inhibitor or the pharmaceutical formulation that comprises the JAK inhibitor is released from the device to the descending colon. In some embodiments, the disease or condition is ulcerative colitis.

In other embodiments, the pre-selected location is proximal to the section or subsection of the GI tract containing the one or more inflammatory disease sites. In some further embodiments, the pre-selected location immediately precedes the section or subsection of the subject's GI tract containing the one or more inflammatory disease sites. In yet some further embodiments, the pre-selected location does not contain or has not been determined to contain a disease site.

In some embodiments, the section or subsection of the GI tract of the subject containing the one or more disease sites is the duodenum, and the JAK inhibitor or the pharmaceutical formulation that comprises the JAK inhibitor is released from the device to the stomach. In some embodiments, the disease or condition is Crohn's disease.

In some embodiments, the section or subsection of the GI tract of the subject containing the one or more disease sites is the jejunum, and the JAK inhibitor or the pharmaceutical formulation that comprises the JAK inhibitor is released from the device to the duodenum. In some further embodiments, the duodenum does not contain or has not been determined to contain one or more disease sites. In some embodiments, the disease or condition is Crohn's disease.

In some embodiments, the section or subsection of the GI tract of the subject containing the one or more disease sites is the ileum, and the JAK inhibitor or the pharmaceutical formulation that comprises the JAK inhibitor is released from the device to the jejunum. In some further embodiments, the jejunum does not contain or has not been determined to contain one or more disease sites. In some embodiments, the disease or condition is Crohn's disease. In some further embodiments, the disease or condition is ileal Crohn's disease. In some other embodiments, the disease or condition is ulcerative colitis with at least one or more disease sites in the terminal ileum.

In some embodiments, the section or subsection of the GI tract of the subject containing the one or more disease sites is the cecum, and the JAK inhibitor or the pharmaceutical formulation that comprises the JAK inhibitor is released to the ileum. In some further embodiments, the ileum does not contain or has not been determined to contain one or more disease sites. In some embodiments, the disease or condition is ulcerative colitis.

In some embodiments, the section or subsection of the GI tract of the subject containing the one or more disease sites is the colon, and the JAK inhibitor or the pharmaceutical formulation that comprises the JAK inhibitor is released from the device to the cecum. In some further embodiments, the cecum does not contain or has not been determined to contain one or more disease sites. In some embodiments, the disease or condition is ulcerative colitis.

In some embodiments, the section or subsection of the GI tract of the subject containing the one or more disease sites is the ascending colon, and the JAK inhibitor or the pharmaceutical formulation that comprises the JAK inhibitor is released from the device to the cecum. In some further embodiments, the cecum does not contain or has not been determined to contain one or more disease sites. In some embodiments, the disease or condition is ulcerative colitis.

In some embodiments, the section or subsection of the GI tract of the subject containing the one or more disease sites is the transverse colon, and the JAK inhibitor or the pharmaceutical formulation that comprises the JAK inhibitor is released from the device to the cecum or ascending colon. In some embodiments, the disease or condition is ulcerative colitis.

In some embodiments, the section or subsection of the GI tract of the subject containing the one or more disease sites is the descending colon, and the JAK inhibitor or the pharmaceutical formulation that comprises the JAK inhibitor is released from the device to the ascending or transverse colon. In some embodiments, the disease or condition is ulcerative colitis.

In some embodiments, the JAK inhibitor, or the pharmaceutical formulation comprising the JAK inhibitor, is released by a mechanism capable of releasing the JAK inhibitor or the pharmaceutical formulation comprising the JAK inhibitor from the device. In some more particular embodiments, the release mechanism is a gas-generating cell capable of generating a gas in an amount sufficient to release the JAK inhibitor, or the pharmaceutical formulation comprising the JAK inhibitor, from the device.

In some embodiments, the ingestible device is equipped with a triggering mechanism for releasing the JAK inhibitor or the pharmaceutical formulation comprising the JAK inhibitor from the ingestible device. In some embodiments, the triggering mechanism comprises a processor or controller communicably coupled to one or more sensors. In some embodiments, the sensor is capable of detecting reflectance (e.g., light reflected from the environment in the GI tract and external to the device). In some embodiments, the sensor capable of detecting muscle contractions and/or peristalsis. In some embodiments, the sensor is not a pH sensor. In some embodiments, the sensor is not a pressure sensor. In some embodiments, the sensor is not a temperature sensor. In some further embodiments, the processor or controller activates the triggering mechanism. In some embodiments, the device is programmed to release the JAK inhibitor or the pharmaceutical formulation comprising the JAK inhibitor to a location in the GI tract of the subject. In some embodiments, the location in the GI tract of the subject is the pre-selected location.

Thus, in some further embodiments, the method further comprises releasing the JAK inhibitor, or the pharmaceutical formulation comprising the JAK inhibitor, from the device, said device comprising the triggering mechanism. In some more particular embodiments, the release is triggered autonomously. In some more particular embodiments, the release is autonomously triggered based on reflectance (light reflectance) detected by the sensor. In some more particular embodiments, the release is autonomously triggered based on one or more pre-established parameters. In some more particular embodiments, the one or more pre-established parameters are selected from reflectance (light reflectance) in the GI tract, time following entry of the device into the GI tract of the subject, and a combination thereof. Additional pre-established parameters optionally include detected muscle contractions in the GI tract, pH in the GI tract, temperature in the GI tract, blood detected in the GI tract, and the level of analyte or biomarker determined in a sample obtained in the GI tract. In some more particular embodiments, the one or more pre-established parameters do not comprise the pH in the GI tract. In some more particular embodiments, the one or more pre-established parameters do not comprise the temperature in the GI tract. In some more particular embodiments, the one or more pre-established parameters do not comprise the pressure in the GI tract. In some more particular embodiments, the JAK inhibitor or the pharmaceutical formulation that comprises the JAK inhibitor is triggered for release from the device within a period of time of equal to or less than about 5 minutes after the device is self-localized at the pre-selected location in the GI tract of the subject.

In some embodiments, the ingestible device contains a therapeutically effective amount of the JAK inhibitor. In some embodiments, the therapeutically effective amount of the JAK inhibitor is an induction dose. In some other embodiments, the therapeutically effective amount of the JAK inhibitor is a maintenance dose.

In some embodiments, the method provides a concentration of the JAK inhibitor in the subject's blood, serum, or plasma of less than about 2000 ng/mL. In some further embodiments, the method provides a concentration of the JAK inhibitor in the subject's blood, serum, or plasma of less than about 1000 ng/mL. In some further embodiments, the method provides a concentration of the JAK inhibitor in the subject's blood, serum, or plasma of less than about 500 ng/mL. In some further embodiments, the method provides a concentration of the JAK inhibitor in the subject's blood, serum, or plasma of less than or equal to about 100 ng/mL. In yet some further embodiments, the method provides a concentration of the JAK inhibitor in the subject's blood, serum, or plasma of less than or equal to about 50 ng/mL. In some even further embodiments, the method provides a concentration of the JAK inhibitor in the subject's blood, serum, or plasma of less than or equal to about 10 ng/mL.

In some embodiments, the method provides a concentration of the JAK inhibitor in the subject's blood, serum, or plasma of about 1 ng/mL to about 100 ng/mL. In some further embodiments, the method provides a concentration of the JAK inhibitor in the subject's blood, serum, or plasma of about 1 ng/mL to about 50 ng/mL, about 1 ng/mL to about 30 ng/mL, about 1 ng/mL to about 10 ng/mL, or about 1 ng/mL to about 5 ng/mL.

In some embodiments, the method provides a ratio of GI tissue concentration of the JAK inhibitor to blood, serum, or plasma concentration of the JAK inhibitor of about 2:1 to about 3000:1, about 2:1 to about 2000:1, about 2:1 to about 1000:1, or about 2:1 to about 600:1.

In some embodiments, the method provides a plasma concentration of the JAK inhibitor that is reduced relative to the plasma concentration after systemic administration of the same amount of the JAK inhibitor.

In some embodiments, the JAK inhibitor is a JAK inhibitor as disclosed herein. In some embodiments, the JAK inhibitor is a small molecule, an antibody, a peptide, a peptide fragment or a nucleic acid. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In some preferred embodiments, the JAK inhibitor is tofacitinib or a pharmaceutically acceptable salt thereof, or more particularly, tofacitinib citrate.

In some embodiments, the JAK inhibitor is a small molecule or peptide, and the formulation is a formulation as disclosed herein. In some embodiments, the concentration of the JAK inhibitor in the formulation is at least about 5 mg/mL, such as at least about 10 mg/mL, such as at least about 15 mg/mL.

In some embodiments, the JAK inhibitor is a therapeutic protein or an antibody, such as a monoclonal antibody, and the formulation is a formulation as disclosed herein. In some embodiments, the concentration of the JAK inhibitor in the formulation is at least about 110 mg/mL, or at least about 125 mg/mL.

Device Localization Comprising Detecting Transition from Stomach to Duodenum

In some embodiments, provided herein is a method of treating an inflammatory disease or condition of the GI tract of a subject, comprising:

- topically administering to the GI tract of the subject (i) a JAK inhibitor or (ii) a pharmaceutical formulation that comprises a JAK inhibitor, said topical administration comprising:
- orally administering to the subject an ingestible device comprising the JAK inhibitor or the pharmaceutical formulation that comprises the JAK inhibitor;
- localizing the device to a pre-selected location of the GI tract of the subject, wherein said pre-selected location is the duodenum; and
- releasing the JAK inhibitor or the pharmaceutical formulation that comprises the JAK inhibitor from the ingestible device to the duodenum;
- wherein the device is self-localized to the pre-selected location based on detecting a transition from the stomach to the duodenum.

In some embodiments, at least one of the one or more disease sites is in the duodenum.

In some other embodiments, at least one of the one or more disease sites is in the jejunum. In some further embodiments, the duodenum does not contain or has not been determined to contain a disease site.

Preferably, the inflammatory disease or condition is an inflammatory bowel disease. In some more particular embodiments, the inflammatory bowel disease is Crohn's disease.

In some embodiments, the detection of the transition from the stomach to the duodenum is based on data comprising light reflectance occurring external to the device and within the GI tract of the subject, elapsed time after entry of the device into the GI tract of the subject, or a combination thereof. In some embodiments, the device comprising the self-localization mechanism (the self-localizing device) comprises a first light source and a second light source. In some embodiments, the first light source is configured to emit light at a first wavelength, and the second light source is configured to emit light at a second wavelength different from the first wavelength. In some embodiments, the self-localizing device further comprises a first detector and a second detector, wherein the first detector is configured to detect light at the first wavelength, and the second detector is configured to detect light at the second wavelength. In some further embodiments, the first wavelength and second wavelength are each independently selected from the group consisting of red light, green light and blue light.

In some more particular embodiments, the detection of the transition from the stomach to the duodenum comprises detecting green and blue light reflectance, wherein an increase in the ratio of the green to blue reflectance detected indicates that the device has transitioned from the stomach to the duodenum.

In some embodiments, the ingestible device further comprises a mechanism to monitor elapsed time. In some embodiments, the elapsed time is a period of time that begins after entry of the ingestible device into the GI tract of the subject. In some embodiments, the elapsed time is a period of time that begins after entry of the ingestible device into the mouth of the subject. In some embodiments, the elapsed time is a period of time that begins after the ingestible device is swallowed by the subject. In some embodiments, the elapsed time is a period of time that ends after the device exits the GI tract. In some embodiments, the elapsed time is a period of time that ends when the device exits the GI tract. In some embodiments, the elapsed time is a period of time that ends after the device has localized to a portion of the GI tract. In some embodiments, the elapsed time is a period of time that ends after the mechanism to monitor elapsed time is inactivated. In some embodiments, the elapsed time includes or consists of time of transition, or the elapsed time during passage of the device from one portion of the GI tract into a second portion of the GI tract. In some embodiments, the elapsed time includes or consists of time following transition, or the elapsed time after passage of the device from one portion of the GI tract into a second portion of the GI tract. In some further embodiments, the elapsed time after entry of the device into the GI tract of the subject comprises time of transition, time following transition, or a combination thereof. In some embodiments, the mechanism configured to monitor elapsed time is a clock circuitry.

In some more particular embodiments, the time of transition is elapsed time during passage of the device from mouth to stomach. In some embodiments, the time of transition is elapsed time during passage of the device from esophagus to stomach. In some embodiments, the time following transition is elapsed time after passage of the device from stomach to duodenum.

In some embodiments, the JAK inhibitor, or the pharmaceutical formulation comprising the JAK inhibitor, is released by a mechanism capable of releasing the JAK inhibitor or the pharmaceutical formulation comprising the JAK inhibitor from the device. In some more particular embodiments, the release mechanism is a gas-generating cell capable of generating a gas in an amount sufficient to release the JAK inhibitor, or the pharmaceutical formulation comprising the JAK inhibitor, from the device.

In some embodiments, the ingestible device is equipped with a triggering mechanism for releasing the JAK inhibitor or the pharmaceutical formulation comprising the JAK inhibitor from the ingestible device. In some embodiments, the triggering mechanism comprises a processor or controller communicably coupled to one or more sensors. In some embodiments, the sensor is capable of detecting reflectance (e.g., light reflected from the environment in the GI tract and external to the device). In some embodiments, the sensor is capable of detecting muscle contractions and/or peristalsis. In some embodiments, the sensor is not a pH sensor. In some embodiments, the sensor is not a pressure sensor. In some embodiments, the sensor is not a temperature sensor. In some further embodiments, the processor or controller activates the triggering mechanism. In some embodiments, the device is programmed to release the JAK inhibitor or the pharmaceutical formulation comprising the JAK inhibitor to a location in the GI tract of the subject. In some embodiments, the location in the GI tract of the subject is the pre-selected location.

Thus, in some further embodiments, the method further comprises releasing the JAK inhibitor, or the pharmaceutical formulation comprising the JAK inhibitor, from the device, said device comprising the triggering mechanism. In some more particular embodiments, the release is triggered autonomously. In some more particular embodiments, the release is autonomously triggered based on reflectance (light reflectance) detected by the sensor. In some more particular embodiments, the release is autonomously triggered based on one or more pre-established parameters. In some more particular embodiments, the one or more pre-established parameters are selected from reflectance (light reflectance) in the GI tract, time following entry of the device into the GI tract of the subject, and a combination thereof. Additional pre-established parameters optionally include detected muscle contractions in the GI tract, pH in the GI tract, temperature in the GI tract, blood detected in the GI tract, and the level of analyte or biomarker determined in a sample obtained in the GI tract. In some more particular embodiments, the one or more pre-established parameters do not comprise the pH in the GI tract. In some more particular embodiments, the one or more pre-established parameters do not comprise the temperature in the GI tract. In some more particular embodiments, the one or more pre-established parameters do not comprise the pressure in the GI tract. In some more particular embodiments, the JAK inhibitor or the pharmaceutical formulation that comprises the JAK inhibitor is triggered for release from the device within a period of time of equal to or less than about 5 minutes after the device is self-localized at the pre-selected location in the GI tract of the subject.

In some embodiments, the ingestible device contains a therapeutically effective amount of the JAK inhibitor. In some embodiments, the therapeutically effective amount of the JAK inhibitor is an induction dose. In some other embodiments, the therapeutically effective amount of the JAK inhibitor is a maintenance dose.

In some embodiments, the method provides a concentration of the JAK inhibitor in the subject's blood, serum, or plasma of less than about 2000 ng/mL. In some further embodiments, the method provides a concentration of the JAK inhibitor in the subject's blood, serum, or plasma of less than about 1000 ng/mL. In some further embodiments, the method provides a concentration of the JAK inhibitor in the subject's blood, serum, or plasma of less than about 500 ng/mL. In some further embodiments, the method provides a concentration of the JAK inhibitor in the subject's blood, serum, or plasma of less than or equal to about 100 ng/mL. In yet some further embodiments, the method provides a concentration of the JAK inhibitor in the subject's blood, serum, or plasma of less than or equal to about 50 ng/mL. In some even further embodiments, the method provides a concentration of the JAK inhibitor in the subject's blood, serum, or plasma of less than or equal to about 10 ng/mL.

In some embodiments, the method provides a concentration of the JAK inhibitor in the subject's blood, serum, or plasma of about 1 ng/mL to about 100 ng/mL. In some further embodiments, the method provides a concentration of the JAK inhibitor in the subject's blood, serum, or plasma of about 1 ng/mL to about 50 ng/mL, about 1 ng/mL to about 30 ng/mL, about 1 ng/mL to about 10 ng/mL, or about 1 ng/mL to about 5 ng/mL.

In some embodiments, the method provides a ratio of GI tissue concentration of the JAK inhibitor to blood, serum, or plasma concentration of the JAK inhibitor of about 2:1 to about 3000:1, about 2:1 to about 2000:1, about 2:1 to about 1000:1, or about 2:1 to about 600:1.

In some embodiments, the method provides a plasma concentration of the JAK inhibitor that is reduced relative to the plasma concentration after systemic administration of the same amount of the JAK inhibitor.

In some embodiments, the JAK inhibitor is a JAK inhibitor as disclosed herein. In some embodiments, the JAK inhibitor is a small molecule, an antibody, a peptide, a peptide fragment or a nucleic acid. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In some preferred embodiments, the JAK inhibitor is tofacitinib or a pharmaceutically acceptable salt thereof, or more particularly, tofacitinib citrate.

In some embodiments, the JAK inhibitor is a small molecule or peptide, and the formulation is a formulation as disclosed herein. In some embodiments, the concentration of the JAK inhibitor in the formulation is at least about 5 mg/mL, such as at least about 10 mg/mL, such as at least about 15 mg/mL.

In some embodiments, the JAK inhibitor is a therapeutic protein or an antibody, such as a monoclonal antibody, and the formulation is a formulation as disclosed herein. In some embodiments, the concentration of the JAK inhibitor in the formulation is at least about 110 mg/mL, or at least about 125 mg/mL.

Device Localization Comprising Detecting Transition from Duodenum to Jejunum

In some embodiments, provided herein is a method of treating an inflammatory disease or condition of the GI tract of a subject, comprising:

topically administering to the GI tract of the subject (i) a JAK inhibitor or (ii) a pharmaceutical formulation that comprises a JAK inhibitor, said topical administration comprising:

orally administering to the subject an ingestible device comprising the JAK inhibitor or the pharmaceutical formulation that comprises the JAK inhibitor;

localizing the device to a pre-selected location of the GI tract of the subject, wherein said pre-selected location is the jejunum; and releasing the JAK inhibitor or the pharmaceutical formulation that comprises the JAK inhibitor from the ingestible device to the jejunum;

wherein the device is self-localized to the pre-selected location based on detecting a transition from the duodenum to the jejunum.

Preferably, the inflammatory disease or condition is an inflammatory bowel disease.

In some embodiments, at least one of the one or more disease sites is in the jejunum. In some further embodiments, the disease or condition is Crohn's disease.

In other embodiments, at least one of the one or more disease sites is in the ileum. In some embodiments, the jejunum does not contain or has not been determined to contain a disease site. In some more particular embodiments, the inflammatory bowel disease is Crohn's disease. In some even more particular embodiments, the Crohn's disease is ileal Crohn's disease. In other particular embodiments, the inflammatory bowel disease is ulcerative colitis and at least one of the one more disease sites is in the terminal ileum.

In some embodiments, the detection of the transition from the duodenum to the jejunum is based on data comprising light reflectance occurring external to the device and within the GI tract of the subject, elapsed time after entry of the device into the GI tract of the subject, or a combination thereof. In some embodiments, the device comprising the self-localization mechanism (the self-localizing device) comprises a first light source and a second light source. In some embodiments, the first light source is configured to emit light at a first wavelength, and the second light source is configured to emit light at a second wavelength different from the first wavelength. In some embodiments, the self-localizing device further comprises a first detector and a second detector, wherein the first detector is configured to detect light at the first wavelength, and the second detector is configured to detect light at the second wavelength. In some further embodiments, the first wavelength and second wavelength are each independently selected from the group consisting of red light, green light and blue light.

In a more particular embodiment, the detection of the transition from the duodenum to the jejunum comprises (i) detecting green light and blue light reflectance, wherein an increase in the ratio of the green to blue reflectance detected indicates that the device has transitioned from the stomach to the duodenum; and (ii) measuring a period of elapsed time after the transition to the duodenum; thereby determining that the device has transitioned from the duodenum to the jejunum. In some embodiments, the period of elapsed time is about 3 minutes. In a further embodiment, the device localization further comprises obtaining peristaltic contraction frequency data.

In some embodiments, the ingestible device further comprises a mechanism to monitor elapsed time. In some embodiments, the elapsed time is a period of time that begins after entry of the ingestible device into the GI tract of the subject. In some embodiments, the elapsed time is a period of time that begins after entry of the ingestible device into the mouth of the subject. In some embodiments, the elapsed time is a period of time that begins after the ingestible device is swallowed by the subject. In some embodiments, the elapsed time is a period of time that ends after the device exits the GI tract. In some embodiments, the elapsed time is a period of time that ends when the device exits the GI tract. In some embodiments, the elapsed time is a period of time that ends after the device has localized to a portion of the GI tract. In some embodiments, the elapsed time is a period of time that ends after the mechanism to monitor elapsed time is inactivated. In some embodiments, the elapsed time includes or consists of time of transition, or the elapsed time during passage of the device from one portion of the GI tract into a second portion of the GI tract. In some embodiments, the elapsed time includes or consists of time following transition, or the elapsed time after passage of the device from one portion of the GI tract into a second portion of the GI tract. In some further embodiments, the elapsed time after entry of the device into the GI tract of the subject comprises time of transition, time following transition, or a combination thereof. In some embodiments, the mechanism configured to monitor elapsed time is a clock circuitry.

In some more particular embodiments, the time of transition is elapsed time during passage of the device from mouth to stomach. In some embodiments, the time of transition is elapsed time during passage of the device from esophagus to stomach. In some embodiments, the time following transition is elapsed time after passage of the device from stomach to duodenum.

In some embodiments, the JAK inhibitor, or the pharmaceutical formulation comprising the JAK inhibitor, is released by a mechanism capable of releasing the JAK inhibitor or the pharmaceutical formulation comprising the JAK inhibitor from the device. In some more particular embodiments, the release mechanism is a gas-generating cell capable of generating a gas in an amount sufficient to release the JAK inhibitor, or the pharmaceutical formulation comprising the JAK inhibitor, from the device.

In some embodiments, the ingestible device is equipped with a triggering mechanism for releasing the JAK inhibitor or the pharmaceutical formulation comprising the JAK inhibitor from the ingestible device. In some embodiments, the triggering mechanism comprises a processor or controller communicably coupled to one or more sensors. In some embodiments, the sensor is capable of detecting reflectance (e.g., light reflected from the environment in the GI tract and external to the device). In some embodiments, the sensor is capable of detecting muscle contractions and/or peristalsis. In some embodiments, the sensor is not a pH sensor. In some embodiments, the sensor is not a pressure sensor. In some embodiments, the sensor is not a temperature sensor. In some further embodiments, the processor or controller activates the triggering mechanism. In some embodiments, the device is programmed to release the JAK inhibitor or the pharmaceutical formulation comprising the JAK inhibitor to a location in the GI tract of the subject. In some embodiments, the location in the GI tract of the subject is the pre-selected location.

Thus, in some further embodiments, the method further comprises releasing the JAK inhibitor, or the pharmaceutical formulation comprising the JAK inhibitor, from the device, said device comprising the triggering mechanism. In some more particular embodiments, the release is triggered autonomously. In some more particular embodiments, the release is autonomously triggered based on reflectance (light reflectance) detected by the sensor. In some more particular embodiments, the release is autonomously triggered based on one or more pre-established parameters. In some more particular embodiments, the one or more pre-established parameters are selected from reflectance (light reflectance) in the GI tract, time following entry of the device into the GI tract of the subject, and a combination thereof. Additional pre-established parameters optionally include detected muscle contractions in the GI tract, pH in the GI tract, temperature in the GI tract, blood detected in the GI tract, and the level of analyte or biomarker determined in a sample obtained in the GI tract. In some more particular embodiments, the one or more pre-established parameters do not comprise the pH in the GI tract. In some more particular embodiments, the one or more pre-established parameters do not comprise the temperature in the GI tract. In some more particular embodiments, the one or more pre-established parameters do not comprise the pressure in the GI tract. In some more particular embodiments, the JAK inhibitor or the pharmaceutical formulation that comprises the JAK inhibitor is triggered for release from the device within a period of time of equal to or less than about 5 minutes after the device is self-localized at the pre-selected location in the GI tract of the subject.

In some embodiments, the ingestible device contains a therapeutically effective amount of the JAK inhibitor. In some embodiments, the therapeutically effective amount of the JAK inhibitor is an induction dose. In some other embodiments, the therapeutically effective amount of the JAK inhibitor is a maintenance dose.

In some embodiments, the method provides a concentration of the JAK inhibitor in the subject's blood, serum, or plasma of less than about 2000 ng/mL. In some further embodiments, the method provides a concentration of the JAK inhibitor in the subject's blood, serum, or plasma of less than about 1000 ng/mL. In some further embodiments, the method provides a concentration of the JAK inhibitor in the subject's blood, serum, or plasma of less than about 500 ng/mL. In some further embodiments, the method provides a concentration of the JAK inhibitor in the subject's blood, serum, or plasma of less than or equal to about 100 ng/mL. In yet some further embodiments, the method provides a concentration of the JAK inhibitor in the subject's blood, serum, or plasma of less than or equal to about 50 ng/mL. In some even further embodiments, the method provides a concentration of the JAK inhibitor in the subject's blood, serum, or plasma of less than or equal to about 10 ng/mL.

In some embodiments, the method provides a concentration of the JAK inhibitor in the subject's blood, serum, or plasma of about 1 ng/mL to about 100 ng/mL. In some further embodiments, the method provides a concentration of the JAK inhibitor in the subject's blood, serum, or plasma of about 1 ng/mL to about 50 ng/mL, about 1 ng/mL to about 30 ng/mL, about 1 ng/mL to about 10 ng/mL, or about 1 ng/mL to about 5 ng/mL.

In some embodiments, the method provides a ratio of GI tissue concentration of the JAK inhibitor to blood, serum, or plasma concentration of the JAK inhibitor of about 2:1 to about 3000:1, about 2:1 to about 2000:1, about 2:1 to about 1000:1, or about 2:1 to about 600:1.

In some embodiments, the method provides a plasma concentration of the JAK inhibitor that is reduced relative to the plasma concentration after systemic administration of the same amount of the JAK inhibitor.

In some embodiments, the JAK inhibitor is a JAK inhibitor as disclosed herein. In some embodiments, the JAK inhibitor is a small molecule, an antibody, a peptide, a peptide fragment or a nucleic acid. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In some preferred embodiments, the JAK inhibitor is tofacitinib or a pharmaceutically acceptable salt thereof, or more particularly, tofacitinib citrate.

In some embodiments, the JAK inhibitor is a small molecule or peptide, and the formulation is a formulation as disclosed herein. In some embodiments, the concentration of the JAK inhibitor in the formulation is at least about 5 mg/mL, such as at least about 10 mg/mL, such as at least about 15 mg/mL.

In some embodiments, the JAK inhibitor is a therapeutic protein or an antibody, such as a monoclonal antibody, and the formulation is a formulation as disclosed herein. In some embodiments, the concentration of the JAK inhibitor in the formulation is at least about 110 mg/mL, or at least about 125 mg/mL.

Device Localization Comprising Detecting Transition from Jejunum to Ileum

In some embodiments, provided herein is a method of treating an inflammatory disease or condition of the GI tract of a subject, comprising:

topically administering to the GI tract of the subject (i) a JAK inhibitor or (ii) a pharmaceutical formulation that comprises a JAK inhibitor, said topical administration comprising:

orally administering to the subject an ingestible device comprising the JAK inhibitor or the pharmaceutical formulation that comprises the JAK inhibitor;

localizing the device to a pre-selected location of the GI tract of the subject, wherein said pre-selected location is the ileum; and releasing the JAK inhibitor or the pharmaceutical formulation that comprises the JAK inhibitor from the ingestible device to the ileum;

wherein the device is self-localized to the pre-selected location based on detecting a transition from the jejunum to the ileum.

Preferably, the inflammatory disease or condition is an inflammatory bowel disease.

In some embodiments, at least one of the one or more disease sites is in the ileum. In some more particular embodiments, the inflammatory bowel disease is Crohn's disease. In some even more particular embodiments, the Crohn's disease is ileal Crohn's disease. In other particular embodiments, the inflammatory bowel disease is ulcerative colitis and at least one of the one more disease sites is in the terminal ileum.

In some embodiments, at least one of the one or more disease sites is in the cecum. In some embodiments, the ileum does not contain or has not been determined to contain a disease site. In some further embodiments, the inflammatory bowel disease is ulcerative colitis In some embodiments, the detection of the transition from the jejunum to the ileum is based on data comprising light reflectance occurring external to the device and within the GI tract of the subject, elapsed time after entry of the device into the GI tract of the subject, or a combination thereof. In some embodiments, the device comprising the self-localization mechanism (the self-localizing device) comprises a first light source and a second light source. In some embodiments, the first light source is configured to emit light at a first wavelength, and the second light source is configured to emit light at a second wavelength different from the first wavelength. In some embodiments, the self-localizing device further comprises a first detector and a second detector, wherein the first detector is configured to detect light at the first wavelength, and the second detector is configured to detect light at the second wavelength. In some further embodiments, the first wavelength and second wavelength are each independently selected from the group consisting of red light, green light and blue light.

In a more particular embodiment, the detection of the transition from the jejunum to the ileum comprises detecting red light reflectance, wherein a decrease in red light reflectance detected indicates that the device has transitioned from the jejunum to the ileum.

In some embodiments, the ingestible device further comprises a mechanism to monitor elapsed time. In some embodiments, the elapsed time is a period of time that begins after entry of the ingestible device into the GI tract of the subject. In some embodiments, the elapsed time is a period of time that begins after entry of the ingestible device into the mouth of the subject. In some embodiments, the elapsed time is a period of time that begins after the ingestible device is swallowed by the subject. In some embodiments, the elapsed time is a period of time that ends after the device exits the GI tract. In some embodiments, the elapsed time is a period of time that ends when the device exits the GI tract. In some embodiments, the elapsed time is a period of time that ends after the device has localized to a portion of the GI tract. In some embodiments, the elapsed time is a period of time that ends after the mechanism to monitor elapsed time is inactivated. In some embodiments, the elapsed time includes or consists of time of transition, or the elapsed time during passage of the device from one portion of the GI tract into a second portion of the GI tract. In some embodiments, the elapsed time includes or consists of time following transition, or the elapsed time after passage of the device from one portion of the GI tract into a second portion of the GI tract. In some further embodiments, the elapsed time after entry of the device into the GI tract of the subject comprises time of transition, time following transition, or a combination thereof. In some embodiments, the mechanism configured to monitor elapsed time is a clock circuitry.

In some more particular embodiments, the time of transition is elapsed time during passage of the device from mouth to stomach. In some embodiments, the time of transition is elapsed time during passage of the device from esophagus to stomach. In some embodiments, the time following transition is elapsed time after passage of the device from stomach to duodenum.

In some embodiments, the JAK inhibitor, or the pharmaceutical formulation comprising the JAK inhibitor, is released by a mechanism capable of releasing the JAK inhibitor or the pharmaceutical formulation comprising the JAK inhibitor from the device. In some more particular embodiments, the release mechanism is a gas-generating cell capable of generating a gas in an amount sufficient to release the JAK inhibitor, or the pharmaceutical formulation comprising the JAK inhibitor, from the device.

In some embodiments, the ingestible device is equipped with a triggering mechanism for releasing the JAK inhibitor or the pharmaceutical formulation comprising the JAK inhibitor from the ingestible device. In some embodiments, the triggering mechanism comprises a processor or controller communicably coupled to one or more sensors. In some embodiments, the sensor is capable of detecting reflectance (e.g., light reflected from the environment in the GI tract and external to the device). In some embodiments, the sensor is capable of detecting muscle contractions and/or peristalsis. In some embodiments, the sensor is not a pH sensor. In some embodiments, the sensor is not a pressure sensor. In some embodiments, the sensor is not a temperature sensor. In some further embodiments, the processor or controller activates the triggering mechanism. In some embodiments, the device is programmed to release the JAK inhibitor or the pharmaceutical formulation comprising the JAK inhibitor to a location in the GI tract of the subject. In some embodiments, the location in the GI tract of the subject is the pre-selected location.

Thus, in some further embodiments, the method further comprises releasing the JAK inhibitor, or the pharmaceutical formulation comprising the JAK inhibitor, from the device, said device comprising the triggering mechanism. In some more particular embodiments, the release is triggered autonomously. In some more particular embodiments, the release is autonomously triggered based on reflectance (light reflectance) detected by the sensor. In some more particular embodiments, the release is autonomously triggered based on one or more pre-established parameters. In some more particular embodiments, the one or more pre-established parameters are selected from reflectance (light reflectance) in the GI tract, time following entry of the device into the GI tract of the subject, and a combination thereof. Additional pre-established parameters optionally include detected muscle contractions in the GI tract, pH in the GI tract, temperature in the GI tract, blood detected in the GI tract, and the level of analyte or biomarker determined in a sample obtained in the GI tract. In some more particular embodiments, the one or more pre-established parameters do not comprise the pH in the GI tract. In some more particular embodiments, the one or more pre-established parameters do not comprise the temperature in the GI tract. In some more particular embodiments, the one or more pre-established parameters do not comprise the pressure in the GI tract. In some more particular embodiments, the JAK inhibitor or the pharmaceutical formulation that comprises the JAK inhibitor is triggered for release from the device within a period of time of equal to or less than about 5 minutes after the device is self-localized at the pre-selected location in the GI tract of the subject.

In some embodiments, the ingestible device contains a therapeutically effective amount of the JAK inhibitor. In some embodiments, the therapeutically effective amount of the JAK inhibitor is an induction dose. In some other embodiments, the therapeutically effective amount of the JAK inhibitor is a maintenance dose.

In some embodiments, the method provides a concentration of the JAK inhibitor in the subject's blood, serum, or plasma of less than about 2000 ng/mL. In some further embodiments, the method provides a concentration of the JAK inhibitor in the subject's blood, serum, or plasma of less than about 1000 ng/mL. In some further embodiments, the method provides a concentration of the JAK inhibitor in the subject's blood, serum, or plasma of less than about 500 ng/mL. In some further embodiments, the method provides a concentration of the JAK inhibitor in the subject's blood, serum, or plasma of less than or equal to about 100 ng/mL. In yet some further embodiments, the method provides a concentration of the JAK inhibitor in the subject's blood, serum, or plasma of less than or equal to about 50 ng/mL. In some even further embodiments, the method provides a concentration of the JAK inhibitor in the subject's blood, serum, or plasma of less than or equal to about 10 ng/mL.

In some embodiments, the method provides a concentration of the JAK inhibitor in the subject's blood, serum, or plasma of about 1 ng/mL to about 100 ng/mL. In some further embodiments, the method provides a concentration of the JAK inhibitor in the subject's blood, serum, or plasma of about 1 ng/mL to about 50 ng/mL, about 1 ng/mL to about 30 ng/mL, about 1 ng/mL to about 10 ng/mL, or about 1 ng/mL to about 5 ng/mL.

In some embodiments, the method provides a ratio of GI tissue concentration of the JAK inhibitor to blood, serum, or plasma concentration of the JAK inhibitor of about 2:1 to about 3000:1, about 2:1 to about 2000:1, about 2:1 to about 1000:1, or about 2:1 to about 600:1.

In some embodiments, the method provides a plasma concentration of the JAK inhibitor that is reduced relative to the plasma concentration after systemic administration of the same amount of the JAK inhibitor.

In some embodiments, the JAK inhibitor is a JAK inhibitor as disclosed herein. In some embodiments, the JAK inhibitor is a small molecule, an antibody, a peptide, a peptide fragment or a nucleic acid. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In some preferred embodiments, the JAK inhibitor is tofacitinib or a pharmaceutically acceptable salt thereof, or more particularly, tofacitinib citrate.

In some embodiments, the JAK inhibitor is a small molecule or peptide, and the formulation is a formulation as disclosed herein. In some embodiments, the concentration of the JAK inhibitor in the formulation is at least about 5 mg/mL, such as at least about 10 mg/mL, such as at least about 15 mg/mL.

In some embodiments, the JAK inhibitor is a therapeutic protein or an antibody, such as a monoclonal antibody, and the formulation is a formulation as disclosed herein. In some embodiments, the concentration of the JAK inhibitor in the formulation is at least about 110 mg/mL, or at least about 125 mg/mL.

Device Localization Comprising Detecting Transition from Ileum to Cecum

In some embodiments, provided herein is a method of treating an inflammatory disease or condition of the GI tract of a subject, comprising:

- topically administering to the GI tract of the subject (i) a JAK inhibitor or (ii) a pharmaceutical formulation that comprises a JAK inhibitor, said topical administration comprising:
- orally administering to the subject an ingestible device comprising the JAK inhibitor or the pharmaceutical formulation that comprises the JAK inhibitor;
- localizing the device to a pre-selected location of the GI tract of the subject, wherein said pre-selected location is the cecum; and
- releasing the JAK inhibitor or the pharmaceutical formulation that comprises the JAK inhibitor from the ingestible device to the cecum;
- wherein the device is self-localized to the pre-selected location based on detecting a transition from the ileum to the cecum.

Preferably, the inflammatory disease or condition is an inflammatory bowel disease. In some more particular embodiments, the inflammatory bowel disease is ulcerative colitis.

In some embodiments, at least one of the one or more disease sites is in the cecum.

In other embodiments, at least one of the one or more disease sites is in the colon. In some embodiments, the cecum does not contain or has not been determined to contain a disease site.

In some embodiments, the detection of the transition from the ileum to the cecum is based on data comprising light reflectance occurring external to the device and within the GI tract of the subject, elapsed time after entry of the device into the GI tract of the subject, or a combination thereof. In some embodiments, the device comprising the self-localization mechanism (the self-localizing device) comprises a first light source and a second light source. In some embodiments, the first light source is configured to emit light at a first wavelength, and the second light source is configured to emit light at a second wavelength different from the first wavelength. In some embodiments, the self-localizing device further comprises a first detector and a second detector, wherein the first detector is configured to detect light at the first wavelength, and the second detector is configured to detect light at the second wavelength. In some further embodiments, the first wavelength and second wavelength are each independently selected from the group consisting of red light, green light and blue light.

In a more particular embodiment, the detection of the transition from the ileum to the cecum comprises detecting red, green and blue light reflectance, wherein a decrease in the ratio of the red to green reflectance detected, together with a decrease in the ratio of the green to blue reflectance detected, indicates that the device has transitioned from the ileum to the cecum.

In some embodiments, the ingestible device further comprises a mechanism to monitor elapsed time. In some embodiments, the elapsed time is a period of time that begins after entry of the ingestible device into the GI tract of the subject. In some embodiments, the elapsed time is a period of time that begins after entry of the ingestible device into the mouth of the subject. In some embodiments, the elapsed time is a period of time that begins after the ingestible device is swallowed by the subject. In some embodiments, the elapsed time is a period of time that ends after the device exits the GI tract. In some embodiments, the elapsed time is a period of time that ends when the device exits the GI tract. In some embodiments, the elapsed time is a period of time that ends after the device has localized to a portion of the GI tract. In some embodiments, the elapsed time is a period of time that ends after the mechanism to monitor elapsed time is inactivated. In some embodiments, the elapsed time includes or consists of time of transition, or the elapsed time during passage of the device from one portion of the GI tract into a second portion of the GI tract. In some embodiments, the elapsed time includes or consists of time following transition, or the elapsed time after passage of the device from one portion of the GI tract into a second portion of the GI tract. In some further embodiments, the elapsed time after entry of the device into the GI tract of the subject comprises time of transition, time following transition, or a combination thereof. In some embodiments, the mechanism configured to monitor elapsed time is a clock circuitry.

In some more particular embodiments, the time of transition is elapsed time during passage of the device from mouth to stomach. In some embodiments, the time of transition is elapsed time during passage of the device from esophagus to stomach. In some embodiments, the time following transition is elapsed time after passage of the device from stomach to duodenum.

In some embodiments, the JAK inhibitor, or the pharmaceutical formulation comprising the JAK inhibitor, is released by a mechanism capable of releasing the JAK inhibitor or the pharmaceutical formulation comprising the JAK inhibitor from the device. In some more particular embodiments, the release mechanism is a gas-generating cell capable of generating a gas in an amount sufficient to release the JAK inhibitor, or the pharmaceutical formulation comprising the JAK inhibitor, from the device.

In some embodiments, the ingestible device is equipped with a triggering mechanism for releasing the JAK inhibitor or the pharmaceutical formulation comprising the JAK inhibitor from the ingestible device. In some embodiments, the triggering mechanism comprises a processor or controller communicably coupled to one or more sensors. In some embodiments, the sensor is capable of detecting reflectance (e.g., light reflected from the environment in the GI tract and external to the device). In some embodiments, the sensor is capable of detecting muscle contractions and/or peristalsis. In some embodiments, the sensor is not a pH sensor. In some embodiments, the sensor is not a pressure sensor. In some embodiments, the sensor is not a temperature sensor. In some further embodiments, the processor or controller activates the triggering mechanism. In some embodiments, the device is programmed to release the JAK inhibitor or the pharmaceutical formulation comprising the JAK inhibitor to a location in the GI tract of the subject. In some embodiments, the location in the GI tract of the subject is the pre-selected location.

Thus, in some further embodiments, the method further comprises releasing the JAK inhibitor, or the pharmaceutical formulation comprising the JAK inhibitor, from the device, said device comprising the triggering mechanism. In some more particular embodiments, the release is triggered autonomously. In some more particular embodiments, the release is autonomously triggered based on reflectance (light reflectance) detected by the sensor. In some more particular embodiments, the release is autonomously triggered based on one or more pre-established parameters. In some more particular embodiments, the one or more pre-established parameters are selected from reflectance (light reflectance) in the GI tract, time following entry of the device into the GI tract of the subject, and a combination thereof. Additional pre-established parameters optionally include detected muscle contractions in the GI tract, pH in the GI tract, temperature in the GI tract, blood detected in the GI tract, and the level of analyte or biomarker determined in a sample obtained in the GI tract. In some more particular embodiments, the one or more pre-established parameters do not comprise the pH in the GI tract. In some more particular embodiments, the one or more pre-established parameters do not comprise the temperature in the GI tract. In some more particular embodiments, the one or more pre-established parameters do not comprise the pressure in the GI tract. In some more particular embodiments, the JAK inhibitor or the pharmaceutical formulation that comprises the JAK inhibitor is triggered for release from the device within a period of time of equal to or less than about 5 minutes after the device is self-localized at the pre-selected location in the GI tract of the subject.

In some embodiments, the ingestible device contains a therapeutically effective amount of the JAK inhibitor. In some embodiments, the therapeutically effective amount of the JAK inhibitor is an induction dose. In some other embodiments, the therapeutically effective amount of the JAK inhibitor is a maintenance dose.

In some embodiments, the method provides a concentration of the JAK inhibitor in the subject's blood, serum, or plasma of less than about 2000 ng/mL. In some further embodiments, the method provides a concentration of the JAK inhibitor in the subject's blood, serum, or plasma of less than about 1000 ng/mL. In some further embodiments, the method provides a concentration of the JAK inhibitor in the subject's blood, serum, or plasma of less than about 500 ng/mL. In some further embodiments, the method provides a concentration of the JAK inhibitor in the subject's blood, serum, or plasma of less than or equal to about 100 ng/mL. In yet some further embodiments, the method provides a concentration of the JAK inhibitor in the subject's blood, serum, or plasma of less than or equal to about 50 ng/mL. In some even further embodiments, the method provides a concentration of the JAK inhibitor in the subject's blood, serum, or plasma of less than or equal to about 10 ng/mL.

In some embodiments, the method provides a concentration of the JAK inhibitor in the subject's blood, serum, or plasma of about 1 ng/mL to about 100 ng/mL. In some further embodiments, the method provides a concentration of the JAK inhibitor in the subject's blood, serum, or plasma of about 1 ng/mL to about 50 ng/mL, about 1 ng/mL to about 30 ng/mL, about 1 ng/mL to about 10 ng/mL, or about 1 ng/mL to about 5 ng/mL.

In some embodiments, the method provides a ratio of GI tissue concentration of the JAK inhibitor to blood, serum, or plasma concentration of the JAK inhibitor of about 2:1 to about 3000:1, about 2:1 to about 2000:1, about 2:1 to about 1000:1, or about 2:1 to about 600:1.

In some embodiments, the method provides a plasma concentration of the JAK inhibitor that is reduced relative to the plasma concentration after systemic administration of the same amount of the JAK inhibitor.

In some embodiments, the JAK inhibitor is a JAK inhibitor as disclosed herein. In some embodiments, the JAK inhibitor is a small molecule, an antibody, a peptide, a peptide fragment or a nucleic acid. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In some preferred embodiments, the JAK inhibitor is tofacitinib or a pharmaceutically acceptable salt thereof, or more particularly, tofacitinib citrate.

In some embodiments, the JAK inhibitor is a small molecule or peptide, and the formulation is a formulation as disclosed herein. In some embodiments, the concentration of the JAK inhibitor in the formulation is at least about 5 mg/mL, such as at least about 10 mg/mL, such as at least about 15 mg/mL.

In some embodiments, the JAK inhibitor is a therapeutic protein or an antibody, such as a monoclonal antibody, and the formulation is a formulation as disclosed herein. In some embodiments, the concentration of the JAK inhibitor in the formulation is at least about 110 mg/mL, or at least about 125 mg/mL.

Device Localization Comprising Detecting Transition from Cecum to Colon

In some embodiments, provided herein is a method of treating an inflammatory disease or condition of the GI tract of a subject, comprising:

topically administering to the GI tract of the subject (i) a JAK inhibitor or (ii) a pharmaceutical formulation that comprises a JAK inhibitor, said topical administration comprising:

orally administering to the subject an ingestible device comprising the JAK inhibitor or the pharmaceutical formulation that comprises the JAK inhibitor;

localizing the device to a pre-selected location of the (GI tract of the subject, wherein said pre-selected location is the colon; and releasing the JAK inhibitor or the pharmaceutical formulation that comprises the JAK inhibitor from the ingestible device to the colon;

wherein the device is self-localized to the pre-selected location based on detecting a transition from the cecum to the colon.

Preferably, the inflammatory disease or condition is an inflammatory bowel disease. In some more particular embodiments, the inflammatory bowel disease is ulcerative colitis.

In some embodiments, the one or more disease sites is in the ascending colon, the transverse colon, the descending colon, or any combination thereof.

In some embodiments, the detection of the transition from the cecum to the colon is based on data comprising light reflectance occurring external to the device and within the GI tract of the subject, elapsed time after entry of the device into the GI tract of the subject, or a combination thereof. In some embodiments, the device comprising the self-localization mechanism (the self-localizing device) comprises a first light source and a second light source. In some embodiments, the first light source is configured to emit light at a first wavelength, and the second light source is configured to emit light at a second wavelength different from the first wavelength. In some embodiments, the self-localizing device further comprises a first detector and a second detector, wherein the first detector is configured to detect light at the first wavelength, and the second detector is configured to detect light at the second wavelength. In some further embodiments, the first wavelength and second wavelength are each independently selected from the group consisting of red light, green light and blue light.

In a more particular embodiment, the detection of the transition from the cecum to the colon comprises detecting red, green and blue light reflectance, wherein a change in the ratio of the red to green reflectance detected, and/or a change in the coefficient of variation (CV) of the detected blue reflectance, indicates that the device has transitioned from the cecum to the colon.

In some embodiments, the ingestible device further comprises a mechanism to monitor elapsed time. In some embodiments, the elapsed time is a period of time that begins after entry of the ingestible device into the GI tract of the subject. In some embodiments, the elapsed time is a period of time that begins after entry of the ingestible device into the mouth of the subject. In some embodiments, the elapsed time is a period of time that begins after the ingestible device is swallowed by the subject. In some embodiments, the elapsed time is a period of time that ends after the device exits the GI tract. In some embodiments, the elapsed time is a period of time that ends when the device exits the GI tract. In some embodiments, the elapsed time is a period of time that ends after the device has localized to a portion of the GI tract. In some embodiments, the elapsed time is a period of time that ends after the mechanism to monitor elapsed time is inactivated. In some embodiments, the elapsed time includes or consists of time of transition, or the elapsed time during passage of the device from one portion of the GI tract into a second portion of the GI tract. In some embodiments, the elapsed time includes or consists of time following transition, or the elapsed time after passage of the device from one portion of the GI tract into a second portion of the GI tract. In some further embodiments, the elapsed time after entry of the device into the GI tract of the subject comprises time of transition, time following transition, or a combination thereof. In some embodiments, the mechanism configured to monitor elapsed time is a clock circuitry.

In some more particular embodiments, the time of transition is elapsed time during passage of the device from mouth to stomach. In some embodiments, the time of transition is elapsed time during passage of the device from esophagus to stomach. In some embodiments, the time following transition is elapsed time after passage of the device from stomach to duodenum.

In some embodiments, the JAK inhibitor, or the pharmaceutical formulation comprising the JAK inhibitor, is released by a mechanism capable of releasing the JAK inhibitor or the pharmaceutical formulation comprising the JAK inhibitor from the device. In some more particular embodiments, the release mechanism is a gas-generating cell capable of generating a gas in an amount sufficient to release the JAK inhibitor, or the pharmaceutical formulation comprising the JAK inhibitor, from the device.

In some embodiments, the ingestible device is equipped with a triggering mechanism for releasing the JAK inhibitor or the pharmaceutical formulation comprising the JAK inhibitor from the ingestible device. In some embodiments, the triggering mechanism comprises a processor or controller communicably coupled to one or more sensors. In some embodiments, the sensor is capable of detecting reflectance (e.g., light reflected from the environment in the GI tract and external to the device). In some embodiments, the sensor is capable of detecting muscle contractions and/or peristalsis. In some embodiments, the sensor is not a pH sensor. In some embodiments, the sensor is not a pressure sensor. In some embodiments, the sensor is not a temperature sensor. In some further embodiments, the processor or controller activates the triggering mechanism. In some embodiments, the device is programmed to release the JAK inhibitor or the pharmaceutical formulation comprising the JAK inhibitor to a location in the GI tract of the subject. In some embodiments, the location in the GI tract of the subject is the pre-selected location.

Thus, in some further embodiments, the method further comprises releasing the JAK inhibitor, or the pharmaceutical formulation comprising the JAK inhibitor, from the device, said device comprising the triggering mechanism. In some more particular embodiments, the release is triggered autonomously. In some more particular embodiments, the release is autonomously triggered based on reflectance (light reflectance) detected by the sensor. In some more particular embodiments, the release is autonomously triggered based on one or more pre-established parameters. In some more particular embodiments, the one or more pre-established parameters are selected from reflectance (light reflectance) in the GI tract, time following entry of the device into the GI tract of the subject, and a combination thereof. Additional pre-established parameters optionally include detected muscle contractions in the GI tract, pH in the GI tract, temperature in the GI tract, blood detected in the GI tract, and the level of analyte or biomarker determined in a sample obtained in the GI tract. In some more particular embodiments, the one or more pre-established parameters do not comprise the pH in the GI tract. In some more particular embodiments, the one or more pre-established parameters do not comprise the temperature in the GI tract. In some more particular embodiments, the one or more pre-established parameters do not comprise the pressure in the GI tract. In some more particular embodiments, the JAK inhibitor or the pharmaceutical formulation that comprises the JAK inhibitor is triggered for release from the device within a period of time of equal to or less than about 5 minutes after the device is self-localized at the pre-selected location in the GI tract of the subject.

In some embodiments, the ingestible device contains a therapeutically effective amount of the JAK inhibitor. In some embodiments, the therapeutically effective amount of the JAK inhibitor is an induction dose. In some other embodiments, the therapeutically effective amount of the JAK inhibitor is a maintenance dose.

In some embodiments, the method provides a concentration of the JAK inhibitor in the subject's blood, serum, or plasma of less than about 2000 ng/mL. In some further embodiments, the method provides a concentration of the JAK inhibitor in the subject's blood, serum, or plasma of less than about 1000 ng/mL. In some further embodiments, the method provides a concentration of the JAK inhibitor in the subject's blood, serum, or plasma of less than about 500 ng/mL. In some further embodiments, the method provides a concentration of the JAK inhibitor in the subject's blood, serum, or plasma of less than or equal to about 100 ng/mL. In yet some further embodiments, the method provides a concentration of the JAK inhibitor in the subject's blood, serum, or plasma of less than or equal to about 50 ng/mL. In some even further embodiments, the method provides a concentration of the JAK inhibitor in the subject's blood, serum, or plasma of less than or equal to about 10 ng/mL.

In some embodiments, the method provides a concentration of the JAK inhibitor in the subject's blood, serum, or plasma of about 1 ng/mL to about 100 ng/mL. In some further embodiments, the method provides a concentration of the JAK inhibitor in the subject's blood, serum, or plasma of about 1 ng/mL to about 50 ng/mL, about 1 ng/mL to about 30 ng/mL, about 1 ng/mL to about 10 ng/mL, or about 1 ng/mL to about 5 ng/mL.

In some embodiments, the method provides a ratio of GI tissue concentration of the JAK inhibitor to blood, serum, or plasma concentration of the JAK inhibitor of about 2:1 to about 3000:1, about 2:1 to about 2000:1, about 2:1 to about 1000:1, or about 2:1 to about 600:1.

In some embodiments, the method provides a plasma concentration of the JAK inhibitor that is reduced relative to the plasma concentration after systemic administration of the same amount of the JAK inhibitor.

In some embodiments, the JAK inhibitor is a JAK inhibitor as disclosed herein. In some embodiments, the JAK inhibitor is a small molecule, an antibody, a peptide, a peptide fragment or a nucleic acid. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In some preferred embodiments, the JAK inhibitor is tofacitinib or a pharmaceutically acceptable salt thereof, or more particularly, tofacitinib citrate.

In some embodiments, the JAK inhibitor is a small molecule or peptide, and the formulation is a formulation as disclosed herein. In some embodiments, the concentration of the JAK inhibitor in the formulation is at least about 5 mg/mL, such as at least about 10 mg/mL, such as at least about 15 mg/mL.

In some embodiments, the JAK inhibitor is a therapeutic protein or an antibody, such as a monoclonal antibody, and the formulation is a formulation as disclosed herein. In some embodiments, the concentration of the JAK inhibitor in the formulation is at least about 110 mg/mL, or at least about 125 mg/mL.

Further Embodiments Directed to a Method of Treating a Disease or Condition of the GI Tract of the Subject, the Method Comprising Topical Administration of Drug to the GI Tract of the Subject In some further embodiments, the method of treating a disease or condition of the GI tract of a subject further comprises one or more of the following features.

Further Non-Limiting Embodiments Related to the Ingestible Device as Disclosed Herein for the Topical Administration of a Drug to the GI Tract of a Subject In some embodiments, the device used in the method of treatment is further configured with at least one environmental sensor. In some embodiments, the environmental sensor is a pH sensor, a temperature sensor, a pressure sensor, or a combination thereof, wherein said pH, temperature and/or pressure sensor monitors the pH, temperature or pressure in the GI tract of the subject, respectively.

In some embodiments, the device used in the method of treatment does not include an environmental pH sensor. In some embodiments, the device used in the method of treatment does not include a temperature sensor. In some embodiments, the device used in the method of treatment does not include a pressure sensor. In some embodiments, the device self-localization mechanism does not require monitoring the pH of the subject's GI tract. In some embodiments, the device self-localization mechanism does not require monitoring the temperature of the subject's GI tract. In some embodiments, the device self-localization mechanism does not require monitoring the pressure of the subject's GI tract.

In some embodiments, the device is self-localized to a pre-selected location in the GI tract of the subject based on data including optical data, elapsed time, or a combination thereof. In some embodiments, the device is self-localized to a pre-selected location in the GI tract of the subject based on data optical data, elapsed time, or a combination thereof. In some further embodiments, the optical data are based on reflected light detected by the device, wherein the reflected light is light reflected within the GI tract of the subject and external to the device.

Further Non-Limiting Embodiments Related to the Release of the JAK Inhibitor, or the Pharmaceutical Formulation that Comprises the JAK Inhibitor, From the Device In some more particular embodiments, the JAK inhibitor or the pharmaceutical formulation that comprises the JAK inhibitor is released from the device within a period of time of equal to or less than about 5 minutes after the device detects or confirms transition to a portion of the GI tract that has been preselected for release of the JAK inhibitor. In some more particular embodiments, the release of the JAK inhibitor or the pharmaceutical formulation that comprises the JAK inhibitor is triggered within a period of time after the device is self-localized to the pre-selected location. In some embodiments, the period of time is equal to or less than about 60 seconds, such as equal to or less than about 30 seconds, equal to or less than about 20 seconds, equal to or less than about 10 seconds, equal to or less than about 5 seconds, or equal to or less than about 1 second. In some more particular embodiments, the release of the JAK inhibitor or the pharmaceutical formulation that comprises the JAK inhibitor is triggered at substantially the same time as the device is self-localized to the pre-selected location. In some more particular embodiments, the JAK inhibitor or the pharmaceutical formulation that comprises the JAK inhibitor, is released as a bolus. In some more particular embodiments, the release of the JAK inhibitor or the pharmaceutical formulation that comprises the JAK inhibitor is triggered within a period of time after the device detects or confirms transition to a portion of the GI tract containing one or more disease sites. In some embodiments, the period of time is equal to or less than about 60 seconds, such as equal to or less than about 30 seconds, equal to or less than about 20 seconds, equal to or less than about 10 seconds, equal to or less than about 5 seconds, or equal to or less than about 1 second. In some more particular embodiments, the release of the JAK inhibitor or the pharmaceutical formulation that comprises the JAK inhibitor is triggered at substantially the same time as the device is self-localized to the pre-selected location. In a more particular embodiment, the JAK inhibitor or the pharmaceutical formulation that comprises the JAK inhibitor is released as a bolus.

In some more particular embodiments, the release of the JAK inhibitor or the pharmaceutical formulation that comprises the JAK inhibitor is triggered within a period of time after the device is self-localized to the pre-selected location. In some embodiments, the period of time is equal to or less than about 60 seconds, such as equal to or less than about 30 seconds, equal to or less than about 20 seconds, equal to or less than about 10 seconds, equal to or less than about 5 seconds, or equal to or less than about 1 second. In some more particular embodiments, the release of the JAK inhibitor or the pharmaceutical formulation that comprises the JAK inhibitor is triggered at substantially the same time as the device is self-localized to the pre-selected location. In a more particular embodiment, the JAK inhibitor or the pharmaceutical formulation that comprises the JAK inhibitor is released from the device over a pre-determined period of time, wherein the pre-determined period of time commences within at most about 5 minutes after the device is self-localized at the pre-selected location. In some particular embodiments, the pre-determined period of time over which the formulation is released from the device is about 8 hours, about 7 hours, about 6 hours, about 5 hours, about 4 hours, about 3 hours, about 2 hours, about 1 hour, about 30 minutes, about 15 minutes, about 10 minutes, or about 5 minutes. In more particular embodiments, the pre-determined period of time commences within at most about 1 minute, at most about 30 seconds, or at most about 1 second after the device detects or confirms a transition to the pre-selected location. In some more particular embodiments, the release of the JAK inhibitor or the pharmaceutical formulation that comprises the JAK inhibitor is triggered within a period of time after the device detects or confirms transition to a portion of the GI tract pre-determined to contain one or more disease sites. In some embodiments, the period of time is equal to or less than about 60 seconds, such as equal to or less than about 30 seconds, equal to or less than about 20 seconds, equal to or less than about 10 seconds, equal to or less than about 5 seconds, or equal to or less than about 1 second. In some more particular embodiments, the release of the JAK inhibitor or the pharmaceutical formulation that comprises the JAK inhibitor is triggered at substantially the same time as the device is self-localized at a pre-selected location. In a more particular embodiment, the JAK inhibitor or the pharmaceutical formulation that comprises the JAK inhibitor is released from the device over a pre-determined period of time, wherein the pre-determined period of time commences within at most about 5 minutes after the device detects or confirms a transition to a pre-selected location. In some particular embodiments, the pre-determined period of time over which the formulation is released from the device is about 8 hours, about 7 hours, about 6 hours, about 5 hours, about 4 hours, about 3 hours, about 2 hours, about 1 hour, about 30 minutes, about 15 minutes, about 10 minutes, or about 5 minutes. In more particular embodiments, the pre-determined period of time commences within at most about 1 minute, at most about 30 seconds, or at most about 1 second after the device detects or confirms a transition to the pre-selected location.

In some embodiments, at least about 50% or more by weight of the JAK inhibitor, or the pharmaceutical formulation that comprises the JAK inhibitor, is released from the ingestible device at the pre-selected location. In some embodiments, at least about 80% or more by weight of the JAK inhibitor, or the pharmaceutical formulation that comprises the JAK inhibitor, is released from the ingestible device at the pre-selected location.

Further Non-Limiting Embodiments Related to Dosing

In some embodiments, the method of treating the disease or condition of the GI tract of the subject comprises administering a therapeutically effective amount of the JAK inhibitor. In some embodiments, the therapeutically effective amount is an induction dose of the JAK inhibitor. In some embodiments, the therapeutically effective amount is a maintenance dose of the JAK inhibitor. In some embodiments, the method comprises administering an induction dose and subsequently administering a maintenance dose of the JAK inhibitor. In some more particular embodiments, the total induction dose for a given period of time is at least about 1.5 times, at least about 2 times, at least about 3 times, at least about 4 times, at least about 5 times, at least about 6 times, at least about 8 times or at least about 10 times greater than a systemic induction dose for the same period of time. In some more particular embodiments, the total induction dose for a 2 week period is at least about 1.5 times, at least about 2 times, at least about 3 times, at least about 4 times, at least about 5 times, at least about 6 times, at least about 8 times or at least about 10 times greater than a systemic induction dose for the same period of time. In some more particular embodiments, the total induction dose for a 4 week period is at least about 1.5 times, at least about 2 times, at least about 3 times, at least about 4 times, at least about 5 times, at least about 6 times, at least about 8 times or at least about 10 times greater than a systemic induction dose for the same period of time. In some more particular embodiments, the total induction dose for a 6 week period is at least about 1.5 times, at least about 2 times, at least about 3 times, at least about 4 times, at least about 5 times, at least about 6 times, at least about 8 times or at least about 10 times greater than a systemic induction dose for the same period of time. In some more particular embodiments, the total induction dose for a 8 week period is at least about 1.5 times, at least about 2 times, at least about 3 times, at least about 4 times, at least about 5 times, at least about 6 times, at least about 8 times or at least about 10 times greater than a systemic induction dose for the same period of time.

In some more particular embodiments, an ingestible device comprising the JAK inhibitor or the pharmaceutical formulation that comprises the JAK inhibitor is administered once per day or more than once per day, for example, 1, 2, 3, 4 or more times per day. In some more particular embodiments, two or more ingestible devices are administered at the same time. In some more particular embodiments, two or more ingestible devices are administered about 1 minute apart, about 2 minutes apart, about 3 minutes apart, about 4 minutes apart, about 5 minutes apart, about 10 minutes apart, about 15 minutes apart, about 30 minutes apart, or about 60 minutes apart. In some more particular embodiments, two or more ingestible devices are administered about 1 hour apart, about 2 hours apart, about 3 hours apart, about 4 hours apart, about 5 hours apart, about 6 hours apart, about 7 hours apart, about 8 hours apart, about 9 hours apart, about 10 hours apart, about 11 hours apart, or about 12 hours apart.

Further Non-Limiting Embodiments Related to a Device Comprising a Reservoir

In some embodiments, the device comprises a reservoir, and the reservoir contains the JAK inhibitor, or a formulation comprising the JAK inhibitor. In some more particular embodiments, the formulation is suitable for introduction and optionally for storage in a reservoir comprised in the device. In some more particular embodiments the reservoir is configured to fit into the device. In some more particular embodiments, the reservoir comprises one or more anchor systems for anchoring the reservoir at a particular location in the GI tract, such as a section or subsection of the GI tract containing one or more disease sites, or proximal to a section or subsection of the GI tract containing one or more disease sites.

Thus, in some further embodiments, the method of treating a disease or condition of the GI tract further comprises releasing the JAK inhibitor or the pharmaceutical formulation that comprises the JAK inhibitor from a reservoir comprised in the device.

In some embodiments, the JAK inhibitor or the pharmaceutical formulation that comprises the JAK inhibitor is released from a reservoir configured to fit into the device.

In some embodiments, the JAK inhibitor or the pharmaceutical formulation that comprises the JAK inhibitor is released from a reservoir comprising one or more anchor systems for anchoring the reservoir at the pre-selected location of the GI tract.

Further Non-Limiting Embodiments Related to Determining a Site of Disease

In some further embodiments, the method further comprises identifying the section or subsection of the GI tract containing at least one of the one or more disease sites. In some embodiments, the one or more disease sites is identified prior to the administration (i.e., the one or more disease sites is pre-determined). In some embodiments, the identification of the one or more disease sites prior to the administration comprises imaging the GI tract, endoscopy, biopsy, computer-aided (CT) enterography, magnetic resonance enterography, sampling the GI tract for one or more disease markers or biomarkers, or a combination of any two or more of the foregoing.

In some embodiments, determining a site of disease is preceded by identifying symptoms or signs indicative of Crohn's disease in a subject, for example, according to American Gastroenterology Association (AGA) clinical guidelines. In some particular embodiments, such one or more symptoms or signs are selected from fever, abdominal pain, GI bleeding, localized tenderness, weight loss, joint pain, and cutaneous signs.

In more particular embodiments, the subject is further evaluated by determining the level of one or more inflammatory markers, for example, according to AGA guidelines. In some particular embodiments, such one or more markers are selected from CBC, CRP, CMP, fecal calprotectin, and ESR.

In some particular embodiments, the subject, having undergone evaluation for symptoms and signs of disease and evaluation for one or more disease markers, is identified as a candidate for further evaluation, e.g., such that imaging is indicated. In some such embodiments, the subject further undergoes CT-enterography or magnetic resonance enterography to determine the location(s) of one or more disease sites.

In more particular embodiments, determining a site of disease is preceded by identifying one or more AGA clinical guideline symptoms or signs indicative of Crohn's disease, and the subject is further evaluated by determining the level of one or more AGA clinical guideline inflammatory markers. Thus, in some particular embodiments, pre-determining a site of disease is preceded by identifying one or more symptoms or signs selected from fever, abdominal pain, GI bleeding, localized tenderness, weight loss, joint pain, and cutaneous signs, and the subject is further evaluated by determining the level of one or more inflammatory markers selected from CBC, CRP, CMP, fecal calprotectin, and ESR.

In more particular embodiments, determining a site of disease is preceded by identifying one or more AGA clinical guideline symptoms or signs indicative of Crohn's disease, the subject is identified as a candidate for further evaluation, and the subject undergoes CT-enterography or magnetic resonance enterography to determine the location(s) of one or more disease sites. Thus, in some particular embodiments, pre-determining a site of disease is preceded by identifying one or more symptoms or signs selected from fever, abdominal pain, GI bleeding, localized tenderness, weight loss, joint pain, and cutaneous signs; the subject is identified as a candidate for further evaluation; and the subject undergoes CT-enterography or magnetic resonance enterography to determine the location(s) of one or more disease sites.

In more particular embodiments, determining a site of disease is preceded by identifying symptoms or signs indicative of ulcerative colitis in a subject, for example, according to American Gastroenterology Association (AGA) clinical guidelines. In some particular embodiments, such one or more symptoms or signs are selected from bloody diarrhea, tenesmus, urgency, fever, abdominal pain, localized abdominal tenderness, weight loss, joint swelling and/or redness, signs of anemia, and cutaneous signs.

In more particular embodiments, the subject is further evaluated by determining the level of one or more inflammatory markers, for example, according to AGA guidelines. In some particular embodiments, such one or more markers are selected from CBC, CRP, CMP, difficile, ESR, and stool culture.

In some particular embodiments, the subject, having undergone evaluation for symptoms and signs of disease and evaluation for one or more disease markers, is identified as a candidate for further evaluation, e.g., such that imaging is indicated. In some such embodiments, the subject further undergoes colonoscopy and/or sigmoidoscopy to determine the location(s) of one or more disease sites.

In more particular embodiments, determining a site of disease is preceded by identifying one or more AGA clinical guideline symptoms or signs indicative of ulcerative colitis, and the subject is further evaluated by determining the level of one or more AGA clinical guideline inflammatory markers. Thus, in some particular embodiments, pre-determining a site of disease is preceded by identifying one or more symptoms or signs selected from bloody diarrhea, tenesmus, urgency, fever, abdominal pain, localized abdominal tenderness, weight loss, joint swelling and/or redness, signs of anemia, and cutaneous signs, and the subject is further evaluated by determining the level of one or more inflammatory markers selected from CBC, CRP, CMP, difficile, ESR, and stool culture.

In more particular embodiments, determining a site of disease is preceded by identifying one or more AGA clinical guideline symptoms or signs indicative of ulcerative colitis, the subject is identified as a candidate for further evaluation, and the subject undergoes colonoscopy and/or sigmoidoscopy to determine the location(s) of one or more disease sites. Thus, in some particular embodiments, pre-determining a site of disease is preceded by identifying one or more symptoms or signs selected from bloody diarrhea, tenesmus, urgency, fever, abdominal pain, localized abdominal tenderness, weight loss, joint swelling and/or redness, signs of anemia, and cutaneous signs; the subject is identified as a candidate for further evaluation; and the subject undergoes colonoscopy and/or sigmoidoscopy to determine the location(s) of one or more disease sites.

In some embodiments, determining a site of disease comprises imaging the GI tract of the subject. In some more particular embodiments, the imaging comprises still imaging, video imaging, or a combination thereof. In some embodiments, pre-determining a site of disease comprises endoscopy. In some more particular embodiments, pre-determining a site of disease comprises endoscopy with imaging. In one particular aspect, pre-determining the site of disease comprises endoscopy with video imaging, still imaging, or both. In some other more particular embodiments, pre-determining a site of disease comprises endoscopy with biopsy. In more particular embodiments, pre-determining a site of disease comprises endoscopy with imaging and biopsy.

In some more particular aspects of the foregoing embodiments for the determination of the site of disease, the ingestible device is configured with at least one sensor. In some more particular embodiments, the at least one sensor is a light sensor. In some more particular embodiments, the sensor is an imaging sensor. In some more particular embodiments, the sensor is an imaging sensor capable of detecting inflamed tissue or lesions in the GI tract. In some more particular embodiments, the sensor is capable of detecting muscle contractions and/or peristalsis. In some more particular embodiments, the sensor is capable of detecting reflectance.

Thus, in some further embodiments, the method of treating one or more inflammatory disease sites comprises using an ingestible device configured with an imaging sensor. In some embodiments, the imaging sensor is capable of detecting inflamed tissue or lesions in the GI tract. In some embodiments, the ingestible device configured with the imaging sensor comprises the JAK inhibitor, or the pharmaceutical formulation comprising the JAK inhibitor. In other embodiments, the ingestible device configured with the imaging sensor is a second ingestible device that does not comprise the JAK inhibitor, or the pharmaceutical formulation comprising the JAK inhibitor.

Thus, in some further embodiments, the method of treating one or more inflammatory disease sites comprises determining or pre-determining one or more inflammatory disease sites;

wherein the ingestible device is configured with an imaging sensor capable of detecting inflamed tissue or lesions in the GI tract, and the determining or pre-determining of the one or more inflammatory disease sites comprises imaging the GI tract via the ingestible device imaging sensor.

In some other embodiments, the method further comprises determining or pre-determining one or more inflammatory disease sites based on the level of an analyte or biomarker in a sample obtained from the GI tract. In some embodiments, the sample is obtained from the GI tract prior to the administration of the ingestible device. In some more particular embodiments, the sample is obtained from the same portion of the GI tract in which the JAK inhibitor is subsequently released. In some embodiments, the sample is obtained from the GI tract after the administration of the ingestible device. In some more particular embodiments, the sample is obtained from the same portion of the GI tract in which the JAK inhibitor was released. In some embodiments, a first sample is obtained from the GI tract prior to the administration of the ingestible device, and a second sample is obtained from the GI tract after the administration of the ingestible device. In some more particular embodiments, the first sample and the second sample are obtained from the same portion of the GI tract in which the JAK inhibitor is released. The concentration of the analyte or biomarker in the sample is determined as disclosed herein.

In some even more particular embodiments, the JAK inhibitor or the pharmaceutical formulation that comprises the JAK inhibitor is released from the ingestible device to the same portion of the GI tract from which the sample is obtained. In some even more particular embodiments, the JAK inhibitor or the pharmaceutical formulation that comprises the JAK inhibitor is released from the ingestible device to a portion of the GI tract proximal to that from which the sample is obtained.

In some even more particular embodiments, the analyte or biomarker is an analyte or biomarker that indicates that a JAK inhibitor is a suitable therapeutic for the treatment of the one or more disease sites. Examples of such analytes or biomarkers include, but are not limited to, pro-inflammatory cytokines that rely on the JAK family for signal transduction.

In some even more particular embodiments, the analyte or biomarker is calprotectin, TNF-alpha, MAdCAM, other cytokines, and/or lactoferrin. Another example of an analyte is blood.

In some even more particular embodiments, the analyte or biomarker is an analyte or biomarker that indicates that a JAK inhibitor may provide a suitable therapeutic for the treatment of the one or more disease sites. Examples of such analytes or biomarkers include pro-inflammatory cytokines that rely on the JAK family for signal transduction.

In some even more particular embodiments, the analyte or biomarker is IL-6, IL-13, IL-15, IL-23 and/or IFNγ. In some even more particular embodiments, the analyte or biomarker is IL-13, IL15, IL-22, IL-24 and/or IL-27. In some even more particular embodiments, the analyte or biomarker is IL-6, IL-13, IL-15, IL-23 and/or IFNγ, and the disease is ulcerative colitis. In some even more particular embodiments, the analyte or biomarker is IL-13, IL15, IL-22, IL-24 and/or IL-27, and the disease is Crohn's disease.

Combination Therapy

The JAK inhibitors disclosed herein may be optionally be used with additional agents in the treatment of the diseases disclosed herein. Nonlimiting examples of such agents for treating or preventing inflammatory bowel disease in such adjunct therapy (e.g., Crohn's disease, ulcerative colitis) include substances that suppress cytokine production, down-regulate or suppress self-antigen expression, or mask the MHC antigens. Examples of such agents include 2-amino-6-aryl-5-substituted pyrimidines (see U.S. Pat. No. 4,665,077); non-steroidal antiinflammatory drugs (NSAIDs); ganciclovir; tacrolimus; lucocorticoids such as Cortisol or aldosterone; anti-inflammatory agents such as a cyclooxygenase inhibitor; a 5-lipoxygenase inhibitor; or a leukotriene receptor antagonist; purine antagonists such as azathioprine or mycophenolate mofetil (MMF); alkylating agents such as cyclophosphamide; bromocryptine; danazol; dapsone; glutaraldehyde (which masks the MHC antigens, as described in U.S. Pat. No. 4,120,649); anti-idiotypic antibodies for MHC antigens and MHC fragments; cyclosporin A; 6-mercaptopurine; steroids such as corticosteroids or glucocorticosteroids or glucocorticoid analogs, e.g., prednisone, methylprednisolone, including SOLU-MEDROL®, methylprednisolone sodium succinate, and dexamethasone; dihydrofolate reductase inhibitors such as methotrexate (oral or subcutaneous); anti-malarial agents such as chloroquine and hydroxychloroquine; sulfasalazine; leflunomide; cytokine or cytokine receptor antibodies or antagonists including anti-interferon-alpha, -beta, or -gamma antibodies, anti-tumor necrosis factor (TNF)-alpha antibodies (infliximab (REMICADE®) or adalimumab), anti-TNF-alpha immunoadhesin (etanercept), anti-TNF-beta antibodies, anti-interleukin-2 (IL-2) antibodies and anti-IL-2 receptor antibodies, and anti-interleukin-6 (IL-6) receptor antibodies and antagonists; anti-LFA-1 antibodies, including anti-CD11a and anti-CD 18 antibodies; anti-L3T4 antibodies; heterologous anti-lymphocyte globulin; pan-T antibodies, anti-CD3 or anti-CD4/CD4a antibodies; soluble peptide containing a LFA-3 binding domain (WO 90/08187 published Jul. 26, 1990); streptokinase; transforming growth factor-beta (TGF-beta); streptodomase; RNA or DNA from the host; FK506; RS-61443; chlorambucil; deoxyspergualin; rapamycin; T-cell receptor (Cohen et al., U.S. Pat. No. 5,114,721); T-cell receptor fragments (Offner et al., Science, 251:430-432 (1991); WO 90/11294; Ianeway, Nature, 341:482 (1989); and WO 91/01133); BAFF antagonists such as BAFF or BR3 antibodies or immunoadhesins and zTNF4 antagonists (for review, see Mackay and Mackay, Trends Immunol., 23:113-5 (2002) and see also definition below); biologic agents that interfere with T cell helper signals, such as anti-CD40 receptor or anti-CD40 ligand (CD 154), including blocking antibodies to CD40-CD40 ligand (e.g., Durie et al., Science, 261:1328-30 (1993); Mohan et al., J. Immunol., 154:1470-80 (1995)) and CTLA4-Ig (Finck et al., Science, 265:1225-7 (1994)); and T-cell receptor antibodies (EP 340,109) such as T10B9. Non-limiting examples of adjunct agents also include the following: budenoside; epidermal growth factor; aminosalicylates; metronidazole; mesalamine; olsalazine; balsalazide; antioxidants; thromboxane inhibitors; IL-1 receptor antagonists; anti-IL-1 monoclonal antibodies; growth factors; elastase inhibitors; pyridinyl-imidazole compounds; TNF antagonists; IL-4, IL-10, IL-13 and/or TGFβ cytokines or agonists thereof (e.g., agonist antibodies); IL-11; glucuronide- or dextran-conjugated prodrugs of prednisolone, dexamethasone or budesonide; ICAM-I antisense phosphorothioate oligodeoxynucleotides (ISIS 2302; Isis Pharmaceuticals, Inc.); soluble complement receptor 1 (TPIO; T Cell Sciences, Inc.); slow-release mesalazine; antagonists of platelet activating factor (PAF); ciprofloxacin; and lignocaine. Examples of agents for UC are sulfasalazine and related salicylate-containing drugs for mild cases and corticosteroid drugs in severe cases. Topical administration of either salicylates or corticosteroids is sometimes effective, particularly when the disease is limited to the distal bowel, and is associated with decreased side effects compared with systemic use. Supportive measures such as administration of iron and antidiarrheal agents are sometimes indicated. Azathioprine, 6-mercaptopurine and methotrexate are sometimes also prescribed for use in refractory corticosteroid-dependent cases.

In other embodiments, a JAK inhibitor as described herein can be administered with a DNA enzyme (DNAzyme). In, some embodiments, the DNAzyme is a GATA-3-specific DNAzyme, for example, SB012, as described in Krug et al., The New England Journal of Medicine (2015) 372(21):1987-1995, which is incorporated by reference herein in its entirety.

In other embodiments, a JAK inhibitor as described herein can be administered with one or more of: a CHST15 inhibitor, a IL-6 receptor inhibitor, an anti-TNF agent, an integrin inhibitor, an IL-12/IL-23 inhibitor, a SMAD7 inhibitor, a IL-13 inhibitor, an IL-1 receptor inhibitor, a TLR agonist (e.g., cobitolimod), an immunosuppressant, a live biotherapeutic such as a stem cell, IL-10 or an IL-10 agonist, copaxone, a CD40 inhibitor, an S1P-inhibitor, a GM-CSF, or a chemokine/chemokine receptor inhibitor. In other embodiments, a JAK inhibitor as described herein can be administered with a vitamin C infusion, one or more corticosteroids, and optionally thiamine.

In some embodiments, the immunosuppressant is an antibody or monoclonal antibody. In some embodiments, the immunosuppressant antibody is daclizumab (e.g., marketed as Zenapax® or Zinbryta®); or a biosimilar thereof. Daclizumab is a humanized monoclonal antibody that binds specifically to the alpha subunit (p55 alpha, CD25, or Tac subunit) of the human high-affinity interleukin-2 (IL-2) receptor that is expressed on the surface of activated lymphocytes (e.g., see Cohan S. L. et al., Biomedicines, 7(1), 18 2019). In some embodiments, the daclizumab is provided in a formulation as disclosed herein.

In some embodiments, the additional agent is a granulocyte-macrophage colony-stimulating factor (GM-CSF; also known as colony-stimulating factor 2 (CSF 2)); or a biosimilar thereof. (See Barahona-Garrido J. and Yamamoto-Furusho J. K., Biologics 2008, 2(3):501-504). GM-CSF is an immunostimulant, and more particularly, a monomeric glycoprotein that functions as a cytokine (white blood cell growth factor) and can stimulate stem cells to produce granulocytes and monocytes. GM-CSF also facilitates immune system development and promotes defense against infections. In some embodiments, the GM-CSF is sargramostim (Leukine®) or molgramostim; or a biosimilar thereof. In some preferred embodiments, the GM-CSF is sargramostim or a biosimilar thereof. In some embodiments, the GM-CSF is administered during maintenance therapy.

Examples of particular combinations include the following. Unless otherwise specified, the first component (component (1)) is administered in an ingestible device, while the second component (component (2)) is administered either topically, for example, via an ingestible device, which may be the same or different ingestible device as the first component, or by another form of administration. Each listed small molecule, peptide or nucleic acid agent optionally includes a pharmaceutically acceptable salt thereof, whether or not such a form is expressly indicated. Each listed antibody agent optionally includes a biosimilar thereof, whether or not such a biosimilar is expressly indicated. Examples of the first component and the second component recited in combinations disclosed below are optionally provided in a formulation as disclosed herein.

(1) JAK inhibitor; (2) a PDE4 inhibitor, an IL-12/IL-23 inhibitor, an S1P modulator, an integrin inhibitor, or an anti-TNF agent. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate.

(1) JAK inhibitor; (2) PDE4 inhibitor. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate. In some embodiments, the PDE4 inhibitor is apremilast, crisaborole, ibudilast, roflumilast or tetomilast; or a pharmaceutically acceptable salt thereof.

(1) JAK inhibitor; (2) PDE4 inhibitor administered topically, for example, via an ingestible device.

In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate. In some embodiments, the PDE4 inhibitor is apremilast, crisaborole, ibudilast, roflumilast or tetomilast; or a pharmaceutically acceptable salt thereof.

(1) JAK inhibitor; (2) PDE4 inhibitor administered systemically. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate. In some embodiments, the PDE4 inhibitor is apremilast, crisaborole, ibudilast, roflumilast or tetomilast; or a pharmaceutically acceptable salt thereof. In some embodiments, the systemic administration is intravenous administration. In some embodiments, the systemic administration is subcutaneous administration.

(1) JAK inhibitor; (2) PDE4 inhibitor administered orally. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate. In some embodiments, the PDE4 inhibitor is apremilast, crisaborole, ibudilast, roflumilast or tetomilast; or a pharmaceutically acceptable salt thereof.

(1) JAK inhibitor; (2) PDE4 inhibitor administered rectally. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate. In some embodiments, the PDE4 inhibitor is apremilast, crisaborole, ibudilast, roflumilast or tetomilast; or a pharmaceutically acceptable salt thereof.

(1) PDE4 inhibitor; (2) JAK inhibitor. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate. In some embodiments, the PDE4 inhibitor is apremilast, crisaborole, ibudilast, roflumilast or tetomilast; or a pharmaceutically acceptable salt thereof.

(1) PDE4 inhibitor; (2) JAK inhibitor administered topically, for example, via an ingestible device. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate. In some embodiments, the PDE4 inhibitor is apremilast, crisaborole, ibudilast, roflumilast or tetomilast; or a pharmaceutically acceptable salt thereof.

(1) PDE4 inhibitor; (2) JAK inhibitor administered systemically. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate. In some embodiments, the PDE4 inhibitor is apremilast, crisaborole, ibudilast, roflumilast or tetomilast; or a pharmaceutically acceptable salt thereof. In some embodiments, the systemic administration is intravenous administration. In some embodiments, the systemic administration is subcutaneous administration.

(1) PDE4 inhibitor; (2) JAK inhibitor administered orally. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate. In some embodiments, the PDE4 inhibitor is apremilast, crisaborole, ibudilast, roflumilast or tetomilast; or a pharmaceutically acceptable salt thereof.

(1) PDE4 inhibitor; (2) JAK inhibitor administered rectally. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate. In some embodiments, the PDE4 inhibitor is apremilast, crisaborole, ibudilast, roflumilast or tetomilast; or a pharmaceutically acceptable salt thereof.

(1) JAK inhibitor; (2) IL-12/IL-23 inhibitor. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate. In some embodiments, the IL-12/IL-23 inhibitor is selected from the group consisting of ustekinumab, guselkumab, risankizumab, brazikumab and mirikizumab; and biosimilars thereof; preferably, the IL-12/IL-23 inhibitor is ustekinumab or a biosimilar thereof. In some embodiments, the JAK inhibitor is tofacitinib or a pharmaceutically acceptable salt thereof, even more particularly, tofacitinib citrate, and the IL-12/IL-23 inhibitor is ustekinumab or a biosimilar thereof.

(1) JAK inhibitor; (2) IL-12/IL-23 inhibitor administered topically, for example, via an ingestible device. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate. In some embodiments, the IL-12/IL-23 inhibitor is selected from the group consisting of ustekinumab, guselkumab, risankizumab, brazikumab and mirikizumab; and biosimilars thereof; preferably, the IL-12/IL-23 inhibitor is ustekinumab or a biosimilar thereof. In some embodiments, the JAK inhibitor is tofacitinib or a pharmaceutically acceptable salt thereof, even more particularly, tofacitinib citrate, and the IL-12/IL-23 inhibitor is ustekinumab or a biosimilar thereof.

(1) JAK inhibitor; (2) IL-12/IL-23 inhibitor administered systemically. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate. In some embodiments, the IL-12/IL-23 inhibitor is selected from the group consisting of ustekinumab, guselkumab, risankizumab, brazikumab and mirikizumab; and biosimilars thereof; preferably, the IL-12/IL-23 inhibitor is ustekinumab or a biosimilar thereof. In some embodiments, the JAK inhibitor is tofacitinib or a pharmaceutically acceptable salt thereof, even more particularly, tofacitinib citrate, and the IL-12/IL-23 inhibitor is ustekinumab or a biosimilar thereof. In some embodiments, the systemic administration is intravenous administration. In some embodiments, the systemic administration is subcutaneous administration.

(1) JAK inhibitor; (2) IL-12/IL-23 inhibitor administered orally. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate. In some embodiments, the IL-12/IL-23 inhibitor is selected from the group consisting of ustekinumab, guselkumab, risankizumab, brazikumab and mirikizumab; and biosimilars thereof; preferably, the IL-12/IL-23 inhibitor is ustekinumab or a biosimilar thereof. In some embodiments, the JAK inhibitor is tofacitinib or a pharmaceutically acceptable salt thereof, even more particularly, tofacitinib citrate, and the IL-12/IL-23 inhibitor is ustekinumab or a biosimilar thereof.

(1) JAK inhibitor; (2) IL-12/IL-23 inhibitor administered rectally. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate. In some embodiments, the IL-12/IL-23 inhibitor is selected from the group consisting of ustekinumab, guselkumab, risankizumab, brazikumab and mirikizumab; and biosimilars thereof; preferably, the IL-12/IL-23 inhibitor is ustekinumab or a biosimilar thereof. In some embodiments, the JAK inhibitor is tofacitinib or a pharmaceutically acceptable salt thereof, even more particularly, tofacitinib citrate, and the IL-12/IL-23 inhibitor is ustekinumab or a biosimilar thereof.

(1) IL-12/IL-23; (2) JAK inhibitor. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate. In some embodiments, the IL-12/IL-23 inhibitor is selected from the group consisting of ustekinumab, guselkumab, risankizumab, brazikumab and mirikizumab; and biosimilars thereof; preferably, the IL-12/IL-23 inhibitor is ustekinumab or a biosimilar thereof. In some embodiments, the JAK inhibitor is tofacitinib or a pharmaceutically acceptable salt thereof, even more particularly, tofacitinib citrate, and the IL-12/IL-23 inhibitor is ustekinumab or a biosimilar thereof.

(1) IL-12/IL-23 inhibitor; (2) JAK inhibitor administered topically, for example, via an ingestible device. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate. In some embodiments, the IL-12/IL-23 inhibitor is selected from the group consisting of ustekinumab, guselkumab, risankizumab, brazikumab and mirikizumab; and biosimilars thereof; preferably, the IL-12/IL-23 inhibitor is ustekinumab or a biosimilar thereof. In some embodiments, the JAK inhibitor is tofacitinib or a pharmaceutically acceptable salt thereof, even more particularly, tofacitinib citrate, and the IL-12/IL-23 inhibitor is ustekinumab or a biosimilar thereof.

(1) IL-12/IL-23 inhibitor; (2) JAK inhibitor administered systemically. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate. In some embodiments, the IL-12/IL-23 inhibitor is selected from the group consisting of ustekinumab, guselkumab, risankizumab, brazikumab and mirikizumab; and biosimilars thereof; preferably, the IL-12/IL-23 inhibitor is ustekinumab or a biosimilar thereof. In some embodiments, the systemic administration is intravenous administration. In some embodiments, the systemic administration is subcutaneous administration. In some embodiments, the JAK inhibitor is tofacitinib or a pharmaceutically acceptable salt thereof, even more particularly, tofacitinib citrate, and the IL-12/IL-23 inhibitor is ustekinumab or a biosimilar thereof.

(1) IL-12/IL-23 inhibitor; (2) JAK inhibitor administered orally. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate. In some embodiments, the IL-12/IL-23 inhibitor is selected from the group consisting of ustekinumab, guselkumab, risankizumab, brazikumab and mirikizumab; and biosimilars thereof; preferably, the IL-12/IL-23 inhibitor is ustekinumab or a biosimilar thereof. In some embodiments, the JAK inhibitor is tofacitinib or a pharmaceutically acceptable salt thereof, even more particularly, tofacitinib citrate, and the IL-12/IL-23 inhibitor is ustekinumab or a biosimilar thereof.

(1) IL-12/IL-23 inhibitor; (2) JAK inhibitor administered rectally. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate. In some embodiments, the IL-12/IL-23 inhibitor is selected from the group consisting of ustekinumab, guselkumab, risankizumab, brazikumab and mirikizumab; and biosimilars thereof; preferably, the IL-12/IL-23 inhibitor is ustekinumab or a biosimilar thereof. In some embodiments, the JAK inhibitor is tofacitinib or a pharmaceutically acceptable salt thereof, even more particularly, tofacitinib citrate, and the IL-12/IL-23 inhibitor is ustekinumab or a biosimilar thereof.

(1) JAK inhibitor; (2) S1P modulator. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate. In some embodiments, the S1P modulator is selected from the group consisting of fingolimod, KRP203, siponimod, ponesimod, cenerimod, ozanimod, ceralifimod, amiselimod, and etrasimod; and pharmaceutically acceptable salts thereof.

(1) JAK inhibitor; (2) S1P modulator administered topically, for example, via an ingestible device. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate. In some embodiments, the S1P modulator is selected from the group consisting of fingolimod, KRP203, siponimod, ponesimod, cenerimod, ozanimod, ceralifimod, amiselimod, and etrasimod; and pharmaceutically acceptable salts thereof.

(1) JAK inhibitor; (2) S1P modulator administered systemically. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate. In some embodiments, the S1P modulator is selected from the group consisting of fingolimod, KRP203, siponimod, ponesimod, cenerimod, ozanimod, ceralifimod, amiselimod, and etrasimod; and pharmaceutically acceptable salts thereof. In some embodiments, the systemic administration is intravenous administration. In some embodiments, the systemic administration is subcutaneous administration.

(1) JAK inhibitor; (2) S1P modulator administered orally. In some embodiments, the JAK inhibitor is selected from the group consisting abrocitinib, baricitinib, BMS-986165, decemotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate. In some embodiments, the S1P modulator is selected from the group consisting of fingolimod, KRP203, siponimod, ponesimod, cenerimod, ozanimod, ceralifimod, amiselimod, and etrasimod; and pharmaceutically acceptable salts thereof.

(1) JAK inhibitor; (2) S1P modulator administered rectally. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate. In some embodiments, the S1P modulator is selected from the group consisting of fingolimod, KRP203, siponimod, ponesimod, cenerimod, ozanimod, ceralifimod, amiselimod, and etrasimod; and pharmaceutically acceptable salts thereof.

(1) S1P modulator; (2) JAK inhibitor. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate. In some embodiments, the S1P modulator is selected from the group consisting of fingolimod, KRP203, siponimod, ponesimod, cenerimod, ozanimod, ceralifimod, amiselimod, and etrasimod; and pharmaceutically acceptable salts thereof.

(1) S1P modulator; (2) JAK inhibitor administered topically, for example, via an ingestible device. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate. In some embodiments, the S1P modulator is selected from the group consisting of fingolimod, KRP203, siponimod, ponesimod, cenerimod, ozanimod, ceralifimod, amiselimod, and etrasimod; and pharmaceutically acceptable salts thereof.

(1) S1P modulator; (2) JAK inhibitor administered systemically. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate. In some embodiments, the S1P modulator is selected from the group consisting of fingolimod, KRP203, siponimod, ponesimod, cenerimod, ozanimod, ceralifimod, amiselimod, and etrasimod; and pharmaceutically acceptable salts thereof. In some embodiments, the systemic administration is intravenous administration. In some embodiments, the systemic administration is subcutaneous administration.

(1) S1P modulator; (2) JAK inhibitor administered orally. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate. In some embodiments, the S1P modulator is selected from the group consisting of fingolimod, KRP203, siponimod, ponesimod, cenerimod, ozanimod, ceralifimod, amiselimod, and etrasimod; and pharmaceutically acceptable salts thereof.

(1) S1P modulator; (2) JAK inhibitor administered rectally. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate. In some embodiments, the S1P modulator is selected from the group consisting of fingolimod, KRP203, siponimod, ponesimod, cenerimod, ozanimod, ceralifimod, amiselimod, and etrasimod; and pharmaceutically acceptable salts thereof.

(1) JAK inhibitor; (2) integrin inhibitor. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate. In some embodiments, the integrin inhibitor is (a) an antibody selected from the group consisting of vedolizumab, natalizumab, etrolizumab, vatelizumab and PF-00547659; and biosimilars thereof; preferably, vedolizumab or a biosimilar thereof, or (b) a small molecule selected from the group consisting ofAJM-300, HCA2969 (carotegrast), firategrast, valategrast, R00270608, CDP-323, CT7758, GW-559090, ELND-004 TBC-4746, DW-908e, PTG-100 (peptide), PN-10943 (peptide; also known as PN-943) and a compound disclosed in US 2005/0209232; U.S. Pat. No. 9,518,091; WO 2005/077914; WO 2005/077915; WO 09/706822; WO 2017/135471; WO 2017/135472; Co et al., Immunotechnol., 4:253-266 (1999); Dubree et al., J. Med. Chem., 45:3451-3457 (2002); Gong et al., J. Med. Chem., 49:3402-3411 (2006); Gong et al., Bioorg. Med. Chem. Lett., 18:1331-1335 (2008); Muz et al., American Society of Hematology Annual Meeting and Exposition, (2014) 56th (December 8) Abs 4758; Sidduri et al., Bioorg. Med. Chem. Lett., 23:1026-1031 (2013); or Xu et al., Bioorg. Med. Chem. Lett., 23:4370-4373 (2013), the disclosures of each of which are incorporated by reference in their entireties; and pharmaceutically acceptable salts thereof. In a preferred embodiment, the JAK inhibitor is tofacitinib or a pharmaceutically acceptable salt thereof, even more particularly, tofacitinib citrate, and the integrin inhibitor is vedolizumab or a biosimilar thereof. In another preferred embodiment, the JAK inhibitor is tofacitinib or a pharmaceutically acceptable salt thereof, even more particularly, tofacitinib citrate, and the integrin inhibitor is HCA2969 (carotegrast) or a pharmaceutically acceptable salt thereof. In another preferred embodiment, the JAK inhibitor is tofacitinib or a pharmaceutically acceptable salt thereof, even more particularly, tofacitinib citrate, and the integrin inhibitor is AJM300 or a pharmaceutically acceptable salt thereof.

(1) JAK inhibitor; (2) integrin inhibitor administered topically, for example, via an ingestible device. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate. In some embodiments, the integrin inhibitor is (a) an antibody selected from the group consisting of vedolizumab, natalizumab, etrolizumab, vatelizumab and PF-00547659; and biosmilars thereof, or (b) a small molecule selected from the group consisting ofAJM-300, HCA2969 (carotegrast), firategrast, valategrast, R00270608, CDP-323, CT7758, GW-559090, ELND-004 TBC-4746, DW-908e, PTG-100 (peptide), PN-10943 (peptide; also known as PN-943) and a compound disclosed in US 2005/0209232; U.S. Pat. No. 9,518,091; WO 2005/077914; WO 2005/077915; WO 09/706822; WO 2017/135471; WO 2017/135472; Co et al., Immunotechnol., 4:253-266 (1999); Dubree et al., J. Med. Chem., 45:3451-3457 (2002); Gong et al., J. Med. Chem., 49:3402-3411 (2006); Gong et al., Bioorg. Med. Chem. Lett., 18:1331-1335 (2008); Muz et al., American Society of Hematology Annual Meeting and Exposition, (2014) 56th (December 8) Abs 4758; Sidduri et al., Bioorg. Med. Chem. Lett., 23:1026-1031 (2013); or Xu et al., Bioorg. Med. Chem. Lett., 23:4370-4373 (2013), the disclosures of each of which are incorporated by reference in their entireties; and pharmaceutically acceptable salts thereof.

In a preferred embodiment, the JAK inhibitor is tofacitinib or a pharmaceutically acceptable salt thereof, even more particularly, tofacitinib citrate, and the integrin inhibitor is vedolizumab or a biosimilar thereof. In another preferred embodiment, the JAK inhibitor is tofacitinib or a pharmaceutically acceptable salt thereof, even more particularly, tofacitinib citrate, and the integrin inhibitor is HCA2969 (carotegrast) or a pharmaceutically acceptable salt thereof. In another preferred embodiment, the JAK inhibitor is tofacitinib or a pharmaceutically acceptable salt thereof, even more particularly, tofacitinib citrate, and the integrin inhibitor is AJM300 or a pharmaceutically acceptable salt thereof.

(1) JAK inhibitor; (2) integrin inhibitor administered systemically. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate. In some embodiments, the integrin inhibitor is (a) an antibody selected from the group consisting of vedolizumab, natalizumab, etrolizumab, vatelizumab and PF-00547659; and biosimilars thereof; preferably, vedolizumab or a biosimilar thereof, or (b) a small molecule selected from the group consisting of AJM-300, HCA2969 (carotegrast), firategrast, valategrast, R00270608, CDP-323, CT7758, GW-559090, ELND-004 TBC-4746, DW-908e, PTG-100 (peptide), PN-10943 (peptide; also known as PN-943) and a compound disclosed in US 2005/0209232; U.S. Pat. No. 9,518,091; WO 2005/077914; WO 2005/077915; WO 09/706822; WO 2017/135471; WO 2017/135472; Co et al., Immunotechnol., 4:253-266 (1999); Dubree et al., J. Med. Chem., 45:3451-3457 (2002); Gong et al., J. Med. Chem., 49:3402-3411 (2006); Gong et al., Bioorg. Med. Chem. Lett., 18:1331-1335 (2008); Muz et al., American Society of Hematology Annual Meeting and Exposition, (2014) 56th (December 8) Abs 4758; Sidduri et al., Bioorg. Med. Chem. Lett., 23:1026-1031 (2013); or Xu et al., Bioorg. Med. Chem. Lett., 23:4370-4373 (2013), the disclosures of each of which are incorporated by reference in their entireties; and pharmaceutically acceptable salts thereof. In some embodiments, the systemic administration is intravenous administration. In some embodiments, the systemic administration is subcutaneous administration.

In a preferred embodiment, the JAK inhibitor is tofacitinib or a pharmaceutically acceptable salt thereof, even more particularly, tofacitinib citrate, and the integrin inhibitor is vedolizumab or a biosimilar thereof. In another preferred embodiment, the JAK inhibitor is tofacitinib or a pharmaceutically acceptable salt thereof, even more particularly, tofacitinib citrate, and the integrin inhibitor is HCA2969 (carotegrast) or a pharmaceutically acceptable salt thereof. In another preferred embodiment, the JAK inhibitor is tofacitinib or a pharmaceutically acceptable salt thereof, even more particularly, tofacitinib citrate, and the integrin inhibitor is AJM300 or a pharmaceutically acceptable salt thereof.

(1) JAK inhibitor; (2) integrin inhibitor administered orally. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate. In some embodiments, the integrin inhibitor is (a) an antibody selected from the group consisting of vedolizumab, natalizumab, etrolizumab, vatelizumab and PF-00547659; and biosimilars thereof; preferably, vedolizumab or a biosimilar thereof, or (b) a small molecule selected from the group consisting ofAJM-300, HCA2969 (carotegrast), firategrast, valategrast, R00270608, CDP-323, CT7758, GW-559090, ELND-004 TBC-4746, DW-908e, PTG-100 (peptide), PN-10943 (peptide; also known as PN-943) and a compound disclosed in US 2005/0209232; U.S. Pat. No. 9,518,091; WO 2005/077914; WO 2005/077915; WO 09/706822; WO 2017/135471; WO 2017/135472; Co et al., Immunotechnol., 4:253-266 (1999); Dubree et al., J. Med. Chem., 45:3451-3457 (2002); Gong et al., J. Med. Chem., 49:3402-3411 (2006); Gong et al., Bioorg. Med. Chem. Lett., 18:1331-1335 (2008); Muz et al., American Society of Hematology Annual Meeting and Exposition, (2014) 56th (December 8) Abs 4758; Sidduri et al., Bioorg. Med. Chem. Lett., 23:1026-1031 (2013); or Xu et al., Bioorg. Med. Chem.

Lett., 23:4370-4373 (2013), the disclosures of each of which are incorporated by reference in their entireties; and pharmaceutically acceptable salts thereof.

In a preferred embodiment, the JAK inhibitor is tofacitinib or a pharmaceutically acceptable salt thereof, even more particularly, tofacitinib citrate, and the integrin inhibitor is vedolizumab or a biosimilar thereof. In another preferred embodiment, the JAK inhibitor is tofacitinib or a pharmaceutically acceptable salt thereof, even more particularly, tofacitinib citrate, and the integrin inhibitor is HCA2969 (carotegrast) or a pharmaceutically acceptable salt thereof. In another preferred embodiment, the JAK inhibitor is tofacitinib or a pharmaceutically acceptable salt thereof, even more particularly, tofacitinib citrate, and the integrin inhibitor is AJM300 or a pharmaceutically acceptable salt thereof.

(1) JAK inhibitor; (2) integrin inhibitor administered rectally. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate. In some embodiments, the integrin inhibitor is (a) an antibody selected from the group consisting of vedolizumab, natalizumab, etrolizumab, vatelizumab and PF-00547659; and biosimilars thereof; preferably, vedolizumab or a biosimilar thereof, or (b) a small molecule selected from the group consisting ofAJM-300, HCA2969 (carotegrast), firategrast, valategrast, R00270608, CDP-323, CT7758, GW-559090, ELND-004 TBC-4746, DW-908e, PTG-100 (peptide), PN-10943 (peptide; also known as PN-943) and a compound disclosed in US 2005/0209232; U.S. Pat. No. 9,518,091; WO 2005/077914; WO 2005/077915; WO 09/706822; WO 2017/135471; WO 2017/135472; Co et al., Immunotechnol., 4:253-266 (1999); Dubree et al., J. Med. Chem., 45:3451-3457 (2002); Gong et al., J. Med. Chem., 49:3402-3411 (2006); Gong et al., Bioorg. Med. Chem. Lett., 18:1331-1335 (2008); Muz et al., American Society of Hematology Annual Meeting and Exposition, (2014) 56th (December 8) Abs 4758; Sidduri et al., Bioorg. Med. Chem. Lett., 23:1026-1031 (2013); or Xu et al., Bioorg. Med. Chem. Lett., 23:4370-4373 (2013), the disclosures of each of which are incorporated by reference in their entireties; and pharmaceutically acceptable salts thereof.

In a preferred embodiment, the JAK inhibitor is tofacitinib or a pharmaceutically acceptable salt thereof, even more particularly, tofacitinib citrate, and the integrin inhibitor is vedolizumab or a biosimilar thereof. In another preferred embodiment, the JAK inhibitor is tofacitinib or a pharmaceutically acceptable salt thereof, even more particularly, tofacitinib citrate, and the integrin inhibitor is HCA2969 (carotegrast) or a pharmaceutically acceptable salt thereof. In another preferred embodiment, the JAK inhibitor is tofacitinib or a pharmaceutically acceptable salt thereof, even more particularly, tofacitinib citrate, and the integrin inhibitor is AJM300 or a pharmaceutically acceptable salt thereof.

(1) Integrin inhibitor; (2) JAK inhibitor. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate. In some embodiments, the integrin inhibitor is (a) an antibody selected from the group consisting of vedolizumab, natalizumab, etrolizumab, vatelizumab and PF-00547659; and biosimilars thereof; preferably, vedolizumab or a biosimilar thereof, or (b) a small molecule selected from the group consisting ofAJM-300, HCA2969 (carotegrast), firategrast, valategrast, R00270608, CDP-323, CT7758, GW-559090, ELND-004 TBC-4746, DW-908e, PTG-100 (peptide), PN-10943 (peptide; also known as PN-943) and a compound disclosed in US 2005/0209232; U.S. Pat. No. 9,518,091; WO 2005/077914; WO 2005/077915; WO 09/706822; WO 2017/135471; WO 2017/135472; Co et al., Immunotechnol., 4:253-266 (1999); Dubree et al., J. Med. Chem., 45:3451-3457 (2002); Gong et al., J. Med. Chem., 49:3402-3411 (2006); Gong et al., Bioorg. Med. Chem. Lett., 18:1331-1335 (2008); Muz et al., American Society of Hematology Annual Meeting and Exposition, (2014) 56th (December 8) Abs 4758; Sidduri et al., Bioorg. Med. Chem. Lett., 23:1026-1031 (2013); or Xu et al., Bioorg. Med. Chem. Lett., 23:4370-4373 (2013), the disclosures of each of which are incorporated by reference in their entireties; and pharmaceutically acceptable salts thereof.

In a preferred embodiment, the JAK inhibitor is tofacitinib or a pharmaceutically acceptable salt thereof, even more particularly, tofacitinib citrate, and the integrin inhibitor is vedolizumab or a biosimilar thereof. In another preferred embodiment, the JAK inhibitor is tofacitinib or a pharmaceutically acceptable salt thereof, even more particularly, tofacitinib citrate, and the integrin inhibitor is HCA2969 (carotegrast) or a pharmaceutically acceptable salt thereof. In another preferred embodiment, the JAK inhibitor is tofacitinib or a pharmaceutically acceptable salt thereof, even more particularly, tofacitinib citrate, and the integrin inhibitor is AJM300 or a pharmaceutically acceptable salt thereof.

(1) Integrin inhibitor; (2) JAK inhibitor administered topically, for example, via an ingestible device. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate. In some embodiments, the integrin inhibitor is (a) an antibody selected from the group consisting of vedolizumab, natalizumab, etrolizumab, vatelizumab and PF-00547659; and biosmilars thereof, or (b) a small molecule selected from the group consisting ofAJM-300, HCA2969 (carotegrast), firategrast, valategrast, R00270608, CDP-323, CT7758, GW-559090, ELND-004 TBC-4746, DW-908e, PTG-100 (peptide), PN-10943 (peptide; also known as PN-943) and a compound disclosed in US 2005/0209232; U.S. Pat. No. 9,518,091; WO 2005/077914; WO 2005/077915; WO 09/706822; WO 2017/135471; WO 2017/135472; Co et al., Immunotechnol., 4:253-266 (1999); Dubree et al., J. Med. Chem., 45:3451-3457 (2002); Gong et al., J. Med. Chem., 49:3402-3411 (2006); Gong et al., Bioorg. Med. Chem. Lett., 18:1331-1335 (2008); Muz et al., American Society of Hematology Annual Meeting and Exposition, (2014) 56th (December 8) Abs 4758; Sidduri et al., Bioorg. Med. Chem. Lett., 23:1026-1031 (2013); or Xu et al., Bioorg. Med. Chem. Lett., 23:4370-4373 (2013), the disclosures of each of which are incorporated by reference in their entireties; and pharmaceutically acceptable salts thereof.

In a preferred embodiment, the JAK inhibitor is tofacitinib or a pharmaceutically acceptable salt thereof, even more particularly, tofacitinib citrate, and the integrin inhibitor is vedolizumab or a biosimilar thereof. In another preferred embodiment, the JAK inhibitor is tofacitinib or a pharmaceutically acceptable salt thereof, even more particularly, tofacitinib citrate, and the integrin inhibitor is HCA2969 (carotegrast) or a pharmaceutically acceptable salt thereof. In another preferred embodiment, the JAK inhibitor is tofacitinib or a pharmaceutically acceptable salt thereof, even more particularly, tofacitinib citrate, and the integrin inhibitor is AJM300 or a pharmaceutically acceptable salt thereof.

(1) Integrin inhibitor; (2) JAK inhibitor administered systemically. In some embodiments, the JAK inhibitor is selected from the group consisting abrocitinib, baricitinib, BMS-986165, decemotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate. In some embodiments, the integrin inhibitor is (a) an antibody selected from the group consisting of vedolizumab, natalizumab, etrolizumab, vatelizumab and PF-00547659; and biosimilars thereof; preferably, vedolizumab or a biosimilar thereof, or (b) a small molecule selected from the group consisting of AJM-300, HCA2969 (carotegrast), firategrast, valategrast, R00270608, CDP-323, CT7758, GW-559090, ELND-004 TBC-4746, DW-908e, PTG-100 (peptide), PN-10943 (peptide; also known as PN-943) and a compound disclosed in US 2005/0209232; U.S. Pat. No. 9,518,091; WO 2005/077914; WO 2005/077915; WO 09/706822; WO 2017/135471; WO 2017/135472; Co et al., Immunotechnol., 4:253-266 (1999); Dubree et al., J. Med. Chem., 45:3451-3457 (2002); Gong et al., J. Med. Chem., 49:3402-3411 (2006); Gong et al., Bioorg. Med. Chem. Lett., 18:1331-1335 (2008); Muz et al., American Society of Hematology Annual Meeting and Exposition, (2014) 56th (December 8) Abs 4758; Sidduri et al., Bioorg. Med. Chem. Lett., 23:1026-1031 (2013); or Xu et al., Bioorg. Med. Chem. Lett., 23:4370-4373 (2013), the disclosures of each of which are incorporated by reference in their entireties; and pharmaceutically acceptable salts thereof. In some embodiments, the systemic administration is intravenous administration. In some embodiments, the systemic administration is subcutaneous administration.

In a preferred embodiment, the JAK inhibitor is tofacitinib or a pharmaceutically acceptable salt thereof, even more particularly, tofacitinib citrate, and the integrin inhibitor is vedolizumab or a biosimilar thereof. In another preferred embodiment, the JAK inhibitor is tofacitinib or a pharmaceutically acceptable salt thereof, even more particularly, tofacitinib citrate, and the integrin inhibitor is HCA2969 (carotegrast) or a pharmaceutically acceptable salt thereof. In another preferred embodiment, the JAK inhibitor is tofacitinib or a pharmaceutically acceptable salt thereof, even more particularly, tofacitinib citrate, and the integrin inhibitor is AJM300 or a pharmaceutically acceptable salt thereof.

(1) Integrin inhibitor; (2) JAK inhibitor administered orally. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate. In some embodiments, the integrin inhibitor is (a) an antibody selected from the group consisting of vedolizumab, natalizumab, etrolizumab, vatelizumab and PF-00547659; and biosimilars thereof; preferably, vedolizumab or a biosimilar thereof, or (b) a small molecule selected from the group consisting of AJM-300, HCA2969 (carotegrast), firategrast, valategrast, R00270608, CDP-323, CT7758, GW-559090, ELND-004 TBC-4746, DW-908e, PTG-100 (peptide), PN-10943 (peptide; also known as PN-943) and a compound disclosed in US 2005/0209232; U.S. Pat. No. 9,518,091; WO 2005/077914; WO 2005/077915; WO 09/706822; WO 2017/135471; WO 2017/135472; Co et al., Immunotechnol., 4:253-266 (1999); Dubree et al., J. Med. Chem., 45:3451-3457 (2002); Gong et al., J. Med. Chem., 49:3402-3411 (2006); Gong et al., Bioorg. Med. Chem. Lett., 18:1331-1335 (2008); Muz et al., American Society of Hematology Annual Meeting and Exposition, (2014) 56th (December 8) Abs 4758; Sidduri et al., Bioorg. Med. Chem. Lett., 23:1026-1031 (2013); or Xu et al., Bioorg. Med. Chem. Lett., 23:4370-4373 (2013), the disclosures of each of which are incorporated by reference in their entireties; and pharmaceutically acceptable salts thereof. In a preferred embodiment, the JAK inhibitor is tofacitinib citrate and the integrin inhibitor is vedolizumab or a biosimilar thereof. In another preferred embodiment, the JAK inhibitor is tofacitinib citrate and the integrin inhibitor is HCA2969 (carotegrast) or a pharmaceutically acceptable salt thereof. In another preferred embodiment, the JAK inhibitor is tofacitinib citrate and the integrin inhibitor is AJM300 or a pharmaceutically acceptable salt thereof.

(1) Integrin inhibitor; (2) JAK inhibitor administered rectally. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate. In some embodiments, the integrin inhibitor is (a) an antibody selected from the group consisting of vedolizumab, natalizumab, etrolizumab, vatelizumab and PF-00547659; and biosimilars thereof; preferably, vedolizumab or a biosimilar thereof, or (b) a small molecule selected from the group consisting ofAJM-300, HCA2969 (carotegrast), firategrast, valategrast, R00270608, CDP-323, CT7758, GW-559090, ELND-004 TBC-4746, DW-908e, PTG-100 (peptide), PN-10943 (peptide; also known as PN-943) and a compound disclosed in US 2005/0209232; U.S. Pat. No. 9,518,091; WO 2005/077914; WO 2005/077915; WO 09/706822; WO 2017/135471; WO 2017/135472; Co et al., Immunotechnol., 4:253-266 (1999); Dubree et al., J. Med. Chem., 45:3451-3457 (2002); Gong et al., J. Med. Chem., 49:3402-3411 (2006); Gong et al., Bioorg. Med. Chem. Lett., 18:1331-1335 (2008); Muz et al., American Society of Hematology Annual Meeting and Exposition, (2014) 56th (December 8) Abs 4758; Sidduri et al., Bioorg. Med. Chem. Lett., 23:1026-1031 (2013); or Xu et al., Bioorg. Med. Chem. Lett., 23:4370-4373 (2013), the disclosures of each of which are incorporated by reference in their entireties; and pharmaceutically acceptable salts thereof. In a preferred embodiment, the JAK inhibitor is tofacitinib or a pharmaceutically acceptable salt thereof, even more particularly, tofacitinib citrate, and the integrin inhibitor is vedolizumab or a biosimilar thereof. In another preferred embodiment, the JAK inhibitor is tofacitinib or a pharmaceutically acceptable salt thereof, even more particularly, tofacitinib citrate, and the integrin inhibitor is HCA2969 (carotegrast) or a pharmaceutically acceptable salt thereof. In another preferred embodiment, the JAK inhibitor is tofacitinib or a pharmaceutically acceptable salt thereof, even more particularly, tofacitinib citrate, and the integrin inhibitor is AJM300 or a pharmaceutically acceptable salt thereof.

(1) JAK inhibitor; (2) anti-TNF agent. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate. In some embodiments, the anti-TNF agent is selected from the group consisting of adalimumab, infliximab, golimumab, certolizumab pegol and etanercept; and biosimilars thereof. In a preferred embodiment, the JAK inhibitor is tofacitinib or a pharmaceutically acceptable salt thereof, or more particularly, tofacitinib citrate, and the anti-TNF agent is adalimumab or a biosimilar thereof.

(1) JAK inhibitor; (2) anti-TNF agent administered topically, for example, via an ingestible device. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate. In some embodiments, the anti-TNF agent is selected from the group consisting of adalimumab, infliximab, golimumab, certolizumab pegol and etanercept; and biosimilars thereof. In a preferred embodiment, the JAK inhibitor is tofacitinib or a pharmaceutically acceptable salt thereof, or more particularly, tofacitinib citrate, and the anti-TNF agent is adalimumab or a biosimilar thereof.

(1) JAK inhibitor; (2) anti-TNF agent administered systemically. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate. In some embodiments, the anti-TNF agent is selected from the group consisting of adalimumab, infliximab, golimumab, certolizumab pegol and etanercept; and biosimilars thereof. In some embodiments, the systemic administration is intravenous administration. In some embodiments, the systemic administration is subcutaneous administration. In a preferred embodiment, the JAK inhibitor is tofacitinib or a pharmaceutically acceptable salt thereof, or more particularly, tofacitinib citrate, and the anti-TNF agent is adalimumab or a biosimilar thereof.

(1) JAK inhibitor; (2) anti-TNF agent administered orally. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate. In some embodiments, the anti-TNF agent is selected from the group consisting of adalimumab, infliximab, golimumab, certolizumab pegol and etanercept; and biosimilars thereof. In a preferred embodiment, the JAK inhibitor is tofacitinib or a pharmaceutically acceptable salt thereof, or more particularly, tofacitinib citrate, and the anti-TNF agent is adalimumab or a biosimilar thereof.

(1) JAK inhibitor; (2) anti-TNF agent administered rectally. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333

(R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate. In some embodiments, the anti-TNF agent is selected from the group consisting of adalimumab, infliximab, golimumab, certolizumab pegol and etanercept; and biosimilars thereof. In a preferred embodiment, the JAK inhibitor is tofacitinib or a pharmaceutically acceptable salt thereof, or more particularly, tofacitinib citrate, and the anti-TNF agent is adalimumab or a biosimilar thereof.

(1) Anti-TNF agent; (2) JAK inhibitor. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate. In another preferred embodiment, the JAK inhibitor is tofacitinib or a pharmaceutically acceptable salt thereof, or more particularly, tofacitinib citrate, and the anti-TNF agent is adalimumab or a biosimilar thereof.

(1) Anti-TNF agent; (2) JAK inhibitor topically, for example, via an ingestible device. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate. In a preferred embodiment, the JAK inhibitor is tofacitinib or a pharmaceutically acceptable salt thereof, or more particularly, tofacitinib citrate, and the anti-TNF agent is adalimumab or a biosimilar thereof.

(1) Anti-TNF agent; (2) JAK inhibitor systemically. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate. In another preferred embodiment, the JAK inhibitor is tofacitinib or a pharmaceutically acceptable salt thereof, or more particularly, tofacitinib citrate, and the anti-TNF agent is adalimumab or a biosimilar thereof.

(1) Anti-TNF agent; (2) JAK inhibitor orally. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate. In another preferred embodiment, the JAK inhibitor is tofacitinib or a pharmaceutically acceptable salt thereof, or more particularly, tofacitinib citrate, and the anti-TNF agent is adalimumab or a biosimilar thereof.

(1) Anti-TNF agent; (2) JAK inhibitor rectally. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate.

(1) JAK inhibitor; (2) neoregulin-4. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting ofbaricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate.

(1) JAK inhibitor; (2) neoregulin-4 topically, for example, via an ingestible device. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate.

(1) JAK inhibitor; (2) neoregulin-4 systemically. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate. In some embodiments, the JAK inhibitor is administered intravenously. In some embodiments, the JAK inhibitor is administered subcutaneously.

(1) JAK inhibitor; (2) neoregulin-4 administered orally. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate.

(1) JAK inhibitor; (2) neoregulin-4 administered rectally. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate.

(1) Neoregulin-4; (2) JAK inhibitor. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate.

(1) Neoregulin-4; (2) JAK inhibitor topically, for example, via an ingestible device. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate.

(1) Neoregulin-4; (2) JAK inhibitor systemically. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate. In some embodiments, the JAK inhibitor is administered intravenously. In some embodiments, the JAK inhibitor is administered subcutaneously.

(1) Neoregulin-4; (2) JAK inhibitor administered orally. In some embodiments, the JAK inhibitor is selected from the group consisting abrocitinib, baricitinib, BMS-986165, decemotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate.

(1) Neoregulin-4; (2) JAK inhibitor administered rectally. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate.

(1) JAK inhibitor; (2) methotrexate. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate.

(1) JAK inhibitor; (2) methotrexate topically, for example, via an ingestible device. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate.

(1) JAK inhibitor; (2) methotrexate administered systemically. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate.

(1) JAK inhibitor; (2) methotrexate administered orally. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate.

(1) JAK inhibitor; (2) methotrexate administered rectally. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate.

(1) Methotrexate; (2) JAK inhibitor. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate.

(1) Methotrexate; (2) JAK inhibitor topically, for example, via an ingestible device. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate.

(1) Methotrexate; (2) JAK inhibitor administered systemically. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate. In some embodiments, the JAK inhibitor is administered intravenously. In other embodiments, the JAK inhibitor is administered subcutaneously.

(1) Methotrexate; (2) JAK inhibitor administered orally. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate.

(1) Methotrexate; (2) JAK inhibitor administered rectally. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate.

(1) JAK inhibitor; (2) Traficet-EN. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate.

(1) JAK inhibitor; (2) Traficet-EN topically, for example, via an ingestible device. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate.

(1) JAK inhibitor; (2) Traficet-EN administered systemically. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate.

(1) JAK inhibitor; (2) Traficet-EN administered orally. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate.

(1) JAK inhibitor; (2) Traficet-EN administered rectally. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate.

(1) Traficet-EN; (2) JAK inhibitor. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate.

(1) Traficet-EN; (2) JAK inhibitor topically, for example, via an ingestible device. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate.

(1) Traficet-EN; (2) JAK inhibitor administered systemically. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate.

(1) Traficet-EN; (2) JAK inhibitor administered orally. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate.

(1) Traficet-EN; (2) JAK inhibitor administered rectally. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate.

(1) JAK inhibitor; (2) alicaforsen (ISIS 2302). In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate.

(1) JAK inhibitor; (2) alicaforsen (ISIS 2302) topically, for example, via an ingestible device. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting ofbaricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate.

(1) JAK inhibitor; (2) alicaforsen (ISIS 2302) administered systemically. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate.

(1) JAK inhibitor; (2) alicaforsen (ISIS 2302) administered orally. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate.

(1) JAK inhibitor; (2) alicaforsen (ISIS 2302) administered rectally. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate.

(1) Alicaforsen (ISIS 2302); (2) JAK inhibitor. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate.

(1) Alicaforsen (ISIS 2302); (2) JAK inhibitor topically, for example, via an ingestible device. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate.

(1) Alicaforsen (ISIS 2302); (2) JAK inhibitor administered systemically. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate.

(1) Alicaforsen (ISIS 2302); (2) JAK inhibitor administered orally. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate.

(1) Alicaforsen (ISIS 2302); (2) JAK inhibitor administered rectally. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate.

(1) JAK inhibitor; (2) SB012. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate.

(1) JAK inhibitor; (2) SB012 topically, for example, via an ingestible device. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate.

(1) JAK inhibitor; (2) SB012 administered systemically. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate.

(1) JAK inhibitor; (2) SB012 administered orally. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate.

(1) JAK inhibitor; (2) SB012 administered rectally. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate.

(1) SB012; (2) JAK inhibitor. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate.

(1) SB012; (2) JAK inhibitor topically, for example, via an ingestible device. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate.

(1) SB012; (2) JAK inhibitor administered systemically. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate.

(1) SB012; (2) JAK inhibitor administered orally. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate.

(1) SB012; (2) JAK inhibitor administered rectally. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate.

(1) JAK inhibitor; (2) a corticosteroid. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate. In some embodiments, the corticosteroid is selected from the group consisting of prednisone, methylprednisolone, hydrocortisone and budesonide.

(1) JAK inhibitor; (2) a corticosteroid topically, for example, via an ingestible device. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate. In some embodiments, the corticosteroid is selected from the group consisting of prednisone, methylprednisolone, hydrocortisone and budesonide.

(1) JAK inhibitor; (2) a corticosteroid administered systemically. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate. In some embodiments, the corticosteroid is selected from the group consisting of prednisone, methylprednisolone, hydrocortisone and budesonide.

(1) JAK inhibitor; (2) a corticosteroid administered orally. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate. In some embodiments, the corticosteroid is selected from the group consisting of prednisone, methylprednisolone, hydrocortisone and budesonide.

(1) JAK inhibitor; (2) a corticosteroid administered rectally. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate. In some embodiments, the corticosteroid is selected from the group consisting of prednisone, methylprednisolone, hydrocortisone and budesonide.

(1) A corticosteroid; (2) JAK inhibitor. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate. In some embodiments, the corticosteroid is selected from the group consisting of prednisone, methylprednisolone, hydrocortisone and budesonide.

(1) A corticosteroid; (2) JAK inhibitor topically, for example, via an ingestible device. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate. In some embodiments, the corticosteroid is selected from the group consisting of prednisone, methylprednisolone, hydrocortisone and budesonide.

(1) A corticosteroid; (2) JAK inhibitor administered systemically. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate. In some embodiments, the corticosteroid is selected from the group consisting of prednisone, methylprednisolone, hydrocortisone and budesonide.

(1) A corticosteroid; (2) JAK inhibitor administered orally. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate. In some embodiments, the corticosteroid is selected from the group consisting of prednisone, methylprednisolone, hydrocortisone and budesonide.

(1) A corticosteroid; (2) JAK inhibitor administered rectally. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate. In some embodiments, the corticosteroid is selected from the group consisting of prednisone, methylprednisolone, hydrocortisone and budesonide.

(1) JAK inhibitor; (2) an aminosalicylate. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate. In some embodiments, the aminosalicylate is mesalazine.

(1) JAK inhibitor; (2) an aminosalicylate topically, for example, via an ingestible device. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting ofbaricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate. In some embodiments, the aminosalicylate is mesalazine.

(1) JAK inhibitor; (2) an aminosalicylate administered systemically. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate. In some embodiments, the aminosalicylate is mesalazine.

(1) JAK inhibitor; (2) an aminosalicylate administered orally. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate. In some embodiments, the aminosalicylate is mesalazine.

(1) JAK inhibitor; (2) an aminosalicylate administered rectally. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate. In some embodiments, the aminosalicylate is mesalazine.

(1) An aminosalicylate; (2) JAK inhibitor. In some embodiments, the JAK inhibitor is selected from the group consisting abrocitinib, baricitinib, BMS-986165, decemotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate. In some embodiments, the aminosalicylate is mesalazine.

(1) An aminosalicylate; (2) JAK inhibitor topically, for example, via an ingestible device. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting ofbaricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate. In some embodiments, the aminosalicylate is mesalazine.

(1) An aminosalicylate; (2) JAK inhibitor administered systemically. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate. In some embodiments, the aminosalicylate is mesalazine.

(1) An aminosalicylate; (2) JAK inhibitor administered orally. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate. In some embodiments, the aminosalicylate is mesalazine.

(1) An aminosalicylate; (2) JAK inhibitor administered rectally. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate. In some embodiments, the aminosalicylate is mesalazine.

(1) JAK inhibitor; (2) tacrolimus. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate.

(1) JAK inhibitor; (2) tacrolimus topically, for example, via an ingestible device. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate.

(1) JAK inhibitor; (2) tacrolimus administered systemically. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate.

(1) JAK inhibitor; (2) tacrolimus administered orally. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate.

(1) JAK inhibitor; (2) tacrolimus administered rectally. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate.

(1) Tacrolimus; (2) JAK inhibitor. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate.

(1) Tacrolimus; (2) JAK inhibitor topically, for example, via an ingestible device. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate.

(1) Tacrolimus; (2) JAK inhibitor administered systemically. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate.

(1) Tacrolimus; (2) JAK inhibitor administered orally. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate.

(1) Tacrolimus; (2) JAK inhibitor administered rectally. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate.

(1) JAK inhibitor; (2) cyclosporin A. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate.

(1) JAK inhibitor; (2) cyclosporin A topically, for example, via an ingestible device. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate.

(1) JAK inhibitor; (2) cyclosporin A administered systemically. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate.

(1) JAK inhibitor; (2) cyclosporin A administered orally. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate.

(1) JAK inhibitor; (2) cyclosporin A administered rectally. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate.

(1) Cyclosporin A; (2) JAK inhibitor. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate.

(1) Cyclosporin A; (2) JAK inhibitor topically, for example, via an ingestible device. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate.

(1) Cyclosporin A; (2) JAK inhibitor administered systemically. In some embodiments, the JAK inhibitor is selected from the group consisting abrocitinib, baricitinib, BMS-986165, decemotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate.

(1) Cyclosporin A; (2) JAK inhibitor administered orally. In some embodiments, the JAK inhibitor is selected from the group consisting abrocitinib, baricitinib, BMS-986165, decemotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate.

(1) Cyclosporin A; (2) JAK inhibitor administered rectally. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate.

(1) JAK inhibitor; (2) GM-CSF. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate. In some embodiments, the GM-CSF is sargramostim (Leukine®) or molgramostim; or a biosimilar thereof. In some preferred embodiments, the GM-CSF is sargramostim or a biosimilar thereof. In some embodiments, the GM-CSF is administered during maintenance therapy.

(1) JAK inhibitor; (2) GM-CSF topically, for example, via an ingestible device. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate. In some embodiments, the GM-CSF is sargramostim (Leukine®) or molgramostim; or a biosimilar thereof. In some preferred embodiments, the GM-CSF is sargramostim or a biosimilar thereof. In some embodiments, the GM-CSF is administered during maintenance therapy.

(1) JAK inhibitor; (2) GM-CSF administered systemically. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate. In some embodiments, the GM-CSF is sargramostim (Leukine®) or molgramostim; or a biosimilar thereof. In some preferred embodiments, the GM-CSF is sargramostim or a biosimilar thereof. In some embodiments, the GM-CSF is administered during maintenance therapy.

(1) JAK inhibitor; (2) GM-CSF administered orally. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate. In some embodiments, the GM-CSF is sargramostim (Leukine®) or molgramostim; or a biosimilar thereof. In some preferred embodiments, the GM-CSF is sargramostim or a biosimilar thereof. In some embodiments, the GM-CSF is administered during maintenance therapy.

(1) JAK inhibitor; (2) GM-CSF administered rectally. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate. In some embodiments, the GM-CSF is sargramostim (Leukine®) or molgramostim; or a biosimilar thereof. In some preferred embodiments, the GM-CSF is sargramostim or a biosimilar thereof. In some embodiments, the GM-CSF is administered during maintenance therapy.

(1) GM-CSF; (2) JAK inhibitor. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate. In some embodiments, the GM-CSF is sargramostim (Leukine®) or molgramostim; or a biosimilar thereof. In some preferred embodiments, the GM-CSF is sargramostim or a biosimilar thereof. In some embodiments, the GM-CSF is administered during maintenance therapy.

(1) GM-CSF; (2) JAK inhibitor topically, for example, via an ingestible device. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate. In some embodiments, the GM-CSF is sargramostim (Leukine®) or molgramostim; or a biosimilar thereof. In some preferred embodiments, the GM-CSF is sargramostim or a biosimilar thereof. In some embodiments, the GM-CSF is administered during maintenance therapy.

(1) GM-CSF; (2) JAK inhibitor administered systemically. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate. In some embodiments, the GM-CSF is sargramostim (Leukine®) or molgramostim; or a biosimilar thereof. In some preferred embodiments, the GM-CSF is sargramostim or a biosimilar thereof. In some embodiments, the GM-CSF is administered during maintenance therapy.

(1) GM-CSF; (2) JAK inhibitor administered orally. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate. In some embodiments, the GM-CSF is sargramostim (Leukine®) or molgramostim; or a biosimilar thereof. In some preferred embodiments, the GM-CSF is sargramostim or a biosimilar thereof. In some embodiments, the GM-CSF is administered during maintenance therapy.

(1) GM-CSF; (2) JAK inhibitor administered rectally. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate. In some embodiments, the GM-CSF is sargramostim (Leukine®) or molgramostim; or a biosimilar thereof. In some preferred embodiments, the GM-CSF is sargramostim or a biosimilar thereof. In some embodiments, the GM-CSF is administered during maintenance therapy.

(1) JAK inhibitor; (2) cyclosporin A. In some embodiments, the JAK inhibitor is selected from the group consisting abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some more particular embodiments, the JAK inhibitor is selected from the group consisting of baricitinib, filgotinib, upadacitinib, TD-1473, TD-3504 and tofacitinib; and pharmaceutically acceptable salts thereof. In a preferred embodiment, the JAK inhibitor is tofacitinib or a pharmaceutically acceptable salt thereof, even more particularly, tofacitinib citrate. In some embodiments, the GM-CSF is sargramostim (Leukine®) or molgramostim; or a biosimilar thereof. In some preferred embodiments, the GM-CSF is sargramostim or a biosimilar thereof. In some embodiments, the GM-CSF is administered during maintenance therapy.

In some embodiments, the methods disclosed herein comprise administering (i) the JAK inhibitor as disclosed herein, and (ii) a second agent orally, intravenously or subcutaneously, wherein the second agent in (ii) is the same JAK inhibitor in (i); a different JAK inhibitor; or an agent having a different biological target from the JAK inhibitor.

In some embodiments, the methods disclosed herein comprise administering (i) the JAK inhibitor in the manner disclosed herein, and (ii) a second agent orally, intravenously or subcutaneously, wherein the second agent in (ii) is an agent suitable for treating an inflammatory bowel disease.

In some embodiments of the methods that include administering a second or additional agent or component, the additional agent is administered together with the JAK inhibitor in the same ingestible device as the JAK inhibitor. In some embodiments of the methods that include administering a second or additional agent or component, the additional agent is administered separately from the JAK inhibitor in a separate ingestible device from the JAK inhibitor.

In some embodiments, the JAK inhibitor is administered prior to the second agent. In some embodiments, the JAK inhibitor is administered after the second agent. In some embodiments, the JAK inhibitor and the second agent are administered substantially at the same time. In some embodiments, the JAK inhibitor is delivered prior to the second agent. In some embodiments, the JAK inhibitor is delivered after the second agent. In some embodiments, the JAK inhibitor and the second agent are delivered substantially at the same time.

In some embodiments, the second agent is an agent suitable for the treatment of a disease of the gastrointestinal tract. In some embodiments, the second agent is an agent suitable for the treatment of an inflammatory bowel disease. In some embodiments, the second agent is administered intravenously. In some embodiments, the second agent is administered subcutaneously. In some embodiments, the second agent is methotrexate.

In some embodiments, delivery of the JAK inhibitor to the location, such as delivery to the location by mucosal contact, results in systemic immunogenicity levels at or below systemic immunogenicity levels resulting from administration of the JAK inhibitor systemically. In some embodiments comprising administering the JAK inhibitor in the manner disclosed herein and a second agent systemically, delivery of the JAK inhibitor to the location, such as delivery to the location by mucosal contact, results in systemic immunogenicity levels at or below systemic immunogenicity levels resulting from administration of the JAK inhibitor systemically and the second agent systemically. In some embodiments, the method comprises administering the JAK inhibitor in the manner disclosed herein and a second agent, wherein the amount of the second agent is less than the amount of the second agent when the JAK inhibitor and the second agent are both administered systemically. In some aspects of these embodiments, the second agent is a JAK inhibitor.

In some embodiments, the method comprises administering the JAK inhibitor in the manner disclosed herein and does not comprise administering a second agent.

Combination Therapy Methods

JAK Inhibitor via Topical Administration

In some embodiments, provided herein is a method of treating an inflammatory disease or condition of the gastrointestinal (GI) tract of a subject comprising:

topically administering to the GI tract of the subject (i) a JAK inhibitor or (ii) a pharmaceutical formulation that comprises a JAK inhibitor; and administering an additional agent useful for treating the disease or condition of the gastrointestinal tract of the subject;

wherein the topical administration comprises releasing the JAK inhibitor, or the pharmaceutical formulation that comprises the JAK inhibitor, to, or proximal to, a section or subsection of the GI tract containing one or more inflammatory disease sites.

In some further embodiments, the topical administration comprises orally administering to the subject an ingestible device as disclosed herein, said device containing the JAK inhibitor, or the pharmaceutical formulation that comprises the JAK inhibitor; and releasing the JAK inhibitor, or the pharmaceutical formulation that comprises the JAK inhibitor from the ingestible device to, or proximal to, the section or subsection of the GI tract containing the one or more disease sites.

In some embodiments, the inflammatory disease or condition is an inflammatory bowel disease. In some embodiments, the inflammatory bowel disease is ulcerative colitis. In some embodiments, the inflammatory bowel disease is Crohn's disease.

In some embodiments, the section or subsection of the GI tract of the subject containing the one or more disease sites is the duodenum, and the JAK inhibitor or the pharmaceutical formulation that comprises the JAK inhibitor is released to the stomach or the duodenum.

In some embodiments, the section or subsection of the GI tract of the subject containing the one or more disease sites is the jejunum, and the JAK inhibitor, or the pharmaceutical formulation that comprises the JAK inhibitor, is released to the duodenum or the jejunum.

In some embodiments, the section or subsection of the GI tract of the subject containing the one or more disease sites is the ileum, and the JAK inhibitor, or the pharmaceutical formulation that comprises the JAK inhibitor, is released to the jejunum or the ileum.

In some embodiments, the section or subsection of the GI tract of the subject containing the one or more disease sites is the cecum, and the JAK inhibitor, or the pharmaceutical formulation that comprises the JAK inhibitor, is released to the ileum or the cecum.

In some embodiments, the section or subsection of the GI tract of the subject containing the one or more disease sites is the colon, and the JAK inhibitor, or the pharmaceutical formulation that comprises the JAK inhibitor, is released to the cecum or the colon. In some more particular embodiments, the JAK inhibitor, or the pharmaceutical formulation that comprises the JAK inhibitor, is released to the ascending colon.

In some embodiments, the JAK inhibitor is a JAK inhibitor as disclosed herein.

In some embodiments, the JAK inhibitor is selected from the group consisting of abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some embodiments, the JAK inhibitor is tofacitinib or a pharmaceutically acceptable salt thereof. In some embodiments, the JAK inhibitor is tofacitinib citrate.

In some embodiments, the additional agent is administered topically (e.g, via an ingestible device as disclosed herein). In some embodiments, the additional agent is administered by another form of administration. In some further embodiments, the additional agent is administered systemically (such as intervenously, subcutaneously, or orally) or rectally.

In some embodiments, the JAK inhibitor is administered prior to administration of the additional agent. In some embodiments, the additional agent is administered prior to administration of the JAK inhibitor. In some embodiments, the JAK inhibitor and the additional agent are administered simultaneously.

In some embodiments, the additional agent is an aminosalicylate, an immunosuppressant (e.g., a corticosteroid), a PDE4 inhibitor, an S1P modulator, an integrin inhibitor, an anti-TNF agent, an IL-12/IL-23 inhibitor, a GM-CSF or a second JAK inhibitor.

In some embodiments, the JAK inhibitor is administered topically (optionally, via an ingestible device as disclosed herein), and an immunosuppressant is administered. In some embodiments, the immunosuppressant is a corticosteroid, optionally selected from the group consisting of budesonide, dexamethasone, hydrocortisone, methylprednisolone, prednisolone and prednisone; and pharmaceutically acceptable salts thereof. In some embodiments, the immunosuppressant is a cytostatic agent, optionally selected from the group consisting of azathioprine, 6-mercaptopurine and methotrexate; and pharmaceutically acceptable salts thereof. In some embodiments, the immunosuppressant is an mTOR inhibitor, optionally selected from the group consisting of rapamycin, everolimus, dactolisib and temsirolimus; and pharmaceutically acceptable salts thereof. In some embodiments, the immunosuppressant is a calcineurin inhibitor, optionally selected from the group consisting of a cyclosporin (such as cyclosporin A), pimecrolimus, sanglifehrin A, tacrolimus and voclosporin; and pharmaceutically acceptable salts thereof.

In some embodiments, the JAK inhibitor is administered topically (optionally, via an ingestible device as disclosed herein), and a PDE4 inhibitor is administered. In some embodiments, the PDE4 inhibitor is selected from the group consisting of apremilast, crisaborole, ibudilast, roflumilast and tetomilast; and pharmaceutically acceptable salts thereof.

In some embodiments, the JAK inhibitor is administered topically (optionally, via an ingestible device as disclosed herein), and an S1P modulator is administered. In some embodiments, the S1P modulator is selected from the group consisting of fingolimod, KRP203, siponimod, ponesimod, cenerimod, ozanimod, ceralifimod, amiselimod, and etrasimod; and pharmaceutically acceptable salts thereof. In some embodiments, the S1P modulator is ozanimod or pharmaceutically acceptable salt thereof. In other embodiments, the S1P modulator is etrasimod or pharmaceutically acceptable salt thereof. In yet other embodiments, the S1P modulator is amiselimod or pharmaceutically acceptable salt thereof.

In some embodiments, the JAK inhibitor is administered topically (optionally, via an ingestible device as disclosed herein), and an integrin inhibitor is administered. In some embodiments, the integrin inhibitor is an antibody. In a further embodiment, the integrin inhibitor is selected from the group consisting of vedolizumab, natalizumab, etrolizumab, vatelizumab and PF-00547659; and biosimilars thereof. In a preferred embodiment, the integrin inhibitor is vedolizumab or a biosimilar thereof. In other embodiments, the integrin inhibitor is a small molecule integrin inhibitor. In some embodiments, the small molecule integrin inhibitor is firategrast, valategrast, R00270608, CDP-323, CT7758, GW-559090, or ELND-004; or pharmaceutically acceptable salt thereof. In further embodiments, the small molecule integrin inhibitor is a compound as disclosed in US 2005/0209232; U.S. Pat. No. 9,518,091; WO 2005/077914; WO 2005/077915; WO 09/706822; WO 2017/135471; WO 2017/135472; Co et al., Immunotechnol., 4:253-266 (1999); Dubree et al., J. Med. Chem., 45:3451-3457 (2002); Gong et al., J. Med. Chem., 49:3402-3411 (2006); Gong et al., Bioorg. Med. Chem. Lett., 18:1331-1335 (2008); Muz et al., American Society of Hematology Annual Meeting and Exposition, (2014) 56th (December 8) Abs 4758; Sidduri et al., Bioorg. Med. Chem. Lett., 23:1026-1031 (2013); or Xu et al., Bioorg. Med. Chem. Lett., 23:4370-4373 (2013), each of which are incorporated by reference in their entireties; or pharmaceutically acceptable salt thereof. In a preferred embodiment, the small molecule integrin inhibitor is AJM-300, or a pharmaceutically acceptable salt thereof. In another preferred embodiment, the small molecule integrin inhibitor is HCA2969 (carotegrast), or a prodrug thereof; or a pharmaceutically acceptable salt thereof; provided that the prodrug of carotegrast is not AJM300. In another preferred embodiment, the small molecule integrin inhibitor is HCA2969 (carotegrast); or a pharmaceutically acceptable salt thereof. In other embodiments, the integrin inhibitor is a peptide integrin inhibitor. In some embodiments, the peptide integrin inhibitor is PTG-100 or PN-10943 (also known as PN-943).

In some embodiments, the JAK inhibitor is administered topically (optionally, via an ingestible device as disclosed herein), and an anti-TNF agent is administered. In some embodiments, the anti-TNF agent is infliximab, golimumab, certolizumab, certolizumab pegol or etanercept; or a biosimilar thereof. In a preferred embodiment, the anti-TNF agent is adalimumab or a biosimilar thereof.

In some embodiments, the JAK inhibitor, or the pharmaceutical formulation that comprises the JAK inhibitor, is administered topically (optionally, via an ingestible device as disclosed herein), and GM-CSF is administered. In some embodiments, the GM-CSF is sargramostim (Leukine®) or molgramostim; or a biosimilar thereof. In some preferred embodiments, the GM-CSF is sargramostim or a biosimilar thereof. In some embodiments, the GM-CSF is administered during maintenance therapy.

In some embodiments, the JAK inhibitor is administered topically (optionally, via an ingestible device as disclosed herein), and an IL-12/IL-23 inhibitor is administered. In some embodiments, the IL-12/IL-23 inhibitor is selected from the group consisting of ustekinumab, guselkumab, risankizumab, brazikumab and mirikizumab; and biosimilars thereof. In a preferred embodiment, the IL-12/IL-23 inhibitor is ustekinumab or a biosimilar thereof. In some embodiments, the IL-12/IL-23 inhibitor is a peptide inhibitor of the IL-23 receptor, such as a peptide disclosed in U.S. Pat. No. 9,624,268, e.g., Compound A (SEQ ID NO: 276), Compound B (SEQ ID NO: 279), or Compound C (SEQ ID NO: 280); or a pharmaceutically acceptable salt thereof. In some embodiments, the IL-12/IL-23 inhibitor is apilomod mesylate.

In some embodiments, the JAK inhibitor is administered topically (optionally, via an ingestible device as disclosed herein), and a GM-CSF is administered. In some embodiments, the GM-CSF is sargramostim (Leukine®) or molgramostim; or a biosimilar thereof. In some preferred embodiments, the GM-CSF is sargramostim or a biosimilar thereof. In some embodiments, the GM-CSF is administered during maintenance therapy.

In some embodiments, a first JAK inhibitor is administered topically (optionally, via an ingestible device as disclosed herein), and a second JAK inhibitor is administered, wherein the second JAK inhibitor is different from the first JAK inhibitor. In some embodiments, the second JAK inhibitor is a JAK inhibitor as disclosed herein. In some embodiments, the second JAK inhibitor is selected from group consisting of abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof.

In some embodiments, the pharmaceutical formulation comprising the JAK inhibitor is a formulation as disclosed herein. In some embodiments, the additional agent is provided in a formulation as disclosed herein.

JAK Inhibitor Topically Administered via an Ingestible Device

In some more particular embodiments, provided herein is a method of treating an inflammatory disease or condition of the gastrointestinal (GI) tract of a subject, comprising:

topically administering to the GI tract of the subject (i) a JAK inhibitor, or (ii) a pharmaceutical formulation that comprises a JAK inhibitor; and administering an additional agent useful for treating the disease or condition of the GI tract of the subject;

wherein the topical administration comprises orally administering to the subject an ingestible device as disclosed herein, said device containing the JAK inhibitor, or the pharmaceutical formulation that comprises the JAK inhibitor; and releasing the JAK inhibitor, or the pharmaceutical formulation that comprises the JAK inhibitor, from the ingestible device to, or proximal to, a section or subsection of the GI tract containing the one or more inflammatory disease sites.

In some embodiments, the inflammatory disease or condition is an inflammatory bowel disease. In some embodiments, the inflammatory bowel disease is ulcerative colitis. In some embodiments, the inflammatory bowel disease is Crohn's disease.

In some embodiments, the section or subsection of the GI tract of the subject containing the one or more disease sites is the duodenum, and the JAK inhibitor or the pharmaceutical formulation that comprises the JAK inhibitor is released to the stomach or the duodenum.

In some embodiments, the section or subsection of the GI tract of the subject containing the one or more disease sites is the jejunum, and the JAK inhibitor, or the pharmaceutical formulation that comprises the JAK inhibitor, is released to the duodenum or the jejunum.

In some embodiments, the section or subsection of the GI tract of the subject containing the one or more disease sites is the ileum, and the JAK inhibitor, or the pharmaceutical formulation that comprises the JAK inhibitor, is released to the jejunum or the ileum.

In some embodiments, the section or subsection of the GI tract of the subject containing the one or more disease sites is the cecum, and the JAK inhibitor, or the pharmaceutical formulation that comprises the JAK inhibitor, is released to the ileum or the cecum.

In some embodiments, the section or subsection of the GI tract of the subject containing the one or more disease sites is the colon, and the JAK inhibitor, or the pharmaceutical formulation that comprises the JAK inhibitor, is released to the cecum or the colon. In some more particular embodiments, the JAK inhibitor, or the pharmaceutical formulation that comprises the JAK inhibitor, is released to the ascending colon.

In some embodiments, the JAK inhibitor is a JAK inhibitor as disclosed herein.

In some embodiments, the JAK inhibitor is selected from the group consisting of abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some embodiments, the JAK inhibitor is tofacitinib or a pharmaceutically acceptable salt thereof. In some embodiments, the JAK inhibitor is tofacitinib citrate.

In some embodiments, the additional agent is administered topically (e.g., via an ingestible device as disclosed herein). In some embodiments, the additional agent is administered by another form of administration. In some further embodiments, the additional agent is administered systemically (such as intervenously, subcutaneously, or orally) or rectally.

In some embodiments, the JAK inhibitor is administered prior to administration of the additional agent. In some embodiments, the additional agent is administered prior to administration of the JAK inhibitor. In some embodiments, the JAK inhibitor and the additional agent are administered simultaneously.

In some embodiments, the additional agent is an aminosalicylate, an immunosuppressant (e.g., a corticosteroid), a PDE4 inhibitor, an S1P modulator, an integrin inhibitor, an anti-TNF agent, an IL-12/IL-23 inhibitor, or a second JAK integrin inhibitor.

In some embodiments, the JAK inhibitor is administered topically via an ingestible device as disclosed herein, and an immunosuppressant is administered. In some embodiments, the immunosuppressant is a corticosteroid, optionally selected from the group consisting of budesonide, dexamethasone, hydrocortisone, methylprednisolone, prednisolone and prednisone; and pharmaceutically acceptable salts thereof. In some embodiments, the immunosuppressant is a cytostatic agent, optionally selected from the group consisting of azathioprine, 6-mercaptopurine and methotrexate; and pharmaceutically acceptable salts thereof. In some embodiments, the immunosuppressant is an mTOR inhibitor, optionally selected from the group consisting of rapamycin, everolimus, dactolisib and temsirolimus; and pharmaceutically acceptable salts thereof. In some embodiments, the immunosuppressant is a calcineurin inhibitor, optionally selected from the group consisting of a cyclosporin (such as cyclosporin A), pimecrolimus, sanglifehrin A, tacrolimus and voclosporin; and pharmaceutically acceptable salts thereof.

In some embodiments, the JAK inhibitor is administered topically via an ingestible device as disclosed herein, and a PDE4 inhibitor is administered. In some embodiments, the PDE4 inhibitor is selected from the group consisting of apremilast, crisaborole, ibudilast, roflumilast and tetomilast; and pharmaceutically acceptable salts thereof.

In some embodiments, the JAK inhibitor is administered topically via an ingestible device as disclosed herein, and a S1P modulator is administered. In some embodiments, the S1P modulator is selected from the group consisting of fingolimod, KRP203, siponimod, ponesimod, cenerimod, ozanimod, ceralifimod, amiselimod, and etrasimod; and pharmaceutically acceptable salts thereof. In some embodiments, the S1P modulator is ozanimod or pharmaceutically acceptable salt thereof. In other embodiments, the S1P modulator is etrasimod or pharmaceutically acceptable salt thereof. In yet other embodiments, the S1P modulator is amiselimod or pharmaceutically acceptable salt thereof.

In some embodiments, the JAK inhibitor is administered topically via an ingestible device as disclosed herein, and an integrin inhibitor is administered. In some embodiments, the integrin inhibitor is an antibody. In a further embodiment, the integrin inhibitor is selected from the group consisting of vedolizumab, natalizumab, etrolizumab, vatelizumab and PF-00547659; and biosimilars thereof. In a preferred embodiment, the integrin inhibitor is vedolizumab or a biosimilar thereof. In other embodiments, the integrin inhibitor is a small molecule integrin inhibitor. In some embodiments, the small molecule integrin inhibitor is firategrast, valategrast, R00270608, CDP-323, CT7758, GW-559090, or ELND-004; or pharmaceutically acceptable salt thereof. In further embodiments, the small molecule integrin inhibitor is a compound as disclosed in US 2005/0209232; U.S. Pat. No. 9,518,091; WO 2005/077914; WO 2005/077915; WO 09/706822; WO 2017/135471; WO 2017/135472; Co et al., Immunotechnol., 4:253-266 (1999); Dubree et al., J. Med. Chem., 45:3451-3457 (2002); Gong et al., J. Med. Chem., 49:3402-3411 (2006); Gong et al., Bioorg. Med. Chem. Lett., 18:1331-1335 (2008); Muz et al., American Society of Hematology Annual Meeting and Exposition, (2014) 56th (December 8) Abs 4758; Sidduri et al., Bioorg. Med. Chem. Lett., 23:1026-1031 (2013); or Xu et al., Bioorg. Med. Chem. Lett., 23:4370-4373 (2013), each of which are incorporated by reference in their entireties; or pharmaceutically acceptable salt thereof. In a preferred embodiment, the small molecule integrin inhibitor is AJM-300, or a pharmaceutically acceptable salt thereof. In another preferred embodiment, the small molecule integrin inhibitor is HCA2969 (carotegrast), or a prodrug thereof; or a pharmaceutically acceptable salt thereof; provided that the prodrug of carotegrast is not AJM300. In another preferred embodiment, the small molecule integrin inhibitor is HCA2969 (carotegrast); or a pharmaceutically acceptable salt thereof. In other embodiments, the integrin inhibitor is a peptide integrin inhibitor. In some embodiments, the peptide integrin inhibitor is PTG-100 or PN-10943 (also known as PN-943).

In some embodiments, the JAK inhibitor is administered topically via an ingestible device as disclosed herein, and an anti-TNF agent is administered. In some embodiments, the anti-TNF agent is infliximab, golimumab, certolizumab, certolizumab pegol or etanercept; or a biosimilar thereof. In a preferred embodiment, the anti-TNF agent is adalimumab or a biosimilar thereof.

In some embodiments, the JAK inhibitor is administered topically via an ingestible device as disclosed herein, and an IL-12/IL-23 inhibitor is administered. In some embodiments, the IL-12/IL-23 inhibitor is selected from the group consisting of ustekinumab, guselkumab, risankizumab, brazikumab and mirikizumab; and biosimilars thereof. In a preferred embodiment, the IL-12/IL-23 inhibitor is ustekinumab or a biosimilar thereof. In some embodiments, the IL-12/IL-23 inhibitor is a peptide inhibitor of the IL-23 receptor, such as a peptide disclosed in U.S. Pat. No. 9,624,268, e.g., Compound A (SEQ ID NO: 276), Compound B (SEQ ID NO: 279), or Compound C (SEQ ID NO: 280); or a pharmaceutically acceptable salt thereof. In some embodiments, the IL-12/IL-23 inhibitor is apilomod mesylate.

In some embodiments, the JAK inhibitor is administered topically via an ingestible device as disclosed herein, and a GM-CSF is administered. In some embodiments, the GM-CSF is sargramostim (Leukine®) or molgramostim; or a biosimilar thereof. In some preferred embodiments, the GM-CSF is sargramostim or a biosimilar thereof. In some embodiments, the GM-CSF is administered during maintenance therapy.

In some embodiments, a first JAK inhibitor is administered topically via an ingestible device as disclosed herein, and a second JAK inhibitor is administered, wherein the second JAK inhibitor is different from the first JAK inhibitor. In some embodiments, the second JAK inhibitor is a JAK inhibitor as disclosed herein. In some embodiments, the second JAK inhibitor is selected from the group consisting of abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof.

In some embodiments, the pharmaceutical formulation comprising the JAK inhibitor is a formulation as disclosed herein. In some embodiments, the additional agent is provided in a formulation as disclosed herein.

JAK Inhibitor Plus Additional Agent via Ingestible Device

In some other embodiments, a method of treating an inflammatory disease or condition of the gastrointestinal (GI) tract of a subject comprises:

- administering to the subject a JAK inhibitor;
- orally administering to the subject an ingestible device comprising (i) an additional agent or (ii) a pharmaceutical formulation that comprises an additional agent, wherein the additional agent is useful for treating a disease or condition of the GI tract of a subject; and
- releasing the additional agent, or the pharmaceutical formulation that comprises the additional agent, from the ingestible device to, or proximal to, a section or subsection of the GI tract containing one or more inflammatory disease sites.

In some embodiments, the inflammatory disease or condition is an inflammatory bowel disease. In some embodiments, the inflammatory bowel disease is ulcerative colitis. In some embodiments, the inflammatory bowel disease is Crohn's disease.

In some embodiments, the section or subsection of the GI tract of the subject containing the one or more disease sites is the duodenum, and the additional agent or the pharmaceutical formulation that comprises the additional agent is released to the stomach or the duodenum.

In some embodiments, the section or subsection of the GI tract of the subject containing the one or more disease sites is the jejunum, and the additional agent, or the pharmaceutical formulation that comprises the additional agent, is released to the duodenum or the jejunum.

In some embodiments, the section or subsection of the GI tract of the subject containing the one or more disease sites is the ileum, and the additional agent, or the pharmaceutical formulation that comprises the additional agent, is released to the jejunum or the ileum.

In some embodiments, the section or subsection of the GI tract of the subject containing the one or more disease sites is the cecum, and the additional agent, or the pharmaceutical formulation that comprises the additional agent, is released to the ileum or the cecum.

In some embodiments, the section or subsection of the GI tract of the subject containing the one or more disease sites is the colon, and the additional agent, or the pharmaceutical formulation that comprises the additional agent, is released to the cecum or the colon. In some more particular embodiments, the additional agent, or the pharmaceutical formulation that comprises the additional agent, is released to the ascending colon.

In some embodiments, the JAK inhibitor is a JAK inhibitor as disclosed herein.

In some embodiments, the JAK inhibitor is selected from the group consisting of abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof. In some embodiments, the JAK inhibitor is tofacitinib or a pharmaceutically acceptable salt thereof. In some embodiments, the JAK inhibitor is tofacitinib citrate.

In some embodiments, the JAK inhibitor is administered in an ingestible device. In some embodiments, the JAK inhibitor is administered by another form of administration. In some further embodiments, the JAK inhibitor is administered systemically (such as intravenously, subcutaneously, or orally) or rectally.

In some embodiments, the JAK inhibitor is administered prior to administration of the additional agent. In some embodiments, the additional agent is administered prior to administration of the JAK inhibitor. In some embodiments, the JAK inhibitor and the additional agent are administered simultaneously.

In some embodiments, the additional agent is an aminosalicylate, an immunosuppressant (e.g., a corticosteroid), a PDE4 inhibitor, an S1P modulator, an integrin inhibitor, an anti-TNF agent, an IL-12/IL-23 inhibitor, a GM-CSF or a second JAK inhibitor.

In some embodiments, the additional agent is an immunosuppressant. In some embodiments, the immunosuppressant is a corticosteroid, optionally selected from the group consisting of budesonide, dexamethasone, hydrocortisone, methylprednisolone, prednisolone and prednisone; and pharmaceutically acceptable salts thereof. In some embodiments, the immunosuppressant is a cytostatic agent, optionally selected from the group consisting of azathioprine, 6-mercaptopurine and methotrexate; and pharmaceutically acceptable salts thereof. In some embodiments, the immunosuppressant is an mTOR inhibitor, optionally selected from the group consisting of rapamycin, everolimus, dactolisib and temsirolimus; and pharmaceutically acceptable salts thereof. In some embodiments, the immunosuppressant is a calcineurin inhibitor, optionally selected from the group consisting of a cyclosporin (such as cyclosporin A), pimecrolimus, sanglifehrin A, tacrolimus and voclosporin; and pharmaceutically acceptable salts thereof.

In some embodiments, the additional agent is a PDE4 inhibitor selected from the group consisting of apremilast, crisaborole, ibudilast, roflumilast and tetomilast; and pharmaceutically acceptable salts thereof.

In some embodiments, the additional agent is an S1P modulator selected from the group consisting of fingolimod, KRP203, siponimod, ponesimod, cenerimod, ozanimod, ceralifimod, amiselimod, and etrasimod; and pharmaceutically acceptable salts thereof. In some embodiments, the S1P modulator is ozanimod or a pharmaceutically acceptable salt thereof. In other embodiments, the S1P modulator is etrasimod or a pharmaceutically acceptable salt thereof. In yet other embodiments, the S1P modulator is amiselimod or a pharmaceutically acceptable salt thereof.

In some embodiments, the additional agent is an integrin inhibitor. In some embodiments, the integrin inhibitor is an antibody. In a further embodiment, the integrin inhibitor is selected from the group consisting of vedolizumab, natalizumab, etrolizumab, vatelizumab and PF-00547659; and biosimilars thereof. In a preferred embodiment, the integrin inhibitor is vedolizumab or a biosimilar thereof. In other embodiments, the integrin inhibitor is a small molecule integrin inhibitor. In some embodiments, the small molecule integrin inhibitor is firategrast, valategrast, R00270608, CDP-323, CT7758, GW-559090, or ELND-004; or pharmaceutically acceptable salt thereof. In further embodiments, the small molecule integrin inhibitor is a compound as disclosed in US 2005/0209232; U.S. Pat. No. 9,518,091; WO 2005/077914; WO 2005/077915; WO 09/706822; WO 2017/135471; WO 2017/135472; Co et al., Immunotechnol., 4:253-266 (1999); Dubree et al., J. Med. Chem., 45:3451-3457 (2002); Gong et al., J. Med. Chem., 49:3402-3411 (2006); Gong et al., Bioorg. Med. Chem. Lett., 18:1331-1335 (2008); Muz et al., American Society of Hematology Annual Meeting and Exposition, (2014) 56th (December 8) Abs 4758; Sidduri et al., Bioorg. Med. Chem. Lett., 23:1026-1031 (2013); or Xu et al., Bioorg. Med. Chem. Lett., 23:4370-4373 (2013), each of which are incorporated by reference in their entireties; or pharmaceutically acceptable salt thereof. In a preferred embodiment, the small molecule integrin inhibitor is AJM-300, or a pharmaceutically acceptable salt thereof. In another preferred embodiment, the small molecule integrin inhibitor is HCA2969 (carotegrast), or a prodrug thereof; or a pharmaceutically acceptable salt thereof; provided that the prodrug of carotegrast is not AJM300. In another preferred embodiment, the small molecule integrin inhibitor is HCA2969 (carotegrast); or a pharmaceutically acceptable salt thereof. In other embodiments, the integrin inhibitor is a peptide integrin inhibitor. In some embodiments, the peptide integrin inhibitor is PTG-100 or PN-10943 (also known as PN-943).

In some embodiments, the additional agent is an anti-TNF agent selected from the group consisting of infliximab, golimumab, certolizumab, certolizumab pegol and etanercept; and biosimilars thereof. In a preferred embodiment, the anti-TNF agent is adalimumab or a biosimilar thereof.

In some embodiments, the additional agent is an IL-12/IL-23 inhibitor selected from the group consisting of ustekinumab, guselkumab, risankizumab, brazikumab and mirikizumab; and biosimilars thereof. In a preferred embodiment, the IL-12/IL-23 inhibitor is ustekinumab or a biosimilar thereof. In some embodiments, the IL-12/IL-23 inhibitor is a peptide inhibitor of the IL-23 receptor, such as a peptide disclosed in U.S. Pat. No. 9,624,268, e.g., Compound A (SEQ ID NO: 276), Compound B (SEQ ID NO: 279), or Compound C (SEQ ID NO: 280); or a pharmaceutically acceptable salt thereof. In some embodiments, the IL-12/IL-23 inhibitor is apilomod mesylate.

In some embodiments, the additional agent is a GM-CSF. In some embodiments, the GM-CSF is sargramostim (Leukine®) or molgramostim; or a biosimilar thereof. In some preferred embodiments, the GM-CSF is sargramostim or a biosimilar thereof. In some embodiments, the GM-CSF is administered during maintenance therapy.

In some embodiments, the additional agent is a second JAK inhibitor, wherein the second JAK inhibitor is different from the first JAK inhibitor. In some embodiments, the second JAK inhibitor is a JAK inhibitor as disclosed herein. In some embodiments, the second JAK inhibitor is selected from group consisting of abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, tofacitinib and upadacitinib; and pharmaceutically acceptable salts thereof.

In some embodiments, the pharmaceutical formulation comprising the JAK inhibitor is a formulation as disclosed herein. In some embodiments, the additional agent is provided in a formulation as disclosed herein.

Tofacitinib Topically Administered Plus Additional Agent

In some more particular embodiments, provided herein is a method of treating an inflammatory disease or condition of the gastrointestinal (GI) tract of a subject comprising:

topically administering to the GI tract of the subject (i) tofacitinib or a pharmaceutically acceptable salt thereof (e.g., tofacitinib citrate), or (ii) a pharmaceutical formulation that comprises tofacitinib or a pharmaceutically acceptable salt thereof (e.g., tofacitinib citrate); and administering an additional agent useful for treating the disease or condition of the GI tract of the subject;

wherein the topical administration comprises releasing the tofacitinib or pharmaceutically acceptable salt thereof (e.g., tofacitinib citrate), or the pharmaceutical formulation that comprises the tofacitinib or pharmaceutically acceptable salt thereof (e.g., tofacitinib citrate), to, or proximal to, a section or subsection of the GI tract containing one or more inflammatory disease sites.

In some further embodiments, the topical administration further comprises orally administering to the subject an ingestible device as disclosed herein, said device containing the tofacitinib or pharmaceutically acceptable salt thereof (e.g., tofacitinib citrate), or the pharmaceutical formulation that comprises the tofacitinib or pharmaceutically acceptable salt thereof (e.g., tofacitinib citrate); and releasing the tofacitinib or pharmaceutically acceptable salt thereof (e.g., tofacitinib citrate), or the pharmaceutical formulation that comprises the tofacitinib or pharmaceutically acceptable salt thereof (e.g., tofacitinib citrate), from the ingestible device to, or proximal to, the section or subsection of the GI tract containing the one or more disease sites.

In some embodiments, the inflammatory disease or condition is an inflammatory bowel disease. In some embodiments, the inflammatory bowel disease is ulcerative colitis. In some embodiments, the inflammatory bowel disease is Crohn's disease.

In some embodiments, the section or subsection of the GI tract of the subject containing the one or more disease sites is the duodenum, and the tofacitinib or pharmaceutically acceptable salt thereof (e.g., tofacitinib citrate), or the pharmaceutical formulation that comprises the tofacitinib or pharmaceutically acceptable salt thereof (e.g., tofacitinib citrate), is released to the stomach or the duodenum.

In some embodiments, the section or subsection of the GI tract of the subject containing the one or more disease sites is the jejunum, and the tofacitinib or pharmaceutically acceptable salt thereof (e.g., tofacitinib citrate), or the pharmaceutical formulation that comprises the tofacitinib or pharmaceutically acceptable salt thereof (e.g., tofacitinib citrate), is released to the duodenum or the jejunum.

In some embodiments, the section or subsection of the GI tract of the subject containing the one or more disease sites is the ileum, and tofacitinib or pharmaceutically acceptable salt thereof (e.g., tofacitinib citrate), or the pharmaceutical formulation that comprises the tofacitinib or pharmaceutically acceptable salt thereof (e.g., tofacitinib citrate), is released to the jejunum or the ileum.

In some embodiments, the section or subsection of the GI tract of the subject containing the one or more disease sites is the cecum, and the tofacitinib or pharmaceutically acceptable salt thereof (e.g., tofacitinib citrate), or the pharmaceutical formulation that comprises the tofacitinib or pharmaceutically acceptable salt thereof (e.g., tofacitinib citrate), is released to the ileum or the cecum.

In some embodiments, the section or subsection of the GI tract of the subject containing the one or more disease sites is the colon, and the tofacitinib or pharmaceutically acceptable salt thereof (e.g., tofacitinib citrate), or the pharmaceutical formulation that comprises the tofacitinib or pharmaceutically acceptable salt thereof (e.g., tofacitinib citrate), is released to the cecum or the colon. In some more particular embodiments, the tofacitinib or pharmaceutically acceptable salt thereof (e.g., tofacitinib citrate), or the pharmaceutical formulation that comprises the tofacitinib or pharmaceutically acceptable salt thereof (e.g., tofacitinib citrate), is released to the ascending colon.

In some embodiments, the additional agent is administered topically (e.g., via an ingestible device as disclosed herein). In some embodiments, the additional agent is administered by another form of administration. In some further embodiments, the additional agent is administered systemically (such as intervenously, subcutaneously, or orally) or rectally.

In some embodiments, the tofacitinib or pharmaceutically acceptable salt thereof (e.g., tofacitinib citrate), or the pharmaceutical formulation that comprises the tofacitinib or pharmaceutically acceptable salt thereof (e.g., tofacitinib citrate), is administered prior to administration of the additional agent. In some embodiments, the additional agent is administered prior to administration of the tofacitinib or pharmaceutically acceptable salt thereof (e.g., tofacitinib citrate), or the pharmaceutical formulation that comprises the tofacitinib or pharmaceutically acceptable salt thereof (e.g., tofacitinib citrate). In some embodiments, the tofacitinib or pharmaceutically acceptable salt thereof (e.g., tofacitinib citrate), or the pharmaceutical formulation that comprises the tofacitinib or pharmaceutically acceptable salt thereof (e.g., tofacitinib citrate), and the additional agent are administered simultaneously.

In some embodiments, the additional agent an aminosalicylate, an immunosuppressant (e.g., a corticosteroid), a PDE4 inhibitor, an S1P modulator, an integrin inhibitor, an anti-TNF agent, an IL-12/IL-23 inhibitor, a GM-CSF or a second JAK inhibitor.

In some embodiments, the tofacitinib or pharmaceutically acceptable salt thereof (e.g., tofacitinib citrate) is administered topically (optionally, via an ingestible device as disclosed herein), and an immunosuppressant is administered. In some embodiments, the immunosuppressant is a corticosteroid, optionally selected from the group consisting of budesonide, dexamethasone, hydrocortisone, methylprednisolone, prednisolone and prednisone; and pharmaceutically acceptable salts thereof. In some embodiments, the immunosuppressant is a cytostatic agent, optionally selected from the group consisting of azathioprine, 6-mercaptopurine and methotrexate; and pharmaceutically acceptable salts thereof. In some embodiments, the immunosuppressant is an mTOR inhibitor, optionally selected from the group consisting of rapamycin, everolimus, dactolisib and temsirolimus; and pharmaceutically acceptable salts thereof. In some embodiments, the immunosuppressant is a calcineurin inhibitor, optionally selected from the group consisting of a cyclosporin (such as cyclosporin A), pimecrolimus, sanglifehrin A, tacrolimus and voclosporin; and pharmaceutically acceptable salts thereof.

In some embodiments, the tofacitinib or pharmaceutically acceptable salt thereof (e.g., tofacitinib citrate), or the pharmaceutical formulation that comprises the tofacitinib or pharmaceutically acceptable salt thereof (e.g., tofacitinib citrate), is administered topically (optionally, via an ingestible device as disclosed herein), and a PDE4 inhibitor is administered. In some embodiments, the PDE4 inhibitor is selected from the group consisting of apremilast, crisaborole, ibudilast, roflumilast and tetomilast; and pharmaceutically acceptable salts thereof.

In some embodiments, the tofacitinib or pharmaceutically acceptable salt thereof (e.g., tofacitinib citrate), or the pharmaceutical formulation that comprises the tofacitinib or pharmaceutically acceptable salt thereof (e.g., tofacitinib citrate), is administered topically (optionally, via an ingestible device as disclosed herein), and a S1P modulator is administered. In some embodiments, the S1P modulator is selected from the group consisting of fingolimod, KRP203, siponimod, ponesimod, cenerimod, ozanimod, ceralifimod, amiselimod, and etrasimod; and pharmaceutically acceptable salts thereof. In some embodiments, the S1P modulator is ozanimod or pharmaceutically acceptable salt thereof. In other embodiments, the S1P modulator is etrasimod or pharmaceutically acceptable salt thereof. In yet other embodiments, the S1P modulator is amiselimod or pharmaceutically acceptable salt thereof.

In some embodiments, the tofacitinib or pharmaceutically acceptable salt thereof (e.g., tofacitinib citrate), or the pharmaceutical formulation that comprises the tofacitinib or pharmaceutically acceptable salt thereof (e.g., tofacitinib citrate), is administered topically (optionally, via an ingestible device as disclosed herein), and an integrin inhibitor is administered. In some embodiments, the integrin inhibitor is an antibody. In a further embodiment, the integrin inhibitor is selected from the group consisting of vedolizumab, natalizumab, etrolizumab, vatelizumab and PF-00547659; and biosimilars thereof. In a preferred embodiment, the integrin inhibitor is vedolizumab or a biosimilar thereof. In some particularly preferred embodiments, the tofacitinib or the pharmaceutically acceptable salt thereof, such as tofacitinib citrate, is administered topically (optionally, via an ingestible device as disclosed herein), and vedolizumab or biosimilar thereof is administered systemically. In some embodiments, the vedolizumab or biosimilar thereof is administered intravenously. In some embodiments, the vedolizumab or biosimilar thereof is administered subcutaneously. In other embodiments, the integrin inhibitor is a small molecule integrin inhibitor. In some embodiments, the small molecule integrin inhibitor is firategrast, valategrast, R00270608, CDP-323, CT7758, GW-559090, or ELND-004; or pharmaceutically acceptable salt thereof. In further embodiments, the small molecule integrin inhibitor is a compound as disclosed in US 2005/0209232; U.S. Pat. No. 9,518,091; WO 2005/077914; WO 2005/077915; WO 09/706822; WO 2017/135471; WO 2017/135472; Co et al., Immunotechnol., 4:253-266 (1999); Dubree et al., J. Med. Chem., 45:3451-3457 (2002); Gong et al., J. Med. Chem., 49:3402-3411 (2006); Gong et al., Bioorg. Med. Chem. Lett., 18:1331-1335 (2008); Muz et al., American Society of Hematology Annual Meeting and Exposition, (2014) 56th (December 8) Abs 4758; Sidduri et al., Bioorg. Med. Chem. Lett., 23:1026-1031 (2013); or Xu et al., Bioorg. Med. Chem. Lett., 23:4370-4373 (2013), each of which are incorporated by reference in their entireties; or pharmaceutically acceptable salt thereof. In a preferred embodiment, the small molecule integrin inhibitor is AJM-300, or a pharmaceutically acceptable salt thereof. In another preferred embodiment, the small molecule integrin inhibitor is HCA2969 (carotegrast), or a prodrug thereof; or a pharmaceutically acceptable salt thereof; provided that the prodrug of carotegrast is not AJM300. In another preferred embodiment, the small molecule integrin inhibitor is HCA2969 (carotegrast); or a pharmaceutically acceptable salt thereof. In other embodiments, the integrin inhibitor is a peptide integrin inhibitor. In some embodiments, the peptide integrin inhibitor is PTG-100 or PN-10943 (also known as PN-943).

In some embodiments, the tofacitinib or pharmaceutically acceptable salt thereof (e.g., tofacitinib citrate), or the pharmaceutical formulation that comprises the tofacitinib or pharmaceutically acceptable salt thereof (e.g., tofacitinib citrate), is administered topically (optionally, via an ingestible device as disclosed herein), and an anti-TNF agent is administered. In some embodiments, the anti-TNF agent is infliximab, golimumab, certolizumab, certolizumab pegol or etanercept; or a biosimilar thereof. In a preferred embodiment, the anti-TNF agent is adalimumab or a biosimilar thereof. In a particularly preferred embodiment, the tofacitinib or the pharmaceutically acceptable salt thereof, such as tofacitinib citrate, is administered topically (optionally, via an ingestible device as disclosed herein), and adalimumab or biosimilar thereof is administered systemically. In some embodiments, the adalimumab or biosimilar thereof is administered intravenously. In some embodiments, the adalimumab or biosimilar thereof is administered subcutaneously. In another particularly preferred embodiment, the tofacitinib or the pharmaceutically acceptable salt thereof, such as tofacitinib citrate, is administered topically (optionally, via an ingestible device as disclosed herein), and adalimumab or biosimilar thereof is administered topically (optionally, via an ingestible device as disclosed herein).

In some embodiments, the tofacitinib or pharmaceutically acceptable salt thereof (e.g., tofacitinib citrate), or the pharmaceutical formulation that comprises the tofacitinib or pharmaceutically acceptable salt thereof (e.g., tofacitinib citrate), is administered topically (optionally, via an ingestible device as disclosed herein), and an IL-12/IL-23 inhibitor is administered. In some embodiments, the IL-12/IL-23 inhibitor is selected from the group consisting of ustekinumab, guselkumab, risankizumab, brazikumab and mirikizumab; and biosimilars thereof. In a preferred embodiment, the IL-12/IL-23 inhibitor is ustekinumab or a biosimilar thereof. In some embodiments, the IL-12/IL-23 inhibitor is a peptide inhibitor of the IL-23 receptor, such as a peptide disclosed in U.S. Pat. No. 9,624,268, e.g., Compound A (SEQ ID NO: 276), Compound B (SEQ ID NO: 279), or Compound C (SEQ ID NO: 280); or a pharmaceutically acceptable salt thereof. In some embodiments, the IL-12/IL-23 inhibitor is apilomod mesylate.

In some embodiments, the tofacitinib or pharmaceutically acceptable salt thereof (e.g., tofacitinib citrate), or the pharmaceutical formulation that comprises the tofacitinib or pharmaceutically acceptable salt thereof (e.g., tofacitinib citrate), is administered topically (optionally, via an ingestible device as disclosed herein), and a GM-CSF is administered. In some embodiments, the GM-CSF is sargramostim (Leukine®) or molgramostim; or a biosimilar thereof. In some preferred embodiments, the GM-CSF is sargramostim or a biosimilar thereof. In some embodiments, the GM-CSF is administered during maintenance therapy.

In some embodiments, the tofacitinib or pharmaceutically acceptable salt thereof (e.g., tofacitinib citrate), or the pharmaceutical formulation that comprises the tofacitinib or pharmaceutically acceptable salt thereof (e.g., tofacitinib citrate), is administered topically (optionally, via an ingestible device as disclosed herein), and a second JAK inhibitor is administered, wherein the second JAK inhibitor is not tofacitinib or pharmaceutically acceptable salt thereof (e.g., tofacitinib citrate). In some embodiments, the second JAK inhibitor is a JAK inhibitor as disclosed herein. In some embodiments, the second JAK inhibitor is selected from the group consisting of abrocitinib, baricitinib, BMS-986165, decernotinib (VX509), filgotinib, itacitinib, oclacitinib, peficitinib, PF-06651600, PF-06700841, R333 (R932333), R348 (R932348), ruxolitinib, solcitinib, TD-1473, TD-3504, and upadacitinib; and pharmaceutically acceptable salts thereof.

In some embodiments, the pharmaceutical formulation comprising the JAK inhibitor is a formulation as disclosed herein. In some embodiments, the additional agent is provided in a formulation as disclosed herein.

Tofacitinib Topically Administered via an Ingestible Device Plus Additional Agent In some more particular embodiments, provided herein is a method of treating an inflammatory disease or condition of the gastrointestinal (GI) tract of a subject, comprising:

- topically administering to the GI tract of the subject tofacitinib or a pharmaceutically acceptable salt thereof (e.g., tofacitinib citrate), or a pharmaceutical formulation that comprises tofacitinib or a pharmaceutically acceptable salt thereof (e.g., tofacitinib citrate); and
- administering an additional agent useful for treating the disease or condition of the GI tract of the subject;
- wherein the topical administration comprises orally administering to the subject an ingestible device as disclosed herein, said device containing the tofacitinib or pharmaceutically acceptable salt thereof (e.g., tofacitinib citrate), or the pharmaceutical formulation that comprises the tofacitinib or pharmaceutically acceptable salt thereof (e.g., tofacitinib citrate); and releasing the tofacitinib or pharmaceutically acceptable salt thereof (e.g., tofacitinib citrate), or the pharmaceutical formulation that comprises the tofacitinib or pharmaceutically acceptable salt thereof (e.g., tofacitinib citrate), from the ingestible device to, or proximal to, a section or subsection of the GI tract containing the one or more inflammatory disease sites.

In some embodiments, the inflammatory disease or condition is an inflammatory bowel disease. In some embodiments, the inflammatory bowel disease is ulcerative colitis. In some embodiments, the inflammatory bowel disease is Crohn's disease.

In some embodiments, the section or subsection of the GI tract of the subject containing the one or more disease sites is the duodenum, and the tofacitinib or pharmaceutically acceptable salt thereof (e.g., tofacitinib citrate), or the pharmaceutical formulation that comprises the tofacitinib or pharmaceutically acceptable salt thereof (e.g., tofacitinib citrate), is released to the stomach or the duodenum.

In some embodiments, the section or subsection of the GI tract of the subject containing the one or more disease sites is the jejunum, and the tofacitinib or pharmaceutically acceptable salt thereof (e.g., tofacitinib citrate), or the pharmaceutical formulation that comprises the tofacitinib or pharmaceutically acceptable salt thereof (e.g., tofacitinib citrate), is released to the duodenum or the jejunum.

In some embodiments, the section or subsection of the GI tract of the subject containing the one or more disease sites is the ileum, and the tofacitinib or pharmaceutically acceptable salt thereof (e.g., tofacitinib citrate), or the pharmaceutical formulation that comprises the tofacitinib or pharmaceutically acceptable salt thereof (e.g., tofacitinib citrate), is released to the jejunum or the ileum.

In some embodiments, the section or subsection of the GI tract of the subject containing the one or more disease sites is the cecum, and the tofacitinib or pharmaceutically acceptable salt thereof (e.g., tofacitinib citrate), or the pharmaceutical formulation that comprises the tofacitinib or pharmaceutically acceptable salt thereof (e.g., tofacitinib citrate), is released to the ileum or the cecum.

In some embodiments, the section or subsection of the GI tract of the subject containing the one or more disease sites is the colon, and the tofacitinib or pharmaceutically acceptable salt thereof (e.g., tofacitinib citrate), or the pharmaceutical formulation that comprises the tofacitinib or pharmaceutically acceptable salt thereof (e.g., tofacitinib citrate), is released to the cecum or the colon. In some more particular embodiments, the tofacitinib or pharmaceutically acceptable salt thereof (e.g., tofacitinib citrate), or the pharmaceutical formulation that comprises the tofacitinib or pharmaceutically acceptable salt thereof (e.g., tofacitinib citrate), is released to the ascending colon.

In some embodiments, the additional agent is administered topically (e.g., via an ingestible device as disclosed herein). In some embodiments, the additional agent is administered by another form of administration. In some further embodiments, the additional agent is administered systemically (such as intravenously, subcutaneously, or orally) or rectally.

In some embodiments, the tofacitinib or pharmaceutically acceptable salt thereof (e.g., tofacitinib citrate), or the pharmaceutical formulation that comprises the tofacitinib or pharmaceutically acceptable salt thereof (e.g., tofacitinib citrate), is administered prior to administration of the additional agent. In some embodiments, the additional agent is administered prior to administration of the tofacitinib or pharmaceutically acceptable salt thereof (e.g., tofacitinib citrate), or the pharmaceutical formulation that comprises the tofacitinib or pharmaceutically acceptable salt thereof (e.g., tofacitinib citrate). In some embodiments, the tofacitinib or pharmaceutically acceptable salt thereof (e.g., tofacitinib citrate), or the pharmaceutical formulation that comprises the tofacitinib or pharmaceutically acceptable salt thereof (e.g., tofacitinib citrate), and the additional agent are administered simultaneously.

In some embodiments, the additional agent is an aminosalicylate, an immunosuppressant (e.g., a corticosteroid), a PDE4 inhibitor, an S1P modulator, an integrin inhibitor, an anti-TNF agent, an IL-12/IL-23 inhibitor a GM-CSF or a second JAK inhibitor.

In some embodiments, the tofacitinib or pharmaceutically acceptable salt thereof (e.g., tofacitinib citrate)f, or the pharmaceutical formulation that comprises the tofacitinib or pharmaceutically acceptable salt thereof (e.g., tofacitinib citrate), is administered topically via an ingestible device as disclosed herein, and an immunosuppressant is administered. In some embodiments, the immunosuppressant is a corticosteroid, optionally selected from the group consisting of budesonide, dexamethasone, hydrocortisone, methylprednisolone, prednisolone and prednisone; and pharmaceutically acceptable salts thereof. In some embodiments, the immunosuppressant is a cytostatic agent, optionally selected from the group consisting of azathioprine, 6-mercaptopurine and methotrexate; and pharmaceutically acceptable salts thereof. In some embodiments, the immunosuppressant is an mTOR inhibitor, optionally selected from the group consisting of rapamycin, everolimus, dactolisib and temsirolimus; and pharmaceutically acceptable salts thereof. In some embodiments, the immunosuppressant is a calcineurin inhibitor, optionally selected from the group consisting of a cyclosporin (such as cyclosporin A), pimecrolimus, sanglifehrin A, tacrolimus and voclosporin; and pharmaceutically acceptable salts thereof.

In some embodiments, the tofacitinib or pharmaceutically acceptable salt thereof (e.g., tofacitinib citrate), or the pharmaceutical formulation that comprises the tofacitinib or pharmaceutically acceptable salt thereof (e.g., tofacitinib citrate), is administered topically via an ingestible device as disclosed herein, and a PDE4 inhibitor is administered. In some embodiments, the PDE4 inhibitor is selected from the group consisting of apremilast, crisaborole, ibudilast, roflumilast and tetomilast; and pharmaceutically acceptable salts thereof.

In some embodiments, the tofacitinib or pharmaceutically acceptable salt thereof (e.g., tofacitinib citrate), or the pharmaceutical formulation that comprises the tofacitinib or pharmaceutically acceptable salt thereof (e.g., tofacitinib citrate), is administered topically via an ingestible device as disclosed herein, and a S1P modulator is administered. In some embodiments, the S1P modulator is selected from the group consisting of fingolimod, KRP203, siponimod, ponesimod, cenerimod, ozanimod, ceralifimod, amiselimod, and etrasimod. In some embodiments, the S1P modulator is ozanimod. In other embodiments, the S1P modulator is etrasimod. In yet other embodiments, the S1P modulator is amiselimod.

In some embodiments, the tofacitinib or pharmaceutically acceptable salt thereof (e.g., tofacitinib citrate), or the pharmaceutical formulation that comprises the tofacitinib or pharmaceutically acceptable salt thereof (e.g., tofacitinib citrate), is administered topically via an ingestible device as disclosed herein, and an integrin inhibitor is administered. In some embodiments, the integrin inhibitor is an antibody. In a further embodiment, the integrin inhibitor is selected from the group consisting of vedolizumab, natalizumab, etrolizumab, vatelizumab and PF-00547659; and biosimilars thereof. In a preferred embodiment, the integrin inhibitor is vedolizumab or a biosimilar thereof. In a particularly preferred embodiment, the tofacitinib or the pharmaceutically acceptable salt thereof, such as tofacitinib citrate, is administered topically via an ingestible device as disclosed herein, and vedolizumab or biosimilar thereof is administered systemically. In some embodiments, the vedolizumab or biosimilar thereof is administered intravenously. In some embodiments, the vedolizumab or biosimilar thereof is administered subcutaneously. In other embodiments, the integrin inhibitor is a small molecule integrin inhibitor. In some embodiments, the small molecule integrin inhibitor is firategrast, valategrast, R00270608, CDP-323, CT7758, GW-559090, or ELND-004; or pharmaceutically acceptable salt thereof. In further embodiments, the small molecule integrin inhibitor is a compound as disclosed in US 2005/0209232; U.S. Pat. No. 9,518,091; WO 2005/077914; WO 2005/077915; WO 09/706822; WO 2017/135471; WO 2017/135472; Co et al., Immunotechnol., 4:253-266 (1999); Dubree et al., J. Med. Chem., 45:3451-3457 (2002); Gong et al., J. Med. Chem., 49:3402-3411 (2006); Gong et al., Bioorg. Med. Chem. Lett., 18:1331-1335 (2008); Muz et al., American Society of Hematology Annual Meeting and Exposition, (2014) 56th (December 8) Abs 4758; Sidduri et al., Bioorg. Med. Chem. Lett., 23:1026-1031 (2013); or Xu et al., Bioorg. Med. Chem. Lett., 23:4370-4373 (2013), each of which are incorporated by reference in their entireties; or pharmaceutically acceptable salt thereof. In a preferred embodiment, the small molecule integrin inhibitor is AJM-300, or a pharmaceutically acceptable salt thereof. In another preferred embodiment, the small molecule integrin inhibitor is HCA2969 (carotegrast), or a prodrug thereof; or a pharmaceutically acceptable salt thereof; provided that the prodrug of carotegrast is not AJM300. In another preferred embodiment, the small molecule integrin inhibitor is HCA2969 (carotegrast); or a pharmaceutically acceptable salt thereof. In other embodiments, the integrin inhibitor is a peptide integrin inhibitor. In some embodiments, the peptide integrin inhibitor is PTG-100 or PN-10943 (also known as PN-943).

In some embodiments, the tofacitinib or pharmaceutically acceptable salt thereof (e.g., tofacitinib citrate), or the pharmaceutical formulation that comprises the tofacitinib or pharmaceutically acceptable salt thereof (e.g., tofacitinib citrate), is administered topically via an ingestible device as disclosed herein, and an anti-TNF agent is administered. In some embodiments, the anti-TNF agent is infliximab, golimumab, certolizumab, certolizumab pegol or etanercept; or a biosimilar thereof. In a preferred embodiment, the anti-TNF agent is adalimumab or a biosimilar thereof. In a particularly preferred embodiment, the tofacitinib or the pharmaceutically acceptable salt thereof, such as tofacitinib citrate, is administered topically via an ingestible device as disclosed herein, and adalimumab or biosimilar thereof is administered systemically. In some embodiments, the adalimumab or biosimilar thereof is administered intravenously. In some embodiments, the adalimumab or biosimilar thereof is administered subcutaneously. In another particularly preferred embodiment, the tofacitinib or the pharmaceutically acceptable salt thereof, such as tofacitinib citrate, is administered topically via an ingestible device as disclosed herein, and adalimumab or biosimilar thereof is administered topically (optionally, via an ingestible device as disclosed herein).

In some embodiments, the tofacitinib or pharmaceutically acceptable salt thereof (e.g., tofacitinib citrate), or the pharmaceutical formulation that comprises the tofacitinib or pharmaceutically acceptable salt thereof (e.g., tofacitinib citrate), is administered topically via an ingestible device as disclosed herein, and an IL-12/IL-23 inhibitor is administered. In some embodiments, the IL-12/IL-23 inhibitor is selected from the group consisting of ustekinumab, guselkumab, risankizumab, brazikumab and mirikizumab; and biosimilars thereof. In a preferred embodiment, the IL-12/IL-23 inhibitor is ustekinumab or a biosimilar thereof. In some embodiments, the IL-12/IL-23 inhibitor is a peptide inhibitor of the IL-23 receptor, such as a peptide disclosed in U.S. Pat. No. 9,624,268, e.g., Compound A (SEQ ID NO: 276), Compound B (SEQ ID NO: 279), or Compound C (SEQ ID NO: 280); or a pharmaceutically acceptable salt thereof. In some embodiments, the IL-12/IL-23 inhibitor is apilomod mesylate.

In some embodiments, the tofacitinib or pharmaceutically acceptable salt thereof (e.g., tofacitinib citrate), or the pharmaceutical formulation that comprises the tofacitinib or pharmaceutically acceptable salt thereof (e.g., tofacitinib citrate), is administered topically via an ingestible device as disclosed herein, and a GM-CSF is administered. In some embodiments, the GM-CSF is sargramostim (Leukine®) or molgramostim; or a biosimilar thereof. In some preferred embodiments, the GM-CSF is sargramostim or a biosimilar thereof. In some embodiments, the GM-CSF is administered during maintenance therapy.

In some embodiments, the tofacitinib or pharmaceutically acceptable salt thereof (e.g., tofacitinib citrate), or the pharmaceutical formulation that comprises the tofacitinib or pharmaceutically acceptable salt thereof (e.g., tofacitinib citrate), is administered topically via an ingestible device as disclosed herein, and a second JAK inhibitor is administered, wherein the second JAK inhibitor is not tofacitinib or a pharmaceutically acceptable salt thereof (e.g., tofacitinib citrate). In some embodiments, the second JAK inhibitor is a JAK inhibitor as disclosed herein. In some embodiments, the second JAK inhibitor is selected from the group consisting of abrocitinib, baricitinib, BMS-986165, decemotinib (VX509), filgotinib, itacitinib, oclacitinib, peficitinib, PF-06651600, PF-06700841, R333 (R932333), R348 (R932348), ruxolitinib, solcitinib, TD-1473, TD-3504, and upadacitinib; and pharmaceutically acceptable salts thereof.

In some embodiments, the pharmaceutical formulation comprising the JAK inhibitor is a formulation as disclosed herein. In some embodiments, the additional agent is provided in a formulation as disclosed herein.

Tofacitinib Plus Additional Agent via Ingestible Device

In some other embodiments, provided herein is a method of treating an inflammatory disease or condition of the gastrointestinal (GI) tract of a subject that comprises:

- administering to the subject tofacitinib or a pharmaceutically acceptable salt thereof (e.g., tofacitinib citrate);
- orally administering to the subject an ingestible device comprising (i) an additional agent or (ii) a pharmaceutical formulation that comprises the additional agent, wherein the additional agent is useful for treating a disease or condition of the GI tract of a subject; and
- releasing the additional agent, or the pharmaceutical formulation that comprises the additional agent, from the ingestible device to, or proximal to, a section or subsection of the GI tract containing one or more inflammatory disease sites.

In some embodiments, the inflammatory disease or condition is an inflammatory bowel disease. In some embodiments, the inflammatory bowel disease is ulcerative colitis. In some embodiments, the inflammatory bowel disease is Crohn's disease.

In some embodiments, the section or subsection of the GI tract of the subject containing the one or more disease sites is the duodenum, and the additional agent, or the pharmaceutical formulation that comprises the additional agent, is released to the stomach or the duodenum.

In some embodiments, the section or subsection of the GI tract of the subject containing the one or more disease sites is the jejunum, and the additional agent, or the pharmaceutical formulation that comprises the additional agent, is released to the duodenum or the jejunum.

In some embodiments, the section or subsection of the GI tract of the subject containing the one or more disease sites is the ileum, and the additional agent, or the pharmaceutical formulation that comprises the additional agent, is released to the jejunum or the ileum.

In some embodiments, the section or subsection of the GI tract of the subject containing the one or more disease sites is the cecum, and the additional agent, or the pharmaceutical formulation that comprises the additional agent, is released to the ileum or the cecum.

In some embodiments, the section or subsection of the GI tract of the subject containing the one or more disease sites is the colon, and the additional agent, or the pharmaceutical formulation that comprises the additional agent, is released to the cecum or the colon. In some more particular embodiments, the additional agent, or the pharmaceutical formulation that comprises the additional agent, is released to the ascending colon.

In some embodiments, the tofacitinib or a pharmaceutically acceptable salt thereof (e.g., tofacitinib citrate), or the pharmaceutical formulation comprising the tofacitinib or a pharmaceutically acceptable salt thereof (e.g., tofacitinib citrate), is administered topically (e.g., via an ingestible device as disclosed herein). In some embodiments, the tofacitinib or a pharmaceutically acceptable salt thereof (e.g., tofacitinib citrate), or the pharmaceutical formulation comprising the tofacitinib or a pharmaceutically acceptable salt thereof (e.g., tofacitinib citrate), is administered by another form of administration. In some embodiments, the tofacitinib or a pharmaceutically acceptable salt thereof (e.g., tofacitinib citrate), or the pharmaceutical formulation comprising the tofacitinib or a pharmaceutically acceptable salt thereof (e.g., tofacitinib citrate), is administered systemically (such as intravenously, subcutaneously, or orally) or rectally.

In some embodiments, the tofacitinib or a pharmaceutically acceptable salt thereof (e.g., tofacitinib citrate), or the pharmaceutical formulation comprising the tofacitinib or a pharmaceutically acceptable salt thereof (e.g., tofacitinib citrate), is administered prior to administration of the additional agent. In some embodiments, the additional agent is administered prior to administration of the tofacitinib or a pharmaceutically acceptable salt thereof (e.g., tofacitinib citrate), or the pharmaceutical formulation comprising the tofacitinib or a pharmaceutically acceptable salt thereof (e.g., tofacitinib citrate). In some embodiments, the tofacitinib or a pharmaceutically acceptable salt thereof (e.g., tofacitinib citrate), or the pharmaceutical formulation comprising the tofacitinib or a pharmaceutically acceptable salt thereof (e.g., tofacitinib citrate), and the additional agent are administered simultaneously.

In some embodiments, the additional agent is an aminosalicylate, an immunosuppressant (e.g., a corticosteroid), a PDE4 inhibitor, an S1P modulator, an integrin inhibitor, an anti-TNF agent, an IL-12/IL-23 inhibitor, a GM-CSF or a second JAK inhibitor.

In some embodiments, the additional agent is an immunosuppressant. In some embodiments, the immunosuppressant is a corticosteroid, optionally selected from the group consisting of budesonide, dexamethasone, hydrocortisone, methylprednisolone, prednisolone and prednisone; and pharmaceutically acceptable salts thereof. In some embodiments, the immunosuppressant is a cytostatic agent, optionally selected from the group consisting of azathioprine, 6-mercaptopurine and methotrexate; and pharmaceutically acceptable salts thereof. In some embodiments, the immunosuppressant is an mTOR inhibitor, optionally selected from the group consisting of rapamycin, everolimus, dactolisib and temsirolimus; and pharmaceutically acceptable salts thereof. In some embodiments, the immunosuppressant is a calcineurin inhibitor, optionally selected from the group consisting of a cyclosporin (such as cyclosporin A), pimecrolimus, sanglifehrin A, tacrolimus and voclosporin; and pharmaceutically acceptable salts thereof.

In some embodiments, the additional agent is a PDE4 inhibitor selected from the group consisting of apremilast, crisaborole, ibudilast, roflumilast and tetomilast; and pharmaceutically acceptable salts thereof.

In some embodiments, the additional agent is an S1P modulator selected from the group consisting of fingolimod, KRP203, siponimod, ponesimod, cenerimod, ozanimod, ceralifimod, amiselimod, and etrasimod; and pharmaceutically acceptable salts thereof. In some embodiments, the S1P modulator is ozanimod or a pharmaceutically acceptable salt thereof. In other embodiments, the S1P modulator is etrasimod or a pharmaceutically acceptable salt thereof. In yet other embodiments, the S1P modulator is amiselimod or a pharmaceutically acceptable salt thereof.

In some embodiments, the additional agent is an integrin inhibitor. In some embodiments, the integrin inhibitor is an antibody. In a further embodiment, the integrin inhibitor is selected from the group consisting of vedolizumab, natalizumab, etrolizumab, vatelizumab and PF-00547659; and biosimilars thereof. In a preferred embodiment, the integrin inhibitor is vedolizumab or a biosimilar thereof. In other embodiments, the integrin inhibitor is a small molecule integrin inhibitor. In some embodiments, the small molecule integrin inhibitor is firategrast, valategrast, R00270608, CDP-323, CT7758, GW-559090, or ELND-004; or pharmaceutically acceptable salt thereof. In further embodiments, the small molecule integrin inhibitor is a compound as disclosed in US 2005/0209232; U.S. Pat. No. 9,518,091; WO 2005/077914; WO 2005/077915; WO 09/706822; WO 2017/135471; WO 2017/135472; Co et al., Immunotechnol., 4:253-266 (1999); Dubree et al., J. Med. Chem., 45:3451-3457 (2002); Gong et al., J. Med. Chem., 49:3402-3411 (2006); Gong et al., Bioorg. Med. Chem. Lett., 18:1331-1335 (2008); Muz et al., American Society of Hematology Annual Meeting and Exposition, (2014) 56th (December 8) Abs 4758; Sidduri et al., Bioorg. Med. Chem. Lett., 23:1026-1031 (2013); or Xu et al., Bioorg. Med. Chem. Lett., 23:4370-4373 (2013), each of which are incorporated by reference in their entireties; or pharmaceutically acceptable salt thereof. In a preferred embodiment, the small molecule integrin inhibitor is AJM-300, or a pharmaceutically acceptable salt thereof. In another preferred embodiment, the small molecule integrin inhibitor is HCA2969 (carotegrast), or a prodrug thereof; or a pharmaceutically acceptable salt thereof; provided that the prodrug of carotegrast is not AJM300. In another preferred embodiment, the small molecule integrin inhibitor is HCA2969 (carotegrast); or a pharmaceutically acceptable salt thereof. In other embodiments, the integrin inhibitor is a peptide integrin inhibitor. In some embodiments, the peptide integrin inhibitor is PTG-100 or PN-10943 (also known as PN-943).

In some embodiments, the additional agent is an anti-TNF agent selected from the group consisting of infliximab, golimumab, certolizumab, certolizumab pegol and etanercept; and biosimilars thereof. In a preferred embodiment, the anti-TNF agent is adalimumab or a biosimilar thereof. In a particularly preferred embodiment, the tofacitinib or the pharmaceutically acceptable salt thereof, such as tofacitinib citrate, is administered topically (optionally, via an ingestible device as disclosed herein), and adalimumab or biosimilar thereof is administered topically via an ingestible device as disclosed herein.

In some embodiments, the additional agent is an IL-12/IL-23 inhibitor selected from the group consisting of ustekinumab, guselkumab, risankizumab, brazikumab and mirikizumab; and biosimilars thereof. In a preferred embodiment, the IL-12/IL-23 inhibitor is ustekinumab or a biosimilar thereof. In some embodiments, the IL-12/IL-23 inhibitor is a peptide inhibitor of the IL-23 receptor, such as a peptide disclosed in U.S. Pat. No. 9,624,268, e.g., Compound A (SEQ ID NO: 276), Compound B (SEQ ID NO: 279), or Compound C (SEQ ID NO: 280); or a pharmaceutically acceptable salt thereof. In some embodiments, the IL-12/IL-23 inhibitor is apilomod mesylate.

In some embodiments, the additional agent is a GM-CSF. In some embodiments, the GM-CSF is sargramostim (Leukine®) or molgramostim; or a biosimilar thereof. In some preferred embodiments, the GM-CSF is sargramostim or a biosimilar thereof. In some embodiments, the GM-CSF is administered during maintenance therapy.

In some embodiments, the additional agent is a second JAK inhibitor, wherein the second JAK inhibitor is not tofacitinib or a pharmaceutically acceptable salt thereof (e.g., tofacitinib citrate). In some embodiments, the second JAK inhibitor is a JAK inhibitor as disclosed herein. In some embodiments, the second JAK inhibitor is selected from the group consisting of abrocitinib, baricitinib, BMS-986165, decernotinib (VX509), filgotinib, itacitinib, oclacitinib, perficitinib, PF-06651600, PF-06700841, R333 (R932333), R348 (R932348), ruxolitinib, solcitinib, TD-1473, TD-3504, and upadacitinib; and pharmaceutically acceptable salts thereof.

In some embodiments, the pharmaceutical formulation comprising the JAK inhibitor is a formulation as disclosed herein. In some embodiments, the additional agent is provided in a formulation as disclosed herein.

Endoscopes, Ingestible Devices, and Reservoirs

As discussed herein, in some embodiments, a method of treating a disease of the gastrointestinal tract comprises administering to the subject a pharmaceutical formulation. In some embodiments, the pharmaceutical formulation is delivered proximate to one or more sites of disease by one of various methods. For example, the pharmaceutical formulation may be delivered via a medical device such as an endoscope, ingestible device, or reservoir; the pharmaceutical formulation may be a solid dosage form, a liquid dosage form, a suppository or an enema for rectal administration with different types of release such as sustained or delayed release.

In one embodiment, the pharmaceutical formulation is delivered proximate to one or more sites of disease by an endoscope, ingestible device, or reservoir containing the pharmaceutical formulation.

The GI tract can be imaged using endoscopes, or more recently, by ingestible devices that are swallowed. Direct visualization of the GI mucosa is useful to detect subtle mucosal alterations, as in inflammatory bowel diseases, as well as any flat or sessile lesions.

The technology behind standard colonoscopy consists of a long, semi-rigid insertion tube with a steerable tip (stiff if compared to the colon), which is pushed by the physician from the outside. However, invasiveness, patient discomfort, fear of pain, and, more often than not, the need for conscious sedation limit the take-up of screening colonoscopy. Diagnosis and treatment in the GI tract are dominated by the use of flexible endoscopes. A few large companies, namely Olympus Medical Systems Co. (Tokyo, Japan), Pentax Medical Co. (Montvale, NJ, USA), Fujinon, Inc. (Wayne, NJ, USA) and Karl Storz GmbH & Co. KG (Tuttlingen, Germany), cover the majority of the market in flexible GI endoscopy.

Endoscopes may comprise a catheter. As an example, the catheter may be a spray catheter. As an example, a spray catheter may be used to deliver dyes for diagnostic purposes. As an example, a spray catheter may be used to deliver a therapeutic agent at the site of disease in the GI tract. For example, the Olypmus PW-205V is a ready-to-use spray catheter that enables efficient spraying for maximal differentiation of tissue structures during endoscopy, but may also be used to deliver drugs diseased tissue.

In a review of robotic endoscopic capsules, Journal of Micro-Bio Robotics 11.1-4 (2016):1-18, Ciuti et al. state that progress in micro-electromechanical systems (MEMS) technologies have led to the development of new endoscopic capsules with enhanced diagnostic capabilities, in addition to traditional visualization of mucosa (embedding, e.g. pressure, pH, blood detection and temperature sensors).

Methods and Mechanisms for Localization

In addition to, or as an alternative, to directly visualizing the GI tract, one or more different mechanisms can be used to determine the location of an ingestible device within the GI tract. Various implementations may be used for localization of ingestible devices within the GI tract.

For example, certain implementations can include one or more electromagnetic sensor coils, magnetic fields, electromagnetic waves, electric potential values, ultrasound positioning systems, gamma scintigraphy techniques or other radio-tracker technology have been described by others. Alternatively, imaging can be used to localize, for example, using anatomical landmarks or more complex algorithms for 3D reconstruction based on multiple images. Other technologies rely on radio frequency, which relies on sensors placed externally on the body to receive the strength of signals emitted by the capsule. Ingestible devices may also be localized based on reflected light in the medium surrounding the device; pH; temperature; time following ingestion; and/or acoustic signals.

The disclosure provides an ingestible device, as well as related systems and methods that provide for determining the position of the ingestible device within the GI tract of a subject with very high accuracy. In some embodiments, the ingestible device can autonomously determine its position within the GI tract of the subject.

Typically, the ingestible device includes one or more processing devices, and one more machine readable hardware storage devices. In some embodiments, the one or more machine readable hardware storage devices store instructions that are executable by the one or more processing devices to determine the location of the ingestible device in a portion of a GI tract of the subject. In certain embodiments, the one or more machine readable hardware storage devices store instructions that are executable by the one or more processing devices to transmit data to an external device (e.g., a base station external to the subject, such as a base station carried on an article worn by the subject) capable of implementing the data to determine the location of the device within the GI tract of the subject.

In some embodiments, the location of the ingestible device within the GI tract of the subject can be determined to an accuracy of at least 85%, e.g., at least 90%, at least 95%, at least 97%, at least 98%, at least 99%, 100%. In some embodiments, the location of the ingestible device within the GI tract of the subject can be determined to an accuracy of at least 85%, e.g., at least 90%, at least 95%, at least 97%, at least 98%, at least 99%, 100%. In such embodiments, the portion of the GI tract of the subject can include, for example, the esophagus, the stomach, duodenum, the jejunum, and/or the terminal ileum, cecum and colon. An exemplary and non-limiting embodiment is provided below in Example 13.

In certain embodiments, the location of the ingestible device within the esophagus of the subject can be determined to an accuracy of at least 85%, e.g., at least 90%, at least 95%, at least 97%, at least 98%, at least 99%, 100%. An exemplary and non-limiting embodiment is provided below in Example 13.

In some embodiments, the location of the ingestible device within the stomach of the subject can be determined to an accuracy of at least 85%, e.g., at least 90%, at least 95%, at least 97%, at least 98%, at least 99%, 100%. An exemplary and non-limiting embodiment is provided below in Example 13.

In certain embodiments, the location of the ingestible device within the duodenum of the subject can be determined to an accuracy of at least 85%, e.g., at least 90%, at least 95%, at least 97%, at least 98%, at least 99%, 100%. An exemplary and non-limiting embodiment is provided below in Example 13.

In some embodiments, the location of the ingestible device within the jejunum of the subject can be determined to an accuracy of at least 85%, e.g., at least 90%, at least 95%, at least 97%, at least 98%, at least 99%, 100%. An exemplary and non-limiting embodiment is provided below in Example 13.

In certain embodiments, the location of the ingestible device within the terminal ileum, cecum and colon of the subject can be determined to an accuracy of at least 85%, e.g., at least 90%, at least 95%, at least 97%, at least 98%, at least 99%, 100%.

In some embodiments, the location of the ingestible device within the cecum of the subject can be determined to an accuracy of at least 85%, e.g., at least 90%, at least 95%, at least 97%, at least 98%, at least 99%, 100%. An exemplary and non-limiting embodiment is provided below in Example 13. In such embodiments, the portion of the portion of the GI tract of the subject can include, for example, the esophagus, the stomach, duodenum, the jejunum, and/or the terminal ileum, cecum and colon.

In certain embodiments, the location of the ingestible device within the esophagus of the subject can be determined to an accuracy of at least 85%, e.g., at least 90%, at least 95%, at least 97%, at least 98%, at least 99%, 100%.

In some embodiments, the location of the ingestible device within the stomach of the subject can be determined to an accuracy of at least 85%, e.g., at least 90%, at least 95%, at least 97%, at least 98%, at least 99%, 100%.

In certain embodiments, the location of the ingestible device within the duodenum of the subject can be determined to an accuracy of at least 85%, e.g., at least 90%, at least 95%, at least 97%, at least 98%, at least 99%, 100%.

In some embodiments, the location of the ingestible device within the jejunum of the subject can be determined to an accuracy of at least 85%, e.g., at least 90%, at least 95%, at least 97%, at least 98%, at least 99%, 100%.

In certain embodiments, the location of the ingestible device within the terminal ileum, cecum and colon of the subject can be determined to an accuracy of at least 85%, e.g., at least 90%, at least 95%, at least 97%, at least 98%, at least 99%, 100%.

In some embodiments, the location of the ingestible device within the cecum of the subject can be determined to an accuracy of at least 85%, e.g., at least 90%, at least 95%, at least 97%, at least 98%, at least 99%, 100%.

As used herein, the term "reflectance" refers to a value derived from light emitted by the device, reflected back to the device, and received by a detector in or on the device. For example, in some embodiments this refers to light emitted by the device, wherein a portion of the light is reflected by a surface external to the device, and the light is received by a detector located in or on the device.

As used herein, the term "illumination" refers to any electromagnetic emission. In some embodiments, an illumination may be within the range of Infrared Light (IR), the visible spectrum and ultraviolet light (UV), and an illumination may have a majority of its power centered at a particular wavelength in the range of 100 nm to 1000 nm. In some embodiments, it may be advantageous to use an illumination with a majority of its power limited to one of the infrared (750 nm-1000 nm), red (600 nm-750 nm), green (495 nm-600 nm), blue (400 nm-495 nm), or ultraviolet (100 nm-400 nm) spectrums. In some embodiments a plurality of illuminations with different wavelengths may be used. For illustrative purposes, the embodiments described herein may refer to the use of green or blue spectrums of light. However, it is understood that these embodiments may use any suitable light having a wavelength that is substantially or approximately within the green or blue spectra defined above, and the localization systems and methods described herein may use any suitable spectra of light.

Figure 1:
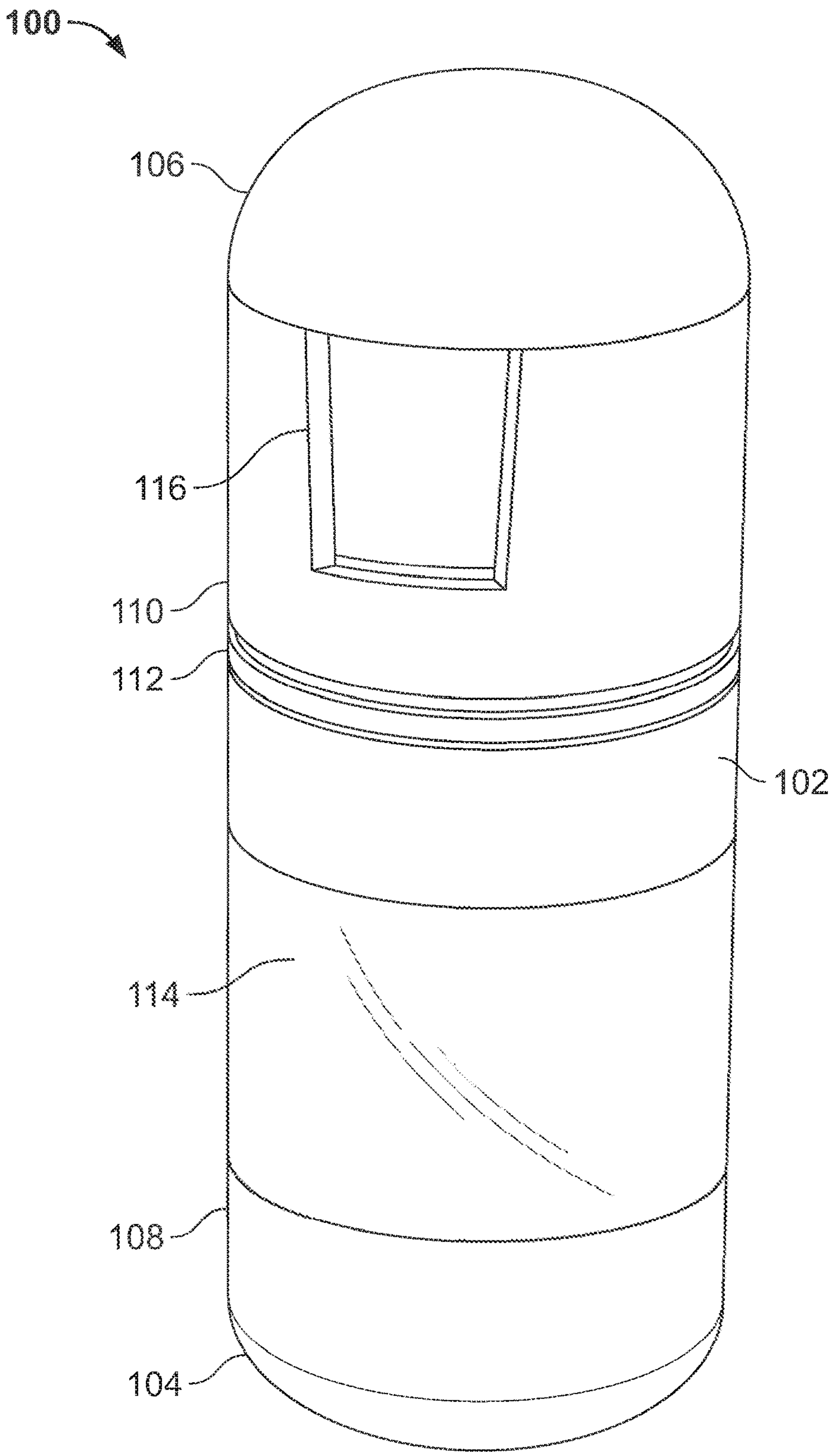
FIG. 1 is a view of an example embodiment of an ingestible device, in accordance with some embodiments of the disclosure.

Referring now to FIG. 1, shown therein is a view of an example embodiment of an ingestible device 100, which may be used to identify a location within a gastrointestinal (GI) tract. In some embodiments, ingestible device 100 may be configured to autonomously determine whether it is located in the stomach, a particular portion of the small intestine such as a duodenum, jejunum, or ileum, or the large intestine by utilizing sensors operating with different wavelengths of light. Additionally, ingestible device 100 may be configured to autonomously determine whether it is located within certain portions of the small intestine or large intestine, such as the duodenum, the jejunum, the cecum, or the colon.

Ingestible device 100 may have a housing 102 shaped similar to a pill or capsule. The housing 102 of ingestible device 100 may have a first end portion 104, and a second end portion 106. The first end portion 104 may include a first wall portion 108, and second end portion 106 may include a second wall portion 110. In some embodiments, first end portion 104 and second end portion 106 of ingestible device 100 may be manufactured separately, and may be affixed together by a connecting portion 112.

In some embodiments, ingestible device 100 may include an optically transparent window 114. Optically transparent window 114 may be transparent to various types of illumination in the visible spectrum, infrared spectrum, or ultraviolet light spectrum, and ingestible device 100 may have various sensors and illuminators located within the housing 102, and behind the transparent window 114. This may allow ingestible device 100 to be configured to transmit illumination at different wavelengths through transparent window 114 to an environment external to housing 102 of ingestible device 100, and to detect a reflectance from a portion of the illumination that is reflected back through transparent window 114 from the environment external to housing 102. Ingestible device 100 may then use the detected level of reflectance in order to determine a location of ingestible device 100 within a GI tract. In some embodiments, optically transparent window 114 may be of any shape and size, and may wrap around the circumference of ingestible device 100. In this case, ingestible device 100 may have multiple sets of sensors and illuminators positioned at different locations azimuthally behind window 114.

In some embodiments, ingestible device 100 may optionally include an opening 116 in the second wall portion 110. In some embodiments, the second wall portion 110 may be configured to rotate around the longitudinal axis of ingestible device 100 (e.g., by means of a suitable motor or other actuator housed within ingestible device 100). This may allow ingestible device 100 to obtain a fluid sample from the GI tract, or release a substance into the GI tract, through opening 116.

Figure 2:
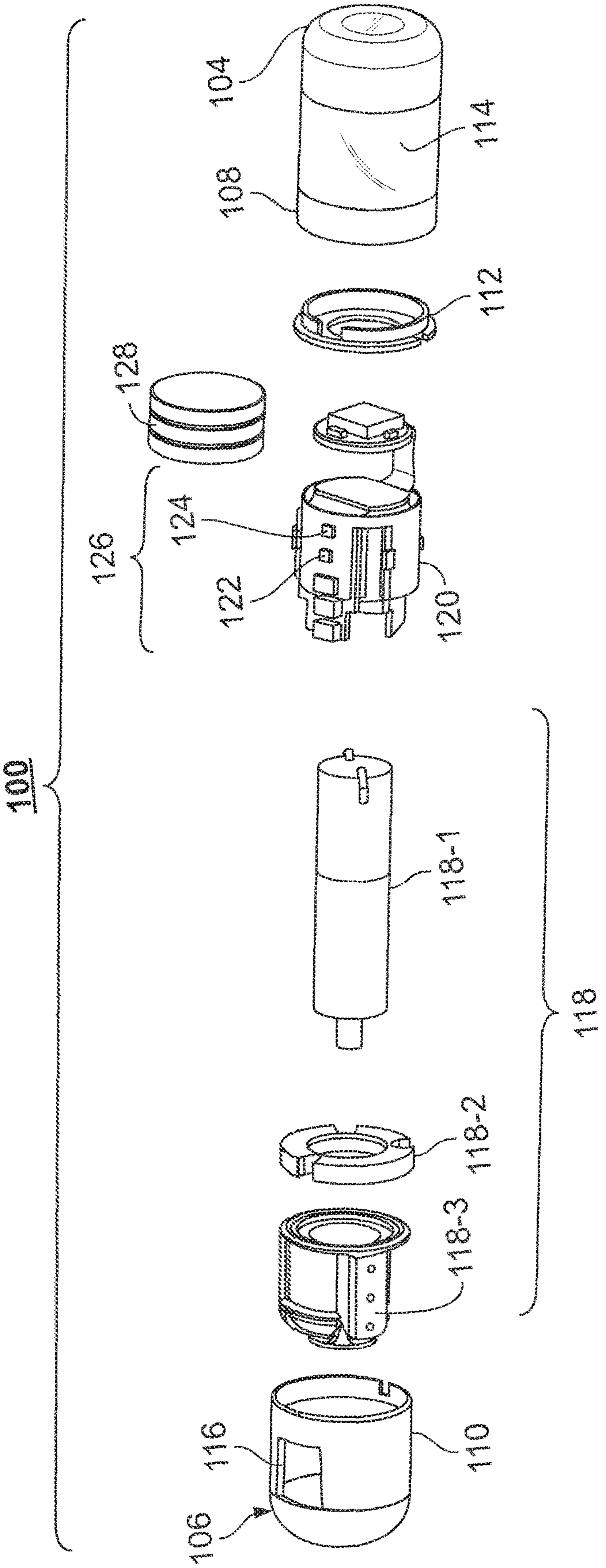
FIG. 2 is an exploded view of the ingestible device of FIG. 1, in accordance with some embodiments of the disclosure.

FIG. 2 shows an exploded view of ingestible device 100. In some embodiments, ingestible device 100 may optionally include a rotation assembly 118. Optional rotation assembly 118 may include a motor 118-1 driven by a microcontroller (e.g., a microcontroller coupled to printed circuit board 120), a rotation position sensing ring 118-2, and a storage sub-unit 118-3 configured to fit snugly within the second end portion 104. In some embodiments, rotation assembly 118 may cause second end portion 104, and opening 116, to rotate relative to the storage sub-unit 118-3. In some embodiments, there may be cavities on the side of storage sub-unit 118-3 that function as storage chambers. When the opening 116 is aligned with a cavity on the side of the storage sub-unit 118-3, the cavity on the side of the storage sub-unit 118-3 may be exposed to the environment external to the housing 102 of ingestible device 100. In some embodiments, the storage sub-unit 118-3 may be loaded with a medicament or other substance prior to the ingestible device 100 being administered to a subject. In this case, the medicament or other substance may be released from the ingestible device 100 by aligning opening 116 with the cavity within storage sub-unit 118-3. In some embodiments, the storage sub-unit 118-3 may be configured to hold a fluid sample obtained from the GI tract. For example, ingestible device 100 may be configured to align opening 116 with the cavity within storage sub-unit 118-3, thus allowing a fluid sample from the GI tract to enter the cavity within storage sub-unit 118-3. Afterwards, ingestible device 100 may be configured to seal the fluid sample within storage sub-unit 118-3 by further rotating the second end portion 106 relative to storage sub-unit 118-3. In some embodiments, storage sub-unit 118-3 may also contain a hydrophilic sponge, which may enable ingestible device 100 to better draw certain types of fluid samples into ingestible device 100. In some embodiments, ingestible device 100 may be configured to either obtain a sample from within the GI tract, or to release a substance into the GI tract, in response to determining that ingestible device 100 has reached a predetermined location within the GI tract. For example, ingestible device 100 may be configured to obtain a fluid sample from the GI tract in response to determining that the ingestible device has entered the jejunum portion of the small intestine (e.g., as determined by process 900 discussed in relation to FIG. 9).

Other ingestible devices capable of obtaining samples or releasing substances are discussed in commonly-assigned PCT Application No. PCT/CA2013/000133 filed Feb. 15, 2013, commonly-assigned U.S. Provisional Application No. 62/385,553, and commonly-assigned U.S. Provisional Application No. 62/376,688, which each are hereby incorporated by reference herein in their entirety. It is understood that any suitable method of obtaining samples or releasing substances may be incorporated into some of the embodiments of the ingestible devices disclosed herein, and that the systems and methods for determining a location of an ingestible device may be incorporated into any suitable type of ingestible device.

Ingestible device 100 may include a printed circuit board (PCB) 120, and a battery 128 configured to power PCB 120. PCB 120 may include a programmable microcontroller, and control and memory circuitry for holding and executing firmware or software for coordinating the operation of ingestible device 100, and the various components of ingestible device 100. For example, PCB 120 may include memory circuitry for storing data, such as data sets of measurements collected by sensing sub-unit 126, or instructions to be executed by control circuitry to implement a localization process, such as, for example, one or more of the processes, discussed herein, including those discussed below in connection with one or more of the associated flow charts. PCB 120 may include a detector 122 and an illuminator 124, which together form sensing sub-unit 126. In some embodiments, control circuitry within PCB 120 may include processing units, communication circuitry, or any other suitable type of circuitry for operating ingestible device 100. For illustrative purposes, only a single detector 122 and a single illuminator 124 forming a single sensing sub-unit 126 are shown. However, it is understood that in some embodiments there may be multiple sensing sub-units, each with a separate illuminator and detector, within ingestible device 100. For example, there may be several sensing sub-units spaced azimuthally around the circumference of the PCB 120, which may enable ingestible device 100 to transmit illumination and detect reflectances or ambient light in all directions around the circumference of the device. In some embodiments, sensing sub-unit 126 may be configured to generate an illumination using illuminator 124, which is directed through the window 114 in a radial direction away from ingestible device 100. This illumination may reflect off of the environment external to ingestible device 100, and the reflected light coming back into ingestible device 100 through window 114 may be detected as a reflectance by detector 122.

In some embodiments, window 114 may be of any suitable shape and size. For example, window 114 may extend around a full circumference of ingestible device 100. In some embodiments there may be a plurality of sensing sub-units (e.g., similar to sensing sub-unit 126) located at different positions behind the window. For example, three sensing sub-units may be positioned behind the window at the same longitudinal location, but spaced 120 degrees apart azimuthally. This may enable ingestible device 100 to transmit illuminations in all directions radially around ingestible device 100, and to measure each of the corresponding reflectances.

In some embodiments, illuminator 124 may be capable of producing illumination at a variety of different wavelengths in the ultraviolet, infrared, or visible spectrum. For example, illuminator 124 may be implemented by using Red-Green-Blue Light-Emitting diode packages (RGB-LED). These types of RGB-LED packages are able to transmit red, blue, or green illumination, or combinations of red, blue, or green illumination. Similarly, detector 122 may be configured to sense reflected light of the same wavelengths as the illumination produced by illuminator 124. For example, if illuminator 124 is configured to produce red, blue, or green illumination, detector 122 may be configured to detect different reflectances produced by red, blue, or green illumination (e.g., through the use of an appropriately configured photodiode). These detected reflectances may be stored by ingestible device 100 (e.g., within memory circuitry of PCB 120), and may then be used by ingestible device 100 in determining a location of ingestible device 100 within the GI tract (e.g., through the use of process 500 (FIG. 5), process 600 (FIG. 6), or process 900 (FIG. 9)).

It is understood that ingestible device 100 is intended to be illustrative, and not limiting. It will be understood that modifications to the general shape and structure of the various devices and mechanisms described in relation to FIG. 1 and FIG. 2 may be made without significantly changing the functions and operations of the devices and mechanisms. For example, ingestible device 100 may have a housing formed from a single piece of molded plastic, rather than being divided into a first end portion 104 and a second end portion 106. As an alternate example, the location of window 114 within ingestible device 100 may be moved to some other location, such as the center of ingestible device 100, or to one of the ends of ingestible device 100. Moreover, the systems and methods discussed in relation to FIGS. 1-10 may be implemented on any suitable type of ingestible device, provided that the ingestible device is capable of detecting reflectances or levels of illumination in some capacity. For example, in some embodiments ingestible device 100 may be modified to replace detector 122 with an image sensor, and the ingestible device may be configured to measure relative levels of red, blue, or green light by decomposing a recorded image into its individual spectral components. Other examples of ingestible devices with localization capabilities, which may be utilized in order to implement the systems and methods discussed in relation to FIG. 1-11, are discussed in co-owned PCT Application No. PCT/US2015/052500 filed on Sep. 25, 2015, which is hereby incorporated by reference herein in its entirety. Furthermore, it should be noted that the features and limitations described in any one embodiment may be applied to any other embodiment herein, and the descriptions and examples relating to one embodiment may be combined with any other embodiment in a suitable manner.

Figure 3:
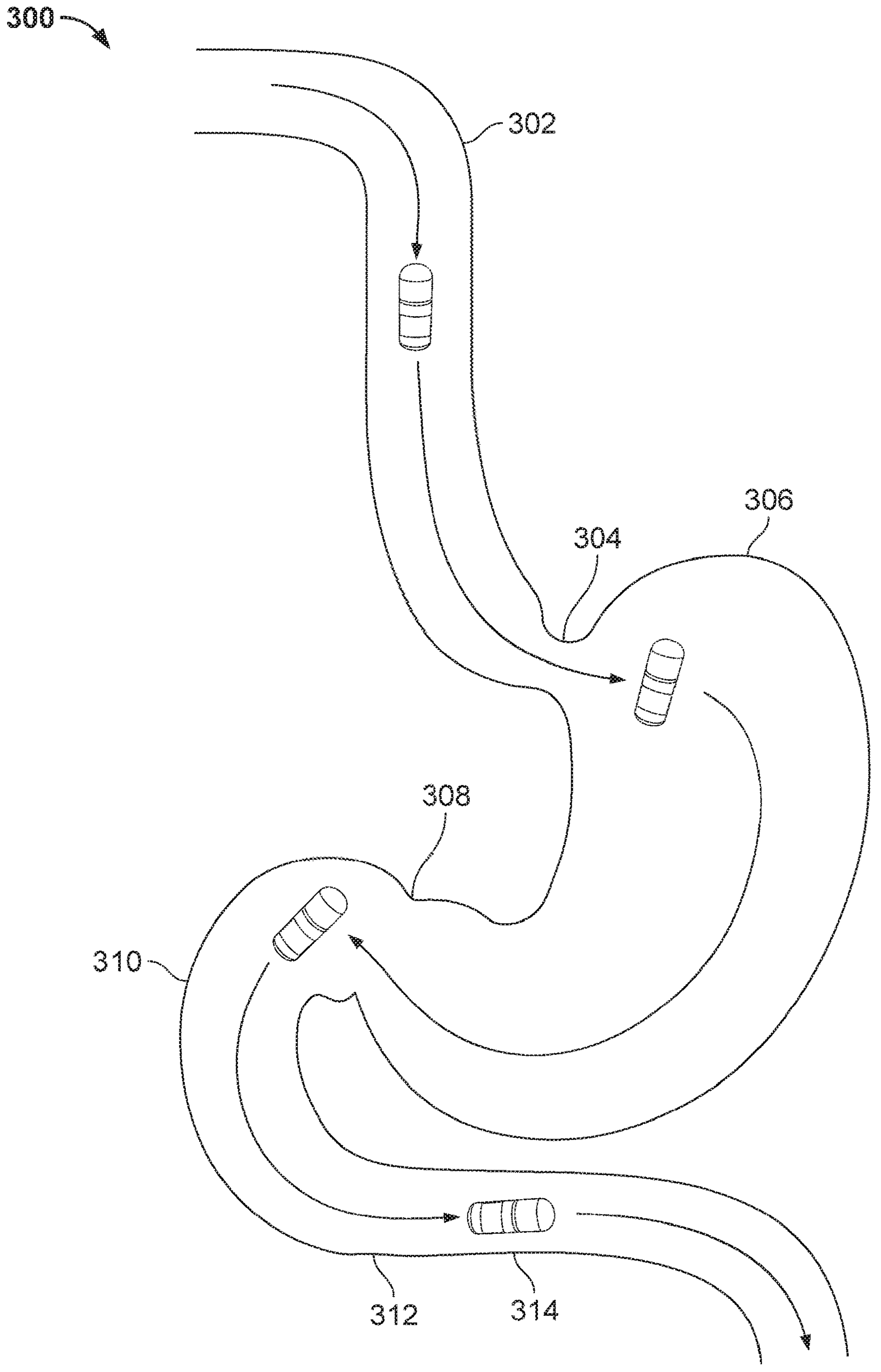
FIG. 3 is a diagram of an ingestible device during an example transit through a GI tract, in accordance with some embodiments of the disclosure.

FIG. 3 is a diagram of an ingestible device during an example transit through a gastrointestinal (GI) tract, in accordance with some embodiments of the disclosure. Ingestible device 300 may include any portion of any other ingestible device discussed in this disclosure (e.g., ingestible device 100 (FIG. 1)), and may be any suitable type of ingestible device with localization capabilities. For example, ingestible device 300 may be one embodiment of ingestible device 100 without the optional opening 116 (FIG. 1) or optional rotation assembly 118 (FIG. 2)). In some embodiments, ingestible device 300 may be ingested by a subject, and as ingestible device 300 traverses the GI tract, ingestible device 300 may be configured to determine its location within the GI tract. For example, the movement of ingestible device 300 and the amount of light detected by ingestible device 300 (e.g., via detector 122 (FIG. 2)) may vary substantially depending on the location of ingestible device 300 within the GI tract, and ingestible device 300 may be configured to use this information to determine a location of ingestible device 300 within the GI tract. For instance, ingestible device 300 may detect ambient light from the surrounding environment, or reflectances based on illumination generated by ingestible device 300 (e.g., generated by illuminator 124 (FIG. 1)), and use this information to determine a location of ingestible device 300 through processes, such as described herein. The current location of ingestible device 300, and the time that ingestible device 300 detected each transition between the various portions of the GI tract, may then be stored by ingestible device 300 (e.g., in memory circuitry of PCB 120 (FIG. 2)), and may be used for any suitable purpose.

Shortly after ingestible device 300 is ingested, ingestible device will traverse the esophagus 302, which may connect the subject's mouth to a stomach 306. In some embodiments, ingestible device 300 may be configured to determine that it has entered the esophagus portion GI tract by measuring the amount and type of light (e.g., via detector 122 (FIG. 2)) in the environment surrounding the ingestible device 300. For instance, ingestible device 300 may detect higher levels of light in the visible spectrum (e.g., via detector 122 (FIG. 2)) while outside the subject's body, as compared to the levels of light detected while within the GI tract. In some embodiments, ingestible device 300 may have previously stored data (e.g., on memory circuitry of PCB 120 (FIG. 2)) indicating a typical level of light detected when outside of the body, and the ingestible device 300 may be configured to determine that entry to the body has occurred when a detected level of light (e.g., detected via detector 122 (FIG. 2)) has been reduced beyond a threshold level (e.g., at least a 20-30% reduction) for a sufficient period of time (e.g., 5.0 seconds).

In some embodiments, ingestible device 300 may be configured to detect a transition from esophagus 302 to stomach 306 by passing through sphincter 304. In some embodiments, ingestible device 300 may be configured to determine whether it has entered stomach 306 based at least in part on a plurality of parameters, such as but not limited to the use of light or temperature measurements (e.g., via detector 122 (FIG. 2) or via a thermometer within ingestible device 300), pH measurements (e.g., via a pH meter within ingestible device 300), time measurements (e.g., as detected through the use of clock circuitry included within PCB 120 (FIG. 2)), or any other suitable information. For instance, ingestible device 300 may be configured to determine that ingestible device 300 has entered stomach 306 after detecting that a measured temperature of ingestible device 300 exceeds 31 degrees Celsius. Additionally, or alternately, ingestible device 300 may be configured to automatically determine it has entered stomach 306 after one minute (or another pre-set time duration parameter, 80 seconds, 90 seconds, etc.) has elapsed from the time that ingestible device 300 was ingested, or one minute (or another pre-set time duration parameter, 80 seconds, 90 seconds, etc.) from the time that ingestible device 300 detected that it has entered the GI tract.

Stomach 306 is a relatively large, open, and cavernous organ, and therefore ingestible device 300 may have a relatively large range of motion. By comparison, the motion of ingestible device 300 is relatively restricted within the tube-like structure of the duodenum 310, the jejunum 314, and the ileum (not shown), all of which collectively form the small intestine. Additionally, the interior of stomach 306 has distinct optical properties from duodenum 310 and jejunum 314, which may enable ingestible device 300 to detect a transition from stomach 306 to duodenum 310 through the appropriate use of measured reflectances (e.g., through the use of reflectances measured by detector 122 (FIG. 2)), as used in conjunction with process 600 (FIG. 6)).

In some embodiments, ingestible device 300 may be configured to detect a pyloric transition from stomach 306 to duodenum 310 through the pylorus 308. For instance, in some embodiments, ingestible device 300 may be configured to periodically generate illumination in the green and blue wavelengths (e.g., via illuminator 124 (FIG. 2)), and measure the resulting reflectances (e.g., via detector 122 (FIG. 2)). Ingestible device 300 may be configured to then use a ratio of the detected green reflectance to the detected blue reflectance to determine whether ingestible device 300 is located within the stomach 306, or duodenum 310 (e.g., via process 600 (FIG. 6)). In turn, this may enable ingestible device 300 to detect a pyloric transition from stomach 306 to duodenum 310, an example of which is discussed in relation to FIG. 6.

Similarly, in some embodiments, ingestible device 300 may be configured to detect a reverse pyloric transition from duodenum 310 to stomach 306. Ingestible device 300 will typically transition naturally from stomach 306 to duodenum 310, and onward to jejunum 314 and the remainder of the GI tract. However, similar to other ingested substances, ingestible device 300 may occasionally transition from duodenum 310 back to stomach 306 as a result of motion of the subject, or due to the natural behavior of the organs with the GI tract. To accommodate this possibility, ingestible device 300 may be configured to continue to periodically generate illumination in the green and blue wavelengths (e.g., via illuminator 124 (FIG. 2)), and measure the resulting reflectances (e.g., via detector 122 (FIG. 2)) to detect whether or not ingestible device 300 has returned to stomach 306. An exemplary detection process is described in additional detail in relation to FIG. 6.

After entering duodenum 310, ingestible device 300 may be configured to detect a transition to the jejunum 314 through the duodenojejunal flexure 312. For example, ingestible device 300 may be configured to use reflectances to detect peristaltic waves within the jejunum 314, caused by the contraction of the smooth muscle tissue lining the walls of the jejunum 314. In particular, ingestible device 300 may be configured to begin periodically transmitting illumination (and measuring the resulting reflectances (e.g., via detector 122 and illuminator 124 of sensing sub-unit 126 (FIG. 2)) at a sufficiently high frequency in order to detect muscle contractions within the jejunum 314. Ingestible device 300 may then determine that it has entered the jejunum 314 in response to having detected either a first muscle contraction, or a predetermined number of muscle contractions (e.g., after having detected three muscle contractions in sequence). The interaction of ingestible device 300 with the walls of jejunum 314 is also discussed in relation to FIG. 4, and an example of this detection process is described in additional detail in relation to FIG. 9.

Figure 4:
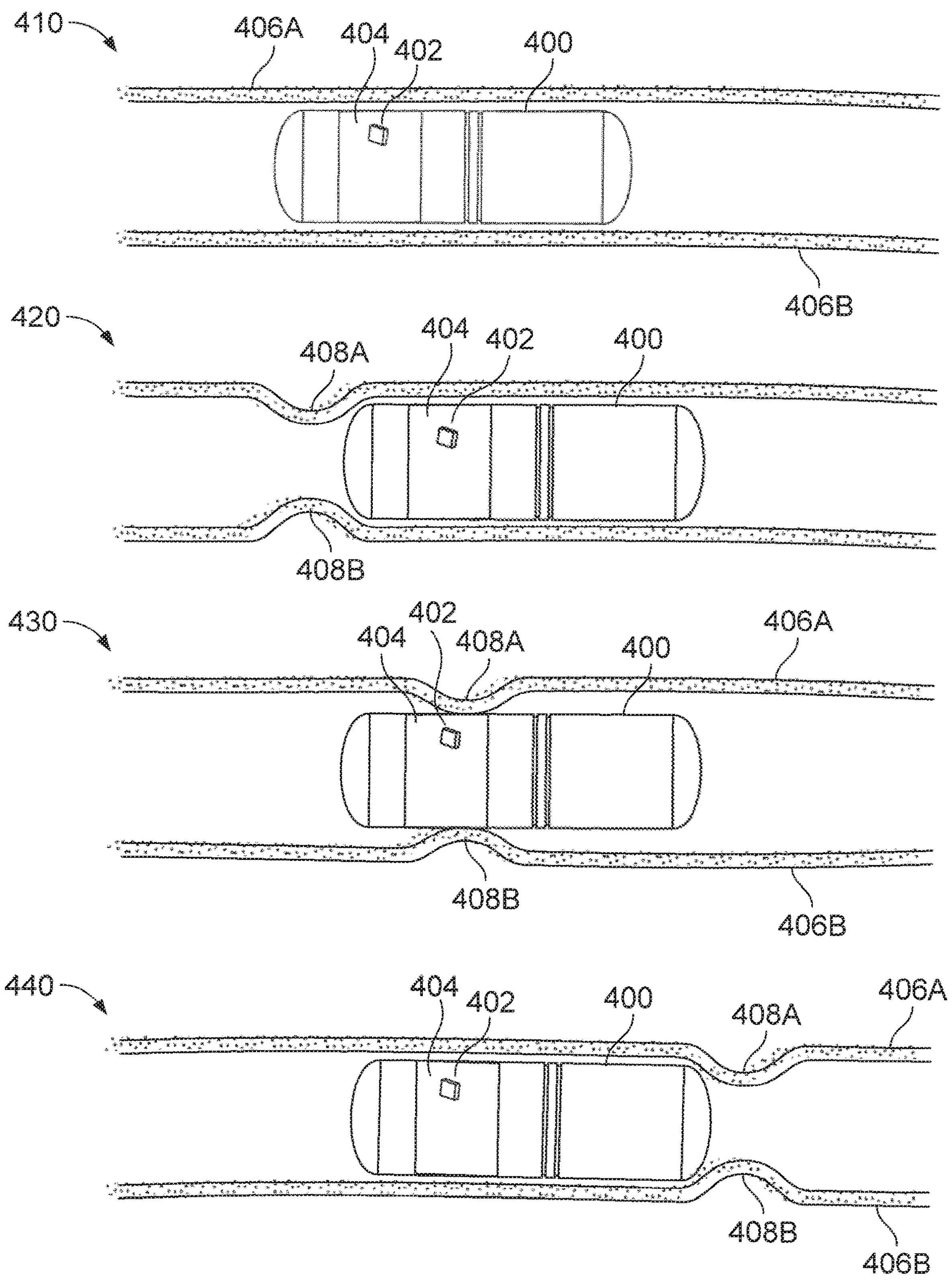
FIG. 4 is a diagram of an ingestible device during an example transit through a jejunum, in accordance with some embodiments of the disclosure.

FIG. 4 is a diagram of an ingestible device during an example transit through a jejunum, in accordance with some embodiments of the disclosure. Diagrams 410, 420, 430, and 440 depict ingestible device 400 as it traverses through a jejunum (e.g., jejunum 314), and how ingestible device 400 interacts with peristaltic waves formed by walls 406A and 406B (collectively, walls 406) of the jejunum. In some implementations, ingestible device 400 may include any portion of any other ingestible device discussed in this disclosure (e.g., ingestible device 100 (FIG. 1) or ingestible device 300 (FIG. 3)), and may be any suitable type of ingestible device with localization capabilities. For example, ingestible device 400 may be substantially similar to the ingestible device 300 (FIG. 3) or ingestible device 100 (FIG. 1), with window 404 being the same as window 114 (FIG. 1), and sensing sub-unit 402 being the same as sensing sub-unit 126 (FIG. 2).

Diagram 410 depicts ingestible device 400 within the jejunum, when the walls 406 of the jejunum are relaxed. In some embodiments, the confined tube-like structure of the jejunum naturally causes ingestible device 400 to be oriented longitudinally along the length of the jejunum, with window 404 facing walls 406. In this orientation, ingestible device 400 may use sensing sub-unit 402 to generate illumination (e.g., via illuminator 124 (FIG. 2)) oriented towards walls 406, and to detect the resulting reflectances (e.g., via detector 122 (FIG. 2)) from the portion of the illumination reflected off of walls 406 and back through window 404. In some embodiments, ingestible device 400 may be configured to use sensing sub-unit 402 to generate illumination and measure the resulting reflectance with sufficient frequency to detect peristaltic waves within the jejunum. For instance, in a healthy human subject, peristaltic waves may occur at a rate of approximately 0.1 Hz to 0.2 Hz. Therefore, the ingestible device 400 may be configured to generate illumination and measure the resulting reflectance at least once every 2.5 seconds (i.e., the minimum rate necessary to detect a 0.2 Hz signal), and preferably at a higher rate, such as once every 0.5 seconds, which may improve the overall reliability of the detection process due to more data points being available. It is understood that the ingestible device 400 need not gather measurements at precise intervals, and in some embodiments the ingestible device 400 may be adapted to analyze data gathered at more irregular intervals, provided that there are still a sufficient number of appropriately spaced data points to detect 0.1 Hz to 0.2 Hz signals.

Diagram 420 depicts ingestible device 400 within the jejunum, when the walls 406 of the jejunum begin to contract and form a peristaltic wave. Diagram 420 depicts contracting portion 408A of wall 406A and contracting portion 408B of wall 406B (collectively, contracting portion 408 of wall 406) that form a peristaltic wave within the jejunum. The peristaltic wave proceeds along the length of the jejunum as different portions of wall 406 contract and relax, causing it to appear as if contracting portions 408 of wall 406 proceed along the length of the jejunum (i.e., as depicted by contracting portions 408 proceeding from left to right in diagrams 410-430). While in this position, ingestible device 400 may detect a similar level of reflectance (e.g., through the use of illuminator 124 and detector 122 of sensing sub-unit 126 (FIG. 2)) as detected when there is no peristaltic wave occurring (e.g., as detected when ingestible device 400 is in the position indicated in diagram 410).

Diagram 430 depicts ingestible device 400 within the jejunum, when the walls 406 of the jejunum continue to contract, squeezing around ingestible device 400. As the peristaltic wave proceeds along the length of the jejunum, contracting portions 408 of wall 406 may squeeze tightly around ingestible device 400, bringing the inner surface of wall 406 into contact with window 404. While in this position, ingestible device 400 may detect a change in a reflectance detected as a result of illumination produced by sensing sub-unit 402. The absolute value of the change in the measured reflectance may depend on several factors, such as the optical properties of the window 404, the spectral components of the illumination, and the optical properties of the walls 406. However, ingestible device 400 may be configured to store a data set with the reflectance values over time, and search for periodic changes in the data set consistent with the frequency of the peristaltic waves (e.g., by analyzing the data set in the frequency domain, and searching for peaks between 0.1 Hz to 0.2 Hz). This may enable ingestible device 400 to detect muscle contractions due to peristaltic waves without foreknowledge of the exact changes in reflectance signal amplitude that may occur as a result of detecting the muscle contractions of the peristaltic wave. An example procedure for detecting muscle contractions is discussed further in relation to FIG. 9, and an example of a reflectance data set gathered while ingestible device 400 is located within the jejunum is discussed in relation to FIG. 10.

Diagram 440 depicts ingestible device 400 within the jejunum, when the peristaltic wave has moved past ingestible device 400. Diagram 440 depicts contracting portions 408 that form the peristaltic wave within the jejunum having moved past the end of ingestible device 400. The peristaltic wave proceeds along the length of the jejunum as different portions of wall 406 contract and relax, causing it to appear as if contracting portions 408 of wall 406 proceed along the length of the jejunum (i.e., as depicted by contracting portions 408 proceeding from left to right in diagrams 410-430). While in this position, ingestible device 400 may detect a similar level of reflectance (e.g., through the use of illuminator 124 and detector 122 of sensing sub-unit 126 (FIG. 2)) as detected when there is no peristaltic wave occurring (e.g., as detected when ingestible device 400 is in the position indicated in diagram 410, or diagram 420).

Depending on the species of the subject, peristaltic waves may occur with relatively predictable regularity. After the peristaltic wave has passed over ingestible device 400 (e.g., as depicted in diagram 440), the walls 406 of the jejunum may relax again (e.g., as depicted in diagram 410), until the next peristaltic wave begins to form. In some embodiments, ingestible device 400 may be configured to continue to gather reflectance value data while it is within the GI tract, and may store a data set with the reflectance values over time. This may allow ingestible device 400 to detect each of the muscle contractions as the peristaltic wave passes over ingestible device 400 (e.g., as depicted in diagram 430), and may enable ingestible device 400 to both count the number of muscle contractions that occur, and to determine that a current location of the ingestible device 400 is within the jejunum. For example, ingestible device 400 may be configured to monitor for possible muscle contractions while is inside either the stomach or the duodenum, and may determine that ingestible device 400 has moved to the jejunum in response to detecting a muscle contraction consistent with a peristaltic wave.

Figure 5:
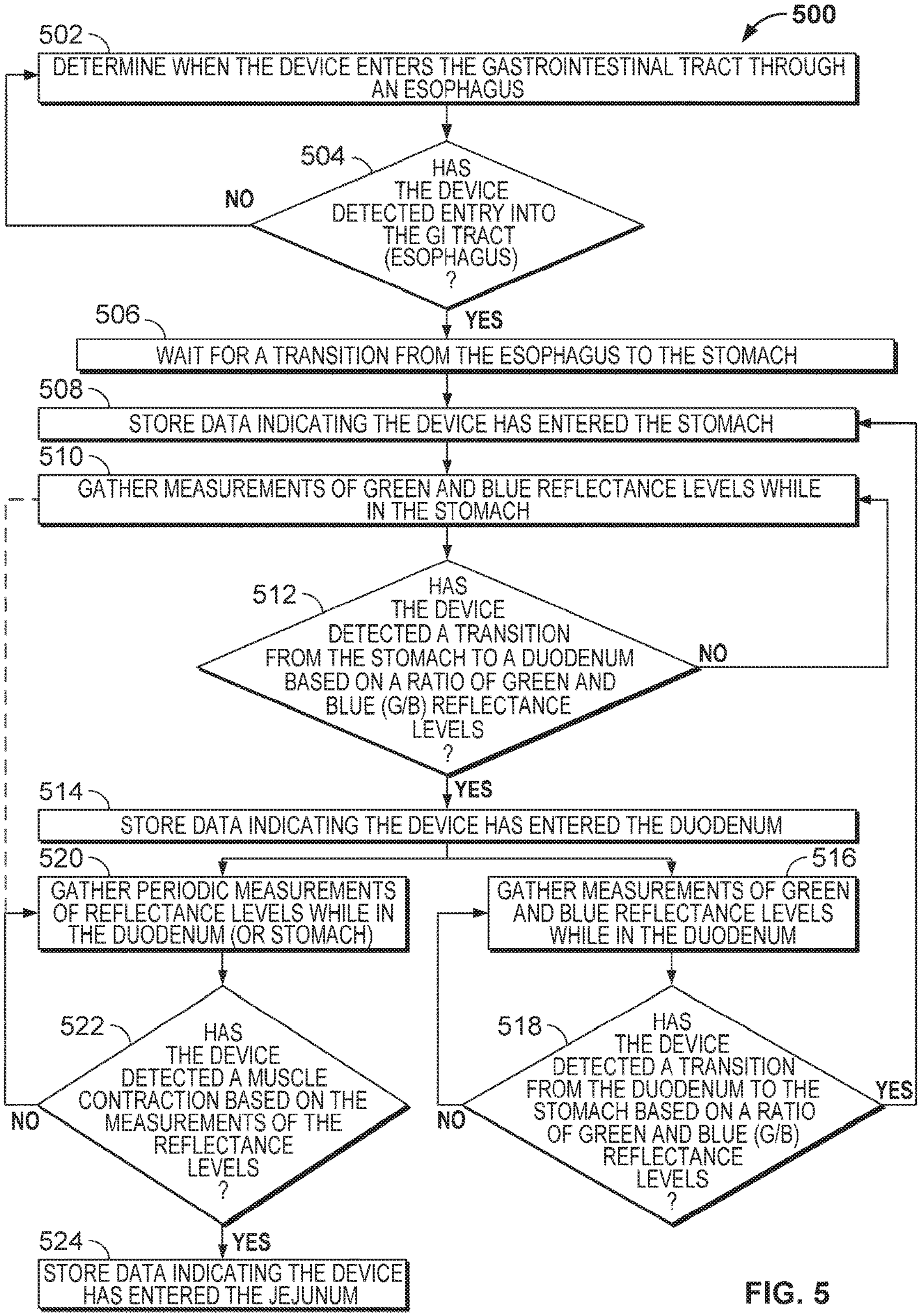
FIG. 5 is a flowchart of illustrative steps for determining a location of an ingestible device as it transits through a GI tract, in accordance with some embodiments of the disclosure.

FIG. 5 is a flowchart illustrating some aspects of a localization process used by the ingestible device. Although FIG. 5 may be described in connection with the ingestible device 100 for illustrative purposes, this is not intended to be limiting, and either portions or the entirety of the localization procedure 500 described in FIG. 5 may be applied to any device discussed in this application (e.g., the ingestible devices 100, 300, and 400), and any of the ingestible devices may be used to perform one or more parts of the process described in FIG. 5. Furthermore, the features of FIG. 5 may be combined with any other systems, methods or processes described in this application. For example, portions of the process in FIG. 5 may be integrated into or combined with the pyloric transition detection procedure described by FIG. 6, or the jejunum detection process described by FIG. 9.

At 502, the ingestible device (e.g., ingestible device 100, 300, or 400) gathers measurements (e.g., through detector 122 (FIG. 2)) of ambient light. For example, ingestible device 100 may be configured to periodically measure (e.g., through detector 122 (FIG. 2)) the level of ambient light in the environment surrounding ingestible device 100. In some embodiments, the type of ambient light being measured may depend on the configuration of detector 122 within ingestible device 100. For example, if detector 122 is configured to measure red, green, and blue wavelengths of light, ingestible device 100 may be configured to measure the ambient amount of red, green, and blue light from the surrounding environment. In some embodiments, the amount of ambient light measured by ingestible device 100 will be larger in the area external to the body (e.g., a well-lit room where ingestible device 100 is being administered to a subject) and in the oral cavity of the subject, as compared to the ambient level of light measured by ingestible device 100 when inside of an esophagus, stomach, or other portion of the GI tract (e.g., esophagus 302, stomach 306, duodenum 310, or jejunum 314 (FIG. 3)).

At 504, the ingestible device (e.g., ingestible device 100, 300, or 400) determines (e.g., via control circuitry within PCB 120 (FIG. 2)) whether the ingestible device has detected entry into the GI tract. For example, ingestible device 100 may be configured to determine when the most recent measurement of ambient light (e.g., the measurement gathered at 502) indicates that the ingestible device has entered the GI tract. For instance, the first time that ingestible device 100 gatherers a measurement of ambient light at 502, ingestible device 100 may store that measurement (e.g., via storage circuitry within PCB 120 (FIG. 2)) as a typical level of ambient light external to the body. Ingestible device 100 may be configured to then compare the most recent measurement of ambient light to the typical level of ambient light external to the body (e.g., via control circuitry within PCB 120 (FIG. 2)), and determine that ingestible device 100 has entered the GI tract when the most recent measurement of ambient light is substantially smaller than the typical level of ambient light external to the body. For example, ingestible device 100 may be configured to detect that it has entered the GI tract in response to determining that the most recent measurement of ambient light is less than or equal to 20% of the typical level of ambient light external to the body. If ingestible device 100 determines that it has detected entry into the GI tract (e.g., that ingestible device 100 has entered at least the esophagus 302 (FIG. 3)), process 500 proceeds to 506. Alternately, if ingestible device 100 determines that it has not detected entry into the GI tract (e.g., as a result of the most recent measurement being similar to the typical level of ambient light external to the body), process 500 proceeds back to 502 where the ingestible device 100 gathers further measurements. For instance, ingestible device 100 may be configured to wait a predetermined amount of time (e.g., five seconds, ten seconds, etc.), and then gather another measurement of the level of ambient light from the environment surrounding ingestible device 100.

At 506, the ingestible device (e.g., ingestible device 100, 300, or 400) waits for a transition from the esophagus to the stomach (e.g., from esophagus 302 to stomach 306 (FIG. 3)). For example, ingestible device 100 may be configured to determine that it has entered the stomach (e.g., stomach 306 (FIG. 3)) after waiting a predetermined period of time after having entered the GI tract. For instance, a typical esophageal transit time in a human patient may be on the order of 15-30 seconds. In this case, after having detected that ingestible device 100 has entered the GI tract at 504 (i.e., after detecting that ingestible device 100 has reached at least esophagus 302 (FIG. 3)), ingestible device 100 may be configured to wait one minute, or a similar amount of time longer than the typical esophageal transmit time (e.g., ninety-seconds), before automatically determining that ingestible device 100 has entered at least the stomach (e.g., stomach 306 (FIG. 3)).

In some embodiments, the ingestible device (e.g., ingestible device 100, 300, or 400) may also determine it has entered the stomach based on measurements of pH or temperature. For example, ingestible device 100 may be configured to determine that it has entered the stomach if a temperature of ingestible device has increased to at least 31 degrees Celsius (i.e., consistent with the temperature inside the stomach), or if a measured pH of the environment surrounding ingestible device 100 is sufficiently acidic (i.e., consistent with the acidic nature of gastric juices that may be found inside the stomach).

At 508, the ingestible device (e.g., ingestible device 100, 300, or 400) stores data indicating the ingestible device has entered the stomach (e.g., stomach 306 (FIG. 3)). For example, after having waited a sufficient amount of time at 506, ingestible device 100 may store data (e.g., within storage circuitry of PCB 120 (FIG. 2)) indicative of ingestible device 100 having entered at least the stomach. Once ingestible device 100 reaches at least the stomach, process 500 proceeds to 510 where ingestible device 100 may be configured to gather data to detect entry into the duodenum (e.g., duodenum 310 (FIG. 3)).

In some embodiments, process 500 may also simultaneously proceed from 508 to 520, where ingestible device 100 may be configured to gather data in order to detect muscle contractions and detect entry into the jejunum (e.g., jejunum 314 (FIG. 3)). In some embodiments, ingestible device 100 may be configured to simultaneously monitor for entry into the duodenum at 516-518, as well as detect for entry into the jejunum at 520-524. This may allow ingestible device 100 to determine when it has entered the jejunum (e.g., as a result of detecting muscle contractions), even when it fails to first detect entry into the duodenum (e.g., as a result of very quick transit times of the ingestible device through the duodenum).

At 510, the ingestible device (e.g., ingestible device 100, 300, or 400) gathers measurements of green and blue reflectance levels (e.g., through the use of illuminator 124 and detector 122 of sensing sub-unit 126 (FIG. 2)) while in the stomach (e.g., stomach 306 (FIG. 3)). For example, ingestible device 100 may be configured to periodically gather measurements of green and blue reflectance levels while in the stomach. For instance, ingestible device 100 may be configured to transmit a green illumination and a blue illumination (e.g., via illuminator 124 (FIG. 2)) every five to fifteen seconds, and measure the resulting reflectance (e.g., via detector 122 (FIG. 2)). Every time that ingestible device 100 gathers a new set of measurements, the measurements may be added to a stored data set (e.g., stored within memory circuitry of PCB 120 (FIG. 2)). The ingestible device 100 may then use this data set to determine whether or not ingestible device 100 is still within a stomach (e.g., stomach 306 (FIG. 3)), or a duodenum (e.g., duodenum 310 (FIG. 3)).

In some embodiments, the ingestible device (e.g., ingestible device 100, 300, or 400) may be configured to detect a first reflectance based on generating an illumination of a first wavelength in approximately the green spectrum of light (between 495-600 nm), and detecting a second reflectance based on generating an illumination of the second wavelength in approximately the blue spectrum of light (between 400-495 nm). In some embodiments, the ingestible device may ensure that the illumination in the green spectrum and the illumination in the blue spectrum have wavelengths separated by at least 50 nm. This may enable ingestible device 100 to sufficiently distinguish between the two wavelengths when detecting the reflectances (e.g., via detector 122 (FIG. 2)). It is understood that the separation of 50 nm is intended to be illustrative, and not limiting, and depending on the accuracy of the detectors within ingestible device 100, smaller separations may be possible to be used.

At 512, the ingestible device (e.g., ingestible device 100, 300, or 400) determines (e.g., using control circuitry within PCB 120 (FIG. 2)) whether the ingestible device has detected a transition from the stomach (e.g., stomach 306 (FIG. 3)) to a duodenum (e.g., duodenum 310 (FIG. 3)) based on a ratio of green and blue (G/B) reflectance levels. For example, ingestible device 100 may obtain (e.g., from memory circuitry of PCB 120 (FIG. 2)) a data set containing historical data for the respective ratio of the green reflectance to the blue reflectance as measured at a respective time. Generally speaking, a duodenum (e.g., duodenum 310 (FIG. 3)) of a human subject reflects a higher ratio of green light to blue light, as compared to the ratio of green light to blue light that is reflected by a stomach (e.g., stomach 306 (FIG. 3)). Based on this, ingestible device 100 may be configured to take a first set of ratios from the data set, representing the result of recent measurements, and compare them to a second set of ratios from the data set, representing the results of past measurements. When the ingestible device 100 determines that the mean value of the first set of ratios is substantially larger than the mean value of the second set of ratios (i.e., that the ratio of reflected green light to reflected blue light has increased), the ingestible device 100 may determine that it has entered the duodenum (e.g., duodenum 310 (FIG. 3)) from the stomach (e.g., stomach 306 (FIG. 3)). If the ingestible device 100 detects a transition from the stomach (e.g., stomach 306 (FIG. 3)) to a duodenum (e.g., duodenum 310 (FIG. 3)), process 500 proceeds to 514, where ingestible device 100 stores data indicating that the ingestible device 100 has entered the duodenum (e.g., duodenum 310 (FIG. 3)). Alternatively, if the ingestible device determines that the ingestible device has not transitioned from the stomach (e.g., stomach 306 (FIG. 3)) to the duodenum (e.g., duodenum 310 (FIG. 3)), process 500 proceeds back to 510 to gather more measurements of green and blue reflectance levels while still in the stomach (e.g., stomach 306 (FIG. 3)). An example procedure for using measurements of green and blue reflectances to monitor for transitions between the stomach and the duodenum is discussed in greater detail in relation to FIG. 6.

In some embodiments, the first time that ingestible device 100 detects a transition from the stomach (e.g., stomach 306 (FIG. 3)) to the duodenum (e.g., duodenum 310 (FIG. 3)), ingestible device 100 may be configured to take a mean of the second set of data, (e.g., the set of data previously recorded while in stomach 306 (FIG. 3)) and store this as a typical ratio of green light to blue light detected within the stomach (e.g., stomach 306 (FIG. 3)) (e.g., within memory circuitry of PCB 120 (FIG. 2)). This stored information may later be used by ingestible device 100 to determine when ingestible device 100 re-enters the stomach (e.g., stomach 306 (FIG. 3)) from the duodenum (e.g., duodenum 310 (FIG. 3)) as a result of a reverse pyloric transition.

At 514, the ingestible device (e.g., ingestible device 100, 300, or 400) stores data indicating that the ingestible device has entered the duodenum (e.g., duodenum 310 (FIG. 3)). For example, ingestible device 100 may store a flag within local memory (e.g., memory circuitry of PCB 120) indicating that the ingestible device 100 is currently in the duodenum. In some embodiments, the ingestible device 100 may also store a timestamp indicating the time when ingestible device 100 entered the duodenum. Once ingestible device 100 reaches the duodenum, process 500 proceeds to 520 where ingestible device 100 may be configured to gather data in order to detect muscle contractions and detect entry into the jejunum (e.g., jejunum 314 (FIG. 3)). Process 500 also proceeds from 514 to 516, where ingestible device 100 may be configured to gather data additional data in order to detect re-entry into the stomach (e.g., stomach 306 (FIG. 3)) from the duodenum (e.g., duodenum 310 (FIG. 3)).

At 516, the ingestible device (e.g., ingestible device 100, 300, or 400) gathers measurements (e.g., via sensing sub-unit 126 (FIG. 2)) of green and blue reflectance levels while in the duodenum (e.g., duodenum 310 (FIG. 3)). For example, ingestible device 100 may be configured to periodically gather measurements (e.g., via sensing sub-unit 126 (FIG. 2)) of green and blue reflectance levels while in the duodenum, similar to the measurements made at 510 while in the stomach. For instance, ingestible device 100 may be configured to transmit a green illumination and a blue illumination (e.g., via illuminator 124 (FIG. 2)) every five to fifteen seconds, and measure the resulting reflectance (e.g., via detector 122 (FIG. 2)). Every time that ingestible device 100 gathers a new set of measurements, the measurements may be added to a stored data set (e.g., stored within memory circuitry of PCB 120 (FIG. 2)). The ingestible device 100 may then use this data set to determine whether or not ingestible device 100 is still within the duodenum (e.g., duodenum 310 (FIG. 3)), or if the ingestible device 100 has transitioned back into the stomach (e.g., stomach 306 (FIG. 3)).

At 518, the ingestible device (e.g., ingestible device 100, 300, or 400) determines a transition from the duodenum (e.g., duodenum 310 (FIG. 3)) to the stomach (e.g., stomach 306 (FIG. 3)) based on a ratio of the measured green reflectance levels to the measured blue reflectance levels. In some embodiments, ingestible device 100 may compare the ratio of the measured green reflectance levels to the measured blue reflectance levels recently gathered by ingestible device 100 (e.g., measurements gathered at 516), and determine whether or not the ratio of the measured green reflectance levels to the measured blue reflectance levels is similar to the average ratio of the measured green reflectance levels to the measured blue reflectance levels seen in the stomach (e.g., stomach 306 (FIG. 3)). For instance, ingestible device 100 may retrieve data (e.g., from memory circuitry of PCB 120 (FIG. 2)) indicative of the average ratio of the measured green reflectance levels to the measured blue reflectance levels seen in the stomach, and determine that ingestible device 100 has transitioned back to the stomach if the recently measured ratio of the measured green reflectance levels to the measured blue reflectance levels is sufficiently similar to the average level in the stomach (e.g., within 20% of the average ratio of the measured green reflectance levels to the measured blue reflectance levels seen in the stomach, or within any other suitable threshold level). If the ingestible device detects a transition from the duodenum (e.g., duodenum 310 (FIG. 3)) to the stomach (e.g., stomach 306 (FIG. 3)), process 500 proceeds to 508 to store data indicating the ingestible device has entered the stomach (e.g., stomach 306 (FIG. 3)), and continues to monitor for further transitions. Alternatively, if the ingestible device does not detect a transition from the duodenum (e.g., duodenum 310 (FIG. 3)) to the stomach (e.g., stomach 306 (FIG. 3)), process 500 proceeds to 516 to gather additional measurements of green and blue reflectance levels while in the duodenum (e.g., duodenum 310 (FIG. 3)), which may be used to continuously monitor for possible transitions back into the stomach. An example procedure for using measurements of green and blue reflectances to monitor for transitions between the stomach and the duodenum is discussed in greater detail in relation to FIG. 6.

At 520, the ingestible device (e.g., ingestible device 100, 300, or 400) gathers periodic measurements of the reflectance levels (e.g., via sensing sub-unit 126 (FIG. 2)) while in the duodenum (e.g., duodenum 310 (FIG. 3)). In some embodiments, the ingestible device (e.g., ingestible device 100, 300, or 400) may gather similar periodic measurements while in the stomach as well. In some embodiments, these periodic measurements may enable ingestible device 100 to detect muscle contractions (e.g., muscle contractions due to a peristaltic wave as discussed in relation to FIG. 4), which may be indicative of entry into a jejunum (e.g., jejunum 314 (FIG. 3)). Ingestible device 100 may be configured to gather periodic measurements using any suitable wavelength of illumination (e.g., by generating illumination using illuminator 124, and detecting the resulting reflectance using detector 122 (FIG. 2)), or combinations of wavelengths of illumination. For example, in some embodiments, ingestible device 100 may be configured to generate red, green, and blue illumination, store separate data sets indicative of red, green, and blue illumination, and analyze each of the data sets separately to search for frequency components in the recorded data indicative of detected muscle contractions. In some embodiments, the measurements gathered by ingestible device 100 at 520 may be sufficiently fast as to detect peristaltic waves in a subject. For instance, in a healthy human subject, peristaltic waves may occur at a rate of approximately 0.1 Hz to 0.2 Hz. Therefore, the ingestible device 400 may be configured to generate illumination and measure the resulting reflectance at least once every 2.5 seconds (i.e., the minimum rate necessary to detect a 0.2 Hz signal), and preferably at a higher rate, such as once every 0.5 seconds or faster, and store values indicative of the resulting reflectances in a data set (e.g., within memory circuitry of PCB 120 (FIG. 2)). After gathering additional data (e.g., after gathering one new data point, or a predetermined number of new data points), process 500 proceeds to 522, where ingestible device 100 determines whether or not a muscle contraction has been detected.

At 522, the ingestible device (e.g., ingestible device 100, 300, or 400) determines (e.g., via control circuitry within PCB 120 (FIG. 0.2)) whether the ingestible device detects a muscle contraction based on the measurements of reflectance levels (e.g., as gathered by sensing sub-unit 126 (FIG. 2)). For example, ingestible device 100 may obtain a fixed amount of data stored as a result of measurements made at 520 (e.g., retrieve the past minute of data from memory circuitry within PCB 120 (FIG. 2)). Ingestible device 100 may then convert the obtained data into the frequency domain, and search for peaks in a frequency range that would be consistent with peristaltic waves. For example, in a healthy human subject, peristaltic waves may occur at a rate of approximately 0.1 Hz to 0.2 Hz, and an ingestible device 100 may be configured to search for peaks in the frequency domain representation of the data between 0.1 Hz and 0.2 Hz above a threshold value. If the ingestible device 100 detects a contraction based on the reflectance levels (e.g., based on detecting peaks in the frequency domain representation of the data between 0.1 Hz and 0.2 Hz), process 500 proceeds to 524 to store data indicating that the device has entered the jejunum. Alternatively, if the ingestible device 100 does not detect a muscle contraction, process 500 proceeds to 520 to gather periodic measurements of the reflectance levels while in the duodenum (e.g., duodenum 310 (FIG. 3)). In some embodiments, the ingestible device (e.g., ingestible device 100, 300, or 400) may store data (e.g., within memory circuitry of PCB 120 (FIG. 2)) indicating that a muscle contraction was detected, and process 500 will not proceed from 522 to 524 until a sufficient number of muscle contractions have been detected.

At 524, the ingestible device (e.g., ingestible device 100, 300, or 400) stores data (e.g., within memory circuitry of PCB 120 (FIG. 2)) indicating that the device has entered the jejunum (e.g., jejunum 314 (FIG. 3)). For example, in response to detecting that muscle contraction has occurred at 522, ingestible device 100 may determine that it has entered the jejunum 314, and is no longer inside of the duodenum (e.g., duodenum 310 (FIG. 3)) or the stomach (e.g., stomach 306 (FIG. 3)). In some embodiments, the ingestible device 100 may continue to measure muscle contractions while in the jejunum, and may store data indicative of the frequency, number, or strength of the muscle contractions over time (e.g., within memory circuitry of PCB 120 (FIG. 2)). In some embodiments, the ingestible device 100 may also be configured to monitor for one or more transitions. Such transitions can include a transition from the jejunum to the ileum, an ileocecal transition from the ileum to the cecum, a transition from the cecum to the colon, or detect exit from the body (e.g., by measuring reflectances, temperature, or levels of ambient light).

In some embodiments, the ingestible device (e.g., ingestible device 100, 300, or 400) may also determine that it has entered the jejunum (e.g., jejunum 314 (FIG. 3)) after a pre-determined amount of time has passed after having detected entry into the duodenum (e.g., duodenum 310 (FIG. 3)). For example, barring a reverse pyloric transition from the duodenum (e.g., duodenum 310 (FIG. 3)) back to the stomach (e.g., stomach 306 (FIG. 3)), the typical transit time for an ingestible device to reach the jejunum from the duodenum in a healthy human subject is less than three minutes. In some embodiments, the ingestible device (e.g., ingestible device 100, 300, or 400) may therefore be configured to automatically determine that it has entered the jejunum after spending at least three minutes within the duodenum. This determination may be made separately from the determination made based on measured muscle contractions (e.g., the determination made at 522), and in some embodiments, ingestible device 100 may determine that it has entered the jejunum in response to either detecting muscle contractions, or after three minutes has elapsed from having entered the duodenum (e.g., as determined by storing data at 514 indicative of the time that ingestible device entered the duodenum).

For illustrative purposes, 512-518 of process 500 describe the ingestible device (e.g., ingestible device 100, 300, or 400) measuring green reflectances and blue reflectances, calculating a ratio of the two reflectances, and using this information to determine when the ingestible device has transitioned between the duodenum and stomach. However, in some embodiments, other wavelengths of light may be used other than green and blue, provided that the wavelengths of light chosen have different reflective properties within the stomach and the duodenum (e.g., as a result of different reflection coefficients of the stomach tissue and the tissue of the duodenum).

It will be understood that the steps and descriptions of the flowcharts of this disclosure, including FIG. 5, are merely illustrative. Any of the steps and descriptions of the flowcharts, including FIG. 5, may be modified, omitted, rearranged, and performed in alternate orders or in parallel, two or more of the steps may be combined, or any additional steps may be added, without departing from the scope of the present disclosure. For example, the ingestible device 100 may calculate the mean and the standard deviation of multiple data sets in parallel in order to speed up the overall computation time. As another example, ingestible device 100 may gather data periodic measurements and detect possible muscle contractions (e.g., at 520-522) while simultaneously gathering green and blue reflectance levels to determine transitions to and from the stomach and duodenum (e.g., at 510-518). Furthermore, it should be noted that the steps and descriptions of FIG. 5 may be combined with any other system, device, or method described in this application, including processes 600 (FIG. 6) and 900 (FIG. 9), and any of the ingestible devices or systems discussed in this application (e.g., ingestible devices 100, 300, or 400) could be used to perform one or more of the steps in FIG. 5.

Figure 6:
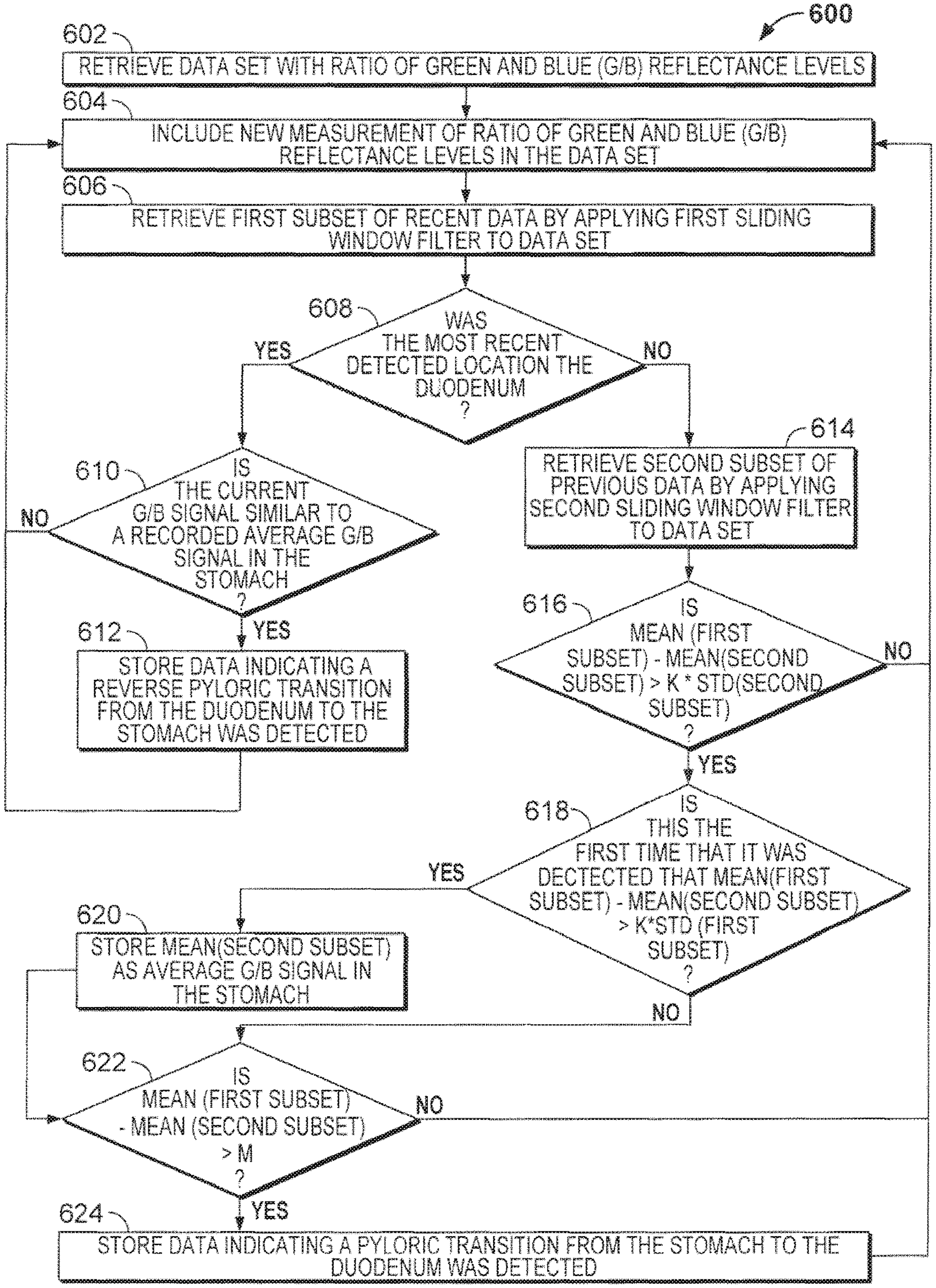
FIG. 6 is a flowchart of illustrative steps for detecting transitions from a stomach to a duodenum and from a duodenum back to a stomach, which may be used when determining a location of an ingestible device as it transits through a GI tract, in accordance with some embodiments of the disclosure.

FIG. 6 is a flowchart illustrating some aspects of a process for detecting transitions from a stomach to a duodenum and from a duodenum back to a stomach, which may be used when determining a location of an ingestible device as it transits through a gastrointestinal (GI) tract, in accordance with some embodiments of the disclosure. In some embodiments, process 600 may begin when an ingestible device first detects that it has entered the stomach, and will continue as long as the ingestible device determines that it is within the stomach or the duodenum. In some embodiments, process 600 may only be terminated when an ingestible device determines that it has entered the jejunum, or otherwise progressed past the duodenum and the stomach. Although FIG. 6 may be described in connection with the ingestible device 100 for illustrative purposes, this is not intended to be limiting, and either portions or the entirety of the duodenum detection process 600 described in FIG. 6 may be applied to any device discussed in this application (e.g., the ingestible devices 100, 300, or 400), and any of the ingestible devices may be used to perform one or more parts of the process described in FIG. 6. Furthermore, the features of FIG. 6 may be combined with any other systems, methods or processes described in this application. For example, portions of the process described by the process in FIG. 6 may be integrated into process 500 discussed in relation to FIG. 5.

At 602, the ingestible device (e.g., ingestible device 100, 300, or 400) retrieves a data set (e.g., from memory circuitry within PCB 120 (FIG. 2)) with ratios of the measured green reflectance levels to the measured blue reflectance levels over time. For example, ingestible device 100 may retrieve a data set from PCB 120 containing recently recorded ratios of the measured green reflectance levels to the measured blue reflectance levels (e.g., as recorded at 510 or 516 of process 500 (FIG. 5)). In some embodiments, the retrieved data set may include the ratios of the measured green reflectance levels to the measured blue reflectance levels over time. Example plots of data sets of ratios of the measured green reflectance levels to the measured blue reflectance levels are discussed further in relation to FIG. 7 and FIG. 8.

At 604, the ingestible device (e.g., ingestible device 100, 300, or 400) includes a new measurement (e.g., as made with sensing sub-unit 126 (FIG. 2)) of a ratio of the measured green reflectance level to the measured blue reflectance level in the data set. For example, ingestible device 100 may be configured to occasionally record new data by transmitting green and blue illumination (e.g., via illuminator 124 (FIG. 2)), detecting the amount of reflectance received due to the green and blue illumination (e.g., via detector 122 (FIG. 2)), and storing data indicative of the amount of the received reflectance (e.g., in memory circuitry of PCB 120 (FIG. 2)). The ingestible device 100 may be configured to record new data every five to fifteen seconds, or at any other convenient interval of time. For illustrative purposes, ingestible device 100 is described as storing and retrieving the ratio of the measured green reflectance levels to the measured blue reflectance levels (e.g., if the amount of detected green reflectance was identical to the amount of detected blue reflectance at a given time, the ratio of the green and blue reflectances would be “1.0” at that given time); however, it is understood that the green reflectance data and the blue reflectance data may be stored separately within the memory of ingestible device 100 (e.g., stored as two separate data sets within memory circuitry of PCB 120 (FIG. 2)).

At 606, the ingestible device (e.g., ingestible device 100, 300, or 400) retrieves a first subset of recent data by applying a first sliding window filter to the data set. For example, ingestible device 100 may use a sliding window filter to obtain a predetermined amount of the most recent data within the data set, which may include any new values of the ratio of the measured green reflectance level to the measured blue reflectance level obtained at 604. For instance, the ingestible device may be configured to select between ten and forty data points from the data set, or ingestible device 100 may be configured to select a predetermined range of data values between fifteen seconds of data and five minutes of data. In some embodiments, other ranges of data may be selected, depending on how frequently measurements are recorded, and the particular application at hand. For instance, any suitable amount of data may be selected in the sliding window, provided that it is sufficient to detect statistically significant differences between the data selected in a second sliding window (e.g., the second subset of data selected at 614).

In some embodiments, the ingestible device (e.g., ingestible device 100, 300, or 400) may also be configured to remove outliers from the data set, or to smooth out unwanted noise in the data set. For example, ingestible device 100 may select the first subset of data, or any other subset of data, by first obtaining a raw set of values by applying a window filter to the data set (e.g., selecting a particular range of data to be included). Ingestible device 100 may then be configured to identify outliers in the raw set of values; for instance, by identifying data points that are over three standard deviations away from the mean value of the raw set of values, or any other suitable threshold. Ingestible device 100 may then determine the subset of data by removing outliers from the raw set of values. This may enable ingestible device 100 to avoid spurious information when determining whether or not it is located within the stomach or the duodenum.

At 608, the ingestible device (e.g., ingestible device 100, 300, or 400) determines whether the most recently detected location was the duodenum (e.g., duodenum 310 (FIG. 3)). In some embodiments, ingestible device 100 may store a data flag (e.g., within memory circuitry of PCB 120 (FIG. 2)) indicating the most recent portion of the GI tract that the ingestible device 100 detected itself to be within. For instance, every time ingestible device 100 detects entry to the stomach (e.g., detects entry into stomach 306 (FIG. 3) as a result of the decision made at 610), a flag is stored in memory indicating the ingestible device 100 is in the stomach (e.g., as part of storing data at 612). If ingestible device 100 subsequently detects entry into the duodenum (e.g., detects entry into duodenum 310 (FIG. 3) as a result of a decision made at 624), another different flag is stored in memory indicating that the ingestible device 100 is in the duodenum (e.g., as part of storing data at 624). In this case, ingestible device 100 may retrieve the most recently stored flag at 608, and determine whether or not the flag indicates that the ingestible device 100 was most recently within the duodenum. If ingestible device 100 detects that it was most recently in the duodenum, process 600 proceeds to 610 where the ingestible device compares the recent measurements of the ratios of the measured green reflectance levels to the measured blue reflectance levels (e.g., measurements that include the recent measurement made at 606) to the typical ratios measured within the stomach, and uses this information to determine whether a reverse pyloric transition from the duodenum back to the stomach has occurred. Alternately, if ingestible device 100 detects that it was not most recently in the duodenum (e.g., because it was in the stomach instead), process 600 proceeds to 614 where the ingestible device compares the recent measurements of the ratios of the measured green reflectance levels to the measured blue reflectance levels (e.g., measurements that include the recent measurement made at 606) to past measurements, and uses this information to determine whether a pyloric transition from the stomach to the duodenum has occurred.

Process 600 proceeds from 608 to 610 when the ingestible device determined that it was most recently in the duodenum. At 610, the ingestible device (e.g., ingestible device 100, 300, or 400) determines (e.g., via control circuitry within PCB 120 (FIG. 2)) whether the current G/B signal is similar to a recorded average G/B signal in the stomach. For example, ingestible device 100 may be configured to have previously stored data (e.g., within memory circuitry of PCB 120 (FIG. 2)) indicative of the average ratio of the measured green reflectance levels to the measured blue reflectance levels measured in the stomach. Ingestible device 100 may then retrieve this stored data indicative of the average ratio of the measured green reflectance levels to the measured blue reflectance levels in the stomach, and compare this against the recent measurements in order to determine whether or not ingestible device 100 has returned back to the stomach from the duodenum. For instance, ingestible device 100 may determine if the mean value of the first subset of recent data (i.e., the average value of the recently measured ratios of the measured green reflectance levels to the measured blue reflectance levels) is less than the average ratio of the measured green reflectance levels to the measured blue reflectance levels within the stomach, or less that the average ratio measured within the stomach plus a predetermined number times the standard deviation of the ratios measured within the stomach. For instance, if the average ratio of the measured green reflectance levels to the measured blue reflectance levels in the stomach was “1,” with a standard deviation of “0.2,” ingestible device 100 may determine whether or not the mean value of the first subset of data is less than “1.0+k*0.2,” where “k” is a number between zero and five. It is understood that, in some embodiments, the ingestible device 100 may be configured to use a different threshold level to determine whether or not the mean value of the first subset of recent data is sufficiently similar to the average ratio of the measured green reflectance levels to the measured blue reflectance levels within the stomach. In response to determining that the recent ratio of the measured green reflectance levels to the measured blue reflectance levels is similar to the average ratio of measured green and blue reflectance levels seen in the stomach, process 600 proceeds to 612 where ingestible device 100 stores data indicating that it has re-entered the stomach from the duodenum. Alternately, in response to determining that the recent ratio of measured green and blue reflectance levels is sufficiently different from the average ratio of measured green and blue reflectance levels seen in the stomach, ingestible device 100 proceeds directly to 604, and continues to obtain new data on an ongoing basis.

At 612, the ingestible device (e.g., ingestible device 100, 300, or 400) stores data indicating a reverse pyloric transition from the duodenum to the stomach was detected. For example ingestible device 100 may store a data flag (e.g., within memory circuitry of PCB 120 (FIG. 2)) indicating that the ingestible device 100 most recently detected itself to be within the stomach portion of the GI tract (e.g., stomach 306 (FIG. 3)). In some embodiments, ingestible device 100 may also store data (e.g., within memory circuitry of PCB 120 (FIG. 2)) indicating a time that ingestible device 100 detected the reverse pyloric transition from the duodenum to the stomach. This information may be used by ingestible device 100 at 608, and as a result process 600 may proceed from 608 to 614, rather than proceeding from 618 to 610. After ingestible device 100 stores the data indicating a reverse pyloric transition from the duodenum to the stomach was detected, process 600 proceeds to 604 where ingestible device 100 continues to gather additional measurements, and continues to monitor for further transitions between the stomach and the duodenum.

Process 600 proceeds from 608 to 614 when the ingestible device determined that it was not most recently in the duodenum (e.g., as a result of having most recently been in the stomach instead). At 614, the ingestible device (e.g., ingestible device 100, 300, or 400) retrieves a second subset of previous data by applying a second sliding window filter to the data set. For example, ingestible device 100 may use a sliding window filter to obtain a predetermined amount of older data from a past time range, which may be separated from recent time range used to select the first subset of data gathered at 606 by a predetermined period of time. In some embodiments, any suitable amount of data may be selected by the first and second window filters, and the first and second window filters may be separated by any appropriate predetermined amount of time. For example, in some embodiments, the first window filter and the second window filter may each be configured to select a predetermined range of data values from the data set, the predetermined range being between fifteen seconds of data and five minutes of data. In some embodiments, the recent measurements and the past measurements may then be separated by a predetermined period of time that is between one to five times the predetermined range of data values. For instance, ingestible device 100 may select the first subset of data and the second subset of data to each be one minute of data selected from the dataset (i.e., selected to have a predetermined range of one minute), and the first subset of data and the second subset of data are selected from recorded measurements that are at least two minutes apart (i.e., the predetermined period of time is two minutes, which is twice the range used to select the subsets of data using the window filters). As another example, ingestible device 100 may select the first subset of data and the second subset of data to each be five minutes of data selected from the dataset (i.e., selected to have a predetermined range of five minutes), and the first subset of data and the second subset of data are selected from recorded measurements that are at least 10 minutes apart (i.e., the predetermined period of time is two minutes, which is twice the range used to select the subsets of data using the window filters).

In some embodiments, if ingestible device 100 recently transitioned to the stomach from the duodenum (e.g., as determined by checking for recent data stored within ingestible device 100 at 612), ingestible device 100 may select the second subset of data at 614 from a time frame when ingestible device 100 is known to be within the stomach. In some embodiments, ingestible device 100 may alternately select a previously recorded average and standard deviation for ratios of green reflectances and blue reflectances within the stomach (e.g., an average and standard deviation typical of data recorded within the stomach, as previously recorded within memory circuitry of PCB 120 at 620) in place of the second subset of data. In this case, ingestible device 100 may simply use the previously recorded average and previously recorded standard deviation when making a determination at 616, rather than expending resources to calculate the mean and standard deviation of the second subset.

At 616, the ingestible device (e.g., ingestible device 100, 300, or 400) determines whether the difference between the mean of the second subset and the mean of the first subset is greater than a predetermined multiple of the standard deviation of the first subset. For example, ingestible device 100 may compute a difference between a mean of the first subset of recent data and a mean of a second subset of past data, and determine whether this difference is greater than three times the standard deviation of the second subset of past data. In some embodiments, it is understood that any convenient threshold level may be used other than three times the standard deviation, such as any value between one and five times the standard deviation. Also, in some embodiments, the ingestible device may instead set the threshold level based on the standard deviation of the second subset instead of the first subset. In response to determining that the difference between the mean of the first subset and the mean of the second subset is greater than a predetermined multiple of the standard deviation of the second subset, process 600 proceeds to 618. Otherwise, process 600 proceeds back to 604, where the ingestible device 604 continues to gather new data to be used in monitoring for transitions between the stomach (e.g., stomach 306 (FIG. 3)) and the duodenum (e.g., duodenum 310 (FIG. 3)).

At 618, the ingestible device (e.g., ingestible device 100, 300, or 400) determines (e.g., via control circuitry within PCB 120 (FIG. 2)) whether the determination made at 616 is the first time that the difference between the mean of the first subset of recent data and the mean of the second subset of past data is calculated to be greater than the standard deviation of the second subset. If the ingestible device determines that this is the first time that the difference between the mean of the first subset and the mean of the second subset is calculated to be greater than the standard deviation of the second subset, process 600 proceeds to 620 to store the mean of the second subset of past data as an average G/B signal in the stomach. Alternatively, if the ingestible device determines that the immediately preceding determination made at 616 is not the first time that the difference between the mean of the first subset of recent data and the mean of the second subset of past data is calculated to be greater than the standard deviation of the second subset, process 600 proceeds directly to 622.

At 620, the ingestible device (e.g., ingestible device 100, 300, or 400) stores the mean of the second subset as an average G/B signal in the stomach. For example, ingestible device 100 may be configured to store the mean of the second subset of past data (e.g., store within memory circuitry of PCB 120 (FIG. 2)) as the average ratio of the measured green reflectance levels to the measured blue reflectance levels measured in the stomach. In some embodiments, ingestible device 100 may also store the standard deviation of the second subset of past data as a typical standard deviation of the ratios of the measured green reflectance levels to the measured blue reflectance levels detected within the stomach. This stored information may be used by the ingestible device later on (e.g., at 610) to compare against future data, which may enable the ingestible device to detect reverse pyloric transitions from the duodenum (e.g., duodenum 310 (FIG. 3)) back to the stomach (e.g., stomach 306 (FIG. 3)), and may generally be used in place of other experimental data gathered from the stomach (e.g., in place of the second subset of data at 616). After storing the mean of the second subset as an average G/B signal in the stomach, process 600 proceeds to 622.

At 622, the ingestible device (e.g., ingestible device 100, 300, or 400) determines whether a difference of the mean of the first subset of recent data to the mean of the second subset of past data is greater than a predetermined threshold, "M". In some embodiments, the predetermined threshold, "M," will be sufficiently large to ensure that the mean of the first subset is substantially larger than the mean of the second subset, and may enable ingestible device 100 to ensure that it detected an actual transition to the duodenum. This may be particularly advantageous when the determination made at 616 is potentially unreliable due to the standard deviation of the second subset of past data being abnormally small. For example, a typical value of the predetermined threshold "M," may be on the order of 0.1 to 0.5. If ingestible device 100 determines that the difference of the mean of the first subset of recent data to the second subset of past data is greater than a predetermined threshold, process 600 proceeds to 624 to store data indicating that a pyloric transition from the stomach to the duodenum (e.g., from stomach 306 to duodenum 310 (FIG. 3)) was detected. Alternatively, if the ingestible device determines that the ratio of the mean of the first subset to the second subset is less than or equal to the predetermined threshold, "M" (i.e., determines that a transition to the duodenum has not occurred), process 600 proceeds directly to 604 where ingestible device 100 continues to make new measurements and monitor for possible transitions between the stomach and the duodenum.

In some embodiments, instead of using a difference of the mean of the first subset of recent data to the mean of the second subset of past data, the ingestible device (e.g., ingestible device 100, 300, or 400) determines whether the ratio of the mean of the first subset of recent data to the mean of the second subset of past data is greater than a predetermined threshold, "M". In some embodiments, the predetermined threshold, "M," will be sufficiently large to ensure that the mean of the first subset is substantially larger than the mean of the second subset, and may enable ingestible device 100 to ensure that it detected an actual transition to the duodenum. This may be particularly advantageous when the determination made at 616 is potentially unreliable due to the standard deviation of the second subset of past data being abnormally small. For example, a typical value of the predetermined threshold "M," may be on the order of 1.2 to 2.0. It is understood any convenient type of threshold or calculation may be used to determine whether or not the first subset of data and the second subset of data are both statistically distinct from one another, and also substantially different from one another in terms of overall average value.

At 624, the ingestible device (e.g., ingestible device 100, 300, or 400) stores data indicating a pyloric transition from the stomach to the duodenum was detected. For example ingestible device 100 may store a data flag (e.g., within memory circuitry of PCB 120 (FIG. 2)) indicating that the ingestible device 100 most recently detected itself to be within the duodenum portion of the GI tract (e.g., duodenum 310 (FIG. 3)). In some embodiments, ingestible device 100 may also store data (e.g., within memory circuitry of PCB 120 (FIG. 2)) indicating a time that ingestible device 100 detected the pyloric transition from the stomach to the duodenum. This information may be used by ingestible device 100 at 608, and as a result process 600 may proceed from 608 to 610, rather than proceeding from 618 to 614. After ingestible device 100 stores the data indicating a pyloric transition from the stomach to the duodenum was detected, process 600 proceeds to 604 where ingestible device 100 continues to gather additional measurements, and continues to monitor for further transitions between the stomach and the duodenum.

It will be understood that the steps and descriptions of the flowcharts of this disclosure, including FIG. 6, are merely illustrative. Any of the steps and descriptions of the flowcharts, including FIG. 6, may be modified, omitted, rearranged, and performed in alternate orders or in parallel, two or more of the steps may be combined, or any additional steps may be added, without departing from the scope of the present disclosure. For example, the ingestible device 100 may calculate the mean and the standard deviation of multiple data sets in parallel in order to speed up the overall computation time. Furthermore, it should be noted that the steps and descriptions of FIG. 6 may be combined with any other system, device, or method described in this application, and any of the ingestible devices or systems discussed in this application could be used to perform one or more of the steps in FIG. 6. For example, portions of process 600 may be incorporated into 508-516 of process 500 (FIG. 5), and may be part of a more general process for determining a location of the ingestible device. As another example, the ratio of detected blue and green light (e.g., as measured and added to the data set at 604) may continue even outside of the stomach or duodenum, and similar information may be recorded by the ingestible device throughout its transit in the GI tract. Example plots of data sets of ratios of measured green and blue reflectance levels, which may be gathered throughout the GI tract, are discussed further in relation to FIG. 7 and FIG. 8 below.

Figure 7:
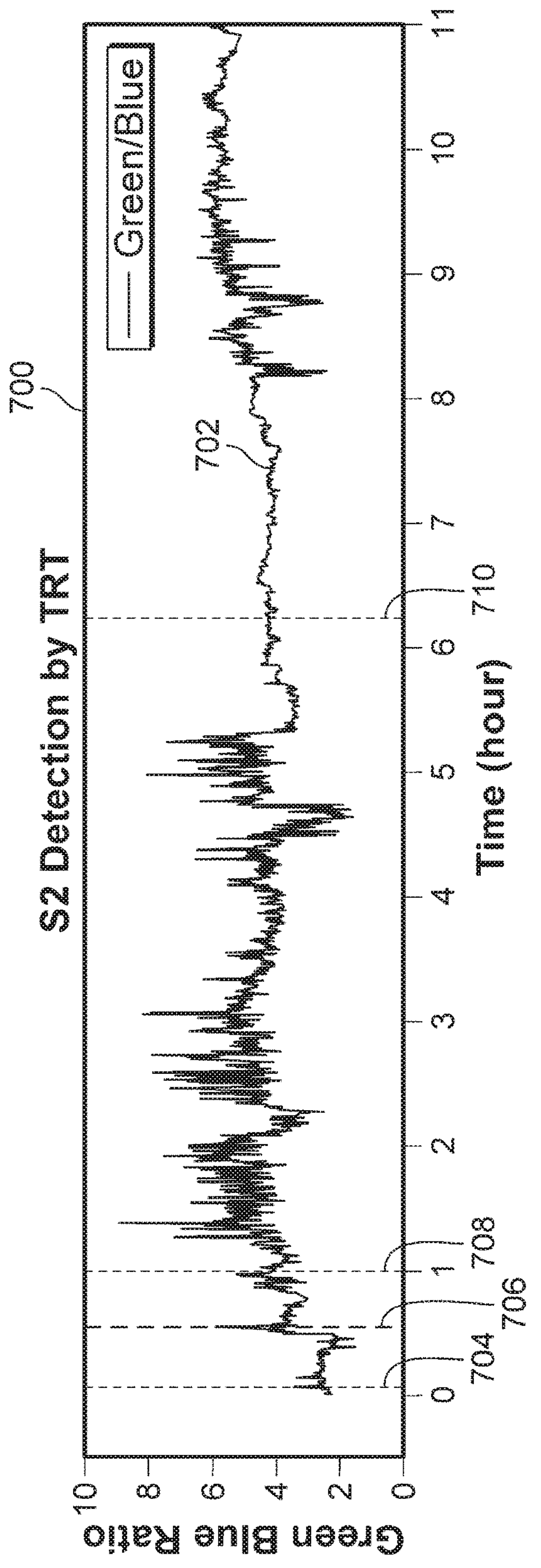
FIG. 7 is a plot illustrating data collected during an example operation of an ingestible device, which may be used when determining a location of an ingestible device as it transits through a GI tract, in accordance with some embodiments of the disclosure.

FIG. 7 is a plot illustrating data collected during an example operation of an ingestible device (e.g., ingestible device 100, 300, or 400), which may be used when determining a location of an ingestible device as it transits through a gastrointestinal (GI) tract, in accordance with some embodiments of the disclosure.

Although FIG. 7 may be described in connection with ingestible device 100 for illustrative purposes, this is not intended to be limiting, and plot 700 and data set 702 may be typical of data gathered by any device discussed in this application. Plot 700 depicts the ratios of the measured green reflectance levels to the measured blue reflectance levels over time. For example, ingestible device 100 may have computed the value for each point in the data set 702 by transmitting green and blue illumination at a given time (e.g., via illuminator 124 (FIG. 2)), measuring the resulting green and blue reflectances (e.g., via detector 122 (FIG. 2)), calculating the ratio of the resulting reflectances, and storing the ratio in the data set along with a timestamp indicating the time that the reflectances were gathered.

At 704, shortly after ingestible device 100 begins operation, ingestible device 100 determines that it has reached at least the stomach (e.g., as a result of making a determination similar to the determination discussed in relation to 506 in process 500 (FIG. 5)). Ingestible device 100 continues to gather additional measurements of green and blue reflectance levels, and at 706 ingestible device 100, determines that a pyloric transition has occurred from the stomach to the duodenum (e.g., as a result of making a determination similar to the determinations discussed in relation to 616-624 of process 600 (FIG. 6)). Notably, the values in data set 702 around 706 jump up precipitously, which is indicative of the higher ratios of measured green reflectance levels to measured blue reflectance levels typical of the duodenum.

The remainder of the data set 702 depicts the ratios of the measured green reflectance levels to the measured blue reflectance levels throughout the remainder of the GI tract. At 708, ingestible device 100 has reached the jejunum (e.g., as determined through measurements of muscle contractions, as discussed in relation to FIG. 9), and by 710, ingestible device 100 has reached the cecum. It is understood that, in some embodiments, the overall character and appearance of data set 702 changes within the small intestine (i.e., the duodenum, jejunum, and ileum) versus the cecum. Within the jejunum and ileum, there may typically be a wide variation in the ratios of the measured green reflectance levels to the measured blue reflectance levels, resulting in relatively noisy data with a high standard deviation. By comparison, within the cecum ingestible device 100 may measure a relatively stable ratio of the measured green reflectance levels to the measured blue reflectance levels. In some embodiments, ingestible device 100 may be configured to determine transitions from the small intestine to the cecum based on these differences. For example, ingestible device 100 may compare recent windows of data to past windows of data, and detect a transition to the cecum in response to determining that the standard deviation of the ratios in the recent window of data is substantially less than the standard deviation of the ratios in the past window of data.

Figure 8:
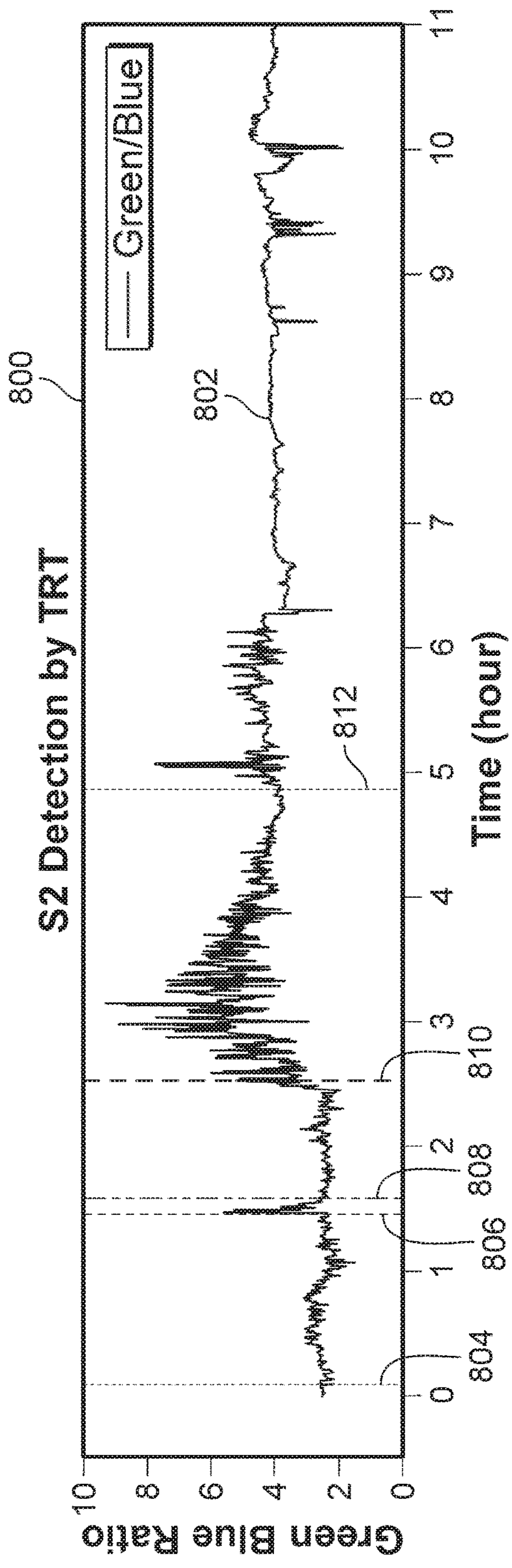
FIG. 8 is another plot illustrating data collected during an example operation of an ingestible device, which may be used when determining a location of an ingestible device as it transits through a GI tract, in accordance with some embodiments of the disclosure.

FIG. 8 is another plot illustrating data collected during an example operation of an ingestible device, which may be used when determining a location of an ingestible device as it transits through a gastrointestinal (GI) tract, in accordance with some embodiments of the disclosure. Similar to FIG. 7, FIG. 8 may be described in connection with the ingestible device 100 for illustrative purposes. However, this is not intended to be limiting, and plot 800 and data set 802 may be typical of data gathered by any device discussed in this application.

At 804, shortly after ingestible device 100 begins operation, ingestible device 100 determines that it has reached at least the stomach (e.g., as a result of making a determination similar to the determination discussed in relation to 506 in process 500 (FIG. 5)). Ingestible device 100 continues to gather additional measurements of green and blue reflectance levels (e.g., via sensing sub-unit 126 (FIG. 2)), and at 806 ingestible device 100 determines that a pyloric transition has occurred from the stomach to the duodenum (e.g., as a result of making a determination similar to the determinations discussed in relation to 616-624 of process 600 (FIG. 6)). Notably, the values in data set 802 around 806 jump up precipitously, which is indicative of the higher ratios of measured green reflectance levels to measured blue reflectance levels typical of the duodenum, before falling shortly thereafter. As a result of the reduced values in data set 802, ingestible device 100 determines that a reverse pyloric transition has occurred from the duodenum back to the stomach at 808 (e.g., as a result of making a determination similar to the determinations discussed in relation to 610-612 of process 600 (FIG. 6)). At 810, as a result of the values in data set 802 increasing again, ingestible device 100 determines that another pyloric transition has occurred from the stomach to the duodenum, and shortly thereafter ingestible device 100 proceeds onwards to the jejunum, ileum, and cecum.

The remainder of the data set 802 depicts the ratios of the measured green reflectance levels to the measured blue reflectance levels throughout the remainder of the GI tract. Notably, at 812, ingestible device reaches the transition point between the ileum and the cecum. As discussed above in relation to FIG. 7, the transition to the cecum is marked by a reduced standard deviation in the ratios of measured green reflectances and measured blue reflectances over time, and ingestible device 100 may be configured to detect a transition to the cecum based on determining that the standard deviation of a recent set of measurements is substantially smaller than the standard deviation of past measurements taken from the jejunum or ileum.

Figure 9:
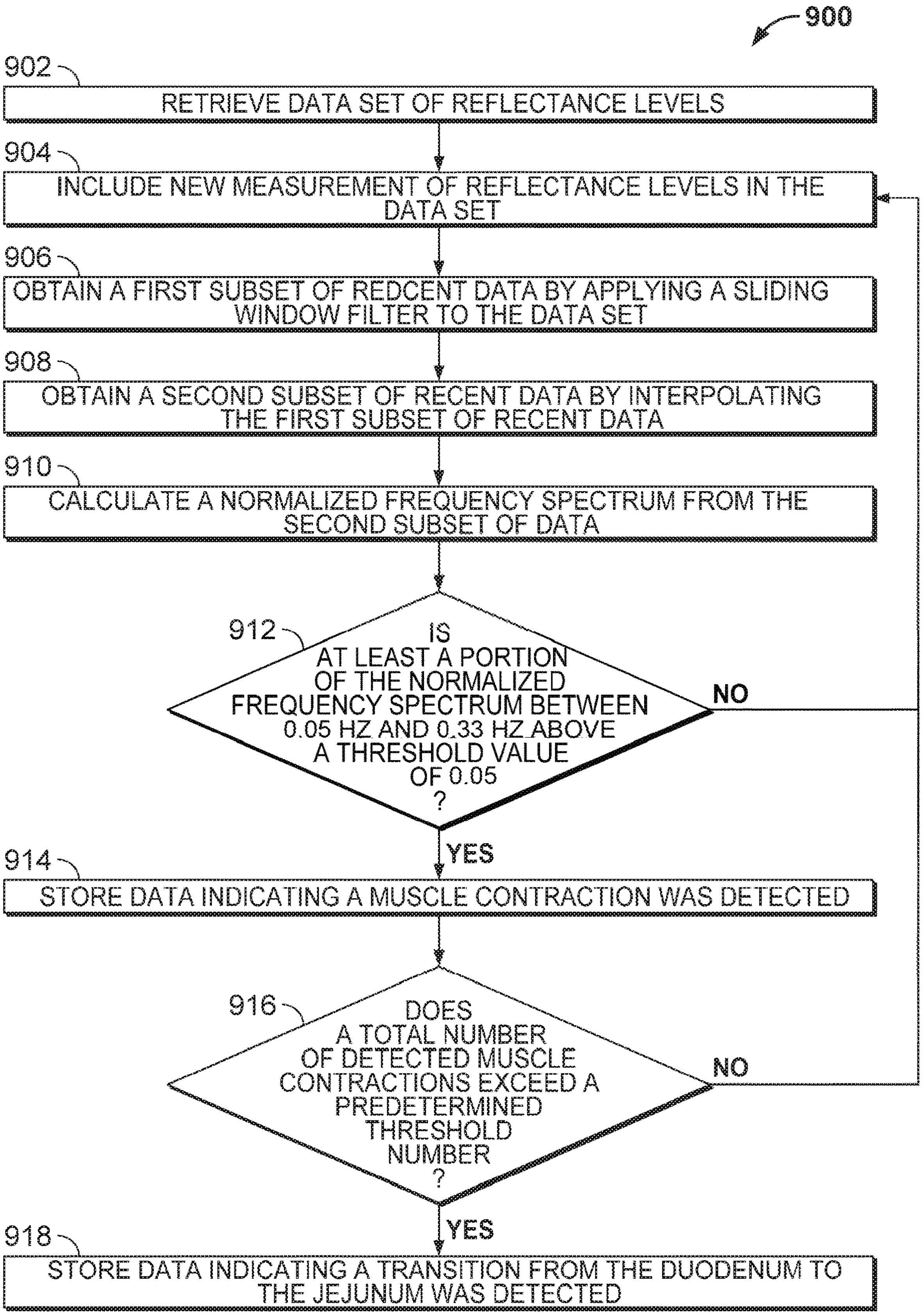
FIG. 9 is a flowchart of illustrative steps for detecting a transition from a duodenum to a jejunum, which may be used when determining a location of an ingestible device as it transits through a GI tract, in accordance with some embodiments of the disclosure.

FIG. 9 is a flowchart of illustrative steps for detecting a transition from a duodenum to a jejunum, which may be used when determining a location of an ingestible device as it transits through a gastrointestinal (GI) tract, in accordance with some embodiments of the disclosure. Although FIG. 9 may be described in connection with the ingestible device 100 for illustrative purposes, this is not intended to be limiting, and either portions or the entirety of process 900 described in FIG. 9 may be applied to any device discussed in this application (e.g., the ingestible devices 100, 300, and 400), and any of these ingestible devices may be used to perform one or more parts of the process described in FIG. 9. Furthermore, the features of FIG. 9 may be combined with any other systems, methods or processes described in this application. For example, portions of the process described by the process in FIG. 9 may be integrated into the localization process described by FIG. 5 (e.g., as part of 520-524 of process 500 (FIG. 5)). In some embodiments, an ingestible device 100 may perform process 900 while in the duodenum, or in response to detecting entry to the duodenum. In other embodiments, an ingestible device 100 may perform process 900 while in the stomach, or in response to detecting entry into the GI tract. It is also understood that process 900 may be performed in parallel with any other process described in this disclosure (e.g., process 600 (FIG. 6)), which may enable ingestible device 100 to detect entry into various portions of the GI tract, without necessarily detecting entry into a preceding portion of the GI tract.

For illustrative purposes, FIG. 9 may be discussed in terms of ingestible device 100 generating and making determinations based on a single set of reflectance levels generated at a single wavelength by a single sensing sub-unit (e.g., sensing sub-unit 126 (FIG. 2)). However, it is understood that ingestible device 100 may generate multiple wavelengths of illumination from multiple different sensing sub-units positioned around the circumference of ingestible device (e.g., multiple sensing sub-units positioned at different locations behind window 114 of ingestible device 100 (FIG. 1), and each of the resulting reflectances may be stored as a separate data set. Moreover, each of these sets of reflectance levels may be used to detect muscle contractions by running multiple versions of process 900, each one of which processes data for a different set of reflectances corresponding to data sets obtained from measurements of different wavelengths or measurements made by different sensing sub-units.

At 902, the ingestible device (e.g., ingestible device 100, 300, or 400) retrieves a set of reflectance levels. For example, ingestible device 100 may retrieve a data set of previously recorded reflectance levels from memory (e.g., from memory circuitry of PCB 120 (FIG. 2)). Each of the reflectance levels may correspond to reflectances previously detected by ingestible device 100 (e.g., via detector 122 (FIG. 2)) from illumination generated by ingestible device 100 (e.g., via illuminator 124 (FIG. 2)), and may represent a value indicative of an amount of light detected in a given reflectance. However, it is understood that any suitable frequency of light may be used, such as light in the infrared, visible, or ultraviolet spectrums. In some embodiments, the reflectance levels may correspond to reflectances previously detected by ingestible device 100 at periodic intervals.

At 904, the ingestible device (e.g., ingestible device 100, 300, or 400) includes new measurements of reflectance levels in the data set. For example, ingestible device 100 may be configured to detect a new reflectance (e.g., transmit illumination and detect the resulting reflectance using sensing sub-unit 126 (FIG. 2)) at regular intervals, or with sufficient speed as to detect peristaltic waves. For example, ingestible device 100 may be configured to generate illumination and measure the resulting reflectance once every three seconds (i.e., the minimum rate necessary to detect a 0.17 Hz signal), and preferably at a higher rate, as fast at 0.1 second or even faster. It is understood that the periodic interval between measurements may be adapted as needed based on the species of the subject, and the expected frequency of the peristaltic waves to be measured. Every time ingestible device 100 makes a new reflectance level measurement at 904, the new data is included to the data set (e.g., a data set stored within memory circuitry of PCB 120 (FIG. 2)).

At 906, the ingestible device (e.g., ingestible device 100, 300, or 400) obtains a first subset of recent data by applying a sliding window filter to the data set. For example, ingestible device 100 may retrieve a one-minute worth of data from the data set. If the data set includes values for reflectances measured every second, this would be approximately 60 data points worth of data. Any suitable type of window size may be used, provided that the size of the window is sufficiently large to detect peristaltic waves (e.g., fluctuations on the order of 0.1 Hz to 0.2 Hz for healthy human subjects). In some embodiments, ingestible device 100 may also clean the data, for example, by removing outliers from the first subset of data obtained through the use of the sliding window filter.

At 908, the ingestible device (e.g., ingestible device 100, 300, or 400) obtains a second subset of recent data by interpolating the first subset of recent data. For example, ingestible device 100 may interpolate the first subset of data in order to generate a second subset of data with a sufficient number of data points (e.g., data points spaced every 0.5 seconds or greater). In some embodiments, this may enable ingestible device 100 to also replace any outlier data points that may have been removed as part of applying the window filter at 906.

At 910, the ingestible device (e.g., ingestible device 100, 300, or 400) calculates a normalized frequency spectrum from the second subset of data. For example, ingestible device 100 may be configured to perform a fast Fourier transform to convert the second subset of data from a time domain representation into a frequency domain representation. It is understood that depending on the application being used, and the nature of the subset of data, any number of suitable procedures (e.g., Fourier transform procedures) may be used to determine a frequency spectrum for the second subset of data. For example, the sampling frequency and size of the second subset of data may be known in advance, and ingestible device 100 may be configured to have pre-stored values of a normalized discreet Fourier transform (DFT) matrix, or the rows of the DFT matrix corresponding to the 0.1 Hz to 0.2 Hz frequency components of interest, within memory (e.g., memory circuitry of PCB 120 (FIG. 2)). In this case, the ingestible device may use matrix multiplication between the DFT matrix and the data set to generate an appropriate frequency spectrum. An example data set and corresponding frequency spectrum that may be obtained by the ingestible device is discussed in greater detail in relation to FIG. 10.

At 912, the ingestible device (e.g., ingestible device 100, 300, or 400) determines whether at least a portion of the normalized frequency spectrum is between 0.1 Hz and 0.2 Hz above a threshold value of 0.5 Hz. Peristaltic waves in a healthy human subject occur at a rate between 0.1 Hz and 0.2 Hz, and an ingestible device experiencing peristaltic waves (e.g., ingestible device 400 detecting contractions in walls 406 of the jejunum (FIG. 4)) may detect sinusoidal variations in the amplitude of detected reflectances levels that follow a similar 0.1 Hz to 0.2 Hz frequency. If the ingestible device determines that a portion of the normalized frequency spectrum between 0.1 Hz and 0.2 Hz is above a threshold value of 0.5, this measurement may be consistent with peristaltic waves in a healthy human subject, and process 900 proceeds to 914 where ingestible device 100 stores data indicating a muscle contraction was detected. Alternatively, if the ingestible device determines that no portion of the normalized frequency spectrum between 0.1 Hz and 0.2 Hz above a threshold value of 0.5, process 900 proceeds directly to 904 to make new measurements and to continue to monitor for new muscle contractions. It is understood that a threshold value other than 0.5 may be used, and that the exact threshold may depend on the sampling frequency and type of frequency spectrum used by ingestible device 100.

At 914, the ingestible device (e.g., ingestible device 100, 300, or 400) stores data indicating a muscle contraction was detected. For example, ingestible device 100 may store data in memory (e.g., memory circuitry of PCB 120 (FIG. 2)) indicating that a muscle contraction was detected, and indicating the time that the muscle contraction was detected. In some embodiments, ingestible device 100 may also monitor the total number of muscle contractions detected, or the number of muscle contractions detected in a given time frame. In some embodiments, detecting a particular number of muscle contractions may be consistent with ingestible device 100 being within the jejunum (e.g., jejunum 314 (FIG. 3)) of a healthy human subject. After detecting a muscle contraction, process 900 proceeds to 916.

At 916, the ingestible device (e.g., ingestible device 100, 300, or 400) determines whether a total number of muscle contractions exceeds a predetermined threshold number. For example, ingestible device 100 may retrieve the total number of muscle contractions detected from memory (e.g., from memory circuitry of PCB 120 (FIG. 2)), and compare the total number to a threshold value. In some embodiments, the threshold value may be one, or any number larger than one. The larger the threshold value, the more muscle contractions need to be detected before ingestible device 100 stores data indicating that it has entered the jejunum. In practice, setting the threshold value as three or higher may prevent the ingestible device from detecting false positives (e.g., due to natural movement of the GI tract organs, or due to movement of the subject). If the total number of contractions exceeds the predetermined threshold number, process 900 proceeds to 918 to store data indicating detection of a transition from the duodenum to the jejunum. Alternatively, if the total number of contractions does not exceed a predetermined threshold number, process 900 proceeds to 904 to include new measurements of reflectance levels in the data set. An example plot of the muscle contractions detected over time is discussed in greater detail in relation to FIG. 11.

At 918, the ingestible device (e.g., ingestible device 100, 300, or 400) stores data indicating detection of a transition from the duodenum to the jejunum. For example, ingestible device 100 may store data in memory (e.g., from memory circuitry of PCB 120 (FIG. 2)) indicating that the jejunum has been reached. In some embodiments, if ingestible device 100 is configured to perform all or part of process 900 while in the stomach, ingestible device 100 may store data at 918 indicating detection of a transition from the stomach directly to the jejunum (e.g., as a result of transitioning too quickly through the duodenum for the pyloric transition to be detected using process 600 (FIG. 6)).

In some embodiments, the ingestible device (e.g., ingestible device 100, 300, or 400) may be configured to obtain a fluid sample from the environment external to a housing of the ingestible device in response to identifying a change in the location of the ingestible device. For example, ingestible device 100 may be configured to obtain a fluid sample from the environment external to the housing of ingestible device 100 (e.g., through the use of optional opening 116 and optional rotating assembly 118 (FIG. 2)) in response to determining that the ingestible device is located within the jejunum (e.g., jejunum 314 (FIG. 3)). In some embodiments, ingestible device 100 may also be equipped with appropriate diagnostics to detect certain medical conditions based on the retrieved fluid sample, such as small intestinal bacterial overgrowth (SIBO).

In some embodiments, the ingestible device (e.g., ingestible device 100, 300, or 400) may be configured to deliver a dispensable substance that is pre-stored within the ingestible device from the ingestible device into the gastrointestinal tract in response to identifying the change in the location of the ingestible device. For example, ingestible device 100 may have a dispensable substance pre-stored within the ingestible device 100 (e.g., within a storage chamber or cavity on optional storage sub-unit 118-3 (FIG. 2)), and ingestible device 100 may be configured to dispense the substance into the gastrointestinal tract (e.g., through the use of optional opening 116 and optional rotating assembly 118 (FIG. 2)) when the ingestible device 100 detects that the ingestible device 100 is located within the jejunum (e.g., jejunum 314 (FIG. 3)). In some embodiments, this may enable ingestible device 100 to deliver substances (e.g., therapeutics and medicaments) at targeted locations within the GI tract.

In some embodiments, the ingestible device (e.g., ingestible device 100, 300, or 400) may be configured to perform an action based on the total number of detected muscle contractions. For example, ingestible device 100 may be configured to retrieve data indicative of the total number of muscle contractions (e.g., from memory circuitry of PCB 120 (FIG. 2)), and compare that to an expected number muscle contractions in a healthy individual. In response, the ingestible device may either dispense a substance into the gastrointestinal tract (e.g., through the use of optional opening 116 and optional rotating assembly 118 (FIG. 2)), or may obtain a fluid sample from the environment external to the housing of ingestible device 100 (e.g., through the use of optional opening 116 and optional rotating assembly 118

(FIG. 2)). For instance, ingestible device 100 may be configured to obtain a sample in response to determining that a number of detected muscle contractions is abnormal, and differs greatly from the expected number. As another example, ingestible device 100 may be configured to deliver a substance into the GI tract (such as a medicament), in response to determining that the detected muscle contractions are consistent with a functioning GI tract in a healthy individual.

It will be understood that the steps and descriptions of the flowcharts of this disclosure, including FIG. 9, are merely illustrative. Any of the steps and descriptions of the flowcharts, including FIG. 9, may be modified, omitted, rearranged, performed in alternate orders or in parallel, two or more of the steps may be combined, or any additional steps may be added, without departing from the scope of the present disclosure. For example, the ingestible device 100 may calculate the mean and the standard deviation of multiple data sets in parallel (e.g., multiple data sets, each one corresponding to a different wavelength of reflectance or different sensing sub-unit used to detect the reflectance) in order to speed up the overall computation time. Furthermore, it should be noted that the steps and descriptions of FIG. 9 may be combined with any other system, device, or method described in this application, and any of the ingestible devices or systems discussed in this application could be used to perform one or more of the steps in FIG. 9.

Figure 10:
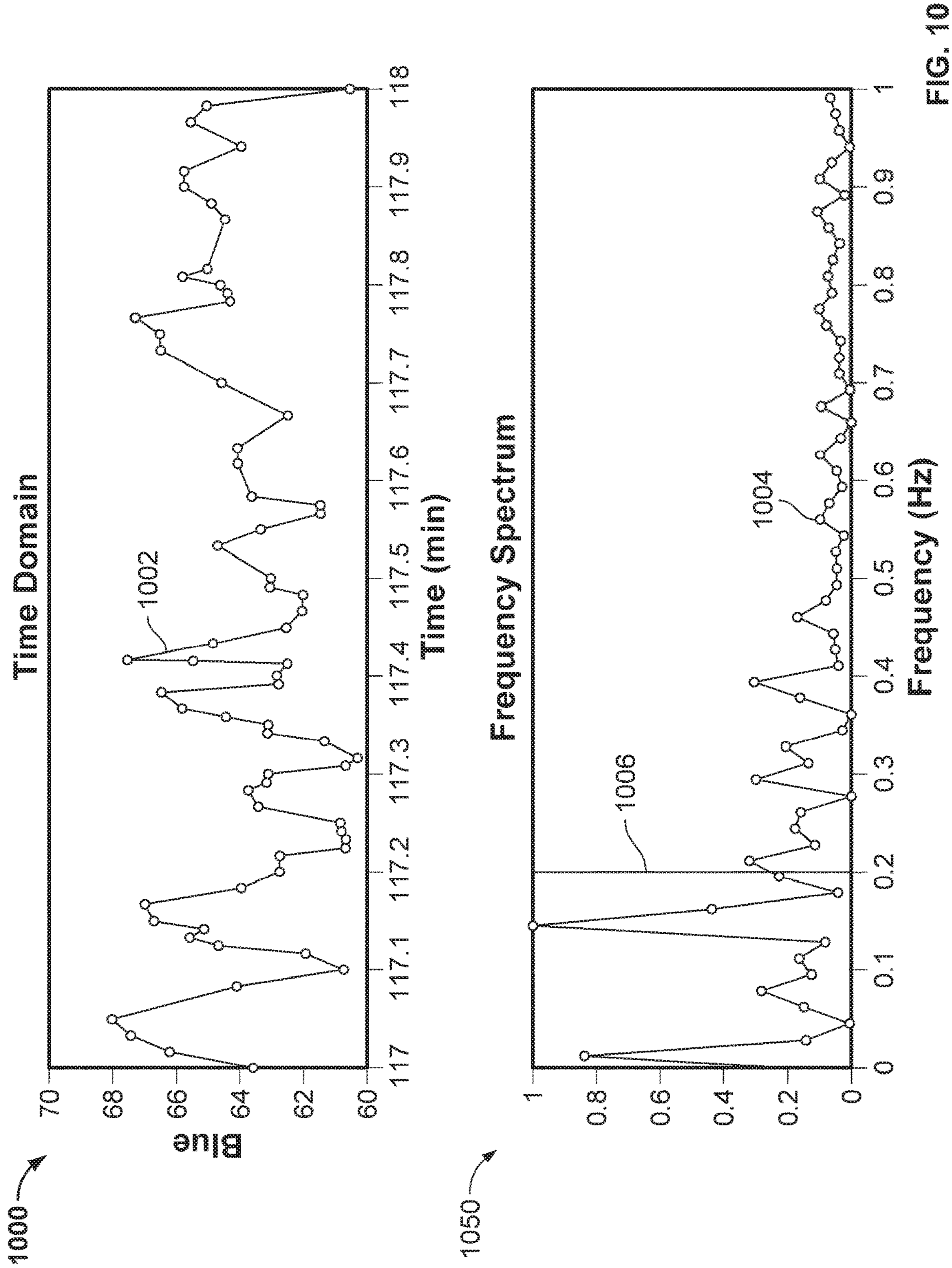
FIG. 10 is a plot illustrating data collected during an example operation of an ingestible device, which may be used when detecting a transition from a duodenum to a jejunum, in accordance with some embodiments of the disclosure.

FIG. 10 is a plot illustrating data collected during an example operation of an ingestible device, which may be used when detecting a transition from a duodenum to a jejunum, in accordance with some embodiments of the disclosure. Diagram 1000 depicts a time domain plot 1002 of a data set of reflectance levels measured by an ingestible device (e.g., the second subset of data discussed in relation to 908 of FIG. 9). In some embodiments, ingestible device 100 may be configured to gather data points at semi-regular intervals approximately 0.5 seconds apart. By comparison, diagram 1050 depicts a frequency domain plot 1004 of the same data set of reflectance levels measured by an ingestible device (e.g., as a result of ingestible device 100 calculating a frequency spectrum at 910 of FIG. 9). In some embodiments, ingestible device 100 may be configured to calculate the frequency spectrum through any convenient means.

In diagram 1050, the range of frequencies 1006 between 0.1 Hz and 0.2 Hz may be the range of frequencies that ingestible device 100 searches in order to detect muscle contractions.

As shown in diagram 1050, there is a strong peak in the frequency domain plot 1004 around 0.14 Hz, which is consistent with the frequency of peristaltic motion in a healthy human individual. In this case, an ingestible device 100 analyzing frequency domain plot 1004 may be configured to determine that the data is consistent with a detected muscle contraction (e.g., using a process similar to 912 of process 900 (FIG. 9)), and may store data (e.g., in memory circuitry of PCB 120 (FIG. 2)) indicating that a muscle contraction has been detected. Because the muscle contraction was detected from the one-minute window of data ending at 118 minutes, ingestible device 100 may also store data indicating that the muscle contraction was detected at the 118-minute mark (i.e., which may indicate that the ingestible device 100 was turned on and ingested by the subject 118 minutes ago).

Figure 11:
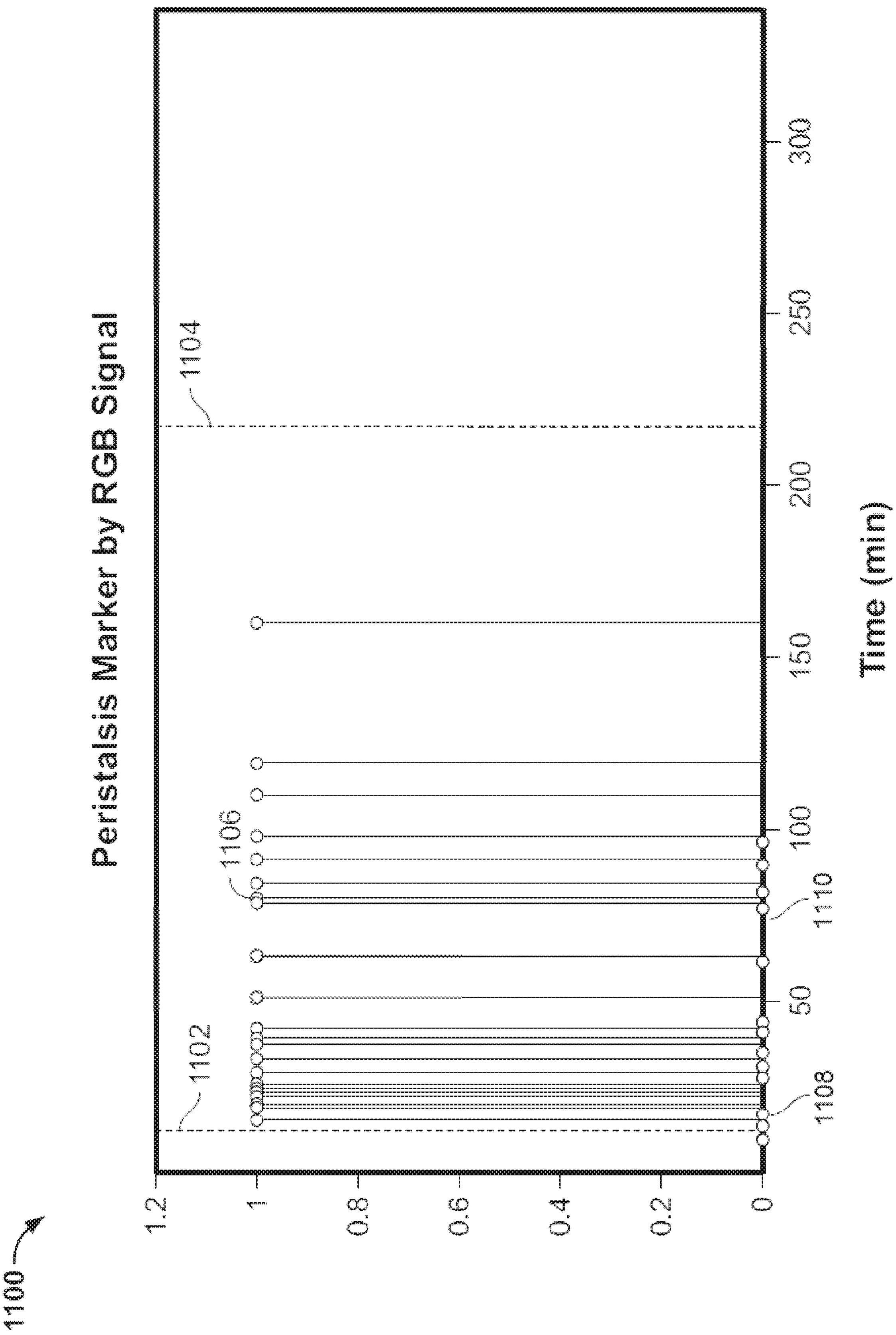
FIG. 11 is a plot illustrating muscle contractions detected by an ingestible device over time, which may be used when determining a location of an ingestible device as it transits through a GI tract, in accordance with some embodiments of the disclosure.

FIG. 11 is a plot illustrating muscle contractions detected by an ingestible device over time, which may be used when determining a location of an ingestible device as it transits through a gastrointestinal (GI) tract, in accordance with some embodiments of the disclosure. In some embodiments, ingestible device 100 may be configured to detect muscle contractions, and store data indicative of when each muscle contraction is detected (e.g., as part of 914 of process 900 (FIG. 9)). Plot 1100 depicts the detected muscle contractions 1106 over time, with each muscle contraction being represented by a vertical line reaching from "0" to "1" on the y-axis.

At 1102, around the 10-minute mark, ingestible device 100 first enters the duodenum (e.g., as determined by ingestible device 100 performing process 600 (FIG. 6)). Shortly thereafter, at 1108, ingestible device 100 begins to detect several muscle contractions 1106 in quick succession, which may be indicative of the strong peristaltic waves that form in the jejunum (e.g., jejunum 314 (FIG. 3)). Later, around 1110, ingestible device 100 continues to detect intermittent muscle contractions, which may be consistent with an ingestible device 100 within the ileum. Finally at 1104, ingestible device 100 transitions out of the small intestine, and into the cecum. Notably, ingestible device 100 detects more frequent muscle contractions in the jejunum portion of the small intestine as compared to the ileum portion of the small intestine, and ingestible device 100 does not measure any muscle contractions after having exited the small intestine. In some embodiments, ingestible device 100 may incorporate this information into a localization process. For example, ingestible device 100 may be configured to detect a transition from a jejunum to an ileum in response to determining that a frequency of detected muscle contractions (e.g., the number of muscle contractions measured in a given 10-minute window) has fallen below a threshold number. As another example, ingestible device 100 may be configured to detect a transition from an ileum to a cecum in response to determining that no muscle contractions have been detected for a threshold period of time. It is understood that these examples are intended to be illustrative, and not limiting, and that measurements of muscle contractions may be combined with any of the other processes, systems, or methods discussed in this disclosure.

Figure 12:
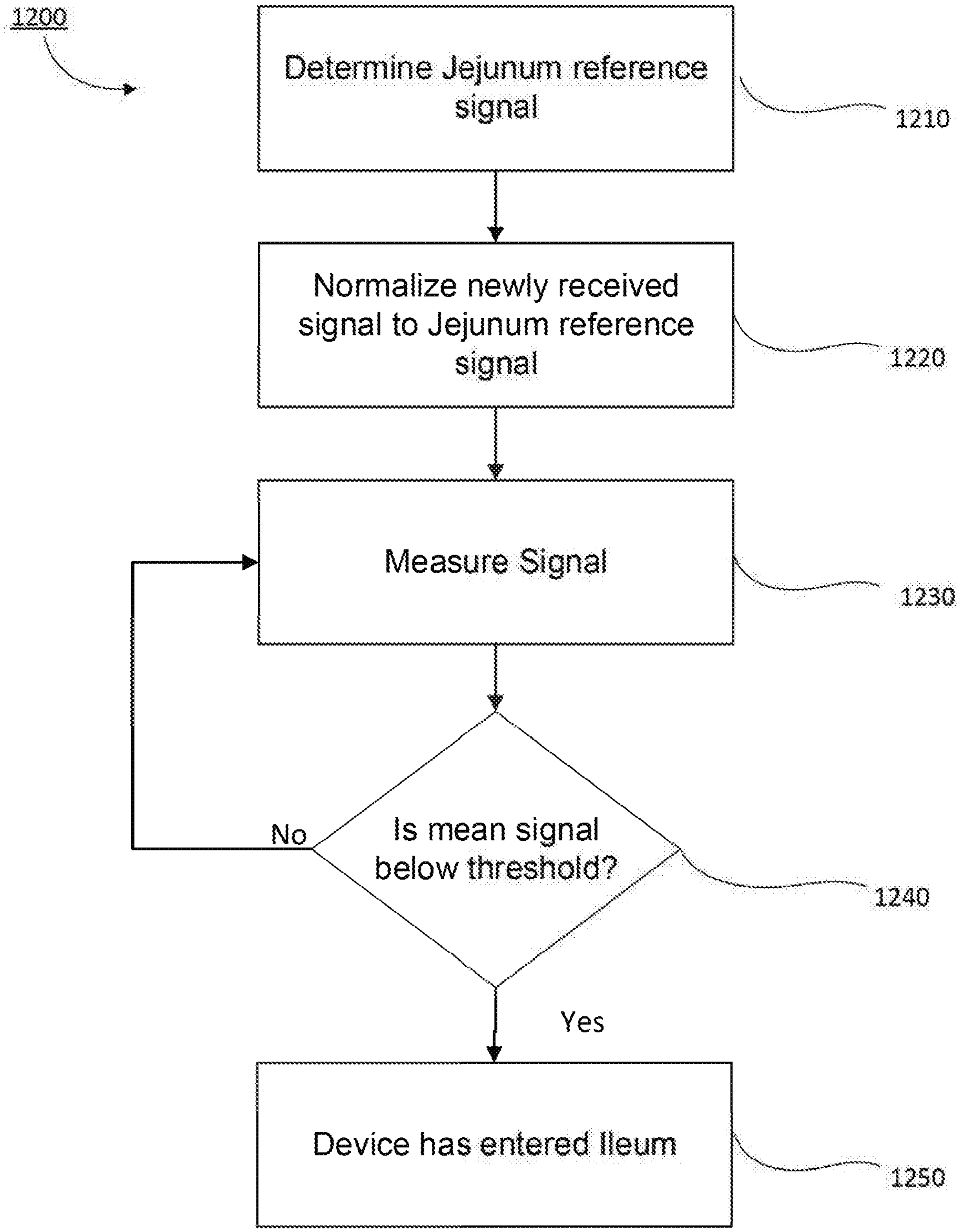
FIG. 12 is a flowchart of illustrative steps for detecting a transition from a jejunum to an ileum, which may be used when determining a location of an ingestible device as it transits through a GI tract, in accordance with some embodiments of the disclosure.

FIG. 12 is a flowchart 1200 for certain embodiments for determining a transition of the device from the jejunum to the ileum. It is to be noted that, in general, the jejunum is redder and more vascular than the ileum. Moreover, generally, in comparison to the ileum, the jejunum has a thicker intestine wall with more messentary fat. These differences between the jejunum and the ileum are expected to result in differences in optical responses in the jejunum relative to the ileum. Optionally, one or more optical signals may be used to investigate the differences in optical responses. For example, the process can include monitoring a change in optical response in reflected red light, blue light, green light, ratio of red light to green light, ratio of red light to blue light, and/or ratio of green light to blue light. In some embodiments, reflected red light is detected in the process.

Flowchart 1200 represents a single sliding window process. In step 1210, the jejunum reference signal is determined based on optical reflection. Typically, this signal is as the average signal (e.g., reflected red light) over a period of time since the device was determined to enter the jejunum. The period of time can be, for example, from five minutes to 40 minutes (e.g., from 10 minutes to 30 minutes, from 15 minutes to 25 minutes). In step 1220, the detected signal (e.g., reflected red light) just after the period of time used in step 1210 is normalized to the reference signal determined in step 1210. In step 1230, the signal (e.g., reflected red light) is detected. In step 1240, the mean signal detected based on the single sliding window is compared to a signal threshold. The signal threshold in step 1240 is generally a fraction of the reference signal of the jejunum reference signal determined in step 1210. For example, the signal threshold can be from 60% to 90% (e.g., from 70% to 80%) of the jejunum reference signal. If the mean signal exceeds the signal threshold, then the process determines that the device has entered the ileum at step 1250. If the mean signal does not exceed the signal threshold, then the process returns to step 1230.

Figure 13:
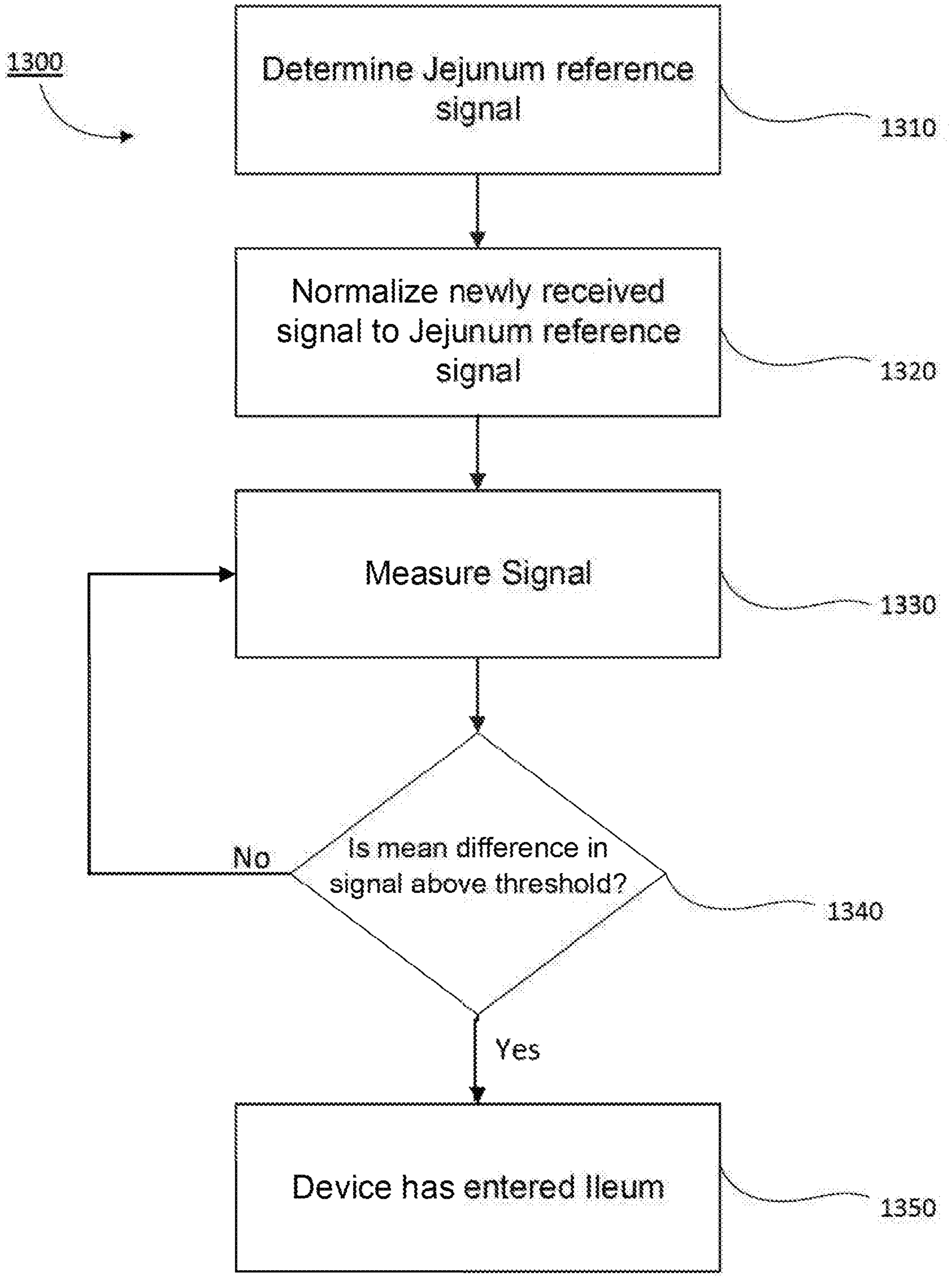
FIG. 13 is a flowchart of illustrative steps for detecting a transition from a jejunum to an ileum, which may be used when determining a location of an ingestible device as it transits through a GI tract, in accordance with some embodiments of the disclosure.

FIG. 13 is a flowchart 1200 for certain embodiments for determining a transition of the device from the jejunum to the ileum using a two sliding window process. In step 1310, the jejunum reference signal is determined based on optical reflection. Typically, this signal is as the average signal (e.g., reflected red light) over a period of time since the device was determined to enter the jejunum. The period of time can be, for example, from five minutes to 40 minutes (e.g., from 10 minutes to 30 minutes, from 15 minutes to 25 minutes). In step 1320, the detected signal (e.g., reflected red light) just after the period of time used in step 1310 is normalized to the reference signal determined in step 1310. In step 1330, the signal (e.g., reflected red light) is detected. In step 1340, the mean difference in the signal detected based on the two sliding windows is compared to a signal threshold. The signal threshold in step 1340 is based on whether the mean difference in the detected signal exceeds a multiple (e.g., from 1.5 times to five times, from two times to four times) of the detected signal of the first window. If signal threshold is exceeded, then the process determines that the device has entered the ileum at step 1350. If the signal threshold is not exceeded, then the process returns to step 1330.

Figure 14:
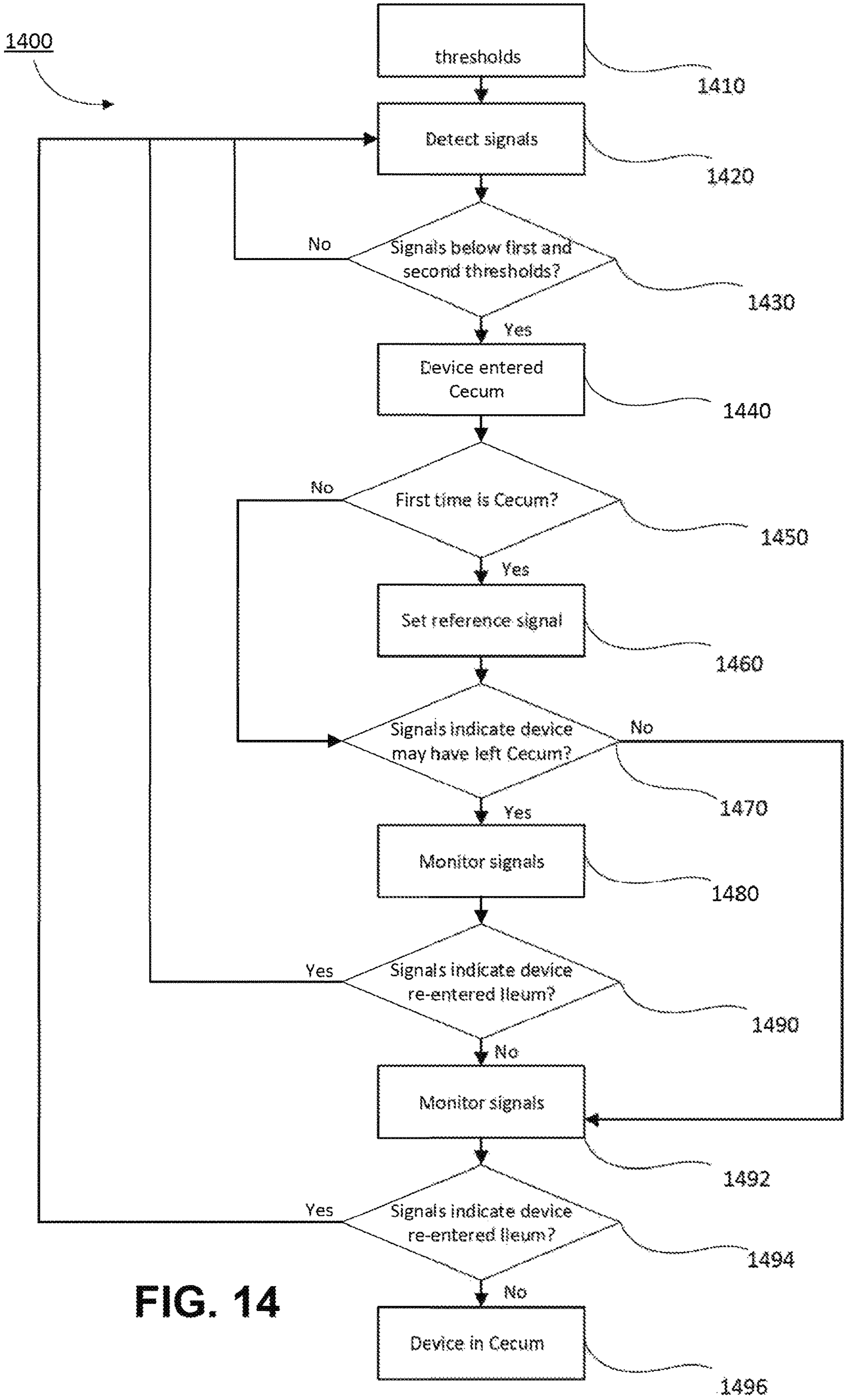
FIG. 14 is a flowchart of illustrative steps for detecting a transition from an ileum to a cecum, which may be used when determining a location of an ingestible device as it transits through a GI tract, in accordance with some embodiments of the disclosure.

FIG. 14 is a flowchart 1400 for a process for certain embodiments for determining a transition of the device from the ileum to the cecum. In general, the process involves detecting changes in the reflected optical signal (e.g., red light, blue light, green light, ratio of red light to green light, ratio of red light to blue light, and/or ratio of green light to blue light). In some embodiments, the process includes detecting changes in the ratio of reflected red light to reflected green light, and also detecting changes in the ratio of reflected green light to reflected blue light. Generally, in the process 1400, the sliding window analysis (first and second windows) discussed with respect to process 600 is continued.

Step 1410 includes setting a first threshold in a detected signal, e.g., ratio of detected red light to detected green light, and setting a second threshold for the coefficient of variation for a detected signal, e.g., the coefficient of variation for the ratio of detected green light to detected blue light. The first threshold can be set to a fraction (e.g., from 0.5 to 0.9, from 0.6 to 0.8) of the average signal (e.g., ratio of detected red light to detected green light) in the first window, or a fraction (e.g., from 0.4 to 0.8, from 0.5 to 0.7) of the mean difference between the detected signal (e.g., ratio of detected red light to detected green light) in the two windows. The second threshold can be set to 0.1 (e.g., 0.05, 0.02).

Step 1420 includes detecting the signals in the first and second windows that are to be used for comparing to the first and second thresholds.

Step 1430 includes comparing the detected signals to the first and second thresholds. If the corresponding value is not below the first threshold or the corresponding value is not below the second threshold, then it is determined that the device has not left the ileum and entered the cecum, and the process returns to step 1420. If the corresponding value is below the first threshold and the corresponding value is below the second threshold, then it is determined that the device has left the ileum and entered the cecum, and the proceeds to step 1440.

Step 1450 includes determining whether it is the first time that that the device was determined to leave the ileum and enter the cecum. If it is the first time that the device was determined to leave the ileum and enter the cecum, then the process proceeds to step 1460. If it is not the first time that the device has left the ileum and entered the cecum, then the process proceeds to step 1470.

Step 1460 includes setting a reference signal. In this step the optical signal (e.g., ratio of detected red light to detected green light) as a reference signal.

Step 1470 includes determining whether the device may have left the cecum and returned to the ileum. The device is determined to have left the cecum and returned to the ileum if the corresponding detected signal (e.g., ratio of detected red light to detected green light) is statistically comparable to the reference signal (determined in step 1460) and the coefficient of variation for the corresponding detected signal (e.g., ratio of detected green light to detected blue light) exceeds the second threshold. If it is determined that the device may have left the cecum and returned to the ileum, the process proceeds to step 1480.

Step 1480 includes continuing to detect the relevant optical signals for a period of time (e.g., at least one minute, from five minutes to 15 minutes).

Step 1490 includes determining whether the signals determined in step 1480 indicate (using the methodology discussed in step 1470) that the device re-entered the ileum. If the signals indicate that the device re-entered the ileum, the process proceeds to step 1420. If the signals indicate that the device is in the cecum, the process proceeds to step 1492.

Step 1492 includes continuing to monitor the relevant optical signals for a period of time (e.g., at least 30 minutes, at least one hour, at least two hours).

Step 1494 includes determining whether the signals determined in step 1492 indicate (using the methodology discussed in step 1470) that the device re-entered the ileum. If the signals indicate that the device re-entered the ileum, the process proceeds to step 1420. If the signals indicate that the device is in the cecum, the process proceeds to step 1496.

At step 1496, the process determines that the device is in the cecum.

Figure 15:
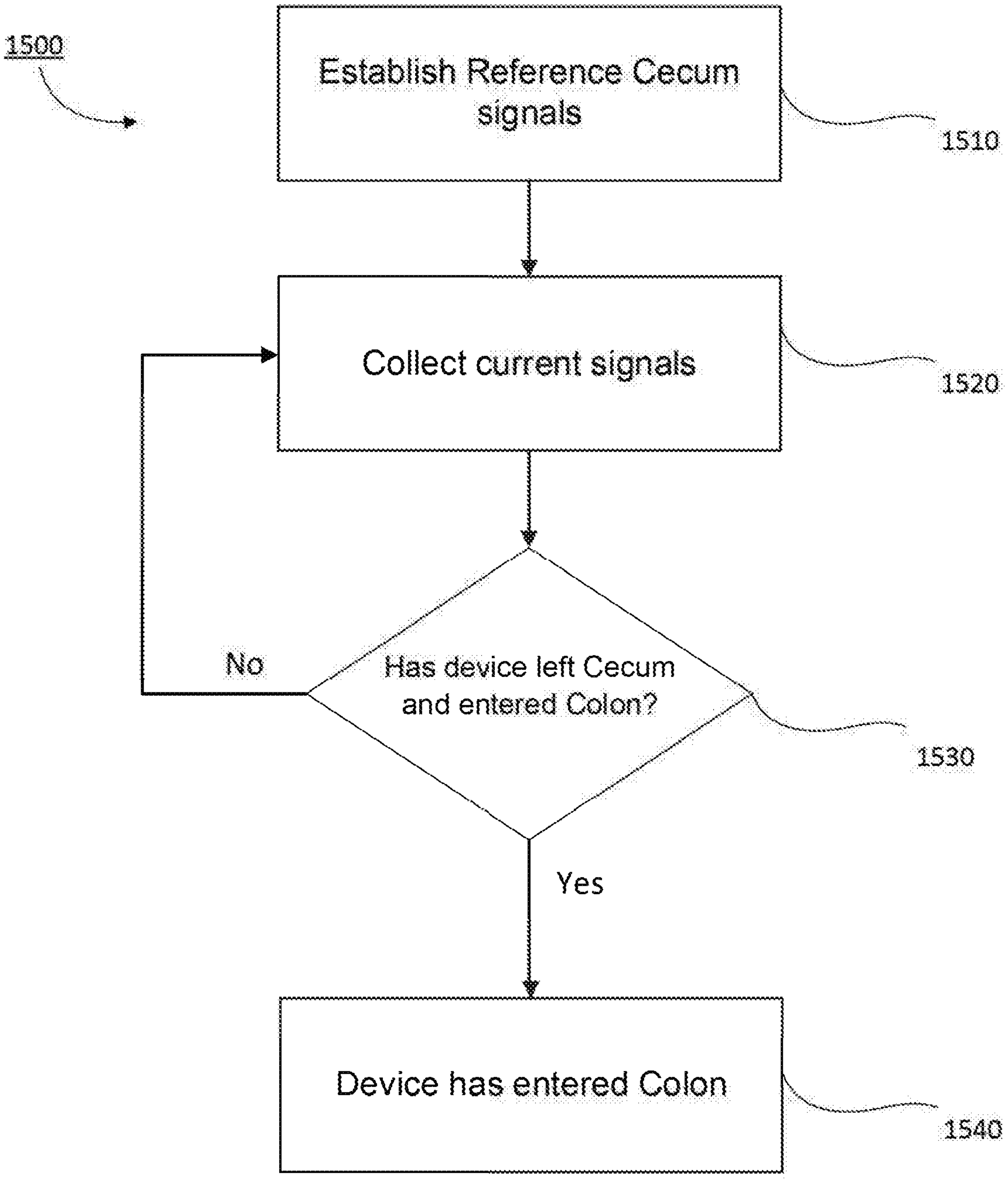
FIG. 15 is a flowchart of illustrative steps for detecting a transition from a cecum to a colon, which may be used when determining a location of an ingestible device as it transits through a GI tract, in accordance with some embodiments of the disclosure.

FIG. 15 is a flowchart 1500 for a process for certain embodiments for determining a transition of the device from the cecum to the colon. In general, the process involves detecting changes in the reflected optical signal (e.g., red light, blue light, green light, ratio of red light to green light, ratio of red light to blue light, and/or ratio of green light to blue light). In some embodiments, the process includes detecting changes in the ratio of reflected red light to reflected green light, and also detecting changes in the ratio of reflected blue light. Generally, in the process 1500, the sliding window analysis (first and second windows) discussed with respect to process 1400 is continued.

In step 1510, optical signals (e.g., the ratio of reflected red signal to reflected green signal, and reflected blue signal) are collected for a period of time (e.g., at least one minute, at least five minutes, at least 10 minutes) while the device is in the cecum (e.g., during step 1480). The average values for the recorded optical signals (e.g., the ratio of reflected red signal to reflected green signal, and reflected blue signal) establish the cecum reference signals.

In step 1520, the optical signals are detected after it has been determined that the device entered the cecum (e.g., at step 1440). The optical signals are normalized to the cecum reference signals.

Step 1530 involves determining whether the device has entered the colon. This includes determining whether any of three different criteria are satisfied. The first criterion is satisfied if the mean difference in the ratio of a detected optical signal (e.g., ratio of detected red signal to the detected green) is a multiple greater than one (e.g., 2×, 3×, 4×) the standard deviation of the corresponding signal (e.g., ratio of detected red signal to the detected green) in the second window. The second criterion is satisfied if the mean of a detected optical signal (e.g., a ratio of detected red light to detected green light) exceeds a given value (e.g., exceeds one). The third criterion is satisfied if the coefficient of variation of an optical signal (e.g., detected blue light) in the first window exceeds a given value (e.g., exceeds 0.2). If any of the three criteria are satisfied, then the process proceeds to step 1540. Otherwise, none of the three criteria are satisfied, the process returns to step 1520.

For illustrative purposes the disclosure focuses primarily on a number of different example embodiments of an ingestible device, and example embodiments of methods for determining a location of an ingestible device within a GI tract. However, the possible ingestible devices that may be constructed are not limited to these embodiments, and variations in the shape and design may be made without significantly changing the functions and operations of the device. Similarly, the possible procedures for determining a location of the ingestible device within the GI tract are not limited to the specific procedures and embodiments discussed (e.g., process 500 (FIG. 5), process 600 (FIG. 6), process 900 (FIG. 9), process 1200 (FIG. 12), process 1300 (FIG. 13), process 1400 (FIG. 14) and process 1500 (FIG. 15)). Also, the applications of the ingestible devices described herein are not limited merely to gathering data, sampling and testing portions of the gastrointestinal tract, or delivering medicament. For example, in some embodiments the ingestible device may be adapted to include a number of chemical, electrical, or optical diagnostics for diagnosing a number of diseases. Similarly, a number of different sensors for measuring bodily phenomenon or other physiological qualities may be included on the ingestible device. For example, the ingestible device may be adapted to measure elevated levels of certain chemical compounds or impurities in the gastrointestinal tract, or the combination of localization, sampling, and appropriate diagnostic and assay techniques incorporated into a sampling chamber may be particularly well suited to determine the presence of small intestinal bacterial overgrowth (SIBO).

At least some of the elements of the various embodiments of the ingestible device described herein that are implemented via software (e.g., software executed by control circuitry within PCB 120 (FIG. 2)) may be written in a high-level procedural language such as object oriented programming, a scripting language or both. Accordingly, the program code may be written in C, $C^{++}$ or any other suitable programming language and may comprise modules or classes, as is known to those skilled in object oriented programming. Alternatively, or in addition, at least some of the elements of the embodiments of the ingestible device described herein that are implemented via software may be written in assembly language, machine language or firmware as needed. In either case, the language may be a compiled or an interpreted language.

At least some of the program code used to implement the ingestible device can be stored on a storage media or on a computer readable medium that is readable by a general or special purpose programmable computing device having a processor, an operating system and the associated hardware and software that is necessary to implement the functionality of at least one of the embodiments described herein. The program code, when read by the computing device, configures the computing device to operate in a new, specific and predefined manner in order to perform at least one of the methods described herein.

Furthermore, at least some of the programs associated with the systems, devices, and methods of the example embodiments described herein are capable of being distributed in a computer program product comprising a computer readable medium that bears computer usable instructions for one or more processors. The medium may be provided in various forms, including non-transitory forms such as, but not limited to, one or more diskettes, compact disks, tapes, chips, and magnetic and electronic storage. In some embodiments, the medium may be transitory in nature such as, but not limited to, wire-line transmissions, satellite transmissions, internet transmissions (e.g., downloads), media, digital and analog signals, and the like. The computer useable instructions may also be in various formats, including compiled and non-compiled code.

The techniques described above can be implemented using software for execution on a computer. For instance, the software forms procedures in one or more computer programs that execute on one or more programmed or programmable computer systems (which may be of various architectures such as distributed, client/server, or grid) each including at least one processor, at least one data storage system (including volatile and non-volatile memory and/or storage elements), at least one input device or port, and at least one output device or port.

The software may be provided on a storage medium, such as a CD-ROM, readable by a general or special purpose programmable computer or delivered (encoded in a propagated signal) over a communication medium of a network to the computer where it is executed. All of the functions may be performed on a special purpose computer, or using special-purpose hardware, such as coprocessors. The software may be implemented in a distributed manner in which different parts of the computation specified by the software are performed by different computers. Each such computer program is preferably stored on or downloaded to a storage media or device (e.g., solid state memory or media, or magnetic or optical media) readable by a general or special purpose programmable computer, for configuring and operating the computer when the storage media or device is read by the computer system to perform the procedures described herein. The inventive system may also be considered to be implemented as a computer-readable storage medium, configured with a computer program, where the storage medium so configured causes a computer system to operate in a specific and predefined manner to perform the functions described herein.

Methods and Mechanisms of Delivery

Figure 16:
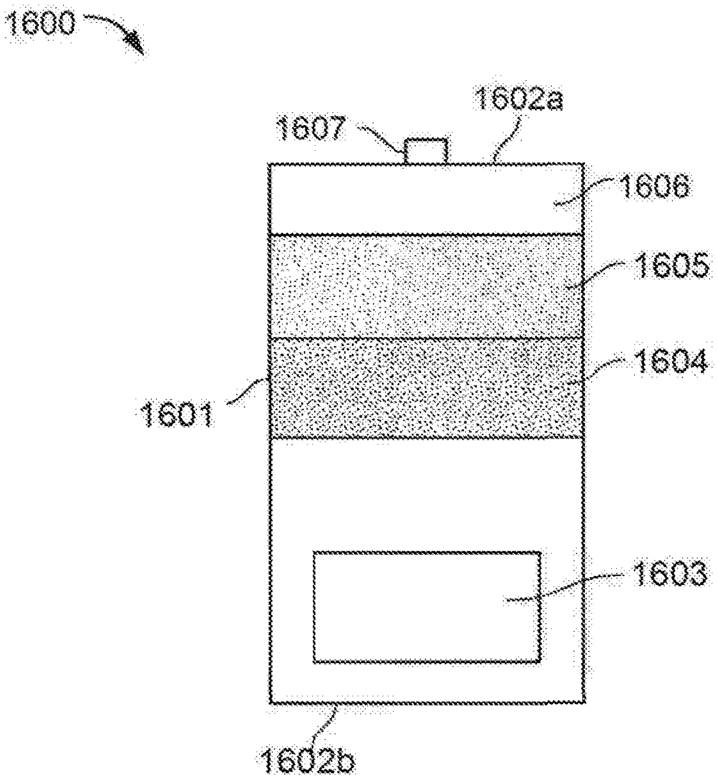
FIG. 16 illustrates an ingestible device for delivering a substance in the GI tract.

FIG. 16 provides an example mock-up diagram illustrating aspects of a structure of an ingestible device 1600 for delivering a dispensable substance, such as a formulation of a therapeutic agent described herein, according to some embodiments described herein. In some embodiments, the ingestible device 1600 may generally be in the shape of a capsule, a pill or any swallowable form that may be orally consumed by an individual. In this way, the ingestible device 1600 may be ingested by a patient and may be prescribed by healthcare practitioners and patients.

The ingestible device 1600 includes a housing 1601 that may take a shape similar to a capsule, a pill, and/or the like, which may include two ends 1602*a-b*. The housing 1601 may be designed to withstand the chemical and mechanical environment of the GI tract (e.g., effects of muscle contractile forces and concentrated hydrochloric acid in the stomach). A broad range of materials that may be used for the housing 1601. Examples of these materials include, but are not limited to, thermoplastics, fluoropolymers, elastomers, stainless steel and glass complying with ISO 10993 and USP Class VI specifications for biocompatibility; and any other suitable materials and combinations thereof.

In some embodiment, the wall of the housing 1601 may have a thickness of 0.5 mm-1 mm, which is sufficient to sustain an internal explosion (e.g., caused by hydrogen ignition or over pressure inside the housing).

The housing 1601 may or may not have a pH-sensitive enteric coating to detect or otherwise be sensitive to a pH level of the environment external to the ingestible device. As discussed elsewhere in the application in more detail, the ingestible device 1600 may additionally or alternatively include one more sensors, e.g., temperature sensor, optical sense.

The housing 1601 may be formed by coupling two enclosure portions together. The ingestible device 1600 may include an electronic component within the housing 1600. The electronic component may be placed proximally to an end 1602*b* of the housing, and includes a printed circuit board (PCB), a battery, an optical sensing unit, and/or the like.

The ingestible device 1600 further includes a gas generating cell 1603 that is configured to generate gas and thus cause an internal pressure within the housing 1601. In some embodiments, the gas generating cell may include or be connected to a separate channel or valve of the ingestible device such that gas may be release through the channel or valve to create a motion to alter the position of the ingestible device within the GI tract. Such gas release can also be used to position the ingestible device relative to the intestinal lining. In another embodiment, gas may be released through the separate channel or valve to alter the surface orientation of the intestinal tissue prior to delivery of the dispensable substance.

A traveling plunger 1604 may be placed on top of the gas generating cell 1603 within the housing 1601. The traveling plunger 1604 is a membrane that separates the gas generating cell 1603 and a storage reservoir that stores the dispensable substance 1605. In some embodiments, the traveling plunger 1604 may be a movable piston. In some embodiments, the traveling plunger 1604 may instead be a flexible membrane such as but not limited to a diaphragm. In some embodiments, the traveling plunger 1604, which may have the form of a flexible diaphragm, may be placed along an axial direction of the housing 1601, instead of being placed on top of the gas generating cell 1603. The traveling plunger or the membrane 1604 may move (when the membrane 1604 is a piston) or deform (when the membrane 1604 is a diaphragm) towards a direction of the end 1602*a* of the housing, when the gas generating cell 1603 generates gas to create an internal pressure that pushes the membrane 1604. In this way, the membrane or traveling plunger 1604 may push the dispensable substance 1605 out of the housing via a dispensing outlet 1607.

The housing 1601 may include a storage reservoir storing one or more dispensable substances 1605 adjacent to the traveling plunger 1604. The dispensable substance 1605 may be a therapeutic or medical agent that may take a form of a powder, a compressed powder, a fluid, a semi-liquid gel, or any other dispensable or deliverable form. The delivery of the dispensable substance 1605 may take a form such as but not limited to bolus, semi-bolus, continuous, burst drug delivery, and/or the like. In some embodiments, a single bolus is delivered proximate to the disease location. In some embodiments, more than one bolus is released at one location or more than one location. In some embodiments the release of more than one bolus is triggered according to a pre-programmed algorithm. In some embodiments the release profile is continuous. In some embodiments the release profile is time-based. In some embodiments the release profile is location-based. In some embodiments, the amount delivered is based on the severity and/or extent of the disease in the following manner. In some embodiments, the bolus is delivered in one or more of the following locations: stomach; duodenum; proximal jejunum; ileum; cecum; ascending colon; transverse colon; descending colon. In some embodiments, the JAK inhibitor is ustekinumab. In some embodiments, the JAK inhibitor is briakinumab. In some embodiments, the JAK inhibitor is guselkumab. In some embodiments, the JAK inhibitor is tildrakizumab. In some embodiments, the JAK inhibitor is brazikumab. In some embodiments, the JAK inhibitor is ustekinumab.

In some embodiments the dispensable substance is a small molecule therapeutic that is released in the cecum and/or other parts of the large intestine. Small molecules that are administerered by typical oral routes are primarily absorbed in the small intestine, with much lower absorption taking place in the large intestine (outside of the rectum). Accordingly, an ingestible device that is capable of releasing a small molecule selectively in the large intestine (e.g., the cecum) with resulting low systemic levels (even when high doses are used) is attractive for subjects with inflammatory bowel disease in the large intestine.

In some embodiments, the storage reservoir may include multiple chambers, and each chamber stores a different dispensable substance. For example, the different dispensable substances can be released at the same time via the dispensing outlet 1607. Alternatively, the multiple chambers may take a form of different layers within the storage reservoir such that the different dispensable substance from each chamber is delivered sequentially in an order. In one example, each of the multiple chambers is controlled by a separate traveling plunger, which may be propelled by gas generation. The electronic component may control the gas generating cell 1603 to generate gas to propel a specific traveling plunger, e.g., via a separate gas generation chamber, etc., to delivery the respective substance. In some embodiments, the content of the multiple chambers may be mixed or combined prior to release, for example, to activate the drug.

The ingestible device 1600 may include a dispensing outlet 1607 at one end 1602*a* of the housing 1601 to direct the dispensable substance 105 out of the housing. The dispensing outlet 1607 may include an exit valve, a slit or a hole, a jet injection nozzle with a syringe, and/or the like. When the traveling plunger 1604 moves towards the end 1602*a* of the housing 1601, an internal pressure within the storage reservoir may increase and push the dispensing outlet to be open to let the dispensable substance 1605 be released out of the housing 1601.

In an embodiment, a pressure relief device 1606 may be placed within the housing 1601, e.g., at the end 1602*a* of the housing 1601.

In some embodiments, the housing 1601 may include small holes (e.g., with a diameter smaller than 2 mm), e.g., on the side of the housing 1601, or at the end 1602*a* to facilitate loading the dispensable substance into the storage reservoir.

In some embodiments, a feedback control circuit (e.g., a feedback resistor, etc.) may be added to send feedback from the gas generating cell 1603 to the electronic component such that when the internal pressure reaches a threshold level, the electronic component may control the gas generating cell 1603 to turn off gas generation, or to activate other safety mechanism (e.g., feedback-controlled release valve, etc.). For example, an internal pressure sensor may be used to measure the internal pressure within the ingestible device and generate feedback to the feedback control circuit.

Figure 17:
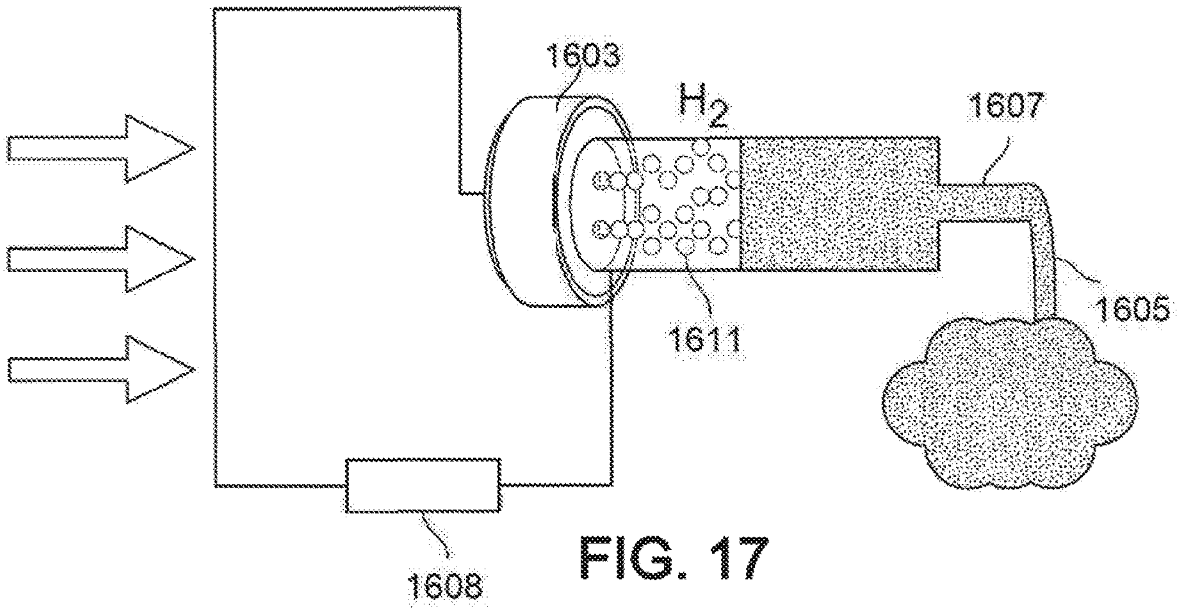
FIG. 17 illustrates aspects of a mechanism for an ingestible device with a gas generating cell configured to generate a gas to dispense a substance.

FIG. 17 provides an example diagram illustrating aspects of a mechanism for a gas generating cell 1603 configured to generate a gas to dispense a substance, according to some embodiments described herein. As shown in FIG. 17, the gas generating cell 1603 generates a gas 1611 which can propel the dispensable substance 1605 out of the dispensing outlet 1607. A variable resistor 1608 may be connected to a circuit with the gas generating cell 1603 such that the variable resistor 1608 may be used to control an intensity and/or an amount of gas 1611 (e.g., hydrogen) generated by the cell 1603. Specifically, the gas generating cell 1603 may be a battery form factor cell that is capable of generating hydrogen when a resistor is applied. In this way, as the gas generating cell 1603 only needs the use of a resistor only without any active power requirements, the gas generating cell 1603 may be integrated into an ingestible device such as a capsule with limited energy/power available. For example, the gas generating cell 1603 may be compatible with a capsule at a size of 26 mm×13 mm or smaller.

In some embodiments, based on the elution rate of gas from the cell, and an internal volume of the ingestible device, it may take time to generate sufficient gas 1611 to deliver the substance 1605, and the time required may be 30 seconds or longer. For example, the time to generate a volume of hydrogen equivalent to 500 μL of fluid would be approximately 5 minutes. A longer period of time may be needed based upon non-ideal conditions within the ingestible device, such as friction, etc. Thus, given that the production of gas (e.g., hydrogen) may take time, gas generation may need to start prior to the ingestible device arriving at the site of delivery to build pressure up within the device. The ingestible device may then need to know when it is approaching the site of delivery. For example, the device may start producing gas on an "entry transition," which is determined by temperature, so as to produce enough gas to be close to the pressure high enough to deliver the dispensable substance. The ingestible device may then only start producing gas again when it arrives at the site of delivery, which will cause the internal pressure within the ingestible device to reach a level required by the dispensing outlet to release the dispensable substance. Also, for regio-specific delivery, the ingestible device may estimate the time it takes to build up enough pressure to deliver the dispensable substance before the ingestible device arrives at a specific location, to activate gas generation.

For example, for systemic delivery, when an internal volume of the ingestible device is around 500 μL, a gas generation time of 2 hours, an initial pressure of approximately 300 pound per square inch absolute (psia) may be generated, with higher and lower pressures possible. The generated pressure may drop when air enters the storage reservoir which was previously occupied by the dispensable substance during the dispensing process. For systemic drug delivery, a force with a generated pressure of approximately 100 to 360 pound per square inch (psi) may be required for dennal penetration, e.g., to penetrate the mucosa or epithelial layer. The pressure may also vary depending on the nozzle design at the dispensing outlet, fluid viscosity, and surrounding tissue proximity and properties.

The gas 1611 that may be generated for a continuous delivery of drug (e.g., 1 cc $H_2$ in 4 hours, 16 breaths per minute at 0.5 L tidal volume) may equate to 1 cc hydrogen in approximately 2000 L of exhaled air, or approximately 0.5 ppm $H_2$, which is below physiologic values of exhaled hydrogen. Reducing this time to 10 minutes equates to approximately 13 ppm hydrogen. Thus, due to the length of intestine that may be covered during this time period, the ingestible device may possess a higher localized value than physiologic.

Figure 18:
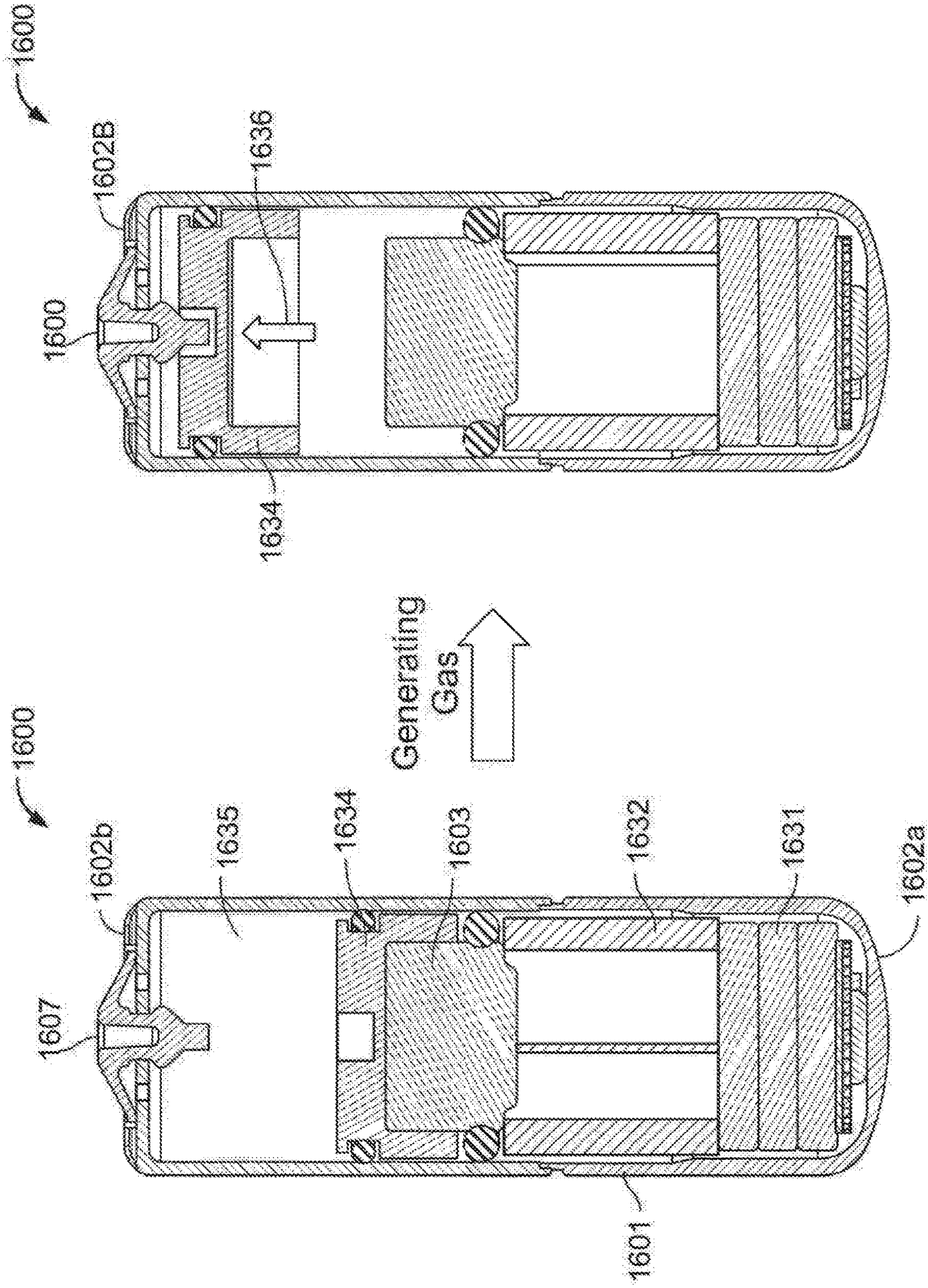
FIG. 18 illustrates an ingestible device having a piston to push for drug delivery.
Figure 19:
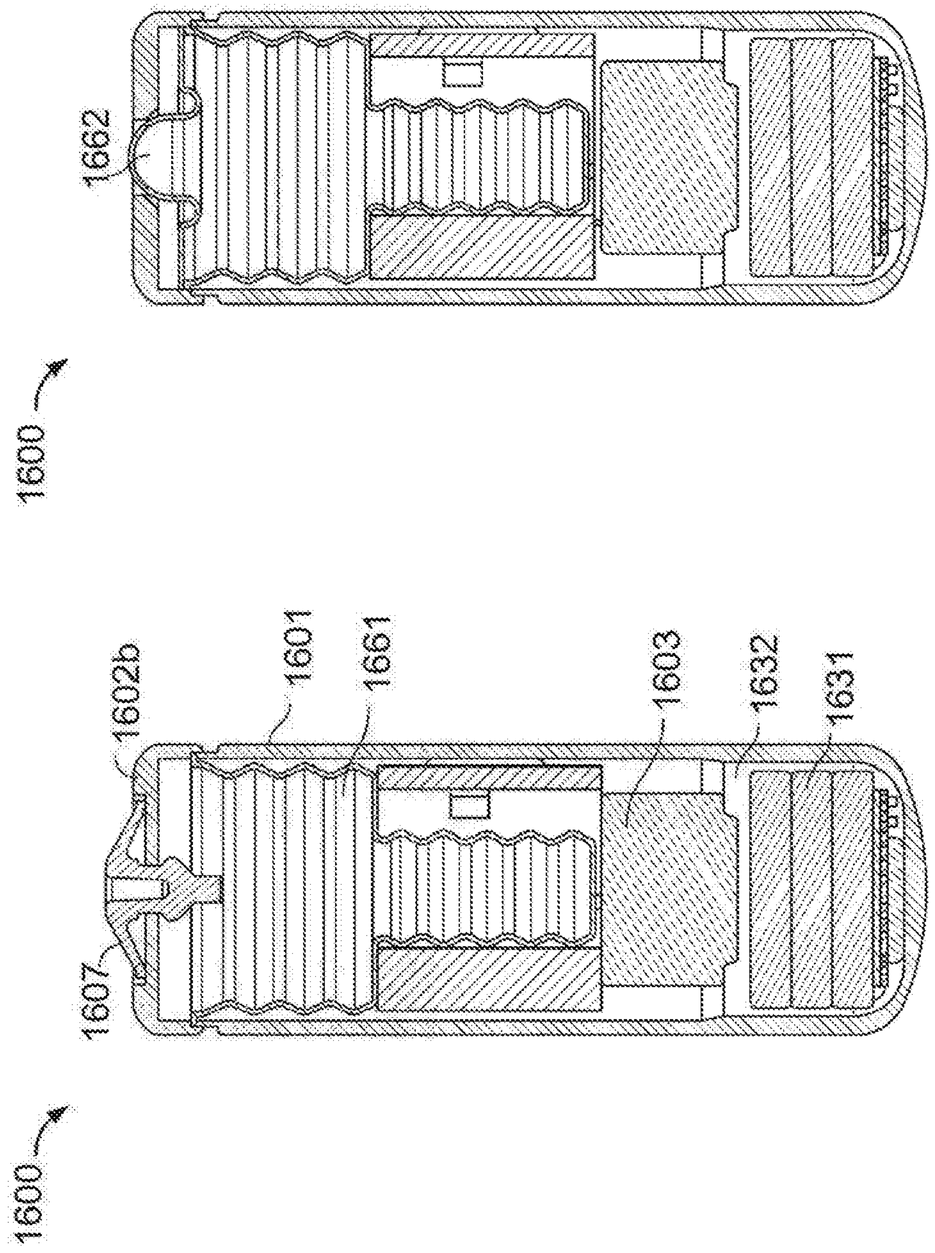
FIG. 19 illustrates an ingestible device having a bellow structure for a storage reservoir of dispensable substances.

FIGS. 18 and 19, disclosed in U.S. Provisional Application No. 62/385,553, incorporated by reference herein in its entirety, illustrates an example of an ingestible device for localized delivery of pharmaceutical compositions disclosed herein, in accordance with particular implementations. The ingestible device 1600 includes a piston or drive element 1634 to push for drug delivery, in accordance with particular implementations described herein. The ingestible device 1600 may have one or more batteries 1631 placed at one end 1602*a* of a housing 1601 to provide power for the ingestible device 1600. A printed circuit board (PCB) 1632 may be placed adjacent to a battery or other power source 1631, and a gas generating cell 1603 may be mounted on or above the PCB 1632. The gas generating cell 1603 may be sealed from the bottom chamber (e.g., space including 1631 and 1632) of the ingestible device 1600. A movable piston 1634 may be placed adjacent to the gas generating cell 1603. In this way, gas generation from the gas generating cell 1603 may propel a piston 1634 to move towards another end 1602*b* of the housing 1601 such that the dispensable substance in a reservoir compartment 1635 can be pushed out of the housing through a dispensing outlet 1607, e.g., the movement is shown at 1636, with the piston 1634 at a position after dispensing the substance. The dispensing outlet 1607 may comprise a plug. The reservoir compartment 1635 can store the dispensable substance (e.g., drug substance), or alternatively the reservoir compartment can house a storage reservoir 1661 which comprises the dispensable substance. The reservoir compartment 1635 or storage reservoir 1661 may have a volume of approximately 600 μL or even more dispensable substance, which may be dispensed in a single bolus, or gradually over a period of time.

The battery cells 1631 may have a height of 1.65 mm each, and one to three batteries may be used. The height of the piston may be reduced with custom molded part for around 1.5 mm to save space. If the gas generating cell 1603 is integrated with the piston 1634, the overall height of the PCB, batteries and gas generating cell in total can be reduced to around 5 mm, thus providing more space for drug storage. For example, for an ingestible device of 7.8 mm in length (e.g., from end 1602*a* to the other end 1602*b*), a reservoir compartment 1635 or a storage reservoir 1661 of approximately 600 μL may be used for drug delivery. For another example, for an ingestible device of 17.5 mm in length, a reservoir compartment 1635 or a storage reservoir 1661 of approximately 1300 μL may be used for drug release.

In some implementations, at the reservoir 1635 or 1661 for storing a therapeutically effective amount of the JAK inhibitor forms at least a portion of the device housing 1601. The therapeutically effective amount of the JAK inhibitor can be stored in the reservoir 1635 or 1661 at a particular pressure, for example, determined to be higher than a pressure inside the GI tract so that once the reservoir 1635 or 1661 is in fluid communication with the GI tract, the JAK inhibitor is automatically released. In certain implementations, the reservoir compartment 1635 includes a plurality of chambers, and each of the plurality of the chambers stores a different dispensable substance or a different storage reservoir 1661.

In certain embodiments, the storage reservoir 1661 is a compressible component or has compressible side walls. In particular embodiments, the compressible component can be composed, at least in part, or coated (e.g., internally) with polyvinyl chloride (PVC), silicone, DEHP (di-2-ethylhexyl phthalate), Tyvek, polyester film, polyolefin, polyethylene, polyurethane, or other materials that inhibit the JAK inhibitor from sticking to the reservoir and provide a sterile reservoir environment for the JAK inhibitor. The storage reservoir 1661 can be hermetically sealed. The reservoir compartment 1635 or storage reservoir 1661 can be configured to store JAK inhibitor in quantities in the range of 0.01 mL-2 mL, such as 0.05 mL-2 mL, such as 0.05 mL-2 mL, such as 0.6 mL-2 mL. In some embodiments, the storage reservoir 1661 is attachable to the device housing 1601, for example, in the reservoir compartment. Accordingly, the storage reservoir 1635 can be loaded with the JAK inhibitor prior to being positioned in and/or coupled to the ingestible device housing 1601. The ingestible device housing 1601 includes one or more openings configured as a loading port to load the dispensable substance into the reservoir compartment. In another embodiment, the ingestible device housing 1601 includes one or more openings configured as a vent.

As noted above, in some embodiments, a storage reservoir (optionally, containing a JAK inhibitor, such as a therapeutically effective amount of JAK inhibitor) is attachable to an ingestible device. In general, in such embodiments the storage reservoir and ingestible device can be designed in any appropriate fashion so that the storage reservoir can attach to the ingestible device when desired. Examples of designs include a storage reservoir that fits entirely within the ingestible device (e.g., in the ingestible device so that the storage reservoir is sealed within the device at the time the device is ingested by a subject), a storage reservoir that fits partially within the ingestible device, and a storage reservoir that is carried by the housing of the device. In some embodiments, the storage reservoir snap fits with the ingestible device. In certain embodiments, the storage reservoir is friction fit with the ingestible device. In some embodiments, the storage reservoir is held together with the ingestible device via a biasing mechanism, such as one or more springs, one or more latches, one or more hooks, one or more magnets, and/or electromagnetic radiation. In certain embodiments, the storage reservoir can be a piercable member. In some embodiments, the ingestible device has a sleeve into which the storage reservoir securely fits. In some embodiments, the storage reservoir is disposed in/on a slidable track/groove so that it can move onto a piercing needle when delivery of the therapeutic agent is desired. In certain embodiments, the storage reservoir is made of a soft plastic coating, which is contacted with a needle at any orientation to deliver the therapeutic agent when desired. Generally, the storage reservoir can be made of one or more appropriate materials, such as, for example, one or more plastics and/or one or more metals or alloys. Exemplary materials include silicone, polyvinyl chloride, polycarbonate and stainless steel. Optionally, the design may be such that the storage reservoir carries some or all of the electrical componentry to be used by the ingestible device. Although the foregoing discussion relates to one storage reservoir, it is to be understood that an ingestible device can be designed to carry any desired number (e.g., two, three, four, five) storage reservoirs. Different storage reservoirs can have the same or different designs. In some embodiments, the ingestible device (when fully assembled and packaged) satisfies the regulatory requirements for marketing a medical device in one or more jurisdictions selected from the United States of America, the European Union or any member state thereof, Japan, China, Brazil, Canada, Mexico, Colombia, Argentina, Chile, Peru, Russia, the UK, Switzerland, Norway, Turkey, Israel, any member state of the Gulf Cooperative Council, South Africa, India, Australia, New Zealand, South Korea, Singapore, Thailand, the Philippines, Malaysia, Viet Nam, Indonesia, Taiwan and Hong Kong.

In certain embodiments, the ingestible device housing 1601 includes one or more actuation systems (e.g., gas generating cell 1603) for pumping the JAK inhibitor from the reservoir 1635. In some embodiments, the actuation system can include a mechanical, electrical, electromechanical, hydraulic, and/or fluid actuation system. For example, a chemical actuation means may use chemical reaction of mixing one or more reagents to generate a sufficient volume of gas to propel the piston or drive element 1634 for drug release. The actuation system can be integrated into the reservoir compartment 1635 or can be an auxiliary system acting on or outside of the reservoir compartment 1635. For example, the actuation system can include pumping system for pushing/pulling the JAK inhibitor out of the reservoir compartment 1635 or the actuation system can be configured to cause the reservoir compartment 1635 to change structurally so that the volume inside of the reservoir compartment 1635 changes, thereby dispensing the JAK inhibitor from the reservoir compartment 1635. The actuation system can include an energy storage component such as a battery or a capacitor for powering the actuation system. The actuation system can be actuated via gas pressure or a system storing potential energy, such as energy from an elastic reservoir component being expanded during loading of the reservoir and after being positioned in the ingestible device housing 1601 being subsequently released from the expanded state when the ingestible device housing is at the location for release within the GI tract. In certain embodiments, the reservoir compartment 1635 can include a membrane portion, whereby the JAK inhibitor is dispensed from the reservoir compartment 1635 or storage reservoir 1661 via osmotic pressure.

In particular embodiments the storage reservoir 1661 is in a form of a bellow that is configured to be compressed via a pressure from the gas generating cell. The JAK inhibitor may be loaded into the bellow, which may be compressed by gas generation from the gas generating cell or other actuation means to dispense the dispensable substance through the dispensing outlet 1607 and out of the housing 1601. In some embodiments, the ingestible device includes a capillary plate placed between the gas generating cell and the first end of the housing, and a wax seal between the gas generating cell and the reservoir, wherein the wax seal is configured to melt and the dispensable substance is pushed through the capillary plate by a pressure from the gas generating cell. The shape of the bellow may aid in controlled delivery. The reservoir compartment 1635 includes a dispensing outlet, such as a valve or dome slit 1662 extending out of an end of the housing 1601, in accordance with particular implementations. Thus when the bellow is being compressed, the dispensable substance may be propelled out of the bellow through the valve or the dome slit.

In certain embodiments, the reservoir compartment 1635 includes one or more valves (e.g., a valve in the dispensing outlet 1607) that are configured to move or open to fluidly couple the reservoir compartment 1635 to the GI tract. In certain embodiments, a housing wall of the housing 1601 can form a portion of the reservoir compartment 1635. In certain embodiments, the housing walls of the reservoir serve as a gasket. One or more of the one or more valves are positioned in the housing wall of the device housing 1601, in accordance with particular implementations. One or more conduits may extend from the reservoir 1635 to the one or more valves, in certain implementations.

In certain embodiments, a housing wall of the housing 1601 can be formed of a material that is configured to dissolve, for example, in response to contact at the disease site. In certain embodiments, a housing wall of the housing 1601 can be configured to dissolve in response to a chemical reaction or an electrical signal. The one or more valves and/or the signals for causing the housing wall of the housing 1601 to dissolve or dissipate can be controlled by one or more processors or controllers positioned on PCB 1632 in the device housing 1601. The controller is communicably coupled to one or more sensors or detectors configured to determine when the device housing 1601 is proximate to a disease site. The sensors or detectors comprise a plurality of electrodes comprising a coating, in certain implementations. Releasing of the JAK inhibitor from the reservoir compartment 1635 is triggered by an electric signal from the electrodes resulting from the interaction of the coating with the one or more sites of disease site. The one or more sensors can include a chemical sensor, an electrical sensor, an optical sensor, an electromagnetic sensor, a light sensor, and/or a radiofrequency sensor.

In particular embodiments, the device housing 1601 can include one or more pumps configured to pump the therapeutically effective amount of the JAK inhibitor from the reservoir compartment 1635. The pump is communicably coupled to the one or more controllers. The controller is configured to activate the pump in response to detection by the one or more detectors of the disease site and activation of the valves to allow the reservoir 1635 to be in fluid communication with the GI tract. The pump can include a fluid actuated pump, an electrical pump, or a mechanical pump.

In certain embodiments, the device housing 1601 comprises one or more anchor systems for anchoring the device housing 1601 or a portion thereof at a particular location in the GI tract adjacent the disease site. In some embodiments, a storage reservoir comprises an anchor system, and the storage reservoir comprising a releasable substance is anchored to the GI tract. The anchor system can be activated by the controller in response to detection by the one or more detectors of the disease site. In certain implementations, the anchor system includes legs or spikes configured to extend from the housing wall(s) of the device housing 1601. The spikes can be configured to retract and/or can be configured to dissolve over time. An example of an attachable device that becomes fixed to the interior surface of the GI tract is described in PCT Patent Application PCT/US2015/012209, "Gastrointestinal Sensor Implantation System," filed Jan. 21, 2015, which is hereby incorporated by reference herein in its entirety.

Figure 20:
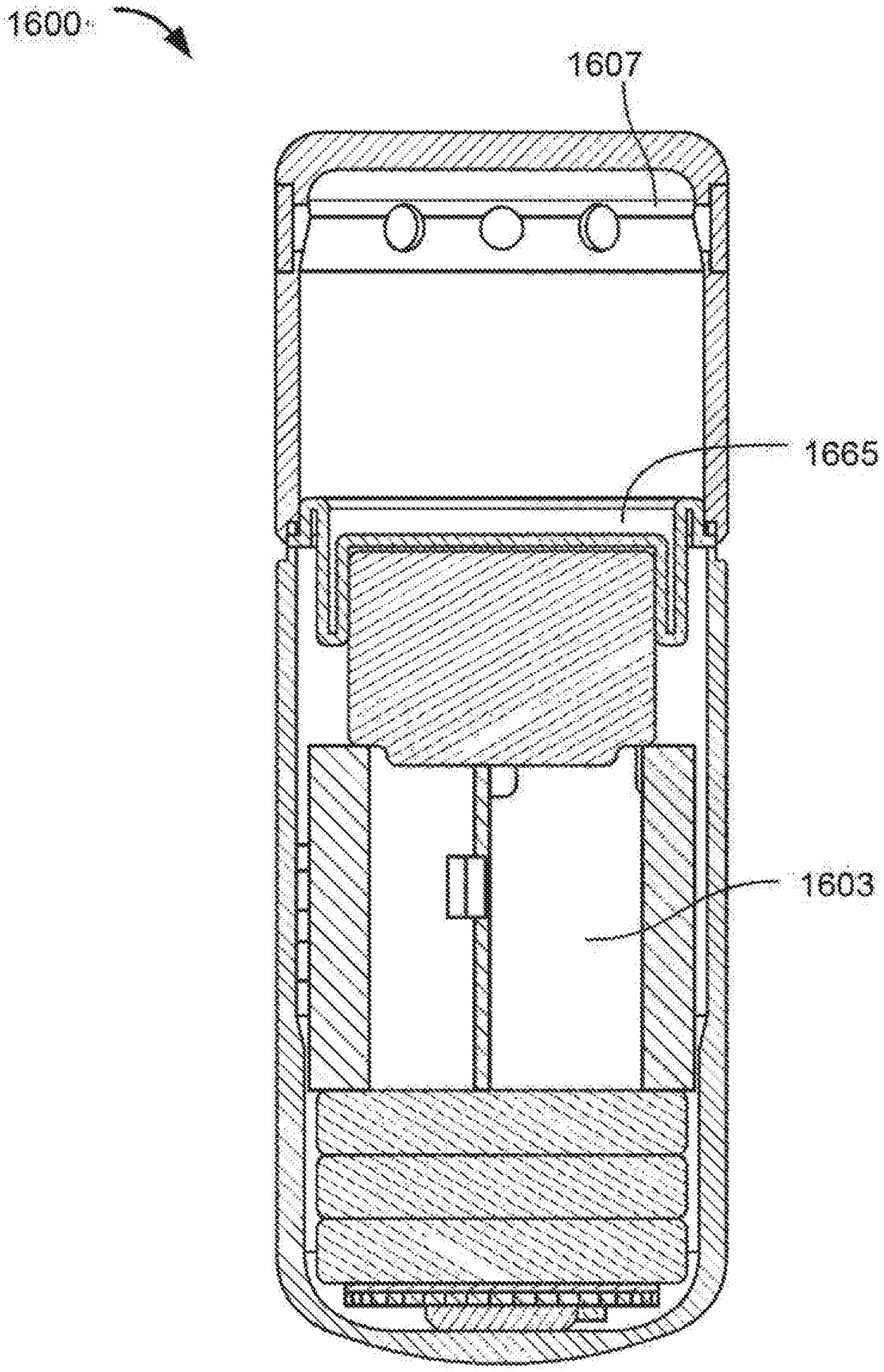
FIG. 20 illustrates an ingestible device having a flexible diaphragm to deform for drug delivery.

FIG. 20 provides an example structural diagram having a flexible diaphragm 1665 that may deform towards the dispensing outlet 1607 when the gas generating cell 1603 generates gas. The dispensable substance may then be propelled by the deformed diaphragm out of the housing through the dispensing outlet 1607. The dispensing outlet 1607 shown at FIG. 20 is in the form of a ring valve, however, any outlet design can be applied.

In some embodiments, an ingestible device can have an umbrella-shaped exit valve structure as a dispensing outlet of the ingestible device. Optionally, an ingestible device can have a flexible diaphragm to deform for drug delivery, and/or an integrated piston and gas generating cell such that the gas generating cell is movable with the piston to push for drug delivery.

In certain embodiments, an ingestible device can be anchored within the intestine by extending hooks from the ingestible device after it has entered the region of interest. For example, when the ingestible device determines it has arrived at a location within the GI tract, the hooks can be actuated to extend outside of the ingestible device to catch in the intestinal wall and hold the ingestible device in the respective location. In some embodiments, the hook can pierce into the intestinal wall to hold the ingestible device 100 in place. The hooks can be hollow. A hollow hook can be used to anchor the ingestible device and/or to dispense a substance from the dispensable substance, e.g., into the intestinal wall.

In some embodiments an ingestible device includes an intestinal gripper to grip a portion of the intestinal wall for delivering the dispensable substance. Such a gripper can include two or more arms configured to out of the device and close to grip a portion of the intestinal wall.

An injecting needle can be used with the anchoring arms to inject dispensable substance into the intestinal wall after a portion of the intestinal wall is gripped.

In some embodiments, when the gas generating cell generates gas to propel the piston to move towards the nozzle such that the dispensable substance can be pushed under the pressure to break a burst disc to be injected via the nozzle.

In some embodiments, an ingestible device has a jet delivery mechanism with enhanced usable volume of dispensable substance. For example, the nozzle may be placed at the center of the ingestible device, and gas channels may be placed longitudinally along the wall of the ingestible device to transport gas from the gas generating cell to propel the piston, which is placed at an end of the ingestible device.

In some embodiments, the ingestible device can use osmotic pressure to adhere a suction device of the ingestible device to the intestinal wall. For example, the ingestible device may have an osmotic mechanism that has a chamber storing salt crystals. The chamber can include a mesh placed in proximate to a burst valve at one end of the chamber, and a reverse osmosis (RO) membrane placed in proximate to a valve on the other end of the chamber. A suction device, e.g., two or more suction fingers, is placed outside of the chamber with an open outlet exposed to luminal fluid in the GI tract. When the osmotic mechanism is inactivated, e.g., the valve is closed so that no luminal fluid is drawn into the osmotic chamber. When the osmotic mechanism is activated by opening the valve, luminal fluid enters the ingestible device through an outlet of the suction device and enters the osmotic chamber through the valve. The salt in the chamber is then dissolved into the fluid. The RO membrane prevents any fluid to flow in the reverse direction, e.g., from inside the chamber to the valve. The fluid continues to flow until all the salt contained in the chamber is dissolved or until intestinal tissue is drawn into the suction device. As luminal fluid keeps flowing into the chamber, the solution of the luminal fluid with dissolved salt in the chamber may reduce osmotic pressure such that the suction force at may also be reduced. In this way, suction of the intestinal tissue may stall before the tissue is in contact with the valve to avoid damage to the intestinal tissue.

An ingestible device employing an osmotic mechanism can also include a suction device as illustrated. The suction device can be two or more suction fingers 347*a*-*b* disposed proximate to the outlet. The outlet can be connected to a storage reservoir storing the dispensable substance (e.g., therapeutic agent). The storage reservoir can contact a piston (similar to 104 in FIG. 16), which can be propelled by pressure generated from the osmotic pump to move towards the outlet. The osmotic pump can be similar to the osmotic mechanism described in the preceding paragraph. A break-away section can be placed in proximate to the other end (opposite to the end where the outlet 107 is disposed) of the ingestible device.

In some embodiments, tumbling suction by an ingestible device is used. Such an ingestible device does not require any electronics or other actuation elements. Such an ingestible device may constantly, intermittently, or periodically tumble when travelling through the intestine. When the ingestible device tumbles to a position that the outlet is in direct contact with the intestinal wall, a suction process similar to that described in the preceding paragraph may occur. Additional structural elements such as fins, flutes or the like may be added to the outer wall of the ingestible device 100 to promote the tumbling motion.

In certain embodiments, the reservoir is an anchorable reservoir, which is a reservoir comprising one or more anchor systems for anchoring the reservoir at a particular location in the GI tract adjacent the disease site. In certain embodiments, the anchor system includes legs or spikes or other securing means such as a piercing element, a gripping element, a magnetic-flux-guiding element, or an adhesive material, configured to extend from the anchorable reservoir of the device housing. The spikes can be configured to retract and/or can be configured to dissolve over time. In some embodiments, the anchorable reservoir is suitable for localizing, positioning and/or anchoring. In some embodiments, the anchorable reservoir is suitable for localizing, and positioning and/or anchoring by an endoscope. In some embodiments, the anchorable reservoir is connected to the endoscope. In some embodiments, the anchorable reservoir is connected to the endoscope in a manner suitable for oral administration. In some embodiments, the anchorable reservoir is connected to the endoscope in a manner suitable for rectal administration. Accordingly, provided herein in some embodiments is an anchorable reservoir is connected to an endoscope wherein the anchorable reservoir comprises a therapeutically effective amount of the JAK inhibitor. In some embodiments the endoscope is fitted with a spray catheter.

Exemplary embodiments of anchorable reservoirs are as follows. In more particular examples of the following exemplary embodiments the reservoir is connected to an endoscope.

In one embodiment, the anchorable reservoir comprises an implant capsule for insertion into a body canal to apply radiation treatment to a selected portion of the body canal. The reservoir includes a body member defining at least one therapeutic treatment material receiving chamber and at least one resilient arm member associated with the body member for removably engaging the body canal when the device is positioned therein.

In one embodiment the anchorable reservoir has multiple suction ports and permits multiple folds of tissue to be captured in the suction ports with a single positioning of the device and attached together by a tissue securement mechanism such as a suture, staple or other form of tissue bonding. The suction ports may be arranged in a variety of configurations on the reservoir to best suit the desired resulting tissue orientation.

In some embodiments an anchorable reservoir comprises a tract stimulator and/or monitor IMD comprising a housing enclosing electrical stimulation and/or monitoring circuitry and a power source and an elongated flexible member extending from the housing to an active fixation mechanism adapted to be fixed into the GI tract wall is disclosed. After fixation is effected, the elongated flexible member bends into a preformed shape that presses the housing against the mucosa so that forces that would tend to dislodge the fixation mechanism are minimized. The IMD is fitted into an esophageal catheter lumen with the fixation mechanism aimed toward the catheter distal end opening whereby the bend in the flexible member is straightened. The catheter body is inserted through the esophagus into the GI tract cavity to direct the catheter distal end to the site of implantation and fix the fixation mechanism to the GI tract wall. The IMD is ejected from the lumen, and the flexible member assumes its bent configuration and lodges the hermetically sealed housing against the mucosa. A first stimulation/sense electrode is preferably an exposed conductive portion of the housing that is aligned with the bend of the flexible member so that it is pressed against the mucosa. A second stimulation/sense electrode is located at the fixation site.

In some embodiments a reservoir for sensing one or more parameters of a patient is anchored to a tissue at a specific site and is released from a device, using a single actuator operated during a single motion. As an example, a delivery device may anchor the capsule to the tissue site and release the reservoir from the delivery device during a single motion of the actuator.

In some embodiments a device is provided comprising: a reservoir configured to contain a fluid, the reservoir having at least one outlet through which the fluid may exit the reservoir; a fluid contained within the reservoir; a primary material contained within the reservoir and having a controllable effective concentration in the fluid; and at least one electromagnetically responsive control element located in the reservoir or in a wall of the reservoir and adapted for modifying the distribution of the primary material between a first active form carried in the fluid and a second form within the reservoir in response to an incident electromagnetic control signal, the effective concentration being the concentration of the first active form in the fluid, whereby fluid exiting the reservoir carries the primary material in the first active form at the effective concentration.

In some embodiments systems and methods are provided for implementing or deploying medical or veterinary devices or reservoirs (a) operable for anchoring at least partly within a digestive tract, (b) small enough to pass through the tract per vias naturales and including a wireless-control component, (c) having one or more protrusions positionable adjacent to a mucous membrane, (d) configured to facilitate redundant modes of anchoring, (e) facilitating a "primary" material supply deployable within a stomach for an extended and/or controllable period, (f) anchored by one or more adaptable extender modules supported by a subject's head or neck, and/or (g) configured to facilitate supporting at least a sensor within a subject's body lumen for up to a day or more.

In certain embodiments, the reservoir is attachable to an ingestible device. In certain embodiments, the ingestible device comprises a housing and the reservoir is attachable to the housing. In certain embodiments, the attachable reservoir is also an anchorable reservoir, such as an anchorable reservoir comprising one or more anchor systems for anchoring the reservoir at a particular location in the GI tract as disclosed hereinabove.

Accordingly, in certain embodiments, provided herein is a JAK inhibitor for use in a method of treating a disease of the gastrointestinal tract as disclosed herein, wherein the JAK inhibitor is contained in a reservoir suitable for attachment to a device housing, and wherein the method comprises attaching the reservoir to the device housing to form the ingestible device, prior to orally administering the ingestible device to the subject.

In certain embodiments, provided herein is an attachable reservoir containing a JAK inhibitor for use in a method of treating a disease of the gastrointestinal tract, wherein the method comprises attaching the reservoir to a device housing to form an ingestible device and orally administering the ingestible device to a subject, wherein the JAK inhibitor is released by device at a location in the gastrointestinal tract of the subject that is proximate to one or more sites of disease.

In certain embodiments, provided herein is an attachable reservoir containing a JAK inhibitor, wherein the reservoir is attachable to a device housing to form an ingestible device that is suitable for oral administration to a subject and that is capable of releasing the JAK inhibitor at a location in the gastrointestinal tract of the subject that is proximate to one or more sites of disease.

In particular implementation the ingestible device includes cameras (e.g., video cameras) that affords inspection of the entire GI tract without discomfort or the need for sedation, thus avoiding many of the potential risks of conventional endoscopy. Video imaging can be used to help determine one or more characteristics of the GI tract, including the location of disease (e.g., presence or location of inflamed tissue and/or lesions associated with inflammatory bowel disease). In some embodiments, the ingestible device 101 may comprise a camera for generating video imaging data of the GI tract which can be used to determine, among other things, the location of the device. Examples of video imaging capsules include Medtronic's PillCam™, Olympus' Endocapsule®, and IntroMedic's MicroCam™. For a review of imaging capsules, see Basar et al. "Ingestible Wireless Capsule Technology: A Review of Development and Future Indication" International Journal of Antennas and Propagation (2012); 1-14). Other imaging technologies implemented with the device 101 can include thermal imaging cameras, and those that employ ultrasound or Doppler principles to generate different images (see Chinese patent application CN104473611: "Capsule endoscope system having ultrasonic positioning function."

Ingestible devices can be equipped with sources for generating reflected light, including light in the Ultraviolet, Visible, Near-infrared and/or Mid-infrared spectrum, and the corresponding detectors for spectroscopy and hyperspectral imaging. Likewise, autofluorescense may be used to characterize GI tissue (e.g., subsurface vessel information), or low-dose radiation (see Check-Cap™) can be used to obtain 3D reconstructed images.

Device Components

An ingestible device in accordance with particular embodiments of the present disclosure may comprise a component made of a non-digestible material and contain the JAK inhibitor. In some embodiments, the material is plastic.

It is envisaged that the device is single-use. The device is loaded with a drug prior to the time of administration. In some embodiments, it may be preferred that there is provided a medicinal product comprising the device pre-filled with the drug.

Anchoring Components

Several systems may actively actuate and control the capsule position and orientation in different sections of the GI tract. Examples include leg-like or anchor-like mechanisms that can be deployed by an ingestible device to resist peristaltic forces in narrowed sections of the GI tract, such as the intestine, and anchor the device to a location. Other systems employ magnetic shields of different shapes that can interact with external magnetic fields to move the device. These mechanisms may be particularly useful in areas outside of the small intestine, like the cecum and large intestine.

An anchoring mechanism may be a mechanical mechanism. For example, a device may be a capsule comprising a plurality of legs configured to steer the capsule. The number of legs in the capsule may be, for example, two, four, six, eight, ten or twelve. The aperture between the legs of the device may be up to about 35 mm; about 30 to about 35 mm; about 35 to about 75 mm; or about 70 to about 75 mm. The contact area of each leg may be varied to reduce impact on the tissue. One or more motors in the capsule may each actuate a set of legs independently from the other. The motors may be battery-powered motors.

An anchoring mechanism may be a non-mechanical mechanism. For example, a device may be a capsule comprising a permanent magnet located inside the capsule. The capsule may be anchored at the desired location of the GI tract by an external magnetic field.

An anchoring mechanism may comprise a non-mechanical mechanism and a mechanical mechanism. For example, a device may be a capsule comprising one or more legs, one or more of which are coated with an adhesive material.

Locomotion Components

Ingestible devices can be active or passive, depending on whether they have controlled or non-controlled locomotion. Passive (non-controlled) locomotion is more commonly used among ingestible devices given the challenges of implementing a locomotion module. Active (controlled) locomotion is more common in endoscopic ingestible capsules. For example, a capsule may comprise a miniaturized locomotion system (internal locomotion).

Internal locomotion mechanisms may employ independent miniaturized propellers actuated by DC brushed motors, or the use of water jets. As an example, a mechanism may comprise flagellar or flap-based swimming mechanisms. As an example, a mechanism may comprise cyclic compression/extension shape-memory alloy (SMA) spring actuators and anchoring systems based on directional micro-needles. As an example, a mechanism may comprise six SMA actuated units, each provided with two SMA actuators for enabling bidirectional motion. As an example, a mechanism may comprise a motor adapted to electrically stimulating the GI muscles to generate a temporary restriction in the bowel.

As an example, a capsule may comprise a magnet and motion of the capsule is caused by an external magnetic field. For example, a locomotion system may comprise an ingestible capsule and an external magnetic field source. For example, the system may comprise an ingestible capsule and magnetic guidance equipment such as, for example, magnetic resonance imaging and computer tomography, coupled to a dedicated control interface. In some embodiments drug release mechanisms may also be triggered by an external condition, such as temperature, pH, movement, acoustics, or combinations thereof.

Sampling Components

In some embodiments, an endoscope or ingestible device is used in biopsy and/or surgery. Ingestible devices may comprise a mechanism adapted to permit the collection of tissue samples. In some examples, this is achieved using electro-mechanical solutions to collect and store the sample inside an ingestible device. As an example, a biopsy mechanism may include a rotational tissue cutting razor fixed to a torsional spring or the use of microgrippers to fold and collect small biopsies. As an example, Over-the-scope clips (OTSC®) may be used to perform endoscopic surgery and/or biopsy. As an example of the methods disclosed herein, the method may comprise releasing a JAK inhibitor and collecting a sample inside the device. As an example, the method may comprise releasing a JAK inhibitor and collecting a sample inside the device in a single procedure.

Figure 21:
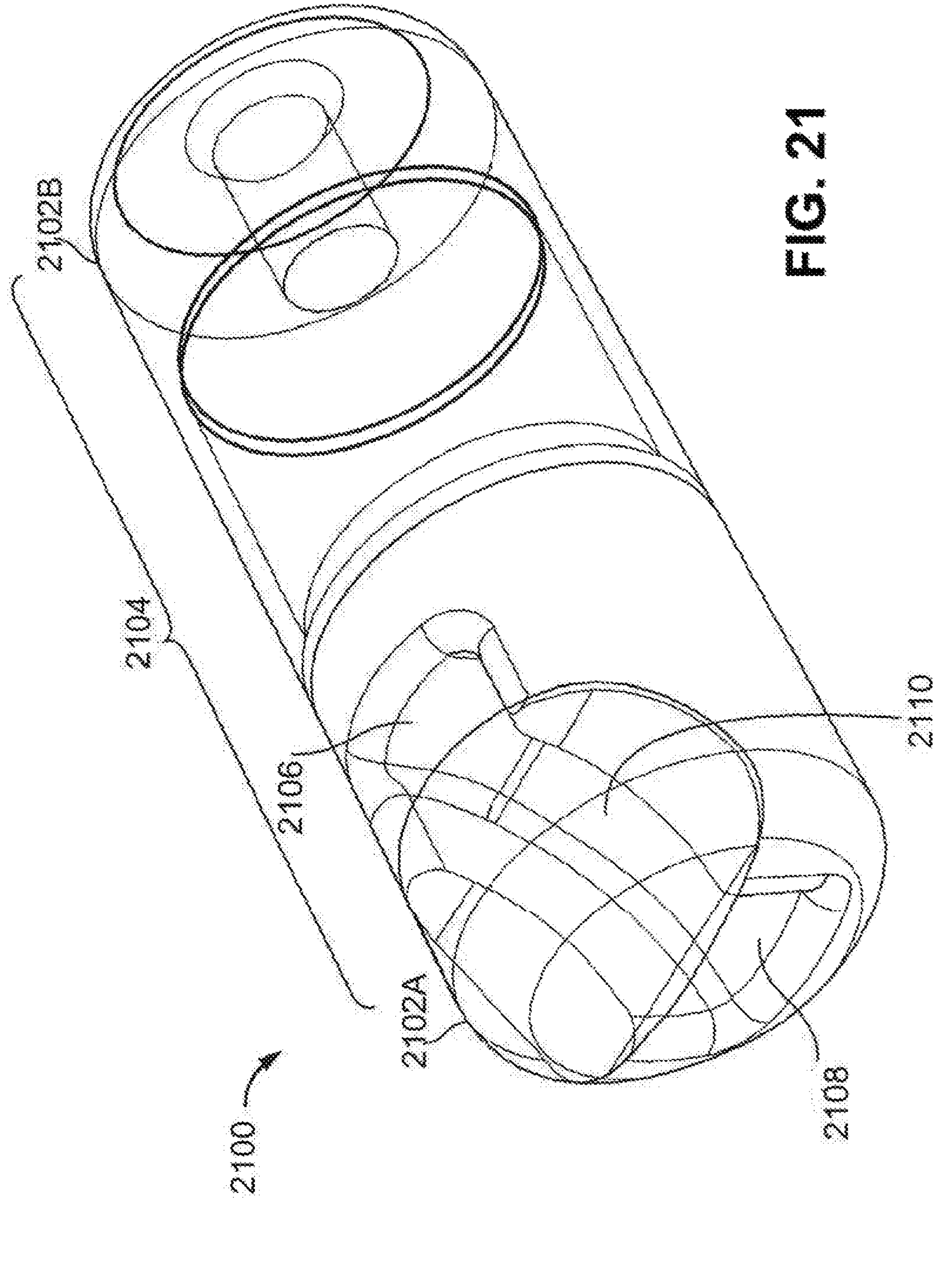
FIG. 21 shows an illustrative embodiment of an ingestible device with multiple openings in the housing.

FIG. 21 illustrates an example ingestible device 2100 with multiple openings in the housing. The ingestible device 2100 has an outer housing with a first end 2102A, a second end 2102B, and a wall 2104 extending longitudinally from the first end 2102A to the second end 2102B. Ingestible device 2100 has a first opening 2106 in the housing, which is connected to a second opening 2108 in the housing. The first opening 2106 of the ingestible device 2100 is oriented substantially perpendicular to the second opening 2108, and the connection between the first opening 2106 and the second opening 2108 forms a curved chamber 2110 within the ingestible device 2100.

The overall shape of the ingestible device 2100, or any of the other ingestible devices discussed in this disclosure, may be similar to an elongated pill or capsule.

In some embodiments, a portion of the curved chamber 2110 may be used as a sampling chamber, which may hold samples obtained from the GI tract. In some embodiments the curved chamber 2110 is subdivided into sub-chambers, each of which may be separated by a series of one or more valves or interlocks.

In some embodiments, the first opening 2106, the second opening 2108, or the curved chamber 2110 include one or more of a hydrophilic or hydrophobic material, a sponge, a valve, or an air permeable membrane.

The use of a hydrophilic material or sponge may allow samples to be retained within the curved chamber 2110, and may reduce the amount of pressure needed for fluid to enter through the first opening 2106 and dislodge air or gas in the curved chamber 2110. Examples of hydrophilic materials that may be incorporated into the ingestible device 2100 include hydrophilic polymers such as polyvinyl alcohol, polyvinyl pyrrolidone, and the like. Similarly, materials that have undergone various types of treatments, such as plasma treatments, may have suitable hydrophilic properties, and may be incorporated into the investible device 2100. Sponges may be made of any suitable material or combination of materials, such as fibers of cotton, rayon, glass, polyester, polyethylene, polyurethane, and the like. Sponges generally may be made from commercially available materials, such as those produced by Porex®.

As discussed in more detail below, in some embodiments, the sponges may be treated in order to change their absorbency or to help preserve samples.

In some embodiments, the sponges may be cut or abraded to change their absorbency or other physical properties.

Hydrophobic materials located near the second opening 2108 may repel liquids, discouraging liquid samples from entering or exiting the curved chamber 2110 through the second opening 2108. This may serve a similar function as an air permeable membrane. Examples of hydrophobic materials which may be incorporated into the ingestible device 2100 include polycarbonate, acrylics, fluorocarbons, styrenes, certain forms of vinyl, stainless steel, silicone, and the like.

The various materials listed above are provided as examples, and are not limiting. In practice, any type of suitable hydrophilic, hydrophobic, or sample preserving material may be used in the ingestible device 2100.

In some embodiments, an ingestible device includes a moveable valve as a diaphragm valve, which uses a mechanical actuator to move a flexible diaphragm in order to seal or unseal an aperture in a second portion of an inlet region, which may effectively block or unblock the inlet region. However, it will be understood that, in some embodiments, the moveable valve may be a different type of valve. For example, in some embodiments the moveable valve may be replaced by a pumping mechanism. As another example, in some embodiments the moveable valve is replaced with an osmotic valve A sampling chamber of an ingestible device can have an exit port to allow air or gas to exit the sampling chamber, while preventing at least a portion of the sample obtained by the ingestible device from exiting the sampling chamber. For example, the exit port may include a gas-permeable membrane. An ingestible device can include one-way valve as part of its exit port.

An ingestible device can include an outlet port connected to the volume within housing of the ingestible device. The outlet port may provide a path for the gas to exit the ingestible device and be released into the environment surrounding the ingestible device. This may prevent pressure from building up within the housing of the ingestible device. In some embodiments, an ingestible device does not include an outlet port, and the gas stays inside the volume of the ingestible device. In some embodiments, the outlet port may contain a gas permeable membrane, a one-way valve, a hydrophobic channel, or some other mechanism to avoid unwanted material, (e.g., fluids and solid particulates from within the GI tract), from entering the ingestible device through the outlet port.

In some embodiments, the ingestible device may include a sensor within or proximate to the sampling chamber. For example, this sensor may be used to detect various properties of a sample contained within the sampling chamber, or this sensor may be used to detect the results of an assay technique applied to the sample contained within the sampling chamber.

In some embodiments, a hydrophilic sponge is located within the sampling chamber, and the hydrophilic sponge may be configured to absorb the sample as the sample enters the sampling chamber. In some embodiments, the hydrophilic sponge fills a substantial portion of the sampling chamber, and holds the sample for an extended period of time. This may be particularly advantageous if the sample is collected from the ingestible device after the ingestible device exits the body. In some embodiments, the hydrophilic sponge is placed on only certain surfaces or fills only certain portions of the sampling chamber. For example, it may be possible to line certain walls (or all walls) of the sampling chamber with a hydrophilic sponge to assist in drawing in the sample, while leaving some (or none) of the walls of the sampling chamber uncovered. Leaving walls uncovered may allow the use of diagnostics or assay techniques that require a relatively un-obscured optical path.

In some embodiments, the ingestible device may include a sealed vacuum chamber connected to the exit port, or connected directly or indirectly to the sampling chamber. In some embodiments a pin valve may be used as a moveable valve (e.g., as moveable valve of ingestible device). In certain embodiments, a rotary valve may be used as a moveable valve (e.g., as moveable valve of ingestible device). In some embodiments, a flexible diaphragm, or diaphragm valve, may be used as a moveable valve (e.g., as moveable valve of ingestible device). In certain embodiments, a mechanism is near the diaphragm or in direct contact with the diaphragm. The spring mechanism may apply pressure to the diaphragm to oppose the pressure applied by the mechanical actuator, which may cause the flexible diaphragm to be moved into an open position when the mechanical actuator is not applying pressure to the flexible diaphragm. Additionally, this may ensure that the diaphragm valve remains open when the mechanical actuator is not applying pressure across the flexible diaphragm. In some embodiments, moving the mechanical actuator from a closed position to an open position causes a volume of the inlet region within the ingestible device to increase. This may cause the pressure within the inlet region to be reduced, generating suction to draw a sample into the inlet region. Similarly, moving the mechanical actuator from an open position to a closed position may cause the volume of the inlet region to be reduced. This may cause the pressure within the inlet region to be increased, pushing the sample out of the inlet region. Depending on the design of the inlet region, the mechanical actuator, and the moveable valve, this may push the sample into the sampling chamber rather than pushing the sample back through the opening in the ingestible device.

Figure 22:
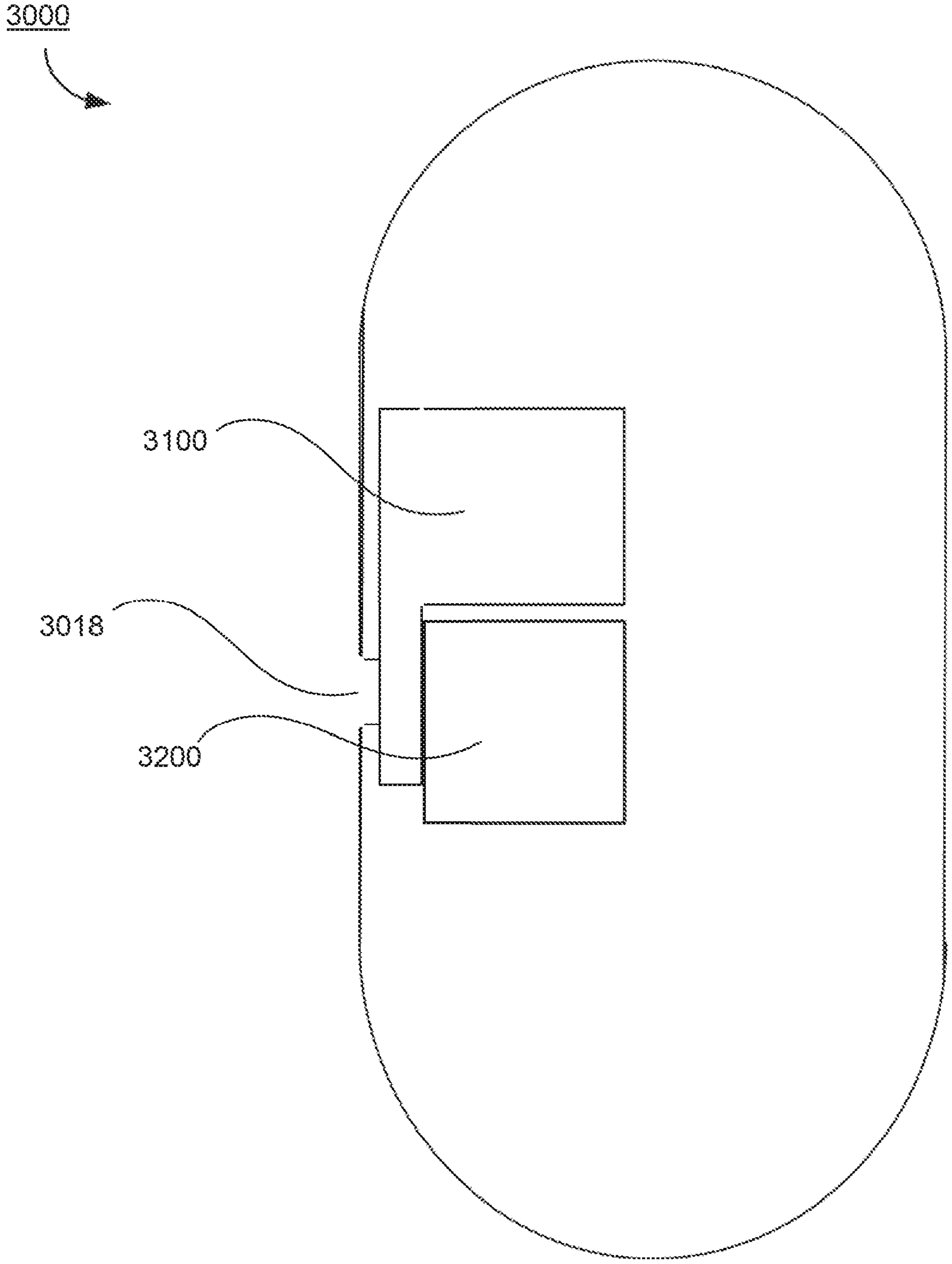
FIG. 22 shows a highly cross-section of an ingestible device including a valve system and a sampling system.

FIG. 22 depicts a cross-sectional view of a portion of the interior of ingestible device 3000. As shown in FIG. 22, the interior of ingestible device 3000 includes a valve system 3100 and a sampling system 3200. Valve system 3100 is depicted as having a portion that is flush with the opening 3018 so that valve system 3100 prevents fluid exterior to ingestible device 2000 from entering sampling system 3200. However, as described in more detail below with reference to FIGS. 22-27, valve system 3100 can change position so that valve system 3100 allows fluid exterior to ingestible device 3000 to enter sampling system 3200.

Figure 23:
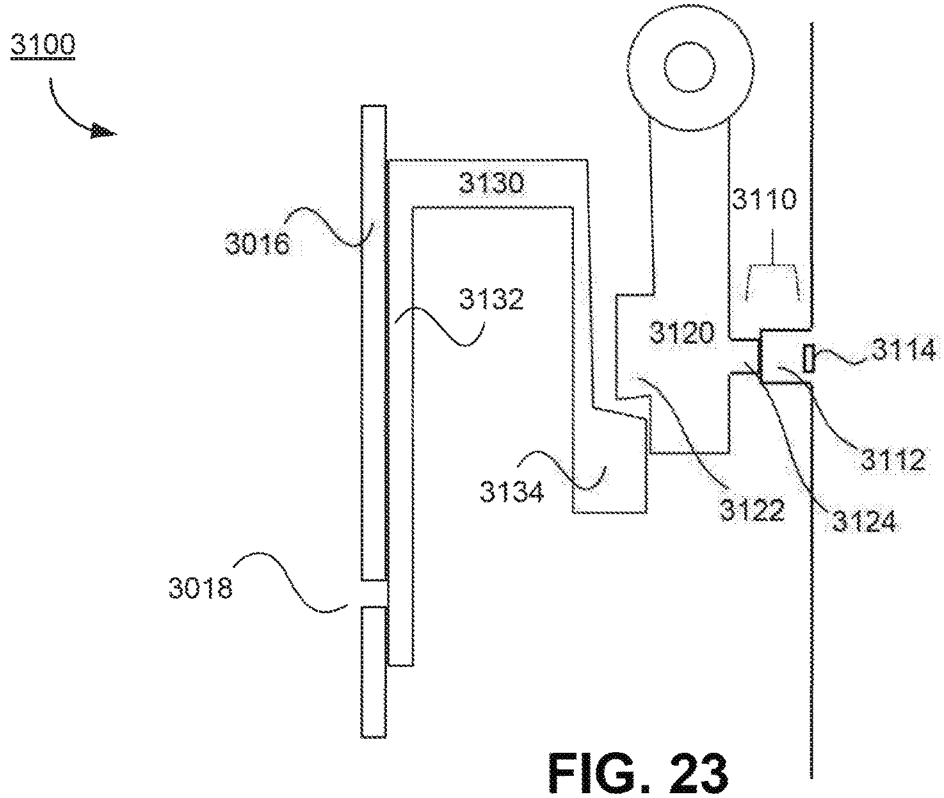
FIG. 23 illustrates a valve system.
Figure 27:
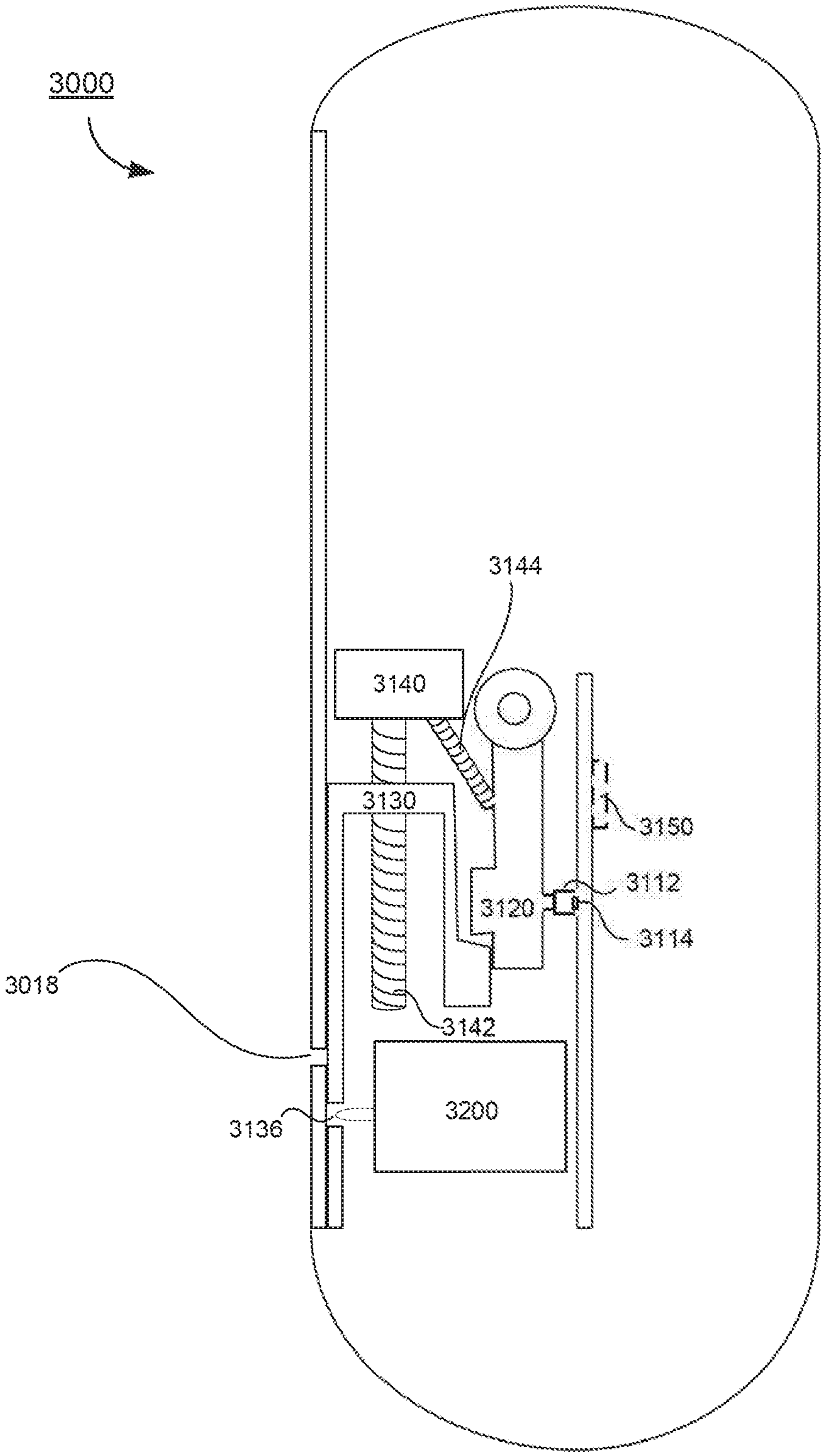
FIG. 27 illustrates a more detailed view of an ingestible device including a valve system and a sampling system.

FIGS. 23 and 27 illustrate valve system 3100 in more detail. As shown in FIG. 23, valve system 3100 includes an actuation mechanism 3110, a trigger 3120, and a gate 3130. In FIGS. 23 and 7, a leg 3132 of gate 3130 is flush against, and parallel with, housing wall 3016 so that gate leg 3132 covers opening 3018 to prevent fluid exterior to ingestible device 3000 (e.g., fluid in the GI tract) from entering the interior of ingestible device 3000. A protrusion 3134 of gate 3130 engages a lip 3122 of trigger 3120. A peg 3124 of trigger 3120 engages a wax pot 3112 of actuation mechanism 3110. Referring to FIG. 27, a biasing mechanism 3140 includes a compression spring 3142 that applies an upward force on gate 3130. Biasing mechanism 3140 also includes a torsion spring 3144 that applies a force on trigger 3120 in the counter-clockwise direction. In FIGS. 23 and 27, the force applied by torsion spring 3144 is counter-acted by the solid wax in pot 3112, and the force applied by compression spring 3142 is counter-acted by lip 3122.

Figure 24A:
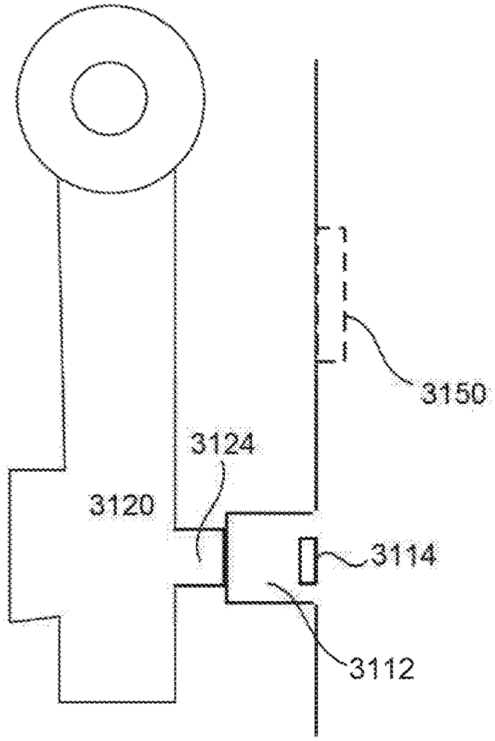
FIGS. 24A and 24B illustrate a portion of a two-stage valve system in its first and second stages, respectively.
Figure 24B:
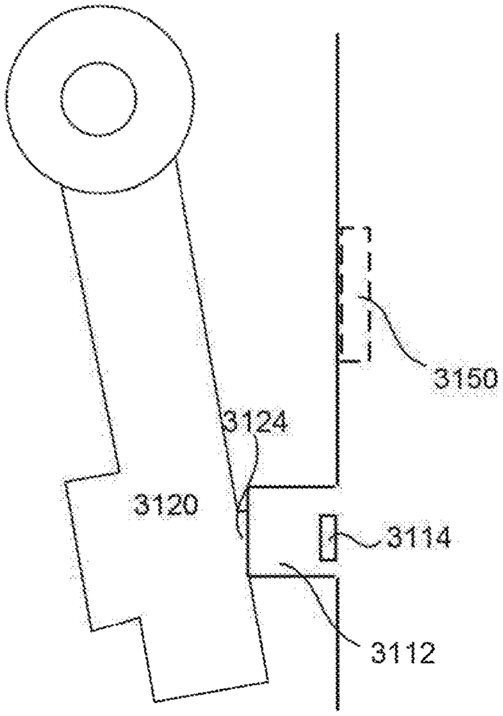

FIG. 24A and FIG. 24B show an embodiment of the manner in which actuation mechanism 3110 actuates movement of trigger 3120. Similar to FIGS. 23 and 27, FIG. 24A shows a configuration in which peg 3124 applies a force against solid wax pot 3112 due to torsion spring 3144, and in which the solid nature of wax pot 3112 resists the force applied by peg 3124. A control unit 3150 is in signal communication with valve system 3100. During use of ingestible device 3000, a control unit 3150 receives a signal, indicating that the position of valve system 3100 should change, e.g., so that ingestible device 3000 can take a sample of a fluid in the GI tract. Control unit 3150 sends a signal that causes a heating system 3114 of actuation system 3100 to heat the wax in pot 3112 so that the wax melts. As shown in FIG. 24B, the melted wax is not able to resist the force applied by peg 3124 so that, under the force of torsion spring 3144, trigger 3120 moves in a counter-clockwise fashion.

Figure 25A:
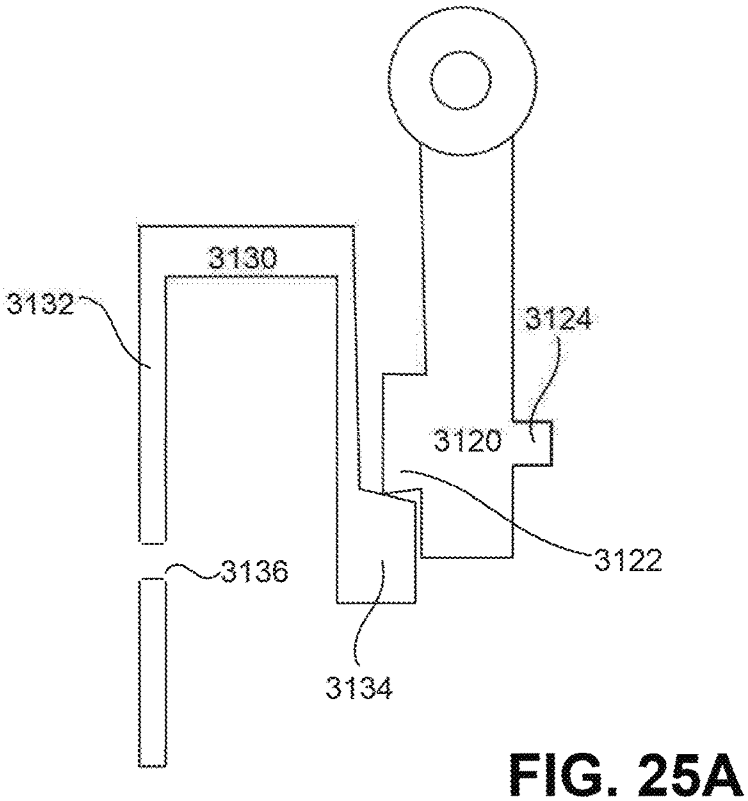
FIGS. 25A and 25B illustrate a portion of a two-stage valve system in its first and second stages, respectively.
Figure 25B:
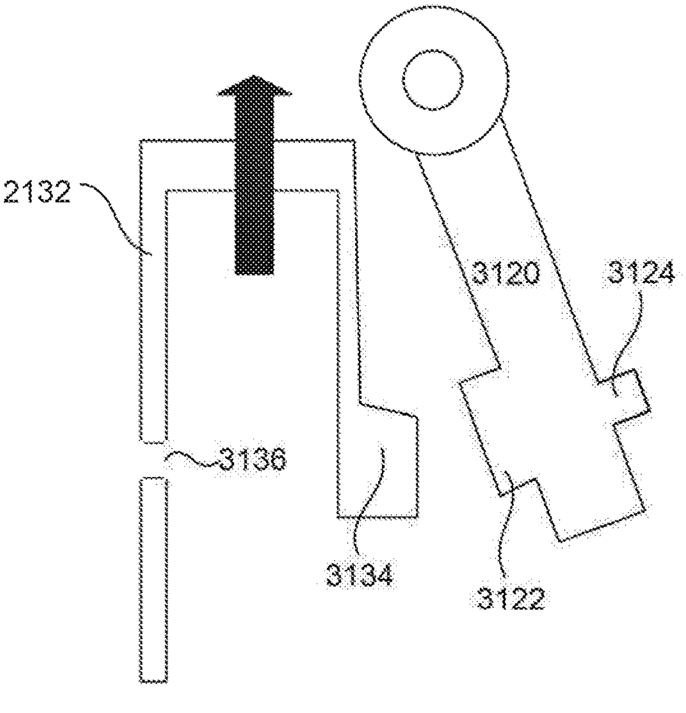

FIGS. 25A and 25B illustrate the interaction of trigger 3120 and gate 3130 before and after actuation. As shown in FIG. 25A, when wax pot 3112 is solid (corresponding to the configuration shown in FIG. 24A), protrusion 3134 engages lip 3122, which prevents the force of compression spring 3142 from moving gate 3130 upward. As shown in FIG. 25B, when the wax in pot 3112 melts (FIG. 24B), trigger 3120 moves counter-clockwise, and lip 3122 disengages from protrusion 3134. This allows the force of compression spring 3142 to move gate 3130 upward. As seen by comparing FIG. 25A to FIG. 25B, the upward movement of gate 3130 results in an upward movement of an opening 3136 in gate leg 3132.

Figure 26A:
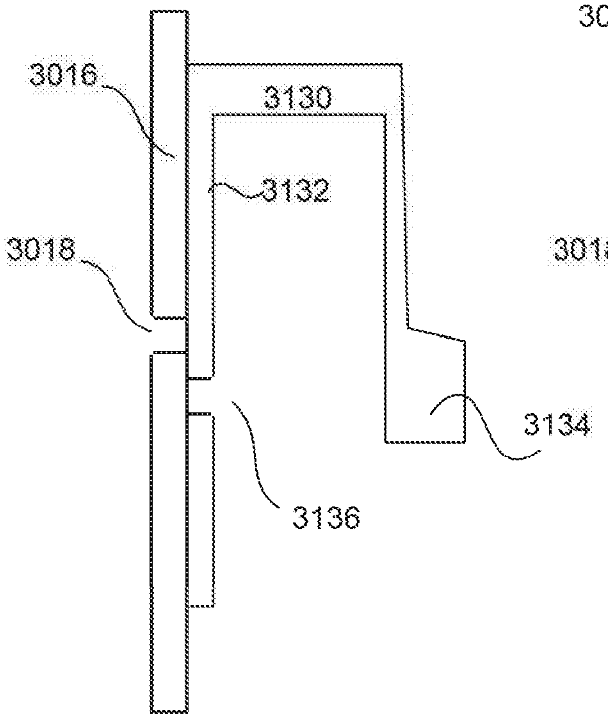
FIGS. 26A and 26B illustrate a portion of a two-stage valve system in its first and second stages, respectively.
Figure 26B:
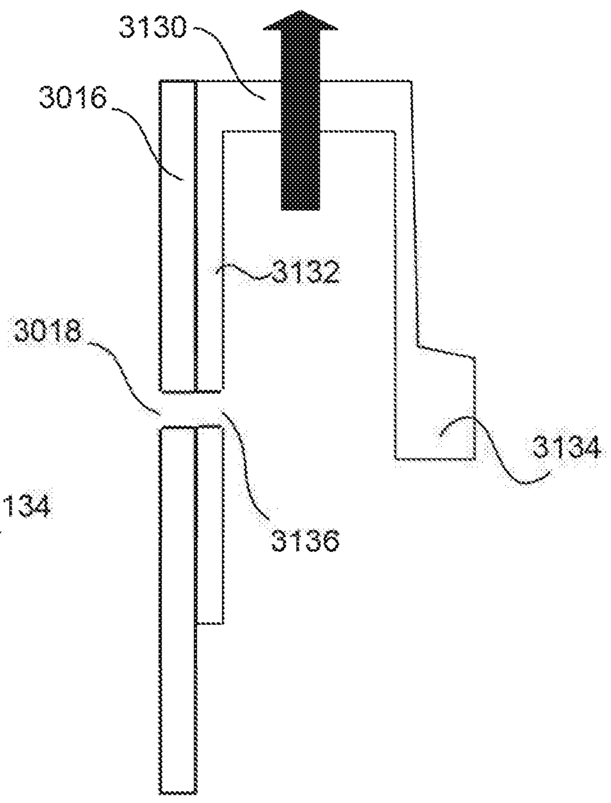

FIGS. 26A and 26B illustrate the impact of the upward movement of opening 3136 on the ability of ingestible device 3000 to obtain a sample. As shown in FIG. 26A, when the wax in pot 3112 is solid (FIGS. 24A and 25A), opening 3136 in is not aligned with opening 3018 in wall 3016 of ingestible device 3000. Instead, gate leg 3132 covers opening 3018 and blocks fluid from entering the interior of ingestible device 3000. As shown in FIG. 26B, when the wax in pot 3112 is melted and trigger 3120 and gate 3130 have moved (FIGS. 24B and 42B), opening 3136 in gate 3130 is aligned with opening 3018 in wall 3016. In this configuration, fluid that is exterior to ingestible device 3000 (e.g., in the GI tract) can enter the interior of ingestible device 3000 via openings 3018 and 3036.

FIG. 27 illustrates a more detailed view of ingestible device 3000 including valve system 3100 and sampling system 3200.

While the foregoing description is made with regard to a valve system having one open position and one closed position (e.g., a two-stage valve system), the disclosure is not limited in this sense. Rather, the concepts described above with regard to a two stage valve system can be implemented with a valve system have more than two stages (e.g., three stages, four stages, five stages, etc.).

Figure 28:
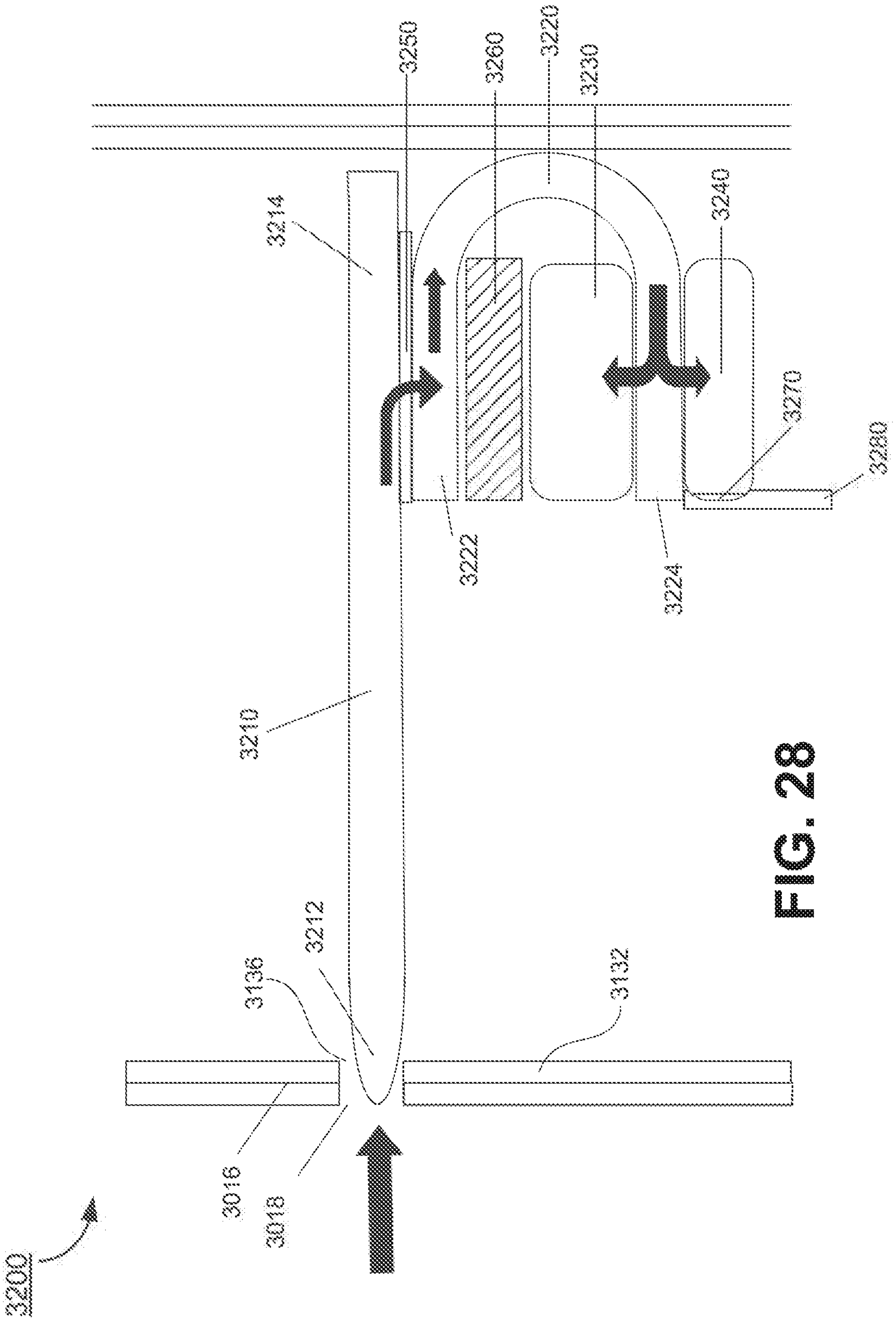
FIG. 28 illustrates a portion of an ingestible device including a sampling system and a two-stage valve system in its second stage.

As noted above in addition to a valve system, an ingestible device includes a sampling system. FIG. 28 illustrates a partial cross sectional view of ingestible device 3000 with sampling system 3200 and certain components of valve system 3100. Sampling system 3200 includes a series of sponges configured to absorb fluid from an opening, move the fluid to a location within the housing, and prepare the fluid for testing. Preparation for testing may include filtering the fluid and combining the fluid with a chemical assay. The assay may be configured to dye cells in the filtered sample. The series of sponges includes a wicking sponge 3210, a transfer sponge 3220, a volume sponge 3230, and an assay sponge 3240. Sampling system 3200 also includes a membrane 3270 located between assay sponge 3240 and a vent 3280 for gases to leave sampling system 3200. A cell filter 3250 is located between distal end 3214 of wicking sponge 3210 and a first end 3222 of transfer sponge 3220. Membrane 3270 is configured to allow one or more gases to leave sampling system 3200 via an opening 3280, while maintaining liquid in sampling system 3200.

Figure 29:
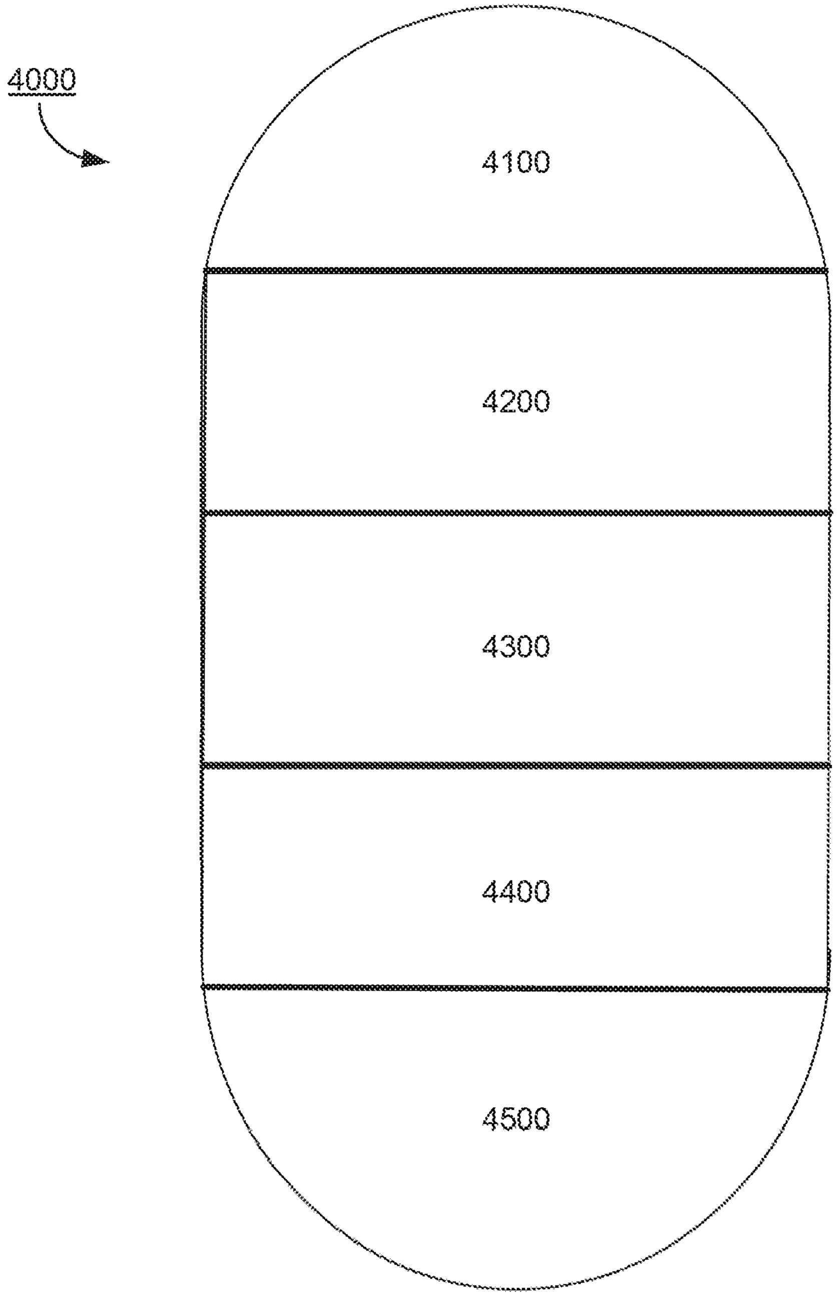
FIG. 29 is a highly schematic illustrate of an ingestible device.

FIG. 29 is a highly schematic illustration of an ingestible device 4000 that contains multiple different systems that cooperate for obtaining a sample and analyzing a sample, e.g., within the GI tract of a subject. Ingestible device 4000 includes a power system 4100 (e.g., one or more batteries), configured to power an electronics system 4200 (e.g., including a control system, optionally in signal communication with an external base station), a valve system 4300, a sampling system 4400, and an analytic system 4500. Exemplary analytical systems include assay systems, such as, for example, optical systems containing one or more sources of radiation and/or one more detectors.

Some or all of the sponges of the above-described sampling systems may contain one or more preservatives (see discussion above). Typically, the assay sponge and/or the volume sponge 3230 and/or the transfer sponge contain one or more preservatives. Typically, the preservative(s) are selected based on the analyte of interest, e.g., an analyte (such as a protein biomarker) for a GI disorder.

Communication Systems

An ingestible device may be equipped with a communication system adapted to transmit and/or receive data, including imaging and/or localization data. As an example, a communication system may employ radiofrequency transmission. Ingestible devices using radiofrequency communication are attractive because of their efficient transmission through the layers of the skin. This is especially true for low frequency transmission (UHF-433 ISM and lower, including the Medical Device Radio Communication Service band (MDRS) band 402-406 MHz). In another embodiment, acoustics are used for communications, including the transmission of data. For example, an ingestible capsule may be able to transmit information by applying one or more base voltages to an electromechanical transducer or piezoelectric (e.g., PZT, PVDF, etc.) device to cause the piezoelectric device to ring at particular frequencies, resulting in an acoustic transmission. A multi-sensor array for receiving the acoustic transmission may include a plurality of acoustic transducers that receive the acoustic transmission from a movable device such as an ingestible capsule as described in U.S. patent application Ser. No. 11/851,214 filed Sep. 6, 2007, incorporated by reference herein in its entirety.

As an example, a communication system may employ human body communication technology. Human body communication technology uses the human body as a conductive medium, which generally requires a large number of sensor electrodes on the skin. As an example, a communication system may integrate a data storage system.

Environmental Sensors

In some embodiments the device may comprise environmental sensors to measure pH, temperature, transit times, or combinations thereof. Other examples of environmental sensors include, but are not limited to a capacitance sensor, an impedance sensor, a heart rate sensor, acoustic sensor such as a microphone or hydrophone, image sensor, and/or a movement sensor. In one embodiment, the ingestible device comprises a plurality of different environmental sensors for generating different kinds of environmental data.

In order to avoid the problem of capsule retention, a thorough past medical and surgical history should be undertaken. In addition, several other steps have been proposed, including performing investigations such as barium follow-through. In cases where it is suspected that there is a high risk of retention, the patient is given a patency capsule a few days before swallowing an ingestible device. Any dissolvable non-endoscopic capsule may be used to determine the patency of the GI tract. The patency capsule is usually the same size as the ingestible device and can be made of cellophane. In some embodiments, the patency capsule contains a mixture of barium and lactose, which allows visualization by x-ray. The patency capsule may also include a radiotag or other label, which allows for it to be detected by radio-scanner externally. The patency capsule may comprise wax plugs, which allow for intestinal fluid to enter and dissolve the content, thereby dividing the capsule into small particles.

Accordingly, in some embodiments, the methods herein comprise (a) identifying a subject having a disease of the gastrointestinal tract and (b) evaluating the subject for suitability to treatment. In some embodiments, the methods herein comprise evaluating for suitability to treatment a subject identified as having a disease of the gastrointestinal tract. In some embodiments, evaluating the subject for suitability to treatment comprises determining the patency of the subject's GI tract.

In some embodiments, an ingestible device comprises a tissue anchoring mechanism for anchoring the ingestible device to a subject's tissue. For example, an ingestible device could be administered to a subject and once it reaches the desired location, the tissue attachment mechanism can be activated or deployed such that the ingestible device, or a portion thereof, is anchored to the desired location. In some embodiments, the tissue anchoring mechanism is reversible such that after initial anchoring, the tissue attachment device is retracted, dissolved, detached, inactivated or otherwise rendered incapable of anchoring the ingestible device to the subject's tissue. In some embodiments the attachment mechanism is placed endoscopically.

In some embodiments, a tissue anchoring mechanism comprises an osmotically-driven sucker. In some embodiments, the osmotically-driven sucker comprises a first valve on the near side of the osmotically-driven sucker (e.g., near the subject's tissue) and a second one-way valve that is opened by osmotic pressure on the far side of the osmotically-driven sucker, and an internal osmotic pump system comprising salt crystals and semi-permeable membranes positioned between the two valves. In such embodiments, osmotic pressure is used to adhere the ingestible device to the subject's tissue without generating a vacuum within the ingestible capsule. After the osmotic system is activated by opening the first valve, fluid is drawn in through the sucker and expelled through the second burst valve. Fluid continues to flow until all the salt contained in the sucker is dissolved or until tissue is drawn into the sucker. As liminal fluid is drawn through the osmotic pump system, solutes build up between the tissue and the first valve, reducing osmotic pressure. In some embodiments, the solute buildup stalls the pump before the tissue contacts the valve, preventing tissue damage. In some embodiments, a burst valve is used on the far side of the osmotically-driven sucker rather than a one-way valve, such that luminal fluid eventually clears the saline chamber and the osmotic flow reverses, actively pushing the subject's tissue out of the sucker. In some embodiments, the ingestible device may be anchored to the interior surface of tissues forming the GI tract of a subject.

In one embodiment, the ingestible device comprises a connector for anchoring the device to the interior surface of the GI tract. The connector may be operable to ingestible device to the interior surface of the GI tract using an adhesive, negative pressure and/or fastener.

In some embodiments a device comprises a tract stimulator and/or monitor IMD comprising a housing enclosing electrical stimulation and/or monitoring circuitry and a power source and an elongated flexible member extending from the housing to an active fixation mechanism adapted to be fixed into the GI tract wall is disclosed. After fixation is effected, the elongated flexible member bends into a preformed shape that presses the housing against the mucosa so that forces that would tend to dislodge the fixation mechanism are minimized. The IMD is fitted into an esophageal catheter lumen with the fixation mechanism aimed toward the catheter distal end opening whereby the bend in the flexible member is straightened. The catheter body is inserted through the esophagus into the GI tract cavity to direct the catheter distal end to the site of implantation and fix the fixation mechanism to the GI tract wall. The IMD is ejected from the lumen, and the flexible member assumes its bent configuration and lodges the hermetically sealed housing against the mucosa. A first stimulation/sense electrode is preferably an exposed conductive portion of the housing that is aligned with the bend of the flexible member so that it is pressed against the mucosa. A second stimulation/sense electrode is located at the fixation site.

In some embodiments a device includes a fixation mechanism to anchor the device to tissue within a body lumen, and a mechanism to permit selective de-anchoring of the device from the tissue anchoring site without the need for endoscopic or surgical intervention. An electromagnetic device may be provided to mechanically actuate the de-anchoring mechanism. Alternatively, a fuse link may be electrically blown to de-anchor the device. As a further alternative, a rapidly degradable bonding agent may be exposed to a degradation agent to de-anchor the device from a bonding surface within the body lumen.

In some embodiments a device is as disclosed in patent publication WO2015/112575A1, incorporated by reference herein in its entirety. The patent publication is directed to a gastrointestinal sensor implantation system. In some embodiments an orally-administrable capsule comprises a tissue capture device or reservoir removably coupled to the orally-administrable capsule, where the tissue capture device including a plurality of fasteners for anchoring the tissue capture device to gastrointestinal tissue within a body.

In some embodiments, the ingestible device contains an electric energy emitting means, a radio signal transmitting means, a medicament storage means and a remote actuatable medicament releasing means. The capsule signals a remote receiver as it progresses through the alimentary tract in a previously mapped route and upon reaching a specified site is remotely triggered to release a dosage of medicament. Accordingly, in some embodiments, releasing the JAK inhibitor is triggered by a remote electromagnetic signal.

In some embodiments, the ingestible device includes a housing introducible into a body cavity and of a material insoluble in the body cavity fluids, but formed with an opening covered by a material which is soluble in body cavity fluids. A diaphragm divides the interior of the housing into a medication chamber including the opening, and a control chamber. An electrolytic cell in the control chamber generates a gas when electrical current is passed therethrough to deliver medication from the medication chamber through the opening into the body cavity at a rate controlled by the electrical current. Accordingly, in some embodiments, releasing the JAK inhibitor is triggered by generation in the composition of a gas in an amount sufficient to expel the JAK inhibitor.

In some embodiments, the ingestible device includes an oral drug delivery device having a housing with walls of water permeable material and having at least two chambers separated by a displaceable membrane. The first chamber receives drug and has an orifice through which the drug is expelled under pressure. The second chamber contains at least one of two spaced apart electrodes forming part of an electric circuit which is closed by the ingress of an aqueous ionic solution into the second chamber. When current flows through the circuit, gas is generated and acts on the displaceable membrane to compress the first chamber and expel the active ingredient through the orifice for progressive delivery to the gastrointestinal tract.

In some embodiments, the ingestible device includes an ingestible device for delivering a substance to a chosen location in the GI tract of a mammal includes a receiver of electromagnetic radiation for powering an openable part of the device to an opened position for dispensing of the substance. The receiver includes a coiled wire that couples the energy field, the wire having an air or ferrite core. In a further embodiment, the device includes an apparatus for generating the electromagnetic radiation, the apparatus including one or more pairs of field coils supported in a housing. The device optionally includes a latch defined by a heating resistor and a fusible restraint. The device may also include a flexible member that may serve one or both the functions of activating a transmitter circuit to indicate dispensing of the substance; and restraining of a piston used for expelling the substance.

In some embodiments, the ingestible device includes an ingestible device for delivering a substance to a chosen location in the GI tract of a mammal includes a receiver of electromagnetic radiation for powering an openable part of the device to an opened position for dispensing of the substance. The receiver includes a coiled wire that couples the energy field, the wire having an air or ferrite core. In a further embodiment, the device includes an apparatus for generating the electromagnetic radiation, the apparatus including one or more pairs of field coils supported in a housing. The device optionally includes a latch defined by a heating resistor and a fusible restraint. The device may also include a flexible member that may serve one or both the functions of activating a transmitter circuit to indicate dispensing of the substance; and restraining of a piston used for expelling the substance.

In some embodiments, the ingestible device is a device a swallowable capsule. A sensing module is disposed in the capsule. A bioactive substance dispenser is disposed in the capsule. A memory and logic component is disposed in the capsule and in communication with the sensing module and the dispenser.

In some embodiments, localized administration is implemented via an electronic probe which is introduced into the intestinal tract of a living organism and which operates autonomously therein, adapted to deliver one or more therapy agents. In one embodiment, the method includes loading the probe with one or more therapy agents, and selectively releasing the agents from the probe at a desired location of the intestinal tract in order to provide increased efficacy over traditional oral ingestion or intravenous introduction of the agent(s).

In some embodiments, the ingestible device includes electronic control means for dispensing the drug substantially to the diseased tissue sites of the GI tract, according to a pre-determined drug release profile obtained prior to administration from the specific mammal. Accordingly, in some embodiments, releasing the JAK inhibitor is triggered by an electromagnetic signal generated within the device. The releasing may occur according to a pre-determined drug release profile.

In some embodiments, the ingestible device can include at least one guide tube, one or more tissue penetrating members positioned in the guide tube, a delivery member, an actuating mechanism and a release element. The release element degrades upon exposure to various conditions in the intestine so as to release and actuate the actuating mechanism. Embodiments of the device are particularly useful for the delivery of drugs which are poorly absorbed, tolerated and/or degraded within the GI tract.

In some embodiments, the ingestible device includes an electronic pill comprising at least one reservoir with a solid powder or granulate medicament or formulation, a discharge opening and an actuator responsive to control circuitry for displacing medicine from the reservoir to the discharge opening. The medicament or formulation comprises a dispersion of one or more active ingredients—e.g., solids in powder or granulate form—in an inert carrier matrix. Optionally, the active ingredients are dispersed using intestinal moisture absorbed into the pill via a semi-permeable wall section.

In some embodiments, the ingestible device includes a sensor comprising a plurality of electrodes having a miniature size and a lower power consumption and a coating exterior to the electrodes, wherein the coating interacts with a target condition thereby producing a change in an electrical property of the electrodes, wherein the change is transduced into an electrical signal by the electrodes. Accordingly, in some embodiments, releasing the JAK inhibitor is triggered by an electric signal by the electrodes resulting from the interaction of the coating with the one or more sites of disease. Further provided herein is a system for medication delivery comprising such sensor and a pill.

In some embodiments, the ingestible device includes an electronic pill comprising a plurality of reservoirs, each of the reservoirs comprising a discharge opening covered by a removable cover. The pill comprises at least one actuator responsive to control circuitry for removing the cover from the discharge opening. The actuator can for example be a spring loaded piston breaking a foil cover when dispensing the medicament. Alternatively, the cover can be a rotatable disk or cylinder with an opening which can be brought in line with the discharge opening of a reservoir under the action of the actuator.

In some embodiments, the ingestible device includes an electronically and remotely controlled pill or medicament delivery system. The pill includes a housing; a reservoir for storing a medicament; an electronically controlled release valve or hatch for dispensing one or more medicaments stored in the reservoir while traversing the gastrointestinal tract; control and timing circuitry for opening and closing the valve; and a battery. The control and timing circuitry opens and closes the valve throughout a dispensing time period in accordance with a preset dispensing timing pattern which is programmed within the control and timing circuitry. RF communication circuitry receives control signals for remotely overriding the preset dispensing timing pattern, reprogramming the control and timing circuitry or terminating the dispensing of the medicament within the body. The pill includes an RFID tag for tracking, identification, inventory and other purposes.

In some embodiments, the ingestible device includes an electronic capsule which has a discrete drive element comprising: a housing, electronics for making the electronic capsule operable, a pumping mechanism for dosing and displacing a substance, a power source for powering the electronic capsule and enabling the electronics and the pumping mechanism to operate, and a locking mechanism; and a discrete payload element comprising: a housing, a reservoir for storing the substance, one or more openings in the housing for releasing the substance from the reservoir and a locking mechanism for engaging the drive element locking mechanism. Engagement of the drive element locking mechanism with the payload element locking mechanism secures the drive element to the payload element, thereby making the electronic capsule operable and specific.

In some embodiments, the ingestible device may be a mucoadhesive device configured for release of an active agent.

In some embodiments, the ingestible device includes an apparatus that includes an ingestible medical treatment device, which is configured to initially assume a contracted state having a volume of less than 4 $cm^3$. The device includes a gastric anchor, which initially assumes a contracted size, and which is configured to, upon coming in contact with a liquid, expand sufficiently to prevent passage of the anchor through a round opening having a diameter of between 1 cm and 3 cm. The device also includes a duodenal unit, which is configured to pass through the opening, and which is coupled to the gastric anchor such that the duodenal unit is held between 1 cm and 20 cm from the gastric anchor.

In some embodiments, the ingestible device includes a medical robotic system and method of operating such comprises taking intraoperative external image data of a patient anatomy, and using that image data to generate a modeling adjustment for a control system of the medical robotic system (e.g., updating anatomic model and/or refining instrument registration), and/or adjust a procedure control aspect (e.g., regulating substance or therapy delivery, improving targeting, and/or tracking performance).

In one embodiment the ingestible device may also include one or more environmental sensors. Environmental sensor may be used to generate environmental data for the environment external to device in the gastrointestinal (GI) tract of the subject. In some embodiments, environmental data is generated at or near the location within the GI tract of the subject where a drug is delivered. Examples of environmental sensor include, but are not limited to a capacitance sensor, a temperature sensor, an impedance sensor, a pH sensor, a heart rate sensor, acoustic sensor, image sensor (e.g., a hydrophone), and/or a movement sensor (e.g., an accelerometer). In one embodiment, the ingestible device comprises a plurality of different environmental sensors for generating different kinds of environmental data.

In one embodiment, the image sensor is a video camera suitable for obtaining images in vivo of the tissues forming the GI tract of the subject. In one embodiment, the environmental data is used to help determine one or more characteristics of the GI tract, including the location of disease (e.g., presence or location of inflamed tissue and/or lesions associated with inflammatory bowel disease). In some embodiments, the ingestible device may comprise a camera for generating video imaging data of the GI tract which can be used to determine, among other things, the location of the device.

In another embodiment, the ingestible device described herein may be localized using a gamma scintigraphy technique or other radio-tracker technology as employed by Phaeton Research's Enterion™ capsule (See Teng, Renli, and Juan Maya, "Absolute bioavailability and regional absorption of ticagrelor in healthy volunteers," Journal of Drug Assessment 3.1 (2014):43-50), or monitoring the magnetic field strength of permanent magnet in the ingestible device (see T. D. Than, et al., "A review of localization systems for robotic endoscopic capsules," IEEE Trans. Biomed. Eng., vol. 59, no. 9, pp. 2387-2399, September 2012).

In one embodiment, drug delivery is triggered when it encounters the site of disease in the GI tract.

In one embodiment, the one or more environmental sensors measure pH, temperature, transit times, or combinations thereof.

In some embodiments, releasing the JAK inhibitor is dependent on the pH at or in the vicinity of the location. In some embodiments the pH in the jejunum is from 6.1 to 7.2, such as 6.6. In some embodiments the pH in the mid small bowel is from 7.0 to 7.8, such as 7.4. In some embodiments the pH in the ileum is from 7.0 to 8.0, such as 7.5. In some embodiments the pH in the right colon is from 5.7 to 7.0, such as 6.4. In some embodiments the pH in the mid colon is from 5.7 to 7.4, such as 6.6. In some embodiments the pH in the left colon is from 6.3 to 7.7, such as 7.0. In some embodiments, the gastric pH in fasting subjects is from about 1.1 to 2.1, such as from 1.4 to 2.1, such as from 1.1 to 1.6, such as from 1.4 to 1.6. In some embodiments, the gastric pH in fed subjects is from 3.9 to 7.0, such as from 3.9 to 6.7, such as from 3.9 to 6.4, such as from 3.9 to 5.8, such as from 3.9 to 5.5, such as from 3.9 to 5.4, such as from 4.3 to 7.0, such as from 4.3 to 6.7, such as from 4.3 to 6.4, such as from 4.3 to 5.8, such as from 4.3 to 5.5, such as from 4.3 to 5.4. In some embodiments, the pH in the duodenum is from 5.8 to 6.8, such as from 6.0 to 6.8, such as from 6.1 to 6.8, such as from 6.2 to 6.8, such as from 5.8 to 6.7, such as from 6.0 to 6.7, such as from 6.1 to 6.7, such as from 6.2 to 6.7, such as from 5.8 to 6.6, such as from 6.0 to 6.6, such as from 6.1 to 6.6, such as from 6.2 to 6.6, such as from 5.8 to 6.5, such as from 6.0 to 6.5, such as from 6.1 to 6.5, such as from 6.2 to 6.5.

In some embodiments, releasing the JAK inhibitor is not dependent on the pH at or in the vicinity of the location. In some embodiments, releasing the JAK inhibitor is triggered by degradation of a release component located in the capsule. In some embodiments, the JAK inhibitor is not triggered by degradation of a release component located in the capsule. In some embodiments, wherein releasing the JAK inhibitor is not dependent on enzymatic activity at or in the vicinity of the location. In some embodiments, releasing the JAK inhibitor is not dependent on bacterial activity at or in the vicinity of the location.

In some embodiments, the pharmaceutical composition is an ingestible device, comprising:

- a housing defined by a first end, a second end substantially opposite from the first end, and a wall extending longitudinally from the first end to the second end;
- a reservoir located within the housing and containing the JAK inhibitor,
  - wherein a first end of the reservoir is attached to the first end of the housing;
- a mechanism for releasing the JAK inhibitor from the reservoir; and
- an exit valve configured to allow the JAK inhibitor to be released out of the housing from the reservoir.

In some embodiments, the ingestible device further comprises:

- an electronic component located within the housing; and
- a gas generating cell located within the housing and adjacent to the electronic component,
  - wherein the electronic component is configured to activate the gas generating cell to generate gas.

In some embodiments, the ingestible device further comprises:

- a safety device placed within or attached to the housing,
  - wherein the safety device is configured to relieve an internal pressure within the housing when the internal pressure exceeds a threshold level.

In some embodiments, the pharmaceutical composition is an ingestible device, comprising:

- a housing defined by a first end, a second end substantially opposite from the first end, and a wall extending longitudinally from the first end to the second end;
- an electronic component located within the housing;
- a gas generating cell located within the housing and adjacent to the electronic component,
  - wherein the electronic component is configured to activate the gas generating cell to generate gas;
- a reservoir located within the housing,
  - wherein the reservoir stores a dispensable substance and a first end of the reservoir is attached to the first end of the housing;
- an exit valve located at the first end of the housing,
  - wherein the exit valve is configured to allow the dispensable substance to be released out of the first end of the housing from the reservoir; and a safety device placed within or attached to the housing,
  - wherein the safety device is configured to relieve an internal pressure within the housing when the internal pressure exceeds a threshold level.

In some embodiments, the pharmaceutical composition is an ingestible device, comprising:

- a housing defined by a first end, a second end substantially opposite from the first end, and a wall extending longitudinally from the first end to the second end;
- an electronic component located within the housing,
- a gas generating cell located within the housing and adjacent to the electronic component,
  - wherein the electronic component is configured to activate the gas generating cell to generate gas;
- a reservoir located within the housing,
  - wherein the reservoir stores a dispensable substance and a first end of the reservoir is attached to the first end of the housing;
- an injection device located at the first end of the housing,
  - wherein the jet injection device is configured to inject the dispensable substance out of the housing from the reservoir; and
- a safety device placed within or attached to the housing,
  - wherein the safety device is configured to relieve an internal pressure within the housing.

In some embodiments, the pharmaceutical composition is an ingestible device, comprising:

- a housing defined by a first end, a second end substantially opposite from the first end, and a wall extending longitudinally from the first end to the second end;
- an optical sensing unit located on a side of the housing,
  - wherein the optical sensing unit is configured to detect a reflectance from an environment external to the housing;
- an electronic component located within the housing;
- a gas generating cell located within the housing and adjacent to the electronic component,
  - wherein the electronic component is configured to activate the gas generating cell to generate gas in response to identifying a location of the ingestible device based on the reflectance;

a reservoir located within the housing, wherein the reservoir stores a dispensable substance and a first end of the reservoir is attached to the first end of the housing;

a membrane in contact with the gas generating cell and configured to move or deform into the reservoir by a pressure generated by the gas generating cell; and a dispensing outlet placed at the first end of the housing, wherein the dispensing outlet is configured to deliver the dispensable substance out of the housing from the reservoir.

In one embodiment, drug delivery is triggered when it encounters the site of disease in the GI tract.

In one embodiment, the one or more environmental sensors measure pH, temperature, transit times, or combinations thereof.

In some embodiments, releasing the JAK inhibitor is dependent on the pH at or in the vicinity of the location. In some embodiments the pH in the jejunum is from 6.1 to 7.2, such as 6.6. In some embodiments the pH in the mid small bowel is from 7.0 to 7.8, such as 7.4. In some embodiments the pH in the ileum is from 7.0 to 8.0, such as 7.5. In some embodiments the pH in the right colon is from 5.7 to 7.0, such as 6.4. In some embodiments the pH in the mid colon is from 5.7 to 7.4, such as 6.6. In some embodiments the pH in the left colon is from 6.3 to 7.7, such as 7.0. In some embodiments, the gastric pH in fasting subjects is from about 1.1 to 2.1, such as from 1.4 to 2.1, such as from 1.1 to 1.6, such as from 1.4 to 1.6. In some embodiments, the gastric pH in fed subjects is from 3.9 to 7.0, such as from 3.9 to 6.7, such as from 3.9 to 6.4, such as from 3.9 to 5.8, such as from 3.9 to 5.5, such as from 3.9 to 5.4, such as from 4.3 to 7.0, such as from 4.3 to 6.7, such as from 4.3 to 6.4, such as from 4.3 to 5.8, such as from 4.3 to 5.5, such as from 4.3 to 5.4. In some embodiments, the pH in the duodenum is from 5.8 to 6.8, such as from 6.0 to 6.8, such as from 6.1 to 6.8, such as from 6.2 to 6.8, such as from 5.8 to 6.7, such as from 6.0 to 6.7, such as from 6.1 to 6.7, such as from 6.2 to 6.7, such as from 5.8 to 6.6, such as from 6.0 to 6.6, such as from 6.1 to 6.6, such as from 6.2 to 6.6, such as from 5.8 to 6.5, such as from 6.0 to 6.5, such as from 6.1 to 6.5, such as from 6.2 to 6.5.

In some embodiments, releasing the JAK inhibitor is not dependent on the pH at or in the vicinity of the location. In some embodiments, releasing the JAK inhibitor is triggered by degradation of a release component located in the capsule. In some embodiments, the JAK inhibitor is not triggered by degradation of a release component located in the capsule. In some embodiments, wherein releasing the JAK inhibitor is not dependent on enzymatic activity at or in the vicinity of the location. In some embodiments, releasing the JAK inhibitor is not dependent on bacterial activity at or in the vicinity of the location.

In some embodiments, the pharmaceutical composition is an ingestible device, comprising:

a housing defined by a first end, a second end substantially opposite from the first end, and a wall extending longitudinally from the first end to the second end;

a reservoir located within the housing and containing the JAK inhibitor, wherein a first end of the reservoir is attached to the first end of the housing; a mechanism for releasing the JAK inhibitor from the reservoir; and;

an exit valve configured to allow the JAK inhibitor to be released out of the housing from the reservoir.

In some embodiments, the ingestible device further comprises:

an electronic component located within the housing; and a gas generating cell located within the housing and adjacent to the electronic component, wherein the electronic component is configured to activate the gas generating cell to generate gas.

In some embodiments, the ingestible device further comprises:

a safety device placed within or attached to the housing, wherein the safety device is configured to relieve an internal pressure within the housing when the internal pressure exceeds a threshold level.

In some embodiments, the pharmaceutical composition is an ingestible device, comprising:

a housing defined by a first end, a second end substantially opposite from the first end, and a wall extending longitudinally from the first end to the second end;

an electronic component located within the housing;

a gas generating cell located within the housing and adjacent to the electronic component, wherein the electronic component is configured to activate the gas generating cell to generate gas;

a reservoir located within the housing, wherein the reservoir stores a dispensable substance and a first end of the reservoir is attached to the first end of the housing;

an exit valve located at the first end of the housing, wherein the exit valve is configured to allow the dispensable substance to be released out of the first end of the housing from the reservoir; and a safety device placed within or attached to the housing, wherein the safety device is configured to relieve an internal pressure within the housing when the internal pressure exceeds a threshold level.

In some embodiments, the pharmaceutical composition is an ingestible device, comprising:

a housing defined by a first end, a second end substantially opposite from the first end, and a wall extending longitudinally from the first end to the second end;

an electronic component located within the housing, a gas generating cell located within the housing and adjacent to the electronic component, wherein the electronic component is configured to activate the gas generating cell to generate gas;

a reservoir located within the housing, wherein the reservoir stores a dispensable substance and a first end of the reservoir is attached to the first end of the housing;

an injection device located at the first end of the housing, wherein the jet injection device is configured to inject the dispensable substance out of the housing from the reservoir; and a safety device placed within or attached to the housing, wherein the safety device is configured to relieve an internal pressure within the housing.

In some embodiments, the pharmaceutical composition is an ingestible device, comprising:

a housing defined by a first end, a second end substantially opposite from the first end, and a wall extending longitudinally from the first end to the second end;

an optical sensing unit located on a side of the housing, wherein the optical sensing unit is configured to detect a reflectance from an environment external to the housing;

an electronic component located within the housing;

a gas generating cell located within the housing and adjacent to the electronic component,
wherein the electronic component is configured to activate the gas generating cell to generate gas in response to identifying a location of the ingestible device based on the reflectance;
a reservoir located within the housing,
wherein the reservoir stores a dispensable substance and a first end of the reservoir is attached to the first end of the housing;
a membrane in contact with the gas generating cell and configured to move or deform into the reservoir by a pressure generated by the gas generating cell; and
a dispensing outlet placed at the first end of the housing,
wherein the dispensing outlet is configured to deliver the dispensable substance out of the housing from the reservoir.

In some embodiments, the pharmaceutical composition is an ingestible device as disclosed in U.S. Patent Application Ser. No. 62/385,553, incorporated by reference herein in its entirety.

In some embodiments, the pharmaceutical composition is an ingestible device as disclosed in the following applications, each of which is incorporated by reference herein in its entirety: U.S. Ser. Nos. 14/460,893; 15/514,413; 62/376,688; 62/385,344; 62/478,955; 62/434,188; 62/434,320; 62/431,297; 62/434,797; 62/480,187; 62/502,383; and 62/540,873.

In some embodiments, the pharmaceutical composition is an ingestible device comprising a localization mechanism as disclosed in international patent application PCT/US2015/052500, incorporated by reference herein in its entirety.

In some embodiments, the pharmaceutical composition is not a dart-like dosage form.

In some embodiments of any ingestible device disclosed herein comprising a JAK inhibitor, the JAK inhibitor is present in a therapeutically effective amount.

In case of conflict between the present specification and any subject matter incorporated by reference herein, the present specification, including definitions, will control.

Devices and Methods for Detection of Analytes in GI tract

Detection of certain analytes in the GI tract may be useful in the identification of the nature and severity of the disease, in accurately locating the site(s) of disease, and in assessing patient response to a therapeutic agent. The appropriate therapeutic agent may accordingly be released at the correct locations(s), dosage, or timing for the disease. As discussed further herein, analytes may include biomarkers associated with a disease or associated with patient response and/or therapeutic agents previously administered to treat the disease. In some embodiments, the disclosure provides an ingestible device for detecting an analyte in a sample, the ingestible device comprising a sampling chamber that is configured to hold a composition comprising: (1) a plurality of donor particles, each of the plurality of donor particles comprising a photosensitizer and having coupled thereto a first antigen-binding agent that binds to the analyte, wherein the photosensitizer, in its excited state, is capable of generating singlet oxygen; and (2) a plurality of acceptor particles, each of the plurality of acceptor particles comprising a chemiluminescent compound and having coupled thereto a second antigen-binding agent that binds to the analyte, wherein the chemiluminescent compound is capable of reacting with singlet oxygen to emit luminescence. In some embodiments, the first and the second analyte-binding agents are antigen-binding agents (e.g., antibodies). In some embodiments, the first and the second antigen-binding agents bind to the same epitope of the analyte (e.g., a protein). In some embodiments, the first and the second antigen-binding agents bind to separate epitopes of the analyte (e.g., a protein) that spatially overlap. In some embodiments, the first and the second antigen-binding agents bind to the separate epitopes of the analyte (e.g., a protein) that do not spatially overlap.

In some embodiments, this disclcosure provides an ingestible device for detecting an analyte in a sample, the ingestible device comprising a sampling chamber that is configured to hold an absorbable material (e.g., an absorbable pad or sponge) having absorbed therein a composition comprising: (1) a plurality of donor particles, each of the plurality of donor particles comprising a photosensitizer and having coupled thereto a first antigen-binding agent that binds to the analyte, wherein the photosensitizer, in its excited state, is capable of generating singlet oxygen; and (2) a plurality of acceptor particles, each of the plurality of acceptor particles comprising a chemiluminescent compound and having coupled thereto a second antigen-binding agent that binds to the analyte, wherein the chemiluminescent compound is capable of reacting with singlet oxygen to emit luminescence. In some embodiments, the first and the second analyte-binding agents are antigen-binding agents (e.g., antibodies). In some embodiments, the first and the second antigen-binding agents bind to the same epitope of the analyte (e.g., a protein). In some embodiments, the first and the second antigen-binding agents bind to separate epitopes of the analyte (e.g., a protein) that spatially overlap. In some embodiments, the first and the second antigen-binding agents bind to the separate epitopes of the analyte (e.g., a protein) that do not spatially overlap.

In certain embodiments, the disclosure provides a kit comprising an ingestible device as described herein. In some embodiments, the kit further comprises instructions, e.g., for detecting or quantifying an analyte in a sample.

In some embodiments, the disclosure provides methods for determining an analyte in a sample. In certain embodiments, this disclosure provides a method of detecting an analyte in a fluid sample of a subject, comprising: (1) providing an ingestible device; (2) transferring the fluid sample of the subject into the sampling chamber of the ingestible device in vivo; (3) irradiating the composition held in the sampling chamber of the ingestible device with light to excite the photosensitizer; and (4) measuring total luminescence or rate of change of luminescence emitted from the composition held in the sampling chamber of the ingestible device as a function of time, thereby determining the level of the analyte in the fluid sample. In some embodiments, the method further comprises comparing the level of the analyte in the fluid sample with the level of analyte in a reference sample (e.g., a reference sample obtained from a healthy subject). In some embodiments, the level of the analyte in the sample is used to diagnose and/or monitor a disease or disorder in the subject.

In some embodiments, the disclosure provides a method of detecting an analyte in a fluid sample of a subject, comprising: (1) providing an ingestible device, the device comprising a sampling chamber that is configured to hold an absorbable material (e.g., an absorbable pad or sponge) having absorbed therein a composition, as described herein; (2) transferring the fluid sample of the subject into the sampling chamber of the ingestible device in vivo; (3) fully or partially saturating the absorbable material held in the sampling chamber of the ingestible device with the fluid sample; (4) irradiating the absorbable material held in the sampling chamber of the ingestible device with light to excite the photosensitizer; and (5) measuring total luminescence or rate of change of luminescence emitted from the composition held in the sampling chamber of the ingestible device as a function of time, thereby determining the level of the analyte in the fluid sample. In some embodiments, the method further comprises comparing the level of the analyte in the fluid sample with the level of analyte in a reference sample (e.g., a reference sample obtained from a healthy subject). In some embodiments, the level of the analyte in the sample is used to diagnose and/or monitor a disease or disorder in the subject.

In some embodiments, the disclosure provides a method of assessing or monitoring the need to treat a subject suffering from or at risk of overgrowth of bacterial cells in the gastrointestinal (GI) tract, comprising: (1) providing an ingestible device for detecting an analyte; (2) transferring a fluid sample from the GI tract of the subject into the sampling chamber of the ingestible device in vivo; (3) irradiating the composition held in the sampling chamber of the ingestible device with light to excite the photosensitizer; (4) measuring total luminescence or rate of change of luminescence emitted from the composition held in the sampling chamber of the ingestible device as a function of time; (5) correlating the total luminescence or the rate of change of luminescence as a function of time measured in step (4) to the amount of the analyte in the fluid sample; and (6) correlating the amount of the analyte in the fluid sample to the number of viable bacterial cells in the fluid sample. In some embodiments, a number of viable bacterial cells determined in step (6) greater than a control number of viable bacterial cells, indicates a need for treatment (e.g., with an antibiotic agent described herein). In some embodiments, the control number of viable bacterial cells is $10^3$, $10^4$, $10^5$, $10^6$, $10^7$, $10^8$, $10^9$, or more. For example, in some embodiments, a number of viable bacterial cells determined in step (6) greater that about 103 CFU/mL indicates a need for treatment. In some embodiments, a number of viable bacterial cells determined in step (6) greater that about $10^4$ CFU/mL indicates a need for treatment. In some embodiments, a number of the viable bacterial cells determined in step (6) greater than about $10^5$ CFU/mL indicates a need for treatment, e.g., with an antibiotic agent as described herein. In some embodiments, a number of viable bacterial cells determined in step (6) greater that about $10^6$ or more CFU/mL indicates a need for treatment.

In some embodiments, the total luminescence or the rate of change of luminescence as a function of time of the sponge is measured over multiple time points for an extended period of time in step (4). For instance, in some embodiments, the total luminescence or rate of change of luminescence as a function of time of the sample is measured continuously for a period of 0-1800 minutes, 0-1600 minutes, 0-1500 minutes, 0-1440 minutes, 0-1320 minutes, 0-1000 minutes, 0-900 minutes, 0-800 minutes, 0-700 minutes, 0-600 minutes, 0-500 minutes, 0-400 minutes, 0-350 minutes, 0-330 minutes, 0-300 minutes, 0-270 minutes, or 0-220 minutes. In some embodiments, the total luminescence or the rate of change of luminescence as a function of time of said sample is measured continuously for a period of 0-330 minutes. In some embodiments, the method is performed in vivo. In some embodiments, the method includes communicating the results of the onboard assay(s) to an ex vivo receiver. In some embodiments, the total luminescence or the rate of change of luminescence as a function of time of the sponge is measured over multiple time points for an extended period of time in step (5). For instance, in some embodiments, the total luminescence or rate of change of luminescence as a function of time of the sample is measured continuously for a period of 0-1800 minutes, 0-1600 minutes, 0-1500 minutes, 0-1440 minutes, 0-1320 minutes, 0-1000 minutes, 0-900 minutes, 0-800 minutes, 0-700 minutes, 0-600 minutes, 0-500 minutes, 0-400 minutes, 0-350 minutes, 0-330 minutes, 0-300 minutes, 0-270 minutes, or 0-220 minutes. In some embodiments, the total luminescence or the rate of change of luminescence as a function of time of said sample is measured continuously for a period of 0-330 minutes. In some embodiments, the method is performed in vivo. In some embodiments, the method includes communicating the results of the onboard assay(s) to an ex vivo receiver.

In some embodiments, the disclosure provides a method of assessing or monitoring the need to treat a subject suffering from or at risk of overgrowth of bacterial cells in the gastrointestinal tract, comprising: (1) providing an ingestible device for detecting an analyte, the device comprising a sampling chamber that is configured to hold an absorbable material (e.g., an absorbable pad or sponge) having absorbed therein a composition, as described herein; (2) transferring a fluid sample from the GI tract of the subject into the sampling chamber of the ingestible device in vivo; (3) fully or partially saturating the absorbable material held in the sampling chamber of the ingestible device with the fluid sample; (4) irradiating the absorbable material held in the sampling chamber of the ingestible device with light to excite the photosensitizer; (5) measuring total luminescence or rate of change of luminescence emitted from the composition held in the sampling chamber of the ingestible device as a function of time; (6) correlating the total luminescence or the rate of change of luminescence as a function of time measured in step (5) to the amount of the analyte in the fluid sample; and (7) correlating the amount of the analyte in the fluid sample to the number of viable bacterial cells in the fluid sample. In some embodiments, a number of viable bacterial cells determined in step (7) greater than a control number of viable bacterial cells indicates a need for treatment (e.g., with an antibiotic agent described herein). In some embodiments, the control number of viable bacterial cells is 103, $10^4$, $10^5$, $10^6$, $10^7$, $10^8$, $10^9$, or more. For example, in some embodiments, a number of viable bacterial cells determined in step (7) greater that about $10^3$ CFU/mL indicates a need for treatment. In some embodiments, a number of viable bacterial cells determined in step (7) greater that about $10^4$ CFU/mL indicates a need for treatment. In some embodiments, a number of the viable bacterial cells determined in step (7) greater than about $10^5$ CFU/mL indicates a need for treatment, e.g., with an antibiotic agent as described herein. In some embodiments, a number of viable bacterial cells determined in step (7) greater that about $10^6$ or more CFU/mL indicates a need for treatment.

In some embodiments, the disclosure, provides a method of measuring the presence, absence or amount of one or more analytes from one or more samples in the gastrointestinal tract. In some embodiments the one or more analytes are measured multiple times, for example, at different time points or at different locations. In one embodiment, a single device measures one or more analytes or more time points or locations; thereby creating a "molecular map" of a physiological region. Measurements can be taken at any location in the gastrointestinal tract. For example, in one aspect, analytes from samples from one or more of the duodenum, jejunum, ileum, ascending colon, transverse colon or descending colon can be measured to create a molecular map of the small and large intestine. In one aspect, the sample is from the duodenum. In one aspect, In one aspect, the sample is from the jejunum. In one aspect, the sample is from the ileum. In one aspect, the sample is from the ascending colon. In one aspect, the sample is from the transverse colon. In one aspect, the sample is from the descending colon.

In another aspect, a series of measurements can be taken over a shorter distance of the gastrointestinal tract (e.g., the ileum) to create a higher resolution molecular map. In some embodiments, previous endoscopic imaging may identify a diseased area for molecular mapping. For example, a gastroenterologist may use imaging (e.g., an endoscope equipped with a camera) to identify the presence of Crohn's Disease in the ileum and cecum of a patient, and the methods and techniques herein may be used to measure inflammation-associated analytes in this diseased area of the patient. In a related embodiment, the inflammation-associated analytes, or any analyte, may be measured every one or more days to monitor disease flare-ups, or response to therapeutics.

Analytes

The compositions and methods described herein can be used to detect, analyze, and/or quantitate a variety of analytes in a human subject. "Analyte" as used herein refers to a compound or composition to be detected in a sample. Exemplary analytes suitable for use herein include those described in U.S. Pat. No. 6,251,581, which is incorporated by reference herein in its entirety. Broadly speaking, an analyte can be any substance (e.g., a substance with one or more antigens) capable of being detected. An exemplary and non-limiting list of analytes includes ligands, proteins, blood clotting factors, hormones, cytokines, polysaccharides, mucopolysaccharides, microorganisms (e.g., bacteria), microbial antigens, and therapeutic agents (including fragments and metabolites thereof).

For instance, the analyte may be a ligand, which is monovalent (monoepitopic) or polyvalent (polyepitopic), usually antigenic or haptenic, and is a single compound or plurality of compounds which share at least one common epitopic or determinant site. The analyte can be a part of a cell such as bacteria or a cell bearing a blood group antigen such as A, B, D, etc., a human leukocyte antigen (HLA), or other cell surface antigen, or a microorganism, e.g., bacterium (e.g. a pathogenic bacterium), a fungus, protozoan, or a virus (e.g., a protein, a nucleic acid, a lipid, or a hormone). In some embodiments, the analyte can be a part of an exosome (e.g., a bacterial exosome). In some embodiments, the analyte is derived from a subject (e.g., a human subject). In some embodiments, the analyte is derived from a microorganism present in the subject. In some embodiments, the analyte is a nucleic acid (e.g., a DNA molecule or a RNA molecule), a protein (e.g., a soluble protein, a cell surface protein), or a fragment thereof, that can be detected using any of the devices and methods provided herein.

The polyvalent ligand analytes will normally be poly (amino acids), i.e., a polypeptide (i.e., protein) or a peptide, polysaccharides, nucleic acids (e.g., DNA or RNA), and combinations thereof. Such combinations include components of bacteria, viruses, chromosomes, genes, mitochondria, nuclei, cell membranes, and the like.

In some embodiments, the polyepitopic ligand analytes have a molecular weight of at least about 5,000 Da, more usually at least about 10,000 Da. In the poly(amino acid) category, the poly(amino acids) of interest may generally have a molecular weight from about 5,000 Da to about 5,000,000 Da, more usually from about 20,000 Da to 1,000,000 Da; among the hormones of interest, the molecular weights will usually range from about 5,000 Da to 60,000 Da.

In some embodiments, the monoepitopic ligand analytes generally have a molecular weight of from about 100 to 2,000 Da, more usually from 125 to 1,000 Da.

A wide variety of proteins may be considered as to the family of proteins having similar structural features, proteins having particular biological functions, proteins related to specific microorganisms, particularly disease causing microorganisms, etc. Such proteins include, for example, immunoglobulins, cytokines, enzymes, hormones, cancer antigens, nutritional markers, tissue specific antigens, etc.

In some embodiments, the analyte is a protein. In some embodiments, the analyte is a protein, e.g., an enzyme (e.g., a hemolysin, a protease, a phospholipase), a soluble protein, an exotoxin. In some embodiments, the analyte is a fragment of a protein, a peptide, or an antigen. In some embodiments, the analyte is a peptide of at least 5 amino acids (e.g., at least 6, at least 7, at least 8, at least 9, at least 10, at least 25, at least, 50, or at least 100 amino acids). Exemplary lengths include 6, 7, 8, 9, 10, 11, 12, 13, 14, 15, 16, 17, 18, 19, 20, 21, 22, 23, 24, 25, 26, 27, 28, 29, 30, 50, 75, or 100 amino acids. Exemplary classes of protein analytes include, but are not limited to: protamines, histones, albumins, globulins, scleroproteins, phosphoproteins, mucoproteins, chromoproteins, lipoproteins, nucleoproteins, glycoproteins, T-cell receptors, proteoglycans, cell surface receptors, membrane-anchored proteins, transmembrane proteins, secreted proteins, HLA, and unclassified proteins.

In some embodiments, the analyte is an affimer (see, e.g., Tiede et al. (2017) *eLife* 6: e24903, which is expressly incorporated herein by reference).

Exemplary analytes include: Prealbumin, Albumin, $\alpha_1$-Lipoprotein, $\alpha_1$-Antitrypsin, $\alpha_1$-Glycoprotein, Transcortin, 4.6S-Postalbumin, $\alpha_1$-glycoprotein, $\alpha_{1X}$-Glycoprotein, Thyroxin-binding globulin, Inter-$\alpha$-trypsin-inhibitor, Gc-globulin (Gc 1-1, Gc 2-1, Gc 2-2), Haptoglobin (Hp 1-1, Hp 2-1, Hp 2-2), Ceruloplasmin, Cholinesterase, $\alpha_2$-Lipoprotein(s), Myoglobin, C-Reactive Protein, $\alpha_2$-Macroglobulin, $\alpha_2$-HS-glycoprotein, Zn-$\alpha_2$-glycoprotein, $\alpha_2$-Neuramino-glycoprotein, Erythropoietin, (i-lipoprotein, Transferrin, Hemopexin, Fibrinogen, Plasminogen, $\beta_2$-glycoprotein I, $\beta_2$-glycoprotein II, Immunoglobulin G (IgG) or $\gamma$G-globulin, Immunoglobulin A (IgA) or $\gamma$A-globulin, Immunoglobulin M (IgM) or $\gamma$M-globulin, Immunoglobulin D (IgD) or $\gamma$D-Globulin ($\gamma$D), Immunoglobulin E (IgE) or $\gamma$E-Globulin ($\gamma$E), Free $\kappa$ and $\lambda$ light chains, and Complement factors: C'1, (C'1q, C'1r, C'1s, C'2, C'3 ($\beta_1$A, $\alpha_2$D), C'4, C'5, C'6, C'7, C'8, C'9.

Additional examples of analytes include tumor necrosis factor-$\alpha$ (TNF$\alpha$), interleukin-12 (IL-12), IL-23, IL-6, $\alpha2\beta1$ integrin, a1$\beta$1 integrin, $\alpha4\beta7$ integrin, integrin $\alpha4\beta1$ (VLA-4), E-selectin, ICAM-1, $\alpha5\beta1$ integrin, $\alpha4\beta1$ integrin, VLA-4, $\alpha2\beta1$ integrin, $\alpha5\beta3$ integrin, $\alpha5\beta5$ integrin, $\alpha$IIb$\beta$3 integrin, MAdCAM-1, SMAD7, JAK1, JAK2, JAK3, TYK-2, CHST15, IL-1, IL-1$\alpha$, IL-1$\beta$, IL-18, IL-36$\alpha$, IL-36$\beta$, IL-36K, IL-38, IL-33, IL-13, CD40L, CD40, CD3K, CD3$\delta$, CD3$\varepsilon$, CD3$\zeta$, TCR, TCR$\alpha$, TCR$\beta$, TCR$\delta$, TCRK, CD14, CD20, CD25, IL-2, IL-2$\beta$ chain, IL-2 K chain, CD28, CD80, CD86, CD49, MMP1, CD89, IgA, CXCL10, CCL11, an ELR chemokine, CCR2, CCR9, CXCR3, CCR3, CCR5, CCL2, CCL8, CCL16, CCL25, CXCR1m CXCR2m CXCL1, CXCL2, CXCL3, CXCL4, CXCL5, CXCL6, CXCL7, and CXCL8, and a nucleic acid (e.g., mRNA) encoding any of the same.

In some embodiments, the analyte is a blood clotting factor. Exemplary blood clotting factors include, but are not limited to:

| International designation | Name |
|---|---|
| I | Fibrinogen |
| II | Prothrombin |
| IIa | Thrombin |
| III | Tissue thromboplastin |
| V and VI | Proaccelerin, accelerator globulin |
| VII | Proconvertin |
| VIII | Antihemophilic globulin (AHG) |
| IX | Christmas factor plasma thromboplastin component (PTC) |
| X | Stuart-Prower factor, autoprothrombin III |
| XI | Plasma thromboplastin antecedent (PTA) |
| XII | Hagemann factor |
| XIII | Fibrin-stabilizing factor |

In some embodiments, the analyte is a hormone. Exemplary hormones include, but are not limited to: Peptide and Protein Hormones, Parathyroid hormone, (parathromone), Thyrocalcitonin, Insulin, Glucagon, Relaxin, Erythropoietin, Melanotropin (melancyte-stimulating hormone; intermedin), Somatotropin (growth hormone), Corticotropin (adrenocorticotropic hormone), Thyrotropin, Follicle-stimulating hormone, Luteinizing hormone (interstitial cell-stimulating hormone), Luteomammotropic hormone (luteotropin, prolactin), Gonadotropin (chorionic gonadotropin), Secretin, Gastrin, Angiotensin I and II, Bradykinin, and Human placental lactogen, thyroxine, cortisol, triiodothyronine, testosterone, estradiol, estrone, progestrone, luteinizing hormone-releasing hormone (LHRH), and immunosuppressants such as cyclosporin, FK506, mycophenolic acid, and so forth.

In some embodiments, the analyte is a peptide hormone (e.g., a peptide hormone from the neurohypophysis). Exemplary peptide hormones from the neurohypophysis include, but are not limited to: Oxytocin, Vasopressin, and releasing factors (RF) (e.g., corticotropin releasing factor (CRF), luteinizing hormone releasing factor (LRF), thyrotropin releasing factor (TRF), Somatotropin-RF, growth hormone releasing factor (GRF), follicle stimulating hormone-releasing factor (FSH-RF), prolactin inhibiting factor (PIF), and melanocyte stimulating hormone inhibiting factor (MIF)).

In some embodiments, the analyte is a cytokine or a chemokine. Exemplary cytokines include, but are not limited to: interleukin-1 (IL-1), interleukin-2 (IL-2), interleukin-6 (IL-6), epidermal growth factor (EGF), tumor necrosis factor (TNF, e.g., TNF-α or TNF-β), and nerve growth factor (NGF).

In some embodiments, the analyte is a cancer antigen. Exemplary cancer antigens include, but are not limited to: prostate-specific antigen (PSA), carcinoembryonic antigen (CEA), α-fetoprotein, Acid phosphatase, CA19.9, and CA125.

In some embodiments, the analyte is a tissue-specific antigen. Exemplary tissue specific antigens include, but are not limited to: alkaline phosphatase, myoglobin, CPK-MB, calcitonin, and myelin basic protein.

In some embodiments, the analyte is a mucopolysaccharide or a polysaccharide.

In some embodiments, the analyte is a microorganism, or a molecule derived from or produced by a microorganism (e.g., a bacteria, a virus, prion, or a protozoan). For example, in some embodiments, the analyte is a molecule (e.g., an protein or a nucleic acid) that is specific for a particular microbial genus, species, or strain (e.g., a specific bacterial genus, species, or strain). In some embodiments, the microorganism is pathogenic (i.e., causes disease). In some embodiments, the microorganism is non-pathogenic (e.g., a commensal microorganism). Exemplary microorganisms include, but are not limited to:

| | |
|---|---|
| Corynebacteria | |
| *Corynebacterium diphtheria* | |
| Pneumococci | |
| *Diplococcus pneumoniae* | |
| Streptococci | |
| *Streptococcus pyrogenes* | |
| *Streptococcus salivarus* | |
| Staphylococci | |
| *Staphylococcus aureus* | |
| *Staphylococcus albus* | |
| Neisseria | |
| *Neisseria meningitidis* | |
| *Neisseria gonorrhea* | |
| Enterobacteriaciae | |
| *Escherichia coli* | |
| *Aerobacter aerogenes* | The coliform bacteria |
| *Klebsiella pneumoniae* | |
| *Salmonella typhosa* | The Salmonellae |
| *Salmonella choleraesuis* | |
| *Salmonella typhimurium* | |
| *Shigella dysenteria* | The Shigellae |
| *Shigella schmitzii* | |
| *Shigella arabinotarda* | |
| *Shigella flexneri* | |
| *Shigella boydii* | |
| *Shigella sonnei* | |
| Other enteric bacilli | |
| *Proteus vulgaris* | Proteus species |
| *Proteus mirabilis* | |
| *Proteus morgani* | |
| *Pseudomonas aeruginosa* | |
| *Alcaligenes faecalis* | |
| *Vibrio cholerae* | |
| Hemophilus-Bordetella group | *Rhizopus oryzae* |
| Hemophilus influenza, *H. ducryi* | *Rhizopus arrhizua* |
| | Phycomycetes |
| *Hemophilus hemophilus* | *Rhizopus nigricans* |
| *Hemophilus aegypticus* | *Sporotrichum schenkii* |
| *Hemophilus parainfluenza* | *Flonsecaea pedrosoi* |
| *Bordetella pertussis* | *Fonsecacea compact* |
| Pasteurellae | *Fonsecacea dermatidis* |
| *Pasteurella pestis* | *Cladosporium carrionii* |
| *Pasteurella tulareusis* | *Phialophora verrucosa* |
| Brucellae | *Aspergillus nidulans* |
| *Brucella melltensis* | *Madurella mycetomi* |
| *Brucella abortus* | *Madurella grisea* |
| *Brucella suis* | *Allescheria boydii* |
| Aerobic Spore-forming Bacilli | *Phialophora jeanselmei* |
| *Bacillus anthracis* | *Microsporum gypseum* |
| *Bacillus subtilis* | *Trichophyton mentagrophytes* |
| *Bacillus megaterium* | *Keratinomyces ajelloi* |
| *Bacillus cereus* | *Microsporum canis* |
| Anaerobic Spore-forming Bacilli | *Trichophyton rubrum* |
| *Clostridium botulinum* | *Microsporum adouini* |
| *Clostridium tetani* | Viruses |
| *Clostridium perfringens* | Adenoviruses |
| *Clostridium novyi* | Herpes Viruses |
| *Clostridium septicum* | *Herpes simplex* |
| *Clostridium histoyticum* | Varicella (Chicken pox) |
| *Clostridium tertium* | Herpes Zoster (Shingles) |
| *Clostridium bifermentans* | Virus B |
| Clostridium sporogenes | Cytomegalovirus |
| Mycobacteria | Pox Viruses |
| *Mycobacterium tuberculosis* hominis | Variola (smallpox) |
| *Mycobacterium bovis* | Vaccinia |
| *Mycobacterium avium* | *Poxvirus bovis* |

-continued

| | |
|---|---|
| *Mycobacterium leprae* | Paravaccinia |
| *Mycobacterium paratuberculosis* | *Molluscum contagiosum* |
| Actinomycetes (fungus-ike bacteria) | Picornaviruses |
| *Actinomyces Isaeli* | Poliovirus |
| *Actinomyces bovis* | Coxsackievirus |
| *Actinomyces naeslundii* | Echoviruses |
| *Nocardia asteroides* | Rhinoviruses |
| *Nocardia brasiliensis* | Myxoviruses |
| The Spirochetes | Influenza (A, B, and C) |
| *Treponema pallidum* | Parainfluenza (1-4) |
| *Treponema pertenue* | Mumps Virus |
| *Spirillum minus* | |
| *Streptobacillus monoiliformis* | Newcastle Disease Virus |
| *Treponema carateum* | Measles Virus |
| *Borrelia recurrentis* | Rinderpest Virus |
| *Leptospira icterohemorrhagiae* | Canine Distemper Virus |
| *Leptospira canicola* | Respiratory Syncytial Virus |
| Trypanasomes | Rubella Virus |
| Mycoplasmas | Arboviruses |
| *Mycoplasma pneumoniae* | |
| Other pathogens | Eastern Equine Encephalitis Virus |
| *Listeria monocytogenes* | Western Equine Encephalitis Virus |
| *Erysipeothrix rhusiopathiae* | Sindbis Virus |
| *Streptobacillus moniliformis* | Chikugunya Virus |
| *Donvania granulomatis* | Semliki Forest Virus |
| *Entamoeba histolytica* | Mayora Virus |
| *Plasmodium falciparum* | St. Louis Encephalitis |
| *Plasmodium japonicum* | California Encephalitis Virus |
| *Bartonella bacilliformis* | Colorado Tick Fever Virus |
| Rickettsia (bacteria-like parasites) | Yellow Fever Virus |
| *Rickettsia prowazekii* | Dengue Virus |
| *Rickettsia mooseri* | Reoviruses |
| *Rickettsia rickettsii* | Reovirus Types 1-3 |
| *Rickettsia conori* | Retroviruses |
| *Rickettsia australis* | Human Immunodeficiency |
| *Rickettsia sibiricus* | Viruses I and II (HTLV) |
| *Rickettsia akari* | Human T-cell Lymphotrophic |
| *Rickettsia tsutsugamushi* | Virus I & II (HIV) |
| *Rickettsia burnetti* | Hepatitis |
| *Rickettsia quintana* | Hepatitis A Virus |
| Chlamydia (unclassifiable parasites bacterial/viral) | Hepatitis B Virus |
| | Hepatitis C Virus |
| Chlamydia agents (naming uncertain) | Tumor Viruses |
| *Chlamydia trachomatis* | |
| Fungi | Rauscher Leukemia Virus |
| *Cryptococcus neoformans* | Gross Virus |
| *Blastomyces dermatidis* | Maloney Leukemia Virus |
| *Histoplasma capsulatum* | |
| *Coccidioides immitis* | Human Papilloma Virus |
| *Paracoccidioides brasliensis* | |
| *Candida albicans* | |
| *Aspergillus fumigatus* | |
| *Mucor corymbifer* (*Absidia corymbifera*) | |

In some embodiments, the analyte is a bacterium. Exemplary bacteria include, but are not limited to: *Escherichia coli* (or *E. coli*), *Bacillus anthracis, Bacillus cereus, Clostridium botulinum, Clostridium difficile, Yersinia pestis, Yersinia enterocolitica, Francisella tularensis, Brucella species, Clostridium perfringens, Burkholderia mallei, Burkholderia pseudomallei, Staphylococcus species, Mycobacterium* species, Group A *Streptococcus*, Group B *Streptococcus, Streptococcus pneumoniae, Helicobacter pylori, Salmonella enteritidis, Mycoplasma hominis, Mycoplasma orale, Mycoplasma salivarium, Mycoplasma fermentans, Mycoplasma pneumoniae, Mycobacterium bovis, Mycobacterium tuberculosis, Mycobacterium avium, Mycobacterium leprae, Rickettsia rickettsii, Rickettsia akari, Rickettsia prowazekii, Rickettsia canada, Bacillus subtilis, Bacillus subtilis niger, Bacillus thuringiensis, Coxiella burnetti, Faecalibacterium prausnitzii* (also known as *Bacteroides praussnitzii*), *Roseburia hominis, Eubacterium rectale, Dialister invisus, Ruminococcus albus, Ruminococcus callidus*, and *Ruminococcus bromii*. Additional exemplary bacteria include bacteria of the phyla Firmicutes (e.g., *Clostridium* clusters XIVa and IV), bacteria of the phyla Bacteroidetes (e.g., *Bacteroides fragilis* or *Bacteroides* vulgatus), and bacteria of the phyla Actinobacteria (e.g., Coriobacteriaceae spp. or *Bifidobacterium adolescentis*). Bacteria of the *Clostridium* cluster XIVa includes species belonging to, for example, the *Clostridium, Ruminococcus, Lachnospira, Roseburia, Eubacterium, Coprococcus, Dorea*, and *Butyrivibrio* genera. Bacteria of the *Clostridium* cluster IV includes species belonging to, for example, the *Clostridium, Ruminococcus, Eubacterium* and *Anaerofilum* genera. In some embodiments, the analyte is *Candida*, e.g., *Candida albicans*. In some embodiments, the analyte is a byproduct from a bacterium or other microorganism, e.g., helminth ova, enterotoxin (*Clostridium difficile* toxin A; TcdA) or cytotoxin (*Clostridium difficile* toxin B; TcdB).

In some embodiments, the bacterium is a pathogenic bacterium. Non-limiting examples of pathogenic bacteria belong to the genera *Bacillus, Bordetella, Borrelia, Brucella, Campylobacter, Chlamydia, Chlamydophila, Clostridium, Corynebacterium, Enterobacter, Enterococcus, Escherichia, Francisella, Haemophilus, Helicobacter, Legionella, Leptospira, Listeria, Mycobacterium, Mycoplasma, Neisseria, Pseudomonas, Rickettsia, Salmonella, Shigella, Staphylococcus, Streptococcus, Treponema, Vibrio*, and *Yersinia*. Non-limiting examples of specific pathogenic bacterial species include a strain of *Bacillus anthracis*, a strain of a strain of *Bordetella pertussis*, a strain of a strain of *Borrelia burgdorferi*, a strain of a strain of *Brucella abortus*, a strain of a strain of *Brucella canis*, a strain of a strain of *Brucella melitensis*, a strain of a strain of *Brucella suis*, a strain of a strain of *Campylobacter jejuni*, a strain of *Chlamydia pneumoniae*, a strain of *Chlamydia trachomatis*, a strain of *Chlamydophila psittaci*, a strain of *Clostridium botulinum*, a strain of *Clostridium difficile*, a strain of *Clostridium perfringens*, a strain of *Clostridium tetani*, a strain of *Corynebacterium diphtheria*, a strain of *Enterobacter* sakazakii, a strain of *Enterococcus faecalis*, a strain of *Enterococcus faecium*, a strain of *Escherichia coli* (e.g., *E. coli* O157 H7), a strain of *Francisella tularensis*, a strain of *Haemophilus influenza*, a strain of *Helicobacter pylori*, a strain of *Legionella pneumophila*, a strain of Leptospira interrogans, a strain of *Listeria monocytogenes*, a strain of *Mycobacterium leprae*, a strain of *Mycobacterium tuberculosis*, a strain of *Mycobacterium ulcerans*, a strain of *Mycoplasma* pneumonia, a strain of *Neisseria gonorrhoeae*, a strain of *Neisseria meningitides*, a strain of *Pseudomonas aeruginosa*, a strain of *Rickettsia rickettsia*, a strain of *Salmonella typhi* and *Salmonella typhimurium*, a strain of *Shigella sonnei*, a strain of *Staphylococcus aureus*, a strain of *Staphylococcus epidermidis*, a strain of *Staphylococcus saprophyticus*, a strain of *Streptococcus agalactiae*, a strain of *Streptococcus pneumonia*, a strain of *Streptococcus pyogenes*, a strain of *Treponema pallidum*, a strain of *Vibrio cholera*, a strain of *Yersinia enterocolitica*, and, a strain of *Yersinia pestis*.

In some embodiments, the bacterium is a commensal bacterium (e.g., a probiotic). In some embodiments, the bacterium has been previously administered to a subject, e.g., as a live biotherapeutic agent. Exemplary commensal bacteria include, but are not limited to, *Faecalibacterium prausnitzii* (also referred to as *Bacteroides praussnitzii*), *Roseburia hominis, Eubacterium rectale, Dialister invisus, Ruminococcus albus, Ruminococcus gnavus, Ruminococcus torques, Ruminococcus callidus*, and *Ruminococcus bromii*.

In some embodiments, the analyte is a virus. In some embodiments, the virus is a pathogenic virus. Non-limiting examples of pathogenic viruses belong to the families Adenoviridae, Picomaviridae, Herpesviridae, Hepadnaviridae, Flaviviridae, Retroviridae, Orthomyxoviridae, Paramyxoviridae, Papovaviridae, Polyomavirus, Rhabdoviridae, and Togaviridae.

In some embodiments, the analyte is a fungus. In some embodiments, the fungi is a pathogenic fungus. Non-limiting examples of pathogenic fungi belong to the genera *Asperfillus, Canidia, Cryptococcus, Histoplasma, Pneumocystis*, and *Stachybotrys*. Non-limiting examples of specific pathogenic fungi species include a strain of *Aspergillus clavatus, Aspergillus fumigatus, Aspergillus flavus, Canidia albicans, Cryptococcus albidus, Cryptococcus gattii, Cryptococcus laurentii, Cryptococcus neoformans, Histoplasma capsulatum, Pneumocystis jirovecii, Pneumocystis carinii*, and *Stachybotrys chartarum.*

In some embodiments, the analyte is a protozoan. In some embodiments, the analyte is a pathogenic protozoan. Non-limiting examples of pathogenic protozoa belong to the genera *Acanthamoeba, Balamuthia, Cryptosporidium, Dientamoeba, Endolimax, Entamoeba, Giardia, lodamoeba, Leishmania, Naegleria, Plasmodium, Sappinia, Toxoplasma, Trichomonas*, and *Trypanosoma*. Non-limiting examples of specific pathogenic protozoa species include a strain of *Acanthamoeba* spp., *Balamuthia mandrillaris, Cryptosporidium canis, Cryptosporidium felis, Cryptosporidium hominis, Cryptosporidium meleagridis, Cryptosporidium muris, Cryptosporidium parvum, Dientamoeba fragilis, Endolimax nana, Entamoeba dispar, Entamoeba hartmanni, Entamoeba histolytica, Entamoeba coi, Entamoeba moshkovskii, Giardia lamblia, Iodamoeba butschlii, Leishmania aethiopica, Leishmania braziliensis, Leishmania chagasi, Leishmania donovani, Leishmania infantum, Leishmania major, Leishmania mexicana, Leishmania tropica, Naegleriafowleri, Plasmodium falciparum, Plasmodium knowlesi, Plasmodium malariae, Plasmodium ovale, Plasmodium vivax, Sappinia diploidea, Toxoplasma gondii, Trichomonas vaginalis, Trypanosoma brucei*, and *Trypanosoma cruzi.*

In some embodiments, the analyte is secreted by or expressed on the cell surface of a microorganism (e.g., a bacterium, a colonic bacterium, a viable bacterium, a dead bacterium, a parasite (e.g., *Giardia lamblia, Cryptosporidium, Cystoisosporiasis belli*, and *Balantidium coli*), a virus (e.g., a herpes virus, a cytomegalovirus, a herpes simplex virus, an Epstein-Barr virus, a human papilloma virus, a rotavirus, a human herpesvirus-8; Goodgame (1999) Curr. Gastroenterol. Rep. 1(4): 292-300). In some embodiments, the analyte is secreted by or expressed on the cell surface of a Gram-negative bacterium (e.g., *E. coli, Helicobacter pylori*). In some embodiments, the analyte is secreted by or expressed on the cell surface (e.g., a bacterial surface epitope) of a Gram-positive bacterium (e.g., *Staphylococcus aureus, Clostridium botulinum, Clostridium difficile*).

In some embodiments, the analyte is a molecule expressed on the surface of a bacterial cell (e.g., a bacterial cell surface protein). In some embodiments, the analyte is a bacterial toxin (e.g., TcdA and/or TcdB from *Clostridium difficile*). In some embodiments, the analyte is CFA/I fimbriae, flagella, lipopolysaccharide (LPS), lipoteichoic acid, or a peptidoglycan. Non-limiting examples of bacterium that may express an analyte that can be detected using any of the devices and methods described herein include: *Bacillus anthracis, Bacillus cereus, Clostridium botulinum, Clostridium difficile, Escherichia coli, Yersinia pestis, Yersinia enterocolitica, Francisella tularensis, Brucella species, Clostridium perfringens, Burkholderia mallei, Burkholderia pseudomallei, Helicobacter pylori, Staphylococcus species, Mycobacterium* species, Group A *Streptococcus*, Group B *Streptococcus, Streptococcus pneumoniae, Francisella tularensis, Salmonella enteritidis, Mycoplasma hominis, Mycoplasma orale, Mycoplasma salivarium, Mycoplasma fermentans, Mycoplasma pneumoniae, Mycobacterium bovis, Mycobacterium tuberculosis, Mycobacterium avium, Mycobacterium leprae, Rickettsia rickettsii, Rickettsia akari, Rickettsia prowazekii, Rickettsia canada, Bacillus subtilis, Bacillus subtilis niger, Bacillus thuringiensis, Coxiella bumetti, Candida albicans, Bacteroides fragilis, Leptospira interrogans, Listeria monocytogenes, Pasteurella multocida, Salmonella typhi, Salmonella typhimurium, Shigella dysenteriae, Shigella flexneria, Shigella sonnei, Vibrio cholera*, and *Vibrio parahaemolyticus.*

In some embodiments, the analyte is a byproduct from a bacterium or another microorganism, e.g., helminth ova, enterotoxin (*Clostridium difficile* toxin A; TcdA), cytotoxin (*Clostridium difficile* toxin B; TcdB), ammonia. In some embodiments, the analyte is an antigen from a microorganism (e.g., a bacteria, virus, prion, fungus, protozoan or a parasite).

In some embodiments, the analytes include drugs, metabolites, pesticides, pollutants, and the like. Included among drugs of interest are the alkaloids. Among the alkaloids are morphine alkaloids, which includes morphine, codeine, heroin, dextromethorphan, their derivatives and metabolites; cocaine alkaloids, which include cocaine and benzyl ecgonine, their derivatives and metabolites; ergot alkaloids, which include the diethylamide of lysergic acid; steroid alkaloids; iminazoyl alkaloids; quinazoline alkaloids; isoquinoline alkaloids; quinoline alkaloids, which include quinine and quinidine; diterpene alkaloids, their derivatives and metabolites.

In some embodiments, the analyte is a steroid selected from the estrogens, androgens, andreocortical steroids, bile acids, cardiotonic glycosides and aglycones, which includes digoxin and digoxigenin, saponins and sapogenins, their derivatives and metabolites. Also included are the steroid mimetic substances, such as diethylstilbestrol.

In some embodiments, the analyte is a bile acid. In some embodiments, the presence, absence, and/or a specific level of one or more bile acids in the GI tract of a subject is indicative of a condition or disease state (e.g., a GI disorder and/or a non-GI disorder (e.g., a systemic disorder). For example, in some embodiments, the compositions and methods described herein may be used to detect and/or quantify a bile acid in the GI tract of the subject to diagnose a condition such as bile acid malabsorption (also known as bile acid diarrhea). In some embodiments, the analyte is a metabolite in the serotonin, tryptophan and/or kynurenine pathways, including but not limited to, serotonin (5-HT), 5-hydroxyindole acetic acid (5-HIAA), 5-hydroxytryptophan (5-HTP), kynurenine (K), kynurenic acid (KA), 3-hydroxykynurenine (3-HK), 3-hydroxyanthranilic acid (3-HAA), quinolinic acid, anthranilic acid, and combinations thereof. 5-HT is a molecule that plays a role in the regulation of gastrointestinal motility, secretion, and sensation. Imbalances in the levels of 5-HT are associated with several diseases including inflammatory bowel syndrome (IBS), autism, gastric ulcer formation, non-cardiac chest pain, and functional dyspepsia (see, e.g., Faure et al. (2010) *Gastroenterology* 139(1): 249-58 and Muller et al. (2016) Neuroscience 321: 24-41, and International Publication No. WO 2014/188377, each of which are incorporated herein by reference). Conversion of metabolites within the serotonin, tryptophan and/or kynurenine pathways affects the levels of 5-HT in a subject. Therefore, measuring the levels of one or more of the metabolites in this pathway may be used for the diagnosis, management and treatment of a disease or disorder associated with 5-HT imbalance including but not limited to IBS, autism, carcinoid syndrome, depression, hypertension, Alzheimer's disease, constipation, migraine, and serotonin syndrome. One or more analytes in the serotonin, tryptophan and/or kynurenine pathways can be detected and/or quantitated using, for example, methods and analyte-binding agents that bind to these metabolites including, e.g., antibodies, known in the art (see, e.g., International Publication No. WO 2014/188377, which is incorporated herein by reference in its entirety).

In some embodiments, the analyte is a lactam having from 5 to 6 annular members selected from barbituates, e.g., phenobarbital and secobarbital, diphenylhydantonin, primidone, ethosuximide, and metabolites thereof.

In some embodiments, the analyte is an aminoalkylbenzene, with alkyl of from 2 to 3 carbon atoms, selected from the amphetamines; catecholamines, which includes ephedrine, L-dopa, epinephrine; narceine; papaverine; and metabolites thereof.

In some embodiments, the analyte is a benzheterocyclic selected from oxazepam, chlorpromazine, tegretol, their derivatives and metabolites, the heterocyclic rings being azepines, diazepines and phenothiazines.

In some embodiments, the analyte is a purine selected from theophylline, caffeine, their metabolites and derivatives.

In some embodiments, the analyte is marijuana, cannabinol or tetrahydrocannabinol.

In some embodiments, the analyte is a vitamin such as vitamin A, vitamin B, e.g. vitamin $B_{12}$, vitamin C, vitamin D, vitamin E and vitamin K, folic acid, thiamine.

In some embodiments, the analyte is selected from prostaglandins, which differ by the degree and sites of hydroxylation and unsaturation.

In some embodiments, the analyte is a tricyclic antidepressant selected from imipramine, dismethylimipramine, amitriptyline, nortriptyline, protriptyline, trimipramine, chlomipramine, doxepine, and desmethyldoxepin.

In some embodiments, the analyte is selected from antineoplastics, including methotrexate.

In some embodiments, the analyte is an antibiotic as described herein, including, but not limited to, penicillin, chloromycetin, actinomycetin, tetracycline, terramycin, and metabolites and derivatives.

In some embodiments, the analyte is a nucleoside and nucleotide selected from ATP, NAD, FMN, adenosine, guanosine, thymidine, and cytidine with their appropriate sugar and phosphate substituents.

In some embodiments, the analyte is selected from methadone, meprobamate, serotonin, meperidine, lidocaine, procainamide, acetylprocainamide, propranolol, griseofulvin, valproic acid, butyrophenones, antihistamines, chloramphenicol, anticholinergic drugs, such as atropine, their metabolites and derivatives.

In some embodiments, the analyte is a metabolite related to a diseased state. Such metabolites include, but are not limited to spermine, galactose, phenylpyruvic acid, and porphyrin Type 1.

In some embodiments, the analyte is an aminoglycoside, such as gentamicin, kanamicin, tobramycin, or amikacin.

In some embodiments, the analyte is a pesticide. Among pesticides of interest are polyhalogenated biphenyls, phosphate esters, thiophosphates, carbamates, polyhalogenated sulfenamides, their metabolites and derivatives.

In some embodiments, the analyte has a molecular weight of about 500 Da to about 1,000,000 Da (e.g., about 500 to about 500,000 Da, about 1,000 to about 100,000 Da).

In some embodiments, the analyte is a receptor, with a molecular weight ranging from 10,000 to $2\times10^8$ Da, more usually from 10,000 to $10^6$ Da. For immunoglobulins, IgA, IgG, IgE and IgM, the molecular weights will generally vary from about 160,000 Da to about $10^6$ Da. Enzymes will normally range in molecular weight from about 10,000 Da to about 1,000,000 Da. Natural receptors vary widely, generally having a molecular weight of at least about 25,000 Da and may be $10^6$ or higher Da, including such materials as avidin, DNA, RNA, thyroxine binding globulin, thyroxine binding prealbumin, transcortin, etc.

In some embodiments, the term "analyte" further includes polynucleotide analytes such as those polynucleotides defined below. These include m-RNA, r-RNA, t-RNA, DNA, DNA-RNA duplexes, etc. The term analyte also includes polynucleotide-binding agents, such as, for example, restriction enzymes, trascription factors, transcription activators, transcription repressors, nucleases, polymerases, histones, DNA repair enzymes, intercalating gagents, chemotherapeutic agents, and the like.

In some embodiments, the analyte may be a molecule found directly in a sample such as a body fluid from a host. The sample can be examined directly or may be pretreated to render the analyte more readily detectible. Furthermore, the analyte of interest may be determined by detecting an agent probative of the analyte of interest (i.e., an analyte-binding agent), such as a specific binding pair member complementary to the analyte of interest, whose presence will be detected only when the analyte of interest is present in a sample. Thus, the agent probative of the analyte becomes the analyte that is detected in an assay.

In some embodiments, the analyte a nucleic acid (e.g., a bacterial DNA molecule or a bacterial RNA molecule (e.g., a bacterial tRNA, a transfer-messenger RNA (tmRNA)). See, e.g., Sjostrom et al. (2015) Scientific Reports 5:15329; Ghosal (2017) Microbial Pathogenesis 104:161-163; Shen et al. (2012) Cell Host Microbe. 12(4):509-520.

In some embodiments, the analyte is a component of an outer membrane vesicle (OMV) (e.g., an OmpU protein, Elluri et al. (2014) PloS One 9:e106731). See, e.g., Kulp and Kuehn (2010) Annual Review of microbiology 64:163-184; Berleman and Auer (2013) Environmental Microbiology 15:347-354; Wai et al. (1995) Microbiology and Immunology 39:451-456; Lindmark et al. (2009) BMC Microbiology 9:220; Sjostrom et al. (2015) Scientific Reports 5:15329.

In some embodiments, the analyte is G-CSF, which can stimulate the bone marrow to produce granulocytes and stem cells and release them into the bloodstream.

In some embodiments, the analyte is an enzyme such as glutathione S-transferase. For example, the ingestible device can include P28GST, a 28 kDa helminth protein from *Schistosoma* with potent immunogenic and antioxidant properties. P28GST prevents intestinal inflammation in experimental colitis through a Th2-type response with mucosal eosinophils and can be recombinantly produced (e.g., in *S. cerevisiae*). See, for example, U.S. Pat. No. 9,593,313, Driss et al., Mucosal Immunology, 2016, 9:322-335; and Capron et al., Gastroenterology, 146(5):S-638.

In some embodiments, the analyte is a metabolite in the serotonin, tryptophan and/or kynurenine pathways, including but not limited to, serotonin (5-HT), 5-hydroxyindole acetic acid (5-HIAA), 5-hydroxytryptophan (5-HTP), kynurenine (K), kynurenic acid (KA), 3-hydroxykynurenine (3-HK), 3-hydroxyanthranilic acid (3-HAA), quinolinic acid, anthranilic acid, and combinations thereof.

In some embodiments, analytes are therapeutic agents or drugs. In some embodiments, analytes are biomarkers. The therapeutic agents disclosed herein are can also be analytes. Examples of biomarkers are provided herein.

In some embodiments, analytes are therapeutic agents, fragments thereof, and metabolites thereof (e.g., antibiotics). In some embodiments, the analytes are antibodies. In some embodiments, the analytes are antibiotics. Additional exemplary analytes (e.g., antibodies and antibiotics) are provided below.

Antibodies

In some embodiments, the analyte or the analyte-binding agent is an antibody. In some embodiments, the antibody can be a humanized antibody, a chimeric antibody, a multivalent antibody, or a fragment thereof. In some embodiments, an antibody can be a scFv-Fc (Sokolowska-Wedzina et al., *Mol. Cancer Res.* 15(8):1040-1050, 2017), a VHH domain (Li et al., *Immunol. Lett.* 188:89-95, 2017), a VNAR domain (Hasler et al., *Mol. Immunol.* 75:28-37, 2016), a $(scFv)_2$, a minibody (Kim et al., *PLoS One* 10(1):el13442, 2014), or a BiTE. In some embodiments, an antibody can be a DVD-Ig (Wu et al., *Nat. Biotechnol.* 25(11):1290-1297, 2007; WO 08/024188; WO 07/024715), and a dual-affinity re-targeting antibody (DART) (Tsai et al., *Mol. Ther. Oncolytics* 3:15024, 2016), a triomab (Chelius et al., *MAbs* 2(3):309-319, 2010), kih IgG with a common LC (Kontermann et al., *Drug Discovery Today* 20(7):838-847, 2015), a crossmab (Regula et al., *EMBO Mol. Med.* 9(7):985, 2017), an ortho-Fab IgG (Kontermann et al., *Drug Discovery Today* 20(7): 838-847, 2015), a 2-in-1-IgG (Kontermann et al., *Drug Discovery Today* 20(7):838-847, 2015), IgG-scFv (Cheal et al., *Mol. Cancer Ther.* 13(7):1803-1812, 2014), scFv2-Fc (Natsume et al., *J. Biochem.* 140(3):359-368, 2006), a bi-nanobody (Kontermann et al., *Drug Discovery Today* 20(7):838-847, 2015), tanden antibody (Kontermann et al., *Drug Discovery Today* 20(7):838-847, 2015), a DART-Fc (Kontermann et al., *Drug Discovery Today* 20(7):838-847, 2015), a scFv-HSA-scFv (Kontermann et al., *Drug Discovery Today* 20(7):838-847, 2015), DNL-Fab3 (Kontermann et al., *Drug Discovery Today* 20(7):838-847, 2015), DAF (two-in-one or four-in-one), DutaMab, DT-IgG, knobs-in-holes common LC, knobs-in-holes assembly, charge pair antibody, Fab-arm exchange antibody, SEEDbody, Triomab, LUZ-Y, Fcab, kλ-body, orthogonal Fab, DVD-IgG, IgG(H)-scFv, scFv-(H)IgG, IgG(L)-scFv, scFv-(L)-IgG, IgG (L,H)-Fc, IgG(H)-V, V(H)-IgG, IgG(L)-V, V(L)-IgG, KIH IgG-scFab, 2scFv-IgG, IgG-2scFv, scFv4-Ig, Zybody, DVI-IgG, nanobody (e.g., antibodies derived from *Camelus bactriamus, Calelus dromaderius*, or *Lama paccos*) (U.S. Pat. No. 5,759,808; Stijlemans et al., *J. Biol. Chem.* 279:1256-1261, 2004; Dumoulin et al., *Nature* 424:783-788, 2003; and Pleschberger et al., *Bioconjugate Chem.* 14:440-448, 2003), nanobody-HSA, a diabody (e.g., Poljak, Structure 2(12): 1121-1123, 1994; Hudson et al., J. *Immunol. Methods* 23(1-2):177-189, 1999), a TandAb (Reusch et al., *mAbs* 6(3):727-738, 2014), seDiabody (Cuesta et al., *Trends in Biotechnol.* 28(7):355-362, 2010), scDiabody-CH3 (Sanz et al., *Trends in Immunol.* 25(2):85-91, 2004), Diabody-CH3 (Guo et al.), Triple Body, miniantibody, minibody, TriBi minibody, scFv-CH3 KIH, Fab-scFv, scFv-CH-CL-scFv, F(ab')2-scFV2, scFv-KIH, Fab-scFv-Fc, tetravalent HCAb, scDiabody-Fc, diabody-Fc, tandem scFv-Fc, intrabody (Huston et al., *Human Antibodies* 10(3-4):127-142, 2001; Wheeler et al., *Mol. Ther.* 8(3):355-366, 2003; Stocks, *Drug Discov. Today* 9(22):960-966, 2004), dock and lock bispecific antibody, ImmTAC, HSAbody, scDiabody-HSA, tandem scFv, IgG-IgG, Cov-X-Body, and scFvl-PEG-scFv2.

In some embodiments, an antibody can be an IgNAR, a bispecific antibody (Milstein and Cuello, *Nature* 305:537-539, 1983; Suresh et al., *Methods in Enzymology* 121:210, 1986; WO 96/27011; Brennan et al., *Science* 229:81, 1985; Shalaby et al., *J. Exp. Med.* 175:217-225, 1992; Kolstelny et al., *J. Immunol.* 148(5):1547-1553, 1992; Hollinger et al., *Proc. Natl. Acad. Sci. U.S.A.* 90:6444-6448, 1993; Gruber et al., *J. Immunol.* 152:5368, 1994; Tutt et al., *J. Immunol.* 147:60, 1991), a bispecific diabody, a triabody (Schoonooghe et al., *BMC Biotechnol.* 9:70, 2009), a tetrabody, scFv-Fc knobs-into-holes, a scFv-Fc-scFv, a $(Fab'scFv)_2$, a V-IgG, a IvG-V, a dual V domain IgG, a heavy chain immunoglobulin or a camelid (Holt et al., *Trends Biotechnol.* 21(11):484-490, 2003), an intrabody, a monoclonal antibody (e.g., a human or humanized monoclonal antibody), a heteroconjugate antibody (e.g., U.S. Pat. No. 4,676,980), a linear antibody (Zapata et al., *Protein Eng.* 8(10: 1057-1062, 1995), a trispecific antibody (Tutt et al., *J. Immunol.* 147:60, 1991), a Fabs-in-Tandem immunoglobulin (WO 15/103072), or a humanized camelid antibody.

In some embodiments, the antibody binds specifically to a metabolite in the serotonin, tryptophan and/or kynurenine pathways, including but not limited to, serotonin (5-HT), 5-hydroxyindole acetic acid (5-HIAA), 5-hydroxytryptophan (5-HTP), kynurenine (K), kynurenic acid (KA), 3-hydroxykynurenine (3-HK), 3-hydroxyanthranilic acid (3-HAA), quinolinic acid, anthranilic acid. Exemplary antibodies that bind to metabolites in these pathways are disclosed, for example, in International Publication No. WO 2014/188377, which is incorporated herein by reference in its entirety.

In some embodiments, the antibody is specific for a particular genus, species, or strain of a microorganism, and may therefore be used for the detection, analysis and/or quantitation of the microorganism using the detection methods described below. In some embodiments, the antibody specifically binds to a surface-specific biomolecule (e.g., a pilus subunit or a flagella protein) present in a particular genus, species or strain of microorganism, and does not cross-react with other microorganisms. In some embodiments, these antibodies may be used in the methods described herein to diagnose a subject with a particular infection or disease, or to monitor an infection (e.g., during or after treatment). In some embodiments, the antibody specifically binds to an antigen present in a particular genera, species or strain of a microorganism. Exemplary antigens, the corresponding microorganism that can be detected, and the disease caused by the microorganism (in parentheticals) include: outer membrane protein A OmpA (*Acinetobacter baumannii, Acinetobacter* infections)); HIV p24 antigen, HIV envelope proteins (Gp120, Gp41, Gp160) (HIV (Human immunodeficiency virus), AIDS (Acquired immunodeficiency syndrome)); galactose-inhibitable adherence protein GIAP, 29 kDa antigen Eh29, GaVGalNAc lectin, protein CRT, 125 kDa immunodominant antigen, protein M17, adhesin ADH112, protein STIRP (*Entamoeba histolytica*, Amoebiasis); protective Antigen PA, edema factor EF, lethal facotor LF, the S-layer homology proteins SLH (*Bacillus anthracis*, Anthrax); nucleocapsid protein NP, glycoprotein precursor GPC, glycoprotein GP1, glycoprotein GP2 (Junin virus, Argentine hemorrhagic fever); 41 kDa allergen Asp v13, allergen Asp f3, major conidial surface protein rodlet A, protease Pep1p, GPI-anchored protein Gel1p, GPI-anchored protein Crf1p (*Aspergillus* genus, Aspergillosis); outer surface protein A OspA, outer surface protein OspB, outer surface protein OspC, decorin binding protein A DbpA, flagellar filament 41 kDa core protein Fla, basic membrane protein A precursor BmpA (Immunodominant antigen P39), outer surface 22 kDa lipoprotein precursor (antigen IPLA7), variable surface lipoprotein vIsE (*Borrelia* genus, *Borrelia* infection); OmpA-like transmembrane domain-containing protein Omp31, immunogenic 39-kDa protein M5 P39, 25 kDa outer-membrane immunogenic protein precursor Omp25, outer membrane protein MotY Omp16, conserved outer membrane protein D15, malate dehydrogenase Mdh, component of the Type-IV secretion system (T4SS) VirJ, lipoprotein of unknown function BABI-0187 (*Brucella* genus, Brucellosis); major outer membrane protein PorA, flagellin FIaA, surface antigen CjaA, fibronectin binding protein CadF, aspartate/glutamate-binding ABC transporter protein PeblA, protein FspAl, protein FspA2 (*Campylobacter* genus, Campylobacteriosis); glycolytic enzyme enolase, secreted aspartyl proteinases SAPI-10, glycophosphatidylinositol (GPI)-linked cell wall protein, adhesin Als3p, cell surface hydrophobicity protein CSH (usually *Candida albicans* and other *Candida* species, Candidiasis); envelope glycoproteins (gB, gC, gE, gH, gI, gK, gL) (Varicella zoster virus (VZV), Chickenpox); major outer membrane protein MOMP, probable outer membrane protein PMPC, outer membrane complex protein B OmcB (*Chlamydia trachomatis, Chlamydia*); major outer membrane protein MOMP, outer membrane protein 2 Omp2, (*Chlamydophila pneumoniae, Chlamydophila pneumoniae* infection); outer membrane protein U Porin ompU, (*Vibrio cholerae*, Cholera); surface layer proteins SLPs, Cell Wall Protein CwpV, flagellar protein FliC, flagellar protein FliD (*Clostridium difficile, Clostridium difficile* infection); acidic ribosomal protein P2 CpP2, mucin antigens Mudl, Muc2, Muc3 Muc4, Muc5, Muc6, Muc7, surface adherence protein CP20, surface adherence protein CP23, surface protein CP12, surface protein CP21, surface protein CP40, surface protein CP60, surface protein CP15, surface-associated glycopeptides gp40, surface-associated glycopeptides gp15, oocyst wall protein AB, profilin PRF, apyrase (*Cryptosporidium* genus, Cryptosporidiosis); membrane protein pp15, capsid-proximal tegument protein pp150 (Cytomegalovirus, Cytomegalovirus infection); prion protein (vCJD prion, Variant Creutzfeldt-Jakob disease (vCJD, nvCJD)); cyst wall proteins CWP1, CWP2, CWP3, variant surface protein VSP, VSP1, VSP2, VSP3, VSP4, VSP5, VSP6, 56 kDa antigen (Giardia intestinalis, Giardiasis); minor pilin-associated subunit pilC, major pilin subunit and variants pilE, pilS (*Neisseria gonorrhoeae*, Gonorrhea); outer membrane protein A OmpA, outer membrane protein C OmpC, outer membrane protein K17 OmpK17 (*Klebsiella granulomatis*, Granuloma inguinale (Donovanosis)); fibronectin-binding protein Sfb (*Streptococcus pyogenes*, Group A streptococcal infection); outer membrane protein P6 (*Haemophilus influenzae, Haemophilus influenzae* infection); integral membrane proteins, aggregation-prone proteins, 0-antigen, toxin-antigens Stx2B, toxin-antigen StxlB, adhesion-antigen fragment Int28, protein EspA, protein EspB, Intimin, protein Tir, protein IntC300, protein Eae (*Escherichia coli* O157: H7, 0111 and 0104:H4, Hemolytic-uremic syndrome (HUS)); hepatitis A surface antigen HBAg (Hepatitis A Virus, Hepatitis A); hepatitis B surface antigen HBsAg (Hepatitis B Virus, Hepatitis B); envelope glycoprotein E1 gp32 gp35, envelope glycoprotein E2 NSl gp68 gp70, capsid protein C, (Hepatitis C Virus, Hepatitis C); type IV pilin PilE, outer membrane protein MIP, major outer membrane protein MompS (*Legionella pneumophila*, Legionellosis (Legionnaires' disease, Pontiac fever)); minor pilin-associated subunit pilC, major pilin subunit and variants pilE, pilS (*Neisseria meningitidis*, Meningococcal disease); adhesin P1, adhesion P30 (*Mycoplasma pneumoniae, Mycoplasma* pneumonia); F1 capsule antigen, outer membrane protease Pla, (*Yersinia pestis*, Plague); surface adhesin PsaA, cell wall surface anchored protein psrP (*Streptococcus pneumoniae*, Pneumococcal infection); flagellin FliC, invasion protein SipC, glycoprotein gp43, outer membrane protein LamB, outer membrane protein PagC, outer membrane protein TolC, outer membrane protein NmpC, outer membrane protein FadL, transport protein SadA (*Salmonella* genus, *Salmonellosis*); collagen adhesin Cna, fibronectin-binding protein A FnbA, secretory antigen SssA (*Staphylococcus* genus, Staphylococcal food poisoning); collagen adhesin Can (*Staphylococcus* genus, Staphylococcal infection); fibronectin-binding protein A FbpA (Ag85A), fibronectin-binding protein D FbpD, fibronectin-binding protein C FbpCl, heat-shock protein HSP65, protein PST-S (*Mycobacterium tuberculosis*, Tuberculosis); and outer membrane protein FobA, outer membrane protein FobB, type IV pili glycosylation protein, outer membrane protein tolC, protein TolQ (*Francisella tularensis*, Tularemia). Additional exemplary microorganisms and corresponding antigens are disclosed, e.g., in U.S. Publication No. 2015/0118264, which is incorporated herein by reference in its entirety.

In some embodiments, a plurality of antibodies (e.g., 2, 3, 4, 5, 6, 7, 8, 9, 10, 15, 20, 25, 30, or more antibodies) are used as analyte-binding agents in any of the methods described herein (e.g., to detect the presence of one or more analytes in a sample). In some embodiments, the plurality of antibodies bind to the same analyte (e.g., an antigen). In some embodiments, the plurality of antibodes bind to the same epitope present on the analyte (e.g., an antigen). In some embodiments, the plurality of antibodies bind to different epitopes present on the same analyte. In some embodiments, the plurality of antibodies bind to overlapping epitopes present on the same analyte. In some embodiments, the plurality of antibodies bind to non-overlapping epitopes present on the same analyte.

Antibiotics

In some embodiments, the analyte or analyte-binding agent is an antibiotic. An "antibiotic" or "antibiotic agent" refers to a substance that has the capacity to inhibit or slow down the growth of, or to destroy bacteria and/or other microorganisms. In some embodiments, the antibiotic agent is a bacteriostatic antibiotic agent. In some embodiments, the antibiotic is a bacteriolytic antibiotic agent. Exemplary antibiotic agents are set forth in the U.S. Patent Publication US 2006/0269485, which is hereby incorporated by reference herein in its entirety.

In some embodiments, the antibiotic agent is selected from the classes consisting of beta-lactam antibiotics, aminoglycosides, ansa-type antibiotics, anthraquinones, antibiotic azoles, antibiotic glycopeptides, macrolides, antibiotic nucleosides, antibiotic peptides, antibiotic polyenes, antibiotic polyethers, quinolones, antibiotic steroids, sulfonamides, tetracycline, dicarboxylic acids, antibiotic metals, oxidizing agents, substances that release free radicals and/or active oxygen, cationic antimicrobial agents, quaternary ammonium compounds, biguanides, triguanides, bisbiguanides and analogs and polymers thereof and naturally occurring antibiotic compounds. In some embodiments, the antibiotic is rifaximin.

Beta-lactam antibiotics include, but are not limited to, 2-(3-alanyl)clavam, 2-hydroxymethylclavam, 8-epi-thienamycin, acetyl-thienamycin, amoxicillin, amoxicillin sodium, amoxicillin trihydrate, amoxicillin-potassium clavulanate combination, ampicillin, ampicillin sodium, ampicillin trihydrate, ampicillin-sulbactam, apalcillin, aspoxicillin, azidocillin, azlocillin, aztreonam, bacampicillin, biapenem, carbenicillin, carbenicillin disodium, carfecillin, carindacillin, carpetimycin, cefacetril, cefaclor, cefadroxil, cefalexin, cefaloridine, cefalotin, cefamandole, cefamandole, cefapirin, cefatrizine, cefatrizine propylene glycol, cefazedone, cefazolin, cefbuperazone, cefcapene, cefcapene pivoxil hydrochloride, cefdinir, cefditoren, cefditoren pivoxil, cefepime, cefetamet, cefetamet pivoxil, cefixime, cefinenoxime, cefinetazole, cefminox, cefminox, cefmolexin, cefodizime, cefonicid, cefoperazone, ceforanide, cefoselis, cefotaxime, cefotetan, cefotiam, cefoxitin, cefozopran, cefpiramide, cefpirome, cefpodoxime, cefpodoxime proxetil, cefprozil, cefquinome, cefradine, cefroxadine, cefsulodin, ceftazidime, cefteram, cefteram pivoxil, ceftezole, ceftibuten, ceftizoxime, ceftriaxone, cefuroxime, cefuroxime axetil, cephalosporin, cephamycin, chitinovorin, ciclacillin, clavulanic acid, clometocillin, cloxacillin, cycloserine, deoxy pluracidomycin, dicloxacillin, dihydro pluracidomycin, epicillin, epithienamycin, ertapenem, faropenem, flomoxef, flucloxacillin, hetacillin, imipenem, lenampicillin, loracarbef, mecillinam, meropenem, metampicillin, meticillin, mezlocillin, moxalactam, nafcillin, northienamycin, oxacillin, panipenem, penamecillin, penicillin, phenethicillin, piperacillin, tazobactam, pivampicillin, pivcefalexin, pivmecillinam, pivmecillinam hydrochloride, pluracidomycin, propicillin, sarmoxicillin, sulbactam, sulbenicillin, talampicillin, temocillin, terconazole, thienamycin, ticarcillin and analogs, salts and derivatives thereof.

Aminoglycosides include, but are not limited to, 1,2'-N-DL-isoseryl-3',4'-dideoxykanamycin B, 1,2'-N-DL-isoseryl-kanamycin B, 1,2'-N—[(S)-4-amino-2-hydroxybutyryl]-3',4'-dideoxykanamycin B, 1,2'-N—[(S)-4-amino-2-hydroxybutyryl]-kanamycin B, 1-N-(2-Aminobutanesulfonyl) kanamycin A, 1-N-(2-aminoethanesulfonyl)3',4'-dideoxyribostamycin, 1-N-(2-Aminoethanesulfonyl)3'-deoxyribostamycin, 1-N-(2-aminoethanesulfonyl)3'4'-dideoxykanamycin B, 1-N-(2-aminoethanesulfonyl)kanamycin A, 1-N-(2-aminoethanesulfonyl)kanamycin B, 1-N-(2-aminoethanesulfonyl)ribostamycin, 1-N-(2-aminopropanesulfonyl)3'-deoxykanamycin B, 1-N-(2-aminopropanesulfonyl)3'4'-dideoxykanamycin B, 1-N-(2-aminopropanesulfonyl)kanamycin A, 1-N-(2-aminopropanesulfonyl)kanamycin B, 1-N-(L-4-amino-2-hydroxy-butyryl)2,'3'-dideoxy-2'-fluorokanamycin A, 1-N-(L-4-amino-2-hydroxy-propionyl)2,'3'-dideoxy-2'-fluorokanamycin A, 1-N-DL-3',4'-dideoxy-isoserylkanamycin B, 1-N-DL-isoserylkanamycin, 1-N-DL-isoserylkanamycin B, 1-N-[L-(−)-(alpha-hydroxy-gamma-aminobutyryl)]-XK-62-2,2',3'-dideoxy-2'-fluorokanamycin A,2-hydroxygentamycin A3,2-hydroxygentamycin B, 2-hydroxygentamycin B1, 2-hydroxygentamycin JI-20A, 2-hydroxygentamycin JI-20B, 3"-N-methyl-4"-C-methyl-3',4'-dodeoxy kanamycin A, 3"-N-methyl-4"-C-methyl-3',4'-dodeoxy kanamycin B, 3"-N-methyl-4"-C-methyl-3',4'-dodeoxy-6'-methyl kanamycin B, 3',4'-Dideoxy-3'-eno-ribostamycin,3',4'-dideoxyneamine,3',4'-dideoxyribostamycin, 3'-deoxy-6'-N-methyl-kanamycin B,3'-deoxyneamine,3'-deoxyribostamycin, 3'-oxysaccharocin,3,3'-nepotrehalosadiamine, 3-demethoxy-2"-N-formimidoylistamycin B disulfate tetrahydrate, 3-demethoxyistamycin B,3-O-demethyl-2-N-formimidoylistamycin B, 3-O-demethylistamycin B,3-trehalosamine,4",6"-dideoxydibekacin, 4-N-glycyl-KA-6606VI, 5"-Amino-3',4',5"-trideoxy-butirosin A, 6"-deoxydibekacin,6'-epifortimicin A, 6-deoxy-neomycin (structure 6-deoxy-neomycin B), 6-deoxy-neomycin B, 6-deoxy-neomycin C, 6-deoxy-paromomycin, acmimycin, AHB-3',4'-dideoxyribostamycin, AHB-3'-deoxykanamycin B, AHB-3'-deoxyneamine, AHB-3'-deoxyribostamycin, AHB-4"-6"-dideoxydibekacin, AHB-6"-deoxydibekacin, AHB-dideoxyneamine, AHB-kanamycin B, AHB-methyl-3'-deoxykanamycin B, amikacin, amikacin sulfate, apramycin, arbekacin, astromicin, astromicin sulfate, bekanamycin, bluensomycin, boholmycin, butirosin, butirosin B, catenulin, coumamidine gammal, coumamidine gamma2,D,L-1-N-(alpha-hydroxy-beta-aminopropionyl)-XK-62-2, dactimicin, de-O-methyl-4-N-glycyl-KA-6606VI, de-O-methyl-KA-6606I, de-O-methyl-KA-7038I, destomycin A, destomycin B, di-N6',O3-demethylistamycin A, dibekacin, dibekacin sulfate, dihydrostreptomycin, dihydrostreptomycin sulfate, epi-formamidoylglycidylfortimicin B, epihygromycin, formimidoyl-istamycin A, formimidoyl-istamycin B, fortimicin B, fortimicin C, fortimicin D, fortimicin KE, fortimicin KF, fortimicin KG, fortimicin KGl (stereoisomer KGl/KG2), fortimicin KG2 (stereoisomer KG1/KG2), fortimicin KG3, framycetin, framycetin sulphate, gentamicin, gentamycin sulfate, globeomycin, hybrimycin A1, hybrimycin A2, hybrimycin B1, hybrimycin B2, hybrimycin C1, hybrimycin C2, hydroxystreptomycin, hygromycin, hygromycin B, isepamicin, isepamicin sulfate, istamycin, kanamycin, kanamycin sulphate, kasugamycin, lividomycin, marcomycin, micronomicin, micronomicin sulfate, mutamicin, myomycin, N-demethyl-7-O-demethylcelesticetin, demethylcelesticetin, methanesulfonic acid derivative of istamycin, nebramycin, nebramycin, neomycin, netilmicin, oligostatin, paromomycin, quintomycin, ribostamycin, saccharocin, seldomycin, sisomicin, sorbistin, spectinomycin, streptomycin, tobramycin, trehalosmaine, trestatin, validamycin, verdamycin, xylostasin, zygomycin and analogs, salts and derivatives thereof.

Ansa-type antibiotics include, but are not limited to, 21-hydroxy-25-demethyl-25-methylth ioprotostreptovaricin. 3-methylth iorifamycin, ansamitocin, atropisostreptovaricin, awamycin, halomicin, maytansine, naphthomycin, rifabutin, rifamide, rifampicin, rifamycin, rifapentine, rifaximin (e.g., Xifaxan®), rubradirin, streptovaricin, tolypomycin and analogs, salts and derivatives thereof.

Antibiotic anthraquinones include, but are not limited to, auramycin, cinerubin, ditrisarubicin, ditrisarubicin C, figaroic acid fragilomycin, minomycin, rabelomycin, rudolfomycin, sulfurmycin and analogs, salts and derivatives thereof.

Antibiotic azoles include, but are not limited to, azanidazole, bifonazole, butoconazol, chlormidazole, chlormidazole hydrochloride, cloconazole, cloconazole monohydrochloride, clotrimazol, dimetridazole, econazole, econazole nitrate, enilconazole, fenticonazole, fenticonazole nitrate, fezatione, fluconazole, flutrimazole, isoconazole, isoconazole nitrate, itraconazole, ketoconazole, lanoconazole, metronidazole, metronidazole benzoate, miconazole, miconazole nitrate, neticonazole, nimorazole, niridazole, omoconazol, ornidazole, oxiconazole, oxiconazole nitrate, propenidazole, secnidazol, sertaconazole, sertaconazole nitrate, sulconazole, sulconazole nitrate, tinidazole, tioconazole, voriconazol and analogs, salts and derivatives thereof.

Antibiotic glycopeptides include, but are not limited to, acanthomycin, actaplanin, avoparcin, balhimycin, bleomycin B (copper bleomycin), chloroorienticin, chloropolysporin, demethylvancomycin, enduracidin, galacardin, guanidylfungin, hachimycin, demethylvancomycin, N-nonanoyl-teicoplanin, phleomycin, platomycin, ristocetin, staphylocidin, talisomycin, teicoplanin, vancomycin, victomycin, xylocandin, zorbamycin and analogs, salts and derivatives thereof.

Macrolides include, but are not limited to, acetylleucomycin, acetylkitasamycin, angolamycin, azithromycin, bafilomycin, brefeldin, carbomycin, chalcomycin, cirramycin, clarithromycin, concanamycin, deisovaleryl-niddamycin, demycinosyl-mycinamycin, Di-O-methyltiacumicidin, dirithromycin, erythromycin, erythromycin estolate, erythromycin ethyl succinate, erythromycin lactobionate, erythromycin stearate, flurithromycin, focusin, foromacidin, haterumalide, haterumalide, josamycin, josamycin ropionate, juvenimycin, juvenimycin, kitasamycin, ketotiacumicin, lankavacidin, lankavamycin, leucomycin, machecin, maridomycin, megalomicin, methylleucomycin, methymycin, midecamycin, miocamycin, mycaminosyltylactone, mycinomycin, neutramycin, niddamycin, nonactin, oleandomycin, phenylacetyideltamycin, pamamycin, picromycin, rokitamycin, rosaramicin, roxithromycin, sedecamycin, shincomycin, spiramycin, swalpamycin, tacrolimus, telithromycin, tiacumicin, tilmicosin, treponemycin, troleandomycin, tylosin, venturicidin and analogs, salts and derivatives thereof.

Antibiotic nucleosides include, but are not limited to, amicetin, angustmycin, azathymidine, blasticidin S, epiroprim, flucytosine, gougerotin, mildiomycin, nikkomycin, nucleocidin, oxanosine, oxanosine, puromycin, pyrazomycin, showdomycin, sinefungin, sparsogenin, spicamycin, tunicamycin, uracil polyoxin, vengicide and analogs, salts and derivatives thereof.

Antibiotic peptides include, but are not limited to, actinomycin, aculeacin, alazopeptin, amfomycin, amythiamycin, antifungal from *Zalerion arboricola*, antrimycin, apid, apidaecin, aspartocin, auromomycin, bacileucin, bacillomycin, bacillopeptin, bacitracin, bagacidin, beminamycin, beta-alanyl-L-tyrosine, bottromycin, capreomycin, caspofungine, cepacidine, cerexin, cilofungin, circulin, colistin, cyclodepsipeptide, cytophagin, dactinomycin, daptomycin, decapeptide, desoxymulundocandin, echanomycin, echinocandin B, echinomycin, ecomycin, enniatin, etamycin, fabatin, ferrimycin, ferrimycin, ficellomycin, fluoronocathiacin, fusaricidin, gardimycin, gatavalin, globopeptin, glyphomycin, gramicidin, herbicolin, iomycin, iturin, iyomycin, izupeptin, janiemycin, janthinocin, jolipeptin, katanosin, killertoxin, lipopeptide antibiotic, lipopeptide from *Zalerion* sp., lysobactin, lysozyme, macromomycin, magainin, melittin, mersacidin, mikamycin, mureidomycin, mycoplanecin, mycosubtilin, neopeptifluorin, neoviridogrisein, netropsin, nisin, nocathiacin, nocathiacin 6-deoxyglycoside, nosiheptide, octapeptin, pacidamycin, pentadecapeptide, peptifluorin, permetin, phytoactin, phytostreptin, planothiocin, plusbacin, polcillin, polymyxin antibiotic complex, polymyxin B, polymyxin B1, polymyxin F, preneocarzinostatin, quinomycin, quinupristin-dalfopristin, safracin, salmycin, salmycin, salmycin, sandramycin, saramycetin, siomycin, sperabillin, sporamycin, a *Streptomyces* compound, subtilin, teicoplanin aglycone, telomycin, thermothiocin, thiopeptin, thiostrepton, tridecaptin, tsushimycin, tuberactinomycin, tuberactinomycin, tyrothricin, valinomycin, viomycin, virginiamycin, zervacin and analogs, salts and derivatives thereof.

In some embodiments, the antibiotic peptide is a naturally-occurring peptide that possesses an antibacterial and/or an antifungal activity. Such peptide can be obtained from an herbal or a vertebrate source.

Polyenes include, but are not limited to, amphotericin, amphotericin, aureofungin, ayfactin, azalomycin, blasticidin, candicidin, candicidin methyl ester, candimycin, candimycin methyl ester, chinopricin, filipin, flavofungin, fradicin, hamycin, hydropricin, levorin, lucensomycin, lucknomycin, mediocidin, mediocidin methyl ester, mepartricin, methylamphotericin, natamycin, niphimycin, nystatin, nystatin methyl ester, oxypricin, partricin, pentamycin, perimycin, pimaricin, primycin, proticin, rimocidin, sistomycosin, sorangicin, trichomycin and analogs, salts and derivatives thereof.

Polyethers include, but are not limited to, 20-deoxy-epinarasin, 20-deoxysalinomycin, carriomycin, dianemycin, dihydrolonomycin, etheromycin, ionomycin, iso-lasalocid, lasalocid, lenoremycin, lonomycin, lysocellin, monensin, narasin, oxolonomycin, a polycyclic ether antibiotic, salinomycin and analogs, salts and derivatives thereof.

Quinolones include, but are not limited to, an alkyl-methylendioxy-4(1H)-oxocinnoline-3-carboxylic acid, alatrofloxacin, cinoxacin, ciprofloxacin, ciprofloxacin hydrochloride, danofloxacin, dermofongin A, enoxacin, enrofloxacin, fleroxacin, flumequine, gatifloxacin, gemifloxacin, grepafloxacin, levofloxacin, lomefloxacin, lomefloxacin, hydrochloride, miloxacin, moxifloxacin, nadifloxacin, nalidixic acid, nifuroquine, norfloxacin, ofloxacin, orbifloxacin, oxolinic acid, pazufloxacine, pefloxacin, pefloxacin mesylate, pipemidic acid, piromidic acid, premafloxacin, rosoxacin, rufloxacin, sparfloxacin, temafloxacin, tosufloxacin, trovafloxacin and analogs, salts and derivatives thereof.

Antibiotic steroids include, but are not limited to, aminosterol, ascosteroside, cladosporide A, dihydrofusidic acid, dehydro-dihydrofusidic acid, dehydrofusidic acid, fusidic acid, squalamine and analogs, salts and derivatives thereof.

Sulfonamides include, but are not limited to, chloramine, dapsone, mafenide, phthalylsulfathiazole, succinylsulfathiazole, sulfabenzamide, sulfacetamide, sulfachlorpyridazine, sulfadiazine, sulfadiazine silver, sulfadicramide, sulfadimethoxine, sulfadoxine, sulfaguanidine, sulfalene, sulfamazone, sulfamerazine, sulfamethazine, sulfamethizole, sulfamethoxazole, sulfamethoxypyridazine, sulfamonomethoxine, sulfamoxol, sulfanilamide, sulfaperine, sulfaphenazol, sulfapyridine, sulfaquinoxaline, sulfasuccinamide, sulfathiazole, sulfathiourea, sulfatolamide, sulfatriazin, sulfisomidine, sulfisoxazole, sulfisoxazole acetyl, sulfacarbamide and analogs, salts and derivatives thereof.

Tetracyclines include, but are not limited to, dihydrosteffimycin, demethyltetracycline, aclacinomycin, akrobomycin, baumycin, bromotetracycline, cetocyclin, chlortetracycline, clomocycline, daunorubicin, demeclocycline, doxorubicin, doxorubicin hydrochloride, doxycycline, lymecyclin, marcellomycin, meclocycline, meclocycline sulfosalicylate, methacycline, minocycline, minocycline hydrochloride, musettamycin, oxytetracycline, rhodirubin, rolitetracycline, rubomycin, serirubicin, steffimycin, tetracycline and analogs, salts and derivatives thereof.

Dicarboxylic acids, having between about 6 and about 14 carbon atoms in their carbon atom skeleton are particularly useful in the treatment of disorders of the skin and mucosal membranes that involve microbial. Suitable dicarboxylic acid moieties include, but are not limited to, adipic acid, pimelic acid, suberic acid, azelaic acid, sebacic acid, 1,11-undecanedioic acid, 1,12-dodecanedioic acid, 1,13-tridecanedioic acid and 1,14-tetradecanedioic acid. Thus, in one or more embodiments of the present disclosure, dicarboxylic acids, having between about 6 and about 14 carbon atoms in their carbon atom skeleton, as well as their salts and derivatives (e.g., esters, amides, mercapto-derivatives, anhydraides), are useful immunomodulators in the treatment of disorders of the skin and mucosal membranes that involve inflammation. Azelaic acid and its salts and derivatives are preferred. It has antibacterial effects on both aerobic and anaerobic organisms, particularly *Propionibacterium acnes* and *Staphylococcus epidermidis*, normalizes keratinization, and has a cytotoxic effect on malignant or hyperactive melanocytes. In a preferred embodiment, the dicarboxylic acid is azelaic acid in a concentration greater than 10%. Preferably, the concentration of azelaic acid is between about 10% and about 25%. In such concentrates, azelaic acid is suitable for the treatment of a variety of skin disorders, such as acne, rosacea and hyperpigmentation.

In some embodiments, the antibiotic agent is an antibiotic metal. A number of metals ions have been shown to possess antibiotic activity, including silver, copper, zinc, mercury, tin, lead, bismutin, cadmium, chromium and ions thereof. It has been theorized that these antibiotic metal ions exert their effects by disrupting respiration and electron transport systems upon absorption into bacterial or fungal cells. Anti-microbial metal ions of silver, copper, zinc, and gold, in particular, are considered safe for in vivo use. Anti-microbial silver and silver ions are particularly useful due to the fact that they are not substantially absorbed into the body. Thus, in one or more embodiment, the antibiotic metal consists of an elemental metal, selected from the group consisting of silver, copper, zinc, mercury, tin, lead, bismutin, cadmium, chromium and gold, which is suspended in the composition as particles, microparticles, nanoparticles or colloidal particles. The antibiotic metal can further be intercalated in a chelating substrate.

In further embodiments, the antibiotic metal is ionic. The ionic antibiotic metal can be presented as an inorganic or organic salt (coupled with a counterion), an organometallic complex or an intercalate. Non-binding examples of counter inorganic and organic ions are sulfadiazine, acetate, benzoate, carbonate, iodate, iodide, lactate, laurate, nitrate, oxide, and palmitate, a negatively charged protein. In preferred embodiments, the antibiotic metal salt is a silver salt, such as silver acetate, silver benzoate, silver carbonate, silver iodate, silver iodide, silver lactate, silver laurate, silver nitrate, silver oxide, silver palmitate, silver protein, and silver sulfadiazine.

In one or more embodiments, the antibiotic metal or metal ion is embedded into a substrate, such as a polymer, or a mineral (such as zeolite, clay and silica).

In one or more embodiments, the antibiotic agent includes strong oxidants and free radical liberating compounds, such as oxygen, hydrogen peroxide, benzoyl peroxide, elemental halogen species, as well as oxygenated halogen species, bleaching agents (e.g., sodium, calcium or magnesium hypochloride and the like), perchlorite species, iodine, iodate, and benzoyl peroxide. Organic oxidizing agents, such as quinones, are also included. Such agents possess a potent broad-spectrum activity.

In one or more embodiments, the antibiotic agent is a cationic antimicrobial agent. The outermost surface of bacterial cells universally carries a net negative charge, making them sensitive to cationic substances. Examples of cationic antibiotic agents include: quaternary ammonium compounds (QAC's) —QAC's are surfactants, generally containing one quaternary nitrogen associated with at least one major hydrophobic moiety; alkyltrimethyl ammonium bromides are mixtures of where the alkyl group is between 8 and 18 carbons long, such as cetrimide (tetradecyltrimethylammonium bromide); benzalkonium chloride, which is a mixture of n-alkyldimethylbenzyl ammonium chloride where the alkyl groups (the hydrophobic moiety) can be of variable length; dialkylmethyl ammonium halides; dialkylbenzyl ammonium halides; and QAC dimmers, which bear bi-polar positive charges in conjunction with interstitial hydrophobic regions.

In one or more embodiments, the cationic antimicrobial agent is a polymer. Cationic antimicrobial polymers include, for example, guanide polymers, biguanide polymers, or polymers having side chains containing biguanide moieties or other cationic functional groups, such as benzalkonium groups or quarternium groups (e.g., quaternary amine groups). It is understood that the term "polymer" as used herein includes any organic material including three or more repeating units, and includes oligomers, polymers, copolymers, block copolymers, terpolymers, etc. The polymer backbone may be, for example a polyethylene, ploypropylene or polysilane polymer.

In one or more embodiments, the cationic antimicrobial polymer is a polymeric biguanide compound. When applied to a substrate, such a polymer is known to form a barrier film that can engage and disrupt a microorganism. An exemplary polymeric biguanide compound is polyhexamethylene biguanide (PHMB) salts. Other exemplary biguanide polymers include, but are not limited to poly(hexamethylenebiguanide), poly(hexamethylenebiguanide) hydrochloride, poly(hexamethylenebiguanide) gluconate, poly(hexamethylenebiguanide) stearate, or a derivative thereof. In one or more embodiments, the antimicrobial material is substantially water-insoluble.

In some embodiments, the antibiotic agent is selected from the group of biguanides, triguanides, bisbiguanides and analogs thereof.

Guanides, biguanides, biguanidines and triguanides are unsaturated nitrogen containing molecules that readily obtain one or more positive charges, which make them effective antimicrobial agents. The basic structures a guanide, a biguanide, a biguanidine and a triguanide are provided below.

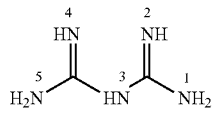

Biguanide

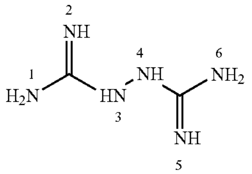

Biguanidine

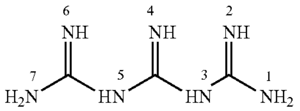

Triguanide

In some embodiments, the guanide, biguanide, biguanidine or triguanide, provide bi-polar configurations of cationic and hydrophobic domains within a single molecule.

Examples of guanides, biguanides, biguanidines and triguanides that are currently been used as antibacterial agents include chlorhexidine and chlorohexidine salts, analogs and derivatives, such as chlorhexidine acetate, chlorhexidine gluconate and chlorhexidine hydrochloride, picloxydine, alexidine and polihexanide. Other examples of guanides, biguanides, biguanidines and triguanides that can conceivably be used according to the present disclosure are chlorproguanil hydrochloride, proguanil hydrochloride (currently used as antimalarial agents), mefformin hydrochloride, phenformin and buformin hydrochloride (currently used as antidiabetic agents).

Yet, in one or more embodiments, the antibiotic is a non-classified antibiotic agent, including, without limitation, aabomycin, acetomycin, acetoxycycloheximide, acetyl-nanaomycin, an *Actinoplanes* sp. compound, actinopyrone, aflastatin, albacarcin, albacarcin, albofungin, albofungin, alisamycin, alpha-R,S-methoxycarbonylbenzylmonate, altromycin, amicetin, amycin, amycin demanoyl compound, amycine, amycomycin, anandimycin, anisomycin, anthramycin, anti-syphilis immune substance, anti-tuberculosis immune substance, an antibiotic from *Escherichia coli*, an antibiotic from *Streptomyces refuineus*, anticapsin, antimycin, aplasmomycin, aranorosin, aranorosinol, arugomycin, ascofuranone, ascomycin, ascosin, *Aspergillus flavus* antibiotic, asukamycin, aurantinin, an Aureolic acid antibiotic substance, aurodox, avilamycin, azidamfenicol, azidimycin, bacillaene, a *Bacillus larvae* antibiotic, bactobolin, benanomycin, benzanthrin, benzylmonate, bicozamycin, bravomicin, brodimoprim, butalactin, calcimycin, calvatic acid, candiplanecin, carumonam, carzinophilin, celesticetin, cepacin, cerulenin, cervinomycin, chartreusin, chloramphenicol, chloramphenicol palmitate, chloramphenicol succinate sodium, chlorflavonin, chlorobiocin, chlorocarcin, chromomycin, ciclopirox, ciclopirox olamine, citreamicin, cladosporin, clazamycin, clecarmycin, clindamycin, coliformin, collinomycin, copiamycin, corallopyronin, corynecandin, coumermycin, culpin, cuprimyxin, cyclamidomycin, cycloheximide, dactylomycin, danomycin, danubomycin, delaminomycin, demethoxyrapamycin, demethylscytophycin, dermadin, desdamethine, dexylosylbenanomycin, pseudoaglycone, dihydromocimycin, dihydronancimycin, diumycin, dnacin, dorrigocin, dynemycin, dynemycin triacetate, ecteinascidin, efrotomycin, endomycin, ensanchomycin, equisetin, ericamycin, esperamicin, ethylmonate, eveminomicin, feldamycin, flambamycin, flavensomycin, florfenicol, fluvomycin, fosfomycin, fosfonochlorin, fredericamycin, frenolicin, fumagillin, fumifungin, funginon, fusacandin, fusafungin, gelbecidine, glidobactin, grahamimycin, granaticin, griseofulvin, griseoviridin, grisonomycin, hayumicin, hayumicin, hazymicin, hedamycin, heneicomycin, heptelicid acid, holomycin, humidin, isohematinic acid, karnatakin, kazusamycin, kristenin, L-dihydrophenylalanine, a L-isoleucyl-L-2-amino-4-(4'-amino-2',5'-cyclohexadienyl) derivative, lanomycin, leinamycin, leptomycin, libanomycin, lincomycin, lomofungin, lysolipin, magnesidin, manumycin, melanomycin, methoxycarbonylmethylmonate, methoxycarbonylethylmonate, methoxycarbonylphenylmonate, methyl pseudomonate, methylmonate, microcin, mitomalcin, mocimycin, moenomycin, monoacetyl cladosporin, monomethyl cladosporin, mupirocin, mupirocin calcium, mycobacidin, myriocin, myxopyronin, pseudoaglycone, nanaomycin, nancimycin, nargenicin, neocarcinostatin, neoenactin, neothramycin, nifurtoinol, nocardicin, nogalamycin, novobiocin, octylmonate, olivomycin, orthosomycin, oudemansin, oxirapentyn, oxoglaucine methiodide, pactacin, pactamycin, papulacandin, paulomycin, phaeoramularia fungicide, phenelfamycin, phenyl, cerulenin, phenylmonate, pholipomycin, pirlimycin, pleuromutilin, a polylactone derivative, polynitroxin, polyoxin, porfiromycin, pradimicin, prenomycin, prop-2-enylmonate, protomycin, *Pseudomonas* antibiotic, pseudomonic acid, purpuromycin, pyrinodemin, pyrrolnitrin, pyrrolomycin, amino, chloro pentenedioic acid, rapamycin, rebeccamycin, resistomycin, reuterin, reveromycin, rhizocticin, roridin, rubiflavin, naphthyridinomycin, saframycin, saphenamycin, sarkomycin, sarkomycin, sclopularin, selenomycin, siccanin, spartanamicin, spectinomycin, spongistatin, stravidin, streptolydigin, *Streptomyces arenae* antibiotic complex, streptonigrin, streptothricins, streptovitacin, streptozotocine, a strobilurin derivative, stubomycin, sulfamethoxazol-trimethoprim, sakamycin, tejeramycin, terpentecin, tetrocarcin, thermorubin, thermozymocidin, thiamphenicol, thioaurin, thiolutin, thiomarinol, thiomarinol, tirandamycin, tolytoxin, trichodermin, trienomycin, trimethoprim, trioxacarcin, tyrissamycin, umbrinomycin, unphenelfamycin, urauchimycin, usnic acid, uredolysin, variotin, vermisporin, verrucarin and analogs, salts and derivatives thereof.

In one or more embodiments, the antibiotic agent is a naturally occurring antibiotic compound. As used herein, the term "naturally-occurring antibiotic agent" includes all antibiotics that are obtained, derived or extracted from plant or vertebrate sources. Non-limiting examples of families of naturally-occurring antibiotic agents include phenol, resorcinol, antibiotic aminoglycosides, anamycin, quinines, anthraquinones, antibiotic glycopeptides, azoles, macrolides, avilamycin, agropyrene, enicin, aucubin antibioticsaponin fractions, berberine (isoquinoline alkaloid), arctiopicrin (sesquiterpene lactone), lupulone, humulone (bitter acids), allicin, hyperforin, echinacoside, coniosetin, tetramic acid, imanine and novoimanine.

Ciclopirox and ciclopiroxolamine possess fungicidal, fungistatic and sporicidal activity. They are active against a broad spectrum of dermatophytes, yeasts, moulds and other fungi, such as Trichophytons species, *Microsporum* species, *Epidermophyton* species and yeasts (*Candida albicans*, *Candida glabrata*, other *candida* species and *Cryptococcus neoformans*). Some *Aspergillus* species are sensitive to ciclopirox as are some *Penicillium*. Likewise, ciclopirox is effective against many Gram-positive and Gram-negative bacteria (e.g., *Escherichia coli*, *Proteus mirabilis*, *Pseudomonas aeruginosa*, *Staphylococcus* and *Streptococcus* species), as well as *Mycoplasma* species, *Trichomonas vaginalis* and *Actinomyces*.

Plant oils and extracts which contain antibiotic agents are also useful. Non-limiting examples of plants that contain agents include thyme, *Perilla*, lavender, tea tree, *Terfezia clayeryi*, *Micromonospora*, *Putterlickia verrucosa*, *Putterlickia pyracantha*, *Putterlickia retrospinosa*, *Maytenus ilicifolia*, *Maytenus evonymoides*, *Maytenus aquifolia*, *Faenia interjecta*, *Cordyceps sinensis*, couchgrass, holy thistle, plantain, burdock, hops, *echinacea*, buchu, chaparral, myrrh, red clover and yellow dock, garlic, and St. John's wort. Mixtures of the antibiotic agents as described herein may also be employed.

Combination Detection

Any combination of the analytes disclosed herein can be detected using any of the methods described herein. In particular, any combination disclosed herein can be detected using any of the methods described herein.

A "photosensitizer" as used herein refers to a sensitizer for generation of singlet oxygen usually by excitation with light. Exemplary photosensitizers suitable for use include those described in U.S. Pat. Nos. 6,251,581, 5,516,636, 8,907,081, 6,545,012, 6,331,530, 8,247,180, 5,763,602, 5,705,622, 5,516,636, 7,217,531, and U.S. Patent Publication No. 2007/0059316, all of which are herein expressly incorporated by reference in their entireties. The photosensitizer can be photoactivatable (e.g., dyes and aromatic compounds) or chemiactivated (e.g., enzymes and metal salts). When excited by light the photosensitizer is usually a compound comprised of covalently bonded atoms, usually with multiple conjugated double or triple bonds. The compound should absorb light in the wavelength range of 200-1100 nm, usually 300-1000 nm, e.g., 450-950 nm, with an extinction coefficient at its absorbance maximum greater than 500 $M^{-1}$ $cm^{-1}$, e.g., at least 5000 $M^{-1}$ $cm^{-1}$, or at least 50,000 $M^{-1}$ $cm^{-1}$ at the excitation wavelength. The lifetime of an excited state produced following absorption of light in the absence of oxygen will usually be at least 100 nsec, e.g., at least 1 gsec. In general, the lifetime must be sufficiently long to permit energy transfer to oxygen, which will normally be present at concentrations in the range of $10^{-5}$ to $10^{31}$ $^{3}$M depending on the medium. The sensitizer excited state will usually have a different spin quantum number (s) than its ground state and will usually be a triplet (s=1) when, as is usually the case, the ground state is a singlet (s=0). In some embodiments, the sensitizer will have a high intersystem crossing yield. That is, photoexcitation of a sensitizer will produce the long lived state (usually triplet) with an efficiency of at least 10%, at least 40%, e.g., greater than 80%. The photosensitizer will usually be at most weakly fluorescent under the assay conditions (quantum yield usually less that 0.5, or less that 0.1).

Photosensitizers that are to be excited by light will be relatively photostable and will not react efficiently with singlet oxygen. Several structural features are present in most useful sensitizers. Most sensitizers have at least one and frequently three or more conjugated double or triple bonds held in a rigid, frequently aromatic structure. They will frequently contain at least one group that accelerates intersystem crossing such as a carbonyl or imine group or a heavy atom selected from rows 3-6 of the periodic table, especially iodine or bromine, or they may have extended aromatic structures. Typical sensitizers include acetone, benzophenone, 9-thioxanthone, eosin, 9,10-dibromoanthracene, methylene blue, metallo-porphyrins, such as hematoporphyrin, phthalocyanines, chlorophylls, rose bengal, buckminsterfullerene, etc., and derivatives of these compounds having substituents of 1 to 50 atoms for rendering such compounds more lipophilic or more hydrophilic and/or as attaching groups for attachment. Examples of other photosensitizers that may be utilized are those that have the above properties and are enumerated in N. J. Turro, "Molecular Photochemistry," page 132, W. A. Benjamin Inc., N.Y. 1965.

In some embodiments, the photosensitizers are relatively non-polar to assure dissolution into a lipophilic member when the photosensitizer is incorporated in an oil droplet, liposome, latex particle, etc.

In some embodiments, the photosensitizers suitable for use herein include other substances and compositions that can produce singlet oxygen with or without activation by an external light source. Thus, for example, molybdate ($MoO_4$) salts and chloroperoxidase and myeloperoxidase plus bromide or chloride ion (Kanofsky, *J. Biol. Chem.* (1983) 259 5596) have been shown to catalyze the conversion of hydrogen peroxide to singlet oxygen and water. Either of these compositions can, for example, be included in particles and used in the assay method wherein hydrogen peroxide is included as an ancillary reagebly, chloroperoxidase is bound to a surface and molybdate is incorporated in the aqueous phase of a liposome. Also included within the scope of the disclosure as photosensitizers are compounds that are not true sensitizers but which on excitation by heat, light, or chemical activation will release a molecule of singlet oxygen. The best known members of this class of compounds includes the endoperoxides such as 1,4-biscarboxyethyl-1,4-naphthalene endoperoxide, 9,10-diphenylanthracene-9,10-endoperoxide and 5,6,11,12-tetraphenylnaphthalene 5,12-endoperoxide. Heating or direct absorption of light by these compounds releases singlet oxygen.

A "chemiluminescent compound" as used herein refers to a substance that undergoes a chemical reaction with singlet oxygen to form a metastable intermediate that can decompose with the simultaneous or subsequent emission of light within the wavelength range of 250 to 1200 nm. Exemplary chemiluminescent compounds suitable for use include those described in U.S. Pat. Nos. 6,251,581 and 7,709,273, and Patent Cooperatio Treaty (PCT) International Application Publication No. WO1999/042838. Examplery chemiluminescent compound includes the following:

| Chemiluminescent | Half-Life | Emission Max |
|---|---|---|
| Thioxene + Diphenyl anthracence: | 0.6 seconds | 430 nm |
| Thioxene + Umbelliferone derivative | 0.6 seconds | 500 nm |
| Thioxene + Europium chelate | 0.6 seconds | 615 nm |
| Thioxene + Samarium Chelate | 0.6 seconds | 648 nm |
| Thioxene + terbium Chelate | 0.6 seconds | 540 nm |
| N-Phenyl Oxazine + Umbelliferone derivative | 30 seconds | 500 nm |
| N-Phenyl Oxazine + Europium chelate | 30 seconds | 613 nm |
| N-phenyl Oxazine + Samarium Chelate | 30 seconds | 648 nm |
| N-phenyl Oxazine + terbium Chelate | 30 seconds | 540 nm |
| Dioxene + Umbelliferone derivative | 300 seconds | 500 nm |
| Dioxene + Europium chelate | 300 seconds | 613 nm |
| Dioxene + Samarium Chelate | 300 seconds | 648 nm |
| N-phenyl Oxazine + terbium Chelate | 300 seconds | 540 nm |

All of the above mentioned applications are herey expressly incorporated by reference herein in their entireties. Emission will usually occur without the presence of an energy acceptor or catalyst to cause decomposition and light emission. In some embodiments, the intermediate decomposes spontaneously without heating or addition of ancillary reagents following its formation. However, addition of a reagent after formation of the intermediate or the use of elevated temperature to accelerate decomposition will be required for some chemiluminescent compounds. The chemiluminescent compounds are usually electron rich compounds that react with singlet oxygen, frequently with formation of dioxetanes or dioxetanones. Exemplary of such compounds are enol ethers, enamines, 9-alkylidenexanthans, 9-alkylidene-N-alkylacridans, aryl vinyl ethers, dioxenes, arylimidazoles and lucigenin. Other chemiluminescent compounds give intermediates upon reaction with singlet oxygen, which subsequently react with another reagent with light emission. Exemplary compounds are hydrazides such as luminol and oxalate esters.

The chemiluminescent compounds of interest will generally emit at wavelengths above 300 nanometers and usually above 400 nm. Compounds that alone or together with a fluorescent molecule emit light at wavelengths beyond the region where serum components absorb light will be of particular use. The fluorescence of serum drops off rapidly above 500 nm and becomes relatively unimportant above 550 nm. Therefore, when the analyte is in serum, chemiluminescent compounds that emit light above 550 nm, e.g., above 600 nm may be suitable for use. In order to avoid autosensitization of the chemiluminescent compound, in some embodiments, the chemiluminescent compounds do not absorb light used to excite the photosensitizer. In some embodiments, the sensitizer is excited with light wavelengths longer than 500 nm, it will therefore be desirable that light absorption by the chemiluminescent compound be very low above 500 nm.

Where long wave length emission from the chemiluminescent compound is desired, a long wavelength emitter such as a pyrene, bound to the chemiluminescent compound can be used. Alternatively, a fluorescent molecule can be included in the medium containing the chemiluminescent compound. In some embodiments, fluorescent molecules will be excited by the activated chemiluminescent compound and emit at a wavelength longer than the emission wavelength of the chemiluminescent compound, usually greater that 550 nm. It is usually also desirable that the fluorescent molecules do not absorb at the wavelengths of light used to activate the photosensitizer. Examples of useful dyes include rhodamine, ethidium, dansyl, Eu(fod)$_3$, Eu(TTA)$_3$, Ru(bpy)$_3^{++}$ (wherein bpy=2,2'-dipyridyl, etc. In general these dyes act as acceptors in energy transfer processes and in some embodiments, have high fluorescent quantum yields and do not react rapidly with singlet oxygen. They can be incorporated into particles simultaneously with the incorporation of the chemiluminescent compound into the particles.

In some embodiments, the disclosure provides diffractive optics detection technology that can be used with, for example, ingestible device technology. In certain embodiments, an ingestible device includes the diffractive optics technology (e.g., diffractive optics detection system). In certain embodiments, the disclosure provides diffractive optics technology (e.g., diffractive optics detection systems) that are used outside the body of subject. As an example, an ingestible device can be used to obtain one more samples in the body (e.g., in the gastrointestinal tract) of a subject, and the diffractive optics technology can be used to analyze the sample(s). Such analysis can be performed in vivo (e.g., when the ingestible device contains the diffractive optics).

Diffraction is a phenomenon that occurs due to the wave nature of light. When light hits an edge or passes through a small aperture, it is scattered in different directions. But light waves can interfere to add (constructively) and subtract (destructively) from each other, so that if light hits a non-random pattern of obstacles, the subsequent constructive and destructive interference will result in a clear and distinct diffraction pattern. A specific example is that of a diffraction grating, which is of uniformly spaced lines, typically prepared by ruling straight, parallel grooves on a surface. Light incident on such a surface produces a pattern of evenly spaced spots of high light intensity. This is called Bragg scattering, and the distance between spots (or 'Bragg scattering peaks') is a unique function of the diffraction pattern and the wavelength of the light source. Diffraction gratings, like focusing optics, can be operated in both transmission and reflection modes.

In general, the light used in the diffractive optics can be of any appropriate wavelength. Exemplary wavelengths include visible light, infrared red (IR) and ultraviolet (UV). Optionally, the light can be monochromatic or polychromatic. The light can be coherent or incoherent. The light can be collimated or non-collimated. In some embodiments, the light is coherent and collimated. Generally, any appropriate light source may be used, such as, for example, a laser (e.g., a laser diode) or a light emitting diode. In some embodiments, the light source is a laser diode operating at 670 nm wavelength, e.g., at 3 mWatts power. Optionally, an operating wavelength of a laser diode can be 780 nm, e.g., when larger grating periods are used. In certain embodiments, the light source is a laser, such as, for example, a He—Ne laser, a Nd:YVO4 laser, or an argon-ion laser. In some embodiments, the light source is a low power, continuous waver laser.

The diffracted light can be detected using any appropriate light detector(s). Examples of light detectors include photodetectors, such as, for example, position sensitive photodiodes, photomultiplier tubes (PMTs), photodiodes (PDs), avalanche photodiodes (APDs), charged-coupled device (CCD) arrays, and CMOS detectors. In some embodiments, the diffracted light is detected via one or more individual photodiodes.

In general, the diffraction grating is made of a material that is transparent in the wavelength of the radiation used to illuminate the sensor. Any appropriate material may be used for the diffraction grating substrate, such as glass or a polymer. Exemplary polymers include polystyrene polymers (PSEs), cyclo-olefin polymers (COPs), polycarbonate polymers, polymethyl methacrylates, and methyl methacrylate styrene copolymers. Exemplary COPs include Zeonex (e.g., Zeonex E48R, Zeonex F52R).

The light may be incident on the diffraction grating any appropriate angle. In some embodiments, the light is incident on the diffraction grating with an angle of incidence of from 30° to 80° (e.g., from 40° to 80°, from 50° to 70°, from 55° to 65°, 60°). Optionally, the system is configured so that that diffractive grating and light source can move relative to each other In general, the light detector can be positioned with respect to the diffractive grating so that the diffraction grating can be illuminated at a desired angle of incidence and/or so that diffracted light can be detected at a desired angle and/or so that diffracted light of a desired order can be detected.

The period P of the diffraction grating can be selected as desired. In some embodiments, the period P is from 0.5 microns to 50 microns (e.g., from one micron to 15 microns, from one micron to five microns). In some embodiments, the grating is a repeating patter of 1.5 micron and 4.5 micron lines with a period of 15 microns.

The height h of the diffraction grating can be selected as desired. In certain embodiments, the height h is from one nanometer to about 1000 nanometers (e.g., from about five nanometers to about 250 nanometers, from five nanometers to 100 nanometers).

In general, the diffractive optics can be prepared using any appropriate method, such as, for example, surface ablation, photolithograph (e.g., UV photolithography), laser etching, electron beam etching, nano-imprint molding, or microcontact printing.

Optionally, the diffractive optics system can include one or more additional optical elements, such as, for example, one or more mirrors, filters and/or lenses. Such optical elements can, for example, be arranged between the light source and the diffractive grating and/or between the diffractive grating and the detector.

In some of the embodiments of the devices described herein, a primary binding partner specifically binds to a secondary binding partner through non-covalent interactions (e.g., electrostatic, van der Waals, hydrophobic effect). In some embodiments, a primary binding partner specifically binds to a secondary binding partner via a covalent bond (e.g., a polar covalent bond or a non-polar covalent bond). In some embodiments of any of the devices described herein, the primary and the secondary binding partner can be interchanged. For example, the primary binding partner can be biotin, or a derivative thereof, and the secondary binding partner is avidin, or a derivative thereof. In other examples, the primary binding partner can be avidin, or a derivative thereof, and the secondary binding partner is biotin.

In some embodiments, the binding of the primary and the secondary binding partner is essentially irreversible. In some embodiments, the binding of the primary and the secondary binding partner is reversible. In some embodiments, the primary binding partner is CaptAvidin™ biotin-binding protein and the secondary binding partner is biotin, or vice versa. In some embodiments, the primary binding partner is DSB-X™ biotin and the secondary binding partner is avidin, or vice versa. In some embodiments, the primary binding partner is desthiobiotin and the secondary binding partner is avidin, or vice versa (Hirsch et al., *Anal Biochem.* 308(2): 343-357, 2002). In some embodiments, the primary binding partner is glutathione (GSH) or a derivative thereof, and the secondary binding partner is glutathione-S-transferase (GST).

In some embodiments, the primary binding partner can bind to a target analyte that is a nucleic acid (e.g., a DNA molecule, a RNA molecule). In some embodiments, the primary binding partner comprises a portion of a nucleic acid that is complementary to the nucleic acid sequence of the target analyte.

In some embodiments of any of the devices described herein, the device can include a label that binds to the target analyte and does not prevent binding of the target analyte to the primary binding partner. In some embodiments, the label can amplify the diffraction signal of the target analyte.

In some embodiments, the label is from about 1 nm to 200 nm (e.g., about 50 nm to about 200 nm).

In some embodiments, the label (e.g., any of the labels described herein) includes one or more antibodies (e.g., any of the antibodies and/or antibody fragments described herein).

In some embodiments, the label is a nanoparticle (e.g., a gold nanoparticle) that includes the primary binding partner that has a nucleic acid sequence that is complementary to the target analyte, and is covalently linked to the nanoparticle.

One or more additional steps can be performed in any of the methods described herein. In some embodiments, the one or more additional steps are performed: prior to the binding of the primary binding partner to the secondary binding partner, after the binding of the primary binding partner to the secondary binding partner, prior to the binding of the primary binding partner to the target analyte, or after the binding of the primary binding partner to the target analyte.

In some embodiments of any of the methods described herein, the determining step (during which the primary binding partner binds to the target analyte is detected) can occur in at least 15 seconds. In some embodiments, the binding of the primary binding partner to the target analyte can occur during a period of time of, for example, five at least seconds.

In some embodiments, the one or more additional steps can include: a blocking of the sensors step, at least one wash step, a capturing step, and/or a filtering step. In some embodiments, the blocking step can include blocking a sensor within the ingestible device with a solution comprising at least 1% bovine serum albumin (BSA) in a buffered solution (e.g., phosphate buffered saline (PBS), Tris buffered saline (TBS)). In some embodiments, the at least one wash step can include washing with a buffered solution (e.g., phosphate buffered saline (PBS), Tris buffered saline (TBS)). In general, blocking is performed during capsule manufacture, rather than in vivo.

In some embodiments, the capturing step includes enriching the target analyte. In some embodiments, the capturing step includes physically separating the target analyte from the remaining sample using a filter, a pore, or a magnetic bead. In some embodiments, the target analyte is captured by size exclusion.

In some embodiments, the disclosure provides methods of obtaining, culturing, and/or detecting target cells and/or target analytes in vivo within the gastrointestinal (GI) tract or reproductive tract of a subject. Associated devices are also disclosed. The methods and devices described provide a number of advantages for obtaining and/or analyzing fluid samples from a subject. In some embodiments, diluting the fluid sample increases the dynamic range of analyte detection and/or reduces background signals or interference within the sample. For example, interference may be caused by the presence of non-target analytes or non-specific binding of a dye or label within the sample. In some embodiments, culturing the sample increases the concentration of target cells and/or target analytes produced by the target cells thereby facilitating their detection and/or characterization.

In certain embodiments, the methods and devices a described herein may be used to obtain information regarding bacteria populations in the GI tract of a subject. This has a number of advantages and is less invasive than surgical procedures such as intubation or endoscopy to obtain fluid samples from the GI tract. The use of an ingestible device as described herein also allows for fluid samples to be obtained and data to be generated on bacterial populations from specific regions of the GI tract.

In some embodiments, the methods and devices described herein may be used to generate data such as by analyzing the fluid sample, dilutions thereof or cultured samples for one or more target cells and/or target analytes. The data may include, but is not limited to, the types of bacteria present in the fluid sample or the concentration of bacteria in specific regions of the GI tract. Such data may be used to determine whether a subject has an infection, such as Small Intestinal Bacterial Overgrowth (SIBO), or to characterize bacterial populations within the GI tract for diagnostic or other purposes. Thus, in some embodiments, analytes disclosed herein are indicative of disorders of the gastrointestinal tract associated with anomalous bacterial populations.

For example, in one aspect, the data may include, but is not limited to, the concentration of bacteria in a specific region of the GI tract that is one or more of the duodenum, jejunum, ileum, ascending colon, transverse colon or descending colon. In one aspect, the specific region of the GI tract is the duodenum. In one aspect, the specific region of the GI tract is the jejunum. In one aspect, the specific region of the GI tract is the ileum. In one aspect, the specific region of the GI tract is the ascending colon. In one aspect, the specific region of the GI tract is the transverse colon. In one aspect, the specific region of the GI tract is the descending colon. In a related embodiment, the data may be generated every one or more days to monitor disease flare-ups, or response to the therapeutic agents disclosed herein.

Data may be generated after the device has exited the subject, or the data may be generated in vivo and stored on the device and recovered ex vivo. Alternatively, the data can be transmitted wirelessly from the device while the device is passing through the GI tract of the subject or in place within the reproductive tract of the subject.

In some embodiments, a method comprises: providing a device comprising one or more dilution chambers and dilution fluid; transferring all or part of a fluid sample obtained from the GI tract or reproductive tract of the subject into the one or more dilution chambers in vivo; and combining the fluid sample and the dilution fluid to produce one or more diluted samples in the one or more dilution chambers.

In certain embodiments, a method comprises: providing an ingestible device comprising one or more dilution chambers; transferring all or part of a fluid sample obtained from the GI tract into the one or more dilution chambers comprising sterile media; culturing the sample in vivo within the one or more dilution chambers to produce one or more cultured samples; and detecting bacteria in the one or more cultured samples.

In some embodiments, a method comprises: providing a device comprising one or more dilution chambers; transferring all or part of a fluid sample obtained from the GI tract or reproductive tract into the one or more dilution chambers; combining all or part of the fluid sample with a dilution fluid in the one or more dilution chambers; and detecting the target analyte in the one or more diluted samples.

In certain embodiments, a device comprises: one or more dilution chambers for diluting a fluid sample obtained from the GI tract or reproductive tract; and dilution fluid for diluting the sample within the one or more dilution chambers.

In some embodiments, the device comprises: one or more dilution chambers for culturing a fluid sample obtained from the GI tract; sterile media for culturing the sample within the one or more dilution chambers; and a detection system for detecting bacteria.

In certain embodiments, a device comprises: one or more dilution chambers for culturing a fluid sample obtained from the GI tract; sterile media for culturing the sample within the one or more dilution chambers; and a detection system for detecting bacteria.

Also provided is the use of a device as described herein for diluting one or more samples obtained from the GI tract or reproductive tract of a subject. In one embodiment, there is provided the use of an ingestible device as described herein for detecting target cells and/or target analytes in vivo within the gastrointestinal (GI) tract of a subject.

Further provided is a system comprising a device as described herein and a base station. In one embodiment, the device transmits data to the base station, such as data indicative of the concentration and/or types of bacteria in the GI tract of the subject. In one embodiment, the device receives operating parameters from the base station. Some embodiments described herein provide an ingestible device for obtaining one or more samples from the GI tract or reproductive tract of a subject and diluting and/or culturing all or part of the one or more samples. The ingestible device includes a cylindrical rotatable element having a port on the wall of the cylindrical rotatable element. The ingestible device further includes a shell element wrapping around the cylindrical rotatable element to form a first dilution chamber between the cylindrical rotatable element and the shell element. The shell element has an aperture that exposes a portion of the wall of the cylindrical rotatable element to an exterior of the ingestible device.

In certain embodiments, the medical device comprises one or more dilution chambers for receiving a fluid sample from the GI tract or reproductive tract of a subject or a dilution thereof. In some embodiments, one or more dilutions of the fluid sample are cultured in one or more dilution chambers. In certain embodiments, the dilution chambers each define a known volume, optionally the same volume or different volumes. In some embodiments, the dilution chambers define a fluid volume ranging from about 10 μL to about 1 mL. The dilution chambers may define a fluid volume less than or equal to about 500 μL, less than or equal to about 250 μL, less than or equal to about 100 μL, or less than or equal to about 50 μL. In certain embodiments, the dilution chambers define a fluid volume of greater than or equal to about 10 μL, greater than or equal to about 20 μL, greater than or equal to about 30 μL, or greater than or equal to about 50 μL. In some embodiments, the dilution chambers define a fluid volume between about 10 μL and 500 μL, between about 20 μL and 250 μL, between about 30 μL and 100 μL or about 50 μL.

In some embodiments, dilution fluid in the device is combined with all or part of the fluid sample, or dilution thereof, to produce one or more dilutions. In certain embodiments, the dilution fluid is sterile media suitable for culturing one or more target cells within the dilution chambers.

In certain embodiments, the one or more dilution chambers may be filled with the dilution fluid prior to a patient ingesting the ingestible device. In some embodiments, the dilution fluid may be added into the one or more dilution chambers in vivo from a reservoir of the ingestible device. Sampling and dilution of the GI fluid sample may take place in vivo. For example, an actuator of the ingestible device may pump the dilution fluid from the reservoir into a dilution chamber when it is determined that the ingestible device is located at a predetermined location within the GI tract. In some embodiments, the dilution chambers each contain a volume of sterile media suitable for culturing a fluid sample from the GI tract or reproductive tract. In certain embodiments, the dilution chambers are at least 95%, at least 97%, at least 98%, or at least 99% full of sterile media. In some embodiments, the dilution chambers each contain oxygen to facilitate aerobic bacteria growth. In certain embodiments, a non-dilution chamber comprises oxygen and is added to one or more of the dilution chambers to facilitate aerobic bacteria growth.

In some embodiments, the culturing may take place in vivo immediately after the GI fluid sample has been diluted. Or alternatively, the culturing may take place ex vivo, e.g., when the ingestible device has been evacuated and recovered such that the dilution chamber containing the diluted GI fluid sample may be extracted and the culturing may be performed in a laboratory. The recovery of the ingestible device may be performed in a similar manner as embodiments described in U.S. Provisional Application No. 62/434,188, filed on Dec. 14, 2016, which is herein expressly incorporated by reference in its entirety.

As used herein "culturing" refers to maintaining target cells in an environment that allows a population of one or more target cells to increase in number through cell division. For example, in some embodiments, "culturing" may include combining the cells with media in an dilution chamber at a temperature that permits cell growth, optionally a temperature found in vivo within the GI tract or reproductive tract of a subject. In certain embodiments, the cells are cultured at a temperature between about 35° C. and 42° C.

As used herein "dilution fluid" refers to a fluid within the device for diluting a fluid sample from the GI tract or reproductive tract. In some embodiments, the dilution fluid is an aqueous solution. In certain embodiments, the dilution fluid comprises one or more agents that promote or inhibit the growth of an organism, such as a fungus or bacteria. In some embodiments, the dilution fluid comprises one or more agents that facilitate the detection of a target analyte, such as dyes or binding agents for target analytes.

In some embodiments, the dilution fluid is a sterile media. As used herein, “sterile media” refers to media that does not contain any viable bacteria or other cells that would grow and increase in number through cell division. Media may be rendered sterile by various techniques known in the art such as, but not limited to, autoclaving and/or preparing the media using asceptic techniques. In certain embodiments, the media is a liquid media. Examples of media suitable for culturing bacteria include nutrient broth, Lysogeny Broth (LB) (also known as Luria Broth), Wilkins chalgren, and Tryptic Soy Broth (TSB), Other growth or culture media known in the art may also be used in the methods and devices described herein. In some embodiments, the media has a carbon source, such as glucose or glycerol, a nitrogen source such as ammonium salts or nitrates or amino acids, as well as salts and/or trace elements and vitamins required for microbial growth. In certain embodiments, the media is suitable for maintaining eukaryotic cells. In some embodiments, the media comprises one or more agents that promote or inhibit the growth of bacteria, optionally agents that promote or inhibit the growth of specific types of bacteria.

In certain embodiments, the media is a selective media. As used herein, “selective media” refers to a media that allows certain types of target cells to grow and inhibits the growth of other organisms. Accordingly, the growth of cells in a selective media indicates the presence of certain types of cells within the cultured sample. For example, in some embodiments, the media is selective for gram-positive or gram-negative bacteria. In certain embodiments, the media contains crystal violet and bile salts (such as found in MacConkey agar) that inhibit the growth of gram-positive organisms and allows for the selection and isolation of gram-negative bacteria. In some embodiments, the media contains a high concentration of salt (NaCl) (such as found in Mannitol salt agar) and is selective for Gram-positive bacteria. In some embodiments, the media selectively kills eukaryotic cells or only grows prokaryotic cells, for example, using a media comprising Triton™ X-100. In certain embodiments, the media selectively kills prokaryotic cells (or alternatively only grows eukaryotic cells), for example, using a media that comprises antibiotics.

In some embodiments, the media is an indicator media. As used herein, “indicator media” refers to a media that contains specific nutrients or indicators (such as, but not limited to neutral red, phenol red, eosin Y, or methylene blue) that produce a detectable signal when a certain type of cells are cultured in the indicator media.

In some embodiments, the disclosure provides a composition comprising a dye and optionally a reagent for selective lysis of eukaryotic cells. In certain embodiments, the composition comprises both a dye and a reagent for selective lysis of eukaryotic cells. In some embodiments, the composition further comprises one or more reagents independently selected from the group consisting of: a second reagent for selective lysis of eukaryotic cells (e.g., Triton X-100), an electrolyte (e.g., $MgCl_2$), an anti-fungi reagent (e.g., amphotericin-B), and an antibiotic. In some embodiments, the composition comprises water and is in the form of an aqueous solution. In some embodiments, the composition is a solid or semi-solid. In some embodiments, the compositions described here are suitable for use in a kit or device for detecting or quantifying viable bacterial cells in a sample. In some embodiments, such a device is an ingestible device for detecting or quantifying viable bacterial cells in vivo (e.g., in the GI tract). In some embodiments, viable bacterial cells in a sample are detected or quantified in the presence of one or more antibiotics to determine antibiotic resistance of the bacteria in the sample. In some embodiments, anomalous bacterial populations in a sample may be detected or quantified, for example through the use of one a composition comprising a dye as disclosed herein, to determine whether a subject has an infection, such as Small Intestinal Bacterial Overgrowth (SIBO), or to characterize bacterial populations within the GI tract for diagnostic or other purposes.

In some embodiments, a method comprises: (a) contacting the sample with a composition as described herein; and (b) measuring total fluorescence or rate of change of fluorescence as a function of time of said sample, thereby detecting viable bacterial cells in said sample. In some embodiments, a control as described herein may be employed in the method. In some embodiments, the total fluorescence or the rate of change of fluorescence as a function of time of the sample is measured over multiple time points for an extended period of time in step (b), thereby detecting viable bacterial cells in said sample. In some embodiments, the method further comprises correlating the total fluorescence or the rate of change of fluorescence as a function of time determined in step (b) to the number of viable bacterial cells in the sample. In some embodiments, the rate of change of fluorescence as a function of time of the sample measured over multiple time points is determined and compared to the rate of change of fluorescence as a function of time of a control measured over the same time points to determine the number of viable bacterial cells in the sample. In some embodiments, the method does not require ex vivo plating or culturing. In some embodiments, the method does not require aspiration. In some embodiments, the method is performed in vivo (e.g., in an ingestible device in vivo). In some embodiments, the method comprises communicating the results of the onboard assay(s) to an ex vivo receiver.

In certain embodiments, a kit comprises a composition as described herein and instructions, e.g., for detecting or quantifying viable bacterial cells in a sample. In some embodiments, a device comprises a composition as described herein, e.g., for detecting or quantifying viable bacterial cells in a sample. The detection of live cells, as opposed to the detection of bacterial components (such as endotoxins) which can be present in the sample environment and lead to conflicting results, is the gold standard of viable plate counting and represents one of the advantages of the compositions and methods described herein.

The systems employ methods, compositions and detection systems found to accurately and reliably correlate fluorescence to total bacteria count (TBC) in an autonomous, ingestible device, or other similarly-sized device. The compositions include novel combinations of dyes, buffers and detergents that allow for the selective staining of viable bacterial cells in samples that comprise non-bacterial cells and other components that otherwise make detecting or quantifying live bacterial cells challenging. In some embodiments, the systems allow for bacteria to be quantified in near real-time and the results to be shared telemetrically outside of the device.

In certain embodiments, the disclosure provides a method of assessing or monitoring the need to treat a subject suffering from or at risk of overgrowth of bacterial cells in the gastrointestinal tract, which comprises: (a) obtaining a sample from the gastrointestinal tract of said subject; (b) contacting the sample with a composition as described herein; (c) measuring total fluorescence or rate of change of fluorescence as a function of time of said sample; and (d) correlating the total fluorescence or the rate of change of fluorescence as a function of time measured in step (c) to the number of viable bacterial cells in the sample, wherein the number of the viable bacterial cells determined in step (e) greater than about 105 CFU/mL indicates a need for treatment, e.g., with an antibiotic agent as described herein. In some embodiments, a control as described herein may be employed in the method. In some embodiments, the total fluorescence or the rate of change of fluorescence as a function of time of the sample is measured over multiple time points for an extended period of time in step (c). In some embodiments, the rate of change of fluorescence as a function of time of the sample measured over multiple time points is determined and compared to the rate of change of fluorescence as a function of time of a control measured over the same time points to determine the number of viable bacterial cells in the sample. In some embodiments, the method does not require ex vivo plating or culturing. In some embodiments, the method does not require aspiration. In some embodiments, the method is performed in vivo (e.g., in an ingestible device in vivo). In some embodiments, the method comprises communicating the results of the onboard assay(s) to an ex vivo receiver. In some embodiments, the method may be further used to monitor the subject after the treatment (e.g., with an antibiotic). In some embodiments, the method may be used to assess the efficacy of the treatment. For example, efficacious treatment may be indicated by the decrease of the number of viable bacterial cells in a sample from the GI tract of the subject post-treatment. Efficacy of the treatment may be evaluated by the rate of decrease of the number of viable bacterial cells in a sample from the GI tract of the subject post-treatment. In some embodiments, the method may be used to detect infection with antibiotic-resistant strains of bacteria in a subject. For instance, such infection may be indicated where the number of viable bacterial cells in a sample from the GI tract of the subject does not substantially decrease after antibiotic treatment.

In some embodiments, the disclosure provides an absorbable material, (e.g., absorbable sponge), having absorbed therein a composition as described herein. In some embodiments, the absorbable sponge is Ahlstrom Grade 6613H (Lot 150191) or Porex PSU-567, having absorbed therein a composition as described herein. In some embodiments, the absorbable sponge may be prepared by injecting into the absorbable sponge an aqueous solution comprising a composition as described herein, and optionally further comprising a step of drying the resulting absorbable sponge.

In certain embodiments, the disclosure provides a method for detecting the presence of viable bacterial cells in a sample, which comprises: (a) fully or partially saturating an absorbable sponge as described herein, or an absorbable sponge prepared as described herein, with the sample; and (b) measuring total fluorescence or rate of change of fluorescence as a function of time of the fully or partially saturated sponge prepared in step (a), thereby detecting viable bacterial cells. In some embodiments, a control as described herein may be employed in the method. In some embodiments, the total fluorescence or the rate of change of fluorescence as a function of time of the fully or partially saturated sponge is measured over multiple time points for an extended period of time in step (b), thereby detecting viable bacterial cells in said sample. In some embodiments, the method further comprises correlating the total fluorescence or the rate of change of fluorescence as a function of time measured in step (b) to the number of viable bacterial cells in the sample. In some embodiments, the rate of change of fluorescence as a function of time of the fully or partially saturated sponge measured over multiple time points is determined and compared to the rate of change of fluorescence as a function of time of a control measured over the same time points to determine the number of viable bacterial cells in the sample. In some embodiments, the method does not require ex vivo plating or culturing. In some embodiments, the method does not require aspiration. In some embodiments, the method is performed in vivo (e.g., in an ingestible device in vivo). In some embodiments, the method comprises communicating the results of the onboard assay(s) to an ex vivo receiver.

In one aspect, provided herein is a kit comprising an absorbable sponge as described herein and instructions, e.g., for detecting or quantifying viable bacterial cells in a sample. In another aspect, provided herein is a device comprising an absorbable sponge as described herein, e.g., for detecting or quantifying viable bacterial cells in a sample.

In certain embodiments, the disclosure provides a method of assessing or monitoring the need to treat a subject suffering from or at risk of overgrowth of bacterial cells in the gastrointestinal tract, which comprises: (a) obtaining a sample from the gastrointestinal tract of said subject; (b) fully or partially saturating an absorbable sponge described herein, or an absorbable sponge prepared as described herein, with the sample; (c) measuring total fluorescence or rate of change of fluorescence as a function of time of the fully or partially saturated sponge prepared in step (b); (d) correlating the total fluorescence or the rate of change of fluorescence as a function of time measured in step (c) to the number of viable bacterial cells in the sample, wherein the number of the viable bacterial cells as determined in step (e) greater than about $10^5$ CFU/mL indicates a need for treatment, e.g., with an antibiotic agent as described herein. In some embodiments, a control as described herein may be employed in the method. In some embodiments, the total fluorescence or the rate of change of fluorescence as a function of time of the fully or partially saturated sponge is measured over multiple time points for an extended period of time in step (c). In some embodiments, the rate of change of fluorescence as a function of time of the fully or partially saturated sponge measured over multiple time points is determined and compared to the rate of change of fluorescence as a function of time of a control measured over the same time points to determine the number of viable bacterial cells in the sample. In some embodiments, the method does not require ex vivo plating or culturing. In some embodiments, the method does not require aspiration. In some embodiments, the method is performed in vivo (e.g., in an ingestible device in vivo). In some embodiments, the method comprises communicating the results of the onboard assay(s) to an ex vivo receiver. In some embodiments, the method may be further used to monitor the subject after the treatment (e.g., with an antibiotic). In some embodiments, the method may be used to assess the efficacy of the treatment. For example, efficacious treatment may be indicated by the decrease of the number of viable bacterial cells in a sample from the GI tract of the subject post-treatment. Efficacy of the treatment may be evaluated by the rate of decrease of the number of viable bacterial cells in a sample from the GI tract of the subject post-treatment. In some embodiments, the method may be used to detect infection with antibiotic-resistant strains of bacteria in a subject. For instance, such infection may be indicated where the number of viable bacterial cells in a sample from the GI tract of the subject does not substantially decrease after antibiotic treatment In certain embodiments, the disclosure provides and ingestible device comprising a housing; a first opening in the wall of the housing; a second opening in the first end of the housing; and a chamber connecting the first opening and the second opening, wherein at least a portion of the chamber forms a sampling chamber within the ingestible device. In some embodiments, the sampling chamber is configured to hold an absorbable sponge described herein. In some embodiments, the sampling chamber is configured to hold a sample obtained from a gastrointestinal (GI) tract of a body. In some embodiments, the ingestible device is individually calibrated (for example, by comparing to a positive or negative control as described herein), wherein the fluorescent properties of the absorbable sponge held in the sampling chamber of the device are determined prior to the introduction of the sample. The ingestible device as described herein is useful for detecting or quantifying viable bacterial cells in vivo. In some embodiments, provided herein is a method for detecting or quantifying viable bacterial cells in a GI tract sample in vivo using an ingestible device as described herein. In some embodiments, provided herein is a method of assessing or monitoring the need to treat a subject suffering from or at risk of overgrowth of bacterial cells in the GI tract in vivo using an ingestible device as described herein. In some embodiments, provided herein is a method of altering the treatment regimen of a subject suffering from or at risk of overgrowth of bacterial cells in the GI tract in vivo using an ingestible device as described herein. In one aspect, the subject is a subject suffering from or at risk of overgrowth of bacterial cells in the duodenum. In one aspect, the subject is a subject suffering from or at risk of overgrowth of bacterial cells in the jejunum. In one aspect, the subject is a subject suffering from or at risk of overgrowth of bacterial cells in the ileum. In one aspect, the subject is a subject suffering from or at risk of overgrowth of bacterial cells in the ascending colon. In one aspect, the subject is a subject suffering from or at risk of overgrowth of bacterial cells in the transverse colon. In one aspect, the subject is a subject suffering from or at risk of overgrowth of bacterial cells in the descending colon. In some embodiments, the method may be further used to monitor the subject after the treatment (e.g., with an antibiotic). In some embodiments, the method may be used to assess the efficacy of the treatment. For example, efficacious treatment may be indicated by the decrease of the number of viable bacterial cells in a sample from the GI tract of the subject post-treatment. Efficacy of the treatment may be evaluated by the rate of decrease of the number of viable bacterial cells in a sample from the GI tract of the subject post-treatment. In some embodiments, the method may be used to detect infection with antibiotic-resistant strains of bacteria in a subject. For instance, such infection may be indicated where the number of viable bacterial cells in a sample from the GI tract of the subject does not substantially decrease after antibiotic treatment. In some embodiments, the method is performed autonomously and does not require instructions, triggers or other inputs from outside the body after the device has been ingested.

"Eukaryotic" as recited herein relates to any type of eukaryotic organism excluding fungi, such as animals, in particular animals containing blood, and comprises invertebrate animals such as crustaceans and vertebrates. Vertebrates comprise both cold-blooded (fish, reptiles, amphibians) and warm blooded animal (birds and mammals). Mammals comprise in particular primates and more particularly humans "Selective lysis" as used herein is obtained in a sample when the percentage of bacterial cells in that sample that remain intact is significantly higher (e.g. 2, 5, 10, 20, 50, 100, 250, 500, or 1,000 times more) than the percentage of the eukaryotic cells in that sample that remain intact, upon treatment of or contact with a composition or device as described herein.

In some embodiments, the dye suitable for use herein is a dye that is capable of being internalized by a viable cell, binding to or reacting with a target component of the viable cell, and having fluorescence properties that are measurably altered when the dye is bound to or reacted with the target component of the viable cell. In some embodiments, the dye herein is actively internalized by penetrating viable cells through a process other than passible diffusion across cell membranes. Such internalization includes, but is not limited to, internalization through cell receptors on cell surfaces or through channels in cell membranes. In some embodiments, the target component of a viable cell to which the dye is bound to or reacted with is selected from the group consisting of: nucleic acids, actin, tubulin, enzymes, nucleotide-binding proteins, ion-transport proteins, mitochondria, cytoplasmic components, and membrane components. In some embodiments, the dye suitable for use herein is a fluorogenic dye that is capable of being internalized and metabolized by a viable cell, and wherein said dye fluoresces when metabolized by the viable cell. In some embodiments, the dye is a chemiluminescent dye that is capable of being internalized and metabolized by a viable cell, and wherein said dye becomes chemiluminescent when metabolized by the viable cell.

In some embodiments, the composition comprises a dye that fluoresces when bond to nucleic acids. Examples of such dyes include, but are not limited to, acridine orange (U.S. Pat. No. 4,190,328); calcein-AM (U.S. Pat. No. 5,314, 805); DAPI; Hoechst 33342; Hoechst 33258; PicoGreen™; SYTO® 16; SYBR® Green I; Texas Red®; Redmond Red™; Bodipy® Dyes; Oregon Green™; ethidium bromide; and propidium iodide.

In some embodiments, the composition comprises a lipophilic dye that fluoresces when metabolized by a cell. In some embodiments, the dye fluoresces when reduced by a cell or a cell component. Examples of dyes that fluoresce when reduced include, but are not limited to, resazurin; $C^{12}$-resazurin; 7-hydroxy-9H-(1,3 dichloro-9,9-dimethylacridin-2-ol)N-oxide; 6-chloro-9-nitro-5-oxo-5H-benzo[a]phenoxazine; and tetrazolium salts. In some embodiment, the dye fluoresces when oxidized by a cell or a cell component. Examples of such dyes include, but are not limited to, dihydrocalcein AM; dihydrorhodamine 123; dihydroethidium; 2,3,4,5,6-pentafluorotetramethyldihydrorosamine; and 3'-(p-aminophenyl) fluorescein.

In some embodiments, the composition comprises a dye that becomes chemiluminescent when oxidized by a cell or a cell component, such as luminol.

In some embodiments, the composition comprises a dye that fluoresces when de-acetylated and/or oxidized by a cell or a cell component. Examples of such dyes include, but are not limited to, dihydrorhodamines; dihydrofluoresceins; 2',7'-dichlorodihydrofluorescein diacetate; 5-(and 6-)carboxy-2',7'-dichlorodihydrofluorescein diacetate; and chloromethyl-2',7'-dichlorodihydrofluorescein diacetate acetyl ester.

In some embodiments, the composition comprises a dye that fluoresces when reacted with a peptidase. Examples of such dyes include, but are not limited to, (CBZ-Ala-Ala-Ala-Ala)2-R110 elastase 2; (CBZ-Ala-Ala-Asp)2-R110 granzyme B; and 7-amino-4-methylcoumarin, N-CBZ-L-aspartyl-L-glutamyl-L-valyl-L-aspartic acid amide.

In some embodiments, the composition comprises a dye selected from the group consisting of resazurin, FDA, Calcein AM, and SYTO® 9. In some embodiments, the dye is FDA or SYTO® 9.

SYTO® 9, when used alone, labels the nucleic acid of bacteria cells. The excitation/emission wavelengths for SYTO® 9 is 480/500 nm, with the background remaining non-fluorescent. See, e.g., J. Appl. Bacteriol. 72, 410 (1992); Lett. Appl. Microbiol. 13, 58 (1991); Curr. Microbiol. 4, 321 (1980); J. Microbiol. Methods 13, 87 (1991); and Microbiol. Rev. 51, 365 (1987); and J. Med. Microbiol. 39, 147 (1993).

FDA is a non-polar, non-fluorescent compound that can cross the membranes of mammalian and bacterial cells. The acetyl esterases (present only within viable cells) hydrolyze the FDA into the fluorescent compound fluorescein. Fluorescein is a fluorescent polar compound that is retained within these cells. Living cells can be visualized in a photospectrometer when assayed with an excitation wavelength of 494 nm and an emission wavelength of 518 nm. See, e.g., Brunius, G. (1980). *Technical aspects of the use of 3',6'—Diacetylfluorescein for vita/fluorescent staining of bacteria*. Current Microbiol. 4: 321-323; Jones, K. H. and Senft, J. A. (1985). *An improved method to determine cellviability by simultaneous staining with fluorescein diacetate-propidium iodide*. J. Histochem. Cytochem. 33: 77-79; Ross, R. D., Joneckis, C. C., Ordonez, J. V., Sisk, A. M., Wu, R. K., Hamburger, A. W., and Nora, R. E. (1989). *Estimation of cell survival by flow cytometric quantification of fluorescein diacetate/propidium iodide viable cell number*. Cancer Research. 49: 3776-3782.

Calcein-AM, which is an acetoxylmethyl ester of calcein, is highly lipophilic and cell permeable. Calcein-AM in itself is not fluorescent, but the calcein generated by esterase in a viable cell emits a green fluorescence with an excitation wavelength of 490 nm and an emission of 515 nm. Therefore, Calcein-AM can only stain viable cells. See, e.g., Kimura, K., et al., *Neurosci. Lett.*, 208, 53 (1998); Shimokawa, I., et al., *J. Geronto.*, 51a, b49 (1998); Yoshida, S., et al., *Clin. Nephrol.*, 49, 273 (1998); and Tominaga, H., et al., *Anal. Commun.*, 36, 47 (1999).

Resazuirn (also known as Alamar Blue) is a blue compound that can be reduced to pink resorufin which is fluorescent. This dye is mainly used in viability assays for mammalian cells. $C^{12}$-resazurin has better cell permeability than resazurin. When lipohilic $C^{12}$-resazurin crosses the cell membranes, it is subsequently reduced by living cells to make a red fluorescent resorufin. The adsorption/emission of $C^{12}$-resazurin is 563/587 nm. See, e.g., Appl Environ Microbiol 56, 3785 (1990); J Dairy Res 57, 239 (1990); J Neurosci Methods 70, 195 (1996); J Immunol Methods 210, 25 (1997); J Immunol Methods 213, 157 (1998); Antimicrob Agents Chemother 41, 1004 (1997).

In some embodiments, the composition optionally further comprises a reagent for selective lysis of eukaryotic cells. In some embodiments, the composition comprises a dye as described herein and a reagent for selective lysis of eukaryotic cells. In some embodiments, the reagent for selective lysis of eukaryotic cells is a detergent, such as a non-ionic or an ionic detergent. Examples of the reagent for selective lysis of eukaryotic cells include, but are not limited to, alkylglycosides, Brij 35 (C12E23 Polyoxyethyleneglycol dodecyl ether), Brij 58 (C16E20 Polyoxyethyleneglycol dodecyl ether), Genapol, glucanids such as MEGA-8, -9, -10, octylglucoside, Pluronic F127, Triton X-100 ($C_{14}H_{22}O(C_2H_4O)_n$), Triton X-114 ($C_{24}H_{42}O_6$), Tween 20 (Polysorbate 20) and Tween 80 (Polysorbate 80), Nonidet P40, deoxycholate, reduced Triton X-100 and/or Igepal CA 630. In some embodiments, the composition comprises a dye as described herein and deoxycholate (e.g., sodium deoxycholate) as a reagent for selective lysis of eukaryotic cells. In some embodiments, the composition comprises deoxycholate at a concentration selected from 0.0001% to 1 wt %. In some embodiments, the composition comprises deoxycholate at a concentration of 0.005 wt %. In some embodiments, the composition may comprise more than one reagent for selective lysis of eukaryotic cells.

In some embodiments, the composition may comprise two different reagents for selective lysis of eukaryotic cells. In some instances, when more than one selective lysis reagents are used, more effective and/or complete selective lysis of eukaryotic cells in a sample may be achieved. For example, the composition may comprise deoxycholate (e.g., sodium deoxycholate) and Triton X-100 as two different reagents for selective lysis of eukaryotic cells. In some embodiments, the composition comprises deoxycholate (e.g., sodium deoxycholate) at a concentration selected from 0.0001% to 1 wt % (e.g., 0.005 wt %) and Triton X-100 at a concentration selected from 0.1 to 0.05 wt %.

In some embodiments, after a sample (e.g., a biological sample) is treated or contacted with a composition comprising a dye and one or more reagents for selective lysis of eukaryotic cells as described herein, the eukaryotic cells (e.g., animal cells) in the sample are selectively lysed whereby a substantial percentage (e.g., more than 20%, 40%, 60%, 80%, 90% or even more that 95%) of the bacterial cells in the same sample remains intact or alive.

In some embodiments, the composition does not comprise a reagent for selective lysis of eukaryotic cells, and such a composition is useful for detecting or quantifying viable bacterial cells in a sample (e.g., an environmental sample such as a water sample) that does not contain any eukaryotic cells.

In some embodiments, the composition further comprises an electrolyte, such as a divalent electrolyte (e.g., $MgCl_2$). In some embodiments, the composition comprises $MgCl_2$ at a concentration selected from 0.1 mM to 100 mM (e.g., a concentration selected from 0.5 mM to 50 mM).

In some embodiments, the composition further comprises water and is in a form of an aqueous solution. In some embodiments, the composition has a pH selected from 5-8 (e.g., a pH selected from 6-7.8, such as pH being 6.0). In some embodiments, the composition is a solid or a semi-solid.

In some embodiments, the composition further comprises an anti-fungal agent. Suitable anti-fungal agents for use herein include, but are not limited to, fungicidal and fungistatic agents including terbinafine, itraconazole, micronazole nitrate, thiapendazole, tolnaftate, clotrimazole and griseofulvin. In some embodiments, the anti-fungal agent is a polyene anti-fungal agent, such as amphotericin-B, nystatin, and pimaricin.

In some embodiments, the composition does not contain any anti-fungal agent. In some embodiments, the composition contains broad spectrum antibiotics but not any anti-fungal agent. Such compositions that do not contain anti-fungal agents but contain broad spectrum antibiotics may be useful in detecting or quantifying fungi (e.g., yeast) in a sample.

In some embodiments, the composition does not contain any anti-fungal agent, any antibiotics or any anti-mammalian agent. Such compositions that do not selectively lyse mammalian cells may be useful in detecting or quantifying mammalian cells (e.g., cells from the GI tract) in a sample since many dyes have a higher affinity for mammalian as compared to bacteria or fungi cells. In some embodiments, the composition contains broad spectrum antibiotics and one or more anti-fungal agents. Such compositions that contain anti-fungal agents and broad spectrum antibiotics may be useful in detecting or quantifying mammalian cells (e.g., cells from the GI tract) in a sample. The detection or quantification of mammalian cells may be useful for determining cell turnover in a subject. High cell turnover is sometimes associated with a GI injury (e.g., lesion), the presence of a tumor(s), or radiation-induced colitis or radiation enteropathy.

In some embodiments, the composition further comprises an antibiotic agent as described herein. Such a composition may be useful in detecting or quantifying antibiotic-resistant strains of bacteria in a sample.

In certain embodiments, the composition comprises Triton X-100, deoxycholate, resazurin, and $MgCl_2$. In some embodiments, the composition comprises Triton X-100, deoxycholate, resazurin, amphotericin-B and $MgCl_2$. In some embodiments, the composition comprises 0.1 wt % or 0.05 wt % Triton X-100; 0.005 wt % deoxycholate; 10 mM resazurin; 2.5 mg/L amphotericin-B and 50 mM $MgCl_2$. In some embodiments, the composition has a pH of 6.0.

In certain embodiments, the compositions are suitable for use in a kit or device, e.g., for detecting or quantifying viable bacterial cells in a sample. In some embodiments, such a device is an ingestible device for detecting or quantifying viable bacterial cells in vivo (e.g., in the GI tract).

FIG. 62 illustrates a nonlimiting example of a system for collecting, communicating and/or analyzing data about a subject, using an ingestible device as disclosed herein. For example, an ingestible device may be configured to communicate with an external base station. As an example, an ingestible device can have a communications unit that communicates with an external base station which itself has a communications unit. FIG. 62 illustrates exemplary implementation of such an ingestible device. As shown in FIG. 62, a subject ingests an ingestible device as disclosed herein. Certain data about the subject (e.g., based on a collected sample) and/or the location of the ingestible device in the GI tract of the subject is collected or otherwise available and provided to a mobile device, which then forwards the data via the internet and a server/data store to a physician's office computer. The information collected by the ingestible device is communicated to a receiver, such as, for example, a watch or other object worn by the subject. The information is then communicated from the receiver to the mobile device which then forwards the data via the internet and a server/data store to a physician's office computer. The physician is then able to analyze some or all of the data about the subject to provide recommendations, such as, for example, delivery a therapeutic agent. While FIG. 62 shows a particular approach to collecting and transferring data about a subject, the disclosure is not limited. As an example, one or more of the receiver, mobile device, internet, and/or server/data store can be excluded from the data communication channel. For example, a mobile device can be used as the receiver of the device data, e.g., by using a dongle. In such embodiments, the item worn by the subject need not be part of the communication chain. As another example, one or more of the items in the data communication channel can be replaced with an alternative item. For example, rather than be provided to a physician's office computer, data may be provided to a service provider network, such as a hospital network, an HMO network, or the like. In some embodiments, subject data may be collected and/or stored in one location (e.g., a server/data store) while device data may be collected and/or stored in a different location (e.g., a different server/data store).

Locations of Treatment

In some embodiments, the JAK inhibitor is delivered at a location in the large intestine of the subject. In some embodiments, the location is in the proximal portion of the large intestine. In some embodiments, the location is in the distal portion of the large intestine.

In some embodiments, the JAK inhibitor is delivered at a location in the ascending colon of the subject. In some embodiments, the location is in the proximal portion of the ascending colon. In some embodiments, the location is in the distal portion of the ascending colon.

In some embodiments, the JAK inhibitor is delivered at a location in the cecum of the subject. In some embodiments, the location is in the proximal portion of the cecum. In some embodiments, the location is in the distal portion of the cecum.

In some embodiments, the JAK inhibitor is delivered at a location in the sigmoid colon of the subject. In some embodiments, the location is in the proximal portion of the sigmoid colon. In some embodiments, the location is in the distal portion of the sigmoid colon.

In some embodiments, the JAK inhibitor is delivered at a location in the transverse colon of the subject. In some embodiments, the location is in the proximal portion of the transverse colon. In some embodiments, the location is in the distal portion of the transverse colon.

In some embodiments, the JAK inhibitor is delivered at a location in the descending colon of the subject. In some embodiments, the location is in the proximal portion of the descending colon. In some embodiments, the location is in the distal portion of the descending colon.

In some embodiments, the JAK inhibitor is delivered at a location in the small intestine of the subject. In some embodiments, the location is in the proximal portion of the small intestine. In some embodiments, the location is in the distal portion of the small intestine.

In some embodiments, the JAK inhibitor is delivered at a location in the duodenum of the subject. In some embodiments, the location is in the proximal portion of the duodenum. In some embodiments, the location is in the distal portion of the duodenum.

In some embodiments, the JAK inhibitor is delivered at a location in the jejunum of the subject. In some embodiments, the location is in the proximal portion of the jejunum. In some embodiments, the location is in the distal portion of the jejunum.

In some embodiments, the JAK inhibitor is delivered at a location in the duodenum of the subject and is not delivered at other locations in the gastrointestinal tract. In some embodiments, the JAK inhibitor is delivered at a location in the duodenum of the subject and is not delivered at other locations in the gastrointestinal tract, wherein a site of disease is in the duodenum and no site of disease is present at other locations in the gastrointestinal tract.

In some embodiments, the JAK inhibitor is delivered at a location in the duodenum of the subject and is not delivered at other locations in the gastrointestinal tract, wherein a first site of disease is in the duodenum and a second site of disease is in the stomach and no site of disease is present at other locations in the gastrointestinal tract.

In some embodiments, the JAK inhibitor is delivered at a location in the proximal duodenum of the subject and is not delivered at other locations in the gastrointestinal tract. In some embodiments, the JAK inhibitor is delivered at a location in the proximal duodenum of the subject and is not delivered at other locations in the gastrointestinal tract, wherein a site of disease is in the duodenum and no site of disease is present at other locations in the gastrointestinal tract. In some embodiments, the JAK inhibitor is delivered at a location in the proximal duodenum of the subject and is not delivered at other locations in the gastrointestinal tract, wherein a first site of disease is in the duodenum and a second site of disease is in the stomach and no site of disease is present at other locations in the gastrointestinal tract.

In some embodiments, the JAK inhibitor is delivered at a location in the jejunum of the subject and is not delivered at other locations in the gastrointestinal tract. In some embodiments, the JAK inhibitor is delivered at a location in the jejunum of the subject and is not delivered at other locations in the gastrointestinal tract, wherein a site of disease is in the jejunum and no site of disease is present at other locations in the gastrointestinal tract. In some embodiments, the JAK inhibitor is delivered at a location in the jejunum of the subject and is not delivered at other locations in the gastrointestinal tract, wherein a first site of disease is in the jejunum and a second site of disease is in the ileum and no site of disease is present at other locations in the gastrointestinal tract.

In some embodiments, the JAK inhibitor is delivered at a location in the proximal portion of the jejunum of the subject and is not delivered at other locations in the gastrointestinal tract. In some embodiments, the JAK inhibitor is delivered at a location in the proximal portion of the jejunum of the subject and is not delivered at other locations in the gastrointestinal tract, wherein a site of disease is in the jejunum and no site of disease is present at other locations in the gastrointestinal tract. In some embodiments, the JAK inhibitor is delivered at a location in the proximal portion of the jejunum of the subject and is not delivered at other locations in the gastrointestinal tract, wherein a first site of disease is in the jejunum and a second site of disease is in the ileum and no site of disease is present at other locations in the gastrointestinal tract.

In some embodiments, the JAK inhibitor is delivered at a location in the distal portion of the jejunum of the subject and is not delivered at other locations in the gastrointestinal tract. In some embodiments, the JAK inhibitor is delivered at a location in the distal portion of the jejunum of the subject and is not delivered at other locations in the gastrointestinal tract, wherein a site of disease is in the jejunum and no site of disease is present at other locations in the gastrointestinal tract. In some embodiments, the JAK inhibitor is delivered at a location in the distal portion of the jejunum of the subject and is not delivered at other locations in the gastrointestinal tract, wherein a first site of disease is in the jejunum and a second site of disease is in the ileum and no site of disease is present at other locations in the gastrointestinal tract.

In some embodiments, the JAK inhibitor is delivered at a location in the ileum of the subject. In some embodiments, the location is in the proximal portion of the ileum. In some embodiments, the location is in the distal portion of the ileum.

In some embodiments, the JAK inhibitor is delivered at a location in the ileum of the subject and is not delivered at other locations in the gastrointestinal tract. In some embodiments, the JAK inhibitor is delivered at a location in the ileum of the subject and is not delivered at other locations in the gastrointestinal tract, wherein a site of disease is in the ileum and no site of disease is present at other locations in the gastrointestinal tract. In some embodiments, the JAK inhibitor is delivered at a location in the ileum of the subject and is not delivered at other locations in the gastrointestinal tract, wherein a first site of disease is in the ileum and a second site of disease is in the cecum and no site of disease is present at other locations in the gastrointestinal tract. In some embodiments, the JAK inhibitor is delivered at a location in the ileum of the subject and is not delivered at other locations in the gastrointestinal tract, wherein a first site of disease is in the ileum and a second site of disease is in the cecum and/or ascending colon, and no site of disease is present at other locations in the gastrointestinal tract.

In some embodiments, the JAK inhibitor is delivered at a location in the proximal portion of the ileum of the subject and is not delivered at other locations in the gastrointestinal tract. In some embodiments, the JAK inhibitor is delivered at a location in the proximal portion of the ileum of the subject and is not delivered at other locations in the gastrointestinal tract, wherein a site of disease is in the ileum and no site of disease is present at other locations in the gastrointestinal tract. In some embodiments, the JAK inhibitor is delivered at a location in the proximal portion of the ileum of the subject and is not delivered at other locations in the gastrointestinal tract, wherein a first site of disease is in the ileum and a second site of disease is in the cecum and no site of disease is present at other locations in the gastrointestinal tract. In some embodiments, the JAK inhibitor is delivered at a location in the proximal portion of the ileum of the subject and is not delivered at other locations in the gastrointestinal tract, wherein a first site of disease is in the ileum and a second site of disease is in the cecum and/or ascending colon, and no site of disease is present at other locations in the gastrointestinal tract.

In some embodiments, the JAK inhibitor is delivered at a location in the distal portion of the ileum of the subject and is not delivered at other locations in the gastrointestinal tract. In some embodiments, the JAK inhibitor is delivered at a location in the distal portion of the ileum of the subject and is not delivered at other locations in the gastrointestinal tract, wherein a site of disease is in the ileum and no site of disease is present at other locations in the gastrointestinal tract. In some embodiments, the JAK inhibitor is delivered at a location in the distal portion of the ileum of the subject and is not delivered at other locations in the gastrointestinal tract, wherein a first site of disease is in the ileum and a second site of disease is in the cecum and no site of disease is present at other locations in the gastrointestinal tract. In some embodiments, the JAK inhibitor is delivered at a location in the distal portion of the ileum of the subject and is not delivered at other locations in the gastrointestinal tract, wherein a first site of disease is in the ileum and a second site of disease is in the cecum and/or ascending colon, and no site of disease is present at other locations in the gastrointestinal tract.

In some embodiments, the JAK inhibitor is delivered at a location in the cecum of the subject and is not delivered at other locations in the gastrointestinal tract. In some embodiments, the JAK inhibitor is delivered at a location in the distal portion of the cecum of the subject and is not delivered at other locations in the gastrointestinal tract, wherein a site of disease is in the cecum and/or ascending colon, and no site of disease is present at other locations in the gastrointestinal tract. In some embodiments, the JAK inhibitor is delivered at a location in the distal portion of the ileum or the proximal portion of the ascending colon of the subject and is not delivered at other locations in the gastrointestinal tract, wherein a first site of disease is in the cecum and a second site of disease is in the ascending colon, and no site of disease is present at other locations in the gastrointestinal tract.

In some embodiments, a site of disease is in the colon and the JAK inhibitor is released in the colon, such as in the cecum. In some embodiments, a site of disease is in the ascending colon and the JAK inhibitor is released in the ascending colon, such as in the cecum. In some embodiments, a site of disease is in the ileum and the JAK inhibitor is released in the ileum.

In some embodiments the subject is diagnosed with ileal Crohn's disease and the JAK inhibitor is released in the ileum.

In some embodiments the subject is diagnosed with ileal colonic Crohn's disease and the JAK inhibitor is released in both the ileum and the colon. In some more particular embodiments, the JAK inhibitor is released in both the ileum and the colon from the same ingestble device. In some more particular embodiments, the JAK inhibitor is released in the ileum from a first ingestble device and in the colon from a second ingestible device, wherein the first ingestble device and the second ingestible device are ingested at substantially the same time or at different times.

In some embodiments the subject is diagnosed with colitis throughout the colon and the JAK inhibitor is released (a) in the cecum, (b) in the cecum and in the transverse colon, and/or release (c) in the descending colon.

In some embodiments the subject is diagnosed with right sided colitis and the JAK inhibitor is released in the transverse colon or in the descending colon.

In some embodiments the subject is diagnosed with rectosigmoidal colitis and the JAK inhibitor is released in the descending colon.

In some embodiments, the location at which the JAK inhibitor is delivered is proximate to a site of disease. The site of disease may be, for example, an injury, inflamed tissue, or one or more lesions. In some embodiments, the location at which the JAK inhibitor is delivered is proximate to one or more sites of disease. In some embodiments, the JAK inhibitor is delivered 150 cm or less from the one or more sites of disease. In some embodiments, the JAK inhibitor is delivered 125 cm or less from the one or more sites of disease. In some embodiments, the JAK inhibitor is delivered 100 cm or less from the one or more sites of disease. In some embodiments, the JAK inhibitor is delivered 50 cm or less from the one or more sites of disease. In some embodiments, the JAK inhibitor is delivered 40 cm or less from the one or more sites of disease. In some embodiments, the JAK inhibitor is delivered 30 cm or less from the one or more sites of disease. In some embodiments, the JAK inhibitor is delivered 20 cm or less from the one or more sites of disease. In some embodiments, the JAK inhibitor is delivered 10 cm or less from the one or more sites of disease. In some embodiments, the JAK inhibitor is delivered 5 cm or less from the one or more sites of disease. In some embodiments, the JAK inhibitor is delivered 2 cm or less from the one or more sites of disease. In some embodiments, the proximate location for drug release is the same section or subsection of the gastrointestinal tract containing the one or more disease site. In some embodiments, the proximate location for drug release is a different section or subsection of the GI tract than that containing the disease site; for example, the drug release may be proximal to the disease site. In some embodiments, the method further comprises using an ingestible device to deliver the JAK inhibitor and using localization methods disclosed herein (e.g., such as discussed in Example 13 below) to determine the location of the ingestible device within the GI tract (e.g., relative to the site of disease). In some embodiments, the method further comprises using an ingestible device to deliver the JAK inhibitor and determining the period of time since the ingestible device was ingested to determine the location of the ingestible device within the GI tract (e.g., relative to the site of disease). In some embodiments, the method further comprises identifying the one or more sites of disease by a method comprising imaging of the gastrointestinal tract. In some embodiments, imaging of the gastrointestinal tract comprises video imaging. In some embodiments, imaging of the gastrointestinal tract comprises thermal imaging. In some embodiments, imaging of the gastrointestinal tract comprises ultrasound imaging. In some embodiments, imaging of the gastrointestinal tract comprises Doppler imaging.

In some embodiments the method does not comprise releasing more than 20% of the JAK inhibitor at a location that is not proximate to a site of disease. In some embodiments the method does not comprise releasing more than 10% of the JAK inhibitor at a location that is not proximate to a site of disease. In some embodiments the method does not comprise releasing more than 5% of the JAK inhibitor at a location that is not proximate to a site of disease. In some embodiments the method does not comprise releasing more than 4% of the JAK inhibitor at a location that is not proximate to a site of disease. In some embodiments the method does not comprise releasing more than 3% of the JAK inhibitor at a location that is not proximate to a site of disease. In some embodiments the method does not comprise releasing more than 2% of the JAK inhibitor at a location that is not proximate to a site of disease.

In some embodiments the method comprises releasing at least 80% of the JAK inhibitor at a location proximate to a site of disease. In some embodiments the method comprise releasing at least 90% of the JAK inhibitor at a location proximate to a site of disease. In some embodiments the method comprises releasing at least 95% of the JAK inhibitor at a location proximate to a site of disease. In some embodiments the method comprises releasing at least 96% of the JAK inhibitor at a location proximate to a site of disease. In some embodiments the method comprises releasing at least 97% of the JAK inhibitor at a location proximate to a site of disease. In some embodiments the method comprises releasing at least 98% of the JAK inhibitor at a location proximate to a site of disease. In some embodiments, the at least 80%, at least 90%, at least 95%, at least 96%, at least 97%, or at least 98% of the JAK inhibitor is delivered 150 cm or less from the one or more sites of disease. In some embodiments, the at least 80%, at least 90%, at least 95%, at least 96%, at least 97%, or at least 98% of the JAK inhibitor is delivered 125 cm or less from the one or more sites of disease. In some embodiments, the at least 80%, at least 90%, at least 95%, at least 96%, at least 97%, or at least 98% of the JAK inhibitor is delivered 100 cm or less from the one or more sites of disease. In some embodiments, the at least 80%, at least 90%, at least 95%, at least 96%, at least 97%, or at least 98% of the JAK inhibitor is delivered 50 cm or less from the one or more sites of disease. In some embodiments, the at least 80%, at least 90%, at least 95%, at least 96%, at least 97%, or at least 98% of the JAK inhibitor is delivered 40 cm or less from the one or more sites of disease. In some embodiments, the at least 80%, at least 90%, at least 95%, at least 96%, at least 97%, or at least 98% of the JAK inhibitor is delivered 30 cm or less from the one or more sites of disease. In some embodiments, the at least 80%, at least 90%, at least 95%, at least 96%, at least 97%, or at least 98% of the JAK inhibitor is delivered 20 cm or less from the one or more sites of disease. In some embodiments, the at least 80%, at least 90%, at least 95%, at least 96%, at least 97%, or at least 98% of the JAK inhibitor is delivered 10 cm or less from the one or more sites of disease. In some embodiments, the at least 80%, at least 90%, at least 95%, at least 96%, at least 97%, or at least 98% of the JAK inhibitor is delivered 5 cm or less from the one or more sites of disease. In some embodiments, the at least 80%, at least 90%, at least 95%, at least 96%, at least 97%, or at least 98% of the JAK inhibitor is delivered 2 cm or less from the one or more sites of disease. In some embodiments, the method further comprises using an ingestible device to deliver the JAK inhibitor and using localization methods disclosed herein (e.g., such as discussed in Example 13 below) to determine the location of the ingestible device within the GI tract (e.g., relative to the site of disease). In some embodiments, the method further comprises using an ingestible device to deliver the JAK inhibitor and determining the period of time since the ingestible device was ingested to determine the location of the ingestible device within the GI tract (e.g., relative to the site of disease).

In some embodiments, the amount of JAK inhibitor that is delivered is a Human Equivalent Dose.

In some embodiments the method comprises releasing the JAK inhibitor at a location that is proximate to a site of disease, wherein the JAK inhibitor and, if applicable, any carriers, excipients or stabilizers admixed with the JAK inhibitor, are substantially unchanged, at the time of release of the JAK inhibitor at the location, relatively to the time of administration of the composition to the subject.

In some embodiments the method comprises releasing the JAK inhibitor at a location that is proximate to a site of disease, wherein the JAK inhibitor and, if applicable, any carriers, excipients or stabilizers admixed with the JAK inhibitor, are substantially unchanged by any physiological process (such as, but not limited to, degradation in the stomach), at the time of release of the JAK inhibitor at the location, relatively to the time of administration of the composition to the subject.

In some embodiments, the JAK inhibitor is delivered to the location by mucosal contact.

In some embodiments, a method of treatment disclosed herein includes determining the level of JAK inhibitor at a site of disease or a location in the gastrointestinal tract of the subject that is proximate to one or more sites of disease. In some examples, a method of treatment as described herein can include determining the level of JAK inhibitor at a site of disease or a location in the gastrointestinal tract of the subject that is proximate to one or more sites of disease within a time period of about 10 minutes to about 10 hours following administration of the device.

In some examples, a method of treatment disclosed herein includes determining the level of the JAK inhibitor at a site of disease or a location in the gastrointestinal tract of the subject that is proximate to one or more sites of disease at a time point following administration of the device that is elevated as compared to a level of the JAK inhibitor at the same site of disease or location at substantially the same time point in a subject following systemic administration of an equal amount of the JAK inhibitor.

In some examples where the JAK inhibitor is administered to a subject using any of the compositions or devices described herein, the JAK inhibitor can penetrate the GI tissue of the subject. As used herein, "GI tissue" refers to tissue in the gastrointestinal (GI) tract, such as tissue in one or more of duodenum, jejunum, ileum, cecum, ascending colon, transverse colon, descending colon, sigmoid colon, and rectum. In one particular embodiment, GI tissue refers to tissue in the proximal portion of one or more of duodenum, jejunum, ileum, cecum, ascending colon, transverse colon, descending colon, and sigmoid colon. In one particular embodiment, GI tissue refers to tissue in the distal portion of one or more of duodenum, jejunum, ileum, cecum, ascending colon, transverse colon, descending colon, and sigmoid colon. The GI tissue may be, for example, GI tissue proximate to one or more sites of disease. Accordingly, in some embodiments the JAK inhibitor can penetrate the dudodenum tissue proximate to one or more sites of disease. In some embodiments the JAK inhibitor can penetrate the jejunum tissue proximate to one or more sites of disease. In some embodiments the JAK inhibitor can penetrate the ileum tissue proximate to one or more sites of disease. In some embodiments the JAK inhibitor can penetrate the cecum tissue proximate to one or more sites of disease. In some embodiments the JAK inhibitor can penetrate the ascending colon tissue proximate to one or more sites of disease. In some embodiments the JAK inhibitor can penetrate the transverse colon tissue proximate to one or more sites of disease. In some embodiments the JAK inhibitor can penetrate the descending colon tissue proximate to one or more sites of disease. In some embodiments the JAK inhibitor can penetrate the sigmoid colon tissue proximate to one or more sites of disease. For example, a JAK inhibitor can penetrate one or more (e.g., two, three, or four) of the lumen/superficial mucosa, the lamina propria, the submucosa, and the tunica muscularis/serosa.

In some examples, administration of a JAK inhibitor using any of the compositions or devices described herein results in penetration (e.g., a detectable level of penetration) of GI tissue (e.g., one or more (e.g., two, three, or four) of the lumen/superficial mucosa, the lamina propria, the submucosa, and the tunica muscularis/serosa) within a time period of about 10 minutes to about 10 hours, about 10 minutes to about 9 hours, about 10 minutes to about 8 hours, about 10 minutes to about 7 hours, about 10 minutes to about 6 hours, about 10 minutes to about 5 hours, about 10 minutes to about 4.5 hours, about 10 minutes to about 4 hours, about 10 minutes to about 3.5 hours, about 10 minutes to about 3 hours, about 10 minutes to about 2.5 hours, about 10 minutes to about 2 hours, about 10 minutes to about 1.5 hours, about 10 minutes to about 1 hour, about 10 minutes to about 55 minutes, about 10 minutes to about 50 minutes, about 10 minutes to about 45 minutes, about 10 minutes to about 40 minutes, about 10 minutes to about 35 minutes, about 10 minutes to about 30 minutes, about 10 minutes to about 25 minutes, about 10 minutes to about 20 minutes, about 10 minutes to about 15 minutes, about 15 minutes to about 10 hours, about 15 minutes to about 9 hours, about 15 minutes to about 8 hours, about 15 minutes to about 7 hours, about 15 minutes to about 6 hours, about 15 minutes to about 5 hours, about 15 minutes to about 4.5 hours, about 15 minutes to about 4 hours, about 15 minutes to about 3.5 hours, about 15 minutes to about 3 hours, about 15 minutes to about 2.5 hours, about 15 minutes to about 2 hours, about 15 minutes to about 1.5 hours, about 15 minutes to about 1 hour, about 15 minutes to about 55 minutes, about 15 minutes to about 50 minutes, about 15 minutes to about 45 minutes, about 15 minutes to about 40 minutes, about 15 minutes to about 35 minutes, about 15 minutes to about 30 minutes, about 15 minutes to about 25 minutes, about 15 minutes to about 20 minutes, about 20 minutes to about 10 hours, about 20 minutes to about 9 hours, about 20 minutes to about 8 hours, about 20 minutes to about 7 hours, about 20 minutes to about 6 hours, about 20 minutes to about 5 hours, about 20 minutes to about 4.5 hours, about 20 minutes to about 4 hours, about 20 minutes to about 3.5 hours, about 20 minutes to about 3 hours, about 20 minutes to about 2.5 hours, about 20 minutes to about 2 hours, about 20 minutes to about 1.5 hours, about 20 minutes to about 1 hour, about 20 minutes to about 55 minutes, about 20 minutes to about 50 minutes, about 20 minutes to about 45 minutes, about 20 minutes to about 40 minutes, about 20 minutes to about 35 minutes, about 20 minutes to about 30 minutes, about 20 minutes to about 25 minutes, about 25 minutes to about 10 hours, about 25 minutes to about 9 hours, about 25 minutes to about 8 hours, about 25 minutes to about 7 hours, about 25 minutes to about 6 hours, about 25 minutes to about 5 hours, about 25 minutes to about 4.5 hours, about 25 minutes to about 4 hours, about 25 minutes to about 3.5 hours, about 25 minutes to about 3 hours, about 25 minutes to about 2.5 hours, about 25 minutes to about 2 hours, about 25 minutes to about 1.5 hours, about 25 minutes to about 1 hour, about 25 minutes to about 55 minutes, about 25 minutes to about 50 minutes, about 25 minutes to about 45 minutes, about 25 minutes to about 40 minutes, about 25 minutes to about 35 minutes, about 25 minutes to about 30 minutes, about 30 minutes to about 10 hours, about 30 minutes to about 9 hours, about 30 minutes to about 8 hours, about 30 minutes to about 7 hours, about 30 minutes to about 6 hours, about 30 minutes to about 5 hours, about 30 minutes to about 4.5 hours, about 30 minutes to about 4 hours, about 30 minutes to about 3.5 hours, about 30 minutes to about 3 hours, about 30 minutes to about 2.5 hours, about 30 minutes to about 2 hours, about 30 minutes to about 1.5 hours, about 30 minutes to about 1 hour, about 30 minutes to about 55 minutes, about 30 minutes to about 50 minutes, about 30 minutes to about 45 minutes, about 30 minutes to about 40 minutes, about 30 minutes to about 35 minutes, about 35 minutes to about 10 hours, about 35 minutes to about 9 hours, about 35 minutes to about 8 hours, about 35 minutes to about 7 hours, about 35 minutes to about 6 hours, about 35 minutes to about 5 hours, about 35 minutes to about 4.5 hours, about 35 minutes to about 4 hours, about 35 minutes to about 3.5 hours, about 35 minutes to about 3 hours, about 35 minutes to about 2.5 hours, about 35 minutes to about 2 hours, about 35 minutes to about 1.5 hours, about 35 minutes to about 1 hour, about 35 minutes to about 55 minutes, about 35 minutes to about 50 minutes, about 35 minutes to about 45 minutes, about 35 minutes to about 40 minutes, about 40 minutes to about 10 hours, about 40 minutes to about 9 hours, about 40 minutes to about 8 hours, about 40 minutes to about 7 hours, about 40 minutes to about 6 hours, about 40 minutes to about 5 hours, about 40 minutes to about 4.5 hours, about 40 minutes to about 4 hours, about 40 minutes to about 3.5 hours, about 40 minutes to about 3 hours, about 40 minutes to about 2.5 hours, about 40 minutes to about 2 hours, about 40 minutes to about 1.5 hours, about 40 minutes to about 1 hour, about 40 minutes to about 55 minutes, about 40 minutes to about 50 minutes, about 40 minutes to about 45 minutes, about 45 minutes to about 10 hours, about 45 minutes to about 9 hours, about 45 minutes to about 8 hours, about 45 minutes to about 7 hours, about 45 minutes to about 6 hours, about 45 minutes to about 5 hours, about 45 minutes to about 4.5 hours, about 45 minutes to about 4 hours, about 45 minutes to about 3.5 hours, about 45 minutes to about 3 hours, about 45 minutes to about 2.5 hours, about 45 minutes to about 2 hours, about 45 minutes to about 1.5 hours, about 45 minutes to about 1 hour, about 45 minutes to about 55 minutes, about 45 minutes to about 50 minutes, about 50 minutes to about 10 hours, about 50 minutes to about 9 hours, about 50 minutes to about 8 hours, about 50 minutes to about 7 hours, about 50 minutes to about 6 hours, about 50 minutes to about 5 hours, about 50 minutes to about 4.5 hours, about 50 minutes to about 4 hours, about 50 minutes to about 3.5 hours, about 50 minutes to about 3 hours, about 50 minutes to about 2.5 hours, about 50 minutes to about 2 hours, about 50 minutes to about 1.5 hours, about 50 minutes to about 1 hour, about 50 minutes to about 55 minutes, about 55 minutes to about 10 hours, about 55 minutes to about 9 hours, about 55 minutes to about 8 hours, about 55 minutes to about 7 hours, about 55 minutes to about 6 hours, about 55 minutes to about 5 hours, about 55 minutes to about 4.5 hours, about 55 minutes to about 4 hours, about 55 minutes to about 3.5 hours, about 55 minutes to about 3 hours, about 55 minutes to about 2.5 hours, about 55 minutes to about 2 hours, about 55 minutes to about 1.5 hours, about 55 minutes to about 1 hour, about 1 hour to about 10 hours, about 1 hour to about 9 hours, about 1 hour to about 8 hours, about 1 hour to about 7 hours, about 1 hour to about 6 hours, about 1 hour to about 5 hours, about 1 hour to about 4.5 hours, about 1 hour to about 4 hours, about 1 hour to about 3.5 hours, about 1 hour to about 3 hours, about 1 hour to about 2.5 hours, about 1 hour to about 2 hours, about 1 hour to about 1.5 hours, about 1.5 hours to about 10 hours, about 1.5 hours to about 9 hours, about 1.5 hours to about 8 hours, about 1.5 hours to about 7 hours, about 1.5 hours to about 6 hours, about 1.5 hours to about 5 hours, about 1.5 hours to about 4.5 hours, about 1.5 hours to about 4 hours, about 1.5 hours to about 3.5 hours, about 1.5 hours to about 3 hours, about 1.5 hours to about 2.5 hours, about 1.5 hours to about 2 hours, about 2 hours to about 10 hours, about 2 hours to about 9 hours, about 2 hours to about 8 hours, about 2 hours to about 7 hours, about 2 hours to about 6 hours, about 2 hours to about 5 hours, about 2 hours to about 4.5 hours, about 2 hours to about 4 hours, about 2 hours to about 3.5 hours, about 2 hours to about 3 hours, about 2 hours to about 2.5 hours, about 2.5 hours to about 10 hours, about 2.5 hours to about 9 hours, about 2.5 hours to about 8 hours, about 2.5 hours to about 7 hours, about 2.5 hours to about 6 hours, about 2.5 hours to about 5 hours, about 2.5 hours to about 4.5 hours, about 2.5 hours to about 4 hours, about 2.5 hours to about 3.5 hours, about 2.5 hours to about 3 hours, about 3 hours to about 10 hours, about 3 hours to about 9 hours, about 3 hours to about 8 hours, about 3 hours to about 7 hours, about 3 hours to about 6 hours, about 3 hours to about 5 hours, about 3 hours to about 4.5 hours, about 3 hours to about 4 hours, about 3 hours to about 3.5 hours, about 3.5 hours to about 10 hours, about 3.5 hours to about 9 hours, about 3.5 hours to about 8 hours, about 3.5 hours to about 7 hours, about 3.5 hours to about 6 hours, about 3.5 hours to about 5 hours, about 3.5 hours to about 4.5 hours, about 3.5 hours to about 4 hours, about 4 hours to about 10 hours, about 4 hours to about 9 hours, about 4 hours to about 8 hours, about 4 hours to about 7 hours, about 4 hours to about 6 hours, about 4 hours to about 5 hours, about 4 hours to about 4.5 hours, about 4.5 hours to about 10 hours, about 4.5 hours to about 9 hours, about 4.5 hours to about 8 hours, about 4.5 hours to about 7 hours, about 4.5 hours to about 6 hours, about 4.5 hours to about 5 hours, about 5 hours to about 10 hours, about 5 hours to about 9 hours, about 5 hours to about 8 hours, about 5 hours to about 7 hours, about 5 hours to about 6 hours, about 6 hours to about 10 hours, about 6 hours to about 9 hours, about 6 hours to about 8 hours, about 6 hours to about 7 hours, about 7 hours to about 10 hours, about 7 hours to about 9 hours, about 7 hours to about 8 hours, about 8 hours to about 10 hours, about 8 hours to about 9 hours, or about 9 hours to about 10 hours. Penetration of GI tissue by a JAK inhibitor can be detected by administering a labeled JAK inhibitor, and performing imaging on the subject (e.g., ultrasound, computed tomography, or magnetic resonance imaging). For example, the label can be a radioisotope, a heavy metal, a fluorophore, or a luminescent agent (e.g., any suitable radioisotopes, heavy metals, fluorophores, or luminescent agents used for imaging known in the art).

While not wishing to be bound to a particular theory, the inventors contemplate that at or near the site of release a concentration gradient of the JAK inhibitor is generated in the mucosa, and that administration of a JAK inhibitor using a device as described herein advantageously results in a "reverse" concentration gradient when compared to the concentration gradient resulting from systemic administration. In such "reverse" concentration gradient, the drug concentration is highest from superficial to deep with respect to the mucosal surface. Systemic administration instead typically results in concentrations of the drug being highest from deep to superficial. A "reverse" concentration gradient as described above aligns more favorably with the pathophysiology of IBD.

In some embodiments, administration of a JAK inhibitor can provide for treatment (e.g., a reduction in the number, severity, and/or duration of one or more symptoms of any of the disorders described herein in a subject) for a time period of between about 1 hour to about 30 days, about 1 hour to about 28 days, about 1 hour to about 26 days, about 1 hour to about 24 days, about 1 hour to about 22 days, about 1 hour to about 20 days, about 1 hour to about 18 days, about 1 hour to about 16 days, about 1 hour to about 14 days, about 1 hour to about 12 days, about 1 hour to about 10 days, about 1 hour to about 8 days, about 1 hour to about 6 days, about 1 hour to about 5 days, about 1 hour to about 4 days, about 1 hour to about 3 days, about 1 hour to about 2 days, about 1 hour to about 1 day, about 1 hour to about 12 hours, about 1 hour to about 6 hours, about 1 hour to about 3 hours, about 3 hours to about 30 days, about 3 hours to about 28 days, about 3 hours to about 26 days, about 3 hours to about 24 days, about 3 hours to about 22 days, about 3 hours to about 20 days, about 3 hours to about 18 days, about 3 hours to about 16 days, about 3 hours to about 14 days, about 3 hours to about 12 days, about 3 hours to about 10 days, about 3 hours to about 8 days, about 3 hours to about 6 days, about 3 hours to about 5 days, about 3 hours to about 4 days, about 3 hours to about 3 days, about 3 hours to about 2 days, about 3 hours to about 1 day, about 3 hours to about 12 hours, about 3 hours to about 6 hours, about 6 hours to about 30 days, about 6 hours to about 28 days, about 6 hours to about 26 days, about 6 hours to about 24 days, about 6 hours to about 22 days, about 6 hours to about 20 days, about 6 hours to about 18 days, about 6 hours to about 16 days, about 6 hours to about 14 days, about 6 hours to about 12 days, about 6 hours to about 10 days, about 6 hours to about 8 days, about 6 hours to about 6 days, about 6 hours to about 5 days, about 6 hours to about 4 days, about 6 hours to about 3 days, about 6 hours to about 2 days, about 6 hours to about 1 day, about 6 hours to about 12 hours, about 12 hours to about 30 days, about 12 hours to about 28 days, about 12 hours to about 26 days, about 12 hours to about 24 days, about 12 hours to about 22 days, about 12 hours to about 20 days, about 12 hours to about 18 days, about 12 hours to about 16 days, about 12 hours to about 14 days, about 12 hours to about 12 days, about 12 hours to about 10 days, about 12 hours to about 8 days, about 12 hours to about 6 days, about 12 hours to about 5 days, about 12 hours to about 4 days, about 12 hours to about 3 days, about 12 hours to about 2 days, about 12 hours to about 1 day, about 1 day to about 30 days, about 1 day to about 28 days, about 1 day to about 26 days, about 1 day to about 24 days, about 1 day to about 22 days, about 1 day to about 20 days, about 1 day to about 18 days, about 1 day to about 16 days, about 1 day to about 14 days, about 1 day to about 12 days, about 1 day to about 10 days, about 1 day to about 8 days, about 1 day to about 6 days, about 1 day to about 5 days, about 1 day to about 4 days, about 1 day to about 3 days, about 1 day to about 2 days, about 2 days to about 30 days, about 2 days to about 28 days, about 2 days to about 26 days, about 2 days to about 24 days, about 2 days to about 22 days, about 2 days to about 20 days, about 2 days to about 18 days, about 2 days to about 16 days, about 2 days to about 14 days, about 2 days to about 12 days, about 2 days to about 10 days, about 2 days to about 8 days, about 2 days to about 6 days, about 2 days to about 5 days, about 2 days to about 4 days, about 2 days to about 3 days, about 3 days to about 30 days, about 3 days to about 28 days, about 3 days to about 26 days, about 3 days to about 24 days, about 3 days to about 22 days, about 3 days to about 20 days, about 3 days to about 18 days, about 3 days to about 16 days, about 3 days to about 14 days, about 3 days to about 12 days, about 3 days to about 10 days, about 3 days to about 8 days, about 3 days to about 6 days, about 3 days to about 5 days, about 3 days to about 4 days, about 4 days to about 30 days, about 4 days to about 28 days, about 4 days to about 26 days, about 4 days to about 24 days, about 4 days to about 22 days, about 4 days to about 20 days, about 4 days to about 18 days, about 4 days to about 16 days, about 4 days to about 14 days, about 4 days to about 12 days, about 4 days to about 10 days, about 4 days to about 8 days, about 4 days to about 6 days, about 4 days to about 5 days, about 5 days to about 30 days, about 5 days to about 28 days, about 5 days to about 26 days, about 5 days to about 24 days, about 5 days to about 22 days, about 5 days to about 20 days, about 5 days to about 18 days, about 5 days to about 16 days, about 5 days to about 14 days, about 5 days to about 12 days, about 5 days to about 10 days, about 5 days to about 8 days, about 5 days to about 6 days, about 6 days to about 30 days, about 6 days to about 28 days, about 6 days to about 26 days, about 6 days to about 24 days, about 6 days to about 22 days, about 6 days to about 20 days, about 6 days to about 18 days, about 6 days to about 16 days, about 6 days to about 14 days, about 6 days to about 12 days, about 6 days to about 10 days, about 6 days to about 8 days, about 8 days to about 30 days, about 8 days to about 28 days, about 8 days to about 26 days, about 8 days to about 24 days, about 8 days to about 22 days, about 8 days to about 20 days, about 8 days to about 18 days, about 8 days to about 16 days, about 8 days to about 14 days, about 8 days to about 12 days, about 8 days to about 10 days, about 10 days to about 30 days, about 10 days to about 28 days, about 10 days to about 26 days, about 10 days to about 24 days, about 10 days to about 22 days, about 10 days to about 20 days, about 10 days to about 18 days, about 10 days to about 16 days, about 10 days to about 14 days, about 10 days to about 12 days, about 12 days to about 30 days, about 12 days to about 28 days, about 12 days to about 26 days, about 12 days to about 24 days, about 12 days to about 22 days, about 12 days to about 20 days, about 12 days to about 18 days, about 12 days to about 16 days, about 12 days to about 14 days, about 14 days to about 30 days, about 14 days to about 28 days, about 14 days to about 26 days, about 14 days to about 24 days, about 14 days to about 22 days, about 14 days to about 20 days, about 14 days to about 18 days, about 14 days to about 16 days, about 16 days to about 30 days, about 16 days to about 28 days, about 16 days to about 26 days, about 16 days to about 24 days, about 16 days to about 22 days, about 16 days to about 20 days, about 16 days to about 18 days, about 18 days to about 30 days, about 18 days to about 28 days, about 18 days to about 26 days, about 18 days to about 24 days, about 18 days to about 22 days, about 18 days to about 20 days, about 20 days to about 30 days, about 20 days to about 28 days, about 20 days to about 26 days, about 20 days to about 24 days, about 20 days to about 22 days, about 22 days to about 30 days, about 22 days to about 28 days, about 22 days to about 26 days, about 22 days to about 24 days, about 24 days to about 30 days, about 24 days to about 28 days, about 24 days to about 26 days, about 26 days to about 30 days, about 26 days to about 28 days, or about 28 days to about 30 days in a subject following first administration of a JAK inhibitor using any of the compositions or devices described herein. Non-limiting examples of symptoms of a disease described herein are described below.

For example, treatment can result in a decrease (e.g., about 1% to about 99% decrease, about 1% to about 95% decrease, about 1% to about 90% decrease, about 1% to about 85% decrease, about 1% to about 80% decrease, about 1% to about 75% decrease, about 1% to about 70% decrease, about 1% to about 65% decrease, about 1% to about 60% decrease, about 1% to about 55% decrease, about 1% to about 50% decrease, about 1% to about 45% decrease, about 1% to about 40% decrease, about 1% to about 35% decrease, about 1% to about 30% decrease, about 1% to about 25% decrease, about 1% to about 20% decrease, about 1% to about 15% decrease, about 1% to about 10% decrease, about 1% to about 5% decrease, about 5% to about 99% decrease, about 5% to about 95% decrease, about 5% to about 90% decrease, about 5% to about 85% decrease, about 5% to about 80% decrease, about 5% to about 75% decrease, about 5% to about 70% decrease, about 5% to about 65% decrease, about 5% to about 60% decrease, about 5% to about 55% decrease, about 5% to about 50% decrease, about 5% to about 45% decrease, about 5% to about 40% decrease, about 5% to about 35% decrease, about 5% to about 30% decrease, about 5% to about 25% decrease, about 5% to about 20% decrease, about 5% to about 15% decrease, about 5% to about 10% decrease, about 10% to about 99% decrease, about 10% to about 95% decrease, about 10% to about 90% decrease, about 10% to about 85% decrease, about 10% to about 80% decrease, about 10% to about 75% decrease, about 10% to about 70% decrease, about 10% to about 65% decrease, about 10% to about 60% decrease, about 10% to about 55% decrease, about 10% to about 50% decrease, about 10% to about 45% decrease, about 10% to about 40% decrease, about 10% to about 35% decrease, about 10% to about 30% decrease, about 10% to about 25% decrease, about 10% to about 20% decrease, about 10% to about 15% decrease, about 15% to about 99% decrease, about 15% to about 95% decrease, about 15% to about 90% decrease, about 15% to about 85% decrease, about 15% to about 80% decrease, about 15% to about 75% decrease, about 15% to about 70% decrease, about 15% to about 65% decrease, about 15% to about 60% decrease, about 15% to about 55% decrease, about 15% to about 50% decrease, about 15% to about 45% decrease, about 15% to about 40% decrease, about 15% to about 35% decrease, about 15% to about 30% decrease, about 15% to about 25% decrease, about 15% to about 20% decrease, about 20% to about 99% decrease, about 20% to about 95% decrease, about 20% to about 90% decrease, about 20% to about 85% decrease, about 20% to about 80% decrease, about 20% to about 75% decrease, about 20% to about 70% decrease, about 20% to about 65% decrease, about 20% to about 60% decrease, about 20% to about 55% decrease, about 20% to about 50% decrease, about 20% to about 45% decrease, about 20% to about 40% decrease, about 20% to about 35% decrease, about 20% to about 30% decrease, about 20% to about 25% decrease, about 25% to about 99% decrease, about 25% to about 95% decrease, about 25% to about 90% decrease, about 25% to about 85% decrease, about 25% to about 80% decrease, about 25% to about 75% decrease, about 25% to about 70% decrease, about 25% to about 65% decrease, about 25% to about 60% decrease, about 25% to about 55% decrease, about 25% to about 50% decrease, about 25% to about 45% decrease, about 25% to about 40% decrease, about 25% to about 35% decrease, about 25% to about 30% decrease, about 30% to about 99% decrease, about 30% to about 95% decrease, about 30% to about 90% decrease, about 30% to about 85% decrease, about 30% to about 80% decrease, about 30% to about 75% decrease, about 30% to about 70% decrease, about 30% to about 65% decrease, about 30% to about 60% decrease, about 30% to about 55% decrease, about 30% to about 50% decrease, about 30% to about 45% decrease, about 30% to about 40% decrease, about 30% to about 35% decrease, about 35% to about 99% decrease, about 35% to about 95% decrease, about 35% to about 90% decrease, about 35% to about 85% decrease, about 35% to about 80% decrease, about 35% to about 75% decrease, about 35% to about 70% decrease, about 35% to about 65% decrease, about 35% to about 60% decrease, about 35% to about 55% decrease, about 35% to about 50% decrease, about 35% to about 45% decrease, about 35% to about 40% decrease, about 40% to about 99% decrease, about 40% to about 95% decrease, about 40% to about 90% decrease, about 40% to about 85% decrease, about 40% to about 80% decrease, about 40% to about 75% decrease, about 40% to about 70% decrease, about 40% to about 65% decrease, about 40% to about 60% decrease, about 40% to about 55% decrease, about 40% to about 50% decrease, about 40% to about 45% decrease, about 45% to about 99% decrease, about 45% to about 95% decrease, about 45% to about 90% decrease, about 45% to about 85% decrease, about 45% to about 80% decrease, about 45% to about 75% decrease, about 45% to about 70% decrease, about 45% to about 65% decrease, about 45% to about 60% decrease, about 45% to about 55% decrease, about 45% to about 50% decrease, about 50% to about 99% decrease, about 50% to about 95% decrease, about 50% to about 90% decrease, about 50% to about 85% decrease, about 50% to about 80% decrease, about 50% to about 75% decrease, about 50% to about 70% decrease, about 50% to about 65% decrease, about 50% to about 60% decrease, about 50% to about 55% decrease, about 55% to about 99% decrease, about 55% to about 95% decrease, about 55% to about 90% decrease, about 55% to about 85% decrease, about 55% to about 80% decrease, about 55% to about 75% decrease, about 55% to about 70% decrease, about 55% to about 65% decrease, about 55% to about 60% decrease, about 60% to about 99% decrease, about 60% to about 95% decrease, about 60% to about 90% decrease, about 60% to about 85% decrease, about 60% to about 80% decrease, about 60% to about 75% decrease, about 60% to about 70% decrease, about 60% to about 65% decrease, about 65% to about 99% decrease, about 65% to about 95% decrease, about 65% to about 90% decrease, about 65% to about 85% decrease, about 65% to about 80% decrease, about 65% to about 75% decrease, about 65% to about 70% decrease, about 70% to about 99% decrease, about 70% to about 95% decrease, about 70% to about 90% decrease, about 70% to about 85% decrease, about 70% to about 80% decrease, about 70% to about 75% decrease, about 75% to about 99% decrease, about 75% to about 95% decrease, about 75% to about 90% decrease, about 75% to about 85% decrease, about 75% to about 80% decrease, about 80% to about 99% decrease, about 80% to about 95% decrease, about 80% to about 90% decrease, about 80% to about 85% decrease, about 85% to about 99% decrease, about 85% to about 95% decrease, about 85% to about 90% decrease, about 90% to about 99% decrease, about 90% to about 95% decrease, or about 95% to about 99% decrease) in one or more (e.g., two, three, four, five, six, seven, eight, or nine) of: the level of interferon-K in GI tissue, the level of IL-1p in GI tissue, the level of IL-6 in GI tissue, the level of IL-22 in GI tissue, the level of IL-17A in the GI tissue, the level of TNFI in GI tissue, the level of IL-2 in GI tissue, the number of Th memory cells in Peyer's patches, and the number of Th memory cells in mesentery lymph nodes, and endoscopy score in a subject (e.g., as compared to the level in the subject prior to treatment or compared to a subject or population of subjects having a similar disease but receiving a placebo or a different treatment) (e.g., for a time period of between about 1 hour to about 30 days (e.g., or any of the subranges herein) following the first administration of a JAK inhibitor using any of the compositions or devices described herein. Exemplary methods for determining the endoscopy score are described herein and other methods for determining the endoscopy score are known in the art. Exemplary methods for determining the levels of interferon-K, IL-1p, IL-6, IL-22, IL-17A, TNFI, and IL-2 are described herein. Additional methods for determining the levels of these cytokines are known in the art. Exemplary methods for determining the number of Th memory cells in Peyer's patches and mesentery lymph nodes are described herein. Additional methods for determining the number of Th memory cells in Peyer's patches and mesentery lymph nodes are known in the art.

In some examples, treatment can result in an increase (e.g., about 1% to about 500% increase, about 1% to about 400% increase, about 1% to about 300% increase, about 1% to about 200% increase, about 1% to about 150% increase, about 1% to about 100% increase, about 1% to about 90% increase, about 1% to about 80% increase, about 1% to about 70% increase, about 1% to about 60% increase, about 1% to about 50% increase, about 1% to about 40% increase, about 1% to about 30% increase, about 1% to about 20% increase, about 1% to about 10% increase, a 10% to about 500% increase, about 10% to about 400% increase, about 10% to about 300% increase, about 10% to about 200% increase, about 10% to about 150% increase, about 10% to about 100% increase, about 10% to about 90% increase, about 10% to about 80% increase, about 10% to about 70% increase, about 10% to about 60% increase, about 10% to about 50% increase, about 10% to about 40% increase, about 10% to about 30% increase, about 10% to about 20% increase, about 20% to about 500% increase, about 20% to about 400% increase, about 20% to about 300% increase, about 20% to about 200% increase, about 20% to about 150% increase, about 20% to about 100% increase, about 20% to about 90% increase, about 20% to about 80% increase, about 20% to about 70% increase, about 20% to about 60% increase, about 20% to about 50% increase, about 20% to about 40% increase, about 20% to about 30% increase, about 30% to about 500% increase, about 30% to about 400% increase, about 30% to about 300% increase, about 30% to about 200% increase, about 30% to about 150% increase, about 30% to about 100% increase, about 30% to about 90% increase, about 30% to about 80% increase, about 30% to about 70% increase, about 30% to about 60% increase, about 30% to about 50% increase, about 30% to about 40% increase, about 40% to about 500% increase, about 40% to about 400% increase, about 40% to about 300% increase, about 40% to about 200% increase, about 40% to about 150% increase, about 40% to about 100% increase, about 40% to about 90% increase, about 40% to about 80% increase, about 40% to about 70% increase, about 40% to about 60% increase, about 40% to about 50% increase, about 50% to about 500% increase, about 50% to about 400% increase, about 50% to about 300% increase, about 50% to about 200% increase, about 50% to about 150% increase, about 50% to about 100% increase, about 50% to about 90% increase, about 50% to about 80% increase, about 50% to about 70% increase, about 50% to about 60% increase, about 60% to about 500% increase, about 60% to about 400% increase, about 60% to about 300% increase, about 60% to about 200% increase, about 60% to about 150% increase, about 60% to about 100% increase, about 60% to about 90% increase, about 60% to about 80% increase, about 60% to about 70% increase, about 70% to about 500% increase, about 70% to about 400% increase, about 70% to about 300% increase, about 70% to about 200% increase, about 70% to about 150% increase, about 70% to about 100% increase, about 70% to about 90% increase, about 70% to about 80% increase, about 80% to about 500% increase, about 80% to about 400% increase, about 80% to about 300% increase, about 80% to about 200% increase, about 80% to about 150% increase, about 80% to about 100% increase, about 80% to about 90% increase, about 90% to about 500% increase, about 90% to about 400% increase, about 90% to about 300% increase, about 90% to about 200% increase, about 90% to about 150% increase, about 90% to about 100% increase, about 100% to about 500% increase, about 100% to about 400% increase, about 100% to about 300% increase, about 100% to about 200% increase, about 100% to about 150% increase, about 150% to about 500% increase, about 150% to about 400% increase, about 150% to about 300% increase, about 150% to about 200% increase, about 200% to about 500% increase, about 200% to about 400% increase, about 200% to about 300% increase, about 300% to about 500% increase, about 300% to about 400% increase, or about 400% to about 500% increase) in one or both of stool consistency score and weight of a subject (e.g., as compared to the level in the subject prior to treatment or compared to a subject or population of subjects having a similar disease but receiving a placebo or a different treatment) (e.g., for a time period of between about 1 hour to about 30 days (e.g., or any of the subranges herein) following the first administration of a JAK inhibitor using any of the compositions or devices described herein. Exemplary methods for determining stool consistency score are described herein. Additional methods for determining a stool consistency score are known in the art.

In some embodiments, administration of a JAK inhibitor using any of the devices or compositions described herein can result in a ratio of GI tissue concentration of the JAK inhibitor to the blood, serum, or plasma concentration of the JAK inhibitor that is higher than the same ratio when the JAK inhibitor is administered by traditional means (e.g., systemically or orally). Examples of a ratio of GI tissue concentration of the JAK inhibitor to the blood, serum, or plasma concentration of the JAK inhibitor include about 2 to about 600, about 2 to about 580, about 2 to about 560, about 2 to about 540, about 2 to about 520, about 2 to about 500, about 2 to about 480, about 2 to about 460, about 4 to about 440, about 2 to about 420, about 2 to about 400, about 2 to about 380, about 2 to about 360, about 2 to about 340, about 2 to about 320, about 2 to about 300, about 2 to about 280, about 2 to about 260, about 2 to about 240, about 2 to about 220, about 2 to about 200, about 2 to about 190, about 2 to about 180, about 2 to about 170, about 2 to about 160, about 2 to about 150, about 2 to about 140, about 2 to about 130, about 2 to about 120, about 2 to about 110, about 2 to about 100, about 2 to about 90, about 2 to about 80, about 2 to about 70, about 2 to about 60, about 2 to about 50, about 2 to about 40, about 2 to about 30, about 2 to about 20, about 2 to about 15, about 2 to about 10, about 2 to about 5, about 5 to about 600, about 5 to about 580, about 5 to about 560, about 5 to about 540, about 5 to about 520, about 5 to about 500, about 5 to about 480, about 5 to about 460, about 5 to about 440, about 5 to about 420, about 5 to about 400, about 5 to about 380, about 5 to about 360, about 5 to about 340, about 5 to about 320, about 5 to about 300, about 5 to about 280, about 5 to about 260, about 5 to about 240, about 5 to about 220, about 5 to about 200, about 5 to about 190, about 5 to about 180, about 5 to about 170, about 5 to about 160, about 5 to about 150, about 5 to about 140, about 5 to about 130, about 5 to about 120, about 5 to about 110, about 5 to about 100, about 5 to about 90, about 5 to about 80, about 5 to about 70, about 5 to about 60, about 5 to about 50, about 5 to about 40, about 5 to about 30, about 5 to about 20, about 5 to about 15, about 5 to about 10, about 10 to about 600, about 10 to about 580, about 10 to about 560, about 10 to about 540, about 10 to about 520, about 10 to about 500, about 10 to about 480, about 10 to about 460, about 10 to about 440, about 10 to about 420, about 10 to about 400, about 10 to about 380, about 10 to about 360, about 10 to about 340, about 10 to about 320, about 10 to about 300, about 10 to about 280, about 10 to about 260, about 10 to about 240, about 10 to about 220, about 10 to about 200, about 10 to about 190, about 10 to about 180, about 10 to about 170, about 10 to about 160, about 10 to about 150, about 10 to about 140, about 10 to about 130, about 10 to about 120, about 10 to about 110, about 10 to about 100, about 10 to about 90, about 10 to about 80, about 10 to about 70, about 10 to about 60, about 10 to about 50, about 10 to about 40, about 10 to about 30, about 10 to about 20, about 10 to about 15, about 15 to about 600, about 15 to about 580, about 15 to about 560, about 15 to about 540, about 15 to about 520, about 15 to about 500, about 15 to about 480, about 15 to about 460, about 15 to about 440, about 15 to about 420, about 15 to about 400, about 15 to about 380, about 15 to about 360, about 15 to about 340, about 15 to about 320, about 15 to about 300, about 15 to about 280, about 15 to about 260, about 15 to about 240, about 15 to about 220, about 15 to about 200, about 15 to about 190, about 15 to about 180, about 15 to about 170, about 15 to about 160, about 15 to about 150, about 15 to about 140, about 15 to about 130, about 15 to about 120, about 15 to about 110, about 15 to about 100, about 15 to about 90, about 15 to about 80, about 15 to about 70, about 15 to about 60, about 15 to about 50, about 15 to about 40, about 15 to about 30, about 15 to about 20, about 20 to about 600, about 20 to about 580, about 20 to about 560, about 20 to about 540, about 20 to about 520, about 20 to about 500, about 20 to about 480, about 20 to about 460, about 20 to about 440, about 20 to about 420, about 20 to about 400, about 20 to about 380, about 20 to about 360, about 20 to about 340, about 20 to about 320, about 20 to about 300, about 20 to about 280, about 20 to about 260, about 20 to about 240, about 20 to about 220, about 20 to about 200, about 20 to about 190, about 20 to about 180, about 20 to about 170, about 20 to about 160, about 20 to about 150, about 20 to about 140, about 20 to about 130, about 20 to about 120, about 20 to about 110, about 20 to about 100, about 20 to about 90, about 20 to about 80, about 20 to about 70, about 20 to about 60, about 20 to about 50, about 20 to about 40, about 20 to about 30, about 30 to about 600, about 30 to about 580, about 30 to about 560, about 30 to about 540, about 30 to about 520, about 30 to about 500, about 30 to about 480, about 30 to about 460, about 30 to about 440, about 30 to about 420, about 30 to about 400, about 30 to about 380, about 30 to about 360, about 30 to about 340, about 30 to about 320, about 30 to about 300, about 30 to about 280, about 30 to about 260, about 30 to about 240, about 30 to about 220, about 30 to about 200, about 30 to about 190, about 30 to about 180, about 30 to about 170, about 30 to about 160, about 30 to about 150, about 30 to about 140, about 30 to about 130, about 30 to about 120, about 30 to about 110, about 30 to about 100, about 30 to about 90, about 30 to about 80, about 30 to about 70, about 30 to about 60, about 30 to about 50, about 30 to about 40, about 40 to about 600, about 40 to about 580, about 40 to about 560, about 40 to about 540, about 40 to about 520, about 40 to about 500, about 40 to about 480, about 40 to about 460, about 40 to about 440, about 40 to about 420, about 40 to about 400, about 40 to about 380, about 40 to about 360, about 40 to about 340, about 40 to about 320, about 40 to about 300, about 40 to about 280, about 40 to about 260, about 40 to about 240, about 40 to about 220, about 40 to about 200, about 40 to about 190, about 40 to about 180, about 40 to about 170, about 40 to about 160, about 40 to about 150, about 40 to about 140, about 40 to about 130, about 40 to about 120, about 40 to about 110, about 40 to about 100, about 40 to about 90, about 40 to about 80, about 40 to about 70, about 40 to about 60, about 40 to about 50, about 50 to about 600, about 50 to about 580, about 50 to about 560, about 50 to about 540, about 50 to about 520, about 50 to about 500, about 50 to about 480, about 50 to about 460, about 50 to about 440, about 50 to about 420, about 50 to about 400, about 50 to about 380, about 50 to about 360, about 50 to about 340, about 50 to about 320, about 50 to about 300, about 50 to about 280, about 50 to about 260, about 50 to about 240, about 50 to about 220, about 50 to about 200, about 50 to about 190, about 50 to about 180, about 50 to about 170, about 50 to about 160, about 50 to about 150, about 50 to about 140, about 50 to about 130, about 50 to about 120, about 50 to about 110, about 50 to about 100, about 50 to about 90, about 50 to about 80, about 50 to about 70, about 50 to about 60, about 60 to about 600, about 60 to about 580, about 60 to about 560, about 60 to about 540, about 60 to about 520, about 60 to about 500, about 60 to about 480, about 60 to about 460, about 60 to about 440, about 60 to about 420, about 60 to about 400, about 60 to about 380, about 60 to about 360, about 60 to about 340, about 60 to about 320, about 60 to about 300, about 60 to about 280, about 60 to about 260, about 60 to about 240, about 60 to about 220, about 60 to about 200, about 60 to about 190, about 60 to about 180, about 60 to about 170, about 60 to about 160, about 60 to about 150, about 60 to about 140, about 60 to about 130, about 60 to about 120, about 60 to about 110, about 60 to about 100, about 60 to about 90, about 60 to about 80, about 60 to about 70, about 70 to about 600, about 70 to about 580, about 70 to about 560, about 70 to about 540, about 70 to about 520, about 70 to about 500, about 70 to about 480, about 70 to about 460, about 70 to about 440, about 70 to about 420, about 70 to about 400, about 70 to about 380, about 70 to about 360, about 70 to about 340, about 70 to about 320, about 70 to about 300, about 70 to about 280, about 70 to about 260, about 70 to about 240, about 70 to about 220, about 70 to about 200, about 70 to about 190, about 70 to about 180, about 70 to about 170, about 70 to about 160, about 70 to about 150, about 70 to about 140, about 70 to about 130, about 70 to about 120, about 70 to about 110, about 70 to about 100, about 70 to about 90, about 70 to about 80, about 80 to about 600, about 80 to about 580, about 80 to about 560, about 80 to about 540, about 80 to about 520, about 80 to about 500, about 80 to about 480, about 80 to about 460, about 80 to about 440, about 80 to about 420, about 80 to about 400, about 80 to about 380, about 80 to about 360, about 80 to about 340, about 80 to about 320, about 80 to about 300, about 80 to about 280, about 80 to about 260, about 80 to about 240, about 80 to about 220, about 80 to about 200, about 80 to about 190, about 80 to about 180, about 80 to about 170, about 80 to about 160, about 80 to about 150, about 80 to about 140, about 80 to about 130, about 80 to about 120, about 80 to about 110, about 80 to about 100, about 80 to about 90, about 90 to about 600, about 90 to about 580, about 90 to about 560, about 90 to about 540, about 90 to about 520, about 90 to about 500, about 90 to about 480, about 90 to about 460, about 90 to about 440, about 90 to about 420, about 90 to about 400, about 90 to about 380, about 90 to about 360, about 90 to about 340, about 90 to about 320, about 90 to about 300, about 90 to about 280, about 90 to about 260, about 90 to about 240, about 90 to about 220, about 90 to about 200, about 90 to about 190, about 90 to about 180, about 90 to about 170, about 90 to about 160, about 90 to about 150, about 90 to about 140, about 90 to about 130, about 90 to about 120, about 90 to about 110, about 90 to about 100, about 100 to about 600, about 100 to about 580, about 100 to about 560, about 100 to about 540, about 100 to about 520, about 100 to about 500, about 100 to about 480, about 100 to about 460, about 100 to about 440, about 100 to about 420, about 100 to about 400, about 100 to about 380, about 100 to about 360, about 100 to about 340, about 100 to about 320, about 100 to about 300, about 100 to about 280, about 100 to about 260, about 100 to about 240, about 100 to about 220, about 100 to about 200, about 100 to about 190, about 100 to about 180, about 100 to about 170, about 100 to about 160, about 100 to about 150, about 100 to about 140, about 100 to about 130, about 100 to about 120, about 100 to about 110, about 110 to about 600, about 110 to about 580, about 110 to about 560, about 110 to about 540, about 110 to about 520, about 110 to about 500, about 110 to about 480, about 110 to about 460, about 110 to about 440, about 110 to about 420, about 110 to about 400, about 110 to about 380, about 110 to about 360, about 110 to about 340, about 110 to about 320, about 110 to about 300, about 110 to about 280, about 110 to about 260, about 110 to about 240, about 110 to about 220, about 110 to about 200, about 110 to about 190, about 110 to about 180, about 110 to about 170, about 110 to about 160, about 110 to about 150, about 110 to about 140, about 110 to about 130, about 110 to about 120, about 120 to about 600, about 120 to about 580, about 120 to about 560, about 120 to about 540, about 120 to about 520, about 120 to about 500, about 120 to about 480, about 120 to about 460, about 120 to about 440, about 120 to about 420, about 120 to about 400, about 120 to about 380, about 120 to about 360, about 120 to about 340, about 120 to about 320, about 120 to about 300, about 120 to about 280, about 120 to about 260, about 120 to about 240, about 120 to about 220, about 120 to about 200, about 120 to about 190, about 120 to about 180, about 120 to about 170, about 120 to about 160, about 120 to about 150, about 120 to about 140, about 120 to about 130, about 130 to about 600, about 130 to about 580, about 130 to about 560, about 130 to about 540, about 130 to about 520, about 130 to about 500, about 130 to about 480, about 130 to about 460, about 130 to about 440, about 130 to about 420, about 130 to about 400, about 130 to about 380, about 130 to about 360, about 130 to about 340, about 130 to about 320, about 130 to about 300, about 130 to about 280, about 130 to about 260, about 130 to about 240, about 130 to about 220, about 130 to about 200, about 130 to about 190, about 130 to about 180, about 130 to about 170, about 130 to about 160, about 130 to about 150, about 130 to about 140, about 140 to about 600, about 140 to about 580, about 140 to about 560, about 140 to about 540, about 140 to about 520, about 140 to about 500, about 140 to about 480, about 140 to about 460, about 140 to about 440, about 140 to about 420, about 140 to about 400, about 140 to about 380, about 140 to about 360, about 140 to about 340, about 140 to about 320, about 140 to about 300, about 140 to about 280, about 140 to about 260, about 140 to about 240, about 140 to about 220, about 140 to about 200, about 140 to about 190, about 140 to about 180, about 140 to about 170, about 140 to about 160, about 140 to about 150, about 150 to about 600, about 150 to about 580, about 150 to about 560, about 150 to about 540, about 150 to about 520, about 150 to about 500, about 150 to about 480, about 150 to about 460, about 150 to about 440, about 150 to about 420, about 150 to about 400, about 150 to about 380, about 150 to about 360, about 150 to about 340, about 150 to about 320, about 150 to about 300, about 150 to about 280, about 150 to about 260, about 150 to about 240, about 150 to about 220, about 150 to about 200, about 150 to about 190, about 150 to about 180, about 150 to about 170, about 150 to about 160, about 160 to about 600, about 160 to about 580, about 160 to about 560, about 160 to about 540, about 160 to about 520, about 160 to about 500, about 160 to about 480, about 160 to about 460, about 160 to about 440, about 160 to about 420, about 160 to about 400, about 160 to about 380, about 160 to about 360, about 160 to about 340, about 160 to about 320, about 160 to about 300, about 160 to about 280, about 160 to about 260, about 160 to about 240, about 160 to about 220, about 160 to about 200, about 160 to about 190, about 160 to about 180, about 160 to about 170, about 170 to about 600, about 170 to about 580, about 170 to about 560, about 170 to about 540, about 170 to about 520, about 170 to about 500, about 170 to about 480, about 170 to about 460, about 170 to about 440, about 170 to about 420, about 170 to about 400, about 170 to about 380, about 170 to about 360, about 170 to about 340, about 170 to about 320, about 170 to about 300, about 170 to about 280, about 170 to about 260, about 170 to about 240, about 170 to about 220, about 170 to about 200, about 170 to about 190, about 170 to about 180, about 180 to about 600, about 180 to about 580, about 180 to about 560, about 180 to about 540, about 180 to about 520, about 180 to about 500, about 180 to about 480, about 180 to about 460, about 180 to about 440, about 180 to about 420, about 180 to about 400, about 180 to about 380, about 180 to about 360, about 180 to about 340, about 180 to about 320, about 180 to about 300, about 180 to about 280, about 180 to about 260, about 180 to about 240, about 180 to about 220, about 180 to about 200, about 180 to about 190, about 190 to about 600, about 190 to about 580, about 190 to about 560, about 190 to about 540, about 190 to about 520, about 190 to about 500, about 190 to about 480, about 190 to about 460, about 190 to about 440, about 190 to about 420, about 190 to about 400, about 190 to about 380, about 190 to about 360, about 190 to about 340, about 190 to about 320, about 190 to about 300, about 190 to about 280, about 190 to about 260, about 190 to about 240, about 190 to about 220, about 190 to about 200, about 200 to about 600, about 200 to about 580, about 200 to about 560, about 200 to about 540, about 200 to about 520, about 200 to about 500, about 200 to about 480, about 200 to about 460, about 200 to about 440, about 200 to about 420, about 200 to about 400, about 200 to about 380, about 200 to about 360, about 200 to about 340, about 200 to about 320, about 200 to about 300, about 200 to about 280, about 200 to about 260, about 200 to about 240, about 200 to about 220, about 220 to about 600, about 220 to about 580, about 220 to about 560, about 220 to about 540, about 220 to about 520, about 220 to about 500, about 220 to about 480, about 220 to about 460, about 220 to about 440, about 220 to about 420, about 220 to about 400, about 220 to about 380, about 220 to about 360, about 220 to about 340, about 220 to about 320, about 220 to about 300, about 220 to about 280, about 220 to about 260, about 220 to about 240, about 240 to about 600, about 240 to about 580, about 240 to about 560, about 240 to about 540, about 240 to about 520, about 240 to about 500, about 240 to about 480, about 240 to about 460, about 240 to about 440, about 240 to about 420, about 240 to about 400, about 240 to about 380, about 240 to about 360, about 240 to about 340, about 240 to about 320, about 240 to about 300, about 240 to about 280, about 240 to about 260, about 260 to about 600, about 260 to about 580, about 260 to about 560, about 260 to about 540, about 260 to about 520, about 260 to about 500, about 260 to about 480, about 260 to about 460, about 260 to about 440, about 260 to about 420, about 260 to about 400, about 260 to about 380, about 260 to about 360, about 260 to about 340, about 260 to about 320, about 260 to about 300, about 260 to about 280, about 280 to about 600, about 280 to about 580, about 280 to about 560, about 280 to about 540, about 280 to about 520, about 280 to about 500, about 280 to about 480, about 280 to about 460, about 280 to about 440, about 280 to about 420, about 280 to about 400, about 280 to about 380, about 280 to about 360, about 280 to about 340, about 280 to about 320, about 280 to about 300, about 300 to about 600, about 300 to about 580, about 300 to about 560, about 300 to about 540, about 300 to about 520, about 300 to about 500, about 300 to about 480, about 300 to about 460, about 300 to about 440, about 300 to about 420, about 300 to about 400, about 300 to about 380, about 300 to about 360, about 300 to about 340, about 300 to about 320, about 320 to about 600, about 320 to about 580, about 320 to about 560, about 320 to about 540, about 320 to about 520, about 320 to about 500, about 320 to about 480, about 320 to about 460, about 320 to about 440, about 320 to about 420, about 320 to about 400, about 320 to about 380, about 320 to about 360, about 320 to about 340, about 340 to about 600, about 340 to about 580, about 340 to about 560, about 340 to about 540, about 340 to about 520, about 340 to about 500, about 340 to about 480, about 340 to about 460, about 340 to about 440, about 340 to about 420, about 340 to about 400, about 340 to about 380, about 340 to about 360, about 360 to about 600, about 360 to about 580, about 360 to about 560, about 360 to about 540, about 360 to about 520, about 360 to about 500, about 360 to about 480, about 360 to about 460, about 360 to about 440, about 360 to about 420, about 360 to about 400, about 360 to about 380, about 380 to about 600, about 380 to about 580, about 380 to about 560, about 380 to about 540, about 380 to about 520, about 380 to about 500, about 380 to about 480, about 380 to about 460, about 380 to about 440, about 380 to about 420, about 380 to about 400, about 400 to about 600, about 400 to about 580, about 400 to about 560, about 400 to about 540, about 400 to about 520, about 400 to about 500, about 400 to about 480, about 400 to about 460, about 400 to about 440, about 400 to about 420, about 420 to about 600, about 420 to about 580, about 420 to about 560, about 420 to about 540, about 420 to about 520, about 420 to about 500, about 420 to about 480, about 420 to about 460, about 420 to about 440, about 440 to about 600, about 440 to about 580, about 440 to about 560, about 440 to about 540, about 440 to about 520, about 440 to about 500, about 440 to about 480, about 440 to about 460, about 460 to about 600, about 460 to about 580, about 460 to about 560, about 460 to about 540, about 460 to about 520, about 460 to about 500, about 460 to about 480, about 480 to about 600, about 480 to about 580, about 480 to about 560, about 480 to about 540, about 480 to about 520, about 480 to about 500, about 500 to about 600, about 500 to about 580, about 500 to about 560, about 500 to about 540, about 500 to about 520, about 520 to about 600, about 520 to about 580, about 520 to about 560, about 520 to about 540, about 540 to about 600, about 540 to about 580, about 540 to about 560, about 560 to about 600, about 560 to about 580, or about 580 to about 600.

Additional examples of a ratio of GI tissue concentration of the JAK inhibitor to the blood, serum, or plasma concentration of the JAK inhibitor include to 1.1 to 600, 1.2 to 600, 1.3 to 600, 1.4 to 600, 1.5 to 600, 1.6 to 600, 1.7 to 600, 1.8 to 600, or 1.9 to 600, such as 1.1, 1.2, 1.3, 1.4, 1.5, 1.6, 1.7, 1.8, or 1.9.

In some examples, administration of a JAK inhibitor using any of the devices or compositions described herein can result in a ratio of GI tissue concentration of the JAK inhibitor to the blood, serum, or plasma concentration of the JAK inhibitor of, e.g., about 2.8 to about 6.0, about 2.8 to about 5.8, about 2.8 to about 5.6, about 2.8 to about 5.4, about 2.8 to about 5.2, about 2.8 to about 5.0, about 2.8 to about 4.8, about 2.8 to about 4.6, about 2.8 to about 4.4, about 2.8 to about 4.2, about 2.8 to about 4.0, about 2.8 to about 3.8, about 2.8 to about 3.6, about 2.8 to about 3.4, about 2.8 to about 3.2, about 2.8 to about 3.0, about 3.0 to about 6.0, about 3.0 to about 5.8, about 3.0 to about 5.6, about 3.0 to about 5.4, about 3.0 to about 5.2, about 3.0 to about 5.0, about 3.0 to about 4.8, about 3.0 to about 4.6, about 3.0 to about 4.4, about 3.0 to about 4.2, about 3.0 to about 4.0, about 3.0 to about 3.8, about 3.0 to about 3.6, about 3.0 to about 3.4, about 3.0 to about 3.2, about 3.2 to about 6.0, about 3.2 to about 5.8, about 3.2 to about 5.6, about 3.2 to about 5.4, about 3.2 to about 5.2, about 3.2 to about 5.0, about 3.2 to about 4.8, about 3.2 to about 4.6, about 3.2 to about 4.4, about 3.2 to about 4.2, about 3.2 to about 4.0, about 3.2 to about 3.8, about 3.2 to about 3.6, about 3.2 to about 3.4, about 3.4 to about 6.0, about 3.4 to about 5.8, about 3.4 to about 5.6, about 3.4 to about 5.4, about 3.4 to about 5.2, about 3.4 to about 5.0, about 3.4 to about 4.8, about 3.4 to about 4.6, about 3.4 to about 4.4, about 3.4 to about 4.2, about 3.4 to about 4.0, about 3.4 to about 3.8, about 3.4 to about 3.6, about 3.6 to about 6.0, about 3.6 to about 5.8, about 3.6 to about 5.6, about 3.6 to about 5.4, about 3.6 to about 5.2, about 3.6 to about 5.0, about 3.6 to about 4.8, about 3.6 to about 4.6, about 3.6 to about 4.4, about 3.6 to about 4.2, about 3.6 to about 4.0, about 3.6 to about 3.8, about 3.8 to about 6.0, about 3.8 to about 5.8, about 3.8 to about 5.6, about 3.8 to about 5.4, about 3.8 to about 5.2, about 3.8 to about 5.0, about 3.8 to about 4.8, about 3.8 to about 4.6, about 3.8 to about 4.4, about 3.8 to about 4.2, about 3.8 to about 4.0, about 4.0 to about 6.0, about 4.0 to about 5.8, about 4.0 to about 5.6, about 4.0 to about 5.4, about 4.0 to about 5.2, about 4.0 to about 5.0, about 4.0 to about 4.8, about 4.0 to about 4.6, about 4.0 to about 4.4, about 4.0 to about 4.2, about 4.2 to about 6.0, about 4.2 to about 5.8, about 4.2 to about 5.6, about 4.2 to about 5.4, about 4.2 to about 5.2, about 4.2 to about 5.0, about 4.2 to about 4.8, about 4.2 to about 4.6, about 4.2 to about 4.4, about 4.4 to about 6.0, about 4.4 to about 5.8, about 4.4 to about 5.6, about 4.4 to about 5.4, about 4.4 to about 5.2, about 4.4 to about 5.0, about 4.4 to about 4.8, about 4.4 to about 4.6, about 4.6 to about 6.0, about 4.6 to about 5.8, about 4.6 to about 5.6, about 4.6 to about 5.4, about 4.6 to about 5.2, about 4.6 to about 5.0, about 4.6 to about 4.8, about 4.8 to about 6.0, about 4.8 to about 5.8, about 4.8 to about 5.6, about 4.8 to about 5.4, about 4.8 to about 5.2, about 4.8 to about 5.0, about 5.0 to about 6.0, about 5.0 to about 5.8, about 5.0 to about 5.6, about 5.0 to about 5.4, about 5.0 to about 5.2, about 5.2 to about 6.0, about 5.2 to about 5.8, about 5.2 to about 5.6, about 5.2 to about 5.4, about 5.4 to about 6.0, about 5.4 to about 5.8, about 5.4 to about 5.6, about 5.6 to about 6.0, about 5.6 to about 5.8, or about 5.8 to about 6.0. Accordingly, in some embodiments, a method of treatment disclosed herein can include determining the ratio of the level of the JAK inhibitor in the GI tissue to the level of the JAK inhibitor in the blood, serum, or plasma of a subject at substantially the same time point following administration of the device is about 2.8 to about 6.0. Exemplary methods for measuring the concentration of a JAK inhibitor in the plasma or the GI tissue of a subject are described herein. Additional methods for measuring the concentration of a JAK inhibitor in the plasma or the GI tissue of a subject are known in the art.

Accordingly, in some embodiments, a method of treatment disclosed herein includes determining the level of the JAK inhibitor in the GI tissue (e.g., one or more of any of the exemplary GI tissues described herein). In some embodiments, a method of treatment disclosed herein can include determining the level of JAK inhibitor in one or more (e.g., two, three, or four) of the lumen/superficial mucosa, the lamina propria, the submucosa, and the tunica muscularis/serosa.

In some embodiments, a method of treatment disclosed herein includes determining that the level of the JAK inhibitor in the GI tissue (e.g., one or more of any of the exemplary types of GI tissues described herein) at a time point following administration of the device is higher than the level of JAK inhibitor in the GI tissue at substantially the same time point following systemic administration of an equal amount of the JAK inhibitor. In some embodiments, a method of treatment disclosed herein can include determining that the level of the JAK inhibitor in one or more (e.g., two, three, or four) of the lumen/superficial mucosa, the lamina propria, the submucosa, and the tunica muscularis/serosa at a time point following administration of the device is higher than the level of the JAK inhibitor in one or more (e.g., two, three, or four) of the lumen/superficial mucosa, the lamina propria, the submucosa, and the tunica muscularis/serosa at substantially the same time point following systemic administration of an equal amount of the JAK inhibitor.

In some embodiments, a method of treatment disclosed herein includes determining the level of JAK inhibitor in the feces of the subject. In some embodiments, a method of treatment disclosed herein includes determining the level of JAK inhibitor in the GI tissue, e.g., in one or more (e.g., two, three, or four) of the lumen/superficial mucosa, the lamina propria, the submucosa, and the tunica muscularis/serosa within a time period of about 10 minutes to about 10 hours following administration of the device.

In some embodiments, a method of treatment as disclosed herein comprises determining the level of the JAK inhibitor at the location of disease following administration of the device.

In some embodiments, a method of treatment as disclosed herein comprises determining that the level of JAK inhibitor at the location of disease at a time point following administration of the device is higher than the level of the JAK inhibitor at the same location of disease at substantially the same time point following systemic administration of an equal amount of the JAK inhibitor.

In some embodiments, a method of treatment as disclosed herein comprises determining that the level of JAK inhibitor in plasma in a subject at a time point following administration of the device is lower than the level of the JAK inhibitor in plasma in a subject at substantially the same time point following systemic administration of an equal amount of the JAK inhibitor.

In some embodiments, a method of treatment as disclosed herein comprises determining the level of the JAK inhibitor in the tissue of the subject within a time period of about 10 minutes to 10 hours following administration of the device.

Some examples of any of the methods described herein can, e.g., result in a selective suppression of a local inflammatory response (e.g., an inflammatory response in local GI tissue), while maintaining the systemic immune response (e.g., blood). The GI tissue may be, for example, GI tissue proximate to one or more sites of disease. FAs used herein, "GI content" refers to the content of the gastrointestinal (GI) tract, such as the content of one or more of duodenum, jejunum, ileum, cecum, ascending colon, transverse colon, descending colon, sigmoid colon, and rectum, more particularly of the proximal portion of one or more of duodenum, jejunum, ileum, cecum, ascending colon, transverse colon, descending colon, and sigmoid colon, or of the distal portion of one or more of duodenum, jejunum, ileum, cecum, ascending colon, transverse colon, descending colon, and sigmoid colon. Accordingly, in some embodiments, the methods described herein can result in a selective suppression of the inflammatory response in the dudodenum tissue proximate to one or more sites of disease, while maintaining the systemic immune response. In some embodiments, the methods described herein can result in a selective suppression of the inflammatory response in the jejunum tissue proximate to one or more sites of disease, while maintaining the systemic immune response. In some embodiments, the methods described herein can result in a selective suppression of the inflammatory response in the ileum tissue proximate to one or more sites of disease, while maintaining the systemic immune response. In some embodiments, the methods described herein can result in a selective suppression of the inflammatory response in the cecum tissue proximate to one or more sites of disease, while maintaining the systemic immune response. In some embodiments, the methods described herein can result in a selective suppression of the inflammatory response in the ascending colon tissue proximate to one or more sites of disease, while maintaining the systemic immune response. In some embodiments, the methods described herein can result in a selective suppression of the inflammatory response in the transverse colon tissue proximate to one or more sites of disease, while maintaining the systemic immune response. In some embodiments, the methods described herein can result in a selective suppression of the inflammatory response in the descending colon tissue proximate to one or more sites of disease, while maintaining the systemic immune response. In some embodiments, the methods described herein can result in a selective suppression of the inflammatory response in the sigmoid colon tissue proximate to one or more sites of disease, while maintaining the systemic immune response. In some examples, the methods described herein can result in a 1% increase to 500% increase (e.g., a 1% increase to 450% increase, a 1% increase to 400% increase, a 1% increase to 350% increase, a 1% increase to 300% increase, a 1% increase to 250% increase, a 1% increase to 200% increase, a 1% increase to 190% increase, a 1% increase to 180% increase, a 1% increase to 170% increase, a 1% increase to 160% increase, a 1% increase to 150% increase, a 1% increase to 140% increase, a 1% increase to 130% increase, a 1% increase to 120% increase, a 1% increase to 110% increase, a 1% increase to 100% increase, a 1% increase to 90% increase, a 1% increase to 80% increase, a 1% increase to 70% increase, a 1% increase to 60% increase, a 1% increase to 50% increase, a 1% increase to 40% increase, a 1% increase to 30% increase, a 1% increase to 25% increase, a 1% increase to 20% increase, a 1% increase to 15% increase, a 1% increase to 10% increase, a 1% increase to 5% increase, a 5% increase to 500% increase, a 5% increase to 450% increase, a 5% increase to 400% increase, a 5% increase to 350% increase, a 5% increase to 300% increase, a 5% increase to 250% increase, a 5% increase to 200% increase, a 5% increase to 190% increase, a 5% increase to 180% increase, a 5% increase to 170% increase, a 5% increase to 160% increase, a 5% increase to 150% increase, a 5% increase to 140% increase, a 5% increase to 130% increase, a 5% increase to 120% increase, a 5% increase to 110% increase, a 5% increase to 100% increase, a 5% increase to 90% increase, a 5% increase to 80% increase, a 5% increase to 70% increase, a 5% increase to 60% increase, a 5% increase to 50% increase, a 5% increase to 40% increase, a 5% increase to 30% increase, a 5% increase to 25% increase, a 5% increase to 20% increase, a 5% increase to 15% increase, a 5% increase to 10% increase, a 10% increase to 500% increase, a 10% increase to 450% increase, a 10% increase to 400% increase, a 10% increase to 350% increase, a 10% increase to 300% increase, a 10% increase to 250% increase, a 10% increase to 200% increase, a 10% increase to 190% increase, a 10% increase to 180% increase, a 10% increase to 170% increase, a 10% increase to 160% increase, a 10% increase to 150% increase, a 10% increase to 140% increase, a 10% increase to 130% increase, a 10% increase to 120% increase, a 10% increase to 110% increase, a 10% increase to 100% increase, a 10% increase to 90% increase, a 10% increase to 80% increase, a 10% increase to 70% increase, a 10% increase to 60% increase, a 10% increase to 50% increase, a 10% increase to 40% increase, a 10% increase to 30% increase, a 10% increase to 25% increase, a 10% increase to 20% increase, a 10% increase to 15% increase, a 15% increase to 500% increase, a 15% increase to 450% increase, a 15% increase to 400% increase, a 15% increase to 350% increase, a 15% increase to 300% increase, a 15% increase to 250% increase, a 15% increase to 200% increase, a 15% increase to 190% increase, a 15% increase to 180% increase, a 15% increase to 170% increase, a 15% increase to 160% increase, a 15% increase to 150% increase, a 15% increase to 140% increase, a 15% increase to 130% increase, a 15% increase to 120% increase, a 15% increase to 110% increase, a 15% increase to 100% increase, a 15% increase to 90% increase, a 15% increase to 80% increase, a 15% increase to 70% increase, a 15% increase to 60% increase, a 15% increase to 50% increase, a 15% increase to 40% increase, a 15% increase to 30% increase, a 15% increase to 25% increase, a 15% increase to 20% increase, a 20% increase to 500% increase, a 20% increase to 450% increase, a 20% increase to 400% increase, a 20% increase to 350% increase, a 20% increase to 300% increase, a 20% increase to 250% increase, a 20% increase to 200% increase, a 20% increase to 190% increase, a 20% increase to 180% increase, a 20% increase to 170% increase, a 20% increase to 160% increase, a 20% increase to 150% increase, a 20% increase to 140% increase, a 20% increase to 130% increase, a 20% increase to 120% increase, a 20% increase to 110% increase, a 20% increase to 100% increase, a 20% increase to 90% increase, a 20% increase to 80% increase, a 20% increase to 70% increase, a 20% increase to 60% increase, a 20% increase to 50% increase, a 20% increase to 40% increase, a 20% increase to 30% increase, a 20% increase to 25% increase, a 25% increase to 500% increase, a 25% increase to 450% increase, a 25% increase to 400% increase, a 25% increase to 350% increase, a 25% increase to 300% increase, a 25% increase to 250% increase, a 25% increase to 200% increase, a 25% increase to 190% increase, a 25% increase to 180% increase, a 25% increase to 170% increase, a 25% increase to 160% increase, a 25% increase to 150% increase, a 25% increase to 140% increase, a 25% increase to 130% increase, a 25% increase to 120% increase, a 25% increase to 110% increase, a 25% increase to 100% increase, a 25% increase to 90% increase, a 25% increase to 80% increase, a 25% increase to 70% increase, a 25% increase to 60% increase, a 25% increase to 50% increase, a 25% increase to 40% increase, a 25% increase to 30% increase, a 30% increase to 500% increase, a 30% increase to 450% increase, a 30% increase to 400% increase, a 30% increase to 350% increase, a 30% increase to 300% increase, a 30% increase to 250% increase, a 30% increase to 200% increase, a 30% increase to 190% increase, a 30% increase to 180% increase, a 30% increase to 170% increase, a 30% increase to 160% increase, a 30% increase to 150% increase, a 30% increase to 140% increase, a 30% increase to 130% increase, a 30% increase to 120% increase, a 30% increase to 110% increase, a 30% increase to 100% increase, a 30% increase to 90% increase, a 30% increase to 80% increase, a 30% increase to 70% increase, a 30% increase to 60% increase, a 30% increase to 50% increase, a 30% increase to 40% increase, a 40% increase to 500% increase, a 40% increase to 450% increase, a 40% increase to 400% increase, a 40% increase to 350% increase, a 40% increase to 300% increase, a 40% increase to 250% increase, a 40% increase to 200% increase, a 40% increase to 190% increase, a 40% increase to 180% increase, a 40% increase to 170% increase, a 40% increase to 160% increase, a 40% increase to 150% increase, a 40% increase to 140% increase, a 40% increase to 130% increase, a 40% increase to 120% increase, a 40% increase to 110% increase, a 40% increase to 100% increase, a 40% increase to 90% increase, a 40% increase to 80% increase, a 40% increase to 70% increase, a 40% increase to 60% increase, a 40% increase to 50% increase, a 50% increase to 500% increase, a 50% increase to 450% increase, a 50% increase to 400% increase, a 50% increase to 350% increase, a 50% increase to 300% increase, a 50% increase to 250% increase, a 50% increase to 200% increase, a 50% increase to 190% increase, a 50% increase to 180% increase, a 50% increase to 170% increase, a 50% increase to 160% increase, a 50% increase to 150% increase, a 50% increase to 140% increase, a 50% increase to 130% increase, a 50% increase to 120% increase, a 50% increase to 110% increase, a 50% increase to 100% increase, a 50% increase to 90% increase, a 50% increase to 80% increase, a 50% increase to 70% increase, a 50% increase to 60% increase, a 60% increase to 500% increase, a 60% increase to 450% increase, a 60% increase to 400% increase, a 60% increase to 350% increase, a 60% increase to 300% increase, a 60% increase to 250% increase, a 60% increase to 200% increase, a 60% increase to 190% increase, a 60% increase to 180% increase, a 60% increase to 170% increase, a 60% increase to 160% increase, a 60% increase to 150% increase, a 60% increase to 140% increase, a 60% increase to 130% increase, a 60% increase to 120% increase, a 60% increase to 110% increase, a 60% increase to 100% increase, a 60% increase to 90% increase, a 60% increase to 80% increase, a 60% increase to 70% increase, a 70% increase to 500% increase, a 70% increase to 450% increase, a 70% increase to 400% increase, a 70% increase to 350% increase, a 70% increase to 300% increase, a 70% increase to 250% increase, a 70% increase to 200% increase, a 70% increase to 190% increase, a 70% increase to 180% increase, a 70% increase to 170% increase, a 70% increase to 160% increase, a 70% increase to 150% increase, a 70% increase to 140% increase, a 70% increase to 130% increase, a 70% increase to 120% increase, a 70% increase to 110% increase, a 70% increase to 100% increase, a 70% increase to 90% increase, a 70% increase to 80% increase, a 80% increase to 500% increase, a 80% increase to 450% increase, a 80% increase to 400% increase, a 80% increase to 350% increase, a 80% increase to 300% increase, a 80% increase to 250% increase, a 80% increase to 200% increase, a 80% increase to 190% increase, a 80% increase to 180% increase, a 80% increase to 170% increase, a 80% increase to 160% increase, a 80% increase to 150% increase, a 80% increase to 140% increase, a 80% increase to 130% increase, a 80% increase to 120% increase, a 80% increase to 110% increase, a 80% increase to 100% increase, a 80% increase to 90% increase, a 90% increase to 500% increase, a 90% increase to 450% increase, a 90% increase to 400% increase, a 90% increase to 350% increase, a 90% increase to 300% increase, a 90% increase to 250% increase, a 90% increase to 200% increase, a 90% increase to 190% increase, a 90% increase to 180% increase, a 90% increase to 170% increase, a 90% increase to 160% increase, a 90% increase to 150% increase, a 90% increase to 140% increase, a 90% increase to 130% increase, a 90% increase to 120% increase, a 90% increase to 110% increase, a 90% increase to 100% increase, a 100% increase to 500% increase, a 100% increase to 450% increase, a 100% increase to 400% increase, a 100% increase to 350% increase, a 100% increase to 300% increase, a 100% increase to 250% increase, a 100% increase to 200% increase, a 100% increase to 190% increase, a 100% increase to 180% increase, a 100% increase to 170% increase, a 100% increase to 160% increase, a 100% increase to 150% increase, a 100% increase to 140% increase, a 100% increase to 130% increase, a 100% increase to 120% increase, a 100% increase to 110% increase, a 110% increase to 500% increase, a 110% increase to 450% increase, a 110% increase to 400% increase, a 110% increase to 350% increase, a 110% increase to 300% increase, a 110% increase to 250% increase, a 110% increase to 200% increase, a 110% increase to 190% increase, a 110% increase to 180% increase, a 110% increase to 170% increase, a 110% increase to 160% increase, a 110% increase to 150% increase, a 110% increase to 140% increase, a 110% increase to 130% increase, a 110% increase to 120% increase, a 120% increase to 500% increase, a 120% increase to 450% increase, a 120% increase to 400% increase, a 120% increase to 350% increase, a 120% increase to 300% increase, a 120% increase to 250% increase, a 120% increase to 200% increase, a 120% increase to 190% increase, a 120% increase to 180% increase, a 120% increase to 170% increase, a 120% increase to 160% increase, a 120% increase to 150% increase, a 120% increase to 140% increase, a 120% increase to 130% increase, a 130% increase to 500% increase, a 130% increase to 450% increase, a 130% increase to 400% increase, a 130% increase to 350% increase, a 130% increase to 300% increase, a 130% increase to 250% increase, a 130% increase to 200% increase, a 130% increase to 190% increase, a 130% increase to 180% increase, a 130% increase to 170% increase, a 130% increase to 160% increase, a 130% increase to 150% increase, a 130% increase to 140% increase, a 140% increase to 500% increase, a 140% increase to 450% increase, a 140% increase to 400% increase, a 140% increase to 350% increase, a 140% increase to 300% increase, a 140% increase to 250% increase, a 140% increase to 200% increase, a 140% increase to 190% increase, a 140% increase to 180% increase, a 140% increase to 170% increase, a 140% increase to 160% increase, a 140% increase to 150% increase, a 150% increase to 500% increase, a 150% increase to 450% increase, a 150% increase to 400% increase, a 150% increase to 350% increase, a 150% increase to 300% increase, a 150% increase to 250% increase, a 150% increase to 200% increase, a 150% increase to 190% increase, a 150% increase to 180% increase, a 150% increase to 170% increase, a 150% increase to 160% increase, a 160% increase to 500% increase, a 160% increase to 450% increase, a 160% increase to 400% increase, a 160% increase to 350% increase, a 160% increase to 300% increase, a 160% increase to 250% increase, a 160% increase to 200% increase, a 160% increase to 190% increase, a 160% increase to 180% increase, a 160% increase to 170% increase, a 170% increase to 500% increase, a 170% increase to 450% increase, a 170% increase to 400% increase, a 170% increase to 350% increase, a 170% increase to 300% increase, a 170% increase to 250% increase, a 170% increase to 200% increase, a 170% increase to 190% increase, a 170% increase to 180% increase, a 180% increase to 500% increase, a 180% increase to 450% increase, a 180% increase to 400% increase, a 180% increase to 350% increase, a 180% increase to 300% increase, a 180% increase to 250% increase, a 180% increase to 200% increase, a 180% increase to 190% increase, a 190% increase to 500% increase, a 190% increase to 450% increase, a 190% increase to 400% increase, a 190% increase to 350% increase, a 190% increase to 300% increase, a 190% increase to 250% increase, a 190% increase to 200% increase, a 200% increase to 500% increase, a 200% increase to 450% increase, a 200% increase to 400% increase, a 200% increase to 350% increase, a 200% increase to 300% increase, a 200% increase to 250% increase, a 250% increase to 500% increase, a 250% increase to 450% increase, a 250% increase to 400% increase, a 250% increase to 350% increase, a 250% increase to 300% increase, a 300% increase to 500% increase, a 300% increase to 450% increase, a 300% increase to 400% increase, a 300% increase to 350% increase, a 350% increase to 500% increase, a 350% increase to 450% increase, a 350% increase to 400% increase, a 400% increase to 500% increase, a 400% increase to 450% increase, or a 450% increase to 500% increase) in one or more (e.g., two, three, four, five, six, seven, eight, nine, or ten) of: the plasma, serum, or blood level of IL-6; the plasma, serum, or blood level of IL-2; the plasma, serum, or blood level of IL-1β; the plasma, serum, or blood level of TNFα; the plasma, serum, or blood level of IL-17A; the plasma, serum, or blood level of IL-22; the plasma, serum, or blood level of interferon-K; the level of blood Th memory cells ($CD44^{+}CD45RB^{-}CD4^{+}$ cells); and the level of α4β7 expression in blood cells; e.g., each as compared to the corresponding level in a subject systemically administered the same dose of the same JAK inhibitor. Methods for determining the plasma, serum, or blood level of IL-6; the plasma, serum, or blood level of IL-2; the plasma, serum, or blood level of IL-1β; the plasma, serum, or blood level of TNFα; the plasma, serum, or blood level of IL-17A; the plasma, serum, or blood level of IL-22; the plasma, serum, or blood level of interferon-K; the level of blood Th memory cells ($CD44^{+}CD45RB^{-}CD4^{+}$ cells); and the level of α4β7 expression in blood cells are known in the art.

In some examples of any of the methods described herein can result, e.g., in a 1% to 99% decrease (or any of the subranges of this range described herein) in one or more (e.g., two, three, four, five, six, or seven) of: the level of interferon-K in GI tissue or GI content; the level of IL-1β in GI tissue or GI content; the level of IL-6 in GI tissue or GI content; the level of IL-22 in GI tissue or GI content; the level of IL-17A in GI tissue or GI content; the level of TNFα in GI tissue or GI content; and the level of IL-2 in GI tissue or GI content, e.g., as compared to the corresponding level in a subject not administered a treatment, or not administered a JAK inhibitor locally as disclosed herein. Accordingly, in some embodiments, the methods described herein can result, e.g., in a 1% to 99% decrease (or any of the subranges of this range described herein) in one or more (e.g., two, three, four, five, six, or seven) of the level of interferon-K; the level of IL-1β; the level of IL-6; the level of IL-22; the level of IL-17A; the level of TNFα; and the level of IL-2, in the duodenum tissue proximate to one or more sites of disease. Accordingly, in some embodiments, the methods described herein can result, e.g., in a 1% to 99% decrease (or any of the subranges of this range described herein) in one or more (e.g., two, three, four, five, six, or seven) of the level of interferon-K; the level of IL-1β; the level of IL-6; the level of IL-22; the level of IL-17A; the level of TNFα; and the level of IL-2, in the ileum tissue proximate to one or more sites of disease. Accordingly, in some embodiments, the methods described herein can result, e.g., in a 1% to 99% decrease (or any of the subranges of this range described herein) in one or more (e.g., two, three, four, five, six, or seven) of the level of interferon-K; the level of IL-1β; the level of IL-6; the level of IL-22; the level of IL-17A; the level of TNFα; and the level of IL-2, in the jejunum tissue proximate to one or more sites of disease. Accordingly, in some embodiments, the methods described herein can result, e.g., in a 1% to 99% decrease (or any of the subranges of this range described herein) in one or more (e.g., two, three, four, five, six, or seven) of the level of interferon-K; the level of IL-1β; the level of IL-6; the level of IL-22; the level of IL-17A; the level of TNFα; and the level of IL-2, in the cecum tissue proximate to one or more sites of disease. Accordingly, in some embodiments, the methods described herein can result, e.g., in a 1% to 99% decrease (or any of the subranges of this range described herein) in one or more (e.g., two, three, four, five, six, or seven) of the level of interferon-K; the level of IL-1β; the level of IL-6; the level of IL-22; the level of IL-17A; the level of TNFα; and the level of IL-2, in the ascending colon tissue proximate to one or more sites of disease. Accordingly, in some embodiments, the methods described herein can result, e.g., in a 1% to 99% decrease (or any of the subranges of this range described herein) in one or more (e.g., two, three, four, five, six, or seven) of the level of interferon-K; the level of IL-1β; the level of IL-6; the level of IL-22; the level of IL-17A; the level of TNFα; and the level of IL-2, in the transverse colon tissue proximate to one or more sites of disease. Accordingly, in some embodiments, the methods described herein can result, e.g., in a 1% to 99% decrease (or any of the subranges of this range described herein) in one or more (e.g., two, three, four, five, six, or seven) of the level of interferon-K; the level of IL-1β; the level of IL-6; the level of IL-22; the level of IL-17A; the level of TNFα; and the level of IL-2, in the descending colon tissue proximate to one or more sites of disease. Accordingly, in some embodiments, the methods described herein can result, e.g., in a 1% to 99% decrease (or any of the subranges of this range described herein) in one or more (e.g., two, three, four, five, six, or seven) of the level of interferon-K; the level of IL-1β; the level of IL-6; the level of IL-22; the level of IL-17A; the level of TNFα; and the level of IL-2, in the sigmoid colon tissue proximate to one or more sites of disease.

In some embodiments, the JAK inhibitor is delivered to the location by a process that does not comprise systemic transport of the JAK inhibitor.

In some embodiments, the amount of the JAK inhibitor that is administered is from about 1 mg to about 500 mg. In some embodiments, the amount of the JAK inhibitor that is administered is from about 1 mg to about 100 mg. In some embodiments, the amount of the JAK inhibitor that is administered is from about 10 mg to about 300 mg. In some embodiments, the amount of the JAK inhibitor that is administered is from about 5 mg to about 50 mg. In some embodiments, the amount of the JAK inhibitor that is administered is from about 10 mg to about 50 mg. In some embodiments, the amount of the JAK inhibitor that is administered is from about 5 mg to about 40 mg.

In some embodiments, the amount of the JAK inhibitor is administered as an escalating dose of 10 mg, followed by 20 mg, followed by 30 mg; or an escalating dose of 20 mg, followed by 30 mg, followed by 50 mg.

In some embodiments, the amount of the JAK inhibitor is administered in a dose of, e.g., about 1 mg to about 300 mg, about 1 mg to about 250 mg, about 1 mg to about 200 mg, about 1 mg to about 195 mg, about 1 mg to about 190 mg, about 1 mg to about 185 mg, about 1 mg to about 180 mg, about 1 mg to about 175 mg, about 1 mg to about 170 mg, about 1 mg to about 165 mg, about 1 mg to about 160 mg, about 1 mg to about 155 mg, about 1 mg to about 150 mg, about 1 mg to about 145 mg, about 1 mg to about 140 mg, about 1 mg to about 135 mg, about 1 mg to about 130 mg, about 1 mg to about 125 mg, about 1 mg to about 120 mg, about 1 mg to about 115 mg, about 1 mg to about 110 mg, about 1 mg to about 105 mg, about 1 mg to about 100 mg, about 1 mg to about 95 mg, about 1 mg to about 90 mg, about 1 mg to about 85 mg, about 1 mg to about 80 mg, about 1 mg to about 75 mg, about 1 mg to about 70 mg, about 1 mg to about 65 mg, about 1 mg to about 60 mg, about 1 mg to about 55 mg, about 1 mg to about 50 mg, about 1 mg to about 45 mg, about 1 mg to about 40 mg, about 1 mg to about 35 mg, about 1 mg to about 30 mg, about 1 mg to about 25 mg, about 1 mg to about 20 mg, about 1 mg to about 15 mg, about 1 mg to about 10 mg, about 1 mg to about 5 mg, about 5 mg to about 200 mg, about 5 mg to about 195 mg, about 5 mg to about 190 mg, about 5 mg to about 185 mg, about 5 mg to about 180 mg, about 5 mg to about 175 mg, about 5 mg to about 170 mg, about 5 mg to about 165 mg, about 5 mg to about 160 mg, about 5 mg to about 155 mg, about 5 mg to about 150 mg, about 5 mg to about 145 mg, about 5 mg to about 140 mg, about 5 mg to about 135 mg, about 5 mg to about 130 mg, about 5 mg to about 125 mg, about 5 mg to about 120 mg, about 5 mg to about 115 mg, about 5 mg to about 110 mg, about 5 mg to about 105 mg, about 5 mg to about 100 mg, about 5 mg to about 95 mg, about 5 mg to about 90 mg, about 5 mg to about 85 mg, about 5 mg to about 80 mg, about 5 mg to about 75 mg, about 5 mg to about 70 mg, about 5 mg to about 65 mg, about 5 mg to about 60 mg, about 5 mg to about 55 mg, about 5 mg to about 50 mg, about 5 mg to about 45 mg, about 5 mg to about 40 mg, about 5 mg to about 35 mg, about 5 mg to about 30 mg, about 5 mg to about 25 mg, about 5 mg to about 20 mg, about 5 mg to about 15 mg, about 5 mg to about 10 mg, about 10 mg to about 200 mg, about 10 mg to about 195 mg, about 10 mg to about 190 mg, about 10 mg to about 185 mg, about 10 mg to about 180 mg, about 10 mg to about 175 mg, about 10 mg to about 170 mg, about 10 mg to about 165 mg, about 10 mg to about 160 mg, about 10 mg to about 155 mg, about 10 mg to about 150 mg, about 10 mg to about 145 mg, about 10 mg to about 140 mg, about 10 mg to about 135 mg, about 10 mg to about 130 mg, about 10 mg to about 125 mg, about 10 mg to about 120 mg, about 10 mg to about 115 mg, about 10 mg to about 110 mg, about 10 mg to about 105 mg, about 10 mg to about 100 mg, about 10 mg to about 95 mg, about 10 mg to about 90 mg, about 10 mg to about 85 mg, about 10 mg to about 80 mg, about 10 mg to about 75 mg, about 10 mg to about 70 mg, about 10 mg to about 65 mg, about 10 mg to about 60 mg, about 10 mg to about 55 mg, about 10 mg to about 50 mg, about 10 mg to about 45 mg, about 10 mg to about 40 mg, about 10 mg to about 35 mg, about 10 mg to about 30 mg, about 10 mg to about 25 mg, about 10 mg to about 20 mg, about 10 mg to about 15 mg, about 15 mg to about 200 mg, about 15 mg to about 195 mg, about 15 mg to about 190 mg, about 15 mg to about 185 mg, about 15 mg to about 180 mg, about 15 mg to about 175 mg, about 15 mg to about 170 mg, about 15 mg to about 165 mg, about 15 mg to about 160 mg, about 15 mg to about 155 mg, about 15 mg to about 150 mg, about 15 mg to about 145 mg, about 15 mg to about 140 mg, about 15 mg to about 135 mg, about 15 mg to about 130 mg, about 15 mg to about 125 mg, about 15 mg to about 120 mg, about 15 mg to about 115 mg, about 15 mg to about 110 mg, about 15 mg to about 105 mg, about 15 mg to about 100 mg, about 15 mg to about 95 mg, about 15 mg to about 90 mg, about 15 mg to about 85 mg, about 15 mg to about 80 mg, about 15 mg to about 75 mg, about 15 mg to about 70 mg, about 15 mg to about 65 mg, about 15 mg to about 60 mg, about 15 mg to about 55 mg, about 15 mg to about 50 mg, about 15 mg to about 45 mg, about 15 mg to about 40 mg, about 15 mg to about 35 mg, about 15 mg to about 30 mg, about 15 mg to about 25 mg, about 15 mg to about 20 mg, about 20 mg to about 200 mg, about 20 mg to about 195 mg, about 20 mg to about 190 mg, about 20 mg to about 185 mg, about 20 mg to about 180 mg, about 20 mg to about 175 mg, about 20 mg to about 170 mg, about 20 mg to about 165 mg, about 20 mg to about 160 mg, about 20 mg to about 155 mg, about 20 mg to about 150 mg, about 20 mg to about 145 mg, about 20 mg to about 140 mg, about 20 mg to about 135 mg, about 20 mg to about 130 mg, about 20 mg to about 125 mg, about 20 mg to about 120 mg, about 20 mg to about 115 mg, about 20 mg to about 110 mg, about 20 mg to about 105 mg, about 20 mg to about 100 mg, about 20 mg to about 95 mg, about 20 mg to about 90 mg, about 20 mg to about 85 mg, about 20 mg to about 80 mg, about 20 mg to about 75 mg, about 20 mg to about 70 mg, about 20 mg to about 65 mg, about 20 mg to about 60 mg, about 20 mg to about 55 mg, about 20 mg to about 50 mg, about 20 mg to about 45 mg, about 20 mg to about 40 mg, about 20 mg to about 35 mg, about 20 mg to about 30 mg, about 20 mg to about 25 mg, about 25 mg to about 200 mg, about 25 mg to about 195 mg, about 25 mg to about 190 mg, about 25 mg to about 185 mg, about 25 mg to about 180 mg, about 25 mg to about 175 mg, about 25 mg to about 170 mg, about 25 mg to about 165 mg, about 25 mg to about 160 mg, about 25 mg to about 155 mg, about 25 mg to about 150 mg, about 25 mg to about 145 mg, about 25 mg to about 140 mg, about 25 mg to about 135 mg, about 25 mg to about 130 mg, about 25 mg to about 125 mg, about 25 mg to about 120 mg, about 25 mg to about 115 mg, about 25 mg to about 110 mg, about 25 mg to about 105 mg, about 25 mg to about 100 mg, about 25 mg to about 95 mg, about 25 mg to about 90 mg, about 25 mg to about 85 mg, about 25 mg to about 80 mg, about 25 mg to about 75 mg, about 25 mg to about 70 mg, about 25 mg to about 65 mg, about 25 mg to about 60 mg, about 25 mg to about 55 mg, about 25 mg to about 50 mg, about 25 mg to about 45 mg, about 25 mg to about 40 mg, about 25 mg to about 35 mg, about 25 mg to about 30 mg, about 30 mg to about 200 mg, about 30 mg to about 195 mg, about 30 mg to about 190 mg, about 30 mg to about 185 mg, about 30 mg to about 180 mg, about 30 mg to about 175 mg, about 30 mg to about 170 mg, about 30 mg to about 165 mg, about 30 mg to about 160 mg, about 30 mg to about 155 mg, about 30 mg to about 150 mg, about 30 mg to about 145 mg, about 30 mg to about 140 mg, about 30 mg to about 135 mg, about 30 mg to about 130 mg, about 30 mg to about 125 mg, about 30 mg to about 120 mg, about 30 mg to about 115 mg, about 30 mg to about 110 mg, about 30 mg to about 105 mg, about 30 mg to about 100 mg, about 30 mg to about 95 mg, about 30 mg to about 90 mg, about 30 mg to about 85 mg, about 30 mg to about 80 mg, about 30 mg to about 75 mg, about 30 mg to about 70 mg, about 30 mg to about 65 mg, about 30 mg to about 60 mg, about 30 mg to about 55 mg, about 30 mg to about 50 mg, about 30 mg to about 45 mg, about 30 mg to about 40 mg, about 30 mg to about 35 mg, about 35 mg to about 200 mg, about 35 mg to about 195 mg, about 35 mg to about 190 mg, about 35 mg to about 185 mg, about 35 mg to about 180 mg, about 35 mg to about 175 mg, about 35 mg to about 170 mg, about 35 mg to about 165 mg, about 35 mg to about 160 mg, about 35 mg to about 155 mg, about 35 mg to about 150 mg, about 35 mg to about 145 mg, about 35 mg to about 140 mg, about 35 mg to about 135 mg, about 35 mg to about 130 mg, about 35 mg to about 125 mg, about 35 mg to about 120 mg, about 35 mg to about 115 mg, about 35 mg to about 110 mg, about 35 mg to about 105 mg, about 35 mg to about 100 mg, about 35 mg to about 95 mg, about 35 mg to about 90 mg, about 35 mg to about 85 mg, about 35 mg to about 80 mg, about 35 mg to about 75 mg, about 35 mg to about 70 mg, about 35 mg to about 65 mg, about 35 mg to about 60 mg, about 35 mg to about 55 mg, about 35 mg to about 50 mg, about 35 mg to about 45 mg, about 35 mg to about 40 mg, about 40 mg to about 200 mg, about 40 mg to about 195 mg, about 40 mg to about 190 mg, about 40 mg to about 185 mg, about 40 mg to about 180 mg, about 40 mg to about 175 mg, about 40 mg to about 170 mg, about 40 mg to about 165 mg, about 40 mg to about 160 mg, about 40 mg to about 155 mg, about 40 mg to about 150 mg, about 40 mg to about 145 mg, about 40 mg to about 140 mg, about 40 mg to about 135 mg, about 40 mg to about 130 mg, about 40 mg to about 125 mg, about 40 mg to about 120 mg, about 40 mg to about 115 mg, about 40 mg to about 110 mg, about 40 mg to about 105 mg, about 40 mg to about 100 mg, about 40 mg to about 95 mg, about 40 mg to about 90 mg, about 40 mg to about 85 mg, about 40 mg to about 80 mg, about 40 mg to about 75 mg, about 40 mg to about 70 mg, about 40 mg to about 65 mg, about 40 mg to about 60 mg, about 40 mg to about 55 mg, about 40 mg to about 50 mg, about 40 mg to about 45 mg, about 45 mg to about 200 mg, about 45 mg to about 195 mg, about 45 mg to about 190 mg, about 45 mg to about 185 mg, about 45 mg to about 180 mg, about 45 mg to about 175 mg, about 45 mg to about 170 mg, about 45 mg to about 165 mg, about 45 mg to about 160 mg, about 45 mg to about 155 mg, about 45 mg to about 150 mg, about 45 mg to about 145 mg, about 45 mg to about 140 mg, about 45 mg to about 135 mg, about 45 mg to about 130 mg, about 45 mg to about 125 mg, about 45 mg to about 120 mg, about 45 mg to about 115 mg, about 45 mg to about 110 mg, about 45 mg to about 105 mg, about 45 mg to about 100 mg, about 45 mg to about 95 mg, about 45 mg to about 90 mg, about 45 mg to about 85 mg, about 45 mg to about 80 mg, about 45 mg to about 75 mg, about 45 mg to about 70 mg, about 45 mg to about 65 mg, about 45 mg to about 60 mg, about 45 mg to about 55 mg, about 45 mg to about 50 mg, about 50 mg to about 200 mg, about 50 mg to about 195 mg, about 50 mg to about 190 mg, about 50 mg to about 185 mg, about 50 mg to about 180 mg, about 50 mg to about 175 mg, about 50 mg to about 170 mg, about 50 mg to about 165 mg, about 50 mg to about 160 mg, about 50 mg to about 155 mg, about 50 mg to about 150 mg, about 50 mg to about 145 mg, about 50 mg to about 140 mg, about 50 mg to about 135 mg, about 50 mg to about 130 mg, about 50 mg to about 125 mg, about 50 mg to about 120 mg, about 50 mg to about 115 mg, about 50 mg to about 110 mg, about 50 mg to about 105 mg, about 50 mg to about 100 mg, about 50 mg to about 95 mg, about 50 mg to about 90 mg, about 50 mg to about 85 mg, about 50 mg to about 80 mg, about 50 mg to about 75 mg, about 50 mg to about 70 mg, about 50 mg to about 65 mg, about 50 mg to about 60 mg, about 50 mg to about 55 mg, about 55 mg to about 200 mg, about 55 mg to about 195 mg, about 55 mg to about 190 mg, about 55 mg to about 185 mg, about 55 mg to about 180 mg, about 55 mg to about 175 mg, about 55 mg to about 170 mg, about 55 mg to about 165 mg, about 55 mg to about 160 mg, about 55 mg to about 155 mg, about 55 mg to about 150 mg, about 55 mg to about 145 mg, about 55 mg to about 140 mg, about 55 mg to about 135 mg, about 55 mg to about 130 mg, about 55 mg to about 125 mg, about 55 mg to about 120 mg, about 55 mg to about 115 mg, about 55 mg to about 110 mg, about 55 mg to about 105 mg, about 55 mg to about 100 mg, about 55 mg to about 95 mg, about 55 mg to about 90 mg, about 55 mg to about 85 mg, about 55 mg to about 80 mg, about 55 mg to about 75 mg, about 55 mg to about 70 mg, about 55 mg to about 65 mg, about 55 mg to about 60 mg, about 60 mg to about 200 mg, about 60 mg to about 195 mg, about 60 mg to about 190 mg, about 60 mg to about 185 mg, about 60 mg to about 180 mg, about 60 mg to about 175 mg, about 60 mg to about 170 mg, about 60 mg to about 165 mg, about 60 mg to about 160 mg, about 60 mg to about 155 mg, about 60 mg to about 150 mg, about 60 mg to about 145 mg, about 60 mg to about 140 mg, about 60 mg to about 135 mg, about 60 mg to about 130 mg, about 60 mg to about 125 mg, about 60 mg to about 120 mg, about 60 mg to about 115 mg, about 60 mg to about 110 mg, about 60 mg to about 105 mg, about 60 mg to about 100 mg, about 60 mg to about 95 mg, about 60 mg to about 90 mg, about 60 mg to about 85 mg, about 60 mg to about 80 mg, about 60 mg to about 75 mg, about 60 mg to about 70 mg, about 60 mg to about 65 mg, about 65 mg to about 200 mg, about 65 mg to about 195 mg, about 65 mg to about 190 mg, about 65 mg to about 185 mg, about 65 mg to about 180 mg, about 65 mg to about 175 mg, about 65 mg to about 170 mg, about 65 mg to about 165 mg, about 65 mg to about 160 mg, about 65 mg to about 155 mg, about 65 mg to about 150 mg, about 65 mg to about 145 mg, about 65 mg to about 140 mg, about 65 mg to about 135 mg, about 65 mg to about 130 mg, about 65 mg to about 125 mg, about 65 mg to about 120 mg, about 65 mg to about 115 mg, about 65 mg to about 110 mg, about 65 mg to about 105 mg, about 65 mg to about 100 mg, about 65 mg to about 95 mg, about 65 mg to about 90 mg, about 65 mg to about 85 mg, about 65 mg to about 80 mg, about 65 mg to about 75 mg, about 65 mg to about 70 mg, about 70 mg to about 200 mg, about 70 mg to about 195 mg, about 70 mg to about 190 mg, about 70 mg to about 185 mg, about 70 mg to about 180 mg, about 70 mg to about 175 mg, about 70 mg to about 170 mg, about 70 mg to about 165 mg, about 70 mg to about 160 mg, about 70 mg to about 155 mg, about 70 mg to about 150 mg, about 70 mg to about 145 mg, about 70 mg to about 140 mg, about 70 mg to about 135 mg, about 70 mg to about 130 mg, about 70 mg to about 125 mg, about 70 mg to about 120 mg, about 70 mg to about 115 mg, about 70 mg to about 110 mg, about 70 mg to about 105 mg, about 70 mg to about 100 mg, about 70 mg to about 95 mg, about 70 mg to about 90 mg, about 70 mg to about 85 mg, about 70 mg to about 80 mg, about 70 mg to about 75 mg, about 75 mg to about 200 mg, about 75 mg to about 195 mg, about 75 mg to about 190 mg, about 75 mg to about 185 mg, about 75 mg to about 180 mg, about 75 mg to about 175 mg, about 75 mg to about 170 mg, about 75 mg to about 165 mg, about 75 mg to about 160 mg, about 75 mg to about 155 mg, about 75 mg to about 150 mg, about 75 mg to about 145 mg, about 75 mg to about 140 mg, about 75 mg to about 135 mg, about 75 mg to about 130 mg, about 75 mg to about 125 mg, about 75 mg to about 120 mg, about 75 mg to about 115 mg, about 75 mg to about 110 mg, about 75 mg to about 105 mg, about 75 mg to about 100 mg, about 75 mg to about 95 mg, about 75 mg to about 90 mg, about 75 mg to about 85 mg, about 75 mg to about 80 mg, about 80 mg to about 200 mg, about 80 mg to about 195 mg, about 80 mg to about 190 mg, about 80 mg to about 185 mg, about 80 mg to about 180 mg, about 80 mg to about 175 mg, about 80 mg to about 170 mg, about 80 mg to about 165 mg, about 80 mg to about 160 mg, about 80 mg to about 155 mg, about 80 mg to about 150 mg, about 80 mg to about 145 mg, about 80 mg to about 140 mg, about 80 mg to about 135 mg, about 80 mg to about 130 mg, about 80 mg to about 125 mg, about 80 mg to about 120 mg, about 80 mg to about 115 mg, about 80 mg to about 110 mg, about 80 mg to about 105 mg, about 80 mg to about 100 mg, about 80 mg to about 95 mg, about 80 mg to about 90 mg, about 80 mg to about 85 mg, about 85 mg to about 200 mg, about 85 mg to about 195 mg, about 85 mg to about 190 mg, about 85 mg to about 185 mg, about 85 mg to about 180 mg, about 85 mg to about 175 mg, about 85 mg to about 170 mg, about 85 mg to about 165 mg, about 85 mg to about 160 mg, about 85 mg to about 155 mg, about 85 mg to about 150 mg, about 85 mg to about 145 mg, about 85 mg to about 140 mg, about 85 mg to about 135 mg, about 85 mg to about 130 mg, about 85 mg to about 125 mg, about 85 mg to about 120 mg, about 85 mg to about 115 mg, about 85 mg to about 110 mg, about 85 mg to about 105 mg, about 85 mg to about 100 mg, about 85 mg to about 95 mg, about 85 mg to about 90 mg, about 90 mg to about 200 mg, about 90 mg to about 195 mg, about 90 mg to about 190 mg, about 90 mg to about 185 mg, about 90 mg to about 180 mg, about 90 mg to about 175 mg, about 90 mg to about 170 mg, about 90 mg to about 165 mg, about 90 mg to about 160 mg, about 90 mg to about 155 mg, about 90 mg to about 150 mg, about 90 mg to about 145 mg, about 90 mg to about 140 mg, about 90 mg to about 135 mg, about 90 mg to about 130 mg, about 90 mg to about 125 mg, about 90 mg to about 120 mg, about 90 mg to about 115 mg, about 90 mg to about 110 mg, about 90 mg to about 105 mg, about 90 mg to about 100 mg, about 90 mg to about 95 mg, about 95 mg to about 200 mg, about 95 mg to about 195 mg, about 95 mg to about 190 mg, about 95 mg to about 185 mg, about 95 mg to about 180 mg, about 95 mg to about 175 mg, about 95 mg to about 170 mg, about 95 mg to about 165 mg, about 95 mg to about 160 mg, about 95 mg to about 155 mg, about 95 mg to about 150 mg, about 95 mg to about 145 mg, about 95 mg to about 140 mg, about 95 mg to about 135 mg, about 95 mg to about 130 mg, about 95 mg to about 125 mg, about 95 mg to about 120 mg, about 95 mg to about 115 mg, about 95 mg to about 110 mg, about 95 mg to about 105 mg, about 95 mg to about 100 mg, about 100 mg to about 200 mg, about 100 mg to about 195 mg, about 100 mg to about 190 mg, about 100 mg to about 185 mg, about 100 mg to about 180 mg, about 100 mg to about 175 mg, about 100 mg to about 170 mg, about 100 mg to about 165 mg, about 100 mg to about 160 mg, about 100 mg to about 155 mg, about 100 mg to about 150 mg, about 100 mg to about 145 mg, about 100 mg to about 140 mg, about 100 mg to about 135 mg, about 100 mg to about 130 mg, about 100 mg to about 125 mg, about 100 mg to about 120 mg, about 100 mg to about 115 mg, about 100 mg to about 110 mg, about 100 mg to about 105 mg, about 105 mg to about 200 mg, about 105 mg to about 195 mg, about 105 mg to about 190 mg, about 105 mg to about 185 mg, about 105 mg to about 180 mg, about 105 mg to about 175 mg, about 105 mg to about 170 mg, about 105 mg to about 165 mg, about 105 mg to about 160 mg, about 105 mg to about 155 mg, about 105 mg to about 150 mg, about 105 mg to about 145 mg, about 105 mg to about 140 mg, about 105 mg to about 135 mg, about 105 mg to about 130 mg, about 105 mg to about 125 mg, about 105 mg to about 120 mg, about 105 mg to about 115 mg, about 105 mg to about 110 mg, about 110 mg to about 200 mg, about 110 mg to about 195 mg, about 110 mg to about 190 mg, about 110 mg to about 185 mg, about 110 mg to about 180 mg, about 110 mg to about 175 mg, about 110 mg to about 170 mg, about 110 mg to about 165 mg, about 110 mg to about 160 mg, about 110 mg to about 155 mg, about 110 mg to about 150 mg, about 110 mg to about 145 mg, about 110 mg to about 140 mg, about 110 mg to about 135 mg, about 110 mg to about 130 mg, about 110 mg to about 125 mg, about 110 mg to about 120 mg, about 110 mg to about 115 mg, about 115 mg to about 200 mg, about 115 mg to about 195 mg, about 115 mg to about 190 mg, about 115 mg to about 185 mg, about 115 mg to about 180 mg, about 115 mg to about 175 mg, about 115 mg to about 170 mg, about 115 mg to about 165 mg, about 115 mg to about 160 mg, about 115 mg to about 155 mg, about 115 mg to about 150 mg, about 115 mg to about 145 mg, about 115 mg to about 140 mg, about 115 mg to about 135 mg, about 115 mg to about 130 mg, about 115 mg to about 125 mg, about 115 mg to about 120 mg, about 120 mg to about 200 mg, about 120 mg to about 195 mg, about 120 mg to about 190 mg, about 120 mg to about 185 mg, about 120 mg to about 180 mg, about 120 mg to about 175 mg, about 120 mg to about 170 mg, about 120 mg to about 165 mg, about 120 mg to about 160 mg, about 120 mg to about 155 mg, about 120 mg to about 150 mg, about 120 mg to about 145 mg, about 120 mg to about 140 mg, about 120 mg to about 135 mg, about 120 mg to about 130 mg, about 120 mg to about 125 mg, about 125 mg to about 200 mg, about 125 mg to about 195 mg, about 125 mg to about 190 mg, about 125 mg to about 185 mg, about 125 mg to about 180 mg, about 125 mg to about 175 mg, about 125 mg to about 170 mg, about 125 mg to about 165 mg, about 125 mg to about 160 mg, about 125 mg to about 155 mg, about 125 mg to about 150 mg, about 125 mg to about 145 mg, about 125 mg to about 140 mg, about 125 mg to about 135 mg, about 125 mg to about 130 mg, about 130 mg to about 200 mg, about 130 mg to about 195 mg, about 130 mg to about 190 mg, about 130 mg to about 185 mg, about 130 mg to about 180 mg, about 130 mg to about 175 mg, about 130 mg to about 170 mg, about 130 mg to about 165 mg, about 130 mg to about 160 mg, about 130 mg to about 155 mg, about 130 mg to about 150 mg, about 130 mg to about 145 mg, about 130 mg to about 140 mg, about 130 mg to about 135 mg, about 135 mg to about 200 mg, about 135 mg to about 195 mg, about 135 mg to about 190 mg, about 135 mg to about 185 mg, about 135 mg to about 180 mg, about 135 mg to about 175 mg, about 135 mg to about 170 mg, about 135 mg to about 165 mg, about 135 mg to about 160 mg, about 135 mg to about 155 mg, about 135 mg to about 150 mg, about 135 mg to about 145 mg, about 135 mg to about 140 mg, about 140 mg to about 200 mg, about 140 mg to about 195 mg, about 140 mg to about 190 mg, about 140 mg to about 185 mg, about 140 mg to about 180 mg, about 140 mg to about 175 mg, about 140 mg to about 170 mg, about 140 mg to about 165 mg, about 140 mg to about 160 mg, about 140 mg to about 155 mg, about 140 mg to about 150 mg, about 140 mg to about 145 mg, about 145 mg to about 200 mg, about 145 mg to about 195 mg, about 145 mg to about 190 mg, about 145 mg to about 185 mg, about 145 mg to about 180 mg, about 145 mg to about 175 mg, about 145 mg to about 170 mg, about 145 mg to about 165 mg, about 145 mg to about 160 mg, about 145 mg to about 155 mg, about 145 mg to about 150 mg, about 150 mg to about 200 mg, about 150 mg to about 195 mg, about 150 mg to about 190 mg, about 150 mg to about 185 mg, about 150 mg to about 180 mg, about 150 mg to about 175 mg, about 150 mg to about 170 mg, about 150 mg to about 165 mg, about 150 mg to about 160 mg, about 150 mg to about 155 mg, about 155 mg to about 200 mg, about 155 mg to about 195 mg, about 155 mg to about 190 mg, about 155 mg to about 185 mg, about 155 mg to about 180 mg, about 155 mg to about 175 mg, about 155 mg to about 170 mg, about 155 mg to about 165 mg, about 155 mg to about 160 mg, about 160 mg to about 200 mg, about 160 mg to about 195 mg, about 160 mg to about 190 mg, about 160 mg to about 185 mg, about 160 mg to about 180 mg, about 160 mg to about 175 mg, about 160 mg to about 170 mg, about 160 mg to about 165 mg, about 165 mg to about 200 mg, about 165 mg to about 195 mg, about 165 mg to about 190 mg, about 165 mg to about 185 mg, about 165 mg to about 180 mg, about 165 mg to about 175 mg, about 165 mg to about 170 mg, about 170 mg to about 200 mg, about 170 mg to about 195 mg, about 170 mg to about 190 mg, about 170 mg to about 185 mg, about 170 mg to about 180 mg, about 170 mg to about 175 mg, about 175 mg to about 200 mg, about 175 mg to about 195 mg, about 175 mg to about 190 mg, about 175 mg to about 185 mg, about 175 mg to about 180 mg, about 180 mg to about 200 mg, about 180 mg to about 195 mg, about 180 mg to about 190 mg, about 180 mg to about 185 mg, about 185 mg to about 200 mg, about 185 mg to about 195 mg, about 185 mg to about 190 mg, about 190 mg to about 200 mg, about 190 mg to about 195 mg, or about 195 mg to about 200 mg.

In some embodiments the amount of the JAK inhibitor that is administered corresponds to a concentration as disclosed in US patent publication 20170260533A1, incorporated by reference herein in its entirety. In some embodiments the amount of the JAK inhibitor that is administered corresponds to a concentration of 25 nM per volume of mouse large intestine, 250 nM per volume of mouse large intestine, or 2500 nM per volume of mouse large intestine.

For example, the amount of the JAK inhibitor that, when administered, is calculated to result in, or results in, a concentration of the JAK inhibitor in one of the following ranges of concentrations in a human large intestine (e.g., an average adult human large intestine) of, e.g., about 5 nM to about 5000 nM, about 5 nM to about 4500 nM, about 5 nM to about 4,000 nM, about 5 nM to about 3,500 nM, about 5 nM to about 3,000 nM, about 5 nM to about 2,500 nM, about 5 nM to about 2,000 nM, about 5 nM to about 1,500 nM, about 5 nM to about 1,000 nM, about 5 nM to about 750 nM, about 5 nM to about 500 nM, about 5 nM to about 450 nM, about 5 nM to about 400 nM, about 5 nM to about 350 nM, about 5 nM to about 300 nM, about 5 nM to about 250 nM, about 5 nM to about 200 nM, about 5 nM to about 150 nM, about 5 nM to about 100 nM, about 5 nM to about 50 nM, about 5 nM to about 25 nM, about 25 nM to about 5000 nM, about 25 nM to about 4500 nM, about 25 nM to about 4,000 nM, about 25 nM to about 3,500 nM, about 25 nM to about 3,000 nM, about 25 nM to about 2,500 nM, about 25 nM to about 2,000 nM, about 25 nM to about 1,500 nM, about 25 nM to about 1,000 nM, about 25 nM to about 750 nM, about 25 nM to about 500 nM, about 25 nM to about 450 nM, about 25 nM to about 400 nM, about 25 nM to about 350 nM, about 25 nM to about 300 nM, about 25 nM to about 250 nM, about 25 nM to about 200 nM, about 25 nM to about 150 nM, about 25 nM to about 100 nM, about 25 nM to about 50 nM, about 50 nM to about 5000 nM, about 50 nM to about 4500 nM, about 50 nM to about 4,000 nM, about 50 nM to about 3,500 nM, about 50 nM to about 3,000 nM, about 50 nM to about 2,500 nM, about 50 nM to about 2,000 nM, about 50 nM to about 1,500 nM, about 50 nM to about 1,000 nM, about 50 nM to about 750 nM, about 50 nM to about 500 nM, about 50 nM to about 450 nM, about 50 nM to about 400 nM, about 50 nM to about 350 nM, about 50 nM to about 300 nM, about 50 nM to about 250 nM, about 50 nM to about 200 nM, about 50 nM to about 150 nM, about 50 nM to about 100 nM, about 100 nM to about 5000 nM, about 100 nM to about 4500 nM, about 100 nM to about 4,000 nM, about 100 nM to about 3,500 nM, about 100 nM to about 3,000 nM, about 100 nM to about 2,500 nM, about 100 nM to about 2,000 nM, about 100 nM to about 1,500 nM, about 100 nM to about 1,000 nM, about 100 nM to about 750 nM, about 100 nM to about 500 nM, about 100 nM to about 450 nM, about 100 nM to about 400 nM, about 100 nM to about 350 nM, about 100 nM to about 300 nM, about 100 nM to about 250 nM, about 100 nM to about 200 nM, about 100 nM to about 150 nM, about 150 nM to about 5000 nM, about 150 nM to about 4500 nM, about 150 nM to about 4,000 nM, about 150 nM to about 3,500 nM, about 150 nM to about 3,000 nM, about 150 nM to about 2,500 nM, about 150 nM to about 2,000 nM, about 150 nM to about 1,500 nM, about 150 nM to about 1,000 nM, about 150 nM to about 750 nM, about 150 nM to about 500 nM, about 150 nM to about 450 nM, about 150 nM to about 400 nM, about 150 nM to about 350 nM, about 150 nM to about 300 nM, about 150 nM to about 250 nM, about 150 nM to about 200 nM, about 200 nM to about 5000 nM, about 200 nM to about 4500 nM, about 200 nM to about 4,000 nM, about 200 nM to about 3,500 nM, about 200 nM to about 3,000 nM, about 200 nM to about 2,500 nM, about 200 nM to about 2,000 nM, about 200 nM to about 1,500 nM, about 200 nM to about 1,000 nM, about 200 nM to about 750 nM, about 200 nM to about 500 nM, about 200 nM to about 450 nM, about 200 nM to about 400 nM, about 200 nM to about 350 nM, about 200 nM to about 300 nM, or about 200 nM to about 250 nM.

In some embodiments the the amount of the JAK inhibitor that is administered corresponds to a concentration of 25 nM in 0.225 mL, 250 nM in 0.225 mL, or 2500 nM in 0.225 mL. In some embodiments the amount of the JAK inhibitor that is administered corresponds to a concentration of 25 nM in 1 $cm^3$, 250 nM in 1 $cm^3$, or 2500 nM in 1 $cm^3$. In some embodiments the amount of the JAK inhibitor that is administered corresponds to a concentration of 25 nM in 1.34 $cm^3$, 250 nM in 1.34 $cm^3$, or 2500 nM in 1.34 $cm^3$. In some embodiments, the the amount of the JAK inhibitor that is administered corresponds to a concentration of 25 nM in 0.225 mL, 250 nM in 0.225 mL, or 2500 nM in 0.225 mL. In some embodiments the the amount of the JAK inhibitor that is administered corresponds to a concentration of 0.005 mg/mL, 0.05 mg/mL, or 0.5 mg/mL. In some embodiments the JAK inhibitor is administered at a dose of 25 nM, 250 nM, or 2500 nM.

In some aspects of the foregoing embodiments the JAK inhibitor is a siRNA (e.g., a shRNA).

In some embodiments, the amount of the JAK inhibitor that is administered is less than an amount that is effective when the JAK inhibitor is delivered systemically.

In some embodiments, the subject is administered the dose of the JAK inhibitor once a day. In some embodiments, the subject is administered the dose of the JAK inhibitor once every two days.

In some embodiments, the amount of the JAK inhibitor that is administered is an induction dose. In some embodiments, such induction dose is effective to induce remission of the TNF and cytokine storm and healing of acute inflammation and lesions. In some embodiments, the induction dose is administered once a day. In some embodiments, the induction dose is administered once every two days. In some embodiments, the induction dose is administered once every three days. In some embodiments, the induction dose is administered once a week. In some embodiments, the induction dose is administered once a day, once every three days, or once a week, over a period of about 6-8 weeks.

In some embodiments, the method comprises administering (i) an amount of the JAK inhibitor that is an induction dose, and (ii) an amount of the JAK inhibitor that is a maintenance dose, in this order. In some embodiments, step (ii) is repeated one or more times. In some embodiments, the induction dose is equal to the maintenance dose. In some embodiments, the induction dose is greater than the maintenance dose. In some embodiments, the induction dose is five times greater than the maintenance dose. In some embodiments, the induction dose is two times greater than the maintenance dose.

In some embodiments, the induction dose is the same as or higher than an induction dose administered systemically for treatment of the same disorder to a subject. In more particular embodiments, the induction dose is the same as or higher than an induction dose administered systemically for treatment of the same disorder to a subject, and the maintenance dose is lower than the maintenance dose administered systemically for treatment of the same disorder to a subject. In some embodiments, the induction dose is the same as or higher than an induction dose administered systemically for treatment of the same disorder to a subject, and the maintenance dose is higher than the maintenance dose administered systemically for treatment of the same disorder to a subject.

In some embodiments an induction dose of JAK inhibitor and a maintenance dose of JAK inhibitor are each administered to the subject by administering a pharmaceutical composition comprising a therapeutically effective amount of the JAK inhibitor, wherein the pharmaceutical composition is a device. In some embodiments an induction dose of JAK inhibitor is administered to the subject in a different manner from the maintenance dose. As an example, the induction dose may be administered systemically. In some embodiments, the induction dose may be administered other than orally. As an example, the induction dose may be administered rectally. As an example, the induction dose may be administered intravenously. As an example, the induction dose may be administered subcutaneously. In some embodiments, the induction dose may be administered by spray catheter.

In some embodiments, the concentration of the JAK inhibitor delivered at the location in the gastrointestinal tract is 10%, 25%, 50%, 75%, 100%, 200%, 300%, 400%, 500%, 1000%, 2000% greater than the concentration of JAK inhibitor in plasma.

In some embodiments, the method provides a concentration of the JAK inhibitor at a location that is a site of disease or proximate to a site of disease that is 2-100 times greater than at a location that is not a site of disease or proximate to a site of disease.

In some embodiments, the method comprises delivering the JAK inhibitor at the location in the gastrointestinal tract as a single bolus.

In some embodiments, the method comprises delivering the JAK inhibitor at the location in the gastrointestinal tract as more than one bolus.

In some embodiments, the method comprises delivering the JAK inhibitor at the location in the gastrointestinal tract in a continuous manner.

In some embodiments, the method comprises delivering the JAK inhibitor at the location in the gastrointestinal tract over a time period of 20 or more minutes.

In some embodiments, the method provides a concentration of the JAK inhibitor in the plasma of the subject that is less than 10 μg/mL. In some embodiments, the method provides a concentration of the JAK inhibitor in the plasma of the subject that is less than 3 μg/mL. In some embodiments, the method provides a concentration of the JAK inhibitor in the plasma of the subject that is less than 1 μg/mL. In some embodiments, the method provides a concentration of the JAK inhibitor in the plasma of the subject that is less than 0.3 μg/mL. In some embodiments, the method provides a concentration of the JAK inhibitor in the plasma of the subject that is less than 0.1 μg/mL. In some embodiments, the method provides a concentration of the JAK inhibitor in the plasma of the subject that is less than 0.01 μg/mL. In some embodiments, the values of the concentration of the JAK inhibitor in the plasma of the subject provided herein refer to $C_{trough}$, that is, the lowest value of the concentration prior to administration of the next dose.

In some embodiments, the method provides a concentration of the JAK inhibitor in the plasma of the subject that is, e.g., about 1 ng/L to about 100 ng/mL, about 1 ng/mL to about 95 ng/mL, about 1 ng/mL to about 90 ng/mL, about 1 ng/mL to about 85 ng/mL, about 1 ng/mL to about 80 ng/mL, about 1 ng/mL to about 75 ng/mL, about 1 ng/mL to about 70 ng/mL, about 1 ng/mL to about 65 ng/mL, about 1 ng/mL to about 60 ng/mL, about 1 ng/mL to about 55 ng/mL, about 1 ng/mL to about 50 ng/mL, about 1 ng/mL to about 45 ng/mL, about 1 ng/mL to about 40 ng/mL, about 1 ng/mL to about 35 ng/mL, about 1 ng/mL to about 30 ng/mL, about 1 ng/mL to about 25 ng/mL, about 1 ng/mL to about 20 ng/mL, about 1 ng/mL to about 15 ng/mL, about 1 ng/mL to about 10 ng/mL, about 1 ng/mL to about 5 ng/mL, about 2 ng/L to about 100 ng/mL, about 2 ng/mL to about 95 ng/mL, about 2 ng/mL to about 90 ng/mL, about 2 ng/mL to about 85 ng/mL, about 2 ng/mL to about 80 ng/mL, about 2 ng/mL to about 75 ng/mL, about 2 ng/mL to about 70 ng/mL, about 2 ng/mL to about 65 ng/mL, about 2 ng/mL to about 60 ng/mL, about 2 ng/mL to about 55 ng/mL, about 2 ng/mL to about 50 ng/mL, about 2 ng/mL to about 45 ng/mL, about 2 ng/mL to about 40 ng/mL, about 2 ng/mL to about 35 ng/mL, about 2 ng/mL to about 30 ng/mL, about 2 ng/mL to about 25 ng/mL, about 2 ng/mL to about 20 ng/mL, about 2 ng/mL to about 15 ng/mL, about 2 ng/mL to about 10 ng/mL, about 2 ng/mL to about 5 ng/mL, about 5 ng/L to about 100 ng/mL, about 5 ng/mL to about 95 ng/mL, about 5 ng/mL to about 90 ng/mL, about 5 ng/mL to about 85 ng/mL, about 5 ng/mL to about 80 ng/mL, about 5 ng/mL to about 75 ng/mL, about 5 ng/mL to about 70 ng/mL, about 5 ng/mL to about 65 ng/mL, about 5 ng/mL to about 60 ng/mL, about 5 ng/mL to about 55 ng/mL, about 5 ng/mL to about 50 ng/mL, about 5 ng/mL to about 45 ng/mL, about 5 ng/mL to about 40 ng/mL, about 5 ng/mL to about 35 ng/mL, about 5 ng/mL to about 30 ng/mL, about 5 ng/mL to about 25 ng/mL, about 5 ng/mL to about 20 ng/mL, about 5 ng/mL to about 15 ng/mL, about 5 ng/mL to about 10 ng/mL, about 10 ng/L to about 100 ng/mL, about 10 ng/mL to about 95 ng/mL, about 10 ng/mL to about 90 ng/mL, about 10 ng/mL to about 85 ng/mL, about 10 ng/mL to about 80 ng/mL, about 10 ng/mL to about 75 ng/mL, about 10 ng/mL to about 70 ng/mL, about 10 ng/mL to about 65 ng/mL, about 10 ng/mL to about 60 ng/mL, about 10 ng/mL to about 55 ng/mL, about 10 ng/mL to about 50 ng/mL, about 10 ng/mL to about 45 ng/mL, about 10 ng/mL to about 40 ng/mL, about 10 ng/mL to about 35 ng/mL, about 10 ng/mL to about 30 ng/mL, about 10 ng/mL to about 25 ng/mL, about 10 ng/mL to about 20 ng/mL, about 10 ng/mL to about 15 ng/mL, about 15 ng/L to about 100 ng/mL, about 15 ng/mL to about 95 ng/mL, about 15 ng/mL to about 90 ng/mL, about 15 ng/mL to about 85 ng/mL, about 15 ng/mL to about 80 ng/mL, about 15 ng/mL to about 75 ng/mL, about 15 ng/mL to about 70 ng/mL, about 15 ng/mL to about 65 ng/mL, about 15 ng/mL to about 60 ng/mL, about 15 ng/mL to about 55 ng/mL, about 15 ng/mL to about 50 ng/mL, about 15 ng/mL to about 45 ng/mL, about 15 ng/mL to about 40 ng/mL, about 15 ng/mL to about 35 ng/mL, about 15 ng/mL to about 30 ng/mL, about 15 ng/mL to about 25 ng/mL, about 15 ng/mL to about 20 ng/mL, about 20 ng/L to about 100 ng/mL, about 20 ng/mL to about 95 ng/mL, about 20 ng/mL to about 90 ng/mL, about 20 ng/mL to about 85 ng/mL, about 20 ng/mL to about 80 ng/mL, about 20 ng/mL to about 75 ng/mL, about 20 ng/mL to about 70 ng/mL, about 20 ng/mL to about 65 ng/mL, about 20 ng/mL to about 60 ng/mL, about 20 ng/mL to about 55 ng/mL, about 20 ng/mL to about 50 ng/mL, about 20 ng/mL to about 45 ng/mL, about 20 ng/mL to about 40 ng/mL, about 20 ng/mL to about 35 ng/mL, about 20 ng/mL to about 30 ng/mL, about 20 ng/mL to about 25 ng/mL, about 25 ng/L to about 100 ng/mL, about 25 ng/mL to about 95 ng/mL, about 25 ng/mL to about 90 ng/mL, about 25 ng/mL to about 85 ng/mL, about 25 ng/mL to about 80 ng/mL, about 25 ng/mL to about 75 ng/mL, about 25 ng/mL to about 70 ng/mL, about 25 ng/mL to about 65 ng/mL, about 25 ng/mL to about 60 ng/mL, about 25 ng/mL to about 55 ng/mL, about 25 ng/mL to about 50 ng/mL, about 25 ng/mL to about 45 ng/mL, about 25 ng/mL to about 40 ng/mL, about 25 ng/mL to about 35 ng/mL, about 25 ng/mL to about 30 ng/mL, about 30 ng/L to about 100 ng/mL, about 30 ng/mL to about 95 ng/mL, about 30 ng/mL to about 90 ng/mL, about 30 ng/mL to about 85 ng/mL, about 30 ng/mL to about 80 ng/mL, about 30 ng/mL to about 75 ng/mL, about 30 ng/mL to about 70 ng/mL, about 30 ng/mL to about 65 ng/mL, about 30 ng/mL to about 60 ng/mL, about 30 ng/mL to about 55 ng/mL, about 30 ng/mL to about 50 ng/mL, about 30 ng/mL to about 45 ng/mL, about 30 ng/mL to about 40 ng/mL, about 30 ng/mL to about 35 ng/mL, about 35 ng/L to about 100 ng/mL, about 35 ng/mL to about 95 ng/mL, about 35 ng/mL to about 90 ng/mL, about 35 ng/mL to about 85 ng/mL, about 35 ng/mL to about 80 ng/mL, about 35 ng/mL to about 75 ng/mL, about 35 ng/mL to about 70 ng/mL, about 35 ng/mL to about 65 ng/mL, about 35 ng/mL to about 60 ng/mL, about 35 ng/mL to about 55 ng/mL, about 35 ng/mL to about 50 ng/mL, about 35 ng/mL to about 45 ng/mL, about 35 ng/mL to about 40 ng/mL, about 40 ng/L to about 100 ng/mL, about 40 ng/mL to about 95 ng/mL, about 40 ng/mL to about 90 ng/mL, about 40 ng/mL to about 85 ng/mL, about 40 ng/mL to about 80 ng/mL, about 40 ng/mL to about 75 ng/mL, about 40 ng/mL to about 70 ng/mL, about 40 ng/mL to about 65 ng/mL, about 40 ng/mL to about 60 ng/mL, about 40 ng/mL to about 55 ng/mL, about 40 ng/mL to about 50 ng/mL, about 40 ng/mL to about 45 ng/mL, about 45 ng/L to about 100 ng/mL, about 45 ng/mL to about 95 ng/mL, about 45 ng/mL to about 90 ng/mL, about 45 ng/mL to about 85 ng/mL, about 45 ng/mL to about 80 ng/mL, about 45 ng/mL to about 75 ng/mL, about 45 ng/mL to about 70 ng/mL, about 45 ng/mL to about 65 ng/mL, about 45 ng/mL to about 60 ng/mL, about 45 ng/mL to about 55 ng/mL, about 45 ng/mL to about 50 ng/mL, about 50 ng/L to about 100 ng/mL, about 50 ng/mL to about 95 ng/mL, about 50 ng/mL to about 90 ng/mL, about 50 ng/mL to about 85 ng/mL, about 50 ng/mL to about 80 ng/mL, about 50 ng/mL to about 75 ng/mL, about 50 ng/mL to about 70 ng/mL, about 50 ng/mL to about 65 ng/mL, about 50 ng/mL to about 60 ng/mL, about 50 ng/mL to about 55 ng/mL, about 55 ng/L to about 100 ng/mL, about 55 ng/mL to about 95 ng/mL, about 55 ng/mL to about 90 ng/mL, about 55 ng/mL to about 85 ng/mL, about 55 ng/mL to about 80 ng/mL, about 55 ng/mL to about 75 ng/mL, about 55 ng/mL to about 70 ng/mL, about 55 ng/mL to about 65 ng/mL, about 55 ng/mL to about 60 ng/mL, about 60 ng/L to about 100 ng/mL, about 60 ng/mL to about 95 ng/mL, about 60 ng/mL to about 90 ng/mL, about 60 ng/mL to about 85 ng/mL, about 60 ng/mL to about 80 ng/mL, about 60 ng/mL to about 75 ng/mL, about 60 ng/mL to about 70 ng/mL, about 60 ng/mL to about 65 ng/mL, about 65 ng/L to about 100 ng/mL, about 65 ng/mL to about 95 ng/mL, about 65 ng/mL to about 90 ng/mL, about 65 ng/mL to about 85 ng/mL, about 65 ng/mL to about 80 ng/mL, about 65 ng/mL to about 75 ng/mL, about 65 ng/mL to about 70 ng/mL, about 70 ng/L to about 100 ng/mL, about 70 ng/mL to about 95 ng/mL, about 70 ng/mL to about 90 ng/mL, about 70 ng/mL to about 85 ng/mL, about 70 ng/mL to about 80 ng/mL, about 70 ng/mL to about 75 ng/mL, about 75 ng/L to about 100 ng/mL, about 75 ng/mL to about 95 ng/mL, about 75 ng/mL to about 90 ng/mL, about 75 ng/mL to about 85 ng/mL, about 75 ng/mL to about 80 ng/mL, about 80 ng/L to about 100 ng/mL, about 80 ng/mL to about 95 ng/mL, about 80 ng/mL to about 90 ng/mL, about 80 ng/mL to about 85 ng/mL, about 85 ng/L to about 100 ng/mL, about 85 ng/mL to about 95 ng/mL, about 85 ng/mL to about 90 ng/mL, about 90 ng/L to about 100 ng/mL, about 90 ng/mL to about 95 ng/mL, or about 95 ng/mL to about 100 ng/mL.

In some embodiments, the method provides a concentration $C_{max}$ of the JAK inhibitor in the plasma of the subject that is less than 10 μg/mL. In some embodiments, the method provides a concentration $C_{max}$ of the JAK inhibitor in the plasma of the subject that is less than 3 μg/mL. In some embodiments, the method provides a concentration $C_{max}$ of the JAK inhibitor in the plasma of the subject that is less than 1 μg/mL. In some embodiments, the method provides a concentration $C_{max}$ of the JAK inhibitor in the plasma of the subject that is less than 0.3 μg/mL. In some embodiments, the method provides a concentration $C_{max}$ of the JAK inhibitor in the plasma of the subject that is less than 0.1 μg/mL. In some embodiments, the method provides a concentration $C_{max}$ of the JAK inhibitor in the plasma of the subject that is less than 0.01 μg/mL.

In some embodiments, the method does not comprise delivering a JAK inhibitor rectally to the subject.

In some embodiments, the method does not comprise delivering a JAK inhibitor via an enema to the subject.

In some embodiments, the method does not comprise delivering a JAK inhibitor via suppository to the subject.

In some embodiments, the method does not comprise delivering a JAK inhibitor via instillation to the rectum of a subject.

In some embodiments, the methods disclosed herein comprise producing a therapeutically effective degradation product of the JAK inhibitor in the gastrointestinal tract.

In some embodiments, a therapeutically effective amount of the degradation product is produced.

In some embodiments, the methods comprising administering the JAK inhibitor in the manner disclosed herein disclosed herein result in a reduced immunosuppressive properties relative to methods of administration of the JAK inhibitor systemically.

In some embodiments, the methods comprising administering the JAK inhibitor in the manner disclosed herein disclosed herein result in reduced immunogenicity relative to methods of administration of the JAK inhibitor systemically.

Methods for Treating Colitis in Subjects in Immune-Oncology Therapy

In some embodiments, provided herein is a method for treating colitis as disclosed herein in a subject, comprising releasing a JAK inhibitor at a location in the gastrointestinal tract of the subject that is proximate to one or more sites of disease, wherein the method comprises administering to the subject a pharmaceutical composition comprising a therapeutically effective amount of the JAK inhibitor, wherein the colitis is associated with treatment of the subject with one or more immuno-oncology agents. In some embodiments, the pharmaceutical composition is an ingestible device. In some embodiments, the pharmaceutical composition is an ingestible device and the method comprises administering orally to the subject the pharmaceutical composition.

In some embodiments, at least one of the one or more immuno-oncology agents is a chemotherapeutic agent. In some embodiments, the chemotherapeutic agent is a chemotherapeutic immunomodulator. In some embodiments, the chemotherapeutic immunomodulator is an immune checkpoint inhibitor.

In some embodiments, the immune checkpoint inhibitor targets an immune checkpoint protein or decreases an activity of an immune checkpoint protein selected from the group of CTLA-4, PD-1, PD-L1, PD-1-PD-L1, PD-1-PD-L2, interleukin 2 (IL 2), indoleamine 2,3-dioxygenase (IDO), IL 10, transforming growth factor-β (TGFβ), T cell immunoglobulin and mucin 3 (TIM3 or HAVCR2), Galectin 9-TIM3, Phosphatidylserine-TIM3, lymphocyte activation gene 3 protein (LAG3), MHC class II-LAG3, 4 113B-4 1BB ligand, OX40-OX40 ligand, GITR, GITR ligand-GITR, CD27, CD70-CD27, TNFRSF25, TNFRSF25-TL1A, CD40L, CD40-CD40 ligand, HVEM-LIGHT-LTA, HVEM, HVEM-BTLA, HVEM-CD160, HVEM-LIGHT, HVEM- BTLA-CD160, CD80, CD80-PDL-1, PDL2-CD80, CD244, CD48-CD244, CD244, ICOS, ICOS-ICOS ligand, B7 H3, B7 H4, VISTA, TMIGD2, HHLA2-TMIGD2, Butyrophilins, including BTNL2, Siglec family, TIGIT and PVR family members, KIRs, ILTs and LIRs, NKG2D and NKG2A, MICA and MICB, CD244, CD28, CD86-CD28, CD86-CTLA, CD80-CD28, CD39, CD73 Adenosine-CD39-CD73, CXCR4-CXCL12, Phosphatidylserine, TIM3, Phosphatidylserine-TIM3, SIRPA-CD47, VEGF, Neuropilin, CD160, CD30, and CD155.

In some examples, the immune checkpoint inhibitor is selected from the group consisting of: Urelumab, PF 05082566, MEDI6469, TRX518, Varlilumab, CP 870893, Pembrolizumab (PD1), Nivolumab (PD1), Atezolizumab (formerly MPDL3280A) (PDL1), MEDI4736 (PD-L1), Avelumab (PD-L 1), PDR001 (PD1), BMS 986016, MGA271, Lirilumab, IPH2201, Emactuzumab, INCB024360, Galunisertib, Ulocuplumab, BKT140, Bavituximab, CC 90002, Bevacizumab, and MNRP1685A, and MGA271.

In some examples, the immune checkpoint inhibitor targets or decreases an activity of CTLA-4. In some embodiments, the immune checkpoint inhibitor is an antibody. In some embodiments, the antibody is ipilimumab or tremelimumab.

In some examples, the immune checkpoint inhibitor targets PD1 or PD-L1. In some examples, the immune checkpoint inhibitor is selected from nivolumab, lambroizumab, and BMS-936559.

In some embodiments, at least one of the one or more immuno-oncology agents is a T-cell capable of expressing a chimeric antigen receptor (CAR). In some embodiments, at least one of the one or more immuno-oncology agents is a PI-3-kinase inhibitor.

In some embodiments, the treatment of the subject with one or more immuno-oncology agents further comprises treatment of the subject with an immunosuppressant.

In some embodiments, provided herein is a method for reducing the development of colitis in a subject administered an immuno-oncology agent, comprising releasing a JAK inhibitor at a location in the gastrointestinal tract of the subject that is proximate to one or more sites of disease, wherein the method comprises administering to the subject a pharmaceutical composition comprising a therapeutically effective amount of the JAK inhibitor. In some embodiments, the pharmaceutical composition is an ingestible device. In some embodiments, the pharmaceutical composition is an ingestible device and the method comprises administering orally to the subject the pharmaceutical composition.

In some embodiments of these methods, a subject is administered at least one dose of an immuno-oncology agent prior to administering a pharmaceutical composition comprising any of the devices described herein as described herein to the subject. In some embodiments of these methods, a subject is first administered any of the devices as described herein, prior to administration of the first dose of the immuno-oncology agent. In some embodiments of these methods, the immuno-oncology agent is administered at substantially the same time as the device described herein.

Also provided herein are methods of treating a subject having a cancer that include: administering a first dose of an immuno-oncology agent to the subject; monitoring one or more biomarkers, markers, or symptoms of colitis (e.g., any of the biomarkers, markers, or symptoms of colitis described herein or known in the art); identifying a subject having a level of a biomarker or marker, or having a symptom of colitis; and releasing a JAK inhibitor at a location in the gastrointestinal tract of the subject that is proximate to one or more sites of disease, wherein the method comprises administering to the subject a pharmaceutical composition comprising a therapeutically effective amount of the JAK inhibitor. In some embodiments, the pharmaceutical composition is an ingestible device. In some embodiments, the pharmaceutical composition is an ingestible device and the method comprises administering orally to the subject the pharmaceutical composition.

Also provided herein are methods of reducing the severity of colitis in a subject having a cancer and administered an immuno-oncology agent that include administering to the subject any of the devices described herein.

In some embodiments, provided herein is a method for treating colitis in a subject comprising:

- determining that the subject has colitis associated with treatment of the subject with one or more immuno-oncology agents; and
- releasing a JAK inhibitor at a location in the gastrointestinal tract of the subject that is proximate to one or more sites of colitis, wherein the method comprises administering to the subject a pharmaceutical composition comprising a therapeutically effective amount of the JAK inhibitor. In some embodiments, the pharmaceutical composition is an ingestible device.

In some embodiments, the pharmaceutical composition is an ingestible device and the method comprises administering orally to the subject the pharmaceutical composition.

In some embodiments, provided herein is a method for treating colitis in a subject comprising:

- determining that the subject has colitis associated with treatment of the subject with one or more immuno-oncology agents; and
- administering to the subject an ingestible device comprising any of the JAK inhibitors described herein, to treat the colitis.

In some embodiments, provided herein is a method for treating colitis,

- comprising releasing a JAK inhibitor at a location in the gastrointestinal tract of a subject who has been determined to have colitis associated with treatment of the subject with one or more immuno-oncology agents, wherein the location is proximate to one or more sites of colitis, wherein the method comprises administering to the subject a pharmaceutical composition comprising a therapeutically effective amount of the JAK inhibitor. In some embodiments, the pharmaceutical composition is an ingestible device. In some embodiments, the pharmaceutical composition is an ingestible device and the method comprises administering orally to the subject the pharmaceutical composition.

In some embodiments, provided herein is a method for treating colitis, comprising administering an ingestible device comprising any of the JAK inhibitors described herein to a subject who has been determined to have colitis associated with treatment of the subject with one or more immuno-oncology agents.

In some embodiments, provided herein is an ingestible device comprising any of the JAK inhibitors described herein for treating colitis associated with treatment of a subject with one or more immuno-oncology agents.

Monitoring Progress of Disease

In some embodiments, the methods provided herein comprise monitoring the progress of the disease. In some embodiments, monitoring the progress of the disease comprises measuring the levels of IBD serological markers. In some embodiments, monitoring the progress of the disease comprises determining mucosal healing at the location of release. In some embodiments, monitoring the progress of the disease comprises determining the Crohn's Disease Activity Index (CDAI) over a period of about 6-8 weeks, or over a period of about 52 weeks, following administration of the JAK inhibitor. In some embodiments, monitoring the progress of the disease comprises determining the Harvey-Bradshaw Index (HBI) following administration of the JAK inhibitor. Possible markers may include the following: anti-glycan antibodies: anti-*Saccharomices cerevisiae* (ASCA); anti-laminaribioside (ALCA); anti-chitobioside (ACCA); anti-mannobioside (AMCA); anti-laminarin (anti-L); anti-chitin (anti-C) antibodies: anti-outer membrane porin C (anti-OmpC), anti-Cbirl flagellin; anti-12 antibody; autoantibodies targeting the exocrine pancreas (PAB); perinuclear anti-neutrophil antibody (pANCA). In some embodiments, monitoring the progress of the disease comprises measuring JAK inhibitor levels in serum over a period of about 1-14 weeks, such as about 6-8 weeks following administration of the JAK inhibitor, including at the 6-8 week time point. In some embodiments, monitoring the progress of the disease comprises measuring JAK inhibitor levels in serum over a period of about 52 weeks following administration of the JAK inhibitor, including at the 52 week time point.

Patient Condition, Diagnosis and Treatment

In some embodiments herein, the method of treating a disease of the gastrointestinal tract that comprises releasing a JAK inhibitor at a location in the gastrointestinal tract that is proximate to one or more sites of disease comprises one or more of the following:

a) identifying a subject having a disease of the gastrointestinal tract, for example by endoscopy or colonoscopy;
b) determining the severity of the disease, for example with reference to the Mayo Clinic Score, the Crohn's Disease Activity Index (CDAI), the Harvey-Bradshaw Index (HBI), or a combination of the above;
c) determining the location of the disease, for example as determined by the presence of lesions indicative of the disease;
d) evaluating the subject for suitability to treatment, for example by determining the patency of the subject's GI tract, for example if the indication is small intestinal diseases, pancolitis, Crohn's disease, or if the patients has strictures or fistulae;
e) administering an induction dose or of a maintenance dose of a drug, such as the JAK inhibitor or such as another drug that is effective in the treatment of IBD conditions;
f) monitoring the progress of the disease, for example with reference to the Mayo Clinic Score, the Crohn's Disease Activity Index (CDAI), the Harvey-Bradshaw Index (HBI), the PRO, PRO2 or PRO3 tools, or a combination of the above; and/or
g) optionally repeating steps e) and f) one or more times, for example over a period of about 1-14 weeks, such as about 6-8 weeks following administration of the JAK inhibitor, including at the 6-8 week time point, or over a period of about 52 weeks following administration of the JAK inhibitor, including at the 52 week time point.

As used herein, an induction dose is a dose of drug that may be administered, for example, at the beginning of a course of treatment, and that is higher than the maintenance dose administered during treatment. An induction dose may also be administered during treatment, for example if the condition of the patients becomes worse.

As used herein, a maintenance dose is a dose of drug that is provided on a repetitive basis, for example at regular dosing intervals.

In some embodiments the JAK inhibitor is released from an ingestible device.

In some embodiments herein, the method of treating a disease of the gastrointestinal tract that comprises releasing a JAK inhibitor at a location in the gastrointestinal tract that is proximate to one or more sites of disease comprises a) hereinabove.

In some embodiments herein, the method of treating a disease of the gastrointestinal tract that comprises releasing a JAK inhibitor at a location in the gastrointestinal tract that is proximate to one or more sites of disease comprises b) hereinabove.

In some embodiments herein, the method of treating a disease of the gastrointestinal tract that comprises releasing a JAK inhibitor at a location in the gastrointestinal tract that is proximate to one or more sites of disease comprises c) hereinabove.

In some embodiments herein, the method of treating a disease of the gastrointestinal tract that comprises releasing a JAK inhibitor at a location in the gastrointestinal tract that is proximate to one or more sites of disease comprises d) hereinabove.

In some embodiments herein, the method of treating a disease of the gastrointestinal tract that comprises releasing a JAK inhibitor at a location in the gastrointestinal tract that is proximate to one or more sites of disease comprises e) hereinabove.

In some embodiments herein, the method of treating a disease of the gastrointestinal tract that comprises releasing a JAK inhibitor at a location in the gastrointestinal tract that is proximate to one or more sites of disease comprises f) hereinabove.

In some embodiments herein, the method of treating a disease of the gastrointestinal tract that comprises releasing a JAK inhibitor at a location in the gastrointestinal tract that is proximate to one or more sites of disease comprises g) hereinabove.

In some embodiments herein, the method of treating a disease of the gastrointestinal tract that comprises releasing a JAK inhibitor at a location in the gastrointestinal tract that is proximate to one or more sites of disease comprises a) and b) hereinabove. In some embodiments herein, the method of treating a disease of the gastrointestinal tract that comprises releasing a JAK inhibitor at a location in the gastrointestinal tract that is proximate to one or more sites of disease comprises a) and c) hereinabove. In some embodiments herein, the method of treating a disease of the gastrointestinal tract that comprises releasing a JAK inhibitor at a location in the gastrointestinal tract that is proximate to one or more sites of disease comprises a) and d) hereinabove. In some embodiments herein, the method of treating a disease of the gastrointestinal tract that comprises releasing a JAK inhibitor at a location in the gastrointestinal tract that is proximate to one or more sites of disease comprises a) and e) hereinabove. In some embodiments herein, the method of treating a disease of the gastrointestinal tract that comprises releasing a JAK inhibitor at a location in the gastrointestinal tract that is proximate to one or more sites of disease comprises a) and f) hereinabove. In some embodiments herein, the method of treating a disease of the gastrointestinal tract that comprises releasing a JAK inhibitor at a location in the gastrointestinal tract that is proximate to one or more sites of disease comprises a) and g) hereinabove. In some embodiments herein, the method of treating a disease of the gastrointestinal tract that comprises releasing a JAK inhibitor at a location in the gastrointestinal tract that is proximate to one or more sites of disease comprises b) and c) hereinabove. In some embodiments herein, the method of treating a disease of the gastrointestinal tract that comprises releasing a JAK inhibitor at a location in the gastrointestinal tract that is proximate to one or more sites of disease comprises b) and d) hereinabove. In some embodiments herein, the method of treating a disease of the gastrointestinal tract that comprises releasing a JAK inhibitor at a location in the gastrointestinal tract that is proximate to one or more sites of disease comprises b) and e) hereinabove. In some embodiments herein, the method of treating a disease of the gastrointestinal tract that comprises releasing a JAK inhibitor at a location in the gastrointestinal tract that is proximate to one or more sites of disease comprises b) and f) hereinabove. In some embodiments herein, the method of treating a disease of the gastrointestinal tract that comprises releasing a JAK inhibitor at a location in the gastrointestinal tract that is proximate to one or more sites of disease comprises b) and g) hereinabove. In some embodiments herein, the method of treating a disease of the gastrointestinal tract that comprises releasing a JAK inhibitor at a location in the gastrointestinal tract that is proximate to one or more sites of disease comprises c) and d) hereinabove. In some embodiments herein, the method of treating a disease of the gastrointestinal tract that comprises releasing a JAK inhibitor at a location in the gastrointestinal tract that is proximate to one or more sites of disease comprises c) and e) hereinabove. In some embodiments herein, the method of treating a disease of the gastrointestinal tract that comprises releasing a JAK inhibitor at a location in the gastrointestinal tract that is proximate to one or more sites of disease comprises c) and f) hereinabove. In some embodiments herein, the method of treating a disease of the gastrointestinal tract that comprises releasing a JAK inhibitor at a location in the gastrointestinal tract that is proximate to one or more sites of disease comprises c) and g) hereinabove. In some embodiments herein, the method of treating a disease of the gastrointestinal tract that comprises releasing a JAK inhibitor at a location in the gastrointestinal tract that is proximate to one or more sites of disease comprises d) and e) hereinabove. In some embodiments herein, the method of treating a disease of the gastrointestinal tract that comprises releasing a JAK inhibitor at a location in the gastrointestinal tract that is proximate to one or more sites of disease comprises d) and f) hereinabove. In some embodiments herein, the method of treating a disease of the gastrointestinal tract that comprises releasing a JAK inhibitor at a location in the gastrointestinal tract that is proximate to one or more sites of disease comprises d) and g) hereinabove. In some embodiments herein, the method of treating a disease of the gastrointestinal tract that comprises releasing a JAK inhibitor at a location in the gastrointestinal tract that is proximate to one or more sites of disease comprises e) and f) hereinabove. In some embodiments herein, the method of treating a disease of the gastrointestinal tract that comprises releasing a JAK inhibitor at a location in the gastrointestinal tract that is proximate to one or more sites of disease comprises g) hereinabove.

In some embodiments, one or more steps a) to e) herein comprise endoscopy of the gastrointestinal tract. In some embodiments, one or more steps a) to e) herein comprise colonoscopy of the gastrointestinal tract. In some embodiments, one or more steps a) to e) herein is performed one or more times. In some embodiments, such one or more of such one or more steps a) to e) is performed after releasing the JAK inhibitor at the location in the gastrointestinal tract that is proximate to one or more sites of disease.

In some embodiments, the method comprises administering one or more maintenance doses following administration of the induction dose in step e). In some embodiments an induction dose of JAK inhibitor and a maintenance dose of JAK inhibitor are each administered to the subject by administering a pharmaceutical composition comprising a therapeutically effective amount of the JAK inhibitor. In some embodiments an induction dose of JAK inhibitor is administered to the subject in a different manner from the maintenance dose. As an example, the maintenance dose may be administered systemically, while the maintenance dose is administered locally using a device. In one embodiment, a maintenance dose is administered systemically, and an induction dose is administered using a device every 1, 2, 3, 4, 5, 6, 7, 10, 15, 20, 25, 30, 35, 40, or 45 days. In another embodiment, a maintenance dose is administered systemically, and an induction dose is administered when a disease flares up is detected or suspected.

In some embodiments, the induction dose is a dose of the JAK inhibitor administered in an ingestible device as disclosed herein. In some embodiments, the maintenance dose is a dose of the JAK inhibitor administered in an ingestible device as disclosed herein.

In some embodiments, the induction dose is a dose of the JAK inhibitor administered in an ingestible device as disclosed herein. In some embodiments, the maintenance dose is a dose of the JAK inhibitor delivered systemically, such as orally with a tablet or capsule, or subcutaneously, or intravenously.

In some embodiments, the induction dose is a dose of the JAK inhibitor delivered systemically, such as orally with a tablet or capsule, or subcutaneously, or intravenously. In some embodiments, the maintenance dose is a dose of the JAK inhibitor administered in an ingestible device as disclosed herein.

In some embodiments, the induction dose is a dose of the JAK inhibitor administered in an ingestible device as disclosed herein. In some embodiments, the maintenance dose is a dose of a second agent as disclosed herein delivered systemically, such as orally with a tablet or capsule, or subcutaneously, or intravenously.

In some embodiments, the induction dose is a dose of a second agent as disclosed herein delivered systemically, such as orally with a tablet or capsule, or subcutaneously, or intravenously. In some embodiments, the maintenance dose is a dose of the JAK inhibitor administered in an ingestible device as disclosed herein.

In one embodiment of the methods provided herein, the patient is not previously treated with a JAK inhibitor. In one embodiment, the gastrointestinal inflammatory disorder is an inflammatory bowel disease. In one embodiment, the inflammatory bowel disease is ulcerative colitis or Crohn's disease. In one embodiment, the inflammatory bowel disease is ulcerative colitis and the response is selected from clinical response, mucosal healing and remission. In certain embodiments, remission in the patient is determined to be induced when the Mayo Clinic Score <2 and no individual subscore >1, which is also referred to as clinical remission. In certain embodiments, mucosal healing is determined to have occurred when the patient is determined to have an endoscopy subscore of 0 or 1 as assessed by flexible sigmoidoscopy. In certain such embodiments, patients who experience mucosal healing are determined to have an endoscopy subscore of 0. In certain embodiments, clinical response is determined to have occurred when the patient experiences a 3-point decrease and 30% reduction from baseline in MCS and >1-point decrease in rectal bleeding subscore or absolute rectal bleeding score of 0 or 1.

In some embodiments, the method comprises identifying the disease site substantially at the same time as releasing the JAK inhibitor.

In some embodiments, the method comprises monitoring the progress of the disease. In some embodiments, monitoring the progress of the disease comprises measuring the weight of the subject over a period of about 1-14 weeks, such as about 6-8 weeks following administration of the JAK inhibitor, including at the 6-8 week time point, or over a period of about 52 weeks following administration of the JAK inhibitor, including at the 52 week time point. In some embodiments, monitoring the progress of the disease comprises measuring the food intake of the subject; measuring the level of blood in the feces of the subject; measuring the level of abdominal pain of the subject; and/or a combination of the above, for example over a period of about 1-14 weeks, such as about 6-8 weeks following administration of the JAK inhibitor, including at the 6-8 week time point, or over a period of about 52 weeks following administration of the JAK inhibitor, including at the 52 week time point.

In some embodiments, the method comprises administering a JAK inhibitor with a spray catheter. For example, administering a JAK inhibitor with a spray catheter may be performed in step (e) hereinabove.

In some embodiments, the method does not comprise administering a JAK inhibitor with a spray catheter.

In some embodiments, data obtained from cell culture assays and animal studies can be used in formulating an appropriate dosage of any given JAK inhibitor. The effectiveness and dosing of any JAK inhibitor can be determined by a health care professional or veterinary professional using methods known in the art, as well as by the observation of one or more disease symptoms in a subject (e.g., a human). Certain factors may influence the dosage and timing required to effectively treat a subject (e.g., the severity of the disease or disorder, previous treatments, the general health and/or age of the subject, and the presence of other diseases).

In some embodiments, the subject is further administered an additional therapeutic agent (e.g., any of the additional therapeutic agents described herein). The additional therapeutic agent can be administered to the subject at substantially the same time as the JAK inhibitor or pharmaceutical composition comprising it is administered and/or at one or more other time points. In some embodiments, the additional therapeutic agent is formulated together with the JAK inhibitor (e.g., using any of the examples of formulations described herein).

In some embodiments, the subject is administered a dose of the JAK inhibitor at least once a month (e.g., at least twice a month, at least three times a month, at least four times a month, at least once a week, at least twice a week, three times a week, once a day, or twice a day). The JAK inhibitor may be administered to a subject chronically. Chronic treatments include any form of repeated administration for an extended period of time, such as repeated administrations for one or more months, between a month and a year, one or more years, more than five years, more than 10 years, more than 15 years, more than 20 years, more than 25 years, more than 30 years, more than 35 years, more than 40 years, more than 45 years, or longer. Alternatively, or in addition, chronic treatments may be administered. Chronic treatments can involve regular administrations, for example one or more times a day, one or more times a week, or one or more times a month. For example, chronic treatment can include administration (e.g., intravenous administration) about every two weeks (e.g., between about every 10 to 18 days).

A suitable dose may be the amount that is the lowest dose effective to produce a desired therapeutic effect. Such an effective dose will generally depend upon the factors described herein. If desired, an effective daily dose of JAK inhibitor can be administered as two, three, four, five, or six or more sub-doses administered separately at appropriate intervals throughout the day, optionally, in unit dosage forms.

In some examples, administration of a JAK inhibitor using any of the compositions or devices described herein can result in the onset of treatment (e.g., a reduction in the number, severity, or duration of one or more symptoms and/or markers of any of the diseases described herein) or drug-target engagement in a subject within a time period of about 10 minutes to about 10 hours, about 10 minutes to about 9 hours, about 10 minutes to about 8 hours, about 10 minutes to about 7 hours, about 10 minutes to about 6 hours, about 10 minutes to about 5 hours, about 10 minutes to about 4.5 hours, about 10 minutes to about 4 hours, about 10 minutes to about 3.5 hours, about 10 minutes to about 3 hours, about 10 minutes to about 2.5 hours, about 10 minutes to about 2 hours, about 10 minutes to about 1.5 hours, about 10 minutes to about 1 hour, about 10 minutes to about 55 minutes, about 10 minutes to about 50 minutes, about 10 minutes to about 45 minutes, about 10 minutes to about 40 minutes, about 10 minutes to about 35 minutes, about 10 minutes to about 30 minutes, about 10 minutes to about 25 minutes, about 10 minutes to about 20 minutes, about 10 minutes to about 15 minutes, about 15 minutes to about 10 hours, about 15 minutes to about 9 hours, about 15 minutes to about 8 hours, about 15 minutes to about 7 hours, about 15 minutes to about 6 hours, about 15 minutes to about 5 hours, about 15 minutes to about 4.5 hours, about 15 minutes to about 4 hours, about 15 minutes to about 3.5 hours, about 15 minutes to about 3 hours, about 15 minutes to about 2.5 hours, about 15 minutes to about 2 hours, about 15 minutes to about 1.5 hours, about 15 minutes to about 1 hour, about 15 minutes to about 55 minutes, about 15 minutes to about 50 minutes, about 15 minutes to about 45 minutes, about 15 minutes to about 40 minutes, about 15 minutes to about 35 minutes, about 15 minutes to about 30 minutes, about 15 minutes to about 25 minutes, about 15 minutes to about 20 minutes, about 20 minutes to about 10 hours, about 20 minutes to about 9 hours, about 20 minutes to about 8 hours, about 20 minutes to about 7 hours, about 20 minutes to about 6 hours, about 20 minutes to about 5 hours, about 20 minutes to about 4.5 hours, about 20 minutes to about 4 hours, about 20 minutes to about 3.5 hours, about 20 minutes to about 3 hours, about 20 minutes to about 2.5 hours, about 20 minutes to about 2 hours, about 20 minutes to about 1.5 hours, about 20 minutes to about 1 hour, about 20 minutes to about 55 minutes, about 20 minutes to about 50 minutes, about 20 minutes to about 45 minutes, about 20 minutes to about 40 minutes, about 20 minutes to about 35 minutes, about 20 minutes to about 30 minutes, about 20 minutes to about 25 minutes, about 25 minutes to about 10 hours, about 25 minutes to about 9 hours, about 25 minutes to about 8 hours, about 25 minutes to about 7 hours, about 25 minutes to about 6 hours, about 25 minutes to about 5 hours, about 25 minutes to about 4.5 hours, about 25 minutes to about 4 hours, about 25 minutes to about 3.5 hours, about 25 minutes to about 3 hours, about 25 minutes to about 2.5 hours, about 25 minutes to about 2 hours, about 25 minutes to about 1.5 hours, about 25 minutes to about 1 hour, about 25 minutes to about 55 minutes, about 25 minutes to about 50 minutes, about 25 minutes to about 45 minutes, about 25 minutes to about 40 minutes, about 25 minutes to about 35 minutes, about 25 minutes to about 30 minutes, about 30 minutes to about 10 hours, about 30 minutes to about 9 hours, about 30 minutes to about 8 hours, about 30 minutes to about 7 hours, about 30 minutes to about 6 hours, about 30 minutes to about 5 hours, about 30 minutes to about 4.5 hours, about 30 minutes to about 4 hours, about 30 minutes to about 3.5 hours, about 30 minutes to about 3 hours, about 30 minutes to about 2.5 hours, about 30 minutes to about 2 hours, about 30 minutes to about 1.5 hours, about 30 minutes to about 1 hour, about 30 minutes to about 55 minutes, about 30 minutes to about 50 minutes, about 30 minutes to about 45 minutes, about 30 minutes to about 40 minutes, about 30 minutes to about 35 minutes, about 35 minutes to about 10 hours, about 35 minutes to about 9 hours, about 35 minutes to about 8 hours, about 35 minutes to about 7 hours, about 35 minutes to about 6 hours, about 35 minutes to about 5 hours, about 35 minutes to about 4.5 hours, about 35 minutes to about 4 hours, about 35 minutes to about 3.5 hours, about 35 minutes to about 3 hours, about 35 minutes to about 2.5 hours, about 35 minutes to about 2 hours, about 35 minutes to about 1.5 hours, about 35 minutes to about 1 hour, about 35 minutes to about 55 minutes, about 35 minutes to about 50 minutes, about 35 minutes to about 45 minutes, about 35 minutes to about 40 minutes, about 40 minutes to about 10 hours, about 40 minutes to about 9 hours, about 40 minutes to about 8 hours, about 40 minutes to about 7 hours, about 40 minutes to about 6 hours, about 40 minutes to about 5 hours, about 40 minutes to about 4.5 hours, about 40 minutes to about 4 hours, about 40 minutes to about 3.5 hours, about 40 minutes to about 3 hours, about 40 minutes to about 2.5 hours, about 40 minutes to about 2 hours, about 40 minutes to about 1.5 hours, about 40 minutes to about 1 hour, about 40 minutes to about 55 minutes, about 40 minutes to about 50 minutes, about 40 minutes to about 45 minutes, about 45 minutes to about 10 hours, about 45 minutes to about 9 hours, about 45 minutes to about 8 hours, about 45 minutes to about 7 hours, about 45 minutes to about 6 hours, about 45 minutes to about 5 hours, about 45 minutes to about 4.5 hours, about 45 minutes to about 4 hours, about 45 minutes to about 3.5 hours, about 45 minutes to about 3 hours, about 45 minutes to about 2.5 hours, about 45 minutes to about 2 hours, about 45 minutes to about 1.5 hours, about 45 minutes to about 1 hour, about 45 minutes to about 55 minutes, about 45 minutes to about 50 minutes, about 50 minutes to about 10 hours, about 50 minutes to about 9 hours, about 50 minutes to about 8 hours, about 50 minutes to about 7 hours, about 50 minutes to about 6 hours, about 50 minutes to about 5 hours, about 50 minutes to about 4.5 hours, about 50 minutes to about 4 hours, about 50 minutes to about 3.5 hours, about 50 minutes to about 3 hours, about 50 minutes to about 2.5 hours, about 50 minutes to about 2 hours, about 50 minutes to about 1.5 hours, about 50 minutes to about 1 hour, about 50 minutes to about 55 minutes, about 55 minutes to about 10 hours, about 55 minutes to about 9 hours, about 55 minutes to about 8 hours, about 55 minutes to about 7 hours, about 55 minutes to about 6 hours, about 55 minutes to about 5 hours, about 55 minutes to about 4.5 hours, about 55 minutes to about 4 hours, about 55 minutes to about 3.5 hours, about 55 minutes to about 3 hours, about 55 minutes to about 2.5 hours, about 55 minutes to about 2 hours, about 55 minutes to about 1.5 hours, about 55 minutes to about 1 hour, about 1 hour to about 10 hours, about 1 hour to about 9 hours, about 1 hour to about 8 hours, about 1 hour to about 7 hours, about 1 hour to about 6 hours, about 1 hour to about 5 hours, about 1 hour to about 4.5 hours, about 1 hour to about 4 hours, about 1 hour to about 3.5 hours, about 1 hour to about 3 hours, about 1 hour to about 2.5 hours, about 1 hour to about 2 hours, about 1 hour to about 1.5 hours, about 1.5 hours to about 10 hours, about 1.5 hours to about 9 hours, about 1.5 hours to about 8 hours, about 1.5 hours to about 7 hours, about 1.5 hours to about 6 hours, about 1.5 hours to about 5 hours, about 1.5 hours to about 4.5 hours, about 1.5 hours to about 4 hours, about 1.5 hours to about 3.5 hours, about 1.5 hours to about 3 hours, about 1.5 hours to about 2.5 hours, about 1.5 hours to about 2 hours, about 2 hours to about 10 hours, about 2 hours to about 9 hours, about 2 hours to about 8 hours, about 2 hours to about 7 hours, about 2 hours to about 6 hours, about 2 hours to about 5 hours, about 2 hours to about 4.5 hours, about 2 hours to about 4 hours, about 2 hours to about 3.5 hours, about 2 hours to about 3 hours, about 2 hours to about 2.5 hours, about 2.5 hours to about 10 hours, about 2.5 hours to about 9 hours, about 2.5 hours to about 8 hours, about 2.5 hours to about 7 hours, about 2.5 hours to about 6 hours, about 2.5 hours to about 5 hours, about 2.5 hours to about 4.5 hours, about 2.5 hours to about 4 hours, about 2.5 hours to about 3.5 hours, about 2.5 hours to about 3 hours, about 3 hours to about 10 hours, about 3 hours to about 9 hours, about 3 hours to about 8 hours, about 3 hours to about 7 hours, about 3 hours to about 6 hours, about 3 hours to about 5 hours, about 3 hours to about 4.5 hours, about 3 hours to about 4 hours, about 3 hours to about 3.5 hours, about 3.5 hours to about 10 hours, about 3.5 hours to about 9 hours, about 3.5 hours to about 8 hours, about 3.5 hours to about 7 hours, about 3.5 hours to about 6 hours, about 3.5 hours to about 5 hours, about 3.5 hours to about 4.5 hours, about 3.5 hours to about 4 hours, about 4 hours to about 10 hours, about 4 hours to about 9 hours, about 4 hours to about 8 hours, about 4 hours to about 7 hours, about 4 hours to about 6 hours, about 4 hours to about 5 hours, about 4 hours to about 4.5 hours, about 4.5 hours to about 10 hours, about 4.5 hours to about 9 hours, about 4.5 hours to about 8 hours, about 4.5 hours to about 7 hours, about 4.5 hours to about 6 hours, about 4.5 hours to about 5 hours, about 5 hours to about 10 hours, about 5 hours to about 9 hours, about 5 hours to about 8 hours, about 5 hours to about 7 hours, about 5 hours to about 6 hours, about 6 hours to about 10 hours, about 6 hours to about 9 hours, about 6 hours to about 8 hours, about 6 hours to about 7 hours, about 7 hours to about 10 hours, about 7 hours to about 9 hours, about 7 hours to about 8 hours, about 8 hours to about 10 hours, about 8 hours to about 9 hours, or about 9 hours to about 10 hours of administration of a dose of a JAK inhibitor using any of the devices or compositions described herein. Drug-target engagement may be determined, for example, as disclosed in Simon G M, Niphakis M J, Cravatt B F, *Nature chemical biology.* 2013; 9(4):200-205, incorporated by reference herein in its entirety.

In some embodiments, administration of a JAK inhibitor using any of the devices or compositions described herein can provide for treatment (e.g., a reduction in the number, severity, and/or duration of one or more symptoms and/or markers of any of the disorders described herein in a subject) for a time period of between about 1 hour to about 30 days, about 1 hour to about 28 days, about 1 hour to about 26 days, about 1 hour to about 24 days, about 1 hour to about 22 days, about 1 hour to about 20 days, about 1 hour to about 18 days, about 1 hour to about 16 days, about 1 hour to about 14 days, about 1 hour to about 12 days, about 1 hour to about 10 days, about 1 hour to about 8 days, about 1 hour to about 6 days, about 1 hour to about 5 days, about 1 hour to about 4 days, about 1 hour to about 3 days, about 1 hour to about 2 days, about 1 hour to about 1 day, about 1 hour to about 12 hours, about 1 hour to about 6 hours, about 1 hour to about 3 hours, about 3 hours to about 30 days, about 3 hours to about 28 days, about 3 hours to about 26 days, about 3 hours to about 24 days, about 3 hours to about 22 days, about 3 hours to about 20 days, about 3 hours to about 18 days, about 3 hours to about 16 days, about 3 hours to about 14 days, about 3 hours to about 12 days, about 3 hours to about 10 days, about 3 hours to about 8 days, about 3 hours to about 6 days, about 3 hours to about 5 days, about 3 hours to about 4 days, about 3 hours to about 3 days, about 3 hours to about 2 days, about 3 hours to about 1 day, about 3 hours to about 12 hours, about 3 hours to about 6 hours, about 6 hours to about 30 days, about 6 hours to about 28 days, about 6 hours to about 26 days, about 6 hours to about 24 days, about 6 hours to about 22 days, about 6 hours to about 20 days, about 6 hours to about 18 days, about 6 hours to about 16 days, about 6 hours to about 14 days, about 6 hours to about 12 days, about 6 hours to about 10 days, about 6 hours to about 8 days, about 6 hours to about 6 days, about 6 hours to about 5 days, about 6 hours to about 4 days, about 6 hours to about 3 days, about 6 hours to about 2 days, about 6 hours to about 1 day, about 6 hours to about 12 hours, about 12 hours to about 30 days, about 12 hours to about 28 days, about 12 hours to about 26 days, about 12 hours to about 24 days, about 12 hours to about 22 days, about 12 hours to about 20 days, about 12 hours to about 18 days, about 12 hours to about 16 days, about 12 hours to about 14 days, about 12 hours to about 12 days, about 12 hours to about 10 days, about 12 hours to about 8 days, about 12 hours to about 6 days, about 12 hours to about 5 days, about 12 hours to about 4 days, about 12 hours to about 3 days, about 12 hours to about 2 days, about 12 hours to about 1 day, about 1 day to about 30 days, about 1 day to about 28 days, about 1 day to about 26 days, about 1 day to about 24 days, about 1 day to about 22 days, about 1 day to about 20 days, about 1 day to about 18 days, about 1 day to about 16 days, about 1 day to about 14 days, about 1 day to about 12 days, about 1 day to about 10 days, about 1 day to about 8 days, about 1 day to about 6 days, about 1 day to about 5 days, about 1 day to about 4 days, about 1 day to about 3 days, about 1 day to about 2 days, about 2 days to about 30 days, about 2 days to about 28 days, about 2 days to about 26 days, about 2 days to about 24 days, about 2 days to about 22 days, about 2 days to about 20 days, about 2 days to about 18 days, about 2 days to about 16 days, about 2 days to about 14 days, about 2 days to about 12 days, about 2 days to about 10 days, about 2 days to about 8 days, about 2 days to about 6 days, about 2 days to about 5 days, about 2 days to about 4 days, about 2 days to about 3 days, about 3 days to about 30 days, about 3 days to about 28 days, about 3 days to about 26 days, about 3 days to about 24 days, about 3 days to about 22 days, about 3 days to about 20 days, about 3 days to about 18 days, about 3 days to about 16 days, about 3 days to about 14 days, about 3 days to about 12 days, about 3 days to about 10 days, about 3 days to about 8 days, about 3 days to about 6 days, about 3 days to about 5 days, about 3 days to about 4 days, about 4 days to about 30 days, about 4 days to about 28 days, about 4 days to about 26 days, about 4 days to about 24 days, about 4 days to about 22 days, about 4 days to about 20 days, about 4 days to about 18 days, about 4 days to about 16 days, about 4 days to about 14 days, about 4 days to about 12 days, about 4 days to about 10 days, about 4 days to about 8 days, about 4 days to about 6 days, about 4 days to about 5 days, about 5 days to about 30 days, about 5 days to about 28 days, about 5 days to about 26 days, about 5 days to about 24 days, about 5 days to about 22 days, about 5 days to about 20 days, about 5 days to about 18 days, about 5 days to about 16 days, about 5 days to about 14 days, about 5 days to about 12 days, about 5 days to about 10 days, about 5 days to about 8 days, about 5 days to about 6 days, about 6 days to about 30 days, about 6 days to about 28 days, about 6 days to about 26 days, about 6 days to about 24 days, about 6 days to about 22 days, about 6 days to about 20 days, about 6 days to about 18 days, about 6 days to about 16 days, about 6 days to about 14 days, about 6 days to about 12 days, about 6 days to about 10 days, about 6 days to about 8 days, about 8 days to about 30 days, about 8 days to about 28 days, about 8 days to about 26 days, about 8 days to about 24 days, about 8 days to about 22 days, about 8 days to about 20 days, about 8 days to about 18 days, about 8 days to about 16 days, about 8 days to about 14 days, about 8 days to about 12 days, about 8 days to about 10 days, about 10 days to about 30 days, about 10 days to about 28 days, about 10 days to about 26 days, about 10 days to about 24 days, about 10 days to about 22 days, about 10 days to about 20 days, about 10 days to about 18 days, about 10 days to about 16 days, about 10 days to about 14 days, about 10 days to about 12 days, about 12 days to about 30 days, about 12 days to about 28 days, about 12 days to about 26 days, about 12 days to about 24 days, about 12 days to about 22 days, about 12 days to about 20 days, about 12 days to about 18 days, about 12 days to about 16 days, about 12 days to about 14 days, about 14 days to about 30 days, about 14 days to about 28 days, about 14 days to about 26 days, about 14 days to about 24 days, about 14 days to about 22 days, about 14 days to about 20 days, about 14 days to about 18 days, about 14 days to about 16 days, about 16 days to about 30 days, about 16 days to about 28 days, about 16 days to about 26 days, about 16 days to about 24 days, about 16 days to about 22 days, about 16 days to about 20 days, about 16 days to about 18 days, about 18 days to about 30 days, about 18 days to about 28 days, about 18 days to about 26 days, about 18 days to about 24 days, about 18 days to about 22 days, about 18 days to about 20 days, about 20 days to about 30 days, about 20 days to about 28 days, about 20 days to about 26 days, about 20 days to about 24 days, about 20 days to about 22 days, about 22 days to about 30 days, about 22 days to about 28 days, about 22 days to about 26 days, about 22 days to about 24 days, about 24 days to about 30 days, about 24 days to about 28 days, about 24 days to about 26 days, about 26 days to about 30 days, about 26 days to about 28 days, or about 28 days to about 30 days in a subject following first administration of a JAK inhibitor using any of the compositions or devices described herein. Non-limiting examples of symptoms and/or markers of a disease described herein are described below.

For example, treatment can result in a decrease (e.g., about 1% to about 99% decrease, about 1% to about 95% decrease, about 1% to about 90% decrease, about 1% to about 85% decrease, about 1% to about 80% decrease, about 1% to about 75% decrease, about 1% to about 70% decrease, about 1% to about 65% decrease, about 1% to about 60% decrease, about 1% to about 55% decrease, about 1% to about 50% decrease, about 1% to about 45% decrease, about 1% to about 40% decrease, about 1% to about 35% decrease, about 1% to about 30% decrease, about 1% to about 25% decrease, about 1% to about 20% decrease, about 1% to about 15% decrease, about 1% to about 10% decrease, about 1% to about 5% decrease, about 5% to about 99% decrease, about 5% to about 95% decrease, about 5% to about 90% decrease, about 5% to about 85% decrease, about 5% to about 80% decrease, about 5% to about 75% decrease, about 5% to about 70% decrease, about 5% to about 65% decrease, about 5% to about 60% decrease, about 5% to about 55% decrease, about 5% to about 50% decrease, about 5% to about 45% decrease, about 5% to about 40% decrease, about 5% to about 35% decrease, about 5% to about 30% decrease, about 5% to about 25% decrease, about 5% to about 20% decrease, about 5% to about 15% decrease, about 5% to about 10% decrease, about 10% to about 99% decrease, about 10% to about 95% decrease, about 10% to about 90% decrease, about 10% to about 85% decrease, about 10% to about 80% decrease, about 10% to about 75% decrease, about 10% to about 70% decrease, about 10% to about 65% decrease, about 10% to about 60% decrease, about 10% to about 55% decrease, about 10% to about 50% decrease, about 10% to about 45% decrease, about 10% to about 40% decrease, about 10% to about 35% decrease, about 10% to about 30% decrease, about 10% to about 25% decrease, about 10% to about 20% decrease, about 10% to about 15% decrease, about 15% to about 99% decrease, about 15% to about 95% decrease, about 15% to about 90% decrease, about 15% to about 85% decrease, about 15% to about 80% decrease, about 15% to about 75% decrease, about 15% to about 70% decrease, about 15% to about 65% decrease, about 15% to about 60% decrease, about 15% to about 55% decrease, about 15% to about 50% decrease, about 15% to about 45% decrease, about 15% to about 40% decrease, about 15% to about 35% decrease, about 15% to about 30% decrease, about 15% to about 25% decrease, about 15% to about 20% decrease, about 20% to about 99% decrease, about 20% to about 95% decrease, about 20% to about 90% decrease, about 20% to about 85% decrease, about 20% to about 80% decrease, about 20% to about 75% decrease, about 20% to about 70% decrease, about 20% to about 65% decrease, about 20% to about 60% decrease, about 20% to about 55% decrease, about 20% to about 50% decrease, about 20% to about 45% decrease, about 20% to about 40% decrease, about 20% to about 35% decrease, about 20% to about 30% decrease, about 20% to about 25% decrease, about 25% to about 99% decrease, about 25% to about 95% decrease, about 25% to about 90% decrease, about 25% to about 85% decrease, about 25% to about 80% decrease, about 25% to about 75% decrease, about 25% to about 70% decrease, about 25% to about 65% decrease, about 25% to about 60% decrease, about 25% to about 55% decrease, about 25% to about 50% decrease, about 25% to about 45% decrease, about 25% to about 40% decrease, about 25% to about 35% decrease, about 25% to about 30% decrease, about 30% to about 99% decrease, about 30% to about 95% decrease, about 30% to about 90% decrease, about 30% to about 85% decrease, about 30% to about 80% decrease, about 30% to about 75% decrease, about 30% to about 70% decrease, about 30% to about 65% decrease, about 30% to about 60% decrease, about 30% to about 55% decrease, about 30% to about 50% decrease, about 30% to about 45% decrease, about 30% to about 40% decrease, about 30% to about 35% decrease, about 35% to about 99% decrease, about 35% to about 95% decrease, about 35% to about 90% decrease, about 35% to about 85% decrease, about 35% to about 80% decrease, about 35% to about 75% decrease, about 35% to about 70% decrease, about 35% to about 65% decrease, about 35% to about 60% decrease, about 35% to about 55% decrease, about 35% to about 50% decrease, about 35% to about 45% decrease, about 35% to about 40% decrease, about 40% to about 99% decrease, about 40% to about 95% decrease, about 40% to about 90% decrease, about 40% to about 85% decrease, about 40% to about 80% decrease, about 40% to about 75% decrease, about 40% to about 70% decrease, about 40% to about 65% decrease, about 40% to about 60% decrease, about 40% to about 55% decrease, about 40% to about 50% decrease, about 40% to about 45% decrease, about 45% to about 99% decrease, about 45% to about 95% decrease, about 45% to about 90% decrease, about 45% to about 85% decrease, about 45% to about 80% decrease, about 45% to about 75% decrease, about 45% to about 70% decrease, about 45% to about 65% decrease, about 45% to about 60% decrease, about 45% to about 55% decrease, about 45% to about 50% decrease, about 50% to about 99% decrease, about 50% to about 95% decrease, about 50% to about 90% decrease, about 50% to about 85% decrease, about 50% to about 80% decrease, about 50% to about 75% decrease, about 50% to about 70% decrease, about 50% to about 65% decrease, about 50% to about 60% decrease, about 50% to about 55% decrease, about 55% to about 99% decrease, about 55% to about 95% decrease, about 55% to about 90% decrease, about 55% to about 85% decrease, about 55% to about 80% decrease, about 55% to about 75% decrease, about 55% to about 70% decrease, about 55% to about 65% decrease, about 55% to about 60% decrease, about 60% to about 99% decrease, about 60% to about 95% decrease, about 60% to about 90% decrease, about 60% to about 85% decrease, about 60% to about 80% decrease, about 60% to about 75% decrease, about 60% to about 70% decrease, about 60% to about 65% decrease, about 65% to about 99% decrease, about 65% to about 95% decrease, about 65% to about 90% decrease, about 65% to about 85% decrease, about 65% to about 80% decrease, about 65% to about 75% decrease, about 65% to about 70% decrease, about 70% to about 99% decrease, about 70% to about 95% decrease, about 70% to about 90% decrease, about 70% to about 85% decrease, about 70% to about 80% decrease, about 70% to about 75% decrease, about 75% to about 99% decrease, about 75% to about 95% decrease, about 75% to about 90% decrease, about 75% to about 85% decrease, about 75% to about 80% decrease, about 80% to about 99% decrease, about 80% to about 95% decrease, about 80% to about 90% decrease, about 80% to about 85% decrease, about 85% to about 99% decrease, about 85% to about 95% decrease, about 85% to about 90% decrease, about 90% to about 99% decrease, about 90% to about 95% decrease, or about 95% to about 99% decrease) in one or more (e.g., two, three, four, five, six, seven, eight, or nine) of: the level of interferon-K in GI tissue, the level of IL-1β in GI tissue, the level of IL-6 in GI tissue, the level of IL-22 in GI tissue, the level of IL-17A in the GI tissue, the level of TNFI in GI tissue, the level of IL-2 in GI tissue, and endoscopy score in a subject (e.g., as compared to the level in the subject prior to treatment or compared to a subject or population of subjects having a similar disease but receiving a placebo or a different treatment) (e.g., for a time period of between about 1 hour to about 30 days (e.g., or any of the subranges herein) following the first administration of a JAK inhibitor using any of the compositions or devices described herein. As used herein, "GI tissue" refers to tissue in the gastrointestinal (GI) tract, such as tissue in one or more of duodenum, jejunum, ileum, cecum, ascending colon, transverse colon, descending colon, sigmoid colon, and rectum, more particularly in the proximal portion of one or more of duodenum, jejunum, ileum, cecum, ascending colon, transverse colon, descending colon, and sigmoid colon, or in the distal portion of one or more of duodenum, jejunum, ileum, cecum, ascending colon, transverse colon, descending colon, and sigmoid colon. The GI tissue may be, for example, GI tissue proximate to one or more sites of disease. Exemplary methods for determining the endoscopy score are described herein and other methods for determining the endoscopy score are known in the art. Exemplary methods for determining the levels of interferon-K, IL-1p, IL-6, IL-22, IL-17A, TNFI, and IL-2 are described herein. Additional methods for determining the levels of these cytokines are known in the art.

In some examples, treatment can result in an increase (e.g., about 1% to about 500% increase, about 1% to about 400% increase, about 1% to about 300% increase, about 1% to about 200% increase, about 1% to about 150% increase, about 1% to about 100% increase, about 1% to about 90% increase, about 1% to about 80% increase, about 1% to about 70% increase, about 1% to about 60% increase, about 1% to about 50% increase, about 1% to about 40% increase, about 1% to about 30% increase, about 1% to about 20% increase, about 1% to about 10% increase, a 10% to about 500% increase, about 10% to about 400% increase, about 10% to about 300% increase, about 10% to about 200% increase, about 10% to about 150% increase, about 10% to about 100% increase, about 10% to about 90% increase, about 10% to about 80% increase, about 10% to about 70% increase, about 10% to about 60% increase, about 10% to about 50% increase, about 10% to about 40% increase, about 10% to about 30% increase, about 10% to about 20% increase, about 20% to about 500% increase, about 20% to about 400% increase, about 20% to about 300% increase, about 20% to about 200% increase, about 20% to about 150% increase, about 20% to about 100% increase, about 20% to about 90% increase, about 20% to about 80% increase, about 20% to about 70% increase, about 20% to about 60% increase, about 20% to about 50% increase, about 20% to about 40% increase, about 20% to about 30% increase, about 30% to about 500% increase, about 30% to about 400% increase, about 30% to about 300% increase, about 30% to about 200% increase, about 30% to about 150% increase, about 30% to about 100% increase, about 30% to about 90% increase, about 30% to about 80% increase, about 30% to about 70% increase, about 30% to about 60% increase, about 30% to about 50% increase, about 30% to about 40% increase, about 40% to about 500% increase, about 40% to about 400% increase, about 40% to about 300% increase, about 40% to about 200% increase, about 40% to about 150% increase, about 40% to about 100% increase, about 40% to about 90% increase, about 40% to about 80% increase, about 40% to about 70% increase, about 40% to about 60% increase, about 40% to about 50% increase, about 50% to about 500% increase, about 50% to about 400% increase, about 50% to about 300% increase, about 50% to about 200% increase, about 50% to about 150% increase, about 50% to about 100% increase, about 50% to about 90% increase, about 50% to about 80% increase, about 50% to about 70% increase, about 50% to about 60% increase, about 60% to about 500% increase, about 60% to about 400% increase, about 60% to about 300% increase, about 60% to about 200% increase, about 60% to about 150% increase, about 60% to about 100% increase, about 60% to about 90% increase, about 60% to about 80% increase, about 60% to about 70% increase, about 70% to about 500% increase, about 70% to about 400% increase, about 70% to about 300% increase, about 70% to about 200% increase, about 70% to about 150% increase, about 70% to about 100% increase, about 70% to about 90% increase, about 70% to about 80% increase, about 80% to about 500% increase, about 80% to about 400% increase, about 80% to about 300% increase, about 80% to about 200% increase, about 80% to about 150% increase, about 80% to about 100% increase, about 80% to about 90% increase, about 90% to about 500% increase, about 90% to about 400% increase, about 90% to about 300% increase, about 90% to about 200% increase, about 90% to about 150% increase, about 90% to about 100% increase, about 100% to about 500% increase, about 100% to about 400% increase, about 100% to about 300% increase, about 100% to about 200% increase, about 100% to about 150% increase, about 150% to about 500% increase, about 150% to about 400% increase, about 150% to about 300% increase, about 150% to about 200% increase, about 200% to about 500% increase, about 200% to about 400% increase, about 200% to about 300% increase, about 300% to about 500% increase, about 300% to about 400% increase, or about 400% to about 500% increase) in one or both of stool consistency score and weight of a subject (e.g., as compared to the level in the subject prior to treatment or compared to a subject or population of subjects having a similar disease but receiving a placebo or a different treatment) (e.g., for a time period of between about 1 hour to about 30 days (e.g., or any of the subranges herein) following the first administration of a JAK inhibitor using any of the compositions or devices described herein. Exemplary methods for determining stool consistency score are described herein. Additional methods for determining a stool consistency score are known in the art.

Accordingly, in some embodiments, a method of treatment disclosed herein includes determining the level of a marker at the location of disease in a subject (e.g., either before and/or after administration of the device). In some embodiments, the marker is a biomarker and the method of treatment disclosed herein comprises determining that the level of a biomarker at the location of disease is a subject following administration of the device is decreased as compared to the level of the biomarker at the same location of disease in a subject either before administration or at the same time point following systemic administration of an equal amount of the JAK inhibitor. In some examples, the level of the biomarker at the same location of disease following administration of the device is 1% decreased to 99% decreased as compared to the level of the biomarker at the same location of disease in a subject either before administration or at the same time point following systemic administration of an equal amount of the JAK inhibitor. In some embodiments, the level of the marker is one or more of: the level of interferon-K in GI tissue, the level of IL-17A in the GI tissue, the level of TNFα in the GI tissue, the level of IL-2 in the GI tissue, and the endoscopy score in a subject.

In some embodiments, the method of treatment disclosed herein includes determining that the level of a marker at a time point following administration of a device is lower than the level of the marker at a time point following administration of the device is lower than the level of the marker in a subject prior to administration of the device or in a subject at substantially the same time point following systemic administration of an equal amount of the JAK inhibitor. In some examples, the level of the marker following administration of the device is 1% decreased to 99% decreased as compared to the level of the marker in a subject prior to administration of the device or in a subject at the same time point following systemic administration of an equal amount of the JAK inhibitor. In some examples, a method of treatment disclosed herein includes determining the level of the biomarker at the location of disease in a subject within a time period of about 10 minutes to 10 hours following administration of the device.

In some embodiments, a method of treatment described herein includes: (i) determining the ratio $R_B$ of the level $L_{1B}$ of a biomarker at the location of disease at a first time point following administration of the device and the level $L_{2B}$ of the biomarker at the same location of disease in a subject at substantially the same time point following systemic administration of an equal amount of the JAK inhibitor; (ii) determining the ratio of $R_D$ of the level of $L_{1D}$ of the JAK inhibitor at the same location and the substantially the same time point as in (i) and the level $L_{2D}$ of the JAK inhibitor at the same location of disease in a subject at substantially the same time point following systemic administration of an equal amount of the JAK inhibitor; and (iii) determining the ratio of $R_B/R_D$.

In some embodiments, a method of treatment disclosed herein can include: (i) determining the ratio $R_B$ of the level $L_{1B}$ of a biomarker at the location of disease at a time point following administration of the device and the level $L_{2B}$ of the biomarker at the same location of disease in a subject at substantially the same time point following systemic administration of an equal amount of the JAK inhibitor; (ii) determining the ratio $R_D$ of the level $L_{1D}$ of the JAK inhibitor at the same location and at substantially the time point as in (i) and the level $L_{2D}$ of the JAK inhibitor in a subject at the same location of disease at substantially the same time point following systemic administration of an equal amount of the JAK inhibitor; and (iii) determining the product $R_B \times R_D$.

In some embodiments, a method of treatment disclosed herein can include determining that the level of a marker in a subject at a time point following administration of the device is elevated as compared to a level of the marker in a subject prior to administration of the device or a level at substantially the same time point in a subject following systemic administration of an equal amount of the JAK inhibitor. In some examples, the level of the marker at a time point following administration of the device is 1% increased or 400% increased as compared to the level of the marker in a subject prior to administration of the device or a level at substantially the same time point in a subject following systemic administration of an equal amount of the JAK inhibitor. In some examples, the level of the marker is one or more of subject weight and stool consistency (e.g., stool consistency score). In some examples, a method of treatment disclosed herein includes determining the level of the marker in a subject within a period of about 10 minutes to about 10 hours following administration of the device.

In some embodiments, a method of treatment disclosed herein can include determining the level of a marker in a subject's blood, serum or plasma.

An illustrative list of examples of biomarkers for GI disorders includes, but is not limited to, interferon-K; IL-1β; IL-6; IL-22; IL-17A; TNFI; IL-2; memory cells ($CD44^+$ $CD45RB^-CD4^+$ cells); α4β7; VEGF; ICAM; VCAM; Calprotectin; lactoferrin; FGF2; TGFb; ANG-1; ANG-2; PLGF; biologics (e.g., Infliximab; Humira® (adalimumab); Stelara® (ustekinumab); vedolizumab; Simponi® (golimumab); JAK inhibitors); EGF; IL12/23p40; GM-CSF; AeB7; CRP; HB-EGF; HRG; TGFα; SCF; TWEAK; MMP-9; MMP-6; Ceacam CD66; IL-10; ADA; MAdCAM-1; CD166 (AL CAM); FGF2; FGF7; FGF9; FGF19; ANCA (Antineutrophil cytoplasmic antibody); ASCAA (Anti-*Saccharomyces Cerevisiae* Antibody IgA); ASCAG (Anti-*Saccharomyces Cerevisiae* Antibody IgG); CBirl (Anti-*Clostridium* cluster XIVa flagellin CBirl antibody); A4-Fla2 (Anti-*Clostridium* cluster XIVa flagellin 2 antibody); FlaX (Anti-*Clostridium* cluster XIVa flagellin X antibody); OmpC (Anti-*Escherichia coli* Outer Membrane Protein C); ANCA (Perinuclear AntiNeutrophil Cytoplasmic Antibody); AREG (Amphiregulin Protein); BTC (Betacellulin Protein); EGF (Epidermal Growth Factor); EREG (Epiregulin Protein); HBEGF (Heparin Binding Epidermal Growth Factors); HGF (Hepatocyte Growth Factor); NRG1 (Neuregulin-1); TGFA (Transforming Growth Factor alpha); CRP (C-Reactive Protein); SAA (Serum Amyloid A); ICAM-1 (Intercellular Adhesion Molecule 1); VCAM-1 (Vascular Cell Adhesion Molecule 1); and fibroblasts underlying the intestinal epithelium.

In some embodiments, a marker is an IBD biomarker, such as, for example: anti-glycan; anti-*Saccharomices cerevisiae* (ASCA); anti-laminaribioside (ALCA); anti-chitobioside (ACCA); anti-mannobioside (AMCA); anti-laminarin (anti-L); anti-chitin (anti-C) antibodies: anti-outer membrane porin C (anti-OmpC), anti-Cbirl flagellin; anti-12 antibody; autoantibodies targeting the exocrine pancreas (PAB); and perinuclear anti-neutrophil antibody (pANCA); and calprotectin.

In some embodiments, a biomarker is associated with membrane repair, fibrosis, angiogenesis. In certain embodiments, a biomarker is an inflammatory biomarker, an anti-inflammatory biomarker, an MMP biomarker, an immune marker, or a TNF pathway biomarker. In some embodiments, a biomarker is gut specific.

For tissue samples, HER2 can be used as a biomarker relating to cytotoxic T cells. Additionally, other cytokine levels can be used as biomarkers in tissue (e.g., phospho STAT 1, STAT 3 and STAT 5), in plasma (e.g., VEGF, VCAM, ICAM, IL-6), or both.

In some embodiments, the biomarkers include one or more immunoglobulins, such as, for example, immunoglobulin M (IgM), immunoglobulin D (IgD), immunoglobulin G (IgG), immunoglobulin E (IgE) and/or immunoglobulin A (IgA). In some embodiments, IgM is a biomarker of infection and/or inflammation. In some embodiments, IgD is a biomarker of autoimmune disease. In some embodiments, IgG is a biomarker of Alzheimer's disease and/or for cancer. In some embodiments, IgE is a biomarker of asthma and/or allergen immunotherapy. In some embodiments, IgA is a biomarker of kidney disease.

In some embodiments, the biomarker is High Sensitivity C-reactive Protein (hsCRP); 7 α-hydroxy-4-cholesten-3-one (7C4); Anti-Endomysial IgA (EMA IgA); Anti-Human Tissue Transglutaminase IgA (tTG IgA); Total Serum IgA by Nephelometry; Fecal Calprotectin; or Fecal Gastrointestinal Pathogens.

In some embodiments, the biomarker is a) an anti-gliadin IgA antibody, an anti-gliadin IgG antibody, an anti-tissue transglutaminase (tTG) antibody, an anti-endomysial antibody;

b)i) a serological marker that is ASCA-A, ASCA-G, ANCA, pANCA, anti-OmpC antibody, anti-CBirl antibody, anti-FlaX antibody, or anti-A4-Fla2 antibody;

b)ii) an inflammation marker that is VEGF, ICAM, VCAM, SAA, or CRP;

b)iii) the genotype of the genetic markers ATG16L1, ECM1, NKX2-3, or STAT3;

c) a bacterial antigen antibody marker;

d) a mast cell marker;

e) an inflammatory cell marker;

f) a bile acid malabsorption (BAM) marker;

g) a kynurenine marker; or h) a serotonin marker.

In some embodiments, the bacterial antigen antibody marker is selected from the group consisting of an anti-Fla1 antibody, anti-Fla2 antibody, anti-FlaA antibody, anti-FliC antibody, anti-FliC2 antibody, anti-FliC3 antibody, anti-YBaNl antibody, anti-ECFliC antibody, anti-EcOFliC antibody, anti-SeFljB antibody, anti-CjFlaA antibody, anti-CjFlaB antibody, anti-SfFliC antibody, anti-CjCgtA antibody, anti-Cjdmh antibody, anti-CjGT-A antibody, anti-EcYidX antibody, anti-EcEra antibody, anti-EcFrvX antibody, anti-EcGabT antibody, anti-EcYedK antibody, anti-EcYbaN antibody, anti-EcYhgN antibody, anti-RtMaga antibody, anti-RbCpaF antibody, anti-RgPilD antibody, anti-LaFrc antibody, anti-LaEno antibody, anti-LjEFTu antibody, anti-BfOmpa antibody, anti-PrOmpA antibody, anti-CpIObA antibody, anti-CpSpA antibody, anti-EfSant antibody, anti-LmOsp antibody, anti-SfET-2 antibody, anti-Cpatox antibody, anti-Cpbtox antibody, anti-EcSta2 antibody, anti-EcOStx2A antibody, anti-CjcdtB/C antibody, anti-CdtcdA/B antibody, and combinations thereof.

In some embodiments, the mast cell marker is selected from the group consisting of beta-tryptase, histamine, prostaglandin E2 (PGE2), and combinations thereof.

In some embodiments, the inflammatory marker is selected from the group consisting of CRP, ICAM, VCAM, SAA, GRO.alpha., and combinations thereof.

In some embodiments, the bile acid malabsorption marker is selected from the group consisting of 7α-hydroxy-4-cholesten-3-one, FGF19, and a combination thereof.

In some embodiments, the kynurenine marker is selected from the group consisting of kynurenine (K), kynurenic acid (KyA), anthranilic acid (AA), 3-hydroxykynurenine (3-HK), 3-hydroxyanthranilic acid (3-HAA), xanthurenic acid (XA), quinolinic acid (QA), tryptophan, 5-hydroxytryptophan (5-HTP), and combinations thereof.

In some embodiments, the serotonin marker is selected from the group consisting of serotonin (5-HT), 5-hydroxyindoleacetic acid (5-HIAA), serotonin-O-sulfate, serotonin-O-phosphate, and combinations thereof.

In some embodiments, the biomarker is a biomarker as disclosed in U.S. Pat. No. 9,739,786, incorporated by reference herein in its entirety.

The following markers can be expressed by mesenchymal stem cells (MSC): CD105, CD73, CD90, CD13, CD29, CD44, CD10, Stro-1, CD271, SSEA-4, CD146, CD49f, CD349, GD2, 3G5, SSEA-3, SISD2, Stro-4, MSCA-1, CD56, CD200, PODX1, Sox 11, or TM4SF1 (e.g., 2 or more, 3 or more, 4 or more, 5 or more, 6 or more, 7 or more, 8 or more, 9 or more, or 10 or more of such markers), and lack expression of one or more of CD45, CD34, CD14, CD19, and HLA-DR (e.g., lack expression of two or more, three or more, four or more, or five or more such markers). In some embodiments, MSC can express CD105, CD73, and CD90. In some embodiments, MSC can express CD105, CD73, CD90, CD13, CD29, CD44, and CD10. In some embodiments, MSC can express CD105, CD73, and CD90 and one or more stemness markers such as Stro-1, CD271, SSEA-4, CD146, CD49f, CD349, GD2, 3G5, SSEA-3. SISD2, Stro-4, MSCA-1, CD56, CD200, PODX1, Sox 11, or TM4SF1. In some embodiments, MSC can express CD105, CD73, CD90, CD13, CD29, CD44, and CD10 and one or more stemness markers such as Stro-1, CD271, SSEA-4, CD146, CD49f, CD349, GD2, 3G5, SSEA-3. SISD2, Stro-4, MSCA-1, CD56, CD200, PODX1, Sox 11, or TM4SF1. See, e.g., Lv, et al., *Stem Cells,* 2014, 32:1408-1419.

Intestinal stem cells (ISC) can be positive for one or more markers such as Musashi-1 (Msi-1), Ascl2, Bmi-1, Doublecortin and Ca2+/calmodulin-dependent kinase-like 1 (DCAMKL1), and Leucin-rich repeat-containing G-protein-coupled receptor 5 (Lgr5). See, e.g., Mohamed, et al., Cytotechnology, 2015 67(2):177-189.

Any of the foregoing biomarkers can be used as a biomarker for one or more of other conditions as appropriate.

In some embodiments of the methods herein, the methods comprise determining the time period of onset of treatment following administration of the device.

EXAMPLES

Example 1—Preclinical Murine Colitis Model

Experimental Induction of Colitis

Colitis is experimentally induced to mice via the dextran sulfate sodium (DSS)-induced colitis model. This model is widely used because of its simplicity and many similarities with human ulcerative colitis. Briefly, mice are subjected to DSS via cecal catheterization, which is thought to be directly toxic to colonic epithelial cells of the basal crypts, for several days until colitis is induced.

Groups

Mice are allocated to one of seven cohorts, depending on the agent that is administered:

1. Control (no agent)
2. Adalimumab (2.5 mg/kg)
3. Adalimumab (5 mg/kg)
4. Adalimumab (10 mg/kg)

The control or agent is applied to a damaged mucosal surface of the bowel via administration through a cecal catheter at the dose levels described above.

Additionally, for each cohort, the animals are separated into two groups. One group receives a single dose of the control or agent on day 10 or 12. The other group receives daily (or similar) dosing of the control or agent.

Analysis

For each animal, efficacy is determined (e.g., by endoscopy, histology, etc.), and cytotoxic T-cell levels are determined in blood, feces, and tissue (tissue levels are determined after animal sacrifice). For tissue samples, levels HER2 are additionally determined, and the level of cytotoxic T cells is normalized to the level of HER2. Additionally, other cytokine levels are determined in tissue (e.g., phospho STAT 1, STAT 3 and STAT 5), in plasma (e.g., VEGF, VCAM, ICAM, IL-6), or both.

Pharmacokinetics are determined both systemically (e.g., in the plasma) and locally (e.g., in colon tissue). For systemic pharmacokinetic analysis, blood and/or feces is collected from the animals at one or more timepoints after administration (e.g., plasma samples are collected at 15 minutes, 30 minutes, 1 hour, 2 hours, 4 hours, and/or 8 hours after administration). Local/colon tissue samples are collected once after animal sacrifice.

Example 2a—Development of Preclinical Porcine Colitis Model

Experimental Induction of Colitis

Female swine weighing approximately 35 to 45 kg at study start are fasted at least 24 hours prior to intra-rectal administration of trinitrobenzene sulfonic acid (TNBS). Animals are lightly anesthetized during the dosing and endoscopy procedure. An enema to clean the colon is used, if necessary. One animal is administered 40 mL of 100% EtOH mixed with 5 grams of TNBS diluted in 10 mL of water via an enema using a ball-tipped catheter. The enema is deposited in the proximal portion of the descending colon just past the bend of the transverse colon. The TNBS is retained at the dose site for 12 minutes by use of two Foley catheters with 60-mL balloons placed in the mid-section of the descending colon below the dose site. A second animal is similarly treated, but with a solution containing 10 grams of TNBS. An Endoscope is employed to positively identify the dose site in both animals prior to TNBS administration. Dosing and endoscopy are performed by a veterinary surgeon.

Seven (7) days after TNBS administration, after light anesthesia, the dose site and mucosal tissues above and below the dose site are evaluated by the veterinary surgeon using an endoscope. Pinch Biopsies are obtained necessary, as determined by the surgeon. Based on the endoscopy findings, the animals may be euthanized for tissue collection on that day, or may proceed on study pending the results of subsequent endoscopy exams for 1 to 4 more days. Macroscopic and microscopic alterations of colonic architecture, possible necrosis, thickening of the colon, and substantial histologic changes are observed at the proper TNBS dose.

Clinical signs (e.g., ill health, behavioral changes, etc.) are recorded at least daily during acclimation and throughout the study. Additional pen-side observations are conducted twice daily (once-daily on weekends). Body weight is measured for both animals Days 1 and 7 (and on the day of euthanasia if after Day 7).

On the day of necropsy, the animals are euthanized via injection of a veterinarian-approved euthanasia solution. Immediately after euthanasia in order to avoid autolytic changes, colon tissues are collected, opened, rinsed with saline, and a detailed macroscopic examination of the colon is performed to identify macroscopic finings related to TNBS-damage. Photos are taken. Tissue samples are taken from the proximal, mid, and distal transverse colon; the dose site; the distal colon; the rectum; and the anal canal. Samples are placed into NBF and evaluated by a board certified veterinary pathologist.

Example 2b—Pharmacokinetic/Pharmacodynamic and Bioavailability of Adalimumab After Topical Application Groups Sixteen (16) swine (approximately 35 to 45 kg at study start) are allocated to one of five groups:

1. Vehicle Control: (3.2 mL saline); intra-rectal; (n=2)
2. Treated Control: Adalimumab (40 mg in 3.2 mL saline); subcutaneous; (n=2)
3. Adalimumab (low): Adalimumab (40 mg in 3.2 mL saline); intra-rectal; (n=4)
4. Adalimumab (med): Adalimumab (80 mg in 3.2 mL saline); intra-rectal; (n=4)
5. Adalimumab (high): Adalimumab (160 mg in 3.2 mL saline); intra-rectal; (n=4)

On Day 0, the test article is applied to a damaged mucosal surface of the bowel via intra-rectal administration or subcutaneous injection by a veterinary surgeon at the dose levels and volume described above.

Clinical Observations and Body Weight

Clinical observations are conducted at least once daily. Clinical signs (e.g., ill health, behavioral changes, etc.) are recorded on all appropriate animals at least daily prior to the initiation of experiment and throughout the study until termination. Additional clinical observations may be performed if deemed necessary. Animals whose health condition warrants further evaluation are examined by a Clinical Veterinarian. Body weight is measured for all animals Days −6, 0, and after the last blood collections.

Samples

Blood: Blood is collected (cephalic, jugular, and/or catheter) into EDTA tubes during acclimation on Day-7, just prior to dose on Day 0, and 0.5, 1, 2, 4, 6, 8, 12, 24, and 48 hours post-dose. The EDTA samples are split into two aliquots and one is centrifuged for pharmacokinetic plasma and either analyzed immediately, or stored frozen (−80° C.) for later pharmacokinetic analyses. The remaining sample of whole blood is used for pharmacodynamic analyses.

Feces: Feces is collected Day −7, 0 and 0.5, 1, 2, 4, 6, 8, 12, 24 and 48 hours post-dose, and either analyzed immediately, or flash-frozen on liquid nitrogen and stored frozen at −70° C. pending later analysis of drug levels and inflammatory cytokines.

Tissue: Immediately after euthanasia in order to avoid autolytic changes, colon tissues are collected, opened, rinsed with saline, and a detailed macroscopic examination of the colon is performed to identify macroscopic finings related to TNBS-damage. Triplicate samples of normal and damaged tissues are either analyzed immediately, or are flash-frozen on liquid nitrogen and stored frozen at −70° C. pending later analysis of drug concentration, inflammatory cytokines and histology.

Samples are analyzed for adalimumab levels (local mucosal tissue levels and systemic circulation levels), and for levels of inflammatory cytokines including TNF-alpha.

Terminal Procedures

Animals are euthanized as per the schedule in Table 5, where one animal each of Vehicle and Treated Control groups is euthanized at 6 and 48 hours post-dose, and one animal of each the adalimumab groups are euthanized at 6, 12, 24 and 48 hours post-dose. Animals are discarded after the last blood collection unless retained for a subsequent study.

TABLE 5

| | Sample | | | Days | | | | | | | | Hours | | | | | | | | |
|---|---|---|---|---|---|---|---|---|---|---|---|---|---|---|---|---|---|---|---|---|
| | size | Dose | Route | −7 | −6 | −5 | −4 | −3 | −2 | −1 | 0 | 0.5 | 1 | 2 | 4 | 6 | 8 | 12 | 24 | 48 |
| General | | | | | | | | | | | | | | | | | | | | |
| Fast | | | | • | | | | | | | | | | | | | | | | |
| Food/Water | | ad libidum | oral | | • | • | • | • | • | • | • | • | • | • | • | • | • | • | • | • |
| Observations | | | | | | | | | | | | | | | | | | | | |
| clinical observations | | | | • | • | • | • | • | • | • | • | | | | | | | | • | • |
| body weight | | | | • | | | | | | | • | | | | | | | | • | • |
| Treatments (groups) | | | | | | | | | | | | | | | | | | | | |
| TNBS (all animals) | | | intra rectal | | • | | | | | | | | | | | | | | | |

TABLE 5-continued

| | Sample | | | Days | | | | | | | | Hours | | | | | | | | |
|---|---|---|---|---|---|---|---|---|---|---|---|---|---|---|---|---|---|---|---|---|
| | size | Dose | Route | −7 | −6 | −5 | −4 | −3 | −2 | −1 | 0 | 0.5 | 1 | 2 | 4 | 6 | 8 | 12 | 24 | 48 |
| 1. Vehicle control | n = 2 | 1.6 mL saline (vehicle) | intra rectal | | | | | | | | • | | | | | | | | | |
| euthanized | | | | | | | | | | | | | | | | n = 1 | | | | n = 1 |
| 2. Treated control | n = 2 | 40 mg in 1.6 mL saline | sub-cutaneous | | | | | | | | | | | | | | | | | |
| euthanized | | | | | | | | | | | | | | | | n = 1 | | | | n = 1 |
| 3. Adalimumab (low) | n = 4 | 40 mg in 1.6 mL saline | intra rectal | | | | | | | | • | | | | | | | | | |
| euthanized | | | | | | | | | | | | | | | | n = 1 | | n = 1 | n = 1 | n = 1 |
| 4. adalimumab (med) | n = 4 | 80 mg in 1.6 mL saline | intra rectal | | | | | | | | • | | | | | | | | | |
| euthanized | | | | | | | | | | | | | | | | n = 1 | | n = 1 | n = 1 | n = 1 |
| 5. Adalimumab (high) | n = 4 | 160 mg in 1.6 mL saline | intra rectal | | | | | | | | • | | | | | | | | | |
| euthanized | | | | | | | | | | | | | | | | n = 1 | | n = 1 | n = 1 | n = 1 |
| Adalimumab (required) | | 1200 | | | | | | | | | | | | | | | | | | |
| Samples | | | | | | | | | | | | | | | | | | | | |
| Blood | | | cephalic, jugular, or catheter | • | | | | | | | • | • | • | • | • | • | • | • | • | • |
| Fecal | | | rectal | • | | | | | | | • | • | • | • | • | • | • | • | • | • |
| Tissue | | | necropsy | • | | | | | | | | | | | | • | | • | • | • |

Example 2c—Pharmacokinetic/Pharmacodynamic and Bioavailability of Adalimumab After Topical Application Groups DSS-induced colitis Yorkshire-Cross Farm Swine (approximately 5-10 kg at study start) are allocated to one of five groups:

1. Vehicle Control: (saline); intra-rectal;
2. Treated Control: Adalimumab (13 mg in saline); subcutaneous;
3. Adalimumab: Adalimumab (13 mg in saline); intra-rectal.

At t=0, the test article is applied to a damaged mucosal surface of the bowel via intra-rectal administration or subcutaneous injection by a veterinary surgeon at the dose levels and volume described above.

Clinical Observations

Clinical signs (e.g., ill health, behavioral changes, etc.) are recorded on all appropriate animals at least daily prior to the initiation of experiment and throughout the study until termination. Additional clinical observations may be performed if deemed necessary. Animals whose health condition warrants further evaluation are examined by a Clinical Veterinarian.

Samples

Blood: Blood is collected (cephalic, jugular, and/or catheter) into EDTA tubes during acclimation on Day-7, just prior to dose on Day 0, and 12 hours post-dose. The EDTA samples are split into two aliquots and one is centrifuged for pharmacokinetic plasma and either analyzed immediately, or stored frozen (−80° C.) for later pharmacokinetic analyses. The remaining sample of whole blood is used for pharmacodynamic analyses.

Feces: Feces is collected Day −7, 0 and 12 hours post-dose, and either analyzed immediately, or flash-frozen on liquid nitrogen and stored frozen at −70° C. pending later analysis of drug levels and inflammatory cytokines.

Tissue: Immediately after euthanasia (12 hours after dosing) in order to avoid autolytic changes, colon tissues are collected, opened, rinsed with saline, and a detailed macroscopic examination of the colon is performed to identify macroscopic finings related to DSS-damage. Triplicate samples of normal and damaged tissues are either analyzed immediately, or are flash-frozen on liquid nitrogen and stored frozen at −70° C. pending later analysis of drug concentration, inflammatory cytokines and histology.

Samples are analyzed for adalimumab levels (local mucosal tissue levels and systemic circulation levels), and for levels of inflammatory cytokines including TNF-alpha.

Terminal Procedures

Animals are euthanized at 12 hours post-dose.

Example 3—Comparison of Systemic Versus Intracecal Delivery of an Anti-IL-12 Antibody The objective of this study was to compare the efficacy of an IL-12 inhibitor (anti-IL-12 p40; anti-p40 mAb; BioXCell (Cat #: BE0051)), when dosed systemically versus intracecally, to the treat dextran sulfate sodium salt (DSS)-induced colitis in male C57Bl/6 mice.

Materials and Methods

Mice

Normal male C57Bl/6 mice between the ages of 6-8 weeks old, weighing 20-24 g, were obtained from Charles River Laboratories. The mice were randomized into thirteen groups of twelve animals and two groups of eight animals, and housed in groups of 6-8 per cage, and acclimatized for at least three days prior to entering the study. Animal rooms were set to maintain a minimum of 12 to 15 air changes per hour, with an automatic timer for a light/dark cycle of 12 hours on/off, and fed with Labdiet 5053 sterile rodent chow, with water administered ad libitum.

Cecal Cannulation

Animals were placed under isoflurane anesthesia, with the cecum exposed via a midline incision in the abdomen. A small point incision was made in the distal cecum where 1-2 cm of the cannula was inserted. The incision was closed with a purse string suture using 5-0 silk. An incision was then made in the left abdominal wall through which the distal end of the cannula was inserted and pushed subcutaneously to the dorsal aspect of the back. The site was then washed copiously with warmed saline prior to closing the abdominal wall. A small incision was also made in the skin of the back between the shoulder blades, exposing the tip of the cannula. The cannula was secured in place using suture, wound clips, and tissue glue. All animals received 1 mL of warm sterile saline (subcutaneous injection) and were monitored closely until recovery before returning to their cage. All animals received 0.6 mg/kg BID buprenorphine for the first 3 days, and Baytril® at 10 mg/kg every day for the first 5 days post-surgery.

Induction of Colitis

Colitis was induced in male C57Bl/6 mice by exposure to 3% DSS drinking water (MP Biomedicals #0260110) from Day 0 to Day 5. Fresh DSS/water solutions were made again on Day 3 and any of the remaining original DSS solution will be discarded.

Assessment of Colitis

All animals were weighed daily and visually assessed for the presence of diarrhea and/or bloody stool at the time of dosing. The mice underwent two video endoscopies, one on day 10 and one on day 14, to assess colitis severity. Images were captured from each animal at the most severe region of disease identified during the endoscopy, and assessed using the rubric demonstrated in Table 6. Additionally, stool consistency was scored during the endoscopy using this rubric (Table 7) (0=Normal, well-formed pellet, 1=Loose stool, soft, staying in shape, 2=Loose stool, abnormal form with excess moisture, 3=Watery or diarrhea, 4=Bloody diarrhea). At necropsy, intestinal contents, peripheral blood, and tissue, and cecum/colon contents were collected for analysis.

TABLE 6

Endoscopy Scoring

| Score | Description of Endoscopy Score |
|---|---|
| 0 | Normal |
| 1 | Loss of vascularity |
| 2 | Loss of vascularity and friability |
| 3 | Friability and erosions |
| 4 | Ulcerations and bleeding |

TABLE 7

Stool Consistency Score

| Score | Description of Stool Consistency |
|---|---|
| 0 | Normal, well-formed pellet |
| 1 | Loose stool, soft, staying in shape |
| 2 | Loose stool, abnormal form with excess moisture |
| 3 | Watery or diarrhea |
| 4 | Bloody diarrhea |

Treatment of Colitis

Mice were treated with anti-IL-12 p40 during the acute phase of colitis due to its efficacy in the treatment of DSS-induced colitis. The test article was dosed at a volume of 0.1 mL/20 g from days 0 to 14. Anti-IL-12 p40 was administered intraperitoneally at a dose of 10 mg/kg every 3 days, and intracecally at a dose of 10 mg/kg, either every 3 days or every day. There was also a lower dose of 1 mg/kg given every day intracecally. The control groups were not administered drugs, and the vehicles (sterile PBS) were administered the placebo drug intraperitoneally and intracecally every day. These drugs were given from days 5-14, which is 9 days of administration. A more detailed explanation of dosing and groups can be seen in Table 8.

TABLE 8

Groups of Animals

| Group # | # of Animals | DSS | Cecal Cannula | Treatment | Dose (mg/kg) | Route | Dosing Schedule |
|---|---|---|---|---|---|---|---|
| 1 | 8 males | — | NO | — | — | — | — |
| 2 | 8 males | — | YES | — | — | — | — |
| 3 | 12 males | 3% DSS (day 0-5) | NO | Vehicle | — | PO | QD day 0-14 |
| 4 | 12 males | 3% DSS (day 0-5) | YES | Vehicle | — | IC | QD day 0-14 |
| 5 | 12 males | 3% DSS (day 0-5) | NO | Anti-p40 | 10 | IP | Q3 0, 3, 6, 9, 12 |
| 6 | 12 males | 3% DSS (day 0-5) | YES | Anti-p40 | 10 | IC | Q3 0, 3, 6, 9, 12 |
| 7 | 12 males | 3% DSS (day 0-5) | YES | Anti-p40 | 10 | IC | QD day 0-14 |
| 8 | 12 males | 3% DSS (day 0-5) | YES | Anti-p40 | 1 | IC | QD day 0-14 |

Sample Collection

Intestinal contents, peripheral blood, and tissue were collected at sacrifice on day 14, as follows: at the end of each study period, mice were euthanized by $CO_2$ inhalation immediately following endoscopy on day 14. The blood was collected via cardiac puncture into $K_2$EDTA-coated tubes and centrifuged at 4000×g for 10 minutes. The blood cell pellet was retained and snapped frozen. The resulting plasma was then split into two separate cryotubes, with 100 μL in one tube and the remainder in the second. Plasma and cell pellet were also collected, flash frozen, and stored at −80 degrees Celsius.

The cecum and colon were removed from each animal and contents were collected, weighed, and snap frozen in separate cryovials. The colon was excised, rinsed, measured, weighed, and then trimmed to 6 cm in length and divided into 5 pieces. The most proximal 1 cm of colon was snapped frozen for subsequent bioanalysis of test article levels. Of the remaining 5 cm of colon, the most distal and proximal 1.5-cm sections was placed in formalin for 24 hours then transferred to 70% ethanol for subsequent histological evaluation. The middle 2-cm portion was bisected longitudinally and placed into two separate cryotubes, weighed, and snap frozen in liquid nitrogen.

Results

Figure 30:
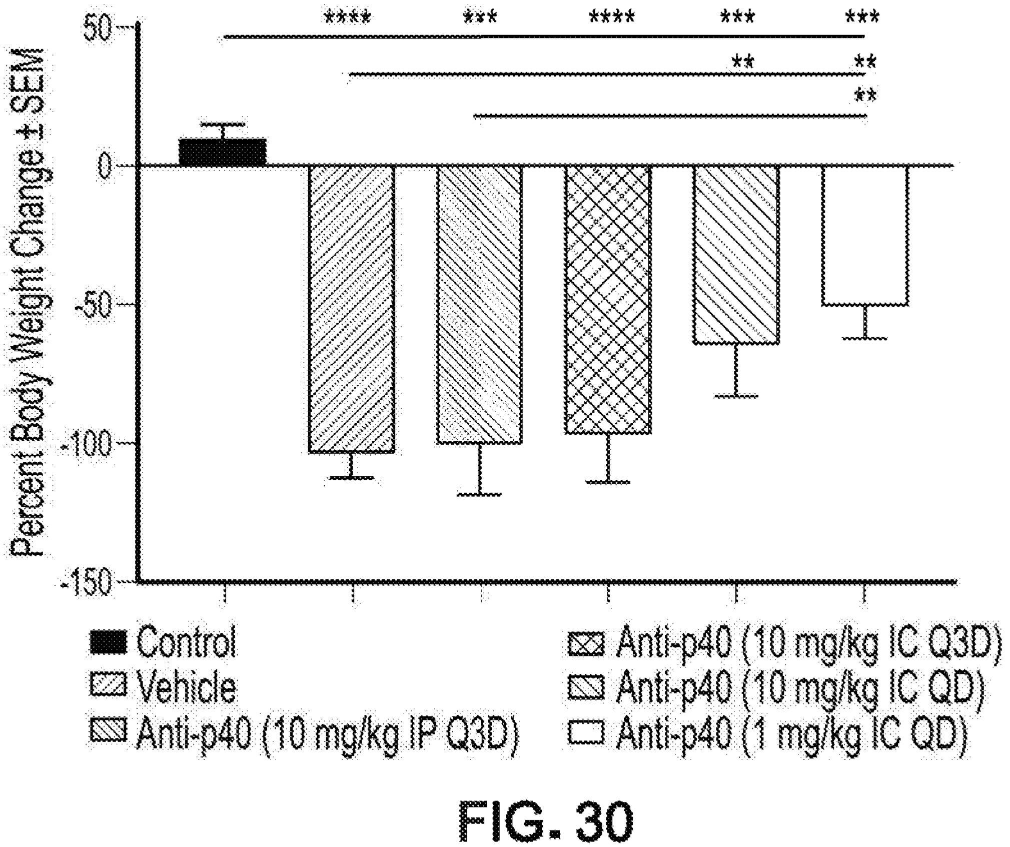
FIG. 30 is a graph showing the percentage (%) change in body weight at day 14 (±SEM) for DSS mice treated with anti-IL-12 p40 antibody intraperitoneally (10 mg/kg) every third day (Q3D) or intracecally (10 mg/kg or 1 mg/kg) daily (QD), when compared to mice treated with anti-IL-12 p40 antibody intraperitoneally (10 mg/kg) every third day (Q3D) and vehicle control (Vehicle). Mann-Whitney's U¬-test and Student's t-test were used for statistical analysis on non-Gaussian and Gaussian data respectively. A value of $p<0.05$ was considered significant (Graph Pad Software, Inc.).

The data in FIG. 30 show that the DSS mice that were intracecally administered an anti-IL-12 p40 (IgG2A) antibody had decreased weight loss as compared to DSS mice that were intraperitoneally administered the anti-IL-12 p40 antibody.

Figure 31:
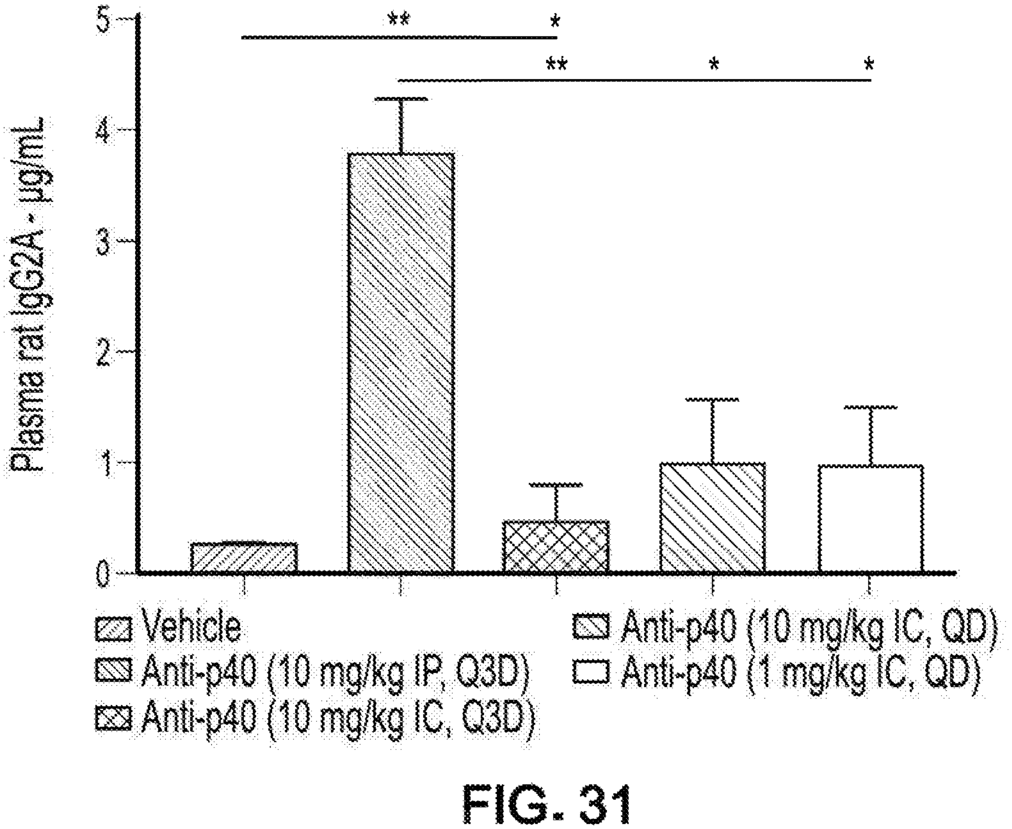
FIG. 31 is a graph showing the concentration of anti-IL-12 p40 rat IgG2A (μg/mL) in plasma of anti-IL-12 p40 intraperitoneally (10 mg/kg) and intracecally (10 mg/kg and 1 mg/kg) administered treatment groups given daily (QD) or every third day (Q3D) when compared to vehicle control (Vehicle) and when IP is compared to IC. ELISA analysis was used to determine the concentration of anti-IL-12 p40 (IgG2A). Data presented as mean±SEM. Mann-Whitney's U¬-test and Student's t-test were used for statistical analysis on non-Gaussian and Gaussian data respectively. A value of $p<0.05$ was considered significant (Graph Pad Software, Inc.).
Figure 32:
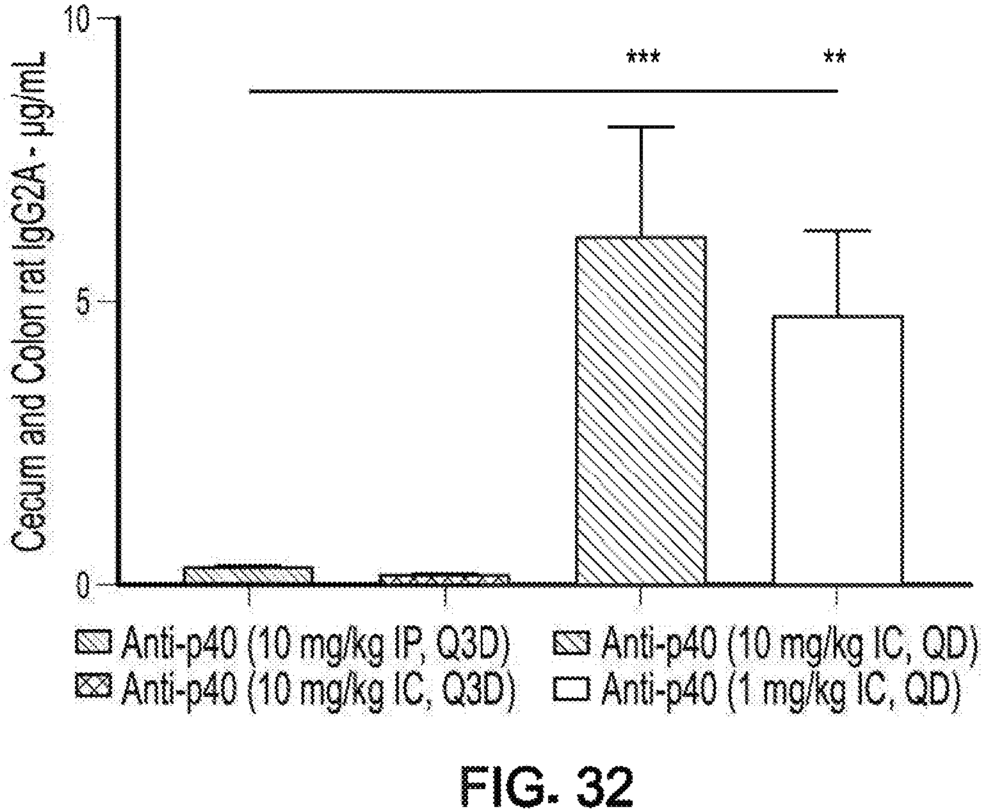
FIG. 32 is a graph showing the concentration of anti-IL-12 p40 antibody (IgG2A) (μg/mL) in the cecum and colon content of anti-IL-12 p40 antibody intraperitoneally (10 mg/kg) and intracecally (10 mg/kg and 1 mg/kg) administered treatment groups given daily (QD) or every third day (Q3D), when compared to vehicle control (Vehicle) and when IP is compared to IC. ELISA analysis was used to determine the concentration of rat IgG2A. Data presented as mean±SEM. Mann-Whitney's U-test and Student's t-test were used for statistical analysis on non-Gaussian and Gaussian data respectively. A value of $p<0.05$ was considered significant (Graph Pad Software, Inc.).

The data in FIG. 31 show that the plasma concentration of the anti-IL-12 p40 antibody was decreased in DSS mice that were intracecally administered the anti-IL-12 p40 antibody as compared to DSS mice that were intraperitoneally administered the anti-IL-12 p40 antibody. The data in FIG. 32 show that the cecum and colon concentration of the anti-IL-12 p40 antibody is increased in DSS mice that were intracecally administered the anti-IL-12 p40 antibody as compared to the DSS mice that were intraperitoneally administered the anti-IL-12 p40 antibody.

Figure 33:
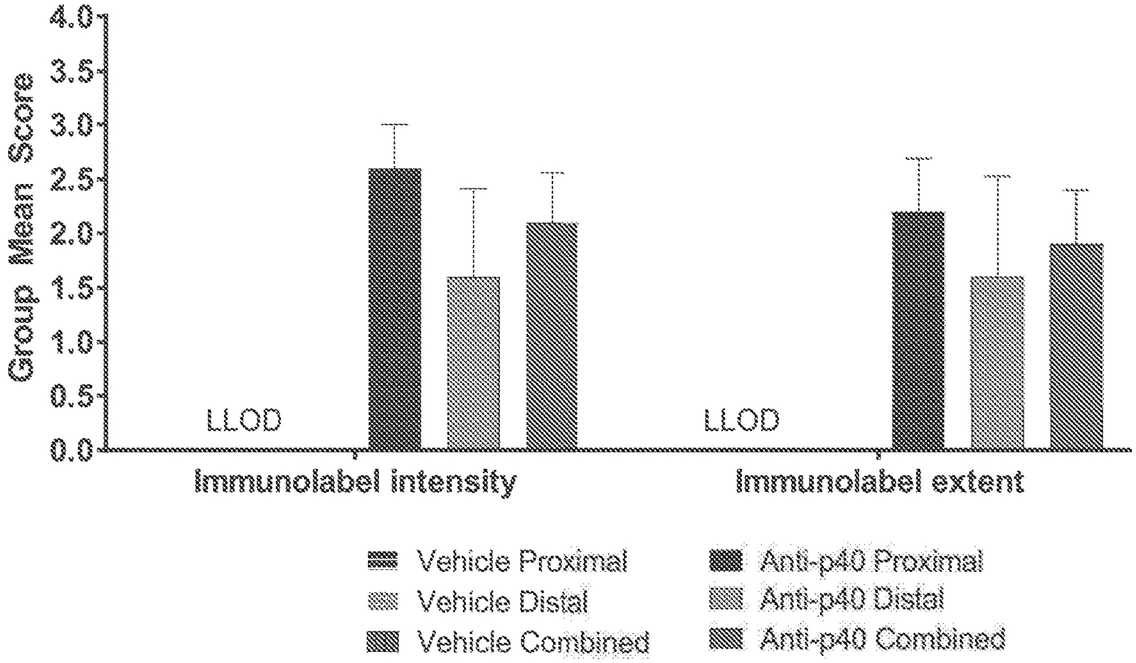
FIG. 33 is a graph showing the mean overall tissue immunolabel scores (intensity and extent) in acute DSS colitis mouse colon of anti-IL-12 p40 antibody intracecally-treated versus vehicle control-treated DSS mice. Data presented as mean±SEM.
Figure 34:
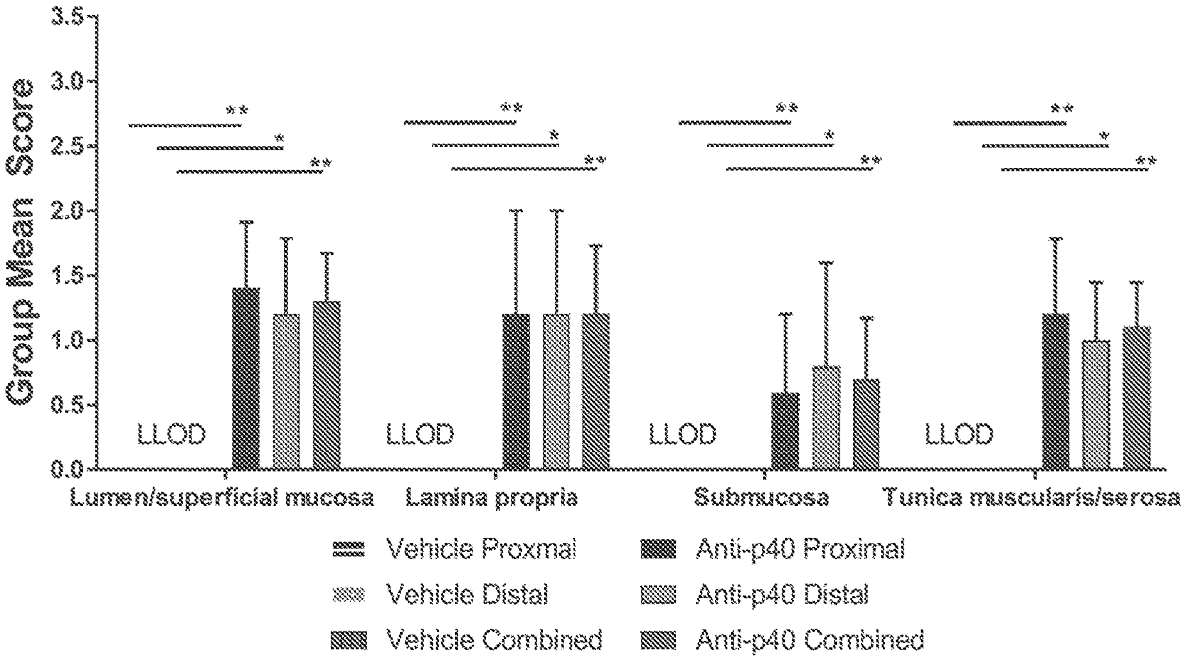
FIG. 34 is a graph showing the mean location-specific immunolabel scores in acute DSS colitis mouse colon of anti-IL-12 p40 intracecally-treated versus vehicle control-treated DSS mice. Data presented as mean±SEM. Mann-Whitney's U-test and Student's t-test were used for statistical analysis on non-Gaussian and Gaussian data respectively. A value of $p<0.05$ was considered significant (Graph Pad Software, Inc.).
Figure 35:
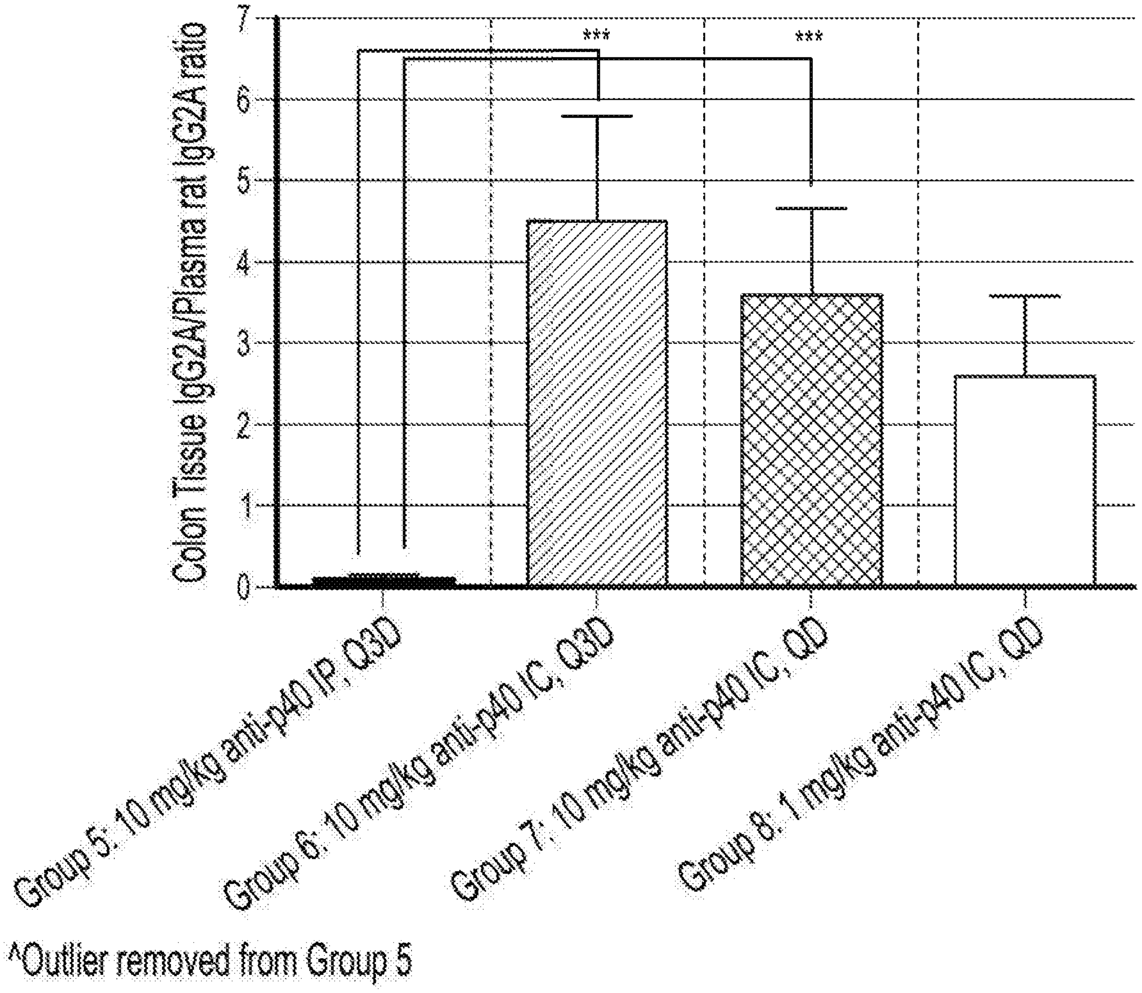
FIG. 35 is a graph showing the ratio of anti-IL-12 p40 antibody in the colon tissue to the plasma concentration of the anti-IL-12 p40 antibody in mice treated with the anti-IL-12 p40 antibody on day 0 (Q0) or day 3 (Q3D) of the study, when measured at the same time point after the initial dosing. An outlier animal was removed from Group 5.

The data in FIGS. 33 and 34 show that the anti-IL-12 p40 antibody is able to penetrate colon tissues (the lumen superficial, lamina propria, submucosa, and tunica muscularis/serosa) in DSS mice intracecally administered the anti-IL-12 p40 antibody, while the anti-IL-12 p40 antibody did not detectably penetrate the colon tissues of DSS mice intraperitoneally administered the anti-IL-12 p40 antibody. The data in FIG. 35 also show that the ratio of the concentration of anti-IL-12 p40 antibody in colon tissue to the concentration of the anti-IL-12 p40 antibody in plasma is increased in DSS mice intracecally administered the anti-IL-12 p40 antibody as compared to the ratio in DSS mice intraperitoneally administered the anti-IL-12 p40 antibody.

Figure 36:
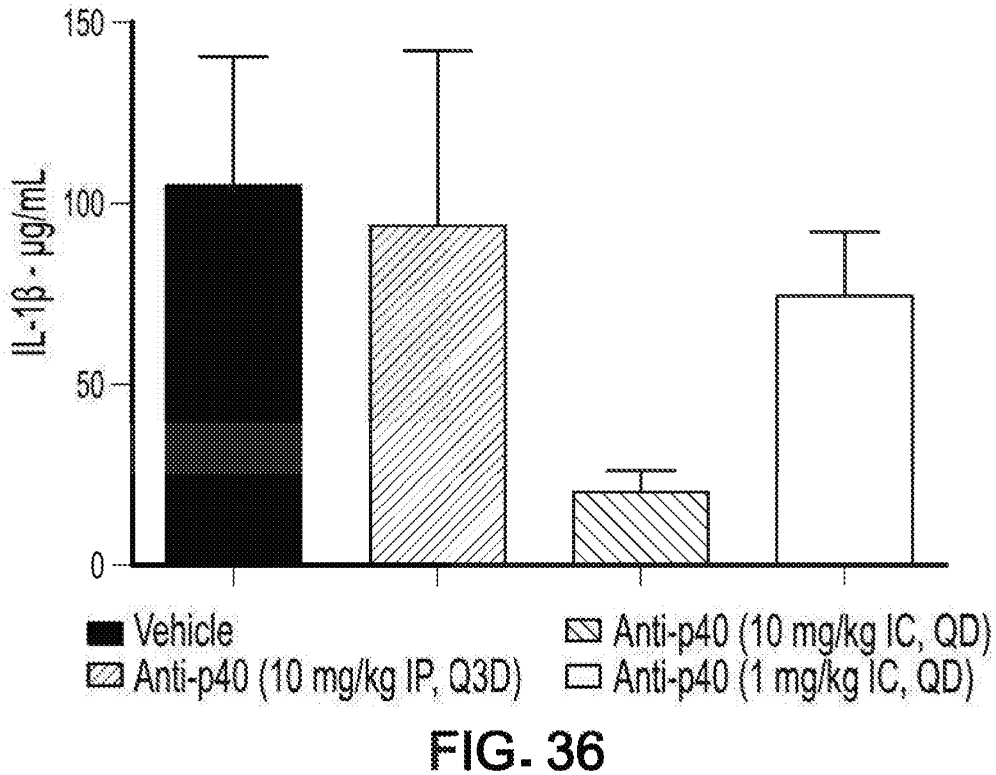
FIG. 36 is a graph showing the concentration of Il-1β (μg/mL) in colon tissue lysate of acute DSS colitis mice treated with anti-IL-12 p40 intraperitoneally (10 mg/kg) every third day (Q3D) or intracecally (10 mg/kg or 1 mg/kg) adminitsered daily (QD), when compared to vehicle control (Vehicle). Data presented as mean±SEM. Mann-Whitney's U-test and Student's t-test were used for statistical analysis on non-Gaussian and Gaussian data respectively. A value of $p<0.05$ was considered significant (Graph Pad Software, Inc.).
Figure 37:
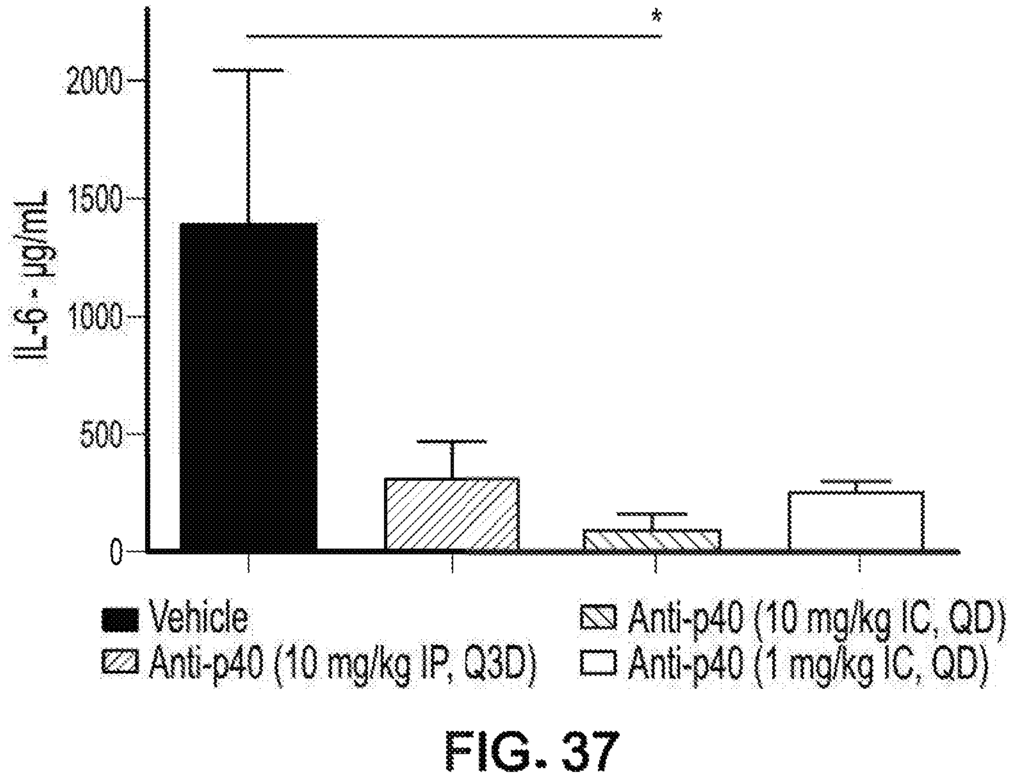
FIG. 37 is a graph showing the concentration of 11-6 (ptg/mL) in colon tissue lysate of acute DSS colitis mice treated with anti-IL-12 p40 intraperitoneally (10 mg/kg) every third day (Q3D) or intracecally (10 mg/kg or 1 mg/kg) administered daily (QD), when compared to vehicle control (Vehicle). Data presented as mean±SEM. Mann-Whitney's U-test and Student's t-test were used for statistical analysis on non-Gaussian and Gaussian data respectively. A value of $p<0.05$ was considered significant (Graph Pad Software, Inc.
Figure 38:
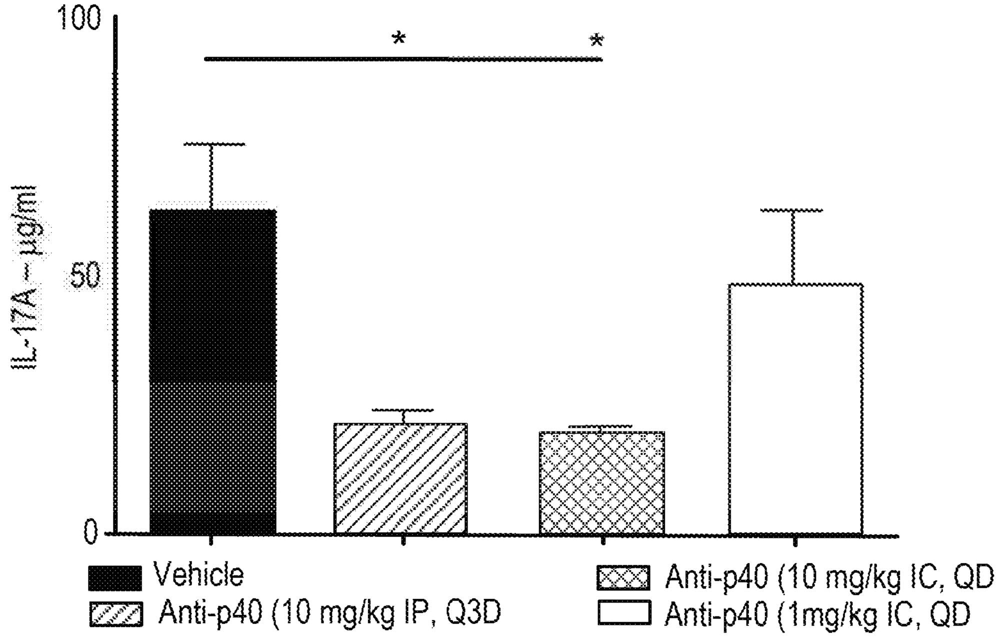
FIG. 38 is a graph showing the concentration of Il-17A (μg/mL) in colon tissue lysate of acute DSS colitis mice treated with anti-IL-12 p40 intraperitoneally (10 mg/kg)

The data in FIG. 36 show that the concentration of IL-1β in colon tissue is decreased in DSS mice intracecally administered the anti-IL-12 p40 antibody as compared to the concentration of IL-1β in colon tissue in DSS mice intraperitoneally administered the anti-IL-12 p40 antibody. The data in FIG. 37 show that the concentration of IL-6 in colon tissue is decreased in DSS mice intracecally administered the anti-IL-12 p'antibody as compared to the concentration of IL-6 in colon tissue in DSS mice intraperitoneally administered the anti-IL-12 p40 antibody. The data in FIG. 38 show that the concentration of IL-17A in colon tissue is decreased in DSS mice intracecally administered the anti-IL-12 p40 antibody as compared to the concentration of IL-17A in colon tissue in DSS mice intraperitoneally administered the anti-IL-12 p40 antibody.

No significant differences in clinical observations or gastrointestinal-specific adverse effects, including stool consistency and/or bloody stool, were observed due to cannulation or intra-cecal treatments when compared with vehicle. No toxicity resulting from the treatments was reported. A significant reduction in body weight-loss (AUC) was found in groups treated with anti-IL-12 p40 antibody (10 mg/kg and 1 mg/kg, QD) via intra-cecal delivery when compared with vehicle control and intraperitoneal delivery (10 mg/kg, Q3D). The immunohistochemistry staining in anti-IL-12 p40 antibody (10 mg/kg, QD) treatment groups showed penetration of the antibody in all layers of colon tissue, including lumen mucosa, lamina propria, submucosa, tunica muscularis, via intra-cecal delivery. The distribution of anti-IL-12 p40 antibody was found in all segments of the colon, however, higher levels were detected in the proximal region. A significantly higher mean concentration of anti-IL-12 p40 antibody was found in the gastrointestinal contents and colon tissues when delivered via intra-cecal administration (Anti-p40: 10 mg/kg and 1 mg/kg, QD) compared with intraperitoneal administration (anti-p40: 10 mg/kg, Q3D). The blood level of anti-IL-12 p40 antibody was significantly higher when delivered via intraperitoneal administration (Q3D) as compared to intra-cecal administration (Q3D & QD). The concentrations of inflammatory cytokines, including IL-1p, IL-6, and IL-17, were significantly reduced by anti-IL-12 p40 antibody (10 mg/kg, QD) treatment when delivered via intra-cecal administration as compared to vehicle controls.

In sum, these data show that the compositions and devices provided herein can suppress the local immune response in the intestine, while having less of a suppressive effect on the systemic immune response of an animal. These data also suggest that the presently claimed compositions and devices will provide for treatment of colitis and other pro-inflammatory disorders of the intestine.

Example 4—Comparison of Systemic Versus Intracecal Delivery of an Anti-Integrin α4β7 Antibody The objective of this study was to compare the efficacy of an integrin inhibitor (anti-integrin α4β7; anti-LPAM1; DATK-32 mAb; BioXCell (Cat #: BE0034)) when dosed systemically versus intracecally for treating dextran sulfate sodium salt (DSS)-induced colitis in male C57Bl/6 mice.

Materials and Methods

Mice

Normal male C57Bl/6 mice between the ages of 6-8 weeks old, weighing 20-24 g, were obtained from Charles River Laboratories. The mice were randomized into thirteen groups of twelve animals and two groups of eight animals, and housed in groups of 6-8 per cage, and acclimatized for at least three days prior to entering the study. Animal rooms were set to maintain a minimum of 12 to 15 air changes per hour, with an automatic timer for a light/dark cycle of 12 hours on/off, and fed with Labdiet 5053 sterile rodent chow, with water administered ad libitum.

Cecal Cannulation

The animals were placed under isoflurane anesthesia, with the cecum exposed via a midline incision in the abdomen. A small point incision was made in the distal cecum where 1-2 cm of the cannula was inserted. The incision was closed with a purse string suture using 5-0 silk. An incision was then made in the left abdominal wall through which the distal end of the cannula was inserted and pushed subcutaneously to the dorsal aspect of the back. The site was then washed copiously with warmed saline prior to closing the abdominal wall. A small incision was also made in the skin of the back between the shoulder blades, exposing the tip of the cannula. The cannula was secured in place using suture, wound clips, and tissue glue. All animals received 1 mL of warm sterile saline (subcutaneous injection) and were monitored closely until recovery before returning to their cage. All animals received 0.6 mg/kg BID buprenorphine for the first 3 days, and Baytril® at 10 mg/kg every day for the first 5 days post-surgery.

Induction of Colitis

Colitis was induced in male C57Bl/6 mice by exposure to 3% DSS drinking water (MP Biomedicals #0260110) from day 0 to day 5. Fresh DSS/water solutions were made again on day 3 and any of the remaining original DSS solution will be discarded.

Assessment of Colitis

All animals were weighed daily and visually assessed for the presence of diarrhea and/or bloody stool at the time of dosing. Mice underwent two video endoscopies, one on day 10 and one on day 14, to assess colitis severity. Images were captured from each animal at the most severe region of disease identified during the endoscopy, and assessed using the rubric demonstrated in Table 9. Additionally, stool consistency was scored during the endoscopy using this rubric (Table 10) (0=Normal, well-formed pellet, 1=Loose stool, soft, staying in shape, 2=Loose stool, abnormal form with excess moisture, 3=Watery or diarrhea, 4=Bloody diarrhea). At necropsy, intestinal contents, peripheral blood and tissue, and cecum/colon contents were collected for analysis.

TABLE 9

| Endoscopy Score | |
|---|---|
| Score | Description of Endoscopy Score |
| 0 | Normal |
| 1 | Loss of vascularity |
| 2 | Loss of vascularity and friability |
| 3 | Friability and erosions |
| 4 | Ulcerations and bleeding |

TABLE 10

| Stool Consistency Score | |
|---|---|
| Score | Description of Stool Consistency |
| 0 | Normal, well-formed pellet |
| 1 | Loose stool, soft, staying in shape |
| 2 | Loose stool, abnormal form with excess moisture |
| 3 | Watery or diarrhea |
| 4 | Bloody diarrhea |

Treatment of Colitis

Mice were treated with DATK32 during the acute phase of colitis due to its efficacy in the treatment of DSS-induced colitis. The test article was dosed at a volume of 0.1 mL/20 g from days 0 to 14. DATK32 was administered intraperitoneally at a dose of25 mg/kg every 3 days, and intracecally at a dose of 25 mg/kg, either every 3 days or every day. There was also a lower dose of 5 mg/kg given every day intracecally. The control groups were not administered drugs, and the vehicle (sterile PBS) was administered as the placebo drug intraperitoneally and intracecally every day. These drugs were given from days 5-14, which is 9 days of administration. A more detailed explanation of dosing and groups can be seen in Table 11.

TABLE 11

Groups of Mice

| Group # | # of Animals | DSS | Cecal Cannula | Treatment | Dose (mg/kg) | Route | Dosing Schedule |
|---|---|---|---|---|---|---|---|
| 1 | 8 males | — | NO | — | — | — | — |
| 2 | 8 males | — | YES | — | — | — | — |
| 3 | 12 males | 3% DSS (day 0-5) | NO | Vehicle | — | PO | QD day 0-14 |
| 4 | 12 males | 3% DSS (day 0-5) | YES | Vehicle | — | IC | QD day 0-14 |
| 9 | 12 males | 3% DSS (day 0-5) | NO | DATK32 | 25 | IP | Q3 0, 3, 6, 9, 12 |
| 10 | 12 males | 3% DSS (day 0-5) | YES | DATK32 | 25 | IC | Q3 0, 3, 6, 9, 12 |
| 11 | 12 males | 3% DSS (day 0-5) | YES | DATK32 | 25 | IC | QD day 0-14 |
| 12 | 12 males | 3% DSS (day 0-5) | YES | DATK32 | 5 | IC | QD day 0-14 |

Sample Collection

Intestinal contents, peripheral blood, and tissue were collected at sacrifice on day 14, as follows: at the end of each study period, mice were euthanized by $CO_2$ inhalation immediately following endoscopy on day 14. The blood was collected via cardiac puncture into $K_2$EDTA-coated tubes and centrifuged at 4000×g for 10 minutes. The blood cell pellet was retained and snapped frozen. The resulting plasma was then split into two separate cryotubes, with 100 μL in one tube and the remainder in the second. Plasma and the cell pellet were also collected, flash frozen, and stored at −80 degrees Celsius. An ELISA was used to determine the level of rat IgG2A.

The cecum and colon were removed from each animal and contents were collected, weighed, and snap frozen in separate cryovials. The colon was excised, rinsed, measured, weighed, and then trimmed to 6 cm in length and divided into 5 pieces. The most proximal 1 cm of colon was snapped frozen for subsequent bioanalysis of anti-DATK32 levels. Of the remaining 5 cm of colon, the most distal and proximal 1.5-cm sections was placed in formalin for 24 hours then transferred to 70% ethanol for subsequent histological evaluation. The middle 2-cm portion was bisected longitudinally and placed into two separate cryotubes, weighed, and snap frozen in liquid nitrogen.

There was an additional collection of 100 μL of whole blood from all animals and processed for FACS analysis of α4 and β7 expression on T-helper memory cells. Tissue and blood were immediately placed in FACS buffer (1×PBS containing 2.5% fetal calf serum) and analyzed using the following antibody panel (Table 12).

TABLE 12

Fluorophore-Labelled Antibodies Used in FACS Analysis

| Antibody Target | Fluorochrome | Purpose |
| --- | --- | --- |
| CD4 | APC-Vio770 | Defines T-Helper Cells |
| CD44 | VioBlue | Memory/Naive Discrimination |
| CD45RB | FITC | Memory/Naive Discrimination |
| α4 | APC | Defines T-helper memory subset of interest |
| β7 | PE | Defines T-helper memory subset of interest |
| CD16/32 | — | Fc Block |

Results

The data in FIG. 39 show decreased weight loss in DSS mice intracecally administered DATK antibody as compared to DSS mice that were intraperitoneally administered the DATK antibody. The data in FIG. 40 show that DSS mice intracecally administered DATK antibody have a decreased plasma concentration of DATK antibody as compared to DSS mice that were intraperitoneally administered DATK antibody. The data in FIGS. 41 and 42 show that DSS mice intracecally administered DATK antibody have an increased concentration of DATK antibody in the cecum and colon content as compared to DSS mice intraperitoneally administered DATK antibody. The data in FIGS. 43 and 44 show that DSS mice intracecally administered DATK antibody have an increased concentration of DATK antibody in colon tissue as compared to DSS mice intraperitoneally administered DATK antibody. The data in FIGS. 45 and 46 show an increased level of penetration of DATK antibody into colon tissue in DSS mice intracecally administered the DATK antibody as compared to an intracecal vehicle control (PBS). The data in FIG. 47 show that DSS mice intracecally administered DATK antibody have an increased ratio of the concentration of DATK antibody in colon tissue to the plasma concentration of the DATK antibody, as compared to the same ratio in DSS mice intraperitoneally administered the DATK antibody.

The data in FIG. 48 show that DSS mice intracecally administered the DATK antibody have an increased percentage of blood Th memory cells as compared to DSS mice intraperitoneally administered the DATK antibody. The data in FIG. 101 show that the relative number of Peyer's Patch Th memory cells is decreased in the animals that were intracecally administered the DATK32 antibody as compared to the animals that were intraperitoneally administered the DATK32 antibody. The data in FIG. 102 show a decrease in the relative number of mesenteric lymph node (mLN) Th memory cells in the animals that were intracecally administered the DATK32 antibody as compared to the animals that were intraperitoneally administered the DATK32 antibody.

No significant differences in clinical observations or gastrointestinal-specific adverse effects, including stool consistency and/or bloody stool, were observed due to cannulation or intra-cecal treatments when compared with vehicle. No toxicity resulting from the treatments was reported. A significant reduction in body weight-loss was also found with DATK32 (5 mg/kg, QD) treatment (IC) when compared to vehicle control at the endpoint (day 14). The immunohistochemistry staining in DATK32 (25 mg/kg, QD) treatment groups showed penetration of DATK32 in all layers of colon tissue, including lumen mucosa, lamina propria, submucosa, tunica muscularis, via intra-cecal delivery. The distribution of DATK32 was found in all segments of the colon, however, higher levels were detected in the proximal region. A significantly higher mean concentration of DATK32 was found in gastrointestinal contents and colon tissues when delivered via intra-cecal administration (DATK32: 25 mg/kg and 5 mg/kg, QD) as compared to intraperitoneal administration (DATK32: 25 mg/kg, Q3D). The blood level of DATK32 was significantly higher when delivered via intraperitoneal administration (Q3D) as compared to intra-cecal administration (Q3D & QD). The pharmacokinetics of DATK32 (25 mg/kg, QD) showed significantly higher mean concentrations of DATK32 when delivered via intra-cecal administration at 1, 2, and 4 h post-dose in the gastrointestinal contents, and 1, 2, 4 and 24 h in colon tissue as compared with the mean concentrations of DATK32 following intraperitoneal administration. The mean number of gut-homing T cells (Th memory cells) was significantly higher in the blood of groups treated with DATK32 via intra-cecal administration (QD 25 mg/kg and QD 5 mg/kg) as compared to the groups treated with DATK32 via intraperitoneal administration (Q3D 25 mg/kg). The mean number of Th memory cells was significantly lower in the Peyer's Patches of groups treated with DATK32 via intra-cecal administration (QD 25 mg/kg and 5 mg/kg) as compared to the groups treated with DATK32 via intraperitoneal administration (Q3D 25 mg/kg). The mean number of Th memory cells in mesenteric lymph nodes (MLN) was significantly lower in groups treated with DATK32 via intra-cecal administration (QD and Q3D 25 mg/kg and QD 5 mg/kg) as compared to the groups treated with DATK32 via intraperitoneal administration (Q3D 25 mg/kg).

In sum, these data show that the compositions and devices provided herein can suppress the local immune response in the intestine, while having less of a suppressive effect on the systemic immune response of an animal. These data also show that the release of DATK-32 antibody in the colon can result in a suppression of leukocyte recruitment and may provide for the treatment of colitis and other pro-inflammatory diseases of the intestine.

Example 5—An Assessment of DATK32 Bio-Distribution Following Intracecal Administration in Male C57Bl/6 Mice The objective of this study is to assess DATK32 biodistribution when dosed intracecally in male C57Bl/6 mice. A minimum of 10 days prior to the start of the experiment a cohort of animals will undergo surgical implantation of a cecal cannula. A sufficient number of animals will undergo implantation to allow for 24 cannulated animals to be enrolled in the main study (e.g., 31 animals). Animals were dosed with vehicle or test article via intracecal injection (IC) on Day 0 as indicated in Table 13. Animals from all groups were sacrificed for terminal sample collection three hours following test article administration.

Materials and Methods

Mice

Normal male C57Bl/6 mice between the ages of 6-8 weeks old, weighing 20-24 g, were obtained from Charles River Laboratories. The mice were randomized into two groups of twelve animals, and housed in groups of 12 per cage, and acclimatized for at least three days prior to entering the study. Animal rooms were set to maintain a minimum of 12 to 15 air changes per hour, with an automatic timer for a light/dark cycle of 12 hours on/off, and fed with Labdiet 5053 sterile rodent chow, with water administered ad libitum.

Cecal Cannulation

The animals were placed under isoflurane anesthesia, with the cecum exposed via a midline incision in the abdomen. A small point incision was made in the distal cecum where 1-2 cm of the cannula was inserted. The incision was closed with a purse string suture using 5-0 silk. An incision was then made in the left abdominal wall through which the distal end of the cannula was inserted and pushed subcutaneously to the dorsal aspect of the back. The site was then washed copiously with warmed saline prior to closing the abdominal wall. A small incision was also made in the skin of the back between the shoulder blades, exposing the tip of the cannula. The cannula was secured in place using suture, wound clips, and tissue glue. All animals received 1 mL of warm sterile saline (subcutaneous injection) and were monitored closely until recovery before returning to their cage. All animals received 0.6 mg/kg BID buprenorphine for the first 3 days, and Baytril® at 10 mg/kg every day for the first 5 days post-surgery.

Dosing

Animals were dosed IC at a volume of 0.075 mL/animal on Days 0 as indicated in Table 13.

Sacrifice

All animals were euthanized by $CO_2$ inhalation three hours after dosing on Day 0.

Sample Collection

Terminal blood was collected and prepared for plasma using $K_2EDTA$ as the anti-coagulant. The plasma will be split into two cryotubes, with 50 μL in one tube (PK analysis) and the remainder in another (other). Both samples were flash-frozen in liquid nitrogen. Plasma was stored at −80° C. for downstream analysis. Mesenteric lymph nodes (mLN) were collected, weighed, and flash-frozen in liquid nitrogen. Mesenteric lymph nodes were stored at −80° C. for downstream analysis. The small intestine was excised and rinsed, and the most distal 1 cm of ilium was dissected, weighed, and flash-frozen in liquid nitrogen. The samples were stored at −80° C. for downstream analysis. The cecum and colon were removed from each animal and contents collected, weighed, and snap frozen in separate cryovials. The samples were stored at −80° C. for downstream analysis. The colon was rinsed, and the most proximal 1 cm of colon was weighed and flash-frozen in liquid nitrogen. The snap frozen tissues were stored at −80° C.

TABLE 13

Study Design

| Group | No. Animals | Treatment | Route | Schedule | Terminal Collections Day 0 |
|---|---|---|---|---|---|
| 1 | 12 | Vehicle (PBS) | IC | Day 0 ** | Blood (plasma) Small intestine mLN |
| 2 | 12 | DATK32 (625 μg)* | | | Colon<br>Colon Contents<br>Cecum Contents |

*Per mouse. TA was administered in 0.075 mL/animal. DATK32 was delivered in sterile PBS.

** Animals were dosed on Day 0 and collections were performed 3 hours later.

Results

The data in FIGS. 63A-63F show no significant differences in clinical observations. No gastrointestinal-specific or adverse effects were found in the group administered DATK32 via intra-cecal administration as compared to the group administered a vehicle control. No toxicity resulting from the treatments was reported. The level of DATK32 in the group intra-cecally administered DATK32 was significantly higher in cecum and colon content, and colon tissue compared to the group administered a vehicle control at 3 h post-dose. A small amount of DATK32 was also detected in plasma, small intestine, and mesenteric lymph node in the group intra-cecally administered DATK32.

Example 6—Pharmacokinetics/Pharmacodynamics and Bioavailability of Adalimumab when Applied to a TNBS-damaged Mucosal Surface (Induced Colitis) in Swine The purpose of this non-Good Laboratory Practice (GLP) study was to explore the PK/PD, and bioavailability of adalimumab when applied to a TNBS-damaged mucosal surface (induced colitis) in Yorkshire-Cross farm swine, and to determine an appropriate dose and frequency for studies where a drug will be delivered by the ingestible device system. The ingestible device system will be capable of delivering a TNF inhibitor (adalimumab) topically and locally to damaged mucosa in human patients with inflammatory bowel disease (IBD). The TNBS-induced colitis model was validated when a single administration on Day 1 of 40 mL of 100% ethanol (EtOH) mixed with 5 grams of TNBS diluted in 10 mL of water via an enema using a rubber catheter resulted in the intended reproducible induction of damaged mucosal surface (induced colitis) in Yorkshire-Cross farm swine.

This study investigated whether topical delivery of adalimumab would result in increased local mucosal tissue levels with limited drug reaching systemic circulation, as compared to subcutaneous administration; whether local mucosal tissue levels of drug would be greater in damaged tissues when compared to normal tissues; whether increasing the dose of drug would result in increased mucosal tissue levels in local and distal TNBS-damaged tissues; and whether topical delivery of adalimumab would result in reductions in inflammatory cytokines such as TNF-α in damaged tissues, feces, and possibly blood.

All animals were subjected to intra-rectal administration of trinitrobenzene sulfonic acid (TNBS) to induce chronic colitis on day −2. All animals were fasted prior to colitis induction. Bedding was removed and replaced with rubber mats on day −3 to prevent ingestion of straw bedding material. The dose was 40 mL of 100% EtOH mixed with 5 grams of TNBS diluted in 10 mL of water, then instilled into the colon intra-rectally using a flexible gavage tube by a veterinary surgeon (deposited in a 10-cm portion of the distal colon and proximal rectum, and retained for 12 minutes by use of two Foley catheters with 60-mL balloons). Approximately 3 days after induction, macroscopic and microscopic alterations of colonic architecture were apparent: some necrosis, thickening of the colon, and substantial histologic changes were observed (FIGS. 49 and 50). The study employed 15 female swine (approximately 35 to 45 kg at study start) allocated to one of five groups. Group 1 employed three animals that were the treated controls. Each animal in Group 1 was administered adalimumab by subcutaneous injection at 40 mg in 0.8 mL saline. Groups 2, 3, 4, and 5 employed 3 animals in each group. Animals in these groups were administered intra-rectal adalimumab at 40 mg in 0.8 mL saline. The test drug (adalimumab) was administered to all groups on study day 1. The intra-rectal administrations (Groups 2-5) were applied to damaged mucosal surface of the bowel vial intra-rectal administration by a veterinary surgeon. Blood (EDTA) was collected from all animals (cephalic, jugular, or catheter) on day −3 (n=15), −1 (n=15), and 6 (n=15), 12 (n=12), 24 (n=9), and 48 (n=6) hours post-dose (87 bleeds total). The EDTA samples were split into two aliquots, and one was centrifuged for PK plasma, and stored frozen (−80° C.) for PK analyses and reporting. Fecal samples were collected for the same timepoints (87 fecal collections). Fecal samples were flash-frozen in liquid nitrogen and then stored at −80° C. for analysis of drug levels and inflammatory cytokines. Groups 2, 3, 4, and 5 were euthanized and subjected to gross necropsy and tissue collection 6, 12, 24, and 48 hours post-dose, respectively. Group 1 was similarly euthanized and necropsied 48 hours post-dose. The animals were euthanized via injection of a veterinarian-approved euthanasia solution as per the schedule. Immediately after euthanasia in order to avoid aiutolytic changes, colon tissues were collected, opened, rinsed with saline, and a detailed macroscopic examination of the colon were performed to identify macroscopic findings related to TNBS-damage. Tissue samples were taken from the proximal, mid, and distal transverse colon; the dose site; and the distal colon. Each tissue sample was divided into two approximate halves; one tissue section was placed into 10% neutral buffered formalin (NBF) and evaluated by a Board certified veterinary pathologist, and the remaining tissue section was flash frozen in liquid nitrogen and stored frozen at −80° C. Clinical signs (ill health, behavioral changes, etc.) were recorded daily beginning on day −3. Additional pen-side observations were conducted once or twice daily. Animals observed to be in ill health were examined by a veterinarian. Body weight was measured for all animals on day −3, and prior to scheduled euthanasia. Table 14 shows the study design.

Materials and Methods

Test Article

Adalimumab (EXEMPTIA™) is a tumor necrosis factor (TNF) inhibitor. A single dose was pre-filled in a syringe (40 mg in a volume of 0.8 mL).

TABLE 14

Study Design

| | | | | Days | | | | Hours | | | | | | | | |
|---|---|---|---|---|---|---|---|---|---|---|---|---|---|---|---|---|
| | Sample size | Dose | Route | −3 | −2 | −1 | 1 | 0.5 | 1 | 2 | 4 | 6 | 8 | 12 | 24 | 48 |
| General | | | | | | | | | | | | | | | | |
| Fast | | | | • | | | | | | | | | | | | |
| Food/Water | | ad libidum | oral | | • | • | • | • | • | • | • | • | • | • | • | • |
| Observations | | | | | | | | | | | | | | | | |
| clinical observations | | | | • | • | • | • | | | | | | | | • | • |
| body weight | | | | • | | | • | | | | | | | | • | • |
| Treatments (groups) | | | | | | | | | | | | | | | | |
| TNBS (all animals) | | | intra rectal | | • | | | | | | | | | | | |
| 1. Treated control | n = 3 | 40 mg in 0.8 mL saline | sub-cutaneous | | | | • | | | | | | | | | |
| euthanized | | | | | | | | | | | | | | | | n = 3 |
| 2. Adalimumab | n = 3 | 40 mg in 0.8 mL saline | intra rectal | | | | • | | | | | | | | | |
| euthanized | | | | | | | | | | | | n = 3 | | | | |
| 3. Adalimumab | n = 3 | 40 mg in 0.8 mL saline | intra rectal | | | | • | | | | | | | | | |
| euthanized | | | | | | | | | | | | | | n = 3 | | |
| 4. Adalimumab | n = 3 | 40 mg in 0.8 mL saline | intra rectal | | | | • | | | | | | | | | |
| euthanized | | | | | | | | | | | | | | | n = 3 | |
| 5. Adalimumab | n = 3 | 40 mg in 0.8 mL saline | intra rectal | | | | • | | | | | | | | | |
| euthanized | | | | | | | | | | | | | | | | n = 3 |
| Adalimumab (required) | | 600 | | | | | | | | | | | | | | |
| Samples | | | | | | | | | | | | | | | | |
| PBMCs | | | cephalic, jugular or catheter | | | | • | | | | | • | | • | • | • |
| Serum | | | cephalic, jugular or catheter | • | | • | • | | | | | • | | • | | • |
| Fecal | | | rectal | • | | • | • | | | | | • | | • | • | • |
| Tissue | | | necropsy | | | | | | | | | • | | • | • | • |

TABLE 14-continued

Study Design

| | Sample size | Dose | Route | Days | | | | Hours | | | | | | | | |
|---|---|---|---|---|---|---|---|---|---|---|---|---|---|---|---|---|
| | | | | −3 | −2 | −1 | 1 | 0.5 | 1 | 2 | 4 | 6 | 8 | 12 | 24 | 48 |
| **Analysis** | | | | | | | | | | | | | | | | |
| Histopathology | 1 location | 4 locations | | | | | | | | | | | | | | |
| inflammed | 45 | 180 | H&E | | | | | | | | | | | | | |
| normal | 45 | 180 | H&E | | | | | | | | | | | | | |
| **Blood** | | | | | | | | | | | | | | | | |
| adalimumab | 57 | | pbl | | | | 15 | | | | | 15 | | 12 | 9 | 6 |
| TNFα | 87 | | pbl | 15 | | 15 | 15 | | | | | 15 | | 12 | 9 | 6 |
| **Feces** | | | | | | | | | | | | | | | | |
| adalimumab | 57 | | pbl | | | | 15 | | | | | 15 | | 12 | 9 | 6 |
| TNFα | 87 | | pbl | 15 | | 15 | 15 | | | | | 15 | | 12 | 9 | 6 |
| **Tissue Inflammed** | | | | | | | | | | | | | | | | |
| adalimumab | 45 | 180 | pbl | | | | | | | | | 3 | | 3 | 3 | 6 |
| TNFα | 45 | 180 | pbl | | | | | | | | | 3 | | 3 | 3 | 6 |
| HER2 | 45 | 180 | pbl | | | | | | | | | 3 | | 3 | 3 | 6 |
| **Normal** | | | | | | | | | | | | | | | | |
| adalimumab | 45 | 180 | pbl | | | | | | | | | 3 | | 3 | 3 | 6 |
| TNFα | 45 | 180 | pbl | | | | | | | | | 3 | | 3 | 3 | 6 |
| HER2 | 45 | 180 | pbl | | | | | | | | | 3 | | 3 | 3 | 6 |

Results

While subcutaneously administered adalimumab was detected at all times points tested in plasma, topically administered adalimumab was barely detectable in plasma (FIGS. 51 and 52). Both topical delivery and subcutaneous delivery of adalimumab resulted in reduced levels of TNF-α in colon tissue of TNBS-induced colitis animals, yet topical delivery of adalimumab was able to achieve a greater reduction in TNF-α levels (FIGS. 53 and 54).

Either subcutaneous or intra-rectal administration of adalimumab was well tolerated and did not result in death, morbidity, adverse clinical observations, or body weight changes. A decreased level of total TNBS-related inflammatory response was observed by adalimumab treatment via intra-rectal administration when applied to the damaged mucosal surface of the bowel when compared to subcutaneous delivery. A significantly higher concentration of adalimumab was measured in blood following subcutaneous delivery as compared to the blood concentration following intra-rectal administration. Intra-rectal administration of adalimumab decreased the total and normalized TNFα concentration over time (6~48 h) and was more effective at reducing TNFα at the endpoint (48 h) as compared to groups administered adalimumab subcutaneously.

In sum, these data show that the compositions and devices provided herein can suppress the local immune response in the intestine, while having less of a suppressive effect on the systemic immune response of an animal. For example, these data show that intracecal administration of adalimumab using a device as described herein can provide for local delivery of adalimumab to the site of disease, without suppressing the systemic immune response. These data also show that local administration of adalimumab using a device as described herein can result in a significant reduction of the levels of TNFα in diseases animals.

Example 7—Comparison of Systemic Versus Intracecal Delivery of Cyclosporin A

The objective of this study was to compare the efficacy of an immunosuppressant agent (cyclosporin A; CsA) when dosed systemically versus intracecally to treat dextran sulfate sodium salt (DSS)-induced colitis in male C57Bl/6 mice.

Experimental Design

A minimum of 10 days prior to the start of the experiment a cohort of animals underwent surgical implantation of a cecal cannula. A sufficient number of animals underwent implantation to allow for 44 cannulated animals to be enrolled in the main study (e.g., 76 animals). Colitis was induced in 60 male C5Bl/6 mice by exposure to 3% DSS-treated drinking water from day 0 to day 5. Two groups of eight additional animals (cannulated and non-cannulated) served as no-disease controls (Groups 1 and 2). Animals were dosed with cyclosporin A via intraperitoneal injection (IP), oral gavage (PO), or intracecal injection (IC) from day 0 to 14 as indicated in Table 15. All animals were weighed daily and assessed visually for the presence of diarrhea and/or bloody stool at the time of dosing. Mice underwent video endoscopy on days 10 and 14 to assess colitis severity. Images were captured from each animal at the most severe region of disease identified during endoscopy. Additionally, stool consistency was scored during endoscopy using the parameters defined in Table 16. Following endoscopy on day 14, animals from all groups were sacrificed and underwent terminal sample collection.

Specifically, animals in all treatment groups dosed on day 14 were sacrificed at a pre-dosing time point, or 1, 2, and 4 hours after dosing (n=3/group/time point). Terminal blood was collected via cardiac puncture and prepared for plasma using $K_2EDTA$ as the anti-coagulant. The blood cell pellet was retained and snap frozen while the resulting plasma was split into two separate cryotubes, with 100 μL in one tube and the remainder in the second. Additionally, the cecum and colon were removed from all animals; the contents were collected, weighed, and snap frozen in separate cyrovials. The colon was then rinsed, measured, weighed, and then trimmed to 6 cm in length and divided into five pieces. The most proximal 1 cm of colon was snap frozen for subsequent bioanalysis of cyclosporin A levels. Of the remaining 5 cm of colon, the most distal and proximal 1.5-cm sections were each placed in formalin for 24 hours, then transferred to 70% ethanol for subsequent histological evaluation. The middle 2-cm portion was bisected longitudinally and placed into two separate cryotubes, weighed, and snap frozen in liquid nitrogen. All plasma and frozen colon tissue were stored at −80° C. for selected end point analysis. For all control animals in Groups 1-4, there was an additional collection of 100 μL of whole blood from all animals which was then processed for FACS analysis of α4 and β7 expression on Th memory cells. The details of the study are shown in Table 15.

TABLE 15

Study Design

| Group Number | 1 | 2 | 3 | 4 | 13 | 14 | 15 |
|---|---|---|---|---|---|---|---|
| Number of Animals | 8 | 8 | 12 | 12 | 12 | 12 | 12 |
| Cecal Cannula | NO | YES | NO | YES | NO | YES | YES |
| DSS | N/A | N/A | 3% DSS on Day 0 to Day 5 | | | | |
| Treatment | none | none | vehicle | vehicle | CsA | CsA | CsA |
| Dose (mg/kg) | N/A | N/A | N/A | N/A | 10 | 10 | 3 |
| Route | N/A | N/A | N/A | N/A | PO | IC | IC |
| Dosing Schedule | N/A | N/A | QD: Day 0 to 14 | QD: Day 0 to 14 | QD: Day 0 to 14 | QD: Day 0 to 14 | QD: Day 0 to 14 |
| Endoscopy Schedule* | Days 10 and 14 | | | | | | |
| Endpoints Day 14 | Endoscopy, Colon weight/length, stool score<br>Terminal Collection (all groups): Cecal contents, colon contents, plasma, and colon tissue<br>FACS analysis collection of Groups 1-4:<br>Whole blood for the following FACS panel: CD4, CD44, CD45RB, α4, (β7, CD16/32 | | | | | | |
| PK Sacrifice (Day 14) | N = 3/time points<br>At pre-dose and 1, 2, and 4 hours post-dosing | | | | | | |

*Animals were dosed once (QD) on Day 14 and plasma collected (K2EDTA) at pre-dosing, 1, 2, and 4 hours post-dosing from n = 3/group/time point. Each collection was terminal.

Dosing

Animals were dosed by oral gavage (PO), intraperitoneal injection (IP), or intracecal injection (IC) at a volume of 0.1 mL/20 g on days 0 to 14 as indicated in Table 15.

Body Weight and Survival

Animals were observed daily (weight, morbidity, survival, presence of diarrhea, and/or bloody stool) in order to assess possible differences among treatment groups and/or possible toxicity resulting from the treatments.

Animals Found Dead or Moribund

Animals were monitored on a daily basis and those exhibiting weight loss greater than 30% were euthanized, and samples were not collected from these animals.

Experimental Procedures

Cecal Cannulation

Animals were placed under isoflurane anesthesia, and the cecum exposed via a mid-line incision in the abdomen. A small point incision was made in the distal cecum through which 1-2 cm of the cannula was inserted. The incision was closed with a purse-string suture using 5-0 silk. An incision was made in the left abdominal wall through which the distal end of the cannula was inserted and pushed subcutaneously to the dorsal aspect of the back. The site was washed copiously with warmed saline prior to closing the abdominal wall. A small incision was made in the skin of the back between the shoulder blades, exposing the tip of the cannula. The cannula was secured in place using suture, wound clips, and tissue glue. All animals received 1 mL of warm sterile saline (subcutaneous injection) and were monitored closely until fully recovered before returning to the cage. All animals received buprenorphine at 0.6 mg/kg BID for the first 3 days, and Baytril® at 10 mg/kg QD for the first 5 days following surgery.

Disease Induction

Colitis was induced on day 0 via addition of 3% DSS (MP Biomedicals, Cat #0260110) to the drinking water. Fresh DSS/water solutions were made on day 3 and any of the remaining original DSS solution was discarded.

Endoscopy

Each mouse underwent video endoscopy on days 10 and 14 using a small animal endoscope (Karl Storz Endoskope, Germany) under isoflurane anesthesia. During each endoscopic procedure still images as well as video were recorded to evaluate the extent of colitis and the response to treatment. Additionally, we attempted to capture an image from each animal at the most severe region of disease identified during endoscopy. Colitis severity was scored using a 0-4 scale (0=normal; 1=loss of vascularity; 2=loss of vascularity and friability; 3=friability and erosions; 4=ulcerations and bleeding). Additionally, stool consistency was scored during endoscopy using the parameters defined in Table 16.

TABLE 16

Stool Consistency

| Score | Description |
|---|---|
| 0 | Normal, well-formed pellet |
| 1 | Loose stool, soft, staying in shape |
| 2 | Loose stool, abnormal form with excess moisture |
| 3 | Watery or diarrhea |
| 4 | Bloody diarrhea |

Tissue/Blood for FACS

Tissue and blood were immediately placed in FACS buffer (1× phosphate-buffered saline (PBS) containing 2.5% fetal calf serum (FCS)) and analyzed using the antibody panel in Table 17.

TABLE 17

| FACS Antibody Panel | | |
|---|---|---|
| Antibody Target | Fluorochrome | Purpose |
| CD4 | APC-Vio770 | Defines $T_H$ cells |
| CD44 | VioBlue | Memory/Naive discrimination |
| CD45RB | FITC | Memory/Naive discrimination |
| α4 | APC | Defines $T_H$-memory subset of interest |
| β7 | PE | Defines $T_H$-memory subset of interest |
| CD16/32 | — | Fc block |

Results

The data in FIG. 55 show a decrease in weight loss is observed in DSS mice intracecally administered cyclosporin A as compared to DSS mice orally administered cyclosporin A. The data in FIG. 56 show a decrease in plasma concentration of cyclosporin A in DSS mice intracecally administered cyclosporin A as compared to DSS mice orally administered cyclosporin A. The data in FIGS. 57-59 show an increased concentration of cyclosporin A in the colon tissue of DSS mice intracecally administered cyclosporin A as compared to the concentration of cyclosporin A in the colon tissue of DSS mice orally administered cyclosporin A.

The data in FIG. 60 show that DSS mice intracecally administered cyclosporin A have an increased concentration of IL-2 in colon tissue as compared to DSS mice orally administered cyclosporin A. The data in FIG. 61 show that DSS mice intracecally administered cyclosporin A have a decreased concentration of IL-6 in colon tissue as compared to DSS mice orally administered cyclosporin A.

In sum, these data show that the compositions and devices provided herein can suppress the local immune response in the intestine, while having less of a suppressive effect on the systemic immune response of an animal. For example, these data demonstrate that the present compositions and devices can be used to release cyclosporin A to the intestine and that this results in a selective immune suppression in the colon, while having less of an effect on the immune system outside of the intestine. These data also suggest that the present compositions and devices will provide for the treatment of colitis and other pro-inflammatory disorders of the intestine.

Example 8—Bellows Testing: Drug Stability Bench Test

Experiments were run to evaluate the effects that bellows material would have on the function of a drug used as the dispensable substance. The experiments also evaluated the effects on drug function due to shelf life in the bellows.

The adalimumab was loaded into simulated device jigs containing either tapered silicone bellows or smooth PVC bellows and allowed to incubate for 4, 24, or 336 hours at room temperature while protected from light. FIG. 64 illustrates the tapered silicone bellows, and FIG. 65 illustrates the tapered silicone bellows in the simulated device jig. FIG. 66 illustrates the smooth PVC bellows, and FIG. 67 illustrates the smooth PVC in the simulated device jig.

The drug was subsequently extracted using the respective dispensing systems and tested by a competitive inhibition assay. The test method has been developed from the literature (Velayudhan et al., "Demonstration of functional similarity of proposed biosimilar ABP501 to adalimumab," BioDrugs 30:339-351 (2016) and Barbeauet et al., "Application Note: Screening for inhibitors of TNFα/s TNFR1 Binding using AlphaScreen™ Technology," PerkinElmer Technical Note ASC-016 (2002)), as well as pre-testing development work using control drug and experiments using the provided AlphaLISA test kits. FIGS. 68A-68B demonstrate the principle of the competition assay performed in the experiment. FIG. 68A shows binding of anti-TNFα to TNFα receptor without drug, where uninhibited binding brings the Donor and Acceptor beads into close proximity for singlet oxygen transfer detection. FIG. 68B shows binding of anti-TNFα to TNFα that is inhibited by drug binding to TNFα and preventing binding to anti-TNFα antibodies, which prevents proximity oxygen singlet transfer detection.

The bellows were loaded as follows: aseptically wiped the dispensing port of the simulated ingestible device jig with 70% ethanol; allowed to air dry for one minute; used an adalimumab delivery syringe to load each set of bellows with 200 μL of drug; took a photo of the loaded device; gently rotated the device such that the drug is allowed to come in contact with all bellows surfaces; protected the bellows from light; and incubate at room temperature for the predetermined time period to allow full contact of the drug with all bellows' surfaces.

The drug was extracted as follows: after completion of the incubation period; the device jig was inverted such that the dispensing port was positioned over a sterile collection microfuge tube and petri dish below; five cubic centimeters of air was drawn into an appropriate syringe; the lure lock was attached to the device jig; the syringe was used to gently apply positive pressure to the bellow with air such that the drug was recovered in the collection microfuge tube; where possible, a video of drug dispensing was taken; samples were collected from each bellows type; a control drug sample was collected by directly dispensing 200 μL of drug from the commercial dispensing syringe into a sterile microfuge tube; the control drug-free sample was collected by directly dispensing 200 μL of PBS using a sterile pipette into a sterile microfuge tube; the collected drug was protected from light; and the drug was diluted over the following dilution range (250, 125, 25, 2.5, 0.25, 0.025, 0.0125, 0.0025 μg) in sterile PBS to determine the $IC_{50}$ range of the drug.

To determine any effects storage conditions may have on drug efficacy in the device, the drug (stored either in the syringe, silicon bellows, PVC bellows) was stored at room temperature while protected from light for 24 hours and 72 hours. Samples were then extracted and the steps in the preceding paragraph were repeated.

The AlphaLISA (LOCI™) test method was used. Human TNFα standard dilution ranges were prepared as described in Table 18.

TABLE 18

| Tube | Vol of human TNFα (μL) | Vol. of diluent (μL) * | [human TNFα] in standard curve (g/mL in 5 μL) | (pg/mL in 5 μL) |
|---|---|---|---|---|
| A | 10 μL of reconstituted human TNFα | 90 | 1E-07 | 100 000 |
| B | 60 μL of tube A | 140 | 3E−08 | 30 000 |
| C | 60 μL of tube B | 120 | 1E−08 | 10 000 |
| D | 60 μL of tube C | 140 | 3E−09 | 3 000 |
| E | 60 μL of tube D | 120 | 1E−09 | 1 000 |
| F | 60 μL of tube E | 140 | 3E−10 | 300 |
| G | 60 μL of tube F | 120 | 1E−10 | 100 |
| H | 60 μL of tube G | 140 | 3E−11 | 30 |
| I | 60 μL of tube H | 120 | 1E−11 | 10 |
| J | 60 μL of tube I | 140 | 3E−12 | 3 |
| K | 60 μL of tube J | 120 | 1E−12 | 1 |
| L | 60 μL of tube K | 140 | 3E−13 | 0.3 |
| M ** (background) | 0 | 100 | 0 | 0 |
| N ** (background) | 0 | 100 | 0 | 0 |
| O ** (background) | 0 | 100 | 0 | 0 |
| P ** (background) | 0 | 100 | 0 | 0 |

The test was performed as follows: the above standard dilution ranges were in a separate 96-well plate; to ensure consistent mixing, samples were mixed up and down gently with a pipette five times; a 384-well test plate was prepared according to the test layout diagram depicted Table 19; five microliters of 10,000 pg/mL TNFα standard from the previously made dilution plate was added to each corresponding concentration as shown in Table 18 five microliters of recovered drug (directly from the commercial syringe (A), from the silicone bellows (B Si), from the PVC bellows (B PVC), or from the PBS control (C) was added into the corresponding wells described in Table 19; the test plate was incubated for one hour at room temperature while protected from light; 10 microliters of acceptor beads were added to each previously accessed well; the wells were incubated for 30 minutes at room temperature while protected from light; 10 μL of biotinylated antibody was added to each previously accessed well; the wells were incubated for 15 minutes at room temperature, while protected from light; the room lights were darkened and 25 microliters of streptavidin (SA) donor beads were added to each previously accessed well; the wells were incubated for 30 minutes at room temperature while protected from light; the plate was read in Alpha Mode; and the results were recorded. Upon addition of reagent(s) in the various steps, each well was pipetted up and down three times to achieve good mixing.

TABLE 19

| | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| A | STD2 1.00E+05 | | STD10 10 | 250 A | 250 A | 250 A | 250 A | 250 A | 250 B Si | 250 B Si | 250 B Si | 250 B Si | 250 B Si | 250 B PVC | 250 B PVC |
| B | | | | | | | | | | | | | | | |
| C | STD3 30000 | | STD11 3 | 125 A | 125 A | 125 A | 125 A | 125 A | 125 B Si | 125 B Si | 125 B Si | 125 B Si | 125 B Si | 125 B PVC | 125 B PVC |
| D | | | | | | | | | | | | | | | |
| E | STD4 10000 | | STD12 1 | 25 A | 25 A | 25 A | 25 A | 25 AB | 25 Si | 25 B Si | 25 B Si | 25 B Si | 25 B Si | 25 B PVC | 25 B PVC |
| F | | | | | | | | | | | | | | | |
| G | STD5 3000 | | STD13 0.333 | 2.5 A | 2.5 A | 2.5 A | 2.5 A | 2.5 AB | 2.5 Si | 2.5 B Si | 2.5 B Si | 2.5 B Si | 2.5 B Si | 25 B PVC | 2.5 B PVC |
| H | | | | | | | | | | | | | | | |
| I | STD6 1000 | | Blank 0 | 0.25 A | 0.25 A | 0.25 A | 0.25 A | 0.25 A | 0.25 B Si | 0.25 B Si | 0.25 B Si | 0.25 B Si | 0.25 B Si | 0.25 B PVC | 0.25 B PVC |
| J | | | | | | | | | | | | | | | |
| K | STD7 300 | | Blank 0 | 0.025 A | 0.025 A | 0.025 A | 0.025 A | 0.025 A | 0.025 B Si | 0.025 B Si | 0.025 B Si | 0.025 B Si | 0.025 B Si | 0.025 B PVC | 0.025 B PVC |
| L | | | | | | | | | | | | | | | |
| M | STD8 100 | | Blank 0 | 0.013 A | 0.013 A | 0.013 A | 0.013 A | 0.013 A | 0.013 B Si | 0.013 B Si | 0.013 B Si | 0.013 B Si | 0.013 B Si | 0.013 B PVC | 0.013 B PVC |
| N | | | | | | | | | | | | | | | |
| O | STD9 30 | | Blank 0 | 0.003 A | 0.003 A | 0.003 A | 0.003 A | 0.003 A | 0.003 B Si | 0.003 B Si | 0.003 B Si | 0.003 B Si | 0.003 B Si | 0.003 B PVC | 0.003 B PVC |
| P | | | | | | | | | | | | | | | |

| | 16 | 17 | 18 | 19 | 20 | 21 | 22 | 23 |
|---|---|---|---|---|---|---|---|---|
| A | 250 B PVC | 250 B PVC | 250 B PVC | 250 C | 250 C | 250 C | 250 C | 250 C |
| B | | | | | | | | |
| C | 125 B PVC | 125 B PVC | 125 B PVC | 125 C | 125 C | 125 C | 125 C | 125 C |
| D | | | | | | | | |
| E | 25 B PVC | 25 B PVC | 25 B PVC | 25 C | 25 C | 25 C | 25 C | 25 C |
| F | | | | | | | | |
| G | 2.5 B PVC | 2.5 B PVC | 2.5 B PVC | 2.5 C | 2.5 C | 2.5 C | 2.5 C | 25 C |
| H | | | | | | | | |
| I | 0.25 B PVC | 0.25 B PVC | 0.25 B PVC | 0.25 C | 0.25 C | 0.25 C | 0.25 C | 0.25 C |
| J | | | | | | | | |
| K | 0.025 B PVC | 0.025 B PVC | 0.025 B PVC | 0.025 C | 0.025 C | 0.025 C | 0.025 C | 0.025 C |
| L | | | | | | | | |
| M | 0.013 B PVC | 0.013 B PVC | 0.013 B PVC | 0.013 C | 0.013 C | 0.013 C | 0.013 C | 0.013 C |

TABLE 19-continued

| | | | | | | | | |
|---|---|---|---|---|---|---|---|---|
| N | | | | | | | | |
| O | 0.003<br>B PVC | 0.003<br>B PVC | 0.003<br>B PVC | 0.003<br>C | 0.003<br>C | 0.003<br>C | 0.003<br>C | 0.003<br>C |
| P | | | | | | | | |

The data are shown in FIGS. 69-71. The data demonstrate that the bellows do not negatively impact the drug function after shelf lives of 4 hours, 24 hours, or 336 hours. The $IC_{50}$ values of the drug dispensed from the bellows were comparable to the $IC_{50}$ values of the standard dispensation method (Table 18). A slight right shift was noted in the bellows curves after 24 hours (FIG. 70), but this shift was well within the error bars of the curves. Tables 20-23 represent data of FIGS. 69-71, respectively. Of note, when comparing mean (n=5) RFU data between test articles over the concentration ranges significant differences ($p<0.05$) were discerned. However, these significant differences did not favor either test article over time, suggesting that they were not related to the performance of the material in response to the drug (FIGS. 69-71).

TABLE 20

| | Needle control (A) | Silicone Bellows (B) | PVC Bellows (C) |
|---|---|---|---|
| 4 Hours | 0.0174 | 0.0169 | 0.0172 |
| 24 Hours | 0.0180 | 0.0180 | 0.0180 |
| 336 Hours | 0.0144 | 0.0159 | 0.0163 |

TABLE 21

| Statistics (Student's T-test, 2 tailed, non-pair-wise, for significance p < 0.05) | | | |
|---|---|---|---|
| Drug (micrograms) | Needle control (A) vs. Silicone (B) | Needle control (A) vs. PVC | Silicone vs. PVC |
| 0.0001 | 0.911 | 0.008* | 0.268 |
| 0.0025 | 0.138 | 0.390 | 0.822 |
| 0.0125 | 0.122 | 0.118 | 0.771 |
| 0.025 | 0.143 | 0.465 | 0.020* |
| 0.25 | 0.591 | 0.984 | 0.350 |
| 2.5 | 0.243 | 0.124 | 0.169 |
| 125 | 0.867 | 0.688 | 0.182 |
| 250 | 0.681 | 0.184 | 0.108 |

*p < 0.5 data set

TABLE 22

| Statistics (Student's T-test, 2 tailed, non-pair-wise, for significance p < 0.05) | | | |
|---|---|---|---|
| Drug (micrograms) | Needle control (A) vs. Silicone (B) | Needle control (A) vs. PVC | Silicone vs. PVC |
| 0.0001 | 0.132 | 0.038* | 0.292 |
| 0.0025 | 0.003* | 0.076 | 0.575 |
| 0.0125 | 0.161 | 0.022* | 0.783 |
| 0.025 | 0.058 | 0.078 | 0.538 |
| 0.25 | 0.974 | 0.384 | 0.198 |
| 2.5 | 0.714 | 0.080 | 0.017* |
| 125 | 0.873 | 0.731 | 0.269 |
| 250 | 0.798 | 0.956 | 0.903 |

*p < 0.5 data set

TABLE 23

| Statistics (Student's T-test, 2 tailed, non-pair-wise, for significance p < 0.05) | | | |
|---|---|---|---|
| Drug (micrograms) | Needle control (A) vs. Silicone (B) | Needle control (A) vs. PVC | Silicone vs. PVC |
| 0.0001 | 0.858449 | 0.036847* | 0.026444* |
| 0.0025 | 0.087379 | 0.280302 | 0.046767* |
| 0.0125 | 0.469282 | 0.057232 | 0.117194 |

TABLE 23-continued

| Statistics (Student's T-test, 2 tailed, non-pair-wise, for significance p < 0.05) | | | |
|---|---|---|---|
| Drug (micrograms) | Needle control (A) vs. Silicone (B) | Needle control (A) vs. PVC | Silicone vs. PVC |
| 0.025 | 0.02758* | 0.078234 | 0.373419 |
| 0.25 | 0.411548 | 0.258928 | 0.400498 |
| 2.5 | 0.368959 | 0.156574 | 0.006719* |
| 125 | 0.948649 | 0.246702 | 0.463735 |
| 250 | 0.485046 | 0.128993 | 0.705543 |

*p < 0.5 data set

Example 9—A Comparison Study of Systemic vs Intracecal Delivery of SMAD7 Bio-Distribution in DSS-Induced Colitis in Male C57Bl/6 Mice The objective of this study was to compare the efficacy of novel test articles, e.g., fluorescent SMAD7 antisense oligonucleotides (SMAD7 AS), when dosed systemically versus intracecally in the treatment of DSS-induced colitis, in male C57Bl/6 mice.

Experimental Design

A minimum of 10 days prior to the start of the experiment a cohort of animals underwent surgical implantation of a cecal cannula. A sufficient number of animals underwent implantation to allow for 12 cannulated animals to be enrolled in the main study (i.e., 16 animals).

Colitis was induced in 12 male C57Bl/6 mice (Groups 4-5) by exposure to 3% DSS-treated drinking water from Day 0 to Day 5. Three groups of six additional animals per group (n=6 cannulated; n=12 non-cannulated; Groups 1-3) served as no-disease controls (Groups 1-3). All animals were weighed daily and assessed visually for the presence of diarrhea and/or bloody stool during this time.

Animals were dosed with test-article via oral gavage (PO) or intracecal injection (IC) once on Day 9 as indicated in Table 24. The animals in Group 0 were not dosed. The animals in Groups 2 and 4 were dosed PO with SMAD7 antisense. The animals in Groups 3 and 5 were dosed IC with SMAD7 antisense.

All animals were euthanized by $CO_2$ inhalation 12 hours after dosing, on Day 10. Terminal blood was collected into two $K_2EDTA$ tubes and processed for plasma. Both plasma and pellet samples were snap-frozen in liquid nitrogen and stored at −80° C. Cecum contents were removed and the contents were split into two aliquots. Both aliquots were weighed and snap frozen in separate cryovials in liquid nitrogen. The cecum was excised and bisected longitudinally; each piece is separately weighed and flash-frozen in liquid nitrogen. The colon contents were removed and the contents were split into two aliquots. Both aliquots were weighed and snap frozen in separate cryovials in liquid nitrogen. The colon was then rinsed, and the most proximal 2 cm of colon was collected. This 2-cm portion was bisected longitudinally; each piece was separately weighed and flash-frozen in liquid nitrogen. Snap-frozen blood pellet, cecum/colon contents, and tissue samples were used for downstream fluorimetry or RP-HPLC. The details of the study design are shown in Table 24.

TABLE 24

| Study design | | | | | | | |
|---|---|---|---|---|---|---|---|
| Group | No Animals | Cecal Cannula | Colitis Induction | Treatment | Route | Schedule | Terminal Collections Day 10 |
| 1 | 6 | NO | — | — | — | — | Whole blood, |
| 2 | 6 | NO | | Fluorescently | PO | QD | plasma, cecal |
| 3 | 6 | YES | | labeled | IC | Day 9** | contents, colon |
| 4 | 6 | NO | 3% DSS | SMAD7 | PO | | contents, cecal |
| 5 | 6 | YES | Days 0-5 | antisense | IC | | tissue, colon |
| | | | | 50 μg* | | | tissue |

*Per mouse. TA is administered in 0.075 mL/animal.

**Animals are dosed on Day 9 and collections are performed 12 hours later.

Materials and Methods

Mice

Normal male C57Bl/6 mice between the ages of 6-8 weeks old, weighing 20-24 g, were obtained from Charles River Laboratories. The mice were randomized into five groups of six mice each, and housed in groups of 8-15 per cage, and acclimatized for at least three days prior to entering the study. Animal rooms were set to maintain a minimum of 12 to 15 air changes per hour, with an automatic timer for a light/dark cycle of 12 hours on/off, and fed with Labdiet 5053 sterile rodent chow, with water administered ad libitum.

Cecal Cannulation

The animals were placed under isoflurane anesthesia, with the cecum exposed via a midline incision in the abdomen. A small point incision was made in the distal cecum, where 1-2 cm of the cannula was inserted. The incision was closed with a purse string suture using 5-0 silk. An incision was then made in the left abdominal wall through which the distal end of the cannula was inserted and pushed subcutaneously to the dorsal aspect of the back. The site was then washed copiously with warmed saline prior to closing the abdominal wall. A small incision was also made in the skin of the back between the shoulder blades, exposing the tip of the cannula. The cannula was secured in place using suture, wound clips, and tissue glue. All animals were administered 1 mL of warm sterile saline (subcutaneous injection) and were monitored closely until recovery before returning to their cage. All animals were administered 0.6 mg/kg BID buprenorphine for the first 3 days, and Baytril® at 10 mg/kg every day for the first 5 days post-surgery.

Disease Induction

Colitis was induced on Day 0 via addition of 3% DSS (MP Biomedicals, Cat #0260110) to the drinking water. Fresh DSS/water solutions was provided on Day 3 and any of the remaining original DSS solution is discarded.

Body Weight and Survival

Animals were observed daily (weight, morbidity, survival, presence of diarrhea and/or bloody stool) in order to assess possible differences among treatment groups and/or possible toxicity resulting from the treatments.

Animals Found Dead or Moribund

Animals were monitored on a daily basis. Animals exhibiting weight loss greater than 30% were euthanized, and samples were not collected from these animals.

Dosing

Animals were dosed with test-article via oral gavage (PO) or intracecal injection (IC) once on Day 9 as indicated in Table 24. Animals in Group 0 were not dosed. Animals in Groups 2 and 4 were dosed PO with SMAD7 antisense. Animals in Groups 3 and 5 were dosed IC with SMAD7 antisense.

Sacrifice

All animals were euthanized by $CO_2$ inhalation 12 hours after dosing, on Day 10.

Sample Collection

Intestinal contents, peripheral blood and tissue were collected at sacrifice on Day 10, as follows:

Blood/Plasma: Terminal blood was collected into two $K_2$EDTA tubes and processed for plasma. The approximate volume of each blood sample was recorded prior to centrifugation. Both plasma and pellet samples were snap-frozen in liquid nitrogen and stored at −80° C. The first pellet sample (sample 1) was used for fluorimetry. The second pellet sample (sample 2) was used for RP-HPLC.

Cecum Contents: Cecum contents was removed and contents were split into two aliquots. Both aliquots were weighed and snap frozen in separate cryovials in liquid nitrogen. The first sample (sample 1) was used for fluorimetry. The second sample (sample 2) was used for RP-HPLC.

Cecum: The cecum was excised and bisected longitudinally; each piece was separately weighed and snap-frozen. The first sample (sample 1) was used for fluorimetry. The second sample (sample 2) was used for RP-HPLC.

Colon Contents: Colon contents were removed and contents were split into two aliquots. Both aliquots were weighed and snap frozen in separate cryovials in liquid nitrogen. The first sample (sample 1) was used for fluorimetry. The second sample (sample 2) was used for RP-HPLC.

Colon: The colon was rinsed, and the most proximal 2 cm of colon was collected and bisected longitudinally. Each piece was separately weighed and flash-frozen in liquid nitrogen. The first sample (sample 1) was used for fluorimetry. The second sample (sample 2) was used for RP-HPLC.

SMAD7 Antisense Bioanalysis

Samples flash-frozen for fluorimetry were homogenized in 0.5 mL buffer RLT+(Qiagen). Homogenate was centrifuged (4000×g; 10 minutes), and supernatant was collected. Forty microliters of the sample was diluted 1:6 in 200 μL of bicarbonate solution and 100 μL of diluted supernatant was analyzed on a fluorescent plate reader (485 excitation; 535 emission) in duplicate.

Prior to the above, assay development was performed as follows. Samples (as indicated in Sample Collection) were harvested from a naïve animal and flash-frozen. Samples were then homogenized in 0.5 mL buffer RLT+, homogenate was centrifuged (4000×g; 10 minutes) and supernatant was collected and diluted 1:6 with bicarbonate solution (i.e., 0.5 mL supernatant was added to 2.5 mL of PBS). An aliquot (0.200 mL (90 μL for each duplicate) of each diluted sample was pipetted into 15 (14 dilution of FAM-AS-SAMD7+ blank control) Eppendorf tubes. One tube was set-aside to be used as a blank sample. Ten microliters of fluorescently-labeled SMAD7 antisense was then spiked into all other sample to achieve final concentrations of 50 μg/mL, 16.67 μg/mL, 5.56 μg/mL, 1.85 μg/mL, 0.62 μg/mL, 0.21 μg/mL, 0.069 μg/mL, 0.023 μg/mL, 7.6 ng/mL, 2.5 ng/mL, 0.847 ng/mL, 0.282 ng/mL, 0.094 ng/mL, and 0.024 ng/mL respectively. The fluorescently-labeled SMAD7 antisense was prepared and serially diluted such that the volume added to each organ homogenate sample was the same for each of the above concentrations. These samples were analyzed on a fluorescent plate reader (485 excitation; 535 emission) in duplicate.

Processing for RP-HPLC

Samples flash-frozen for RP-HPLC were homogenized in buffer RLT+ (Qiagen). Homogenate was centrifuged (4000× g; 10 minutes), and supernatant was used to perform RP-HPLC analysis.

Results

The data in FIGS. 73 and 74 show that significantly more SMAD7 antisense oligonucleotide was present in cecum tissue and colon tissue for mice with or without DSS treatment that were intra-cecally administered the SMAD7 antisense oligonucleotide as compared to mice with or without DSS treatment that were orally administered the SMAD7 antisense oligonucleotide. The data in FIG. 75 show that there is about the same level of SMAD7 antisense oligonucleotide in the cecum contents of mice with or without DSS treatment that were orally or intra-cecally administered the SMAD7 antisense oligonucleotide. No SMAD7 antisense oligonucleotide was found in the plasma or white blood cell pellet of SMAD7 antisense oligonucleotide treated mice.

No significant differences were observed in clinical observations, GI-specific adverse effects or toxicity due to FAM-AS-SMAD7 treatment via PO vs IC. No fluorescent detection of FAM-AS-SMAD7 was found in plasma and whole blood cell pellets across all treatment groups. A significant higher fluorescent signal (RFU) of FAM-AS-SMAD7 was found in cecum tissue when delivered intra-cecally compared with PO in both normal and DSS-induced models (FIG. 83). A slight higher RFU was also found in colon tissue when delivered intra-cecally, however, the overall signal is 10 times lower (FIG. 84). A significant higher RFU was found in colon content when delivered intra-cecally compared with PO in a normal mouse model (FIG. 85). This result was not seen in cecum content across all treatment groups (FIG. 86), indicating a better tissue absorption of oligos in cecum tissue from cecal content when delivered intra-cecally, but not in colon content at 12 hours post-treatment.

Example 10—Comparison of the Tissue, Plasma, and GI Content Pharmacokinetics of Tacrolimus Through Oral Vs. Intra-Cecal Ingestible Device Delivery in Yorkshire-Cross Farm Swine The primary objective of this study was to compare the tissue, plasma, rectal sample, and GI content pharmacokinetics of tacrolimus through oral versus intra-cecal ingestible device delivery in normal Yorkshire-Cross farm swine.

This study compares the effects of administration of: a single intra-cecal administration of an ingestible device containing 0.8 mL sterile vehicle solution (80% alcohol, 20% castor oil (HCO-60)); a single oral dose of tacrolimus at 4 mg/0.8 mL (in sterile vehicle solution); and a single intra-cecal administration of an ingestible device containing either 1 mg/0.8 mL (in sterile vehicle solution), 2 mg/0.8 mL (in sterile vehicle solution), or 4 mg/0.8 mL (in sterile vehicle solution).

This study employed five groups of three female swine weighing approximately 45 to 50 kg at study start. Swine were randomly placed into animal rooms/pens as they are transferred from the delivery vehicle without regard to group. Group numbers were assigned to the rooms in order of room number. No further randomization procedure was employed. The study design is provided in Table 25.

TABLE 25

| | | | | Days Pre-Dose | | | | | Hours Post-dose | | | | | | |
|---|---|---|---|---|---|---|---|---|---|---|---|---|---|---|---|
| | Group size | Dose | Route | −11 | −10 | −5 | −1 | 1 | 0.5 | 1 | 2 | 3 | 4 | 6 | 12 |
| General | | | | | | | | | | | | | | | |
| Fast | | | | • | | | • | | | | | | | | |
| Food/Water | | Ad libidum | | | • | • | | • | • | • | • | • | • | • | • |
| Observations | | | | | | | | | | | | | | | |
| Clinical observations | | Daily from Day 10-5 | | | | • | | • | • | • | • | • | • | • | • |
| Body weight* | | | | | • | • | | • | | | | | | | • |
| Treatments | | | | | | | | | | | | | | | |
| 1. Vehicle control | n = 3 | 0.8 mL (20% HCO-60, 80% EtOH) | IC | | | | | | | | | | | | |
| Surgical placement of IC port** | | | | | • | | | | | | | | | | |
| Euthanized | | (1 Capsule) | | | | | | | | | | | | | |
| 2. Tacrolimus (PO) | n = 3 | 4 mg in 0.8 mL | Oral | | | | | • | | | | | | | |
| Surgical placement of IC port** | | −0.08 mg/kg | | | • | | | | | | | | | | |
| Euthanized | | (1 Capsule) | | | | | | | | | | | | | |
| 3. Tacrolimus (IC) | n = 3 | 1 mg in 0.8 mL | IC | | | | | • | | | | | | | |
| Surgical placement of IC port** | | −0.02 mg/kg | | | • | | | | | | | | | | |
| Euthanized | | (1 Capsule) | | | | | | | | | | | | | |
| 4. Tacrolimus (IC) | n = 3 | 2 mg in 0.8 mL | IC | | | | | • | | | | | | | |
| Surgical placement of IC port** | | −0.04 mg/kg | | | • | | | | | | | | | | |
| Euthanized | | (1 Capsule) | | | | | | | | | | | | | |
| 5. Tacrolimus (IC) | n = 3 | 4 mg in 0.8 mL | IC | | | | | • | | | | | | | |
| Euthanized | | (1 Capsule) | | | | | | | | | | | | | |

TABLE 25-continued

| | Group size | Dose | Route | Days Pre-Dose −11 | −10 | −5 | −1 | 1 | Hours Post-dose 0.5 | 1 | 2 | 3 | 4 | 6 | 12 |
|---|---|---|---|---|---|---|---|---|---|---|---|---|---|---|---|
| Samples***** | | | | | | | | | | | | | | | |
| Plasma | | | cephalic, jugular, or catheter | | | | | • | | • | • | • | • | • | • |
| Rectal contents | | | rectal | | | | | | | • | | • | | • | • |
| Tissue*** | x5 | | necrospy | | | | | | | | | | | | • |
| Luminal contents**** | x5 | | necrospy | | | | | | | | | | | | • |

*Animal weight was ~45-50 kg for drug doses proposed.

**Surgical placement of IC port in all animals to control.

***Tissue samples [drug] (five GI section cecum (CAC); proximal colon (PCN); transverse colon (TCN); distal colon (DCN); rectum (RTM), plus mesenteric lymph nodes and Peyer's Patch).

****Luminal contents (cecum (CAC); proximal colon (PCN); transverse colon (TCN); distal colon (DCN); rectum (RTM)).

Animals in Group 1 received an ingestible device containing 0.8 mL of vehicle solution (80% alcohol, 20% HCO-60). Animals in Group 2 received orally 4 mL liquid formulation of tacrolimus at 4 mg/0.8 mL per animal (Prograf: 5 mg/mL). Animals in Group 3 received intra-cecally an ingestible device containing tacrolimus at 1 mg in 0.8 mL per ingestible device. Animals in Group 4 received intra-cecally an ingestible device containing tacrolimus at 2 mg in 0.8 mL per ingestible device. Animals in Group 5 received intra-cecally an ingestible device containing tacrolimus at 4 mg in 0.8 mL per ingestible device. To control for potential confounding effects of the surgery, all groups fast on Day −11 at least 24 hr before being subjected to anesthesia followed by surgical placements of a cecal port by a veterinary surgeon at Day −10. All animals were fasted for at least 12 hr prior to dosing on Day 1. Animals were dosed via either intra-cecal dosing (IC) or oral dosing (PO) at Day 1 (between 6-8 p.m.). All animals resumed feeding at approximately 4 hours after dose (11-12 p.m. after dosing).

Animals in Group 1 (Vehicle Control) were administered a single intra-cecal ingestible device containing 0.8 mL Vehicle solution (80% alcohol, 20% castor oil (HCO-60) on Day 1. On Day −10 the animals were anesthetized, and a veterinary surgeon surgically placed an intra-cecal port in each animal. On Day 1, each animal was placed into a sling then a single intra-cecal ingestible device containing 0.8 mL vehicle solution (80% alcohol, 20% castor oil (HCO-60)) is introduced by the veterinary surgeon into the cecum via the cecal port in each animal. Following ingestible device placement, the animals were removed from the slings and placed back into their pens with water. All animals resumed feeding at approximately 4 hours after dose. Samples of rectal contents were collected for pharmacokinetic analyses from each animal at each of 1, 3, 6, and 12 hours post-ingestible device placement using a fecal swab (rectal swab). A total of 60 samples were collected.

Approximately 200~400 mg of rectal content were collected, if available, with a fecal swab (Copan Diagnostics Nylon Flocked Dry Swabs, 502CS01). The fecal swab was pre-weighed and weighed after collection in the collection tube (Sterile Tube and Cap No Media, PFPM913S), and the sample weight was recorded. The fecal swab was broken via the breakpoint, and was stored in the collection tube, and immediately frozen at −70° C. Whole blood (2 mL) was collected into $K_2$EDTA coated tubes for pharmacokinetics at each time-point of pre-dose and 1, 2, 3, 4, 6 and 12 hours post-dose. Immediately following euthanasia, tissue was collected. A total of 105 samples were collected.

For tissue necropsy, small intestine fluid and cecal fluid were collected separately from all the animals into two separate square plastic bottles, and stored at −20° C. The length and diameter of the cecum and the colon was measured from one animal in each group and recorded for reference. Tissues were collected for pharmacokinetic analyses and include mesenteric lymph nodes, a Peyer's Patch, and five gastrointestinal sections, including cecum, proximal colon, transverse colon, distal colon, and rectum. All samples were weighed, and the tissue sample weights were recorded. In each of the five gastrointestinal sections, tissue samples were collected in three different areas where the mucosal surface was visible and not covered by luminal content by using an 8.0-mm punch biopsy tool. Around 3 grams of the total punched sample were collected into a pre-weighed 15-mL conical tube, and the tissue weight was recorded. Three mesenteric lymph nodes were collected from different areas and weighed. At least one Peyer's Patch was collected and weighed. Tissues were snap-frozen in liquid nitrogen and stored frozen at approximately −70° C. or below (total of 105 samples).

Luminal contents were collected for pharmacokinetic analyses from the surface of the tissue from each of five gastrointestinal sections: cecum, proximal colon, transverse colon, distal colon, and rectum (total of 75). The contents were collected in pre-weighed 15-mL conical tubes and the sample weights were recorded. Samples were snap-frozen in liquid nitrogen stored frozen at approximately −70° C. or below.

After removing the luminal content, another set of tissue samples from 3 different areas were collected via an 8.0-mm punch biopsy in each section of the five tissue gastrointestinal sections described above. Around 3 grams of the total punched sample were collected into a pre-weighed 15-mL conical tube, and the tissue weight was recorded (total of 75). Tissues were snap-frozen in liquid nitrogen and stored frozen at approximately −70° C. or below.

A 30-cm length of jejunum (separated into two 15 cm lengths), and the remaining distal and transverse colon tissue sample (after tissue and luminal content were collected for PK) were collected in one animal in each group of treatment, snap-frozen in liquid nitrogen and stored frozen at approximately −70° C. or below. All samples for pharmacokinetic analyses were stored on dry ice before analyses.

Group 2 animals were administered a single oral dose of tacrolimus at 4 mg/0.8 mL (0.08-mg/kg) (in the vehicle solution) on Day 1. Plasma, rectal content sample, tissue collection, GI content collection and related procedures/storage/shipments was the same as those employed in Group 1.

Group 3 animals were administered a single intra-cecal ingestible device containing tacrolimus at 1-mg/0.8 mL (0.02 mg/kg) (in the vehicle solution) on Day 1 by a veterinary surgeon. Plasma, rectal content sample, tissue collection, GI content collection and related procedures/storage/shipments was the same as those employed in Group 1. All samples were analyzed for tacrolimus.

Group 4 animals were administered a single intra-cecal ingestible device of tacrolimus at 2 mg/0.8 mL (0.04 mg/kg) (in sterile vehicle solution) on Day 1 by a veterinary surgeon. Plasma, rectal content sample, tissue collection, GI content collection and related procedures/storage/shipments were the same as those employed in Group 1. All samples were analyzed for tacrolimus.

Group 5 animals are administered a single intra-cecal ingestible device containing tacrolimus at 4 mg/0.8 mL (0.08 mg/kg) (in the vehicle solution) on Day 1 by a veterinary surgeon. Plasma, rectal content sample, tissue collection, GI content collection and related procedures/storage/shipments were the same as those employed in Group 1. All samples were analyzed for tacrolimus.

Detailed clinical observations were conducted daily from Day −10 to −5, and on Day 1. Additional pen-side observations were conducted at least once each day. The animals remained under constant clinical observation for the entire 12 hours from dose until euthanasia. Body weights were collected on Day −10, Day −5, and pre-dose on Day 1. Animals were euthanized via injection of a veterinarian-approved euthanasia.

Test Article and Formulation

1. Vehicle Solution, 20 mL

Description: 80% alcohol, 20% PEG-60 castor oil

Physical characteristics: clear liquid solution.

2. Prograf (Tacrolimus Injection), 10 Ampules

Description: A sterile solution containing the equivalent of 5 mg anhydrous tacrolimus in 1 mL. Tacrolimus is macrolide immunosuppressant and the active ingredient of Prograf. 0.8 mL of Prograf (5 mg/mL) was administrated through oral gavage per animal in group 2. Prograf (5 mg/mL) was diluted 2× folds (2.5 mg/mL) and 4× folds (1.25 mg/mL) by using vehicle solution. 0.8 mL of each concentration, 1.25 mg/mL, 2.5 mg/mL, and 5 mg/mL of Prograf, was injected into a DSS ingestible device for group 3, 4, and 5.

Formulation: Each mL contained polyoxyl 60 hydrogenated castor oil (HCO-60), 200 mg, and dehydrated alcohol, USP, 80.0% v/v.

Physical characteristics: clear liquid solution.

3. DDS Ingestible Device Containing Tacrolimus

Description: Three (3) DDS ingestible devices containing vehicle solution for Group 1, three (3) DSS ingestible devices containing 1 mg tacrolimus for Group 3, three (3) DDS ingestible devices containing 2 mg tacrolimus for Group 4, and three (3) DDS ingestible devices containing 4 mg tacrolimus for Group 5.

Acclimation

Animals were acclimated prior to study initiation for at least 7 days. Animals in obvious poor health were not placed on study.

Concurrent Medication

Other than veterinary-approved anesthetics and medications used during surgery to install the ileocecal ports, or for vehicle or test article administration, and analgesia and antibiotics post-surgery, no further medications were employed.

Feed

All swine were fasted at least 24 hours before being anesthetized and properly medicated for surgery or overnight before dosing. Otherwise, animals were fed ad-libitum. Tap water was pressure-reduced and passed through a particulate filter, then a carbon filter prior to supply to an automatic watering system. Water was supplied ad libitum. There were no known contaminants in the feed or water that would be expected to interfere with this study.

Results

The data in FIG. 76 show that the mean concentration of tacrolimus in the cecum tissue and the proximate colon tissue were higher in swine that were intra-cecally administered tacrolimus as compared to swine that were orally administered tacrolimus. All blood trough concentrations were <10 ng/mL and exposure AUC <2000–12 ng·h/mL (FIGS. 87-89 and Table 26).

TABLE 26

| Route | PO | IC | IC | IC |
|---|---|---|---|---|
| Dose (mg · kg) | 0.09 | 0.02 | 0.04 | 0.09 |
| Tmax | 1 | 1 | 1 | 1 |
| Cmax | 3.531 ± 3.84 | 2.39 ± 0.565 | 9.197 ± 3.30 | 21.8 ± 4.73 |
| Trough (12 hr) | 0.568 ± 0.291 | 0.746 ± 0.038 | 1.96 ± 0.491 | 4.35 ± 0.516 |
| AUC 0-12 hr (ng*h/ml) | 16.83 ± 3.641 | 15.29 ± 2.356 | 51.35 ± 4.04 | 129.6 ± 7.827 |

Significantly higher $C_{max}$ values (9.20±3.30 and 21.80±4.73 ng/mL) were observed in groups treated with high (0.09 mg/kg) and moderate (0.04 mg/kg) dose of tacrolimus when delivered through IC capsule as compared to the $C_{max}$ values following PO delivery of tacrolimus (0.09 mg/kg). Significantly higher tissue (spiral and transverse colon) and luminal content (spiral, transverse, and distal colon) concentrations were observed in groups treated with high and moderate dose tacrolimus delivered through IC capsule as compared to the levels observed in animals administered tacrolimus via PO. No measurable level of tacrolimus was detected in tissue when animals were delivered tacrolimus via PO, despite systemic concentrations equivalent to low dose IC group (0.02 mg/kg) (FIGS. 90 and 91). A higher rectal content concentration was observed at 12 hours post-treatment in the IC capsule groups (FIG. 92), while no detectable level was observed in the PO group.

These data suggest that intra-cecal administration of tacrolimus is able to locally deliver tacrolimus to the tissues in the GI tract of a mammal, while not decreasing the systemic immune system of a mammal.

Example 11—Comparison of the Tissue, Plasma, and GI Content Pharmacokinetics of Adalimumab Through SC Vs. Intra-Cecal Ingestible Device Delivery in Yorkshire-Cross Farm Swine in DSS-Induced Colitis The purpose of this non-Good Laboratory Practice (GLP) study was to explore the PK/PD and bioavailability of adalimumab when applied to (Dextran Sulfate Sodium Salt) DSS-induced colitis in Yorkshire-cross farm swine, and to evaluate topical Humira® (adalimumab or ADA) in DSS-colitis in swine. Colitis was induced in weanling Yorkshire-Cross farm swine by administering DSS once daily for 7 consecutive days via oral gastric intubation. The dose levels were chosen based on the doses and regimens used to induce colitis in weanling pigs. The doses of DSS were 1.275 or 2.225 g/k/day for Groups 2 and 3, respectively. This study used one group of 19- to 21-day old weanling swine, and 2 groups of three, 19- to 20-day old weanling swine that weighed from 6.5 to 7.5 kg on arrival. To induce colitis, on study day 1 through and including day 7, animals in Groups 2 and 3 were administered once daily oral (gastric intubation) doses of DSS at 8.5% or 15% w/v for dose levels of 1.275 or 2.25 g/kg/day, respectively (Groups 2 and 3, respectively, 2 hours before morning feeding). The Group 1 control animal was administered sterile saline only. Each animal was placed in a sling for dosing. Animals were fasted at least 6 hours prior to each dose. See Table 27.

TABLE 27

Study Design

| Group | Route | Animal #[1] | DSS % w/v | mg/mL | Vol. (mL) | Total g[2] | g/kg | Frequency[3] | Total DSS needed | ADA treatment[4] |
|---|---|---|---|---|---|---|---|---|---|---|
| 1 (Animal 1501) | oral/gastric intubation | 1 | 0 | 0 | 105 | 0 | 0 | QD, 7 day | 0 | Day 8 (Vehicle) |
| 2 (Animals 2501, 2502, and 2504) | oral/gastric intubation | 3 | 8.5% | 85 | 105 | 8.925 | 1.275 | QD, 7 day | 187.425 | Day 8 (rectal 13 mg) |
| 3 | oral/gastric intubation | 3 | 15% | 150 | 105 | 15.75 | 2.25 | QD, 7 day | 330.75 | Day 8 (rectal 13 mg) |

[1]Animal weighed around 6.5-7.5 kg.

[2]Daily clinical signs and body weight were closely monitored throughout the study. If severe clinical signs or body weight loss is observed at day 1~3 after dosing, the DSS dosing was shortened to 5 days.

[3]0.8 mL of ADA solution was dosed rectally to the colon via an endoscope.

[4]Necropsy was done to observe GI inflammation and overall histopathology.

The day following the last DSS dose, using endoscopy and a catheter, at 13 mg adalimumab/0.8 mL/pig (one 40 mg adalimumab/0.8 mL dosage syringe was divided into 3 parts and diluted with PBS) was placed in the proximal portion of the descending colon just past the bend of the transverse colon. Alternatively, 13 mg of adalimumab was diluted with PBS to a volume suitable for dosing post-weanling swine. Prior to dosing, endoscopy photographs were taken of the mucosal surface of the colon. Animals were anesthetized during adalimumab dosing. Prior to adalimumab dosing, animals were housed on rubber mats to prevent ingestion of bedding material, and were fasted at least 24 hours. The colon was cleansed using an enema prior to the procedure.

All animals were properly euthanized approximately 3 hours post-adalimumab-dose for tissue collections and subjected to a gross necropsy with emphasis on the severity of colitis (immediately after euthanasia, in order to avoid autolytic changes). All samples for histology were fixed in a fixation medium and the punch-biopsy sample snap-frozen in liquid nitrogen and stored frozen (−70° C.).

To measure drug content, tissue samples and luminal content were collected by gently removing and collecting luminal content first, then using an 8.0 mm-punch biopsy tool. Biopsies from three different areas at the site of adalimumab administration were collected in each animal. Additional tissue biopsy samples were collected from three different areas at the proximal colon, and the proximal region of transverse colon in each animal. Approximately 3 g of total punched sample and 200 mg of luminal content were collected in a pre-weighed conical tubes and the tissue weighed was recorded.

Approximately, a 5-cm length of open gastrointestinal tissue sample including terminal ileum, cecum (CAC); proximal colon (PCN); transverse colon (TCN); spiral colon, distal colon (DCN), and rectum was collected, gently rinsed in saline to remove luminal material, and individually fixed in fixation buffer (10% neutral buffered formalin). Also, a 5-cm length of open gastrointestinal tissue from 3 different areas near the site of adalimumab administration was collected and fixed in formalin in the same manner for immunohistochemical staining for adalimumab. Tissue samples for histopathology were fixed in 10% neutral buffered formalin for 18-24 hr, and transferred to 70% ethanol.

HUMIRA® was supplied in single-use, 1-mL pre-filled glass syringes, as a sterile, preservative-free solution for subcutaneous administration. The solution of HUMIRA® was clear and colorless, with a pH of about 5.2. Each syringe delivered 0.8 mL (40 mg adalimumab) of drug product. Each vial contained approximately 0.9 mL of solution to deliver 0.8 mL (40 mg adalimumab) of drug product. Each 0.8 mL HUMIRA® contained 40 mg adalimumab, 4.93 mg sodium chloride, 0.69 mg monobasic sodium phosphate dihydrate, 1.22 mg dibasic sodium phosphate dihydrate, 0.24 mg sodium citrate, 1.04 mg citric acid monohydrate, 9.6 mg mannitol, 0.8 mg polysorbate 80, and water for injection. Sodium hydroxide was added as necessary to adjust pH.

All animals were randomized into groups of three. Animals were dosed once with adalimumab via subcutaneous (SC), perirectal (PR), or intracecal (IC) administration.

The concentration of adalimumab and TNFα was measured in plasma at 1, 2, 3, 4, 6, and 12 hours post-dose. The concentration of adalimumab was measured in rectal contents at 1, 3, 6, and 12 hours post-dose and in luminal content at 12 hours post-dose. Concentration of adalimumab and TNFα, HER2, and total protein was measured in gastrointestinal tissue, e.g., cecum sample (CAC), proximal colon sample (PCN), transverse colon sample (TCN), distal colon sample (DCNi) inflamed, distal colon non-inflamed sample (DCNn), and rectum sample (RTM), at 12 hours post-dose.

Treatment with 8.5% DSS (oral; Day 1 to Day 7) induced mild body weight loss, hemorrhage diarrhea, soft bloody stool, and moderate colitis in swine. Necropsy revealed marked edema and full thickness of mucosal erosion from the proximal colon through the distal rectum. The 8.5% DSS-induced animals were treated with adalimumab at day 8. No significant differences in clinical observations, GI-specific adverse effects or toxicity due to adalimumab treatment were observed. The 15% DSS (oral; Day 1 to Day 7)-induced animals had marked mucosal sloughing and hemorrhage from cecum to rectum and severe colitis. All of the animals were euthanized early on Day 5.

Significant lesions of colitis were found in animals treated with 8.5% DSS and were characterized by inflammation that involved mucosa and submucosa, loss of surface epithelium (erosion), and intestinal crypts (FIGS. 93 and 94). Table 28 shows the quantitative histological grading of colitis that was used.

TABLE 28

| Feature graded | Grade | Description |
|---|---|---|
| Inflammation | 0 | None |
| | 1 | Slight |
| | 2 | Moderate |
| | 3 | Severe |
| Extent | 0 | None |
| | 1 | Mucosa |
| | 2 | Mucosa and submucosa |
| | 3 | Transmural |
| Regeneration | 0 | Complete regeneration or normal tissue |
| | 1 | Almost complete regeneration |
| | 2 | Regeneration with crypt depletion |
| | 3 | Surface epithelium not intact |
| | 4 | No tissue repair |
| Crypt damage | 0 | None |
| | 1 | Basal 1/3 damaged |
| | 2 | Basal 2/3 damaged |
| | 3 | Only surface epithelium intact |
| | 4 | Entire crypt and epithelium lost |
| Percent involvement | 1 | 1-25% |
| | 2 | 26-50% |
| | 3 | 51-75% |
| | 4 | 76-100% |

There was little, if any, evidence of regeneration. The ileum and cecum were unremarkable in all animals except cecum from one animal (animal 2504) that was treated with 8.5% DSS, which had lesions of inflammation and loss of surface and crypt epithelium (FIGS. 95-99). Lesions of colitis were significant and consistent in all other segments of the large intestine from animals treated with 8.5% DSS. The severity and character of the changes were not remarkably different among the different segments or among these animals. Staining for human IgG was most consistent and intense at the adalimumab administration site and localized to the luminal surface of the mucosal epithelium or inflammatory exudate at the luminal surface, and penetration of adalimumab is found in the lamina propria near the luminal surface (FIG. 100).

Example 12—Human Clinical Trial of Treatment of Ulcerative Colitis Using Adalimumab As a proof of concept, the patient population of this study is patients that (1) have moderate to severe ulcerative colitis, regardless of extent, and (2) have had an insufficient response to a previous treatment, e.g., a conventional therapy (e.g., 5-ASA, corticosteroid, and/or immunosuppressant) or a FDA-approved treatment. In this placebo-controlled eight-week study, patients are randomized. All patient undergo a colonoscopy at the start of the study (baseline) and at week 8. Patients enrolled in the study are assessed for clinical status of disease by stool frequency, rectal bleeding, abdominal pain, physician's global assessment, and biomarker levels such as fecal calprotectin and hsCRP. The primary endpoint is a shift in endoscopy scores from Baseline to Week 8. Secondary and exploratory endpoints include safety and tolerability, change in rectal bleeding score, change in abdominal pain score, change in stool frequency, change in partial Mayo score, change in Mayo score, proportion of subjects achieving endoscopy remission, proportion of subjects achieving clinical remission, change in histology score, change in biomarkers of disease such as fecal calprotectin and hsCRP, level of adalimumab in the blood/tissue/stool, change in cytokine levels (e.g., TNFα, IL-6) in the blood and tissue.

FIG. 72 describes an exemplary process of what would occur in clinical practice, and when, where, and how the ingestible device will be used. Briefly, a patient displays symptoms of ulcerative colitis, including but not limited to: diarrhea, bloody stool, abdominal pain, high c-reactive protein (CRP), and/or high fecal calprotectin. A patient may or may not have undergone a colonoscopy with diagnosis of ulcerative colitis at this time. The patient's primary care physician refers the patient. The patient undergoes a colonoscopy with a biopsy, CT scan, and/or MRI. Based on this testing, the patient is diagnosed with ulcerative colitis. Most patients are diagnosed with ulcerative colitis by colonoscopy with biopsy. The severity based on clinical symptoms and endoscopic appearance, and the extent, based on the area of involvement on colonoscopy with or without CT/MRI is documented. Treatment is determined based on diagnosis, severity and extent.

For example, treatment for a patient that is diagnosed with ulcerative colitis is an ingestible device programmed to release a single bolus of a therapeutic agent, e.g., 40 mg adalimumab, in the cecum or proximal to the cecum. Prior to administration of the treatment, the patient is fasted overnight and is allowed to drink clear fluids. Four hours after swallowing the ingestible device, the patient can resume a normal diet. An ingestible device is swallowed at the same time each day. The ingestible device is not recovered.

In some embodiments, there may be two different ingestible devices: one including an induction dose (first 8 to 12 weeks) and a different ingestible device including a different dose or a different dosing interval.

In some examples, the ingestible device can include a mapping tool, which can be used after 8 to 12 weeks of induction therapy, to assess the response status (e.g., based on one or more of the following: drug level, drug antibody level, biomarker level, and mucosal healing status). Depending on the response status determined by the mapping tool, a subject may continue to receive an induction regimen or maintenance regimen of adalimumab.

In different clinical studies, the patients may be diagnosed with Crohn's disease and the ingestible devices (including adalimumab) can be programmed to release adalimumab in the cecum, or in both the cecum and transverse colon.

In different clinical studies, the patients may be diagnosed with ileocolonic Crohn's disease and the ingestible devices (including adalimumab) can be programmed to release adalimumab in the late jejunum or in the jejunum and transverse colon.

Example 13—Pharmacokinetic Study of Oral vs. Intra-Cecal Administration of Tacrolimus in Yorkshire-Cross Farm Swine The primary objective of this study was to study the pharmacokinetics of oral versus intra-cecal administration of tacrolimus in normal Yorkshire-Cross farm swine.

This study compares the effects of administration of: a single intra-cecal administration of a device containing 0.8 mL sterile vehicle solution (80% alcohol, 20% castor oil (HCO-60)); a single oral dose of tacrolimus at 0.09 mg/kg (in sterile vehicle solution); and a single intra-cecal administration of a device containing either 0.02 mg/kg (in sterile vehicle solution), 0.04 mg/kg (in sterile vehicle solution), or 0.09 mg/kg (in sterile vehicle solution).

This study employed five groups of three female swine weighing approximately 45 to 50 kg at study start. Swine were randomly placed into animal rooms/pens as they are transferred from the delivery vehicle without regard to group. Group numbers were assigned to the rooms in order of room number. No further randomization procedure was employed. The study design is provided in Table 29.

TABLE 29

| Study Design | | | | | | |
|---|---|---|---|---|---|---|
| Treatments | | | Dosage mg/kg | HED mg | Route | Endpoints |
| Group 1 | Vehicle control | n = 3 | 0 | 0 | Intra-cecal capsule | [Tacrolimus] in blood and rectal content at 1~12 hr post dose, and GI tissue & GI content at 12 hr post dose |
| Group 2 | Tacrolimus | n = 3 | 0.09 | 6.60 | Oral solution | |
| Group 3 | Tacrolimus | n = 3 | 0.02 | 1.65 | Intra-cecal capsule | |
| Group 4 | Tacrolimus | n = 3 | 0.04 | 3.30 | Intra-cecal capsule | |
| Group 5 | Tacrolimus | n = 3 | 0.09 | 6.60 | Intra-cecal capsule | |

Animals in Group 1 received intra-cecally a device containing a vehicle solution (80% alcohol, 20% HCO-60). Animals in Group 2 received orally a liquid formulation of tacrolimus at 0.09 mg/kg per animal. Animals in Group 3 received intra-cecally a device containing tacrolimus at 0.02 mg/kg per device. Animals in Group 4 received intra-cecally a device containing tacrolimus 0.04 mg/kg per device. Animals in Group 5 received intra-cecally a device containing tacrolimus 0.09 mg/kg per device.

Samples of rectal contents were collected for pharmacokinetic analyses from each animal at each of 1, 3, 6, and 12 hours post-device placement using a fecal swab (rectal swab).

The concentration of tacrolimus measured was measured in the blood at 1-, 2-, 3-, 4-, 6-, and 12-hours post-dose. The concentration of tacrolimus was measured in rectal contents at 1-, 3-, 6-, and 12-hours post-dose, and in the gastrointestinal tissue and luminal content, e.g., the cecum tissue and lumen, the proximal colon tissue and lumen, the spiral colon tissue and lumen, the transverse colon tissue and lumen, and the distal colon tissue and lumen, at 12 hours post-dose.

Results

The data in FIGS. 77 and 78 show that the mean concentration and AUCO-12 hours of tacrolimus in the blood was higher in swine that were intra-cecally administered tacrolimus as compared to swine that were orally administered tacrolimus even at the same concentration (0.09 mg/kg). The data in FIG. 79 show that the mean concentration of tacrolimus in the spiral colon tissue and the transverse colon tissue were statistically higher in swine that were intra-cecally administered tacrolimus as compared to swine that were orally administered tacrolimus. The data in FIG. 80 show that the mean concentration of tacrolimus in the spiral colon lumen, the transverse colon lumen, and the distal colon lumen were statistically higher in swine that were intra-cecally administered tacrolimus as compared to swine that were orally administered tacrolimus. The data in FIGS. 81 and 82 show that the mean concentration of tacrolimus in the rectal content was higher in swine that were intra-cecally administered tacrolimus as compared to swine that were orally administered tacrolimus even at the same concentration, particularly at 12 hours post-dose.

These data suggest that intra-cecal administration of tacrolimus is able to locally deliver tacrolimus to the tissues in the GI tract of a mammal.

A summary of the results are shown in Table 30.

TABLE 30

| Summary of Results | | | | |
|---|---|---|---|---|
| Route | PO | IC | IC | IC |
| Dosage (mg/kg) | 0.09 | 0.02 | 0.04 | 0.09 |
| Cmax (ng/mL) | 3.53 ± 3.84 | 2.39 ± 0.57 | 9.197 ± 3.30 | 21.8 ± 4.73 |
| Trough (12 hr) (ng/mL) | 0.568 ± 0.291 | 0.746 ± 0.038 | 1.96 ± 0.491 | 4.35 ± 0.561 |
| $AUC_{0-12\ hr}$ (ng · hr/mL) | 16.83 ± 3.641 | 15.29 ± 2.36 | 51.35 ± 4.04 | 129.6 ± 7.83 |

Tables 31 and 32 provide the tissue and plasma ratios of the animals in Groups 2-5.

TABLE 31-1

| $Tissue_{(mean)}$ (ng/g)/$AUG_{(0-12\ hr)}$ (ng · hr/mL) ratios | | | | | | |
|---|---|---|---|---|---|---|
| | Group 2 PO (0.09 mg/kg) | | | Group 3 IC (0.02 mg/kg) | | |
| | Tissue (ng/g) | AUC 0-12 hr (ng · hr/mL) | Ratio | Tissue (ng/g) | AUC 0-12 hr (ng · hr/mL) | Ratio |
| Cecum | | 16.83 | 0 | | 15.29 | 0.00 |
| Proximal Colon | | 16.83 | 0 | 50.20 | 15.29 | 3.28 |
| Spiral colon | | 16.83 | 0 | 204.00 | 15.29 | 13.34 |
| Transverse colon | | 16.83 | 0 | 128.20 | 15.29 | 8.38 |
| Distal Colon | | 16.83 | 0 | 44.70 | 15.29 | 2.92 |

TABLE 31-2

| Tissue$_{(mean)}$ (ng/g)/AUG$_{(0\text{-}12\ hr)}$ (ng · hr/mL) ratios | | | | | | |
|---|---|---|---|---|---|---|
| | Group 4 IC (0.04 mg/kg) | | | Group 5 IC (0.09 mg/kg) | | |
| | Tissue (ng/g) | AUC 0-12 hr (ng · hr/mL) | Ratio | Tissue (ng/g) | AUC 0-12 hr (ng · hr/mL) | Ratio |
| Cecum | 52.3 | 51.35 | 1.019 | 77.3 | 129.6 | 0.60 |
| Proximal Colon | 98.3 | 51.35 | 1.914 | 157.0 | 129.6 | 1.21 |
| Spiral colon | 342.3 | 51.35 | 6.667 | 783.3 | 129.6 | 6.04 |
| Transverse colon | 85.8 | 51.35 | 1.670 | 272.0 | 129.6 | 2.10 |
| Distal Colon | 28.7 | 51.35 | 0.559 | 67.7 | 129.6 | 0.52 |

TABLE 32-1

| Tissue$_{(mean)}$ (ng/g)/Trough$_{(12\ hr)}$(ng/mL) | | | | | | |
|---|---|---|---|---|---|---|
| | Group 2 PO (0.09 mg/kg) | | | Group 3 IC (0.02 mg/kg) | | |
| | Tissue (ng/g) | Trough level (12 hr) | Ratio | Tissue (ng/g) | Trough level (12 hr) | Ratio |
| Cecum | | 0.568 | 0 | | 0.746 | 0.00 |
| Proximal Colon | | 0.568 | 0 | 50.20 | 0.746 | 67.29 |
| Spiral colon | | 0.568 | 0 | 204.00 | 0.746 | 273.46 |
| Transverse colon | | 0.568 | 0 | 128.20 | 0.746 | 171.85 |
| Distal Colon | | 0.568 | 0 | 44.70 | 0.746 | 59.92 |

TABLE 32-2

| Tissue$_{(mean)}$ (ng/g)/Trough$_{(12\ hr)}$(ng/mL) | | | | | | |
|---|---|---|---|---|---|---|
| | Group 4 IC (0.04 mg/kg) | | | Group 5 IC (0.09 mg/kg) | | |
| | Tissue (ng/g) | Trough level (12 hr) | Ratio | Tissue (ng/g) | Trough level (12 hr) | Ratio |
| Cecum | 52.3 | 1.96 | 26.684 | 77.3 | 4.35 | 17.78 |
| Proximal Colon | 98.3 | 1.96 | 50.136 | 157.0 | 4.35 | 36.09 |
| Spiral colon | 342.3 | 1.96 | 174.660 | 783.3 | 4.35 | 180.08 |
| Transverse colon | 85.8 | 1.96 | 43.759 | 272.0 | 4.35 | 62.53 |
| Distal Colon | 28.7 | 1.96 | 14.643 | 67.7 | 4.35 | 15.56 |

Example 14

An ingestible medical device according to the disclosure ("TLC1") was tested on 20 subjects to investigate its localization ability. TLC1 was a biocompatible polycarbonate ingestible device that contained a power supply, electronics and software. An onboard software algorithm used time, temperature and reflected light spectral data to determine the location of the ingestible device as it traveled the GI tract. The ingestible device is 0.51×1.22 inches which is larger than a vitamin pill which is 0.4×0.85 inches. The subjects fasted overnight before participating in the study. Computerized tomography ("CT") were used as a basis for determining the accuracy of the localization data collected with TLC1. One of the 20 subjects did not follow the fasting rule. CT data was lacking for another one of the 20 subjects. Thus, these two subjects were excluded from further analysis. TLC1 sampled RGB data (radially transmitted) every 15 seconds for the first 14 hours after it entered the subject's stomach, and then samples every five minutes after that until battery dies. TLC1 did not start to record optical data until it reached the subject's stomach. Thus, there was no RGB-based data for the mouth-esophagus transition for any of the subjects.

In addition, a PillCarn® SB (Given Imaging) device was tested on 57 subjects. The subjects fasted overnight before joining the study. PillCam videos were recorded within each subject. The sampling frequency of PillCam is velocity dependent. The faster PillCam travels, the faster it would sample data. Each video is about seven to eight hours long, starting from when the ingestible device was administrated into the subject's mouth. RGB optical data were recorded in a table. A physician provided notes on where stomach-duodenum transition and ileum-cecum transition occurred in each video. Computerized tomography ("CT") was used as a basis for determining the accuracy of the localization data collected with PillCam.

Esophagus-Stomach Transition

For TLC1, it was assumed that this transition occurred one minute after the patient ingested the device. For PillCam, the algorithm was as follows:

1. Start mouth-esophagus transition detection after ingestible device is activated/administrated 2. Check whether Green <102.3 and Blue <94.6
   a. If yes, mark as mouth-esophagus transition
   b. If no, continue to scan the data
3. After detecting mouth-esophagus transition, continue to monitor Green and Blue signals for another 30 seconds, in case of location reversal
   a. If either Green >110.1 or Blue >105.5, mark it as mouth-esophagus location reversal
   b. Reset the mouth-esophagus flag and loop through step 2 and 3 until the confirmed mouth-esophagus transition detected
4. Add one minute to the confirmed mouth-esophagus transition and mark it as esophagus-stomach transition For one of the PillCam subjects, there was not a clear cut difference between the esophagus and stomach, so this subject was excluded from future analysis of stomach localization. Among the 56 valid subjects, 54 of them have correct esophagus-stomach transition localization. The total agreement is 54/56=96%. Each of the two failed cases had prolonged esophageal of greater than one minute. Thus, adding one minute to mouth-esophagus transition was not enough to cover the transition in esophagus for these two subjects.

Stomach-Duodenum

For both TLC1 and PillCam, a sliding window analysis was used. The algorithm used a dumbbell shape two-sliding-window approach with a two-minute gap between the front (first) and back (second) windows. The two-minute gap was designed, at least in part, to skip the rapid transition from stomach to small intestine and capture the small intestine signal after ingestible device settles down in small intestine. The algorithm was as follows:

1. Start to check for stomach-duodenum transition after ingestible device enters stomach
2. Setup the two windows (front and back)
   a. Time length of each window: 3 minutes for TLC1; 30 seconds for PillCam
   b. Time gap between two windows: 2 minutes for both devices
   c. Window sliding step size: 0.5 minute for both devices
3. Compare signals in the two sliding windows
   a. If difference in mean is higher than 3 times the standard deviation of Green/Blue signal in the back window
      i. If this is the first time ever, record the mean and standard deviation of signals in the back window as stomach reference
      ii. If mean signal in the front window is higher than stomach reference signal by a certain threshold (0.3 for TLC1 and 0.18 for PillCam), mark this as a possible stomach-duodenum transition
   b. If a possible pyloric transition is detected, continue to scan for another 10 minutes in case of false positive flag
      i. If within this 10 minutes, location reversal is detected, the previous pyloric transition flag is a false positive flag. Clear the flag and continue to check
      ii. If no location reversal has been identified within 10 minutes following the possible pyloric transition flag, mark it as a confirmed pyloric transition
   c. Continue monitoring Green/Blue data for another 2 hours after the confirmed pyloric transition, in case of location reversal
      i. If a location reversal is identified, flag the timestamp when reversal happened and then repeat steps a-c to look for the next pyloric transition
      ii. If the ingestible device has not gone back to stomach 2 hours after previously confirmed pyloric transition, stops location reversal monitoring and assume the ingestible device would stay in intestinal area For TLC1, one of the 18 subjects had too few samples (<3 minutes) taken in the stomach due to the delayed esophagus-stomach transition identification by previously developed localization algorithm. Thus, this subject was excluded from the stomach-duodenum transition algorithm test. For the rest of the TLC1 subjects, CT images confirmed that the detected pyloric transitions for all the subjects were located somewhere between stomach and jejunum. Two out of the 17 subjects showed that the ingestible device went back to stomach after first the first stomach-duodenum transition. The total agreement between the TLC1 algorithm detection and CT scans was 17/17=100%.

For one of the PillCam subjects, the ingestible device stayed in the subject's stomach all the time before the video ended. For another two of the PillCam subjects, too few samples were taken in the stomach to run the localization algorithm. These three PillCam subjects were excluded from the stomach-duodenum transition localization algorithm performance test. The performance summary of pyloric transition localization algorithm for PillCam was as follows:

1. Good cases (48 subjects):
   a. For 25 subjects, our detection matches exactly with the physician's notes
   b. For 19 subjects, the difference between the two detections is less than five minutes
   c. For four subjects, the difference between the two detections is less than 10 minutes (The full transition could take up to 10 minutes before the G/B signal settled)
2. Failed cases (6 subjects):
   a. Four subjects had high standard deviation of Green/Blue signal in the stomach
   b. One subject had bile in the stomach, which greatly affected Green/Blue in stomach
   c. One subject had no Green/Blue change at pyloric transition The total agreement for the PillCam stomach-duodenum transition localization algorithm detection and physician's notes was 48/54=89%.

Duodenum-Jejunum Transition

For TLC1, it was assumed that the device left the duodenum and entered the jejunum three minutes after it was determined that the device entered the duodenum. Of the 17 subjects noted above with respect to the TLC1 investigation of the stomach-duodenum transition, 16 of the subjects mentioned had CT images that confirmed that the duodenum-jejunum transition was located somewhere between stomach and jejunum. One of the 17 subjects had a prolonged transit time in duodenum. The total agreement between algorithm detection and CT scans was 16/17=94%.

For PillCam, the duodenum-jejunum transition was not determined.

Jejunum-Ileum Transition

It is to be noted that the jejunum is redder and more vascular than ileum, and that the jejunum has a thicker intestine wall with more mesentery fat. These differences can cause various optical responses between jejunum and ileum, particularly for the reflected red light signal. For both TLC1 and PillCam, two different approaches were explored to track the change of red signal at the jejunum-ileum transition. The first approach was a single-sliding-window analysis, where the window is 10 minutes long, and the mean signal was compared with a threshold value while the window was moving along. The second approach was a two-sliding-window analysis, where each window was 10 minutes long with a 20 minute spacing between the two windows. The algorithm for the jejunum-ileum transition localization was as follows:

1. Obtain 20 minutes of Red signal after the duodenum-jejunum transition, average the data and record it as the jejunum reference signal
2. Start to check the jejunum-ileum transition 20 minutes after the device enters the jejunum
   a. Normalize the newly received data by the jejunum reference signal
   b. Two approaches:
      i. Single-sliding-window analysis
         Set the transition flag if the mean of reflected red signal is less than 0.8
      ii. Two-sliding-window analysis:
         Set the transition flag if the mean difference in reflected red is higher than 2× the standard deviation of the reflected red signal in the front window For TLC1, 16 of the 18 subjects had CT images that confirmed that the detected jejunum-ileum transition fell between jejunum and cecum. The total agreement between algorithm and CT scans was 16/18=89%. This was true for both the single-sliding-window and double-sliding-window approaches, and the same two subjects failed in both approaches.

The performance summary of the jejunum-ileum transition detection for PillCam is listed below:

1. Single-sliding-window analysis:
   a. 11 cases having jejunum-ileum transition detected somewhere between jejunum and cecum
   b. 24 cases having jejunum-ileum transition detected after cecum
   c. 19 cases having no jejunum-ileum transition detected
   d. Total agreement: 11/54=20%
2. Two-sliding-window analysis:
   a. 30 cases having jejunum-ileum transition detected somewhere between jejunum and cecum
   b. 24 cases having jejunum-ileum transition detected after cecum
   c. Total agreement: 30/54=56%

Ileum-Cecum Transition

Data demonstrated that, for TLC1, mean signal of reflected red/green provided the most statistical difference before and after the ileum-cecum transition. Data also demonstrated that, for TLC1, the coefficient of variation of reflected green/blue provided the most statistical contrast at ileum-cecum transition. The analysis based on PillCam videos showed very similar statistical trends to those results obtained with TLC1 device. Thus, the algorithm utilized changes in mean value of reflected red/green and the coefficient of variation of reflected green/blue. The algorithm was as follows:

1. Start to monitor ileum-cecum transition after the ingestible device enters the stomach
2. Setup the two windows (front (first) and back (second))
   a. Use a five-minute time length for each window
   b. Use a 10-minute gap between the two windows
   c. Use a one-minute window sliding step size
3. Compare signals in the two sliding windows
   a. Set ileum-cecum transition flag if
      i. Reflected red/green has a significant change or is lower than a threshold
      ii. Coefficient of variation of reflected green/blue is lower than a threshold
   b. If this is the first ileum-cecum transition detected, record average reflected red/green signal in small intestine as small intestine reference signal
   c. Mark location reversal (i.e., ingestible device returns to terminal ileum) if
      i. Reflected red/green is statistically comparable with small intestine reference signal
      ii. Coefficient of variation of reflected green/blue is higher than a threshold
   d. If a possible ileum-cecum transition is detected, continue to scan for another 10 minutes for TLC1 (15 minutes for PillCam) in case of false positive flag
      i. If within this time frame (10 minutes for TLC1, 15 minutes for PillCam), location reversal is detected, the previous ileum-cecum transition flag is a false positive flag. Clear the flag and continue to check
      ii. If no location reversal has been identified within this time frame (10 minutes for TLC1, 15 minutes for PillCam) following the possible ileum-cecum transition flag, mark it as a confirmed ileum-cecum transition
   e. Continue monitoring data for another 2 hours after the confirmed ileum-cecum transition, in case of location reversal
      i. If a location reversal is identified, flag the time-stamp when reversal happened and then repeat steps a-d to look for the next ileum-cecum transition
      ii. If the ingestible device has not gone back to small intestine 2 hours after previously confirmed ileum-cecum transition, stop location reversal monitoring and assume the ingestible device would stay in large intestinal area The flag setting and location reversal criteria particularly designed for TLC1 device were as follows:

1. Set ileum-cecum transition flag if
   a. The average reflected red/Green in the front window is less than 0.7 or mean difference between the two windows is higher than 0.6
   b. And the coefficient of variation of reflected green/blue is less than 0.02
2. Define as location reversal if a. The average reflected red/green in the front window is higher than small intestine reference signal
   b. And the coefficient of variation of reflected green/blue is higher than 0.086

For TLC1, 16 of the 18 subjects had CT images that confirmed that the detected ileum-cecum transition fell between terminal ileum and colon. The total agreement between algorithm and CT scans was 16/18=89%. Regarding those two subject where the ileum-cecum transition localization algorithm failed, for one subject the ileum-cecum transition was detected while TLC1 was still in the subject's terminal ileum, and for the other subject the ileum-cecum transition was detected when the device was in the colon.

Among the 57 available PillCam endoscopy videos, for three subjects the endoscopy video ended before PillCam reached cecum, and another two subjects had only very limited video data (less than five minutes) in the large intestine. These five subjects were excluded from ileum-cecum transition localization algorithm performance test. The performance summary of ileum-cecum transition detection for PillCam is listed below:

1. Good cases (39 subjects):
    a. For 31 subjects, the difference between the PillCam detection and the physician's notes was less than five minutes
    b. For 3 subjects, the difference between the PillCam detection and the physician's notes was less than 10 minutes
    c. For 5 subjects, the difference between the PillCam detection and the physician's notes was less than 20 minutes (the full transition can take up to 20 minutes before the signal settles)
2. Marginal/bad cases (13 subjects):
    a. Marginal cases (9 subjects)
        i. The PillCam ileum-cecum transition detection appeared in the terminal ileum or colon, but the difference between the two detections was within one hour
    b. Failed cases (4 subjects)
        i. Reasons of failure:
            1. The signal already stabilized in the terminal ileum
            2. The signal was highly variable from the entrance to exit
            3. There was no statistically significant change in reflected red/green at ileum-cecum transition The total agreement between ileocecal transition localization algorithm detection and the physician's notes is 39/52=75% if considering good cases only. Total agreement including possibly acceptable cases is 48/52=92.3%.

Cecum-Colon Transition

Data demonstrated that, for TLC1, mean signal of reflected red/green provided the most statistical difference before and after the cecum-colon transition. Data also demonstrated that, for TLC1, the coefficient of variation of reflected blue provided the most statistical contrast at cecum-colon transition. The same signals were used for PillCam. The cecum-colon transition localization algorithm was as follows:

1. Obtain 10 minutes of reflected red/green and reflected blue signals after ileum-cecum transition, average the data and record it as the cecum reference signals
2. Start to check cecum-colon transition after ingestible device enters cecum (The cecum-colon transition algorithm is dependent on the ileum-cecum transition flag)
    a. Normalize the newly received data by the cecum reference signals
    b. Two-sliding-window analysis:
        i. Use two adjacent 10 minute windows
        ii. Set the transition flag if any of the following criteria were met
            The mean difference in reflected red/green was more than 4× the standard deviation of reflected red/green in the back (second) window
            The mean of reflected red/green in the front (first) window was higher than 1.03
            The coefficient of variation of reflected blue signal in the front (first) window was greater than 0.23

The threshold values above were chosen based on a statistical analysis of data taken by TLC1.

For TLC1, 15 of the 18 subjects had the cecum-colon transition detected somewhere between cecum and colon. One of the subjects had the cecum-colon transition detected while TLC1 was still in cecum. The other two subjects had both wrong ileum-cecum transition detection and wrong cecum-colon transition detection. The total agreement between algorithm and CT scans was 15/18=83%.

For PillCam, for three subjects the endoscopy video ended before PillCam reached cecum, and for another two subjects there was very limited video data (less than five minutes) in the large intestine. These five subjects were excluded from cecum-colon transition localization algorithm performance test. The performance summary of cecum-colon transition detection for PillCam is listed below:

1. 27 cases had the cecum-colon transition detected somewhere between the cecum and the colon
2. one case had the cecum-colon transition detected in the ileum
3. 24 cases had no cecum-colon transition localized The total agreement: 27/52=52%.

Table 33 summarizes the localization accuracy results.

TABLE 33

| Location accuracy | | |
|---|---|---|
| Transition | TLC1 | PillCam |
| Stomach-Duodenum | 100% (17/17) | 89% (48/54) |
| Duodenum-Jejunum | 94% (16/17) | N/A |
| Ileum-Cecum | 89% (16/18) | 75% (39/52) |
| Ileum-terminal ileum/cecum/colon | 100% (18/18) | 92% (48/52) |

Example 15

In the following cases, each subject is treated by administering an ingestible device as disclosed herein, said device containing a drug, or a pharmaceutical formulation containing the drug. The device has a self-localization mechanism that autonomously determines the device location within the subject's GI tract. The device localization mechanism includes one or more sensors associated with the device that detects light reflectance that is external to the device and present in the GI tract. Based on pre-determined identification of disease site(s) in a particular section or subsection of the GI tract, as disclosed in each case, the device is pre-programmed with instructions to release the drug, or the pharmaceutical formulation containing the drug, to or proximal to the section of the GI tract containing the disease site(s). The instructions are provided from at least one processor and/or at least one controller associated with the at least one sensor. The device contains a therapeutically effective amount of the drug (preferably, tofacitinib or a pharmaceutically acceptable salt thereof, or more particularly, tofacitinib citrate).

In some cases, a second agent is administered. In some particular cases, the second agent is an immunosuppressant (e.g., a corticosteroid), an aminosalicylate, an S1P modulator, a PDE4 inhibitor, an IL-12/IL-23 inhibitor, an integrin inhibitor, a GM-CSF, an anti-TNF agent, or a second JAK inhibitor. In some embodiments, the GM-CSF is administered during maintenance therapy.

Example 15-1a—Treatment of Inflammatory Disease Site(s) in the Duodenum by Releasing Drug in the Duodenum In the following 4 cases, based on pre-determined identification of disease site(s) in the duodenum, the device is pre-programmed with instructions to release the drug to the duodenum to treat the disease site(s).

(i) A 34-year old male subject suffering from symptoms of gastrointestinal inflammation walks into a clinic. The subject returns for an endoscopy, which reveals that he has disease site(s) in the tissue in the duodenum. Subsequently, the subject is orally administered the ingestible device containing the therapeutically effective amount of the drug. After ingestion of the device, data collected from at least one of the light sensors, optionally in conjunction with elapsed time through the GI tract after the oral administration, indicate that the device has transitioned from the stomach into the duodenum with at least about 90% accuracy. In this particular case, the light reflectance detected by the sensors includes green light and blue light; an increase in the ratio of the green to blue reflectance is used to determine that the device has transitioned from the stomach to the duodenum. The drug or pharmaceutical formulation containing the drug is then released from the device based on the instructions, providing topical delivery of the drug, or the pharmaceutical formulation containing the drug, to the duodenum containing one or more disease sites. In a follow-up visit, the subject undergoes a repeat endoscopy to determine the effect of the treatment.

(ii) Treatment of diffuse duodenitis associated with pancolonic ulcerative colitis in the duodenum by releasing drug in the duodenum. A 45-year old subject with a history of pancolonic ulcerative colitis undergoes laparoscopy-assisted proctocolectomy due to severe steroid-resistant disease. Two weeks after the surgery, the subject complains of epigastralia and tarry stool. The subject undergoes an endoscopy of the upper gastrointestinal tract with biopsy and histology, which reveals that the subject has disease site(s) in the tissue in the duodenum. Subsequently, the subject is orally administered the ingestible device containing the therapeutically effective amount of the drug. After ingestion of the device, data collected from at least one of the light sensors, optionally in conjunction with elapsed time through the GI tract after the oral administration, indicate that the device has transitioned from the stomach into the duodenum with at least about 90% accuracy. In this particular case, the light reflectance detected by the sensors includes green light and blue light; an increase in the ratio of the green to blue reflectance is used to determine that the device has transitioned from the stomach to the duodenum. The drug, or the pharmaceutical formulation containing the drug, is then released from the device based on the instructions, providing topical delivery of the drug, or the pharmaceutical formulation containing the drug, to the duodenum containing one or more disease sites. The subject subsequently undergoes an endoscopy to determine the effect of the treatment.

(iii) Treatment of gastroduodenal Crohn's disease by releasing drug in the duodenum. A 33-year old subject suffering from one month of epigastric pain and dyspepsia visits an outpatient clinic. The subject undergoes esophagogastroduodenoscopy (EGD) with biopsy, which reveals multiple progressive ulcers and erosions in the tissue in the duodenum. Subsequently, the subject is orally administered the ingestible device containing the therapeutically effective amount of the drug. After ingestion of the device, data collected from at least one of the light sensors, optionally in conjunction with elapsed time through the GI tract after the oral administration, indicate that the device has transitioned from the stomach into the duodenum with at least about 90% accuracy. In this particular case, the light reflectance detected by the sensors includes green light and blue light; an increase in the ratio of the green to blue reflectance is used to determine that the device has transitioned from the stomach to the duodenum. The drug, or the pharmaceutical formulation containing the drug, is then released from the device based on the instructions, providing topical delivery of the drug, or the pharmaceutical formulation containing the drug, to the duodenum containing one or more disease sites. The subject subsequently undergoes an endoscopy to determine the effect of the treatment.

(iv) Treatment of gastroduodenal Crohn's disease by releasing drug in the duodenum. A 26-year old female subject suffering from nausea, weight loss and loss of appetite sees a gastroenterologist. The subject undergoes an endoscopy, which reveals gastroduodenal Crohn's disease affecting the subject's duodenum. Subsequently, the subject is orally administered the ingestible device containing the therapeutically effective amount of the drug. ingestion of the device, data collected from at least one of the light sensors, optionally in conjunction with elapsed time through the GI tract after the oral administration, indicate that the device has transitioned from the stomach into the duodenum with at least about 90% accuracy. In this particular case, the light reflectance detected by the sensors includes green light and blue light; an increase in the ratio of the green to blue reflectance is used to determine that the device has transitioned from the stomach to the duodenum. The drug, or the pharmaceutical formulation containing the drug, is then released from the device based on the instructions, providing topical delivery of the drug, or the pharmaceutical formulation containing the drug, to the duodenum containing one or more disease sites. In a follow-up visit, the subject undergoes a repeat endoscopy to determine the effect of the treatment.

Example 15-1b—Treatment of Inflammatory Disease Site(s) in the Jejunum by Releasing Drug in the Jejunum In the following 2 cases, based on pre-determined identification of disease site(s) in the jejunum, as disclosed in each case, the device is pre-programmed with instructions to release the drug to the jejunum to treat the disease site(s).

(i) A 68-year old female subject suffering from symptoms of gastrointestinal pain and discomfort goes to see her doctor. The subject subsequently undergoes a video endoscopy, which reveals disease site(s) in the tissue in the jejunum. Subsequently, the subject is orally administered the ingestible device containing the therapeutically effective amount of the drug. After ingestion of the device, data collected from at least one of the light sensors, together with elapsed time through the GI tract after the oral administration, indicates that the device has transitioned into the jejunum with at least about 90% accuracy. In this particular case, the light reflectance detected by the sensors includes green light and blue light; an increase in the ratio of the green to blue reflectance is used to determine that the device has transitioned from the stomach to the duodenum; a period of elapsed time (about 3 minutes) after the transition to the duodenum is then used to determine that the device has transitioned from the duodenum to the jejunum. Optionally, peristaltic contraction frequency data are used to corroborate that the device has entered the jejunum. The drug, or the pharmaceutical formulation containing the drug, is then released from the device based on the instructions, providing topical delivery of the drug, or the pharmaceutical formulation containing the drug, to the jejunum containing one or more disease sites. The subject subsequently undergoes an endoscopy to determine the effect of the treatment.

(ii) Treatment of Crohn's disease in the jejunum by releasing drug in the jejunum. A subject having unexplained weight loss and fever goes to urgent care. The subject later undergoes an endoscopy, which reveals that the subject has disease site(s) in the tissue in the jejunum associated with Crohn's disease. Subsequently, the subject is orally administered the ingestible device containing the therapeutically effective amount of the drug. After ingestion of the device, data collected from at least one of the light sensors, together with elapsed time through the GI tract after the oral administration, indicates that the device has transitioned into the jejunum with at least about 90% accuracy. In this particular case, the light reflectance detected by the sensors includes green light and blue light; an increase in the ratio of the green to blue reflectance is used to determine that the device has transitioned from the stomach to the duodenum; a period of elapsed time (about 3 minutes) after the transition to the duodenum is then used to determine that the device has transitioned from the duodenum to the jejunum. Optionally, peristaltic contraction frequency data are used to corroborate that the device has entered the jejunum. The drug, or the pharmaceutical formulation containing the drug, is then released from the device based on the instructions, providing topical delivery of the drug, or the pharmaceutical formulation containing the drug, to the jejunum containing one or more disease sites. The subject subsequently undergoes an endoscopy to determine the effect of the treatment.

Example 15-1c—Treatment of Inflammatory Disease Site(s) in the Ileum by Releasing Drug in the Ileum In the following 3 cases, based on pre-determined identification of disease site(s) in the ileum, as disclosed in each case, the device is pre-programmed with instructions to release the drug to the ileum to treat the disease site(s).

(i) A 42-year old female subject suffering from gastrointestinal cramping and fatigue makes an appointment with a gastroenterologist. The subject undergoes an endoscopy, which reveals that she has disease site(s) in the tissue in the ileum. Subsequently, the subject is orally administered the ingestible device containing the therapeutically effective amount of the drug. After ingestion of the device, data collected from at least one of the light sensors, together with elapsed time through the GI tract after the oral administration, indicates that the device has transitioned from the jejunum into the ileum with at least about 80% accuracy. In this particular case, the light reflectance detected by the sensors includes red light. Once the device has reached the jejunum (essentially as determined in Example 15-1b (i)), a detected decrease in red light reflectance is used to determine that the device has transitioned from the jejunum to the ileum. The drug, or the pharmaceutical formulation containing the drug, is then released from the device based on the instructions, providing topical delivery of the drug, or the pharmaceutical formulation containing the drug, to the ileum containing one or more disease sites. The subject subsequently undergoes an endoscopy to determine the effect of the treatment.

(ii) Treatment of ulcerative colitis with backwash ileitis by releasing drug in the ileum. A 42-year old female subject with a history of pancolitis visits her treating physician. The subject undergoes an endoscopy, which reveals that the subject has patchy cryptitis and crypt abscesses in the distal ileum thought to be due to backwash of cecal contents ("backwash ileitis"). Subsequently, the subject is orally administered the ingestible device containing the therapeutically effective amount of the drug. After ingestion of the device, data collected from at least one of the light sensors, together with elapsed time through the GI tract after the oral administration, indicates that the device has transitioned from the jejunum into the ileum with at least about 80% accuracy. In this particular case, the light reflectance detected by the sensors includes red light. Once the device has reached the jejunum (essentially as determined in Example 15-1b(i)), a detected decrease in red light reflectance is used to determine that the device has transitioned from the jejunum to the ileum. The drug, or the pharmaceutical formulation containing the drug, is then released from the device based on the instructions, providing topical delivery of the drug, or the pharmaceutical formulation containing the drug, to the ileum containing one or more disease sites. The subject subsequently undergoes an endoscopy to determine the effect of the treatment.

(iii) Treatment of Crohn's disease in the ileum by releasing drug in the ileum. A subject suffering from symptoms of Crohn's disease, including abdominal pain and cramping, walks into a clinic. The subject undergoes an endoscopy, which reveals that the subject has disease site(s) in the tissue in the ileum. Subsequently, the subject is orally administered the ingestible device containing the therapeutically effective amount of the drug. After ingestion of the device, data collected from at least one of the light sensors, together with elapsed time through the GI tract after the oral administration, indicates that the device has transitioned from the jejunum to the ileum with at least about 80% accuracy. In this particular case, the light reflectance detected by the sensors includes red light. Once the device has reached the jejunum (essentially as determined in Example 15-1b(i)), a detected decrease in red light reflectance is used to determine that the device has transitioned from the jejunum to the ileum. The drug, or the pharmaceutical formulation containing the drug, is then released from the device based on the instructions, providing topical delivery of the drug, or the pharmaceutical formulation containing the drug, to the ileum containing one or more disease sites. The subject subsequently undergoes an endoscopy to determine the effect of the treatment.

Example 15-1d—Treatment of Inflammatory Disease Site(s) in the Cecum by Releasing Drug in the Cecum In the following 3 cases, based on pre-determined identification of disease site(s) in the cecum, as disclosed in each case, the device is pre-programmed with instructions to release the drug to the cecum to treat the disease site(s).

(i) A 25-year old male subject suffering from symptoms of gastrointestinal inflammation walks into a clinic. The subject undergoes an endoscopy, which reveals disease site(s) in the tissue in the cecum. Subsequently, the subject is orally administered the ingestible device containing the therapeutically effective amount of the drug. After ingestion of the device, data collected from at least one of the light sensors, optionally in conjunction with elapsed time through the GI tract after the oral administration, indicates that the device has transitioned into the cecum with at least about 80% accuracy. In this particular case, the light reflectance detected by the sensors includes red, green and blue light. A decrease in the ratio of the red to green reflectance, together with a decrease in the ratio of the green to blue reflectance, are used to determine that the device has transitioned from the ileum to the cecum. The drug, or the pharmaceutical formulation containing the drug, is then released from the device based on the instructions, providing topical delivery of the drug, or the pharmaceutical formulation containing the drug, to the cecum containing one or more disease sites. The subject subsequently undergoes an endoscopy to determine the effect of the treatment.

(ii) Treatment of ulcerative colitis in the cecum by releasing drug in the cecum. A subject with a history of ulcerative colitis returns to the clinic. The subject undergoes an endoscopy, which reveals that the subject has disease site(s) in the tissue in the cecum. Subsequently, the subject is orally administered the ingestible device containing the therapeutically effective amount of the drug. After ingestion of the device, data collected from at least one of the light sensors, optionally in conjunction with elapsed time through the GI tract after the oral administration, indicates that the device has transitioned into the cecum with at least about 80% accuracy. In this particular case, the light reflectance detected by the sensors includes red, green and blue light. A decrease in the ratio of the red to green reflectance, together with a decrease in the ratio of the green to blue reflectance, are used to determine that the device has transitioned from the ileum to the cecum. The drug, or the pharmaceutical formulation containing the drug, is then released from the device based on the instructions, providing topical delivery of the drug, or the pharmaceutical formulation containing the drug, to the cecum containing one or more disease sites. The subject subsequently undergoes an endoscopy to determine the effect of the treatment.

(iii) Treatment of Crohn's disease in the cecum by releasing drug in the cecum. A subject suffering from symptoms of Crohn's disease, including fatigue, reduced appetite and frequent, recurring diarrhea goes to a local clinic. The subject undergoes an endoscopy, which reveals that the subject has disease site(s) in the tissue in the cecum. Subsequently, the subject is orally administered the ingestible device containing the therapeutically effective amount of the drug. After ingestion of the device, data collected from at least one of the light sensors, optionally in conjunction with elapsed time through the GI tract after the oral administration, indicates that the device has transitioned into the cecum with at least about 80% accuracy. In this particular case, the light reflectance detected by the sensors includes red, green and blue light. A decrease in the ratio of the red to green reflectance, together with a decrease in the ratio of the green to blue reflectance, are used to determine that the device has transitioned from the ileum to the cecum. The drug, or the pharmaceutical formulation containing the drug, is then released from the device based on the instructions, providing topical delivery of the drug, or the pharmaceutical formulation containing the drug, to the cecum containing one or more disease sites. The subject subsequently undergoes an endoscopy to determine the effect of the treatment.

Example 15-1e—Treatment of Inflammatory Disease Site(s) in the Colon by Releasing Drug in the Colon In the following 3 cases, based on pre-determined identification of disease site(s) in the colon, as disclosed in each case, the device is pre-programmed with instructions to release the drug to the colon to treat the disease site(s).

(i) A 57-year old male subject suffering frequent, recurring diarrhea goes to an outpatient facility for an endoscopy, which reveals disease site(s) in the tissue in the colon. The subject undergoes an endoscopy, which reveals that the subject has disease site(s) in the tissue in the colon. Subsequently, the subject is orally administered the ingestible device containing the therapeutically effective amount of the drug. After ingestion of the device, data collected from at least one of the light sensors, together with elapsed time through the GI tract after the oral administration, indicates that the device has transitioned into the colon with at least about 80% accuracy. In this particular case, the light reflectance detected by the sensors includes red light, green light and blue light. Once the device is localized to the cecum (essentially as described in Example 15-1d(i)), a change in the ratio of the red to green reflectance is used to determine that the device has transitioned from the cecum further into the colon. Alternatively or additionally, a change in the coefficient of variation (CV) of the detected blue reflectance is used to determine that the device has transitioned from the cecum further into the colon. The drug, or the pharmaceutical formulation containing the drug, is then released from the device based on the instructions, providing topical delivery of the drug, or the pharmaceutical formulation containing the drug, to the colon containing one or more disease sites. The subject subsequently undergoes an endoscopy to determine the effect of the treatment.

(ii) Treatment of ulcerative colitis in the colon by releasing drug in the colon. A subject suffering from tenesmus and rectal bleeding sees a gastroenterologist. The subject undergoes an endoscopy, which reveals that the subject has disease site(s) in the tissue in the colon. Subsequently, the subject is orally administered the ingestible device containing the therapeutically effective amount of the drug. After ingestion of the device, data collected from at least one of the light sensors, together with elapsed time through the GI tract after the oral administration, indicates that the device has transitioned into the colon with at least about 80% accuracy. In this particular case, the light reflectance detected by the sensors includes red light, green light and blue light. Once the device is localized to the cecum (essentially as described in Example 15-1d(i)), a change in the ratio of the red to green reflectance is used to determine that the device has transitioned from the cecum to the colon. Alternatively or additionally, a change in the coefficient of variation (CV) of the detected blue reflectance is used to determine that the device has transitioned from the cecum to the colon. The drug, or the pharmaceutical formulation containing the drug, is then released from the device based on the instructions, providing topical delivery of the drug, or the pharmaceutical formulation containing the drug, to the jejunum containing one or more disease sites. The subject subsequently undergoes an endoscopy to determine the effect of the treatment.

(iii) Treatment of Crohn's disease in the colon by releasing drug in the colon. A subject suffering from Crohn's disease undergoes an endoscopy, which reveals disease site(s) in the tissue in the colon. Subsequently, the subject is orally administered the ingestible device containing the therapeutically effective amount of the drug. After ingestion of the device, data collected from at least one of the light sensors, together with elapsed time through the GI tract after the oral administration, indicates that the device has transitioned into the colon with at least about 80% accuracy. In this particular case, the light reflectance detected by the sensors includes red light, green light and blue light. Once the device is localized to the cecum (essentially as described in Example 15-1d(i)), a change in the ratio of the red to green reflectance is used to detennine that the device has transitioned from the cecum to the colon. Alternatively or additionally, a change in the coefficient of variation (CV) of the detected blue reflectance is used to determine that the device has transitioned from the cecum to the colon. The drug, or the pharmaceutical formulation containing the drug, is then released from the device based on the instructions, providing topical delivery of the drug, or the pharmaceutical formulation containing the drug, to the colon containing one or more disease sites. The subject subsequently undergoes an endoscopy to determine the effect of the treatment.

Example 15-1f—Treatment of Inflammatory Disease Site(s) in the Stomach by Releasing Drug in the Stomach A subject suffering from nausea, weight loss and loss of appetite sees a gastroenterologist. The subject undergoes an endoscopy, which reveals disease site(s) in the stomach. Subsequently the subject is orally administered an ingestible device as disclosed herein containing a therapeutically effective amount of drug. The device contains a self-localization mechanism that autonomously determines the device location within the subject's GI tract. The device localization mechanism includes one or more sensors associated with the device that detects light reflectance that is external to the device and present in the GI tract. The device is pre-programmed with instructions to release the drug to the stomach. The instructions are provided from at least one processor and/or at least one controller associated with the at least one sensor. After ingestion of the device, data collected from at least one of the light sensors, in conjunction with elapsed time (about 1 minute) after the oral administration, indicates that the device has entered the stomach. The drug, or the pharmaceutical formulation containing the drug, is then released from the device based on the instructions, providing topical delivery of the drug, or the pharmaceutical formulation containing the drug, to the stomach containing one or more disease sites. The subject subsequently undergoes an endoscopy to determine the effect of the treatment.

Example 15-2a—Treatment of Inflammatory Disease Site(s) in the Jejunum by Releasing Drug in the Duodenum In the following 2 cases, based on pre-determined identification of disease site(s) in the jejunum, as disclosed in each case, the device is pre-programmed with instructions to release the drug to the duodenum to treat the disease site(s).

(i) A subject suffering from symptoms of a gastrointestinal inflammatory disease walks sees her doctor. The subject later undergoes an endoscopy with biopsy, which reveals disease site(s) in the tissue in the jejunum. Subsequently, the subject is orally administered the ingestible device containing the therapeutically effective amount of the drug. After ingestion of the device, data collected from at least one of the light sensors, optionally in conjunction with elapsed time through the GI tract after the oral administration, indicate that the device has transitioned from the stomach into the duodenum with at least about 90% accuracy. In this particular case, the light reflectance detected by the sensors includes green light and blue light; an increase in the ratio of the green to blue reflectance is used to determine that the device has transitioned from the stomach to the duodenum. The drug, or the pharmaceutical formulation containing the drug, is then released from the device based on the instructions, providing topical delivery of the drug, or the pharmaceutical formulation containing the drug, to the jejunum containing one or more disease sites. The subject subsequently undergoes an endoscopy to determine the effect of the treatment.

(ii) Treatment of Crohn's disease in the jejunum by releasing drug in the duodenum. A subject suffering from abdominal pain, cramping after meals, and diarrhea is diagnosed by endoscopy with jejunoileitis, a form of Crohn's disease that affects the jejunum. Subsequently, the subject is orally administered the ingestible device containing the therapeutically effective amount of the drug. After ingestion of the device, data collected from at least one of the light sensors, optionally in conjunction with elapsed time through the GI tract after the oral administration, indicate that the device has transitioned from the stomach into the duodenum with at least about 90% accuracy. In this particular case, the light reflectance detected by the sensors includes green light and blue light; an increase in the ratio of the green to blue reflectance is used to determine that the device has transitioned from the stomach to the duodenum. The drug, or the pharmaceutical formulation containing the drug, is then released from the device based on the instructions, providing topical delivery of the drug, or the pharmaceutical formulation containing the drug, to the jejunum containing one or more disease sites. The subject subsequently undergoes an endoscopy to determine the effect of the treatment.

Example 15-2b—Treatment of Inflammatory Disease Site(s) in the Ileum by Releasing Drug in the Jejunum In the following 3 cases, each subject is treated by administering a device as disclosed herein containing a self-localization mechanism that autonomously determines the device location within the subject's GI tract. The device localization mechanism includes one or more sensors associated with the device that detects light reflectance that is external to the device and present in the GI tract. Based on pre-determined identification of disease site(s) in the ileum, as disclosed in each case, the device is pre-programmed with instructions to release the drug to the jejunum to treat the disease site(s). The instructions are provided from at least one processor and/or at least one controller associated with the at least one sensor. The device contains a therapeutically effective amount of drug.

(i) A subject suffering from symptoms of gastrointestinal inflammation and recent weight loss walks into a clinic. The subject undergoes an endoscopy, which reveals that the subject has disease site(s) in the tissue in the ileum. Subsequently, the subject is orally administered the ingestible device containing the therapeutically effective amount of the drug. After ingestion of the device, data collected from at least one of the light sensors, together with elapsed time through the GI tract after the oral administration, indicates that the device has transitioned into the jejunum with at least about 90% accuracy. In this particular case, the light reflectance detected by the sensors includes green light and blue light; an increase in the ratio of the green to blue reflectance is used to determine that the device has transitioned from the stomach to the duodenum; a period of elapsed time (about 3 minutes) after the transition to the duodenum is then used to determine that the device has transitioned from the duodenum to the jejunum. Optionally, peristaltic contraction frequency data are used to corroborate that the device has entered the jejunum. The drug, or the pharmaceutical formulation containing the drug, is then released from the device based on the instructions, providing topical delivery of the drug, or the pharmaceutical formulation containing the drug, to the ileum containing one or more disease sites. The subject subsequently undergoes an endoscopy to determine the effect of the treatment.

(ii) Treatment of ulcerative colitis with backwash ileitis by releasing drug in the jejunum. A 47-year old male subject who previously underwent total proctocolectomy returns to the clinic for a follow-up visit. The subject undergoes an endoscopy, which reveals that the subject has increased neutrophilic and mononuclear inflammation in the lamina propria, along with patchy cryptitis in the ileum. Subsequently, the subject is orally administered the ingestible device containing the therapeutically effective amount of the drug. After ingestion of the device, data collected from at least one of the light sensors, together with elapsed time through the GI tract after the oral administration, indicates that the device has transitioned into the jejunum with at least about 90% accuracy. In this particular case, the light reflectance detected by the sensors includes green light and blue light; an increase in the ratio of the green to blue reflectance is used to determine that the device has transitioned from the stomach to the duodenum; a period of elapsed time (about 3 minutes) after the transition to the duodenum is then used to determine that the device has transitioned from the duodenum to the jejunum. Optionally, peristaltic contraction frequency data are used to corroborate that the device has entered the jejunum. The drug, or the pharmaceutical formulation containing the drug, is then released from the device based on the instructions, providing topical delivery of the drug, or the pharmaceutical formulation containing the drug, to the ileum containing one or more disease sites. The subject subsequently undergoes an endoscopy to determine the effect of the treatment.

(iii) Treatment of Crohn's disease in the ileum (ileocolitis) by releasing drug in the jejunum. A subject suffering from diarrhea and cramping in the lower right part of the abdomen undergoes an endoscopy, which reveals that the subject has ileocolitis. Subsequently, the subject is orally administered the ingestible device containing the therapeutically effective amount of the drug. After ingestion of the device, data collected from at least one of the light sensors, together with elapsed time through the GI tract after the oral administration, indicates that the device has transitioned into the jejunum with at least about 90% accuracy. In this particular case, the light reflectance detected by the sensors includes green light and blue light; an increase in the ratio of the green to blue reflectance is used to determine that the device has transitioned from the stomach to the duodenum; a period of elapsed time (about 3 minutes) after the transition to the duodenum is then used to determine that the device has transitioned from the duodenum to the jejunum. Optionally, peristaltic contraction frequency data are used to corroborate that the device has entered the jejunum. The drug, or the pharmaceutical formulation containing the drug, is then released from the device based on the instructions, providing topical delivery of the drug, or the pharmaceutical formulation containing the drug, to the ileum containing one or more disease sites. The subject subsequently undergoes an endoscopy to determine the effect of the treatment.

Example 15-2c—Treatment of Inflammatory Disease Site(s) in the Cecum by Releasing Drug in the Ileum In the following 3 cases, based on pre-determined identification of disease site(s) in the cecum, as disclosed in each case, the device is pre-programmed with instructions to release the drug to the ileum to treat the disease site(s). The instructions are provided from at least one processor and/or at least one controller associated with the at least one sensor. The device contains a therapeutically effective amount of drug.

(i) A subject having diarrhea, pain and fatigue walks into a clinic. The subject undergoes an endoscopy, which reveals that the subject has disease site(s) in the tissue in the cecum. Subsequently, the subject is orally administered the ingestible device containing the therapeutically effective amount of the drug. After ingestion of the device, data collected from at least one of the light sensors, together with elapsed time through the GI tract after the oral administration, indicates that the device has transitioned from the jejunum to the ileum with at least about 80% accuracy. In this particular case, the light reflectance detected by the sensors includes red light. Once the device has reached the jejunum (essentially as determined in Example 15-1b(i)), a detected decrease in red light reflectance is used to determine that the device has transitioned from the jejunum to the ileum. The drug, or the pharmaceutical formulation containing the drug, is then released from the device based on the instructions, providing topical delivery of the drug, or the pharmaceutical formulation containing the drug, to the cecum containing the one or more disease sites. The subject subsequently undergoes an endoscopy to determine the effect of the treatment.

(ii) Treatment ofulcerative colitis in the cecum by releasing drug in the ileum. A subject suffering from symptoms of ulcerative colitis, including diarrhea, pain and fatigue walks into a clinic. The subject undergoes an endoscopy, which reveals that the subject has disease site(s) in the tissue in the cecum. Subsequently, the subject is orally administered the ingestible device containing the therapeutically effective amount of the drug. After ingestion of the device, data collected from at least one of the light sensors, together with elapsed time through the GI tract after the oral administration, indicates that the device has transitioned from the jejunum to the ileum with at least about 80% accuracy. In this particular case, the light reflectance detected by the sensors includes red light. Once the device has reached the jejunum (essentially as determined in Example 15-1b(i)), a detected decrease in red light reflectance is used to determine that the device has transitioned from the jejunum to the ileum. The drug, or the pharmaceutical formulation containing the drug, is then released from the device based on the instructions, providing topical delivery of the drug, or the pharmaceutical formulation containing the drug, to the cecum containing one or more disease sites. The subject subsequently undergoes an endoscopy to determine the effect of the treatment.

(iii) Treatment of Crohn's disease in the cecum by releasing drug in the ileum. A subject suffering from symptoms of Crohn's disease walks into a clinic. The subject undergoes an endoscopy, which reveals that the subject has disease site(s) in the tissue in the cecum. Subsequently, the subject is orally administered the ingestible device containing the therapeutically effective amount of the drug. After ingestion of the device, data collected from at least one of the light sensors, together with elapsed time through the GI tract after the oral administration, indicates that the device has transitioned from the jejunum to the ileum with at least about 80% accuracy. In this particular case, the light reflectance detected by the sensors includes red light. Once the device has reached the jejunum (essentially as determined in Example 15-1b(i)), a detected decrease in red light reflectance is used to determine that the device has transitioned from the jejunum to the ileum. The drug, or the pharmaceutical formulation containing the drug, is then released from the device based on the instructions, providing topical delivery of the drug, or the pharmaceutical formulation containing the drug, to the cecum containing one or more disease sites. The subject subsequently undergoes an endoscopy to determine the effect of the treatment.

Example 15-2d—Treatment of Inflammatory Disease Site(s) in the Colon by Releasing Drug in the Cecum In the following 3 cases, based on pre-determined identification of disease site(s) in the colon, as disclosed in each case, the device is pre-programmed with instructions to release the drug to the cecum to treat the disease site(s). The instructions are provided from at least one processor and/or at least one controller associated with the at least one sensor. The device contains a therapeutically effective amount of drug.

(i) A subject having abdominal pain and bloody bowel movements sees a gastroenterologist. The subject undergoes an endoscopy, which reveals disease site(s) in the tissue in the colon. Subsequently, the subject is orally administered the ingestible device containing the therapeutically effective amount of the drug. After ingestion of the device, data collected from at least one of the light sensors, optionally in conjunction with elapsed time through the GI tract after the oral administration, indicates that the device has transitioned into the cecum with at least about 80% accuracy. In this particular case, the light reflectance detected by the sensors includes red, green and blue light. A decrease in the ratio of the red to green reflectance, together with a decrease in the ratio of the green to blue reflectance, are used to determine that the device has transitioned from the ileum to the cecum. The drug, or the pharmaceutical formulation containing the drug, is then released from the device based on the instructions, providing topical delivery of the drug, or the pharmaceutical formulation containing the drug, to the colon containing one or more disease sites. The subject subsequently undergoes an endoscopy to determine the effect of the treatment.

(ii) Treatment of ulcerative colitis in the colon by releasing drug in the cecum. A subject suffering from a recurrent urge to have a bowel movement sees a specialist. The subject undergoes an endoscopy, which reveals that the subject has disease site(s) in the tissue in the colon. Subsequently, the subject is orally administered the ingestible device containing the therapeutically effective amount of the drug. After ingestion of the device, data collected from at least one of the light sensors, optionally in conjunction with elapsed time through the GI tract after the oral administration, indicates that the device has transitioned into the cecum with at least about 80% accuracy. In this particular case, the light reflectance detected by the sensors includes red, green and blue light. A decrease in the ratio of the red to green reflectance, together with a decrease in the ratio of the green to blue reflectance, are used to determine that the device has transitioned from the ileum to the cecum. The drug, or the pharmaceutical formulation containing the drug, is then released from the device based on the instructions, providing topical delivery of the drug, or the pharmaceutical formulation containing the drug, to the colon containing one or more disease sites. The subject subsequently undergoes an endoscopy to determine the effect of the treatment.

(iii) Treatment of Crohn's disease in the colon by releasing drug in the cecum. A subject suffering from skin lesions, joint pain, diarrhea, and pain around the anus undergoes an endoscopy and is diagnosed with Crohn's (granulomatous) colitis. Subsequently, the subject is orally administered the ingestible device containing the therapeutically effective amount of the drug. After ingestion of the device, data collected from at least one of the light sensors, optionally in conjunction with elapsed time through the GI tract after the oral administration, indicates that the device has transitioned into the cecum with at least about 80% accuracy. In this particular case, the light reflectance detected by the sensors includes red, green and blue light. A decrease in the ratio of the red to green reflectance, together with a decrease in the ratio of the green to blue reflectance, are used to determine that the device has transitioned from the ileum to the cecum. The drug, or the pharmaceutical formulation containing the drug, is then released from the device based on the instructions, providing topical delivery of the drug, or the pharmaceutical formulation containing the drug, to the colon containing one or more disease sites. The subject subsequently undergoes an endoscopy to determine the effect of the treatment.

Example 15-2e—Treatment of Gastroduodenal Crohn's Disease by Releasing Drug in the Stomach A subject suffering from nausea, weight loss and loss of appetite sees a gastroenterologist. The subject undergoes an endoscopy, which reveals gastroduodenal Crohn's disease affecting the stomach and duodenum. Subsequently the subject is orally administered an ingestible device as disclosed herein containing a therapeutically effective amount of drug. The device contains a self-localization mechanism that autonomously determines the device location within the subject's GI tract. The device localization mechanism includes one or more sensors associated with the device that detects light reflectance that is external to the device and present in the GI tract. The device is pre-programmed with instructions to release the drug to the stomach. The instructions are provided from at least one processor and/or at least one controller associated with the at least one sensor. After ingestion of the device, data collected from at least one of the light sensors, in conjunction with elapsed time (about 1 minute) after the oral administration, indicates that the device has entered the stomach. The drug, or the pharmaceutical formulation containing the drug, is then released from the device based on the instructions, providing topical delivery of the drug, or the pharmaceutical formulation containing the drug, to the stomach and distal to the duodenum containing one or more disease sites. The subject subsequently undergoes an endoscopy to determine the effect of the treatment.

Example 16—Intracecal Administration of Therapeutic Antibodies in a Colitis Animal Model that has Previously Received an Adoptive T-cell Transfer A set of experiments was performed to compare the efficacy of targeted intracecal (IC) anti-mouse-TNFα antibody (a surrogate for adalimumab) and anti-mouse-interleukin (IL) 12p40 antibody (a surrogate of anti-human-IL12p40 antibody) with systemic intraperitoneal (IP) injection in an adoptive T cell transfer induced chronic colitis mouse model.

Materials

Test System

- Species/strain: Mice, C57Bl/6 (donors) and RAG2$^{-/-}$ (recipients; C57Bl/6 background)
- Physiological state: Normal/immunodeficient
- Age/weight range at start of study: 6-8 weeks (20-24 g)
- Animal supplier: Taconic
- Randomization: Mice were randomized into seven groups of 15 mice each, and two groups of eight mice each.
- Justification: T cells isolated from male C57Bl/6 wild type donors were transferred into male RAG2$^{-/-}$ recipient mice to induce colitis.
- Replacement: Animals were not replaced during the course of the study.

Animal Housing and Environment

- Housing: Mice were housed in groups of 8-15 animals per cage prior to cannulation surgery. After cannulation surgery, cannulated animals were single-housed for seven days post-surgery. After this point, animals were again group-housed as described above. Non-cannulated animals (Group 9) were housed at 8 mice per cage. ALPHA-Dri® bedding was used. Prior to colitis induction (i.e., during the cannulation surgeries), bedding was changed a minimum of once per week. After colitis induction, bedding was changed every two weeks, with % A of dirty cage material captured and transferred to the new cage. Additionally, bedding from Group 9 animals was used to supplement the bedding for all other groups at the time of cage change.
- Acclimation: Animals were acclimatized for a minimum of 7 days prior to study commencement. During this period, the animals were observed daily in order to reject animals that presented in poor condition.
- Environmental conditions: The study was performed in animal rooms provided with filtered air at a temperature of 70+/−5° F. and 50%+/−20% relative humidity. Animal rooms were set to maintain a minimum of 12 to 15 air changes per hour. The room was on an automatic timer for a light/dark cycle of 12 hours on and 12 hours off, with no twilight.
- Food/water and contaminants: Animals were maintained with Labdiet 5053 sterile rodent chow. Sterile water was provided ad libitum.

Test Article: IgG Control

- Name of the Test Article: InVivoMAb polyclonal rat IgG
- Source: BioXCell, catalog #BP0290
- Storage conditions: 4° C.
- Vehicle: Sterile PBS
- Dose: 0.625 mg/mouse; 0.110 mL/mouse IP and IC
- Formulation:
  - Formulation Stability: Prepare fresh daily
  - For Group 3: On each day of dosing, dilute stock pAb to achieve 2.145 mL of a 5.68 mg/mL solution.
  - For Group 4: On each day of dosing, dilute stock pAb to achieve 2.145 mL of a 5.68 mg/mL solution Test Article: Anti-IL12 p40

- Name of the Test Article: InVivoMAb anti-mouse IL-12 p40
- Source: BioXCell, catalog #BE0051
- Storage conditions: 4° C.
- Vehicle: Sterile PBS
- Dose: 0.625 mg/mouse (IP and IC); 0.110 mL/mouse IP and IC
- Formulation:
  - Formulation Stability: Prepare fresh daily
  - For Group 5: On each dosing day, the stock mAb was diluted to achieve 1.716 mL of a 5.68 mg/mL solution.
  - For Group 6: On each dosing day, the stock mAb was diluted to achieve 1.716 mL of a 5.68 mg/mL solution.

Test Article: anti-TNFα

- Name of the Test Article: In VivoPlus anti-mouse TNFα, clone XT3.11
- Source: BioXCell, catalog #BP0058
- Storage conditions: 4° C.
- Vehicle: Sterile PBS
- Dose: 0.625 mg/mouse (IP and IC); 0.110 mL/mouse IP and IC
- Formulation:
  - Formulation Stability: Prepare fresh daily
  - For Group 7: On each dosing day, the stock mAb was diluted to achieve 1.716 mL of a 5.68 mg/mL solution.

For Group 8: On each dosing day, the stock mAb was diluted to achieve 1.716 mL of a 5.68 mg/mL solution.

Methods

The details of the study design are summarized in Table 34. A detailed description of the methods used in this study is provided below.

TABLE 34

Study Design

| Group | No. Animals | Cecal Cannula | Cell Transfer (Day 0) | Treatment | Dose* | Route | Schedule (Days 0-42**) | Blood Collection (RO) | Endoscopy | Endpoints (Day 42) |
|---|---|---|---|---|---|---|---|---|---|---|
| 1 | 8 | YES | — | — | — | — | — | Day 13 | Days 14, 28, 42 | 3 Hours Post Dose: Colon weight/length, stool score Terminal collection (all groups) Cecal Contents, Colon Contents, Plasma, small intestinal tissue, colon tissue, mLN, and Peyer's Patches |
| 2 | 15 | | 0.5 × $10^6$ naïve $T_H$ cells | Vehicle (PBS; IP) Vehicle (PBS; IC) | — | IP, IC | IP: 3x/week IC: QD | | | |
| 3 | 15 | | | IgG Control (IP) Vehicle (PBS; IC) | 625 μg | | IP: 3x/week IC: QD | | | |
| 4 | 15 | | | Vehicle (PBS; IP) IgG Control (IC) | 625 μg | | IP: 3x/week IC: QD | | | |
| 5 | 15 | | | Anti-IL 12p40 (IP) Vehicle (PBS; IC) | 625 μg | | IP: 3x/week IC: QD | | | |
| 6 | 15 | | | Vehicle (PBS; IP) Anti-IL 12p40 (IC) | 625 μg | | IP: 3x/week IC: QD | | | |
| 7 | 15 | | | Anti-TNFα (IP) Vehicle (PBS; IC) | 625 μg | | IP: 3x/week IC: QD | | | |
| 8 | 15 | | | Vehicle (PBS; IP) Anti-TNFα (IC) | 625 μg | | IP: 3x/week IC: QD | | | |
| 9 | 8 | NO | — | — | — | — | — | — | — | — |

*Per mouse;

**Test Article was administered in 0.110 mL/animal IC or IP from Day 0-42;

IC = intracecal injection;

IP = intraperitoneal injection;

QD = once a day;

RO = Retro-Oribital eye bleed

A cohort of animals underwent surgical implantation of a cecal cannula at least 10 days to 2 weeks prior to the experiment for the ease of bolus topical delivery to the cecum. A sufficient number of animals underwent implantation to allow for enough cannulated animals to be enrolled in the main study. An additional n=8 animals (Group 9) served as no surgery/no disease controls.

Colitis was induced by intraperitoneal (IP) injection of 0.5×$10^6$ CD44/CD62L+ T-cells from C57BL/6 donor mice to male RAG2$^{-/-}$ recipient mice in Groups 2 to 8 on Day 0. The donor cells were processed by first harvesting spleens from 80 C57Bl/6 mice and then isolating the CD44$^-$/CD62L$^+$ T cells using Miltenyi Magnetic-Activated Cell Sorting (MACS) columns.

To minimize variation due to methods of administration, animals were treated both by IP injection every third day (3×/wk) and IC injection once daily for 42 consecutive days (qdx42d) of either the test article or the control (vehicle solution or IgG control). Groups were as outlined in Table 38, also summarized as follows: Group 1=untreated (no disease controls); Group 2=vehicle [phosphate buffer saline (PBS)] (IP)+vehicle (IC); Group 3=IgG (IP)+vehicle (IC); Group 4=vehicle (IP)+IgG (IC); Group 5=anti-IL12p40 (IP)+vehicle (IC); Group 6=vehicle (IC)+anti-IL12p40 (IC); Group 7=anti-TNFα (IP)+vehicle (IC); Group 8=vehicle (IP)+anti-TNFα (IC); Group 9=no surgery, untreated (no-cannulation and no-disease controls (sentinel animals for bedding)). Treatment with test article was initiated on Day 0 and was continued until Day 42 as outlined in Table 34.

All recipient mice were weighed daily and assessed visually for the presence of diarrhea and/or bloody stool. The cages were changed every two weeks starting on Day 7, with care taken to capture ¼ of dirty cage material for transfer to the new cage. On Day 13, blood was collected via RO eye bleed, centrifuged, and plasma was aliquoted (50 μL and remaining) and frozen for downstream analysis. The pelleted cells were re-suspended in buffer to determine the presence of T cells by FACS analysis of CD45$^+$/CD4$^+$ events.

On Day 13, after dosing, peripheral blood from all surviving mice was analyzed by flow cytometry from the presence of CD45$^+$/CD4$^+$ T cells.

The mice underwent high definition video endoscopy on Days 14 (pre-dosing; baseline), 28, and 42 (before euthanasia) to assess the extent of colitis severity. Images were captured from each animal at the most severe region of disease identified during endoscopy. Stool consistency was scored during endoscopy using the parameters described herein on Days 14, 18 and 42.

Disease Activity Index (DAI) was calculated using a combination of body weight (BW) loss score, colitis score, stool consistency score. The DAI (combined value from 0 to 13) was calculated using colitis score, stool consistency score, and BW loss score to provide an overall evaluation of the disease intensity (see Table 35). The score from animals with unscheduled death was carried forward to limit any bias that may be introduced by mortality.

The animals from all groups were euthanized by $CO_2$ inhalation on Day 42 following endoscopy and three hours after dosing. Terminal blood samples were collected for bioanalysis of inflammatory cytokines, and tissues samples were collected and fixed for histopathological evaluation. Plasma obtained from these samples was split into two separate cryotubes, with 50 μL in one tube (Bioanalysis) and the remainder in a second tube (TBD). The cecum and colon contents were removed and the contents collected, weighed, and snap frozen in separate cryovials. The mesenteric lymph nodes were collected and flash-frozen in liquid nitrogen. The small intestine were excised and rinsed, and the most distal 2-cm of ileum was placed in formalin for 24 hours and then transferred to 70% ethanol for subsequent histological evaluation. The Peyer's patches were collected from the small intestine, and were flash-frozen in liquid nitrogen. The colon was rinsed, measured, weighed, and then trimmed to 6-cm in length and divided into 5 pieces as described in the above Examples. The most proximal 1-cm of colon was separately weighed, and flash-frozen for subsequent bioanalysis (PK) of test article levels. Of the remaining 5-cm of colon, the most distal and proximal 1.5-cm sections were each placed in formalin for 24 hours and then transferred to 70% ethanol for subsequent histological evaluation. The middle 2-cm portion was bisected longitudinally, and each piece was weighed, placed into two separate cryotubes, and snap frozen in liquid nitrogen; one of the samples was used for cytokine analysis and the other was used for myeloperoxidase (MPO) analysis. All plasma and frozen colon tissue samples were stored at −80° C. until used for endpoint analysis.

The colon weight (mg) to length (cm) ratio was calculated for individual mice.

A more detailed description of the protocols used in this study are described below.

Cecal Cannulation

Animals were placed under isoflurane anesthesia, and the cecum was exposed via a mid-line incision in the abdomen. A small point incision was made in the distal cecum through which 1-2 cm of the cannula was inserted. The incision was closed with a purse-string suture using 5-0 silk. An incision was made in the left abdominal wall through which the distal end of the cannula was inserted and pushed subcutaneously to the dorsal aspect of the back. The site was washed copiously with warmed saline prior to closing the abdominal wall. A small incision was made in the skin of the back between the shoulder blades, exposing the tip of the cannula. The cannula was secured in place using suture, wound clips, and tissue glue. All of the animals received 1 mL of warm sterile saline (subcutaneous injection) and were monitored closely until fully recovered before returning to the cage. All animals received buprenorphine at 0.6 mg/kg BID for the first 3 days, and Baytril at 10 mg/kg QD for the first 5 days following surgery.

Disease Induction

Colitis was induced on Day 0 in male $RAG2^{-/-}$ mice by IP injection (200 μL) of $0.5\times10^6$ $CD44^-/CD62L^+$ T cells (in PBS) isolated and purified from C57Bl/6 recipients.

Donor Cell Harvest

Whole spleens were excised from C57Bl/6 mice and immediately placed in ice-cold PBS. The spleens were dissociated to yield a single cell suspension and the red blood cells were lysed. The spleens were then processed for $CD4^+$ enrichment prior to $CD44^-CD62L^+$ sorting by MACS.

Dosing

See Table 34.

Body Weight and Survival

The animals were observed daily (morbidity, survival, presence of diarrhea and/or bloody stool) in order to assess possible differences among treatment groups and/or possible toxicity resulting from the treatments. Animals were weighed daily and their percent body weight relative to Day 0 was calculated.

Animals Found Dead or Moribund

The animals were monitored on a daily basis and those exhibiting weight loss greater than 30% were euthanized, and did not have samples collected.

Endoscopy

Each mouse underwent video endoscopy on Days 14 (pre-dosing; baseline), 28, and 42 (before euthanasia) using a small animal endoscope (Karl Storz Endoskope, Germany), under isoflurane anesthesia. During each endoscopic procedure, still images as well as video were recorded to evaluate the extent of colitis and the response to treatment. Additionally, an image from each animal at the most severe region of disease identified during endoscopy was captured. Colitis severity was scored using a 0-4 scale (0=normal; 1=loss of vascularity; 2=loss of vascularity and friability; 3=friability and erosions; 4=ulcerations and bleeding). Additionally, stool consistency was scored during endoscopy using the scoring system described herein.

Sample Collection

Terminal blood (plasma and cell pellet), Peyer's patches (Groups 1-8 only), small intestine and colon mLN (Groups 1-8 only), cecum contents, colon contents, small intestine, and colon were collected at euthanasia, as follows.

Blood: Terminal blood was collected by cardiac puncture and plasma generated from these samples. The resulting plasma was split into two separate cryotubes with 50 μL in one tube (Bioanalysis), and the remainder in a second tube (TBD).

Mesenteric Lymph Nodes: The mesenteric lymph nodes were collected, weighed, snap-frozen in liquid nitrogen, and stored at −80° C.

Small Intestine: The small intestine was excised and rinsed, and the most distal 2-cm of ileum will be placed in formalin for 24 hours and then transferred to 70% ethanol for subsequent histological evaluation.

Peyer's Patches: The Peyer's patches were collected from the small intestine. The collected Peyer's patches were weighed, snap-frozen in liquid nitrogen, and stored at −80° C.

Cecum/Colon Contents: The cecum and colon were removed from each animal and contents collected, weighed, and snap-frozen in separate cryovials.

Colon: Each colon was rinsed, measured, weighed, and then trimmed to 6-cm in length and divided into 5 pieces as outlined herein. The most proximal 1-cm of colon was separately weighed, and snap frozen for subsequent bioanalysis (PK) of test article levels. Of the remaining 5-cm of colon, the most distal and proximal 1.5-cm sections were placed in formalin for 24 hours and then transferred to 70% ethanol for subsequent histological evaluation. The middle 2-cm portion was bisected longitudinally, and each piece weighed, placed into two separate cryotubes, and snap-frozen in liquid nitrogen; one of these samples was used for cytokine analysis and the other sample was used for myeloperoxidase analysis.

Cytokine Levels in Colon Tissue

Cytokine levels (IFNγ, IL-2, IL-4, IL-5, IL-1β, IL-6, IL-12 p40, and TNFα) were assessed in colon tissue homogenate (all groups) by multiplex analysis. Myeloperoxidase levels were assessed by ELISA in colon tissue homogenate (all groups).

Histopatholoy

Ileum, proximal colon, and distal colon samples from seventy-one mice were fixed in 10% neutral buffered formalin. Samples were trimmed into three cross sections per portion and processed routinely into two blocks per animal (ileum in one block, proximal and distal colon in a second block). One slide from each block was sectioned at approximately 5 microns and stained with hematoxylin and eosin (H&E). Glass slides were evaluated with light microscopy by a board-certified veterinary pathologist. Ileum, proximal colon, and distal colon samples were scored individually. Lesions in H&E-stained samples were given a severity score 0-51 (0=not present/normal, 1=minimal, <10% of tissue affected; 2=mild, 10-25% of tissue affected; 3=moderate, 26-50% of tissue affected; 4=marked, 51-79% of tissue affected; 5=severe, >75% of the tissue affected). Inflammation, crypt damage, erosion, and hyperplasia scores were added together to determine a sum colitis score for each sample.

Lymphocyte counts were performed in a subset of samples: proximal and distal colon from Groups 2 (vehicle), 7 (anti-TNF alpha IP; vehicle IC), and 8 (anti-TNF alpha IC; vehicle IP). In each piece of tissue, a randomly identified site was divided into approximately four segments extending from the lumen to the muscularis mucosae; 100 μm2 fields were used in the proximal colon, and 50 μm2 fields were used in the distal colon due to the differences in mucosal thickness. Using H&E-stained slides, the number of cells with lymphocyte morphology (small round nucleus with condensed chromatin) were counted within the overlying surface epithelium, in each field from lumen to muscularis mucosae, and within a 100 μm2 field surrounding an adjacent submucosal blood vessel.

Statistical Analysis

As presented in the figures, non-parametric data was analyzed by Kruskal-Wallis test with Dunn's multiple comparisons test used to compare all groups to one another and individual pair-wise comparisons was analyzed by Mann Whitney U-Test. All statistical analyses were performed using GraphPad Prism7 (La Jolla, CA).

Results

Survival

The observed mortality rate was within the expected range given the design including surgical intervention, T-cell transfer in immunologically compromised animals followed by chronic development of colitis over a 6-week study period (Ostanin D V et al. Am J Physiol Gastrointest Liver Physiol. 2009, 296(2):G 135-G146).

The survival of animals was compared; no significant difference in survival rate was found in treatments of anti-IL12p40 and anti-TNFα with either route of administration compared to vehicle or IgG controls (p>0.08, log-rank; Kaplan-Meier). The timing of animal deaths did not correspond to changes in efficacy endpoints, such as body weight, that were evaluated longitudinally. As noted above, changes in DAI score which includes, BW loss, stool consistency and colitis severity were carried forward to limit any bias that may be introduced by mortality.

Colon Weight:Length Ratio

The mean colon weight:length ratio was significantly elevated in vehicle control animals (Group 2) compared to naïve (Group 1); no other significant differences in mean colon weight:length ratio were observed.

Disease Activity Index

The Disease Activity Index was determined in each mouse using a total score from the scoring system depicted in Table 35.

TABLE 35

Disease Activity Index scoring system

| Disease Activity Index | Description | Score |
|---|---|---|
| Colitis Severity | Normal | 0 |
| | Loss of vascularity | 1 |
| | Loss of vascularity and friability | 2 |
| | Friability and erosions | 3 |
| | Ulcerations and bleeding | 4 |
| Stool Consistency | Normal | 0 |
| | Loose stool, soft, staying in shape | 1 |
| | Abnormal form with excess moisture | 2 |
| | Watery or diarrhea | 3 |
| | Bloody diarrhea | 4 |
| Body Weight Loss (%) | X < 0% or gain weight | 0 |
| | 2% ≤ X < 5% | 1 |
| | 5% ≤ X < 10% | 2 |
| | 10% ≤ X < 15% | 3 |
| | 15% ≤ X < 20% | 4 |
| | 20% ≤ X < 25% | 5 |
| | 25% ≤ X < 30% | 6 |
| | X ≥ 35% | 7 |
| Total Score | | 15 |

The data in FIG. 103 show that mice intracecally administered anti-TNFα antibody (Group 8) had decreased disease activity index (DAI) as compared to mice intraperitoneally administered anti-TNFα antibody (Group 7) at Day 42 of the study. The data in FIG. 105 show that mice intracecally administered anti-IL12 p40 antibody (Group 6) had decreased disease activity index (DAI) as compared to mice intraperitoneally administered anti-IL12 p40 antibody (Group 5) at Day 28 and Day 42 of the study.

Inflammatory Cytokines in Colonic Tissue

The concentration of inflammatory cytokines was evaluated in the colonic tissue in vehicle or IgG control groups.

A significant reduction of inflammatory cytokines, including IL 17A, IL-4, TNFα, and IL-22, were found in groups treated with anti-TNFα (IC (Group 8) or IP (Group 7)) when compared with vehicle (IP/IC) control or its respective IgG controls (IC or IP) in colon tissue (FIG. 104). Mice treated with anti-TNFα antibody IC (Group 8) had decreased levels of TNFα, IL-17A, and IL-4 in colonic tissue as compared to the levels in colonic tissue of mice treated with anti-TNFα IP (Group 7) when assessed at Day 42 of the study.

A significant reduction of IL-22, IL-6, IL17A, TNFα, IL-1b, and IFNγ cytokine was found in groups treated with anti-IL12p40 (IP or IC) when compared with vehicle (IP/IC) control in colon tissue (FIG. 106). Mice intracecally administered anti-IL12 p40 antibody (Group 6) had decreased levels of IFNK, IL-6, IL-17A, TNFα, IL-22, and IL-1b in colonic tissue as compared to the levels in colonic tissue in vehicle-administered control mice (Group 2).

Body Weight Loss

Treatments with either systemic (IP) or topical (IC) administration of an anti-TNFα antibody or anti-IL12p40 antibody led to a significant decrease in body weight (BW) loss over time from Day 0 to Day 42.

The change in body weight over the course of the experiment from Day 0 through Day 42 is shown in FIGS. 107A and 107B. No apparent signs of disease were observed within the first week after induction of colitis. In control groups treated with PBS vehicle and/or IgG, BW loss did not begin until Days 14 through 16 and continued in the 3rd and 4th week following transfer during the acute phase. The weight loss was maintained until study termination on Day 42. Administration of anti-TNFα antibody or anti-IL12p40 antibody through either IP or IC had a significant reduction in AUC of the BW loss (%) from Day 0 to Day 42 along with the weight increase maintained from Day 21 to Day 42 (FIGS. 107A and 107B). Overall, intracecal administration of anti-IL12p40 antibody had the earliest recovery of weight loss and most significant reduction in overall BW loss from Day 0-Day 42 in comparison to the vehicle control group amount of all treatment groups (FIG. 107B).

Histopathology Colitis Score

Lesions of ileitis and colitis, including inflammation, crypt damage, occasional erosions, and epithelial hyperplasia, were induced with the T-cell transfer in this model. Lesions were the least severe in ileum sections and the most severe in the proximal colon. Both IP and IC administration of anti-IL12p40 and anti-TNFα resulted in a reduction in sum ileitis/colitis scores compared to PBS vehicle control. Targeted IC anti-TNFα treatment showed a significant improvement in the mean histopathologic score when compared with the vehicle controls given by either route (IP or IC) in proximal and distal colon tissues (FIG. 108).

Lymphocyte Counts

Targeted IC anti-TNFα treatment showed the greatest magnitude of lymphocyte reductions in all counted fields, from inner lumen to submucosa of proximal colon when compared to the vehicle control group (Group 8 vs. Group 2, P<0.05*, FIG. 109A). A similar trend in lymphocyte count reductions was found in the distal colon, although to a lesser degree. Results are shown in FIG. 109. Mean counts and scores for all fields were generally the highest in vehicle-treated animals (Group 2, data not shown) and lower in those given anti-TNFα by IP (Group 7, data not shown) or IC (Group 8, FIG. 109B).

Thus, significantly reduced body weight loss (%), decreased Disease Activity Index, improved histological score and reduced tissue inflammatory cytokines were found in animals receiving targeted (IC) anti-TNFα antibody when compared with vehicle controls. Targeted IC delivery was significantly more efficacious when compared to systemic (IP) anti-TNFα antibody in end points of total histologic score and lymphocyte count from inner lumen to submucosa of proximal colon.

Example 17—Pharmacokinetic and Pharmacodynamic Assessment of Tofacitinib Citrate Dosed Orally Versus Intracecally in a Dextran Sulfate Sodium (DSS)-Induced Colitis Mouse Model Study Design The overall study design is summarized in Table 36. Briefly, at least 10 days prior to the start of the study (Day −10), a cohort of male C57BL/6 mice underwent surgical implantation of a cecal cannula. Colitis was induced in 110 mice (Groups 2-7) by exposure to 3% DSS-treated drinking water from Day 0 to Day 5. Five animals (Group 1) served as no-disease controls; the other animals received a single dose of vehicle (Group 2) or tofacitinib citrate suspension containing about 0.5% excipients via oral gavage (PO; Groups 3 and 4) or intracecal injection via the surgically implanted indwelling catheter (IC; Groups 5, 6 and 7) once on Day 12 (peak disease status). All animals were weighed daily and assessed visually for the presence of diarrhea and/or blood in stool. A subset of animals per group was sacrificed for terminal PK collections at various time points post-dose. Terminal samples (plasma, cecal contents, colon contents, cecal tissue and colon tissue) were collected at terminal sacrifice. All $K_2$EDTA plasma and tissue homogenate (proximal colon, cecum and associated lumen contents) were stored at −80° C. until further analysis.

TABLE 36

Description of Treatment Groups

| Group Number | Number of Animals | Cecal Cannula | Colitis Induction | Treatment | Dose (mg/kg) (Day 12)[1] | Route | PK Schedule |
|---|---|---|---|---|---|---|---|
| 1 | 5 | no | (a) | (a) | (a) | (a) | 24 h post-dose (n = 5) 24 h |
| 2 | 10 | | 3% DSS in drinking water Days 0-5 | Control vehicle | 0 | PO | 1 and 24 h post-dose (n = 5 per timepoint) |
| 3 | 20 | | | Tofacitinib citrate suspension | 15 | | 1, 3, 12, 24 h post-dose (n = 5 per timepoint) |
| 4 | 20 | | | | 45 | | |
| 5 | 20 | yes | | | 1 | IC | |
| 6 | 20 | | | | 3 | | |
| 7 | 20 | | | | 10 | | |

DSS = dextran sulfate sodium;
IC = Intracecal injection;
PK = Pharmacokinetics;
PO = oral gavage
(a) Five animals served as no-disease controls.
[1]All dose levels are expressed based on tofacitinib citrate salt form.

Sample Bioanalysis

Plasma samples and tissue homogenate (proximal colon, cecum and associated lumen contents) were assessed for tofacitinib. Briefly, samples were analyzed by LC-MS/MS against matrix-matched standard curves. Three additional samples were above their respective quantitation limits, and extrapolated data was reported.

To evaluate pharmacodynamic (PD) effects of tofacitinib in the DSS-induced colitis mouse model, several cytokines involved in the JAK/STAT signaling pathway, i.e., IL-6, GM-CSF, IL-15, IL-2, IL-12, IL-13, TNF-α, and INF-γ, were measured in both plasma and colon tissue by ELISA.

The study design was complex and involved surgical procedure in a disease model The PK/PD parameters were derived from limited timepoints and should be considered best estimates only.

All PK/PD concentrations are expressed as active drug moiety (anhydrous tofacitinib free base).

Pharmacokinetic Statistical Analysis

PK modeling was performed using mean plasma or tissue concentrations of tofacitinib versus time curves. The following PK parameters were calculated with a one-compartmental model using Excel software: time to maximum concentration: $T_{max}$; half-life: $t_{1/2}$, maximum concentration: $C_{max}$; clearance (Cl), area under the concentration-time curve from the start of dosing to the last protocol-specified time point: $AUC_{(0\text{-}24\ h)}$. The absolute oral bioavailability was estimated to be 74% based on: Xeljanz® (Tofacitinib tablets for oral administration) Prescribing Information Revised 11/2012.

Results

Drug Tissue Concentrations

Animals dosed PO with tofacitinib citrate (Groups 3-4) demonstrated the highest mean plasma tofacitinib concentrations at all timepoints, while limited blood exposure was observed in animals treated IC (Groups 5-6) (See FIG. 110). Plasma $T_{max}$ occurred between 1.2 and 1.6 h post-dose in all groups, regardless of dosing route. Colon tissue $T_{max}$ occurred between 1.43 and 1.86 h post-dose in all IC groups, and at 2.25 and 2.33 h post-dose in PO groups (Table 37). At similar dose levels, IC delivery of tofacitinib citrate (IC, 10 mg/kg) resulted in an 18-fold higher tofacitinib AUC colon tissue/plasma ratio when compared to PO delivery (PO, 15 mg/kg) (AUC ratio 193.76 vs. 10.6, respectively; Table 37). Plasma and tissue tofacitinib exposure ($AUC_{0\text{-}24\ h}$) are also shown in FIG. 111.

112B). Recovery from IL-6 inhibition was observed in the low dose PO group (15 mg/kg) by 12 h post-dose.

The concentration of GM-CSF was not significantly different between the DSS-treatment groups and the naïve group, nor was there a significant difference in GM-CSF levels between IC and PO treatment groups in either plasma or colon tissue, despite high exposure of tofacitinib found in colon tissue of IC groups dosed at 3 and 10 mg/kg (data not shown).

Exemplary Embodiments

Exemplary embodiments include:

1) A method of treating a disease of the gastrointestinal tract in a subject, comprising:

administering to the subject a pharmaceutical formulation that comprises a JAK inhibitor, wherein the pharmaceutical formulation is released at a location in the gastrointestinal tract of the subject that is proximate to one or more sites of disease.

TABLE 37

Pharmacokinetic and pharmacodynamic parameters for tofacitinib over 24 hours after a single dose administration of tofacitinib citrate suspension on Day 12 in DSS-induced colitis mouse model

| | | | Pharmacokinetic parameters | | | | | | Pharmacodynamics | | |
|---|---|---|---|---|---|---|---|---|---|---|---|
| Group | Route/ | Biological | $C_{max}$ | AUC | Tissue/ | $T_{max}$ | $T_{1/2}$ | Clearance | $IC_{50}$ coverage (h)[a] | | |
| Number | Dose | Matrix | (ng/mL) | (ng · h/mL) | Plasma ratio | (h) | (h) | (mL/h) | JAK1/3[b] | JAK1/2[c] | JAK2/2[d] |
| 3 | PO/15 | Plasma | 65.5 | 372.09 | 10.6 | 1.61 | 2.53 | 656.28 | 1 | 0 | 0 |
| | mg/kg | Colon tissue | 552.7 | 3954.9 | | 2.25 | 3.23 | 61.82 | 12 | 3 | 0 |
| 4 | PO/45 | Plasma | 467.1 | 1976.24 | 7.09 | 1.36 | 1.64 | 370.7 | 1 | 3 | 1 |
| | mg/kg | Colon tissue | 1774.9 | 14006.55 | | 2.33 | 3.4 | 52.3 | 12 | 12 | 3 |
| 5 | IC/1 | Plasma | 1.3 | 6.13 | 253.05 | 1.56 | 1.73 | 2653.91 | 0 | 0 | 0 |
| | mg/kg | Colon tissue | 271.7 | 1551.21 | | 1.61 | 2.56 | 10.5 | 3 | 3 | 0 |
| 6 | IC/3 | Plasma | 33.2 | 115.45 | 128.76 | 1.21 | 1.19 | 423.05 | 1 | 0 | 0 |
| | mg/kg | Colon tissue | 2960.2 | 14865.55 | | 1.43 | 2.23 | 3.29 | 24 | 3 | 3 |
| 7 | IC/10 | Plasma | 57.8 | 223.27 | 193.76 | 1.27 | 1.47 | 729.17 | 3 | 0 | 0 |
| | mg/kg | Colon tissue | 7644.9 | 43261.18 | | 1.86 | 2.16 | 3.76 | 24 | 12 | 3 |

PO = oral gavage;
IC = Intra-cecal injection;
$IC_{50}$ = Half-maximum inhibitory concentration;
Groups 1 and 2: not applicable
[a]Concentrations above the $IC_{50}$ over the 24-hour period;
[b]$IC_{50}$ of JAK1/3 heterodimer = 56 nM (28.25 ng/mL)
[c]$IC_{50}$ of JAK1/2 heterodimer = 406 nM[e] (204.83 ng/mL);
[d]$IC_{50}$ ofJAK2/2 homodimer inhibition = 1377 nM[e] (694.7 ng/mL)
[e]Meyer et al. (2010) J. Inflamm. 7-41.

Cytokines

Inflammatory cytokine IL-6 has been shown to play a critical role in the response of uncontrolled intestinal inflammation through JAK1/JAK2 and JAK1/TYK2 signaling pathways (Meyer et al. (2010) J.Inflamm. 7-41).

FIG. 112 shows results obtained for IL-6 in colon tissue on Day 12. IL-6 expression was induced by DSS treatment in both plasma (data not shown) and colon tissue (FIG. 109A) of PO and IC treatment groups; significant induction ($p<0.05$) was observed on Day 12 when compared with naïve animals (Group 1).

In plasma, inhibition of IL-6 expression was observed in groups treated with tofacitinib citrate via PO or IC administration at 1 h and 3 h post-treatment; recovery of IL-6 expression (50 to 100%) was observed at 12 h and 24 h post-treatment (data not shown).

In colon tissue, inhibition of IL-6 expression was sustained through 24 h post-dose in colon tissue in all IC treated groups and in the high dose PO group (45 mg/kg) (FIG.

2) The method of embodiment 1, wherein the pharmaceutical formulation is administered in an ingestible device.

3) The method of embodiment 1, wherein the pharmaceutical formulation is released from an ingestible device.

4) The method of embodiment 2 or 3, wherein the ingestible device comprises a housing, a reservoir containing the pharmaceutical formulation, and a release mechanism for releasing the pharmaceutical formulation from the device, wherein the reservoir is releasably or permanently attached to the exterior of the housing or internal to the housing.

5) The method of embodiment 2 or 3, wherein the ingestible device comprises a housing, a reservoir containing the pharmaceutical formulation, and a release mechanism for releasing the pharmaceutical formulation from the device, wherein the reservoir is internal to the device.

6) A method of treating a disease of the gastrointestinal tract in a subject, comprising:

administering to the subject an ingestible device comprising a housing, a reservoir containing a pharmaceutical formulation, and a release mechanism for releasing the pharmaceutical formulation from the device; wherein:

the reservoir is releasably or permanently attached to the exterior of the housing or internal to the housing; and the pharmaceutical formulation comprises a JAK inhibitor, and the ingestible device releases the pharmaceutical formulation at a location in the gastrointestinal tract of the subject that is proximate to one or more sites of disease.

7) A method of treating a disease of the gastrointestinal tract in a subject, comprising:

administering to the subject an ingestible device comprising a housing, a reservoir containing a pharmaceutical formulation, and a release mechanism for releasing the pharmaceutical formulation from the device;

wherein the reservoir is internal to the device; the pharmaceutical formulation comprises a JAK inhibitor, and the ingestible device releases the pharmaceutical formulation at a location in the gastrointestinal tract of the subject that is proximate to one or more sites of disease.

8) The method of any one of embodiments 4 to 7, wherein the housing is non-biodegradable in the GI tract.

9) The method of any one of embodiments 2 to 8, wherein the release of the formulation is triggered autonomously.

10) The method of any one of embodiments 2 to 9, wherein the device is programmed to release the formulation with one or more release profiles that may be the same or different at one or more locations in the GI tract.

11) The method of any one of embodiments 2 to 10, wherein the device is programmed to release the formulation at a location proximate to one or more sites of disease.

12) The method of embodiment 11, wherein the location of one or more sites of disease is predetermined.

13) The method of any one of embodiments 4 to 12, wherein the reservoir is made of a material that allows the formulation to leave the reservoir.

14) The method of embodiment 13, wherein the material is a biodegradable material.

15) The method of any one of embodiments 2 to 14, wherein the release of the formulation is triggered by a pre-programmed algorithm.

16) The method of any one of embodiments 2 to 15, wherein the release of the formulation is triggered by data from a sensor or detector to identify the location of the device.

17) The method of embodiment 16, wherein the data is not based solely on a physiological parameter.

18) The method of any one of embodiments 2 to 17, wherein the device comprises a detector configured to detect light reflectance from an environment external to the housing.

19) The method of embodiment 18, wherein the release is triggered autonomously or based on the detected reflectance.

20) The method of any one of embodiments 2 to 19, wherein the device releases the formulation at substantially the same time as one or more sites of disease are detected.

21) The method of any one of embodiments 4 to 20, wherein the release mechanism is an actuation system.

22) The method of embodiment 21, wherein the actuation system is a chemical actuation system.

23) The method of embodiment 21, wherein the actuation system is a mechanical actuation system.

24) The method of embodiment 21, wherein the actuation system is an electrical actuation system.

25) The method of embodiment 21, wherein the actuation system comprises a pump and releasing the formulation comprises pumping the formulation out of the reservoir.

26) The method of embodiment 21, wherein the actuation system comprises a gas generating cell.

27) The method of any one of embodiments 2 to 26, wherein the device comprises an anchoring mechanism.

28) The method of any one of embodiments 1 to 27, wherein the formulation comprises a therapeutically effective amount of the JAK inhibitor.

29) The method of any one of the preceding embodiments, wherein the formulation comprises a human equivalent dose (HED) of the JAK inhibitor.

30) A method of treating a disease of the gastrointestinal tract in a subject, comprising:

releasing a JAK inhibitor at a location in the gastrointestinal tract of the subject that is proximate to one or more sites of disease, wherein the method comprises administering to the subject a pharmaceutical composition comprising a JAK inhibitor.

31) The method of embodiment 30, wherein the pharmaceutical composition is an ingestible device and the method comprises administering orally to the subject the pharmaceutical composition.

32) The method of embodiment 30 or 31, wherein the method does not comprise releasing more than 10% of the JAK inhibitor at a location that is not proximate to a site of disease.

33) The method of embodiment 30 or 31, wherein the method provides a concentration of the JAK inhibitor at a location that is a site of disease or proximate to a site of disease that is 2-100 times greater than at a location that is not proximate to a site of disease.

34) The method of any one of the preceding embodiments, wherein the method provides a concentration of the JAK inhibitor in the plasma of the subject that is less than 3 μg/mL.

35) The method of embodiment 34, wherein the method provides a concentration of the JAK inhibitor in the plasma of the subject that is less than 0.3 μg/mL.

36) The method of embodiment 35, wherein the method provides a concentration of the JAK inhibitor in the plasma of the subject that is less than 0.01 μg/mL.

37) The method of any one of embodiments 30 to 33, wherein the method provides a $C_{24}$ value of the JAK inhibitor in the plasma of the subject that is less than 3 μg/mL.

38) The method of embodiment 8, wherein the method provides a $C_{24}$ value of the JAK inhibitor in the plasma of the subject that is less than 0.3 μg/mL.

39) The method of any one of embodiments 30 to 38, wherein the JAK inhibitor is present in a therapeutically effective amount.

40) The method of any one of embodiments 30 to 39, wherein the JAK inhibitor decreases the expression of JAK1.

41) The method of any one of embodiments 30 to 39, wherein the JAK inhibitor decreases the expression of JAK2.

42) The method of any one of embodiments 30 to 39, wherein the JAK inhibitor decreases the expression of JAK3.

43) The method of any one of embodiments 30 to 39, wherein the JAK inhibitor decreases the expression of TYK-2.

44) The method of any one of embodiments 30 to 39, wherein the JAK inhibitor decreases the kinase activity of TYK-2.

45) The method of any one of embodiments 31 to 44, wherein the JAK inhibitor is present in a pharmaceutical formulation within the device.

46) The method of embodiment 45, wherein the formulation is a solution of the JAK inhibitor in a liquid medium.

47) The method of embodiment 46, wherein the formulation is a suspension of the JAK inhibitor in a liquid medium.

48) The method of any one of embodiments 30 to 47, wherein the disease of the GI tract is an inflammatory bowel disease.

49) The method of any one of embodiments 30 to 47, wherein the disease of the GI tract is ulcerative colitis.

50) The method of any one of embodiments 30 to 47, wherein the disease of the GI tract is Crohn's disease.

51) The method of any one of embodiments 30 to 50, wherein the JAK inhibitor is released at a location in the large intestine of the subject.

52) The method of embodiment 51, wherein the location is in the proximal portion of the large intestine.

53) The method of embodiment 51, wherein the location is in the distal portion of the large intestine.

54) The method of any one of embodiments 30 to 50, wherein the JAK inhibitor is released at a location in the ascending colon of the subject.

55) The method of embodiment 54, wherein the location is in the proximal portion of the ascending colon.

56) The method of embodiment 54, wherein the location is in the distal portion of the ascending colon.

57) The method of any one of embodiments 30 to 50, wherein the JAK inhibitor is released at a location in the cecum of the subject.

58) The method of embodiment 57, wherein the location is in the proximal portion of the cecum.

59) The method of embodiment 57, wherein the location is in the distal portion of the cecum 60) The method of any one of embodiments 30 to 50, wherein the JAK inhibitor is released at a location in the sigmoid colon of the subject.

61) The method of embodiment 60, wherein the location is in the proximal portion of the sigmoid colon.

62) The method of embodiment 60, wherein the location is in the distal portion of the sigmoid colon.

63) The method of any one of embodiments 30 to 50, wherein the JAK inhibitor is released at a location in the transverse colon of the subject.

64) The method of embodiment 63, wherein the location is in the proximal portion of the transverse colon.

65) The method of embodiment 63, wherein the location is in the distal portion of the transverse colon.

66) The method of any one of embodiments 30 to 50, wherein the JAK inhibitor is released at a location in the descending colon of the subject.

67) The method of embodiment 66, wherein the location is in the proximal portion of the descending colon.

68) The method of embodiment 66, wherein the location is in the distal portion of the descending colon.

69) The method of any one of embodiments 30 to 50, wherein the JAK inhibitor is released at a location in the small intestine of the subject.

70) The method of embodiment 69, wherein the location is in the proximal portion of the small intestine.

71) The method of embodiment 69, wherein the location is in the distal portion of the small intestine.

72) The method of any one of embodiments 30 to 50, wherein the JAK inhibitor is released at a location in the duodenum of the subject.

73) The method of embodiment 72, wherein the location is in the proximal portion of the duodenum.

74) The method of embodiment 72, wherein the location is in the distal portion of the duodenum.

75) The method of any one of embodiments 30 to 50, wherein the JAK inhibitor is released at a location in the jejunum of the subject.

76) The method of embodiment 75, wherein the location is in the proximal portion of the jejunum.

77) The method of embodiment 75, wherein the location is in the distal portion of the jejunum.

78) The method of any one of embodiments 30 to 50, wherein the JAK inhibitor is released at a location in the ileum of the subject.

79) The method of embodiment 78, wherein the location is in the proximal portion of the ileum.

80) The method of embodiment 78, wherein the location is in the distal portion of the ileum.

81) The method of any one of the preceding embodiments, wherein the location at which the JAK inhibitor is released is 10 cm or less from one or more sites of disease.

82) The method of any one of the preceding embodiments, wherein the location at which the JAK inhibitor is released is 5 cm or less from one or more sites of disease.

83) The method of any one of the preceding embodiments, wherein the location at which the JAK inhibitor is released is 2 cm or less from one or more sites of disease.

84) The method of any one of the preceding embodiments, wherein the JAK inhibitor is released by mucosal contact.

85) The method of any one of the preceding embodiments, wherein the JAK inhibitor is delivered to the location by a process that does not comprise systemic transport of the JAK inhibitor.

86) The method of any one of the preceding embodiments, further comprising identifying the one or more sites of disease by a method comprising imaging of the gastrointestinal tract.

87) The method of any one of the preceding embodiments, wherein the method comprises identifying the disease site prior to administering the pharmaceutical composition.

88) The method of embodiment 87, wherein the method comprises releasing the JAK inhibitor substantially at the same time as identifying the disease site.

89) The method of any one of the preceding embodiments, comprising (a) identifying a subject having a disease of the gastrointestinal tract and (b) evaluating the subject for suitability to treatment.

90) The method of any one of embodiments 30 or 32 to 44 or 46 to 89, wherein releasing the JAK inhibitor is triggered by one or more of: a pH in the jejunum from 6.1 to 7.2, a pH in the mid small bowel from 7.0 to 7.8, a pH in the ileum from 7.0 to 8.0, a pH in the right colon from 5.7 to 7.0, a pH in the mid colon from 5.7 to 7.4, a pH in the left colon from 6.3 to 7.7, such as 7.0.

91) The method of any one of embodiments 30 to 89, wherein releasing the JAK inhibitor is not dependent on the pH at or in the vicinity of the location.

92) The method of any one of embodiments 30 or 32 to 44 or 46 to 89, wherein releasing the JAK inhibitor is triggered by degradation of a release component located in the device.

93) The method of any one of embodiments 30 to 89, wherein releasing the JAK inhibitor is not triggered by degradation of a release component located in the device.

94) The method of any one of embodiments 30 to 89, wherein releasing the JAK inhibitor is not dependent on enzymatic activity at or in the vicinity of the location.

95) The method of any one of embodiments 30 to 89, wherein releasing the JAK inhibitor is not dependent on bacterial activity at or in the vicinity of the location.

96) The method of any one of embodiments 30 to 89, wherein the composition comprises a plurality of electrodes comprising a coating, and releasing the JAK inhibitor is triggered by an electric signal by the electrodes resulting from the interaction of the coating with the one or more sites of disease.

97) The method of any one of embodiments 30 to 89, wherein releasing the JAK inhibitor is triggered by a remote electromagnetic signal.

98) The method of any one of embodiments 30 to 89, wherein releasing the JAK inhibitor is triggered by generation in the composition of a gas in an amount sufficient to expel the JAK inhibitor.

99) The method of any one of embodiments 30 to 89, wherein releasing the JAK inhibitor is triggered by an electromagnetic signal generated within the device according to a pre-determined drug release profile.

100) The method of any one of embodiments 31 to 89, wherein the ingestible device comprises an ingestible housing, wherein a reservoir storing the JAK inhibitor is attached to the housing.

101) The method of embodiment 100, further comprising:
 detecting when the ingestible housing is proximate to a respective disease site of the one of the one or more sites of disease,
 wherein releasing the JAK inhibitor comprises releasing the therapeutically effective amount of the JAK inhibitor from the reservoir proximate the respective disease site in response to the detection.

102) The method of embodiment 101, wherein detecting comprises detecting via one or more sensors coupled to the ingestible housing.

103) The method of embodiment 102, wherein the one or more sensors comprise a plurality of coated electrodes and wherein detecting comprises receiving an electric signal by one or more of the coated electrodes responsive to the one or more electrode contacting the respective disease site.

104) The method of embodiment 101, wherein releasing comprises opening one or more valves in fluid communication with the reservoir.

105) The method of embodiment 104, wherein the one or more valves is communicably coupled to a processor positioned in the housing, the processor communicably coupled to one or more sensors configured to detect the one or more sites of disease.

106) The method of embodiment 101, wherein releasing comprises pumping the therapeutically effective amount of the JAK inhibitor from the reservoir via pump positioned in the ingestible housing.

107) The method of embodiment 106, wherein the pump is communicably coupled to a processor positioned in the housing, the processor communicably coupled to one or more sensors configured to detect the one or more sites of disease.

108) The method of embodiment 100, wherein the therapeutically effective amount of the JAK inhibitor is stored in the reservoir at a reservoir pressure higher than a pressure in the gastrointestinal tract of the subject.

109) The method of embodiment 100, further comprising anchoring the ingestible housing at a location proximate to the respective disease site in response to the detection.

110) The method of embodiment 109, wherein anchoring the ingestible housing comprises one or more legs to extend from the ingestible housing.

111) The method of any one of the preceding embodiments, wherein the amount of the JAK inhibitor that is administered is from about 1 mg to about 500 mg.

112) The method of any one of the preceding embodiments, wherein the JAK inhibitor is selected from tofacitinib (Xeljanz®), filgotinib (GLPG0634, Galapagos NV); TD-1473 (Theravance Biopharma, Inc.); ruxolitinib; and generic equivalents thereof.

113) The method of any one of the preceding embodiments, wherein the JAK inhibitor is ruxolitinib.

114) The method of any one of embodiments 30 to 113, wherein the amount of the JAK inhibitor is less than an amount that is effective when JAK inhibitor is administered systemically.

115) The method of any one of the preceding embodiments, comprising administering (i) an amount of the JAK inhibitor that is an induction dose.

116) The method of embodiment 115, further comprising (ii) administering an amount of the JAK inhibitor that is a maintenance dose following the administration of the induction dose.

117) The method of embodiment 115 or 116, wherein the induction dose is administered once a day.

118) The method of embodiment 115 or 116, wherein the induction dose is administered once every three days.

119) The method of embodiment 115 or 116, wherein the induction dose is administered once a week.

120) The method of embodiment 116, wherein step (ii) is repeated one or more times.

121) The method of embodiment 116, wherein step (ii) is repeated once a day over a period of about 6-8 weeks.

122) The method of embodiment 116, wherein step (ii) is repeated once every three days over a period of about 6-8 weeks.

123) The method of embodiment 116, wherein step (ii) is repeated once a week over a period of about 6-8 weeks.

124) The method of embodiment 116, wherein the induction dose is equal to the maintenance dose.

125) The method of embodiment 116, wherein the induction dose is greater than the maintenance dose.

126) The method of embodiment 116, wherein the induction dose is 5 times greater than the maintenance dose.

127) The method of embodiment 116, wherein the induction dose is 2 times greater than the maintenance dose.

128) The method of any one of the preceding embodiments, wherein the method comprises releasing the JAK inhibitor at the location in the gastrointestinal tract as a single bolus.

129) The method of any one of embodiments 30 to 127, wherein the method comprises releasing the JAK inhibitor at the location in the gastrointestinal tract as more than one bolus.

130) The method of any one of embodiments 30 to 127, wherein the method comprises delivering the JAK inhibitor at the location in the gastrointestinal tract in a continuous manner.

131) The method of embodiment 130, wherein the method comprises delivering the JAK inhibitor at the location in the gastrointestinal tract over a time period of 20 or more minutes.

132) The method of any one of embodiments 30 to 131, wherein the method does not comprise delivering a JAK inhibitor rectally to the subject.

133) The method of any one of embodiments 30 to 131, wherein the method does not comprise delivering a JAK inhibitor via an enema to the subject.

134) The method of any one of embodiments 30 to 131, wherein the method does not comprise delivering a JAK inhibitor via suppository to the subject.

135) The method of any one of embodiments 30 to 131, wherein the method does not comprise delivering a JAK inhibitor via instillation to the rectum of the subject.

136) The method of any one of embodiments 30 to 131, wherein the method does not comprise surgical implantation.

137) The method of any one of embodiments 30 to 136, wherein the JAK inhibitor decreases the kinase activity of JAK1.

138) The method of any one of embodiments 30 to 136, wherein the JAK inhibitor decreases the kinase activity of JAK2.

139) The method of any one of embodiments 30 to 136, wherein the JAK inhibitor decreases the kinase activity of JAK3.

140) The method of any one of embodiments 30 to 136, wherein the JAK inhibitor decreases the kinase activity of a single JAK isoform.

141) The method of any one of embodiments 30 to 136, wherein the JAK inhibitor decreases the kinase activity of two or more (e.g., 3 or 4) of: JAK1, JAK2, JAK3 and TYK2.

142) The method of any one of embodiments 30 to 96 or 98 to 141, wherein the composition is an autonomous device.

143) The method of any one of embodiments 30 to 142, wherein the composition comprises a mechanism capable of releasing the JAK inhibitor.

144) The method of any one of embodiments 30 to 143, wherein the composition comprises a tissue anchoring mechanism for anchoring the composition to the location.

145) The method of embodiment 144, wherein the tissue anchoring mechanism is capable of activation for anchoring to the location.

146) The method of embodiment 144 to 145, wherein the tissue anchoring mechanism comprises an osmotically-driven sucker.

147) The method of embodiment 144, 145, or 146, wherein the tissue anchoring mechanism comprises a connector operable to anchor the composition to the location.

148) The method of embodiment 147, wherein the connector is operable to anchor the composition to the location using an adhesive, negative pressure and/or fastener.

149) The method of embodiment 100, wherein the reservoir is an anchorable reservoir.

150) The method of any one of embodiments 30 to 89, wherein the pharmaceutical composition is an ingestible device, comprising:

a) a housing;

b) a reservoir located within the housing and containing the JAK inhibitor, c) a mechanism for releasing the JAK inhibitor from the reservoir; and d) an exit valve configured to allow the JAK inhibitor to be released out of the housing from the reservoir.

151) The method of embodiment 150, wherein the ingestible device further comprises:

an electronic component located within the housing; and a gas generating cell located within the housing and adjacent to the electronic component, wherein the electronic component is configured to activate the gas generating cell to generate gas.

152) The method of embodiment 150 or 151, wherein the ingestible device further comprises: a safety device placed within or attached to the housing, wherein the safety device is configured to relieve an internal pressure within the housing when the internal pressure exceeds a threshold level.

153) The method of embodiment 30 to 89, wherein the pharmaceutical composition is an ingestible device, comprising:

a). a housing defined by a first end, a second end substantially opposite from the first end, and a wall extending longitudinally from the first end to the second end;

b) an electronic component located within the housing;

c) a gas generating cell located within the housing and adjacent to the electronic component, wherein the electronic component is configured to activate the gas generating cell to generate gas;

d) a reservoir located within the housing,wherein the reservoir stores a dispensable substance and a first end of the reservoir is attached to the first end of the housing;

e) an exit valve located at the first end of the housing, wherein the exit valve is configured to allow the dispensable substance to be released out of the first end of the housing from the reservoir; and f) a safety device placed within or attached to the housing, wherein the safety device is configured to relieve an internal pressure within the housing when the internal pressure exceeds a threshold level.

154) The method of embodiment 30 to 89, wherein the pharmaceutical composition is an ingestible device, comprising:

a) a housing defined by a first end, a second end substantially opposite from the first end, and a wall extending longitudinally from the first end to the second end;

b) an electronic component located within the housing, c) a gas generating cell located within the housing and adjacent to the electronic component, wherein the electronic component is configured to activate the gas generating cell to generate gas;

d) a reservoir located within the housing, wherein the reservoir stores a dispensable substance and a first end of the reservoir is attached to the first end of the housing;

e) an injection device located at the first end of the housing, wherein the jet injection device is configured to inject the dispensable substance out of the housing from the reservoir; and f) a safety device placed within or attached to the housing, wherein the safety device is configured to relieve an internal pressure within the housing.

155) The method of embodiment 30 to 89, wherein the pharmaceutical composition is an ingestible device, comprising:

a) a housing defined by a first end, a second end substantially opposite from the first end, and a wall extending longitudinally from the first end to the second end;

b) an optical sensing unit located on a side of the housing, wherein the optical sensing unit is configured to detect a reflectance from an environment external to the housing;

c) an electronic component located within the housing;

d) a gas generating cell located within the housing and adjacent to the electronic component, wherein the electronic component is configured to activate the gas generating cell to generate gas in response to identifying a location of the ingestible device based on the reflectance;

e) a reservoir located within the housing, wherein the reservoir stores a dispensable substance and a first end of the reservoir is attached to the first end of the housing;

f) a membrane in contact with the gas generating cell and configured to move or deform into the reservoir by a pressure generated by the gas generating cell; and g) a dispensing outlet placed at the first end of the housing, wherein the dispensing outlet is configured to deliver the dispensable substance out of the housing from the reservoir.

156) The method of any one of embodiments 30 to 89, wherein the pharmaceutical composition is an ingestible device as disclosed in U.S. Patent Application Ser. No. 62/385,553, incorporated by reference herein in its entirety.

157) The method of any one of embodiments 30 to 89, wherein the pharmaceutical composition is an ingestible device as disclosed in U.S. Patent Application Ser. No. 62/478,955, incorporated by reference herein in its entirety.

158) The method of any one of embodiments 30 to 89, wherein the pharmaceutical composition is an ingestible device comprising a localization mechanism as disclosed in international patent application PCT/US2015/052500, incorporated by reference herein in its entirety.

159) A method of treating a disease of the large intestine of a subject, comprising:

releasing a JAK inhibitor at a location in the proximal portion of the large intestine of the subject that is proximate to one or more sites of disease, wherein the method comprises administering endoscopically to the subject a therapeutically effective amount of the JAK inhibitor, wherein the method does not comprise releasing more than 20% of the JAK inhibitor at a location that is not proximate to a site of disease.

160) A method of treating a disease of the gastrointestinal tract in a subject, comprising:

releasing a JAK inhibitor at a location in the proximal portion of the large intestine of the subject that is proximate to one or more sites of disease, wherein the method comprises administering endoscopically to the subject a pharmaceutical composition comprising a therapeutically effective amount of the JAK inhibitor, wherein the pharmaceutical composition is an ingestible device.

161) The method of embodiment 159 or 160, wherein the method does not comprise releasing more than 20% of the JAK inhibitor at a location that is not proximate to a site of disease 162) The method of embodiment 159, 160 or 161 wherein the method does not comprise releasing more than 10% of the JAK inhibitor at a location that is not proximate to a site of disease.

163) The method of any one of embodiments 159, 160 or 161, wherein the method provides a concentration of the JAK inhibitor at a location that is a site of disease or proximate to a site of disease that is 2-100 times greater than at a location that is not proximate to a site of disease.

164) The method of any one of embodiments 159 to 163, wherein the method provides a concentration of the JAK inhibitor in the plasma of the subject that is less than 5000 ng/mL, or less than 3000 ng/mL.

165) The method of embodiment 164, wherein the method provides a concentration of the JAK inhibitor in the plasma of the subject that is less than 500 ng/mL, or less than 300 ng/mL.

166) The method of embodiment 165, wherein the method provides a concentration of the JAK inhibitor in the plasma of the subject that is less than 50 ng/mL, or less than 10 ng/mL.

167) The method of any one of embodiments 159 to 163, wherein the method provides a $C_{24}$ value of the JAK inhibitor in the plasma of the subject that is less than 5000 ng/mL, or less than 3000 ng/mL.

168) The method of any one of embodiments 159 to 163, wherein the method provides a $C_{24}$ value of the JAK inhibitor in the plasma of the subject that is less than 500 ng/mL, or less than 300 ng/mL.

169) The method of any one of embodiments 159 to 163, wherein the method provides a $C_{24}$ value of the JAK inhibitor in the plasma of the subject that is less than 50 ng/mL, or less than 10 ng/mL.

170) The method of any one of embodiments 159 to 163, wherein the composition does not comprise an enteric coating.

171) The method of any one of embodiments 159 to 170, wherein the JAK inhibitor is not a cyclic peptide.

172) The method of any one of embodiments 159 to 170, wherein the JAK inhibitor is present in a pharmaceutical formulation within the device.

173) The method of embodiment 172, wherein the formulation is a solution of the JAK inhibitor in a liquid medium.

174) The method of embodiment 172, wherein the formulation is a suspension of the JAK inhibitor in a liquid medium.

175) The method of any one of embodiments 159 to 174, wherein the disease of the large intestine is an inflammatory bowel disease.

176) The method of any one of embodiments 159 to 174, wherein the disease of the large intestine is ulcerative colitis.

177) The method of any one of embodiments 159 to 174, wherein the disease the large intestine is Crohn's disease.

178) The method of any one of embodiments 159 to 177, wherein the JAK inhibitor is released at a location in the proximal portion of the ascending colon.

179) The method of any one of embodiments 159 to 177, wherein the JAK inhibitor is released at a location in the proximal portion of the cecum.

180) The method of any one of embodiments 159 to 177, wherein the JAK inhibitor is released at a location in the proximal portion of the sigmoid colon.

181) The method of any one of embodiments 159 to 177, wherein the JAK inhibitor is released at a location in the proximal portion of the transverse colon.

182) The method of any one of embodiments 159 to 177, wherein the JAK inhibitor is released at a location in the proximal portion of the descending colon.

183) The method of any one of embodiments 159 to 177, wherein the method comprises administering to the subject a reservoir comprising the therapeutically effective amount of the JAK inhibitor, wherein the reservoir is connected to the endoscope.

184) The method of any one of the preceding embodiments, further comprising administering a second agent orally, intravenously or subcutaneously, wherein the second agent is the same JAK inhibitor; a different JAK inhibitor; or an agent having a different biological target from the JAK inhibitor, wherein the second agent is an agent suitable for treating an inflammatory bowel disease.

185) The method of embodiment 184, wherein the JAK inhibitor is administered prior to the second agent.

186) The method of embodiment 184, wherein the JAK inhibitor is administered after the second agent.

187) The method of embodiment 184, wherein the JAK inhibitor and the second agent are administered substantially at the same time.

188) The method of embodiment 184, wherein the second agent is administered intravenously.

189) The method of embodiment 184, wherein the second agent is administered subcutaneously.

190) The method of any one of embodiments 184 to 189, wherein the amount of the second agent is less than the amount of the second agent when the JAK inhibitor and the second agent are both administered systemically.

191) The method of embodiment 190, wherein the second agent is a JAK inhibitor.

192) The method of embodiment 190, wherein second agent is methotrexate.

193) The method of any one of embodiments 30 to 183, wherein the method does not comprise administering a second agent.

194) The method of any one of embodiments 148 to 193, wherein the method comprises identifying the disease site prior to endoscopic administration.

195) The method of any one of embodiments 148 to 193, wherein the method comprises identifying the disease site substantially at the same time as releasing the JAK inhibitor.

196) The method of any one of the preceding embodiments, wherein the method comprising monitoring the progress of the disease.

197) The method of embodiment 196, wherein monitoring the progress of the disease comprises measuring the weight of the subject over a period of about 1-14 weeks, such as about 6-8 weeks following administration of the JAK inhibitor.

198) The method of embodiment 196 or 197, wherein monitoring the progress of the disease comprises measuring the food intake of the subject over a period of about 1-14 weeks, such as about 6-8 weeks following administration of the JAK inhibitor.

199) The method of embodiment 196, 197 or 198, wherein monitoring the progress of the disease comprises measuring the level of blood in the feces of the subject over a period of about 1-14 weeks, such as about 6-8 weeks following administration of the JAK inhibitor.

200) The method of embodiment 196, 197 or 198, wherein monitoring the progress of the disease comprises measuring the level of abdominal pain of the subject over a period of about 1-14 weeks, such as about 6-8 weeks following administration of the JAK inhibitor.

201) The method of any one of embodiments 30 to 200, wherein the method does not comprise administering a JAK inhibitor with a spray catheter.

202) The method of any one of embodiments 30 to 201, wherein the method comprises administering a JAK inhibitor with a spray catheter.

203) A method of treating a disease of the gastrointestinal tract in a subject, comprising:

releasing a JAK inhibitor at a location in the gastrointestinal tract of the subject that is proximate to one or more sitcs of disease, wherein the method comprises administering to the subject a pharmaceutical composition comprising a therapeutically effective amount of the JAK inhibitor the method comprising one or more of the following steps:

a) identifying a subject having a disease of the gastrointestinal tract;

b) determination of the severity of the disease;

c) determination of the location of the disease;

d) evaluating the subject for suitability to treatment;

e) administration of an induction dose of the JAK inhibitor;

f) monitoring the progress of the disease; and/or g) optionally repeating steps e) and f) one or more times.

204) The method of embodiment 203, wherein the pharmaceutical composition is an ingestible device and the method comprises administering orally to the subject the pharmaceutical composition.

205) The method of embodiment 203 or 204, wherein the method comprises administering one or more maintenance doses following administration of the induction dose in step e).

206) The method of embodiment 205, wherein the induction dose is a dose of the JAK inhibitor administered in an ingestible device.

207) The method of embodiment 205 or 206, wherein the maintenance dose is a dose of the JAK inhibitor administered in an ingestible device as disclosed herein.

208) The method of embodiment 205 or 206, wherein the maintenance dose is a dose of the JAK inhibitor delivered systemically.

209) The method of embodiment 205, wherein the induction dose is a dose of the JAK inhibitor delivered systemically.

210) The method of embodiment 205 or 209, wherein the maintenance dose is a dose of the JAK inhibitor administered in an ingestible device.

211) The method of embodiment 205, wherein the induction dose is a dose of a second agent as delivered systemically.

212) The method of embodiment 205 or 209, wherein the maintenance dose is a dose of the JAK inhibitor administered in an ingestible device.

213) A JAK inhibitor delivery apparatus comprising:

a) an ingestible housing comprising a reservoir having a pharmaceutical composition comprising a therapeutically effective amount of the JAK inhibitor stored therein;

b) a detector coupled to the ingestible housing, the detector configured to detect when the ingestible housing is proximate to a respective disease site of the one of the one or more sites of disease;

c) a valve system in fluid communication with the reservoir system; and d) a controller communicably coupled to the valve system and the detector, the controller configured to cause the valve system to open in response to the detector detecting that the ingestible housing is proximate to the respective disease site so as to release the therapeutically effective amount of the JAK inhibitor at the respective disease site.

214) The JAK inhibitor delivery apparatus according to embodiment 213, further comprising a pump positioned in the ingestible housing, the pump configured to pump the therapeutically effective amount of the JAK inhibitor from the reservoir in response to activation of the pump by the controller responsive to detection by the detector of the ingestible housing being proximate to the respective disease site.

215) The JAK inhibitor delivery apparatus according to embodiment 214, wherein the controller is configured to cause the pump to pump the therapeutically effective amount of the JAK inhibitor from the reservoir according to the following protocol.

216) The JAK inhibitor delivery apparatus according to embodiment 213, wherein the valve system comprises a dissolvable coating.

217) The JAK inhibitor delivery apparatus according to embodiment 213, wherein the valve system comprises one or more doors configured for actuation by at least one of sliding, pivoting, and rotating.

218) The JAK inhibitor delivery apparatus according to embodiment 213, wherein the valve system comprises an electrostatic shield.

219) The JAK inhibitor delivery apparatus according to embodiment 213, wherein the reservoir comprises a pressurized cell.

220) The JAK inhibitor delivery apparatus according to embodiment 213, further comprising at least one actuatable anchor configured to retain the ingestible housing at the respective disease site upon actuation.

221) The JAK inhibitor delivery apparatus according to embodiment 213, herein the actuatable anchor is retractable.

222) A composition comprising a therapeutically effective amount of the JAK inhibitor of any one of the preceding embodiments, wherein the composition is capable of releasing the JAK inhibitor at a location in the gastrointestinal tract of the subject.

223) The composition of embodiment 222, wherein the composition comprises a tissue anchoring mechanism for anchoring the composition to the location.

224) The composition of embodiment 223, wherein the tissue anchoring mechanism is capable of anchoring for anchoring to the location.

225) The composition of embodiment 223 or 224, wherein the tissue anchoring mechanism comprises an osmotically-driven sucker.

226) The composition of embodiment 223, 224 or 225, wherein the tissue anchoring mechanism comprises a connector operable to anchor the composition to the location.

227) The composition of embodiment 226, wherein the connector is operable to anchor the composition to the location using an adhesive, negative pressure and/or fastener.

228) A JAK inhibitor for use in a method of treating a disease of the gastrointestinal tract in a subject, wherein the method comprises orally administering to the subject an ingestible device loaded with the JAK inhibitor, wherein the JAK inhibitor is released by the device at a location in the gastrointestinal tract of the subject that is proximate to one or more sites of disease.

229) The JAK inhibitor for use of embodiment 228, wherein the JAK inhibitor is contained in a reservoir suitable for attachment to a device housing, and wherein the method comprises attaching the reservoir to the device housing to form the ingestible device, prior to orally administering the ingestible device to the subject.

230) An attachable reservoir containing a JAK inhibitor for use in a method of treating a disease of the gastrointestinal tract, wherein the method comprises attaching the reservoir to a device housing to form an ingestible device and orally administering the ingestible device to a subject, wherein the JAK inhibitor is released by device at a location in the gastrointestinal tract of the subject that is proximate to one or more sites of disease.

231) A composition comprising or consisting of an ingestible device loaded with a therapeutically effective amount of a JAK inhibitor, for use in a method of treatment, wherein the method comprises orally administering the composition to the subject, wherein the JAK inhibitor is released by the device at a location in the gastrointestinal tract of the subject that is proximate to one or more sites of disease.

232) The JAK inhibitor for use according to embodiment 228 or 229, the attachable reservoir compartment for use according to embodiment 230, or the composition for use according to embodiment 231, wherein the sites of disease have been pre-determined.

233) The JAK inhibitor for use according to embodiment 228 or 229, the attachable reservoir compartment for use according to embodiment 230, or the composition for use according to embodiment 231, wherein the ingestible device further comprises an environmental sensor and the method further comprises using the environmental sensor to identify the location of one or more sites of disease.

234) The JAK inhibitor for use, the attachable reservoir compartment for use the composition for use, according to embodiment 233, wherein the environmental sensor is an imaging sensor and the method further comprising imaging the gastrointestinal tract to identify the location of one or more sites of disease.

235) The JAK inhibitor for use, the attachable reservoir compartment for use, or the composition for use, according to embodiment 234, wherein the imaging detects inflamed tissue and/or lesions associated with a disease of the gastrointestinal tract.

236) The JAK inhibitor for use, the attachable reservoir compartment for use or the composition for use, according to any one of embodiments 228 to 234, wherein the disease of the GI tract is one or more of an inflammatory bowel disease, ulcerative colitis and Crohn's disease.

237) An ingestible device loaded with a therapeutically effective amount of a JAK inhibitor, wherein the device is controllable to release the JAK inhibitor at a location in the gastrointestinal tract of the subject that is proximate to one or more sites of disease.

238) The device of embodiment 237 for use in a method of treatment of the human or animal body.

239) The JAK inhibitor for use, the attachable reservoir compartment for use or the composition for use according to any one of embodiments 228 to 236, or the device according to embodiment 237 or embodiment 238, wherein the ingestible device comprises:

a) a housing defined by a first end, a second end substantially opposite from the first end, and a wall extending longitudinally from the first end to the second end;

b) a reservoir located within the housing and containing the JAK inhibitor wherein a first end of the reservoir is connected to the first end of the housing;

c) a mechanism for releasing the JAK inhibitor from the reservoir; and d) an exit value configured to allow the JAK inhibitor to be released out of the housing from the reservoir.

240) The JAK inhibitor for use, the attachable reservoir compartment for use or the composition for use according to any one of embodiments 228 to 236, or the device according to embodiment 237 or embodiment 238, wherein the ingestible device comprises:

a) an ingestible housing comprising a reservoir compartment having a therapeutically effective amount of the JAK inhibitor stored therein;

b) a release mechanism having a closed state which retains the JAK inhibitor in the reservoir and an open state which releases the JAK inhibitor from the reservoir to the exterior of the device; and c) an actuator which changes the state of the release mechanism from the closed to the open state.

241) The JAK inhibitor for use, the attachable reservoir compartment for use, the composition for use, or the device according to embodiments 239 or 240, wherein the ingestible device further comprises an environmental sensor for detecting the location of the device in the gut and/or for detecting the presence of disease in the GI tract.

242) The JAK inhibitor for use, the attachable reservoir compartment for use, the composition for use, or the device according to embodiment 241, wherein the ingestible device further comprises a communication system for transmitting data from the environmental sensor to an external receiver.

243) The JAK inhibitor for use, the attachable reservoir compartment for use, the composition for use, or the device according to embodiment 241 or 242, wherein the ingestible device further comprises a processor or controller which is coupled to the environmental sensor and to the actuator and which triggers the actuator to cause the release mechanism to transition from its closed state to its open state when it is determined that the device is in the presence of diseased tissue and/or is in a location in the gut that has been predetermined to be proximal to diseased tissue.

244) The JAK inhibitor for use, the attachable reservoir compartment for use, the composition for use, or the device according to embodiment 242, wherein the communication system further comprises means for receiving a signal from an external transmitter, and wherein the actuator is adapted to be triggered in response to the signal.

245) The JAK inhibitor for use, the attachable reservoir compartment for use, the composition for use, or the device according to any one of embodiments 239 to 244, wherein the ingestible device further comprises a communication system for transmitting localization data to an external receiver.

246) The JAK inhibitor for use, the attachable reservoir compartment for use, the composition for use, or the device according to any one of embodiments 239 to 242, wherein the ingestible device further comprises a communication system for transmitting localization data to an external receiver and for receiving a signal from an external transmitter; wherein the actuator is adapted to be triggered in response to the signal.

247) The JAK inhibitor for use, the attachable reservoir compartment for use, the composition for use, or the device according to any one of embodiments 148 to 246, wherein the ingestible device further comprises a deployable anchoring system and an actuator for deploying the anchoring system, wherein the anchoring system is capable of anchoring or attaching the ingestible device to the subject's tissue.

248) The method of any one of embodiments 31 to 221, wherein the method comprises determining the level of the JAK inhibitor at the location of disease following administration of the device.

249) The method of any one of embodiments 31 to 221 or 248, wherein the method comprises determining that the level of JAK inhibitor at the location of disease at the time point following administration of the device is higher than the level of the JAK inhibitor at the same location of disease at substantially the same time point following systemic administration of an equal amount of the JAK inhibitor.

250) The method of embodiment 248, wherein the method comprises determining the level of the JAK inhibitor in the GI tissue of the subject at a time point following administration of the device.

251) The method of embodiment of any one of embodiments 31 to 221 or 250, wherein the method comprises determining the level of the JAK inhibitor in one or more of the lumen/superficial mucosa, the lamina propria, the submucosa, and the tunica muscularis/serosa in the subject at a time point following administration of the device.

252) The method of any one of embodiments 31 to 221 or 250, wherein the method comprises determining that the level of the JAK inhibitor in the GI tissue at a time point following administration of the device is higher than the level of the JAK inhibitor in the GI tissue of a subject at substantially the same time point following systemic administration of an equal amount of the JAK inhibitor.

253) The method of any one of embodiments 31 to 221 or 251, wherein the method comprises determining that the level of the JAK inhibitor in the lumen/superficial mucosa in the subject following administration of the device is elevated as compared to the level of JAK inhibitor in the lumen/superficial mucosa in a subject at substantially the same time point following systemic administration of an equal amount of the JAK inhibitor.

254) The method of any one of embodiments 31 to 221 or 248 to 253, wherein the method comprises determining the level of the JAK inhibitor in the tissue of the subject within a time period of about 10 minutes to 10 hours following administration of the device.

255) The method of any one of embodiments 31 to 221 or 248 to 254, wherein the method comprises determining a level of a marker at the location of disease in the subject following administration of the device.

256) The method of embodiment 255, wherein the marker is a biomarker and the method comprises determining that the level of the biomarker at the location of disease in the subject at a time point following administration of the device is decreased as compared to a level of the biomarker in the subject prior to administration of the device or a level of the biomarker in a subject at the same location of disease at substantially the same time point following systemic administration of an equal amount of the JAK inhibitor.

257) The method of embodiment 256, wherein the level of the biomarker in the subject at a time point following administration of the device is 1% decreased to 99% decreased as compared to the level of the biomarker in the subject prior to administration of the device or the level of the biomarker in a subject at the same location of disease at substantially the same time point following systemic administration of an equal amount of the JAK inhibitor.

258) The method of embodiment 256 or 257, wherein the method comprises determining the level of the biomarker in the subject at a time point that is 10 minutes to 10 hours following administration of the device.

259) The method of embodiment 256, 257, or 258, wherein the level of the biomarker is one or more of: the level of interferon-K in GI tissue, the level of IL-1 P in GI tissue, the level of IL-6 in GI tissue, the level of IL-22 in GI tissue, the level of IL-17A in the GI tissue, the level of TNFα in GI tissue, the level of IL-2 in GI tissue.

260) The method of embodiment 255, wherein the method comprises determining that the level of the marker at the time point following administration of the device is decreased relative to the level of the marker in the subject prior to administration of the device or the level of the marker in a subject at the same location of disease at substantially the same time point following systemic administration of an equal amount of the JAK inhibitor.

261) The method of embodiment 260, wherein the level of the marker in the subject at the time point following administration of the device is 1% decreased to 99% decreased as compared to the level of the marker in the subject prior to administration of the device or the level of the marker in a subject at the same location of disease at substantially the same time point following systemic administration of an equal amount of the JAK inhibitor.

262) The method of embodiment 260 or 261, wherein the method comprises determining the level of the marker in the subject within a time period of about 10 minutes to about 10 hours following administration of the device.

263) The method of embodiment 260, 261 or 262, wherein the level of the marker is an endoscopy score in the subject.

264) The method of embodiment 238, wherein the method comprises determining that the level of the marker in the subject at the time point following administration of the device is elevated as compared to the level of the marker in the subject prior to administration of the device or the level of the marker in a subject at the same location of disease at substantially the same time point following systemic administration of an equal amount of the JAK inhibitor.

265) The method of embodiment 247, wherein the level of the marker in the subject following administration of the device is 1% increased to 400% increased as compared to the level of the marker in the subject prior to administration of the device or the level of the marker in a subject at the same location of disease at substantially the same time point following systemic administration of an equal amount of the JAK inhibitor.

266) The method of embodiment 264 or 265, wherein the method comprises determining the level of the marker in the subject within a time period of about 10 minutes to about 10 hours of administration of the device.

267) The method of embodiment 264, 265 or 266 wherein the level of the marker is one or both of subject weight and stool consistency.

268) The method of any one of embodiments 31 to 221 or 248 to 267, wherein the method comprises determining the time period of onset of treatment following administration of the device.

269) A method for treating colitis in a subject, wherein the colitis is associated with treatment of the subject with one or more immuno-oncology agents, the method comprising releasing a JAK inhibitor at a location in the gastrointestinal tract of the subject that is proximate to one or more sites of disease, wherein the method comprises administering to the subject a pharmaceutical composition comprising a therapeutically effective amount of the JAK inhibitor.

270) The method of embodiment 269, wherein the pharmaceutical composition is an ingestible device and the method comprises administering orally to the subject the pharmaceutical composition.

271) The method of embodiment 269 or 270, wherein at least one of the one or more immuno-oncology agents is a chemotherapeutic agent.

272) The method of embodiment 271, wherein the chemotherapeutic agent is a chemotherapeutic immunomodulator.

273) The method of embodiment 272, wherein the chemotherapeutic immunomodulatory is an immune checkpoint inhibitor.

274) The method of embodiment 273, wherein the immune checkpoint inhibitor targets or decreases an activity of an immune checkpoint protein selected from the group consisting of: CTLA-4, PD-1, PD-L1, PD-1-PD-L1, PD-1-PD-L2, interleukin 2 (IL 2), indoleamine 2,3-dioxygenase (IDO), IL 10, transforming growth factor-β (TGFβ), T cell immunoglobulin and mucin 3 (TIM3 or HAVCR2), Galectin 9-TIM3, Phosphatidylserine-TIM3, lymphocyte activation gene 3 protein (LAG3), MHC class II-LAG3, 4 1BB-4 1BB ligand, OX40-OX40 ligand, GITR, GITR ligand-GITR, CD27, CD70-CD27, TNFRSF25, TNFRSF25-TL1A, CD40L, CD40-CD40 ligand, HVEM-LIGHT-LTA, HVEM, HVEM-BTLA, HVEM-CD160, HVEM-LIGHT, HVEM-BTLA-CD160, CD80, CD80-PDL-1, PDL2-CD80, CD244, CD48-CD244, CD244, ICOS, ICOS-ICOS ligand, B7 H3, B7 H4, VISTA, TMIGD2, HHLA2-TMIGD2, Butyrophilins, including BTNL2, Siglec family, TIGIT and PVR family members, KIRs, ILTs and LIRs, NKG2D and NKG2A, MICA and MICB, CD244, CD28, CD86-CD28, CD86-CTLA, CD80-CD28, CD39, CD73 Adenosine-CD39-CD73, CXCR4-CXCL12, Phosphatidylserine, TIM3, Phosphatidylserine-TIM3, SIRPA-CD47, VEGF, Neuropilin, CD160, CD30, and CD155.

275) The method of embodiment 273, wherein the immune checkpoint inhibitor is selected from the group consisting of: Urelumab, PF 05082566, MED16469, TRX518, Varlilumab, CP 870893, Pembrolizumab (PD1), Nivolumab (PD1), Atezolizumab (formerly MPDL3280A) (PDL1), MED14736 (PD-L1), Avelumab (PD-L1), PDR001 (PD1), BMS 986016, MGA271, Lirilumab, IPH2201, Emactuzumab, INCB024360, Galunisertib, Ulocuplumab, BKT140, Bavituximab, CC 90002, Bevacizumab, and MNRP1685A, and MGA271.

276) The method of embodiment 273, wherein the immune checkpoint inhibitor targets CTLA-4.

277) The method of embodiment 273, wherein the immune checkpoint inhibitor is an antibody.

278) The method of embodiment 277, wherein the antibody is ipilimumab or tremelimumab.

279) The method of embodiment 273, wherein the immune checkpoint inhibitor targets PD1 or PD-L1.

280) The method of embodiment 273, wherein the immune checkpoint inhibitor is selected from the group of: nivolumab, lambroizumab, and BMS-936559.

281) The method of embodiment 269, wherein at least one of the one or more immuno-oncology agents is a T-cell that expresses a chimeric antigen receptor (a CAR-T cell).

282) The method of any one of embodiments 269 to 281, wherein the treatment of the subject with one or more immuno-oncology agents further includes treatment of the patient with an immunosuppressant.

283) The method of embodiment 269, wherein at least one of the one or more immuno-oncology agents is a PI-3 kinase inhibitor.

284) A method for treating colitis in a subject comprising:

a) determining that the subject has colitis associated with treatment of the subject with one or more immuno-oncology agents; and b) releasing a JAK inhibitor at a location in the gastrointestinal tract of the subject that is proximate to one or more sites of colitis, wherein the method comprises administering to the subject a pharmaceutical composition comprising a therapeutically effective amount of the JAK inhibitor. In some embodiments, the pharmaceutical composition is an ingestible device. In some embodiments, the pharmaceutical composition is an ingestible device and the method comprises administering orally to the subject the pharmaceutical composition.

285) A method for treating colitis, comprising releasing a JAK inhibitor at a location in the gastrointestinal tract of a subject who has been determined to have colitis associated with treatment of the subject with one or more immuno-oncology agents, wherein the location is proximate to one or more sites of colitis, wherein the method comprises administering to the subject a pharmaceutical composition comprising a therapeutically effective amount of the JAK inhibitor.

286) The method of embodiment 254 or 285, wherein the pharmaceutical composition is an ingestible device and the method comprises administering orally to the subject the pharmaceutical composition.

287) An ingestible device, comprising:

a) a JAK inhibitor;

b) one or more processing devices; and c) one more machine readable hardware storage devices storing instructions that are executable by the one or more processing devices to determine a location of the ingestible device in a portion of a GI tract of a subject to an accuracy of at least 85%.

288) The ingestible device of embodiment 287, wherein the accuracy is at least 90%.

289) The ingestible device of embodiment 287, wherein the accuracy is at least 95%.

290) The ingestible device of embodiment 287, wherein the accuracy is at least 97%.

291) The ingestible device of embodiment 287, wherein the accuracy is at least 98%

292) The ingestible device of embodiment 287, wherein the accuracy is at least 99%.

293) The ingestible device of embodiment 287, wherein the accuracy is 100%.

294) The ingestible device of embodiment 287, wherein the portion of the GI tract of the subject comprises the duodenum.

295) The ingestible device of embodiment 287, wherein the portion of the GI tract of the subject comprises the jejunum.

296) The ingestible device of embodiment 287, wherein the portion of the GI tract of the subject comprises the terminal ileum, cecum and colon.

297) The ingestible device of any of embodiments 287-296, further comprising first and second light sources, wherein the first light source is configured to emit light at a first wavelength, and the second light source is configured to emit light at a second wavelength different from the first wavelength.

298) The ingestible device of embodiment 297, further comprising first and second detectors, wherein the first detector is configured to detect light at the first wavelength, and the second detector is configured to detect light at the second wavelength.

299) An ingestible device, comprising:

a) a JAK inhibitor;

b) one or more processing devices; and c) one more machine readable hardware storage devices storing instructions that are executable by the one or more processing devices to determine that the ingestible device is in the cecum of a subject to an accuracy of at least 70%, 300) The ingestible device of embodiment 299, wherein the accuracy is at least 75%, 301) The ingestible device of embodiment 299, wherein the accuracy is at least 80%, 302) The ingestible device of embodiment 299, wherein the accuracy is at least 85%, 303) The ingestible device of embodiment 299, wherein the accuracy is at least 88%

304) The ingestible device of embodiment 299, wherein the accuracy is at least 89%, 305) An ingestible device, comprising:

a) a JAK inhibitor;

b) one or more processing devices; and c) one more machine readable hardware storage devices storing instructions that are executable by the one or more processing devices to transmit data to a device capable of implementing the data to determine a location of the medical device in a portion of a GI tract of a subject to an accuracy of at least 85%.

306) The ingestible device of embodiment 305, wherein the accuracy is at least 90%.

307) The ingestible device of embodiment 305, wherein the accuracy is at least 95%.

308) The ingestible device of embodiment 305, wherein the accuracy is at least 97%.

309) The ingestible device of embodiment 305, wherein the accuracy is at least 98%

310) The ingestible device of embodiment 305, wherein the accuracy is at least 99%.

311) The ingestible device of embodiment 305, wherein the accuracy is 100%.

312) The ingestible device of embodiment 305, wherein the portion of the portion of the GI tract of the subject comprises the duodenum.

313) The ingestible device of embodiment 305, wherein the portion of the portion of the GI tract of the subject comprises the jejunum.

314) The ingestible device of embodiment 305, wherein the portion of the portion of the GI tract of the subject comprises the terminal ileum, cecum and colon.

315) The ingestible device of any of embodiments 305 to 314, further comprising first and second light sources, wherein the first light source is configured to emit light at a first wavelength, and the second light source is configured to emit light at a second wavelength different from the first wavelength.

316) The ingestible device of embodiment 315, further comprising first and second detectors, wherein the first detector is configured to detect light at the first wavelength, and the second detector is configured to detect light at the second wavelength.

317) The ingestible device of any of embodiments 305 to 315, wherein the data comprise intensity data for at least two different wavelengths of light.

318) An ingestible device, comprising:

a) a JAK inhibitor;

b) one or more processing devices; and c) one more machine readable hardware storage devices storing instructions that are executable by the one or more processing devices to transmit data to an external device capable of implementing the data to determine that the ingestible device is in the cecum of subject to an accuracy of at least 70%.

319) The ingestible device of embodiment 318, wherein the accuracy is at least 75%.

320) The ingestible device of embodiment 318, wherein the accuracy is at least 80%.

321) The ingestible device of embodiment 318, wherein the accuracy is at least 85%.

322) The ingestible device of embodiment 318, wherein the accuracy is at least 88%

323) The ingestible device of embodiment 318, wherein the accuracy is at least 89%.

324) The device of any one of embodiments 287 to 317, wherein the JAK inhibitor is present in a therapeutically effective amount.

325) A method of treating a disease of the gastrointestinal tract in a subject, comprising:

releasing a JAK inhibitor at a location in the gastrointestinal tract of the subject that is proximate to one or more sites of disease, wherein the method comprises administering orally to the subject the ingestible device of any one of embodiments 287 to 324, the method further comprising determining a location of the ingestible medical device in a portion of a GI tract of a subject to an accuracy of at least 85%.

326) The method of embodiment 325, wherein the accuracy is at least 90%.

327) The method of embodiment 325, wherein the accuracy is at least 95%.

328) The method of embodiment 325, wherein the accuracy is at least 97%.

329) The method of embodiment 325, wherein the accuracy is at least 98%

330) The method of embodiment 325, wherein the accuracy is at least 99%.

331) The method of embodiment 325, wherein the accuracy is 100%.

332) The method of embodiment 325, wherein the portion of the portion of the GI tract of the subject comprises the duodenum.

333) The method of embodiment 325, wherein the portion of the portion of the GI tract of the subject comprises the jejunum.

334) The method of embodiment 325, wherein the portion of the portion of the GI tract of the subject comprises the terminal ileum, cecum and colon.

335) The method of embodiment 325, wherein determining the location of the ingestible device within the GI tract of a subject comprises determining reflected light signals within the GI tract, wherein the reflected signals comprise light of at least two different wavelengths.

336) The method of embodiment 335, wherein the reflected signals comprise light of at least three different wavelengths.

337) The method of embodiment 335 or 336, wherein:

a) the reflected light comprise first and second wavelengths;

b) the first wavelength is between 495-600 nm; and c) the second wavelength is between 400-495 nm.

338) The method of embodiment 337, wherein the first and second wavelengths are separated by at least 50 nm.

339) A method of treating a disease of the gastrointestinal tract in a subject, comprising:

releasing a JAK inhibitor at a location in the gastrointestinal tract of the subject that is proximate to one or more sites of disease, wherein the method comprises administering orally to the subject the ingestible device of any one of embodiments 287 to 324, the method further comprising determining a location of an ingestible medical device within the GI tract of a subject based on measured reflected light signals within the GI tract, wherein the reflected signals comprise light of at least two different wavelengths.

340) The method of embodiment 339, wherein the reflected signals comprise light of at least three different wavelengths.

341) The method of embodiment 339, wherein:

a) the at least two different wavelengths comprise first and second wavelengths;

b) the first wavelength is between 495-600 nm; and c) the second wavelength is between 400-495 nm.

342) The method of embodiment 341, wherein the first and second wavelengths are separated by at least 50 nm.

343) The method of any one of embodiments 325 to 342, wherein the JAK inhibitor is present in a therapeutically effective amount 344) An ingestible device, comprising:

a) a housing;

b) a gas generating cell located within the housing; and c) a storage reservoir located within the housing, wherein:

the storage reservoir stores a JAK inhibitor; and the ingestible device is configured so that, when the gas generating cell generates a gas, the JAK inhibitor exits the ingestible device via an opening in the ingestible device.

345) The ingestible device of embodiment 344, further comprising an injection device configured so that, when the gas generating cell generates the gas, the gas moves the injection device to force the JAK inhibitor out of the ingestible device via the opening.

346) The ingestible device of embodiment 345, wherein the injection device comprises a syringe.

347) The ingestible device of embodiment 345 or 346, further comprising a component configured to position the injection device at an epithelial layer and spread the epithelial layer prior to a delivery of the JAK inhibitor.

348) The ingestible device of any one of embodiments 344 to 347, further comprising a membrane configured so that, when the gas generating cell generates the gas, the gas moves the membrane to force the JAK inhibitor out of the ingestible device via the opening.

349) The ingestible device of embodiment 348, wherein the membrane comprises a piston configured so that, when the gas generating cell generates the gas, the gas moves the membrane to force the JAK inhibitor out of the ingestible device via the opening.

350) The ingestible device of any one of embodiments 344 to 349, further comprising an optical sensing unit supported by the housing, wherein the optical sensing unit is configured to detect a reflectance from an environment external to the housing.

351) The ingestible device of embodiment 350, wherein the ingestible device is configured to determine a location of the ingestible device based on the reflectance detected by the optical sensing unit.

352) The ingestible device of embodiment 350 or embodiment 351, wherein the gas generating cell generates the gas based on the reflectance detected by the optical sensing unit.

353) The ingestible device of any one of embodiments 344 to 352, further comprising an electronic component within the housing, wherein the electronic component is configured to active the gas generating cell.

354) The ingestible device of embodiment 353, wherein the gas generating cell is adjacent the electronic component.

355) The ingestible device of any one of embodiments 344 to 354, further comprising a safety device configured to relieve an internal pressure within the housing.

356) The ingestible device of any one of embodiments 344 to 355, wherein:

a) the housing has a first end, a second end and a wall extending between the first and second ends; and b) the storage reservoir is adjacent to the first end.

357) The ingestible device of any one of embodiments 344 to 356, wherein the storage reservoir stores a therapeutically effective amount of the JAK inhibitor.

358) A reservoir configured for use in an ingestible device, wherein the reservoir comprises a therapeutic agent.

359) The reservoir of embodiment 358, wherein the reservoir comprises a housing and the housing comprises a plastic.

360) The reservoir of embodiment 358 or 359, wherein the plastic comprises at least one material selected from the group consisting of PVC, silicone and polycarbonate.

361) The reservoir of any of embodiments 358 to 360, wherein the ingestible device when fully assembled and packaged satisfies the regulatory requirements for marketing a medical device in the United States of America.

362) The reservoir of any one of embodiments 358 to 361, wherein the therapeutic agent comprises a JAK inhibitor.

363) The reservoir of any one of embodiments 358 to 362, wherein the reservoir is configured to partially fit within the housing of the ingestible device.

364) The reservoir of any one of embodiments 358 to 363, wherein the reservoir is configured to entirely fit within the housing of the ingestible device 365) The reservoir of any of embodiments 358 to 362, wherein the reservoir is configured to attach to the housing of the ingestible device.

366) The reservoir of any one of embodiments 358 to 365, wherein the reservoir is configured to friction fit with the ingestible device.

367) The reservoir of any one of embodiments 358 to 366, wherein the reservoir is configured to be held to the ingestible device via a biasing mechanism.

368) The reservoir of embodiment 367, wherein the biasing mechanism comprises at least one member selected from the group consisting of a spring, a latch, a hook, a magnet, and electromagnetic radiation.

369) The reservoir of any one of embodiments 358 to 368, wherein the reservoir is configured to fit into a groove or a track in the housing of the ingestible device.

370) The reservoir of any one of embodiments 358 to 369, wherein the reservoir is configured to snap fit to the ingestible device.

371) The reservoir of any one of embodiments 358 to 370, wherein the reservoir is configured to be pierced.

372) The reservoir of any one of embodiments 358 to 371, wherein the reservoir comprises a plastic.

373) The reservoir of any one of embodiments 358 to 372, wherein the reservoir comprises at least one material selected from the group consisting of PVC, polycarbonate and silicone.

374) The reservoir of any one of embodiments 358 to 373, wherein the reservoir comprises a metal or an alloy.

375) The reservoir of embodiment 374, wherein the reservoir comprises stainless steel.

376) The reservoir of any one of embodiments 358 to 375, wherein the reservoir is configured to carry electronic components.

377) A kit, comprising:

a) an ingestible device; and b) a reservoir configured for use in an ingestible device, wherein the reservoir comprises a therapeutic agent.

378) The ingestible device of any one of embodiments 287 to 298, further comprising one or more elements of a device as recited in any one of embodiments 100, 151, 152, 233, or 239 to 247.

379) The ingestible device of any one of embodiments 299 to 304, further comprising one or more elements of a device as recited in any one of embodiments 100, 151, 152, 233, or 239 to 247.

380) The ingestible device of any one of embodiments 305 to 317, further comprising one or more elements of a device as recited in any one of embodiments 100, 151, 152, 233, or 239 to 247.

381) The ingestible device of any one of embodiments 318 to 324, further comprising one or more elements of a device as recited in any one of embodiments 100, 151, 152, 233, or 239 to 247.

382) The ingestible device of any one of embodiments 344 to 357, further comprising one or more elements of a device as recited in any one of embodiments 100, 151, 152, 233, or 239 to 247.

383) The reservoir of any one of embodiments 358 to 376, wherein the reservoir is configured for use in a device of any one of embodiments 287 to 324, 344 to 357, or 378 to 382.

Other Embodiments

The various embodiments of systems, processes and apparatuses have been described herein by way of example only. It is contemplated that the features and limitations described in any one embodiment may be applied to any other embodiment herein, and flowcharts or examples relating to one embodiment may be combined with any other embodiment in a suitable manner, done in different orders, or done in parallel. It should be noted, the systems and/or methods described above may be applied to, or used in accordance with, other systems and/or methods. Various modifications and variations may be made to these example embodiments without departing from the spirit and scope of the embodiments, and the appended listing of embodiments should be given the broadest interpretation consistent with the description as a whole.

What is claimed is:

1. A method of treating a gastrointestinal (GI) inflammatory disease or condition in a subject in need thereof, comprising:

topically administering to the subject a pharmaceutical formulation comprising a therapeutically effective amount of a Janus Kinase (JAK) inhibitor selected from abrocitinib, baricitinib, decernotinib (VX509), filgotinib, itacitinib, lestaurtinib, momelotinib, cerdulatinib, oclacitinib, peficitinib, pacritinib, cucurbitacin I, PF-06651600, PF-06700841, R333 (R932333), R348 (R932348), ruxolitinib, solcitinib, ustekinumab, guselkumab, brazikumab, TD-1473, TD-3504, tofacitinib and upadacitinib, or a pharmaceutically acceptable salt, solvate, prodrug or metabolite thereof, said topical administration comprising:

orally administering an ingestible device to the subject, said device containing the pharmaceutical formulation, wherein the device comprises a self-localization mechanism configured to determine a location of the device based on anatomy; and releasing the pharmaceutical formulation from the device (a) to a section or subsection of the subject's GI tract containing one or more inflammatory disease sites; or (b) proximal to a section or subsection of the subject's GI tract containing one or more inflammatory disease sites;

thereby providing a ratio of the JAK inhibitor concentration in the subject's GI tissue to the JAK inhibitor concentration in the subject's blood, serum, or plasma ranging from about 2:1 to about 3000:1 and treating at least one of the one or more disease sites.

2. The method of claim 1, wherein the method further comprises determining the device location within the subject's GI tract via the device self-localization mechanism.

3. The method of claim 2, wherein determining the device location within the subject's GI tract via the device self-localization mechanism comprises detecting one or more device transitions between portions of the subject's GI tract; optionally, the one or more device transitions occurs between portions of the GI tract selected from the group consisting of: mouth and stomach; esophagus and stomach; stomach and duodenum; duodenum and jejunum; jejunum and ileum; ileum and cecum; and cecum and ascending colon; and combinations of any two or more of the foregoing.

4. The method of claim 3, wherein the device self-localizes to the stomach, duodenum, jejunum, ileum, cecum, ascending colon, or traverse colon with at least 80% accuracy; optionally, with at least 85% accuracy.

5. The method of claim 1, wherein the release of the formulation from the device is autonomously triggered based on the self-localization of the device to a pre-selected location within the subject's GI tract; optionally, the pre-selected location is selected from the group consisting of the stomach, the duodenum, the jejunum, the ileum, the cecum, the ascending colon, and the traverse colon.

6. The method of claim 5, wherein the release of the formulation from the device occurs at substantially the same time as the device self-localizes to the pre-selected location.

7. The method of claim 1, wherein the method provides a ratio of JAK inhibitor concentration in the subject's GI tissue to JAK inhibitor concentration in the subject's blood, serum, or plasma ranging from about 2:1 to about 2000:1, about 2:1 to about 1000:1, or about 2:1 to about 600:1.

8. The method of claim 1, wherein the therapeutically effective amount of the JAK inhibitor is an induction dose.

9. The method of claim 1, wherein the therapeutically effective amount of the JAK inhibitor is a maintenance dose.

10. The method of claim 1, wherein the JAK inhibitor is present in the pharmaceutical formulation at a concentration of at least about 75% (w/w), about 80% (w/w), about 85% (w/w), or at least about 90% (w/w); optionally, at least about 95%, about 96%, about 97%, about 98% or about 99% (w/w).

11. The method of claim 1, wherein the small molecule is tofacitinib or a pharmaceutically acceptable salt, solvate, prodrug or metabolite thereof.

12. A method of treating an inflammatory bowel disease (IBD) in a subject in need thereof, the method comprising:

topically administering a pharmaceutical formulation from an ingestible device comprising a self-localization mechanism configured to determine a location of the device based on anatomy, the pharmaceutical formulation comprising a therapeutically effective amount of tofacitinib or a pharmaceutically acceptable salt thereof, (a) to a section or subsection of the gastrointestinal (GI) tract of the subject; or (b) proximal to a section or subsection of the GI tract of the subject; wherein said section or subsection contains one or more inflammatory disease sites, thereby providing a ratio of the tofacitinib or pharmaceutically acceptable salt thereof concentration in the subject's GI tissue to the tofacitinib or pharmaceutically acceptable salt thereof concentration in the subject's blood, serum, or plasma ranging from about 2:1 to about 3000:1 and treating at least one of the one or more inflammatory disease sites.

13. The method of claim 12, wherein the pharmaceutical formulation is contained in an ingestible device, and the method further comprises determining the device location within the subject's GI tract via the device self-localization mechanism.

14. The method of claim 13, wherein determining the device location within the subject's GI tract via the device self-localization mechanism comprises detecting one or more device transitions between portions of the subject's GI tract; optionally, the one or more device transitions occurs between portions of the GI tract selected from the group consisting of: mouth and stomach; esophagus and stomach; stomach and duodenum; duodenum and jejunum; jejunum and ileum; ileum and cecum; and cecum and ascending colon; and combinations of any two or more of the foregoing.

15. The method of claim 12, wherein the topical administration comprises:

orally administering the ingestible device to the subject; and releasing the pharmaceutical formulation from the device (a) to a section or subsection of the subject's GI tract containing one or more inflammatory disease sites; or (b) proximal to a section or subsection of the subject's GI tract containing one or more inflammatory disease sites.

16. The method of claim 12, wherein the method provides a ratio of the tofacitinib or pharmaceutically acceptable salt thereof concentration in the subject's GI tissue to the tofacitinib or pharmaceutically acceptable salt thereof concentration in the subject's blood, serum, or plasma ranging from about 2:1 to about 2000:1, about 2:1 to about 1000:1, or about 2:1 to about 600:1.

17. An ingestible device comprising:

a pharmaceutical formulation comprising a therapeutically effective amount of a Janus Kinase (JAK) inhibitor selected from abrocitinib, baricitinib, decernotinib (VX509), filgotinib, itacitinib, lestaurtinib, momelotinib, cerdulatinib, oclacitinib, peficitinib, pacritinib, cucurbitacin I, PF-06651600, PF-06700841, R333 (R932333), R348 (R932348), ruxolitinib, solcitinib, ustekinumab, guselkumab, brazikumab, TD-1473, TD-3504, tofacitinib and upadacitinib, or a pharmaceutically acceptable salt, solvate, prodrug or metabolite thereof;

one or more processing devices; and one more machine-readable hardware storage devices storing instructions that are executable by the one or more processing devices to (a) determine a location of the ingestible device based on anatomy in the GI tract of the subject; and (b) release the formulation from the device at a pre-selected location of the GI tract to provide a ratio of the JAK inhibitor concentration in the subject's GI tissue to the JAK inhibitor concentration in the subject's blood, serum, or plasma ranging from about 2:1 to about 3000:1;

wherein the ingestible device is a self-localizing ingestible device configured for use in treating an inflammatory gastrointestinal disease or condition in a subject.

18. The ingestible device of claim 17, wherein the device self-localizes in the pre-selected location of the GI tract of the subject with an accuracy of at least 80%; optionally, the pre-selected location is selected from the group consisting of stomach, duodenum, jejunum, ileum, cecum, ascending colon, and traverse colon.

19. The ingestible device of claim 18, further comprising:

a housing;

a force generator located within the housing; and a storage reservoir located within the housing, wherein the storage reservoir stores the pharmaceutical formulation;

wherein the ingestible device is configured such that the force generator generates a force, thereby initiating the release of the formulation from the ingestible device into the pre-selected location of the GI tract.

* * * * *

SEQUENCE LISTING

```
<160> NUMBER OF SEQ ID NOS: 15

<210> SEQ ID NO 1
<211> LENGTH: 5118
<212> TYPE: DNA
<213> ORGANISM: Homo sapiens

<400> SEQUENCE: 1

ggggcgggac gggaggcggt gcgtcgctga gcgcaggccg cggcggccgc ggagtatcct      60

ggagctgcag acagtgcggg cctgcgccca gtcccggctg tcctcgccgc gacccctcct     120

cagccctggg cgcgcgcacg ctggggcccc gcggggctgg ccgcctagcg agcctgccgg     180

tcgaccccag ccagcgcagc gacggggcgc tgcctggccc aggcgcacac ggaagtgcgc     240
```

-continued

```
ttctctgaag tagctttgga aagtagagaa gaaaatccag tttgcttctt ggagaacact    300
ggacagctga ataaatgcag tatctaaata taaaagagga ctgcaatgcc atggctttct    360
gtgctaaaat gaggagctcc aagaagactg aggtgaacct ggaggcccct gagccagggg    420
tggaagtgat cttctatctg tcggacaggg agcccctccg gctgggcagt ggagagtaca    480
cagcagagga actgtgcatc agggctgcac aggcatgccg tatctctcct ctttgtcaca    540
acctctttgc cctgtatgac gagaacacca agctctggta tgctccaaat cgcaccatca    600
ccgttgatga caagatgtcc ctccggctcc actaccggat gaggttctat ttcaccaatt    660
ggcatggaac caacgacaat gagcagtcag tgtggcgtca ttctccaaag aagcagaaaa    720
atggctacga gaaaaaaaag attccagatg caacccctct ccttgatgcc agctcactgg    780
agtatctgtt tgctcaggga cagtatgatt tggtgaaatg cctggctcct attcgagacc    840
ccaagaccga gcaggatgga catgatattg agaacgagtg tctagggatg gctgtcctgg    900
ccatctcaca ctatgccatg atgaagaaga tgcagttgcc agaactgccc aaggacatca    960
gctacaagcg atatattcca gaaacattga ataagtccat cagacagagg aaccttctca   1020
ccaggatgcg gataaataat gttttcaagg atttcctaaa ggaatttaac aacaagacca   1080
tttgtgacag cagcgtgtcc acgcatgacc tgaaggtgaa atacttggct accttggaaa   1140
ctttgacaaa acattacggt gctgaaatat ttgagacttc catgttactg atttcatcag   1200
aaaatgagat gaattggttt cattcgaatg acggtggaaa cgttctctac tacgaagtga   1260
tggtgactgg gaatcttgga atccagtgga ggcataaacc aaatgttgtt tctgttgaaa   1320
aggaaaaaaa taaactgaag cggaaaaaac tggaaaataa acacaagaag gatgaggaga   1380
aaaacaagat ccgggaagag tggaacaatt tttcttactt ccctgaaatc actcacattg   1440
taataaagga gtctgtggtc agcattaaca agcaggacaa caagaaaatg gaactgaagc   1500
tctcttccca cgaggaggcc ttgtcctttg tgtccctggt agatggctac ttccggctca   1560
cagcagatgc ccatcattac ctctgcaccg acgtggcccc cccgttgatc gtccacaaca   1620
tacagaatgg ctgtcatggt ccaatctgta cagaatacgc catcaataaa ttgcggcaag   1680
aaggaagcga ggaggggatg tacgtgctga ggtggagctg caccgacttt gacaacatcc   1740
tcatgaccgt cacctgcttt gagaagtctg agcaggtgca gggtgcccag aagcagttca   1800
agaactttca gatcgaggtg cagaagggcc gctacagtct gcacggttcg gaccgcagct   1860
tccccagctt gggagacctc atgagccacc tcaagaagca gatcctgcgc acggataaca   1920
tcagcttcat gctaaaacgc tgctgccagc ccaagccccg agaaatctcc aacctgctgg   1980
tggctactaa gaaagcccag gagtggcagc ccgtctaccc catgagccag ctgagtttcg   2040
atcggatcct caagaaggat ctggtgcagg gcgagcacct tgggagaggc acgagaacac   2100
acatctattc tgggaccctg atggattaca aggatgacga aggaacttct gaagagaaga   2160
agataaaagt gatcctcaaa gtcttagacc ccagccacag ggatatttcc ctggccttct   2220
tcgaggcagc cagcatgatg agacaggtct cccacaaaca catcgtgtac ctctatggcg   2280
tctgtgtccg cgacgtggag aatatcatgg tggaagagtt tgtggaaggg ggtcctctgg   2340
atctcttcat gcaccggaaa agcgatgtcc ttaccacacc atggaaattc aaagttgcca   2400
aacagctggc cagtgccctg agctacttgg aggataaaga cctggtccat ggaaatgtgt   2460
gtactaaaaa cctcctcctg gcccgtgagg gcatcgacag tgagtgtggc ccattcatca   2520
agctcagtga ccccggcatc cccattacgg tgctgtctag gcaagaatgc attgaacgaa   2580
```

-continued

```
tcccatggat tgctcctgag tgtgttgagg actccaagaa cctgagtgtg gctgctgaca   2640
agtggagctt tggaaccacg ctctgggaaa tctgctacaa tggcgagatc cccttgaaag   2700
acaagacgct gattgagaaa gagagattct atgaaagccg gtgcaggcca gtgacaccat   2760
catgtaagga gctggctgac ctcatgaccc gctgcatgaa ctatgacccc aatcagaggc   2820
ctttcttccg agccatcatg agagacatta ataagcttga agagcagaat ccagatattg   2880
tttcagaaaa aaaaccagca actgaagtgg accccacaca ttttgaaaag cgcttcctaa   2940
agaggatccg tgacttggga gagggccact ttgggaaggt tgagctctgc aggtatgacc   3000
ccgaagggga caatacaggg gagcaggtgg ctgttaaatc tctgaagcct gagagtggag   3060
gtaaccacat agctgatctg aaaaaggaaa tcgagatctt aaggaacctc tatcatgaga   3120
acattgtgaa gtacaaagga atctgcacag aagacggagg aaatggtatt aagctcatca   3180
tggaatttct gccttcggga agccttaagg aatatcttcc aaagaataag aacaaaataa   3240
acctcaaaca gcagctaaaa tatgccgttc agatttgtaa ggggatggac tatttgggtt   3300
ctcggcaata cgttcaccgg gacttggcag caagaaatgt ccttgttgag agtgaacacc   3360
aagtgaaaat tggagacttc ggtttaacca aagcaattga aaccgataag gagtattaca   3420
ccgtcaagga tgaccgggac agccctgtgt tttggtatgc tccagaatgt ttaatgcaat   3480
ctaaatttta tattgcctct gacgtctggt cttttggagt cactctgcat gagctgctga   3540
cttactgtga ttcagattct agtcccatgg ctttgttcct gaaaatgata ggcccaaccc   3600
atggccagat gacagtcaca agacttgtga atacgttaaa agaaggaaaa cgcctgccgt   3660
gcccacctaa ctgtccagat gaggtttatc aacttatgag gaaatgctgg gaattccaac   3720
catccaatcg gacaagcttt cagaacctta ttgaaggatt tgaagcactt ttaaaataag   3780
aagcatgaat aacatttaaa ttccacagat tatcaagtcc ttctcctgca acaaatgccc   3840
aagtcatttt ttaaaaattt ctaatgaaag aagtttgtgt tctgtccaaa aagtcactga   3900
actcatactt cagtacatat acatgtataa ggcacactgt agtgcttaat atgtgtaagg   3960
acttcctctt taaatttggt accagtaact tagtgacaca taatgacaac caaaatattt   4020
gaaagcactt aagcactcct ccttgtggaa agaatatacc accatttcat ctggctagtt   4080
caccatcaca actgcattac caaaagggga tttttgaaaa cgaggagttg accaaaataa   4140
tatctgaaga tgattgcttt tccctgctgc cagctgatct gaaatgtttt gctggcacat   4200
taatcataga taaagaaaga ttgatggact tagccctcaa atttcagtat ctatacagta   4260
ctagaccatg cattcttaaa atattagata ccaggtagta tatattgttt ctgtacaaaa   4320
atgactgtat tctctcacca gtaggactta aactttgttt ctccagtggc ttagctcctg   4380
ttcctttggg tgatcactag cacccatttt tgagaaagct ggttctacat ggggggatag   4440
ctgtggaata gataatttgc tgcatgttaa ttctcaagaa ctaagcctgt gccagtgctt   4500
tcctaagcag tataccttta atcagaactc attcccagaa cctggatgct attacacatg   4560
cttttaagaa acgtcaatgt atatcctttt ataactctac cactttgggg caagctattc   4620
cagcactggt tttgaatgct gtatgcaacc agtctgaata ccacatacgc tgcactgttc   4680
ttagagggtt tccatactta ccaccgatct acaagggttg atccctgttt ttaccatcaa   4740
tcatcaccct gtggtgcaac acttgaaaga cccggctaga ggcactatgg acttcaggat   4800
ccactagaca gttttcagtt tgcttggagg tagctgggta atcaaaaatg tttagtcatt   4860
gattcaatgt gaacgattac ggtctttatg accaagagtc tgaaaatctt tttgttatgc   4920
tgtttagtat tcgtttgata ttgttacttt tcacctgttg agcccaaatt caggattggt   4980
```

-continued

```
tcagtggcag caatgaagtt gccatttaaa tttgttcata gcctacatca ccaaggtctc   5040

tgtgtcaaac ctgtggccac tctatatgca ctttgtttac tctttataca aataaatata   5100

ctaaagactt tacatgca                                                 5118


<210> SEQ ID NO 2
<211> LENGTH: 5021
<212> TYPE: DNA
<213> ORGANISM: Homo sapiens

<400> SEQUENCE: 2

agaagcggag cgtatacgga ggaggcggga tgcatttctg catcgagcgc acaaagttat     60

ctaaaacagt tcatgctgct gaaaacctcc ttcctggcag atgtccctca accctactgg    120

tgcctggctt ctgagacaca cgcttctctg aagtagcttt ggaaagtaga gaagaaaatc    180

cagtttgctt cttggagaac actggacagc tgaataaatg cagtatctaa atataaaaga    240

ggactgcaat gccatggctt tctgtgctaa aatgaggagc tccaagaaga ctgaggtgaa    300

cctggaggcc cctgagccag gggtggaagt gatcttctat ctgtcggaca gggagcccct    360

ccggctgggc agtggagagt acacagcaga ggaactgtgc atcagggctg cacaggcatg    420

ccgtatctct cctctttgtc acaacctctt tgccctgtat gacgagaaca ccaagctctg    480

gtatgctcca aatcgcacca tcaccgttga tgacaagatg tccctccggc tccactaccg    540

gatgaggttc tatttcacca attggcatgg aaccaacgac aatgagcagt cagtgtggcg    600

tcattctcca aagaagcaga aaaatggcta cgagaaaaaa aagattccag atgcaacccc    660

tctccttgat gccagctcac tggagtatct gtttgctcag ggacagtatg atttggtgaa    720

atgcctggct cctattcgag accccaagac cgagcaggat ggacatgata ttgagaacga    780

gtgtctaggg atggctgtcc tggccatctc acactatgcc atgatgaaga agatgcagtt    840

gccagaactg cccaaggaca tcagctacaa gcgatatatt ccagaaacat tgaataagtc    900

catcagacag aggaaccttc tcaccaggat gcggataaat aatgttttca aggatttcct    960

aaaggaattt aacaacaaga ccatttgtga cagcagcgtg tccacgcatg acctgaaggt   1020

gaaatacttg gctaccttgg aaactttgac aaaacattac ggtgctgaaa tatttgagac   1080

ttccatgtta ctgatttcat cagaaaatga gatgaattgg tttcattcga atgacggtgg   1140

aaacgttctc tactacgaag tgatggtgac tgggaatctt ggaatccagt ggaggcataa   1200

accaaatgtt gtttctgttg aaaaggaaaa aaataaactg aagcggaaaa aactggaaaa   1260

taaacacaag aaggatgagg agaaaaacaa gatccgggaa gagtggaaca atttttctta   1320

cttccctgaa atcactcaca ttgtaataaa ggagtctgtg gtcagcatta acaagcagga   1380

caacaagaaa atggaactga agctctcttc ccacgaggag gccttgtcct ttgtgtccct   1440

ggtagatggc tacttccggc tcacagcaga tgcccatcat tacctctgca ccgacgtggc   1500

ccccccgttg atcgtccaca acatacagaa tggctgtcat ggtccaatct gtacagaata   1560

cgccatcaat aaattgcggc aagaaggaag cgaggagggg atgtacgtgc tgaggtggag   1620

ctgcaccgac tttgacaaca tcctcatgac cgtcacctgc tttgagaagt ctgagcaggt   1680

gcagggtgcc cagaagcagt tcaagaactt tcagatcgag gtgcagaagg gccgctacag   1740

tctgcacggt tcggaccgca gcttccccag cttgggagac ctcatgagcc acctcaagaa   1800

gcagatcctg cgcacggata acatcagctt catgctaaaa cgctgctgcc agcccaagcc   1860

ccgagaaatc tccaacctgc tggtggctac taagaaagcc caggagtggc agcccgtcta   1920
```

-continued

```
ccccatgagc cagctgagtt tcgatcggat cctcaagaag gatctggtgc agggcgagca   1980
ccttgggaga ggcacgagaa cacacatcta ttctgggacc ctgatggatt acaaggatga   2040
cgaaggaact tctgaagaga agaagataaa agtgatcctc aaagtcttag accccagcca   2100
cagggatatt tccctggcct tcttcgaggc agccagcatg atgagacagg tctcccacaa   2160
acacatcgtg tacctctatg gcgtctgtgt ccgcgacgtg gagaatatca tggtggaaga   2220
gtttgtggaa gggggtcctc tggatctctt catgcaccgg aaaagcgatg tccttaccac   2280
accatggaaa ttcaaagttg ccaaacagct ggccagtgcc ctgagctact tggaggataa   2340
agacctggtc catggaaatg tgtgtactaa aaacctcctc ctggcccgtg agggcatcga   2400
cagtgagtgt ggcccattca tcaagctcag tgaccccggc atccccatta cggtgctgtc   2460
taggcaagaa tgcattgaac gaatcccatg gattgctcct gagtgtgttg aggactccaa   2520
gaacctgagt gtggctgctg acaagtggag ctttggaacc acgctctggg aaatctgcta   2580
caatggcgag atccccttga aagacaagac gctgattgag aaagagagat tctatgaaag   2640
ccggtgcagg ccagtgacac catcatgtaa ggagctggct gacctcatga cccgctgcat   2700
gaactatgac cccaatcaga ggcctttctt ccgagccatc atgagagaca ttaataagct   2760
tgaagagcag aatccagata ttgtttcaga aaaaaaacca gcaactgaag tggaccccac   2820
acattttgaa aagcgcttcc taaagaggat ccgtgacttg ggagagggcc actttgggaa   2880
ggttgagctc tgcaggtatg accccgaagg ggacaataca ggggagcagg tggctgttaa   2940
atctctgaag cctgagagtg gaggtaacca catagctgat ctgaaaaagg aaatcgagat   3000
cttaaggaac ctctatcatg agaacattgt gaagtacaaa ggaatctgca cagaagacgg   3060
aggaaatggt attaagctca tcatggaatt tctgccttcg ggaagcctta aggaatatct   3120
tccaaagaat aagaacaaaa taaacctcaa acagcagcta aaatatgccg ttcagatttg   3180
taaggggatg gactatttgg gttctcggca atacgttcac cgggacttgg cagcaagaaa   3240
tgtccttgtt gagagtgaac accaagtgaa aattggagac ttcggtttaa ccaaagcaat   3300
tgaaaccgat aaggagtatt acaccgtcaa ggatgaccgg gacagccctg tgttttggta   3360
tgctccagaa tgtttaatgc aatctaaatt ttatattgcc tctgacgtct ggtcttttgg   3420
agtcactctg catgagctgc tgacttactg tgattcagat tctagtccca tggctttgtt   3480
cctgaaaatg ataggcccaa cccatggcca gatgacagtc acaagacttg tgaatacgtt   3540
aaaagaagga aaacgcctgc cgtgcccacc taactgtcca gatgaggttt atcaacttat   3600
gaggaaatgc tgggaattcc aaccatccaa tcggacaagc tttcagaacc ttattgaagg   3660
atttgaagca cttttaaaat aagaagcatg aataacattt aaattccaca gattatcaag   3720
tccttctcct gcaacaaatg cccaagtcat ttttaaaaa tttctaatga aagaagtttg   3780
tgttctgtcc aaaaagtcac tgaactcata cttcagtaca tatacatgta taaggcacac   3840
tgtagtgctt aatatgtgta aggacttcct ctttaaattt ggtaccagta acttagtgac   3900
acataatgac aaccaaaata tttgaaagca cttaagcact cctccttgtg gaaagaatat   3960
accaccattt catctggcta gttcaccatc acaactgcat taccaaaagg ggatttttga   4020
aaacgaggag ttgaccaaaa taatatctga agatgattgc ttttccctgc tgccagctga   4080
tctgaaatgt tttgctggca cattaatcat agataaagaa agattgatgg acttagccct   4140
caaatttcag tatctataca gtactagacc atgcattctt aaaatattag ataccaggta   4200
gtatatattg tttctgtaca aaaatgactg tattctctca ccagtaggac ttaaactttg   4260
tttctccagt ggcttagctc ctgttccttt gggtgatcac tagcacccat tttgagaaa    4320
```

gctggttcta catgggggga tagctgtgga atagataatt tgctgcatgt taattctcaa 4380
gaactaagcc tgtgccagtg ctttcctaag cagtatacct ttaatcagaa ctcattccca 4440
gaacctggat gctattacac atgcttttaa gaaacgtcaa tgtatatcct tttataactc 4500
taccactttg gggcaagcta ttccagcact ggttttgaat gctgtatgca accagtctga 4560
ataccacata cgctgcactg ttcttagagg gtttccatac ttaccaccga tctacaaggg 4620
ttgatccctg tttttaccat caatcatcac cctgtggtgc aacacttgaa agacccggct 4680
agaggcacta tggacttcag gatccactag acagttttca gtttgcttgg aggtagctgg 4740
gtaatcaaaa atgtttagtc attgattcaa tgtgaacgat tacggtcttt atgaccaaga 4800
gtctgaaaat ctttttgtta tgctgtttag tattcgtttg atattgttac ttttcacctg 4860
ttgagcccaa attcaggatt ggttcagtgg cagcaatgaa gttgccattt aaatttgttc 4920
atagcctaca tcaccaaggt ctctgtgtca aacctgtggc cactctatat gcactttgtt 4980
tactctttat acaaataaat atactaaaga ctttacatgc a 5021

<210> SEQ ID NO 3
<211> LENGTH: 5024
<212> TYPE: DNA
<213> ORGANISM: Homo sapiens

<400> SEQUENCE: 3
atctatcaca tggcagagat agaataaaaa cagaaaaatg gcgacggtca cgttgtggcg 60
agccttgctg cgtcattaga taatcctcat gcaaatagcg ggaagaacaa aggaagggga 120
gcccgggacc cccgggggcg cagcgcttct ctgaagtagc tttggaaagt agagaagaaa 180
atccagtttg cttcttggag aacactggac agctgaataa atgcagtatc taaatataaa 240
agaggactgc aatgccatgg ctttctgtgc taaaatgagg agctccaaga agactgaggt 300
gaacctggag gcccctgagc caggggtgga agtgatcttc tatctgtcgg acagggagcc 360
cctccggctg ggcagtggag agtacacagc agaggaactg tgcatcaggg ctgcacaggc 420
atgccgtatc tctcctcttt gtcacaacct ctttgccctg tatgacgaga acaccaagct 480
ctggtatgct ccaaatcgca ccatcaccgt tgatgacaag atgtccctcc ggctccacta 540
ccggatgagg ttctatttca ccaattggca tggaaccaac gacaatgagc agtcagtgtg 600
gcgtcattct ccaaagaagc agaaaaatgg ctacgagaaa aaaaagattc cagatgcaac 660
ccctctcctt gatgccagct cactggagta tctgtttgct cagggacagt atgatttggt 720
gaaatgcctg gctcctattc gagaccccaa gaccgagcag gatggacatg atattgagaa 780
cgagtgtcta gggatggctg tcctggccat ctcacactat gccatgatga agaagatgca 840
gttgccagaa ctgcccaagg acatcagcta caagcgatat attccagaaa cattgaataa 900
gtccatcaga cagaggaacc ttctcaccag gatgcggata aataatgttt tcaaggattt 960
cctaaaggaa tttaacaaca agaccatttg tgacagcagc gtgtccacgc atgacctgaa 1020
ggtgaaatac ttggctacct tggaaacttt gacaaaacat tacggtgctg aaatatttga 1080
gacttccatg ttactgattt catcagaaaa tgagatgaat tggtttcatt cgaatgacgg 1140
tggaaacgtt ctctactacg aagtgatggt gactgggaat cttggaatcc agtggaggca 1200
taaaccaaat gttgtttctg ttgaaaagga aaaaaataaa ctgaagcgga aaaaactgga 1260
aaataaacac aagaaggatg aggagaaaaa caagatccgg gaagagtgga acaatttttc 1320
ttacttccct gaaatcactc acattgtaat aaaggagtct gtggtcagca ttaacaagca 1380

-continued

```
ggacaacaag aaaatggaac tgaagctctc ttcccacgag gaggccttgt cctttgtgtc   1440
cctggtagat ggctacttcc ggctcacagc agatgcccat cattacctct gcaccgacgt   1500
ggcccccccg ttgatcgtcc acaacataca gaatggctgt catggtccaa tctgtacaga   1560
atacgccatc aataaattgc ggcaagaagg aagcgaggag gggatgtacg tgctgaggtg   1620
gagctgcacc gactttgaca acatcctcat gaccgtcacc tgctttgaga agtctgagca   1680
ggtgcagggt gcccagaagc agttcaagaa ctttcagatc gaggtgcaga agggccgcta   1740
cagtctgcac ggttcggacc gcagcttccc cagcttggga gacctcatga gccacctcaa   1800
gaagcagatc ctgcgcacgg ataacatcag cttcatgcta aaacgctgct gccagcccaa   1860
gccccgagaa atctccaacc tgctggtggc tactaagaaa gcccaggagt ggcagcccgt   1920
ctaccccatg agccagctga gtttcgatcg gatcctcaag aaggatctgg tgcagggcga   1980
gcaccttggg agaggcacga gaacacacat ctattctggg accctgatgg attacaagga   2040
tgacgaagga acttctgaag agaagaagat aaaagtgatc ctcaaagtct tagaccccag   2100
ccacagggat atttccctgg ccttcttcga ggcagccagc atgatgagac aggtctccca   2160
caaacacatc gtgtacctct atggcgtctg tgtccgcgac gtggagaata tcatggtgga   2220
agagtttgtg gaagggggtc ctctggatct cttcatgcac cggaaaagcg atgtccttac   2280
cacaccatgg aaattcaaag ttgccaaaca gctggccagt gccctgagct acttggagga   2340
taaagacctg gtccatggaa atgtgtgtac taaaaacctc ctcctggccc gtgagggcat   2400
cgacagtgag tgtggcccat tcatcaagct cagtgacccc ggcatcccca ttacggtgct   2460
gtctaggcaa gaatgcattg aacgaatccc atggattgct cctgagtgtg ttgaggactc   2520
caagaacctg agtgtggctg ctgacaagtg gagctttgga accacgctct gggaaatctg   2580
ctacaatggc gagatcccct tgaaagacaa gacgctgatt gagaaagaga gattctatga   2640
aagccggtgc aggccagtga caccatcatg taaggagctg gctgacctca tgacccgctg   2700
catgaactat gaccccaatc agaggccttt cttccgagcc atcatgagag acattaataa   2760
gcttgaagag cagaatccag atattgtttc agaaaaaaaa ccagcaactg aagtggaccc   2820
cacacatttt gaaaagcgct tcctaaagag gatccgtgac ttgggagagg gccactttgg   2880
gaaggttgag ctctgcaggt atgaccccga aggggacaat acaggggagc aggtggctgt   2940
taaatctctg aagcctgaga gtggaggtaa ccacatagct gatctgaaaa aggaaatcga   3000
gatcttaagg aacctctatc atgagaacat tgtgaagtac aaaggaatct gcacagaaga   3060
cggaggaaat ggtattaagc tcatcatgga atttctgcct tcgggaagcc ttaaggaata   3120
tcttccaaag aataagaaca aaataaacct caaacagcag ctaaaatatg ccgttcagat   3180
ttgtaagggg atggactatt tgggttctcg gcaatacgtt caccgggact tggcagcaag   3240
aaatgtcctt gttgagagtg aacaccaagt gaaaattgga gacttcggtt taaccaaagc   3300
aattgaaacc gataaggagt attacaccgt caaggatgac cgggacagcc ctgtgttttg   3360
gtatgctcca gaatgtttaa tgcaatctaa attttatatt gcctctgacg tctggtcttt   3420
tggagtcact ctgcatgagc tgctgactta ctgtgattca gattctagtc ccatggcttt   3480
gttcctgaaa atgataggcc caacccatgg ccagatgaca gtcacaagac ttgtgaatac   3540
gttaaaagaa ggaaaacgcc tgccgtgccc acctaactgt ccagatgagg tttatcaact   3600
tatgaggaaa tgctgggaat tccaaccatc caatcggaca agctttcaga accttattga   3660
aggatttgaa gcacttttaa aataagaagc atgaataaca tttaaattcc acagattatc   3720
aagtccttct cctgcaacaa atgcccaagt catttttttaa aaatttctaa tgaaagaagt   3780
```

```
ttgtgttctg tccaaaaagt cactgaactc atacttcagt acatatacat gtataaggca   3840
cactgtagtg cttaatatgt gtaaggactt cctctttaaa tttggtacca gtaacttagt   3900
gacacataat gacaaccaaa atatttgaaa gcacttaagc actcctcctt gtggaaagaa   3960
tataccacca tttcatctgg ctagttcacc atcacaactg cattaccaaa aggggatttt   4020
tgaaaacgag gagttgacca aaataatatc tgaagatgat tgcttttccc tgctgccagc   4080
tgatctgaaa tgttttgctg gcacattaat catagataaa gaaagattga tggacttagc   4140
cctcaaattt cagtatctat acagtactag accatgcatt cttaaaatat tagataccag   4200
gtagtatata ttgtttctgt acaaaaatga ctgtattctc tcaccagtag gacttaaact   4260
ttgtttctcc agtggcttag ctcctgttcc tttgggtgat cactagcacc catttttgag   4320
aaagctggtt ctacatgggg ggatagctgt ggaatagata atttgctgca tgttaattct   4380
caagaactaa gcctgtgcca gtgctttcct aagcagtata cctttaatca gaactcattc   4440
ccagaacctg gatgctatta cacatgcttt taagaaacgt caatgtatat ccttttataa   4500
ctctaccact ttggggcaag ctattccagc actggttttg aatgctgtat gcaaccagtc   4560
tgaataccac atacgctgca ctgttcttag agggtttcca tacttaccac cgatctacaa   4620
gggttgatcc ctgtttttac catcaatcat caccctgtgg tgcaacactt gaaagacccg   4680
gctagaggca ctatggactt caggatccac tagacagttt tcagtttgct tggaggtagc   4740
tgggtaatca aaaatgttta gtcattgatt caatgtgaac gattacggtc tttatgacca   4800
agagtctgaa aatctttttg ttatgctgtt tagtattcgt ttgatattgt tacttttcac   4860
ctgttgagcc caaattcagg attggttcag tggcagcaat gaagttgcca tttaaatttg   4920
ttcatagcct acatcaccaa ggtctctgtg tcaaacctgt ggccactcta tatgcacttt   4980
gtttactctt tatacaaata aatatactaa agactttaca tgca                    5024
```

<210> SEQ ID NO 4
<211> LENGTH: 5283
<212> TYPE: DNA
<213> ORGANISM: Homo sapiens

<400> SEQUENCE: 4

```
atctatcaca tggcagagat agaataaaaa cagaaaaatg gcgacggtca cgttgtggcg     60
agccttgctg cgtcattaga taatcctcat gcaaatagcg ggaagaacaa aggaagggga    120
gcccgggacc cccgggggcg caggatccgg cgggaggagt ctaagaggag gaggcggcgg    180
tgccggagga ggaggaggag ggagggagaa gagaggaaga ccggagtccc cgcggcggcg    240
gcggtccgga gagagggcga gccccgcgcg gcgccgggga ccgggcgcta ccacgaggcc    300
gggacgctgg agtctgggtt atctaaaaca gttcatgctg ctgaaaacct ccttcctggc    360
agatgtccct caaccctact ggtgcctggc ttctgagaca cacgcttctc tgaagtagct    420
ttggaaagta gagaagaaaa tccagtttgc ttcttggaga acactggaca gctgaataaa    480
tgcagtatct aaatataaaa gaggactgca atgccatggc tttctgtgct aaaatgagga    540
gctccaagaa gactgaggtg aacctggagg cccctgagcc aggggtggaa gtgatcttct    600
atctgtcgga cagggagccc ctccggctgg gcagtggaga gtacacagca gaggaactgt    660
gcatcagggc tgcacaggca tgccgtatct ctcctctttg tcacaacctc tttgccctgt    720
atgacgagaa caccaagctc tggtatgctc caaatcgcac catcaccgtt gatgacaaga    780
tgtccctccg gctccactac cggatgaggt tctatttcac caattggcat ggaaccaacg    840
```

-continued

```
acaatgagca gtcagtgtgg cgtcattctc caaagaagca gaaaaatggc tacgagaaaa    900
aaaagattcc agatgcaacc cctctccttg atgccagctc actggagtat ctgtttgctc    960
agggacagta tgatttggtg aaatgcctgg ctcctattcg agaccccaag accgagcagg   1020
atggacatga tattgagaac gagtgtctag ggatggctgt cctggccatc tcacactatg   1080
ccatgatgaa gaagatgcag ttgccagaac tgcccaagga catcagctac aagcgatata   1140
ttccagaaac attgaataag tccatcagac agaggaacct tctcaccagg atgcggataa   1200
ataatgtttt caaggatttc ctaaaggaat ttaacaacaa gaccatttgt gacagcagcg   1260
tgtccacgca tgacctgaag gtgaaatact tggctacctt ggaaactttg acaaaacatt   1320
acggtgctga aatatttgag acttccatgt tactgatttc atcagaaaat gagatgaatt   1380
ggtttcattc gaatgacggt ggaaacgttc tctactacga agtgatggtg actgggaatc   1440
ttggaatcca gtggaggcat aaaccaaatg ttgtttctgt tgaaaaggaa aaaaataaac   1500
tgaagcggaa aaaactggaa aataaacaca agaaggatga ggagaaaaac aagatccggg   1560
aagagtggaa caatttttct tacttccctg aaatcactca cattgtaata aaggagtctg   1620
tggtcagcat taacaagcag gacaacaaga aaatggaact gaagctctct tcccacgagg   1680
aggccttgtc ctttgtgtcc ctggtagatg gctacttccg gctcacagca gatgcccatc   1740
attacctctg caccgacgtg gcccccccgt tgatcgtcca caacatacag aatggctgtc   1800
atggtccaat ctgtacagaa tacgccatca ataaattgcg gcaagaagga agcgaggagg   1860
ggatgtacgt gctgaggtgg agctgcaccg actttgacaa catcctcatg accgtcacct   1920
gctttgagaa gtctgagcag gtgcagggtg cccagaagca gttcaagaac tttcagatcg   1980
aggtgcagaa gggccgctac agtctgcacg gttcggaccg cagcttcccc agcttgggag   2040
acctcatgag ccacctcaag aagcagatcc tgcgcacgga taacatcagc ttcatgctaa   2100
aacgctgctg ccagcccaag ccccgagaaa tctccaacct gctggtggct actaagaaag   2160
cccaggagtg gcagcccgtc taccccatga gccagctgag tttcgatcgg atcctcaaga   2220
aggatctggt gcagggcgag caccttggga gaggcacgag aacacacatc tattctggga   2280
ccctgatgga ttacaaggat gacgaaggaa cttctgaaga gaagaagata aaagtgatcc   2340
tcaaagtctt agaccccagc cacagggata tttccctggc cttcttcgag gcagccagca   2400
tgatgagaca ggtctcccac aaacacatcg tgtacctcta tggcgtctgt gtccgcgacg   2460
tggagaatat catggtggaa gagtttgtgg aaggggggtcc tctggatctc ttcatgcacc  2520
ggaaaagcga tgtccttacc acaccatgga aattcaaagt tgccaaacag ctggccagtg   2580
ccctgagcta cttggaggat aaagacctgg tccatggaaa tgtgtgtact aaaaacctcc   2640
tcctggcccg tgagggcatc gacagtgagt gtggcccatt catcaagctc agtgaccccg   2700
gcatccccat tacggtgctg tctaggcaag aatgcattga acgaatccca tggattgctc   2760
ctgagtgtgt tgaggactcc aagaacctga gtgtggctgc tgacaagtgg agctttggaa   2820
ccacgctctg ggaaatctgc tacaatggcg agatcccctt gaaagacaag acgctgattg   2880
agaaagagag attctatgaa agccggtgca ggccagtgac accatcatgt aaggagctgg   2940
ctgacctcat gacccgctgc atgaactatg accccaatca gaggcctttc ttccgagcca   3000
tcatgagaga cattaataag cttgaagagc agaatccaga tattgtttca gaaaaaaaac   3060
cagcaactga agtggacccc acacattttg aaaagcgctt cctaaagagg atccgtgact   3120
tgggagaggg ccactttggg aaggttgagc tctgcaggta tgaccccgaa ggggacaata   3180
caggggagca ggtggctgtt aaatctctga agcctgagag tggaggtaac cacatagctg   3240
```

-continued atctgaaaaa ggaaatcgag atcttaagga acctctatca tgagaacatt gtgaagtaca 3300
aaggaatctg cacagaagac ggaggaaatg gtattaagct catcatggaa tttctgcctt 3360
cgggaagcct taaggaatat cttccaaaga ataagaacaa aataaacctc aaacagcagc 3420
taaaatatgc cgttcagatt tgtaagggga tggactattt gggttctcgg caatacgttc 3480
accgggactt ggcagcaaga aatgtccttg ttgagagtga acaccaagtg aaaattggag 3540
acttcggttt aaccaaagca attgaaaccg ataaggagta ttacaccgtc aaggatgacc 3600
gggacagccc tgtgttttgg tatgctccag aatgtttaat gcaatctaaa ttttatattg 3660
cctctgacgt ctggtctttt ggagtcactc tgcatgagct gctgacttac tgtgattcag 3720
attctagtcc catggctttg ttcctgaaaa tgataggccc aacccatggc cagatgacag 3780
tcacaagact tgtgaatacg ttaaaagaag gaaaacgcct gccgtgccca cctaactgtc 3840
cagatgaggt ttatcaactt atgaggaaat gctgggaatt ccaaccatcc aatcggacaa 3900
gctttcagaa ccttattgaa ggatttgaag cacttttaaa ataagaagca tgaataacat 3960
ttaaattcca cagattatca agtccttctc ctgcaacaaa tgcccaagtc atttttttaaa 4020 aatttctaat gaaagaagtt tgtgttctgt ccaaaaagtc actgaactca tacttcagta 4080
catatacatg tataaggcac actgtagtgc ttaatatgtg taaggacttc ctctttaaat 4140
ttggtaccag taacttagtg acacataatg acaaccaaaa tatttgaaag cacttaagca 4200
ctcctccttg tggaaagaat ataccaccat ttcatctggc tagttcacca tcacaactgc 4260
attaccaaaa ggggattttt gaaaacgagg agttgaccaa aataatatct gaagatgatt 4320
gcttttccct gctgccagct gatctgaaat gttttgctgg cacattaatc atagataaag 4380
aaagattgat ggacttagcc ctcaaatttc agtatctata cagtactaga ccatgcattc 4440
ttaaaatatt agataccagg tagtatatat tgtttctgta caaaaatgac tgtattctct 4500
caccagtagg acttaaactt tgtttctcca gtggcttagc tcctgttcct ttgggtgatc 4560
actagcaccc atttttgaga aagctggttc tacatggggg gatagctgtg gaatagataa 4620
tttgctgcat gttaattctc aagaactaag cctgtgccag tgctttccta agcagtatac 4680
ctttaatcag aactcattcc cagaacctgg atgctattac acatgctttt aagaaacgtc 4740
aatgtatatc cttttataac tctaccactt tggggcaagc tattccagca ctggttttga 4800
atgctgtatg caaccagtct gaataccaca tacgctgcac tgttcttaga gggtttccat 4860
acttaccacc gatctacaag ggttgatccc tgtttttacc atcaatcatc accctgtggt 4920
gcaacacttg aaagacccgg ctagaggcac tatggacttc aggatccact agacagtttt 4980
cagtttgctt ggaggtagct gggtaatcaa aaatgtttag tcattgattc aatgtgaacg 5040
attacggtct ttatgaccaa gagtctgaaa atctttttgt tatgctgttt agtattcgtt 5100
tgatattgtt acttttcacc tgttgagccc aaattcagga ttggttcagt ggcagcaatg 5160
aagttgccat ttaaatttgt tcatagccta catcaccaag gtctctgtgt caaacctgtg 5220
gccactctat atgcactttg tttactcttt atacaaataa atatactaaa gactttacat 5280
gca 5283

<210> SEQ ID NO 5
<211> LENGTH: 5199
<212> TYPE: DNA
<213> ORGANISM: Homo sapiens

<400> SEQUENCE: 5

-continued

```
atctatcaca tggcagagat agaataaaaa cagaaaaatg gcgacggtca cgttgtggcg     60
agccttgctg cgtcattaga taatcctcat gcaaatagcg ggaagaacaa aggaagggga    120
gcccgggacc cccgggggcg caggatccgg cgggaggagt ctaagaggag gaggcggcgg    180
tgccggagga ggaggaggag ggagggagaa gagaggaaga ccggagtccc cgcggcggcg    240
gcggtccgga gagagggcga gccccgcgcg gcgccgggga ccgggcgcta ccacgaggcc    300
gggacgctgg agtctgggcg cttctctgaa gtagctttgg aaagtagaga agaaaatcca    360
gtttgcttct tggagaacac tggacagctg aataaatgca gtatctaaat ataaaagagg    420
actgcaatgc catggctttc tgtgctaaaa tgaggagctc caagaagact gaggtgaacc    480
tggaggcccc tgagccaggg gtggaagtga tcttctatct gtcggacagg gagcccctcc    540
ggctgggcag tggagagtac acagcagagg aactgtgcat cagggctgca caggcatgcc    600
gtatctctcc tctttgtcac aacctctttg ccctgtatga cgagaacacc aagctctggt    660
atgctccaaa tcgcaccatc accgttgatg acaagatgtc cctccggctc cactaccgga    720
tgaggttcta tttcaccaat tggcatggaa ccaacgacaa tgagcagtca gtgtggcgtc    780
attctccaaa gaagcagaaa aatggctacg agaaaaaaaa gattccagat gcaacccctc    840
tccttgatgc cagctcactg gagtatctgt ttgctcaggg acagtatgat ttggtgaaat    900
gcctggctcc tattcgagac cccaagaccg agcaggatgg acatgatatt gagaacgagt    960
gtctagggat ggctgtcctg gccatctcac actatgccat gatgaagaag atgcagttgc   1020
cagaactgcc caaggacatc agctacaagc gatatattcc agaaacattg aataagtcca   1080
tcagacagag gaaccttctc accaggatgc ggataaataa tgttttcaag gatttcctaa   1140
aggaatttaa caacaagacc atttgtgaca gcagcgtgtc cacgcatgac ctgaaggtga   1200
aatacttggc taccttggaa actttgacaa aacattacgg tgctgaaata tttgagactt   1260
ccatgttact gatttcatca gaaaatgaga tgaattggtt tcattcgaat gacggtggaa   1320
acgttctcta ctacgaagtg atggtgactg ggaatcttgg aatccagtgg aggcataaac   1380
caaatgttgt ttctgttgaa aaggaaaaaa ataaactgaa gcggaaaaaa ctggaaaata   1440
aacacaagaa ggatgaggag aaaaacaaga tccgggaaga gtggaacaat ttttcttact   1500
tccctgaaat cactcacatt gtaataaagg agtctgtggt cagcattaac aagcaggaca   1560
acaagaaaat ggaactgaag ctctcttccc acgaggaggc cttgtccttt gtgtccctgg   1620
tagatggcta cttccggctc acagcagatg cccatcatta cctctgcacc gacgtggccc   1680
ccccgttgat cgtccacaac atacagaatg gctgtcatgg tccaatctgt acagaatacg   1740
ccatcaataa attgcggcaa gaaggaagcg aggaggggat gtacgtgctg aggtggagct   1800
gcaccgactt tgacaacatc ctcatgaccg tcacctgctt tgagaagtct gagcaggtgc   1860
agggtgccca gaagcagttc aagaactttc agatcgaggt gcagaagggc cgctacagtc   1920
tgcacggttc ggaccgcagc ttccccagct tgggagacct catgagccac ctcaagaagc   1980
agatcctgcg cacggataac atcagcttca tgctaaaacg ctgctgccag cccaagcccc   2040
gagaaatctc caacctgctg gtggctacta agaaagccca ggagtggcag cccgtctacc   2100
ccatgagcca gctgagtttc gatcggatcc tcaagaagga tctggtgcag ggcgagcacc   2160
ttgggagagg cacgagaaca cacatctatt ctgggaccct gatggattac aaggatgacg   2220
aaggaacttc tgaagagaag aagataaaag tgatcctcaa agtcttagac cccagccaca   2280
gggatatttc cctggccttc ttcgaggcag ccagcatgat gagacaggtc tcccacaaac   2340
acatcgtgta cctctatggc gtctgtgtcc gcgacgtgga gaatatcatg gtggaagagt   2400
```

-continued

```
ttgtggaagg gggtcctctg gatctcttca tgcaccggaa aagcgatgtc cttaccacac   2460
catggaaatt caaagttgcc aaacagctgg ccagtgccct gagctacttg gaggataaag   2520
acctggtcca tggaaatgtg tgtactaaaa acctcctcct ggcccgtgag ggcatcgaca   2580
gtgagtgtgg cccattcatc aagctcagtg accccggcat ccccattacg gtgctgtcta   2640
ggcaagaatg cattgaacga atcccatgga ttgctcctga gtgtgttgag gactccaaga   2700
acctgagtgt ggctgctgac aagtggagct ttggaaccac gctctgggaa atctgctaca   2760
atggcgagat ccccttgaaa gacaagacgc tgattgagaa agagagattc tatgaaagcc   2820
ggtgcaggcc agtgacacca tcatgtaagg agctggctga cctcatgacc cgctgcatga   2880
actatgaccc caatcagagg cctttcttcc gagccatcat gagagacatt aataagcttg   2940
aagagcagaa tccagatatt gtttcagaaa aaaaaccagc aactgaagtg gaccccacac   3000
attttgaaaa gcgcttccta aagaggatcc gtgacttggg agagggccac tttgggaagg   3060
ttgagctctg caggtatgac cccgaagggg acaatacagg ggagcaggtg gctgttaaat   3120
ctctgaagcc tgagagtgga ggtaaccaca tagctgatct gaaaaaggaa atcgagatct   3180
taaggaacct ctatcatgag aacattgtga agtacaaagg aatctgcaca gaagacggag   3240
gaaatggtat taagctcatc atggaatttc tgccttcggg aagccttaag gaatatcttc   3300
caaagaataa gaacaaaata aacctcaaac agcagctaaa atatgccgtt cagatttgta   3360
aggggatgga ctatttgggt tctcggcaat acgttcaccg ggacttggca gcaagaaatg   3420
tccttgttga gagtgaacac caagtgaaaa ttggagactt cggtttaacc aaagcaattg   3480
aaaccgataa ggagtattac accgtcaagg atgaccggga cagccctgtg ttttggtatg   3540
ctccagaatg tttaatgcaa tctaaatttt atattgcctc tgacgtctgg tcttttggag   3600
tcactctgca tgagctgctg acttactgtg attcagattc tagtcccatg gctttgttcc   3660
tgaaaatgat aggcccaacc catggccaga tgacagtcac aagacttgtg aatacgttaa   3720
aagaaggaaa acgcctgccg tgcccaccta actgtccaga tgaggtttat caacttatga   3780
ggaaatgctg ggaattccaa ccatccaatc ggacaagctt tcagaacctt attgaaggat   3840
ttgaagcact ttttaaaataa gaagcatgaa taacatttaa attccacaga ttatcaagtc   3900
cttctcctgc aacaaatgcc caagtcattt tttaaaaatt tctaatgaaa gaagtttgtg   3960
ttctgtccaa aaagtcactg aactcatact tcagtacata tacatgtata aggcacactg   4020
tagtgcttaa tatgtgtaag gacttcctct ttaaatttgg taccagtaac ttagtgacac   4080
ataatgacaa ccaaaatatt tgaaagcact taagcactcc tccttgtgga aagaatatac   4140
caccatttca tctggctagt tcaccatcac aactgcatta ccaaaagggg atttttgaaa   4200
acgaggagtt gaccaaaata atatctgaag atgattgctt ttccctgctg ccagctgatc   4260
tgaaatgttt tgctggcaca ttaatcatag ataaagaaag attgatggac ttagccctca   4320
aatttcagta tctatacagt actagaccat gcattcttaa aatattagat accaggtagt   4380
atatattgtt tctgtacaaa aatgactgta ttctctcacc agtaggactt aaactttgtt   4440
tctccagtgg cttagctcct gttcctttgg gtgatcacta gcacccattt ttgagaaagc   4500
tggttctaca tggggggata gctgtggaat agataatttg ctgcatgtta attctcaaga   4560
actaagcctg tgccagtgct ttcctaagca gtatacctt aatcagaact cattcccaga   4620
acctggatgc tattacacat gcttttaaga aacgtcaatg tatatccttt tataactcta   4680
ccactttggg gcaagctatt ccagcactgg ttttgaatgc tgtatgcaac cagtctgaat   4740
```

accacatacg ctgcactgtt cttagagggt ttccatactt accaccgatc tacaagggtt 4800
gatccctgtt tttaccatca atcatcaccc tgtggtgcaa cacttgaaag acccggctag 4860
aggcactatg gacttcagga tccactagac agttttcagt ttgcttggag gtagctgggt 4920
aatcaaaaat gtttagtcat tgattcaatg tgaacgatta cggtctttat gaccaagagt 4980
ctgaaaatct ttttgttatg ctgtttagta ttcgtttgat attgttactt ttcacctgtt 5040
gagcccaaat tcaggattgg ttcagtggca gcaatgaagt tgccatttaa atttgttcat 5100
agcctacatc accaaggtct ctgtgtcaaa cctgtggcca ctctatatgc actttgttta 5160
ctctttatac aaataaatat actaaagact ttacatgca 5199

<210> SEQ ID NO 6
<211> LENGTH: 5202
<212> TYPE: DNA
<213> ORGANISM: Homo sapiens

<400> SEQUENCE: 6
ggggcgggac gggaggcggt gcgtcgctga gcgcaggccg cggcggccgc ggagtatcct 60
ggagctgcag acagtgcggg cctgcgccca gtcccggctg tcctcgccgc gacccctcct 120
cagccctggg cgcgcgcacg ctggggcccc gcggggctgg ccgcctagcg agcctgccgg 180
tcgaccccag ccagcgcagc gacggggcgc tgcctggccc aggcgcacac ggaagtgtta 240
tctaaaacag ttcatgctgc tgaaaacctc cttcctggca gatgtccctc aaccctactg 300
gtgcctggct tctgagacac acgcttctct gaagtagctt tggaaagtag agaagaaaat 360
ccagtttgct tcttggagaa cactggacag ctgaataaat gcagtatcta aatataaaag 420
aggactgcaa tgccatggct ttctgtgcta aaatgaggag ctccaagaag actgaggtga 480
acctggaggc ccctgagcca ggggtggaag tgatcttcta tctgtcggac agggagcccc 540
tccggctggg cagtggagag tacacagcag aggaactgtg catcagggct gcacaggcat 600
gccgtatctc tcctctttgt cacaacctct ttgccctgta tgacgagaac accaagctct 660
ggtatgctcc aaatcgcacc atcaccgttg atgacaagat gtccctccgg ctccactacc 720
ggatgaggtt ctatttcacc aattggcatg gaaccaacga caatgagcag tcagtgtggc 780
gtcattctcc aaagaagcag aaaaatggct acgagaaaaa aaagattcca gatgcaaccc 840
ctctccttga tgccagctca ctggagtatc tgtttgctca gggacagtat gatttggtga 900
aatgcctggc tcctattcga gaccccaaga ccgagcagga tggacatgat attgagaacg 960
agtgtctagg gatggctgtc ctggccatct cacactatgc catgatgaag aagatgcagt 1020
tgccagaact gcccaaggac atcagctaca agcgatatat tccagaaaca ttgaataagt 1080
ccatcagaca gaggaacctt ctcaccagga tgcggataaa taatgttttc aaggatttcc 1140
taaaggaatt taacaacaag accatttgtg acagcagcgt gtccacgcat gacctgaagg 1200
tgaaatactt ggctaccttg gaaactttga caaaacatta cggtgctgaa atatttgaga 1260
cttccatgtt actgatttca tcagaaaatg agatgaattg gtttcattcg aatgacggtg 1320
gaaacgttct ctactacgaa gtgatggtga ctgggaatct tggaatccag tggaggcata 1380
aaccaaatgt tgtttctgtt gaaaaggaaa aaaataaact gaagcggaaa aaactggaaa 1440
ataaacacaa gaaggatgag gagaaaaaca agatccggga agagtggaac aatttttctt 1500
acttccctga aatcactcac attgtaataa aggagtctgt ggtcagcatt aacaagcagg 1560
acaacaagaa aatggaactg aagctctctt cccacgagga ggccttgtcc tttgtgtccc 1620
tggtagatgg ctacttccgg ctcacagcag atgcccatca ttacctctgc accgacgtgg 1680

```
cccccccgtt gatcgtccac aacatacaga atggctgtca tggtccaatc tgtacagaat   1740
acgccatcaa taaattgcgg caagaaggaa gcgaggaggg gatgtacgtg ctgaggtgga   1800
gctgcaccga ctttgacaac atcctcatga ccgtcacctg ctttgagaag tctgagcagg   1860
tgcagggtgc ccagaagcag ttcaagaact ttcagatcga ggtgcagaag ggccgctaca   1920
gtctgcacgg ttcggaccgc agcttcccca gcttgggaga cctcatgagc cacctcaaga   1980
agcagatcct gcgcacggat aacatcagct tcatgctaaa acgctgctgc cagcccaagc   2040
cccgagaaat ctccaacctg ctggtggcta ctaagaaagc ccaggagtgg cagcccgtct   2100
accccatgag ccagctgagt ttcgatcgga tcctcaagaa ggatctggtg cagggcgagc   2160
accttgggag aggcacgaga acacacatct attctgggac cctgatggat tacaaggatg   2220
acgaaggaac ttctgaagag aagaagataa aagtgatcct caaagtctta gaccccagcc   2280
acagggatat ttccctggcc ttcttcgagg cagccagcat gatgagacag gtctcccaca   2340
aacacatcgt gtacctctat ggcgtctgtg tccgcgacgt ggagaatatc atggtggaag   2400
agtttgtgga agggggtcct ctggatctct tcatgcaccg gaaaagcgat gtccttacca   2460
caccatggaa attcaaagtt gccaaacagc tggccagtgc cctgagctac ttggaggata   2520
aagacctggt ccatggaaat gtgtgtacta aaaacctcct cctggcccgt gagggcatcg   2580
acagtgagtg tggcccattc atcaagctca gtgaccccgg catccccatt acggtgctgt   2640
ctaggcaaga atgcattgaa cgaatcccat ggattgctcc tgagtgtgtt gaggactcca   2700
agaacctgag tgtggctgct gacaagtgga gctttggaac cacgctctgg gaaatctgct   2760
acaatggcga gatccccttg aaagacaaga cgctgattga gaaagagaga ttctatgaaa   2820
gccggtgcag gccagtgaca ccatcatgta aggagctggc tgacctcatg acccgctgca   2880
tgaactatga ccccaatcag aggcctttct tccgagccat catgagagac attaataagc   2940
ttgaagagca gaatccagat attgtttcag aaaaaaaacc agcaactgaa gtggacccca   3000
cacattttga aaagcgcttc ctaaagagga tccgtgactt gggagagggc cactttggga   3060
aggttgagct ctgcaggtat gaccccgaag gggacaatac aggggagcag gtggctgtta   3120
aatctctgaa gcctgagagt ggaggtaacc acatagctga tctgaaaaag gaaatcgaga   3180
tcttaaggaa cctctatcat gagaacattg tgaagtacaa aggaatctgc acagaagacg   3240
gaggaaatgg tattaagctc atcatggaat ttctgccttc gggaagcctt aaggaatatc   3300
ttccaaagaa taagaacaaa ataaacctca aacagcagct aaaatatgcc gttcagattt   3360
gtaaggggat ggactatttg ggttctcggc aatacgttca ccgggacttg gcagcaagaa   3420
atgtccttgt tgagagtgaa caccaagtga aaattggaga cttcggttta accaaagcaa   3480
ttgaaaccga taaggagtat tacaccgtca aggatgaccg ggacagccct gtgttttggt   3540
atgctccaga atgtttaatg caatctaaat tttatattgc ctctgacgtc tggtcttttg   3600
gagtcactct gcatgagctg ctgacttact gtgattcaga ttctagtccc atggctttgt   3660
tcctgaaaat gataggccca acccatggcc agatgacagt cacaagactt gtgaatacgt   3720
taaaagaagg aaaacgcctg ccgtgcccac ctaactgtcc agatgaggtt tatcaactta   3780
tgaggaaatg ctgggaattc caaccatcca atcggacaag ctttcagaac cttattgaag   3840
gatttgaagc acttttaaaa taagaagcat gaataacatt taaattccac agattatcaa   3900
gtccttctcc tgcaacaaat gcccaagtca ttttttaaaa atttctaatg aaagaagttt   3960
gtgttctgtc caaaaagtca ctgaactcat acttcagtac atatacatgt ataaggcaca   4020
```

```
ctgtagtgct taatatgtgt aaggacttcc tctttaaatt tggtaccagt aacttagtga   4080

cacataatga caaccaaaat atttgaaagc acttaagcac tcctccttgt ggaaagaata   4140

taccaccatt tcatctggct agttcaccat cacaactgca ttaccaaaag ggattttttg   4200

aaaacgagga gttgaccaaa ataatatctg aagatgattg cttttccctg ctgccagctg   4260

atctgaaatg ttttgctggc acattaatca tagataaaga aagattgatg gacttagccc   4320

tcaaatttca gtatctatac agtactagac catgcattct taaaatatta gataccaggt   4380

agtatatatt gtttctgtac aaaaatgact gtattctctc accagtagga cttaaacttt   4440

gtttctccag tggcttagct cctgttcctt tgggtgatca ctagcaccca tttttgagaa   4500

agctggttct acatgggggg atagctgtgg aatagataat ttgctgcatg ttaattctca   4560

agaactaagc ctgtgccagt gctttcctaa gcagtatacc tttaatcaga actcattccc   4620

agaacctgga tgctattaca catgctttta agaaacgtca atgtatatcc ttttataact   4680

ctaccacttt ggggcaagct attccagcac tggttttgaa tgctgtatgc aaccagtctg   4740

aataccacat acgctgcact gttcttagag ggtttccata cttaccaccg atctacaagg   4800

gttgatccct gtttttacca tcaatcatca ccctgtggtg caacacttga aagacccggc   4860

tagaggcact atggacttca ggatccacta gacagttttc agtttgcttg gaggtagctg   4920

ggtaatcaaa aatgtttagt cattgattca atgtgaacga ttacggtctt tatgaccaag   4980

agtctgaaaa tctttttgtt atgctgttta gtattcgttt gatattgtta cttttcacct   5040

gttgagccca aattcaggat tggttcagtg gcagcaatga agttgccatt taaatttgtt   5100

catagcctac atcaccaagg tctctgtgtc aaacctgtgg ccactctata tgcactttgt   5160

ttactcttta tacaaataaa tatactaaag actttacatg ca                      5202
```

<210> SEQ ID NO 7
<211> LENGTH: 4937
<212> TYPE: DNA
<213> ORGANISM: Homo sapiens

<400> SEQUENCE: 7

```
agaagcggag cgtatacgga ggaggcggga tgcatttctg catcgagcgc acaaagcgct     60

tctctgaagt agctttggaa agtagagaag aaaatccagt ttgcttcttg gagaacactg    120

gacagctgaa taaatgcagt atctaaatat aaaagaggac tgcaatgcca tggctttctg    180

tgctaaaatg aggagctcca agaagactga ggtgaacctg gaggcccctg agccaggggt    240

ggaagtgatc ttctatctgt cggacaggga gcccctccgg ctgggcagtg gagagtacac    300

agcagaggaa ctgtgcatca gggctgcaca ggcatgccgt atctctcctc tttgtcacaa    360

cctctttgcc ctgtatgacg agaacaccaa gctctggtat gctccaaatc gcaccatcac    420

cgttgatgac aagatgtccc tccggctcca ctaccggatg aggttctatt tcaccaattg    480

gcatggaacc aacgacaatg agcagtcagt gtggcgtcat tctccaaaga agcagaaaaa    540

tggctacgag aaaaaaaaga ttccagatgc aacccctctc cttgatgcca gctcactgga    600

gtatctgttt gctcagggac agtatgattt ggtgaaatgc ctggctccta ttcgagaccc    660

caagaccgag caggatggac atgatattga gaacgagtgt ctagggatgg ctgtcctggc    720

catctcacac tatgccatga tgaagaagat gcagttgcca gaactgccca aggacatcag    780

ctacaagcga tatattccag aaacattgaa taagtccatc agacagagga accttctcac    840

caggatgcgg ataaataatg ttttcaagga tttcctaaag gaatttaaca acaagaccat    900

ttgtgacagc agcgtgtcca cgcatgacct gaaggtgaaa tacttggcta ccttggaaac    960
```

-continued

```
tttgacaaaa cattacggtg ctgaaatatt tgagacttcc atgttactga tttcatcaga   1020
aaatgagatg aattggtttc attcgaatga cggtggaaac gttctctact acgaagtgat   1080
ggtgactggg aatcttggaa tccagtggag gcataaacca aatgttgttt ctgttgaaaa   1140
ggaaaaaaat aaactgaagc ggaaaaaact ggaaaataaa cacaagaagg atgaggagaa   1200
aaacaagatc cgggaagagt ggaacaattt ttcttacttc cctgaaatca ctcacattgt   1260
aataaaggag tctgtggtca gcattaacaa gcaggacaac aagaaaatgg aactgaagct   1320
ctcttcccac gaggaggcct tgtcctttgt gtccctggta gatggctact tccggctcac   1380
agcagatgcc catcattacc tctgcaccga cgtggccccc ccgttgatcg tccacaacat   1440
acagaatggc tgtcatggtc caatctgtac agaatacgcc atcaataaat tgcggcaaga   1500
aggaagcgag gaggggatgt acgtgctgag gtggagctgc accgactttg acaacatcct   1560
catgaccgtc acctgctttg agaagtctga gcaggtgcag ggtgcccaga agcagttcaa   1620
gaactttcag atcgaggtgc agaagggccg ctacagtctg cacggttcgg accgcagctt   1680
ccccagcttg ggagacctca tgagccacct caagaagcag atcctgcgca cggataacat   1740
cagcttcatg ctaaaacgct gctgccagcc caagccccga gaaatctcca acctgctggt   1800
ggctactaag aaagcccagg agtggcagcc cgtctacccc atgagccagc tgagtttcga   1860
tcggatcctc aagaaggatc tggtgcaggg cgagcacctt gggagaggca cgagaacaca   1920
catctattct gggaccctga tggattacaa ggatgacgaa ggaacttctg aagagaagaa   1980
gataaaagtg atcctcaaag tcttagaccc cagccacagg gatatttccc tggccttctt   2040
cgaggcagcc agcatgatga gacaggtctc ccacaaacac atcgtgtacc tctatggcgt   2100
ctgtgtccgc gacgtggaga atatcatggt ggaagagttt gtggaagggg gtcctctgga   2160
tctcttcatg caccggaaaa gcgatgtcct taccacacca tggaaattca aagttgccaa   2220
acagctggcc agtgccctga gctacttgga ggataaagac ctggtccatg gaaatgtgtg   2280
tactaaaaac ctcctcctgg cccgtgaggg catcgacagt gagtgtggcc cattcatcaa   2340
gctcagtgac cccggcatcc ccattacggt gctgtctagg caagaatgca ttgaacgaat   2400
cccatggatt gctcctgagt gtgttgagga ctccaagaac ctgagtgtgg ctgctgacaa   2460
gtggagcttt ggaaccacgc tctgggaaat ctgctacaat ggcgagatcc ccttgaaaga   2520
caagacgctg attgagaaag agagattcta tgaaagccgg tgcaggccag tgacaccatc   2580
atgtaaggag ctggctgacc tcatgacccg ctgcatgaac tatgacccca atcagaggcc   2640
tttcttccga gccatcatga gagacattaa taagcttgaa gagcagaatc cagatattgt   2700
ttcagaaaaa aaaccagcaa ctgaagtgga ccccacacat tttgaaaagc gcttcctaaa   2760
gaggatccgt gacttgggag agggccactt tgggaaggtt gagctctgca ggtatgaccc   2820
cgaaggggac aatacagggg agcaggtggc tgttaaatct ctgaagcctg agagtggagg   2880
taaccacata gctgatctga aaaaggaaat cgagatctta aggaacctct atcatgagaa   2940
cattgtgaag tacaaaggaa tctgcacaga agacggagga aatggtatta agctcatcat   3000
ggaatttctg ccttcgggaa gccttaagga atatcttcca aagaataaga acaaaataaa   3060
cctcaaacag cagctaaaat atgccgttca gatttgtaag gggatggact atttgggttc   3120
tcggcaatac gttcaccggg acttggcagc aagaaatgtc cttgttgaga gtgaacacca   3180
agtgaaaatt ggagacttcg gtttaaccaa agcaattgaa accgataagg agtattacac   3240
cgtcaaggat gaccgggaca gccctgtgtt ttggtatgct ccagaatgtt taatgcaatc   3300
```

-continued

```
taaattttat attgcctctg acgtctggtc ttttggagtc actctgcatg agctgctgac   3360

ttactgtgat tcagattcta gtcccatggc tttgttcctg aaaatgatag gcccaaccca   3420

tggccagatg acagtcacaa gacttgtgaa tacgttaaaa gaaggaaaac gcctgccgtg   3480

cccacctaac tgtccagatg aggtttatca acttatgagg aaatgctggg aattccaacc   3540

atccaatcgg acaagctttc agaaccttat tgaaggattt gaagcacttt taaaataaga   3600

agcatgaata acatttaaat tccacagatt atcaagtcct tctcctgcaa caaatgccca   3660

agtcattttt taaaaatttc taatgaaaga agtttgtgtt ctgtccaaaa agtcactgaa   3720

ctcatacttc agtacatata catgtataag gcacactgta gtgcttaata tgtgtaagga   3780

cttcctcttt aaatttggta ccagtaactt agtgacacat aatgacaacc aaaatatttg   3840

aaagcactta agcactcctc cttgtggaaa gaatatacca ccatttcatc tggctagttc   3900

accatcacaa ctgcattacc aaaaggggat ttttgaaaac gaggagttga ccaaaataat   3960

atctgaagat gattgctttt ccctgctgcc agctgatctg aaatgttttg ctggcacatt   4020

aatcatagat aaagaaagat tgatggactt agccctcaaa tttcagtatc tatacagtac   4080

tagaccatgc attcttaaaa tattagatac caggtagtat atattgtttc tgtacaaaaa   4140

tgactgtatt ctctcaccag taggacttaa actttgtttc tccagtggct tagctcctgt   4200

tcctttgggt gatcactagc acccattttt gagaaagctg gttctacatg gggggatagc   4260

tgtggaatag ataatttgct gcatgttaat tctcaagaac taagcctgtg ccagtgcttt   4320

cctaagcagt ataccttttaa tcagaactca ttcccagaac ctggatgcta ttacacatgc   4380

ttttaagaaa cgtcaatgta tatcctttta taactctacc actttggggc aagctattcc   4440

agcactggtt ttgaatgctg tatgcaacca gtctgaatac cacatacgct gcactgttct   4500

tagagggttt ccatacttac caccgatcta caagggttga tccctgtttt taccatcaat   4560

catcaccctg tggtgcaaca cttgaaagac ccggctagag gcactatgga cttcaggatc   4620

cactagacag ttttcagttt gcttggaggt agctgggtaa tcaaaaatgt ttagtcattg   4680

attcaatgtg aacgattacg gtctttatga ccaagagtct gaaaatcttt ttgttatgct   4740

gtttagtatt cgtttgatat tgttactttt cacctgttga gcccaaattc aggattggtt   4800

cagtggcagc aatgaagttg ccatttaaat ttgttcatag cctacatcac caaggtctct   4860

gtgtcaaacc tgtggccact ctatatgcac tttgtttact ctttatacaa ataaatatac   4920

taaagacttt acatgca                                                  4937
```

<210> SEQ ID NO 8
<211> LENGTH: 5115
<212> TYPE: DNA
<213> ORGANISM: Homo sapiens

<400> SEQUENCE: 8

```
ggggcgggac gggaggcggt gcgtcgctga gcgcaggccg cggcggccgc ggagtatcct     60

ggagctgcag acagtgcggg cctgcgccca gtcccggctg tcctcgccgc gacccctcct    120

cagccctggg cgcgcgcacg ctggggcccc gcggggctgg ccgcctagcg agcctgccgg    180

tcgaccccag ccagcgcagc gacggggcgc tgcctggccc aggcgcacac ggaagtgcgc    240

ttctctgaag tagctttgga aagtagagaa gaaaatccag tttgcttctt ggagaacact    300

ggacagctga ataaatgcag tatctaaata taaaagagga ctgcaatgcc atggctttct    360

gtgctaaaat gaggagctcc aagaagactg aggtgaacct ggaggcccct gagccagggg    420

tggaagtgat cttctatctg tcggacaggg agcccctccg gctgggcagt ggagagtaca    480
```

-continued

```
cagcagagga actgtgcatc agggctgcac aggcatgccg tatctctcct ctttgtcaca    540
acctctttgc cctgtatgac gagaacacca agctctggta tgctccaaat cgcaccatca    600
ccgttgatga caagatgtcc ctccggctcc actaccggat gaggttctat ttcaccaatt    660
ggcatggaac caacgacaat gagcagtcag tgtggcgtca ttctccaaag aagcagaaaa    720
atggctacga gaaaaaaaag attccagatg caacccctct ccttgatgcc agctcactgg    780
agtatctgtt tgctcaggga cagtatgatt tggtgaaatg cctggctcct attcgagacc    840
ccaagaccga gcaggatgga catgatattg agaacgagtg tctagggatg gctgtcctgg    900
ccatctcaca ctatgccatg atgaagaaga tgcagttgcc agaactgccc aaggacatca    960
gctacaagcg atatattcca gaaacattga ataagtccat cagacagagg aaccttctca   1020
ccaggatgcg gataaataat gttttcaagg atttcctaaa ggaatttaac aacaagacca   1080
tttgtgacag cagcgtgtcc acgcatgacc tgaaggtgaa atacttggct accttggaaa   1140
ctttgacaaa acattacggt gctgaaatat ttgagacttc catgttactg atttcatcag   1200
aaaatgagat gaattggttt cattcgaatg acggtggaaa cgttctctac tacgaagtga   1260
tggtgactgg gaatcttgga atccagtgga ggcataaacc aaatgttgtt tctgttgaaa   1320
aggaaaaaaa taaactgaag cggaaaaaac tggaaaataa acacaagaag gatgaggaga   1380
aaaacaagat ccgggaagag tggaacaatt tttcttactt ccctgaaatc actcacattg   1440
taataaagga gtctgtggtc agcattaaca agcaggacaa caagaaaatg gaactgaagc   1500
tctcttccca cgaggaggcc ttgtcctttg tgtccctggt agatggctac ttccggctca   1560
cagcagatgc ccatcattac ctctgcaccg acgtggcccc cccgttgatc gtccacaaca   1620
tacagaatgg ctgtcatggt ccaatctgta cagaatacgc catcaataaa ttgcggcaag   1680
aaggaagcga ggaggggatg tacgtgctga ggtggagctg caccgacttt gacaacatcc   1740
tcatgaccgt cacctgcttt gagaagtctg aggtgcaggg tgcccagaag cagttcaaga   1800
actttcagat cgaggtgcag aagggccgct acagtctgca cggttcggac cgcagcttcc   1860
ccagcttggg agacctcatg agccacctca agaagcagat cctgcgcacg gataacatca   1920
gcttcatgct aaaacgctgc tgccagccca agccccgaga aatctccaac ctgctggtgg   1980
ctactaagaa agcccaggag tggcagcccg tctaccccat gagccagctg agtttcgatc   2040
ggatcctcaa gaaggatctg gtgcagggcg agcaccttgg gagaggcacg agaacacaca   2100
tctattctgg gaccctgatg gattacaagg atgacgaagg aacttctgaa gagaagaaga   2160
taaaagtgat cctcaaagtc ttagacccca gccacaggga tatttccctg gccttcttcg   2220
aggcagccag catgatgaga caggtctccc acaaacacat cgtgtacctc tatggcgtct   2280
gtgtccgcga cgtggagaat atcatggtgg aagagtttgt ggaaggggggt cctctggatc   2340
tcttcatgca ccggaaaagc gatgtcctta ccacaccatg gaaattcaaa gttgccaaac   2400
agctggccag tgccctgagc tacttggagg ataaagacct ggtccatgga aatgtgtgta   2460
ctaaaaacct cctcctggcc cgtgagggca tcgacagtga gtgtggccca ttcatcaagc   2520
tcagtgaccc cggcatcccc attacggtgc tgtctaggca agaatgcatt gaacgaatcc   2580
catggattgc tcctgagtgt gttgaggact ccaagaacct gagtgtggct gctgacaagt   2640
ggagctttgg aaccacgctc tgggaaatct gctacaatgg cgagatcccc ttgaaagaca   2700
agacgctgat tgagaaagag agattctatg aaagccggtg caggccagtg acaccatcat   2760
gtaaggagct ggctgacctc atgacccgct gcatgaacta tgaccccaat cagaggcctt   2820
```

-continued

```
tcttccgagc catcatgaga gacattaata agcttgaaga gcagaatcca gatattgttt   2880
cagaaaaaaa accagcaact gaagtggacc ccacacattt tgaaaagcgc ttcctaaaga   2940
ggatccgtga cttgggagag ggccactttg ggaaggttga gctctgcagg tatgaccccg   3000
aaggggacaa tacaggggag caggtggctg ttaaatctct gaagcctgag agtggaggta   3060
accacatagc tgatctgaaa aaggaaatcg agatcttaag gaacctctat catgagaaca   3120
ttgtgaagta caaaggaatc tgcacagaag acggaggaaa tggtattaag ctcatcatgg   3180
aatttctgcc ttcgggaagc cttaaggaat atcttccaaa gaataagaac aaaataaacc   3240
tcaaacagca gctaaaatat gccgttcaga tttgtaaggg gatggactat ttgggttctc   3300
ggcaatacgt tcaccgggac ttggcagcaa gaaatgtcct tgttgagagt gaacaccaag   3360
tgaaaattgg agacttcggt ttaaccaaag caattgaaac cgataaggag tattacaccg   3420
tcaaggatga ccgggacagc cctgtgtttt ggtatgctcc agaatgttta atgcaatcta   3480
aattttatat tgcctctgac gtctggtctt ttggagtcac tctgcatgag ctgctgactt   3540
actgtgattc agattctagt cccatggctt tgttcctgaa aatgataggc ccaacccatg   3600
gccagatgac agtcacaaga cttgtgaata cgttaaaaga aggaaaacgc ctgccgtgcc   3660
cacctaactg tccagatgag gtttatcaac ttatgaggaa atgctgggaa ttccaaccat   3720
ccaatcggac aagctttcag aaccttattg aaggatttga agcactttta aaataagaag   3780
catgaataac atttaaattc cacagattat caagtccttc tcctgcaaca aatgcccaag   3840
tcatttttta aaaatttcta atgaaagaag tttgtgttct gtccaaaaag tcactgaact   3900
catacttcag tacatataca tgtataaggc acactgtagt gcttaatatg tgtaaggact   3960
tcctctttaa atttggtacc agtaacttag tgacacataa tgacaaccaa aatatttgaa   4020
agcacttaag cactcctcct tgtggaaaga atataccacc atttcatctg gctagttcac   4080
catcacaact gcattaccaa aaggggattt ttgaaaacga ggagttgacc aaaataatat   4140
ctgaagatga ttgcttttcc ctgctgccag ctgatctgaa atgttttgct ggcacattaa   4200
tcatagataa agaaagattg atggacttag ccctcaaatt tcagtatcta tacagtacta   4260
gaccatgcat tcttaaaata ttagatacca ggtagtatat attgtttctg tacaaaaatg   4320
actgtattct ctcaccagta ggacttaaac tttgtttctc cagtggctta gctcctgttc   4380
ctttgggtga tcactagcac ccatttttga gaaagctggt tctacatggg ggatagctg   4440
tggaatagat aatttgctgc atgttaattc tcaagaacta agcctgtgcc agtgctttcc   4500
taagcagtat acctttaatc agaactcatt cccagaacct ggatgctatt acacatgctt   4560
ttaagaaacg tcaatgtata tccttttata actctaccac tttggggcaa gctattccag   4620
cactggtttt gaatgctgta tgcaaccagt ctgaatacca catacgctgc actgttctta   4680
gagggtttcc atacttacca ccgatctaca agggttgatc cctgttttta ccatcaatca   4740
tcaccctgtg gtgcaacact tgaaagaccc ggctagaggc actatggact tcaggatcca   4800
ctagacagtt ttcagtttgc ttggaggtag ctgggtaatc aaaaatgttt agtcattgat   4860
tcaatgtgaa cgattacggt ctttatgacc aagagtctga aaatcttttt gttatgctgt   4920
ttagtattcg tttgatattg ttacttttca cctgttgagc ccaaattcag gattggttca   4980
gtggcagcaa tgaagttgcc atttaaattt gttcatagcc tacatcacca aggtctctgt   5040
gtcaaacctg tggccactct atatgcactt tgtttactct ttatacaaat aaatatacta   5100
aagactttac atgca                                                    5115
```

<210> SEQ ID NO 9
<211> LENGTH: 5285
<212> TYPE: DNA
<213> ORGANISM: Homo sapiens

<400> SEQUENCE: 9
ctgcaggaag gagagaggaa gaggagcaga agggggcagc agcggacgcc gctaacggcc 60
tccctcggcg ctgacaggct gggccggcgc ccggctcgct tgggtgttcg cgtcgccact 120
tcggcttctc ggccggtcgg gcccctcggc ccgggcttgc ggcgcgcgtc ggggctgagg 180
gctgctgcgg cgcagggaga ggcctggtcc tcgctgccga gggatgtgag tgggagctga 240
gcccacactg gagggccccc gagggcccag cctggaggtc gttcagagcc gtgcccgtcc 300
cggggcttcg cagaccttga cccgccgggt aggagccgcc cctgcgggct cgagggcgcg 360
ctctggtcgc ccgatctgtg tagccggttt cagaagcagg caacaggaac aagatgtgaa 420
ctgtttctct tctgcagaaa aagaggctct tcctcctcct cccgcgacgg caaatgttct 480
gaaaaagact ctgcatggga atggcctgcc ttacgatgac agaaatggag ggaacatcca 540
cctcttctat atatcagaat ggtgatattt ctggaaatgc caattctatg aagcaaatag 600
atccagttct tcaggtgtat ctttaccatt cccttgggaa atctgaggca gattatctga 660
cctttccatc tggggagtat gttgcagaag aaatctgtat tgctgcttct aaagcttgtg 720
gtatcacacc tgtgtatcat aatatgtttg ctttaatgag tgaaacagaa aggatctggt 780
atccacccaa ccatgtcttc catatagatg agtcaaccag gcataatgta ctctacagaa 840
taagatttta ctttcctcgt tggtattgca gtggcagcaa cagagcctat cggcatggaa 900
tatctcgagg tgctgaagct cctcttcttg atgactttgt catgtcttac ctctttgctc 960
agtggcggca tgattttgtg cacggatgga taaaagtacc tgtgactcat gaaacacagg 1020
aagaatgtct tgggatggca gtgttagata tgatgagaat agccaaagaa aacgatcaaa 1080
ccccactggc catctataac tctatcagct acaagacatt cttaccaaaa tgtattcgag 1140
caaagatcca agactatcat attttgacaa ggaagcgaat aaggtacaga tttcgcagat 1200
ttattcagca attcagccaa tgcaaagcca ctgccagaaa cttgaaactt aagtatctta 1260
taaatctgga aactctgcag tctgccttct acacagagaa atttgaagta aaagaacctg 1320
gaagtggtcc ttcaggtgag gagatttttg caaccattat aataactgga aacggtggaa 1380
ttcagtggtc aagagggaaa cataaagaaa gtgagacact gacagaacag gatttacagt 1440
tatattgcga ttttcctaat attattgatg tcagtattaa gcaagcaaac caagagggtt 1500
caaatgaaag ccgagttgta actatccata agcaagatgg taaaaatctg gaaattgaac 1560
ttagctcatt aagggaagct ttgtctttcg tgtcattaat tgatggatat tatagattaa 1620
ctgcagatgc acatcattac ctctgtaaag aagtagcacc tccagccgtg cttgaaaata 1680
tacaaagcaa ctgtcatggc ccaatttcga tggattttgc cattagtaaa ctgaagaaag 1740
caggtaatca gactggactg tatgtacttc gatgcagtcc taaggacttt aataaatatt 1800
ttttgacttt tgctgtcgag cgagaaaatg tcattgaata taaacactgt ttgattacaa 1860
aaaatgagaa tgaagagtac aacctcagtg ggacaaagaa gaacttcagc agtcttaaag 1920
atcttttgaa ttgttaccag atggaaactg ttcgctcaga caatataatt ttccagttta 1980
ctaaatgctg tcccccaaag ccaaaagata aatcaaacct tctagtcttc agaacgaatg 2040
gtgtttctga tgtaccaacc tcaccaacat tacagaggcc tactcatatg aaccaaatgg 2100
tgtttcacaa aatcagaaat gaagatttga tatttaatga aagccttggc caaggcactt 2160

-continued

```
ttacaaagat ttttaaaggc gtacgaagag aagtaggaga ctacggtcaa ctgcatgaaa   2220
cagaagttct tttaaaagtt ctggataaag cacacagaaa ctattcagag tctttctttg   2280
aagcagcaag tatgatgagc aagctttctc acaagcattt ggttttaaat tatggagtat   2340
gtgtctgtgg agacgagaat attctggttc aggagtttgt aaaatttgga tcactagata   2400
catatctgaa aaagaataaa aattgtataa atatattatg gaaacttgaa gttgctaaac   2460
agttggcatg ggccatgcat tttctagaag aaaacaccct tattcatggg aatgtatgtg   2520
ccaaaaatat tctgcttatc agagaagaag acaggaagac aggaaatcct cctttcatca   2580
aacttagtga tcctggcatt agtattacag ttttgccaaa ggacattctt caggagagaa   2640
taccatgggt accacctgaa tgcattgaaa atcctaaaaa tttaaatttg gcaacagaca   2700
aatggagttt tggtaccact ttgtgggaaa tctgcagtgg aggagataaa cctctaagtg   2760
ctctggattc tcaaagaaag ctacaatttt atgaagatag gcatcagctt cctgcaccaa   2820
agtgggcaga attagcaaac cttataaata attgtatgga ttatgaacca gatttcaggc   2880
cttctttcag agccatcata cgagatctta acagtttgtt tactccagat tatgaactat   2940
taacagaaaa tgacatgtta ccaaatatga ggataggtgc cctggggttt tctggtgcct   3000
ttgaagaccg ggatcctaca cagtttgaag agagacattt gaaatttcta cagcaacttg   3060
gcaagggtaa ttttgggagt gtggagatgt gccggtatga ccctctacag gacaacactg   3120
gggaggtggt cgctgtaaaa aagcttcagc atagtactga agagcaccta agagactttg   3180
aaagggaaat tgaaatcctg aaatccctac agcatgacaa cattgtaaag tacaagggag   3240
tgtgctacag tgctggtcgg cgtaatctaa aattaattat ggaatattta ccatatggaa   3300
gtttacgaga ctatcttcaa aaacataaag aacggataga tcacataaaa cttctgcagt   3360
acacatctca gatatgcaag ggtatggagt atcttggtac aaaaaggtat atccacaggg   3420
atctggcaac gagaaatata ttggtggaga acgagaacag agttaaaatt ggagattttg   3480
ggttaaccaa agtcttgcca caagacaaag aatactataa agtaaaagaa cctggtgaaa   3540
gtcccatatt ctggtatgct ccagaatcac tgacagagag caagttttct gtggcctcag   3600
atgtttggag ctttggagtg gttctgtatg aacttttcac atacattgag aagagtaaaa   3660
gtccaccagc ggaatttatg cgtatgattg gcaatgacaa acaaggacag atgatcgtgt   3720
tccatttgat agaacttttg aagaataatg gaagattacc aagaccagat ggatgcccag   3780
atgagatcta tatgatcatg acagaatgct ggaacaataa tgtaaatcaa cgcccctcct   3840
ttagggatct agctcttcga gtggatcaaa taagggataa catggctgga tgaaagaaat   3900
gaccttcatt ctgagaccaa agtagattta cagaacaaag ttttatattt cacattgctg   3960
tggactatta ttacatatat cattattata taaatcatga tgctagccag caaagatgtg   4020
aaaatatctg ctcaaaactt tcaaagttta gtaagttttt cttcatgagg ccaccagtaa   4080
aagacattaa tgagaattcc ttagcaagga ttttgtaaga agtttcttaa acattgtcag   4140
ttaacatcac tcttgtctgg caaaagaaaa aaaatagact tttcaactc agcttttga     4200
gacctgaaaa aattattatg taaattttgc aatgttaaag atgcacagaa tatgtatgta   4260
tagtttttac cacagtggat gtataatacc ttggcatctt gtgtgatgtt ttacacacat   4320
gagggctggt gttcattaat actgttttct aatttttcca tagttaatct ataattaatt   4380
acttcactat acaaacaaat taagatgttc agataattga ataagtacct ttgtgtcctt   4440
gttcatttat atcgctggcc agcattataa gcaggtgtat acttttagct tgtagttcca   4500
tgtactgtaa atatttttca cataaaggga acaaatgtct agttttattt gtataggaaa   4560
```

```
tttccctgac cctaaataat acattttgaa atgaaacaag cttacaaaga tataatctat   4620
tttattatgg tttcccttgt atctatttgt ggtgaatgtg ttttttaaat ggaactatct   4680
ccaaattttt ctaagactac tatgaacagt tttcttttaa aattttgaga ttaagaatgc   4740
caggaatatt gtcatccttt gagctgctga ctgccaataa cattcttcga tctctgggat   4800
ttatgctcat gaactaaatt taagcttaag ccataaaata gattagattg tttttttaaaa   4860
atggatagct cattaagaag tgcagcaggt taagaatttt ttcctaaaga ctgtatattt   4920
gaggggtttc agaattttgc attgcagtca tagaagagat ttatttcctt tttagagggg   4980
aaatgaggta aataagtaaa aaagtatgct tgttaatttt attcaagaat gccagtagaa   5040
aattcataac gtgtatcttt aagaaaaatg agcatacatc ttaaatcttt tcaattaagt   5100
ataaggggtt gttcgttgtt gtcatttgtt atagtgctac tccactttag acaccatagc   5160
taaaataaaa tatggtgggt tttgtgtgtg tgtgtgtgtg tgtgtgtgtg tgtgtgtgtg   5220
tgttatttat acaaaactta aaatacttgc tgttttgatt aaaaagaaaa tagtttctta   5280
cttta                                                               5285
```

<210> SEQ ID NO 10
<211> LENGTH: 5386
<212> TYPE: DNA
<213> ORGANISM: Homo sapiens

<400> SEQUENCE: 10

```
attcggggag actgcaggcc aaccgggagg ctgagttcga agctagcagg gcggcgaagc     60
cagtgtcgcc cgcggcgttg agaagacggt gtggccccgg agagggtgga gacaactgtg    120
acgggcttcc cggctgcccg aagtgggagt ggtgtggggc tgcaggaagg agagaggaag    180
aggagcagaa gggggcagca gcggacgccg ctaacggcct ccctcggcgc tgacaggctg    240
ggccggcgcc cggctcgctt gggtgttcgc gtcgccactt cggcttctcg gccggtcggg    300
cccctcggcc cgggcttgcg gcgcgcgtcg gggctgaggg ctgctgcggc gcagggagag    360
gcctggtcct cgctgccgag ggatgtgagt gggagctgag cccacactgg agggcccccg    420
agggcccagc ctggaggtcg ttcagagccg tgcccgtccc ggggcttcgc agaccttgac    480
ccgccgggtt tcagaagcag gcaacaggaa caagatgtga actgtttctc ttctgcagaa    540
aaagaggctc ttcctcctcc tcccgcgacg gcaaatgttc tgaaaaagac tctgcatggg    600
aatggcctgc cttacgatga cagaaatgga gggaacatcc acctcttcta tatatcagaa    660
tggtgatatt tctggaaatg ccaattctat gaagcaaata gatccagttc ttcaggtgta    720
tctttaccat tcccttggga aatctgaggc agattatctg acctttccat ctggggagta    780
tgttgcagaa gaaatctgta ttgctgcttc taaagcttgt ggtatcacac ctgtgtatca    840
taatatgttt gctttaatga gtgaaacaga aaggatctgg tatccaccca accatgtctt    900
ccatatagat gagtcaacca ggcataatgt actctacaga ataagatttt actttcctcg    960
ttggtattgc agtggcagca acagagccta tcggcatgga atatctcgag gtgctgaagc   1020
tcctcttctt gatgactttg tcatgtctta cctctttgct cagtggcggc atgattttgt   1080
gcacggatgg ataaaagtac ctgtgactca tgaaacacag gaagaatgtc ttgggatggc   1140
agtgttagat atgatgagaa tagccaaaga aaacgatcaa accccactgg ccatctataa   1200
ctctatcagc tacaagacat tcttaccaaa atgtattcga gcaaagatcc aagactatca   1260
tattttgaca aggaagcgaa taaggtacag atttcgcaga tttattcagc aattcagcca   1320
```

-continued

```
atgcaaagcc actgccagaa acttgaaact taagtatctt ataaatctgg aaactctgca   1380
gtctgccttc tacacagaga aatttgaagt aaaagaacct ggaagtggtc cttcaggtga   1440
ggagattttt gcaaccatta taataactgg aaacggtgga attcagtggt caagagggaa   1500
acataaagaa agtgagacac tgacagaaca ggatttacag ttatattgcg attttcctaa   1560
tattattgat gtcagtatta agcaagcaaa ccaagagggt tcaaatgaaa gccgagttgt   1620
aactatccat aagcaagatg gtaaaaatct ggaaattgaa cttagctcat taagggaagc   1680
tttgtctttc gtgtcattaa ttgatggata ttatagatta actgcagatg cacatcatta   1740
cctctgtaaa gaagtagcac ctccagccgt gcttgaaaat atacaaagca actgtcatgg   1800
cccaatttcg atggattttg ccattagtaa actgaagaaa gcaggtaatc agactggact   1860
gtatgtactt cgatgcagtc ctaaggactt taataaatat tttttgactt ttgctgtcga   1920
gcgagaaaat gtcattgaat ataaacactg tttgattaca aaaaatgaga atgaagagta   1980
caacctcagt gggacaaaga agaacttcag cagtcttaaa gatcttttga attgttacca   2040
gatggaaact gttcgctcag acaatataat tttccagttt actaaatgct gtcccccaaa   2100
gccaaaagat aaatcaaacc ttctagtctt cagaacgaat ggtgtttctg atgtaccaac   2160
ctcaccaaca ttacagaggc ctactcatat gaaccaaatg gtgtttcaca aaatcagaaa   2220
tgaagatttg atatttaatg aaagccttgg ccaaggcact tttacaaaga tttttaaagg   2280
cgtacgaaga gaagtaggag actacggtca actgcatgaa acagaagttc ttttaaaagt   2340
tctggataaa gcacacagaa actattcaga gtctttcttt gaagcagcaa gtatgatgag   2400
caagctttct cacaagcatt tggttttaaa ttatggagta tgtgtctgtg gagacgagaa   2460
tattctggtt caggagtttg taaaatttgg atcactagat acatatctga aaaagaataa   2520
aaattgtata aatatattat ggaaacttga agttgctaaa cagttggcat gggccatgca   2580
ttttctagaa gaaaacaccc ttattcatgg gaatgtatgt gccaaaaata ttctgcttat   2640
cagagaagaa gacaggaaga caggaaatcc tcctttcatc aaacttagtg atcctggcat   2700
tagtattaca gttttgccaa aggacattct tcaggagaga ataccatggg taccacctga   2760
atgcattgaa aatcctaaaa atttaaattt ggcaacagac aaatggagtt ttggtaccac   2820
tttgtgggaa atctgcagtg gaggagataa acctctaagt gctctggatt ctcaaagaaa   2880
gctacaattt tatgaagata ggcatcagct tcctgcacca aagtgggcag aattagcaaa   2940
ccttataaat aattgtatgg attatgaacc agatttcagg ccttctttca gagccatcat   3000
acgagatctt aacagtttgt ttactccaga ttatgaacta ttaacagaaa atgacatgtt   3060
accaaatatg aggataggtg ccctggggtt ttctggtgcc tttgaagacc gggatcctac   3120
acagtttgaa gagagacatt tgaaatttct acagcaactt ggcaagggta attttgggag   3180
tgtggagatg tgccggtatg accctctaca ggacaacact ggggaggtgg tcgctgtaaa   3240
aaagcttcag catagtactg aagagcacct aagagacttt gaaagggaaa ttgaaatcct   3300
gaaatcccta cagcatgaca acattgtaaa gtacaaggga gtgtgctaca gtgctggtcg   3360
gcgtaatcta aaattaatta tggaatattt accatatgga agtttacgag actatcttca   3420
aaaacataaa gaacggatag atcacataaa acttctgcag tacacatctc agatatgcaa   3480
gggtatggag tatcttggta caaaaaggta tatccacagg gatctggcaa cgagaaatat   3540
attggtggag aacgagaaca gagttaaaat tggagatttt gggttaacca aagtcttgcc   3600
acaagacaaa gaatactata aagtaaaaga acctggtgaa agtcccatat tctggtatgc   3660
tccagaatca ctgacagaga gcaagttttc tgtggcctca gatgtttgga gctttggagt   3720
```

```
ggttctgtat gaacttttca catacattga gaagagtaaa agtccaccag cggaatttat   3780

gcgtatgatt ggcaatgaca aacaaggaca gatgatcgtg ttccatttga tagaactttt   3840

gaagaataat ggaagattac caagaccaga tggatgccca gatgagatct atatgatcat   3900

gacagaatgc tggaacaata atgtaaatca acgcccctcc tttagggatc tagctcttcg   3960

agtggatcaa ataagggata acatggctgg atgaaagaaa tgaccttcat tctgagacca   4020

aagtagattt acagaacaaa gttttatatt tcacattgct gtggactatt attacatata   4080

tcattattat ataaatcatg atgctagcca gcaaagatgt gaaaatatct gctcaaaact   4140

ttcaaagttt agtaagtttt tcttcatgag gccaccagta aaagacatta atgagaattc   4200

cttagcaagg attttgtaag aagtttctta aacattgtca gttaacatca ctcttgtctg   4260

gcaaaagaaa aaaaatagac tttttcaact cagctttttg agacctgaaa aaattattat   4320

gtaaattttg caatgttaaa gatgcacaga atatgtatgt atagttttta ccacagtgga   4380

tgtataatac cttggcatct tgtgtgatgt tttacacaca tgagggctgg tgttcattaa   4440

tactgttttc taatttttcc atagttaatc tataattaat tacttcacta tacaaacaaa   4500

ttaagatgtt cagataattg aataagtacc tttgtgtcct tgttcattta tatcgctggc   4560

cagcattata agcaggtgta tacttttagc ttgtagttcc atgtactgta aatatttttc   4620

acataaaggg aacaaatgtc tagttttatt tgtataggaa atttccctga ccctaaataa   4680

tacattttga aatgaaacaa gcttacaaag atataatcta ttttattatg gtttcccttg   4740

tatctatttg tggtgaatgt gtttttttaaa tggaactatc tccaaatttt tctaagacta   4800

ctatgaacag ttttctttta aaattttgag attaagaatg ccaggaatat tgtcatcctt   4860

tgagctgctg actgccaata acattcttcg atctctggga tttatgctca tgaactaaat   4920

ttaagcttaa gccataaaat agattagatt gtttttttaaa aatggatagc tcattaagaa   4980

gtgcagcagg ttaagaattt tttcctaaag actgtatatt tgaggggttt cagaattttg   5040

cattgcagtc atagaagaga tttatttcct ttttagaggg gaaatgaggt aaataagtaa   5100

aaaagtatgc ttgttaattt tattcaagaa tgccagtaga aaattcataa cgtgtatctt   5160

taagaaaaat gagcatacat cttaaatctt ttcaattaag tataaggggt tgttcgttgt   5220

tgtcatttgt tatagtgcta ctccacttta gacaccatag ctaaaataaa atatggtggg   5280

ttttgtgtgt gtgtgtgtgt gtgtgtgtgt gtgtgtgtgt gtgttattta tacaaaactt   5340

aaaatacttg ctgttttgat taaaaagaaa atagtttctt acttta                  5386
```

<210> SEQ ID NO 11
<211> LENGTH: 4904
<212> TYPE: DNA
<213> ORGANISM: Homo sapiens

<400> SEQUENCE: 11

```
attcggggag actgcaggcc aaccgggagg ctgagttcga agctagcagg gcggcgaagc     60

cagtgtcgcc cgcggcgttg agaagacggc aaatgttctg aaaaagactc tgcatgggaa    120

tggcctgcct tacgatgaca gaaatggagg gaacatccac ctcttctata tatcagaatg    180

gtgatatttc tggaaatgcc aattctatga agcaaataga tccagttctt caggtgtatc    240

tttaccattc ccttgggaaa tctgaggcag attatctgac ctttccatct ggggagtatg    300

ttgcagaaga aatctgtatt gctgcttcta aagcttgtgg tatcacacct gtgtatcata    360

atatgtttgc tttaatgagt gaaacagaaa ggatctggta tccacccaac catgtcttcc    420
```

-continued

```
atatagatga gtcaaccagg cataatgtac tctacagaat aagattttac tttcctcgtt    480
ggtattgcag tggcagcaac agagcctatc ggcatggaat atctcgaggt gctgaagctc    540
ctcttcttga tgactttgtc atgtcttacc tctttgctca gtggcggcat gattttgtgc    600
acggatggat aaaagtacct gtgactcatg aaacacagga agaatgtctt gggatggcag    660
tgttagatat gatgagaata gccaaagaaa acgatcaaac cccactggcc atctataact    720
ctatcagcta caagacattc ttaccaaaat gtattcgagc aaagatccaa gactatcata    780
ttttgacaag gaagcgaata aggtacagat ttcgcagatt tattcagcaa ttcagccaat    840
gcaaagccac tgccagaaac ttgaaactta agtatcttat aaatctggaa actctgcagt    900
ctgccttcta cacagagaaa tttgaagtaa aagaacctgg aagtggtcct tcaggtgagg    960
agatttttgc aaccattata ataactggaa acggtggaat tcagtggtca agagggaaac   1020
ataaagaaag tgagacactg acagaacagg atttacagtt atattgcgat tttcctaata   1080
ttattgatgt cagtattaag caagcaaacc aagagggttc aaatgaaagc cgagttgtaa   1140
ctatccataa gcaagatggt aaaaatctgg aaattgaact tagctcatta agggaagctt   1200
tgtctttcgt gtcattaatt gatggatatt atagattaac tgcagatgca catcattacc   1260
tctgtaaaga agtagcacct ccagccgtgc ttgaaaatat acaaagcaac tgtcatggcc   1320
caatttcgat ggattttgcc attagtaaac tgaagaaagc aggtaatcag actggactgt   1380
atgtacttcg atgcagtcct aaggacttta ataaatattt tttgactttt gctgtcgagc   1440
gagaaaatgt cattgaatat aaacactgtt tgattacaaa aaatgagaat gaagagtaca   1500
acctcagtgg gacaaagaag aacttcagca gtcttaaaga tcttttgaat tgttaccaga   1560
tggaaactgt tcgctcagac aatataattt tccagtttac taaatgctgt cccccaaagc   1620
caaaagataa atcaaacctt ctagtcttca gaacgaatgg tgtttctgat gtaccaacct   1680
caccaacatt acagaggcct actcatatga accaaatggt gtttcacaaa atcagaaatg   1740
aagatttgat atttaatgaa agccttggcc aaggcacttt tacaaagatt tttaaaggcg   1800
tacgaagaga agtaggagac tacggtcaac tgcatgaaac agaagttctt ttaaaagttc   1860
tggataaagc acacagaaac tattcagagt ctttctttga agcagcaagt atgatgagca   1920
agctttctca caagcatttg gttttaaatt atggagtatg tgtctgtgga gacgagaata   1980
ttctggttca ggagtttgta aaatttggat cactagatac atatctgaaa aagaataaaa   2040
attgtataaa tatattatgg aaacttgaag ttgctaaaca gttggcatgg gccatgcatt   2100
ttctagaaga aaacaccctt attcatggga atgtatgtgc caaaaatatt ctgcttatca   2160
gagaagaaga caggaagaca ggaaatcctc ctttcatcaa acttagtgat cctggcatta   2220
gtattacagt tttgccaaag gacattcttc aggagagaat accatgggta ccacctgaat   2280
gcattgaaaa tcctaaaaat ttaaatttgg caacagacaa atggagtttt ggtaccactt   2340
tgtgggaaat ctgcagtgga ggagataaac ctctaagtgc tctggattct caaagaaagc   2400
tacaatttta tgaagatagg catcagcttc ctgcaccaaa gtgggcagaa ttagcaaacc   2460
ttataaataa ttgtatggat tatgaaccag atttcaggcc ttctttcaga gccatcatac   2520
gagatcttaa cagtttgttt actccagatt atgaactatt aacagaaaat gacatgttac   2580
caaatatgag gataggtgcc ctggggtttt ctggtgcctt tgaagaccgg gatcctacac   2640
agtttgaaga gagacatttg aaatttctac agcaacttgg caagggtaat tttgggagtg   2700
tggagatgtg ccggtatgac cctctacagg acaacactgg ggaggtggtc gctgtaaaaa   2760
agcttcagca tagtactgaa gagcacctaa gagactttga aagggaaatt gaaatcctga   2820
```

```
aatccctaca gcatgacaac attgtaaagt acaagggagt gtgctacagt gctggtcggc   2880
gtaatctaaa attaattatg gaatatttac catatggaag tttacgagac tatcttcaaa   2940
aacataaaga acggatagat cacataaaac ttctgcagta cacatctcag atatgcaagg   3000
gtatggagta tcttggtaca aaaaggtata tccacaggga tctggcaacg agaaatatat   3060
tggtggagaa cgagaacaga gttaaaattg gagattttgg gttaaccaaa gtcttgccac   3120
aagacaaaga atactataaa gtaaaagaac ctggtgaaag tcccatattc tggtatgctc   3180
cagaatcact gacagagagc aagttttctg tggcctcaga tgtttggagc tttggagtgg   3240
ttctgtatga acttttcaca tacattgaga agagtaaaag tccaccagcg gaatttatgc   3300
gtatgattgg caatgacaaa caaggacaga tgatcgtgtt ccatttgata gaacttttga   3360
agaataatgg aagattacca agaccagatg gatgcccaga tgagatctat atgatcatga   3420
cagaatgctg gaacaataat gtaaatcaac gcccctcctt tagggatcta gctcttcgag   3480
tggatcaaat aagggataac atggctggat gaaagaaatg accttcattc tgagaccaaa   3540
gtagatttac agaacaaagt tttatatttc acattgctgt ggactattat tacatatatc   3600
attattatat aaatcatgat gctagccagc aaagatgtga aaatatctgc tcaaaacttt   3660
caaagtttag taagtttttc ttcatgaggc caccagtaaa agacattaat gagaattcct   3720
tagcaaggat tttgtaagaa gtttcttaaa cattgtcagt taacatcact cttgtctggc   3780
aaaagaaaaa aaatagactt tttcaactca gctttttgag acctgaaaaa attattatgt   3840
aaattttgca atgttaaaga tgcacagaat atgtatgtat agtttttacc acagtggatg   3900
tataatacct tggcatcttg tgtgatgttt tacacacatg agggctggtg ttcattaata   3960
ctgttttcta atttttccat agttaatcta taattaatta cttcactata caaacaaatt   4020
aagatgttca gataattgaa taagtacctt tgtgtccttg ttcatttata tcgctggcca   4080
gcattataag caggtgtata cttttagctt gtagttccat gtactgtaaa tatttttcac   4140
ataaagggaa caaatgtcta gttttatttg tataggaaat ttccctgacc ctaaataata   4200
cattttgaaa tgaaacaagc ttacaaagat ataatctatt ttattatggt ttcccttgta   4260
tctatttgtg gtgaatgtgt tttttaaatg gaactatctc caaatttttc taagactact   4320
atgaacagtt ttcttttaaa attttgagat taagaatgcc aggaatattg tcatcctttg   4380
agctgctgac tgccaataac attcttcgat ctctgggatt tatgctcatg aactaaattt   4440
aagcttaagc cataaaatag attagattgt tttttaaaaa tggatagctc attaagaagt   4500
gcagcaggtt aagaattttt tcctaaagac tgtatatttg aggggtttca gaattttgca   4560
ttgcagtcat agaagagatt tatttccttt ttagagggga aatgaggtaa ataagtaaaa   4620
aagtatgctt gttaatttta ttcaagaatg ccagtagaaa attcataacg tgtatcttta   4680
agaaaaatga gcatacatct taaatctttt caattaagta taaggggttg ttcgttgttg   4740
tcatttgtta tagtgctact ccactttaga caccatagct aaaataaaat atggtgggtt   4800
ttgtgtgtgt gtgtgtgtgt gtgtgtgtgt gtgtgtgtgt gttatttata caaaacttaa   4860
aatacttgct gttttgatta aaaagaaaat agtttcttac ttta                    4904
```

<210> SEQ ID NO 12
<211> LENGTH: 5217
<212> TYPE: DNA
<213> ORGANISM: Homo sapiens

<400> SEQUENCE: 12

-continued

```
gggagtggtg tggggctgca ggaaggagag aggaagagga gcagaagggg gcagcagcgg     60
acgccgctaa cggcctccct cggcgctgac aggctgggcc ggcgcccggc tcgcttgggt    120
gttcgcgtcg ccacttcggc ttctcggccg gtcgggcccc tcggcccggg cttgcggcgc    180
gcgtcggggc tgagggctgc tgcggcgcag ggagaggcct ggtcctcgct gccgagggat    240
gtgagtggga gctgagccca cactggaggg cccccgaggg cccagcctgg aggtcgttca    300
gagccgtgcc cgtcccgggg cttcgcagac cttgacccgc cgggtaggag ccgcccctgc    360
gggctcgagg gcgcgctctg gtcgcccgat ctgtgtagcc ggcaaatgtt ctgaaaaaga    420
ctctgcatgg gaatggcctg ccttacgatg acagaaatgg agggaacatc cacctcttct    480
atatatcaga atggtgatat ttctggaaat gccaattcta tgaagcaaat agatccagtt    540
cttcaggtgt atctttacca ttcccttggg aaatctgagg cagattatct gacctttcca    600
tctggggagt atgttgcaga agaaatctgt attgctgctt ctaaagcttg tggtatcaca    660
cctgtgtatc ataatatgtt tgctttaatg agtgaaacag aaaggatctg gtatccaccc    720
aaccatgtct tccatataga tgagtcaacc aggcataatg tactctacag aataagattt    780
tactttcctc gttggtattg cagtggcagc aacagagcct atcggcatgg aatatctcga    840
ggtgctgaag ctcctcttct tgatgacttt gtcatgtctt acctctttgc tcagtggcgg    900
catgattttg tgcacggatg gataaaagta cctgtgactc atgaaacaca ggaagaatgt    960
cttgggatgg cagtgttaga tatgatgaga atagccaaag aaaacgatca aaccccactg   1020
gccatctata actctatcag ctacaagaca ttcttaccaa aatgtattcg agcaaagatc   1080
caagactatc atattttgac aaggaagcga ataaggtaca gatttcgcag atttattcag   1140
caattcagcc aatgcaaagc cactgccaga aacttgaaac ttaagtatct tataaatctg   1200
gaaactctgc agtctgcctt ctacacagag aaatttgaag taaaagaacc tggaagtggt   1260
ccttcaggtg aggagatttt tgcaaccatt ataataactg gaaacggtgg aattcagtgg   1320
tcaagaggga aacataaaga aagtgagaca ctgacagaac aggatttaca gttatattgc   1380
gattttccta atattattga tgtcagtatt aagcaagcaa accaagaggg ttcaaatgaa   1440
agccgagttg taactatcca taagcaagat ggtaaaaatc tggaaattga acttagctca   1500
ttaagggaag ctttgtcttt cgtgtcatta attgatggat attatagatt aactgcagat   1560
gcacatcatt acctctgtaa agaagtagca cctccagccg tgcttgaaaa tatacaaagc   1620
aactgtcatg gcccaatttc gatggatttt gccattagta aactgaagaa agcaggtaat   1680
cagactggac tgtatgtact tcgatgcagt cctaaggact ttaataaata tttttgact    1740
tttgctgtcg agcgagaaaa tgtcattgaa tataaacact gtttgattac aaaaaatgag   1800
aatgaagagt acaacctcag tgggacaaag aagaacttca gcagtcttaa agatcttttg   1860
aattgttacc agatggaaac tgttcgctca gacaatataa ttttccagtt tactaaatgc   1920
tgtcccccaa agccaaaaga taaatcaaac cttctagtct tcagaacgaa tggtgtttct   1980
gatgtaccaa cctcaccaac attacagagg cctactcata tgaaccaaat ggtgtttcac   2040
aaaatcagaa atgaagattt gatatttaat gaaagccttg gccaaggcac ttttacaaag   2100
atttttaaag gcgtacgaag agaagtagga gactacggtc aactgcatga aacagaagtt   2160
cttttaaaag ttctggataa agcacacaga aactattcag agtctttctt tgaagcagca   2220
agtatgatga gcaagctttc tcacaagcat ttggttttaa attatggagt atgtgtctgt   2280
ggagacgaga atattctggt tcaggagttt gtaaaatttg gatcactaga tacatatctg   2340
aaaaagaata aaaattgtat aaatatatta tggaaacttg aagttgctaa acagttggca   2400
```

-continued

```
tgggccatgc atttctaga agaaaacacc cttattcatg ggaatgtatg tgccaaaaat   2460
attctgctta tcagagaaga agacaggaag acaggaaatc ctcctttcat caaacttagt   2520
gatcctggca ttagtattac agttttgcca aaggacattc ttcaggagag aataccatgg   2580
gtaccacctg aatgcattga aaatcctaaa aatttaaatt tggcaacaga caaatggagt   2640
tttggtacca ctttgtggga aatctgcagt ggaggagata aacctctaag tgctctggat   2700
tctcaaagaa agctacaatt ttatgaagat aggcatcagc ttcctgcacc aaagtgggca   2760
gaattagcaa accttataaa taattgtatg gattatgaac cagatttcag gccttctttc   2820
agagccatca tacgagatct taacagtttg tttactccag attatgaact attaacagaa   2880
aatgacatgt taccaaatat gaggataggt gccctggggt tttctggtgc ctttgaagac   2940
cgggatccta cacagtttga agagagacat ttgaaatttc tacagcaact tggcaagggt   3000
aattttggga gtgtggagat gtgccggtat gaccctctac aggacaacac tggggaggtg   3060
gtcgctgtaa aaaagcttca gcatagtact gaagagcacc taagagactt tgaaagggaa   3120
attgaaatcc tgaaatccct acagcatgac aacattgtaa agtacaaggg agtgtgctac   3180
agtgctggtc ggcgtaatct aaaattaatt atggaatatt taccatatgg aagtttacga   3240
gactatcttc aaaaacataa agaacggata gatcacataa aacttctgca gtacacatct   3300
cagatatgca agggtatgga gtatcttggt acaaaaaggt atatccacag ggatctggca   3360
acgagaaata tattggtgga gaacgagaac agagttaaaa ttggagattt tgggttaacc   3420
aaagtcttgc cacaagacaa agaatactat aaagtaaaag aacctggtga aagtcccata   3480
ttctggtatg ctccagaatc actgacagag agcaagtttt ctgtggcctc agatgtttgg   3540
agctttggag tggttctgta tgaacttttc acatacattg agaagagtaa aagtccacca   3600
gcggaattta tgcgtatgat tggcaatgac aaacaaggac agatgatcgt gttccatttg   3660
atagaacttt tgaagaataa tggaagatta ccaagaccag atggatgccc agatgagatc   3720
tatatgatca tgacagaatg ctggaacaat aatgtaaatc aacgcccctc ctttagggat   3780
ctagctcttc gagtggatca aataagggat aacatggctg gatgaaagaa atgaccttca   3840
ttctgagacc aaagtagatt tacagaacaa agttttatat ttcacattgc tgtggactat   3900
tattacatat atcattatta tataaatcat gatgctagcc agcaaagatg tgaaaatatc   3960
tgctcaaaac tttcaaagtt tagtaagttt ttcttcatga ggccaccagt aaaagacatt   4020
aatgagaatt ccttagcaag gattttgtaa gaagtttctt aaacattgtc agttaacatc   4080
actcttgtct ggcaaaagaa aaaaaataga ctttttcaac tcagcttttt gagacctgaa   4140
aaaattatta tgtaaatttt gcaatgttaa agatgcacag aatatgtatg tatagttttt   4200
accacagtgg atgtataata ccttggcatc ttgtgtgatg ttttacacac atgagggctg   4260
gtgttcatta atactgtttt ctaatttttc catagttaat ctataattaa ttacttcact   4320
atacaaacaa attaagatgt tcagataatt gaataagtac ctttgtgtcc ttgttcattt   4380
atatcgctgg ccagcattat aagcaggtgt atacttttag cttgtagttc catgtactgt   4440
aaatattttt cacataaagg gaacaaatgt ctagttttat ttgtatagga aatttccctg   4500
accctaaata atacattttg aaatgaaaca agcttacaaa gatataatct attttattat   4560
ggtttccctt gtatctattt gtggtgaatg tgttttttaa atggaactat ctccaaattt   4620
ttctaagact actatgaaca gttttctttt aaaattttga gattaagaat gccaggaata   4680
ttgtcatcct ttgagctgct gactgccaat aacattcttc gatctctggg atttatgctc   4740
```

-continued

```
atgaactaaa tttaagctta agccataaaa tagattagat tgttttttaa aaatggatag   4800
ctcattaaga agtgcagcag gttaagaatt ttttcctaaa gactgtatat ttgaggggtt   4860
tcagaatttt gcattgcagt catagaagag atttatttcc tttttagagg ggaaatgagg   4920
taaataagta aaaaagtatg cttgttaatt ttattcaaga atgccagtag aaaattcata   4980
acgtgtatct ttaagaaaaa tgagcataca tcttaaatct tttcaattaa gtataagggg   5040
ttgttcgttg ttgtcatttg ttatagtgct actccacttt agacaccata gctaaaataa   5100
aatatggtgg gttttgtgtg tgtgtgtgtg tgtgtgtgtg tgtgtgtgtg tgtgttattt   5160
atacaaaact taaaatactt gctgttttga ttaaaaagaa aatagtttct tacttta      5217
```

<210> SEQ ID NO 13
<211> LENGTH: 5449
<212> TYPE: DNA
<213> ORGANISM: Homo sapiens

<400> SEQUENCE: 13

```
cacacaggaa ggagccgagt gggactttcc tctcgctgcc tcccggctct gcccgccctt     60
cgaaagtcca gggtccctgc ccgctaggca agttgcactc atggcacctc caagtgaaga    120
gacgcccctg atccctcagc gttcatgcag cctcttgtcc acggaggctg gtgccctgca    180
tgtgctgctg cccgctcggg gccccgggcc cccccagcgc ctatctttct cctttgggga    240
ccacttggct gaggacctgt gcgtgcaggc tgccaaggcc agcggcatcc tgcctgtgta    300
ccactccctc tttgctctgg ccacggagga cctgtcctgc tggttccccc cgagccacat    360
cttctccgtg gaggatgcca gcacccaagt cctgctgtac aggattcgct tttacttccc    420
caattggttt gggctggaga agtgccaccg cttcgggcta cgcaaggatt tggccagtgc    480
tatccttgac ctgccagtcc tggagcacct ctttgcccag caccgcagtg acctggtgag    540
tgggcgcctc cccgtgggcc tcagtctcaa ggagcagggt gagtgtctca gcctggccgt    600
gttggacctg gcccggatgg cgcgagagca ggcccagcgg ccgggagagc tgctgaagac    660
tgtcagctac aaggcctgcc taccccccaag cctgcgcgac ctgatccagg gcctgagctt    720
cgtgacgcgg aggcgtattc ggaggacggt gcgcagagcc ctgcgccgcg tggccgcctg    780
ccaggcagac cggcactcgc tcatggccaa gtacatcatg gacctggagc ggctggatcc    840
agccggggcc gccgagacct tccacgtggg cctccctggg gcccttggtg gccacgacgg    900
gctggggctg ctccgcgtgg ctggtgacgg cggcatcgcc tggacccagg gagaacagga    960
ggtcctccag cccttctgcg actttccaga aatcgtagac attagcatca agcaggcccc   1020
gcgcgttggc ccggccggag agcaccgcct ggtcactgtt accaggacag acaaccagat   1080
tttagaggcc gagttcccag ggctgcccga ggctctgtcg ttcgtggcgc tcgtggacgg   1140
ctacttccgg ctgaccacgg actcccagca cttcttctgc aaggaggtgg caccgccgag   1200
gctgctggag gaagtggccg agcagtgcca cggccccatc actctggact ttgccatcaa   1260
caagctcaag actgggggct cacgtcctgg ctcctatgtt ctccgccgca gcccccagga   1320
ctttgacagc ttcctcctca ctgtctgtgt ccagaacccc cttggtcctg attataaggg   1380
ctgcctcatc cggcgcagcc ccacaggaac cttccttctg gttggcctca gccgacccca   1440
cagcagtctt cgagagctcc tggcaacctg ctgggatggg ggctgcacg tagatggggt   1500
ggcagtgacc ctcacttcct gctgtatccc cagacccaaa gaaaagtcca acctgatcgt   1560
ggtccagaga ggtcacagcc cacccacatc atccttggtt cagccccaat cccaatacca   1620
gctgagtcag atgacatttc acaagatccc tgctgacagc ctggagtggc atgagaacct   1680
```

-continued

```
gggccatggg tccttcacca agatttaccg gggctgtcgc catgaggtgg tggatgggga   1740
ggcccgaaag acagaggtgc tgctgaaggt catggatgcc aagcacaaga actgcatgga   1800
gtcattcctg gaagcagcga gcttgatgag ccaagtgtcg taccggcatc tcgtgctgct   1860
ccacggcgtg tgcatggctg gagacagcac catggtgcag gaatttgtac acctgggggc   1920
catagacatg tatctgcgaa aacgtggcca cctggtgcca gccagctgga agctgcaggt   1980
ggtcaaacag ctggcctacg ccctcaacta tctggaggac aaaggcctgc cccatggcaa   2040
tgtctctgcc cggaaggtgc tcctggctcg ggaggggggct gatgggagcc cgcccttcat   2100
caagctgagt gaccctgggg tcagccccgc tgtgttaagc ctggagatgc tcaccgacag   2160
gatcccctgg gtggcccccg agtgtctccg ggaggcgcag acacttagct tggaagctga   2220
caagtggggc ttcggcgcca cggtctggga agtgtttagt ggcgtcacca tgcccatcag   2280
tgccctggat cctgctaaga aactccaatt ttatgaggac cggcagcagc tgccggcccc   2340
caagtggaca gagctggccc tgctgattca acagtgcatg gcctatgagc cggtccagag   2400
gccctccttc cgagccgtca ttcgtgacct caatagcctc atctcttcag actatgagct   2460
cctctcagac cccacacctg gtgccctggc acctcgtgat gggctgtgga atggtgccca   2520
gctctatgcc tgccaagacc ccacgatctt cgaggagaga cacctcaagt acatctcaca   2580
gctgggcaag ggcaactttg gcagcgtgga gctgtgccgc tatgacccgc taggcgacaa   2640
tacaggtgcc ctggtggccg tgaaacagct gcagcacagc gggccagacc agcagaggga   2700
ctttcagcgg gagattcaga tcctcaaagc actgcacagt gatttcattg tcaagtatcg   2760
tggtgtcagc tatggcccgg gccgccagag cctgcggctg gtcatggagt acctgcccag   2820
cggctgcttg cgcgacttcc tgcagcggca ccgcgcgcgc ctcgatgcca gccgcctcct   2880
tctctattcc tcgcagatct gcaagggcat ggagtacctg ggctcccgcc gctgcgtgca   2940
ccgcgacctg gccgcccgaa acatcctcgt ggagagcgag gcacacgtca agatcgctga   3000
cttcggccta gctaagctgc tgccgcttga caaagactac tacgtggtcc gcgagccagg   3060
ccagagcccc attttctggt atgcccccga atccctctcg gacaacatct tctctcgcca   3120
gtcagacgtc tggagcttcg gggtcgtcct gtacgagctc ttcacctact gcgacaaaag   3180
ctgcagcccc tcggccgagt tcctgcggat gatgggatgt gagcgggatg tccccgccct   3240
ctgccgcctc ttggaactgc tggaggaggg ccagaggctg ccggcgcctc ctgcctgccc   3300
tgctgaggtt cacgagctca tgaagctgtg ctgggcccct agcccacagg accggccatc   3360
attcagcgcc ctgggccccc agctggacat gctgtggagc ggaagccggg ggtgtgagac   3420
tcatgccttc actgctcacc cagagggcaa acaccactcc ctgtcctttt catagctcct   3480
gcccgcagac ctctggatta ggtctctgtt gactggctgt gtgaccttag gcccggagct   3540
gcccctctct gggcctcaga ggccttatga gggtcctcta cttcaggaac acccccatga   3600
cattgcattt ggggggctc ccgtggcctg tagaatagcc tgtggccttt gcaatttgtt   3660
aaggttcaag acagatgggc atatgtgtca gtggggctct ctgagtcctg gcccaaagaa   3720
gcaaggaacc aaatttaaga ctctcgcatc ttcccaaccc cttaagccct ggccccctga   3780
gtttcctttt ctgtctctct ctttttattt tttttatttt tatttttatt tttgagacag   3840
agcctcgctc tgttacccag ggtggagtgc agtggtgcga tctcggctca gtgcaacctc   3900
tgcttcccag gttcaagcga ttctcctgcc tcagcctccc gagtagctgg gattacaggt   3960
gtgcaccacc acacccggct aattttttt atttttaata gagatgaggt ttcaccatga   4020
```

tggccaggct gatctcgaac tcctaacctc aagtgatcct cccacctcag cctcccaaag 4080
tgttggaata ataggcatga gccactgcac ccaggctttt ttttttttaa atttattatt 4140
attattttta agagacagga tcttgctacg ttgcccaggc tggtcttgaa ctcctgggct 4200
acagtgatcc tcctgcctta tcctcctaaa tagctgggac tacagcacct agttttgagt 4260
ttcctgtctt atttccaatg gggacattca tgtagctttt tttttttttt tttttttgag 4320
acggagtctc gctctgtcgc ccaggctgga gtacagtggc gcaatctagg ctcactgcaa 4380
gctccgcctc ctgggttcac accattctct cgcctcagcc tcccaagtag ctgggactac 4440
aggcgcccgc caccacaccc ggctaatttt ttgtattttt agtagagacg gggtttcacc 4500
ttgttagcca ggatggtttc catctcctga cctcgtgatc tgcccgtctc ggcctcccaa 4560
agtgctggga ttacaggcat gagccactgc gcccggccct catgtagctt taaatgtatg 4620
atctgacttc tgctccccga tctctgtttc tctggaggaa gccaaggaca agagcagttg 4680
ctgtggctgg gactctgcct tttaggggag cccgtgtatc tctttgggat cctgaaaggg 4740
ggcaggaaag gctggggtcc cagtccaccc taatggtatc tgagtgtcct agggcttcag 4800
ttttcccacc tgtccaatgg gaccctttct gtcctcaccc tacaaggggc acaaagggat 4860
gacaccaaac ctggcaggaa cttttcacgc aatcaaggga aggaaaggca ttcctggcag 4920
agggaacagc atgccaagcg tgagaaggct cagagtaagg aggttaagag cccaagtatt 4980
ggagcctaca gttttgcccc ttccatgcag tgtgacagtg ggcaagttcc tttccctctc 5040
tgggtctcag ttctgtcccc tgcaaaatgg tcagagctta ccccttggct gtgcagggtc 5100
aactttctga ctggtgagag ggattctcat gcaggttaag cttctgctgc tcctcctcac 5160
ctgcaaagct tttctgccac ttttgcctcc ttggaaaact cttatccatc tctcaaaact 5220
ccagctacca catccttgca gccttccctc atataccccc actactactg tagccctgtc 5280
cttccctcca gccccactct ggccctgggg ctggggaagt gtctgtgtcc agctgtctcc 5340
cctgacctca gggttccttg ggggctgggc tgaggcctca gtacagaggg ggctctggaa 5400
atgtttgttg actgaataaa ggaattcagt ggaaaaaaaa aaaaaaaaa 5449

<210> SEQ ID NO 14
<211> LENGTH: 4064
<212> TYPE: DNA
<213> ORGANISM: Homo sapiens

<400> SEQUENCE: 14
ccctctgacc aggactgagg ggctttttct ctctgtgccc caggcaagtt gcactcatta 60
tggaattccg gcggcccgct aggcaagttg cactcatggc acctccaagt gaagagacgc 120
ccctgatccc tcagcgttca tgcagcctct tgtccacgga ggctggtgcc ctgcatgtgc 180
tgctgcccgc tcgggccccg gggccccccc agcgcctatc tttctccttt ggggaccact 240
tggctgagga cctgtgcgtg caggctgcca aggccagcgg catcctgcct gtgtaccact 300
ccctctttgc tctggccacg gaggacctgt cctgctggtt ccccccgagc cacatcttct 360
ccgtggagga tgccagcacc caagtcctgc tgtacaggat tcgcttttac ttccccaatt 420
ggtttgggct ggagaagtgc caccgcttcg ggctacgcaa ggatttggcc agtgctatcc 480
ttgacctgcc agtcctggag cacctctttg cccagcaccg cagtgacctg gtgagtgggc 540
gcctccccgt gggcctcagt ctcaaggagc agggtgagtg tctcagcctg gccgtgttgg 600
acctggcccg gatggcgcga gagcaggccc agcggccggg agagctgctg aagactgtca 660
gctacaaggc ctgcctaccc ccaagcctgc gcgacctgat ccagggcctg agcttcgtga 720

-continued

```
cgcggagggc tattcggagg acggtgcgca gagccctgcc gcgcgtggcc gcctgccagg    780
cagaccggca ctcgctcatg gccaagtaca tcatggacct ggagcggctg gatccagccg    840
gggccgccga gaccttccac gtgggcctcc ctggggccct tggtggccac gacgggctgg    900
ggctgctccg cgtggctggt gacggcggca tcgcctggac ccagggagaa caggaggtcc    960
tccagccctt ctgcgacttt ccagaaatcg tagacattag catcaagcag gccccgcgcg   1020
ttggcccggc cggagagcac cgcctggtca ctgttaccag gacagacaac cagattttag   1080
aggccgagtt cccagggctg cccgaggctc tgtcgttcgt ggcgctcgtg gacggctact   1140
tccggctgac cacggactcc cagcacttct tctgcaagga ggtggcaccg ccgaggctgc   1200
tggaggaagt ggccgagcag tgccacggcc ccatcactct ggactttgcc atcaacaagc   1260
tcaagactgg gggctcacgt cctggctcct atgttctccg ccgcagcccc caggactttg   1320
acagcttcct cctcactgtc tgtgtccaga accccccttgg tcctgattat aagggctgcc   1380
tcatccggcg cagccccaca ggaaccttcc ttctggttgg cctcagccga ccccacagca   1440
gtcttcgaga gctcctggca acctgctggg atggggggct gcacgtagat ggggtggcag   1500
tgaccctcac ttcctgctgt atccccagac ccaaagaaaa gtccaacctg atcgtggtcc   1560
agagaggtca cagcccaccc acatcatcct tggttcagcc ccaatcccaa taccagctga   1620
gtcagatgac atttcacaag atccctgctg acagcctgga gtggcatgag aacctgggcc   1680
atgggtcctt caccaagatt taccggggct gtcgccatga ggtggtggat ggggaggccc   1740
gaaagacaga ggtgctgctg aaggtcatgg atgccaagca caagaactgc atggagtcat   1800
tcctggaagc agcgagcttg atgagccaag tgtcgtaccg gcatctcgtg ctgctccacg   1860
gcgtgtgcat ggctggagac agcaccatgg tgcaggaatt tgtacacctg gggggccatag   1920
acatgtatct gcgaaaacgt ggccacctgg tgccagccag ctggaagctg caggtggtca   1980
aacagctggc ctacgccctc aactatctgg aggacaaagg cctgccccat ggcaatgtct   2040
ctgcccggaa ggtgctcctg gctcgggagg gggctgatgg gagcccgccc ttcatcaagc   2100
tgagtgaccc tggggtcagc cccgctgtgt taagcctgga gatgctcacc gacaggatcc   2160
cctgggtggc ccccgagtgt ctccgggagg cgcagacact tagcttggaa gctgacaagt   2220
ggggcttcgg cgccacggtc tgggaagtgt ttagtggcgt caccatgccc atcagtgccc   2280
tggatcctgc taagaaactc caattttatg aggaccggca gcagctgccg gccccccaagt   2340
ggacagagct ggccctgctg attcaacagt gcatggccta tgagccggtc cagaggccct   2400
ccttccgagc cgtcattcgt gacctcaata gcctcatctc ttcagactat gagctcctct   2460
cagaccccac acctggtgcc ctggcacctc gtgatgggct gtggaatggt gcccagctct   2520
atgcctgcca agaccccacg atcttcgagg agagacacct caagtacatc tcacagctgg   2580
gcaagggcaa ctttggcagc gtggagctgt gccgctatga cccgctagcc cacaatacag   2640
gtgccctggt ggccgtgaaa cagctgcagc acagcgggcc agaccagcag agggactttc   2700
agcgggagat tcagatcctc aaagcactgc acagtgattt cattgtcaag tatcgtggtg   2760
tcagctatgg cccgggccgg ccagagctgc ggctggtcat ggagtacctg cccagcggct   2820
gcttgcgcga cttcctgcag cggcaccgcg cgcgcctcga tgccagccgc ctccttctct   2880
attcctcgca gatctgcaag ggcatggagt acctgggctc ccgccgctgc gtgcaccgcg   2940
acctggccgc ccgaaacatc ctcgtggaga gcgaggcaca cgtcaagatc gctgacttcg   3000
gcctagctaa gctgctgccg cttgacaaag actactacgt ggtccgcgag ccaggccaga   3060
```

gccccatttt ctggtatgcc cccgaatccc tctcggacaa catcttctct cgccagtcag 3120
acgtctggag cttcggggtc gtcctgtacg agctcttcac ctactgcgac aaaagctgca 3180
gcccctcggc cgagttcctg cggatgatgg gatgtgagcg ggatgtcccc gccctctgcc 3240
gcctcttgga actgctggag gagggccaga ggctgccggc gcctcctgcc tgccctgctg 3300
aggttcacga gctcatgaag ctgtgctggg cccctagccc acaggaccgg ccatcattca 3360
gcgccctggg cccccagctg gacatgctgt ggagcggaag ccgggggtgt gagactcatg 3420
ccttcactgc tcacccagag ggcaaacacc actccctgtc cttttcatag ctcctgcccg 3480
cagacctctg gattaggtct ctgttgactg gctgtgtgac cttaggcccg gagctgcccc 3540
tctctgggcc tcagaggcct tatgagggtc ctctacttca ggaacacccc catgacattg 3600
catttggggg ggctcccgtg gcctgtagaa tagcctgtgg cctttgcaat ttgttaaggt 3660
tcaagacaga tgggcatatg tgtcagtggg gctctctgag tcctggccca aagaagcaag 3720
gaaccaaatt taagactctc gcatcttccc aaccccttaa gccctggccc cctgagtttc 3780
cttttctcgt ctctctcttt ttattttttt tatttttatt tttatttttg agacagagcc 3840
tcgctcgtta cccagggtgg agtgcagtgg tagcgatctc ggctcacagt gcaacctctg 3900
cttcccaggt tcaagcgatt ctcctgcctc agcctcccga gtagctggga ttacaggtgt 3960
gcaccaccac acccggctaa ttttttttat ttttaataga gatgaggttt caccatgatg 4020
gccaggctga tctcgaactc ctaacctcaa gtgatcctcc cacc 4064

<210> SEQ ID NO 15
<211> LENGTH: 4262
<212> TYPE: DNA
<213> ORGANISM: Homo sapiens

<400> SEQUENCE: 15
aagcagtagc tacccgcggg agcggggagg ggtccgggtt cgagcttgtg ttcccccgga 60
agggtgagtc tggacgcggg cgcggaagga gcgcggccgg aggtcctcag gaagaagccg 120
cggggactgg ctgcgcttga caggctgcac ttggatggga gcacctggtg cctcgggact 180
gctccgatgc ccgggtctgt gctgaatgtg taatatgcgg aactatattg aaacattaca 240
accatctttt gatggcaaca ccctgaggac ctcccttttc cagatgggga aactgaggcc 300
cagaattgct aagtggcttg cttgagttga cacagggagc tccaggactc accctcagct 360
gagccacctg ccgggagcat gcctctgcgc cactgggggga tggccagggg cagtaagccc 420
gttggggatg gagcccagcc catggctgcc atgggaggcc tgaaggtgct tctgcactgg 480
gctggtccag gcggcgggga gccctgggtc actttcagtg agtcatcgct gacagctgag 540
gaagtctgca tccacattgc acataaagtt ggtatcactc ctccttgctt caatctcttt 600
gccctcttcg atgctcaggc ccaagtctgg ttgcccccaa accacatcct agagatcccc 660
agagatgcaa gcctgatgct atatttccgc ataaggtttt atttccggaa ctggcatggc 720
atgaatcctc gggaaccggc tgtgtaccgt tgtgggcccc caggaaccga ggcatcctca 780
gatcagacag cacaggggat gcaactcctg gacccagcct catttgagta cctctttgag 840
cagggcaagc atgagtttgt gaatgacgtg gcatcactgt gggagctgtc gaccgaggag 900
gagatccacc actttaagaa tgagagcctg ggcatggcct ttctgcacct ctgtcacctc 960
gctctccgcc atggcatccc cctggaggag gtggccaaga agaccagctt caaggactgc 1020
atcccgcgct ccttccgccg gcatatccgg cagcacagcg ccctgacccg gctgcgcctt 1080
cggaacgtct tccgcaggtt cctgcgggac ttccagccgg gccgactctc ccagcagatg 1140

-continued

```
gtcatggtca aatacctagc cacactcgag cggctggcac cccgcttcgg cacagagcgt   1200
gtgcccgtgt gccacctgag gctgctggcc caggccgagg gggagccctg ctacatccgg   1260
gacagtgggg tggcccctac agaccctggc cctgagtctg ctgctgggcc cccaacccac   1320
gaggtgctgg tgacaggcac tggtggcatc cagtggtggc cagtagagga ggaggtgaac   1380
aaggaggagg gttctagtgg cagcagtggc aggaaccccc aagccagcct gtttgggaag   1440
aaggccaagg ctcacaaggc agtcggccag ccggcagaca ggccgcggga gccactgtgg   1500
gcctacttct gtgacttccg ggacatcacc cacgtggtgc tgaaagagca ctgtgtcagc   1560
atccaccggc aggacaacaa gtgcctggag ctgagcttgc cttcccgggc tgcggcgctg   1620
tccttcgtgt cgctggtgga cggctatttc cgcctgacgg ccgactccag ccactacctg   1680
tgccacgagg tggctccccc acggctggtg atgagcatcc gggatgggat ccacggaccc   1740
ctgctggagc catttgtgca ggccaagctg cggcccgagg acggcctgta cctcattcac   1800
tggagcacca gccacccccta ccgcctgatc ctcacagtgg cccagcgtag ccaggcacca   1860
gacggcatgc agagcttgcg gctccgaaag ttccccattg agcagcagga cggggccttc   1920
gtgctggagg gctggggccg gtccttcccc agcgttcggg aacttggggc tgccttgcag   1980
ggctgcttgc tgagggccgg ggatgactgc ttctctctgc gtcgctgttg cctgccccaa   2040
ccaggagaaa cctccaatct catcatcatg cggggggctc gggccagccc caggacactc   2100
aacctcagcc agctcagctt ccaccgggtt gaccagaagg agatcaccca gctgtcccac   2160
ttgggccagg gcacaaggac caacgtgtat gagggccgcc tgcgagtgga gggcagcggg   2220
gaccctgagg agggcaagat ggatgacgag gaccccctcg tgcctggcag ggaccgtggg   2280
caggagctac gagtggtgct caaagtgctg gaccctagtc accatgacat cgccctggcc   2340
ttctacgaga cagccagcct catgagccag gtctcccaca cgcacctggc cttcgtgcat   2400
ggcgtctgtg tgcgcggccc tgaaaatatc atggtgacag agtacgtgga gcacggaccc   2460
ctggatgtgt ggctgcggag ggagcggggc catgtgccca tggcttggaa gatggtggtg   2520
gcccagcagc tggccagcgc cctcagctac ctggagaaca agaacctggt tcatggtaat   2580
gtgtgtggcc ggaacatcct gctggcccgg ctggggttgg cagagggcac cagccccttc   2640
atcaagctga gtgatcctgg cgtgggcctg ggcgccctct ccagggagga gcgggtggag   2700
aggatcccct ggctggcccc cgaatgccta ccaggtgggg ccaacagcct aagcaccgcc   2760
atggacaagt gggggtttgg cgccaccctc ctggagatct gctttgacgg agaggcccct   2820
ctgcagagcc gcagtccctc cgagaaggag catttctacc agaggcagca ccggctgccc   2880
gagccctcct gcccacagct ggccacactc accagccagt gtctgaccta tgagccaacc   2940
cagaggccat cattccgcac catcctgcgt gacctcaccc ggctgcagcc ccacaatctt   3000
gctgacgtct tgactgtgaa cccggactca ccggcgtcgg accctacggt tttccacaag   3060
cgctatttga aaaagatccg agatctgggc gagggtcact tcggcaaggt cagcttgtac   3120
tgctacgatc cgaccaacga cggcactggc gagatggtgg cggtgaaagc cctcaaggca   3180
gactgcggcc cccagcaccg ctcgggctgg aagcaggaga ttgacattct gcgcacgctc   3240
taccacgagc acatcatcaa gtacaagggc tgctgcgagg accaaggcga gaagtcgctg   3300
cagctggtca tggagtacgt gcccctgggc agcctccgag actacctgcc ccggcacagc   3360
atcgggctgg cccagctgct gctcttcgcc cagcagatct gcgagggcat ggcctatctg   3420
cacgcgcagc actacatcca ccgagaccta gccgcgcgca acgtgctgct ggacaacgac   3480
```

-continued

```
aggctggtca agatcgggga ctttggccta gccaaggccg tgcccgaagg ccacgagtac   3540

taccgcgtgc gcgaggatgg ggacagcccc gtgttctggt atgccccaga gtgcctgaag   3600

gagtataagt tctactatgc gtcagatgtc tggtccttcg gggtgaccct gtatgagctg   3660

ctgacgcact gtgactccag ccagagcccc cccacgaaat tccttgagct cataggcatt   3720

gctcagggtc agatgacagt tctgagactc actgagttgc tggaacgagg ggagaggctg   3780

ccacggcccg acaaatgtcc ctgtgaggtc tatcatctca tgaagaactg ctgggagaca   3840

gaggcgtcct ttcgcccaac cttcgagaac ctcataccca ttctgaagac agtccatgag   3900

aagtaccaag gccaggcccc ttcagtgttc agcgtgtgct gaggcacaat ggcagccctg   3960

cctgggagga ctggaccagg cagtggctgc agagggagcc tcctgctccc tgctccagga   4020

tgaaaccaag agggggatgt cagcctcacc cacaccgtgt gccttactcc tgtctagaga   4080

ccccacctct gtgaacttat ttttctttct tggccgtgag cctaaccatg atcttgaggg   4140

acccaacatt tgtaggggca ctaatccagc ccttaaatcc cccagcttcc aaacttgagg   4200

cccaccatct ccaccatctg gtaataaact catgttttct ctgctggaaa aaaaaaaaaa   4260

aa                                                                  4262
```